(12) United States Patent
Rife et al.

(10) Patent No.: US 9,273,299 B2
(45) Date of Patent: Mar. 1, 2016

(54) ISOPRENE SYNTHASE VARIANTS WITH IMPROVED SOLUBILITY FOR PRODUCTION OF ISOPRENE

(71) Applicants: Danisco US Inc., Palo Alto, CA (US); The Goodyear Tire & Rubber Company, Akron, OH (US)

(72) Inventors: Christopher L. Rife, Redwood City, CA (US); Derek H. Wells, Palo Alto, CA (US)

(73) Assignees: DANISCO US INC., Palo Alto, CA (US); THE GOODYEAR & TIRE RUBBER COMPANY, Akron, OH (US)

( * ) Notice: Subject to any disclaimer, the term of this patent is extended or adjusted under 35 U.S.C. 154(b) by 81 days.

(21) Appl. No.: 14/251,311

(22) Filed: Apr. 11, 2014

(65) Prior Publication Data

US 2014/0315275 A1     Oct. 23, 2014

Related U.S. Application Data

(62) Division of application No. 13/662,328, filed on Oct. 26, 2012, now Pat. No. 8,735,134.

(60) Provisional application No. 61/552,453, filed on Oct. 27, 2011.

(51) Int. Cl.

| | |
|---|---|
| C12P 5/02 | (2006.01) |
| C12N 9/88 | (2006.01) |
| C07H 21/04 | (2006.01) |
| C12N 15/82 | (2006.01) |
| C12P 5/00 | (2006.01) |
| C08L 7/00 | (2006.01) |

(52) U.S. Cl.
CPC .............. *C12N 9/88* (2013.01); *C12N 15/8243* (2013.01); *C12P 5/007* (2013.01); *C12Y 402/03007* (2013.01); *C08L 7/00* (2013.01)

(58) Field of Classification Search
None
See application file for complete search history.

(56) References Cited

U.S. PATENT DOCUMENTS

| | | | |
|---|---|---|---|
| 4,570,029 A | 2/1986 | Kulprathipanja et al. | |
| 4,703,007 A | 10/1987 | Mulholland et al. | |
| 6,106,888 A | 8/2000 | Dale et al. | |
| 6,176,176 B1 | 1/2001 | Dale et al. | |
| 8,288,148 B2 | 10/2012 | Cervin et al. | |
| 8,420,360 B2 | 4/2013 | Calabria et al. | |
| 8,420,759 B2 | 4/2013 | Feher et al. | |
| 8,735,134 B2 | 5/2014 | Rife et al. | |
| 2008/0038805 A1 | 2/2008 | Melis | |
| 2009/0076743 A1 | 3/2009 | Moseson et al. | |
| 2010/0003716 A1 | 1/2010 | Cervin et al. | |
| 2010/0086978 A1 | 4/2010 | Beck et al. | |
| 2010/0285549 A1 | 11/2010 | Muramatsu et al. | |

FOREIGN PATENT DOCUMENTS

| | | |
|---|---|---|
| JP | 2008/061506 A | 3/2008 |
| WO | WO-96/35796 A1 | 11/1996 |
| WO | WO-98/02550 A2 | 1/1998 |
| WO | WO-98/02550 A3 | 1/1998 |
| WO | WO-02/10398 A2 | 2/2002 |
| WO | WO-02/10398 A3 | 2/2002 |
| WO | WO-2004/033646 A2 | 4/2004 |
| WO | WO-2004/033646 A3 | 4/2004 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2011/075534 A2 | 6/2011 |
| WO | WO-2011/075534 A3 | 6/2011 |
| WO | WO-2011/075748 A1 | 6/2011 |
| WO | WO-2011/079314 A2 | 6/2011 |
| WO | WO-2011/079314 A3 | 6/2011 |
| WO | WO-2012/058494 A2 | 5/2012 |
| WO | WO-2012/058494 A3 | 5/2012 |

OTHER PUBLICATIONS

Altschul, S.F. et al. "Basic Local Alignment Search Tool." *J. Mol. Biol.* 1990, 215(3):403-410.
Altschul, S.F. et al., "Local Alignment Statistics," Chapter 27 in *Multiple Alignment and Phylogenetic Trees*, American Press, Inc., 1996, 266:460-480.
Altschul, et al. "Gapped BLAST and PSI-BLAST: A New Generation of Protein Database Search Programs," *Nucleic Acids Res.* 1997, 25(17):3389-3402.
Ausubel, F.M. et al. (1997). "Introduction of DNA into Mammalian Cells," Chapter 9 in *Current Protocols in Molecular Biology*, Contributed by R.E. Kingston, John Wiley & Sons, Inc., 205 pages.

(Continued)

*Primary Examiner* — Iqbal H Chowdhury
(74) *Attorney, Agent, or Firm* — Mintz, Levin, Cohn, Ferris, Glovsky and Popeo, P.C.

(57) ABSTRACT

The present invention provides methods and compositions of variant polypeptides having isoprene synthase activity with improved solubility. In particular, the present invention provides isoprene synthase variant for increased isoprene production in recombinant host cells.

14 Claims, 26 Drawing Sheets

(56) References Cited

OTHER PUBLICATIONS

Bellion, E. et al., "Methylamine Utilization in Yeast and Bacteria: Studies Using in vivo NMR," Chapter 32 in Microbial Growth C1 Compounds, Muerrell, J.C. et al. eds, Intercept Ltd: Andover, UK, 1993, pp. 415-432.
Campbell, et al., "Improved Transformation Efficiency of *Aspergillus niger* Using the Homologus *nia*D Gene for Nitrate Reductase," *Current Genetics* 1989, 16:53-56.
Collaborative Computational Project, No. 4, "The CCP4 Suite: Programs for Protein Crystallography," *Acta Crystallographica* Section D50, 1994, 760-763.
Davis, I. W., et al. "MolProbity: All-Atom Contacts and Structure Validation for Proteins and Nucleic Acids," *Nucl. Acids Research* 2007, 35:W375-W383.
Devereux, et al., "A Comprehensive Set of Sequence Analysis Programs for the VAX," *Nucl. Acid Research* 1984, 12:387-395.
Emsley, P. et al. (2010). "Features and Development of *Coot*," *Acta Crystallographica* Section D66, 486-501.
Feng, D.-F. et al. "Progressive Sequence Alignment as a Prerequisite to Correct Phylogenetic Trees," *J. Mol. Evol.* 1987, 35:351-360.
Gottschalk, G., Bacterial Metabolism, Second Edition, Springer Verlag: New York, NY, 1986, pp. xi-xiii. (Table of Contents Only).
Greenberg, J.P. et al. "Sub-Parts Per Billion Detection of Isoprene Using a Reduction Gas Detector with a Portable Gas Chromatograph," *Atmos. Environ.* 1993, 27A(16):2689-2692.
Hedl, et al. "*Enterococcus faecalis* Acetoacetyl-Coenzyme a Thiolase/3-Hydroxy-3-Methyglutaryl-Coenzyme a Reductase, a Dual-Function Protein of Isopentenyl Diphosphate Biosynthesis," *Journal of Bacteriology* Apr. 2002, 184(8):2116-2122.
Henikoff, S. et al. (Nov. 1992). "Amino Acid Substitution Matrices from Protein Blocks," *Proc. Natl. Acad. Sci. USA* 89:10915-10919.
Higgins, D.G. et al. "Fast and Sensitive Multiple Sequence Alignments on a Microcomputer," *Cabios Communications* 1989, 5(2):151-153.
Hunter, B.K., "Formaldehyde Metabolism by *Escherichia coli.* Carbon and Solvent Deuterium Incorporation into Glycerol, 1,2-Propanediol, and 1,3-Propanediol," *Biochemistry* 1985, 24(15):4148-4155.
Ilmen, M. et al., "Regulation of Cellulase Gene Expression in the Filamentous Fungus *Trichoderma reesei*," *Appl. Environ. Microbiol.* Apr. 1997, 63(4):1298-1306.
Jeong, et al., "Cloning and Characterization of a Gene Encoding Phosphoketolase in a *Lactobacillus paraplantarum* Isolated from *Kimchi,*" *J. Microbiol. Biotechnol.* 2007, 17:5, 822-829.
Karlin, S. et al. (Jun. 1993). "Applications and Statistics for Multiple High Scoring Segments in Molecular Sequences," *Proc. Natl. Acad. Sci. USA* 90:5873-5877.
Meile, et al., "Characterization of the D-Xylulose 5-Phosphate/D-Fructose 6-Phosphate Phosphoketolase Gene (*xfp*) from *Bifidobacterium lactis,*" *Journal of Bacteriology* May 2001, 183(9):2929-2936.
Miller, B. et al. (2001, e-pub. May 10, 2001) "First Isolation of an Isoprene Synthase Gene from Poplar and Successful Expression of the Gene in *Escherichia coli*," *Planta* 213:483-487.
Needleman, S.B. et al. (1970). "A General Method Applicable to the Search for Similarities in the Amino Add Sequence of Two Proteins," *J. Mol. Biol.* 48:443-453.
Okamura, et al. (Jun. 22, 2010). "Unprecedented Acetoacetyl-Coenzyme A Synthesizing Enzyme of the Thiolase Superfamily Involved in the Mevalonate Pathway," *PNAS* 107(25):11265-11270.
Pearson, W.R. et al. (Apr. 1988). "Improved Tools for Biological Sequence Comparison," *Proc. Natl. Acad. Sci. USA* 85:2444-2448.
Pourquié, J. et al. "Scale Up of Cellulase Production and Utilization," in *Biochemistry and Genetics of Cellulose Degradation*, Aubert, J.-P. et al. eds., Academic Press: San Diego, CA, 1988, pp. 71-86.
Read, R.J. et al. (2011). "Using SAD Data in *Phaser*," *Acta Crystallographica* Section D67, 338-344.
Sharkey, T.D. et al. (Feb. 2005). "Evolution of the Isoprene Biosynthetic Pathway in Kudzu," *Plant Physiology* 137(2):700-712.
Sharkey, T.D. et al. (Feb. 2005). "Evolution of the Isoprene Biosynthetic Pathway in Kudzu," *Plant Physiology* 137(2):700-712, Supplemental Data, four pages.
Silver, et al. "Characterization of Aspen Isoprene Synthase, an Enzyme Responsible for Leaf Isoprene Emission to the Atmosphere," *J. Biol. Chem.* Jun. 2, 1995, 270(22):13010-13016.
Silver, G.M. et al., "Enzymatic Synthesis of Isoprene from Dimethylallyl Diphosphate in Aspen Leaf Extracts," *Plant Physiol.* 1991, 97:1588-1591.
Smith, T.F. et al. "Comparison of Biosequences," *Adv. Appl. Math.* 1981, 2:482-489.
Steller, et al., "An Algorithm for Automatic Indexing of Oscillation Images using Fourier Analysis," *J. Appl. Cryst.* 1997, 30:1036-1040.
Sulter, et al. (1990). "Proliferation and Metabolic Significance of Peroxisomes in *Candida boidinii* During Growth on D-Alanine or Oleic Acid as the Sole Carbon Source," *Arch. Microbiol.* 153(5):485-489.
Teymouri, et al. "Optimization of the Ammonia Fiber Explosion (AFEX) Treatment Parameters for Enzymatic Hydrolysis of Corn Stover," *Bioresource Technology* 2005, 96(18):2014-2018.
Vagin, A., et al. (1997). "*MOLREP*: an Automated Program for Molecular Replacement," *J. of Appl. Crystallography* 30:1022-1025.
Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.
Yamada, K. et al. "Production of Glycerol from Methanol by a Mutant Strain of *Candida boidinii* No. 2201," *Agric. Biol. Chem.* 1989, 53(2):541-543.
International Search Report mailed on Apr. 26, 2013 for PCT Patent Application No. PCT/US2012/062308, filed on Oct. 26, 2012, five pages.
EMBL-EBI Accession No. AY341431, last updated Apr. 16, 2005, located at <http://www.ebi.ac.uk/cgi-bin/dbfetch?db=embl&id=AY341431∈ . . . >, last visited on Nov. 26, 2009, 2 pages.
EMBL-EBI Accession No. AB198180, last updated May 10, 2005, located at <http://www.ebi.ac.uk/cgi-bin/dbfetch?db=embl&id=ab198180&Subm . . . >, last visited on Aug. 7, 2009, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AJ294819.1, last updated Apr. 15, 2005, located at <http://www.ncbi.nlm.nih.gov/nuccore/AJ294819.1>, last visited on Dec. 7, 2011, 2 pages.
GenBank Accession No. EU693027.1, last updated on May 27, 2008, located at <http://www.ncbi.nlm.nih.gov/nuccore/189017053>, last visited on Jun. 2, 2010, 2 pages.
GenBank Accession No. EF638224.1, last updated May 3, 2010, located at <http://www.ncbi.nlm.nih.gov/nuccore/EF638224.1>, last visited on Dec. 7, 2011, 2 pages.
GenBank Accession No. AM410988.1, last updated Aug. 14, 2008, located at <http://www.ncbi.nlm.nih.gov/nuccore/AM410988.1>, last visited on Dec. 7, 2011, 2 pages.
GenBank Accession No. EF147555.1, last updated Mar. 24, 2009, located at <http://www.ncbi.nlm.nih.gov/nuccore/EF147555.1>, last visited on Dec. 7, 2011, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AY182241, last updated on May 4, 2004, located at <http://www.ncbi.nlm.nih.gov/nuccore/32265057>, last visited on Jun. 2, 2010, 2 pages.

Lane
1. S288C soluble fraction
2. S288C insoluble fraction
3. MEA (WT) soluble fraction
4. MEA (WT) insoluble fraction

Figure 7

Total alignment length: 544
Number of identity: 499
Number of residues aligned: 544
BLAST style alignment length: 544
Pecent identity (BLAST style): 91.73%
Pecent identity (GAP style): 91.73%
Pecent identity (Needle style): 91.73%

---

```
CLUSTAL W (1.83) multiple sequence alignment

P.alba    MEARRSANYEPNSWDYDYLLSSDTDESIEVYKDKAKKLEAEVRREINNEKAEFLTLLELI    (SEQ ID NO.44)
S.alba    METRRSANYEPNSWDYDYLLSSDTEDAIEVYKDKAKKLDAEVRSKINNETAEFLTQLELI    (SEQ ID NO.45)
          **:****************:::**********:****.****.*****.****

P.alba    DNVQRLGLGYRFESDIRGALDRJVSSGGFDAVTKTSLHGTALSFRLLRQHGFEVSQEAFS    (SEQ ID NO.44)
S.alba    DTIQRLGLGYRFESDIRRALDRJVSSGGFEAVAKTSLQATALSFRLLRQHGFEVSQEVFN    (SEQ ID NO.45)
          *.:**************.************:**:***:.***********.*.

P.alba    GFKDQNGNFLENLKEDIKAILSLYEASFLALEGENILDEAKVFAISHLKELSEEKIGKEL    (SEQ ID NO.44)
S.alba    GFKDQNGNFMEDLKEDIKALLSLHEASFLALEGENILDEAKVFTISHLKELNEEKIGKDM    (SEQ ID NO.45)
          *********:*:*******:***:*****************:******:*****::

P.alba    AEQVNHALELPLHRRTQRLEAVWSIEAYRKKEDANQVLLELAILDYNMIQSVYQRDLRET    (SEQ ID NO.44)
S.alba    VEQVNHALELPLHRRTQRLEAVWSIEAYRKKEDANRVLLELAILDYNMVQSVYQRDLRET    (SEQ ID NO.45)
          .**********************************.************:***********

P.alba    SRWWRRVCLATKLHFARDRLIESFYWAVCVAFEPQYSDCRNSVAKMFSFVTIIDDIYDVY    (SEQ ID NO.44)
S.alba    SRWWRRVCLATKLHFARDRLIESFYWAVCVAFEPQYSDCRISVAKMFSFVTIIDDIYDVY    (SEQ ID NO.45)
          ****************************************.*******************

P.alba    GTLDELELFTDAVERWDVNAINDLPDYMKLCFLALYNTINEIAYDNLKDKGENILPYLTK    (SEQ ID NO.44)
S.alba    GTLEELELFTDAVERWDVSAIDDLPDYMKLCFLALYNTINEIAYDNLKEKGENILPYLTK    (SEQ ID NO.45)
          ***:**************.**:****************************:********

P.alba    AWADLCNAFLQEAKWLYNKSTPTFDDYFGNAWKSSSGPLQLVFAYFAVVQNIKKEEIENL    (SEQ ID NO.44)
S.alba    AWADLCNAFLQEARFLYNKSTPTFSDYFGNAWKSSSGPLQLVFAYFAVVQNIKKEEIENL    (SEQ ID NO.45)
          *************::********.************************************ ***

P.alba    QKYHDTISRPSHIFRLCNDLASASAEIARGETANSVSCYMRTKGISEELATESVMNLIDE    (SEQ ID NO.44)
S.alba    LKYHDIISWPSYIFRLCNDLASASAEIARGETANSVSCYMRTKGISEELATESVMNLIDE    (SEQ ID NO.45)
          ****  **:************************************

P.alba    TWKKMNKEKLGGSLFAKPFVETAINLARQSHCTYHNGDAHTSPDELTRKRVLSVITEPLL    (SEQ ID NO.44)
S.alba    TWKKMNKEKLGDSLFAKHFVETAINLARQSHCTYHNGDAHTSPDELTRKRVLSVITEPTL    (SEQ ID NO.45)
          ***********.*****.*****************************************

P.alba    PFER    (SEQ ID NO.44)
S.alba    PLER    (SEQ ID NO.45)
          *:**
```

Figure 10

Total alignment length: 544
Number of identity: 502
Number of residues aligned: 544
BLAST style alignment length: 544
Pecent identity (BLAST style): 92.28%
Pecent identity (GAP style): 92.28%
Pecent identity (Needle style): 92.28%

```
CLUSTAL W (1.83) multiple sequence alignment

P.alba       MEARRSANYEPNSWDYDYLLSSDTDESIEVYKDKAKKLEAEVRREINNEKAEFLTLLELI   (SEQ ID NO.46)
S.babylonica METRRTANYEPNSWDYDYLLSSDNDDAIELYKDKAKKLDAEVRSKINNEKAEFLTQLELI   (SEQ ID NO.47)
             **:**:*****************.*::**:*******:**** :********** ****

P.alba       DNVQRLGLGYRFESDIRGALDRFVSSGGFDAVTKTSLEGTALSFRLLRQHGFEVSQEAFS   (SEQ ID NO.46)
S.babylonica DTIQRLGLGYRFESDIRRAIDRYVSSGGFEAVAKTSLEATALSFRLLRQHGFEVSQEVFS   (SEQ ID NO.47)
             *.:************* *:**:******:**:*****.************.**

P.alba       GFKDQNGNFLENLKEDIKAILSLYEASFLALEGENILDEAKVFAISHLKELSEEKIGKEL   (SEQ ID NO.46)
S.babylonica GFKDQNGNFMENIKEDIKATLSLYEASFLALEGENILDEAKVFTISHLKEINEEKIGKDL   (SEQ ID NO.47)
             *********:**:******:*********************:*******:.****** *

P.alba       AEQVNHALELPLHRRTQRLEAVWSIEAYRKKEDANQVLLELAILDYNMIQSVYQRDLRET   (SEQ ID NO.46)
S.babylonica ADQVNHALELPLHRRTQRLEAVWSIEAYRKKEGANRALLELAILDYNMVQSVYQRDLRET   (SEQ ID NO.47)
             *:******************************.**: ***********:***********

P.alba       SRWWRRVGLATKLHFARDRLIESFYWAVGVAFEPQYSDCRNSVAKMFSFVTIIDDIYDVY   (SEQ ID NO.46)
S.babylonica SRWWRRVGLATKLHFARDRLIESFYWAVGVAFEPQYSDCRKSVAKMFSFVTIIDDIYDVY   (SEQ ID NO.47)
             ****************************************:*******************

P.alba       GTLDELELFTDAVERWDVNAINDLPDYMKLCFLALYNTINEIAYDNLKDKGENILPYLTK   (SEQ ID NO.46)
S.babylonica GTLDELELFTDAVERWDVSAVDDLPDYMKLCFLALYNTINEIAYDNLKEKGENILPYLTK   (SEQ ID NO.47)
             ******************.*:.*************************:************

P.alba       AWADLCNAFLQEAKWLYNKSTPIFDDYFGNAWKSSSGPLQLVFAYFAVVQNIKKEEIENL   (SEQ ID NO.46)
S.babylonica AWADLCNAFLQEAKFLYNKSTPIFDDYFGNAWKSSSGPLQLVFAYFAVVQNIKKEETENL   (SEQ ID NO.47)
             **************:***************************************** ***

P.alba       QKYHDTISRPSHIFRLCNDLASASAEIARGETANSVSCYMRTKGISEELATESVMNLIDE   (SEQ ID NO.46)
S.babylonica QKYHDIISWPSYIFRLCNDLASASAEIARGETANSVSCYIRTKGISEELATESVMNLIDE   (SEQ ID NO.47)
             ***** ** **:**********************.****************

P.alba       TWKKMNKEKLGGSLFAKPFVETAINLARQSHCTYHNGDAHTSPDELTRKRVLSVITEPIL   (SEQ ID NO.46)
S.babylonica TWKKMNKEKVGDSLFAKQFVETAINLARQSHCTYHNGDAHTSPDELTRKRVLSVITEPIL   (SEQ ID NO.47)
             ********:*.***** ***********************************

P.alba       PFER    (SEQ ID NO.46)
S.babylonica PFER    (SEQ ID NO.47)
             ****
```

1 – DW194 supernatent
2 – EWL900 supernatent
3 – EWL903 supernatent
4 – DW194 pellet
5 – EWL900 pellet
6 – EWL903 pellet
7 – 0.4ug P. alba IspS standard
8 – 0.2ug P. alba IspS standard
9 – 0.1ug P. alba IspS standard
10 – 0.05ug P. alba IspS standard

US 9,273,299 B2

ISOPRENE SYNTHASE VARIANTS WITH IMPROVED SOLUBILITY FOR PRODUCTION OF ISOPRENE

CROSS-REFERENCE TO RELATED APPLICATIONS

This application is a divisional of U.S. patent application Ser. No. 13/662,328, now U.S. Pat. No. 8,735,134, filed Oct. 26, 2012, which claims priority to U.S. Provisional Patent Application No. 61/552,453, filed Oct. 27, 2011, the disclosures of which are herein incorporated by reference in their entirety.

INCORPORATION BY REFERENCE

The content of the following submission on ASCII text file is incorporated herein by reference in its entirety: a computer readable form (CRF) of the Sequence Listing (filename: "643842004110_Sequence_Listing.txt", date recorded: Jul. 8, 2014, size: 143,146 bytes.)

FIELD OF THE INVENTION

The present invention provides methods and compositions comprising isoprene synthase variants. In particular, the present invention provides variant plant isoprene synthases for increased isoprene production in host cells.

BACKGROUND OF THE INVENTION

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, $4^{th}$ ed., Wiley-VCH, pp. 117-122, 2003). The C5 skeleton can also be synthesized from smaller subunits. It would be desirable, however, to have a commercially viable method of producing isoprene that was independent of nonrenewable resources.

Isoprene monomer is employed in the manufacture of polyisoprene and various copolymers (with isobutylene, butadiene, styrene, or other monomers). Building a strain (prokaryotic or eukaryotic) capable of producing commercially viable levels of isoprene requires optimization of part of or the entire DXP or MVA pathway or both MVA and DXP pathways. A key enzyme in the pathway is isoprene synthase (IspS), which converts the precursor DMAPP to isoprene. Isoprene synthases (IspS) that have been identified include those from plants such as poplar, English oak and kudzu vine. Some of the plant IspS enzymes identified have been partially characterized in part by expression in *E. coli* and some of the kinetic parameters of these enzymes have been determined in vitro with purified protein. However, the solubility of the native IspS enzymes and even some of the recombinant enzymes are insufficient for commercial production of isoprene in a biological host. Thus, one problem to be solved is the provision of isoprene synthase variants (e.g. with substitutions at specific residues) which have improved solubility such that a greater amount of isoprene can be biologically produced. To solve this problem as described herein, an isoprene synthase with improved solubility may be expressed in a host (e.g. a bacterial host).

All patents, patent applications, articles and publications mentioned herein are hereby expressly incorporated herein by reference.

SUMMARY OF THE INVENTION

The invention provides compositions of variant polypeptides having isoprene activity with improved solubility and methods for making and using such variants for the production of isoprene.

Accordingly, in one aspect, the invention provides for isolated polypeptides having isoprene synthase activity, wherein the polypeptide variant comprises a substitution at residue X288 corresponding to SEQ ID NO:1, and wherein the polypeptide has increased protein solubility compared a parent polypeptide which does not comprise the substitution at residue X288. In one embodiment, the substitution is at S288. In another embodiment, the substitution is S288C. In another embodiment, the polypeptide has at least about 5% to at least about 75% increased protein solubility compared to the parent polypeptide. In another embodiment, the polypeptide is derived from a parent polypeptide isolated from a plant. In another embodiment, the parent polypeptide is isolated from a plant species selected from poplar (*Populus* sp.), kudzu (*Pueraria* sp.), English oak (*Quercus* sp.) or willow (*Salix* sp.). In another embodiment, the parent species is *Populus* sp. In another embodiment, in the parent is *P. alba, P. tremuloides, P. trichocharpa, P. nigra*. In another embodiment, the parent species is *Pueraria* sp. In another embodiment, in the parent species is *Pueraria montana*. In another embodiment, the parent species is *Quercus* sp. In another embodiment, the parent species is *Quercus rubur*. In another embodiment, the parent species is *Salix* sp. In another embodiment, the parent species is *S. alba* or *S. baylonica*.

In another aspect, the invention provides for recombinant host cells comprising any of the polypeptides described herein. In one embodiment, the host cell is selected from the group consisting of a bacterial, algal, fungal, yeast, cyanobacterial, or Clostridial cell. In another embodiment, the host cell is a bacterial cell. In another embodiment, the bacterial cell is a gram-positive bacterial cell or gram-negative bacterial cell. In another embodiment, the bacterial cell is selected from the group consisting of *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cells. In another embodiment, the host cell is an algal cell. In another embodiment, the algal cell is selected from the group consisting of green algae, red algae, glaucophytes, chlorarachniophytes, euglenids, chromista, or dinoflagellates. In another embodiment, the host cell is a fungal cell. In another embodiment, the fungal cell is a filamentous fungi. In another embodiment, the host cell is a yeast cell. In another embodiment, the yeast cell is selected from the group consisting of *Saccharomyces* sp., *Schizosaccharomyces* sp., *Pichia* sp., or *Candida* sp. In another embodiment, the yeast cell is a *Saccharomyces cerevisiae* cell.

In another aspect, the invention provides for a crystalline form of a polypeptide comprising the amino acid residues of SEQ ID NO:2 (DW614). In another aspect, the invention provides for a polynucleotide that encodes for isolated polypeptides having isoprene synthase activity, wherein the polypeptide variant comprises a substitution at residue X288 corresponding to SEQ ID NO:1, and wherein the polypeptide has increased protein solubility compared a parent polypeptide which does not comprise the substitution at residue X288. In another aspect, the invention provides for a vector comprising a polynucleotide that encodes for isolated polypeptides having isoprene synthase activity, wherein the polypeptide variant comprises a substitution at residue X288 corresponding to SEQ ID NO:1, and wherein the polypeptide has increased protein solubility compared a parent polypeptide which does not comprise the substitution at residue X288. In another aspect, the invention provides for a recombinant host cell comprising the vector described above. In another aspect, the invention provides for methods of producing isoprene comprising: (a) culturing the recombinant cell of above under conditions suitable for the production of isoprene and (b) producing isoprene.

In another aspect, the invention provides for methods of producing isoprene comprising: (a) culturing the recombinant cell comprising polypeptides having isoprene synthase activity, wherein the polypeptide variant comprises a substitution at residue X288 corresponding to SEQ ID NO:1, and wherein the polypeptide has increased protein solubility compared a parent polypeptide which does not comprise the substitution at residue X288 under conditions suitable for the production of isoprene and (b) producing isoprene.

BRIEF DESCRIPTION OF THE DRAWINGS

FIG. 7 shows Clustal W alignment between *P. alba* IspS and *S. alba* IspS.

FIG. 10 shows Clustal W alignment between *P. alba* IspS and *S. babylonica* IspS.

DETAILED DESCRIPTION OF THE INVENTION

Figure 1:
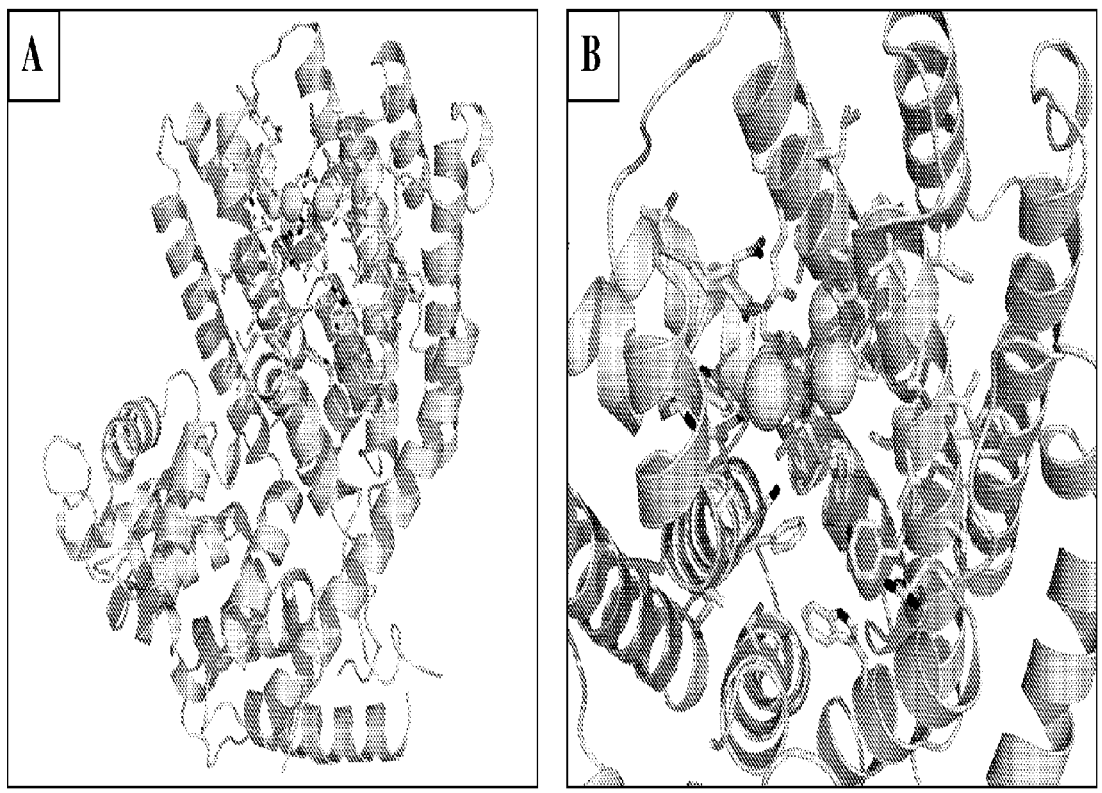
FIG. 1 shows a monomer view of wild type IspS showing the location of sites located approximately 8 Å from the active site (A). Dimethylallyl s-thiolodiphosphate and $Mg^{2+}$ (spheres) are placed based on a structural alignment with PDB 3N0G. B) Close-up view of sites in A.

The invention provides compositions of variant polypeptides having isoprene activity with improved solubility and methods for making and using such variants for the production of isoprene. In one embodiment, the variant polypeptide has a substitution at X288 residue corresponding to reference sequence SEQ ID NO:1. The sequence of MEA *P. alba* isoprene synthase is as follows:

(SEQ ID NO: 1)
MEARRSANYEPNSWDYDYLLSSDTDESIEVYKDKAKKLEAEVRREINNE

KAEFLTLLELIDNVQRLGLGYRFESDIRGALDRFVSSGGFDAVTKTSLH

GTALSFRLLRQHGFEVSQEAFSGFKDQNGNFLENLKEDIKAILSLYEAS

FLALEGENILDEAKVFAISHLKELSEEKIGKELAEQVNHALELPLHRRT

QRLEAVWSIEAYRKKEDANQVLLELAILDYNMIQSVYQRDLRETSRWWR

RVGLATKLHFARDRLIESFYWAVGVAFEPQYSDCRNSVAKMFSFVTIID

DIYDVYGTLDELELFTDAVERWDVNAINDLPDYMKLCFLALYNTINEIA

YDNLKDKGENILPYLTKAWADLCNAFLQEAKWLYNKSTPTFDDYFGNAW

KSSSGPLQLVFAYFAVVQNIKKEEIENLQKYHDTISRPSHIFRLCNDLA

SASAEIARGETANSVSCYMRTKGISEELATESVMNLIDETWKKMNKEKL

GGSLFAKPFVETAINLARQSHCTYHNGDAHTSPDELTRKRVLSVITEPI

LPFER.

The practice of the present invention will employ, unless otherwise indicated, conventional techniques of protein chemistry, molecular biology (including recombinant techniques), microbiology, cell biology, biochemistry, nucleic acid chemistry, and enzymology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly and individually referred to herein as "Sambrook"). *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Nucleic Acid Chemistry* John Wiley & Sons, Inc., New York, 2000); and Agrawal, ed., *Protocols for Oligonucleotides and Analogs, Synthesis and Properties* Humana Press Inc., New Jersey, 1993). Accordingly, the terms defined immediately below are more fully described by reference to the Specification as a whole.

Furthermore, the headings provided herein are not limitations of the various aspects or embodiments of the invention, which can be had by reference to the specification as a whole. Accordingly, the terms defined immediately below are more fully defined by reference to the specification as a whole.

Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

"X" refers to any amino acid residue. However, when in the context of an amino acid substitution (e.g. "X003C"), it is to be understood that "X" refers to an amino acid residue other than the amino acid residue resulting from the substitution (e.g., X is an amino acid residue other than C). In some embodiments, the additional zeros in front of the residue position are not included, thus for example "X003" can also be referred to as "X3" to refer to residue position 3.

"Isoprene" refers to 2-methyl-1,3-butadiene (CAS#78-79-5). It can refer to the direct and final volatile C5 hydrocarbon product from the elimination of pyrophosphate from 3,3-dimethylallyl pyrophosphate (DMAPP). It may not involve the linking or polymerization of one or more isopentenyl diphosphate (IPP) molecules to one or more DMAPP molecules. Isoprene is not limited by the method of its manufacture.

As used herein, the terms "isoprene synthase," "isoprene synthase variant", and "IspS," refer to enzymes that catalyze the elimination of pyrophosphate from dimethylallyl diphosphate (DMAPP) to form isoprene. An "isoprene synthase" may be a wild type sequence or an isoprene synthase variant.

An "isoprene synthase variant" indicates a non-wild type polypeptide having isoprene synthase activity. One skilled in the art can measure isoprene synthase activity using known methods. See, for example, by GC-MS (see, e.g., WO 2009/132220, Example 3) or Silver et al., J. Biol. Chem. 270: 13010-13016, 1995. Variants may have substitutions, additions, deletions, and/or truncations from a wild type isoprene synthase sequence. Variants may have substitutions, additions, deletions, and/or truncations from a non-wild type isoprene synthase sequence. The variants described herein contain at least one amino acid residue substitution from a parent isoprene synthase polypeptide. In some embodiments, the parent isoprene synthase polypeptide is a wild type sequence. In some embodiments, the parent isoprene synthase polypeptide is a non-wild type sequence. In various embodiments, the variant will have at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild type isoprene synthase. In various embodiments, the variant will have at least about 40%, at least about 50%, at least about 60%, at least about 70%, at least about 80%, at least about 90%, at least about 91%, at least about 92%, at least about 93%, at least about 94%, at least about 95%, at least about 96%, at least about 97%, at least about 98%, at least about 99% sequence identity to a wild type isoprene synthase. In various embodiments, the number of differing amino acid residues between the variant and the wild type may be one or more, e.g. 1, 2, 3, 4, 5, 10, 15, 20, 30, 40, 50, or more amino acid residues. Wild type isoprene synthases can include any isoprene synthases from plants, for example, kudzu isoprene synthases, poplar isoprene synthases, English oak isoprene synthases, and willow isoprene synthases.

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of an isoprene synthase polypeptide may be aligned with that of a reference sequence (e.g. SEQ ID NO: 1 using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure (see, for example, PCT/US2010/032134 (WO 2010/124146)). In another aspect, equivalent residues may be identified by determining homology at the level of tertiary structure. Using such methods, the amino acid residues of an isoprene synthase polypeptide or isoprene synthase variant may be numbered according to the corresponding amino acid residue position numbering of the reference sequence. For example, the amino acid sequence of SEQ ID NO: 1 may be used for determining amino acid residue position numbering of each amino acid residue of an isoprene synthase variant of interest.

The term "identical" in the context of two nucleic acids or polypeptide sequences refers to the residues in the two sequences that are the same when aligned for maximum correspondence, as measured using one of the following sequence comparison or analysis algorithms.

As used herein, "homology" refers to sequence similarity or identity, with identity being preferred. Homology may be determined using standard techniques known in the art (see, e.g., Smith and Waterman, Adv. Appl. Math. 2:482 [1981]; Needleman and Wunsch, J. Mol. Biol. 48:443 [1970\; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (see Feng and Doolittle, J. Mol. Evol. 35:351-360 [1987]). The method is similar to that described by Higgins and Sharp (see Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (see Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (see Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11.

The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 [1992]) alignments (B) of 50, expectation (E) of 10, M'5, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a isoprene synthase nucleic acid of this invention if the smallest sum probability in a comparison of the test nucleic acid to a isoprene synthase nucleic acid is less than about 0.1, more preferably less than about 0.01, and most preferably less than about 0.001. Where the test nucleic acid encodes an isoprene synthase polypeptide, it is considered similar to a specified isoprene synthase nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity" of a subject nucleic acid sequence to a reference nucleic acid sequence means that the subject nucleic acid sequence is identical (i.e., on a nucleotide-by-nucleotide basis for a polynucleotide sequence) by a specified percentage to the reference sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

The "percent sequence identity" or "% sequence identity" or "% identity" of a subject sequence to a reference sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the reference sequence). The resulting number is multiplied by 100 to yield the percent sequence identity of the subject sequence to the reference sequence.

"Optimal alignment" or "optimally aligned" refers to the alignment of two (or more) sequences giving the highest percent identity score. For example, optimal alignment of two polypeptide sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

Two sequences (e.g., polypeptide sequences) may be deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (see Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to e.g., the BLASTP program for amino acid sequences and the BLASTN program for nucleic acid sequences (see, e.g., Altschul et al., Nucleic Acids Res. 25(17):3389-3402 (1997); see also the National Center for Biotechnology Information (NCBI) website) or CLUSTALW program.

A polypeptide of interest may be said to be "substantially identical" to a reference polypeptide if the polypeptide of interest comprises an amino acid sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, e.g., where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A "nucleic acid" refers to two or more deoxyribonucleotides and/or ribonucleotides in either single or double-stranded form. It is to be understood that mutations, including single nucleotide mutations, can occur within a nucleic acid as defined herein.

A "recombinant nucleic acid" refers to a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of an anaerobic microorganism, or which exists as a separate molecule (e.g., a cDNA, a genomic DNA fragment, or a cDNA fragment produced by PCR or restriction endonuclease digestion) independent of other sequences. A recombinant nucleic acid may be obtained using molecular biology techniques that are known in the art, or part or all of a recombinant nucleic acid may be chemically synthesized.

A "heterologous nucleic acid" can be a nucleic acid whose nucleic acid sequence is from another species than the host cell or another strain of the same species of the host cell. In some embodiments, the sequence is not identical to that of another nucleic acid naturally found in the same host cell. In some embodiments, a heterologous nucleic acid is not identical to a wild-type nucleic acid that is found in the same host cell in nature.

An "endogenous nucleic acid" is a nucleic acid whose nucleic acid sequence is naturally found in the host cell. In some embodiments, an endogenous nucleic acid is identical to a wild-type nucleic acid that is found in the host cell in nature. In some embodiments, one or more copies of endogenous nucleic acids are introduced into a host cell.

A nucleic acid or protein of the invention may be in isolated or purified form. As used herein, "isolated," with respect to nucleic acid or protein, means separated from other components, such as, but not limited to a cell or cell culture. It is preferably in a homogeneous state although it can be in either a dry or aqueous solution. Purity and homogeneity are typically determined using analytical chemistry techniques, such as polyacrylamide gel electrophoresis or high performance liquid chromatography. A protein or nucleic acid that is the predominant species present in a preparation is substantially purified. The term "purified" denotes that a nucleic acid or protein gives rise to essentially one band in an electrophoretic gel. Particularly, "purified" means that when isolated, the isolate contains at least 90%, at least 95%, at least 98%, or more preferably at least 99% of nucleic acid or protein by weight of the isolate.

Purified polypeptides may be obtained by a number of methods including, for example, laboratory synthesis, chromatography, preparative electrophoresis, gel electrophoresis, centrifugation, precipitation, affinity purification, etc. (see, generally, R Scopes, Protein Purification, Springer-Verlag, N.Y. (1982), Deutscher, Methods in Enzymology Vol. 182: Guide to Protein Purification, Academic Press, Inc. N.Y. (1990)).

"Polypeptides" includes polypeptides, proteins, peptides, fragments of polypeptides, and fusion polypeptides. It is also understood that a polypeptide may be coded for by more than one nucleotide sequence due to the degeneracy of the genetic code.

A "heterologous polypeptide" is a polypeptide encoded by a heterologous nucleic acid. In some embodiments, the sequence is not identical to that of another polypeptide encoded by a nucleic acid naturally found in the same host cell. Examples of heterologous proteins include enzymes such as isoprene synthases. In some embodiments, the genes encoding the proteins are naturally occurring genes, while in other embodiments mutated and/or synthetic genes are used.

An "endogenous polypeptide" is a polypeptide whose amino acid sequence is naturally found in the host cell. In some embodiments, an endogenous polypeptide is identical to a wild-type polypeptide that is found in the host cell in nature.

As used herein, the singular terms "a," "an," and "the" include the plural reference unless the context clearly indicates otherwise.

Unless otherwise indicated, nucleic acids are written left to right in 5' to 3' orientation; amino acid sequences are written left to right in amino to carboxy orientation, respectively.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Reference to "about" a value or parameter herein also includes (and describes) embodiments that are directed to that value or parameter per se.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions. It is to be understood that this invention is not limited to the particular methodology, protocols, and reagents described, as these may vary, depending upon the context they are used by those of skill in the art.

Isoprene Synthase Variants with Improved Solubility

The invention features compositions of variant polypeptides having isoprene synthase activity and having improved solubility as well as methods for making such polypeptides and methods for producing increased amounts of isoprene. In some embodiments, the polypeptide has at least about 5% to at least about 75% increased protein solubility compared to a parent polypeptide. In some embodiments, the polypeptide has at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% increased protein solubility compared to a parent polypeptide. In particular, these compositions and methods may increase the rate of isoprene production and the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) variant into the cells.

Additionally, isoprene production by cells containing a heterologous isoprene synthase nucleic acid can be enhanced by increasing the amount of one or more DXP pathway polypeptides (e.g., a 1-deoxy-D-xylulose-5-phosphate synthase (DXS) polypeptide) and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

The encoded DXS and IDI polypeptides are part of the DXP pathway for the biosynthesis of isoprene. DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

As is further detailed below, in some embodiments, the production of isoprene by cells containing a heterologous isoprene synthase nucleic acid can be augmented by increasing expression of one or more MVA polypeptide(s) in the cells. Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, other DXP pathway and/or MVA pathway nucleic acids for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, other DXP pathway and/or MVA pathway nucleic acids also comprises a selective marker, such as a kanamycin, ampicillin, carbenicillin, gentamicin, hygromycin, phleomycin, bleomycin, neomycin, or chloramphenicol antibiotic resistance nucleic acid Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein.

In one embodiment, DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA or by heat inactivation, and isoprene is quantified by GC/MS.

Isoprene Synthase Parent Sequences

Isoprene synthase variants may be generated from a parent isoprene synthase, wherein the parent isoprene synthase may be an isoprene synthase as described herein, including wild type and non-wild type isoprene synthases. Exemplary parent isoprene synthase nucleic acids include nucleic acids that encode a polypeptide, fragment of a polypeptide, peptide, or fusion polypeptide that has at least one activity of an isoprene synthase polypeptide. Exemplary parent isoprene synthase polypeptides and nucleic acids include naturally-occurring polypeptides and nucleic acids from any of the source organisms described herein as well as variant polypeptides and nucleic acids derived from any of the source organisms described herein.

In some embodiments, the parent isoprene synthase is from the family Fabaceae, the family Salicaceae, or the family Fagaceae. In some embodiments, the parent isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba×tremula* CAC35696, Miller et al., Planta 213: 483-487, 2001) or *Populus alba*, aspen (such as *Populus tremuloides*) Silver et al., JBC 270(22): 13010-1316, 1995), or English Oak (*Quercus robur*) (Zimmer et al., WO 98/02550). Suitable parent isoprene synthases include, but are not limited to, those identified by GenBank Accession Nos. AY341431, AY316691, AB198180, AJ294819.1, EU693027.1, EF638224.1, AM410988.1, EF147555.1, AY279379, AJ457070, and AY182241. Additional parent sequences are described in PCT/US2009/041581 (WO 2009/132220) and PCT/US2010/032134 (WO 2010/124146).

In various embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with MEA *P. alba*. In other embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with full-length *P. alba* or complete *P. alba*.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Variants with improved solubility can be made by including a mutation at X288 corresponding to SEQ ID NO:1. In one aspect, X288 is S288. In another aspect, the mutation is S288C. Exemplary methods of measuring solubility is described below in the Examples.

Exemplary Nucleic Acids

Nucleic acids encoding the isoprene synthase variants of the invention are provided and contemplated within the scope of the invention. In various embodiments, the nucleic acid is a recombinant nucleic acid. For instance, in some embodiments, an isoprene synthase variant nucleic acid is operably linked to another nucleic acid encoding all or a portion of another polypeptide such that the recombinant nucleic acid encodes a fusion polypeptide that includes an isoprene synthase variant and all or part of another polypeptide (e.g., a peptide that facilitates purification or detection of the fusion polypeptide, such as a His-tag). In some embodiments, part or all of a recombinant nucleic acid is chemically synthesized. In some aspects, the nucleic acid is a heterologous nucleic acid. By "heterologous nucleic acid" is meant a nucleic acid whose nucleic acid sequence is not identical to that of another nucleic acid naturally found in the same host cell.

In some embodiments, the nucleic acid includes at least or about 50, 100, 150, 200, 300, 400, 500, 600, 700, 800, or more contiguous nucleotides from a naturally-occurring isoprene synthase nucleic acid. In some aspects, the nucleic acid has one or more mutations compared to the sequence of a wild-type (i.e., a sequence occurring in nature) isoprene synthase nucleic acid. In some embodiments, the nucleic acid has one or more mutations (e.g., a silent mutation) that increase the transcription or translation of isoprene synthase nucleic acid. In some embodiments, the nucleic acid is a degenerate variant of any nucleic acid encoding an isoprene synthase polypeptide.

An isoprene synthase nucleic acid can be incorporated into a vector, such as an expression vector, using standard techniques known to one of skill in the art. Methods used to ligate the DNA construct comprising a nucleic acid of interest such as isoprene synthase, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express isoprene synthase nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2nd ed., Cold Spring Harbor, 2001.

Exemplary Pathway Polypeptides

As noted above, one or more polypeptides from the DXP pathway and/or MVA pathway can be used to increase the production of isoprene in conjunction with using the isoprene synthase variants described herein. Accordingly, in certain aspects, the one or more nucleic acids encoding one or more MVA pathway polypeptides is a heterologous nucleic acid. In other aspects, the one or more nucleic acids encoding one or more MVA pathway polypeptides is a copy of an endogenous nucleic acid. In any of the aspects herein, one or more MVA pathway polypeptides can be selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; (f) an enzyme that converts mevalonate 5-pyrophosphate to isopentenyl pyrophosphate; and (g) an enzyme that converts isopentenyl pyrophosphate to dimethylallyl diphosphate. In any of the aspects herein, one or more MVA pathway polypeptides is selected from (a) an enzyme that condenses acetoacetyl-CoA with acetyl-CoA to form HMG-CoA (e.g., HMG synthase); (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

In any of the aspects herein, the enzyme that phosphorylates mevalonate to mevalonate 5-phosphate can be selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, and *Streptomyces* mevalonate kinase polypeptide, *M. Burtonii* mevalonate kinase, or *Streptomyces* CL190 mevalonate kinase polypeptide. In any of the aspects herein, the enzyme that phosphorylates mevalonate to mevalonate 5-phosphate is *M. mazei* mevalonate kinase.

Upper MVA Pathway Polypeptides

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated in can be expressed in recombinant cells in any of the ways described herein.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In *L. grayi, E. faecium, E. gallinarum, E. casseliflavus*, and *E. faecalis*, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol*. 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis*, to produce mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

In any of the aspects herein, the recombinant host cells can further comprise one or more nucleic acids encoding one or more 1-deoxy-D-xylulose 5-phosphate (DXP) pathway polypeptides. In one aspect, one or more nucleic acids that encode for one or more DXP pathway polypeptides is a heterologous nucleic acid. In another aspect, the one or more nucleic acids encoding one or more DXP pathway polypeptides is a copy of an endogenous nucleic acid. In another aspect, the one or more DXP pathway polypeptides is selected from (a) 1-deoxy-D-xylulose-5-phosphate synthase (DXS), (b) 1-deoxy-D-xylulose-5-phosphate reductoisomerase (DXR), (c) 4-diphosphocytidyl-2C-methyl-D-erythritol synthase (MCT), (d) 4-diphosphocytidyl-2-C-methyl-D-erythritol kinase (CMK), (e) 2C-methyl-D-erythritol 2,4-cyclodiphosphate synthase (MCS), (f) 1-hydroxy-2-methyl-2-(E)-butenyl 4-diphosphate synthase (HDS), and (g) 1-hydroxy-2-methyl-2-(E)-butenyl 4-diphosphate reductase (HDR). In another aspect, the DXP pathway polypeptide is DXS.

In another aspect, one of skill in the art can use an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms, particularly among Bifidobacteria [see, for example, Biology of the Prokaryotes (ed. Lengeler, Drews and Schlegel); Blackwell Science, New York, 1999, p. 299-301; Meile et al., *J. of Bacteriology*, 2001, 183:9, 2929-36; Jeong et al., *J. Microbiol. Biotechnol.*, 2007, 17:5, 822-829]. Phosphoketolase enzymes allow for formation of acetyl-CoA (via acetyl-phosphate) from xylulose 5-phosphate or fructose 6-phosphate rather than through oxidation of pyruvate as in typical metabolism. Increased biosynthesis of acetyl CoA by the use of a phosphoketolase polypeptide can result in increased productivity of the upper mevalonate-dependent biosynthetic pathway which can substantially increase biosynthesis of mevalonate and, consequently, of downstream isoprenoid precursor molecules such as DMAPP and IPP. Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity is suitable for use in the present invention. Exemplary phosphoketolase nucleic acids include, but are not limited to, a phosphoketolase isolated from *Lactobacillus reuteri, Bifidobacterium longum, Ferrimonas balearica, Pedobactor saltans, Streptomyces griseus*, and/or *Nocardiopsis dassonvillei*.

Lower MVA Pathway Polypeptides

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *M. Burtonii* mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. In some embodiments, the lower MVK polypeptide can be from *M. burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variant.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, *Methanosarcina mazei* mevalonate kinase polypeptide, and *M. Burtonii* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Acetoacetyl-CoA Synthase Gene

In another aspect, acetoacetyl-CoA synthase gene (aka nphT7) can be used. The acetoacetyl-CoA synthase gene is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., PNAS Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In any of the aspects or embodiments described herein, an enzyme that has the ability to synthesize acetoacetyl-CoA from malonyl-CoA and acetyl-CoA can be used. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

Exemplary Host Cells

A variety of host cells can be used to make a recombinant host cell that can express isoprene synthase variants and to produce isoprene in the methods of the claimed invention. The host cell may be a cell that naturally produces isoprene or a cell that does not naturally produce isoprene. In some embodiments, the host cell naturally produces isoprene using the DXP pathway, and an isoprene synthase variant, DXP pathway polypeptide (e.g., DXS), and/or IDI nucleic acid is added to enhance production of isoprene using this pathway. In some embodiments, the host cell naturally produces isoprene using the MVA pathway, and an isoprene synthase variant and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase variants, DXS, IDI, or MVA pathway nucleic acids are added to enhance production of isoprene by one or both of these pathways.

In some embodiments, the host cell is a yeast, such as *Saccharomyces* sp., *Schizosaccharomyces* sp., *Pichia* sp., *Candida* sp. or *Y. lipolytica*.

In some embodiments, the host cell is a bacterium, such as strains of *Bacillus* such as *B. licheniformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, strains of Archaea such as *Methanosarcina mazei* or strains of *Corynebacterium* such as *C. glutamicum*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the host cell is a gram-positive bacterium. Non-limiting examples include strains of *Streptomyces* (e.g., *S. lividans*, *S. coelicolor*, or *S. griseus*) and *Bacillus*. In some embodiments, the source organism is a gram-negative bacterium, such as *E. coli* or *Pseudomonas* sp.

In some embodiments, the host cell is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), or *Quercus robur*.

In some embodiments, the host cell is an algae, such as a green algae, red algae, glaucophytes, chlorarachniophytes, euglenids, chromista, or dinoflagellates.

In some embodiments, the host cell is a cyanobacteria, such as cyanobacteria classified into any of the following groups based on morphology: *Chroococcales, Pleurocapsales, Oscillatoriales, Nostocales,* or *Stigonematales*.

In some embodiments, the host cell is an anaerobic organisms. An "anaerobe" is an organism that does not require oxygen for growth. An anaerobe can be an obligate anaerobe, a facultative anaerobe, or an aerotolerant organism. Such organisms can be any of the organisms listed above, bacteria, yeast, etc. An "obligate anaerobe" is an anaerobe for which atmospheric levels of oxygen can be lethal. Examples of obligate anaerobes include, but are not limited to, *Clostridium, Eurobacterium, Bacteroides, Peptostreptococcus, Butyribacterium, Veillonella,* and *Actinomyces*. In one embodiment, the obligate anaerobes can be any one or combination selected from the group consisting of *Clostridium ljungdahlii, Clostridium autoethanogenum, Eurobacterium limosum, Clostridium carboxydivorans, Peptostreptococcus productus,* and *Butyribacterium methylotrophicum*. A "facultative anaerobe" is an anaerobe that is capable of performing aerobic respiration in the presence of oxygen and is capable of performing anaerobic fermentation under oxygen-limited or oxygen-free conditions. Examples of facultative anaerobes include, but are not limited to, *Escherichia, Pantoea*, yeast, and *Yarrowia*.

In some embodiments, the host cell is a photosynthetic cell. In other embodiments, the host cell is a non-photosynthetic cell.

Other exemplary host cells that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, 3rd ed., Cold Spring Harbor, 2001; and Campbell et al., Curr Genet, 16:53-56, 1989, which are each hereby incorporated by reference in their entireties, particularly with respect to transformation methods). The introduced nucleic acids may be integrated into chromosomal DNA or maintained as extrachromosomal replicating sequences.

Other exemplary transformation methods that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Cell Culture Media

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more C12-C22 fatty acids, such as a C12 saturated fatty acid, a C14 saturated fatty acid, a C16 saturated fatty acid, a C18 saturated fatty acid, a C20 saturated fatty acid, or a C22 saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., Bioresource Technology 96 (18): 2014-2018, 2005; U.S. Pat. No. 6,176,176; U.S. Pat. No. 6,106,888). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., Agric. Biol. Chem., 53(2) 541-543, 1989) and in bacteria (Hunter et. al., Biochemistry, 24, 4148-4155, 1985). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth Cl Compd., Int. Symp., 7th ed., 415-32. Editors: Murrell et al., Publisher: Intercept, Andover, UK, 1993). Similarly, various species of *Candida* metabolize alanine or oleic acid (Sulter et al., Arch. Microbiol. 153(5), 485-9, 1990).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., Appl. Environ. Microbiol. 63:1298-1306, 1997). Exemplary growth media are common commercially prepared media such as Luria Bertani (LB) broth, Sabouraud Dextrose (SD) broth, or Yeast medium (YM) broth. One skilled in the art of microbiology or fermentation science would know other defined or synthetic growth media that may also be used, and the appropriate medium for growth of particular host cells.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Other exemplary cell culture media that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, 1993; Silver et al., Plant Physiol. 97:1588-1591, 1991). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\% \text{ Carbon Yield} = (\text{moles carbon in isoprene produced})/(\text{moles carbon in carbon source})*100 \quad \text{Equation 1}$$

For this calculation, yeast extract can be assumed to contain 50% w/w carbon.

$$\% \text{ Carbon Yield} = (39.1 \text{ g isoprene}*1/68.1 \text{ mol/g}*5 \text{ C/mol})/[(181221 \text{ g glucose}*1/180 \text{ mol/g}*6 \text{ C/mol})+(17780 \text{ g yeast extract}*0.5*1/12 \text{ mol/g})]*100 = 0.042\% \quad \text{Equation 2}$$

One skilled in the art can readily convert the rates of isoprene production or amount of isoprene produced into any other units. Exemplary equations are listed below for inter-converting between units.

Units for Rate of Isoprene Production (Total and Specific)

$$1 \text{ g isoprene}/L_{broth}/\text{hr} = 14.7 \text{ mmol isoprene}/L_{broth}/\text{hr} \text{ (total volumetric rate)} \quad \text{Equation 3}$$

$$1 \text{ nmol isoprene}/g_{wcm}/\text{hr} = 1 \text{ nmol isoprene}/L_{broth}/\text{hr}/OD_{600} \text{(This conversion assumes that one liter of broth with an } OD_{600} \text{ value of 1 has a wet cell weight of 1 gram.)} \quad \text{Equation 4}$$

$$1 \text{ nmol isoprene}/g_{wcm}/\text{hr} = 68.1 \text{ ng isoprene}/g_{wcm}/\text{hr} \text{ (given the molecular weight of isoprene)} \quad \text{Equation 5}$$

$$1 \text{ nmol isoprene}/L_{gas}O_2/\text{hr} = 90 \text{ nmol isoprene}/L_{broth}/\text{hr} \text{ (at an } O_2 \text{ flow rate of 90 L/hr per L of culture broth)} \quad \text{Equation 6}$$

$$1 \text{ μg isoprene}/L_{gas} \text{ isoprene in off-gas} = 60 \text{ μg isoprene}/L_{broth}/\text{hr at a flow rate of 60 } L_{gas} \text{ per } L_{broth}(1 \text{ vvm}) \quad \text{Equation 7}$$

Units for Titer (Total and Specific)

$$1 \text{ nmol isoprene/mg cell protein} = 150 \text{ nmol isoprene}/L_{broth}/OD_{600} \text{(This conversion assumes that one liter of broth with an } OD_{600} \text{ value of 1 has a total cell protein of approximately 150 mg)(specific productivity)} \quad \text{Equation 8}$$

$$1 \text{ g isoprene}/L_{broth} = 14.7 \text{ mmol isoprene}/L_{broth} \text{(total titer)} \quad \text{Equation 9}$$

If desired, Equation 10 can be used to convert any of the units that include the wet weight of the cells into the corresponding units that include the dry weight of the cells.

$$\text{Dry weight of cells} = (\text{wet weight of cells})/3.3 \quad \text{Equation 10}$$

In some embodiments encompassed by the invention, a cell comprising a heterologous nucleic acid encoding an isoprene synthase variant polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase variant polypeptide.

In some embodiments encompassed by the invention, a cell comprising a heterologous nucleic acid encoding an isoprene synthase variant polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques, such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene. In some embodiments, the recovery is performed as described in U.S. Provisional Patent Appl. No. 61/288,142, filed on Dec. 18, 2009.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No. 2009/0203102, PCT publication WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

EXAMPLES

A pool of mutants located near the active site of MEA *P. alba* was screened for the ability to convert DMAPP to isoprene and confer improved growth to the host expression strain. After several rounds of enrichment, the S288C mutation was the predominant variant in the mutant pool. S288C conferred significantly increased solubility to MEA *P. alba* when expressed in host cells. S288C conferred increased solubility to IspS during large scale fermentation, and also significantly increased the solubility of IspS enzymes derived from *Salix alba* and *Salix babylonica* willow species.

Example 1

Enrichment of a Pool of MEA *P. alba* Mutants Near the Enzyme Active Site Identified the S288C Mutation A pool of mutants located near the active site of MEA *P. alba* was screened for the ability to convert DMAPP to isoprene and confer improved growth to the host expression strain.

Methods

The entire MEA *P. alba* IspS enzyme (544 positions) was mutagenized by QuikChange (Stratagene) PCR using NNK/MNN oligonucleotide primer pairs at every position. Substitution of NNK (32 possible codons) at each position in the coding sequence of MEA *P. alba* allowed for all 20 possible amino acids to be represented in mutant pools. NNK primers were systematically generated to have 10 bases upstream and 20 bases downstream of the codon to be mutagenized. The complementary MNN primers were systematically generated in the exact same way with a 23 base overlap between the primer pair. Quikchange PCR reactions were carried out according to the manufacturer's recommended protocol. Recombinant mutants were generated after transformation of the PCR products.

To identify individual variants of MEA *P. alba* IspS that allow for increased activity within the host, 51 positions within an approximate radius of 8 angstroms from the active site (PDB 3N0G) were selected for pooling (see Table 1 and FIG. 1). NNK PCR products from each of these positions were pooled and transformed into electrocompetent MD09-170 cells. Approximately 7,500 independent transformants were isolated and then pooled prior to the enrichment procedure. The 7,500 transformants represented an approximate 5-fold oversampling of the possible mutants at each position (32 codons for NNK at each position, 1,632 possible codons in a pool of 51 positions). This pool was then subjected to several rounds of enrichment by growth under MVA supplement and induction of IspS by IPTG as previously described in US 2010/0003716. After round three of enrichment, the IspS ORF in either 8 or 16 individual isolates was fully sequenced prior to the next round of enrichment. The enrichment procedure was stopped after round six.

Results

Enrichment of the pool of individual mutants in the 51 positions near the active site of MEA *P. alba* IspS (see Table 1) identified the S288C variant as the predominant mutation after 5 rounds of selection. Table 2 shows that 13 out of 16 sequenced variants randomly isolated after round 5 harbored the S288C mutation. S288C was not present in any of 8 isolated variants post earlier rounds 3 or 4, and was only present in 2 isolated variants (out of 16) after round 6. Table 2 also shows that after round 6, the predominant mutation was a silent R435R (CGT to CGG), which likely caused a simple IspS expression increase in the host strain. This indicates that in the enrichment procedure there is a narrow window for identification of variants that convey beneficial properties to IspS, prior to the proliferation of variants that simply improve expression.

TABLE 1

Positions near the enzyme active site located approximately 8 Å from the active site as defined by the substrate analog and coordinated metals in the PDB 3N0G.

| Residue | Position |
| --- | --- |
| ARG | 259 |
| SER | 263 |
| TRP | 266 |
| MET | 286 |
| PHE | 287 |
| SER | 288 |
| PHE | 289 |
| VAL | 290 |
| THR | 291 |
| ILE | 292 |
| ILE | 293 |
| ASP | 294 |
| ASP | 295 |
| ILE | 296 |
| TYR | 297 |
| ASP | 298 |
| VAL | 299 |
| LEU | 365 |
| CYS | 366 |
| ALA | 368 |
| PHE | 369 |
| LEU | 370 |
| GLN | 371 |
| GLU | 372 |
| ALA | 373 |
| ASN | 390 |
| ALA | 391 |
| TRP | 392 |
| LYS | 393 |
| SER | 394 |
| SER | 395 |
| SER | 396 |
| GLY | 397 |
| GLN | 400 |
| PHE | 434 |

TABLE 1-continued

Positions near the enzyme active site located approximately 8 Å from the active site as defined by the substrate analog and coordinated metals in the PDB 3N0G.

| Residue | Position |
|---|---|
| ARG | 435 |
| LEU | 436 |
| CYS | 437 |
| ASN | 438 |
| ASP | 439 |
| LEU | 440 |
| ALA | 441 |
| SER | 442 |
| ALA | 443 |
| GLU | 446 |
| GLU | 451 |
| THR | 452 |
| ALA | 453 |
| ASN | 454 |
| SER | 455 |
| SER | 510 |

TABLE 2

Variants isolated in each round of enrichment of active site pool. Isolates that did not produce clear sequencing results are labeled "ND."

| | Round 3 | Round 4 | Round 5 | Round 6 |
|---|---|---|---|---|
| Isolate 1 | A368T | T452H | S288C | R435R (cgt-cgg) |
| Isolate 2 | T452Y | N390W | S288C | R435R (cgt-cgg) |
| Isolate 3 | A368T | A391A (gca-gct) | S288C | V299L |
| Isolate 4 | C437Q | T452E | ND | R435R (cgt-cgg) |
| Isolate 5 | V299V (gta-gtt) | N390W | S288C | R435R (cgt-cgg) |
| Isolate 6 | A368N | R435R (cgt-cgg) | S288C | R435R (cgt-cgg) |
| Isolate 7 | T452S | N390W | S288C | R435R (cgt-cgg) |
| Isolate 8 | ND | ND | S288C | R435R (cgt-cgg) |
| Isolate 9 | | | S288C | V299L |
| Isolate 10 | | | S288C | S288C |
| Isolate 11 | | | S288C | R435R (cgt-cgg) |
| Isolate 12 | | | S288C | R435R (cgt-cgg) |
| Isolate 13 | | | S288C | S288C |
| Isolate 14 | | | A443G | R435R (cgt-cgg) |
| Isolate 15 | | | V299L | I292L |
| Isolate 16 | | | S288C | V299L |

Example 2

The S288C Variant Confers Solubility to MEA *P. alba* Isoprene Synthase

A pool of mutants located near the active site of MEA *P. alba* was screened for the ability to convert DMAPP to isoprene and confer improved growth to the host expression strain. Since S288C was the predominant mutation after several rounds of enrichment (described in Example 1), and conveyed a clear benefit to intracellular activity of IspS, various strains harboring the mutation were isolated for further analysis.

Methods

Figure 2:
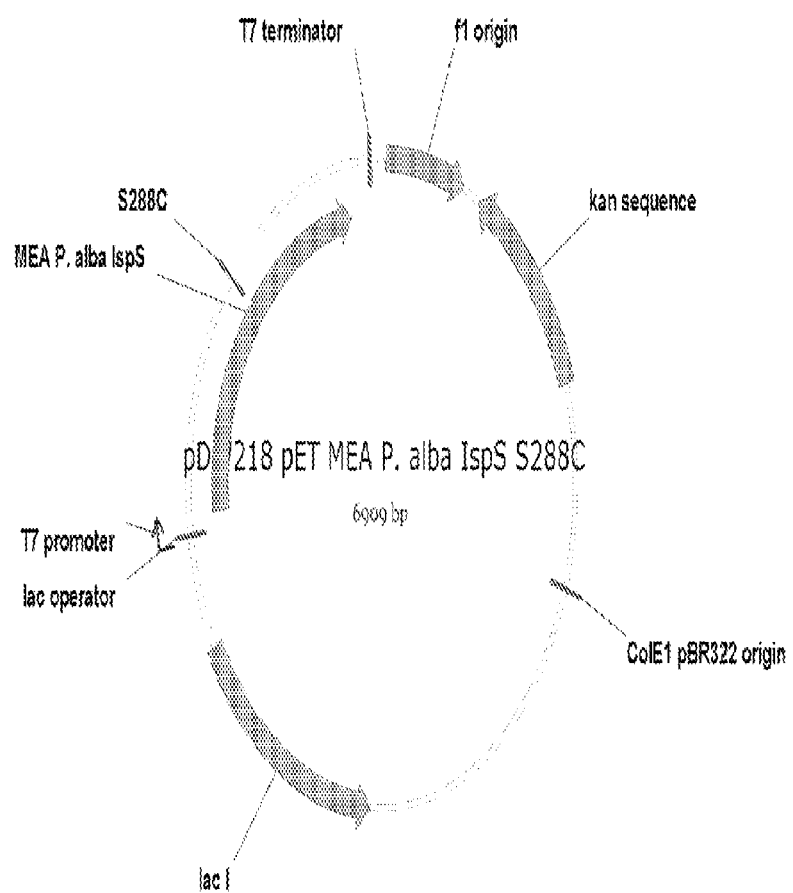
FIG. 2 shows a plasmid maps for pDW218—MEA *P. alba* IspS S288C.
Figure 3:
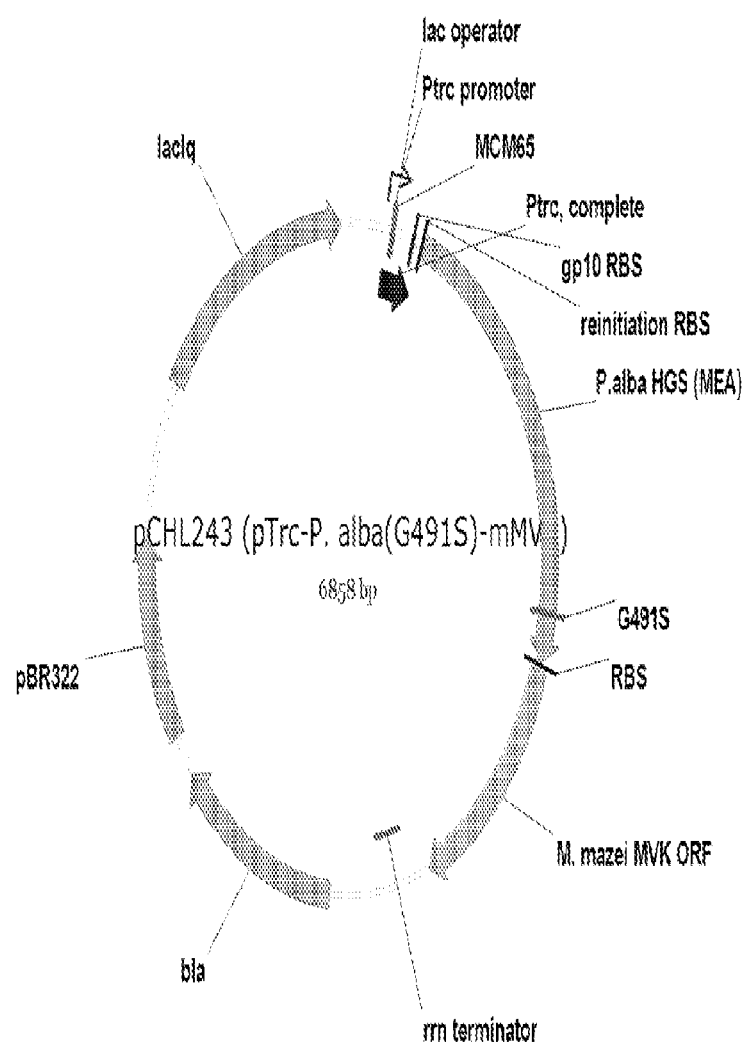
FIG. 3 shows a map of pCHL243, containing *P. alba* Isoprene Synthase with the G491S mutation.

To examine solubility of the MEA *P. alba* IspS S288C variant in comparison to wild type, strain DW425 containing the pCL201 plasmid encoding wild type IspS and strain DW526 containing the pDW218 plasmid encoding the S288C variant (FIG. 2) were inoculated into LB medium, grown, and induced with IPTG according to standard molecular biology practices (See Table 5 and Table 6). The S288C mutation was introduced into pCHL243 (FIG. 3), which contains the G491S variant of isoprene synthase, by the QuikChange procedure described above using primers shown in Table 4. The pCHL243 was generated by introduction of the G491S mutation into pDW34 (see below for pDW34 generation), which encodes the wild-type isoprene synthase, by QuikChange (Stratagene) mutagenesis (see below for PCR cycling parameters).

PCR Mixture for QuikChange Reaction:

| | |
|---|---|
| Template DNA (pTrc-MEA-Alba-mMVK) | ~100 ng |
| G507S QC 2 For | 50 uM |
| G507S QC 2 Rev | 50 uM |
| dNTPs (Roche) | 1 ul |
| 10X pfu II fusion buffer | 5 ul |
| Pfu Ultra II | 1 ul |
| Water | add enough to reach 50 ul total |

PCR Cycling Parameters for QuikChange Reaction:
95° C.—1 minute
(95° C. 50 seconds, 60° C. 50 seconds, 68° C. 3 minutes) 18 rounds
68° C.—10 minutes

TABLE 3

| Primers | |
|---|---|
| G507S QC 2 For | GAAAAACTGAGTGGTAGCCTGTTCGCGAAAC |
| G507S QC 2 Rev | AGGCTACCACTCAGTTTTTCCTTGTTCATCT |

Figure 4:
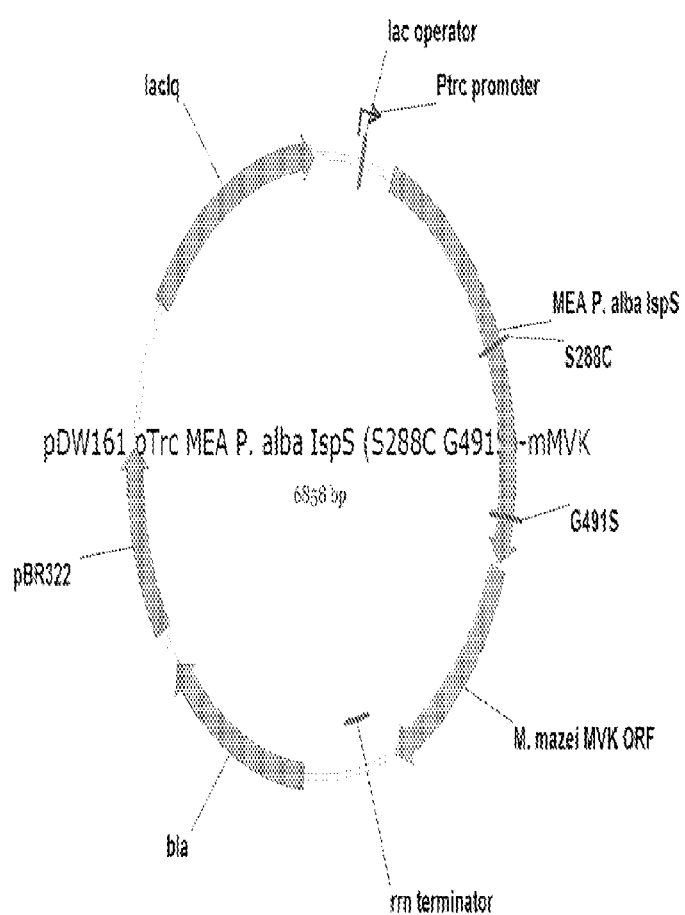
FIG. 4 shows a plasmid map for B. pDW161 pTrc MEA *P. alba* IspS (S288C G491S)-mMVK.

The resultant plasmid from introduction of S288C into pCHL243 was termed pDW161 and was confirmed by sequencing to harbor the MEA *P. alba* S288C G491S variant of IspS (See FIG. 4 and Table 4). Strain DW532 was generated by co-transformation of plasmid pMCM82 and pDW161 into strain CMP451 using standard molecular biology practices (Table 6). Positive strains resistant to both carbenicillin and spectinomycin were selected for fermentation at the 14 L scale. Samples from either shake flask experiments or fermentation were subjected to centrifugation and frozen at −80° C. prior to analysis.

Frozen samples were thawed and resuspended in lysis buffer (100 mM Tris, 100 mM NaCl pH 7.6 buffer, 0.1 mg/ml DNase, 0.5 mM PMSF/AEBSF, 5 mM MgCl2) and passed through a French pressure cell as previously described. Lysed cultures were then spun at full speed in a table-top microcentrifuge for 10 minutes at 4° C. The supernatants were removed, and the pellets were washed 1× in lysis buffer before a second centrifugation step in the microcentrifuge. Samples were removed from the centrifuge, and pellets were resuspended in lysis buffer to exactly the same volume as the supernatant from the first centrifugation step. Equivalent volumes were then treated with loading buffer (Invitrogen) and run on Coomassie gels according to the manufacturer's recommended protocol (Invitrogen, NuPage). Proteins that were soluble were present in the lane carrying samples from supernatants, and insoluble proteins were present in the lanes carrying samples from resuspended pellets. Samples from fermentation strains CMP563 (see Table 6) and DW532 were also fractionated following the procedure described above, in order to observe the effect of the S288C variant at large scale. Soluble and insoluble IspS fractions from fermentation samples were detected by Western blot analysis (Invitrogen, WesternBreeze) and quantification using a Storm 860 Molecular Imager (GMI, Inc.), as previously described and according to the manufacturer's recommended protocol. Generation of plasmids pDW34 and pMCM82, and strains CMP563, DW532, and CMP451 was previously described in WO2009/076676, WO2010/003007, WO2009132220, WO2010/031062, WO2010/031068, WO2010/031076, WOWO2010/031077, WO2010/031079, WO2010/148150, WO2010/005525, WO2010/078457, WO2010/124146, WO2011/075534, WO2010/148144, WO2011/079314, WO2011/075748, and WO2002/010398 all incorporated herein for reference.

TABLE 4

Primers used for QuikChange mutagenesis

| Primer | Sequence |
|---|---|
| HgS QC S288C Forward | AAAAATGTTTTGTTTCGTAACCATTATCGACGA |
| HgS QC S288C Reverse | TGGTTACGAAACAAAACATTTTTGCGACGGAGT |

TABLE 5

Plasmids used in this study

| Plasmid | Resistance | Description |
|---|---|---|
| pDW218 | Kan | pET MEA *P. alba* IspS S288C |
| pDW161 | Carb | pTrc MEA *P. alba* IspS G491S S288C |

TABLE 6

Strains used in this study

| Strain | Plasmid(s) | Description |
|---|---|---|
| DW425 | pCL201 | BL21 (DE3) PL.2-mKKDyI, pET MEA *P. alba* IspS (control) |
| DW526 | pDW218 | BL21 (DE3) PL.2-mKKDyI, pET MEA *P. alba* IspS S288C |
| CMP563 | pMCM82, pCHL243 | BL21 pgl+ PL.2 mKKDyI GI1.2 gltA, pTrc-MEA *P. alba* (G491S)-mMVK, MCM82 (pCL-Upper MVA pathway) |
| DW532 | pMCM82, pDW161 | BL21 pgl+ PL.2 mKKDyI GI1.2 gltA, pTrc-MEA *P. alba* (S288C G491S)-mMVK, MCM82 (pCL-Upper MVA pathway) |

Results

Figure 5:
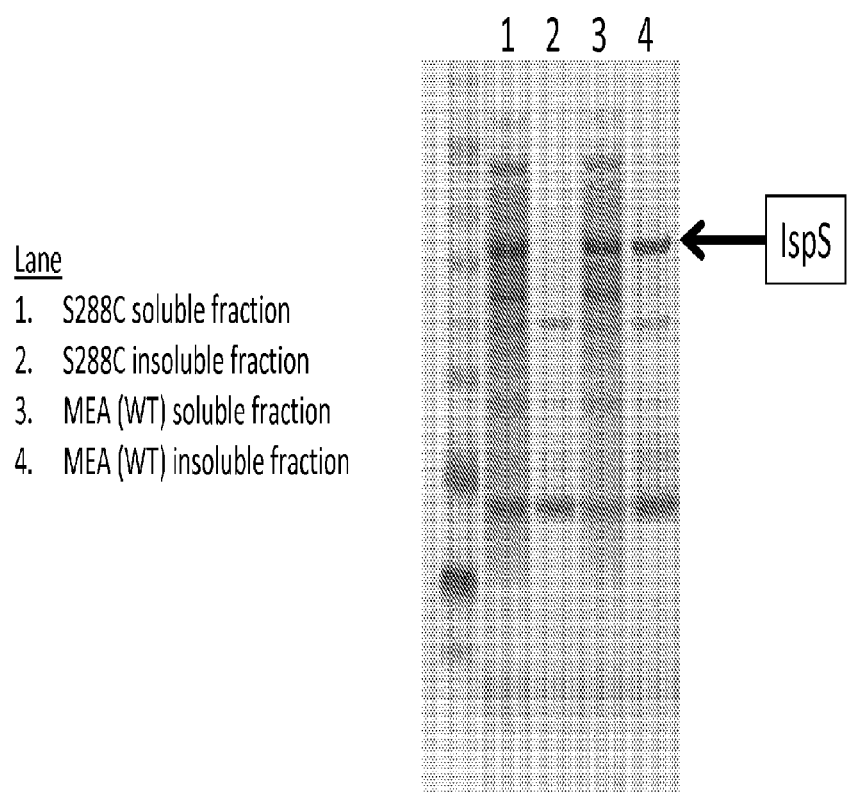
FIG. 5 shows MEA *P. alba* IspS containing the S288C mutation is soluble.
Figure 6:
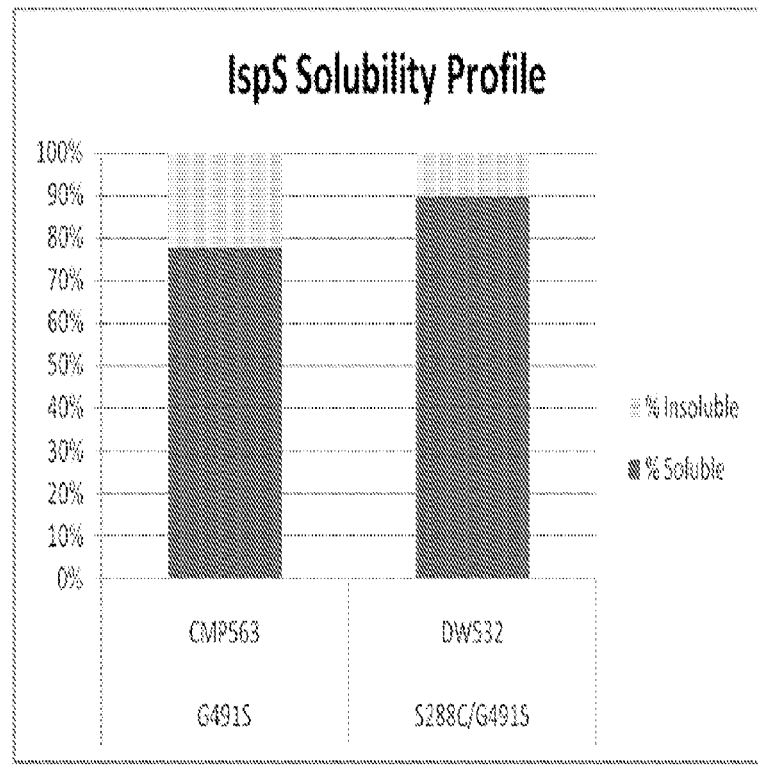
FIG. 6 shows MEA *P. alba* IspS S288C G491S is significantly more soluble than the G491S parent enzyme.

Strain DW526 was isolated directly from the enrichment pool, induced and fractionated to determine the effect of S288C on solubility in comparison to wild type. FIG. 5 shows that the MEA *P. alba* IspS S288C variant is absent from the insoluble fraction compared to the control molecule (lane 2 compared to lane 4 of the Coomassie gel). FIG. 5 also shows that the control IspS enzyme was present in the soluble and insoluble fractions at an approximate ratio of 1:1, while the S288C was found exclusively in the soluble fraction. FIG. 6 shows the effect of the S288C mutation on the solubility of IspS in a larger scale fermentation experiment. In this study, the parental IspS enzyme harbored the G491S mutation, which previously was shown to have a positive effect on cell viability, yet no effect on solubility. In comparison to the parent enzyme, the IspS G491S S288C enzyme displayed significantly increased solubility in a fermentation strain. FIG. 6 shows that solubility of the S288C G491S molecule was increased to 90% of the total amount of IspS, in comparison to the G491S molecule alone, which was only 78% soluble.

Amino acid sequence of MEA *P. alba* IspS S288C
MEARRSANYEPNSWDYDYLLSSDTDESIEVYKDKAKKLEAEVRREINNE
KAEFLTLLELIDNVQRLGLGYRFESDIRGALDRFVSSGGFDAVTKTSLH
GTALSFRLLRQHGFEVSQEAFSGFKDQNGNFLENLKEDIKAILSLYEAS
FLALEGENILDEAKVFAISHLKELSEEKIGKELAEQVNHALELPLHRRT
QRLEAVWSIEAYRKKEDANQVLLELAILDYNMIQSVYQRDLRETSRWWR
RVGLATKLHFARDRLIESFYWAVGVAFEPQYSDCRNSVAKMFCFVTIID
DIYDVYGTLDELELFTDAVERWDVNAINDLPDYMKLCFLALYNTINEIA
YDNLKDKGENILPYLTKAWADLCNAFLQEAKWLYNKSTPTFDDYFGNAW
KSSSGPLQLVFAYFAVVQNIKKEEIENLQKYHDTISRPSHIFRLCNDLA
SASAEIARGETANSVSCYMRTKGISEELATESVMNLIDETWKKMNKEKL
GGSLFAKPFVETAINLARQSHCTYHNGDAHTSPDELTRKRVLSVITEPI
LPFER DNA sequence of pDW218 harboring MEA *P. alba* IspS S288C
tggcgaatgggacgcgccctgtagcggcgcattaagcgcggcgggtgtg
gtggttacgcgcagcgtgaccgctacacttgccagcgccctagcgcccg
ctcctttcgctttcttcccttcctttctcgccacgttcgccggctttcc
ccgtcaagctctaaatcggggctccctttagggttccgatttagtgct
ttacggcacctcgaccccaaaaaacttgattagggtgatggttcacgta
gtgggccatcgccctgatagacggttttcgccctttgacgttggagtc
cacgttctttaatagtggactcttgttccaaactggaacaacactcaac
cctatctcggtctattcttttgatttataagggattttgccgatttcgg
cctattggttaaaaaatgagctgatttaacaaaaatttaacgcgaattt
taacaaaatattaacgtttacaatttcaggtggcacttttcggggaaat
gtgcgcggaacccctatttgtttattttctaaatacattcaaatatgt
atccgctcatgaattaattcttagaaaaactcatcgagcatcaaatgaa
actgcaatttattcatatcaggattatcataccatattttgaaaaag
ccgtttctgtaatgaaggagaaaactcaccgaggcagttccataggatg
gcaagatcctggtatcggtctgcgattccgactcgtccaacatcaatac
aacctattaatttccctcgtcaaaaataaggttatcaagtgagaaatc
accatgagtgacgactgaatccggtgagaatggcaaaagtttatgcatt
tcttccagacttgttcaacaggccagccattacgctcgtcatcaaaat
cactcgcatcaaccaaaccgttattcattcgtgattgcgcctgagcgag
acgaaatacgcgatcgctgttaaaaggacaattacaaacaggaatcgaa
tgcaaccggcgcaggaacactgccagcgcatcaacaatattttcacctg
aatcaggatattcttctaatacctggaatgctgttttcccggggatcgc
agtggtgagtaaccatgcatcatcaggagtacggataaaatgcttgatg
gtcggaagaggcataaattccgtcagccagtttagtctgaccatctcat
ctgtaacatcattggcaacgctacctttgccatgtttcagaaacaactc
tggcgcatcgggcttcccatacaatcgatagattgtcgcacctgattgc
ccgacattatcgcgagcccatttatacccatataaatcagcatccatgt -continued tggaatttaatcgcggcctagagcaagacgtttcccgttgaatatggct
cataacacccccttgtattactgtttatgtaagcagacagttttattgtt
catgaccaaaatcccttaacgtgagttttcgttccactgagcgtcagac
cccgtagaaaagatcaaaggatcttcttgagatcctttttttctgcgcg
taatctgctgcttgcaaacaaaaaaaccaccgctaccagcggtggtttg
tttgccggatcaagagctaccaactctttttccgaaggtaactggcttc
agcagagcgcagataccaaatactgtccttctagtgtagccgtagttag
gccaccacttcaagaactctgtagcaccgcctacatacctcgctctgct
aatcctgttaccagtggctgctgccagtggcgataagtcgtgtcttacc
gggttggactcaagacgatagttaccggataaggcgcagcggtcgggct
gaacggggggttcgtgcacacagcccagcttggagcgaacgacctacac
cgaactgagatacctacagcgtgagctatgagaaagcgccacgcttccc
gaagggagaaaggcggacaggtatccggtaagcggcagggtcggaacag
gagagcgcacgagggagcttccaggggggaaacgcctggtatctttatag
tcctgtcgggtttcgccacctctgacttgagcgtcgatttttgtgatgc
tcgtcagggggcggagcctatggaaaaacgccagcaacgcggccttttt
tacgttcctgccttttgctggccttttgctcacatgttctttcctgc
gttatcccctgattctgtggataaccgtattaccgcctttgagtgagct
gataccgctcgccgcagccgaacgaccgagcgcagcgagtcagtgagcg
aggaagcggaagagcgcctgatgcggtattttctccttacgcatctgtg
cggtatttcacaccgcatatatggtgcactctcagtacaatctgctctg
atgccgcatagttaagccagtatacactccgctatcgctacgtgactgg
gtcatggctgcgccccgacacccgccaacacccgctgacgcgccctgac
gggcttgtctgctcccggcatccgcttacagacaagctgtgaccgtctc
cgggagctgcatgtgtcagaggttttcaccgtcatcaccgaaacgcgcg
aggcagctgcggtaaagctcatcagcgtggtcgtgaagcgattcacaga
tgtctgcctgttcatccgcgtccagctcgttgagtttctccagaagcgt
taatgtctggcttctgataaagcgggccatgttaagggcggttttttcc
tgtttggtcactgatgcctccgtgtaaggggggatttctgttcatggggg
taatgataccgatgaaacgagagaggatgctcacgatacgggttactga
tgatgaacatgcccggttactggaacgttgtgagggtaaacaactggcg
gtatggatgcggcgggaccagagaaaaatcactcagggtcaatgccagc
gcttcgttaatacagatgtaggtgttccacagggtagccagcagcatcc
tgcgatgcagatccggaacataatggtgcagggcgctgacttccgcgtt
tccagactttacgaaacacggaaaccgaagaccattcatgttgttgctc
aggtcgcagacgttttgcagcagcagtcgcttcacgttcgctcgcgtat
cggtgattcattctgctaaccagtaaggcaacccccgccagcctagccgg
gtcctcaacgacaggagcacgatcatgcgcacccgtgggggccgccatgc
ggcgataatggcctgcttctcgccgaaacgtttggtggcgggaccagt
gacgaaggcttgagcgagggcgtgcaagattccgaataccgcaagcgac
aggccgatcatcgtcgcgctccagcgaaagcggtcctcgccgaaaatga -continued cccagagcgctgccggcacctgtcctacgagttgcatgataaagaagac
agtcataagtgcggcgacgatagtcatgcccgcgcccaccggaaggag
ctgactgggttgaaggctctcaagggcatcggtcgagatcccggtgcct
aatgagtgagctaacttacattaattgcgttgcgctcactgcccgcttt
ccagtcgggaaacctgtcgtgccagctgcattaatgaatcggccaacgc
gcggggagaggcggtttgcgtattgggcgccagggtggttttcttttc
accagtgagacgggcaacagctgattgcccttcaccgcctggccctgag
agagttgcagcaagcggtccacgctggtttgcccagcaggcgaaaatc
ctgtttgatggtggttaacggcgggatataacatgagctgtcttcggta
tcgtcgtatcccactaccgagatatccgcaccaacgcgcagcccggact
cggtaatggcgcgcattgcgcccagcgccatctgatcgttggcaaccag
catcgcagtggggaacgatgccctcattcagcatttgcatggtttgttga
aaaccggacatggcactccagtcgccttcccgttccgctatcggctgaa
tttgattgcgagtgagatatttatgccagccagccagacgcagacgcgc
cgagacagaacttaatgggcccgctaacagcgcgatttgctggtgaccc
aatgcgaccagatgctccacgcccagtcgcgtaccgtcttcatgggaga
aaataatactgttgatgggtgtctggtcagagacatcaagaaataacgc
cggaacattagtgcaggcagcttccacagcaatggcatcctggtcatcc
agcggatagttaatgatcagcccactgacgcgttgcgcgagaagattgt
gcaccgccgctttacaggcttcgacgccgcttcgttctaccatcgacac
caccacgctggcacccagttgatcggcgcgagatttaatcgccgcgaca
atttgcgacgcgcgtgcagggccagactggaggtggcaacgccaatca
gcaacgactgtttgcccgccagttgttgtgccacgcggttgggaatgta
attcagctccgccatcgccgcttccactttttcccgcgttttcgcagaa
acgtggctggcctggttcaccacgcgggaaacgtctgataagagacac
cggcatactctgcgacatcgtataacgttactggtttcacattcaccac
cctgaattgactctcttccgggcgctatcatgccataccgcgaaaggtt
ttgcgccattcgatggtgtccgggatctcgacgctctcccttatgcgac
tcctgcattaggaagcagcccagtagtaggttgaggccgttgagcaccg
ccgccgcaaggaatggtgcatgcaaggagatggcgcccaacagtccccc
ggccacggggcctgccaccatacccacgccgaaacaagcgctcatgagc
ccgaagtggcgagcccgatcttccccatcggtgatgtcggcgatatagg
cgccagcaaccgcacctgtggcgccggtgatgccggccacgatgcgtcc
ggcgtagaggatcgagatctcgatcccgcgaaattaatacgactcacta
tagggggaattgtgagcggataacaattccctctagaaataattttgtt
taactttaagaaggagatatacatatggaagcacgtcgctctgcgaact
acgaacctaacagctgggactatgattacctgctgtcctccgacacgga
cgagtccatcgaagtatacaaagacaaagcgaaaaagctggaagccgaa
gttcgtcgcgagattaataacgaaaaagcagaatttctgaccctgctgg
aactgattgacaacgtccagcgcctgggcctgggttaccgtttcgagtc -continued tgatatccgtggtgcgctggatcgcttcgtttcctccggcggcttcgat
gcggtaaccaagacttccctgcacggtacggcactgtctttccgtctgc
tgcgtcaacacggttttgaggtttctcaggaagcgttcagcggcttcaa
agaccaaaacggcaacttcctggagaacctgaaggaagatatcaaagct
atcctgagcctgtacgaggccagcttcctggctctggaaggcgaaaaca
tcctggacgaggcgaaggttttcgcaatctctcatctgaaagaactgtc
tgaagaaagatcggtaaagagctggcagaacaggtgaaccatgcactg
gaactgccactgcatcgccgtactcagcgtctggaagcagtatggtcta
tcgaggcctaccgtaaaaggaggacgcgaatcaggttctgctggagct
ggcaattctggattacaacatgatccagtctgtataccagcgtgatctg
cgtgaaacgtcccgttggtggcgtcgtgtgggtctggcgaccaaactgc
actttgctcgtgaccgcctgattgagagcttctactgggccgtgggtgt
agcattcgaaccgcaatactccgactgccgtaactccgtcgcaaaaatg
ttttgtttcgtaaccattatcgacgatatctacgatgtatacggcaccc
tggacgaactggagctgtttactgatgcagttgagcgttgggacgtaaa
cgccatcaacgacctgccggattacatgaaactgtgctttctggctctg
tataacactattaacgaaatcgcctacgacaacctgaaagataaaggtg
agaacatcctgccgtatctgaccaaagcctgggctgacctgtgcaacgc
tttcctgcaagaagccaagtggctgtacaacaaatctactccgaccttt
gacgactacttcggcaacgcatggaaatcctcttctggcccgctgcaac
tggtgttcgcttacttcgctgtcgtgcagaacattaaaaaggaagagat
cgaaaacctgcaaaaataccatgacaccatctctcgtccttcccatatc
ttccgtctgtgcaatgacctggctagcgcgtctgcggaaattgcgcgtg
gtgaaaccgcaaatagcgtttcttgttacatgcgcactaaaggtatctc
cgaagaactggctaccgaaagcgtgatgaatctgatcgatgaaacctgg
aaaagatgaacaaggaaaaactgggtggtagcctgttcgcgaaaccgt
tcgtggaaaccgcgatcaacctggcacgtcaatctcactgcacttatca
taacggcgacgcgcatacctctccggatgagctgacccgcaaacgcgtt
ctgtctgtaatcactgaaccgattctgccgtttgaacgctaaggatccg
aattcgagctccgtcgacaagcttgcggccgcactcgagcaccaccac
caccactgagatccggctgctaacaaagcccgaaaggaagctgagtt
ggctgctgccaccgctgagcaataactagcataaccccttggggcctct
aaacgggtcttgaggggttttttgctgaaaggaggaactatatccggat DNA sequence of pCHL243 harboring MEA P. alba
IspS G491S
gtttgacagcttatcatcgactgcacggtgcaccaatgcttctggcgtc
aggcagccatcggaagctgtggtatggctgtgcaggtcgtaaatcactg
cataattcgtgtcgctcaaggcgcactcccgttctggataatgttttt
gcgccgacatcataacggttctggcaaatattctgaaatgagctgttga
caattaatcatccggctcgtataatgtgtggaattgtgagcggataaca
atttcacacaggaaacagcgccgctgagaaaaagcgaagcggcactgct
ctttaacaatttatcagacaatctgtgtgggcactcgaccggaattatc -continued gattaactttattattaaaaattaaagaggtatatattaatgtatcgat
taaataaggaggaataaaccatggaagctcgtcgttctgcgaactacga
acctaacagctgggactatgattacctgctgtcctccgacacggacgag
tccatcgaagtatacaaagacaaagcgaaaaagctggaagccgaagttc
gtcgcgagattaataacgaaaaagcagaatttctgaccctgctggaact
gattgacaacgtccagcgcctgggcctggttaccgtttcgagtctgat
atccgtggtgcgctggatcgcttcgtttcctccggcggcttcgatgcgg
taaccaagacttccctgcacggtacggcactgtctttccgtctgctgcg
tcaacacggttttgaggtttctcaggaagcgttcagcggcttcaaagac
caaaacggcaacttcctggagaacctgaaggaagatatcaaagctatcc
tgagcctgtacgaggccagcttcctggctctggaaggcgaaaacatcct
ggacgaggcgaaggttttcgcaatctctcatctgaaagaactgtctgaa
gaaaagatcggtaaagagctggcagaacaggtgaaccatgcactggaac
tgccactgcatcgccgtactcagcgtctggaagcagtatggtctatcga
ggcctaccgtaaaaggaggacgcgaatcaggttctgctggagctggca
attctggattacaacatgatccagtctgtataccagcgtgatctgcgtg
aaacgtcccgttggtggcgtcgtgtgggtctggcgaccaaactgcactt
tgctcgtgaccgcctgattgagagcttctactgggccgtgggtgtagca
ttcgaaccgcaatactccgactgccgtaactccgtcgcaaaaatgtttt
ctttcgtaaccattatcgacgatatctacgatgtatacggcaccctgga
cgaactggagctgtttactgatgcagttgagcgttgggacgtaaacgcc
atcaacgacctgccggattacatgaaactgtgctttctggctctgtata
acactattaacgaaatcgcctacgacaacctgaaagataaaggtgagaa
catcctgccgtatctgaccaaagcctgggctgacctgtgcaacgctttc
ctgcaagaagccaagtggctgtacaacaaatctactccgacctttgacg
actacttcggcaacgcatggaaatcctcttctggcccgctgcaactggt
gttcgcttacttcgctgtcgtgcagaacattaaaaaggaagagatcgaa
aacctgcaaaaataccatgacaccatctctcgtccttcccatatcttcc
gtctgtgcaatgacctggctagcgcgtctgcggaaattgcgcgtggtga
aaccgcaaatagcgtttcttgttacatgcgcactaaaggtatctccgaa
gaactggctaccgaaagcgtgatgaatctgatcgatgaaacctggaaaa
gatgaacaaggaaaaactgagtggtagcctgttcgcgaaaccgttcgt
ggaaaccgcgatcaacctggcacgtcaatctcactgcacttatcataac
ggcgacgcgcatacctctccggatgagctgacccgcaaacgcgttctgt
ctgtaatcactgaaccgattctgccgtttgaacgctaactgcataaagg
aggtaaaaaaacatggtatcctgttctgcgccgggtaagatttacctgt
tcggtgaacacgccgtagtttatggcgaaactgcaattgcgtgtgcggt
ggaactgcgtacccgtgttcgcgcggaactcaatgactctatcactatt
cagagccagatcggccgcaccggtctggatttcgaaaagcacccttatg
tgtctgcggtaattgagaaaatgcgcaaatctattcctattaacggtgt -continued

```
tttcttgaccgtcgattccgacatcccggtgggctccggtctgggtagc
agcgcagccgttactatcgcgtctattggtgcgctgaacgagctgttcg
gctttggcctcagcctgcaagaaatcgctaaactgggccacgaaatcga
aattaaagtacaggtgccgcgtcccaaccgatacgtatgtttctacc
ttcggcggcgtggttaccatcccggaacgtcgcaaactgaaaactccgg
actgcggcattgtgattggcgataccggcgttttctcctccaccaaaga
gttagtagctaacgtacgtcagctgcgcgaaagctacccggatttgatc
gaaccgctgatgacctctattggcaaaatctctcgtatcggcgaacaac
tggttctgtctggcgactacgcatccatcggccgcctgatgaacgtcaa
ccagggtctcctggacgccctgggcgttaacatcttagaactgagccag
ctgatctattccgctcgtgcggcaggtgcgtttggcgctaaaatcacgg
gcgctgcggcggtggctgtatggttgcgctgaccgctccggaaaaatg
caaccaagtggcagaagcggtagcaggcgctggcggtaaagtgactatc
actaaaccgaccgagcaaggtctgaaagtagattaaagtctagttaaag
tttaaacggtctccagcttggctgttttggcggatgagagaagatttttc
agcctgatacagattaaatcagaacgcagaagcggtctgataaaacaga
atttgcctggcggcagtagcgcggtggtcccacctgaccccatgccgaa
ctcagaagtgaaacgccgtagcgccgatggtagtgtggggtctccccat
gcgagagtagggaactgccaggcatcaaataaaacgaaaggctcagtcg
aaagactgggcctttcgttttatctgttgtttgtcggtgaacgctctcc
tgagtaggacaaatccgccgggagcggatttgaacgttgcgaagcaacg
gcccggagggtggcgggcaggacgcccgccataaactgccaggcatcaa
attaagcagaaggccatcctgacggatggcctttttgcgtttctacaaa
ctcttttttgtttatttttctaaatacattcaaatatgtatccgctcatg
agacaataaccctgataaatgcttcaataatattgaaaaaggaagagta
tgagtattcaacatttccgtgtcgcccttattcccttttttgcggcatt
ttgccttcctgtttttgctcacccagaaacgctggtgaaagtaaaagat
gctgaagatcagttgggtgcacgagtgggttacatcgaactggatctca
acagcggtaagatccttgagagttttcgccccgaagaacgttttccaat
gatgagcacttttaaagttctgctatgtggcgcggtattatcccgtgtt
gacgccgggcaagagcaactcggtcgccgcatacactattctcagaatg
acttggttgagtactcaccagtcacagaaaagcatcttacggatggcat
gacagtaagagaattatgcagtgctgccataaccatgagtgataacact
gcggccaacttacttctgacaacgatcggaggaccgaaggagctaaccg
cttttttgcacaacatgggggatcatgtaactcgccttgatcgttggga
accggagctgaatgaagccataccaaacgacgagcgtgacaccacgatg
cctgtagcaatggcaacaacgttgcgcaaactattaactggcgaactac
ttactctagcttcccggcaacaattaatagactggatggaggcggataa
agttgcaggaccacttctgcgctcggcccttccggctggctggtttatt
gctgataaatctggagccggtgagcgtgggtctcgcggtatcattgcag
cactggggccagatggtaagccctcccgtatcgtagttatctacacgac
```

```
ggggagtcaggcaactatggatgaacgaaatagacagatcgctgagata
ggtgcctcactgattaagcattggtaactgtcagaccaagtttactcat
atatactttagattgatttaaaacttcatttttaatttaaaaggatcta
ggtgaagatcctttttgataatctcatgaccaaaatcccttaacgtgag
ttttcgttccactgagcgtcagaccccgtagaaaagatcaaaggatctt
cttgagatcctttttttctgcgcgtaatctgctgcttgcaaacaaaaaa
accaccgctaccagcggtggtttgtttgccggatcaagagctaccaact
cttttttccgaaggtaactggcttcagcagagcgcagataccaaatactg
tccttctagtgtagccgtagttaggccaccacttcaagaactctgtagc
accgcctacatacctcgctctgctaatcctgttaccagtggctgctgcc
agtggcgataagtcgtgtcttaccgggttggactcaagacgatagttac
cggataaggcgcagcggtcgggctgaacggggggttcgtgcacacagcc
cagcttggagcgaacgacctacaccgaactgagatacctacagcgtgag
ctatgagaaagcgccacgcttcccgaagggagaaaggcggacaggtatc
cggtaagcggcagggtcggaacaggagagcgcacgagggagcttccagg
gggaaacgcctggtatctttatagtcctgtcgggtttcgccacctctga
cttgagcgtcgatttttgtgatgctcgtcaggggggcggagcctatgga
aaaacgccagcaacgcggcctttttacggttcctggccttttgctggcc
ttttgctcacatgttctttcctgcgttatcccctgattctgtggataac
cgtattaccgcctttgagtgagctgataccgctcgccgcagccgaacga
ccgagcgcagcgagtcagtgagcgaggaagcggaagagcgcctgatgcg
gtattttctccttacgcatctgtgcggtatttcacaccgcatatggtgc
actctcagtacaatctgctctgatgccgcatagttaagccagtatacac
tccgctatcgctacgtgactgggtcatggctgcgccccgacacccgcca
acacccgctgacgcgccctgacgggcttgtctgctcccggcatccgctt
acagacaagctgtgaccgtctccgggagctgcatgtgtcagaggttttc
accgtcatcaccgaaacgcgcgaggcagcagatcaattcgcgcgcgaag
gcgaagcggcatgcatttacgttgacaccatcgaatggtgcaaaacctt
tcgcggtatggcatgatagcgcccggaagagagtcaattcagggtggtg
aatgtgaaaccagtaacgttatacgatgtcgcagagtatgccggtgtct
cttatcagaccgtttcccgcgtggtgaaccaggccagccacgtttctgc
gaaaacgcgggaaaaagtggaagcggcgatggcggagctgaattacatt
cccaaccgcgtggcacaacaactggcgggcaaacagtcgttgctgattg
gcgttgccacctccagtctggccctgcacgcgccgtcgcaaattgtcgc
ggcgattaaatctcgcgccgatcaactgggtgccagcgtggtggtgtcg
atggtagaacgaagcggcgtcgaagcctgtaaagcggcggtgcacaatc
ttctcgcgcaacgcgtcagtgggctgatcattaactatccgctggatga
ccaggatgccattgctgtggaagctgcctgcactaatgttccggcgtta
tttcttgatgtctctgaccagacacccatcaacagtattattttctccc
atgaagacggtacgcgactgggcgtggagcatctggtcgcattgggtca
```

-continued

```
ccagcaaatcgcgctgttagcgggcccattaagttctgtctcggcgcgt
ctgcgtctggctggctggcataaatatctcactcgcaatcaaattcagc
cgatagcggaacgggaaggcgactggagtgccatgtccggttttcaaca
aaccatgcaaatgctgaatgagggcatcgttcccactgcgatgctggtt
gccaacgatcagatggcgctgggcgcaatgcgcgccattaccgagtccg
ggctgcgcgttggtgcggatatctcggtagtgggatacgacgataccga
agacagctcatgttatatcccgccgtcaaccaccatcaaacaggatttt
cgcctgctggggcaaaccagcgtggaccgcttgctgcaactctctcagg
gccaggcggtgaagggcaatcagctgttgcccgtctcactggtgaaaag
aaaaaccaccctggcgcccaatacgcaaaccgcctctccccgcgcgttg
gccgattcattaatgcagctggcacgacaggtttcccgactggaaagcg
ggcagtgagcgcaacgcaattaatgtgagttagcgcgaattgatctg
```

Amino acid sequence of MEA P. alba IspS
S288C G491S

```
MEARRSANYEPNSWDYDYLLSSDTDESIEVYKDKAKKLEAEVRREINNE
KAEFLTLLELIDNVQRLGLGYRFESDIRGALDRFVSSGGFDAVTKTSLH
GTALSFRLLRQHGFEVSQEAFSGFKDQNGNFLENLKEDIKAILSLYEAS
FLALEGENILDEAKVFAISHLKELSEEKIGKELAEQVNHALELPLHRRT
QRLEAVWSIEAYRKKEDANQVLLELAILDYNMIQSVYQRDLRETSRWWR
RVGLATKLHFARDRLIESFYWAVGVAFEPQYSDCRNSVAKMFCFVTIID
DIYDVYGTLDELELFTDAVERWDVNAINDLPDYMKLCFLALYNTINEIA
YDNLKDKGENILPYLTKAWADLCNAFLQEAKWLYNKSTPTFDDYFGNAW
KSSSGPLQLVFAYFAVVQNIKKEEIENLQKYHDTISRPSHIFRLCNDLA
SASAEIARGETANSVSCYMRTKGISEELATESVMNLIDETWKKMNKEKL
SGSLFAKPFVETAINLARQSHCTYHNGDAHTSPDELTRKRVLSVITEPI
LPFER
```

DNA sequence of pDW161 harboring MEA P. alba
IspS S288C G491S

```
gtttgacagcttatcatcgactgcacggtgcaccaatgcttctggcgtc
aggcagccatcggaagctgtggtatggctgtgcaggtcgtaaatcactg
cataattcgtgtcgctcaaggcgcactcccgttctggataatgtttttt
gcgccgacatcataacggttctggcaaatattctgaaatgagctgttga
caattaatcatccggctcgtataatgtgtggaattgtgagcggataaca
atttcacacaggaaacagcgccgctgagaaaaagcgaagcggcactgct
ctttaacaatttatcagacaatctgtgtgggcactcgaccggaattatc
gattaactttattattaaaaattaaagaggtatatattaatgtatcgat
taaataaggaggaataaaccatggaagctcgtcgttctgcgaactacga
acctaacagctgggactatgattacctgctgtcctccgacacggacgag
tccatcgaagtatacaaagacaaagcgaaaaagctggaagccgaagttc
gtcgcgagattaataacgaaaagcagaatttctgaccctgctggaact
gattgacaacgtccagcgcctgggcctgggttaccgtttcgagtctgat
atccgtggtgcgctggatcgcttcgtttcctccggcggcttcgatgcgg
taaccaagacttccctgcacggtacggcactgtctttccgtctgctgcg
```

```
tcaacacggttttgaggtttctcaggaagcgttcagcggcttcaaagac
caaaacggcaacttcctggagaacctgaaggaagatatcaaagctatcc
tgagcctgtacgaggccagcttcctggctctggaaggcgaaaacatcct
ggacgaggcgaaggttttcgcaatctctcatctgaaagaactgtctgaa
gaaaagatcggtaaagagctggcagaacaggtgaaccatgcactggaac
tgccactgcatcgccgtactcagcgtctggaagcagtatggtctatcga
ggcctaccgtaaaaaggaggacgcgaatcaggttctgctggagctggca
attctggattacaacatgatccagtctgtataccagcgtgatctgcgtg
aaacgtcccgttggtggcgtcgtgtgggtctggcgaccaaactgcactt
tgctcgtgaccgcctgattgagagcttctactgggccgtgggtgtagca
ttcgaaccgcaatactccgactgccgtaactccgtcgcaaaaatgtttt
gtttcgtaaccattatcgacgatatctacgatgtatacggcaccctgga
cgaactggagctgtttactgatgcagttgagcgttgggacgtaaacgcc
atcaacgacctgccggattacatgaaactgtgctttctggctctgtata
acactattaacgaaatcgcctacgacaacctgaaagataaaggtgagaa
catcctgccgtatctgaccaaagcctgggctgacctgtgcaacgctttc
ctgcaagaagccaagtggctgtacaacaaatctactccgacctttgacg
actacttcggcaacgcatggaaatcctcttctggcccgctgcaactggt
gttcgcttacttcgctgtcgtgcagaacattaaaaaggaagagatcgaa
aacctgcaaaaatatcatgacaccatctctcgtccttcccatatcttcc
gtctgtgcaatgacctggctagcgcgtctgcggaaattgcgcgtggtga
aaccgcaaatagcgtttcttgttacatgcgcactaaaggtatctccgaa
gaactggctaccgaaagcgtgatgaatctgatcgatgaaacctggaaaa
agatgaacaaggaaaaactgagtggtagcctgttcgcgaaaccgttcgt
ggaaaccgcgatcaacctggcacgtcaatctcactgcacttatcataac
ggcgacgcgcataccctctccggatgagctgacccgcaaacgcgttctgt
ctgtaatcactgaaccgattctgccgtttgaacgctaactgcataaagg
aggtaaaaaaacatggtatcctgttctgcgccgggtaagatttacctgt
tcggtgaacacgccgtagtttatggcgaaactgcaattgcgtgtgcggt
ggaactgcgtaccgtgttcgcgcggaactcaatgactctatcactatt
cagagccagatcggccgcaccggtctggatttcgaaaagcacccttatg
tgtctgcggtaattgagaaaatgcgcaaatctattcctattaacggtgt
tttcttgaccgtcgattccgacatcccggtgggctccgtctgggtagc
agcgcagccgttactatcgcgtctattggtgcgctgaacgagctgttcg
gctttggcctcagcctgcaagaaatcgctaaactgggccacgaaatcga
aattaaagtacagggtgccgcgtccccaaccgatacgtatgtttctacc
ttcggcggcgtggttaccatcccggaacgtcgcaaactgaaaactccgg
actgcggcattgtgattggcgataccggcgttttctcctccaccaaaga
gttagtagctaacgtacgtcagctgcgcgaaagctaccggatttgatc
gaaccgctgatgacctctattggcaaaatctctcgtatcggcgaacaac
```

-continued tggttctgtctggcgactacgcatccatcggccgcctgatgaacgtcaa
ccagggtctcctggacgccctgggcgttaacatcttagaactgagccag
ctgatctattccgctcgtgcggcaggtgcgtttggcgctaaaatcacgg
gcgctggcggcggtggctgtatggttgcgctgaccgctccggaaaaatg
caaccaagtggcagaagcggtagcaggcgctggcggtaaagtgactatc
actaaaccgaccgagcaaggtctgaaagtagattaaagtctagttaaag
tttaaacggtctccagcttggctgttttggcggatgagagaagattttc
agcctgatacagattaaatcagaacgcagaagcggtctgataaaacaga
atttgcctggcggcagtagcgcggtggtcccacctgaccccatgccgaa
ctcagaagtgaaacgccgtagcgccgatggtagtgtggggtctcccat
gcgagagtagggaactgccaggcatcaaataaaacgaaaggctcagtcg
aaagactgggcctttcgttttatctgttgtttgtcggtgaacgctctcc
tgagtaggacaaatccgccgggagcggatttgaacgttgcgaagcaacg
gcccggagggtggcgggcaggacgcccgccataaactgccaggcatcaa
attaagcagaaggccatcctgacggatggccttttttgcgtttctacaaa
ctcttttttgtttattttttctaaatacattcaaatatgtatccgctcatg
agacaataaccctgataaatgcttcaataatattgaaaaaggaagagta
tgagtattcaacatttccgtgtcgcccttattcccttttttgcggcatt
ttgccttcctgtttttgctcacccagaaacgctggtgaaagtaaaagat
gctgaagatcagttgggtgcacgagtgggttacatcgaactggatctca
acagcggtaagatccttgagagttttcgccccgaagaacgttttccaat
gatgagcacttttaaagttctgctatgtggcgcggtattatcccgtgtt
gacgccgggcaagagcaactcggtcgccgcatacactattctcagaatg
acttggttgagtactcaccagtcacagaaaagcatcttacggatggcat
gacagtaagagaattatgcagtgctgccataaccatgagtgataacact
gcggccaacttacttctgacaacgatcggaggaccgaaggagctaaccg
cttttttgcacaacatgggggatcatgtaactcgccttgatcgttggga
accggagctgaatgaagccataccaaacgacgagcgtgacaccacgatg
cctgtagcaatggcaacaacgttgcgcaaactattaactggcgaactac
ttactctagcttcccggcaacaattaatagactggatggaggcggataa
agttgcaggaccacttctgcgctcggcccttccggctggctggtttatt
gctgataaatctggagccggtgagcgtgggtctcgcggtatcattgcag
cactggggccagatggtaagccctcccgtatcgtagttatctacacgac
ggggagtcaggcaactatggatgaacgaaatagacagatcgctgagata
ggtgcctcactgattaagcattggtaactgtcagaccaagtttactcat
atatactttagattgatttaaaacttcattttttaattttaaaaggatcta
ggtgaagatcctttttgataatctcatgaccaaaatcccttaacgtgag
ttttcgttccactgagcgtcagaccccgtagaaaagatcaaaggatctt
cttgagatcctttttttctgcgcgtaatctgctgcttgcaaacaaaaaa
accaccgctaccagcggtggtttgtttgccggatcaagagctaccaact
cttttttccgaaggtaactggcttcagcagagcgcagataccaaatactg -continued tccttctagtgtagccgtagttaggccaccacttcaagaactctgtagc
accgcctacatacctcgctctgctaatcctgttaccagtggctgctgcc
agtggcgataagtcgtgtcttaccgggttggactcaagacgatagttac
cggataagcgcagcggtcgggctgaacgggggggttcgtgcacacagcc
cagcttggagcgaacgacctacaccgaactgagatacctacagcgtgag
ctatgagaaagcgccacgcttcccgaagggagaaaggcggacaggtatc
cggtaagcggcagggtcggaacaggagagcgcacgagggagcttccagg
gggaaacgcctggtatctttatagtcctgtcgggtttcgccacctctga
cttgagcgtcgatttttgtgatgctcgtcaggggggcggagcctatgga
aaaacgccagcaacgcggcctttttacggttcctggccttttgctggcc
ttttgctcacatgttctttcctgcgttatcccctgattctgtggataac
cgtattaccgcctttgagtgagctgataccgctcgccgcagccgaacga
ccgagcgcagcgagtcagtgagcgaggaagcggaagagcgcctgatgcg
gtattttctccttacgcatctgtgcggtatttcacaccgcatatggtgc
actctcagtacaatctgctctgatgccgcatagttaagccagtatacac
tccgctatcgctacgtgactgggtcatggctgcgccccgacacccgcca
acacccgctgacgcgccctgacgggcttgtctgctcccggcatccgctt
acagacaagctgtgaccgtctccgggagctgcatgtgtcagaggttttc
accgtcatcaccgaaacgcgcgaggcagcagatcaattcgcgcgcgaag
gcgaagcggcatgcatttacgttgacaccatcgaatggtgcaaaacctt
tcgcggtatggcatgatagcgcccggaagagagtcaattcagggtggtg
aatgtgaaaccagtaacgttatacgatgtcgcagagtatgccggtgtct
cttatcagaccgtttcccgcgtggtgaaccaggccagccacgtttctgc
gaaaacgcgggaaaaagtggaagcggcgatggcggagctgaattacatt
cccaaccgcgtggcacaacaactggcgggcaaacagtcgttgctgattg
gcgttgccacctccagtctggccctgcacgcgccgtcgcaaattgtcgc
ggcgattaaatctcgcgccgatcaactgggtgccagcgtggtggtgtcg
atggtagaacgaagcggcgtcgaagcctgtaaagcggcggtgcacaatc
ttctcgcgcaacgcgtcagtgggctgatcattaactatccgctggatga
ccaggatgccattgctgtggaagctgcctgcactaatgttccggcgtta
tttcttgatgtctctgaccagacacccatcaacagtattattttctccc
atgaagacggtacgcgactgggcgtggagcatctggtcgcattgggtca
ccagcaaatcgcgctgttagcgggcccattaagttctgtctcggcgcgt
ctgcgtctggctggctggcataaatatctcactcgcaatcaaattcagc
cgatagcggaacgggaaggcgactggagtgccatgtccggttttcaaca
aaccatgcaaatgctgaatgagggcatcgttcccactgcgatgctggtt
gccaacgatcagatggcgctgggcgcaatgcgcgccattaccgagtccg
ggctgcgcgttggtgcggatatctcggtagtgggatacgacgataccga
agacagctcatgttatatcccgccgtcaaccaccatcaaacaggatttt
cgcctgctggggcaaaccagcgtggaccgcttgctgcaactctctcagg -continued
```
gccaggcggtgaagggcaatcagctgttgcccgtctcactggtgaaaag aaaaaccaccctggcgcccaatacgcaaaccgcctctccccgcgcgttg gccgattcattaatgcagctggcacgacaggtttcccgactggaaagcg ggcagtgagcgcaacgcaattaatgtgagttagcgcgaattgatctg
```

Example 3

The S288C Mutation Increases the Solubility of IspS Enzymes from *Salix alba* and *Salix babylonica*

The effect of S288C mutation on solubility of IspS from *Salix alba* and *Salix babylonica* was investigated.

Methods and Results

Construction of Plasmid pEWL792 (pTrc *S. alba* IspS)

Generation of a synthetic gene encoding *Salix alba* isoprene synthase (*S. alba* IspS) was performed by Gene Oracle Inc. (Mountain View, Calif.) utilizing a codon optimization method specific for *E. coli* expression. The synthetic gene was cloned into plasmid pGOv4 with an engineered NcoI restriction site on the 5'-end and a PstI restriction site on the 3'-end. Clustal W sequence alignment between *P. alba* IspS and *S. alba* IspS shows 91.73% identity (FIG. 7).

Figure 8:
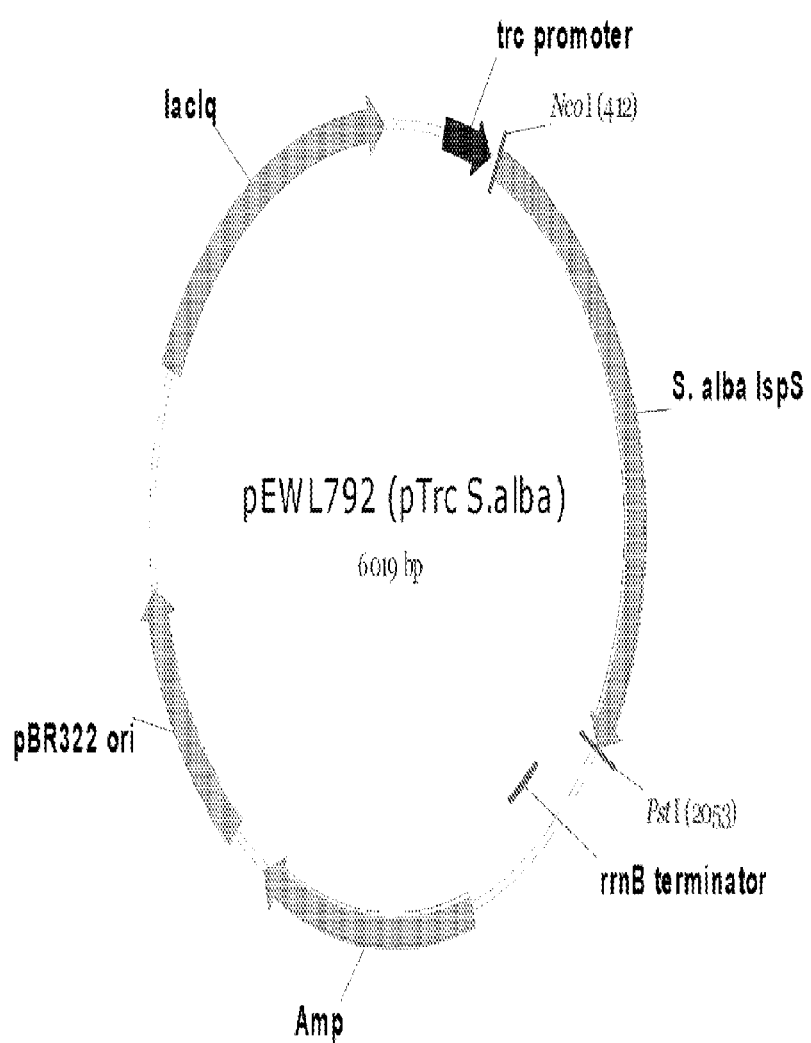
FIG. 8 shows a plasmid map of pEWL792.

1 µg of the pGOv4 *S. alba* IspS plasmid was digested with restriction endonucleases NcoI and PstI (Roche) based on the manufacturer's protocol at 37° C. The digested *S. alba* IspS fragment was then purified using a 1% EX gel (Invitrogen) and extracted using the QIAquick Gel Extraction Kit (Qiagen). 0.5 µg of pTrcHis2B plasmid (Invitrogen) was digested with restriction endonucleases NcoI and PstI based on the manufacturer's protocol at 37° C. The pTrcHis2B plasmid was then purified using a 1% EX gel and extracted using the QIAquick Gel Extraction Kit. The *S. alba* IspS gene was ligated into the pTrcHis2B plasmid using T4 DNA ligase (New England Biolabs) based on the manufacturer's protocol at room temperature. The ligation mixture was desalted by floating a 0.025 µm nitrocellulose membrane filter (Millipore) in a petri dish of ddH$_2$O and applying the ligation mixture gently on top of the nitrocellulose membrane filter for 30 minutes at room temperature. Strain MCM446 cells were grown in LB to midlog phase and then washed three times in ice-cold, sterile water. Mixed 50 µl of cell suspension with 5 µl of desalted pTrc *S. alba* IspS ligation mix. The cell suspension mixture was electroporated in a 2 mm cuvette at 2.5 Volts and 25 µFd using a Gene Pulser Xcell Electroporator (BioRad). Cells were recovered in 1 ml of LB and incubated for 2 hours at 30° C. with shaking. Transformants were selected on LA+50 µg/µl carbenicillin+10 mM mevalonic acid plates and incubated overnight at 37° C. The next day, several transformants were picked and grown in 5 ml LB+50 µg/µl carbenicillin tubes overnight at 30° C. Plasmid preps were performed on the overnight cultures using QIAquick Spin Miniprep Kit (Qiagen). Plasmids were digested with restriction endonucleases NcoI and PstI at 37° C. and analyzed on a 1.2% E-gel (Invitrogen) to ensure correct sized fragments were obtained. Plasmids from several transformants were shipped to Sequetech (Mountain View, Calif.) for sequencing with primers EL1005, EL1006, EL1270, and EL1271 (Table 7). DNA sequencing results showed that plasmids were correct. One plasmid was selected and designated as pEWL792 (FIG. 8, Table 8).

Construction of Plasmid pEWL795 (pTrc *S. alba* IspS-mMVK)

A PCR reaction was performed to amplify the *Methanosarcina mazei* MVK gene using plasmid MCM376 as the template, primers MCM165 and MCM177, and Pfu Ultra II Fusion DNA polymerase (Agilent) according to manufacturer's protocol. PCR conditions were as follows: 95° C. for 2 minutes (first cycle only), 95° C. for 25 seconds, 55° C. for 25 seconds, 72° C. for 18 seconds, repeat for 29 cycles, with final extension at 72° C. for 2 minutes. The *M. mazei* MVK PCR product was purified using QIAquick PCR Purification Kit (Qiagen).

Figure 9:
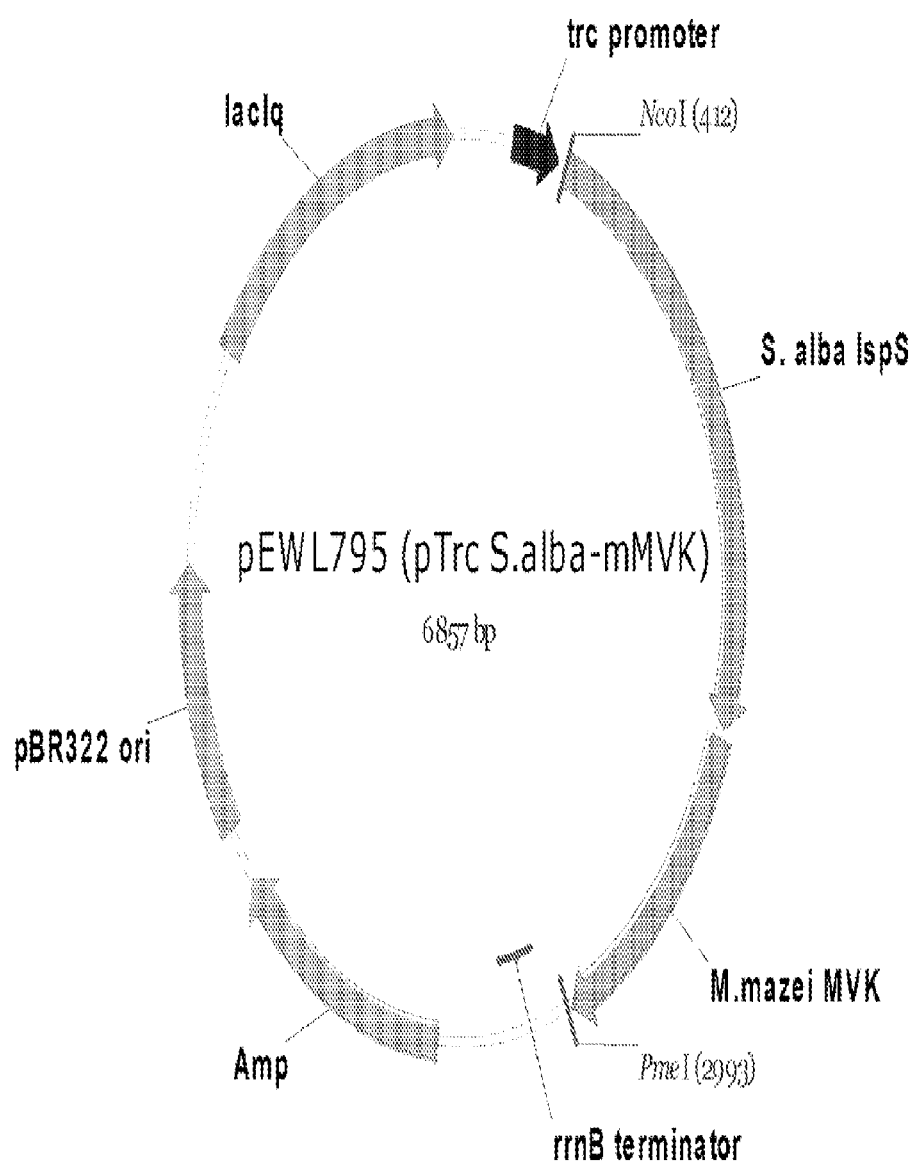
FIG. 9 shows a plasmid map of pEWL795.

The *M. mazei* MVK PCR product was digested with restriction endonuclease PmeI (New England Biolabs) based on manufacturer's protocol at 37° C. The digested PCR fragment was then purified using the QIAquick PCR Purification Kit. A sequential restriction digest was performed with restriction endonuclease NsiI (Roche) based on manufacturer's protocol at 37° C. The digested *M. mazei* MVK fragment was then purified using the QIAquick PCR Purification Kit. Plasmid pEWL792 was digested with restriction endonuclease PmeI based on manufacturer's protocol at 37° C. The digested pEWL792 fragment was then purified using the QIAquick PCR Purification Kit. A sequential restriction digest was performed with restriction endonuclease NsiI based on manufacturer's protocol at 37° C. The digested pEWL792 fragment was then gel purified using a 1% EX gel and extracted using the QIAquick Gel Extraction Kit. The *M. mazei* MVK gene was ligated into the pEWL792 plasmid using T4 DNA ligase based on the manufacturer's protocol overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. Mixed 50 µl of cell suspension with 5 µl of desalted pTrc *S. alba* IspS-mMVK ligation mix. The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+10 mM mevalonic acid plates and incubated overnight at 37° C. The next day, several transformants were picked and grown in 5 ml LB+50 µg/µl carbenicillin tubes overnight at 30° C. Plasmid preps were performed on the overnight cultures using QIAquick Spin Miniprep Kit (Qiagen). Plasmids were digested with restriction endonucleases NcoI (Roche) and PmeI (New England Biolabs) using Buffer 4 (New England Biolabs) at 37° C. and analyzed on a 1.2% E-gel to ensure correct sized fragments were obtained. Plasmids from several transformants were shipped to Sequetech for sequencing with primers EL1003, EL1005, EL1006, EL1270, EL1271, and EL1272 (Table 7). DNA sequencing results showed that plasmids were correct. One plasmid was selected and designated as pEWL795 (FIG. 9, Table 8).

Construction of Strain EWL804 (BL21, pgl+ PL.2-mKKDyI, GI1.2-gltA, pTrc *S. alba* IspS-mMVK)

Strain CMP451 cells were grown in LB to midlog phase and then washed three times in ice-cold, sterile water. Mixed 50 µl of cell suspension with 11 µl of plasmid pEWL795. The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+5 mM mevalonic acid plates and incubated overnight at 37° C. One colony was selected and designated as strain EWL804 (Table 9).

Construction of Strain EWL810 (BL21, pgl+ PL.2-mKKDyI, GI1.2-gltA, pTrc S. alba IspS-mMVK, pCL Ptrc-Upper MVA)

Strain EWL804 cells were grown in LB to midlog phase and then washed three times in ice-cold, sterile water. Mixed 50 µl of cell suspension with 11 µl of plasmid MCM82 (pCL Ptrc Upper MVA). The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+ 50 µg/µl spectinomycin plates and incubated overnight at 37° C. One colony was selected and designated as strain EWL810 (Table 9)

Construction of Plasmid pEWL834 (pTrc S. babylonica IspS)

Generation of a synthetic gene encoding Salix babylonica isoprene synthase (S. babylonica IspS) was performed by Gene Oracle Inc. (Mountain View, Calif.) utilizing a codon optimization method specific for E. coli expression. The synthetic gene was cloned into plasmid pGOv4 with an engineered NcoI restriction site on the 5'-end and a PstI restriction site on the 3'-end. Clustal W sequence alignment between P. alba IspS and S. babylonica IspS shows 92.28% identity (FIG. 10).

Figure 11:
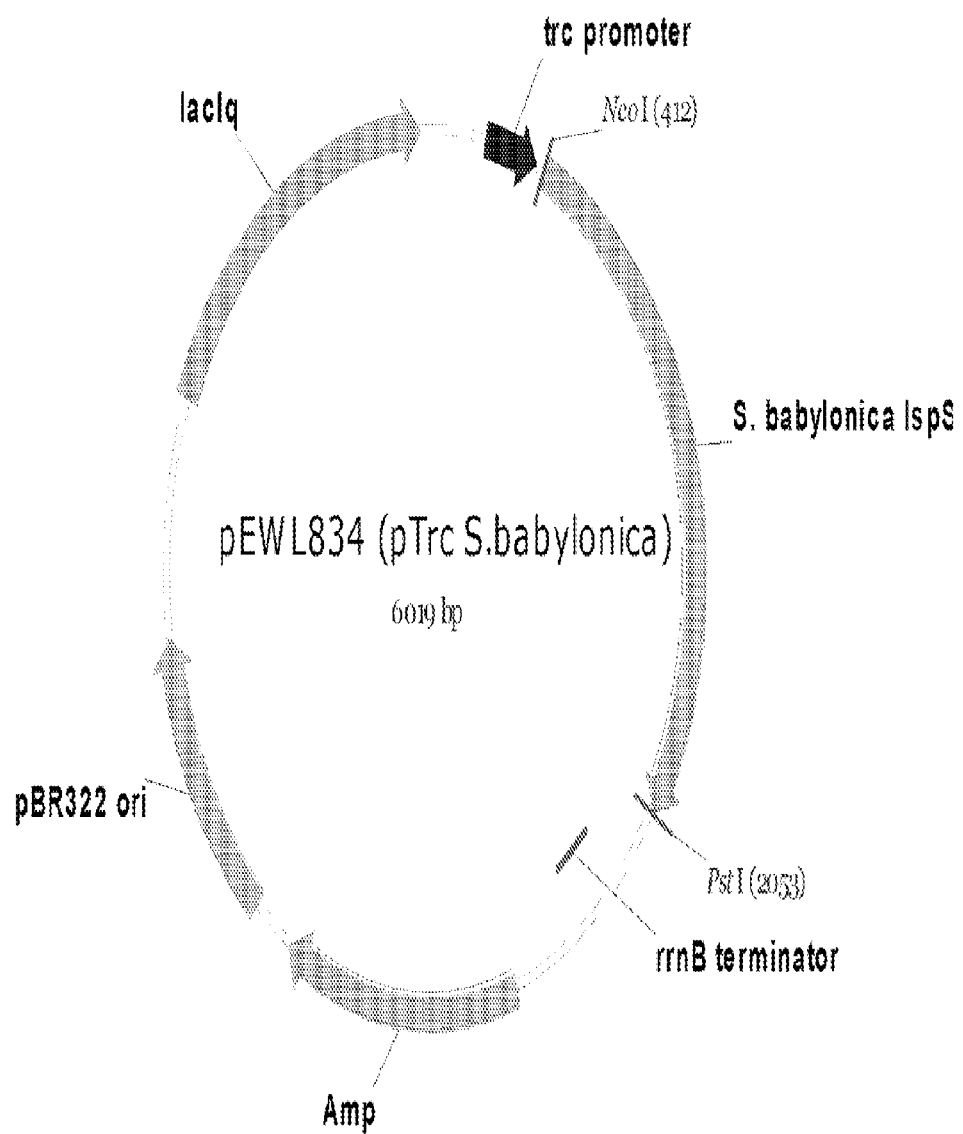
FIG. 11 shows a plasmid map of pEWL834.

1 µg of the pGOv4 S. babylonica IspS plasmid was digested with restriction endonucleases NcoI and PstI based on the manufacturer's protocol at 37° C. The digested S. babylonica IspS fragment was then purified using a 1% EX gel and extracted using the QIAquick Gel Extraction Kit. Digested 0.5 µg of pTrcHis2B plasmid with restriction endonucleases NcoI and PstI based on the manufacturer's protocol at 37° C. The pTrcHis2B plasmid was then purified using a 1% EX gel and extracted using the QIAquick Gel Extraction Kit. The S. babylonica IspS gene was ligated into the pTrcHis2B plasmid using T4 DNA ligase based on the manufacturer's protocol at room temperature. The ligation mixture was desalted by floating a 0.025 µm nitrocellulose membrane filter (Millipore) in a petri dish of ddH$_2$O and applying the ligation mixture gently on top of the nitrocellulose membrane filter for 30 minutes at room temperature. Strain MCM446 cells were grown in LB to midlog phase and then washed three times in ice-cold, sterile water. Mixed 50 µl of cell suspension with 5 µl of desalted pTrc S. baylonica IspS ligation mix. The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+10 mM mevalonic acid plates and incubated overnight at 37° C. The next day, several transformants were picked and grown in 5 ml LB+50 µg/µl carbenicillin tubes overnight at 30° C. Plasmid preps were performed on the overnight cultures using QIAquick Spin Miniprep Kit. Plasmids were digested with restriction endonucleases NcoI and PstI at 37° C. and analyzed on a 1.2% E-gel to ensure correct sized fragments were obtained. Plasmids from several transformants were shipped to Sequetech for sequencing with primers EL1004, EL1006, EL1285, EL1286, EL1287 (Table 7). DNA sequencing results showed that plasmids were correct. One plasmid was selected and designated as pEWL834 (FIG. 11, Table 8).

Construction of Plasmid pEWL851 (pTrc S. babylonica IspS-mMVK)

A PCR reaction was performed to amplify the Methanosarcina mazei MVK gene using plasmid MCM376 as the template, primers MCM165 and MCM177, and Pfu Ultra II Fusion DNA polymerase (Agilent) according to manufacturer's protocol. PCR conditions were as follows: 95° C. for 2 minutes (first cycle only), 95° C. for 25 seconds, 55° C. for 25 seconds, 72° C. for 18 seconds, repeat for 29 cycles, with final extension at 72° C. for 2 minutes. The M. mazei MVK PCR product was purified using QIAquick PCR Purification Kit.

Figure 12:
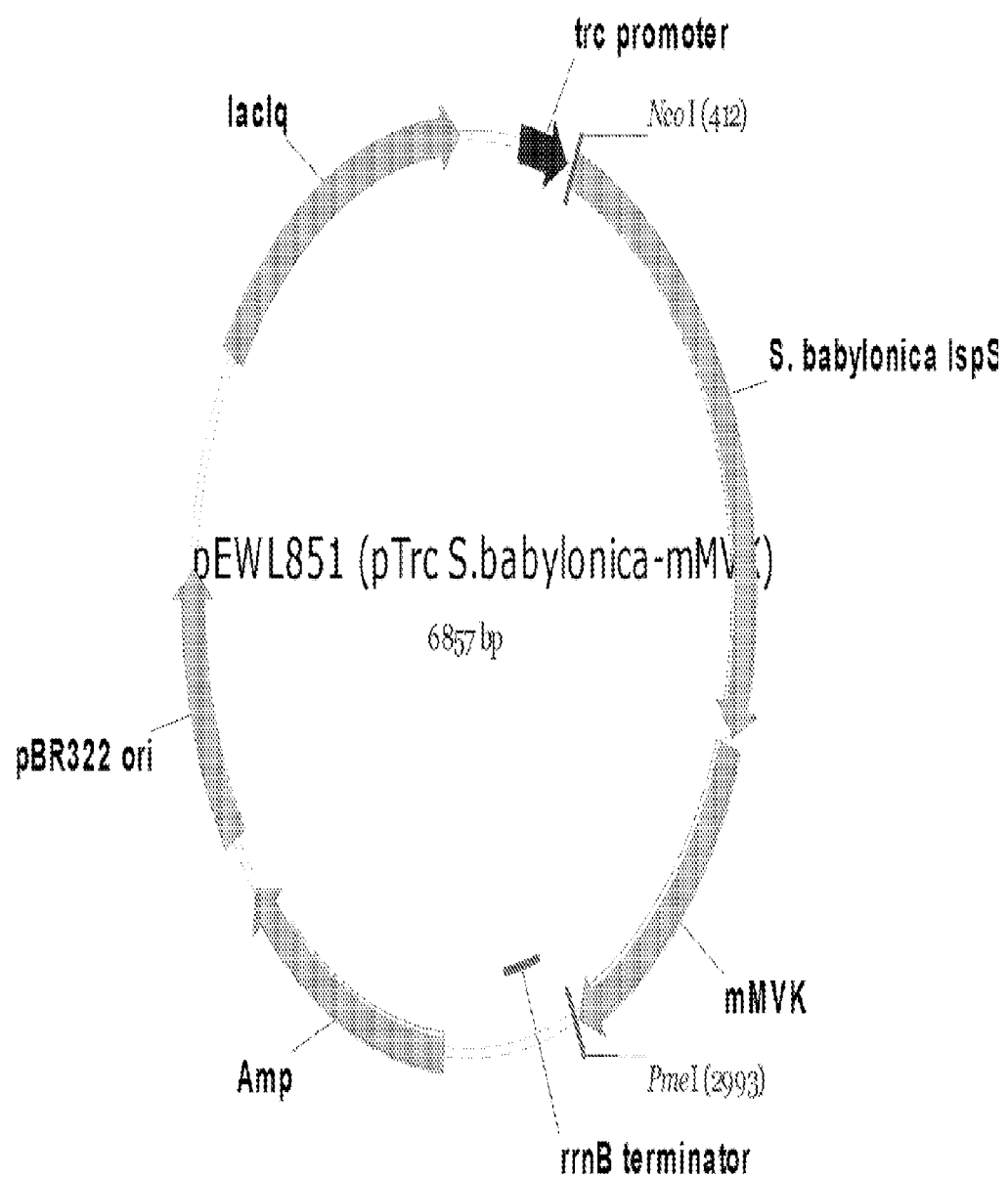
FIG. 12 shows a plasmid map of pEWL851.

The M. mazei MVK PCR product was digested with restriction endonuclease PmeI (New England Biolabs) based on manufacturer's protocol at 37° C. The digested PCR fragment was then purified using the QIAquick PCR Purification Kit. A sequential restriction digest was performed with restriction endonuclease NsiI based on manufacturer's protocol at 37° C. The digested M. mazei MVK fragment was then purified using the QIAquick PCR Purification Kit. Plasmid pEWL834 was digested with restriction endonuclease PmeI based on manufacturer's protocol at 37° C. The digested pEWL834 fragment was then purified using the QIAquick PCR Purification Kit. A sequential restriction digest was performed with restriction endonuclease NsiI based on manufacturer's protocol at 37° C. The digested pEWL834 fragment was then gel purified using a 1% EX gel and extracted using the QIAquick Gel Extraction Kit. The M. mazei MVK gene was ligated into the pEWL834 plasmid using T4 DNA ligase based on the manufacturer's protocol overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. Mixed 50 µl of cell suspension with 5 µl of desalted pTrc S. babylonica IspS-mMVK ligation mix. The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+10 mM mevalonic acid plates and incubated overnight at 37° C. The next day, several transformants were picked and grown in 5 ml LB+50 µg/µl carbenicillin tubes overnight at 30° C. Plasmid preps were performed on the overnight cultures using QIAquick Spin Miniprep Kit. Plasmids were digested with restriction endonucleases NcoI and PmeI using Buffer 4 (New England Biolabs) at 37° C. and analyzed on a 1.2% E-gel to ensure correct sized fragments were obtained. Plasmids from several transformants were shipped to Sequetech for sequencing with primers EL1004, EL1005, EL1006, EL1285, EL1286, and EL1287 (Table 6). DNA sequencing confirmed the plasmid sequences. One plasmid was selected and designated as pEWL851 (FIG. 12, Table 8).

Construction of Strain EWL887 (BL21, pgl+ PL.2-mKKDyI, GI1.2-gltA, pTrc S. babylonica IspS-mMVK)

Strain CMP451 cells were grown in LB to midlog phase and then washed three times in ice-cold, sterile water. Mixed 50 µl of cell suspension with 11 µl of plasmid pEWL851. The cell suspension mixture was electroporated in a 2 mm cuvette at 2.5 Volts and 25 µFd using a Gene Pulser Xcell Electroporator. Cells were recovered in 1 ml of LB and incubated for 2 hours at 30° C. with shaking. Transformants were selected on LA+50 µg/µl carbenicillin+5 mM mevalonic acid plates and incubated overnight at 37° C. One colony was selected and designated as strain EWL887 (Table 9).

Construction of Strain EWL893 (BL21, pgl+ PL.2-mKKDyI, GI1.2-gltA, pTrc S. babylonica IspS-mMVK, MCM82)

Strain EWL887 cells were grown in LB to midlog phase and then washed three times in ice-cold, sterile water. Mixed 50 μl of cell suspension with 11 μl of plasmid MCM82. The cell suspension mixture was electroporated in a 2 mm cuvette at 2.5 Volts and 25 μFd using a Gene Pulser Xcell Electroporator. Cells were recovered in 1 ml of LB and incubated for 2 hours at 30° C. with shaking. Transformants were selected on LA+50 μg/μl carbenicillin+50 μg/μl spectinomycin plates and incubated overnight at 37° C. One colony was selected and designated as strain EWL893 (Table 9).

Construction of Strain EWL900 (BL21, PL.2-mKKDyI, pTrc S. alba IspS) and EWL903 (BL21, PL.2-mKKDyI, pTrc S. babylonica IspS)

Strain MCM531 cells were grown in LB to midlog phase and then washed three times in ice-cold, sterile water. Mixed 50 μl of cell suspension with 11 μl of plasmid pEWL792 (pTrc S. alba IspS) or pEWL834 (pTrc S. babylonica IspS). The cell suspension mixture was electroporated in a 2 mm cuvette at 2.5 Volts and 25 μFd using a Gene Pulser Xcell Electroporator. Cells were recovered in 1 ml of LB and incubated for 2 hours at 30° C. with shaking. Transformants were selected on LA+50 μg/μl carbenicillin+5 mM mevalonic acid plates and incubated overnight at 37° C. For transformants harboring the plasmid pEWL792, one colony was selected and designated as strain EWL900 (Table 9). For transformants harboring the plasmid pEWL834, one colony was selected and designated as strain EWL903 (Table 9).

Comparing Solubility of P. alba IspS, S. alba IspS, and S. babylonica IspS

Figure 13:
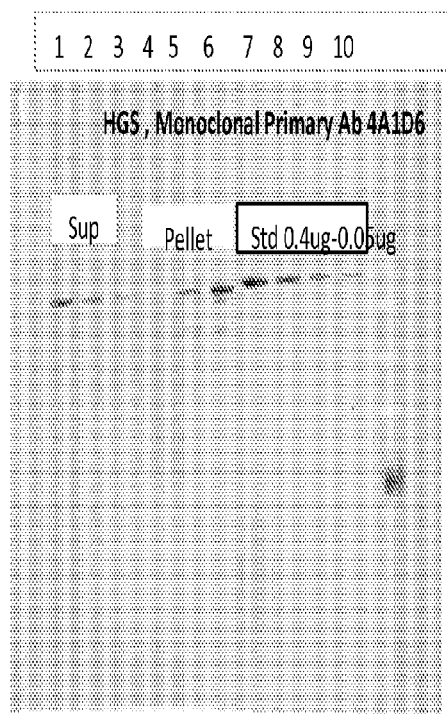
FIG. 13 shows western blot analysis of IspS in the supernatant and pellet fraction.
Figure 14:
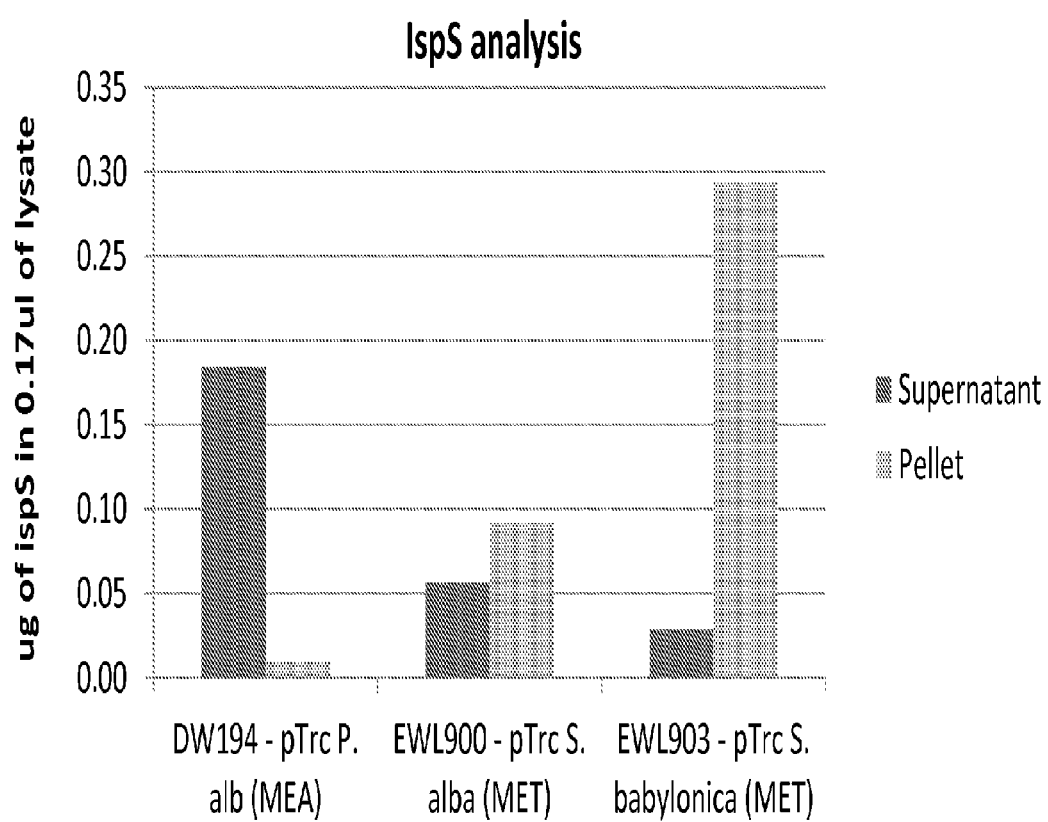
FIG. 14 shows protein solubility analysis of IspS by comparison of IspS in the supernatant and pellet fraction.

Strains expressing pTrc P. alba IspS (DW194), pTrc S. alba IspS (EWL900) and pTrc S. babylonica IspS (EWL903) were grown in LB media, induced at $OD_{600}$~0.5 with 200 μM IPTG, and induced for 4 hours. Cell pellets were collected by centrifugation and stored at −80° C. The cells were lysed by French Press and analyzed for protein solubility by Western Blot. Results showed that S. alba IspS and S. babylonica IspS are more insoluble than P. alba IspS (FIG. 13 and FIG. 14).

Construction of pEWL906 (pTrc S. alba IspS S288C) and pEWL907 (pTrc S. babylonica IspS S288C)

Primers were designed to introduce the S288C mutation into S. alba IspS (primers EL1288 and EL1289, see Table 7) and S. babylonica IspS (primers EL1290 and EL1291, see Table 7). Plasmid pEWL792 (pTrc S. alba IspS) and pEWL834 (pTrc S. babylonica IspS) were used as the starting templates for PCR reactions with the Pfu Ultra II Fusion DNA Polymerase. PCR conditions were as follows: 95° C. for 2 minutes (first cycle only), 95° C. for 30 seconds, 55° C. for 1 minute, 68° C. for 6 minute, repeat for 16 cycles. The parental template for each PCR reaction were digested by addition of 21 μl DpnI restriction endonuclease (Roche) and incubated at 37° C. for 2 hours. Strain MCM531 cells were grown in LB to midlog phase and then washed three times in ice-cold, sterile water. Mixed 50 μl of cell suspension with 21 μl of each PCR reaction. The cell suspension mixture was electroporated in a 2 mm cuvette at 2.5 Volts and 25 μFd using a Gene Pulser Xcell Electroporator. Cells were recovered in 1 ml of LB and incubated for 2 hours at 30° C. with shaking. Transformants were selected on LA+50 μg/μl carbenicillin+5 mM mevalonic acid plates and incubated overnight at 37° C. The next day, several transformants were picked from each and grown in 5 ml LB+50 μg/μl carbenicillin tubes overnight at 30° C. Plasmid preps were performed on the overnight cultures using QIAquick Spin Miniprep Kit. Plasmids from several transformants were shipped to Sequetech for sequencing. Primers EL1005, EL1006, EL1270, EL1271, and EL1272 were used for sequencing pTrc S. alba IspS S288C (see Table 7). Primers EL1005, EL1006, EL1285, EL1286, and EL1287 were used for sequencing pTrc S. babylonica IspS S288C (see Table 7).

Figure 15:
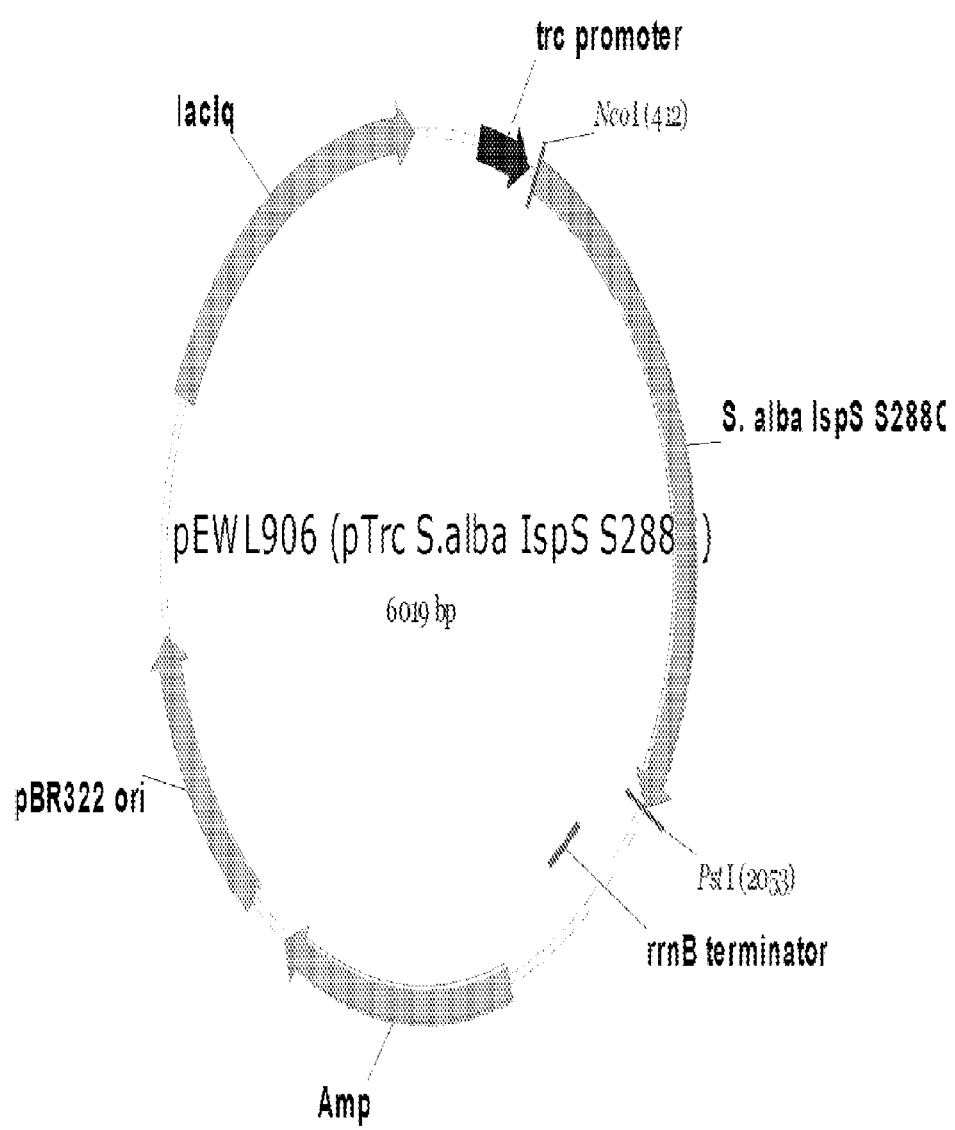
FIG. 15 shows a plasmid map of pEWL906.
Figure 16:
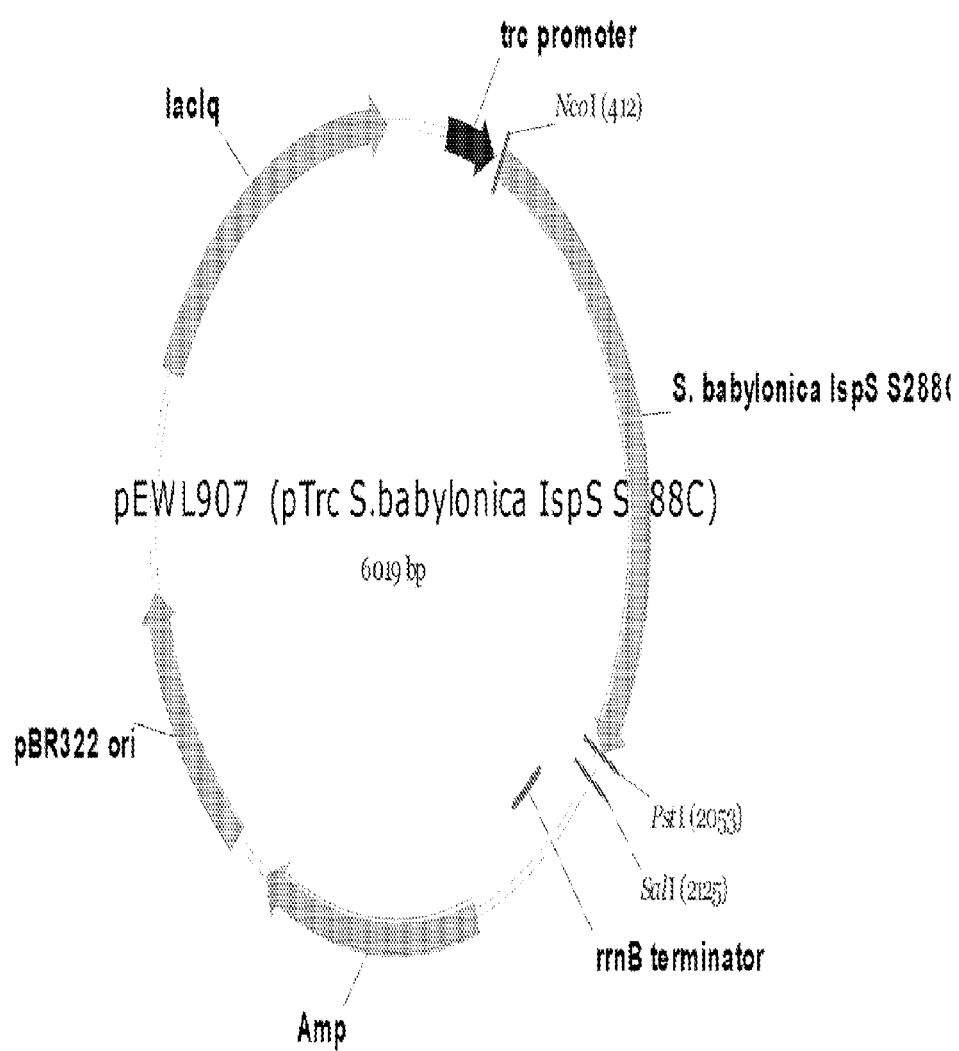
FIG. 16 shows a plasmid map of pEWL907.

DNA sequencing results showed that plasmids were correct and contained the S288C mutation. Plasmid pTrc S. alba IspS S288C was designated pEWL906 (FIG. 15, Table 8). Plasmid pTrc S. babylonica IspS S288C was designated pEWL907 (FIG. 16, Table 8). Plasmid pEWL906 was transformed into MCM531 cells to generate the expression strain EWL913 (Table 9). Plasmid pEWL907 was transformed into MCM531 cells to generate expression strain EWL916 (Table 9).

Figure 17:
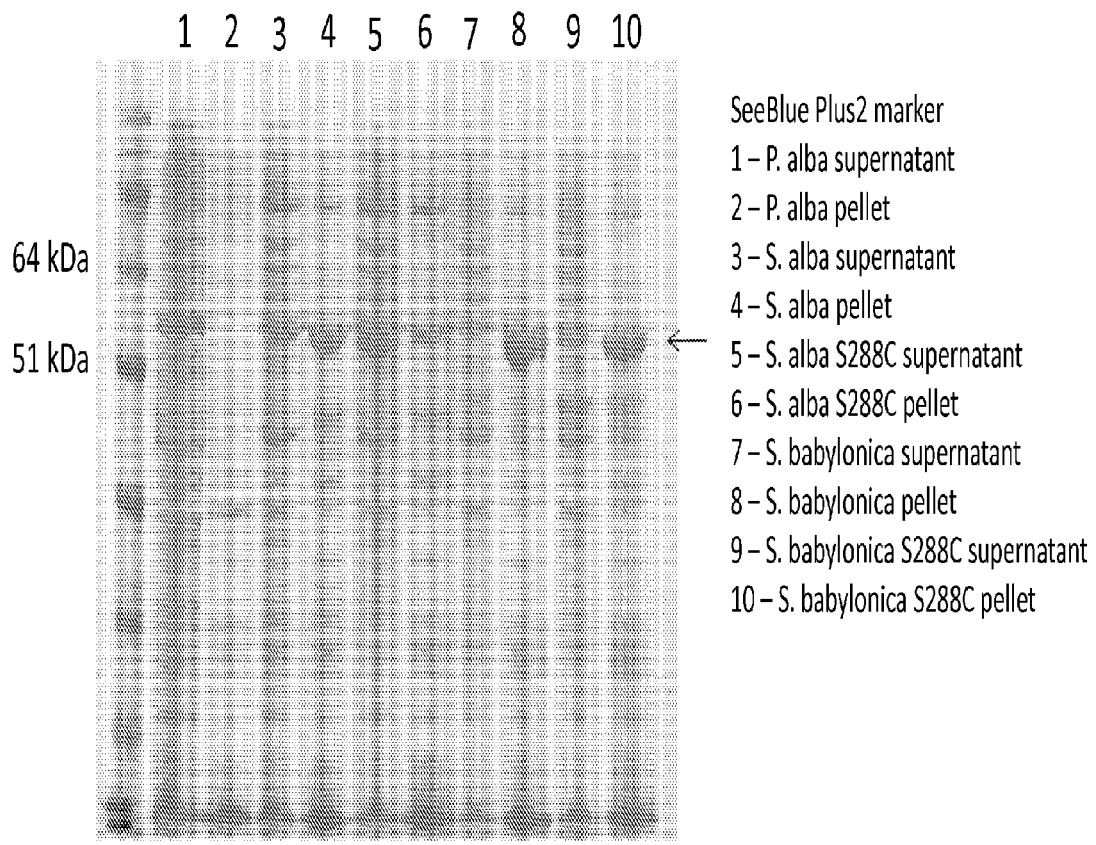
FIG. 17 is a coomassie stained NuPage gel that shows improved *Salix* IspS solubility due to the S288C mutation.
Figure 18:
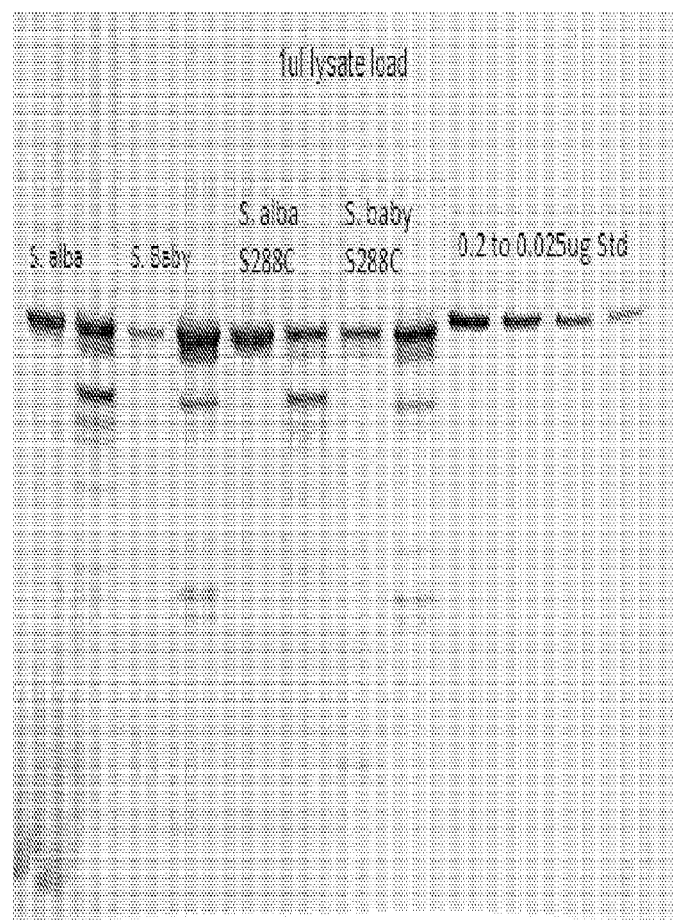
FIG. 18 is a western blot that shows improved *Salix* IspS solubility due to the S288C mutation.

Comparing Solubility of P. alba IspS, S. alba IspS, S. alba IspS S288C, S. babylonica IspS, and S. babylonica IspS S288C Strains expressing P. alba IspS (DW194), S. alba IspS (EWL900), S. alba IspS S288C (EWL913), S. babylonica IspS (EWL903), or S. babylonica IspS S288C (EWL916) were grown in LB+50 μg/μl carbenicillin. Cells were induced with 200 μM IPTG when $OD_{600}$~0.5 and grown for 4 hours at 34° C. Cell pellets were collected by centrifugation and stored at −80° C. The cells were lysed by French Press and analyzed for protein solubility on 10% NuPage gel (Invitrogen) by Coomassie staining (FIG. 17) and Western blot (FIG. 18). Results showed that the S288C mutation improved solubility of both S. alba IspS and S. babylonica IspS.

TABLE 7

Primer sequences

| Primer name | Primer sequence |
|---|---|
| EL1003 | GATAGTAACGGCTGCGCTGCTACC |
| EL1004 | ACAATTTCACACAGGAAACAGC |
| EL1005 | CCAGGCAAATTCTGTTTTATCAG |
| EL1006 | GACAGCTTATCATCGACTGCACG |
| EL1270 | CCTCCTTTCACTTCACGAAGC |
| EL1271 | GCTTTTCACTGACGCAGTTGAG |
| EL1272 | GATAAACAATGAGACCGCAG |
| EL1285 | GGAGAACTTGAAAGAGGAC |
| EL1286 | GTACAACACAATCAATGAGATAG |
| EL1287 | GATGCACATACATCACCTGATG |
| EL1288 | GCAGAATTTCTGTCGCTAAGATGTTCTGTTTCGT AACCATTATCGACGAC |
| EL1289 | GTCGTCGATAATGGTTACGAAACAGAACATCTTA GCGACAGAAATTCTGC |
| EL1290 | CGCAAATCTGTGGCTAAAATGTTTTGTTTCGTGA CCATAATTGATGAC |
| EL1291 | GTCATCAATTATGGTCACGAAACAAAACATTTTA GCCACAGATTTGCG |
| MCM165 | GCGAACGATGCATAAAGGAGGTAAAAAAACATGG TATCCTGTTCTGCGCCGGGTAAGATTTACCTG |
| MCM177 | GGGCCCGTTTAAACTTTAACTAGACTTTAATCTA CTTTCAGACCTTGC |

TABLE 8

Plasmids used in this study

| Plasmid name | Antibiotic resistance | Description |
|---|---|---|
| pEWL792 | Carbenicillin | pTrc S. alba IspS |
| pEWL795 | Carbenicillin | pTrc S. alba IspS-mMVK |
| pEWL834 | Carbenicillin | pTrc S. babylonic IspS |
| pEWL851 | Carbenicillin | pTrc S. babylonic IspS-mMVK |
| pEWL906 | Carbenicillin | pTrc S. alba IspS S288C |
| pEWL907 | Carbenicillin | pTrc S. babylonic IspS S288C |

TABLE 9

Strains used in this study

| Strain name | Antibiotic resistance | Description |
|---|---|---|
| EWL804 | Carbenicillin | BL21, pgl+ PL.2-mKKDyI, GI1.2-gltA, pTrc S. alba IspS-mMVK |
| EWL810 | Carbenicillin, Spectinomycin | BL21, pgl+ PL.2-mKKDyI, GI1.2-gltA, pTrc S. alba IspS-mMVK, pCL Ptrc-Upper MVA |
| EWL887 | Carbenicillin | BL21, pgl+ PL.2-mKKDyI, GI1.2-gltA, pTrc S. babylonica IspS-mMVK |
| EWL893 | Carbenicillin, Spectinomycin | BL21, pgl+ PL.2-mKKDyI, GI1.2-gltA, pTrc S. babylonica IspS-mMVK, pCL Ptrc-Upper MVA |
| EWL900 | Carbenicillin | BL21, PL.2-mKKDyI, pTrc S. alba IspS |
| EWL903 | Carbenicillin | BL21, PL.2-mKKDyI, pTrc S. babylonica IspS |
| EWL913 | Carbenicillin | BL21, PL.2-mKKDyI, pTrc S. alba IspS S288C |
| EWL916 | Carbenicillin | BL21, PL.2-mKKDyI, pTrc S. babylonica IspS S288C |

```
DNA Sequence of pEWL792
GTTTGACAGCTTATCATCGACTGCACGGTGCACCAATGCTTCTGGCGTCAGGCAGCCAT

CGGAAGCTGTGGTATGGCTGTGCAGGTCGTAAATCACTGCATAATTCGTGTCGCTCAAG

GCGCACTCCCGTTCTGGATAATGTTTTTTGCGCCGACATCATAACGGTTCTGGCAAATA

TTCTGAAATGAGCTGTTGACAATTAATCATCCGGCTCGTATAATGTGTGGAATTGTGAG

CGGATAACAATTTCACACAGGAAACAGCGCCGCTGAGAAAAAGCGAAGCGGCACTGC

TCTTTAACAATTTATCAGACAATCTGTGTGGGCACTCGACCGGAATTATCGATTAACTT

TATTATTAAAAATTAAAGAGGTATATATTAATGTATCGATTAAATAAGGAGGAATAAA

CCATGGAAACCAGACGGTCCGCTAATTATGAACCGAACAGTTGGGATTACGATTACCT

GCTTTCTTCGGATACGGAAGATGCCATAGAGGTATACAAAGACAAAGCGAAGAAACTG

GATGCTGAAGTACGCTCGAAGATAAACAATGAGACCGCAGAATTTTTAACGCAATTAG

AACTGATTGACACTATCCAGCGCCTGGGTTTGGGTTATCGTTTCGAAAGCGACATTAGA

CGCGCCTTGGATCGTTTCGTGAGTAGTGGTGGGTTCGAGGCTGTCGCGAAAACTTCACT

GCAAGCTACAGCACTGTCTTTTCGGCTGCTGCGTCAACATGGTTTCGAGGTTAGTCAAG

AAGTGTTTAATGGTTTCAAAGACCAGAACGGTAACTTTATGGAGGATTTAAAAGAAGA

TATTAAGGCCCTCCTTTCACTTCACGAAGCATCTTTTTTAGCTCTGGAAGGCGAGAATA

TTCTGGACGAGGCAAAGGTATTCACAATTAGCCACCTCAAAGAACTGAACGAGGAGAA

AATTGGCAAAGACATGGTGGAACAAGTGAACCATGCTCTGGAATTACCCCTTCATCGT

CGTACGCAGCGTTTGGAGGCTGTGTGGTCTATTGAAGCGTATCGGAAGAAGGAAGATG

CAAACCGCGTCCTTCTGGAACTTGCAATCCTCGATTATAATATGGTCCAATCTGTGTAT

CAGCGCGATTTGCGCGAAACTTCGAGATGGTGGCGCCGCGTGGGATTAGCCACTAAGT

TGCATTTCGCCAGAGACAGACTTATCGAATCCTTCTATTGGGCGGTTGGCGTCGCCTTT

GAACCGCAATACTCAGATTGCAGAATTTCTGTCGCTAAGATGTTCTCTTTCGTAACCAT

TATCGACGACATTTATGATGTGTATGGGACGTTGGAAGAGCTGGAGCTTTTCACTGACG

CAGTTGAGAGATGGGATGTGAGCGCCATTGACGATTTACCCGATTATATGAAACTGTG

CTTCTTGGCGTTGTACAATACTATAAACGAAATCGCTTATGACAATCTTAAAGAAAAG

GCGAAAATATTCTGCCGTATCTGACTAAAGCCTGGGCGGATCTTTGCAATGCTTTCCTG

CAAGAGGCACGTTTTTTATATAACAAGTCGACACCTACCTTCTCAGATTATTTTGGCAA
```

-continued

```
TGCGTGGAAATCTAGTTCTGGGCCACTTCAACTGGTTTTTGCTTACTTTGCCGTAGTGCA

AAACATCAAAAAGGAAGAAACCGAAAATCTGCTGAAATATCATGATATAATCTCTTGG

CCATCGTACATATTTCGGCTGTGTAATGATCTGGCTTCCGCATCGGCAGAAATTGCGCG

GGGTGAGACTGCAAACAGCGTTTCTTGTTACATGCGGACGAAGGGAATTTCCGAAGAA

CTGGCAACCGAATCAGTGATGAATCTTATTGATGAAACGTGGAAAAAGATGAACAAGG

AAAAATTGGGGACTCACTCTTTGCAAAACACTTTGTGGAGACCGCGATAAACCTTGCT

CGCCAATCGCATTGTACGTATCATAATGGAGATGCGCATACTTCGCCTGACGAATTAAC

CCGCAAACGCGTACTGTCAGTGATCACTGAACCGATACTGCCATTGGAACGGTGACTG

CAGCTGGTACCATATGGGAATTCGAAGCTTTCTAGAACAAAAACTCATCTCAGAAGAG

GATCTGAATAGCGCCGTCGACCATCATCATCATCATCATTGAGTTTAAACGGTCTCCAG

CTTGGCTGTTTTGGCGGATGAGAGAAGATTTTCAGCCTGATACAGATTAAATCAGAACG

CAGAAGCGGTCTGATAAAACAGAATTTGCCTGGCGGCAGTAGCGCGGTGGTCCCACCT

GACCCCATGCCGAACTCAGAAGTGAAACGCCGTAGCGCCGATGGTAGTGTGGGGTCTC

CCCATGCGAGAGTAGGGAACTGCCAGGCATCAAATAAAACGAAAGGCTCAGTCGAAA

GACTGGGCCTTTCGTTTTATCTGTTGTTTGTCGGTGAACGCTCTCCTGAGTAGGACAAAT

CCGCCGGGAGCGGATTTGAACGTTGCGAAGCAACGGCCCGGAGGGTGGCGGGCAGGA

CGCCCGCCATAAACTGCCAGGCATCAAATTAAGCAGAAGGCCATCCTGACGGATGGCC

TTTTTGCGTTTCTACAAACTCTTTTGTTTATTTTTCTAAATACATTCAAATATGTATCCGC

TCATGAGACAATAACCCTGATAAATGCTTCAATAATATTGAAAAAGGAAGAGTATGAG

TATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAG

TGGGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCCG

TGTTGACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGAGAAT

TATGCAGTGCTGCCATAACCATGAGTGATAACACTGCGGCCAACTTACTTCTGACAACG

ATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACAC

CACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTA

TCGTAGTTATCTACACGACGGGGAGTCAGGCAACTATGGATGAACGAAATAGACAGAT

CGCTGAGATAGGTGCCTCACTGATTAAGCATTGGTAACTGTCAGACCAAGTTTACTCAT

ATATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGTCA

GACCCCGTAGAAAAGATCAAAGGATCTTCTTGAGATCCTTTTTTTCTGCGCGTAATCTG

CTGCTTGCAAACAAAAAAACCACCGCTACCAGCGGTGGTTTGTTTGCCGGATCAAGAG

CTACCAACTCTTTTTCCGAAGGTAACTGGCTTCAGCAGAGCGCAGATACCAAATACTGT

CCTTCTAGTGTAGCCGTAGTTAGGCCACCACTTCAAGAACTCTGTAGCACCGCCTACAT
```

-continued

```
ACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGGAAA
CGCCTGGTATCTTTATAGTCCTGTCGGGTTTCGCCACCTCTGACTTGAGCGTCGATTTTT
GTGATGCTCGTCAGGGGGCGGAGCCTATGGAAAAACGCCAGCAACGCGGCCTTTTTA
CGGTTCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCTGATGCGGTATTTTC
TCCTTACGCATCTGTGCGGTATTTCACACCGCATATGGTGCACTCTCAGTACAATCTGCT
CTGATGCCGCATAGTTAAGCCAGTATACACTCCGCTATCGCTACGTGACTGGGTCATGG
CTGCGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTC
ACCGTCATCACCGAAACGCGCGAGGCAGCAGATCAATTCGCGCGCGAAGGCGAAGCG
GCATGCATTTACGTTGACACCATCGAATGGTGCAAAACCTTTCGCGGTATGGCATGATA
GCGCCCGGAAGAGAGTCAATTCAGGGTGGTGAATGTGAAACCAGTAACGTTATACGAT
GTCGCAGAGTATGCCGGTGTCTCTTATCAGACCGTTTCCCGCGTGGTGAACCAGGCCAG
CCACGTTTCTGCGAAAACGCGGGAAAAAGTGGAAGCGGCGATGGCGGAGCTGAATTAC
ATTCCCAACCGCGTGGCACAACAACTGGCGGGCAAACAGTCGTTGCTGATTGGCGTTG
CCACCTCCAGTCTGGCCCTGCACGCGCCGTCGCAAATTGTCGCGGCGATTAAATCTCGC
GCCGATCAACTGGGTGCCAGCGTGGTGGTGTCGATGGTAGAACGAAGCGGCGTCGAAG
CCTGTAAAGCGGCGGTGCACAATCTTCTCGCGCAACGCGTCAGTGGGCTGATCATTAAC
TATCCGCTGGATGACCAGGATGCCATTGCTGTGGAAGCTGCCTGCACTAATGTTCCGGC
GTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTG
TTAGCGGGCCCATTAAGTTCTGTCTCGGCGCGTCTGCGTCTGGCTGGCTGGCATAAATA
TCTCACTCGCAATCAAATTCAGCCGATAGCGGAACGGGAAGGCGACTGGAGTGCCATG
TCCGGTTTTCAACAAACCATGCAAATGCTGAATGAGGGCATCGTTCCCACTGCGATGCT
GGTTGCCAACGATCAGATGGCGCTGGGCGCAATGCGCGCCATTACCGAGTCCGGGCTG
CGCGTTGGTGCGGATATCTCGGTAGTGGGATACGACGATACCGAAGACAGCTCATGTT
ATATCCCGCCGTCAACCACCATCAAACAGGATTTTCGCCTGCTGGGGCAAACCAGCGT
GGACCGCTTGCTGCAACTCTCTCAGGGCCAGGCGGTGAAGGGCAATCAGCTGTTGCCC
GTCTCACTGGTGAAAAGAAAAACCACCCTGGCGCCCAATACGCAAACCGCCTCTCCCC
GCGCGTTGGCCGATTCATTAATGCAGCTGGCACGACAGGTTTCCCGACTGGAAAGCGG
GCAGTGAGCGCAACGCAATTAATGTGAGTTAGCGCGAATTGATCTG

DNA sequence of pEWL795
GTTTGACAGCTTATCATCGACTGCACGGTGCACCAATGCTTCTGGCGTCAGGCAGCCAT
CGGAAGCTGTGGTATGGCTGTGCAGGTCGTAAATCACTGCATAATTCGTGTCGCTCAAG
GCGCACTCCCGTTCTGGATAATGTTTTTTGCGCCGACATCATAACGGTTCTGGCAAATA
TTCTGAAATGAGCTGTTGACAATTAATCATCCGGCTCGTATAATGTGTGGAATTGTGAG
```

-continued
```
CGGATAACAATTTCACACAGGAAACAGCGCCGCTGAGAAAAAGCGAAGCGGCACTGC

TCTTTAACAATTTATCAGACAATCTGTGTGGGCACTCGACCGGAATTATCGATTAACTT

TATTATTAAAAATTAAAGAGGTATATATTAATGTATCGATTAAATAAGGAGGAATAAA

CCATGGAAACCAGACGGTCCGCTAATTATGAACCGAACAGTTGGGATTACGATTACCT

GCTTTCTTCGGATACGGAAGATGCCATAGAGGTATACAAAGACAAAGCGAAGAAACTG

GATGCTGAAGTACGCTCGAAGATAAACAATGAGACCGCAGAATTTTTAACGCAATTAG

AACTGATTGACACTATCCAGCGCCTGGGTTTGGGTTATCGTTTCGAAAGCGACATTAGA

CGCGCCTTGGATCGTTTCGTGAGTAGTGGTGGGTTCGAGGCTGTCGCGAAAACTTCACT

GCAAGCTACAGCACTGTCTTTTCGGCTGCTGCGTCAACATGGTTTCGAGGTTAGTCAAG

AAGTGTTTAATGGTTTCAAAGACCAGAACGGTAACTTTATGGAGGATTTAAAAGAAGA

TATTAAGGCCCTCCTTTCACTTCACGAAGCATCTTTTTTAGCTCTGGAAGGCGAGAATA

TTCTGGACGAGGCAAAGGTATTCACAATTAGCCACCTCAAAGAACTGAACGAGGAGAA

AATTGGCAAAGACATGGTGGAACAAGTGAACCATGCTCTGGAATTACCCCTTCATCGT

CGTACGCAGCGTTTGGAGGCTGTGTGGTCTATTGAAGCGTATCGGAAGAAGGAAGATG

CAAACCGCGTCCTTCTGGAACTTGCAATCCTCGATTATAATATGGTCCAATCTGTGTAT

CAGCGCGATTTGCGCGAAACTTCGAGATGGTGGCGCCGCGTGGGATTAGCCACTAAGT

TGCATTTCGCCAGAGACAGACTTATCGAATCCTTCTATTGGGCGGTTGGCGTCGCCTTT

GAACCGCAATACTCAGATTGCAGAATTTCTGTCGCTAAGATGTTCTCTTTCGTAACCAT

TATCGACGACATTTATGATGTGTATGGGACGTTGGAAGAGCTGGAGCTTTTCACTGACG

CAGTTGAGAGATGGGATGTGAGCGCCATTGACGATTTACCCGATTATATGAAACTGTG

CTTCTTGGCGTTGTACAATACTATAAACGAAATCGCTTATGACAATCTTAAAGAAAAG

GCGAAAATATTCTGCCGTATCTGACTAAAGCCTGGGCGGATCTTTGCAATGCTTTCCTG

CAAGAGGCACGTTTTTTATATAACAAGTCGACACCTACCTTCTCAGATTATTTTGGCAA

TGCGTGGAAATCTAGTTCTGGGCCACTTCAACTGGTTTTTGCTTACTTTGCCGTAGTGCA

AAACATCAAAAAGGAAGAAACCGAAAATCTGCTGAAATATCATGATATAATCTCTTGG

CCATCGTACATATTTCGGCTGTGTAATGATCTGGCTTCCGCATCGGCAGAAATTGCGCG

GGGTGAGACTGCAAACAGCGTTTCTTGTTACATGCGGACGAAGGGAATTTCCGAAGAA

CTGGCAACCGAATCAGTGATGAATCTTATTGATGAAACGTGGAAAAAGATGAACAAGG

AAAAATTGGGGGACTCACTCTTTGCAAAACACTTTGTGGAGACCGCGATAAACCTTGCT

CGCCAATCGCATTGTACGTATCATAATGGAGATGCGCATACTTCGCCTGACGAATTAAC

CCGCAAACGCGTACTGTCAGTGATCACTGAACCGATACTGCCATTGGAACGGTGACTG

CATAAAGGAGGTAAAAAAACATGGTATCCTGTTCTGCGCCGGGTAAGATTTACCTGTTC

GGTGAACACGCCGTAGTTTATGGCGAAACTGCAATTGCGTGTGCGGTGGAACTGCGTA

CCCGTGTTCGCGCGGAACTCAATGACTCTATCACTATTCAGAGCCAGATCGGCCGCACC

GGTCTGGATTTCGAAAAGCACCCTTATGTGTCTGCGGTAATTGAGAAAATGCGCAAATC

TATTCCTATTAACGGTGTTTTCTTGACCGTCGATTCCGACATCCCGGTGGGCTCCGGTCT

GGGTAGCAGCGCAGCCGTTACTATCGCGTCTATTGGTGCGCTGAACGAGCTGTTCGGCT

TTGGCCTCAGCCTGCAAGAAATCGCTAAACTGGGCCACGAAATCGAAATTAAAGTACA

GGGTGCCGCGTCCCCAACCGATACGTATGTTTCTACCTTCGGCGGCGTGGTTACCATCC

CGGAACGTCGCAAACTGAAAACTCCGGACTGCGGCATTGTGATTGGCGATACCGGCGT

TTTCTCCTCCACCAAAGAGTTAGTAGCTAACGTACGTCAGCTGCGCGAAAGCTACCCGG
```

-continued

```
ATTTGATCGAACCGCTGATGACCTCTATTGGCAAAATCTCTCGTATCGGCGAACAACTG

GTTCTGTCTGGCGACTACGCATCCATCGGCCGCCTGATGAACGTCAACCAGGGTCTCCT

GGACGCCCTGGGCGTTAACATCTTAGAACTGAGCCAGCTGATCTATTCCGCTCGTGCGG

CAGGTGCGTTTGGCGCTAAAATCACGGGCGCTGGCGGCGGTGGCTGTATGGTTGCGCT

GACCGCTCCGGAAAAATGCAACCAAGTGGCAGAAGCGGTAGCAGGCGCTGGCGGTAA

AGTGACTATCACTAAACCGACCGAGCAAGGTCTGAAAGTAGATTAAAGTCTAGTTAAA

GTTTAAACGGTCTCCAGCTTGGCTGTTTTGGCGGATGAGAGAAGATTTTCAGCCTGATA

CAGATTAAATCAGAACGCAGAAGCGGTCTGATAAAACAGAATTTGCCTGGCGGCAGTA

GCGCGGTGGTCCCACCTGACCCCATGCCGAACTCAGAAGTGAAACGCCGTAGCGCCGA

TGGTAGTGTGGGGTCTCCCCATGCGAGAGTAGGGAACTGCCAGGCATCAAATAAAACG

AAAGGCTCAGTCGAAAGACTGGGCCTTTCGTTTTATCTGTTGTTTGTCGGTGAACGCTC

TCCTGAGTAGGACAAATCCGCCGGGAGCGGATTTGAACGTTGCGAAGCAACGGCCCGG

AGGGTGGCGGGCAGGACGCCCGCCATAAACTGCCAGGCATCAAATTAAGCAGAAGGC

CATCCTGACGGATGGCCTTTTTGCGTTTCTACAAACTCTTTTGTTTATTTTTCTAAATAC

ATTCAAATATGTATCCGCTCATGAGACAATAACCCTGATAAATGCTTCAATAATATTGA

AAAAGGAAGAGTATGAGTATTCAACATTTCCGTGTCGCCCTTATTCCCTTTTTTGCGGC

ATTTTGCCTTCCTGTTTTTGCTCACCCAGAAACGCTGGTGAAAGTAAAAGATGCTGAAG

ATCAGTTGGGTGCACGAGTGGGTTACATCGAACTGGATCTCAACAGCGGTAAGATCCT

TGAGAGTTTTCGCCCCGAAGAACGTTTTCCAATGATGAGCACTTTTAAAGTTCTGCTAT

GTGGCGCGGTATTATCCCGTGTTGACGCCGGGCAAGAGCAACTCGGTCGCCGCATACA

CTATTCTCAGAATGACTTGGTTGAGTACTCACCAGTCACAGAAAAGCATCTTACGGATG

GCATGACAGTAAGAGAATTATGCAGTGCTGCCATAACCATGAGTGATAACACTGCGGC

CAACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCATAC

CAAACGACGAGCGTGACACCACGATGCCTGTAGCAATGGCAACAACGTTGCGCAAACT

ATTAACTGGCGAACTACTTACTCTAGCTTCCCGGCAACAATTAATAGACTGGATGGAGG

CGGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCAG

ATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTG

TCAGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAGTT

TTCGTTCCACTGAGCGTCAGACCCCGTAGAAAAGATCAAAGGATCTTCTTGAGATCCTT

TTTTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACT

CTGTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGACCTA

CACCGAACTGAGATACCTACAGCGTGAGCTATGAGAAAGCGCCACGCTTCCCGAAGGG
```

```
AGAAAGGCGGACAGGTATCCGGTAAGCGGCAGGGTCGGAACAGGAGAGCGCACGAGG

GAGCTTCCAGGGGGAAACGCCTGGTATCTTTATAGTCCTGTCGGGTTTCGCCACCTCTG

ACTTGAGCGTCGATTTTTGTGATGCTCGTCAGGGGGCGGAGCCTATGGAAAAACGCC

AGCAACGCGGCCTTTTTACGGTTCCTGGCCTTTTGCTGGCCTTTTGCTCACATGTTCTTT

CCTGCGTTATCCCCTGATTCTGTGGATAACCGTATTACCGCCTTTGAGTGAGCTGATAC

CGCTCGCCGCAGCCGAACGACCGAGCGCAGCGAGTCAGTGAGCGAGGAAGCGGAAGA

GCGCCTGATGCGGTATTTTCTCCTTACGCATCTGTGCGGTATTTCACACCGCATATGGTG

CACTCTCAGTACAATCTGCTCTGATGCCGCATAGTTAAGCCAGTATACACTCCGCTATC

GCTACGTGACTGGGTCATGGCTGCGCCCCGACACCCGCCAACACCCGCTGACGCGCCC

TGACGGGCTTGTCTGCTCCCGGCATCCGCTTACAGACAAGCTGTGACCGTCTCCGGGAG

CTGCATGTGTCAGAGGTTTTCACCGTCATCACCGAAACGCGCGAGGCAGCAGATCAAT

TCGCGCGCGAAGGCGAAGCGGCATGCATTTACGTTGACACCATCGAATGGTGCAAAAC

CTTTCGCGGTATGGCATGATAGCGCCCGGAAGAGAGTCAATTCAGGGTGGTGAATGTG

AAACCAGTAACGTTATACGATGTCGCAGAGTATGCCGGTGTCTCTTATCAGACCGTTTC

CCGCGTGGTGAACCAGGCCAGCCACGTTTCTGCGAAAACGCGGGAAAAAGTGGAAGC

GGCGATGGCGGAGCTGAATTACATTCCCAACCGCGTGGCACAACAACTGGCGGGCAAA

CAGTCGTTGCTGATTGGCGTTGCCACCTCCAGTCTGGCCCTGCACGCGCCGTCGCAAAT

TGTCGCGGCGATTAAATCTCGCGCCGATCAACTGGGTGCCAGCGTGGTGGTGTCGATG

GTAGAACGAAGCGGCGTCGAAGCCTGTAAAGCGGCGGTGCACAATCTTCTCGCGCAAC

GCGTCAGTGGGCTGATCATTAACTATCCGCTGGATGACCAGGATGCCATTGCTGTGGAA

GCTGCCTGCACTAATGTTCCGGCGTTATTTCTTGATGTCTCTGACCAGACACCCATCAA

CAGTATTATTTTCTCCCATGAAGACGGTACGCGACTGGGCGTGGAGCATCTGGTCGCAT

TGGGTCACCAGCAAATCGCGCTGTTAGCGGGCCCATTAAGTTCTGTCTCGGCGCGTCTG

CGTCTGGCTGGCTGGCATAAATATCTCACTCGCAATCAAATTCAGCCGATAGCGGAAC

GGGAAGGCGACTGGAGTGCCATGTCCGGTTTTCAACAAACCATGCAAATGCTGAATGA

GGGCATCGTTCCCACTGCGATGCTGGTTGCCAACGATCAGATGGCGCTGGGCGCAATG

CGCGCCATTACCGAGTCCGGGCTGCGCGTTGGTGCGGATATCTCGGTAGTGGGATACG

ACGATACCGAAGACAGCTCATGTTATATCCCGCCGTCAACCACCATCAAACAGGATTTT

CGCCTGCTGGGGCAAACCAGCGTGGACCGCTTGCTGCAACTCTCTCAGGGCCAGGCGG

TGAAGGGCAATCAGCTGTTGCCCGTCTCACTGGTGAAAGAAAAACCACCCTGGCGCC

CAATACGCAAACCGCCTCTCCCCGCGCGTTGGCCGATTCATTAATGCAGCTGGCACGAC

AGGTTTCCCGACTGGAAAGCGGGCAGTGAGCGCAACGCAATTAATGTGAGTTAGCGCG

AATTGATCTG
```

Sequence of codon optimized *S. babylonica* IspS with engineered
NcoI restriction site on the 5'-end and an and PstI sites
```
CCATGGAAACCCGCAGAACCGCCAATTATGAACCCAATTCCTGGGATTACGATTACCTT

TTGAGTAGCGATAACGATGACGCCATAGAACTGTACAAAGATAAAGCCAAGAAACTTG

ATGCAGAAGTGCGTAGTAAAATTAATAACGAAAAAGCAGAATTTCTTACACAACTTGA

ACTCATTGATACTATCCAACGTCTCGGCCTCGGATACCGCTTCGAATCAGATATACGGC

GCGCTATCGATAGATATGTTTCATCGGGCGGATTCGAGGCAGTGGCTAAAACGTCGTTA

CACGCAACAGCACTCAGTTTTCGTTTGTTACGCCAACATGGATTCGAAGTGAGCCAAGA

GGTATTTTCGGGTTTCAAGGACCAAAAATGGAAACTTTATGGAGAACTTGAAAGAGGAC
```

-continued

```
ATAAAGGCAATTCTTAGTCTCTATGAAGCGAGTTTCCTTGCTTTAGAAGGCGAGAATAT
ATTGGACGAAGCCAAGGTCTTTACAATCTCCCACCTGAAAGAGCTGAATGAGGAAAAA
ATTGGAAAAGACCTGGCCGACCAAGTGAATCATGCGCTGGAACTTCCTCTGCATCGGC
GTACCCAGCGTCTTGAAGCGGTATGGTCGATAGAAGCCTATCGCAAAAAGGAAGGAGC
GAATCGCGCATTACTGGAACTGGCGATCTTGGACTACAATATGGTCCAATCAGTCTACC
AACGCGATTTGCGCGAAACCTCCCGCTGGTGGCGCCGTGTAGGCTTAGCAACTAAATT
GCATTTTGCACGTGACCGGCTGATTGAATCTTTCTATTGGGCGGTCGGCGTTGCCTTTG
AGCCGCAATATTCTGACTGTCGCAAATCTGTGGCTAAAATGTTTTCATTCGTGACCATA
ATTGATGACATATATGATGTTTATGGGACGTTAGATGAGTTAGAGTTGTTTACCGACGC
AGTTGAACGCTGGGACGTTTCTGCCGTGGATGACCTCCCGGATTATATGAAATTATGCT
TTCTGGCCCTGTACAACACAATCAATGAGATAGCATACGACAATCTGAAAGAAAAAGG
TGAAAACATCCTGCCTTACCTGACTAAAGCATGGGCTGACTTATGCAACGCATTTCTGC
AAGAGGCGAAATTTCTGTACAACAAATCCACTCCAACCTTCGATGACTACTTTGGCAAT
GCCTGGAAAAGTAGCAGTGGCCCGTTGCAGTTAGTGTTCGCTTATTTTGCGGTCGTTCA
AAACATTAAGAAGGAGGAGACGGAGAACCTTCAGAAGTACCACGACATTATTTCGTGG
CCAAGTTATATTTTTCGCTTATGTAATGATCTGGCCTCTGCGTCAGCCGAAATCGCTCG
GGGAGAGACCGCAAATTCTGTTTCTTGCTACATTAGAACTAAGGGCATCTCTGAGGAGT
TAGCAACGGAATCTGTTATGAATCTGATTGATGAGACTTGGAAAAAGATGAATAAAGA
GAAGGTGGGCGATTCACTGTTCGCTAAACAATTTGTAGAAACAGCTATTAATCTGGCTC
GTCAGTCACATTGCACGTATCATAATGGTGATGCACATACATCACCTGATGAGCTGACT
CGTAAACGTGTCTTATCTGTGATCACCGAACCGATCCTTCCGTTTGAAAGATGACTGCAG
```

DNA sequence of pEWL834
```
GTTTGACAGCTTATCATCGACTGCACGGTGCACCAATGCTTCTGGCGTCAGGCAGCCAT
CGGAAGCTGTGGTATGGCTGTGCAGGTCGTAAATCACTGCATAATTCGTGTCGCTCAAG
GCGCACTCCCGTTCTGGATAATGTTTTTTGCGCCGACATCATAACGGTTCTGGCAAATA
TTCTGAAATGAGCTGTTGACAATTAATCATCCGGCTCGTATAATGTGTGGAATTGTGAG
CGGATAACAATTTCACACAGGAAACAGCGCCGCTGAGAAAAAGCGAAGCGGCACTGC
TCTTTAACAATTTATCAGACAATCTGTGTGGGCACTCGACCGGAATTATCGATTAACTT
TATTATTAAAAATTAAAGAGGTATATATTAATGTATCGATTAAATAAGGAGGAATAAA
CCATGGAAACCCGCAGAACCGCCAATTATGAACCCAATTCCTGGGATTACGATTACCTT
TTGAGTAGCGATAACGATGACGCCATAGAACTGTACAAAGATAAAGCCAAGAAACTTG
ATGCAGAAGTGCGTAGTAAAATTAATAACGAAAAAGCAGAATTTCTTACACAACTTGA
ACTCATTGATACTATCCAACGTCTCGGCCTCGGATACCGCTTCGAATCAGATATACGGC
GCGCTATCGATAGATATGTTTCATCGGGCGGATTCGAGGCAGTGGCTAAAACGTCGTTA
CACGCAACAGCACTCAGTTTTCGTTTGTTACGCCAACATGGATTCGAAGTGAGCCAAGA
GGTATTTTCGGGTTTCAAGGACCAAAATGGAAACTTTATGGAGAACTTGAAAGAGGAC
ATAAAGGCAATTCTTAGTCTCTATGAAGCGAGTTTCCTTGCTTTAGAAGGCGAGAATAT
ATTGGACGAAGCCAAGGTCTTTACAATCTCCCACCTGAAAGAGCTGAATGAGGAAAAA
ATTGGAAAAGACCTGGCCGACCAAGTGAATCATGCGCTGGAACTTCCTCTGCATCGGC
GTACCCAGCGTCTTGAAGCGGTATGGTCGATAGAAGCCTATCGCAAAAAGGAAGGAGC
GAATCGCGCATTACTGGAACTGGCGATCTTGGACTACAATATGGTCCAATCAGTCTACC
```

-continued

```
AACGCGATTTGCGCGAAACCTCCCGCTGGTGGCGCCGTGTAGGCTTAGCAACTAAATT

GCATTTTGCACGTGACCGGCTGATTGAATCTTTCTATTGGGCGGTCGGCGTTGCCTTTG

AGCCGCAATATTCTGACTGTCGCAAATCTGTGGCTAAAATGTTTTCATTCGTGACCATA

ATTGATGACATATATGATGTTTATGGGACGTTAGATGAGTTAGAGTTGTTTACCGACGC

AGTTGAACGCTGGGACGTTTCTGCCGTGGATGACCTCCCGGATTATATGAAATTATGCT

TTCTGGCCCTGTACAACACAATCAATGAGATAGCATACGACAATCTGAAAGAAAAAGG

TGAAAACATCCTGCCTTACCTGACTAAAGCATGGGCTGACTTATGCAACGCATTTCTGC

AAGAGGCGAAATTTCTGTACAACAAATCCACTCCAACCTTCGATGACTACTTTGGCAAT

GCCTGGAAAAGTAGCAGTGGCCCGTTGCAGTTAGTGTTCGCTTATTTTGCGGTCGTTCA

AAACATTAAGAAGGAGGAGACGGAGAACCTTCAGAAGTACCACGACATTATTTCGTGG

CCAAGTTATATTTTTCGCTTATGTAATGATCTGGCCTCTGCGTCAGCCGAAATCGCTCG

GGGAGAGACCGCAAATTCTGTTTCTTGCTACATTAGAACTAAGGGCATCTCTGAGGAGT

TAGCAACGGAATCTGTTATGAATCTGATTGATGAGACTTGGAAAAAGATGAATAAAGA

GAAGGTGGGCGATTCACTGTTCGCTAAACAATTTGTAGAAACAGCTATTAATCTGGCTC

GTCAGTCACATTGCACGTATCATAATGGTGATGCACATACATCACCTGATGAGCTGACT

CGTAAACGTGTCTTATCTGTGATCACCGAACCGATCCTTCCGTTTGAAAGATGACTGCA

GCTGGTACCATATGGGAATTCGAAGCTTTCTAGAACAAAAACTCATCTCAGAAGAGGA

TCTGAATAGCGCCGTCGACCATCATCATCATCATCATTGAGTTTAAACGGTCTCCAGCT

TGGCTGTTTTGGCGGATGAGAGAAGATTTTCAGCCTGATACAGATTAAATCAGAACGC

AGAAGCGGTCTGATAAAACAGAATTTGCCTGGCGGCAGTAGCGCGGTGGTCCCACCTG

ACCCCATGCCGAACTCAGAAGTGAAACGCCGTAGCGCCGATGGTAGTGTGGGGTCTCC

CCATGCGAGAGTAGGGAACTGCCAGGCATCAAATAAAACGAAAGGCTCAGTCGAAAG

ACTGGGCCTTTCGTTTTATCTGTTGTTTGTCGGTGAACGCTCTCCTGAGTAGGACAAATC

CGCCGGGAGCGGATTTGAACGTTGCGAAGCAACGGCCCGGAGGGTGGCGGGCAGGAC

GCCCGCCATAAACTGCCAGGCATCAAATTAAGCAGAAGGCCATCCTGACGGATGGCCT

TTTTGCGTTTCTACAAACTCTTTTGTTTATTTTTCTAAATACATTCAAATATGTATCCGCT

CATGAGACAATAACCCTGATAAATGCTTCAATAATATTGAAAAAGGAAGAGTATGAGT

ATTCAACATTTCCGTGTCGCCCTTATTCCCTTTTTTGCGGCATTTTGCCTTCCTGTTTTTG

CTCACCCAGAAACGCTGGTGAAAGTAAAAGATGCTGAAGATCAGTTGGGTGCACGAGT

GGGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCCG

TGTTGACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGAGAAT

TATGCAGTGCTGCCATAACCATGAGTGATAACACTGCGGCCAACTTACTTCTGACAACG

ATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACAC

CACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTA
```

-continued

```
TCGTAGTTATCTACACGACGGGGAGTCAGGCAACTATGGATGAACGAAATAGACAGAT
CGCTGAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTTTTTA
CGGTTCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCTGATGCGGTATTTTC
TCCTTACGCATCTGTGCGGTATTTCACACCGCATATGGTGCACTCTCAGTACAATCTGCT
CTGATGCCGCATAGTTAAGCCAGTATACACTCCGCTATCGCTACGTGACTGGGTCATGG
CTGCGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTC
ACCGTCATCACCGAAACGCGCGAGGCAGCAGATCAATTCGCGCGCGAAGGCGAAGCG
GCATGCATTTACGTTGACACCATCGAATGGTGCAAAACCTTTCGCGGTATGGCATGATA
GCGCCCGGAAGAGAGTCAATTCAGGGTGGTGAATGTGAAACCAGTAACGTTATACGAT
GTCGCAGAGTATGCCGGTGTCTCTTATCAGACCGTTTCCCGCGTGGTGAACCAGGCCAG
CCACGTTTCTGCGAAAACGCGGGAAAAAGTGGAAGCGGCGATGGCGGAGCTGAATTAC
ATTCCCAACCGCGTGGCACAACAACTGGCGGGCAAACAGTCGTTGCTGATTGGCGTTG
CCACCTCCAGTCTGGCCCTGCACGCGCCGTCGCAAATTGTCGCGGCGATTAAATCTCGC
GCCGATCAACTGGGTGCCAGCGTGGTGGTGTCGATGGTAGAACGAAGCGGCGTCGAAG
CCTGTAAAGCGGCGGTGCACAATCTTCTCGCGCAACGCGTCAGTGGGCTGATCATTAAC
TATCCGCTGGATGACCAGGATGCCATTGCTGTGGAAGCTGCCTGCACTAATGTTCCGGC
GTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTG
TTAGCGGGCCCATTAAGTTCTGTCTCGGCGCGTCTGCGTCTGGCTGGCTGGCATAAATA
TCTCACTCGCAATCAAATTCAGCCGATAGCGGAACGGGAAGGCGACTGGAGTGCCATG
TCCGGTTTTCAACAAACCATGCAAATGCTGAATGAGGGCATCGTTCCCACTGCGATGCT
GGTTGCCAACGATCAGATGGCGCTGGGCGCAATGCGCGCCATTACCGAGTCCGGGCTG
CGCGTTGGTGCGGATATCTCGGTAGTGGGATACGACGATACCGAAGACAGCTCATGTT
ATATCCCGCCGTCAACCACCATCAAACAGGATTTTCGCCTGCTGGGGCAAACCAGCGT
GGACCGCTTGCTGCAACTCTCTCAGGGCCAGGCGGTGAAGGGCAATCAGCTGTTGCCC
```

```
GTCTCACTGGTGAAAAGAAAAACCACCCTGGCGCCCAATACGCAAACCGCCTCTCCCC

GCGCGTTGGCCGATTCATTAATGCAGCTGGCACGACAGGTTTCCCGACTGGAAAGCGG

GCAGTGAGCGCAACGCAATTAATGTGAGTTAGCGCGAATTGATCTG

DNA sequence of pEWL851
GTTTGACAGCTTATCATCGACTGCACGGTGCACCAATGCTTCTGGCGTCAGGCAGCCAT

CGGAAGCTGTGGTATGGCTGTGCAGGTCGTAAATCACTGCATAATTCGTGTCGCTCAAG

GCGCACTCCCGTTCTGGATAATGTTTTTTGCGCCGACATCATAACGGTTCTGGCAAATA

TTCTGAAATGAGCTGTTGACAATTAATCATCCGGCTCGTATAATGTGTGGAATTGTGAG

CGGATAACAATTTCACACAGGAAACAGCGCCGCTGAGAAAAAGCGAAGCGGCACTGC

TCTTTAACAATTTATCAGACAATCTGTGTGGGCACTCGACCGGAATTATCGATTAACTT

TATTATTAAAAATTAAAGAGGTATATATTAATGTATCGATTAAATAAGGAGGAATAAA

CCATGGAAACCCGCAGAACCGCCAATTATGAACCCAATTCCTGGGATTACGATTACCTT

TTGAGTAGCGATAACGATGACGCCATAGAACTGTACAAAGATAAAGCCAAGAAACTTG

ATGCAGAAGTGCGTAGTAAAATTAATAACGAAAAAGCAGAATTTCTTACACAACTTGA

ACTCATTGATACTATCCAACGTCTCGGCCTCGGATACCGCTTCGAATCAGATATACGGC

GCGCTATCGATAGATATGTTTCATCGGGCGGATTCGAGGCAGTGGCTAAAACGTCGTTA

CACGCAACAGCACTCAGTTTTCGTTTGTTACGCCAACATGGATTCGAAGTGAGCCAAGA

GGTATTTTCGGGTTTCAAGGACCAAAATGGAAACTTTATGGAGAACTTGAAAGAGGAC

ATAAAGGCAATTCTTAGTCTCTATGAAGCGAGTTTCCTTGCTTTAGAAGGCGAGAATAT

ATTGGACGAAGCCAAGGTCTTTACAATCTCCCACCTGAAAGAGCTGAATGAGGAAAAA

ATTGGAAAAGACCTGGCCGACCAAGTGAATCATGCGCTGGAACTTCCTCTGCATCGGC

GTACCCAGCGTCTTGAAGCGGTATGGTCGATAGAAGCCTATCGCAAAAAGGAAGGAGC

GAATCGCGCATTACTGGAACTGGCGATCTTGGACTACAATATGGTCCAATCAGTCTACC

AACGCGATTTGCGCGAAACCTCCCGCTGGTGGCGCCGTGTAGGCTTAGCAACTAAATT

GCATTTTGCACGTGACCGGCTGATTGAATCTTTCTATTGGGCGGTCGGCGTTGCCTTTG

AGCCGCAATATTCTGACTGTCGCAAATCTGTGGCTAAAATGTTTTCATTCGTGACCATA

ATTGATGACATATATGATGTTTATGGGACGTTAGATGAGTTAGAGTTGTTTACCGACGC

AGTTGAACGCTGGGACGTTTCTGCCGTGGATGACCTCCCGGATTATATGAAATTATGCT

TTCTGGCCCTGTACAACACAATCAATGAGATAGCATACGACAATCTGAAAGAAAAAGG

TGAAAACATCCTGCCTTACCTGACTAAAGCATGGGCTGACTTATGCAACGCATTTCTGC

AAGAGGCGAAATTTCTGTACAACAAATCCACTCCAACCTTCGATGACTACTTTGGCAAT

GCCTGGAAAAGTAGCAGTGGCCCGTTGCAGTTAGTGTTCGCTTATTTTGCGGTCGTTCA

AAACATTAAGAAGGAGGAGACGGAGAACCTTCAGAAGTACCACGACATTATTTCGTGG

CCAAGTTATATTTTTCGCTTATGTAATGATCTGGCCTCTGCGTCAGCCGAAATCGCTCG

GGGAGAGACCGCAAATTCTGTTTCTTGCTACATTAGAACTAAGGGCATCTCTGAGGAGT

TAGCAACGGAATCTGTTATGAATCTGATTGATGAGACTTGGAAAAAGATGAATAAAGA

GAAGGTGGGCGATTCACTGTTCGCTAAACAATTTGTAGAAACAGCTATTAATCTGGCTC

GTCAGTCACATTGCACGTATCATAATGGTGATGCACATACATCACCTGATGAGCTGACT

CGTAAACGTGTCTTATCTGTGATCACCGAACCGATCCTTCCGTTTGAAAGATGACTGCA

TAAAGGAGGTAAAAAAACATGGTATCCTGTTCTGCGCCGGGTAAGATTTACCTGTTCG

GTGAACACGCCGTAGTTTATGGCGAAACTGCAATTGCGTGTGCGGTGGAACTGCGTAC
```

-continued

```
CCGTGTTCGCGCGGAACTCAATGACTCTATCACTATTCAGAGCCAGATCGGCCGCACCG

GTCTGGATTTCGAAAAGCACCCTTATGTGTCTGCGGTAATTGAGAAAATGCGCAAATCT

ATTCCTATTAACGGTGTTTTCTTGACCGTCGATTCCGACATCCCGGTGGGCTCCGGTCTG

GGTAGCAGCGCAGCCGTTACTATCGCGTCTATTGGTGCGCTGAACGAGCTGTTCGGCTT

TGGCCTCAGCCTGCAAGAAATCGCTAAACTGGGCCACGAAATCGAAATTAAAGTACAG

GGTGCCGCGTCCCCAACCGATACGTATGTTTCTACCTTCGGCGGCGTGGTTACCATCCC

GGAACGTCGCAAACTGAAAACTCCGGACTGCGGCATTGTGATTGGCGATACCGGCGTT

TTCTCCTCCACCAAAGAGTTAGTAGCTAACGTACGTCAGCTGCGCGAAAGCTACCCGG

ATTTGATCGAACCGCTGATGACCTCTATTGGCAAAATCTCTCGTATCGGCGAACAACTG

GTTCTGTCTGGCGACTACGCATCCATCGGCCGCCTGATGAACGTCAACCAGGGTCTCCT

GGACGCCCTGGGCGTTAACATCTTAGAACTGAGCCAGCTGATCTATTCCGCTCGTGCGG

CAGGTGCGTTTGGCGCTAAAATCACGGGCGCTGGCGGCGGTGGCTGTATGGTTGCGCT

GACCGCTCCGGAAAAATGCAACCAAGTGGCAGAAGCGGTAGCAGGCGCTGGCGGTAA

AGTGACTATCACTAAACCGACCGAGCAAGGTCTGAAAGTAGATTAAAGTCTAGTTAAA

GTTTAAACGGTCTCCAGCTTGGCTGTTTTGGCGGATGAGAGAAGATTTTCAGCCTGATA

CAGATTAAATCAGAACGCAGAAGCGGTCTGATAAAACAGAATTTGCCTGGCGGCAGTA

GCGCGGTGGTCCCACCTGACCCCATGCCGAACTCAGAAGTGAAACGCCGTAGCGCCGA

TGGTAGTGTGGGGTCTCCCCATGCGAGAGTAGGGAACTGCCAGGCATCAAATAAAACG

AAAGGCTCAGTCGAAAGACTGGGCCTTTCGTTTTATCTGTTGTTTGTCGGTGAACGCTC

TCCTGAGTAGGACAAATCCGCCGGGAGCGGATTTGAACGTTGCGAAGCAACGGCCCGG

AGGGTGGCGGGCAGGACGCCCGCCATAAACTGCCAGGCATCAAATTAAGCAGAAGGC

CATCCTGACGGATGGCCTTTTTGCGTTTCTACAAACTCTTTTGTTTATTTTTCTAAATAC

ATTCAAATATGTATCCGCTCATGAGACAATAACCCTGATAAATGCTTCAATAATATTGA

AAAAGGAAGAGTATGAGTATTCAACATTTCCGTGTCGCCCTTATTCCCTTTTTTGCGGC

ATTTTGCCTTCCTGTTTTTGCTCACCCAGAAACGCTGGTGAAAGTAAAAGATGCTGAAG

ATCAGTTGGGTGCACGAGTGGGTTACATCGAACTGGATCTCAACAGCGGTAAGATCCT

TGAGAGTTTTCGCCCCGAAGAACGTTTTCCAATGATGAGCACTTTTAAAGTTCTGCTAT

GTGGCGCGGTATTATCCCGTGTTGACGCCGGGCAAGAGCAACTCGGTCGCCGCATACA

CTATTCTCAGAATGACTTGGTTGAGTACTCACCAGTCACAGAAAAGCATCTTACGGATG

GCATGACAGTAAGAGAATTATGCAGTGCTGCCATAACCATGAGTGATAACACTGCGGC

CAACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCATAC

CAAACGACGAGCGTGACACCACGATGCCTGTAGCAATGGCAACAACGTTGCGCAAACT

ATTAACTGGCGAACTACTTACTCTAGCTTCCCGGCAACAATTAATAGACTGGATGGAGG

CGGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCAG

ATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTG

TCAGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAGTT
```

-continued

```
TTCGTTCCACTGAGCGTCAGACCCCGTAGAAAAGATCAAAGGATCTTCTTGAGATCCTT

TTTTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACT

CTGTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGACCTA

CACCGAACTGAGATACCTACAGCGTGAGCTATGAGAAAGCGCCACGCTTCCCGAAGGG

AGAAAGGCGGACAGGTATCCGGTAAGCGGCAGGGTCGGAACAGGAGAGCGCACGAGG

GAGCTTCCAGGGGAAACGCCTGGTATCTTTATAGTCCTGTCGGGTTTCGCCACCTCTG

ACTTGAGCGTCGATTTTGTGATGCTCGTCAGGGGGCGGAGCCTATGGAAAAACGCC

AGCAACGCGGCCTTTTTACGGTTCCTGGCCTTTTGCTGGCCTTTTGCTCACATGTTCTTT

CCTGCGTTATCCCCTGATTCTGTGGATAACCGTATTACCGCCTTTGAGTGAGCTGATAC

CGCTCGCCGCAGCCGAACGACCGAGCGCAGCGAGTCAGTGAGCGAGGAAGCGGAAGA

GCGCCTGATGCGGTATTTTCTCCTTACGCATCTGTGCGGTATTTCACACCGCATATGGTG

CACTCTCAGTACAATCTGCTCTGATGCCGCATAGTTAAGCCAGTATACACTCCGCTATC

GCTACGTGACTGGGTCATGGCTGCGCCCCGACACCCGCCAACACCCGCTGACGCGCCC

TGACGGGCTTGTCTGCTCCCGGCATCCGCTTACAGACAAGCTGTGACCGTCTCCGGGAG

CTGCATGTGTCAGAGGTTTTCACCGTCATCACCGAAACGCGCGAGGCAGCAGATCAAT

TCGCGCGCGAAGGCGAAGCGGCATGCATTTACGTTGACACCATCGAATGGTGCAAAAC

CTTTCGCGGTATGGCATGATAGCGCCCGGAAGAGAGTCAATTCAGGGTGGTGAATGTG

AAACCAGTAACGTTATACGATGTCGCAGAGTATGCCGGTGTCTCTTATCAGACCGTTTC

CCGCGTGGTGAACCAGGCCAGCCACGTTTCTGCGAAAACGCGGGAAAAAGTGGAAGC

GGCGATGGCGGAGCTGAATTACATTCCCAACCGCGTGGCACAACAACTGGCGGGCAAA

CAGTCGTTGCTGATTGGCGTTGCCACCTCCAGTCTGGCCCTGCACGCGCCGTCGCAAAT

TGTCGCGGCGATTAAATCTCGCGCCGATCAACTGGGTGCCAGCGTGGTGGTGTCGATG

GTAGAACGAAGCGGCGTCGAAGCCTGTAAAGCGGCGGTGCACAATCTTCTCGCGCAAC

GCGTCAGTGGGCTGATCATTAACTATCCGCTGGATGACCAGGATGCCATTGCTGTGGAA

GCTGCCTGCACTAATGTTCCGGCGTTATTTCTTGATGTCTCTGACCAGACACCCATCAA

CAGTATTATTTTCTCCCATGAAGACGGTACGCGACTGGGCGTGGAGCATCTGGTCGCAT

TGGGTCACCAGCAAATCGCGCTGTTAGCGGGCCCATTAAGTTCTGTCTCGGCGCGTCTG

CGTCTGGCTGGCTGGCATAAATATCTCACTCGCAATCAAATTCAGCCGATAGCGGAAC

GGGAAGGCGACTGGAGTGCCATGTCCGGTTTTCAACAAACCATGCAAATGCTGAATGA

GGGCATCGTTCCCACTGCGATGCTGGTTGCCAACGATCAGATGGCGCTGGGCGCAATG

CGCCAATCGCATTGTACGTATCATAATGGAGATGCGCATACTTCGCCTGACGAATTAAC

CCGCAAACGCGTACTGTCAGTGATCACTGAACCGATACTGCCATTGGAACGGTGACTG

CAGCTGGTACCATATGGGAATTCGAAGCTTTCTAGAACAAAAACTCATCTCAGAAGAG

GATCTGAATAGCGCCGTCGACCATCATCATCATCATCATTGAGTTTAAACGGTCTCCAG

CTTGGCTGTTTTGGCGGATGAGAGAAGATTTTCAGCCTGATACAGATTAAATCAGAACG

CAGAAGCGGTCTGATAAAACAGAATTTGCCTGGCGGCAGTAGCGCGGTGGTCCCACCT

GACCCCATGCCGAACTCAGAAGTGAAACGCCGTAGCGCCGATGGTAGTGTGGGGTCTC
```

```
CCCATGCGAGAGTAGGGAACTGCCAGGCATCAAATAAAACGAAAGGCTCAGTCGAAA

GACTGGGCCTTTCGTTTTATCTGTTGTTTGTCGGTGAACGCTCTCCTGAGTAGGACAAAT

CCGCCGGGAGCGGATTTGAACGTTGCGAAGCAACGGCCCGGAGGGTGGCGGGCAGGA

CGCCCGCCATAAACTGCCAGGCATCAAATTAAGCAGAAGGCCATCCTGACGGATGGCC

TTTTTGCGTTTCTACAAACTCTTTTGTTTATTTTTCTAAATACATTCAAATATGTATCCGC

TCATGAGACAATAACCCTGATAAATGCTTCAATAATATTGAAAAAGGAAGAGTATGAG

TATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAG

TGGGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCCG

TGTTGACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGAGAAT

TATGCAGTGCTGCCATAACCATGAGTGATAACACTGCGGCCAACTTACTTCTGACAACG

ATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACAC

CACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTA

TCGTAGTTATCTACACGACGGGGAGTCAGGCAACTATGGATGAACGAAATAGACAGAT

CGCTGAGATAGGTGCCTCACTGATTAAGCATTGGTAACTGTCAGACCAAGTTTACTCAT

ATATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGTCA

GACCCCGTAGAAAAGATCAAAGGATCTTCTTGAGATCCTTTTTTTCTGCGCGTAATCTG

CTGCTTGCAAACAAAAAAACCACCGCTACCAGCGGTGGTTTGTTTGCCGGATCAAGAG

CTACCAACTCTTTTTCCGAAGGTAACTGGCTTCAGCAGAGCGCAGATACCAAATACTGT

CCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTT

ACCGGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTA

TCCGGTAAGCGGCAGGGTCGGAACAGGAGAGCGCACGAGGGAGCTTCCAGGGGGAAA

CGCCTGGTATCTTTATAGTCCTGTCGGGTTTCGCCACCTCTGACTTGAGCGTCGATTTTT

GTGATGCTCGTCAGGGGGCGGAGCCTATGGAAAAACGCCAGCAACGCGGCCTTTTTA

CGGTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAACG

ACCGAGCGCAGCGAGTCAGTGAGCGAGGAAGCGGAAGAGCGCCTGATGCGGTATTTTC

TCCTTACGCATCTGTGCGGTATTTCACACCGCATATGGTGCACTCTCAGTACAATCTGCT

CTGATGCCGCATAGTTAAGCCAGTATACACTCCGCTATCGCTACGTGACTGGGTCATGG

CTGCGCCCCGACACCCGCCAACACCCGCTGACGCGCCCTGACGGGCTTGTCTGCTCCCG
```

-continued
GCATCCGCTTACAGACAAGCTGTGACCGTCTCCGGGAGCTGCATGTGTCAGAGGTTTTC

ACCGTCATCACCGAAACGCGCGAGGCAGCAGATCAATTCGCGCGCGAAGGCGAAGCG

GCATGCATTTACGTTGACACCATCGAATGGTGCAAAACCTTTCGCGGTATGGCATGATA

GCGCCCGGAAGAGAGTCAATTCAGGGTGGTGAATGTGAAACCAGTAACGTTATACGAT

GTCGCAGAGTATGCCGGTGTCTCTTATCAGACCGTTTCCCGCGTGGTGAACCAGGCCAG

CCACGTTTCTGCGAAAACGCGGGAAAAAGTGGAAGCGGCGATGGCGGAGCTGAATTAC

ATTCCCAACCGCGTGGCACAACAACTGGCGGGCAAACAGTCGTTGCTGATTGGCGTTG

CCACCTCCAGTCTGGCCCTGCACGCGCCGTCGCAAATTGTCGCGGCGATTAAATCTCGC

GCCGATCAACTGGGTGCCAGCGTGGTGGTGTCGATGGTAGAACGAAGCGGCGTCGAAG

CCTGTAAAGCGGCGGTGCACAATCTTCTCGCGCAACGCGTCAGTGGGCTGATCATTAAC

TATCCGCTGGATGACCAGGATGCCATTGCTGTGGAAGCTGCCTGCACTAATGTTCCGGC

GTTATTTCTTGATGTCTCTGACCAGACACCCATCAACAGTATTATTTTCTCCCATGAAGA

CGGTACGCGACTGGGCGTGGAGCATCTGGTCGCATTGGGTCACCAGCAAATCGCGCTG

TTAGCGGGCCCATTAAGTTCTGTCTCGGCGCGTCTGCGTCTGGCTGGCTGGCATAAATA

TCTCACTCGCAATCAAATTCAGCCGATAGCGGAACGGGAAGGCGACTGGAGTGCCATG

TCCGGTTTTCAACAAACCATGCAAATGCTGAATGAGGGCATCGTTCCCACTGCGATGCT

GGTTGCCAACGATCAGATGGCGCTGGGCGCAATGCGCGCCATTACCGAGTCCGGGCTG

CGCGTTGGTGCGGATATCTCGGTAGTGGGATACGACGATACCGAAGACAGCTCATGTT

ATATCCCGCCGTCAACCACCATCAAACAGGATTTTCGCCTGCTGGGGCAAACCAGCGT

GGACCGCTTGCTGCAACTCTCTCAGGGCCAGGCGGTGAAGGGCAATCAGCTGTTGCCC

GTCTCACTGGTGAAAAGAAAAACCACCCTGGCGCCCAATACGCAAACCGCCTCTCCCC

GCGCGTTGGCCGATTCATTAATGCAGCTGGCACGACAGGTTTCCCGACTGGAAAGCGG

GCAGTGAGCGCAACGCAATTAATGTGAGTTAGCGCGAATTGATCTG

```
DNA sequence of pEWL907
```
GTTTGACAGCTTATCATCGACTGCACGGTGCACCAATGCTTCTGGCGTCAGGCAGCCAT

CGGAAGCTGTGGTATGGCTGTGCAGGTCGTAAATCACTGCATAATTCGTGTCGCTCAAG

GCGCACTCCCGTTCTGGATAATGTTTTTTGCGCCGACATCATAACGGTTCTGGCAAATA

TTCTGAAATGAGCTGTTGACAATTAATCATCCGGCTCGTATAATGTGTGGAATTGTGAG

CGGATAACAATTTCACACAGGAAACAGCGCCGCTGAGAAAAAGCGAAGCGGCACTGC

TCTTTAACAATTTATCAGACAATCTGTGTGGGCACTCGACCGGAATTATCGATTAACTT

TATTATTAAAAATTAAAGAGGTATATATTAATGTATCGATTAAATAAGGAGGAATAAA

CCATGGAAACCCGCAGAACCGCCAATTATGAACCCAATTCCTGGGATTACGATTACCTT

TTGAGTAGCGATAACGATGACGCCATAGAACTGTACAAAGATAAAGCCAAGAAACTTG

ATGCAGAAGTGCGTAGTAAAATTAATAACGAAAAAGCAGAATTTCTTACACAACTTGA

ACTCATTGATACTATCCAACGTCTCGGCCTCGGATACCGCTTCGAATCAGATATACGGC

GCGCTATCGATAGATATGTTTCATCGGGCGGATTCGAGGCAGTGGCTAAAACGTCGTTA

CACGCAACAGCACTCAGTTTTCGTTTGTTACGCCAACATGGATTCGAAGTGAGCCAAGA

GGTATTTTCGGGTTTCAAGGACCAAAATGGAAACTTTATGGAGAACTTGAAAGAGGAC

ATAAAGGCAATTCTTAGTCTCTATGAAGCGAGTTTCCTTGCTTTAGAAGGCGAGAATAT

ATTGGACGAAGCCAAGGTCTTTACAATCTCCCACCTGAAAGAGCTGAATGAGGAAAAA

ATTGGAAAAGACCTGGCCGACCAAGTGAATCATGCGCTGGAACTTCCTCTGCATCGGC

-continued

```
GTACCCAGCGTCTTGAAGCGGTATGGTCGATAGAAGCCTATCGCAAAAGGAAGGAGC
GAATCGCGCATTACTGGAACTGGCGATCTTGGACTACAATATGGTCCAATCAGTCTACC
AACGCGATTTGCGCGAAACCTCCCGCTGGTGGCGCCGTGTAGGCTTAGCAACTAAATT
GCATTTTGCACGTGACCGGCTGATTGAATCTTTCTATTGGGCGGTCGGCGTTGCCTTTG
AGCCGCAATATTCTGACTGTCGCAAATCTGTGGCTAAAATGTTTTGTTTCGTGACCATA
ATTGATGACATATATGATGTTTATGGGACGTTAGATGAGTTAGAGTTGTTTACCGACGC
AGTTGAACGCTGGGACGTTTCTGCCGTGGATGACCTCCCGGATTATATGAAATTATGCT
TTCTGGCCCTGTACAACACAATCAATGAGATAGCATACGACAATCTGAAAGAAAAAGG
TGAAAACATCCTGCCTTACCTGACTAAAGCATGGGCTGACTTATGCAACGCATTTCTGC
AAGAGGCGAAATTTCTGTACAACAAATCCACTCCAACCTTCGATGACTACTTTGGCAAT
GCCTGGAAAAGTAGCAGTGGCCCGTTGCAGTTAGTGTTCGCTTATTTTGCGGTCGTTCA
AAACATTAAGAAGGAGGAGACGGAGAACCTTCAGAAGTACCACGACATTATTTCGTGG
CCAAGTTATATTTTTCGCTTATGTAATGATCTGGCCTCTGCGTCAGCCGAAATCGCTCG
GGGAGAGACCGCAAATTCTGTTTCTTGCTACATTAGAACTAAGGGCATCTCTGAGGAGT
TAGCAACGGAATCTGTTATGAATCTGATTGATGAGACTTGGAAAAAGATGAATAAAGA
GAAGGTGGGCGATTCACTGTTCGCTAAACAATTTGTAGAAACAGCTATTAATCTGGCTC
GTCAGTCACATTGCACGTATCATAATGGTGATGCACATACATCACCTGATGAGCTGACT
CGTAAACGTGTCTTATCTGTGATCACCGAACCGATCCTTCCGTTTGAAAGATGACTGCA
GCTGGTACCATATGGGAATTCGAAGCTTTCTAGAACAAAAACTCATCTCAGAAGAGGA
TCTGAATAGCGCCGTCGACCATCATCATCATCATCATTGAGTTTAAACGGTCTCCAGCT
TGGCTGTTTTGGCGGATGAGAGAAGATTTTCAGCCTGATACAGATTAAATCAGAACGC
AGAAGCGGTCTGATAAAACAGAATTTGCCTGGCGGCAGTAGCGCGGTGGTCCCACCTG
ACCCCATGCCGAACTCAGAAGTGAAACGCCGTAGCGCCGATGGTAGTGTGGGGTCTCC
CCATGCGAGAGTAGGGAACTGCCAGGCATCAAATAAAACGAAAGGCTCAGTCGAAAG
ACTGGGCCTTTCGTTTTATCTGTTGTTTGTCGGTGAACGCTCTCCTGAGTAGGACAAATC
CGCCGGGAGCGGATTTGAACGTTGCGAAGCAACGGCCCGGAGGGTGGCGGGCAGGAC
GCCCGCCATAAACTGCCAGGCATCAAATTAAGCAGAAGGCCATCCTGACGGATGGCCT
TTTTGCGTTTCTACAAACTCTTTTGTTTATTTTTCTAAATACATTCAAATATGTATCCGCT
CATGAGACAATAACCCTGATAAATGCTTCAATAATATTGAAAAAGGAAGAGTATGAGT
ATTCAACATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCCG
TGTTGACGCCGGGCAAGAGCAACTCGGTCGCCGCATACACTATTCTCAGAATGACTTG
GTTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAACG
ATCGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGACAC
CACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGAGCCGGT
```

-continued

```
GAGCGTGGGTCTCGCGGTATCATTGCAGCACTGGGGCCAGATGGTAAGCCCTCCCGTA
TCGTAGTTATCTACACGACGGGGAGTCAGGCAACTATGGATGAACGAAATAGACAGAT
CGCTGAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTTTTTA
CGGTTCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCTGATGCGGTATTTTC
TCCTTACGCATCTGTGCGGTATTTCACACCGCATATGGTGCACTCTCAGTACAATCTGCT
CTGATGCCGCATAGTTAAGCCAGTATACACTCCGCTATCGCTACGTGACTGGGTCATGG
CTGCGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTC
ACCGTCATCACCGAAACGCGCGAGGCAGCAGATCAATTCGCGCGCGAAGGCGAAGCG
GCATGCATTTACGTTGACACCATCGAATGGTGCAAAACCTTTCGCGGTATGGCATGATA
GCGCCCGGAAGAGAGTCAATTCAGGGTGGTGAATGTGAAACCAGTAACGTTATACGAT
GTCGCAGAGTATGCCGGTGTCTCTTATCAGACCGTTTCCCGCGTGGTGAACCAGGCCAG
CCACGTTTCTGCGAAAACGCGGGAAAAGTGGAAGCGGCGATGGCGGAGCTGAATTAC
ATTCCCAACCGCGTGGCACAACAACTGGCGGGCAAACAGTCGTTGCTGATTGGCGTTG
CCACCTCCAGTCTGGCCCTGCACGCGCCGTCGCAAATTGTCGCGGCGATTAAATCTCGC
GCCGATCAACTGGGTGCCAGCGTGGTGGTGTCGATGGTAGAACGAAGCGGCGTCGAAG
CCTGTAAAGCGGCGGTGCACAATCTTCTCGCGCAACGCGTCAGTGGGCTGATCATTAAC
TATCCGCTGGATGACCAGGATGCCATTGCTGTGGAAGCTGCCTGCACTAATGTTCCGGC
GTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTG
TTAGCGGGCCCATTAAGTTCTGTCTCGGCGCGTCTGCGTCTGGCTGGCTGGCATAAATA
TCTCACTCGCAATCAAATTCAGCCGATAGCGGAACGGGAAGGCGACTGGAGTGCCATG
TCCGGTTTTCAACAAACCATGCAAATGCTGAATGAGGGCATCGTTCCCACTGCGATGCT
GGTTGCCAACGATCAGATGGCGCTGGGCGCAATGCGCGCCATTACCGAGTCCGGGCTG
CGCGTTGGTGCGGATATCTCGGTAGTGGGATACGACGATACCGAAGACAGCTCATGTT
```

```
ATATCCCGCCGTCAACCACCATCAAACAGGATTTTCGCCTGCTGGGGCAAACCAGCGT

GGACCGCTTGCTGCAACTCTCTCAGGGCCAGGCGGTGAAGGGCAATCAGCTGTTGCCC

GTCTCACTGGTGAAAAGAAAAACCACCCTGGCGCCCAATACGCAAACCGCCTCTCCCC

GCGCGTTGGCCGATTCATTAATGCAGCTGGCACGACAGGTTTCCCGACTGGAAAGCGG

GCAGTGAGCGCAACGCAATTAATGTGAGTTAGCGCGAATTGATCTG
```

Example 4

Crystal Structure of MEA P. alba A3T S288C

Figure 23:
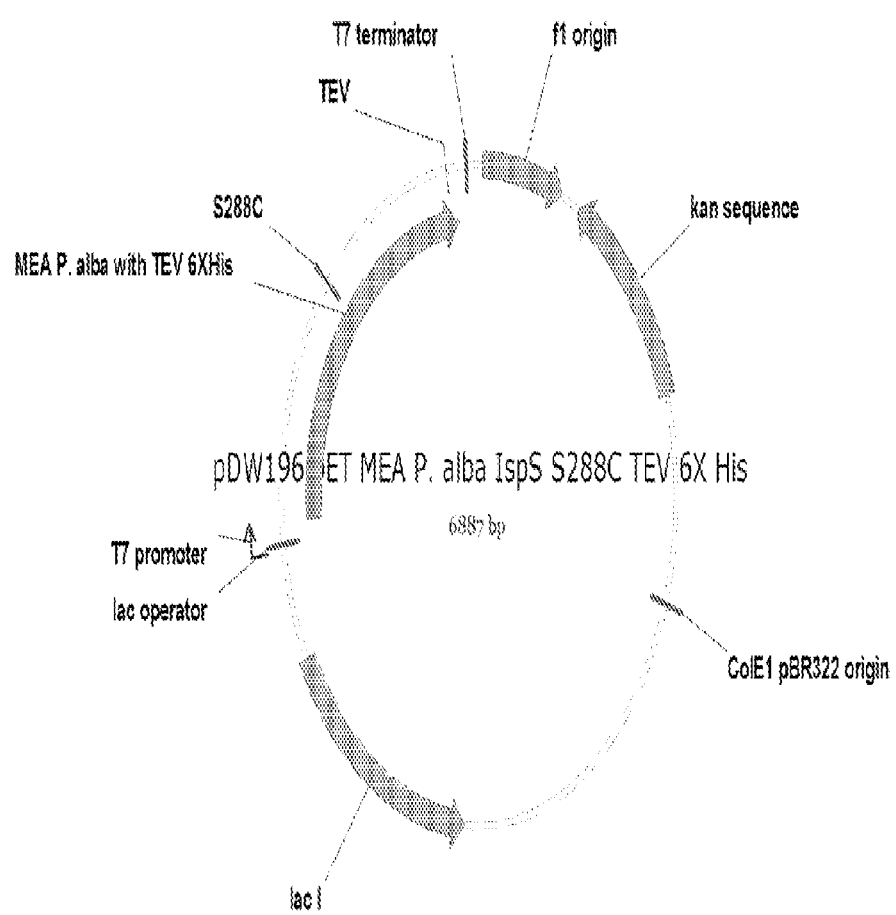
FIG. 23 shows plasmid map pDW196.
Figure 24:
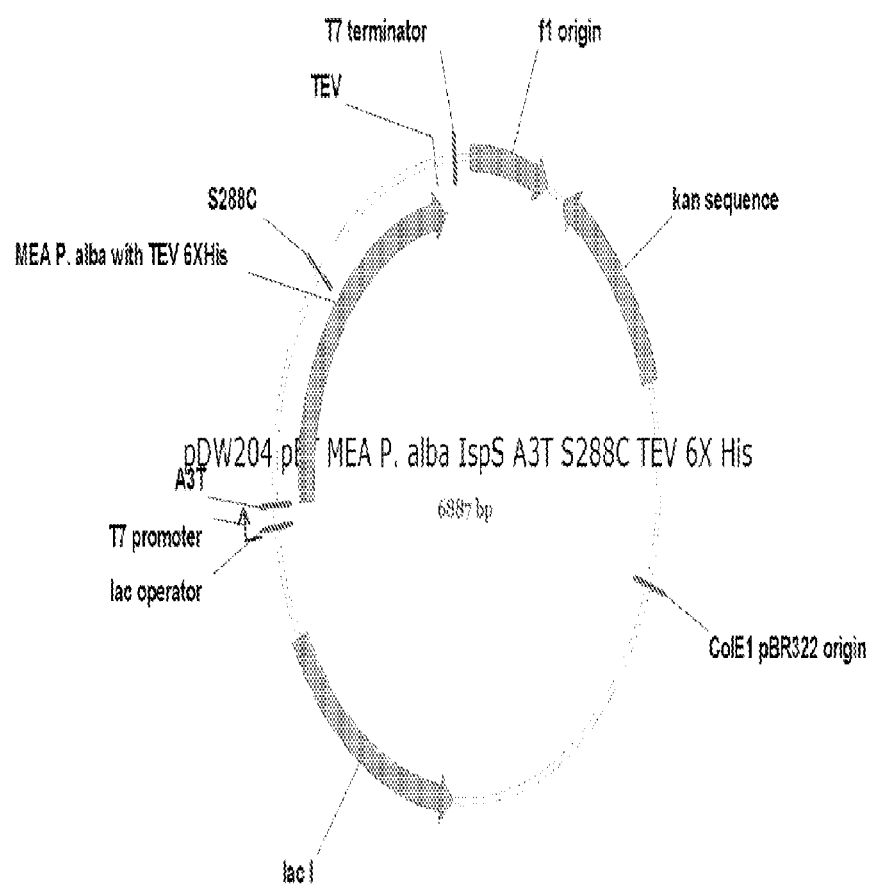
FIG. 24 shows plasmid maps pDW204.

The S288C mutation was introduced into the MD09-163 vector (previously described) by QuikChange (Stratagene) mutagenesis using the primers listed in Table 10. Mutagenesis was carried out according to the manufacturer's recommended protocol. PCR products were transformed into chemically competent Top10 E. coli (Invitrogen) cells, and positive transformants were selected for plasmid isolation and complete sequencing. A single plasmid, pDW196 (Table 11, FIG. 23), was verified and used for additional mutagenesis. The A3T mutation was introduced in the pDW 196 vector by the same procedure as described above. The fully verified plasmid, pDW204 (Table 11, FIG. 24), was transformed into chemically competent BL21 DE3 pLysS cells (Invitrogen) according to the manufacturer's recommended protocol. This strain, DW614 was used for purification and subsequent crystallization for structural analysis of the MEA P. alba IspS A3T S288C variant.

TABLE 10

Primers used in this study

| Primer | Sequence |
| --- | --- |
| HgS pET QC A3T Forward | ACATATGGAAACGCGTCGTTCTGCGAACTACGA |
| HgS pET QC A3T Reverse | CAGAACGACGCGTTTCCATATGTATATCTCCTT |
| HgS QC S288C Forward | AAAAATGTTTTGTTTCGTAACCATTATCGACGA |
| HgS QC S288C Reverse | TGGTTACGAAACAAAACATTTTTGCGACGGAGT |

TABLE 11

Plasmids/Strains used in this study

| Plasmid/Strain | Resistance | Description |
| --- | --- | --- |
| pDW196 | Kan | pET MEA P. alba IspS S288C TEV 6X His |
| pDW204 | Kan | pET MEA P. alba IspS A3T S288C TEV 6X His |
| DW614 | Chlor, Kan | BL21 (DE3), pLysS, pDW204 = pET MEA P. alba IspS A3T S288C TEV 6X His |

```
Amino acid sequence of MEA P. alba IspS S288C TEV 6XHis
MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFCFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVITEPILPFERENLYFQG

LEHHHHHH

DNA sequence of pDW196 harboring MEA P. alba IspS S288C TEV 6XHis
tggcgaatgggacgcgccctgtagcggcgcattaagcgcggcgggtgtggtggttacgcgcagcgtgaccgctacacttgccagcgccctag cgcccgctccttttcgctttcttccttcctttctcgccacgttcgccggctttccccgtcaagctctaaatcgggggctcccttttagggttc cgatttagtgctttacggcacctcgaccccaaaaaacttgattagggtgatggttcacgtagtgggccatcgccctgatagacggttttcg ccctttgacgttggagtccacgttcttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt
```

-continued

```
acaatttcaggtggcacttttcggggaaatgtgcgcggaaccccctatttgtttattttttctaaatacattcaaatatgtatccgctcatgaa
ttaattcttagaaaaactcatcgagcatcaaatgaaactgcaatttattcatatcaggattatcaataccatattttgaaaaagccgtttc
gatcctggtatcggtctgcgattccgactcgtccaacatcaatacaacctattaatttcccctcgtcaaaaataaggttatcaagtgagaaa
tgtaatgaaggagaaaactcaccgaggcagttccataggatggcaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaattaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatccttttttttctgcgcgtaatctgctgcttgcaaacaaaaaaaccaccgctaccagcggtgg
tttgtttgccggatcaagagctaccaactcttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacgggggttcgtgcacacagccca
gcttggagcgaacgacctacaccgaactgagataccctacagcgtgagctatgagaaagcgccacgcttcccgaagggagaaaggcggacagg
tatccggtaagcggcagggtcggaacaggagagcgcacgagggagcttccaggggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttcttttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacaccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaacccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggataaacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
```

-continued

```
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccaaggaatggtgcatgcaaggagat
ggcgcccaacagtccccggccacggggcctgccaccatacccacgccgaaacaagcgctcatgagcccgaagtggcgagcccgatcttccc
catcggtgatgtcggcgatataggcgccagcaaccgcacctgtggccgcggtgatgccggccacgatgcgtccggcgtagaggatcgagatc
tcgatcccgcgaaattaatacgactcactataggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgagtttctcaggaagcgttc
agcggcttcaaagaccaaaacggcaacttcctggagaacctgaaggaagatatcaaagctatcctgagcctgtacgaggccagcttcctggc
tctggaaggcgaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttgtttcgtaaccattatcgacgatatctacgatgtatacggcaccctg
gacgaactggagctgttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgcttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
gaaaaactgggtggtagcctgttcgcgaaaccgttcgtggaaaccgcgatcaacctggcacgtcaatctcactgcacttatcataacggcga
cgcgcatacctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

Amino acid sequence of MEA P. alba IspS A3T S288C TEV 6XHis

METRRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFCFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVITEPILPFERENLYFQG

LEHHHHHH

-continued

```
The sequence of SEQ ID NO: 2 is
METRRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFCFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVITEPILPFERENLYFQGLE

DNA sequence of pDW204 harboring MEA P. alba IspS A3T S288C TEV 6XHis
tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctccctttagggttc cgatttagtgctttacggcacctcgaccccaaaaaacttgattagggtgatggttcacgtagtgggccatcgccctgatagacggttttcg cccctttgacgttggagtccacgttctttaatagtggactcttgttccaaactggaacaacactcaacccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaaccccctatttgtttattttttctaaatacattcaaatatgtatccgctcatgaa ttaattcttagaaaaactcatcgagcatcaaatgaaactgcaatttattcatatcaggattatcaataccatattttttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttcttctcccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatccttttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagataacctacagcgtgagctatgagaaagcgccacgcttcccgaagggagaaaggcggacagg tatccggtaagcggcagggtcggaacaggagagcgcacgagggagcttccagggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggatttctgttcatgggggtaatgataccgatgaa
```

-continued

```
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcaccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcgggagagg
cggtttgcgtattgggcgccagggtggtttttcttttcaccagtgagacgggcaacagctgattgcccttcaccgcctggccctgagagagt
tgcagcaagcggtccacgctggtttgcccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggtgggaatgtaattcagctccgccatcgccgcttccacttttttccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggggaattgtgagcggataacaattcccctctagaaataattttgtttaactttaagaag
gagatatacatatggaaacgcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtctttccgtctgctgcgtcaacacggttttgagggtttctcaggaagcgttc
agcggcttcaaagaccaaaacggcaacttcctggagaaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttgtttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgcttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
```

-continued

```
gaaaaactgggtggtagcctgttcgcgaaaccgttcgtggaaaccgcgatcaacctggcacgtcaatctcactgcacttatcataacggcga cgcgcatacctctccggatgagctgacccgcaaacgcgttctgtctgtaatcactgaaccgattctgccgtttgaacgcgaaaacctgtatt ttcagggcctcgagcaccaccaccaccactgagatccggctgctaacaaagcccgaaaggaagctgagttggctgctgccaccgctgag caataactagcataacccttggggcctctaaacgggtcttgaggggttttttgctgaaaggaggaactatatccggat
```

Expression and Purification of MEA P. Alba A3T S288C
Expression of 6×His-tagged MEA P. Alba A3T S288C N-terminally 6×His-tagged MEA P. Alba A3T S288C was expressed and purified from strain DW614. The growth procedure is suitable for histidine tagged enzymes expressed in BL21(λDE3)pLysS cells. A 10 ml of overnight culture was prepared for each 1 L of planned growth. The appropriate antibiotics (50 mg/ml kanamycin, 50 mg/ml chloramphenicol) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the OD600 reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.
Purification of 6×his-Tagged MEA P. Alba A3T S288C For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM NaH2PO4, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM NaH2PO4, 300 mm NaCl, 20 mM imidazole, ph 8.0). The his-tagged IspS was then eluted from the column using a gradient from 0-100% Ni elution buffer (50 mM NaH2PO4, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE heathcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage of MEA P. Alba A3T S288C from Strain DW614

Strain DW614 is described above. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

Crystal Structure Determination

Construct DW614 was purified as described and a concentrated protein solution was then prepared for surveying possible crystallization conditions. The construct was purified independently and surveyed as described below. At a minimum, the construct was surveyed using the following commercial screens: the Crystal Screen from Hampton Research (Aliso Viejo, Calif.) and the JCSG+ Suite from Qiagen (Valencia, Calif.).

Initial crystallization screens were setup using the Crystal Screen from Hampton Research and the JCSG+ Suite from Qiagen. Crystals from this construct were observed in numerous conditions; optimization included 50 variations of pH, precipitating agents, and concentrations. From the optimization experiments, five different DW614 crystals were screened for diffraction. A crystal composed of MEA P. Alba A3T S288C was obtained that diffracted to 2.5 Å. The large, rod-shaped crystals belong to the tetragonal space group $P4_32_12$, and have unit cell dimensions a=b=156.84, c=143.41. The crystals were grown by mixing 2 μL of protein (9 mg/ml protein) with 2 μL of precipitant solution [0.2 M Malic Acid, pH 7.0, 8% (wt/vol) Polyethylene glycol 8000] and equilibrated against 500 μL of precipitant. Prior to flash-freezing the crystal in liquid nitrogen, the crystals were cryoprotected by swishing through 0.2 M Malic Acid, pH 7.0, 8% (wt/vol) Polyethylene glycol 8000, and 25% (wt/vol) ethylene glycol.

Figure 19:
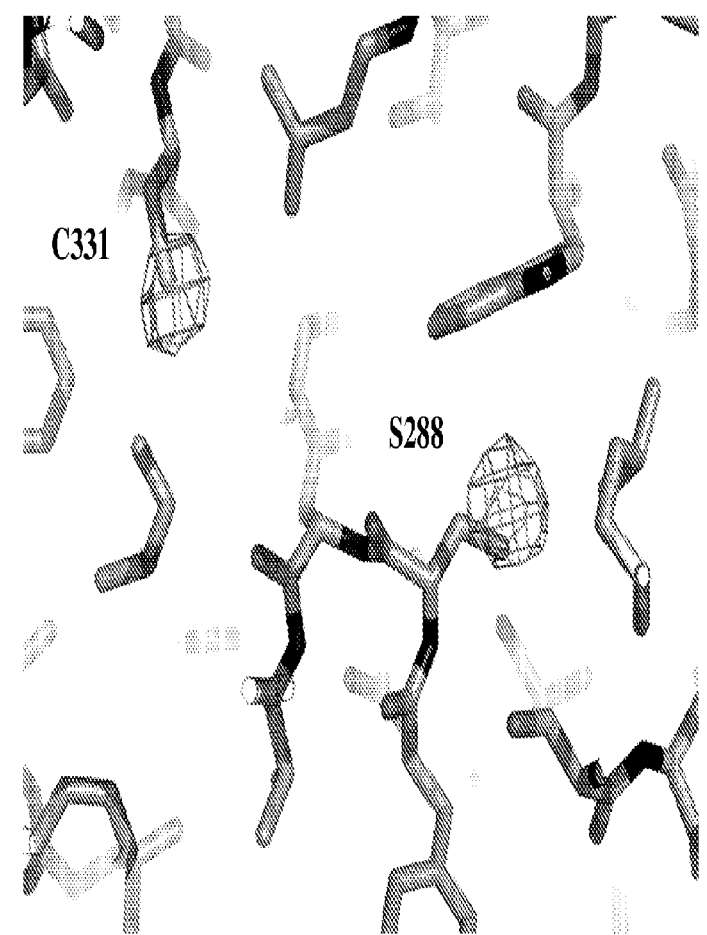
FIG. 19 shows wild type IspS with anomalous difference map contoured at 5σ showing location of sulfur atoms.

Single-wavelength anomalous dispersion data (SAD) were collected to verify the presence of the serine to cysteine substitution. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were phased with MOLREP (Vagin, A., and Teplyakov, A. (1997) J. of Appl. Crystallography 30, 1022-1025), using the previously determined structure of Isoprene synthase from P. alba as the starting model (US2009/0076743). The crystal contains one dimer in the asymmetric unit with a solvent content of 63%. The SAD data were phased using Phaser EP (Read, R. J., and McCoy, A. J. (2011) Acta Crystallographica Section D 67, 338-344). The resulting anomalous difference maps clearly indicate the presence of cysteine at position 288 (FIG. 19).

The same crystal was sent to Stanford Synchrotron Radiation Laboratory, and data were collected at Beamline 11-1 to 1.98 Å resolution. Data were processed as described above and were used for model refinement. Refinement with Refmac5 (Collaborative Computational Project, N. (1994) Acta Crystallographica Section D 50, 760-763) was used with iterative manual rebuilding steps using the visualization program Coot (Emsley, P., et al. (2010) Acta Crystallographica Section D 66, 486-501). During refinement, the geometry of the protein was checked using Molprobity (Davis, I. W., et al. (2007) Nucl. Acids Res., 35:W375-W383). The current model has an RWork value of 17.8% and an RFree value of 20.9%.

Figure 20:
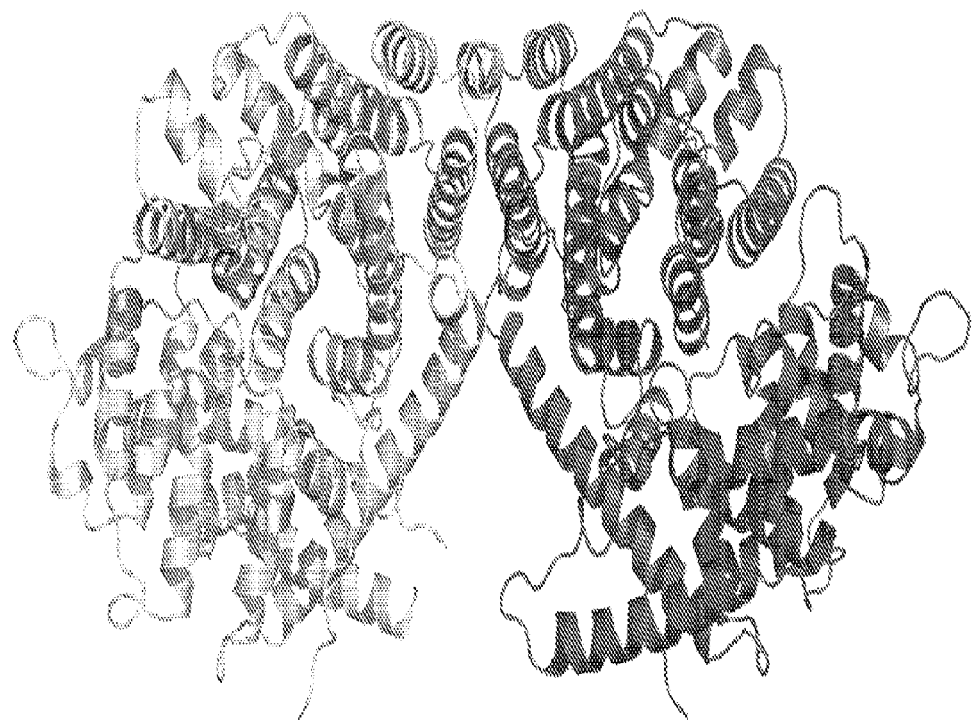
FIG. 20 shows dimer view of IspS variant A3T/S288C. Chain A is light gray, chain B is dark gray.
Figure 21:
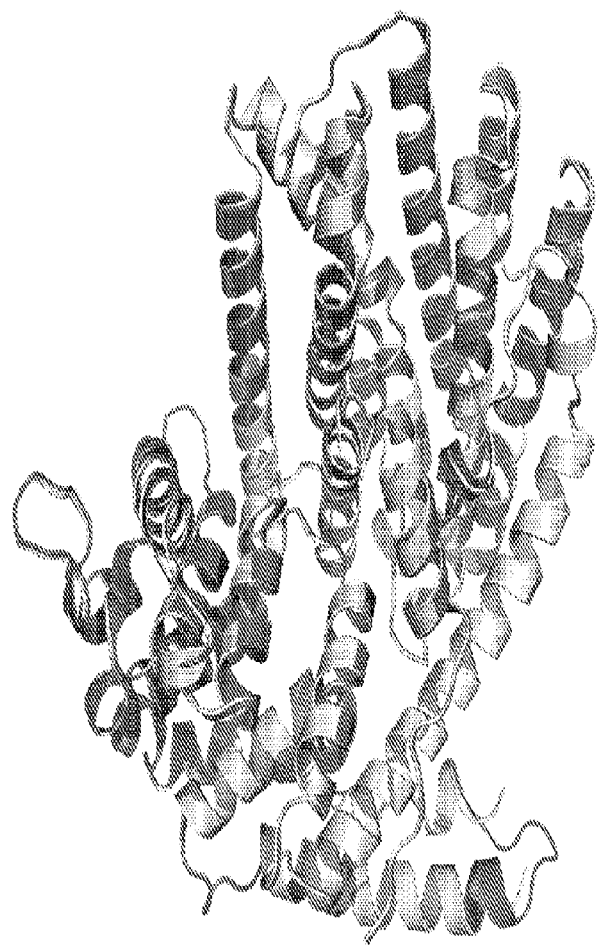
FIG. 21 shows a structural alignment of wild type IspS (dark gray) and variant A3T/S288C (light gray).
Figure 22:
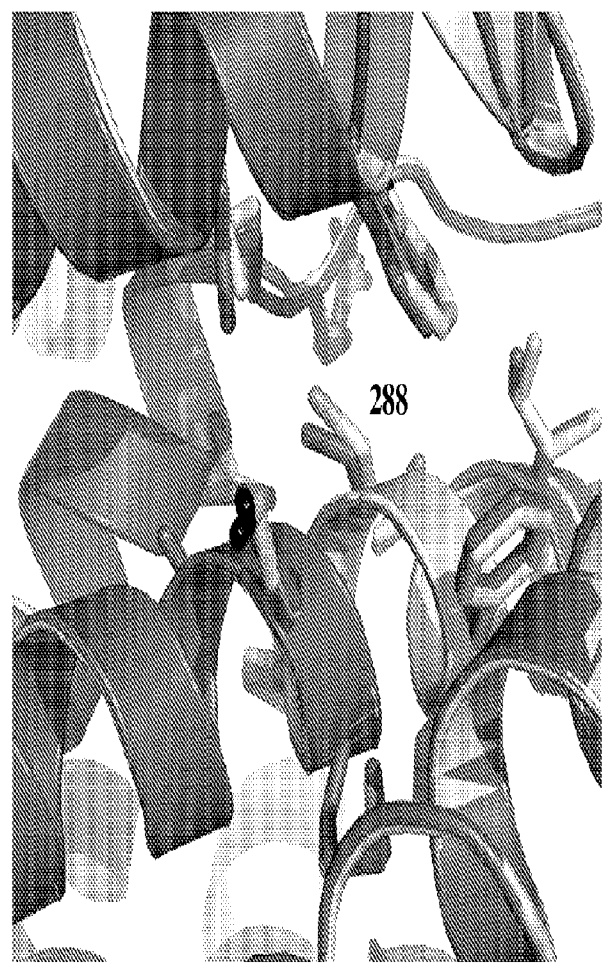
FIG. 22 shows a structural alignment of wild type IspS (light gray) and variant A3T/S288C (dark gray) showing environment around position 288.

The structure consists of a homo dimer in the asymmetric unit (FIG. 20). Each monomer is comprised of two helical domains, a C-terminal domain containing the active site and an N-terminal domain with unknown function. Structural alignment of the wild type IspS and MEA P. Alba A3T S288C shows that the overall fold is unchanged, though the variant structure contains a few residues that were disordered in the previous structure (FIG. 21). The replacement of serine with cysteine does not result in any local structural perturbations (FIG. 22). Coordinates are provided in Appendix A.

Example 5

Differences Between P. alba and Salix Spp. IspS Enzymes

Figure 25:
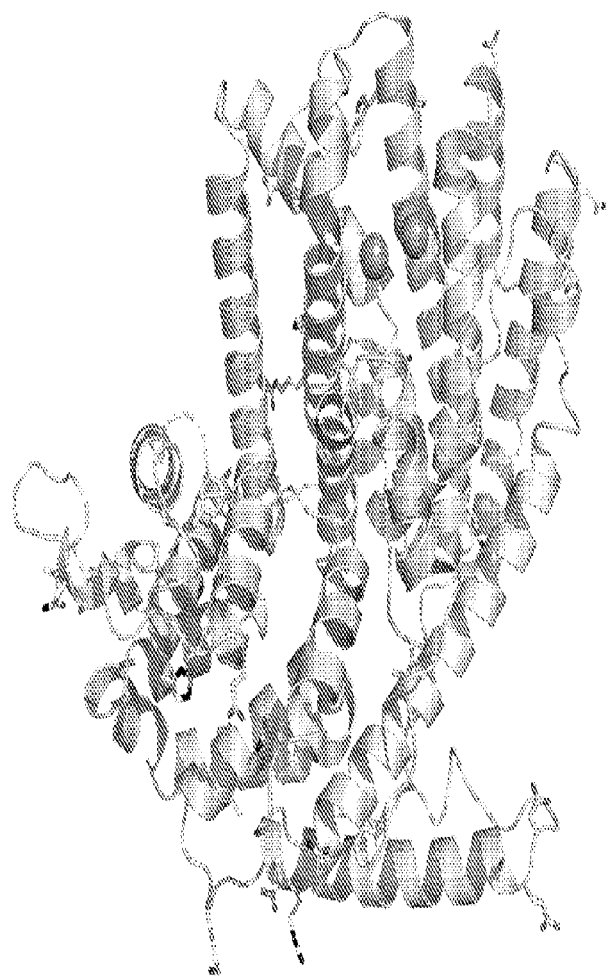
FIG. 25 shows positions where the sequence of *S. alba* differs from *P. alba* are highlighted. $Mg^{2+}$ (spheres) are placed based on a structural alignment with PDB 1N24.
Figure 26:
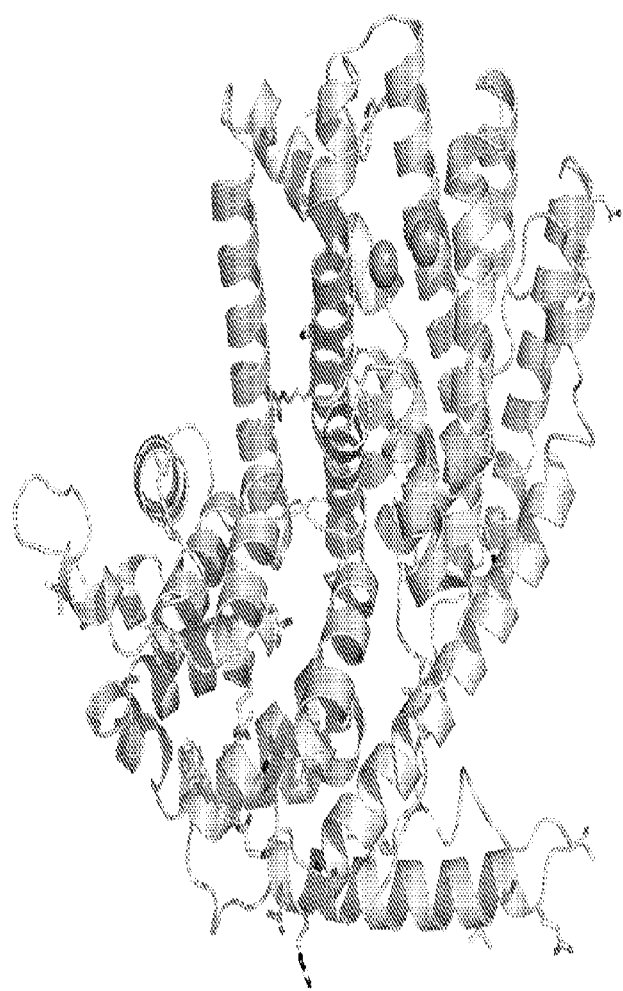
FIG. 26 shows positions where the sequence of *S. babylonica* differs from *P. alba* are highlighted. $Mg^{2+}$ (spheres) are placed based on a structural alignment with PDB 1N24.

Amino acid differences between MEA P. alba and Salix spp. IspS enzymes are listed in Table 12. Charge changes for individual amino acid substitutions are shown in Table 12, as well as % surface accessibility of each position in the crystal structure of MEA P. alba. Surface accessibility was calculated using the program MOE, which is written and supported by the Chemical Computing Group, Inc. An estimate for the water-accessible surface area of each residue was determined using a probe having a specified radius. The estimate was then compared against a library of peptides and the ratio between them was reported as the percent surface accessibility. Positions where the sequence of S. alba differs from P. alba are shown in FIG. 25. Positions where the sequence of S. babylonica differs from P. alba are shown in FIG. 26.

TABLE 12

Differences between P. alba and Salix spp. isoprene synthase enzymes. Charge changes and surface accessibilities of positions in the P. alba MEA crystal structure are indicated.

| Position | MEA P. alba | S. alba | S. babylonica | S. alba Δ Charge | S. babylonica Δ Charge | % Surface Accessibility |
|---|---|---|---|---|---|---|
| 3 | A | T | T | 0 | 0 | Not calc. |
| 6 | S | | T | | 0 | Not calc. |
| 24 | T | | N | | 0 | 84 |
| 25 | D | E | | 0 | | 55 |
| 26 | E | D | D | 0 | 0 | 86 |
| 27 | S | A | A | 0 | 0 | 65 |
| 30 | V | | L | | 0 | 60 |
| 39 | E | D | D | 0 | 0 | 13 |
| 44 | R | S | S | −1 | −1 | 55 |
| 45 | E | K | K | 2 | 2 | 31 |
| 50 | K | T | | −1 | | 89 |
| 56 | L | Q | Q | 0 | 0 | 5 |
| 62 | N | T | T | 0 | 0 | 13 |
| 63 | V | I | I | 0 | 0 | 0 |
| 78 | G | R | R | 1 | 1 | 29 |
| 80 | L | | I | | 0 | 0 |
| 83 | F | | Y | | 0 | 1 |
| 90 | D | E | E | 0 | 0 | 54 |
| 93 | T | A | A | 0 | 0 | 8 |
| 98 | H | Q | | 0 | | 10 |
| 99 | G | A | A | 0 | 0 | 0 |
| 118 | A | V | V | 0 | 0 | 10 |
| 120 | S | N | | 0 | | 52 |
| 130 | L | M | M | 0 | 0 | 33 |
| 132 | N | D | | −1 | | 63 |
| 140 | I | L | | 0 | | 1 |
| 144 | Y | H | | 0 | | 2 |
| 164 | A | T | T | 0 | 0 | 0 |
| 172 | S | N | N | 0 | 0 | 47 |
| 179 | E | D | D | 0 | 0 | 46 |
| 180 | L | M | | 0 | | 28 |
| 181 | A | V | | 0 | | 8 |
| 182 | E | | D | | 0 | 40 |
| 213 | D | | G | | 1 | 83 |
| 216 | Q | R | R | 1 | 1 | 45 |
| 217 | V | | A | | 0 | 20 |
| 229 | I | V | V | 0 | 0 | 0 |
| 281 | N | I | K | 0 | 1 | 10 |
| 304 | D | E | | 0 | | 66 |
| 319 | N | S | S | 0 | 0 | 37 |
| 321 | I | | V | | 0 | 3 |
| 322 | N | D | D | −1 | −1 | 54 |
| 349 | D | E | E | 0 | 0 | 64 |
| 374 | K | R | | 0 | | 23 |
| 375 | W | F | F | 0 | 0 | 14 |
| 385 | D | S | | 1 | | 47 |

TABLE 12-continued

Differences between *P. alba* and *Salix* spp. isoprene synthase enzymes. Charge changes and surface accessibilities of positions in the *P. alba* MEA crystal structure are indicated.

| Position | MEA *P. alba* | *S. alba* | *S. babylonica* | *S. alba* Δ Charge | *S. babylonica* Δ Charge | % Surface Accessibility |
|---|---|---|---|---|---|---|
| 417 | I | T | T | 0 | 0 | 6 |
| 421 | Q | L |   |   | 0 | 23 |
| 426 | T | I | I | 0 | 0 | 0 |
| 429 | R | W | W | −1 | −1 | 5 |
| 432 | H | Y | Y | 0 | 0 | 6 |
| 460 | M |   | I |   | 0 | 21 |
| 490 | L |   | V |   | 0 | 19 |
| 492 | G | D | D | −1 | −1 | 89 |
| 498 | P | H | Q | 0 | 0 | 57 |
| 542 | F | L |   |   | 0 | 17 |

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

APPENDIX A

*P. alba* 3T288C coordinates

| ATOM | 1 | N | SER | A | 6 | 57.986 | −35.273 | −30.156 | 1.00 | 72.58 | A | N |
| ATOM | 2 | CA | SER | A | 6 | 58.480 | −33.880 | −30.355 | 1.00 | 68.61 | A | C |
| ATOM | 3 | CB | SER | A | 6 | 57.316 | −32.894 | −30.340 | 1.00 | 61.40 | A | C |
| ATOM | 4 | OG | SER | A | 6 | 57.743 | −31.589 | −30.698 | 1.00 | 58.19 | A | O |
| ATOM | 5 | C | SER | A | 6 | 59.509 | −33.500 | −29.283 | 1.00 | 75.11 | A | C |
| ATOM | 6 | O | SER | A | 6 | 59.271 | −33.694 | −28.080 | 1.00 | 66.06 | A | O |
| ATOM | 7 | N | ALA | A | 7 | 60.650 | −32.967 | −29.734 | 1.00 | 55.83 | A | N |
| ATOM | 8 | CA | ALA | A | 7 | 61.745 | −32.563 | −28.846 | 1.00 | 37.95 | A | C |
| ATOM | 9 | CB | ALA | A | 7 | 63.101 | −32.683 | −29.571 | 1.00 | 35.03 | A | C |
| ATOM | 10 | C | ALA | A | 7 | 61.520 | −31.137 | −28.346 | 1.00 | 34.22 | A | C |
| ATOM | 11 | O | ALA | A | 7 | 60.884 | −30.305 | −29.015 | 1.00 | 33.25 | A | O |
| ATOM | 12 | N | ASN | A | 8 | 62.042 | −30.855 | −27.159 | 1.00 | 31.53 | A | N |
| ATOM | 13 | CA | ASN | A | 8 | 62.004 | −29.521 | −26.602 | 1.00 | 41.19 | A | C |
| ATOM | 14 | CB | ASN | A | 8 | 61.256 | −29.534 | −25.259 | 1.00 | 43.35 | A | C |
| ATOM | 15 | CG | ASN | A | 8 | 61.257 | −28.175 | −24.574 | 1.00 | 38.99 | A | C |
| ATOM | 16 | OD1 | ASN | A | 8 | 61.277 | −27.124 | −25.221 | 1.00 | 47.85 | A | O |
| ATOM | 17 | ND2 | ASN | A | 8 | 61.227 | −28.195 | −23.246 | 1.00 | 65.44 | A | N |
| ATOM | 18 | C | ASN | A | 8 | 63.431 | −29.020 | −26.417 | 1.00 | 39.96 | A | C |
| ATOM | 19 | O | ASN | A | 8 | 64.147 | −29.495 | −25.529 | 1.00 | 46.00 | A | O |
| ATOM | 20 | N | TYR | A | 9 | 63.845 | −28.090 | −27.272 | 1.00 | 34.27 | A | N |
| ATOM | 21 | CA | TYR | A | 9 | 65.157 | −27.460 | −27.165 | 1.00 | 35.68 | A | C |
| ATOM | 22 | CB | TYR | A | 9 | 65.835 | −27.435 | −28.549 | 1.00 | 30.73 | A | C |
| ATOM | 23 | CG | TYR | A | 9 | 66.034 | −28.818 | −29.146 | 1.00 | 27.98 | A | C |
| ATOM | 24 | CD1 | TYR | A | 9 | 66.744 | −29.815 | −28.449 | 1.00 | 22.86 | A | C |
| ATOM | 25 | CE1 | TYR | A | 9 | 66.919 | −31.070 | −28.996 | 1.00 | 23.00 | A | C |
| ATOM | 26 | CZ | TYR | A | 9 | 66.392 | −31.361 | −30.263 | 1.00 | 19.46 | A | C |
| ATOM | 27 | OH | TYR | A | 9 | 66.559 | −32.617 | −30.842 | 1.00 | 19.25 | A | O |
| ATOM | 28 | CE2 | TYR | A | 9 | 65.680 | −30.412 | −30.944 | 1.00 | 20.38 | A | C |
| ATOM | 29 | CD2 | TYR | A | 9 | 65.515 | −29.138 | −30.403 | 1.00 | 20.74 | A | C |
| ATOM | 30 | C | TYR | A | 9 | 65.053 | −26.029 | −26.583 | 1.00 | 39.07 | A | C |
| ATOM | 31 | O | TYR | A | 9 | 66.045 | −25.297 | −26.512 | 1.00 | 42.20 | A | O |
| ATOM | 32 | N | GLU | A | 10 | 63.862 | −25.632 | −26.144 | 1.00 | 43.68 | A | N |
| ATOM | 33 | CA | GLU | A | 10 | 63.653 | −24.239 | −25.734 | 1.00 | 51.14 | A | C |
| ATOM | 34 | CB | GLU | A | 10 | 62.175 | −23.842 | −25.891 | 1.00 | 63.92 | A | C |
| ATOM | 35 | CG | GLU | A | 10 | 61.624 | −24.061 | −27.347 | 1.00 | 73.92 | A | C |
| ATOM | 36 | CD | GLU | A | 10 | 62.612 | −23.648 | −28.477 | 1.00 | 85.85 | A | C |
| ATOM | 37 | OE1 | GLU | A | 10 | 63.165 | −22.528 | −28.397 | 1.00 | 73.86 | A | O |
| ATOM | 38 | OE2 | GLU | A | 10 | 62.831 | −24.435 | −29.443 | 1.00 | 75.20 | A | O |
| ATOM | 39 | C | GLU | A | 10 | 64.198 | −24.048 | −24.323 | 1.00 | 37.85 | A | C |
| ATOM | 40 | O | GLU | A | 10 | 64.234 | −24.992 | −23.557 | 1.00 | 32.89 | A | O |
| ATOM | 41 | N | PRO | A | 11 | 64.689 | −22.845 | −24.000 | 1.00 | 44.76 | A | N |
| ATOM | 42 | CA | PRO | A | 11 | 65.387 | −22.665 | −22.723 | 1.00 | 46.27 | A | C |
| ATOM | 43 | CB | PRO | A | 11 | 66.119 | −21.335 | −22.922 | 1.00 | 54.27 | A | C |
| ATOM | 44 | CG | PRO | A | 11 | 65.182 | −20.535 | −23.821 | 1.00 | 55.02 | A | C |
| ATOM | 45 | CD | PRO | A | 11 | 64.500 | −21.564 | −24.721 | 1.00 | 51.34 | A | C |
| ATOM | 46 | C | PRO | A | 11 | 64.411 | −22.569 | −21.533 | 1.00 | 42.77 | A | C |
| ATOM | 47 | O | PRO | A | 11 | 63.275 | −22.169 | −21.729 | 1.00 | 45.64 | A | O |
| ATOM | 48 | N | ASN | A | 12 | 64.852 | −22.959 | −20.334 | 1.00 | 36.56 | A | N |
| ATOM | 49 | CA | ASN | A | 12 | 64.098 | −22.713 | −19.087 | 1.00 | 37.47 | A | C |
| ATOM | 50 | CB | ASN | A | 12 | 64.272 | −23.862 | −18.096 | 1.00 | 38.59 | A | C |

APPENDIX A-continued

*P. alba* 3T288C coordinates

| ATOM | 51 | CG | ASN | A | 12 | 64.111 | −25.195 | −18.745 | 1.00 | 49.28 | A | C |
|---|---|---|---|---|---|---|---|---|---|---|---|---|
| ATOM | 52 | OD1 | ASN | A | 12 | 62.997 | −25.608 | −19.041 | 1.00 | 50.88 | A | O |
| ATOM | 53 | ND2 | ASN | A | 12 | 65.227 | −25.877 | −19.000 | 1.00 | 52.57 | A | N |
| ATOM | 54 | C | ASN | A | 12 | 64.496 | −21.418 | −18.389 | 1.00 | 38.56 | A | C |
| ATOM | 55 | O | ASN | A | 12 | 65.646 | −20.955 | −18.485 | 1.00 | 31.10 | A | O |
| ATOM | 56 | N | SER | A | 13 | 63.541 | −20.847 | −17.650 | 1.00 | 38.39 | A | N |
| ATOM | 57 | CA | SER | A | 13 | 63.768 | −19.565 | −16.967 | 1.00 | 47.84 | A | C |
| ATOM | 58 | CB | SER | A | 13 | 62.462 | −19.064 | −16.345 | 1.00 | 42.98 | A | C |
| ATOM | 59 | OG | SER | A | 13 | 61.847 | −20.123 | −15.628 | 1.00 | 43.24 | A | O |
| ATOM | 60 | C | SER | A | 13 | 64.844 | −19.690 | −15.885 | 1.00 | 39.53 | A | C |
| ATOM | 61 | O | SER | A | 13 | 65.430 | −18.690 | −15.484 | 1.00 | 39.12 | A | O |
| ATOM | 62 | N | TRP | A | 14 | 65.106 | −20.923 | −15.437 | 1.00 | 31.26 | A | N |
| ATOM | 63 | CA | TRP | A | 14 | 66.150 | −21.196 | −14.425 | 1.00 | 34.62 | A | C |
| ATOM | 64 | CB | TRP | A | 14 | 65.588 | −22.154 | −13.360 | 1.00 | 31.14 | A | C |
| ATOM | 65 | CG | TRP | A | 14 | 64.834 | −23.336 | −13.913 | 1.00 | 37.51 | A | C |
| ATOM | 66 | CD1 | TRP | A | 14 | 63.461 | −23.457 | −14.081 | 1.00 | 46.88 | A | C |
| ATOM | 67 | NE1 | TRP | A | 14 | 63.143 | −24.667 | −14.618 | 1.00 | 48.46 | A | N |
| ATOM | 68 | CE2 | TRP | A | 14 | 64.251 | −25.407 | −14.820 | 1.00 | 39.74 | A | C |
| ATOM | 69 | CD2 | TRP | A | 14 | 65.385 | −24.609 | −14.375 | 1.00 | 30.24 | A | C |
| ATOM | 70 | CE3 | TRP | A | 14 | 66.651 | −25.128 | −14.491 | 1.00 | 47.63 | A | C |
| ATOM | 71 | CZ3 | TRP | A | 14 | 66.803 | −26.425 | −15.013 | 1.00 | 54.86 | A | C |
| ATOM | 72 | CH2 | TRP | A | 14 | 65.705 | −27.181 | −15.419 | 1.00 | 55.53 | A | C |
| ATOM | 73 | CZ2 | TRP | A | 14 | 64.403 | −26.682 | −15.326 | 1.00 | 52.45 | A | C |
| ATOM | 74 | C | TRP | A | 14 | 67.500 | −21.691 | −14.975 | 1.00 | 35.77 | A | C |
| ATOM | 75 | O | TRP | A | 14 | 68.442 | −21.945 | −14.213 | 1.00 | 29.88 | A | O |
| ATOM | 76 | N | ASP | A | 15 | 67.634 | −21.833 | −16.294 | 1.00 | 31.54 | A | N |
| ATOM | 77 | CA | ASP | A | 15 | 68.926 | −22.238 | −16.858 | 1.00 | 30.12 | A | C |
| ATOM | 78 | CB | ASP | A | 15 | 68.886 | −22.314 | −18.387 | 1.00 | 35.22 | A | C |
| ATOM | 79 | CG | ASP | A | 15 | 68.006 | −23.457 | −18.916 | 1.00 | 35.51 | A | C |
| ATOM | 80 | OD1 | ASP | A | 15 | 67.780 | −24.458 | −18.212 | 1.00 | 39.20 | A | O |
| ATOM | 81 | OD2 | ASP | A | 15 | 67.562 | −23.353 | −20.077 | 1.00 | 46.90 | A | O |
| ATOM | 82 | C | ASP | A | 15 | 70.003 | −21.240 | −16.427 | 1.00 | 29.97 | A | C |
| ATOM | 83 | O | ASP | A | 15 | 69.726 | −20.035 | −16.282 | 1.00 | 27.48 | A | O |
| ATOM | 84 | N | TYR | A | 16 | 71.222 | −21.742 | −16.220 | 1.00 | 24.88 | A | N |
| ATOM | 85 | CA | TYR | A | 16 | 72.355 | −20.905 | −15.817 | 1.00 | 27.41 | A | C |
| ATOM | 86 | CB | TYR | A | 16 | 73.587 | −21.740 | −15.393 | 1.00 | 24.08 | A | C |
| ATOM | 87 | CG | TYR | A | 16 | 73.367 | −22.522 | −14.085 | 1.00 | 21.97 | A | C |
| ATOM | 88 | CD1 | TYR | A | 16 | 73.002 | −21.865 | −12.899 | 1.00 | 20.51 | A | C |
| ATOM | 89 | CE1 | TYR | A | 16 | 72.795 | −22.573 | −11.715 | 1.00 | 17.26 | A | C |
| ATOM | 90 | CZ | TYR | A | 16 | 72.923 | −23.922 | −11.715 | 1.00 | 18.76 | A | C |
| ATOM | 91 | OH | TYR | A | 16 | 72.722 | −24.624 | −10.573 | 1.00 | 23.38 | A | O |
| ATOM | 92 | CE2 | TYR | A | 16 | 73.269 | −24.611 | −12.869 | 1.00 | 20.65 | A | C |
| ATOM | 93 | CD2 | TYR | A | 16 | 73.511 | −23.906 | −14.045 | 1.00 | 21.95 | A | C |
| ATOM | 94 | C | TYR | A | 16 | 72.731 | −19.918 | −16.906 | 1.00 | 29.38 | A | C |
| ATOM | 95 | O | TYR | A | 16 | 73.185 | −18.812 | −16.600 | 1.00 | 32.24 | A | O |
| ATOM | 96 | N | ASP | A | 17 | 72.561 | −20.310 | −18.168 | 1.00 | 28.07 | A | N |
| ATOM | 97 | CA | ASP | A | 17 | 72.813 | −19.388 | −19.284 | 1.00 | 37.53 | A | C |
| ATOM | 98 | CB | ASP | A | 17 | 72.589 | −20.099 | −20.623 | 1.00 | 33.68 | A | C |
| ATOM | 99 | CG | ASP | A | 17 | 73.757 | −21.003 | −21.016 | 1.00 | 33.51 | A | C |
| ATOM | 100 | OD1 | ASP | A | 17 | 74.920 | −20.713 | −20.659 | 1.00 | 39.78 | A | O |
| ATOM | 101 | OD2 | ASP | A | 17 | 73.506 | −22.002 | −21.718 | 1.00 | 33.90 | A | O |
| ATOM | 102 | C | ASP | A | 17 | 71.927 | −18.126 | −19.150 | 1.00 | 38.47 | A | C |
| ATOM | 103 | O | ASP | A | 17 | 72.400 | −17.000 | −19.350 | 1.00 | 39.61 | A | O |
| ATOM | 104 | N | TYR | A | 18 | 70.667 | −18.356 | −18.773 | 1.00 | 36.67 | A | N |
| ATOM | 105 | CA | TYR | A | 18 | 69.679 | −17.312 | −18.474 | 1.00 | 38.99 | A | C |
| ATOM | 106 | CB | TYR | A | 18 | 68.322 | −18.001 | −18.304 | 1.00 | 57.51 | A | C |
| ATOM | 107 | CG | TYR | A | 18 | 67.110 | −17.380 | −18.946 | 1.00 | 76.08 | A | C |
| ATOM | 108 | CD1 | TYR | A | 18 | 66.449 | −16.309 | −18.344 | 1.00 | 93.77 | A | C |
| ATOM | 109 | CE1 | TYR | A | 18 | 65.305 | −15.764 | −18.914 | 1.00 | 99.10 | A | C |
| ATOM | 110 | CZ | TYR | A | 18 | 64.795 | −16.315 | −20.081 | 1.00 | 101.95 | A | C |
| ATOM | 111 | OH | TYR | A | 18 | 63.667 | −15.777 | −20.644 | 1.00 | 100.31 | A | O |
| ATOM | 112 | CE2 | TYR | A | 18 | 65.417 | −17.397 | −20.684 | 1.00 | 93.17 | A | C |
| ATOM | 113 | CD2 | TYR | A | 18 | 66.560 | −17.931 | −20.108 | 1.00 | 85.18 | A | C |
| ATOM | 114 | C | TYR | A | 18 | 70.049 | −16.539 | −17.174 | 1.00 | 42.81 | A | C |
| ATOM | 115 | O | TYR | A | 18 | 70.299 | −15.343 | −17.213 | 1.00 | 34.84 | A | O |
| ATOM | 116 | N | LEU | A | 19 | 70.122 | −17.235 | −16.032 | 1.00 | 39.87 | A | N |
| ATOM | 117 | CA | LEU | A | 19 | 70.283 | −16.598 | −14.704 | 1.00 | 38.49 | A | C |
| ATOM | 118 | CB | LEU | A | 19 | 69.875 | −17.580 | −13.586 | 1.00 | 34.82 | A | C |
| ATOM | 119 | CG | LEU | A | 19 | 68.416 | −18.018 | −13.434 | 1.00 | 37.78 | A | C |
| ATOM | 120 | CD1 | LEU | A | 19 | 68.275 | −19.058 | −12.276 | 1.00 | 29.08 | A | C |
| ATOM | 121 | CD2 | LEU | A | 19 | 67.489 | −16.786 | −13.219 | 1.00 | 30.96 | A | C |
| ATOM | 122 | C | LEU | A | 19 | 71.695 | −16.041 | −14.373 | 1.00 | 40.09 | A | C |
| ATOM | 123 | O | LEU | A | 19 | 71.822 | −15.105 | −13.588 | 1.00 | 36.68 | A | O |
| ATOM | 124 | N | LEU | A | 20 | 72.748 | −16.645 | −14.916 | 1.00 | 38.96 | A | N |
| ATOM | 125 | CA | LEU | A | 20 | 74.113 | −16.187 | −14.645 | 1.00 | 43.59 | A | C |
| ATOM | 126 | CB | LEU | A | 20 | 75.023 | −17.350 | −14.186 | 1.00 | 42.50 | A | C |
| ATOM | 127 | CG | LEU | A | 20 | 74.766 | −18.088 | −12.860 | 1.00 | 42.59 | A | C |
| ATOM | 128 | CD1 | LEU | A | 20 | 75.842 | −19.151 | −12.616 | 1.00 | 34.09 | A | C |

APPENDIX A-continued

*P. alba* 3T288C coordinates

| ATOM | 129 | CD2 | LEU | A | 20 | 74.697 | −17.094 | −11.706 | 1.00 | 45.62 | A | C |
|------|-----|-----|-----|---|----|--------|---------|---------|------|-------|---|---|
| ATOM | 130 | C | LEU | A | 20 | 74.706 | −15.498 | −15.885 | 1.00 | 50.43 | A | C |
| ATOM | 131 | O | LEU | A | 20 | 75.718 | −15.945 | −16.436 | 1.00 | 43.53 | A | O |
| ATOM | 132 | N | SER | A | 21 | 74.056 | −14.433 | −16.339 | 1.00 | 66.73 | A | N |
| ATOM | 133 | CA | SER | A | 21 | 74.699 | −13.479 | −17.256 | 1.00 | 77.64 | A | C |
| ATOM | 134 | CB | SER | A | 21 | 74.005 | −13.478 | −18.617 | 1.00 | 70.83 | A | C |
| ATOM | 135 | OG | SER | A | 21 | 74.122 | −14.749 | −19.235 | 1.00 | 68.52 | A | O |
| ATOM | 136 | C | SER | A | 21 | 74.719 | −12.077 | −16.645 | 1.00 | 88.35 | A | C |
| ATOM | 137 | O | SER | A | 21 | 75.120 | −11.118 | −17.305 | 1.00 | 98.79 | A | O |
| ATOM | 138 | N | SER | A | 22 | 74.305 | −11.976 | −15.379 | 1.00 | 97.10 | A | N |
| ATOM | 139 | CA | SER | A | 22 | 74.314 | −10.721 | −14.634 | 1.00 | 99.45 | A | C |
| ATOM | 140 | CB | SER | A | 22 | 73.092 | −9.875 | −14.992 | 1.00 | 94.35 | A | C |
| ATOM | 141 | OG | SER | A | 22 | 72.999 | −8.745 | −14.147 | 1.00 | 89.75 | A | O |
| ATOM | 142 | C | SER | A | 22 | 74.340 | −11.011 | −13.134 | 1.00 | 93.31 | A | C |
| ATOM | 143 | O | SER | A | 22 | 75.174 | −11.787 | −12.661 | 1.00 | 86.27 | A | O |
| ATOM | 144 | N | GLU | A | 26 | 81.547 | −9.426 | −13.066 | 1.00 | 77.98 | A | N |
| ATOM | 145 | CA | GLU | A | 26 | 81.323 | −9.634 | −14.494 | 1.00 | 81.96 | A | C |
| ATOM | 146 | CB | GLU | A | 26 | 81.137 | −8.290 | −15.197 | 1.00 | 81.82 | A | C |
| ATOM | 147 | CG | GLU | A | 26 | 79.899 | −7.547 | −14.719 | 1.00 | 83.63 | A | C |
| ATOM | 148 | CD | GLU | A | 26 | 79.387 | −6.539 | −15.730 | 1.00 | 86.04 | A | C |
| ATOM | 149 | OE1 | GLU | A | 26 | 80.202 | −5.766 | −16.271 | 1.00 | 81.48 | A | O |
| ATOM | 150 | OE2 | GLU | A | 26 | 78.164 | −6.518 | −15.982 | 1.00 | 99.87 | A | O |
| ATOM | 151 | C | GLU | A | 26 | 82.403 | −10.494 | −15.184 | 1.00 | 82.65 | A | C |
| ATOM | 152 | O | GLU | A | 26 | 82.764 | −10.263 | −16.341 | 1.00 | 72.41 | A | O |
| ATOM | 153 | N | SER | A | 27 | 82.936 | −11.463 | −14.447 | 1.00 | 83.75 | A | N |
| ATOM | 154 | CA | SER | A | 27 | 83.361 | −12.726 | −15.039 | 1.00 | 81.10 | A | C |
| ATOM | 155 | CB | SER | A | 27 | 84.878 | −12.932 | −14.991 | 1.00 | 78.85 | A | C |
| ATOM | 156 | OG | SER | A | 27 | 85.289 | −13.594 | −13.814 | 1.00 | 78.66 | A | O |
| ATOM | 157 | C | SER | A | 27 | 82.577 | −13.797 | −14.276 | 1.00 | 94.31 | A | C |
| ATOM | 158 | O | SER | A | 27 | 83.095 | −14.861 | −13.927 | 1.00 | 100.03 | A | O |
| ATOM | 159 | N | ILE | A | 28 | 81.306 | −13.470 | −14.017 | 1.00 | 92.06 | A | N |
| ATOM | 160 | CA | ILE | A | 28 | 80.292 | −14.426 | −13.590 | 1.00 | 83.46 | A | C |
| ATOM | 161 | CB | ILE | A | 28 | 78.923 | −13.698 | −13.339 | 1.00 | 79.85 | A | C |
| ATOM | 162 | CG1 | ILE | A | 28 | 78.999 | −12.785 | −12.096 | 1.00 | 75.89 | A | C |
| ATOM | 163 | CD1 | ILE | A | 28 | 79.113 | −13.507 | −10.743 | 1.00 | 64.21 | A | C |
| ATOM | 164 | CG2 | ILE | A | 28 | 77.773 | −14.681 | −13.196 | 1.00 | 77.42 | A | C |
| ATOM | 165 | C | ILE | A | 28 | 80.183 | −15.522 | −14.671 | 1.00 | 84.44 | A | C |
| ATOM | 166 | O | ILE | A | 28 | 79.486 | −16.521 | −14.489 | 1.00 | 75.29 | A | O |
| ATOM | 167 | N | GLU | A | 29 | 80.872 | −15.294 | −15.796 | 1.00 | 79.42 | A | N |
| ATOM | 168 | CA | GLU | A | 29 | 81.163 | −16.298 | −16.833 | 1.00 | 69.34 | A | C |
| ATOM | 169 | CB | GLU | A | 29 | 82.075 | −15.677 | −17.898 | 1.00 | 70.95 | A | C |
| ATOM | 170 | CG | GLU | A | 29 | 81.339 | −14.975 | −19.010 | 1.00 | 80.65 | A | C |
| ATOM | 171 | CD | GLU | A | 29 | 80.700 | −15.953 | −19.977 | 1.00 | 78.28 | A | C |
| ATOM | 172 | OE1 | GLU | A | 29 | 81.451 | −16.734 | −20.604 | 1.00 | 63.52 | A | O |
| ATOM | 173 | OE2 | GLU | A | 29 | 79.454 | −15.938 | −20.109 | 1.00 | 67.73 | A | O |
| ATOM | 174 | C | GLU | A | 29 | 81.848 | −17.570 | −16.343 | 1.00 | 67.94 | A | C |
| ATOM | 175 | O | GLU | A | 29 | 81.490 | −18.677 | −16.759 | 1.00 | 54.47 | A | O |
| ATOM | 176 | N | VAL | A | 30 | 82.867 | −17.408 | −15.503 | 1.00 | 66.57 | A | N |
| ATOM | 177 | CA | VAL | A | 30 | 83.629 | −18.554 | −15.006 | 1.00 | 55.26 | A | C |
| ATOM | 178 | CB | VAL | A | 30 | 85.025 | −18.151 | −14.446 | 1.00 | 50.13 | A | C |
| ATOM | 179 | CG1 | VAL | A | 30 | 85.940 | −19.367 | −14.387 | 1.00 | 43.43 | A | C |
| ATOM | 180 | CG2 | VAL | A | 30 | 85.669 | −17.054 | −15.305 | 1.00 | 49.92 | A | C |
| ATOM | 181 | C | VAL | A | 30 | 82.793 | −19.297 | −13.954 | 1.00 | 45.40 | A | C |
| ATOM | 182 | O | VAL | A | 30 | 82.865 | −20.523 | −13.870 | 1.00 | 43.51 | A | O |
| ATOM | 183 | N | TYR | A | 31 | 81.998 | −18.548 | −13.177 | 1.00 | 41.39 | A | N |
| ATOM | 184 | CA | TYR | A | 31 | 80.996 | −19.102 | −12.240 | 1.00 | 43.11 | A | C |
| ATOM | 185 | CB | TYR | A | 31 | 80.376 | −17.939 | −11.430 | 1.00 | 47.10 | A | C |
| ATOM | 186 | CG | TYR | A | 31 | 79.407 | −18.221 | −10.261 | 1.00 | 54.66 | A | C |
| ATOM | 187 | CD1 | TYR | A | 31 | 79.865 | −18.624 | −8.995 | 1.00 | 55.24 | A | C |
| ATOM | 188 | CE1 | TYR | A | 31 | 78.948 | −18.818 | −7.896 | 1.00 | 58.05 | A | C |
| ATOM | 189 | CZ | TYR | A | 31 | 77.565 | −18.576 | −8.070 | 1.00 | 70.02 | A | C |
| ATOM | 190 | OH | TYR | A | 31 | 76.618 | −18.756 | −7.021 | 1.00 | 31.58 | A | O |
| ATOM | 191 | CE2 | TYR | A | 31 | 77.116 | −18.143 | −9.324 | 1.00 | 70.34 | A | C |
| ATOM | 192 | CD2 | TYR | A | 31 | 78.033 | −17.951 | −10.394 | 1.00 | 69.01 | A | C |
| ATOM | 193 | C | TYR | A | 31 | 79.915 | −19.902 | −13.011 | 1.00 | 38.65 | A | C |
| ATOM | 194 | O | TYR | A | 31 | 79.559 | −21.013 | −12.620 | 1.00 | 30.30 | A | O |
| ATOM | 195 | N | LYS | A | 32 | 79.419 | −19.335 | −14.115 | 1.00 | 37.41 | A | N |
| ATOM | 196 | CA | LYS | A | 32 | 78.408 | −19.989 | −14.969 | 1.00 | 32.39 | A | C |
| ATOM | 197 | CB | LYS | A | 32 | 77.920 | −19.032 | −16.068 | 1.00 | 34.41 | A | C |
| ATOM | 198 | CG | LYS | A | 32 | 77.173 | −19.718 | −17.212 | 1.00 | 40.68 | A | C |
| ATOM | 199 | CD | LYS | A | 32 | 76.327 | −18.748 | −18.034 | 1.00 | 49.83 | A | C |
| ATOM | 200 | CE | LYS | A | 32 | 77.138 | −17.767 | −18.852 | 1.00 | 49.40 | A | C |
| ATOM | 201 | NZ | LYS | A | 32 | 77.502 | −18.323 | −20.169 | 1.00 | 53.46 | A | N |
| ATOM | 202 | C | LYS | A | 32 | 78.932 | −21.292 | −15.586 | 1.00 | 24.83 | A | C |
| ATOM | 203 | O | LYS | A | 32 | 78.275 | −22.315 | −15.500 | 1.00 | 25.50 | A | O |
| ATOM | 204 | N | ASP | A | 33 | 80.109 | −21.262 | −16.194 | 1.00 | 24.37 | A | N |
| ATOM | 205 | CA | ASP | A | 33 | 80.701 | −22.478 | −16.752 | 1.00 | 25.75 | A | C |
| ATOM | 206 | CB | ASP | A | 33 | 82.001 | −22.192 | −17.499 | 1.00 | 33.04 | A | C |

APPENDIX A-continued

*P. alba* 3T288C coordinates

| ATOM | 207 | CG | ASP | A | 33 | 81.767 | −21.560 | −18.869 | 1.00 | 40.42 | A | C |
|---|---|---|---|---|---|---|---|---|---|---|---|---|
| ATOM | 208 | OD1 | ASP | A | 33 | 80.634 | −21.654 | −19.398 | 1.00 | 45.69 | A | O |
| ATOM | 209 | OD2 | ASP | A | 33 | 82.729 | −20.981 | −19.421 | 1.00 | 41.92 | A | O |
| ATOM | 210 | C | ASP | A | 33 | 80.941 | −23.532 | −15.677 | 1.00 | 29.91 | A | C |
| ATOM | 211 | O | ASP | A | 33 | 80.847 | −24.721 | −15.956 | 1.00 | 22.59 | A | O |
| ATOM | 212 | N | LYS | A | 34 | 81.229 | −23.088 | −14.454 | 1.00 | 28.83 | A | N |
| ATOM | 213 | CA | LYS | A | 34 | 81.440 | −23.997 | −13.335 | 1.00 | 27.61 | A | C |
| ATOM | 214 | CB | LYS | A | 34 | 82.071 | −23.229 | −12.149 | 1.00 | 33.30 | A | C |
| ATOM | 215 | CG | LYS | A | 34 | 82.285 | −23.993 | −10.832 | 1.00 | 32.01 | A | C |
| ATOM | 216 | CD | LYS | A | 34 | 83.474 | −24.963 | −10.867 | 1.00 | 49.59 | A | C |
| ATOM | 217 | CE | LYS | A | 34 | 83.183 | −26.189 | −11.757 | 1.00 | 50.50 | A | C |
| ATOM | 218 | NZ | LYS | A | 34 | 83.640 | −27.463 | −11.181 | 1.00 | 41.90 | A | N |
| ATOM | 219 | C | LYS | A | 34 | 80.103 | −24.658 | −12.968 | 1.00 | 22.42 | A | C |
| ATOM | 220 | O | LYS | A | 34 | 80.017 | −25.884 | −12.834 | 1.00 | 20.81 | A | O |
| ATOM | 221 | N | ALA | A | 35 | 79.053 | −23.862 | −12.821 | 1.00 | 18.29 | A | N |
| ATOM | 222 | CA | ALA | A | 35 | 77.732 | −24.397 | −12.506 | 1.00 | 18.56 | A | C |
| ATOM | 223 | CB | ALA | A | 35 | 76.730 | −23.280 | −12.355 | 1.00 | 23.87 | A | C |
| ATOM | 224 | C | ALA | A | 35 | 77.252 | −25.393 | −13.555 | 1.00 | 17.36 | A | C |
| ATOM | 225 | O | ALA | A | 35 | 76.787 | −26.498 | −13.228 | 1.00 | 16.12 | A | O |
| ATOM | 226 | N | LYS | A | 36 | 77.418 | −25.038 | −14.821 | 1.00 | 15.09 | A | N |
| ATOM | 227 | CA | LYS | A | 36 | 76.989 | −25.916 | −15.911 | 1.00 | 16.19 | A | C |
| ATOM | 228 | CB | LYS | A | 36 | 77.195 | −25.206 | −17.251 | 1.00 | 20.04 | A | C |
| ATOM | 229 | CG | LYS | A | 36 | 76.070 | −24.130 | −17.446 | 1.00 | 20.11 | A | C |
| ATOM | 230 | CD | LYS | A | 36 | 76.355 | −23.138 | −18.530 | 1.00 | 19.35 | A | C |
| ATOM | 231 | CE | LYS | A | 36 | 76.571 | −23.797 | −19.854 | 1.00 | 21.87 | A | C |
| ATOM | 232 | NZ | LYS | A | 36 | 76.850 | −22.796 | −20.953 | 1.00 | 24.73 | A | N |
| ATOM | 233 | C | LYS | A | 36 | 77.657 | −27.290 | −15.904 | 1.00 | 16.32 | A | C |
| ATOM | 234 | O | LYS | A | 36 | 77.001 | −28.299 | −16.145 | 1.00 | 17.53 | A | O |
| ATOM | 235 | N | LYS | A | 37 | 78.959 | −27.325 | −15.631 | 1.00 | 15.35 | A | N |
| ATOM | 236 | CA | LYS | A | 37 | 79.733 | −28.589 | −15.646 | 1.00 | 15.48 | A | C |
| ATOM | 237 | CB | LYS | A | 37 | 81.247 | −28.252 | −15.606 | 1.00 | 18.37 | A | C |
| ATOM | 238 | CG | LYS | A | 37 | 82.147 | −29.422 | −15.470 | 1.00 | 22.75 | A | C |
| ATOM | 239 | CD | LYS | A | 37 | 83.628 | −29.045 | −15.576 | 1.00 | 26.96 | A | C |
| ATOM | 240 | CE | LYS | A | 37 | 84.463 | −30.314 | −15.779 | 1.00 | 30.90 | A | C |
| ATOM | 241 | NZ | LYS | A | 37 | 85.904 | −30.113 | −15.499 | 1.00 | 41.14 | A | N |
| ATOM | 242 | C | LYS | A | 37 | 79.291 | −29.500 | −14.476 | 1.00 | 14.16 | A | C |
| ATOM | 243 | O | LYS | A | 37 | 79.087 | −30.727 | −14.627 | 1.00 | 12.16 | A | O |
| ATOM | 244 | N | LEU | A | 38 | 79.095 | −28.888 | −13.319 | 1.00 | 12.16 | A | N |
| ATOM | 245 | CA | LEU | A | 38 | 78.557 | −29.611 | −12.169 | 1.00 | 12.46 | A | C |
| ATOM | 246 | CB | LEU | A | 38 | 78.569 | −28.705 | −10.943 | 1.00 | 11.62 | A | C |
| ATOM | 247 | CG | LEU | A | 38 | 79.948 | −28.214 | −10.491 | 1.00 | 13.13 | A | C |
| ATOM | 248 | CD1 | LEU | A | 38 | 79.786 | −27.177 | −9.428 | 1.00 | 13.41 | A | C |
| ATOM | 249 | CD2 | LEU | A | 38 | 80.845 | −29.365 | −10.003 | 1.00 | 15.16 | A | C |
| ATOM | 250 | C | LEU | A | 38 | 77.131 | −30.088 | −12.431 | 1.00 | 12.95 | A | C |
| ATOM | 251 | O | LEU | A | 38 | 76.788 | −31.249 | −12.177 | 1.00 | 11.60 | A | O |
| ATOM | 252 | N | GLU | A | 39 | 76.275 | −29.193 | −12.919 | 1.00 | 11.82 | A | N |
| ATOM | 253 | CA | GLU | A | 39 | 74.891 | −29.586 | −13.221 | 1.00 | 12.20 | A | C |
| ATOM | 254 | CB | GLU | A | 39 | 74.127 | −28.385 | −13.767 | 1.00 | 16.05 | A | C |
| ATOM | 255 | CG | GLU | A | 39 | 72.731 | −28.656 | −14.294 | 1.00 | 21.03 | A | C |
| ATOM | 256 | CD | GLU | A | 39 | 72.130 | −27.381 | −14.877 | 1.00 | 23.31 | A | C |
| ATOM | 257 | OE1 | GLU | A | 39 | 72.820 | −26.681 | −15.648 | 1.00 | 23.15 | A | O |
| ATOM | 258 | OE2 | GLU | A | 39 | 70.986 | −27.071 | −14.533 | 1.00 | 22.30 | A | O |
| ATOM | 259 | C | GLU | A | 39 | 74.816 | −30.756 | −14.184 | 1.00 | 10.69 | A | C |
| ATOM | 260 | O | GLU | A | 39 | 74.012 | −31.673 | −14.001 | 1.00 | 11.30 | A | O |
| ATOM | 261 | N | ALA | A | 40 | 75.685 | −30.741 | −15.197 | 1.00 | 11.54 | A | N |
| ATOM | 262 | CA | ALA | A | 40 | 75.767 | −31.785 | −16.201 | 1.00 | 10.76 | A | C |
| ATOM | 263 | CB | ALA | A | 40 | 76.918 | −31.447 | −17.199 | 1.00 | 12.41 | A | C |
| ATOM | 264 | C | ALA | A | 40 | 76.041 | −33.164 | −15.575 | 1.00 | 14.03 | A | C |
| ATOM | 265 | O | ALA | A | 40 | 75.409 | −34.180 | −15.911 | 1.00 | 10.38 | A | O |
| ATOM | 266 | N | GLU | A | 41 | 77.024 | −33.200 | −14.687 | 1.00 | 16.09 | A | N |
| ATOM | 267 | CA | GLU | A | 41 | 77.390 | −34.441 | −14.017 | 1.00 | 13.91 | A | C |
| ATOM | 268 | CB | GLU | A | 41 | 78.665 | −34.237 | −13.212 | 1.00 | 19.27 | A | C |
| ATOM | 269 | CG | GLU | A | 41 | 79.138 | −35.483 | −12.508 | 1.00 | 25.02 | A | C |
| ATOM | 270 | CD | GLU | A | 41 | 80.607 | −35.425 | −12.091 | 1.00 | 28.02 | A | C |
| ATOM | 271 | OE1 | GLU | A | 41 | 81.375 | −34.548 | −12.576 | 1.00 | 24.47 | A | O |
| ATOM | 272 | OE2 | GLU | A | 41 | 80.970 | −36.273 | −11.257 | 1.00 | 29.52 | A | O |
| ATOM | 273 | C | GLU | A | 41 | 76.272 | −34.965 | −13.108 | 1.00 | 12.87 | A | C |
| ATOM | 274 | O | GLU | A | 41 | 76.090 | −36.165 | −13.024 | 1.00 | 13.64 | A | O |
| ATOM | 275 | N | VAL | A | 42 | 75.532 | −34.091 | −12.434 | 1.00 | 12.85 | A | N |
| ATOM | 276 | CA | VAL | A | 42 | 74.421 | −34.563 | −11.586 | 1.00 | 14.03 | A | C |
| ATOM | 277 | CB | VAL | A | 42 | 73.924 | −33.454 | −10.695 | 1.00 | 14.90 | A | C |
| ATOM | 278 | CG1 | VAL | A | 42 | 72.584 | −33.857 | −10.061 | 1.00 | 13.47 | A | C |
| ATOM | 279 | CG2 | VAL | A | 42 | 74.995 | −33.110 | −9.638 | 1.00 | 12.19 | A | C |
| ATOM | 280 | C | VAL | A | 42 | 73.276 | −35.141 | −12.475 | 1.00 | 15.79 | A | C |
| ATOM | 281 | O | VAL | A | 42 | 72.718 | −36.203 | −12.205 | 1.00 | 14.89 | A | O |
| ATOM | 282 | N | ARG | A | 43 | 73.021 | −34.478 | −13.604 | 1.00 | 16.80 | A | N |
| ATOM | 283 | CA | ARG | A | 43 | 72.115 | −35.001 | −14.629 | 1.00 | 15.60 | A | C |
| ATOM | 284 | CB | ARG | A | 43 | 72.092 | −34.051 | −15.853 | 1.00 | 15.25 | A | C |

APPENDIX A-continued

P. alba 3T288C coordinates

| ATOM | 285 | CG | ARG | A | 43 | 71.211 | −34.540 | −17.003 | 1.00 | 16.80 | A | C |
|------|-----|-----|-----|---|----|--------|---------|---------|------|-------|---|---|
| ATOM | 286 | CD | ARG | A | 43 | 71.932 | −35.504 | −17.942 | 1.00 | 16.08 | A | C |
| ATOM | 287 | NE | ARG | A | 43 | 71.013 | −35.995 | −18.967 | 1.00 | 19.00 | A | N |
| ATOM | 288 | CZ | ARG | A | 43 | 71.278 | −36.953 | −19.843 | 1.00 | 21.10 | A | C |
| ATOM | 289 | NH1 | ARG | A | 43 | 72.472 | −37.567 | −19.874 | 1.00 | 16.27 | A | N |
| ATOM | 290 | NH2 | ARG | A | 43 | 70.323 | −37.315 | −20.694 | 1.00 | 19.98 | A | N |
| ATOM | 291 | C | ARG | A | 43 | 72.536 | −36.396 | −15.060 | 1.00 | 13.27 | A | C |
| ATOM | 292 | O | ARG | A | 43 | 71.722 | −37.295 | −15.093 | 1.00 | 12.89 | A | O |
| ATOM | 293 | N | ARG | A | 44 | 73.819 | −36.583 | −15.386 | 1.00 | 12.23 | A | N |
| ATOM | 294 | CA | ARG | A | 44 | 74.287 | −37.877 | −15.802 | 1.00 | 13.34 | A | C |
| ATOM | 295 | CB | ARG | A | 44 | 75.778 | −37.854 | −16.129 | 1.00 | 13.24 | A | C |
| ATOM | 296 | CG | ARG | A | 44 | 76.300 | −39.154 | −16.657 | 1.00 | 14.52 | A | C |
| ATOM | 297 | CD | ARG | A | 44 | 77.795 | −39.105 | −16.917 | 1.00 | 16.25 | A | C |
| ATOM | 298 | NE | ARG | A | 44 | 78.513 | −38.905 | −15.676 | 1.00 | 15.34 | A | N |
| ATOM | 299 | CZ | ARG | A | 44 | 79.791 | −38.554 | −15.561 | 1.00 | 22.40 | A | C |
| ATOM | 300 | NH1 | ARG | A | 44 | 80.581 | −38.337 | −16.624 | 1.00 | 18.24 | A | N |
| ATOM | 301 | NH2 | ARG | A | 44 | 80.285 | −38.413 | −14.338 | 1.00 | 26.00 | A | N |
| ATOM | 302 | C | ARG | A | 44 | 74.029 | −38.934 | −14.726 | 1.00 | 15.66 | A | C |
| ATOM | 303 | O | ARG | A | 44 | 73.596 | −40.025 | −15.046 | 1.00 | 14.32 | A | O |
| ATOM | 304 | N | GLU | A | 45 | 74.309 | −38.612 | −13.464 | 1.00 | 16.48 | A | N |
| ATOM | 305 | CA | GLU | A | 45 | 74.179 | −39.621 | −12.394 | 1.00 | 15.18 | A | C |
| ATOM | 306 | CB | GLU | A | 45 | 74.884 | −39.173 | −11.117 | 1.00 | 17.44 | A | C |
| ATOM | 307 | CG | GLU | A | 45 | 76.398 | −39.065 | −11.261 | 1.00 | 23.45 | A | C |
| ATOM | 308 | CD | GLU | A | 45 | 77.009 | −40.405 | −11.686 | 1.00 | 30.59 | A | C |
| ATOM | 309 | OE1 | GLU | A | 45 | 76.904 | −41.378 | −10.908 | 1.00 | 41.70 | A | O |
| ATOM | 310 | OE2 | GLU | A | 45 | 77.554 | −40.495 | −12.820 | 1.00 | 34.07 | A | O |
| ATOM | 311 | C | GLU | A | 45 | 72.706 | −39.958 | −12.106 | 1.00 | 14.08 | A | C |
| ATOM | 312 | O | GLU | A | 45 | 72.401 | −41.076 | −11.798 | 1.00 | 12.78 | A | O |
| ATOM | 313 | N | ILE | A | 46 | 71.799 | −39.015 | −12.285 | 1.00 | 15.21 | A | N |
| ATOM | 314 | CA | ILE | A | 46 | 70.360 | −39.321 | −12.129 | 1.00 | 14.92 | A | C |
| ATOM | 315 | CB | ILE | A | 46 | 69.546 | −38.073 | −11.941 | 1.00 | 13.75 | A | C |
| ATOM | 316 | CG1 | ILE | A | 46 | 69.968 | −37.340 | −10.668 | 1.00 | 13.13 | A | C |
| ATOM | 317 | CD1 | ILE | A | 46 | 69.335 | −35.917 | −10.521 | 1.00 | 13.11 | A | C |
| ATOM | 318 | CG2 | ILE | A | 46 | 68.010 | −38.395 | −11.900 | 1.00 | 15.50 | A | C |
| ATOM | 319 | C | ILE | A | 46 | 69.857 | −40.187 | −13.291 | 1.00 | 18.05 | A | C |
| ATOM | 320 | O | ILE | A | 46 | 69.013 | −41.083 | −13.103 | 1.00 | 18.68 | A | O |
| ATOM | 321 | N | ASN | A | 47 | 70.398 | −39.976 | −14.487 | 1.00 | 18.26 | A | N |
| ATOM | 322 | CA | ASN | A | 47 | 69.952 | −40.743 | −15.668 | 1.00 | 16.25 | A | C |
| ATOM | 323 | CB | ASN | A | 47 | 70.181 | −39.936 | −16.926 | 1.00 | 16.08 | A | C |
| ATOM | 324 | CG | ASN | A | 47 | 69.170 | −38.835 | −17.085 | 1.00 | 22.48 | A | C |
| ATOM | 325 | OD1 | ASN | A | 47 | 68.166 | −39.047 | −17.712 | 1.00 | 21.93 | A | O |
| ATOM | 326 | ND2 | ASN | A | 47 | 69.411 | −37.668 | −16.490 | 1.00 | 18.56 | A | N |
| ATOM | 327 | C | ASN | A | 47 | 70.585 | −42.115 | −15.828 | 1.00 | 18.89 | A | C |
| ATOM | 328 | O | ASN | A | 47 | 70.184 | −42.892 | −16.689 | 1.00 | 21.16 | A | O |
| ATOM | 329 | N | ASN | A | 48 | 71.615 | −42.392 | −15.040 | 1.00 | 20.07 | A | N |
| ATOM | 330 | CA | ASN | A | 48 | 72.411 | −43.614 | −15.177 | 1.00 | 21.07 | A | C |
| ATOM | 331 | CB | ASN | A | 48 | 73.524 | −43.561 | −14.128 | 1.00 | 22.12 | A | C |
| ATOM | 332 | CG | ASN | A | 48 | 74.333 | −44.833 | −14.027 | 1.00 | 24.42 | A | C |
| ATOM | 333 | OD1 | ASN | A | 48 | 74.362 | −45.670 | −14.931 | 1.00 | 22.04 | A | O |
| ATOM | 334 | ND2 | ASN | A | 48 | 75.046 | −44.955 | −12.920 | 1.00 | 22.68 | A | N |
| ATOM | 335 | C | ASN | A | 48 | 71.551 | −44.840 | −14.953 | 1.00 | 22.60 | A | C |
| ATOM | 336 | O | ASN | A | 48 | 71.037 | −45.017 | −13.878 | 1.00 | 24.75 | A | O |
| ATOM | 337 | N | GLU | A | 49 | 71.404 | −45.677 | −15.965 | 1.00 | 25.27 | A | N |
| ATOM | 338 | CA | GLU | A | 49 | 70.534 | −46.838 | −15.873 | 1.00 | 31.45 | A | C |
| ATOM | 339 | CB | GLU | A | 49 | 69.971 | −47.183 | −17.248 | 1.00 | 33.69 | A | C |
| ATOM | 340 | CG | GLU | A | 49 | 69.010 | −46.083 | −17.720 | 1.00 | 43.39 | A | C |
| ATOM | 341 | CD | GLU | A | 49 | 68.043 | −46.506 | −18.832 | 1.00 | 49.09 | A | C |
| ATOM | 342 | OE1 | GLU | A | 49 | 68.038 | −47.692 | −19.225 | 1.00 | 45.42 | A | O |
| ATOM | 343 | OE2 | GLU | A | 49 | 67.282 | −45.626 | −19.308 | 1.00 | 40.84 | A | O |
| ATOM | 344 | C | GLU | A | 49 | 71.177 | −48.050 | −15.241 | 1.00 | 34.38 | A | C |
| ATOM | 345 | O | GLU | A | 49 | 70.520 | −49.055 | −15.058 | 1.00 | 37.08 | A | O |
| ATOM | 346 | N | LYS | A | 50 | 72.455 | −47.958 | −14.906 | 1.00 | 31.70 | A | N |
| ATOM | 347 | CA | LYS | A | 50 | 73.159 | −49.048 | −14.255 | 1.00 | 36.67 | A | C |
| ATOM | 348 | CB | LYS | A | 50 | 74.573 | −49.191 | −14.827 | 1.00 | 40.64 | A | C |
| ATOM | 349 | CG | LYS | A | 50 | 74.689 | −49.329 | −16.371 | 1.00 | 51.97 | A | C |
| ATOM | 350 | CD | LYS | A | 50 | 75.923 | −48.546 | −16.896 | 1.00 | 56.91 | A | C |
| ATOM | 351 | CE | LYS | A | 50 | 76.546 | −49.104 | −18.184 | 1.00 | 54.15 | A | C |
| ATOM | 352 | NZ | LYS | A | 50 | 75.666 | −48.933 | −19.373 | 1.00 | 52.48 | A | N |
| ATOM | 353 | C | LYS | A | 50 | 73.275 | −48.787 | −12.758 | 1.00 | 33.26 | A | C |
| ATOM | 354 | O | LYS | A | 50 | 73.835 | −49.595 | −12.057 | 1.00 | 33.42 | A | O |
| ATOM | 355 | N | ALA | A | 51 | 72.780 | −47.654 | −12.270 | 1.00 | 30.39 | A | N |
| ATOM | 356 | CA | ALA | A | 51 | 72.905 | −47.331 | −10.843 | 1.00 | 30.68 | A | C |
| ATOM | 357 | CB | ALA | A | 51 | 72.301 | −45.928 | −10.554 | 1.00 | 29.95 | A | C |
| ATOM | 358 | C | ALA | A | 51 | 72.173 | −48.388 | −10.015 | 1.00 | 26.77 | A | C |
| ATOM | 359 | O | ALA | A | 51 | 71.125 | −48.866 | −10.439 | 1.00 | 23.61 | A | O |
| ATOM | 360 | N | GLU | A | 52 | 72.720 | −48.742 | −8.851 | 1.00 | 25.28 | A | N |
| ATOM | 361 | CA | GLU | A | 52 | 71.998 | −49.553 | −7.854 | 1.00 | 27.96 | A | C |
| ATOM | 362 | CB | GLU | A | 52 | 72.881 | −49.902 | −6.643 | 1.00 | 31.71 | A | C |

APPENDIX A-continued

P. alba 3T288C coordinates

| ATOM | 363 | CG  | GLU | A | 52 | 74.162 | −50.669 | −6.959  | 1.00 | 49.71 | A | C |
| ATOM | 364 | CD  | GLU | A | 52 | 73.925 | −52.024 | −7.623  | 1.00 | 61.36 | A | C |
| ATOM | 365 | OE1 | GLU | A | 52 | 72.763 | −52.463 | −7.743  | 1.00 | 70.03 | A | O |
| ATOM | 366 | OE2 | GLU | A | 52 | 74.920 | −52.659 | −8.033  | 1.00 | 80.38 | A | O |
| ATOM | 367 | C   | GLU | A | 52 | 70.793 | −48.786 | −7.336  | 1.00 | 26.09 | A | C |
| ATOM | 368 | O   | GLU | A | 52 | 70.879 | −47.583 | −7.079  | 1.00 | 24.96 | A | O |
| ATOM | 369 | N   | PHE | A | 53 | 69.682 | −49.490 | −7.160  | 1.00 | 26.53 | A | N |
| ATOM | 370 | CA  | PHE | A | 53 | 68.388 | −48.872 | −6.808  | 1.00 | 35.85 | A | C |
| ATOM | 371 | CB  | PHE | A | 53 | 67.340 | −49.942 | −6.445  | 1.00 | 49.50 | A | C |
| ATOM | 372 | CG  | PHE | A | 53 | 66.862 | −50.770 | −7.617  | 1.00 | 61.54 | A | C |
| ATOM | 373 | CD1 | PHE | A | 53 | 66.522 | −50.159 | −8.837  | 1.00 | 61.58 | A | C |
| ATOM | 374 | CE1 | PHE | A | 53 | 66.072 | −50.919 | −9.922  | 1.00 | 53.87 | A | C |
| ATOM | 375 | CZ  | PHE | A | 53 | 65.942 | −52.308 | −9.794  | 1.00 | 69.22 | A | C |
| ATOM | 376 | CE2 | PHE | A | 53 | 66.265 | −52.937 | −8.574  | 1.00 | 66.79 | A | C |
| ATOM | 377 | CD2 | PHE | A | 53 | 66.718 | −52.163 | −7.494  | 1.00 | 69.27 | A | C |
| ATOM | 378 | C   | PHE | A | 53 | 68.495 | −47.922 | −5.634  | 1.00 | 27.28 | A | C |
| ATOM | 379 | O   | PHE | A | 53 | 68.084 | −46.754 | −5.726  | 1.00 | 22.90 | A | O |
| ATOM | 380 | N   | LEU | A | 54 | 69.065 | −48.423 | −4.544  | 1.00 | 24.77 | A | N |
| ATOM | 381 | CA  | LEU | A | 54 | 69.123 | −47.682 | −3.302  | 1.00 | 28.10 | A | C |
| ATOM | 382 | CB  | LEU | A | 54 | 69.596 | −48.572 | −2.154  | 1.00 | 34.39 | A | C |
| ATOM | 383 | CG  | LEU | A | 54 | 68.736 | −48.556 | −0.887  | 1.00 | 49.21 | A | C |
| ATOM | 384 | CD1 | LEU | A | 54 | 68.322 | −47.145 | −0.451  | 1.00 | 51.57 | A | C |
| ATOM | 385 | CD2 | LEU | A | 54 | 67.515 | −49.439 | −1.132  | 1.00 | 50.67 | A | C |
| ATOM | 386 | C   | LEU | A | 54 | 70.013 | −46.443 | −3.396  | 1.00 | 27.68 | A | C |
| ATOM | 387 | O   | LEU | A | 54 | 69.681 | −45.416 | −2.834  | 1.00 | 23.39 | A | O |
| ATOM | 388 | N   | THR | A | 55 | 71.142 | −46.549 | −4.101  | 1.00 | 23.55 | A | N |
| ATOM | 389 | CA  | THR | A | 55 | 72.040 | −45.423 | −4.318  | 1.00 | 21.92 | A | C |
| ATOM | 390 | CB  | THR | A | 55 | 73.281 | −45.871 | −5.101  | 1.00 | 23.88 | A | C |
| ATOM | 391 | OG1 | THR | A | 55 | 73.801 | −47.016 | −4.452  | 1.00 | 25.50 | A | O |
| ATOM | 392 | CG2 | THR | A | 55 | 74.332 | −44.782 | −5.130  | 1.00 | 23.93 | A | C |
| ATOM | 393 | C   | THR | A | 55 | 71.343 | −44.343 | −5.108  | 1.00 | 17.55 | A | C |
| ATOM | 394 | O   | THR | A | 55 | 71.434 | −43.173 | −4.792  | 1.00 | 18.91 | A | O |
| ATOM | 395 | N   | LEU | A | 56 | 70.607 | −44.748 | −6.113  | 1.00 | 18.24 | A | N |
| ATOM | 396 | CA  | LEU | A | 56 | 69.862 | −43.800 | −6.928  | 1.00 | 20.04 | A | C |
| ATOM | 397 | CB  | LEU | A | 56 | 69.227 | −44.539 | −8.105  | 1.00 | 22.20 | A | C |
| ATOM | 398 | CG  | LEU | A | 56 | 68.464 | −43.635 | −9.061  | 1.00 | 26.34 | A | C |
| ATOM | 399 | CD1 | LEU | A | 56 | 69.434 | −42.666 | −9.723  | 1.00 | 31.96 | A | C |
| ATOM | 400 | CD2 | LEU | A | 56 | 67.690 | −44.445 | −10.097 | 1.00 | 33.31 | A | C |
| ATOM | 401 | C   | LEU | A | 56 | 68.777 | −43.049 | −6.149  | 1.00 | 19.87 | A | C |
| ATOM | 402 | O   | LEU | A | 56 | 68.634 | −41.841 | −6.283  | 1.00 | 17.72 | A | O |
| ATOM | 403 | N   | LEU | A | 57 | 68.017 | −43.771 | −5.330  | 1.00 | 18.78 | A | N |
| ATOM | 404 | CA  | LEU | A | 57 | 66.988 | −43.158 | −4.532  | 1.00 | 17.43 | A | C |
| ATOM | 405 | CB  | LEU | A | 57 | 66.169 | −44.211 | −3.795  | 1.00 | 17.26 | A | C |
| ATOM | 406 | CG  | LEU | A | 57 | 65.336 | −45.160 | −4.639  | 1.00 | 18.53 | A | C |
| ATOM | 407 | CD1 | LEU | A | 57 | 64.868 | −46.280 | −3.736  | 1.00 | 17.73 | A | C |
| ATOM | 408 | CD2 | LEU | A | 57 | 64.168 | −44.475 | −5.338  | 1.00 | 17.09 | A | C |
| ATOM | 409 | C   | LEU | A | 57 | 67.585 | −42.177 | −3.549  | 1.00 | 16.16 | A | C |
| ATOM | 410 | O   | LEU | A | 57 | 67.023 | −41.110 | −3.319  | 1.00 | 14.89 | A | O |
| ATOM | 411 | N   | GLU | A | 58 | 68.693 | −42.559 | −2.927  | 1.00 | 16.26 | A | N |
| ATOM | 412 | CA  | GLU | A | 58 | 69.381 | −41.681 | −2.008  | 1.00 | 17.82 | A | C |
| ATOM | 413 | CB  | GLU | A | 58 | 70.460 | −42.434 | −1.225  | 1.00 | 25.14 | A | C |
| ATOM | 414 | CG  | GLU | A | 58 | 69.819 | −43.406 | −0.193  | 1.00 | 35.32 | A | C |
| ATOM | 415 | CD  | GLU | A | 58 | 70.827 | −44.166 | 0.686   | 1.00 | 48.33 | A | C |
| ATOM | 416 | OE1 | GLU | A | 58 | 72.054 | −44.054 | 0.456   | 1.00 | 40.98 | A | O |
| ATOM | 417 | OE2 | GLU | A | 58 | 70.376 | −44.885 | 1.608   | 1.00 | 38.51 | A | O |
| ATOM | 418 | C   | GLU | A | 58 | 69.973 | −40.453 | −2.712  | 1.00 | 17.55 | A | C |
| ATOM | 419 | O   | GLU | A | 58 | 69.926 | −39.353 | −2.157  | 1.00 | 14.34 | A | O |
| ATOM | 420 | N   | LEU | A | 59 | 70.524 | −40.624 | −3.921  | 1.00 | 14.91 | A | N |
| ATOM | 421 | CA  | LEU | A | 59 | 70.938 | −39.466 | −4.720  | 1.00 | 14.26 | A | C |
| ATOM | 422 | CB  | LEU | A | 59 | 71.528 | −39.906 | −6.055  | 1.00 | 16.83 | A | C |
| ATOM | 423 | CG  | LEU | A | 59 | 71.832 | −38.771 | −7.070  | 1.00 | 17.41 | A | C |
| ATOM | 424 | CD1 | LEU | A | 59 | 72.898 | −37.834 | −6.529  | 1.00 | 14.87 | A | C |
| ATOM | 425 | CD2 | LEU | A | 59 | 72.258 | −39.366 | −8.400  | 1.00 | 17.18 | A | C |
| ATOM | 426 | C   | LEU | A | 59 | 69.780 | −38.486 | −4.976  | 1.00 | 13.47 | A | C |
| ATOM | 427 | O   | LEU | A | 59 | 69.901 | −37.259 | −4.762  | 1.00 | 18.07 | A | O |
| ATOM | 428 | N   | ILE | A | 60 | 68.654 | −39.009 | −5.456  | 1.00 | 14.22 | A | N |
| ATOM | 429 | CA  | ILE | A | 60 | 67.510 | −38.174 | −5.735  | 1.00 | 15.30 | A | C |
| ATOM | 430 | CB  | ILE | A | 60 | 66.311 | −39.013 | −6.215  | 1.00 | 15.27 | A | C |
| ATOM | 431 | CG1 | ILE | A | 60 | 66.569 | −39.514 | −7.634  | 1.00 | 18.44 | A | C |
| ATOM | 432 | CD1 | ILE | A | 60 | 65.650 | −40.585 | −8.070  | 1.00 | 18.66 | A | C |
| ATOM | 433 | CG2 | ILE | A | 60 | 65.001 | −38.220 | −6.118  | 1.00 | 13.95 | A | C |
| ATOM | 434 | C   | ILE | A | 60 | 67.108 | −37.415 | −4.450  | 1.00 | 16.70 | A | C |
| ATOM | 435 | O   | ILE | A | 60 | 66.807 | −36.196 | −4.457  | 1.00 | 16.26 | A | O |
| ATOM | 436 | N   | ASP | A | 61 | 67.064 | −38.145 | −3.358  | 1.00 | 15.80 | A | N |
| ATOM | 437 | CA  | ASP | A | 61 | 66.694 | −37.530 | −2.066  | 1.00 | 18.86 | A | C |
| ATOM | 438 | CB  | ASP | A | 61 | 66.698 | −38.587 | −0.971  | 1.00 | 19.67 | A | C |
| ATOM | 439 | CG  | ASP | A | 61 | 65.989 | −38.130 | 0.318   | 1.00 | 26.40 | A | C |
| ATOM | 440 | OD1 | ASP | A | 61 | 65.096 | −37.229 | 0.280   | 1.00 | 21.55 | A | O |

APPENDIX A-continued

*P. alba* 3T288C coordinates

| | | | | | | | | | | | | |
|---|---|---|---|---|---|---|---|---|---|---|---|---|
| ATOM | 441 | OD2 | ASP | A | 61 | 66.330 | −38.722 | 1.376 | 1.00 | 23.18 | A | O |
| ATOM | 442 | C | ASP | A | 61 | 67.630 | −36.378 | −1.688 | 1.00 | 16.98 | A | C |
| ATOM | 443 | O | ASP | A | 61 | 67.185 | −35.298 | −1.260 | 1.00 | 18.46 | A | O |
| ATOM | 444 | N | ASN | A | 62 | 68.939 | −36.607 | −1.826 | 1.00 | 19.40 | A | N |
| ATOM | 445 | CA | ASN | A | 62 | 69.916 | −35.574 | −1.529 | 1.00 | 15.80 | A | C |
| ATOM | 446 | CB | ASN | A | 62 | 71.364 | −36.120 | −1.610 | 1.00 | 17.49 | A | C |
| ATOM | 447 | CG | ASN | A | 62 | 71.717 | −37.018 | −0.442 | 1.00 | 20.29 | A | C |
| ATOM | 448 | OD1 | ASN | A | 62 | 71.275 | −36.780 | 0.657 | 1.00 | 23.89 | A | O |
| ATOM | 449 | ND2 | ASN | A | 62 | 72.522 | −38.057 | −0.689 | 1.00 | 18.30 | A | N |
| ATOM | 450 | C | ASN | A | 62 | 69.761 | −34.380 | −2.472 | 1.00 | 16.16 | A | C |
| ATOM | 451 | O | ASN | A | 62 | 69.742 | −33.232 | −2.018 | 1.00 | 15.22 | A | O |
| ATOM | 452 | N | VAL | A | 63 | 69.630 | −34.648 | −3.772 | 1.00 | 15.09 | A | N |
| ATOM | 453 | CA | VAL | A | 63 | 69.406 | −33.553 | −4.758 | 1.00 | 14.55 | A | C |
| ATOM | 454 | CB | VAL | A | 63 | 69.167 | −34.127 | −6.161 | 1.00 | 15.48 | A | C |
| ATOM | 455 | CG1 | VAL | A | 63 | 68.662 | −33.057 | −7.117 | 1.00 | 15.19 | A | C |
| ATOM | 456 | CG2 | VAL | A | 63 | 70.487 | −34.805 | −6.685 | 1.00 | 13.61 | A | C |
| ATOM | 457 | C | VAL | A | 63 | 68.235 | −32.660 | −4.332 | 1.00 | 15.51 | A | C |
| ATOM | 458 | O | VAL | A | 63 | 68.340 | −31.431 | −4.333 | 1.00 | 18.72 | A | O |
| ATOM | 459 | N | GLN | A | 64 | 67.133 | −33.285 | −3.920 | 1.00 | 15.10 | A | N |
| ATOM | 460 | CA | GLN | A | 64 | 65.957 | −32.562 | −3.455 | 1.00 | 15.57 | A | C |
| ATOM | 461 | CB | GLN | A | 64 | 64.747 | −33.526 | −3.344 | 1.00 | 17.68 | A | C |
| ATOM | 462 | CG | GLN | A | 64 | 64.318 | −34.015 | −4.711 | 1.00 | 17.50 | A | C |
| ATOM | 463 | CD | GLN | A | 64 | 62.971 | −34.726 | −4.748 | 1.00 | 20.03 | A | C |
| ATOM | 464 | OE1 | GLN | A | 64 | 62.382 | −34.802 | −5.810 | 1.00 | 19.14 | A | O |
| ATOM | 465 | NE2 | GLN | A | 64 | 62.489 | −35.252 | −3.609 | 1.00 | 14.20 | A | N |
| ATOM | 466 | C | GLN | A | 64 | 66.175 | −31.788 | −2.143 | 1.00 | 14.86 | A | C |
| ATOM | 467 | O | GLN | A | 64 | 65.873 | −30.605 | −2.042 | 1.00 | 15.46 | A | O |
| ATOM | 468 | N | ARG | A | 65 | 66.705 | −32.453 | −1.137 | 1.00 | 14.05 | A | N |
| ATOM | 469 | CA | ARG | A | 65 | 66.904 | −31.822 | 0.161 | 1.00 | 15.82 | A | C |
| ATOM | 470 | CB | ARG | A | 65 | 67.355 | −32.847 | 1.196 | 1.00 | 16.25 | A | C |
| ATOM | 471 | CG | ARG | A | 65 | 66.247 | −33.875 | 1.445 | 1.00 | 19.90 | A | C |
| ATOM | 472 | CD | ARG | A | 65 | 66.533 | −34.782 | 2.609 | 1.00 | 20.04 | A | C |
| ATOM | 473 | NE | ARG | A | 65 | 66.639 | −33.958 | 3.802 | 1.00 | 27.75 | A | N |
| ATOM | 474 | CZ | ARG | A | 65 | 66.875 | −34.416 | 5.027 | 1.00 | 47.19 | A | C |
| ATOM | 475 | NH1 | ARG | A | 65 | 67.009 | −35.722 | 5.231 | 1.00 | 44.64 | A | N |
| ATOM | 476 | NH2 | ARG | A | 65 | 66.958 | −33.559 | 6.054 | 1.00 | 35.23 | A | N |
| ATOM | 477 | C | ARG | A | 65 | 67.873 | −30.645 | 0.090 | 1.00 | 15.18 | A | C |
| ATOM | 478 | O | ARG | A | 65 | 67.618 | −29.607 | 0.698 | 1.00 | 18.75 | A | O |
| ATOM | 479 | N | LEU | A | 66 | 68.909 | −30.769 | −0.734 | 1.00 | 14.43 | A | N |
| ATOM | 480 | CA | LEU | A | 66 | 69.898 | −29.699 | −0.937 | 1.00 | 15.85 | A | C |
| ATOM | 481 | CB | LEU | A | 66 | 71.120 | −30.253 | −1.690 | 1.00 | 14.34 | A | C |
| ATOM | 482 | CG | LEU | A | 66 | 71.936 | −31.227 | −0.849 | 1.00 | 16.97 | A | C |
| ATOM | 483 | CD1 | LEU | A | 66 | 72.981 | −31.901 | −1.711 | 1.00 | 21.09 | A | C |
| ATOM | 484 | CD2 | LEU | A | 66 | 72.608 | −30.479 | 0.299 | 1.00 | 18.12 | A | C |
| ATOM | 485 | C | LEU | A | 66 | 69.351 | −28.524 | −1.693 | 1.00 | 18.23 | A | C |
| ATOM | 486 | O | LEU | A | 66 | 70.037 | −27.523 | −1.853 | 1.00 | 18.00 | A | O |
| ATOM | 487 | N | GLY | A | 67 | 68.139 | −28.661 | −2.215 | 1.00 | 17.75 | A | N |
| ATOM | 488 | CA | GLY | A | 67 | 67.432 | −27.546 | −2.817 | 1.00 | 15.94 | A | C |
| ATOM | 489 | C | GLY | A | 67 | 67.409 | −27.543 | −4.328 | 1.00 | 17.22 | A | C |
| ATOM | 490 | O | GLY | A | 67 | 66.988 | −26.556 | −4.918 | 1.00 | 19.11 | A | O |
| ATOM | 491 | N | LEU | A | 68 | 67.851 | −28.634 | −4.963 | 1.00 | 17.17 | A | N |
| ATOM | 492 | CA | LEU | A | 68 | 68.050 | −28.660 | −6.409 | 1.00 | 15.94 | A | C |
| ATOM | 493 | CB | LEU | A | 68 | 69.433 | −29.273 | −6.746 | 1.00 | 14.65 | A | C |
| ATOM | 494 | CG | LEU | A | 68 | 70.654 | −28.481 | −6.265 | 1.00 | 17.60 | A | C |
| ATOM | 495 | CD1 | LEU | A | 68 | 71.899 | −29.411 | −6.237 | 1.00 | 14.01 | A | C |
| ATOM | 496 | CD2 | LEU | A | 68 | 70.888 | −27.248 | −7.175 | 1.00 | 14.30 | A | C |
| ATOM | 497 | C | LEU | A | 68 | 66.955 | −29.409 | −7.148 | 1.00 | 17.27 | A | C |
| ATOM | 498 | O | LEU | A | 68 | 67.045 | −29.590 | −8.371 | 1.00 | 16.93 | A | O |
| ATOM | 499 | N | GLY | A | 69 | 65.902 | −29.851 | −6.447 | 1.00 | 19.21 | A | N |
| ATOM | 500 | CA | GLY | A | 69 | 64.864 | −30.621 | −7.100 | 1.00 | 21.34 | A | C |
| ATOM | 501 | C | GLY | A | 69 | 64.274 | −29.941 | −8.319 | 1.00 | 22.17 | A | C |
| ATOM | 502 | O | GLY | A | 69 | 64.052 | −30.579 | −9.363 | 1.00 | 22.04 | A | O |
| ATOM | 503 | N | TYR | A | 70 | 64.083 | −28.631 | −8.205 | 1.00 | 20.57 | A | N |
| ATOM | 504 | CA | TYR | A | 70 | 63.435 | −27.864 | −9.258 | 1.00 | 24.61 | A | C |
| ATOM | 505 | CB | TYR | A | 70 | 63.178 | −26.404 | −8.827 | 1.00 | 22.29 | A | C |
| ATOM | 506 | CG | TYR | A | 70 | 64.422 | −25.554 | −8.871 | 1.00 | 19.75 | A | C |
| ATOM | 507 | CD1 | TYR | A | 70 | 65.402 | −25.637 | −7.864 | 1.00 | 18.08 | A | C |
| ATOM | 508 | CE1 | TYR | A | 70 | 66.566 | −24.891 | −7.942 | 1.00 | 18.63 | A | C |
| ATOM | 509 | CZ | TYR | A | 70 | 66.746 | −24.025 | −9.014 | 1.00 | 19.34 | A | C |
| ATOM | 510 | OH | TYR | A | 70 | 67.887 | −23.263 | −9.175 | 1.00 | 16.26 | A | O |
| ATOM | 511 | CE2 | TYR | A | 70 | 65.789 | −23.954 | −10.015 | 1.00 | 20.55 | A | C |
| ATOM | 512 | CD2 | TYR | A | 70 | 64.650 | −24.705 | −9.938 | 1.00 | 19.66 | A | C |
| ATOM | 513 | C | TYR | A | 70 | 64.228 | −27.898 | −10.550 | 1.00 | 25.17 | A | C |
| ATOM | 514 | O | TYR | A | 70 | 63.661 | −27.687 | −11.608 | 1.00 | 22.72 | A | O |
| ATOM | 515 | N | ARG | A | 71 | 65.539 | −28.130 | −10.477 | 1.00 | 18.92 | A | N |
| ATOM | 516 | CA | ARG | A | 71 | 66.392 | −28.102 | −11.666 | 1.00 | 18.69 | A | C |
| ATOM | 517 | CB | ARG | A | 71 | 67.809 | −27.634 | −11.190 | 1.00 | 22.29 | A | C |
| ATOM | 518 | CG | ARG | A | 71 | 68.902 | −27.719 | −12.174 | 1.00 | 33.98 | A | C |

APPENDIX A-continued

*P. alba* 3T288C coordinates

| ATOM | 519 | CD   | ARG  | A | 71 | 70.148 | −26.850 | −11.726 | 1.00 | 34.42 | A | C |
| ---- | --- | ---- | ---- | - | -- | ------ | ------- | ------- | ---- | ----- | - | - |
| ATOM | 520 | NE   | ARG  | A | 71 | 69.737 | −25.505 | −11.451 | 1.00 | 22.66 | A | N |
| ATOM | 521 | CZ   | ARG  | A | 71 | 69.603 | −24.529 | −12.349 | 1.00 | 20.28 | A | C |
| ATOM | 522 | NH1  | ARG  | A | 71 | 69.910 | −24.686 | −13.614 | 1.00 | 25.84 | A | N |
| ATOM | 523 | NH2  | ARG  | A | 71 | 69.164 | −23.355 | −11.943 | 1.00 | 18.66 | A | N |
| ATOM | 524 | C    | ARG  | A | 71 | 66.450 | −29.454 | −12.393 | 1.00 | 19.16 | A | C |
| ATOM | 525 | O    | ARG  | A | 71 | 66.865 | −29.549 | −13.549 | 1.00 | 16.93 | A | O |
| ATOM | 526 | N    | PHE  | A | 72 | 66.040 | −30.510 | −11.710 | 1.00 | 19.98 | A | N |
| ATOM | 527 | CA   | PHE  | A | 72 | 66.189 | −31.877 | −12.212 | 1.00 | 18.22 | A | C |
| ATOM | 528 | CB   | PHE  | A | 72 | 67.167 | −32.615 | −11.297 | 1.00 | 18.72 | A | C |
| ATOM | 529 | CG   | PHE  | A | 72 | 68.556 | −32.062 | −11.352 | 1.00 | 15.33 | A | C |
| ATOM | 530 | CD1  | PHE  | A | 72 | 69.334 | −32.258 | −12.476 | 1.00 | 17.79 | A | C |
| ATOM | 531 | CE1  | PHE  | A | 72 | 70.602 | −31.747 | −12.543 | 1.00 | 16.36 | A | C |
| ATOM | 532 | CZ   | PHE  | A | 72 | 71.113 | −30.998 | −11.499 | 1.00 | 16.15 | A | C |
| ATOM | 533 | CE2  | PHE  | A | 72 | 70.350 | −30.793 | −10.385 | 1.00 | 14.98 | A | C |
| ATOM | 534 | CD2  | PHE  | A | 72 | 69.068 | −31.326 | −10.320 | 1.00 | 14.87 | A | C |
| ATOM | 535 | C    | PHE  | A | 72 | 64.925 | −32.662 | −12.295 | 1.00 | 22.11 | A | C |
| ATOM | 536 | O    | PHE  | A | 72 | 64.968 | −33.900 | −12.347 | 1.00 | 20.25 | A | O |
| ATOM | 537 | N    | GLU  | A | 73 | 63.787 | −31.965 | −12.329 | 1.00 | 25.45 | A | N |
| ATOM | 538 | CA   | GLU  | A | 73 | 62.514 | −32.638 | −12.154 | 1.00 | 27.06 | A | C |
| ATOM | 539 | CB   | GLU  | A | 73 | 61.344 | −31.649 | −12.123 | 1.00 | 29.03 | A | C |
| ATOM | 540 | CG   | GLU  | A | 73 | 60.061 | −32.289 | −11.662 | 1.00 | 36.46 | A | C |
| ATOM | 541 | CD   | GLU  | A | 73 | 58.884 | −31.321 | −11.634 | 1.00 | 54.40 | A | C |
| ATOM | 542 | OE1  | GLU  | A | 73 | 59.116 | −30.091 | −11.532 | 1.00 | 48.00 | A | O |
| ATOM | 543 | OE2  | GLU  | A | 73 | 57.728 | −31.805 | −11.711 | 1.00 | 42.07 | A | O |
| ATOM | 544 | C    | GLU  | A | 73 | 62.282 | −33.701 | −13.208 | 1.00 | 23.81 | A | C |
| ATOM | 545 | O    | GLU  | A | 73 | 61.900 | −34.844 | −12.873 | 1.00 | 22.20 | A | O |
| ATOM | 546 | N    | SER  | A | 74 | 62.519 | −33.358 | −14.467 | 1.00 | 22.35 | A | N |
| ATOM | 547 | CA   | ASER | A | 74 | 62.290 | −34.318 | −15.548 | 0.50 | 24.87 | A | C |
| ATOM | 548 | CA   | BSER | A | 74 | 62.341 | −34.306 | −15.575 | 0.50 | 24.62 | A | C |
| ATOM | 549 | CB   | ASER | A | 74 | 62.379 | −33.663 | −16.937 | 0.50 | 27.13 | A | C |
| ATOM | 550 | CB   | BSER | A | 74 | 62.668 | −33.651 | −16.909 | 0.50 | 27.23 | A | C |
| ATOM | 551 | OG   | ASER | A | 74 | 63.690 | −33.692 | −17.476 | 0.50 | 32.13 | A | O |
| ATOM | 552 | OG   | BSER | A | 74 | 61.765 | −32.616 | −17.190 | 0.50 | 30.66 | A | O |
| ATOM | 553 | C    | SER  | A | 74 | 63.227 | −35.526 | −15.419 | 1.00 | 23.45 | A | C |
| ATOM | 554 | O    | SER  | A | 74 | 62.809 | −36.654 | −15.663 | 1.00 | 23.95 | A | O |
| ATOM | 555 | N    | ASP  | A | 75 | 64.477 | −35.303 | −15.017 | 1.00 | 19.65 | A | N |
| ATOM | 556 | CA   | ASP  | A | 75 | 65.427 | −36.412 | −14.826 | 1.00 | 20.84 | A | C |
| ATOM | 557 | CB   | ASP  | A | 75 | 66.835 | −35.869 | −14.535 | 1.00 | 22.51 | A | C |
| ATOM | 558 | CG   | ASP  | A | 75 | 67.319 | −34.911 | −15.609 | 1.00 | 29.28 | A | C |
| ATOM | 559 | OD1  | ASP  | A | 75 | 67.561 | −35.386 | −16.734 | 1.00 | 26.21 | A | O |
| ATOM | 560 | OD2  | ASP  | A | 75 | 67.438 | −33.696 | −15.342 | 1.00 | 35.89 | A | O |
| ATOM | 561 | C    | ASP  | A | 75 | 64.972 | −37.340 | −13.661 | 1.00 | 16.01 | A | C |
| ATOM | 562 | O    | ASP  | A | 75 | 65.069 | −38.559 | −13.741 | 1.00 | 14.80 | A | O |
| ATOM | 563 | N    | ILE  | A | 76 | 64.549 | −36.729 | −12.569 | 1.00 | 13.98 | A | N |
| ATOM | 564 | CA   | ILE  | A | 76 | 64.037 | −37.461 | −11.393 | 1.00 | 14.87 | A | C |
| ATOM | 565 | CB   | ILE  | A | 76 | 63.704 | −36.489 | −10.249 | 1.00 | 14.39 | A | C |
| ATOM | 566 | CG1  | ILE  | A | 76 | 65.026 | −35.919 |  −9.708 | 1.00 | 15.22 | A | C |
| ATOM | 567 | CD1  | ILE  | A | 76 | 64.910 | −34.789 |  −8.807 | 1.00 | 15.21 | A | C |
| ATOM | 568 | CG2  | ILE  | A | 76 | 62.950 | −37.214 |  −9.100 | 1.00 | 12.91 | A | C |
| ATOM | 569 | C    | ILE  | A | 76 | 62.811 | −38.292 | −11.791 | 1.00 | 15.71 | A | C |
| ATOM | 570 | O    | ILE  | A | 76 | 62.735 | −39.470 | −11.500 | 1.00 | 17.94 | A | O |
| ATOM | 571 | N    | ARG  | A | 77 | 61.870 | −37.684 | −12.470 | 1.00 | 18.65 | A | N |
| ATOM | 572 | CA   | AARG | A | 77 | 60.670 | −38.385 | −12.938 | 0.50 | 19.96 | A | C |
| ATOM | 573 | CA   | BARG | A | 77 | 60.672 | −38.409 | −12.891 | 0.50 | 21.56 | A | C |
| ATOM | 574 | CB   | AARG | A | 77 | 59.818 | −37.453 | −13.790 | 0.50 | 22.64 | A | C |
| ATOM | 575 | CB   | BARG | A | 77 | 59.669 | −37.479 | −13.580 | 0.50 | 26.61 | A | C |
| ATOM | 576 | CG   | AARG | A | 77 | 59.104 | −36.376 | −13.062 | 0.50 | 22.43 | A | C |
| ATOM | 577 | CG   | BARG | A | 77 | 58.541 | −37.048 | −12.690 | 0.50 | 33.00 | A | C |
| ATOM | 578 | CD   | AARG | A | 77 | 58.085 | −35.708 | −14.032 | 0.50 | 24.82 | A | C |
| ATOM | 579 | CD   | BARG | A | 77 | 57.233 | −36.819 | −13.483 | 0.50 | 41.27 | A | C |
| ATOM | 580 | NE   | AARG | A | 77 | 57.084 | −36.686 | −14.465 | 0.50 | 27.82 | A | N |
| ATOM | 581 | NE   | BARG | A | 77 | 57.430 | −36.132 | −14.766 | 0.50 | 38.02 | A | N |
| ATOM | 582 | CZ   | AARG | A | 77 | 56.062 | −37.076 | −13.710 | 0.50 | 32.47 | A | C |
| ATOM | 583 | CZ   | BARG | A | 77 | 57.743 | −34.845 | −14.906 | 0.50 | 38.80 | A | C |
| ATOM | 584 | NH1  | AARG | A | 77 | 55.895 | −36.544 | −12.499 | 0.50 | 28.27 | A | N |
| ATOM | 585 | NH1  | BARG | A | 77 | 57.920 | −34.070 | −13.842 | 0.50 | 36.68 | A | N |
| ATOM | 586 | NH2  | AARG | A | 77 | 55.203 | −37.976 | −14.169 | 0.50 | 30.50 | A | N |
| ATOM | 587 | NH2  | BARG | A | 77 | 57.892 | −34.330 | −16.121 | 0.50 | 39.56 | A | N |
| ATOM | 588 | C    | ARG  | A | 77 | 61.001 | −39.588 | −13.783 | 1.00 | 21.28 | A | C |
| ATOM | 589 | O    | ARG  | A | 77 | 60.401 | −40.664 | −13.637 | 1.00 | 23.22 | A | O |
| ATOM | 590 | N    | GLY  | A | 78 | 61.944 | −39.398 | −14.706 | 1.00 | 22.93 | A | N |
| ATOM | 591 | CA   | GLY  | A | 78 | 62.399 | −40.504 | −15.558 | 1.00 | 21.83 | A | C |
| ATOM | 592 | C    | GLY  | A | 78 | 63.046 | −41.619 | −14.781 | 1.00 | 20.05 | A | C |
| ATOM | 593 | O    | GLY  | A | 78 | 62.836 | −42.793 | −15.072 | 1.00 | 19.81 | A | O |
| ATOM | 594 | N    | ALA  | A | 79 | 63.850 | −41.272 | −13.778 | 1.00 | 19.76 | A | N |
| ATOM | 595 | CA   | ALA  | A | 79 | 64.509 | −42.292 | −12.967 | 1.00 | 19.48 | A | C |
| ATOM | 596 | CB   | ALA  | A | 79 | 65.542 | −41.631 | −12.006 | 1.00 | 16.46 | A | C |

APPENDIX A-continued

*P. alba* 3T288C coordinates

| ATOM | 597 | C | ALA | A | 79 | 63.466 | −43.102 | −12.180 | 1.00 | 17.42 | A | C |
|------|-----|------|------|---|----|--------|---------|---------|------|-------|---|---|
| ATOM | 598 | O | ALA | A | 79 | 63.564 | −44.316 | −12.041 | 1.00 | 18.48 | A | O |
| ATOM | 599 | N | LEU | A | 80 | 62.469 | −42.415 | −11.652 | 1.00 | 17.25 | A | N |
| ATOM | 600 | CA | LEU | A | 80 | 61.433 | −43.067 | −10.833 | 1.00 | 17.10 | A | C |
| ATOM | 601 | CB | LEU | A | 80 | 60.588 | −42.013 | −10.113 | 1.00 | 18.65 | A | C |
| ATOM | 602 | CG | LEU | A | 80 | 61.318 | −41.248 | −9.018 | 1.00 | 18.83 | A | C |
| ATOM | 603 | CD1 | LEU | A | 80 | 60.504 | −40.080 | −8.548 | 1.00 | 18.36 | A | C |
| ATOM | 604 | CD2 | LEU | A | 80 | 61.697 | −42.202 | −7.848 | 1.00 | 16.67 | A | C |
| ATOM | 605 | C | LEU | A | 80 | 60.546 | −43.948 | −11.703 | 1.00 | 20.72 | A | C |
| ATOM | 606 | O | LEU | A | 80 | 60.159 | −45.046 | −11.299 | 1.00 | 22.37 | A | O |
| ATOM | 607 | N | ASP | A | 81 | 60.232 | −43.466 | −12.899 | 1.00 | 21.72 | A | N |
| ATOM | 608 | CA | ASP | A | 81 | 59.467 | −44.254 | −13.840 | 1.00 | 22.96 | A | C |
| ATOM | 609 | CB | ASP | A | 81 | 59.214 | −43.462 | −15.118 | 1.00 | 34.55 | A | C |
| ATOM | 610 | CG | ASP | A | 81 | 58.294 | −44.203 | −16.076 | 1.00 | 48.66 | A | C |
| ATOM | 611 | OD1 | ASP | A | 81 | 57.059 | −44.159 | −15.876 | 1.00 | 47.13 | A | O |
| ATOM | 612 | OD2 | ASP | A | 81 | 58.813 | −44.858 | −17.001 | 1.00 | 53.22 | A | O |
| ATOM | 613 | C | ASP | A | 81 | 60.161 | −45.583 | −14.159 | 1.00 | 26.16 | A | C |
| ATOM | 614 | O | ASP | A | 81 | 59.536 | −46.638 | −14.175 | 1.00 | 29.06 | A | O |
| ATOM | 615 | N | ARG | A | 82 | 61.465 | −45.549 | −14.398 | 1.00 | 25.91 | A | N |
| ATOM | 616 | CA | ARG | A | 82 | 62.185 | −46.777 | −14.703 | 1.00 | 26.78 | A | C |
| ATOM | 617 | CB | ARG | A | 82 | 63.562 | −46.481 | −15.281 | 1.00 | 34.17 | A | C |
| ATOM | 618 | CG | ARG | A | 82 | 63.492 | −45.835 | −16.668 | 1.00 | 42.87 | A | C |
| ATOM | 619 | CD | ARG | A | 82 | 64.892 | −45.671 | −17.266 | 1.00 | 49.93 | A | C |
| ATOM | 620 | NE | ARG | A | 82 | 65.763 | −44.879 | −16.390 | 1.00 | 44.21 | A | N |
| ATOM | 621 | CZ | ARG | A | 82 | 65.865 | −43.549 | −16.409 | 1.00 | 37.72 | A | C |
| ATOM | 622 | NH1 | ARG | A | 82 | 65.166 | −42.830 | −17.278 | 1.00 | 35.82 | A | N |
| ATOM | 623 | NH2 | ARG | A | 82 | 66.688 | −42.932 | −15.552 | 1.00 | 29.76 | A | N |
| ATOM | 624 | C | ARG | A | 82 | 62.309 | −47.652 | −13.485 | 1.00 | 29.77 | A | C |
| ATOM | 625 | O | ARG | A | 82 | 62.282 | −48.887 | −13.589 | 1.00 | 31.34 | A | O |
| ATOM | 626 | N | PHE | A | 83 | 62.440 | −47.028 | −12.321 | 1.00 | 24.68 | A | N |
| ATOM | 627 | CA | PHE | A | 83 | 62.444 | −47.775 | −11.076 | 1.00 | 25.58 | A | C |
| ATOM | 628 | CB | PHE | A | 83 | 62.638 | −46.834 | −9.889 | 1.00 | 25.29 | A | C |
| ATOM | 629 | CG | PHE | A | 83 | 62.662 | −47.524 | −8.546 | 1.00 | 25.27 | A | C |
| ATOM | 630 | CD1 | PHE | A | 83 | 63.674 | −48.403 | −8.223 | 1.00 | 31.55 | A | C |
| ATOM | 631 | CE1 | PHE | A | 83 | 63.705 | −49.036 | −6.959 | 1.00 | 33.76 | A | C |
| ATOM | 632 | CZ | PHE | A | 83 | 62.723 | −48.761 | −6.027 | 1.00 | 25.63 | A | C |
| ATOM | 633 | CE2 | PHE | A | 83 | 61.688 | −47.908 | −6.363 | 1.00 | 23.21 | A | C |
| ATOM | 634 | CD2 | PHE | A | 83 | 61.671 | −47.275 | −7.603 | 1.00 | 24.70 | A | C |
| ATOM | 635 | C | PHE | A | 83 | 61.153 | −48.571 | −10.920 | 1.00 | 23.30 | A | C |
| ATOM | 636 | O | PHE | A | 83 | 61.192 | −49.699 | −10.442 | 1.00 | 28.14 | A | O |
| ATOM | 637 | N | VAL | A | 84 | 60.008 | −48.011 | −11.304 | 1.00 | 22.28 | A | N |
| ATOM | 638 | CA | VAL | A | 84 | 58.766 | −48.779 | −11.191 | 1.00 | 24.82 | A | C |
| ATOM | 639 | CB | VAL | A | 84 | 57.544 | −47.879 | −11.140 | 1.00 | 34.14 | A | C |
| ATOM | 640 | CG1 | VAL | A | 84 | 56.265 | −48.737 | −11.170 | 1.00 | 34.45 | A | C |
| ATOM | 641 | CG2 | VAL | A | 84 | 57.610 | −47.028 | −9.895 | 1.00 | 24.63 | A | C |
| ATOM | 642 | C | VAL | A | 84 | 58.648 | −49.778 | −12.355 | 1.00 | 36.68 | A | C |
| ATOM | 643 | O | VAL | A | 84 | 58.466 | −50.966 | −12.117 | 1.00 | 28.56 | A | O |
| ATOM | 644 | N | SER | A | 85 | 58.821 | −49.303 | −13.592 | 1.00 | 37.14 | A | N |
| ATOM | 645 | CA | ASER | A | 85 | 58.620 | −50.142 | −14.794 | 0.50 | 37.10 | A | C |
| ATOM | 646 | CA | BSER | A | 85 | 58.622 | −50.140 | −14.791 | 0.50 | 39.01 | A | C |
| ATOM | 647 | CB | ASER | A | 85 | 58.845 | −49.327 | −16.072 | 0.50 | 32.00 | A | C |
| ATOM | 648 | CB | BSER | A | 85 | 58.830 | −49.307 | −16.061 | 0.50 | 36.25 | A | C |
| ATOM | 649 | OG | ASER | A | 85 | 60.229 | −49.189 | −16.324 | 0.50 | 28.69 | A | O |
| ATOM | 650 | OG | BSER | A | 85 | 58.016 | −48.150 | −16.027 | 0.50 | 36.93 | A | O |
| ATOM | 651 | C | SER | A | 85 | 59.536 | −51.355 | −14.824 | 1.00 | 37.47 | A | C |
| ATOM | 652 | O | SER | A | 85 | 59.177 | −52.400 | −15.354 | 1.00 | 41.76 | A | O |
| ATOM | 653 | N | SER | A | 86 | 60.725 | −51.225 | −14.260 | 1.00 | 36.59 | A | N |
| ATOM | 654 | CA | SER | A | 86 | 61.617 | −52.354 | −14.202 | 1.00 | 33.40 | A | C |
| ATOM | 655 | CB | SER | A | 86 | 63.043 | −51.872 | −13.933 | 1.00 | 32.66 | A | C |
| ATOM | 656 | OG | SER | A | 86 | 63.174 | −51.413 | −12.608 | 1.00 | 38.52 | A | O |
| ATOM | 657 | C | SER | A | 86 | 61.213 | −53.407 | −13.129 | 1.00 | 42.41 | A | C |
| ATOM | 658 | O | SER | A | 86 | 61.752 | −54.504 | −13.116 | 1.00 | 37.89 | A | O |
| ATOM | 659 | N | GLY | A | 87 | 60.286 | −53.085 | −12.229 | 1.00 | 46.93 | A | N |
| ATOM | 660 | CA | GLY | A | 87 | 60.046 | −53.937 | −11.038 | 1.00 | 46.12 | A | C |
| ATOM | 661 | C | GLY | A | 87 | 60.922 | −53.651 | −9.810 | 1.00 | 46.43 | A | C |
| ATOM | 662 | O | GLY | A | 87 | 60.874 | −54.385 | −8.823 | 1.00 | 42.81 | A | O |
| ATOM | 663 | N | GLY | A | 88 | 61.727 | −52.591 | −9.843 | 1.00 | 37.85 | A | N |
| ATOM | 664 | CA | GLY | A | 88 | 62.551 | −52.234 | −8.678 | 1.00 | 30.02 | A | C |
| ATOM | 665 | C | GLY | A | 88 | 61.734 | −51.937 | −7.421 | 1.00 | 27.92 | A | C |
| ATOM | 666 | O | GLY | A | 88 | 62.124 | −52.306 | −6.306 | 1.00 | 27.72 | A | O |
| ATOM | 667 | N | PHE | A | 89 | 60.592 | −51.268 | −7.592 | 1.00 | 28.80 | A | N |
| ATOM | 668 | CA | PHE | A | 89 | 59.756 | −50.909 | −6.437 | 1.00 | 28.02 | A | C |
| ATOM | 669 | CB | PHE | A | 89 | 58.610 | −49.969 | −6.826 | 1.00 | 26.31 | A | C |
| ATOM | 670 | CG | PHE | A | 89 | 57.765 | −49.546 | −5.651 | 1.00 | 25.79 | A | C |
| ATOM | 671 | CD1 | PHE | A | 89 | 58.349 | −48.920 | −4.562 | 1.00 | 22.35 | A | C |
| ATOM | 672 | CE1 | PHE | A | 89 | 57.592 | −48.532 | −3.464 | 1.00 | 24.18 | A | C |
| ATOM | 673 | CZ | PHE | A | 89 | 56.227 | −48.769 | −3.456 | 1.00 | 24.74 | A | C |
| ATOM | 674 | CE2 | PHE | A | 89 | 55.637 | −49.412 | −4.520 | 1.00 | 29.64 | A | C |

APPENDIX A-continued

*P. alba* 3T288C coordinates

| ATOM | 675 | CD2 | PHE | A | 89 | 56.405 | −49.802 | −5.618 | 1.00 | 29.08 | A | C |
|---|---|---|---|---|---|---|---|---|---|---|---|---|
| ATOM | 676 | C | PHE | A | 89 | 59.204 | −52.188 | −5.830 | 1.00 | 30.78 | A | C |
| ATOM | 677 | O | PHE | A | 89 | 59.256 | −52.396 | −4.631 | 1.00 | 24.38 | A | O |
| ATOM | 678 | N | ASP | A | 90 | 58.703 | −53.071 | −6.677 | 1.00 | 34.48 | A | N |
| ATOM | 679 | CA | ASP | A | 90 | 58.272 | −54.369 | −6.178 | 1.00 | 39.02 | A | C |
| ATOM | 680 | CB | ASP | A | 90 | 57.660 | −55.229 | −7.270 | 1.00 | 44.69 | A | C |
| ATOM | 681 | CG | ASP | A | 90 | 56.172 | −55.280 | −7.138 | 1.00 | 62.48 | A | C |
| ATOM | 682 | OD1 | ASP | A | 90 | 55.516 | −54.248 | −7.424 | 1.00 | 68.76 | A | O |
| ATOM | 683 | OD2 | ASP | A | 90 | 55.680 | −56.325 | −6.662 | 1.00 | 53.84 | A | O |
| ATOM | 684 | C | ASP | A | 90 | 59.346 | −55.114 | −5.438 | 1.00 | 33.99 | A | C |
| ATOM | 685 | O | ASP | A | 90 | 59.083 | −55.632 | −4.369 | 1.00 | 40.51 | A | O |
| ATOM | 686 | N | ALA | A | 91 | 60.549 | −55.144 | −5.996 | 1.00 | 35.72 | A | N |
| ATOM | 687 | CA | ALA | A | 91 | 61.684 | −55.738 | −5.321 | 1.00 | 37.79 | A | C |
| ATOM | 688 | CB | ALA | A | 91 | 62.949 | −55.644 | −6.189 | 1.00 | 37.01 | A | C |
| ATOM | 689 | C | ALA | A | 91 | 61.926 | −55.119 | −3.934 | 1.00 | 39.48 | A | C |
| ATOM | 690 | O | ALA | A | 91 | 62.084 | −55.874 | −2.967 | 1.00 | 42.14 | A | O |
| ATOM | 691 | N | VAL | A | 92 | 61.958 | −53.779 | −3.795 | 1.00 | 30.00 | A | N |
| ATOM | 692 | CA | VAL | A | 92 | 62.289 | −53.209 | −2.463 | 1.00 | 21.89 | A | C |
| ATOM | 693 | CB | VAL | A | 92 | 62.599 | −51.672 | −2.377 | 1.00 | 31.87 | A | C |
| ATOM | 694 | CG1 | VAL | A | 92 | 63.882 | −51.298 | −3.087 | 1.00 | 39.58 | A | C |
| ATOM | 695 | CG2 | VAL | A | 92 | 61.418 | −50.850 | −2.847 | 1.00 | 18.63 | A | C |
| ATOM | 696 | C | VAL | A | 92 | 61.206 | −53.499 | −1.442 | 1.00 | 19.55 | A | C |
| ATOM | 697 | O | VAL | A | 92 | 61.519 | −53.618 | −0.261 | 1.00 | 21.56 | A | O |
| ATOM | 698 | N | THR | A | 93 | 59.947 | −53.614 | −1.854 | 1.00 | 21.70 | A | N |
| ATOM | 699 | CA | THR | A | 93 | 58.895 | −53.860 | −0.866 | 1.00 | 22.09 | A | C |
| ATOM | 700 | CB | THR | A | 93 | 57.459 | −53.705 | −1.425 | 1.00 | 25.99 | A | C |
| ATOM | 701 | OG1 | THR | A | 93 | 57.160 | −54.784 | −2.301 | 1.00 | 26.79 | A | O |
| ATOM | 702 | CG2 | THR | A | 93 | 57.287 | −52.384 | −2.193 | 1.00 | 25.32 | A | C |
| ATOM | 703 | C | THR | A | 93 | 59.092 | −55.251 | −0.213 | 1.00 | 29.92 | A | C |
| ATOM | 704 | O | THR | A | 93 | 58.533 | −55.516 | 0.855 | 1.00 | 31.66 | A | O |
| ATOM | 705 | N | LYS | A | 94 | 59.903 | −56.112 | −0.832 | 1.00 | 33.47 | A | N |
| ATOM | 706 | CA | LYS | A | 94 | 60.181 | −57.449 | −0.275 | 1.00 | 35.78 | A | C |
| ATOM | 707 | CB | LYS | A | 94 | 60.334 | −58.483 | −1.392 | 1.00 | 37.52 | A | C |
| ATOM | 708 | CG | LYS | A | 94 | 59.155 | −58.590 | −2.351 | 1.00 | 44.02 | A | C |
| ATOM | 709 | CD | LYS | A | 94 | 57.883 | −59.051 | −1.649 | 1.00 | 53.84 | A | C |
| ATOM | 710 | CE | LYS | A | 94 | 57.079 | −59.996 | −2.537 | 1.00 | 64.77 | A | C |
| ATOM | 711 | NZ | LYS | A | 94 | 56.701 | −59.367 | −3.837 | 1.00 | 57.51 | A | N |
| ATOM | 712 | C | LYS | A | 94 | 61.444 | −57.517 | 0.549 | 1.00 | 39.98 | A | C |
| ATOM | 713 | O | LYS | A | 94 | 61.650 | −58.511 | 1.215 | 1.00 | 42.42 | A | O |
| ATOM | 714 | N | THR | A | 95 | 62.295 | −56.488 | 0.507 | 1.00 | 33.33 | A | N |
| ATOM | 715 | CA | ATHR | A | 95 | 63.656 | −56.589 | 1.055 | 0.50 | 35.43 | A | C |
| ATOM | 716 | CA | BTHR | A | 95 | 63.650 | −56.590 | 1.067 | 0.50 | 33.00 | A | C |
| ATOM | 717 | CB | ATHR | A | 95 | 64.721 | −56.623 | −0.080 | 0.50 | 39.50 | A | C |
| ATOM | 718 | CB | BTHR | A | 95 | 64.721 | −56.620 | −0.047 | 0.50 | 33.60 | A | C |
| ATOM | 719 | OG1 | ATHR | A | 95 | 64.258 | −57.437 | −1.168 | 0.50 | 40.50 | A | O |
| ATOM | 720 | OG1 | BTHR | A | 95 | 64.663 | −55.399 | −0.793 | 0.50 | 26.73 | A | O |
| ATOM | 721 | CG2 | ATHR | A | 95 | 66.052 | −57.167 | 0.437 | 0.50 | 39.23 | A | C |
| ATOM | 722 | CG2 | BTHR | A | 95 | 64.502 | −57.798 | −0.988 | 0.50 | 35.05 | A | C |
| ATOM | 723 | C | THR | A | 95 | 64.039 | −55.461 | 2.013 | 1.00 | 39.07 | A | C |
| ATOM | 724 | O | THR | A | 95 | 64.768 | −55.703 | 2.951 | 1.00 | 35.25 | A | O |
| ATOM | 725 | N | SER | A | 96 | 63.570 | −54.219 | 1.763 | 1.00 | 29.44 | A | N |
| ATOM | 726 | CA | SER | A | 96 | 64.102 | −53.048 | 2.502 | 1.00 | 27.71 | A | C |
| ATOM | 727 | CB | SER | A | 96 | 65.123 | −52.359 | 1.584 | 1.00 | 30.94 | A | C |
| ATOM | 728 | OG | SER | A | 96 | 65.567 | −51.129 | 2.099 | 1.00 | 26.14 | A | O |
| ATOM | 729 | C | SER | A | 96 | 63.040 | −52.033 | 2.950 | 1.00 | 24.39 | A | C |
| ATOM | 730 | O | SER | A | 96 | 62.370 | −51.436 | 2.111 | 1.00 | 22.56 | A | O |
| ATOM | 731 | N | LEU | A | 97 | 62.890 | −51.820 | 4.254 | 1.00 | 19.43 | A | N |
| ATOM | 732 | CA | LEU | A | 97 | 61.966 | −50.803 | 4.758 | 1.00 | 20.25 | A | C |
| ATOM | 733 | CB | LEU | A | 97 | 61.838 | −50.828 | 6.286 | 1.00 | 21.08 | A | C |
| ATOM | 734 | CG | LEU | A | 97 | 60.990 | −49.694 | 6.890 | 1.00 | 23.72 | A | C |
| ATOM | 735 | CD1 | LEU | A | 97 | 59.524 | −49.800 | 6.439 | 1.00 | 23.79 | A | C |
| ATOM | 736 | CD2 | LEU | A | 97 | 61.130 | −49.747 | 8.412 | 1.00 | 21.02 | A | C |
| ATOM | 737 | C | LEU | A | 97 | 62.449 | −49.431 | 4.319 | 1.00 | 21.53 | A | C |
| ATOM | 738 | O | LEU | A | 97 | 61.667 | −48.597 | 3.914 | 1.00 | 19.58 | A | O |
| ATOM | 739 | N | HIS | A | 98 | 63.749 | −49.183 | 4.443 | 1.00 | 20.39 | A | N |
| ATOM | 740 | CA | HIS | A | 98 | 64.302 | −47.908 | 4.040 | 1.00 | 23.40 | A | C |
| ATOM | 741 | CB | HIS | A | 98 | 65.811 | −47.859 | 4.296 | 1.00 | 22.80 | A | C |
| ATOM | 742 | CG | HIS | A | 98 | 66.449 | −46.591 | 3.812 | 1.00 | 26.94 | A | C |
| ATOM | 743 | ND1 | HIS | A | 98 | 65.853 | −45.383 | 3.956 | 1.00 | 31.63 | A | N |
| ATOM | 744 | CE1 | HIS | A | 98 | 66.628 | −44.426 | 3.408 | 1.00 | 26.07 | A | C |
| ATOM | 745 | NE2 | HIS | A | 98 | 67.721 | −45.016 | 2.904 | 1.00 | 39.12 | A | N |
| ATOM | 746 | CD2 | HIS | A | 98 | 67.642 | −46.358 | 3.136 | 1.00 | 41.20 | A | C |
| ATOM | 747 | C | HIS | A | 98 | 63.994 | −47.632 | 2.578 | 1.00 | 18.12 | A | C |
| ATOM | 748 | O | HIS | A | 98 | 63.453 | −46.575 | 2.221 | 1.00 | 18.83 | A | O |
| ATOM | 749 | N | GLY | A | 99 | 64.274 | −48.605 | 1.728 | 1.00 | 19.83 | A | N |
| ATOM | 750 | CA | GLY | A | 99 | 64.028 | −48.451 | 0.296 | 1.00 | 19.95 | A | C |
| ATOM | 751 | C | GLY | A | 99 | 62.559 | −48.225 | −0.023 | 1.00 | 19.49 | A | C |
| ATOM | 752 | O | GLY | A | 99 | 62.215 | −47.410 | −0.890 | 1.00 | 20.61 | A | O |

APPENDIX A-continued

P. alba 3T288C coordinates

| ATOM | 753 | N | THR | A | 100 | 61.680 | −48.937 | 0.682 | 1.00 | 18.03 | A | N |
|---|---|---|---|---|---|---|---|---|---|---|---|---|
| ATOM | 754 | CA | THR | A | 100 | 60.225 | −48.836 | 0.422 | 1.00 | 16.81 | A | C |
| ATOM | 755 | CB | THR | A | 100 | 59.460 | −49.948 | 1.171 | 1.00 | 19.24 | A | C |
| ATOM | 756 | OG1 | THR | A | 100 | 59.892 | −51.230 | 0.697 | 1.00 | 20.71 | A | O |
| ATOM | 757 | CG2 | THR | A | 100 | 57.968 | −49.818 | 0.950 | 1.00 | 15.65 | A | C |
| ATOM | 758 | C | THR | A | 100 | 59.681 | −47.471 | 0.842 | 1.00 | 16.08 | A | C |
| ATOM | 759 | O | THR | A | 100 | 58.909 | −46.822 | 0.109 | 1.00 | 15.43 | A | O |
| ATOM | 760 | N | ALA | A | 101 | 60.054 | −47.040 | 2.038 | 1.00 | 16.07 | A | N |
| ATOM | 761 | CA | ALA | A | 101 | 59.614 | −45.746 | 2.551 | 1.00 | 18.24 | A | C |
| ATOM | 762 | CB | ALA | A | 101 | 59.971 | −45.571 | 4.067 | 1.00 | 15.42 | A | C |
| ATOM | 763 | C | ALA | A | 101 | 60.133 | −44.569 | 1.731 | 1.00 | 16.77 | A | C |
| ATOM | 764 | O | ALA | A | 101 | 59.395 | −43.610 | 1.464 | 1.00 | 17.48 | A | O |
| ATOM | 765 | N | LEU | A | 102 | 61.397 | −44.630 | 1.354 | 1.00 | 19.20 | A | N |
| ATOM | 766 | CA | LEU | A | 102 | 61.989 | −43.597 | 0.558 | 1.00 | 17.07 | A | C |
| ATOM | 767 | CB | LEU | A | 102 | 63.514 | −43.759 | 0.447 | 1.00 | 19.30 | A | C |
| ATOM | 768 | CG | LEU | A | 102 | 64.275 | −42.701 | −0.339 | 1.00 | 20.35 | A | C |
| ATOM | 769 | CD1 | LEU | A | 102 | 63.946 | −41.212 | 0.095 | 1.00 | 18.24 | A | C |
| ATOM | 770 | CD2 | LEU | A | 102 | 65.767 | −42.977 | −0.157 | 1.00 | 21.12 | A | C |
| ATOM | 771 | C | LEU | A | 102 | 61.350 | −43.544 | −0.813 | 1.00 | 19.36 | A | C |
| ATOM | 772 | O | LEU | A | 102 | 60.910 | −42.479 | −1.258 | 1.00 | 18.06 | A | O |
| ATOM | 773 | N | SER | A | 103 | 61.256 | −44.686 | −1.470 | 1.00 | 15.50 | A | N |
| ATOM | 774 | CA | SER | A | 103 | 60.689 | −44.690 | −2.798 | 1.00 | 17.71 | A | C |
| ATOM | 775 | CB | SER | A | 103 | 61.019 | −46.015 | −3.528 | 1.00 | 18.18 | A | C |
| ATOM | 776 | OG | SER | A | 103 | 60.455 | −47.104 | −2.871 | 1.00 | 17.47 | A | O |
| ATOM | 777 | C | SER | A | 103 | 59.188 | −44.382 | −2.765 | 1.00 | 15.07 | A | C |
| ATOM | 778 | O | SER | A | 103 | 58.667 | −43.712 | −3.651 | 1.00 | 16.88 | A | O |
| ATOM | 779 | N | PHE | A | 104 | 58.496 | −44.820 | −1.719 | 1.00 | 17.99 | A | N |
| ATOM | 780 | CA | PHE | A | 104 | 57.087 | −44.477 | −1.573 | 1.00 | 15.40 | A | C |
| ATOM | 781 | CB | PHE | A | 104 | 56.492 | −45.119 | −0.305 | 1.00 | 17.80 | A | C |
| ATOM | 782 | CG | PHE | A | 104 | 55.047 | −44.773 | −0.062 | 1.00 | 17.24 | A | C |
| ATOM | 783 | CD1 | PHE | A | 104 | 54.693 | −43.584 | 0.512 | 1.00 | 14.51 | A | C |
| ATOM | 784 | CE1 | PHE | A | 104 | 53.343 | −43.270 | 0.748 | 1.00 | 18.89 | A | C |
| ATOM | 785 | CZ | PHE | A | 104 | 52.349 | −44.154 | 0.380 | 1.00 | 14.12 | A | C |
| ATOM | 786 | CE2 | PHE | A | 104 | 52.699 | −45.359 | −0.165 | 1.00 | 18.32 | A | C |
| ATOM | 787 | CD2 | PHE | A | 104 | 54.028 | −45.674 | −0.395 | 1.00 | 19.18 | A | C |
| ATOM | 788 | C | PHE | A | 104 | 56.889 | −42.949 | −1.573 | 1.00 | 14.21 | A | C |
| ATOM | 789 | O | PHE | A | 104 | 56.015 | −42.433 | −2.269 | 1.00 | 13.20 | A | O |
| ATOM | 790 | N | ARG | A | 105 | 57.667 | −42.247 | −0.765 | 1.00 | 15.27 | A | N |
| ATOM | 791 | CA | ARG | A | 105 | 57.594 | −40.801 | −0.677 | 1.00 | 14.68 | A | C |
| ATOM | 792 | CB | ARG | A | 105 | 58.499 | −40.268 | 0.421 | 1.00 | 17.00 | A | C |
| ATOM | 793 | CG | ARG | A | 105 | 58.556 | −38.738 | 0.484 | 1.00 | 19.27 | A | C |
| ATOM | 794 | CD | ARG | A | 105 | 59.130 | −38.281 | 1.770 | 1.00 | 17.80 | A | C |
| ATOM | 795 | NE | ARG | A | 105 | 60.520 | −38.658 | 1.963 | 1.00 | 17.60 | A | N |
| ATOM | 796 | CZ | ARG | A | 105 | 61.557 | −38.046 | 1.397 | 1.00 | 22.34 | A | C |
| ATOM | 797 | NH1 | ARG | A | 105 | 61.364 | −37.013 | 0.572 | 1.00 | 19.72 | A | N |
| ATOM | 798 | NH2 | ARG | A | 105 | 62.788 | −38.451 | 1.669 | 1.00 | 21.62 | A | N |
| ATOM | 799 | C | ARG | A | 105 | 57.937 | −40.152 | −2.012 | 1.00 | 13.92 | A | C |
| ATOM | 800 | O | ARG | A | 105 | 57.207 | −39.275 | −2.486 | 1.00 | 14.65 | A | O |
| ATOM | 801 | N | LEU | A | 106 | 59.043 | −40.581 | −2.615 | 1.00 | 13.96 | A | N |
| ATOM | 802 | CA | LEU | A | 106 | 59.471 | −39.954 | −3.871 | 1.00 | 16.38 | A | C |
| ATOM | 803 | CB | LEU | A | 106 | 60.839 | −40.462 | −4.268 | 1.00 | 16.84 | A | C |
| ATOM | 804 | CG | LEU | A | 106 | 61.981 | −40.096 | −3.297 | 1.00 | 16.96 | A | C |
| ATOM | 805 | CD1 | LEU | A | 106 | 63.275 | −40.704 | −3.883 | 1.00 | 19.16 | A | C |
| ATOM | 806 | CD2 | LEU | A | 106 | 62.114 | −38.588 | −3.196 | 1.00 | 14.34 | A | C |
| ATOM | 807 | C | LEU | A | 106 | 58.466 | −40.183 | −4.994 | 1.00 | 14.71 | A | C |
| ATOM | 808 | O | LEU | A | 106 | 58.182 | −39.290 | −5.790 | 1.00 | 15.17 | A | O |
| ATOM | 809 | N | LEU | A | 107 | 57.956 | −41.391 | −5.073 | 1.00 | 15.41 | A | N |
| ATOM | 810 | CA | LEU | A | 107 | 56.965 | −41.740 | −6.101 | 1.00 | 16.47 | A | C |
| ATOM | 811 | CB | LEU | A | 107 | 56.653 | −43.241 | −6.076 | 1.00 | 14.69 | A | C |
| ATOM | 812 | CG | LEU | A | 107 | 57.725 | −44.138 | −6.672 | 1.00 | 17.19 | A | C |
| ATOM | 813 | CD1 | LEU | A | 107 | 57.512 | −45.649 | −6.276 | 1.00 | 18.03 | A | C |
| ATOM | 814 | CD2 | LEU | A | 107 | 57.844 | −43.928 | −8.194 | 1.00 | 16.63 | A | C |
| ATOM | 815 | C | LEU | A | 107 | 55.711 | −40.922 | −5.932 | 1.00 | 15.60 | A | C |
| ATOM | 816 | O | LEU | A | 107 | 55.210 | −40.309 | −6.903 | 1.00 | 16.24 | A | O |
| ATOM | 817 | N | ARG | A | 108 | 55.180 | −40.886 | −4.714 | 1.00 | 15.68 | A | N |
| ATOM | 818 | CA | ARG | A | 108 | 53.935 | −40.108 | −4.511 | 1.00 | 17.82 | A | C |
| ATOM | 819 | CB | ARG | A | 108 | 53.336 | −40.378 | −3.139 | 1.00 | 16.80 | A | C |
| ATOM | 820 | CG | ARG | A | 108 | 52.034 | −39.599 | −2.956 | 1.00 | 20.62 | A | C |
| ATOM | 821 | CD | ARG | A | 108 | 51.224 | −40.093 | −1.772 | 1.00 | 21.54 | A | C |
| ATOM | 822 | NE | ARG | A | 108 | 50.578 | −41.371 | −2.062 | 1.00 | 15.38 | A | N |
| ATOM | 823 | CZ | ARG | A | 108 | 49.816 | −42.031 | −1.185 | 1.00 | 17.50 | A | C |
| ATOM | 824 | NH1 | ARG | A | 108 | 49.653 | −41.589 | 0.055 | 1.00 | 17.78 | A | N |
| ATOM | 825 | NH2 | ARG | A | 108 | 49.260 | −43.161 | −1.528 | 1.00 | 16.16 | A | N |
| ATOM | 826 | C | ARG | A | 108 | 54.151 | −38.613 | −4.684 | 1.00 | 17.00 | A | C |
| ATOM | 827 | O | ARG | A | 108 | 53.341 | −37.933 | −5.282 | 1.00 | 15.18 | A | O |
| ATOM | 828 | N | GLN | A | 109 | 55.282 | −38.102 | −4.198 | 1.00 | 15.43 | A | N |
| ATOM | 829 | CA | GLN | A | 109 | 55.646 | −36.687 | −4.480 | 1.00 | 15.25 | A | C |
| ATOM | 830 | CB | GLN | A | 109 | 57.057 | −36.399 | −3.970 | 1.00 | 18.89 | A | C |

APPENDIX A-continued

*P. alba* 3T288C coordinates

| ATOM | 831 | CG | GLN | A | 109 | 57.597 | −35.012 | −4.344 | 1.00 | 21.63 | A | C |
|------|-----|------|-----|---|-----|--------|---------|---------|------|-------|---|---|
| ATOM | 832 | CD | GLN | A | 109 | 59.039 | −34.827 | −3.929 | 1.00 | 26.03 | A | C |
| ATOM | 833 | OE1 | GLN | A | 109 | 59.661 | −35.719 | −3.314 | 1.00 | 20.78 | A | O |
| ATOM | 834 | NE2 | GLN | A | 109 | 59.581 | −33.631 | −4.227 | 1.00 | 23.99 | A | N |
| ATOM | 835 | C | GLN | A | 109 | 55.597 | −36.324 | −5.991 | 1.00 | 18.63 | A | C |
| ATOM | 836 | O | GLN | A | 109 | 55.168 | −35.217 | −6.367 | 1.00 | 16.12 | A | O |
| ATOM | 837 | N | HIS | A | 110 | 56.041 | −37.249 | −6.829 | 1.00 | 14.77 | A | N |
| ATOM | 838 | CA | HIS | A | 110 | 56.118 | −37.033 | −8.254 | 1.00 | 18.76 | A | C |
| ATOM | 839 | CB | HIS | A | 110 | 57.440 | −37.571 | −8.778 | 1.00 | 18.80 | A | C |
| ATOM | 840 | CG | HIS | A | 110 | 58.607 | −36.694 | −8.382 | 1.00 | 19.46 | A | C |
| ATOM | 841 | ND1 | HIS | A | 110 | 58.915 | −35.561 | −9.062 | 1.00 | 16.75 | A | N |
| ATOM | 842 | CE1 | HIS | A | 110 | 59.958 | −34.950 | −8.464 | 1.00 | 22.03 | A | C |
| ATOM | 843 | NE2 | HIS | A | 110 | 60.273 | −35.659 | −7.354 | 1.00 | 18.94 | A | N |
| ATOM | 844 | CD2 | HIS | A | 110 | 59.454 | −36.747 | −7.293 | 1.00 | 14.42 | A | C |
| ATOM | 845 | C | HIS | A | 110 | 54.906 | −37.567 | −8.983 | 1.00 | 21.66 | A | C |
| ATOM | 846 | O | HIS | A | 110 | 54.937 | −37.766 | −10.194 | 1.00 | 22.45 | A | O |
| ATOM | 847 | N | GLY | A | 111 | 53.809 | −37.778 | −8.244 | 1.00 | 19.21 | A | N |
| ATOM | 848 | CA | GLY | A | 111 | 52.491 | −38.034 | −8.880 | 1.00 | 18.67 | A | C |
| ATOM | 849 | C | GLY | A | 111 | 52.232 | −39.478 | −9.221 | 1.00 | 20.43 | A | C |
| ATOM | 850 | O | GLY | A | 111 | 51.223 | −39.775 | −9.806 | 1.00 | 18.90 | A | O |
| ATOM | 851 | N | PHE | A | 112 | 53.133 | −40.398 | −8.881 | 1.00 | 16.53 | A | N |
| ATOM | 852 | CA | PHE | A | 112 | 52.923 | −41.809 | −9.224 | 1.00 | 18.88 | A | C |
| ATOM | 853 | CB | PHE | A | 112 | 54.206 | −42.618 | −9.179 | 1.00 | 19.65 | A | C |
| ATOM | 854 | CG | PHE | A | 112 | 55.188 | −42.250 | −10.259 | 1.00 | 23.54 | A | C |
| ATOM | 855 | CD1 | PHE | A | 112 | 56.062 | −41.200 | −10.077 | 1.00 | 20.65 | A | C |
| ATOM | 856 | CE1 | PHE | A | 112 | 56.994 | −40.852 | −11.057 | 1.00 | 25.46 | A | C |
| ATOM | 857 | CZ | PHE | A | 112 | 57.021 | −41.536 | −12.241 | 1.00 | 28.69 | A | C |
| ATOM | 858 | CE2 | PHE | A | 112 | 56.124 | −42.597 | −12.452 | 1.00 | 31.25 | A | C |
| ATOM | 859 | CD2 | PHE | A | 112 | 55.224 | −42.953 | −11.457 | 1.00 | 29.23 | A | C |
| ATOM | 860 | C | PHE | A | 112 | 51.987 | −42.405 | −8.200 | 1.00 | 23.31 | A | C |
| ATOM | 861 | O | PHE | A | 112 | 51.922 | −41.949 | −7.065 | 1.00 | 20.49 | A | O |
| ATOM | 862 | N | GLU | A | 113 | 51.300 | −43.461 | −8.614 | 1.00 | 24.49 | A | N |
| ATOM | 863 | CA | GLU | A | 113 | 50.309 | −44.144 | −7.796 | 1.00 | 25.45 | A | C |
| ATOM | 864 | CB | GLU | A | 113 | 49.280 | −44.839 | −8.720 | 1.00 | 37.67 | A | C |
| ATOM | 865 | CG | GLU | A | 113 | 47.845 | −44.840 | −8.204 | 1.00 | 58.64 | A | C |
| ATOM | 866 | CD | GLU | A | 113 | 46.794 | −45.024 | −9.330 | 1.00 | 81.44 | A | C |
| ATOM | 867 | OE1 | GLU | A | 113 | 46.982 | −45.896 | −10.209 | 1.00 | 68.75 | A | O |
| ATOM | 868 | OE2 | GLU | A | 113 | 45.775 | −44.293 | −9.335 | 1.00 | 86.73 | A | O |
| ATOM | 869 | C | GLU | A | 113 | 51.001 | −45.194 | −6.966 | 1.00 | 23.08 | A | C |
| ATOM | 870 | O | GLU | A | 113 | 51.580 | −46.140 | −7.493 | 1.00 | 20.88 | A | O |
| ATOM | 871 | N | VAL | A | 114 | 50.965 | −45.033 | −5.651 | 1.00 | 19.99 | A | N |
| ATOM | 872 | CA | VAL | A | 114 | 51.518 | −46.025 | −4.740 | 1.00 | 16.88 | A | C |
| ATOM | 873 | CB | VAL | A | 114 | 52.871 | −45.623 | −4.092 | 1.00 | 21.01 | A | C |
| ATOM | 874 | CG1 | VAL | A | 114 | 54.053 | −45.879 | −5.042 | 1.00 | 25.38 | A | C |
| ATOM | 875 | CG2 | VAL | A | 114 | 52.874 | −44.171 | −3.610 | 1.00 | 15.30 | A | C |
| ATOM | 876 | C | VAL | A | 114 | 50.478 | −46.235 | −3.655 | 1.00 | 19.88 | A | C |
| ATOM | 877 | O | VAL | A | 114 | 49.692 | −45.345 | −3.373 | 1.00 | 17.02 | A | O |
| ATOM | 878 | N | SER | A | 115 | 50.457 | −47.431 | −3.086 | 1.00 | 18.74 | A | N |
| ATOM | 879 | CA | SER | A | 115 | 49.473 | −47.822 | −2.108 | 1.00 | 20.78 | A | C |
| ATOM | 880 | CB | SER | A | 115 | 48.783 | −49.095 | −2.633 | 1.00 | 28.67 | A | C |
| ATOM | 881 | OG | SER | A | 115 | 48.317 | −49.928 | −1.594 | 1.00 | 27.83 | A | O |
| ATOM | 882 | C | SER | A | 115 | 50.108 | −48.124 | −0.765 | 1.00 | 15.47 | A | C |
| ATOM | 883 | O | SER | A | 115 | 51.221 | −48.652 | −0.693 | 1.00 | 18.09 | A | O |
| ATOM | 884 | N | GLN | A | 116 | 49.376 | −47.894 | 0.318 | 1.00 | 17.33 | A | N |
| ATOM | 885 | CA | GLN | A | 116 | 49.869 | −48.283 | 1.669 | 1.00 | 18.18 | A | C |
| ATOM | 886 | CB | GLN | A | 116 | 48.875 | −47.859 | 2.754 | 1.00 | 19.83 | A | C |
| ATOM | 887 | CG | GLN | A | 116 | 47.500 | −48.590 | 2.766 | 1.00 | 19.69 | A | C |
| ATOM | 888 | CD | GLN | A | 116 | 46.636 | −48.180 | 3.948 | 1.00 | 19.13 | A | C |
| ATOM | 889 | OE1 | GLN | A | 116 | 47.048 | −47.385 | 4.805 | 1.00 | 17.20 | A | O |
| ATOM | 890 | NE2 | GLN | A | 116 | 45.449 | −48.739 | 4.019 | 1.00 | 23.50 | A | N |
| ATOM | 891 | C | GLN | A | 116 | 50.179 | −49.768 | 1.813 | 1.00 | 21.60 | A | C |
| ATOM | 892 | O | GLN | A | 116 | 50.854 | −50.171 | 2.766 | 1.00 | 18.86 | A | O |
| ATOM | 893 | N | GLU | A | 117 | 49.703 | −50.605 | 0.882 | 1.00 | 16.60 | A | N |
| ATOM | 894 | CA | GLU | A | 117 | 50.018 | −52.032 | 0.917 | 1.00 | 18.43 | A | C |
| ATOM | 895 | CB | GLU | A | 117 | 49.217 | −52.835 | −0.141 | 1.00 | 23.92 | A | C |
| ATOM | 896 | CG | GLU | A | 117 | 47.699 | −52.752 | 0.019 | 1.00 | 28.14 | A | C |
| ATOM | 897 | CD | GLU | A | 117 | 46.922 | −53.442 | −1.115 | 1.00 | 42.18 | A | C |
| ATOM | 898 | OE1 | GLU | A | 117 | 47.415 | −54.462 | −1.646 | 1.00 | 41.50 | A | O |
| ATOM | 899 | OE2 | GLU | A | 117 | 45.818 | −52.963 | −1.482 | 1.00 | 41.18 | A | O |
| ATOM | 900 | C | GLU | A | 117 | 51.502 | −52.288 | 0.664 | 1.00 | 21.27 | A | C |
| ATOM | 901 | O | GLU | A | 117 | 51.981 | −53.374 | 0.962 | 1.00 | 19.92 | A | O |
| ATOM | 902 | N | ALA | A | 118 | 52.227 | −51.315 | 0.111 | 1.00 | 19.55 | A | N |
| ATOM | 903 | CA | ALA | A | 118 | 53.695 | −51.444 | −0.034 | 1.00 | 22.80 | A | C |
| ATOM | 904 | CB | ALA | A | 118 | 54.294 | −50.191 | −0.610 | 1.00 | 18.03 | A | C |
| ATOM | 905 | C | ALA | A | 118 | 54.403 | −51.768 | 1.300 | 1.00 | 20.01 | A | C |
| ATOM | 906 | O | ALA | A | 118 | 55.498 | −52.326 | 1.310 | 1.00 | 20.69 | A | O |
| ATOM | 907 | N | PHE | A | 119 | 53.786 | −51.388 | 2.412 | 1.00 | 19.91 | A | N |
| ATOM | 908 | CA | PHE | A | 119 | 54.346 | −51.646 | 3.740 | 1.00 | 18.27 | A | C |

APPENDIX A-continued

*P. alba* 3T288C coordinates

| ATOM | 909 | CB | PHE | A | 119 | 53.972 | −50.475 | 4.640 | 1.00 | 19.18 | A | C |
|---|---|---|---|---|---|---|---|---|---|---|---|---|
| ATOM | 910 | CG | PHE | A | 119 | 54.607 | −49.177 | 4.191 | 1.00 | 22.08 | A | C |
| ATOM | 911 | CD1 | PHE | A | 119 | 55.972 | −48.965 | 4.382 | 1.00 | 17.84 | A | C |
| ATOM | 912 | CE1 | PHE | A | 119 | 56.570 | −47.809 | 3.937 | 1.00 | 20.07 | A | C |
| ATOM | 913 | CZ | PHE | A | 119 | 55.815 | −46.844 | 3.280 | 1.00 | 19.50 | A | C |
| ATOM | 914 | CE2 | PHE | A | 119 | 54.461 | −47.059 | 3.050 | 1.00 | 22.32 | A | C |
| ATOM | 915 | CD2 | PHE | A | 119 | 53.860 | −48.217 | 3.523 | 1.00 | 20.27 | A | C |
| ATOM | 916 | C | PHE | A | 119 | 53.925 | −52.953 | 4.410 | 1.00 | 19.87 | A | C |
| ATOM | 917 | O | PHE | A | 119 | 54.400 | −53.271 | 5.514 | 1.00 | 22.50 | A | O |
| ATOM | 918 | N | SER | A | 120 | 53.061 | −53.726 | 3.766 | 1.00 | 24.30 | A | N |
| ATOM | 919 | CA | SER | A | 120 | 52.478 | −54.936 | 4.418 | 1.00 | 25.36 | A | C |
| ATOM | 920 | CB | SER | A | 120 | 51.376 | −55.544 | 3.542 | 1.00 | 29.84 | A | C |
| ATOM | 921 | OG | SER | A | 120 | 51.975 | −56.159 | 2.408 | 1.00 | 29.25 | A | O |
| ATOM | 922 | C | SER | A | 120 | 53.508 | −56.013 | 4.769 | 1.00 | 27.38 | A | C |
| ATOM | 923 | O | SER | A | 120 | 53.388 | −56.673 | 5.790 | 1.00 | 37.36 | A | O |
| ATOM | 924 | N | GLY | A | 121 | 54.529 | −56.169 | 3.940 | 1.00 | 28.63 | A | N |
| ATOM | 925 | CA | GLY | A | 121 | 55.647 | −57.065 | 4.236 | 1.00 | 29.21 | A | C |
| ATOM | 926 | C | GLY | A | 121 | 56.476 | −56.757 | 5.498 | 1.00 | 34.22 | A | C |
| ATOM | 927 | O | GLY | A | 121 | 57.318 | −57.556 | 5.871 | 1.00 | 30.84 | A | O |
| ATOM | 928 | N | PHE | A | 122 | 56.255 | −55.625 | 6.167 | 1.00 | 29.27 | A | N |
| ATOM | 929 | CA | PHE | A | 122 | 57.066 | −55.273 | 7.353 | 1.00 | 33.84 | A | C |
| ATOM | 930 | CB | PHE | A | 122 | 57.660 | −53.861 | 7.177 | 1.00 | 32.20 | A | C |
| ATOM | 931 | CG | PHE | A | 122 | 58.428 | −53.715 | 5.909 | 1.00 | 29.16 | A | C |
| ATOM | 932 | CD1 | PHE | A | 122 | 59.689 | −54.290 | 5.789 | 1.00 | 25.93 | A | C |
| ATOM | 933 | CE1 | PHE | A | 122 | 60.388 | −54.214 | 4.619 | 1.00 | 25.17 | A | C |
| ATOM | 934 | CZ | PHE | A | 122 | 59.840 | −53.563 | 3.519 | 1.00 | 26.81 | A | C |
| ATOM | 935 | CE2 | PHE | A | 122 | 58.576 | −53.009 | 3.606 | 1.00 | 22.72 | A | C |
| ATOM | 936 | CD2 | PHE | A | 122 | 57.865 | −53.090 | 4.803 | 1.00 | 23.54 | A | C |
| ATOM | 937 | C | PHE | A | 122 | 56.295 | −55.360 | 8.661 | 1.00 | 31.14 | A | C |
| ATOM | 938 | O | PHE | A | 122 | 56.692 | −54.770 | 9.656 | 1.00 | 26.44 | A | O |
| ATOM | 939 | N | LYS | A | 123 | 55.192 | −56.098 | 8.667 | 1.00 | 39.19 | A | N |
| ATOM | 940 | CA | LYS | A | 123 | 54.360 | −56.188 | 9.851 | 1.00 | 38.73 | A | C |
| ATOM | 941 | CB | LYS | A | 123 | 52.932 | −55.746 | 9.513 | 1.00 | 47.70 | A | C |
| ATOM | 942 | CG | LYS | A | 123 | 52.836 | −54.210 | 9.399 | 1.00 | 45.24 | A | C |
| ATOM | 943 | CD | LYS | A | 123 | 51.787 | −53.696 | 8.414 | 1.00 | 64.96 | A | C |
| ATOM | 944 | CE | LYS | A | 123 | 50.467 | −53.329 | 9.085 | 1.00 | 67.08 | A | C |
| ATOM | 945 | NZ | LYS | A | 123 | 50.584 | −52.199 | 10.038 | 1.00 | 69.25 | A | N |
| ATOM | 946 | C | LYS | A | 123 | 54.477 | −57.590 | 10.466 | 1.00 | 43.53 | A | C |
| ATOM | 947 | O | LYS | A | 123 | 54.903 | −58.527 | 9.796 | 1.00 | 37.81 | A | O |
| ATOM | 948 | N | ASP | A | 124 | 54.210 | −57.698 | 11.766 | 1.00 | 38.56 | A | N |
| ATOM | 949 | CA | ASP | A | 124 | 54.230 | −58.999 | 12.466 | 1.00 | 39.95 | A | C |
| ATOM | 950 | CB | ASP | A | 124 | 54.587 | −58.824 | 13.956 | 1.00 | 33.62 | A | C |
| ATOM | 951 | CG | ASP | A | 124 | 53.546 | −58.010 | 14.740 | 1.00 | 39.27 | A | C |
| ATOM | 952 | OD1 | ASP | A | 124 | 52.345 | −58.051 | 14.417 | 1.00 | 40.78 | A | O |
| ATOM | 953 | OD2 | ASP | A | 124 | 53.934 | −57.317 | 15.698 | 1.00 | 44.37 | A | O |
| ATOM | 954 | C | ASP | A | 124 | 52.888 | −59.715 | 12.305 | 1.00 | 42.17 | A | C |
| ATOM | 955 | O | ASP | A | 124 | 51.982 | −59.208 | 11.641 | 1.00 | 30.57 | A | O |
| ATOM | 956 | N | GLN | A | 125 | 52.767 | −60.897 | 12.910 | 1.00 | 50.65 | A | N |
| ATOM | 957 | CA | GLN | A | 125 | 51.522 | −61.676 | 12.898 | 1.00 | 53.07 | A | C |
| ATOM | 958 | CB | GLN | A | 125 | 51.649 | −62.870 | 13.837 | 1.00 | 54.97 | A | C |
| ATOM | 959 | CG | GLN | A | 125 | 52.666 | −63.899 | 13.383 | 1.00 | 73.54 | A | C |
| ATOM | 960 | CD | GLN | A | 125 | 52.683 | −65.136 | 14.270 | 1.00 | 83.04 | A | C |
| ATOM | 961 | OE1 | GLN | A | 125 | 51.999 | −65.200 | 15.297 | 1.00 | 76.17 | A | O |
| ATOM | 962 | NE2 | GLN | A | 125 | 53.467 | −66.130 | 13.871 | 1.00 | 79.73 | A | N |
| ATOM | 963 | C | GLN | A | 125 | 50.297 | −60.856 | 13.305 | 1.00 | 49.63 | A | C |
| ATOM | 964 | O | GLN | A | 125 | 49.229 | −60.995 | 12.715 | 1.00 | 52.74 | A | O |
| ATOM | 965 | N | ASN | A | 126 | 50.461 | −59.997 | 14.309 | 1.00 | 45.11 | A | N |
| ATOM | 966 | CA | ASN | A | 126 | 49.374 | −59.122 | 14.775 | 1.00 | 43.91 | A | C |
| ATOM | 967 | CB | ASN | A | 126 | 49.619 | −58.769 | 16.235 | 1.00 | 42.50 | A | C |
| ATOM | 968 | CG | ASN | A | 126 | 49.596 | −59.982 | 17.103 | 1.00 | 45.99 | A | C |
| ATOM | 969 | OD1 | ASN | A | 126 | 48.573 | −60.658 | 17.196 | 1.00 | 47.17 | A | O |
| ATOM | 970 | ND2 | ASN | A | 126 | 50.732 | −60.305 | 17.709 | 1.00 | 43.81 | A | N |
| ATOM | 971 | C | ASN | A | 126 | 49.128 | −57.835 | 13.976 | 1.00 | 44.06 | A | C |
| ATOM | 972 | O | ASN | A | 126 | 48.339 | −56.983 | 14.403 | 1.00 | 47.73 | A | O |
| ATOM | 973 | N | GLY | A | 127 | 49.792 | −57.684 | 12.831 | 1.00 | 43.62 | A | N |
| ATOM | 974 | CA | GLY | A | 127 | 49.616 | −56.490 | 11.994 | 1.00 | 44.43 | A | C |
| ATOM | 975 | C | GLY | A | 127 | 50.232 | −55.197 | 12.530 | 1.00 | 47.04 | A | C |
| ATOM | 976 | O | GLY | A | 127 | 49.812 | −54.100 | 12.156 | 1.00 | 47.00 | A | O |
| ATOM | 977 | N | ASN | A | 128 | 51.230 | −55.319 | 13.399 | 1.00 | 37.90 | A | N |
| ATOM | 978 | CA | ASN | A | 128 | 51.984 | −54.167 | 13.866 | 1.00 | 36.92 | A | C |
| ATOM | 979 | CB | ASN | A | 128 | 52.093 | −54.194 | 15.390 | 1.00 | 39.55 | A | C |
| ATOM | 980 | CG | ASN | A | 128 | 50.737 | −54.083 | 16.064 | 1.00 | 42.96 | A | C |
| ATOM | 981 | OD1 | ASN | A | 128 | 49.899 | −53.270 | 15.669 | 1.00 | 46.29 | A | O |
| ATOM | 982 | ND2 | ASN | A | 128 | 50.505 | −54.914 | 17.065 | 1.00 | 42.44 | A | N |
| ATOM | 983 | C | ASN | A | 128 | 53.354 | −54.202 | 13.209 | 1.00 | 35.45 | A | C |
| ATOM | 984 | O | ASN | A | 128 | 53.845 | −55.273 | 12.874 | 1.00 | 34.29 | A | O |
| ATOM | 985 | N | PHE | A | 129 | 53.963 | −53.038 | 12.987 | 1.00 | 32.75 | A | N |
| ATOM | 986 | CA | PHE | A | 129 | 55.312 | −53.016 | 12.427 | 1.00 | 28.49 | A | C |

APPENDIX A-continued

P. alba 3T288C coordinates

| ATOM | 987 | CB | PHE | A | 129 | 55.810 | −51.580 | 12.253 | 1.00 | 29.22 | A | C |
|---|---|---|---|---|---|---|---|---|---|---|---|---|
| ATOM | 988 | CG | PHE | A | 129 | 55.204 | −50.885 | 11.092 | 1.00 | 29.65 | A | C |
| ATOM | 989 | CD1 | PHE | A | 129 | 55.786 | −50.992 | 9.836 | 1.00 | 27.09 | A | C |
| ATOM | 990 | CE1 | PHE | A | 129 | 55.219 | −50.342 | 8.749 | 1.00 | 31.01 | A | C |
| ATOM | 991 | CZ | PHE | A | 129 | 54.041 | −49.610 | 8.912 | 1.00 | 28.34 | A | C |
| ATOM | 992 | CE2 | PHE | A | 129 | 53.452 | −49.507 | 10.162 | 1.00 | 30.20 | A | C |
| ATOM | 993 | CD2 | PHE | A | 129 | 54.031 | −50.146 | 11.245 | 1.00 | 28.89 | A | C |
| ATOM | 994 | C | PHE | A | 129 | 56.253 | −53.813 | 13.341 | 1.00 | 28.78 | A | C |
| ATOM | 995 | O | PHE | A | 129 | 56.181 | −53.707 | 14.560 | 1.00 | 29.83 | A | O |
| ATOM | 996 | N | LEU | A | 130 | 57.101 | −54.628 | 12.731 | 1.00 | 32.19 | A | N |
| ATOM | 997 | CA | LEU | A | 130 | 58.044 | −55.487 | 13.451 | 1.00 | 35.11 | A | C |
| ATOM | 998 | CB | LEU | A | 130 | 58.918 | −56.250 | 12.457 | 1.00 | 35.91 | A | C |
| ATOM | 999 | CG | LEU | A | 130 | 58.165 | −57.323 | 11.675 | 1.00 | 38.40 | A | C |
| ATOM | 1000 | CD1 | LEU | A | 130 | 58.839 | −57.597 | 10.323 | 1.00 | 34.13 | A | C |
| ATOM | 1001 | CD2 | LEU | A | 130 | 58.069 | −58.567 | 12.544 | 1.00 | 38.09 | A | C |
| ATOM | 1002 | C | LEU | A | 130 | 58.934 | −54.660 | 14.360 | 1.00 | 37.04 | A | C |
| ATOM | 1003 | O | LEU | A | 130 | 59.544 | −53.674 | 13.929 | 1.00 | 31.94 | A | O |
| ATOM | 1004 | N | GLU | A | 131 | 59.007 | −55.079 | 15.615 | 1.00 | 34.55 | A | N |
| ATOM | 1005 | CA | GLU | A | 131 | 59.765 | −54.383 | 16.651 | 1.00 | 39.68 | A | C |
| ATOM | 1006 | CB | GLU | A | 131 | 59.755 | −55.210 | 17.955 | 1.00 | 38.76 | A | C |
| ATOM | 1007 | CG | GLU | A | 131 | 60.141 | −54.423 | 19.214 | 1.00 | 49.60 | A | C |
| ATOM | 1008 | CD | GLU | A | 131 | 59.132 | −53.343 | 19.593 | 1.00 | 56.31 | A | C |
| ATOM | 1009 | OE1 | GLU | A | 131 | 58.053 | −53.260 | 18.966 | 1.00 | 67.91 | A | O |
| ATOM | 1010 | OE2 | GLU | A | 131 | 59.417 | −52.571 | 20.528 | 1.00 | 59.92 | A | O |
| ATOM | 1011 | C | GLU | A | 131 | 61.206 | −54.119 | 16.260 | 1.00 | 30.94 | A | C |
| ATOM | 1012 | O | GLU | A | 131 | 61.700 | −53.017 | 16.467 | 1.00 | 34.37 | A | O |
| ATOM | 1013 | N | ASN | A | 132 | 61.858 | −55.131 | 15.686 | 1.00 | 31.21 | A | N |
| ATOM | 1014 | CA | AASN | A | 132 | 63.297 | −55.058 | 15.372 | 0.50 | 30.95 | A | C |
| ATOM | 1015 | CA | BASN | A | 132 | 63.289 | −55.084 | 15.356 | 0.50 | 34.00 | A | C |
| ATOM | 1016 | CB | AASN | A | 132 | 63.837 | −56.433 | 15.001 | 0.50 | 31.32 | A | C |
| ATOM | 1017 | CB | BASN | A | 132 | 63.799 | −56.491 | 14.994 | 0.50 | 39.09 | A | C |
| ATOM | 1018 | CG | AASN | A | 132 | 63.341 | −56.903 | 13.653 | 0.50 | 33.96 | A | C |
| ATOM | 1019 | CG | BASN | A | 132 | 62.692 | −57.417 | 14.481 | 0.50 | 47.90 | A | C |
| ATOM | 1020 | OD1 | AASN | A | 132 | 62.496 | −56.254 | 13.027 | 0.50 | 27.33 | A | O |
| ATOM | 1021 | OD1 | BASN | A | 132 | 61.662 | −57.614 | 15.141 | 0.50 | 44.58 | A | O |
| ATOM | 1022 | ND2 | AASN | A | 132 | 63.853 | −58.047 | 13.199 | 0.50 | 32.74 | A | N |
| ATOM | 1023 | ND2 | BASN | A | 132 | 62.911 | −57.999 | 13.307 | 0.50 | 52.36 | A | N |
| ATOM | 1024 | C | ASN | A | 132 | 63.664 | −54.083 | 14.250 | 1.00 | 40.19 | A | C |
| ATOM | 1025 | O | ASN | A | 132 | 64.858 | −53.821 | 14.013 | 1.00 | 32.34 | A | O |
| ATOM | 1026 | N | LEU | A | 133 | 62.659 | −53.549 | 13.546 | 1.00 | 31.58 | A | N |
| ATOM | 1027 | CA | LEU | A | 133 | 62.917 | −52.495 | 12.573 | 1.00 | 31.84 | A | C |
| ATOM | 1028 | CB | LEU | A | 133 | 61.659 | −52.164 | 11.744 | 1.00 | 29.65 | A | C |
| ATOM | 1029 | CG | LEU | A | 133 | 61.133 | −53.293 | 10.858 | 1.00 | 32.70 | A | C |
| ATOM | 1030 | CD1 | LEU | A | 133 | 59.694 | −52.974 | 10.379 | 1.00 | 32.29 | A | C |
| ATOM | 1031 | CD2 | LEU | A | 133 | 62.069 | −53.575 | 9.682 | 1.00 | 33.92 | A | C |
| ATOM | 1032 | C | LEU | A | 133 | 63.403 | −51.237 | 13.314 | 1.00 | 31.94 | A | C |
| ATOM | 1033 | O | LEU | A | 133 | 64.048 | −50.367 | 12.708 | 1.00 | 31.35 | A | O |
| ATOM | 1034 | N | LYS | A | 134 | 63.109 | −51.143 | 14.617 | 1.00 | 30.73 | A | N |
| ATOM | 1035 | CA | LYS | A | 134 | 63.553 | −49.996 | 15.427 | 1.00 | 32.93 | A | C |
| ATOM | 1036 | CB | LYS | A | 134 | 63.018 | −50.085 | 16.850 | 1.00 | 38.53 | A | C |
| ATOM | 1037 | CG | LYS | A | 134 | 63.773 | −51.080 | 17.716 | 1.00 | 42.00 | A | C |
| ATOM | 1038 | CD | LYS | A | 134 | 63.062 | −51.357 | 19.013 | 1.00 | 41.05 | A | C |
| ATOM | 1039 | CE | LYS | A | 134 | 63.823 | −52.399 | 19.828 | 1.00 | 41.23 | A | C |
| ATOM | 1040 | NZ | LYS | A | 134 | 63.541 | −52.187 | 21.252 | 1.00 | 33.39 | A | N |
| ATOM | 1041 | C | LYS | A | 134 | 65.084 | −49.841 | 15.462 | 1.00 | 31.46 | A | C |
| ATOM | 1042 | O | LYS | A | 134 | 65.575 | −48.762 | 15.719 | 1.00 | 33.74 | A | O |
| ATOM | 1043 | N | GLU | A | 135 | 65.819 | −50.909 | 15.171 | 1.00 | 31.04 | A | N |
| ATOM | 1044 | CA | GLU | A | 135 | 67.285 | −50.863 | 15.147 | 1.00 | 40.52 | A | C |
| ATOM | 1045 | CB | GLU | A | 135 | 67.896 | −52.285 | 15.148 | 1.00 | 46.31 | A | C |
| ATOM | 1046 | CG | GLU | A | 135 | 67.394 | −53.259 | 16.234 | 1.00 | 52.23 | A | C |
| ATOM | 1047 | CD | GLU | A | 135 | 67.544 | −52.748 | 17.666 | 1.00 | 65.02 | A | C |
| ATOM | 1048 | OE1 | GLU | A | 135 | 68.300 | −51.773 | 17.907 | 1.00 | 55.43 | A | O |
| ATOM | 1049 | OE2 | GLU | A | 135 | 66.894 | −53.344 | 18.559 | 1.00 | 73.29 | A | O |
| ATOM | 1050 | C | GLU | A | 135 | 67.836 | −50.121 | 13.928 | 1.00 | 40.04 | A | C |
| ATOM | 1051 | O | GLU | A | 135 | 68.993 | −49.709 | 13.920 | 1.00 | 37.69 | A | O |
| ATOM | 1052 | N | ASP | A | 136 | 67.023 | −49.974 | 12.890 | 1.00 | 37.22 | A | N |
| ATOM | 1053 | CA | ASP | A | 136 | 67.463 | −49.352 | 11.647 | 1.00 | 30.48 | A | C |
| ATOM | 1054 | CB | ASP | A | 136 | 66.916 | −50.172 | 10.481 | 1.00 | 32.94 | A | C |
| ATOM | 1055 | CG | ASP | A | 136 | 67.367 | −49.665 | 9.131 | 1.00 | 36.65 | A | C |
| ATOM | 1056 | OD1 | ASP | A | 136 | 67.881 | −48.517 | 9.013 | 1.00 | 35.76 | A | O |
| ATOM | 1057 | OD2 | ASP | A | 136 | 67.167 | −50.431 | 8.174 | 1.00 | 34.74 | A | O |
| ATOM | 1058 | C | ASP | A | 136 | 66.961 | −47.907 | 11.616 | 1.00 | 33.39 | A | C |
| ATOM | 1059 | O | ASP | A | 136 | 65.886 | −47.611 | 11.068 | 1.00 | 24.86 | A | O |
| ATOM | 1060 | N | ILE | A | 137 | 67.749 | −47.001 | 12.191 | 1.00 | 24.88 | A | N |
| ATOM | 1061 | CA | ILE | A | 137 | 67.290 | −45.633 | 12.403 | 1.00 | 24.01 | A | C |
| ATOM | 1062 | CB | ILE | A | 137 | 68.288 | −44.799 | 13.186 | 1.00 | 26.01 | A | C |
| ATOM | 1063 | CG1 | ILE | A | 137 | 68.536 | −45.436 | 14.570 | 1.00 | 36.15 | A | C |
| ATOM | 1064 | CD1 | ILE | A | 137 | 67.278 | −45.976 | 15.270 | 1.00 | 28.86 | A | C |

APPENDIX A-continued

*P. alba* 3T288C coordinates

| ATOM | 1065 | CG2 | ILE | A | 137 | 67.802 | −43.339 | 13.300 | 1.00 | 23.28 | A | C |
|---|---|---|---|---|---|---|---|---|---|---|---|---|
| ATOM | 1066 | C | ILE | A | 137 | 66.954 | −44.931 | 11.089 | 1.00 | 27.36 | A | C |
| ATOM | 1067 | O | ILE | A | 137 | 65.990 | −44.175 | 11.016 | 1.00 | 22.50 | A | O |
| ATOM | 1068 | N | LYS | A | 138 | 67.742 | −45.203 | 10.068 | 1.00 | 25.84 | A | N |
| ATOM | 1069 | CA | LYS | A | 138 | 67.586 | −44.599 | 8.758 | 1.00 | 30.98 | A | C |
| ATOM | 1070 | CB | LYS | A | 138 | 68.696 | −45.145 | 7.867 | 1.00 | 35.77 | A | C |
| ATOM | 1071 | CG | LYS | A | 138 | 69.312 | −44.193 | 6.894 | 1.00 | 51.75 | A | C |
| ATOM | 1072 | CD | LYS | A | 138 | 70.032 | −44.990 | 5.790 | 1.00 | 68.67 | A | C |
| ATOM | 1073 | CE | LYS | A | 138 | 71.089 | −44.167 | 5.070 | 1.00 | 82.46 | A | C |
| ATOM | 1074 | NZ | LYS | A | 138 | 72.392 | −44.194 | 5.792 | 1.00 | 86.22 | A | N |
| ATOM | 1075 | C | LYS | A | 138 | 66.216 | −44.970 | 8.165 | 1.00 | 24.80 | A | C |
| ATOM | 1076 | O | LYS | A | 138 | 65.544 | −44.145 | 7.542 | 1.00 | 23.16 | A | O |
| ATOM | 1077 | N | ALA | A | 139 | 65.859 | −46.241 | 8.317 | 1.00 | 22.69 | A | N |
| ATOM | 1078 | CA | ALA | A | 139 | 64.604 | −46.794 | 7.816 | 1.00 | 19.20 | A | C |
| ATOM | 1079 | CB | ALA | A | 139 | 64.639 | −48.355 | 7.913 | 1.00 | 20.06 | A | C |
| ATOM | 1080 | C | ALA | A | 139 | 63.437 | −46.208 | 8.611 | 1.00 | 22.32 | A | C |
| ATOM | 1081 | O | ALA | A | 139 | 62.407 | −45.830 | 8.055 | 1.00 | 22.17 | A | O |
| ATOM | 1082 | N | ILE | A | 140 | 63.600 | −46.083 | 9.917 | 1.00 | 19.58 | A | N |
| ATOM | 1083 | CA | ILE | A | 140 | 62.562 | −45.451 | 10.730 | 1.00 | 23.10 | A | C |
| ATOM | 1084 | CB | ILE | A | 140 | 62.813 | −45.616 | 12.252 | 1.00 | 25.60 | A | C |
| ATOM | 1085 | CG1 | ILE | A | 140 | 62.907 | −47.096 | 12.627 | 1.00 | 31.81 | A | C |
| ATOM | 1086 | CD1 | ILE | A | 140 | 61.752 | −47.904 | 12.154 | 1.00 | 32.36 | A | C |
| ATOM | 1087 | CG2 | ILE | A | 140 | 61.679 | −44.993 | 13.027 | 1.00 | 29.25 | A | C |
| ATOM | 1088 | C | ILE | A | 140 | 62.357 | −43.966 | 10.391 | 1.00 | 19.14 | A | C |
| ATOM | 1089 | O | ILE | A | 140 | 61.212 | −43.517 | 10.314 | 1.00 | 19.83 | A | O |
| ATOM | 1090 | N | LEU | A | 141 | 63.438 | −43.206 | 10.198 | 1.00 | 16.95 | A | N |
| ATOM | 1091 | CA | LEU | A | 141 | 63.317 | −41.813 | 9.748 | 1.00 | 21.76 | A | C |
| ATOM | 1092 | CB | LEU | A | 141 | 64.682 | −41.174 | 9.505 | 1.00 | 23.37 | A | C |
| ATOM | 1093 | CG | LEU | A | 141 | 65.294 | −40.491 | 10.709 | 1.00 | 29.38 | A | C |
| ATOM | 1094 | CD1 | LEU | A | 141 | 66.716 | −40.101 | 10.366 | 1.00 | 26.91 | A | C |
| ATOM | 1095 | CD2 | LEU | A | 141 | 64.434 | −39.292 | 11.112 | 1.00 | 25.25 | A | C |
| ATOM | 1096 | C | LEU | A | 141 | 62.534 | −41.718 | 8.444 | 1.00 | 19.26 | A | C |
| ATOM | 1097 | O | LEU | A | 141 | 61.665 | −40.862 | 8.277 | 1.00 | 17.44 | A | O |
| ATOM | 1098 | N | SER | A | 142 | 62.909 | −42.587 | 7.511 | 1.00 | 18.27 | A | N |
| ATOM | 1099 | CA | SER | A | 142 | 62.341 | −42.594 | 6.206 | 1.00 | 20.46 | A | C |
| ATOM | 1100 | CB | SER | A | 142 | 63.124 | −43.548 | 5.321 | 1.00 | 26.53 | A | C |
| ATOM | 1101 | OG | SER | A | 142 | 62.814 | −43.271 | 3.988 | 1.00 | 46.16 | A | O |
| ATOM | 1102 | C | SER | A | 142 | 60.847 | −42.966 | 6.271 | 1.00 | 18.21 | A | C |
| ATOM | 1103 | O | SER | A | 142 | 60.037 | −42.395 | 5.534 | 1.00 | 14.69 | A | O |
| ATOM | 1104 | N | LEU | A | 143 | 60.488 | −43.888 | 7.172 | 1.00 | 16.13 | A | N |
| ATOM | 1105 | CA | LEU | A | 143 | 59.100 | −44.268 | 7.381 | 1.00 | 17.04 | A | C |
| ATOM | 1106 | CB | LEU | A | 143 | 59.006 | −45.525 | 8.279 | 1.00 | 15.69 | A | C |
| ATOM | 1107 | CG | LEU | A | 143 | 57.615 | −46.033 | 8.546 | 1.00 | 14.71 | A | C |
| ATOM | 1108 | CD1 | LEU | A | 143 | 57.003 | −46.535 | 7.244 | 1.00 | 16.08 | A | C |
| ATOM | 1109 | CD2 | LEU | A | 143 | 57.657 | −47.149 | 9.631 | 1.00 | 15.44 | A | C |
| ATOM | 1110 | C | LEU | A | 143 | 58.311 | −43.097 | 7.984 | 1.00 | 17.25 | A | C |
| ATOM | 1111 | O | LEU | A | 143 | 57.207 | −42.802 | 7.561 | 1.00 | 15.03 | A | O |
| ATOM | 1112 | N | TYR | A | 144 | 58.912 | −42.395 | 8.934 | 1.00 | 15.40 | A | N |
| ATOM | 1113 | CA | TYR | A | 144 | 58.325 | −41.187 | 9.491 | 1.00 | 16.10 | A | C |
| ATOM | 1114 | CB | TYR | A | 144 | 59.225 | −40.646 | 10.613 | 1.00 | 15.60 | A | C |
| ATOM | 1115 | CG | TYR | A | 144 | 58.902 | −39.282 | 11.170 | 1.00 | 16.31 | A | C |
| ATOM | 1116 | CD1 | TYR | A | 144 | 57.977 | −39.090 | 12.193 | 1.00 | 16.83 | A | C |
| ATOM | 1117 | CE1 | TYR | A | 144 | 57.700 | −37.787 | 12.674 | 1.00 | 19.48 | A | C |
| ATOM | 1118 | CZ | TYR | A | 144 | 58.351 | −36.728 | 12.126 | 1.00 | 19.49 | A | C |
| ATOM | 1119 | OH | TYR | A | 144 | 58.165 | −35.414 | 12.516 | 1.00 | 33.50 | A | O |
| ATOM | 1120 | CE2 | TYR | A | 144 | 59.229 | −36.910 | 11.105 | 1.00 | 23.79 | A | C |
| ATOM | 1121 | CD2 | TYR | A | 144 | 59.496 | −38.164 | 10.630 | 1.00 | 22.71 | A | C |
| ATOM | 1122 | C | TYR | A | 144 | 58.059 | −40.146 | 8.400 | 1.00 | 16.74 | A | C |
| ATOM | 1123 | O | TYR | A | 144 | 56.955 | −39.586 | 8.314 | 1.00 | 14.47 | A | O |
| ATOM | 1124 | N | GLU | A | 145 | 59.041 | −39.909 | 7.530 | 1.00 | 15.21 | A | N |
| ATOM | 1125 | CA | GLU | A | 145 | 58.873 | −38.862 | 6.509 | 1.00 | 15.72 | A | C |
| ATOM | 1126 | CB | GLU | A | 145 | 60.154 | −38.637 | 5.722 | 1.00 | 18.15 | A | C |
| ATOM | 1127 | CG | GLU | A | 145 | 61.344 | −38.139 | 6.595 | 1.00 | 19.87 | A | C |
| ATOM | 1128 | CD | GLU | A | 145 | 61.188 | −36.679 | 7.108 | 1.00 | 24.51 | A | C |
| ATOM | 1129 | OE1 | GLU | A | 145 | 60.171 | −36.021 | 6.801 | 1.00 | 29.03 | A | O |
| ATOM | 1130 | OE2 | GLU | A | 145 | 62.097 | −36.173 | 7.820 | 1.00 | 28.27 | A | O |
| ATOM | 1131 | C | GLU | A | 145 | 57.738 | −39.213 | 5.541 | 1.00 | 16.62 | A | C |
| ATOM | 1132 | O | GLU | A | 145 | 56.952 | −38.359 | 5.182 | 1.00 | 15.05 | A | O |
| ATOM | 1133 | N | ALA | A | 146 | 57.690 | −40.475 | 5.134 | 1.00 | 13.68 | A | N |
| ATOM | 1134 | CA | ALA | A | 146 | 56.692 | −40.980 | 4.200 | 1.00 | 15.91 | A | C |
| ATOM | 1135 | CB | ALA | A | 146 | 56.968 | −42.430 | 3.894 | 1.00 | 12.43 | A | C |
| ATOM | 1136 | C | ALA | A | 146 | 55.265 | −40.849 | 4.755 | 1.00 | 15.88 | A | C |
| ATOM | 1137 | O | ALA | A | 146 | 54.344 | −40.597 | 4.002 | 1.00 | 16.60 | A | O |
| ATOM | 1138 | N | SER | A | 147 | 55.099 | −41.014 | 6.068 | 1.00 | 14.09 | A | N |
| ATOM | 1139 | CA | SER | A | 147 | 53.764 | −41.019 | 6.688 | 1.00 | 14.89 | A | C |
| ATOM | 1140 | CB | SER | A | 147 | 53.879 | −41.395 | 8.172 | 1.00 | 15.06 | A | C |
| ATOM | 1141 | OG | SER | A | 147 | 54.428 | −40.319 | 8.928 | 1.00 | 18.70 | A | O |
| ATOM | 1142 | C | SER | A | 147 | 53.002 | −39.717 | 6.510 | 1.00 | 17.14 | A | C |

APPENDIX A-continued

*P. alba* 3T288C coordinates

| ATOM | 1143 | O   | SER  | A | 147 | 51.777 | −39.709 | 6.490  | 1.00 | 17.46 | A | O |
|------|------|-----|------|---|-----|--------|---------|--------|------|-------|---|---|
| ATOM | 1144 | N   | PHE  | A | 148 | 53.726 | −38.612 | 6.309  | 1.00 | 15.93 | A | N |
| ATOM | 1145 | CA  | PHE  | A | 148 | 53.088 | −37.334 | 6.131  | 1.00 | 15.22 | A | C |
| ATOM | 1146 | CB  | PHE  | A | 148 | 54.047 | −36.189 | 6.491  | 1.00 | 16.39 | A | C |
| ATOM | 1147 | CG  | PHE  | A | 148 | 54.337 | −36.123 | 7.963  | 1.00 | 15.45 | A | C |
| ATOM | 1148 | CD1 | PHE  | A | 148 | 53.478 | −35.439 | 8.819  | 1.00 | 17.42 | A | C |
| ATOM | 1149 | CE1 | PHE  | A | 148 | 53.725 | −35.385 | 10.197 | 1.00 | 19.59 | A | C |
| ATOM | 1150 | CZ  | PHE  | A | 148 | 54.841 | −36.077 | 10.727 | 1.00 | 19.38 | A | C |
| ATOM | 1151 | CE2 | PHE  | A | 148 | 55.653 | −36.791 | 9.881  | 1.00 | 18.32 | A | C |
| ATOM | 1152 | CD2 | PHE  | A | 148 | 55.405 | −36.793 | 8.492  | 1.00 | 17.53 | A | C |
| ATOM | 1153 | C   | PHE  | A | 148 | 52.471 | −37.155 | 4.762  | 1.00 | 15.54 | A | C |
| ATOM | 1154 | O   | PHE  | A | 148 | 51.778 | −36.169 | 4.563  | 1.00 | 15.38 | A | O |
| ATOM | 1155 | N   | LEU  | A | 149 | 52.730 | −38.080 | 3.830  | 1.00 | 15.31 | A | N |
| ATOM | 1156 | CA  | LEU  | A | 149 | 52.150 | −37.987 | 2.482  | 1.00 | 18.47 | A | C |
| ATOM | 1157 | CB  | LEU  | A | 149 | 53.157 | −38.474 | 1.415  | 1.00 | 18.22 | A | C |
| ATOM | 1158 | CG  | LEU  | A | 149 | 54.234 | −37.445 | 1.047  | 1.00 | 21.82 | A | C |
| ATOM | 1159 | CD1 | LEU  | A | 149 | 55.387 | −37.390 | 2.130  | 1.00 | 19.29 | A | C |
| ATOM | 1160 | CD2 | LEU  | A | 149 | 54.819 | −37.691 | −0.339 | 1.00 | 22.36 | A | C |
| ATOM | 1161 | C   | LEU  | A | 149 | 50.836 | −38.752 | 2.370  | 1.00 | 16.60 | A | C |
| ATOM | 1162 | O   | LEU  | A | 149 | 50.307 | −38.944 | 1.252  | 1.00 | 15.30 | A | O |
| ATOM | 1163 | N   | ALA  | A | 150 | 50.317 | −39.173 | 3.517  | 1.00 | 15.81 | A | N |
| ATOM | 1164 | CA  | ALA  | A | 150 | 49.107 | −39.941 | 3.618  | 1.00 | 17.34 | A | C |
| ATOM | 1165 | CB  | ALA  | A | 150 | 48.823 | −40.301 | 5.087  | 1.00 | 15.45 | A | C |
| ATOM | 1166 | C   | ALA  | A | 150 | 47.881 | −39.234 | 3.050  | 1.00 | 18.40 | A | C |
| ATOM | 1167 | O   | ALA  | A | 150 | 47.712 | −38.025 | 3.186  | 1.00 | 16.98 | A | O |
| ATOM | 1168 | N   | LEU  | A | 151 | 46.981 | −40.043 | 2.535  | 1.00 | 14.75 | A | N |
| ATOM | 1169 | CA  | LEU  | A | 151 | 45.632 | −39.599 | 2.206  | 1.00 | 16.19 | A | C |
| ATOM | 1170 | CB  | LEU  | A | 151 | 45.243 | −40.145 | 0.854  | 1.00 | 16.19 | A | C |
| ATOM | 1171 | CG  | LEU  | A | 151 | 46.247 | −40.004 | −0.282 | 1.00 | 19.06 | A | C |
| ATOM | 1172 | CD1 | LEU  | A | 151 | 45.756 | −40.681 | −1.566 | 1.00 | 22.57 | A | C |
| ATOM | 1173 | CD2 | LEU  | A | 151 | 46.541 | −38.559 | −0.537 | 1.00 | 16.77 | A | C |
| ATOM | 1174 | C   | LEU  | A | 151 | 44.652 | −40.073 | 3.254  | 1.00 | 13.22 | A | C |
| ATOM | 1175 | O   | LEU  | A | 151 | 44.974 | −40.943 | 4.082  | 1.00 | 14.48 | A | O |
| ATOM | 1176 | N   | GLU  | A | 152 | 43.417 | −39.593 | 3.181  | 1.00 | 14.18 | A | N |
| ATOM | 1177 | CA  | GLU  | A | 152 | 42.394 | −40.062 | 4.089  | 1.00 | 14.14 | A | C |
| ATOM | 1178 | CB  | GLU  | A | 152 | 41.085 | −39.287 | 3.961  | 1.00 | 18.51 | A | C |
| ATOM | 1179 | CG  | GLU  | A | 152 | 41.129 | −37.846 | 4.564  | 1.00 | 23.96 | A | C |
| ATOM | 1180 | CD  | GLU  | A | 152 | 39.734 | −37.206 | 4.652  | 1.00 | 32.90 | A | C |
| ATOM | 1181 | OE1 | GLU  | A | 152 | 39.168 | −36.845 | 3.585  | 1.00 | 28.65 | A | O |
| ATOM | 1182 | OE2 | GLU  | A | 152 | 39.196 | −37.096 | 5.785  | 1.00 | 31.52 | A | O |
| ATOM | 1183 | C   | GLU  | A | 152 | 42.172 | −41.546 | 3.898  | 1.00 | 17.44 | A | C |
| ATOM | 1184 | O   | GLU  | A | 152 | 42.205 | −42.036 | 2.782  | 1.00 | 14.59 | A | O |
| ATOM | 1185 | N   | GLY  | A | 153 | 41.970 | −42.249 | 5.014  | 1.00 | 15.78 | A | N |
| ATOM | 1186 | CA  | GLY  | A | 153 | 41.818 | −43.699 | 5.015  | 1.00 | 16.99 | A | C |
| ATOM | 1187 | C   | GLY  | A | 153 | 43.081 | −44.544 | 4.948  | 1.00 | 14.91 | A | C |
| ATOM | 1188 | O   | GLY  | A | 153 | 42.992 | −45.752 | 5.026  | 1.00 | 13.14 | A | O |
| ATOM | 1189 | N   | GLU  | A | 154 | 44.258 | −43.937 | 4.852  | 1.00 | 13.94 | A | N |
| ATOM | 1190 | CA  | GLU  | A | 154 | 45.497 | −44.703 | 4.823  | 1.00 | 16.14 | A | C |
| ATOM | 1191 | CB  | GLU  | A | 154 | 46.542 | −44.018 | 3.943  | 1.00 | 16.91 | A | C |
| ATOM | 1192 | CG  | GLU  | A | 154 | 46.197 | −44.125 | 2.469  | 1.00 | 18.41 | A | C |
| ATOM | 1193 | CD  | GLU  | A | 154 | 47.257 | −43.609 | 1.503  | 1.00 | 23.40 | A | C |
| ATOM | 1194 | OE1 | GLU  | A | 154 | 47.955 | −42.590 | 1.798  | 1.00 | 17.72 | A | O |
| ATOM | 1195 | OE2 | GLU  | A | 154 | 47.356 | −44.194 | 0.395  | 1.00 | 19.66 | A | O |
| ATOM | 1196 | C   | GLU  | A | 154 | 45.975 | −44.935 | 6.269  | 1.00 | 17.71 | A | C |
| ATOM | 1197 | O   | GLU  | A | 154 | 46.989 | −44.389 | 6.726  | 1.00 | 14.88 | A | O |
| ATOM | 1198 | N   | ASN  | A | 155 | 45.247 | −45.807 | 6.950  | 1.00 | 16.60 | A | N |
| ATOM | 1199 | CA  | ASN  | A | 155 | 45.489 | −46.075 | 8.350  | 1.00 | 18.90 | A | C |
| ATOM | 1200 | CB  | ASN  | A | 155 | 44.434 | −47.017 | 8.918  | 1.00 | 20.93 | A | C |
| ATOM | 1201 | CG  | ASN  | A | 155 | 44.443 | −48.381 | 8.234  | 1.00 | 18.14 | A | C |
| ATOM | 1202 | OD1 | ASN  | A | 155 | 44.241 | −48.483 | 7.024  | 1.00 | 16.09 | A | O |
| ATOM | 1203 | ND2 | ASN  | A | 155 | 44.679 | −49.435 | 9.014  | 1.00 | 18.65 | A | N |
| ATOM | 1204 | C   | ASN  | A | 155 | 46.871 | −46.650 | 8.630  | 1.00 | 20.12 | A | C |
| ATOM | 1205 | O   | ASN  | A | 155 | 47.401 | −46.426 | 9.701  | 1.00 | 18.62 | A | O |
| ATOM | 1206 | N   | ILE  | A | 156 | 47.436 | −47.399 | 7.682  | 1.00 | 16.20 | A | N |
| ATOM | 1207 | CA  | ILE  | A | 156 | 48.771 | −47.949 | 7.861  | 1.00 | 16.77 | A | C |
| ATOM | 1208 | CB  | ILE  | A | 156 | 49.116 | −48.931 | 6.754  | 1.00 | 18.33 | A | C |
| ATOM | 1209 | CG1 | ILE  | A | 156 | 48.132 | −50.099 | 6.778  | 1.00 | 24.37 | A | C |
| ATOM | 1210 | CD1 | ILE  | A | 156 | 48.422 | −51.119 | 5.712  | 1.00 | 29.91 | A | C |
| ATOM | 1211 | CG2 | ILE  | A | 156 | 50.550 | −49.458 | 6.900  | 1.00 | 21.14 | A | C |
| ATOM | 1212 | C   | ILE  | A | 156 | 49.817 | −46.837 | 7.948  | 1.00 | 19.06 | A | C |
| ATOM | 1213 | O   | ILE  | A | 156 | 50.766 | −46.951 | 8.708  | 1.00 | 16.97 | A | O |
| ATOM | 1214 | N   | LEU  | A | 157 | 49.662 | −45.765 | 7.172  | 1.00 | 17.32 | A | N |
| ATOM | 1215 | CA  | ALEU | A | 157 | 50.602 | −44.648 | 7.251  | 0.50 | 17.81 | A | C |
| ATOM | 1216 | CA  | BLEU | A | 157 | 50.604 | −44.657 | 7.252  | 0.50 | 18.60 | A | C |
| ATOM | 1217 | CB  | ALEU | A | 157 | 50.464 | −43.694 | 6.062  | 0.50 | 16.56 | A | C |
| ATOM | 1218 | CB  | BLEU | A | 157 | 50.473 | −43.735 | 6.042  | 0.50 | 18.39 | A | C |
| ATOM | 1219 | CG  | ALEU | A | 157 | 51.257 | −44.012 | 4.793  | 0.50 | 16.00 | A | C |
| ATOM | 1220 | CG  | BLEU | A | 157 | 50.771 | −44.416 | 4.705  | 0.50 | 18.36 | A | C |

APPENDIX A-continued

*P. alba* 3T288C coordinates

| ATOM | 1221 | CD1 | ALEU | A | 157 | 50.915 | −45.378 | 4.215 | 0.50 | 14.54 | A | C |
|---|---|---|---|---|---|---|---|---|---|---|---|---|
| ATOM | 1222 | CD1 | BLEU | A | 157 | 50.536 | −43.465 | 3.509 | 0.50 | 19.37 | A | C |
| ATOM | 1223 | CD2 | ALEU | A | 157 | 51.039 | −42.915 | 3.747 | 0.50 | 14.62 | A | C |
| ATOM | 1224 | CD2 | BLEU | A | 157 | 52.212 | −44.943 | 4.712 | 0.50 | 22.52 | A | C |
| ATOM | 1225 | C | LEU | A | 157 | 50.439 | −43.913 | 8.583 | 1.00 | 20.05 | A | C |
| ATOM | 1226 | O | LEU | A | 157 | 51.428 | −43.499 | 9.195 | 1.00 | 17.15 | A | O |
| ATOM | 1227 | N | ASP | A | 158 | 49.207 | −43.763 | 9.055 | 1.00 | 16.45 | A | N |
| ATOM | 1228 | CA | ASP | A | 158 | 48.995 | −43.157 | 10.381 | 1.00 | 18.02 | A | C |
| ATOM | 1229 | CB | ASP | A | 158 | 47.495 | −42.962 | 10.675 | 1.00 | 23.70 | A | C |
| ATOM | 1230 | CG | ASP | A | 158 | 46.899 | −41.736 | 9.945 | 1.00 | 36.75 | A | C |
| ATOM | 1231 | OD1 | ASP | A | 158 | 47.640 | −41.003 | 9.246 | 1.00 | 46.65 | A | O |
| ATOM | 1232 | OD2 | ASP | A | 158 | 45.680 | −41.496 | 10.074 | 1.00 | 30.74 | A | O |
| ATOM | 1233 | C | ASP | A | 158 | 49.647 | −43.996 | 11.493 | 1.00 | 21.85 | A | C |
| ATOM | 1234 | O | ASP | A | 158 | 50.281 | −43.456 | 12.407 | 1.00 | 17.84 | A | O |
| ATOM | 1235 | N | GLU | A | 159 | 49.481 | −45.306 | 11.415 | 1.00 | 17.82 | A | N |
| ATOM | 1236 | CA | GLU | A | 159 | 50.149 | −46.251 | 12.356 | 1.00 | 22.88 | A | C |
| ATOM | 1237 | CB | GLU | A | 159 | 49.644 | −47.683 | 12.101 | 1.00 | 21.78 | A | C |
| ATOM | 1238 | CG | GLU | A | 159 | 48.159 | −47.853 | 12.486 | 1.00 | 27.20 | A | C |
| ATOM | 1239 | CD | GLU | A | 159 | 47.455 | −49.026 | 11.768 | 1.00 | 33.26 | A | C |
| ATOM | 1240 | OE1 | GLU | A | 159 | 48.161 | −49.941 | 11.281 | 1.00 | 33.28 | A | O |
| ATOM | 1241 | OE2 | GLU | A | 159 | 46.196 | −49.014 | 11.697 | 1.00 | 41.36 | A | O |
| ATOM | 1242 | C | GLU | A | 159 | 51.682 | −46.221 | 12.217 | 1.00 | 21.29 | A | C |
| ATOM | 1243 | O | GLU | A | 159 | 52.395 | −46.328 | 13.204 | 1.00 | 18.19 | A | O |
| ATOM | 1244 | N | ALA | A | 160 | 52.170 | −46.067 | 10.982 | 1.00 | 18.94 | A | N |
| ATOM | 1245 | CA | ALA | A | 160 | 53.604 | −45.903 | 10.733 | 1.00 | 20.13 | A | C |
| ATOM | 1246 | CB | ALA | A | 160 | 53.902 | −45.809 | 9.257 | 1.00 | 18.72 | A | C |
| ATOM | 1247 | C | ALA | A | 160 | 54.142 | −44.682 | 11.465 | 1.00 | 18.25 | A | C |
| ATOM | 1248 | O | ALA | A | 160 | 55.204 | −44.741 | 12.055 | 1.00 | 20.17 | A | O |
| ATOM | 1249 | N | LYS | A | 161 | 53.422 | −43.569 | 11.413 | 1.00 | 19.03 | A | N |
| ATOM | 1250 | CA | LYS | A | 161 | 53.870 | −42.372 | 12.079 | 1.00 | 16.85 | A | C |
| ATOM | 1251 | CB | LYS | A | 161 | 52.987 | −41.176 | 11.756 | 1.00 | 17.64 | A | C |
| ATOM | 1252 | CG | LYS | A | 161 | 53.497 | −39.838 | 12.266 | 1.00 | 19.23 | A | C |
| ATOM | 1253 | CD | LYS | A | 161 | 52.393 | −38.752 | 12.235 | 1.00 | 21.55 | A | C |
| ATOM | 1254 | CE | LYS | A | 161 | 51.991 | −38.399 | 10.792 | 1.00 | 22.08 | A | C |
| ATOM | 1255 | NZ | LYS | A | 161 | 50.873 | −37.403 | 10.754 | 1.00 | 28.22 | A | N |
| ATOM | 1256 | C | LYS | A | 161 | 53.971 | −42.615 | 13.600 | 1.00 | 19.00 | A | C |
| ATOM | 1257 | O | LYS | A | 161 | 54.974 | −42.238 | 14.208 | 1.00 | 21.46 | A | O |
| ATOM | 1258 | N | VAL | A | 162 | 52.955 | −43.233 | 14.196 | 1.00 | 21.78 | A | N |
| ATOM | 1259 | CA | VAL | A | 162 | 52.939 | −43.495 | 15.637 | 1.00 | 21.10 | A | C |
| ATOM | 1260 | CB | VAL | A | 162 | 51.618 | −44.152 | 16.075 | 1.00 | 25.19 | A | C |
| ATOM | 1261 | CG1 | VAL | A | 162 | 51.737 | −44.735 | 17.525 | 1.00 | 21.82 | A | C |
| ATOM | 1262 | CG2 | VAL | A | 162 | 50.480 | −43.145 | 15.953 | 1.00 | 20.91 | A | C |
| ATOM | 1263 | C | VAL | A | 162 | 54.128 | −44.369 | 16.042 | 1.00 | 22.12 | A | C |
| ATOM | 1264 | O | VAL | A | 162 | 54.817 | −44.096 | 17.018 | 1.00 | 20.45 | A | O |
| ATOM | 1265 | N | PHE | A | 163 | 54.366 | −45.415 | 15.278 | 1.00 | 21.27 | A | N |
| ATOM | 1266 | CA | PHE | A | 163 | 55.483 | −46.320 | 15.521 | 1.00 | 23.48 | A | C |
| ATOM | 1267 | CB | PHE | A | 163 | 55.327 | −47.472 | 14.531 | 1.00 | 20.49 | A | C |
| ATOM | 1268 | CG | PHE | A | 163 | 56.455 | −48.422 | 14.504 | 1.00 | 21.07 | A | C |
| ATOM | 1269 | CD1 | PHE | A | 163 | 56.538 | −49.457 | 15.445 | 1.00 | 23.36 | A | C |
| ATOM | 1270 | CE1 | PHE | A | 163 | 57.573 | −50.363 | 15.398 | 1.00 | 22.92 | A | C |
| ATOM | 1271 | CZ | PHE | A | 163 | 58.538 | −50.251 | 14.390 | 1.00 | 23.85 | A | C |
| ATOM | 1272 | CE2 | PHE | A | 163 | 58.440 | −49.248 | 13.430 | 1.00 | 24.53 | A | C |
| ATOM | 1273 | CD2 | PHE | A | 163 | 57.401 | −48.344 | 13.492 | 1.00 | 21.66 | A | C |
| ATOM | 1274 | C | PHE | A | 163 | 56.857 | −45.607 | 15.401 | 1.00 | 23.17 | A | C |
| ATOM | 1275 | O | PHE | A | 163 | 57.719 | −45.684 | 16.281 | 1.00 | 20.56 | A | O |
| ATOM | 1276 | N | ALA | A | 164 | 57.037 | −44.867 | 14.322 | 1.00 | 19.68 | A | N |
| ATOM | 1277 | CA | ALA | A | 164 | 58.311 | −44.248 | 14.037 | 1.00 | 18.42 | A | C |
| ATOM | 1278 | CB | ALA | A | 164 | 58.285 | −43.579 | 12.677 | 1.00 | 13.78 | A | C |
| ATOM | 1279 | C | ALA | A | 164 | 58.636 | −43.240 | 15.139 | 1.00 | 21.21 | A | C |
| ATOM | 1280 | O | ALA | A | 164 | 59.723 | −43.286 | 15.723 | 1.00 | 22.03 | A | O |
| ATOM | 1281 | N | ILE | A | 165 | 57.682 | −42.371 | 15.446 | 1.00 | 21.64 | A | N |
| ATOM | 1282 | CA | AILE | A | 165 | 57.833 | −41.339 | 16.473 | 0.50 | 20.95 | A | C |
| ATOM | 1283 | CA | BILE | A | 165 | 57.909 | −41.334 | 16.442 | 0.50 | 23.71 | A | C |
| ATOM | 1284 | CB | AILE | A | 165 | 56.517 | −40.537 | 16.650 | 0.50 | 20.64 | A | C |
| ATOM | 1285 | CB | BILE | A | 165 | 56.732 | −40.324 | 16.516 | 0.50 | 27.11 | A | C |
| ATOM | 1286 | CG1 | AILE | A | 165 | 56.443 | −39.411 | 15.618 | 0.50 | 21.15 | A | C |
| ATOM | 1287 | CG1 | BILE | A | 165 | 57.136 | −39.071 | 17.301 | 0.50 | 31.60 | A | C |
| ATOM | 1288 | CD1 | AILE | A | 165 | 55.073 | −38.748 | 15.482 | 0.50 | 18.04 | A | C |
| ATOM | 1289 | CD1 | BILE | A | 165 | 55.959 | −38.281 | 17.848 | 0.50 | 32.38 | A | C |
| ATOM | 1290 | CG2 | AILE | A | 165 | 56.392 | −40.001 | 18.089 | 0.50 | 21.87 | A | C |
| ATOM | 1291 | CG2 | BILE | A | 165 | 55.525 | −40.956 | 17.150 | 0.50 | 36.27 | A | C |
| ATOM | 1292 | C | ILE | A | 165 | 58.224 | −41.952 | 17.815 | 1.00 | 24.18 | A | C |
| ATOM | 1293 | O | ILE | A | 165 | 59.101 | −41.458 | 18.516 | 1.00 | 23.80 | A | O |
| ATOM | 1294 | N | SER | A | 166 | 57.560 | −43.046 | 18.165 | 1.00 | 24.66 | A | N |
| ATOM | 1295 | CA | SER | A | 166 | 57.784 | −43.709 | 19.445 | 1.00 | 25.26 | A | C |
| ATOM | 1296 | CB | SER | A | 166 | 56.838 | −44.917 | 19.587 | 1.00 | 25.78 | A | C |
| ATOM | 1297 | OG | SER | A | 166 | 57.370 | −46.095 | 18.941 | 1.00 | 29.45 | A | O |
| ATOM | 1298 | C | SER | A | 166 | 59.237 | −44.173 | 19.578 | 1.00 | 26.55 | A | C |

APPENDIX A-continued

| | | | | | | | | | | | | |
|---|---|---|---|---|---|---|---|---|---|---|---|---|
| *P. alba* 3T288C coordinates | | | | | | | | | | | | |
| ATOM | 1299 | O | SER | A | 166 | 59.821 | −44.112 | 20.648 | 1.00 | 30.51 | A | O |
| ATOM | 1300 | N | HIS | A | 167 | 59.807 | −44.638 | 18.477 | 1.00 | 25.51 | A | N |
| ATOM | 1301 | CA | HIS | A | 167 | 61.160 | −45.136 | 18.451 | 1.00 | 23.28 | A | C |
| ATOM | 1302 | CB | HIS | A | 167 | 61.278 | −46.258 | 17.447 | 1.00 | 23.58 | A | C |
| ATOM | 1303 | CG | HIS | A | 167 | 60.569 | −47.536 | 17.869 | 1.00 | 34.21 | A | C |
| ATOM | 1304 | ND1 | HIS | A | 167 | 60.813 | −48.150 | 19.048 | 1.00 | 31.37 | A | N |
| ATOM | 1305 | CE1 | HIS | A | 167 | 60.052 | −49.257 | 19.151 | 1.00 | 36.74 | A | C |
| ATOM | 1306 | NE2 | HIS | A | 167 | 59.321 | −49.364 | 18.032 | 1.00 | 40.73 | A | N |
| ATOM | 1307 | CD2 | HIS | A | 167 | 59.604 | −48.309 | 17.222 | 1.00 | 34.62 | A | C |
| ATOM | 1308 | C | HIS | A | 167 | 62.171 | −44.054 | 18.194 | 1.00 | 29.12 | A | C |
| ATOM | 1309 | O | HIS | A | 167 | 63.315 | −44.185 | 18.609 | 1.00 | 36.79 | A | O |
| ATOM | 1310 | N | LEU | A | 168 | 61.772 | −42.951 | 17.561 | 1.00 | 22.31 | A | N |
| ATOM | 1311 | CA | LEU | A | 168 | 62.700 | −41.854 | 17.326 | 1.00 | 21.97 | A | C |
| ATOM | 1312 | CB | LEU | A | 168 | 62.289 | −41.008 | 16.130 | 1.00 | 24.55 | A | C |
| ATOM | 1313 | CG | LEU | A | 168 | 62.324 | −41.692 | 14.762 | 1.00 | 23.28 | A | C |
| ATOM | 1314 | CD1 | LEU | A | 168 | 61.510 | −40.848 | 13.755 | 1.00 | 22.93 | A | C |
| ATOM | 1315 | CD2 | LEU | A | 168 | 63.755 | −41.916 | 14.281 | 1.00 | 20.77 | A | C |
| ATOM | 1316 | C | LEU | A | 168 | 62.839 | −40.917 | 18.528 | 1.00 | 25.89 | A | C |
| ATOM | 1317 | O | LEU | A | 168 | 63.890 | −40.328 | 18.689 | 1.00 | 23.33 | A | O |
| ATOM | 1318 | N | LYS | A | 169 | 61.770 | −40.764 | 19.323 | 1.00 | 22.50 | A | N |
| ATOM | 1319 | CA | LYS | A | 169 | 61.679 | −39.744 | 20.370 | 1.00 | 27.82 | A | C |
| ATOM | 1320 | CB | LYS | A | 169 | 60.250 | −39.667 | 20.937 | 1.00 | 34.22 | A | C |
| ATOM | 1321 | CG | LYS | A | 169 | 59.734 | −38.249 | 21.087 | 1.00 | 50.55 | A | C |
| ATOM | 1322 | CD | LYS | A | 169 | 58.226 | −38.198 | 21.357 | 1.00 | 58.76 | A | C |
| ATOM | 1323 | CE | LYS | A | 169 | 57.572 | −37.025 | 20.621 | 1.00 | 62.12 | A | C |
| ATOM | 1324 | NZ | LYS | A | 169 | 56.090 | −37.061 | 20.706 | 1.00 | 59.64 | A | N |
| ATOM | 1325 | C | LYS | A | 169 | 62.623 | −40.088 | 21.520 | 1.00 | 37.79 | A | C |
| ATOM | 1326 | O | LYS | A | 169 | 63.068 | −39.208 | 22.255 | 1.00 | 38.87 | A | O |
| ATOM | 1327 | N | GLU | A | 170 | 62.915 | −41.374 | 21.668 | 1.00 | 33.46 | A | N |
| ATOM | 1328 | CA | GLU | A | 170 | 63.722 | −41.860 | 22.772 | 1.00 | 50.73 | A | C |
| ATOM | 1329 | CB | GLU | A | 170 | 63.038 | −43.071 | 23.433 | 1.00 | 58.58 | A | C |
| ATOM | 1330 | CG | GLU | A | 170 | 62.410 | −42.749 | 24.796 | 1.00 | 74.37 | A | C |
| ATOM | 1331 | CD | GLU | A | 170 | 60.954 | −42.354 | 24.711 | 1.00 | 82.28 | A | C |
| ATOM | 1332 | OE1 | GLU | A | 170 | 60.228 | −42.912 | 23.857 | 1.00 | 101.69 | A | O |
| ATOM | 1333 | OE2 | GLU | A | 170 | 60.532 | −41.496 | 25.516 | 1.00 | 83.80 | A | O |
| ATOM | 1334 | C | GLU | A | 170 | 65.145 | −42.221 | 22.362 | 1.00 | 53.62 | A | C |
| ATOM | 1335 | O | GLU | A | 170 | 65.836 | −42.921 | 23.099 | 1.00 | 49.28 | A | O |
| ATOM | 1336 | N | LEU | A | 171 | 65.596 | −41.737 | 21.208 | 1.00 | 46.07 | A | N |
| ATOM | 1337 | CA | LEU | A | 171 | 66.975 | −41.966 | 20.799 | 1.00 | 47.42 | A | C |
| ATOM | 1338 | CB | LEU | A | 171 | 67.136 | −41.777 | 19.294 | 1.00 | 39.33 | A | C |
| ATOM | 1339 | CG | LEU | A | 171 | 66.477 | −42.875 | 18.462 | 1.00 | 38.86 | A | C |
| ATOM | 1340 | CD1 | LEU | A | 171 | 66.646 | −42.622 | 16.958 | 1.00 | 29.01 | A | C |
| ATOM | 1341 | CD2 | LEU | A | 171 | 67.026 | −44.265 | 18.848 | 1.00 | 41.31 | A | C |
| ATOM | 1342 | C | LEU | A | 171 | 67.929 | −41.047 | 21.581 | 1.00 | 49.73 | A | C |
| ATOM | 1343 | O | LEU | A | 171 | 67.566 | −39.919 | 21.935 | 1.00 | 42.22 | A | O |
| ATOM | 1344 | N | SER | A | 172 | 69.132 | −41.559 | 21.852 | 1.00 | 55.46 | A | N |
| ATOM | 1345 | CA | SER | A | 172 | 70.192 | −40.818 | 22.558 | 1.00 | 59.52 | A | C |
| ATOM | 1346 | CB | SER | A | 172 | 70.665 | −41.614 | 23.788 | 1.00 | 67.88 | A | C |
| ATOM | 1347 | OG | SER | A | 172 | 71.656 | −40.922 | 24.534 | 1.00 | 70.11 | A | O |
| ATOM | 1348 | C | SER | A | 172 | 71.370 | −40.566 | 21.607 | 1.00 | 47.16 | A | C |
| ATOM | 1349 | O | SER | A | 172 | 71.831 | −41.484 | 20.918 | 1.00 | 38.06 | A | O |
| ATOM | 1350 | N | GLU | A | 173 | 71.846 | −39.324 | 21.572 | 1.00 | 44.33 | A | N |
| ATOM | 1351 | CA | GLU | A | 173 | 72.989 | −38.930 | 20.733 | 1.00 | 48.18 | A | C |
| ATOM | 1352 | CB | GLU | A | 173 | 73.371 | −37.480 | 21.048 | 1.00 | 51.55 | A | C |
| ATOM | 1353 | CG | GLU | A | 173 | 74.686 | −37.024 | 20.417 | 1.00 | 54.88 | A | C |
| ATOM | 1354 | CD | GLU | A | 173 | 74.730 | −35.532 | 20.179 | 1.00 | 65.93 | A | C |
| ATOM | 1355 | OE1 | GLU | A | 173 | 73.946 | −34.790 | 20.812 | 1.00 | 65.86 | A | O |
| ATOM | 1356 | OE2 | GLU | A | 173 | 75.552 | −35.103 | 19.344 | 1.00 | 83.90 | A | O |
| ATOM | 1357 | C | GLU | A | 173 | 74.236 | −39.827 | 20.868 | 1.00 | 49.00 | A | C |
| ATOM | 1358 | O | GLU | A | 173 | 74.931 | −40.082 | 19.870 | 1.00 | 37.80 | A | O |
| ATOM | 1359 | N | GLU | A | 174 | 74.515 | −40.280 | 22.096 | 1.00 | 48.12 | A | N |
| ATOM | 1360 | CA | GLU | A | 174 | 75.612 | −41.220 | 22.363 | 1.00 | 55.68 | A | C |
| ATOM | 1361 | CB | GLU | A | 174 | 75.771 | −41.484 | 23.865 | 1.00 | 58.22 | A | C |
| ATOM | 1362 | CG | GLU | A | 174 | 76.324 | −40.317 | 24.665 | 1.00 | 69.42 | A | C |
| ATOM | 1363 | CD | GLU | A | 174 | 75.241 | −39.438 | 25.253 | 1.00 | 76.47 | A | C |
| ATOM | 1364 | OE1 | GLU | A | 174 | 74.227 | −39.181 | 24.565 | 1.00 | 73.99 | A | O |
| ATOM | 1365 | OE2 | GLU | A | 174 | 75.408 | −39.001 | 26.410 | 1.00 | 85.80 | A | O |
| ATOM | 1366 | C | GLU | A | 174 | 75.392 | −42.552 | 21.660 | 1.00 | 57.03 | A | C |
| ATOM | 1367 | O | GLU | A | 174 | 76.314 | −43.095 | 21.047 | 1.00 | 61.24 | A | O |
| ATOM | 1368 | N | LYS | A | 175 | 74.175 | −43.079 | 21.763 | 1.00 | 57.03 | A | N |
| ATOM | 1369 | CA | LYS | A | 175 | 73.825 | −44.340 | 21.102 | 1.00 | 64.40 | A | C |
| ATOM | 1370 | CB | LYS | A | 175 | 72.351 | −44.714 | 21.353 | 1.00 | 84.22 | A | C |
| ATOM | 1371 | CG | LYS | A | 175 | 71.929 | −44.855 | 22.825 | 1.00 | 94.98 | A | C |
| ATOM | 1372 | CD | LYS | A | 175 | 71.932 | −46.299 | 23.316 | 1.00 | 97.31 | A | C |
| ATOM | 1373 | CE | LYS | A | 175 | 71.585 | −46.374 | 24.798 | 1.00 | 88.82 | A | C |
| ATOM | 1374 | NZ | LYS | A | 175 | 71.600 | −47.764 | 25.317 | 1.00 | 78.69 | A | N |
| ATOM | 1375 | C | LYS | A | 175 | 74.066 | −44.248 | 19.591 | 1.00 | 61.10 | A | C |
| ATOM | 1376 | O | LYS | A | 175 | 74.760 | −45.094 | 19.018 | 1.00 | 53.35 | A | O |

APPENDIX A-continued

P. alba 3T288C coordinates

| ATOM | 1377 | N    | ILE  | A | 176 | 73.517 | −43.208 | 18.954 | 1.00 | 42.18  | A | N |
|------|------|------|------|---|-----|--------|---------|--------|------|--------|---|---|
| ATOM | 1378 | CA   | ILE  | A | 176 | 73.412 | −43.188 | 17.487 | 1.00 | 41.76  | A | C |
| ATOM | 1379 | CB   | ILE  | A | 176 | 71.963 | −42.835 | 17.019 | 1.00 | 39.25  | A | C |
| ATOM | 1380 | CG1  | ILE  | A | 176 | 71.533 | −41.438 | 17.477 | 1.00 | 35.80  | A | C |
| ATOM | 1381 | CD1  | ILE  | A | 176 | 70.242 | −40.971 | 16.809 | 1.00 | 37.64  | A | C |
| ATOM | 1382 | CG2  | ILE  | A | 176 | 70.983 | −43.882 | 17.535 | 1.00 | 45.13  | A | C |
| ATOM | 1383 | C    | ILE  | A | 176 | 74.423 | −42.324 | 16.734 | 1.00 | 37.07  | A | C |
| ATOM | 1384 | O    | ILE  | A | 176 | 74.591 | −42.498 | 15.520 | 1.00 | 35.40  | A | O |
| ATOM | 1385 | N    | GLY  | A | 177 | 75.067 | −41.391 | 17.429 | 1.00 | 35.06  | A | N |
| ATOM | 1386 | CA   | GLY  | A | 177 | 76.065 | −40.512 | 16.812 | 1.00 | 33.17  | A | C |
| ATOM | 1387 | C    | GLY  | A | 177 | 75.500 | −39.146 | 16.501 | 1.00 | 38.96  | A | C |
| ATOM | 1388 | O    | GLY  | A | 177 | 74.287 | −38.986 | 16.355 | 1.00 | 31.32  | A | O |
| ATOM | 1389 | N    | LYS  | A | 178 | 76.389 | −38.163 | 16.383 | 1.00 | 35.12  | A | N |
| ATOM | 1390 | CA   | LYS  | A | 178 | 75.995 | −36.761 | 16.293 | 1.00 | 35.31  | A | C |
| ATOM | 1391 | CB   | LYS  | A | 178 | 77.215 | −35.842 | 16.372 | 1.00 | 39.53  | A | C |
| ATOM | 1392 | CG   | LYS  | A | 178 | 76.882 | −34.354 | 16.392 | 1.00 | 46.00  | A | C |
| ATOM | 1393 | CD   | LYS  | A | 178 | 78.060 | −33.521 | 16.888 | 1.00 | 58.26  | A | C |
| ATOM | 1394 | CE   | LYS  | A | 178 | 77.714 | −32.034 | 16.993 | 1.00 | 68.89  | A | C |
| ATOM | 1395 | NZ   | LYS  | A | 178 | 78.519 | −31.320 | 18.047 | 1.00 | 71.94  | A | N |
| ATOM | 1396 | C    | LYS  | A | 178 | 75.207 | −36.428 | 15.030 | 1.00 | 36.95  | A | C |
| ATOM | 1397 | O    | LYS  | A | 178 | 74.277 | −35.624 | 15.086 | 1.00 | 31.16  | A | O |
| ATOM | 1398 | N    | GLU  | A | 179 | 75.578 | −37.024 | 13.901 | 1.00 | 31.99  | A | N |
| ATOM | 1399 | CA   | GLU  | A | 179 | 74.988 | −36.622 | 12.636 | 1.00 | 42.03  | A | C |
| ATOM | 1400 | CB   | GLU  | A | 179 | 75.912 | −36.968 | 11.452 | 1.00 | 43.93  | A | C |
| ATOM | 1401 | CG   | GLU  | A | 179 | 75.578 | −38.196 | 10.631 | 1.00 | 49.30  | A | C |
| ATOM | 1402 | CD   | GLU  | A | 179 | 76.495 | −38.340 | 9.410  | 1.00 | 62.45  | A | C |
| ATOM | 1403 | OE1  | GLU  | A | 179 | 77.641 | −37.830 | 9.436  | 1.00 | 60.91  | A | O |
| ATOM | 1404 | OE2  | GLU  | A | 179 | 76.069 | −38.961 | 8.416  | 1.00 | 60.25  | A | O |
| ATOM | 1405 | C    | GLU  | A | 179 | 73.573 | −37.211 | 12.520 | 1.00 | 44.22  | A | C |
| ATOM | 1406 | O    | GLU  | A | 179 | 72.636 | −36.510 | 12.145 | 1.00 | 38.74  | A | O |
| ATOM | 1407 | N    | LEU  | A | 180 | 73.427 | −38.485 | 12.883 | 1.00 | 32.17  | A | N |
| ATOM | 1408 | CA   | LEU  | A | 180 | 72.130 | −39.120 | 12.907 | 1.00 | 37.01  | A | C |
| ATOM | 1409 | CB   | LEU  | A | 180 | 72.291 | −40.623 | 13.123 | 1.00 | 36.21  | A | C |
| ATOM | 1410 | CG   | LEU  | A | 180 | 71.215 | −41.550 | 12.596 | 1.00 | 39.58  | A | C |
| ATOM | 1411 | CD1  | LEU  | A | 180 | 70.761 | −41.185 | 11.164 | 1.00 | 39.66  | A | C |
| ATOM | 1412 | CD2  | LEU  | A | 180 | 71.758 | −42.977 | 12.663 | 1.00 | 43.88  | A | C |
| ATOM | 1413 | C    | LEU  | A | 180 | 71.218 | −38.457 | 13.958 | 1.00 | 33.76  | A | C |
| ATOM | 1414 | O    | LEU  | A | 180 | 70.047 | −38.205 | 13.694 | 1.00 | 27.31  | A | O |
| ATOM | 1415 | N    | ALA  | A | 181 | 71.749 | −38.114 | 15.121 | 1.00 | 29.65  | A | N |
| ATOM | 1416 | CA   | ALA  | A | 181 | 70.945 | −37.388 | 16.116 | 1.00 | 28.86  | A | C |
| ATOM | 1417 | CB   | ALA  | A | 181 | 71.716 | −37.212 | 17.394 | 1.00 | 25.84  | A | C |
| ATOM | 1418 | C    | ALA  | A | 181 | 70.455 | −36.028 | 15.597 | 1.00 | 31.37  | A | C |
| ATOM | 1419 | O    | ALA  | A | 181 | 69.320 | −35.584 | 15.893 | 1.00 | 25.03  | A | O |
| ATOM | 1420 | N    | GLU  | A | 182 | 71.304 | −35.359 | 14.825 | 1.00 | 25.42  | A | N |
| ATOM | 1421 | CA   | GLU  | A | 182 | 70.911 | −34.077 | 14.240 | 1.00 | 27.62  | A | C |
| ATOM | 1422 | CB   | GLU  | A | 182 | 72.106 | −33.365 | 13.594 | 1.00 | 33.59  | A | C |
| ATOM | 1423 | CG   | GLU  | A | 182 | 72.999 | −32.617 | 14.607 | 1.00 | 53.21  | A | C |
| ATOM | 1424 | CD   | GLU  | A | 182 | 74.282 | −32.037 | 13.996 | 1.00 | 74.57  | A | C |
| ATOM | 1425 | OE1  | GLU  | A | 182 | 74.532 | −32.231 | 12.783 | 1.00 | 106.13 | A | O |
| ATOM | 1426 | OE2  | GLU  | A | 182 | 75.042 | −31.380 | 14.739 | 1.00 | 82.10  | A | O |
| ATOM | 1427 | C    | GLU  | A | 182 | 69.785 | −34.274 | 13.209 | 1.00 | 19.86  | A | C |
| ATOM | 1428 | O    | GLU  | A | 182 | 68.862 | −33.494 | 13.151 | 1.00 | 18.27  | A | O |
| ATOM | 1429 | N    | GLN  | A | 183 | 69.925 | −35.293 | 12.377 | 1.00 | 20.24  | A | N |
| ATOM | 1430 | CA   | AGLN | A | 183 | 68.906 | −35.650 | 11.404 | 0.50 | 24.85  | A | C |
| ATOM | 1431 | CA   | BGLN | A | 183 | 68.898 | −35.606 | 11.398 | 0.50 | 21.35  | A | C |
| ATOM | 1432 | CB   | AGLN | A | 183 | 69.366 | −36.880 | 10.614 | 0.50 | 29.98  | A | C |
| ATOM | 1433 | CB   | BGLN | A | 183 | 69.355 | −36.749 | 10.483 | 0.50 | 20.81  | A | C |
| ATOM | 1434 | CG   | AGLN | A | 183 | 68.795 | −36.970 | 9.221  | 0.50 | 37.32  | A | C |
| ATOM | 1435 | CG   | BGLN | A | 183 | 70.472 | −36.372 | 9.497  | 0.50 | 19.34  | A | C |
| ATOM | 1436 | CD   | AGLN | A | 183 | 69.349 | −35.886 | 8.313  | 0.50 | 46.36  | A | C |
| ATOM | 1437 | CD   | BGLN | A | 183 | 69.946 | −35.727 | 8.205  | 0.50 | 24.20  | A | C |
| ATOM | 1438 | OE1  | AGLN | A | 183 | 68.603 | −35.049 | 7.809  | 0.50 | 48.56  | A | O |
| ATOM | 1439 | OE1  | BGLN | A | 183 | 68.756 | −35.827 | 7.885  | 0.50 | 23.40  | A | O |
| ATOM | 1440 | NE2  | AGLN | A | 183 | 70.666 | −35.889 | 8.115  | 0.50 | 45.01  | A | N |
| ATOM | 1441 | NE2  | BGLN | A | 183 | 70.836 | −35.076 | 7.456  | 0.50 | 23.18  | A | N |
| ATOM | 1442 | C    | GLN  | A | 183 | 67.589 | −35.942 | 12.138 | 1.00 | 22.31  | A | C |
| ATOM | 1443 | O    | GLN  | A | 183 | 66.529 | −35.497 | 11.740 | 1.00 | 20.24  | A | O |
| ATOM | 1444 | N    | VAL  | A | 184 | 67.668 | −36.693 | 13.242 | 1.00 | 18.60  | A | N |
| ATOM | 1445 | CA   | VAL  | A | 184 | 66.447 | −37.108 | 13.963 | 1.00 | 21.87  | A | C |
| ATOM | 1446 | CB   | VAL  | A | 184 | 66.738 | −38.177 | 15.046 | 1.00 | 21.28  | A | C |
| ATOM | 1447 | CG1  | VAL  | A | 184 | 65.593 | −38.311 | 16.034 | 1.00 | 22.68  | A | C |
| ATOM | 1448 | CG2  | VAL  | A | 184 | 67.040 | −39.504 | 14.410 | 1.00 | 25.19  | A | C |
| ATOM | 1449 | C    | VAL  | A | 184 | 65.769 | −35.888 | 14.567 | 1.00 | 20.78  | A | C |
| ATOM | 1450 | O    | VAL  | A | 184 | 64.541 | −35.696 | 14.458 | 1.00 | 16.58  | A | O |
| ATOM | 1451 | N    | ASN  | A | 185 | 66.563 | −35.018 | 15.159 | 1.00 | 20.29  | A | N |
| ATOM | 1452 | CA   | ASN  | A | 185 | 65.995 | −33.828 | 15.770 | 1.00 | 22.74  | A | C |
| ATOM | 1453 | CB   | ASN  | A | 185 | 67.032 | −33.166 | 16.676 | 1.00 | 25.83  | A | C |
| ATOM | 1454 | CG   | ASN  | A | 185 | 67.369 | −34.038 | 17.885 | 1.00 | 32.89  | A | C |

APPENDIX A-continued

*P. alba* 3T288C coordinates

| ATOM | 1455 | OD1 | ASN | A | 185 | 66.486 | −34.683 | 18.462 | 1.00 | 35.58 | A | O |
|---|---|---|---|---|---|---|---|---|---|---|---|---|
| ATOM | 1456 | ND2 | ASN | A | 185 | 68.638 | −34.061 | 18.273 | 1.00 | 30.79 | A | N |
| ATOM | 1457 | C | ASN | A | 185 | 65.385 | −32.857 | 14.764 | 1.00 | 19.89 | A | C |
| ATOM | 1458 | O | ASN | A | 185 | 64.363 | −32.215 | 15.022 | 1.00 | 18.89 | A | O |
| ATOM | 1459 | N | HIS | A | 186 | 65.986 | −32.748 | 13.604 | 1.00 | 16.79 | A | N |
| ATOM | 1460 | CA | HIS | A | 186 | 65.440 | −31.895 | 12.565 | 1.00 | 18.43 | A | C |
| ATOM | 1461 | CB | HIS | A | 186 | 66.481 | −31.869 | 11.432 | 1.00 | 19.47 | A | C |
| ATOM | 1462 | CG | HIS | A | 186 | 66.096 | −31.083 | 10.223 | 1.00 | 17.10 | A | C |
| ATOM | 1463 | ND1 | HIS | A | 186 | 66.082 | −29.746 | 10.200 | 1.00 | 18.23 | A | N |
| ATOM | 1464 | CE1 | HIS | A | 186 | 65.754 | −29.318 | 8.970 | 1.00 | 19.21 | A | C |
| ATOM | 1465 | NE2 | HIS | A | 186 | 65.519 | −30.394 | 8.197 | 1.00 | 21.37 | A | N |
| ATOM | 1466 | CD2 | HIS | A | 186 | 65.735 | −31.506 | 8.930 | 1.00 | 18.75 | A | C |
| ATOM | 1467 | C | HIS | A | 186 | 64.074 | −32.454 | 12.118 | 1.00 | 17.24 | A | C |
| ATOM | 1468 | O | HIS | A | 186 | 63.100 | −31.701 | 11.979 | 1.00 | 18.68 | A | O |
| ATOM | 1469 | N | ALA | A | 187 | 64.009 | −33.752 | 11.860 | 1.00 | 22.68 | A | N |
| ATOM | 1470 | CA | ALA | A | 187 | 62.779 | −34.390 | 11.372 | 1.00 | 24.59 | A | C |
| ATOM | 1471 | CB | ALA | A | 187 | 63.058 | −35.842 | 11.031 | 1.00 | 21.99 | A | C |
| ATOM | 1472 | C | ALA | A | 187 | 61.667 | −34.277 | 12.434 | 1.00 | 22.96 | A | C |
| ATOM | 1473 | O | ALA | A | 187 | 60.504 | −34.046 | 12.109 | 1.00 | 18.69 | A | O |
| ATOM | 1474 | N | LEU | A | 188 | 62.012 | −34.390 | 13.709 | 1.00 | 21.42 | A | N |
| ATOM | 1475 | CA | LEU | A | 188 | 60.982 | −34.344 | 14.756 | 1.00 | 22.89 | A | C |
| ATOM | 1476 | CB | LEU | A | 188 | 61.480 | −34.957 | 16.080 | 1.00 | 23.79 | A | C |
| ATOM | 1477 | CG | LEU | A | 188 | 61.646 | −36.475 | 16.124 | 1.00 | 22.25 | A | C |
| ATOM | 1478 | CD1 | LEU | A | 188 | 62.268 | −36.936 | 17.462 | 1.00 | 22.43 | A | C |
| ATOM | 1479 | CD2 | LEU | A | 188 | 60.344 | −37.182 | 15.918 | 1.00 | 20.82 | A | C |
| ATOM | 1480 | C | LEU | A | 188 | 60.512 | −32.920 | 14.962 | 1.00 | 24.71 | A | C |
| ATOM | 1481 | O | LEU | A | 188 | 59.382 | −32.685 | 15.358 | 1.00 | 24.58 | A | O |
| ATOM | 1482 | N | GLU | A | 189 | 61.360 | −31.948 | 14.648 | 1.00 | 23.21 | A | N |
| ATOM | 1483 | CA | GLU | A | 189 | 60.919 | −30.562 | 14.682 | 1.00 | 21.78 | A | C |
| ATOM | 1484 | CB | GLU | A | 189 | 62.129 | −29.639 | 14.410 | 1.00 | 22.25 | A | C |
| ATOM | 1485 | CG | GLU | A | 189 | 61.841 | −28.180 | 14.309 | 1.00 | 27.16 | A | C |
| ATOM | 1486 | CD | GLU | A | 189 | 63.068 | −27.386 | 13.845 | 1.00 | 38.35 | A | C |
| ATOM | 1487 | OE1 | GLU | A | 189 | 63.522 | −27.587 | 12.707 | 1.00 | 28.82 | A | O |
| ATOM | 1488 | OE2 | GLU | A | 189 | 63.586 | −26.565 | 14.625 | 1.00 | 35.95 | A | O |
| ATOM | 1489 | C | GLU | A | 189 | 59.823 | −30.339 | 13.653 | 1.00 | 22.39 | A | C |
| ATOM | 1490 | O | GLU | A | 189 | 58.838 | −29.674 | 13.905 | 1.00 | 22.62 | A | O |
| ATOM | 1491 | N | LEU | A | 190 | 60.042 | −30.830 | 12.448 | 1.00 | 20.61 | A | N |
| ATOM | 1492 | CA | LEU | A | 190 | 59.068 | −30.652 | 11.378 | 1.00 | 21.06 | A | C |
| ATOM | 1493 | CB | LEU | A | 190 | 59.029 | −29.194 | 10.897 | 1.00 | 22.31 | A | C |
| ATOM | 1494 | CG | LEU | A | 190 | 57.874 | −28.842 | 9.980 | 1.00 | 24.65 | A | C |
| ATOM | 1495 | CD1 | LEU | A | 190 | 56.530 | −28.855 | 10.791 | 1.00 | 21.42 | A | C |
| ATOM | 1496 | CD2 | LEU | A | 190 | 58.138 | −27.521 | 9.235 | 1.00 | 22.03 | A | C |
| ATOM | 1497 | C | LEU | A | 190 | 59.506 | −31.576 | 10.246 | 1.00 | 22.03 | A | C |
| ATOM | 1498 | O | LEU | A | 190 | 60.673 | −31.522 | 9.828 | 1.00 | 18.81 | A | O |
| ATOM | 1499 | N | PRO | A | 191 | 58.591 | −32.426 | 9.756 | 1.00 | 18.19 | A | N |
| ATOM | 1500 | CA | PRO | A | 191 | 58.901 | −33.331 | 8.653 | 1.00 | 19.53 | A | C |
| ATOM | 1501 | CB | PRO | A | 191 | 57.674 | −34.218 | 8.597 | 1.00 | 17.31 | A | C |
| ATOM | 1502 | CG | PRO | A | 191 | 56.584 | −33.313 | 8.960 | 1.00 | 19.81 | A | C |
| ATOM | 1503 | CD | PRO | A | 191 | 57.155 | −32.489 | 10.095 | 1.00 | 18.14 | A | C |
| ATOM | 1504 | C | PRO | A | 191 | 59.152 | −32.627 | 7.314 | 1.00 | 20.66 | A | C |
| ATOM | 1505 | O | PRO | A | 191 | 58.700 | −31.510 | 7.102 | 1.00 | 18.92 | A | O |
| ATOM | 1506 | N | LEU | A | 192 | 59.912 | −33.291 | 6.446 | 1.00 | 17.57 | A | N |
| ATOM | 1507 | CA | LEU | A | 192 | 60.286 | −32.789 | 5.145 | 1.00 | 20.14 | A | C |
| ATOM | 1508 | CB | LEU | A | 192 | 60.978 | −33.891 | 4.319 | 1.00 | 22.36 | A | C |
| ATOM | 1509 | CG | LEU | A | 192 | 62.413 | −34.264 | 4.632 | 1.00 | 31.34 | A | C |
| ATOM | 1510 | CD1 | LEU | A | 192 | 62.772 | −35.494 | 3.770 | 1.00 | 26.77 | A | C |
| ATOM | 1511 | CD2 | LEU | A | 192 | 63.359 | −33.091 | 4.320 | 1.00 | 29.88 | A | C |
| ATOM | 1512 | C | LEU | A | 192 | 59.094 | −32.340 | 4.341 | 1.00 | 20.79 | A | C |
| ATOM | 1513 | O | LEU | A | 192 | 59.148 | −31.339 | 3.689 | 1.00 | 19.46 | A | O |
| ATOM | 1514 | N | HIS | A | 193 | 57.999 | −33.086 | 4.401 | 1.00 | 17.50 | A | N |
| ATOM | 1515 | CA | HIS | A | 193 | 56.821 | −32.732 | 3.624 | 1.00 | 17.24 | A | C |
| ATOM | 1516 | CB | HIS | A | 193 | 55.788 | −33.837 | 3.780 | 1.00 | 14.61 | A | C |
| ATOM | 1517 | CG | HIS | A | 193 | 54.676 | −33.751 | 2.802 | 1.00 | 18.22 | A | C |
| ATOM | 1518 | ND1 | HIS | A | 193 | 54.894 | −33.665 | 1.458 | 1.00 | 18.97 | A | N |
| ATOM | 1519 | CE1 | HIS | A | 193 | 53.700 | −33.623 | 0.829 | 1.00 | 18.36 | A | C |
| ATOM | 1520 | NE2 | HIS | A | 193 | 52.728 | −33.669 | 1.771 | 1.00 | 19.62 | A | N |
| ATOM | 1521 | CD2 | HIS | A | 193 | 53.299 | −33.743 | 2.987 | 1.00 | 18.95 | A | C |
| ATOM | 1522 | C | HIS | A | 193 | 56.185 | −31.400 | 3.964 | 1.00 | 17.41 | A | C |
| ATOM | 1523 | O | HIS | A | 193 | 55.452 | −30.829 | 3.174 | 1.00 | 19.14 | A | O |
| ATOM | 1524 | N | ARG | A | 194 | 56.414 | −30.930 | 5.178 | 1.00 | 16.56 | A | N |
| ATOM | 1525 | CA | ARG | A | 194 | 55.803 | −29.723 | 5.675 | 1.00 | 17.28 | A | C |
| ATOM | 1526 | CB | ARG | A | 194 | 55.233 | −29.988 | 7.064 | 1.00 | 16.73 | A | C |
| ATOM | 1527 | CG | ARG | A | 194 | 54.028 | −30.930 | 7.015 | 1.00 | 19.35 | A | C |
| ATOM | 1528 | CD | ARG | A | 194 | 53.331 | −31.021 | 8.393 | 1.00 | 18.87 | A | C |
| ATOM | 1529 | NE | ARG | A | 194 | 52.218 | −31.951 | 8.267 | 1.00 | 20.89 | A | N |
| ATOM | 1530 | CZ | ARG | A | 194 | 51.433 | −32.324 | 9.259 | 1.00 | 21.04 | A | C |
| ATOM | 1531 | NH1 | ARG | A | 194 | 51.656 | −31.884 | 10.459 | 1.00 | 20.69 | A | N |
| ATOM | 1532 | NH2 | ARG | A | 194 | 50.448 | −33.169 | 9.039 | 1.00 | 20.03 | A | N |

APPENDIX A-continued

*P. alba* 3T288C coordinates

| ATOM | 1533 | C | ARG | A | 194 | 56.764 | −28.511 | 5.759 | 1.00 | 19.33 | A | C |
|---|---|---|---|---|---|---|---|---|---|---|---|---|
| ATOM | 1534 | O | ARG | A | 194 | 56.309 | −27.377 | 5.976 | 1.00 | 20.35 | A | O |
| ATOM | 1535 | N | ARG | A | 195 | 58.055 | −28.752 | 5.574 | 1.00 | 16.40 | A | N |
| ATOM | 1536 | CA | ARG | A | 195 | 59.078 | −27.720 | 5.665 | 1.00 | 18.30 | A | C |
| ATOM | 1537 | CB | ARG | A | 195 | 60.421 | −28.339 | 6.048 | 1.00 | 19.38 | A | C |
| ATOM | 1538 | CG | ARG | A | 195 | 61.441 | −27.274 | 6.475 | 1.00 | 23.23 | A | C |
| ATOM | 1539 | CD | ARG | A | 195 | 62.767 | −27.849 | 7.050 | 1.00 | 24.25 | A | C |
| ATOM | 1540 | NE | ARG | A | 195 | 62.606 | −28.724 | 8.219 | 1.00 | 20.99 | A | N |
| ATOM | 1541 | CZ | ARG | A | 195 | 62.751 | −28.349 | 9.495 | 1.00 | 26.86 | A | C |
| ATOM | 1542 | NH1 | ARG | A | 195 | 63.093 | −27.113 | 9.823 | 1.00 | 26.57 | A | N |
| ATOM | 1543 | NH2 | ARG | A | 195 | 62.590 | −29.220 | 10.467 | 1.00 | 27.07 | A | N |
| ATOM | 1544 | C | ARG | A | 195 | 59.217 | −26.991 | 4.328 | 1.00 | 19.93 | A | C |
| ATOM | 1545 | O | ARG | A | 195 | 59.170 | −27.617 | 3.293 | 1.00 | 19.84 | A | O |
| ATOM | 1546 | N | THR | A | 196 | 59.429 | −25.672 | 4.355 | 1.00 | 16.30 | A | N |
| ATOM | 1547 | CA | THR | A | 196 | 59.627 | −24.921 | 3.106 | 1.00 | 19.56 | A | C |
| ATOM | 1548 | CB | THR | A | 196 | 59.574 | −23.413 | 3.350 | 1.00 | 19.32 | A | C |
| ATOM | 1549 | OG1 | THR | A | 196 | 60.572 | −23.099 | 4.291 | 1.00 | 20.58 | A | O |
| ATOM | 1550 | CG2 | THR | A | 196 | 58.206 | −23.002 | 3.903 | 1.00 | 18.83 | A | C |
| ATOM | 1551 | C | THR | A | 196 | 60.978 | −25.304 | 2.491 | 1.00 | 16.84 | A | C |
| ATOM | 1552 | O | THR | A | 196 | 61.868 | −25.814 | 3.159 | 1.00 | 19.53 | A | O |
| ATOM | 1553 | N | GLN | A | 197 | 61.086 | −25.091 | 1.198 | 1.00 | 18.95 | A | N |
| ATOM | 1554 | CA | GLN | A | 197 | 62.152 | −25.667 | 0.394 | 1.00 | 17.43 | A | C |
| ATOM | 1555 | CB | GLN | A | 197 | 61.792 | −25.510 | −1.087 | 1.00 | 19.72 | A | C |
| ATOM | 1556 | CG | GLN | A | 197 | 62.470 | −26.467 | −2.029 | 1.00 | 21.47 | A | C |
| ATOM | 1557 | CD | GLN | A | 197 | 63.765 | −25.922 | −2.604 | 1.00 | 24.85 | A | C |
| ATOM | 1558 | OE1 | GLN | A | 197 | 64.341 | −24.948 | −2.093 | 1.00 | 22.95 | A | O |
| ATOM | 1559 | NE2 | GLN | A | 197 | 64.246 | −26.559 | −3.654 | 1.00 | 24.44 | A | N |
| ATOM | 1560 | C | GLN | A | 197 | 63.482 | −24.977 | 0.751 | 1.00 | 18.31 | A | C |
| ATOM | 1561 | O | GLN | A | 197 | 64.481 | −25.656 | 0.934 | 1.00 | 16.91 | A | O |
| ATOM | 1562 | N | ARG | A | 198 | 63.510 | −23.641 | 0.845 | 1.00 | 17.97 | A | N |
| ATOM | 1563 | CA | ARG | A | 198 | 64.771 | −22.925 | 1.163 | 1.00 | 17.51 | A | C |
| ATOM | 1564 | CB | ARG | A | 198 | 64.627 | −21.404 | 1.010 | 1.00 | 18.00 | A | C |
| ATOM | 1565 | CG | ARG | A | 198 | 64.331 | −20.959 | −0.395 | 1.00 | 19.52 | A | C |
| ATOM | 1566 | CD | ARG | A | 198 | 65.652 | −21.070 | −1.293 | 1.00 | 19.02 | A | C |
| ATOM | 1567 | NE | ARG | A | 198 | 65.713 | −22.398 | −1.940 | 1.00 | 17.34 | A | N |
| ATOM | 1568 | CZ | ARG | A | 198 | 66.673 | −22.781 | −2.784 | 1.00 | 20.87 | A | C |
| ATOM | 1569 | NH1 | ARG | A | 198 | 67.691 | −21.975 | −3.039 | 1.00 | 19.28 | A | N |
| ATOM | 1570 | NH2 | ARG | A | 198 | 66.655 | −23.989 | −3.324 | 1.00 | 18.08 | A | N |
| ATOM | 1571 | C | ARG | A | 198 | 65.277 | −23.251 | 2.552 | 1.00 | 18.33 | A | C |
| ATOM | 1572 | O | ARG | A | 198 | 66.478 | −23.429 | 2.741 | 1.00 | 18.01 | A | O |
| ATOM | 1573 | N | LEU | A | 199 | 64.374 | −23.387 | 3.531 | 1.00 | 18.80 | A | N |
| ATOM | 1574 | CA | LEU | A | 199 | 64.797 | −23.716 | 4.898 | 1.00 | 19.16 | A | C |
| ATOM | 1575 | CB | LEU | A | 199 | 63.654 | −23.615 | 5.918 | 1.00 | 26.01 | A | C |
| ATOM | 1576 | CG | LEU | A | 199 | 63.350 | −22.263 | 6.543 | 1.00 | 25.56 | A | C |
| ATOM | 1577 | CD1 | LEU | A | 199 | 62.169 | −22.345 | 7.534 | 1.00 | 29.19 | A | C |
| ATOM | 1578 | CD2 | LEU | A | 199 | 64.632 | −21.665 | 7.204 | 1.00 | 23.04 | A | C |
| ATOM | 1579 | C | LEU | A | 199 | 65.357 | −25.113 | 4.947 | 1.00 | 18.37 | A | C |
| ATOM | 1580 | O | LEU | A | 199 | 66.313 | −25.361 | 5.650 | 1.00 | 18.68 | A | O |
| ATOM | 1581 | N | GLU | A | 200 | 64.751 | −26.050 | 4.218 | 1.00 | 17.37 | A | N |
| ATOM | 1582 | CA | GLU | A | 200 | 65.332 | −27.377 | 4.183 | 1.00 | 16.57 | A | C |
| ATOM | 1583 | CB | GLU | A | 200 | 64.423 | −28.365 | 3.480 | 1.00 | 17.92 | A | C |
| ATOM | 1584 | CG | GLU | A | 200 | 64.969 | −29.777 | 3.325 | 1.00 | 21.36 | A | C |
| ATOM | 1585 | CD | GLU | A | 200 | 65.393 | −30.426 | 4.662 | 1.00 | 29.23 | A | C |
| ATOM | 1586 | OE1 | GLU | A | 200 | 64.777 | −30.107 | 5.682 | 1.00 | 29.79 | A | O |
| ATOM | 1587 | OE2 | GLU | A | 200 | 66.339 | −31.263 | 4.698 | 1.00 | 29.20 | A | O |
| ATOM | 1588 | C | GLU | A | 200 | 66.712 | −27.328 | 3.492 | 1.00 | 16.68 | A | C |
| ATOM | 1589 | O | GLU | A | 200 | 67.635 | −28.029 | 3.914 | 1.00 | 19.27 | A | O |
| ATOM | 1590 | N | ALA | A | 201 | 66.835 | −26.553 | 2.419 | 1.00 | 16.26 | A | N |
| ATOM | 1591 | CA | ALA | A | 201 | 68.099 | −26.503 | 1.657 | 1.00 | 18.75 | A | C |
| ATOM | 1592 | CB | ALA | A | 201 | 67.938 | −25.651 | 0.362 | 1.00 | 16.55 | A | C |
| ATOM | 1593 | C | ALA | A | 201 | 69.238 | −25.975 | 2.506 | 1.00 | 20.06 | A | C |
| ATOM | 1594 | O | ALA | A | 201 | 70.328 | −26.580 | 2.562 | 1.00 | 20.06 | A | O |
| ATOM | 1595 | N | VAL | A | 202 | 68.997 | −24.855 | 3.183 | 1.00 | 20.04 | A | N |
| ATOM | 1596 | CA | VAL | A | 202 | 70.048 | −24.237 | 3.979 | 1.00 | 22.09 | A | C |
| ATOM | 1597 | CB | VAL | A | 202 | 69.667 | −22.787 | 4.489 | 1.00 | 18.59 | A | C |
| ATOM | 1598 | CG1 | VAL | A | 202 | 68.692 | −22.850 | 5.643 | 1.00 | 20.29 | A | C |
| ATOM | 1599 | CG2 | VAL | A | 202 | 70.962 | −21.960 | 4.888 | 1.00 | 24.36 | A | C |
| ATOM | 1600 | C | VAL | A | 202 | 70.486 | −25.181 | 5.089 | 1.00 | 20.38 | A | C |
| ATOM | 1601 | O | VAL | A | 202 | 71.669 | −25.348 | 5.318 | 1.00 | 17.33 | A | O |
| ATOM | 1602 | N | TRP | A | 203 | 69.556 | −25.864 | 5.729 | 1.00 | 20.48 | A | N |
| ATOM | 1603 | CA | TRP | A | 203 | 69.916 | −26.851 | 6.740 | 1.00 | 19.93 | A | C |
| ATOM | 1604 | CB | TRP | A | 203 | 68.652 | −27.360 | 7.456 | 1.00 | 21.30 | A | C |
| ATOM | 1605 | CG | TRP | A | 203 | 68.975 | −28.249 | 8.620 | 1.00 | 19.15 | A | C |
| ATOM | 1606 | CD1 | TRP | A | 203 | 69.089 | −27.877 | 9.965 | 1.00 | 23.17 | A | C |
| ATOM | 1607 | NE1 | TRP | A | 203 | 69.420 | −28.947 | 10.731 | 1.00 | 26.66 | A | N |
| ATOM | 1608 | CE2 | TRP | A | 203 | 69.529 | −30.047 | 9.981 | 1.00 | 23.99 | A | C |
| ATOM | 1609 | CD2 | TRP | A | 203 | 69.253 | −29.660 | 8.596 | 1.00 | 19.28 | A | C |
| ATOM | 1610 | CE3 | TRP | A | 203 | 69.265 | −30.637 | 7.605 | 1.00 | 20.86 | A | C |

APPENDIX A-continued

*P. alba* 3T288C coordinates

| ATOM | 1611 | CZ3 | TRP | A | 203 | 69.597 | −31.925 | 7.967 | 1.00 | 23.16 | A | C |
|---|---|---|---|---|---|---|---|---|---|---|---|---|
| ATOM | 1612 | CH2 | TRP | A | 203 | 69.885 | −32.271 | 9.304 | 1.00 | 23.58 | A | C |
| ATOM | 1613 | CZ2 | TRP | A | 203 | 69.845 | −31.341 | 10.331 | 1.00 | 26.26 | A | C |
| ATOM | 1614 | C | TRP | A | 203 | 70.677 | −28.026 | 6.162 | 1.00 | 24.21 | A | C |
| ATOM | 1615 | O | TRP | A | 203 | 71.669 | −28.502 | 6.737 | 1.00 | 19.37 | A | O |
| ATOM | 1616 | N | SER | A | 204 | 70.205 | −28.545 | 5.034 | 1.00 | 19.86 | A | N |
| ATOM | 1617 | CA | SER | A | 204 | 70.781 | −29.787 | 4.465 | 1.00 | 15.86 | A | C |
| ATOM | 1618 | CB | SER | A | 204 | 69.853 | −30.348 | 3.371 | 1.00 | 17.81 | A | C |
| ATOM | 1619 | OG | SER | A | 204 | 68.780 | −31.055 | 3.959 | 1.00 | 24.34 | A | O |
| ATOM | 1620 | C | SER | A | 204 | 72.162 | −29.573 | 3.882 | 1.00 | 15.58 | A | C |
| ATOM | 1621 | O | SER | A | 204 | 72.984 | −30.467 | 3.932 | 1.00 | 15.50 | A | O |
| ATOM | 1622 | N | ILE | A | 205 | 72.424 | −28.384 | 3.360 | 1.00 | 15.58 | A | N |
| ATOM | 1623 | CA | ILE | A | 205 | 73.743 | −28.077 | 2.769 | 1.00 | 15.73 | A | C |
| ATOM | 1624 | CB | ILE | A | 205 | 73.725 | −26.745 | 2.001 | 1.00 | 14.57 | A | C |
| ATOM | 1625 | CG1 | ILE | A | 205 | 72.923 | −26.884 | 0.700 | 1.00 | 14.65 | A | C |
| ATOM | 1626 | CD1 | ILE | A | 205 | 72.469 | −25.560 | 0.102 | 1.00 | 16.39 | A | C |
| ATOM | 1627 | CG2 | ILE | A | 205 | 75.213 | −26.207 | 1.740 | 1.00 | 16.26 | A | C |
| ATOM | 1628 | C | ILE | A | 205 | 74.790 | −28.051 | 3.900 | 1.00 | 21.28 | A | C |
| ATOM | 1629 | O | ILE | A | 205 | 75.853 | −28.632 | 3.780 | 1.00 | 21.22 | A | O |
| ATOM | 1630 | N | GLU | A | 206 | 74.450 | −27.413 | 5.011 | 1.00 | 23.84 | A | N |
| ATOM | 1631 | CA | GLU | A | 206 | 75.317 | −27.397 | 6.189 | 1.00 | 24.36 | A | C |
| ATOM | 1632 | CB | GLU | A | 206 | 74.727 | −26.476 | 7.265 | 1.00 | 27.57 | A | C |
| ATOM | 1633 | CG | GLU | A | 206 | 75.503 | −26.404 | 8.572 | 1.00 | 34.12 | A | C |
| ATOM | 1634 | CD | GLU | A | 206 | 76.948 | −25.902 | 8.395 | 1.00 | 40.13 | A | C |
| ATOM | 1635 | OE1 | GLU | A | 206 | 77.201 | −25.053 | 7.510 | 1.00 | 41.90 | A | O |
| ATOM | 1636 | OE2 | GLU | A | 206 | 77.825 | −26.372 | 9.146 | 1.00 | 36.22 | A | O |
| ATOM | 1637 | C | GLU | A | 206 | 75.548 | −28.811 | 6.739 | 1.00 | 26.16 | A | C |
| ATOM | 1638 | O | GLU | A | 206 | 76.663 | −29.138 | 7.087 | 1.00 | 25.64 | A | O |
| ATOM | 1639 | N | ALA | A | 207 | 74.525 | −29.660 | 6.800 | 1.00 | 23.96 | A | N |
| ATOM | 1640 | CA | ALA | A | 207 | 74.720 | −31.038 | 7.278 | 1.00 | 25.61 | A | C |
| ATOM | 1641 | CB | ALA | A | 207 | 73.383 | −31.727 | 7.520 | 1.00 | 25.10 | A | C |
| ATOM | 1642 | C | ALA | A | 207 | 75.526 | −31.852 | 6.277 | 1.00 | 27.54 | A | C |
| ATOM | 1643 | O | ALA | A | 207 | 76.380 | −32.651 | 6.650 | 1.00 | 22.60 | A | O |
| ATOM | 1644 | N | TYR | A | 208 | 75.245 | −31.649 | 4.992 | 1.00 | 21.54 | A | N |
| ATOM | 1645 | CA | TYR | A | 208 | 75.901 | −32.439 | 3.977 | 1.00 | 22.48 | A | C |
| ATOM | 1646 | CB | TYR | A | 208 | 75.252 | −32.220 | 2.611 | 1.00 | 21.04 | A | C |
| ATOM | 1647 | CG | TYR | A | 208 | 75.584 | −33.267 | 1.584 | 1.00 | 20.80 | A | C |
| ATOM | 1648 | CD1 | TYR | A | 208 | 75.197 | −34.578 | 1.753 | 1.00 | 23.40 | A | C |
| ATOM | 1649 | CE1 | TYR | A | 208 | 75.505 | −35.553 | 0.790 | 1.00 | 24.71 | A | C |
| ATOM | 1650 | CZ | TYR | A | 208 | 76.171 | −35.188 | −0.356 | 1.00 | 21.51 | A | C |
| ATOM | 1651 | OH | TYR | A | 208 | 76.466 | −36.123 | −1.337 | 1.00 | 23.71 | A | O |
| ATOM | 1652 | CE2 | TYR | A | 208 | 76.540 | −33.885 | −0.544 | 1.00 | 19.95 | A | C |
| ATOM | 1653 | CD2 | TYR | A | 208 | 76.241 | −32.933 | 0.415 | 1.00 | 23.60 | A | C |
| ATOM | 1654 | C | TYR | A | 208 | 77.399 | −32.120 | 3.924 | 1.00 | 18.26 | A | C |
| ATOM | 1655 | O | TYR | A | 208 | 78.193 | −33.017 | 3.780 | 1.00 | 20.93 | A | O |
| ATOM | 1656 | N | ARG | A | 209 | 77.765 | −30.847 | 4.048 | 1.00 | 18.60 | A | N |
| ATOM | 1657 | CA | ARG | A | 209 | 79.175 | −30.438 | 3.930 | 1.00 | 22.43 | A | C |
| ATOM | 1658 | CB | ARG | A | 209 | 79.303 | −28.908 | 3.801 | 1.00 | 25.30 | A | C |
| ATOM | 1659 | CG | ARG | A | 209 | 79.204 | −28.103 | 5.093 | 1.00 | 25.28 | A | C |
| ATOM | 1660 | CD | ARG | A | 209 | 79.052 | −26.620 | 4.805 | 1.00 | 25.54 | A | C |
| ATOM | 1661 | NE | ARG | A | 209 | 80.121 | −26.093 | 3.948 | 1.00 | 20.42 | A | N |
| ATOM | 1662 | CZ | ARG | A | 209 | 80.063 | −24.937 | 3.292 | 1.00 | 19.21 | A | C |
| ATOM | 1663 | NH1 | ARG | A | 209 | 79.010 | −24.153 | 3.373 | 1.00 | 17.64 | A | N |
| ATOM | 1664 | NH2 | ARG | A | 209 | 81.080 | −24.549 | 2.541 | 1.00 | 22.99 | A | N |
| ATOM | 1665 | C | ARG | A | 209 | 80.054 | −30.985 | 5.062 | 1.00 | 21.25 | A | C |
| ATOM | 1666 | O | ARG | A | 209 | 81.276 | −31.024 | 4.918 | 1.00 | 24.92 | A | O |
| ATOM | 1667 | N | LYS | A | 210 | 79.429 | −31.434 | 6.153 | 1.00 | 25.30 | A | N |
| ATOM | 1668 | CA | LYS | A | 210 | 80.128 | −32.031 | 7.309 | 1.00 | 31.88 | A | C |
| ATOM | 1669 | CB | LYS | A | 210 | 79.386 | −31.701 | 8.603 | 1.00 | 30.97 | A | C |
| ATOM | 1670 | CG | LYS | A | 210 | 79.381 | −30.211 | 8.900 | 1.00 | 34.55 | A | C |
| ATOM | 1671 | CD | LYS | A | 210 | 78.957 | −29.897 | 10.320 | 1.00 | 39.50 | A | C |
| ATOM | 1672 | CE | LYS | A | 210 | 77.473 | −29.640 | 10.455 | 1.00 | 40.90 | A | C |
| ATOM | 1673 | NZ | LYS | A | 210 | 77.293 | −28.453 | 11.347 | 1.00 | 46.57 | A | N |
| ATOM | 1674 | C | LYS | A | 210 | 80.314 | −33.540 | 7.196 | 1.00 | 36.30 | A | C |
| ATOM | 1675 | O | LYS | A | 210 | 81.035 | −34.138 | 7.998 | 1.00 | 33.45 | A | O |
| ATOM | 1676 | N | LYS | A | 211 | 79.695 | −34.155 | 6.199 | 1.00 | 29.38 | A | N |
| ATOM | 1677 | CA | LYS | A | 211 | 79.869 | −35.591 | 5.976 | 1.00 | 34.50 | A | C |
| ATOM | 1678 | CB | LYS | A | 211 | 78.766 | −36.148 | 5.098 | 1.00 | 38.26 | A | C |
| ATOM | 1679 | CG | LYS | A | 211 | 77.422 | −36.240 | 5.729 | 1.00 | 42.79 | A | C |
| ATOM | 1680 | CD | LYS | A | 211 | 76.481 | −36.952 | 4.765 | 1.00 | 46.28 | A | C |
| ATOM | 1681 | CE | LYS | A | 211 | 75.039 | −36.901 | 5.231 | 1.00 | 63.15 | A | C |
| ATOM | 1682 | NZ | LYS | A | 211 | 74.856 | −37.288 | 6.655 | 1.00 | 77.84 | A | N |
| ATOM | 1683 | C | LYS | A | 211 | 81.171 | −35.854 | 5.257 | 1.00 | 43.74 | A | C |
| ATOM | 1684 | O | LYS | A | 211 | 81.468 | −35.222 | 4.241 | 1.00 | 40.90 | A | O |
| ATOM | 1685 | N | GLU | A | 212 | 81.930 | −36.824 | 5.749 | 1.00 | 48.80 | A | N |
| ATOM | 1686 | CA | GLU | A | 212 | 83.211 | −37.148 | 5.155 | 1.00 | 47.55 | A | C |
| ATOM | 1687 | CB | GLU | A | 212 | 83.947 | −38.165 | 6.026 | 1.00 | 57.33 | A | C |
| ATOM | 1688 | CG | GLU | A | 212 | 85.324 | −38.528 | 5.502 | 1.00 | 64.50 | A | C |

APPENDIX A-continued

*P. alba* 3T288C coordinates

| ATOM | 1689 | CD  | GLU | A | 212 | 86.295 | −38.925 | 6.598  | 1.00 | 68.42 | A | C |
|------|------|-----|-----|---|-----|--------|---------|--------|------|-------|---|---|
| ATOM | 1690 | OE1 | GLU | A | 212 | 86.427 | −38.173 | 7.585  | 1.00 | 64.80 | A | O |
| ATOM | 1691 | OE2 | GLU | A | 212 | 86.943 | −39.983 | 6.461  | 1.00 | 73.66 | A | O |
| ATOM | 1692 | C   | GLU | A | 212 | 83.052 | −37.682 | 3.734  | 1.00 | 38.45 | A | C |
| ATOM | 1693 | O   | GLU | A | 212 | 83.865 | −37.394 | 2.868  | 1.00 | 40.13 | A | O |
| ATOM | 1694 | N   | ASP | A | 213 | 82.002 | −38.447 | 3.493  | 1.00 | 30.53 | A | N |
| ATOM | 1695 | CA  | ASP | A | 213 | 81.793 | −39.045 | 2.173  | 1.00 | 34.13 | A | C |
| ATOM | 1696 | CB  | ASP | A | 213 | 81.274 | −40.477 | 2.347  | 1.00 | 37.83 | A | C |
| ATOM | 1697 | CG  | ASP | A | 213 | 79.945 | −40.536 | 3.105  | 1.00 | 46.70 | A | C |
| ATOM | 1698 | OD1 | ASP | A | 213 | 79.565 | −39.534 | 3.762  | 1.00 | 46.50 | A | O |
| ATOM | 1699 | OD2 | ASP | A | 213 | 79.282 | −41.591 | 3.047  | 1.00 | 59.21 | A | O |
| ATOM | 1700 | C   | ASP | A | 213 | 80.808 | −38.241 | 1.282  | 1.00 | 27.38 | A | C |
| ATOM | 1701 | O   | ASP | A | 213 | 80.218 | −38.789 | 0.379  | 1.00 | 27.59 | A | O |
| ATOM | 1702 | N   | ALA | A | 214 | 80.633 | −36.954 | 1.542  | 1.00 | 24.53 | A | N |
| ATOM | 1703 | CA  | ALA | A | 214 | 79.766 | −36.093 | 0.706  | 1.00 | 26.48 | A | C |
| ATOM | 1704 | CB  | ALA | A | 214 | 79.820 | −34.662 | 1.216  | 1.00 | 23.28 | A | C |
| ATOM | 1705 | C   | ALA | A | 214 | 80.212 | −36.107 | −0.745 | 1.00 | 23.11 | A | C |
| ATOM | 1706 | O   | ALA | A | 214 | 81.385 | −35.966 | −1.014 | 1.00 | 17.41 | A | O |
| ATOM | 1707 | N   | ASN | A | 215 | 79.290 | −36.226 | −1.689 | 1.00 | 20.40 | A | N |
| ATOM | 1708 | CA  | ASN | A | 215 | 79.662 | −36.045 | −3.091 | 1.00 | 19.94 | A | C |
| ATOM | 1709 | CB  | ASN | A | 215 | 78.481 | −36.438 | −3.979 | 1.00 | 25.05 | A | C |
| ATOM | 1710 | CG  | ASN | A | 215 | 78.811 | −36.376 | −5.455 | 1.00 | 29.07 | A | C |
| ATOM | 1711 | OD1 | ASN | A | 215 | 79.116 | −35.319 | −5.995 | 1.00 | 23.21 | A | O |
| ATOM | 1712 | ND2 | ASN | A | 215 | 78.759 | −37.526 | −6.116 | 1.00 | 39.39 | A | N |
| ATOM | 1713 | C   | ASN | A | 215 | 80.049 | −34.567 | −3.313 | 1.00 | 16.76 | A | C |
| ATOM | 1714 | O   | ASN | A | 215 | 79.233 | −33.686 | −3.091 | 1.00 | 19.63 | A | O |
| ATOM | 1715 | N   | GLN | A | 216 | 81.279 | −34.296 | −3.726 | 1.00 | 18.59 | A | N |
| ATOM | 1716 | CA  | GLN | A | 216 | 81.769 | −32.918 | −3.808 | 1.00 | 19.77 | A | C |
| ATOM | 1717 | CB  | GLN | A | 216 | 83.296 | −32.876 | −3.881 | 1.00 | 21.22 | A | C |
| ATOM | 1718 | CG  | GLN | A | 216 | 84.004 | −33.430 | −2.618 | 1.00 | 25.97 | A | C |
| ATOM | 1719 | CD  | GLN | A | 216 | 83.625 | −32.675 | −1.350 | 1.00 | 27.20 | A | C |
| ATOM | 1720 | OE1 | GLN | A | 216 | 84.041 | −31.531 | −1.137 | 1.00 | 34.44 | A | O |
| ATOM | 1721 | NE2 | GLN | A | 216 | 82.828 | −33.313 | −0.506 | 1.00 | 31.17 | A | N |
| ATOM | 1722 | C   | GLN | A | 216 | 81.171 | −32.104 | −4.970 | 1.00 | 16.13 | A | C |
| ATOM | 1723 | O   | GLN | A | 216 | 81.006 | −30.891 | −4.863 | 1.00 | 15.04 | A | O |
| ATOM | 1724 | N   | VAL | A | 217 | 80.888 | −32.768 | −6.076 | 1.00 | 16.85 | A | N |
| ATOM | 1725 | CA  | VAL | A | 217 | 80.253 | −32.131 | −7.235 | 1.00 | 16.12 | A | C |
| ATOM | 1726 | CB  | VAL | A | 217 | 80.180 | −33.125 | −8.471 | 1.00 | 16.39 | A | C |
| ATOM | 1727 | CG1 | VAL | A | 217 | 79.233 | −32.609 | −9.539 | 1.00 | 14.97 | A | C |
| ATOM | 1728 | CG2 | VAL | A | 217 | 81.618 | −33.384 | −9.101 | 1.00 | 16.56 | A | C |
| ATOM | 1729 | C   | VAL | A | 217 | 78.852 | −31.674 | −6.795 | 1.00 | 14.34 | A | C |
| ATOM | 1730 | O   | VAL | A | 217 | 78.471 | −30.506 | −6.964 | 1.00 | 15.07 | A | O |
| ATOM | 1731 | N   | LEU | A | 218 | 78.118 | −32.552 | −6.121 | 1.00 | 16.11 | A | N |
| ATOM | 1732 | CA  | LEU | A | 218 | 76.761 | −32.202 | −5.681 | 1.00 | 15.34 | A | C |
| ATOM | 1733 | CB  | LEU | A | 218 | 76.050 | −33.463 | −5.170 | 1.00 | 17.72 | A | C |
| ATOM | 1734 | CG  | LEU | A | 218 | 74.639 | −33.315 | −4.635 | 1.00 | 19.99 | A | C |
| ATOM | 1735 | CD1 | LEU | A | 218 | 73.748 | −32.679 | −5.719 | 1.00 | 17.34 | A | C |
| ATOM | 1736 | CD2 | LEU | A | 218 | 74.146 | −34.715 | −4.192 | 1.00 | 20.61 | A | C |
| ATOM | 1737 | C   | LEU | A | 218 | 76.761 | −31.050 | −4.633 | 1.00 | 16.80 | A | C |
| ATOM | 1738 | O   | LEU | A | 218 | 75.990 | −30.073 | −4.754 | 1.00 | 16.08 | A | O |
| ATOM | 1739 | N   | LEU | A | 219 | 77.667 | −31.137 | −3.659 | 1.00 | 16.22 | A | N |
| ATOM | 1740 | CA  | LEU | A | 219 | 77.808 | −30.114 | −2.624 | 1.00 | 15.98 | A | C |
| ATOM | 1741 | CB  | LEU | A | 219 | 78.878 | −30.531 | −1.585 | 1.00 | 19.49 | A | C |
| ATOM | 1742 | CG  | LEU | A | 219 | 79.274 | −29.480 | −0.524 | 1.00 | 20.60 | A | C |
| ATOM | 1743 | CD1 | LEU | A | 219 | 78.007 | −28.966 | 0.234  | 1.00 | 17.64 | A | C |
| ATOM | 1744 | CD2 | LEU | A | 219 | 80.343 | −30.018 | 0.454  | 1.00 | 22.47 | A | C |
| ATOM | 1745 | C   | LEU | A | 219 | 78.154 | −28.773 | −3.243 | 1.00 | 14.57 | A | C |
| ATOM | 1746 | O   | LEU | A | 219 | 77.528 | −27.773 | −2.958 | 1.00 | 15.80 | A | O |
| ATOM | 1747 | N   | GLU | A | 220 | 79.152 | −28.745 | −4.119 | 1.00 | 16.34 | A | N |
| ATOM | 1748 | CA  | GLU | A | 220 | 79.521 | −27.477 | −4.740 | 1.00 | 17.54 | A | C |
| ATOM | 1749 | CB  | GLU | A | 220 | 80.762 | −27.610 | −5.633 | 1.00 | 21.32 | A | C |
| ATOM | 1750 | CG  | GLU | A | 220 | 81.228 | −26.244 | −6.097 | 1.00 | 18.06 | A | C |
| ATOM | 1751 | CD  | GLU | A | 220 | 82.556 | −26.245 | −6.841 | 1.00 | 19.47 | A | C |
| ATOM | 1752 | OE1 | GLU | A | 220 | 83.087 | −27.308 | −7.177 | 1.00 | 22.10 | A | O |
| ATOM | 1753 | OE2 | GLU | A | 220 | 83.063 | −25.137 | −7.085 | 1.00 | 22.89 | A | O |
| ATOM | 1754 | C   | GLU | A | 220 | 78.361 | −26.863 | −5.517 | 1.00 | 17.83 | A | C |
| ATOM | 1755 | O   | GLU | A | 220 | 78.059 | −25.668 | −5.385 | 1.00 | 14.53 | A | O |
| ATOM | 1756 | N   | LEU | A | 221 | 77.673 | −27.671 | −6.298 | 1.00 | 17.91 | A | N |
| ATOM | 1757 | CA  | LEU | A | 221 | 76.504 | −27.169 | −7.040 | 1.00 | 14.02 | A | C |
| ATOM | 1758 | CB  | LEU | A | 221 | 75.938 | −28.265 | −7.935 | 1.00 | 14.70 | A | C |
| ATOM | 1759 | CG  | LEU | A | 221 | 74.714 | −27.934 | −8.808 | 1.00 | 13.25 | A | C |
| ATOM | 1760 | CD1 | LEU | A | 221 | 75.094 | −26.855 | −9.814 | 1.00 | 12.26 | A | C |
| ATOM | 1761 | CD2 | LEU | A | 221 | 74.222 | −29.193 | −9.524 | 1.00 | 13.16 | A | C |
| ATOM | 1762 | C   | LEU | A | 221 | 75.421 | −26.646 | −6.110 | 1.00 | 15.19 | A | C |
| ATOM | 1763 | O   | LEU | A | 221 | 74.817 | −25.598 | −6.358 | 1.00 | 13.89 | A | O |
| ATOM | 1764 | N   | ALA | A | 222 | 75.169 | −27.359 | −5.026 | 1.00 | 15.41 | A | N |
| ATOM | 1765 | CA  | ALA | A | 222 | 74.139 | −26.940 | −4.103 | 1.00 | 14.27 | A | C |
| ATOM | 1766 | CB  | ALA | A | 222 | 73.951 | −28.006 | −2.985 | 1.00 | 14.45 | A | C |

APPENDIX A-continued

P. alba 3T288C coordinates

| | | | | | | | | | | | | |
|---|---|---|---|---|---|---|---|---|---|---|---|---|
| ATOM | 1767 | C | ALA | A | 222 | 74.440 | −25.560 | −3.522 | 1.00 | 14.90 | A | C |
| ATOM | 1768 | O | ALA | A | 222 | 73.558 | −24.691 | −3.439 | 1.00 | 16.28 | A | O |
| ATOM | 1769 | N | ILE | A | 223 | 75.697 | −25.329 | −3.142 | 1.00 | 15.61 | A | N |
| ATOM | 1770 | CA | ILE | A | 223 | 76.075 | −24.058 | −2.519 | 1.00 | 14.09 | A | C |
| ATOM | 1771 | CB | ILE | A | 223 | 77.530 | −24.124 | −2.011 | 1.00 | 14.49 | A | C |
| ATOM | 1772 | CG1 | ILE | A | 223 | 77.614 | −25.106 | −0.823 | 1.00 | 13.12 | A | C |
| ATOM | 1773 | CD1 | ILE | A | 223 | 79.093 | −25.623 | −0.535 | 1.00 | 14.91 | A | C |
| ATOM | 1774 | CG2 | ILE | A | 223 | 78.062 | −22.702 | −1.641 | 1.00 | 13.93 | A | C |
| ATOM | 1775 | C | ILE | A | 223 | 75.926 | −22.963 | −3.559 | 1.00 | 14.88 | A | C |
| ATOM | 1776 | O | ILE | A | 223 | 75.318 | −21.929 | −3.333 | 1.00 | 14.14 | A | O |
| ATOM | 1777 | N | LEU | A | 224 | 76.490 | −23.216 | −4.733 | 1.00 | 16.07 | A | N |
| ATOM | 1778 | CA | LEU | A | 224 | 76.463 | −22.240 | −5.833 | 1.00 | 16.94 | A | C |
| ATOM | 1779 | CB | LEU | A | 224 | 77.185 | −22.875 | −6.990 | 1.00 | 21.43 | A | C |
| ATOM | 1780 | CG | LEU | A | 224 | 77.473 | −22.190 | −8.287 | 1.00 | 33.26 | A | C |
| ATOM | 1781 | CD1 | LEU | A | 224 | 78.682 | −22.921 | −8.853 | 1.00 | 29.28 | A | C |
| ATOM | 1782 | CD2 | LEU | A | 224 | 76.226 | −22.298 | −9.181 | 1.00 | 43.08 | A | C |
| ATOM | 1783 | C | LEU | A | 224 | 75.017 | −21.863 | −6.210 | 1.00 | 14.97 | A | C |
| ATOM | 1784 | O | LEU | A | 224 | 74.681 | −20.676 | −6.349 | 1.00 | 15.99 | A | O |
| ATOM | 1785 | N | ASP | A | 225 | 74.167 | −22.872 | −6.389 | 1.00 | 13.69 | A | N |
| ATOM | 1786 | CA | ASP | A | 225 | 72.779 | −22.639 | −6.794 | 1.00 | 14.56 | A | C |
| ATOM | 1787 | CB | ASP | A | 225 | 72.044 | −23.971 | −7.095 | 1.00 | 18.03 | A | C |
| ATOM | 1788 | CG | ASP | A | 225 | 70.792 | −23.759 | −7.974 | 1.00 | 18.76 | A | C |
| ATOM | 1789 | OD1 | ASP | A | 225 | 70.935 | −23.627 | −9.221 | 1.00 | 22.17 | A | O |
| ATOM | 1790 | OD2 | ASP | A | 225 | 69.674 | −23.721 | −7.410 | 1.00 | 18.19 | A | O |
| ATOM | 1791 | C | ASP | A | 225 | 72.010 | −21.858 | −5.717 | 1.00 | 15.07 | A | C |
| ATOM | 1792 | O | ASP | A | 225 | 71.264 | −20.926 | −6.025 | 1.00 | 13.40 | A | O |
| ATOM | 1793 | N | TYR | A | 226 | 72.198 | −22.244 | −4.462 | 1.00 | 14.97 | A | N |
| ATOM | 1794 | CA | TYR | A | 226 | 71.539 | −21.565 | −3.347 | 1.00 | 15.99 | A | C |
| ATOM | 1795 | CB | TYR | A | 226 | 71.895 | −22.238 | −2.014 | 1.00 | 18.96 | A | C |
| ATOM | 1796 | CG | TYR | A | 226 | 71.124 | −21.654 | −0.849 | 1.00 | 20.01 | A | C |
| ATOM | 1797 | CD1 | TYR | A | 226 | 71.531 | −20.468 | −0.232 | 1.00 | 22.17 | A | C |
| ATOM | 1798 | CE1 | TYR | A | 226 | 70.811 | −19.919 | 0.830 | 1.00 | 19.62 | A | C |
| ATOM | 1799 | CZ | TYR | A | 226 | 69.685 | −20.564 | 1.285 | 1.00 | 21.40 | A | C |
| ATOM | 1800 | OH | TYR | A | 226 | 68.962 | −20.057 | 2.317 | 1.00 | 22.99 | A | O |
| ATOM | 1801 | CE2 | TYR | A | 226 | 69.274 | −21.758 | 0.711 | 1.00 | 17.96 | A | C |
| ATOM | 1802 | CD2 | TYR | A | 226 | 69.990 | −22.288 | −0.364 | 1.00 | 17.80 | A | C |
| ATOM | 1803 | C | TYR | A | 226 | 71.934 | −20.074 | −3.287 | 1.00 | 16.06 | A | C |
| ATOM | 1804 | O | TYR | A | 226 | 71.069 | −19.202 | −3.090 | 1.00 | 16.88 | A | O |
| ATOM | 1805 | N | ASN | A | 227 | 73.218 | −19.782 | −3.461 | 1.00 | 14.97 | A | N |
| ATOM | 1806 | CA | ASN | A | 227 | 73.689 | −18.390 | −3.418 | 1.00 | 18.29 | A | C |
| ATOM | 1807 | CB | ASN | A | 227 | 75.208 | −18.332 | −3.217 | 1.00 | 17.52 | A | C |
| ATOM | 1808 | CG | ASN | A | 227 | 75.601 | −18.718 | −1.803 | 1.00 | 19.83 | A | C |
| ATOM | 1809 | OD1 | ASN | A | 227 | 74.751 | −18.764 | −0.907 | 1.00 | 19.76 | A | O |
| ATOM | 1810 | ND2 | ASN | A | 227 | 76.878 | −18.990 | −1.584 | 1.00 | 17.61 | A | N |
| ATOM | 1811 | C | ASN | A | 227 | 73.218 | −17.584 | −4.611 | 1.00 | 19.68 | A | C |
| ATOM | 1812 | O | ASN | A | 227 | 72.905 | −16.409 | −4.480 | 1.00 | 20.30 | A | O |
| ATOM | 1813 | N | MET | A | 228 | 73.103 | −18.230 | −5.763 | 1.00 | 17.59 | A | N |
| ATOM | 1814 | CA | MET | A | 228 | 72.499 | −17.585 | −6.919 | 1.00 | 19.81 | A | C |
| ATOM | 1815 | CB | MET | A | 228 | 72.586 | −18.489 | −8.115 | 1.00 | 21.31 | A | C |
| ATOM | 1816 | CG | MET | A | 228 | 71.922 | −17.937 | −9.338 | 1.00 | 24.26 | A | C |
| ATOM | 1817 | SD | MET | A | 228 | 71.839 | −19.226 | −10.569 | 1.00 | 31.75 | A | S |
| ATOM | 1818 | CE | MET | A | 228 | 70.334 | −20.104 | −10.032 | 1.00 | 32.05 | A | C |
| ATOM | 1819 | C | MET | A | 228 | 71.029 | −17.237 | −6.679 | 1.00 | 21.09 | A | C |
| ATOM | 1820 | O | MET | A | 228 | 70.575 | −16.114 | −6.923 | 1.00 | 22.56 | A | O |
| ATOM | 1821 | N | ILE | A | 229 | 70.248 | −18.207 | −6.248 | 1.00 | 20.81 | A | N |
| ATOM | 1822 | CA | ILE | A | 229 | 68.850 | −17.912 | −5.976 | 1.00 | 18.17 | A | C |
| ATOM | 1823 | CB | ILE | A | 229 | 68.039 | −19.161 | −5.543 | 1.00 | 19.71 | A | C |
| ATOM | 1824 | CG1 | ILE | A | 229 | 67.902 | −20.131 | −6.713 | 1.00 | 17.07 | A | C |
| ATOM | 1825 | CD1 | ILE | A | 229 | 67.115 | −21.438 | −6.387 | 1.00 | 18.64 | A | C |
| ATOM | 1826 | CG2 | ILE | A | 229 | 66.597 | −18.738 | −5.059 | 1.00 | 16.81 | A | C |
| ATOM | 1827 | C | ILE | A | 229 | 68.766 | −16.773 | −4.941 | 1.00 | 18.94 | A | C |
| ATOM | 1828 | O | ILE | A | 229 | 67.982 | −15.852 | −5.126 | 1.00 | 20.45 | A | O |
| ATOM | 1829 | N | GLN | A | 230 | 69.565 | −16.828 | −3.874 | 1.00 | 19.83 | A | N |
| ATOM | 1830 | CA | GLN | A | 230 | 69.529 | −15.780 | −2.851 | 1.00 | 26.24 | A | C |
| ATOM | 1831 | CB | GLN | A | 230 | 70.548 | −16.041 | −1.742 | 1.00 | 23.79 | A | C |
| ATOM | 1832 | CG | GLN | A | 230 | 70.402 | −15.118 | −0.572 | 1.00 | 24.95 | A | C |
| ATOM | 1833 | CD | GLN | A | 230 | 71.409 | −15.419 | 0.507 | 1.00 | 25.13 | A | C |
| ATOM | 1834 | OE1 | GLN | A | 230 | 72.601 | −15.204 | 0.324 | 1.00 | 27.12 | A | O |
| ATOM | 1835 | NE2 | GLN | A | 230 | 70.944 | −15.958 | 1.626 | 1.00 | 21.51 | A | N |
| ATOM | 1836 | C | GLN | A | 230 | 69.785 | −14.383 | −3.452 | 1.00 | 25.05 | A | C |
| ATOM | 1837 | O | GLN | A | 230 | 69.148 | −13.425 | −3.038 | 1.00 | 24.32 | A | O |
| ATOM | 1838 | N | SER | A | 231 | 70.692 | −14.271 | −4.425 | 1.00 | 20.12 | A | N |
| ATOM | 1839 | CA | SER | A | 231 | 70.944 | −12.970 | −5.061 | 1.00 | 23.39 | A | C |
| ATOM | 1840 | CB | SER | A | 231 | 72.235 | −12.977 | −5.917 | 1.00 | 24.86 | A | C |
| ATOM | 1841 | OG | SER | A | 231 | 72.010 | −13.749 | −7.098 | 1.00 | 38.15 | A | O |
| ATOM | 1842 | C | SER | A | 231 | 69.741 | −12.524 | −5.896 | 1.00 | 22.11 | A | C |
| ATOM | 1843 | O | SER | A | 231 | 69.523 | −11.336 | −6.058 | 1.00 | 19.49 | A | O |
| ATOM | 1844 | N | VAL | A | 232 | 68.953 | −13.453 | −6.425 | 1.00 | 20.92 | A | N |

APPENDIX A-continued

*P. alba* 3T288C coordinates

| ATOM | 1845 | CA | VAL | A | 232 | 67.641 | −13.085 | −7.019 | 1.00 | 22.15 | A | C |
|---|---|---|---|---|---|---|---|---|---|---|---|---|
| ATOM | 1846 | CB | VAL | A | 232 | 67.005 | −14.238 | −7.790 | 1.00 | 21.81 | A | C |
| ATOM | 1847 | CG1 | VAL | A | 232 | 65.573 | −13.889 | −8.300 | 1.00 | 21.93 | A | C |
| ATOM | 1848 | CG2 | VAL | A | 232 | 67.928 | −14.622 | −8.989 | 1.00 | 20.61 | A | C |
| ATOM | 1849 | C | VAL | A | 232 | 66.712 | −12.494 | −5.946 | 1.00 | 24.91 | A | C |
| ATOM | 1850 | O | VAL | A | 232 | 66.149 | −11.407 | −6.113 | 1.00 | 23.40 | A | O |
| ATOM | 1851 | N | TYR | A | 233 | 66.617 | −13.149 | −4.808 | 1.00 | 24.97 | A | N |
| ATOM | 1852 | CA | TYR | A | 233 | 65.789 | −12.616 | −3.724 | 1.00 | 23.17 | A | C |
| ATOM | 1853 | CB | TYR | A | 233 | 65.824 | −13.529 | −2.505 | 1.00 | 20.84 | A | C |
| ATOM | 1854 | CG | TYR | A | 233 | 65.292 | −14.943 | −2.719 | 1.00 | 17.60 | A | C |
| ATOM | 1855 | CD1 | TYR | A | 233 | 64.476 | −15.277 | −3.807 | 1.00 | 16.71 | A | C |
| ATOM | 1856 | CE1 | TYR | A | 233 | 64.019 | −16.589 | −3.967 | 1.00 | 18.85 | A | C |
| ATOM | 1857 | CZ | TYR | A | 233 | 64.370 | −17.529 | −3.020 | 1.00 | 16.53 | A | C |
| ATOM | 1858 | OH | TYR | A | 233 | 63.953 | −18.838 | −3.124 | 1.00 | 19.31 | A | O |
| ATOM | 1859 | CE2 | TYR | A | 233 | 65.151 | −17.207 | −1.969 | 1.00 | 17.10 | A | C |
| ATOM | 1860 | CD2 | TYR | A | 233 | 65.582 | −15.937 | −1.792 | 1.00 | 17.40 | A | C |
| ATOM | 1861 | C | TYR | A | 233 | 66.262 | −11.215 | −3.280 | 1.00 | 26.79 | A | C |
| ATOM | 1862 | O | TYR | A | 233 | 65.442 | −10.334 | −3.009 | 1.00 | 25.17 | A | O |
| ATOM | 1863 | N | GLN | A | 234 | 67.575 | −11.021 | −3.153 | 1.00 | 26.50 | A | N |
| ATOM | 1864 | CA | GLN | A | 234 | 68.093 | −9.703 | −2.738 | 1.00 | 26.52 | A | C |
| ATOM | 1865 | CB | GLN | A | 234 | 69.603 | −9.768 | −2.474 | 1.00 | 25.75 | A | C |
| ATOM | 1866 | CG | GLN | A | 234 | 69.927 | −10.604 | −1.214 | 1.00 | 27.64 | A | C |
| ATOM | 1867 | CD | GLN | A | 234 | 71.356 | −11.093 | −1.178 | 1.00 | 30.47 | A | C |
| ATOM | 1868 | OE1 | GLN | A | 234 | 72.087 | −10.905 | −2.136 | 1.00 | 34.88 | A | O |
| ATOM | 1869 | NE2 | GLN | A | 234 | 71.761 | −11.729 | −0.077 | 1.00 | 30.17 | A | N |
| ATOM | 1870 | C | GLN | A | 234 | 67.689 | −8.590 | −3.739 | 1.00 | 29.34 | A | C |
| ATOM | 1871 | O | GLN | A | 234 | 67.342 | −7.459 | −3.326 | 1.00 | 30.77 | A | O |
| ATOM | 1872 | N | ARG | A | 235 | 67.721 | −8.905 | −5.031 | 1.00 | 24.11 | A | N |
| ATOM | 1873 | CA | ARG | A | 235 | 67.249 | −7.974 | −6.056 | 1.00 | 29.32 | A | C |
| ATOM | 1874 | CB | ARG | A | 235 | 67.585 | −8.460 | −7.467 | 1.00 | 30.12 | A | C |
| ATOM | 1875 | CG | ARG | A | 235 | 67.211 | −7.417 | −8.543 | 1.00 | 42.25 | A | C |
| ATOM | 1876 | CD | ARG | A | 235 | 67.848 | −7.655 | −9.904 | 1.00 | 50.89 | A | C |
| ATOM | 1877 | NE | ARG | A | 235 | 67.654 | −9.034 | −10.339 | 1.00 | 80.51 | A | N |
| ATOM | 1878 | CZ | ARG | A | 235 | 68.596 | −9.984 | −10.361 | 1.00 | 95.81 | A | C |
| ATOM | 1879 | NH1 | ARG | A | 235 | 69.853 | −9.730 | −9.995 | 1.00 | 85.77 | A | N |
| ATOM | 1880 | NH2 | ARG | A | 235 | 68.275 | −11.211 | −10.768 | 1.00 | 87.26 | A | N |
| ATOM | 1881 | C | ARG | A | 235 | 65.740 | −7.693 | −5.936 | 1.00 | 31.87 | A | C |
| ATOM | 1882 | O | ARG | A | 235 | 65.299 | −6.546 | −5.996 | 1.00 | 26.48 | A | O |
| ATOM | 1883 | N | ASP | A | 236 | 64.950 | −8.739 | −5.774 | 1.00 | 26.15 | A | N |
| ATOM | 1884 | CA | ASP | A | 236 | 63.512 | −8.589 | −5.551 | 1.00 | 25.59 | A | C |
| ATOM | 1885 | CB | ASP | A | 236 | 62.856 | −9.930 | −5.212 | 1.00 | 27.19 | A | C |
| ATOM | 1886 | CG | ASP | A | 236 | 62.892 | −10.974 | −6.355 | 1.00 | 28.21 | A | C |
| ATOM | 1887 | OD1 | ASP | A | 236 | 63.016 | −10.622 | −7.529 | 1.00 | 32.32 | A | O |
| ATOM | 1888 | OD2 | ASP | A | 236 | 62.734 | −12.184 | −6.030 | 1.00 | 30.52 | A | O |
| ATOM | 1889 | C | ASP | A | 236 | 63.217 | −7.666 | −4.368 | 1.00 | 22.39 | A | C |
| ATOM | 1890 | O | ASP | A | 236 | 62.342 | −6.826 | −4.438 | 1.00 | 25.74 | A | O |
| ATOM | 1891 | N | LEU | A | 237 | 63.910 | −7.896 | −3.263 | 1.00 | 18.81 | A | N |
| ATOM | 1892 | CA | LEU | A | 237 | 63.675 | −7.218 | −2.040 | 1.00 | 21.93 | A | C |
| ATOM | 1893 | CB | LEU | A | 237 | 64.401 | −7.923 | −0.907 | 1.00 | 25.78 | A | C |
| ATOM | 1894 | CG | LEU | A | 237 | 64.373 | −7.206 | 0.428 | 1.00 | 32.12 | A | C |
| ATOM | 1895 | CD1 | LEU | A | 237 | 62.938 | −7.158 | 0.902 | 1.00 | 33.09 | A | C |
| ATOM | 1896 | CD2 | LEU | A | 237 | 65.279 | −7.873 | 1.452 | 1.00 | 33.88 | A | C |
| ATOM | 1897 | C | LEU | A | 237 | 64.130 | −5.761 | −2.147 | 1.00 | 29.65 | A | C |
| ATOM | 1898 | O | LEU | A | 237 | 63.507 | −4.869 | −1.577 | 1.00 | 30.17 | A | O |
| ATOM | 1899 | N | ARG | A | 238 | 65.196 | −5.506 | −2.898 | 1.00 | 25.49 | A | N |
| ATOM | 1900 | CA | ARG | A | 238 | 65.656 | −4.127 | −3.044 | 1.00 | 34.24 | A | C |
| ATOM | 1901 | CB | ARG | A | 238 | 67.022 | −4.032 | −3.752 | 1.00 | 31.76 | A | C |
| ATOM | 1902 | CG | ARG | A | 238 | 68.209 | −3.896 | −2.789 | 1.00 | 37.91 | A | C |
| ATOM | 1903 | CD | ARG | A | 238 | 69.513 | −3.536 | −3.537 | 1.00 | 38.29 | A | C |
| ATOM | 1904 | NE | ARG | A | 238 | 69.709 | −4.359 | −4.738 | 1.00 | 35.82 | A | N |
| ATOM | 1905 | CZ | ARG | A | 238 | 70.261 | −5.583 | −4.763 | 1.00 | 41.70 | A | C |
| ATOM | 1906 | NH1 | ARG | A | 238 | 70.718 | −6.162 | −3.649 | 1.00 | 35.80 | A | N |
| ATOM | 1907 | NH2 | ARG | A | 238 | 70.363 | −6.243 | −5.923 | 1.00 | 32.91 | A | N |
| ATOM | 1908 | C | ARG | A | 238 | 64.583 | −3.336 | −3.786 | 1.00 | 34.60 | A | C |
| ATOM | 1909 | O | ARG | A | 238 | 64.244 | −2.223 | −3.375 | 1.00 | 28.36 | A | O |
| ATOM | 1910 | N | GLU | A | 239 | 64.026 | −3.931 | −4.840 | 1.00 | 30.53 | A | N |
| ATOM | 1911 | CA | GLU | A | 239 | 62.927 | −3.310 | −5.587 | 1.00 | 38.02 | A | C |
| ATOM | 1912 | CB | GLU | A | 239 | 62.596 | −4.159 | −6.798 | 1.00 | 45.08 | A | C |
| ATOM | 1913 | CG | GLU | A | 239 | 61.458 | −3.618 | −7.638 | 1.00 | 66.28 | A | C |
| ATOM | 1914 | CD | GLU | A | 239 | 61.478 | −4.172 | −9.051 | 1.00 | 88.80 | A | C |
| ATOM | 1915 | OE1 | GLU | A | 239 | 61.348 | −5.403 | −9.209 | 1.00 | 95.01 | A | O |
| ATOM | 1916 | OE2 | GLU | A | 239 | 61.631 | −3.376 | −10.002 | 1.00 | 102.21 | A | O |
| ATOM | 1917 | C | GLU | A | 239 | 61.651 | −3.123 | −4.740 | 1.00 | 37.69 | A | C |
| ATOM | 1918 | O | GLU | A | 239 | 60.985 | −2.089 | −4.779 | 1.00 | 41.09 | A | O |
| ATOM | 1919 | N | THR | A | 240 | 61.308 | −4.132 | −3.973 | 1.00 | 29.30 | A | N |
| ATOM | 1920 | CA | THR | A | 240 | 60.119 | −4.032 | −3.133 | 1.00 | 30.80 | A | C |
| ATOM | 1921 | CB | THR | A | 240 | 59.735 | −5.409 | −2.610 | 1.00 | 35.45 | A | C |
| ATOM | 1922 | OG1 | THR | A | 240 | 59.434 | −6.224 | −3.753 | 1.00 | 34.87 | A | O |

APPENDIX A-continued

*P. alba* 3T288C coordinates

| ATOM | 1923 | CG2 | THR | A | 240 | 58.528 | −5.342 | −1.677 | 1.00 | 31.60 | A | C |
|---|---|---|---|---|---|---|---|---|---|---|---|---|
| ATOM | 1924 | C | THR | A | 240 | 60.340 | −3.000 | −2.021 | 1.00 | 29.08 | A | C |
| ATOM | 1925 | O | THR | A | 240 | 59.404 | −2.285 | −1.637 | 1.00 | 25.40 | A | O |
| ATOM | 1926 | N | SER | A | 241 | 61.574 | −2.927 | −1.523 | 1.00 | 31.82 | A | N |
| ATOM | 1927 | CA | SER | A | 241 | 61.967 | −1.904 | −0.546 | 1.00 | 35.69 | A | C |
| ATOM | 1928 | CB | SER | A | 241 | 63.390 | −2.135 | −0.049 | 1.00 | 38.03 | A | C |
| ATOM | 1929 | OG | SER | A | 241 | 63.376 | −3.275 | 0.796 | 1.00 | 38.86 | A | O |
| ATOM | 1930 | C | SER | A | 241 | 61.811 | −0.492 | −1.092 | 1.00 | 32.52 | A | C |
| ATOM | 1931 | O | SER | A | 241 | 61.262 | 0.355 | −0.407 | 1.00 | 32.27 | A | O |
| ATOM | 1932 | N | ARG | A | 242 | 62.267 | −0.251 | −2.316 | 1.00 | 38.08 | A | N |
| ATOM | 1933 | CA | ARG | A | 242 | 62.095 | 1.061 | −2.939 | 1.00 | 45.47 | A | C |
| ATOM | 1934 | CB | ARG | A | 242 | 62.647 | 1.107 | −4.362 | 1.00 | 55.62 | A | C |
| ATOM | 1935 | CG | ARG | A | 242 | 64.105 | 1.575 | −4.465 | 1.00 | 60.65 | A | C |
| ATOM | 1936 | CD | ARG | A | 242 | 64.540 | 1.737 | −5.922 | 1.00 | 58.46 | A | C |
| ATOM | 1937 | NE | ARG | A | 242 | 64.176 | 0.562 | −6.715 | 1.00 | 63.57 | A | N |
| ATOM | 1938 | CZ | ARG | A | 242 | 64.562 | 0.327 | −7.965 | 1.00 | 71.15 | A | C |
| ATOM | 1939 | NH1 | ARG | A | 242 | 65.362 | 1.172 | −8.605 | 1.00 | 77.17 | A | N |
| ATOM | 1940 | NH2 | ARG | A | 242 | 64.157 | −0.786 | −8.573 | 1.00 | 69.07 | A | N |
| ATOM | 1941 | C | ARG | A | 242 | 60.633 | 1.407 | −2.984 | 1.00 | 36.39 | A | C |
| ATOM | 1942 | O | ARG | A | 242 | 60.243 | 2.473 | −2.544 | 1.00 | 28.12 | A | O |
| ATOM | 1943 | N | TRP | A | 243 | 59.829 | 0.492 | −3.503 | 1.00 | 28.35 | A | N |
| ATOM | 1944 | CA | TRP | A | 243 | 58.361 | 0.657 | −3.551 | 1.00 | 26.03 | A | C |
| ATOM | 1945 | CB | TRP | A | 243 | 57.695 | −0.617 | −4.077 | 1.00 | 29.56 | A | C |
| ATOM | 1946 | CG | TRP | A | 243 | 56.200 | −0.649 | −3.818 | 1.00 | 23.64 | A | C |
| ATOM | 1947 | CD1 | TRP | A | 243 | 55.221 | 0.012 | −4.539 | 1.00 | 22.96 | A | C |
| ATOM | 1948 | NE1 | TRP | A | 243 | 53.992 | −0.215 | −4.013 | 1.00 | 23.68 | A | N |
| ATOM | 1949 | CE2 | TRP | A | 243 | 54.067 | −1.021 | −2.931 | 1.00 | 19.35 | A | C |
| ATOM | 1950 | CD2 | TRP | A | 243 | 55.475 | −1.341 | −2.736 | 1.00 | 21.40 | A | C |
| ATOM | 1951 | CE3 | TRP | A | 243 | 55.839 | −2.117 | −1.658 | 1.00 | 21.11 | A | C |
| ATOM | 1952 | CZ3 | TRP | A | 243 | 54.839 | −2.611 | −0.816 | 1.00 | 21.65 | A | C |
| ATOM | 1953 | CH2 | TRP | A | 243 | 53.499 | −2.292 | −1.025 | 1.00 | 24.12 | A | C |
| ATOM | 1954 | CZ2 | TRP | A | 243 | 53.098 | −1.470 | −2.085 | 1.00 | 20.86 | A | C |
| ATOM | 1955 | C | TRP | A | 243 | 57.748 | 1.020 | −2.212 | 1.00 | 28.47 | A | C |
| ATOM | 1956 | O | TRP | A | 243 | 56.898 | 1.931 | −2.117 | 1.00 | 26.65 | A | O |
| ATOM | 1957 | N | TRP | A | 244 | 58.131 | 0.285 | −1.170 | 1.00 | 21.36 | A | N |
| ATOM | 1958 | CA | TRP | A | 244 | 57.522 | 0.468 | 0.135 | 1.00 | 22.92 | A | C |
| ATOM | 1959 | CB | TRP | A | 244 | 57.903 | −0.689 | 1.044 | 1.00 | 19.70 | A | C |
| ATOM | 1960 | CG | TRP | A | 244 | 57.271 | −0.719 | 2.405 | 1.00 | 23.19 | A | C |
| ATOM | 1961 | CD1 | TRP | A | 244 | 57.923 | −0.793 | 3.634 | 1.00 | 32.70 | A | C |
| ATOM | 1962 | NE1 | TRP | A | 244 | 57.011 | −0.851 | 4.665 | 1.00 | 32.87 | A | N |
| ATOM | 1963 | CE2 | TRP | A | 244 | 55.764 | −0.834 | 4.204 | 1.00 | 24.73 | A | C |
| ATOM | 1964 | CD2 | TRP | A | 244 | 55.837 | −0.768 | 2.746 | 1.00 | 23.81 | A | C |
| ATOM | 1965 | CE3 | TRP | A | 244 | 54.669 | −0.697 | 2.027 | 1.00 | 25.86 | A | C |
| ATOM | 1966 | CZ3 | TRP | A | 244 | 53.466 | −0.723 | 2.708 | 1.00 | 30.63 | A | C |
| ATOM | 1967 | CH2 | TRP | A | 244 | 53.418 | −0.815 | 4.093 | 1.00 | 29.59 | A | C |
| ATOM | 1968 | CZ2 | TRP | A | 244 | 54.568 | −0.864 | 4.867 | 1.00 | 30.60 | A | C |
| ATOM | 1969 | C | TRP | A | 244 | 57.894 | 1.796 | 0.747 | 1.00 | 21.08 | A | C |
| ATOM | 1970 | O | TRP | A | 244 | 57.066 | 2.428 | 1.393 | 1.00 | 20.60 | A | O |
| ATOM | 1971 | N | ARG | A | 245 | 59.131 | 2.228 | 0.536 | 1.00 | 27.20 | A | N |
| ATOM | 1972 | CA | ARG | A | 245 | 59.600 | 3.537 | 1.011 | 1.00 | 31.73 | A | C |
| ATOM | 1973 | CB | ARG | A | 245 | 61.114 | 3.701 | 0.828 | 1.00 | 32.00 | A | C |
| ATOM | 1974 | CG | ARG | A | 245 | 61.957 | 3.111 | 1.957 | 1.00 | 47.72 | A | C |
| ATOM | 1975 | CD | ARG | A | 245 | 63.414 | 3.658 | 1.909 | 1.00 | 65.57 | A | C |
| ATOM | 1976 | NE | ARG | A | 245 | 63.978 | 3.622 | 0.550 | 1.00 | 70.19 | A | N |
| ATOM | 1977 | CZ | ARG | A | 245 | 64.550 | 2.557 | −0.028 | 1.00 | 68.85 | A | C |
| ATOM | 1978 | NH1 | ARG | A | 245 | 64.675 | 1.394 | 0.614 | 1.00 | 60.07 | A | N |
| ATOM | 1979 | NH2 | ARG | A | 245 | 65.007 | 2.655 | −1.273 | 1.00 | 76.75 | A | N |
| ATOM | 1980 | C | ARG | A | 245 | 58.884 | 4.688 | 0.316 | 1.00 | 32.25 | A | C |
| ATOM | 1981 | O | ARG | A | 245 | 58.541 | 5.682 | 0.955 | 1.00 | 25.27 | A | O |
| ATOM | 1982 | N | ARG | A | 246 | 58.657 | 4.557 | −0.981 | 1.00 | 30.10 | A | N |
| ATOM | 1983 | CA | ARG | A | 246 | 57.876 | 5.545 | −1.716 | 1.00 | 35.79 | A | C |
| ATOM | 1984 | CB | ARG | A | 246 | 57.869 | 5.189 | −3.197 | 1.00 | 46.51 | A | C |
| ATOM | 1985 | CG | ARG | A | 246 | 56.789 | 5.862 | −4.038 | 1.00 | 57.62 | A | C |
| ATOM | 1986 | CD | ARG | A | 246 | 57.095 | 5.711 | −5.519 | 1.00 | 77.36 | A | C |
| ATOM | 1987 | NE | ARG | A | 246 | 58.470 | 6.129 | −5.827 | 1.00 | 99.02 | A | N |
| ATOM | 1988 | CZ | ARG | A | 246 | 59.493 | 5.319 | −6.132 | 1.00 | 100.61 | A | C |
| ATOM | 1989 | NH1 | ARG | A | 246 | 59.344 | 3.996 | −6.197 | 1.00 | 99.90 | A | N |
| ATOM | 1990 | NH2 | ARG | A | 246 | 60.690 | 5.849 | −6.382 | 1.00 | 97.80 | A | N |
| ATOM | 1991 | C | ARG | A | 246 | 56.451 | 5.614 | −1.172 | 1.00 | 28.96 | A | C |
| ATOM | 1992 | O | ARG | A | 246 | 55.917 | 6.676 | −0.969 | 1.00 | 27.23 | A | O |
| ATOM | 1993 | N | VAL | A | 247 | 55.842 | 4.472 | −0.908 | 1.00 | 21.35 | A | N |
| ATOM | 1994 | CA | VAL | A | 247 | 54.492 | 4.449 | −0.332 | 1.00 | 21.70 | A | C |
| ATOM | 1995 | CB | VAL | A | 247 | 53.980 | 3.019 | −0.174 | 1.00 | 21.06 | A | C |
| ATOM | 1996 | CG1 | VAL | A | 247 | 52.639 | 2.991 | 0.545 | 1.00 | 24.68 | A | C |
| ATOM | 1997 | CG2 | VAL | A | 247 | 53.840 | 2.363 | −1.563 | 1.00 | 29.20 | A | C |
| ATOM | 1998 | C | VAL | A | 247 | 54.523 | 5.162 | 1.024 | 1.00 | 21.79 | A | C |
| ATOM | 1999 | O | VAL | A | 247 | 53.668 | 6.032 | 1.306 | 1.00 | 17.47 | A | O |
| ATOM | 2000 | N | GLY | A | 248 | 55.514 | 4.807 | 1.853 | 1.00 | 21.84 | A | N |

APPENDIX A-continued

*P. alba* 3T288C coordinates

| ATOM | 2001 | CA  | GLY  | A | 248 | 55.852 | 5.583  | 3.069  | 1.00 | 24.01 | A | C |
|------|------|-----|------|---|-----|--------|--------|--------|------|-------|---|---|
| ATOM | 2002 | C   | GLY  | A | 248 | 54.844 | 5.545  | 4.220  | 1.00 | 25.34 | A | C |
| ATOM | 2003 | O   | GLY  | A | 248 | 54.778 | 6.451  | 5.052  | 1.00 | 31.72 | A | O |
| ATOM | 2004 | N   | LEU  | A | 249 | 54.056 | 4.504  | 4.269  | 1.00 | 26.67 | A | N |
| ATOM | 2005 | CA  | LEU  | A | 249 | 52.901 | 4.445  | 5.142  | 1.00 | 31.07 | A | C |
| ATOM | 2006 | CB  | LEU  | A | 249 | 51.968 | 3.379  | 4.590  | 1.00 | 32.92 | A | C |
| ATOM | 2007 | CG  | LEU  | A | 249 | 50.445 | 3.425  | 4.652  | 1.00 | 34.04 | A | C |
| ATOM | 2008 | CD1 | LEU  | A | 249 | 49.811 | 4.784  | 4.331  | 1.00 | 27.52 | A | C |
| ATOM | 2009 | CD2 | LEU  | A | 249 | 49.936 | 2.336  | 3.719  | 1.00 | 33.60 | A | C |
| ATOM | 2010 | C   | LEU  | A | 249 | 53.327 | 4.192  | 6.615  | 1.00 | 46.12 | A | C |
| ATOM | 2011 | O   | LEU  | A | 249 | 52.834 | 4.864  | 7.544  | 1.00 | 39.23 | A | O |
| ATOM | 2012 | N   | ALA  | A | 250 | 54.280 | 3.276  | 6.815  | 1.00 | 51.58 | A | N |
| ATOM | 2013 | CA  | ALA  | A | 250 | 54.779 | 2.935  | 8.157  | 1.00 | 62.76 | A | C |
| ATOM | 2014 | CB  | ALA  | A | 250 | 55.754 | 1.749  | 8.093  | 1.00 | 57.13 | A | C |
| ATOM | 2015 | C   | ALA  | A | 250 | 55.430 | 4.152  | 8.828  | 1.00 | 61.60 | A | C |
| ATOM | 2016 | O   | ALA  | A | 250 | 55.355 | 4.301  | 10.041 | 1.00 | 69.56 | A | O |
| ATOM | 2017 | N   | THR  | A | 251 | 56.045 | 5.017  | 8.021  | 1.00 | 47.72 | A | N |
| ATOM | 2018 | CA  | THR  | A | 251 | 56.545 | 6.327  | 8.461  | 1.00 | 43.94 | A | C |
| ATOM | 2019 | CB  | THR  | A | 251 | 57.291 | 7.050  | 7.298  | 1.00 | 38.98 | A | C |
| ATOM | 2020 | OG1 | THR  | A | 251 | 58.145 | 6.124  | 6.625  | 1.00 | 60.41 | A | O |
| ATOM | 2021 | CG2 | THR  | A | 251 | 58.107 | 8.197  | 7.788  | 1.00 | 38.02 | A | C |
| ATOM | 2022 | C   | THR  | A | 251 | 55.432 | 7.280  | 8.926  | 1.00 | 44.65 | A | C |
| ATOM | 2023 | O   | THR  | A | 251 | 55.573 | 7.945  | 9.942  | 1.00 | 49.78 | A | O |
| ATOM | 2024 | N   | LYS  | A | 252 | 54.342 | 7.358  | 8.159  | 1.00 | 33.75 | A | N |
| ATOM | 2025 | CA  | LYS  | A | 252 | 53.312 | 8.411  | 8.329  | 1.00 | 29.58 | A | C |
| ATOM | 2026 | CB  | LYS  | A | 252 | 52.721 | 8.780  | 6.938  | 1.00 | 38.55 | A | C |
| ATOM | 2027 | CG  | LYS  | A | 252 | 53.751 | 9.375  | 5.910  | 1.00 | 44.61 | A | C |
| ATOM | 2028 | CD  | LYS  | A | 252 | 54.042 | 10.870 | 6.119  | 1.00 | 38.46 | A | C |
| ATOM | 2029 | CE  | LYS  | A | 252 | 55.237 | 11.331 | 5.273  | 1.00 | 43.27 | A | C |
| ATOM | 2030 | NZ  | LYS  | A | 252 | 55.325 | 12.808 | 5.140  | 1.00 | 40.15 | A | N |
| ATOM | 2031 | C   | LYS  | A | 252 | 52.174 | 8.036  | 9.302  | 1.00 | 25.43 | A | C |
| ATOM | 2032 | O   | LYS  | A | 252 | 51.554 | 8.892  | 9.885  | 1.00 | 36.35 | A | O |
| ATOM | 2033 | N   | LEU  | A | 253 | 51.894 | 6.743  | 9.435  | 1.00 | 28.29 | A | N |
| ATOM | 2034 | CA  | LEU  | A | 253 | 50.964 | 6.233  | 10.425 | 1.00 | 28.58 | A | C |
| ATOM | 2035 | CB  | LEU  | A | 253 | 50.221 | 5.011  | 9.864  | 1.00 | 31.96 | A | C |
| ATOM | 2036 | CG  | LEU  | A | 253 | 48.977 | 5.172  | 8.971  | 1.00 | 37.47 | A | C |
| ATOM | 2037 | CD1 | LEU  | A | 253 | 49.006 | 6.440  | 8.122  | 1.00 | 31.09 | A | C |
| ATOM | 2038 | CD2 | LEU  | A | 253 | 48.798 | 3.903  | 8.130  | 1.00 | 35.88 | A | C |
| ATOM | 2039 | C   | LEU  | A | 253 | 51.809 | 5.811  | 11.646 | 1.00 | 31.04 | A | C |
| ATOM | 2040 | O   | LEU  | A | 253 | 52.552 | 4.821  | 11.581 | 1.00 | 33.71 | A | O |
| ATOM | 2041 | N   | HIS  | A | 254 | 51.636 | 6.515  | 12.758 | 1.00 | 27.06 | A | N |
| ATOM | 2042 | CA  | AHIS | A | 254 | 52.536 | 6.332  | 13.904 | 0.50 | 29.33 | A | C |
| ATOM | 2043 | CA  | BHIS | A | 254 | 52.460 | 6.372  | 13.983 | 0.50 | 31.17 | A | C |
| ATOM | 2044 | CB  | AHIS | A | 254 | 52.490 | 7.564  | 14.820 | 0.50 | 28.81 | A | C |
| ATOM | 2045 | CB  | BHIS | A | 254 | 52.159 | 7.517  | 14.992 | 0.50 | 32.28 | A | C |
| ATOM | 2046 | CG  | AHIS | A | 254 | 52.561 | 8.884  | 14.067 | 0.50 | 32.89 | A | C |
| ATOM | 2047 | CG  | BHIS | A | 254 | 50.831 | 7.378  | 15.741 | 0.50 | 39.44 | A | C |
| ATOM | 2048 | ND1 | AHIS | A | 254 | 53.193 | 9.013  | 12.872 | 0.50 | 30.44 | A | N |
| ATOM | 2049 | ND1 | BHIS | A | 254 | 49.750 | 8.139  | 15.460 | 0.50 | 44.49 | A | N |
| ATOM | 2050 | CE1 | AHIS | A | 254 | 53.081 | 10.287 | 12.450 | 0.50 | 30.02 | A | C |
| ATOM | 2051 | CE1 | BHIS | A | 254 | 48.736 | 7.798  | 16.285 | 0.50 | 39.97 | A | C |
| ATOM | 2052 | NE2 | AHIS | A | 254 | 52.387 | 10.977 | 13.377 | 0.50 | 30.22 | A | N |
| ATOM | 2053 | NE2 | BHIS | A | 254 | 49.170 | 6.817  | 17.100 | 0.50 | 33.73 | A | N |
| ATOM | 2054 | CD2 | AHIS | A | 254 | 52.052 | 10.145 | 14.382 | 0.50 | 29.37 | A | C |
| ATOM | 2055 | CD2 | BHIS | A | 254 | 50.455 | 6.542  | 16.802 | 0.50 | 37.01 | A | C |
| ATOM | 2056 | C   | HIS  | A | 254 | 52.296 | 5.040  | 14.669 | 1.00 | 29.00 | A | C |
| ATOM | 2057 | O   | HIS  | A | 254 | 53.161 | 4.596  | 15.424 | 1.00 | 26.96 | A | O |
| ATOM | 2058 | N   | PHE  | A | 255 | 51.156 | 4.403  | 14.447 | 1.00 | 23.47 | A | N |
| ATOM | 2059 | CA  | PHE  | A | 255 | 50.822 | 3.146  | 15.121 | 1.00 | 27.33 | A | C |
| ATOM | 2060 | CB  | PHE  | A | 255 | 49.305 | 3.062  | 15.358 | 1.00 | 25.32 | A | C |
| ATOM | 2061 | CG  | PHE  | A | 255 | 48.517 | 2.984  | 14.077 | 1.00 | 24.28 | A | C |
| ATOM | 2062 | CD1 | PHE  | A | 255 | 48.347 | 1.777  | 13.432 | 1.00 | 26.59 | A | C |
| ATOM | 2063 | CE1 | PHE  | A | 255 | 47.663 | 1.707  | 12.211 | 1.00 | 29.93 | A | C |
| ATOM | 2064 | CZ  | PHE  | A | 255 | 47.171 | 2.861  | 11.637 | 1.00 | 26.82 | A | C |
| ATOM | 2065 | CE2 | PHE  | A | 255 | 47.332 | 4.065  | 12.270 | 1.00 | 34.44 | A | C |
| ATOM | 2066 | CD2 | PHE  | A | 255 | 48.027 | 4.133  | 13.480 | 1.00 | 30.12 | A | C |
| ATOM | 2067 | C   | PHE  | A | 255 | 51.275 | 1.915  | 14.318 | 1.00 | 30.30 | A | C |
| ATOM | 2068 | O   | PHE  | A | 255 | 51.227 | 0.809  | 14.832 | 1.00 | 29.18 | A | O |
| ATOM | 2069 | N   | ALA  | A | 256 | 51.680 | 2.091  | 13.063 | 1.00 | 32.80 | A | N |
| ATOM | 2070 | CA  | ALA  | A | 256 | 51.890 | 0.933  | 12.166 | 1.00 | 39.26 | A | C |
| ATOM | 2071 | CB  | ALA  | A | 256 | 51.835 | 1.360  | 10.708 | 1.00 | 38.98 | A | C |
| ATOM | 2072 | C   | ALA  | A | 256 | 53.201 | 0.205  | 12.438 | 1.00 | 32.90 | A | C |
| ATOM | 2073 | O   | ALA  | A | 256 | 54.219 | 0.833  | 12.705 | 1.00 | 35.46 | A | O |
| ATOM | 2074 | N   | ARG  | A | 257 | 53.128 | −1.125 | 12.418 | 1.00 | 39.28 | A | N |
| ATOM | 2075 | CA  | ARG  | A | 257 | 54.285 | −2.021 | 12.366 | 1.00 | 43.61 | A | C |
| ATOM | 2076 | CB  | ARG  | A | 257 | 53.852 | −3.479 | 12.677 | 1.00 | 45.99 | A | C |
| ATOM | 2077 | CG  | ARG  | A | 257 | 53.326 | −3.819 | 14.113 | 1.00 | 50.74 | A | C |
| ATOM | 2078 | CD  | ARG  | A | 257 | 52.807 | −5.303 | 14.183 | 1.00 | 48.09 | A | C |

APPENDIX A-continued

| | | | | | P. alba 3T288C coordinates | | | | | | |
|---|---|---|---|---|---|---|---|---|---|---|---|
| ATOM | 2079 | NE | ARG | A | 257 | 51.532 | −5.483 | 13.477 | 1.00 | 37.96 | A | N |
| ATOM | 2080 | CZ | ARG | A | 257 | 51.080 | −6.614 | 12.921 | 1.00 | 48.88 | A | C |
| ATOM | 2081 | NH1 | ARG | A | 257 | 51.799 | −7.737 | 12.951 | 1.00 | 53.81 | A | N |
| ATOM | 2082 | NH2 | ARG | A | 257 | 49.889 | −6.623 | 12.284 | 1.00 | 39.93 | A | N |
| ATOM | 2083 | C | ARG | A | 257 | 54.875 | −2.001 | 10.931 | 1.00 | 46.39 | A | C |
| ATOM | 2084 | O | ARG | A | 257 | 54.136 | −2.233 | 9.960 | 1.00 | 44.76 | A | O |
| ATOM | 2085 | N | ASP | A | 258 | 56.182 | −1.751 | 10.804 | 1.00 | 44.98 | A | N |
| ATOM | 2086 | CA | ASP | A | 258 | 56.916 | −2.010 | 9.540 | 1.00 | 51.71 | A | C |
| ATOM | 2087 | CB | ASP | A | 258 | 58.123 | −1.065 | 9.388 | 1.00 | 55.16 | A | C |
| ATOM | 2088 | CG | ASP | A | 258 | 58.906 | −1.298 | 8.082 | 1.00 | 63.44 | A | C |
| ATOM | 2089 | OD1 | ASP | A | 258 | 58.551 | −2.204 | 7.297 | 1.00 | 55.55 | A | O |
| ATOM | 2090 | OD2 | ASP | A | 258 | 59.895 | −0.576 | 7.838 | 1.00 | 65.16 | A | O |
| ATOM | 2091 | C | ASP | A | 258 | 57.383 | −3.491 | 9.481 | 1.00 | 46.48 | A | C |
| ATOM | 2092 | O | ASP | A | 258 | 58.236 | −3.923 | 10.268 | 1.00 | 47.25 | A | O |
| ATOM | 2093 | N | ARG | A | 259 | 56.824 | −4.265 | 8.553 | 1.00 | 39.72 | A | N |
| ATOM | 2094 | CA | ARG | A | 259 | 57.104 | −5.695 | 8.508 | 1.00 | 36.16 | A | C |
| ATOM | 2095 | CB | ARG | A | 259 | 55.842 | −6.489 | 8.901 | 1.00 | 45.84 | A | C |
| ATOM | 2096 | CG | ARG | A | 259 | 55.467 | −6.478 | 10.387 | 1.00 | 48.37 | A | C |
| ATOM | 2097 | CD | ARG | A | 259 | 56.185 | −7.566 | 11.182 | 1.00 | 58.13 | A | C |
| ATOM | 2098 | NE | ARG | A | 259 | 55.862 | −7.511 | 12.615 | 1.00 | 64.71 | A | N |
| ATOM | 2099 | CZ | ARG | A | 259 | 56.333 | −6.609 | 13.492 | 1.00 | 62.43 | A | C |
| ATOM | 2100 | NH1 | ARG | A | 259 | 57.172 | −5.644 | 13.119 | 1.00 | 60.33 | A | N |
| ATOM | 2101 | NH2 | ARG | A | 259 | 55.952 | −6.663 | 14.765 | 1.00 | 51.48 | A | N |
| ATOM | 2102 | C | ARG | A | 259 | 57.591 | −6.115 | 7.122 | 1.00 | 36.67 | A | C |
| ATOM | 2103 | O | ARG | A | 259 | 57.303 | −7.244 | 6.673 | 1.00 | 27.57 | A | O |
| ATOM | 2104 | N | LEU | A | 260 | 58.341 | −5.256 | 6.436 | 1.00 | 31.46 | A | N |
| ATOM | 2105 | CA | LEU | A | 260 | 58.687 | −5.577 | 5.030 | 1.00 | 31.03 | A | C |
| ATOM | 2106 | CB | LEU | A | 260 | 59.352 | −4.410 | 4.273 | 1.00 | 37.61 | A | C |
| ATOM | 2107 | CG | LEU | A | 260 | 59.622 | −4.758 | 2.789 | 1.00 | 35.78 | A | C |
| ATOM | 2108 | CD1 | LEU | A | 260 | 58.346 | −4.883 | 2.016 | 1.00 | 43.44 | A | C |
| ATOM | 2109 | CD2 | LEU | A | 260 | 60.514 | −3.785 | 2.123 | 1.00 | 49.39 | A | C |
| ATOM | 2110 | C | LEU | A | 260 | 59.554 | −6.825 | 4.887 | 1.00 | 26.61 | A | C |
| ATOM | 2111 | O | LEU | A | 260 | 59.309 | −7.654 | 3.992 | 1.00 | 25.45 | A | O |
| ATOM | 2112 | N | ILE | A | 261 | 60.579 | −6.957 | 5.728 | 1.00 | 25.93 | A | N |
| ATOM | 2113 | CA | ILE | A | 261 | 61.526 | −8.051 | 5.533 | 1.00 | 28.16 | A | C |
| ATOM | 2114 | CB | ILE | A | 261 | 62.790 | −7.905 | 6.400 | 1.00 | 33.56 | A | C |
| ATOM | 2115 | CG1 | ILE | A | 261 | 63.502 | −6.572 | 6.083 | 1.00 | 40.92 | A | C |
| ATOM | 2116 | CD1 | ILE | A | 261 | 64.784 | −6.261 | 6.922 | 1.00 | 42.44 | A | C |
| ATOM | 2117 | CG2 | ILE | A | 261 | 63.742 | −9.071 | 6.120 | 1.00 | 29.08 | A | C |
| ATOM | 2118 | C | ILE | A | 261 | 60.823 | −9.381 | 5.821 | 1.00 | 23.39 | A | C |
| ATOM | 2119 | O | ILE | A | 261 | 60.986 | −10.336 | 5.094 | 1.00 | 21.56 | A | O |
| ATOM | 2120 | N | GLU | A | 262 | 60.037 | −9.405 | 6.891 | 1.00 | 24.38 | A | N |
| ATOM | 2121 | CA | GLU | A | 262 | 59.268 | −10.553 | 7.244 | 1.00 | 26.84 | A | C |
| ATOM | 2122 | CB | GLU | A | 262 | 58.520 | −10.319 | 8.555 | 1.00 | 31.21 | A | C |
| ATOM | 2123 | CG | GLU | A | 262 | 59.428 | −10.144 | 9.758 | 1.00 | 43.65 | A | C |
| ATOM | 2124 | CD | GLU | A | 262 | 59.708 | −8.674 | 10.172 | 1.00 | 56.28 | A | C |
| ATOM | 2125 | OE1 | GLU | A | 262 | 59.880 | −7.742 | 9.317 | 1.00 | 45.34 | A | O |
| ATOM | 2126 | OE2 | GLU | A | 262 | 59.791 | −8.473 | 11.403 | 1.00 | 60.11 | A | O |
| ATOM | 2127 | C | GLU | A | 262 | 58.294 | −10.922 | 6.133 | 1.00 | 21.33 | A | C |
| ATOM | 2128 | O | GLU | A | 262 | 58.098 | −12.110 | 5.869 | 1.00 | 21.38 | A | O |
| ATOM | 2129 | N | SER | A | 263 | 57.663 | −9.929 | 5.486 | 1.00 | 24.13 | A | N |
| ATOM | 2130 | CA | ASER | A | 263 | 56.702 | −10.147 | 4.379 | 0.50 | 21.74 | A | C |
| ATOM | 2131 | CA | BSER | A | 263 | 56.676 | −10.253 | 4.462 | 0.50 | 22.97 | A | C |
| ATOM | 2132 | CB | ASER | A | 263 | 56.159 | −8.799 | 3.850 | 0.50 | 19.44 | A | C |
| ATOM | 2133 | CB | BSER | A | 263 | 55.781 | −9.035 | 4.163 | 0.50 | 23.11 | A | C |
| ATOM | 2134 | OG | ASER | A | 263 | 57.138 | −8.090 | 3.067 | 0.50 | 18.88 | A | O |
| ATOM | 2135 | OG | BSER | A | 263 | 54.803 | −8.878 | 5.208 | 0.50 | 26.26 | A | O |
| ATOM | 2136 | C | SER | A | 263 | 57.380 | −10.850 | 3.218 | 1.00 | 20.26 | A | C |
| ATOM | 2137 | O | SER | A | 263 | 56.815 | −11.700 | 2.517 | 1.00 | 20.01 | A | O |
| ATOM | 2138 | N | PHE | A | 264 | 58.615 | −10.469 | 2.992 | 1.00 | 21.57 | A | N |
| ATOM | 2139 | CA | PHE | A | 264 | 59.363 | −11.043 | 1.893 | 1.00 | 20.69 | A | C |
| ATOM | 2140 | CB | PHE | A | 264 | 60.509 | −10.144 | 1.460 | 1.00 | 27.57 | A | C |
| ATOM | 2141 | CG | PHE | A | 264 | 61.002 | −10.505 | 0.131 | 1.00 | 25.73 | A | C |
| ATOM | 2142 | CD1 | PHE | A | 264 | 60.345 | −10.045 | −0.985 | 1.00 | 30.05 | A | C |
| ATOM | 2143 | CE1 | PHE | A | 264 | 60.746 | −10.412 | −2.222 | 1.00 | 33.90 | A | C |
| ATOM | 2144 | CZ | PHE | A | 264 | 61.807 | −11.301 | −2.357 | 1.00 | 30.18 | A | C |
| ATOM | 2145 | CE2 | PHE | A | 264 | 62.447 | −11.790 | −1.254 | 1.00 | 31.62 | A | C |
| ATOM | 2146 | CD2 | PHE | A | 264 | 62.033 | −11.396 | −0.004 | 1.00 | 33.82 | A | C |
| ATOM | 2147 | C | PHE | A | 264 | 59.893 | −12.452 | 2.214 | 1.00 | 19.81 | A | C |
| ATOM | 2148 | O | PHE | A | 264 | 59.892 | −13.336 | 1.362 | 1.00 | 23.69 | A | O |
| ATOM | 2149 | N | TYR | A | 265 | 60.344 | −12.657 | 3.440 | 1.00 | 23.30 | A | N |
| ATOM | 2150 | CA | TYR | A | 265 | 60.692 | −13.991 | 3.917 | 1.00 | 21.15 | A | C |
| ATOM | 2151 | CB | TYR | A | 265 | 61.113 | −13.875 | 5.379 | 1.00 | 24.47 | A | C |
| ATOM | 2152 | CG | TYR | A | 265 | 61.316 | −15.199 | 6.068 | 1.00 | 26.97 | A | C |
| ATOM | 2153 | CD1 | TYR | A | 265 | 62.466 | −15.948 | 5.852 | 1.00 | 38.07 | A | C |
| ATOM | 2154 | CE1 | TYR | A | 265 | 62.644 | −17.174 | 6.483 | 1.00 | 40.87 | A | C |
| ATOM | 2155 | CZ | TYR | A | 265 | 61.671 | −17.636 | 7.336 | 1.00 | 35.57 | A | C |
| ATOM | 2156 | OH | TYR | A | 265 | 61.837 | −18.829 | 7.985 | 1.00 | 38.87 | A | O |

APPENDIX A-continued

*P. alba* 3T288C coordinates

| ATOM | 2157 | CE2 | TYR | A | 265 | 60.544 | −16.894 | 7.575 | 1.00 | 29.52 | A | C |
|---|---|---|---|---|---|---|---|---|---|---|---|---|
| ATOM | 2158 | CD2 | TYR | A | 265 | 60.371 | −15.691 | 6.953 | 1.00 | 27.61 | A | C |
| ATOM | 2159 | C | TYR | A | 265 | 59.506 | −14.945 | 3.768 | 1.00 | 22.73 | A | C |
| ATOM | 2160 | O | TYR | A | 265 | 59.646 | −16.089 | 3.312 | 1.00 | 19.72 | A | O |
| ATOM | 2161 | N | TRP | A | 266 | 58.326 | −14.464 | 4.132 | 1.00 | 19.94 | A | N |
| ATOM | 2162 | CA | TRP | A | 266 | 57.101 | −15.244 | 3.958 | 1.00 | 18.79 | A | C |
| ATOM | 2163 | CB | TRP | A | 266 | 55.954 | −14.403 | 4.500 | 1.00 | 17.85 | A | C |
| ATOM | 2164 | CG | TRP | A | 266 | 54.610 | −15.023 | 4.318 | 1.00 | 17.80 | A | C |
| ATOM | 2165 | CD1 | TRP | A | 266 | 53.758 | −14.885 | 3.230 | 1.00 | 22.77 | A | C |
| ATOM | 2166 | NE1 | TRP | A | 266 | 52.624 | −15.582 | 3.427 | 1.00 | 22.25 | A | N |
| ATOM | 2167 | CE2 | TRP | A | 266 | 52.650 | −16.228 | 4.610 | 1.00 | 20.79 | A | C |
| ATOM | 2168 | CD2 | TRP | A | 266 | 53.906 | −15.892 | 5.247 | 1.00 | 19.11 | A | C |
| ATOM | 2169 | CE3 | TRP | A | 266 | 54.170 | −16.384 | 6.507 | 1.00 | 22.12 | A | C |
| ATOM | 2170 | CZ3 | TRP | A | 266 | 53.229 | −17.194 | 7.111 | 1.00 | 22.16 | A | C |
| ATOM | 2171 | CH2 | TRP | A | 266 | 52.026 | −17.501 | 6.489 | 1.00 | 20.81 | A | C |
| ATOM | 2172 | CZ2 | TRP | A | 266 | 51.703 | −17.005 | 5.233 | 1.00 | 22.45 | A | C |
| ATOM | 2173 | C | TRP | A | 266 | 56.886 | −15.615 | 2.506 | 1.00 | 20.46 | A | C |
| ATOM | 2174 | O | TRP | A | 266 | 56.628 | −16.777 | 2.161 | 1.00 | 19.38 | A | O |
| ATOM | 2175 | N | ALA | A | 267 | 56.986 | −14.624 | 1.619 | 1.00 | 18.01 | A | N |
| ATOM | 2176 | CA | ALA | A | 267 | 56.777 | −14.838 | 0.180 | 1.00 | 19.40 | A | C |
| ATOM | 2177 | CB | ALA | A | 267 | 56.944 | −13.538 | −0.599 | 1.00 | 18.97 | A | C |
| ATOM | 2178 | C | ALA | A | 267 | 57.724 | −15.896 | −0.418 | 1.00 | 18.10 | A | C |
| ATOM | 2179 | O | ALA | A | 267 | 57.323 | −16.629 | −1.322 | 1.00 | 17.66 | A | O |
| ATOM | 2180 | N | VAL | A | 268 | 58.968 | −15.919 | 0.052 | 1.00 | 20.08 | A | N |
| ATOM | 2181 | CA | VAL | A | 268 | 59.952 | −16.916 | −0.395 | 1.00 | 20.64 | A | C |
| ATOM | 2182 | CB | VAL | A | 268 | 61.320 | −16.651 | 0.233 | 1.00 | 19.24 | A | C |
| ATOM | 2183 | CG1 | VAL | A | 268 | 62.249 | −17.869 | 0.121 | 1.00 | 18.95 | A | C |
| ATOM | 2184 | CG2 | VAL | A | 268 | 61.966 | −15.357 | −0.408 | 1.00 | 18.33 | A | C |
| ATOM | 2185 | C | VAL | A | 268 | 59.485 | −18.357 | −0.107 | 1.00 | 22.76 | A | C |
| ATOM | 2186 | O | VAL | A | 268 | 59.676 | −19.255 | −0.930 | 1.00 | 19.44 | A | O |
| ATOM | 2187 | N | GLY | A | 269 | 58.846 | −18.559 | 1.040 | 1.00 | 18.03 | A | N |
| ATOM | 2188 | CA | GLY | A | 269 | 58.269 | −19.859 | 1.372 | 1.00 | 18.75 | A | C |
| ATOM | 2189 | C | GLY | A | 269 | 57.169 | −20.244 | 0.425 | 1.00 | 21.80 | A | C |
| ATOM | 2190 | O | GLY | A | 269 | 57.007 | −21.425 | 0.116 | 1.00 | 19.54 | A | O |
| ATOM | 2191 | N | VAL | A | 270 | 56.394 | −19.253 | −0.028 | 1.00 | 18.94 | A | N |
| ATOM | 2192 | CA | VAL | A | 270 | 55.251 | −19.515 | −0.892 | 1.00 | 18.32 | A | C |
| ATOM | 2193 | CB | VAL | A | 270 | 54.263 | −18.320 | −0.863 | 1.00 | 18.18 | A | C |
| ATOM | 2194 | CG1 | VAL | A | 270 | 53.186 | −18.527 | −1.904 | 1.00 | 21.04 | A | C |
| ATOM | 2195 | CG2 | VAL | A | 270 | 53.681 | −18.132 | 0.574 | 1.00 | 17.70 | A | C |
| ATOM | 2196 | C | VAL | A | 270 | 55.721 | −19.838 | −2.329 | 1.00 | 21.10 | A | C |
| ATOM | 2197 | O | VAL | A | 270 | 55.186 | −20.733 | −2.986 | 1.00 | 21.08 | A | O |
| ATOM | 2198 | N | ALA | A | 271 | 56.735 | −19.122 | −2.813 | 1.00 | 20.64 | A | N |
| ATOM | 2199 | CA | ALA | A | 271 | 57.201 | −19.324 | −4.187 | 1.00 | 21.72 | A | C |
| ATOM | 2200 | CB | ALA | A | 271 | 56.412 | −18.390 | −5.159 | 1.00 | 26.52 | A | C |
| ATOM | 2201 | C | ALA | A | 271 | 58.681 | −19.052 | −4.273 | 1.00 | 21.93 | A | C |
| ATOM | 2202 | O | ALA | A | 271 | 59.111 | −17.880 | −4.411 | 1.00 | 18.81 | A | O |
| ATOM | 2203 | N | PHE | A | 272 | 59.494 | −20.110 | −4.217 | 1.00 | 16.10 | A | N |
| ATOM | 2204 | CA | PHE | A | 272 | 60.938 | −19.943 | −4.004 | 1.00 | 19.48 | A | C |
| ATOM | 2205 | CB | PHE | A | 272 | 61.488 | −21.031 | −3.094 | 1.00 | 22.36 | A | C |
| ATOM | 2206 | CG | PHE | A | 272 | 61.585 | −22.349 | −3.777 | 1.00 | 25.44 | A | C |
| ATOM | 2207 | CD1 | PHE | A | 272 | 60.505 | −23.180 | −3.805 | 1.00 | 27.84 | A | C |
| ATOM | 2208 | CE1 | PHE | A | 272 | 60.566 | −24.387 | −4.467 | 1.00 | 35.48 | A | C |
| ATOM | 2209 | CZ | PHE | A | 272 | 61.720 | −24.743 | −5.130 | 1.00 | 27.50 | A | C |
| ATOM | 2210 | CE2 | PHE | A | 272 | 62.786 | −23.919 | −5.148 | 1.00 | 36.02 | A | C |
| ATOM | 2211 | CD2 | PHE | A | 272 | 62.725 | −22.699 | −4.473 | 1.00 | 37.34 | A | C |
| ATOM | 2212 | C | PHE | A | 272 | 61.736 | −19.935 | −5.293 | 1.00 | 19.74 | A | C |
| ATOM | 2213 | O | PHE | A | 272 | 62.899 | −19.444 | −5.304 | 1.00 | 21.41 | A | O |
| ATOM | 2214 | N | GLU | A | 273 | 61.160 | −20.529 | −6.354 | 1.00 | 22.36 | A | N |
| ATOM | 2215 | CA | GLU | A | 273 | 61.903 | −20.746 | −7.597 | 1.00 | 23.02 | A | C |
| ATOM | 2216 | CB | GLU | A | 273 | 61.141 | −21.571 | −8.632 | 1.00 | 24.76 | A | C |
| ATOM | 2217 | CG | GLU | A | 273 | 60.815 | −23.024 | −8.243 | 1.00 | 29.20 | A | C |
| ATOM | 2218 | CD | GLU | A | 273 | 59.438 | −23.174 | −7.538 | 1.00 | 37.88 | A | C |
| ATOM | 2219 | OE1 | GLU | A | 273 | 58.927 | −22.222 | −6.837 | 1.00 | 30.65 | A | O |
| ATOM | 2220 | OE2 | GLU | A | 273 | 58.863 | −24.270 | −7.715 | 1.00 | 35.51 | A | O |
| ATOM | 2221 | C | GLU | A | 273 | 62.257 | −19.387 | −8.215 | 1.00 | 27.39 | A | C |
| ATOM | 2222 | O | GLU | A | 273 | 61.493 | −18.426 | −8.098 | 1.00 | 21.35 | A | O |
| ATOM | 2223 | N | PRO | A | 274 | 63.424 | −19.301 | −8.882 | 1.00 | 25.26 | A | N |
| ATOM | 2224 | CA | PRO | A | 274 | 63.913 | −17.956 | −9.207 | 1.00 | 20.90 | A | C |
| ATOM | 2225 | CB | PRO | A | 274 | 65.328 | −18.201 | −9.821 | 1.00 | 29.66 | A | C |
| ATOM | 2226 | CG | PRO | A | 274 | 65.441 | −19.705 | −10.051 | 1.00 | 24.11 | A | C |
| ATOM | 2227 | CD | PRO | A | 274 | 64.454 | −20.343 | −9.068 | 1.00 | 23.74 | A | C |
| ATOM | 2228 | C | PRO | A | 274 | 63.011 | −17.206 | −10.167 | 1.00 | 23.99 | A | C |
| ATOM | 2229 | O | PRO | A | 274 | 62.883 | −15.991 | −10.057 | 1.00 | 29.15 | A | O |
| ATOM | 2230 | N | GLN | A | 275 | 62.330 | −17.922 | −11.044 | 1.00 | 20.49 | A | N |
| ATOM | 2231 | CA | GLN | A | 275 | 61.447 | −17.297 | −12.028 | 1.00 | 23.59 | A | C |
| ATOM | 2232 | CB | GLN | A | 275 | 61.043 | −18.339 | −13.086 | 1.00 | 24.38 | A | C |
| ATOM | 2233 | CG | GLN | A | 275 | 60.258 | −19.538 | −12.540 | 1.00 | 28.37 | A | C |
| ATOM | 2234 | CD | GLN | A | 275 | 61.124 | −20.740 | −12.111 | 1.00 | 30.42 | A | C |

APPENDIX A-continued

*P. alba* 3T288C coordinates

| ATOM | 2235 | OE1 | GLN | A | 275 | 62.284 | −20.608 | −11.701 | 1.00 | 30.37 | A | O |
|---|---|---|---|---|---|---|---|---|---|---|---|---|
| ATOM | 2236 | NE2 | GLN | A | 275 | 60.550 | −21.918 | −12.210 | 1.00 | 32.67 | A | N |
| ATOM | 2237 | C | GLN | A | 275 | 60.154 | −16.683 | −11.472 | 1.00 | 27.96 | A | C |
| ATOM | 2238 | O | GLN | A | 275 | 59.421 | −16.047 | −12.220 | 1.00 | 29.78 | A | O |
| ATOM | 2239 | N | TYR | A | 276 | 59.843 | −16.922 | −10.196 | 1.00 | 25.94 | A | N |
| ATOM | 2240 | CA | TYR | A | 276 | 58.638 | −16.385 | −9.573 | 1.00 | 23.53 | A | C |
| ATOM | 2241 | CB | TYR | A | 276 | 58.012 | −17.459 | −8.649 | 1.00 | 25.20 | A | C |
| ATOM | 2242 | CG | TYR | A | 276 | 57.475 | −18.666 | −9.375 | 1.00 | 29.20 | A | C |
| ATOM | 2243 | CD1 | TYR | A | 276 | 56.704 | −18.530 | −10.528 | 1.00 | 33.14 | A | C |
| ATOM | 2244 | CE1 | TYR | A | 276 | 56.204 | −19.650 | −11.186 | 1.00 | 38.24 | A | C |
| ATOM | 2245 | CZ | TYR | A | 276 | 56.448 | −20.919 | −10.668 | 1.00 | 36.54 | A | C |
| ATOM | 2246 | OH | TYR | A | 276 | 55.940 | −21.987 | −11.312 | 1.00 | 42.13 | A | O |
| ATOM | 2247 | CE2 | TYR | A | 276 | 57.195 | −21.088 | −9.526 | 1.00 | 34.95 | A | C |
| ATOM | 2248 | CD2 | TYR | A | 276 | 57.708 | −19.957 | −8.882 | 1.00 | 31.58 | A | C |
| ATOM | 2249 | C | TYR | A | 276 | 58.834 | −15.077 | −8.782 | 1.00 | 23.42 | A | C |
| ATOM | 2250 | O | TYR | A | 276 | 58.213 | −14.873 | −7.730 | 1.00 | 21.75 | A | O |
| ATOM | 2251 | N | SER | A | 277 | 59.631 | −14.170 | −9.318 | 1.00 | 23.32 | A | N |
| ATOM | 2252 | CA | SER | A | 277 | 59.805 | −12.845 | −8.747 | 1.00 | 23.74 | A | C |
| ATOM | 2253 | CB | SER | A | 277 | 60.778 | −11.992 | −9.604 | 1.00 | 27.94 | A | C |
| ATOM | 2254 | OG | SER | A | 277 | 62.123 | −12.238 | −9.199 | 1.00 | 32.61 | A | O |
| ATOM | 2255 | C | SER | A | 277 | 58.475 | −12.122 | −8.580 | 1.00 | 22.51 | A | C |
| ATOM | 2256 | O | SER | A | 277 | 58.199 | −11.517 | −7.528 | 1.00 | 19.90 | A | O |
| ATOM | 2257 | N | ASP | A | 278 | 57.643 | −12.180 | −9.608 | 1.00 | 20.00 | A | N |
| ATOM | 2258 | CA | ASP | A | 278 | 56.383 | −11.459 | −9.599 | 1.00 | 24.90 | A | C |
| ATOM | 2259 | CB | ASP | A | 278 | 55.651 | −11.604 | −10.926 | 1.00 | 27.70 | A | C |
| ATOM | 2260 | CG | ASP | A | 278 | 56.296 | −10.798 | −12.041 | 1.00 | 31.73 | A | C |
| ATOM | 2261 | OD1 | ASP | A | 278 | 57.159 | −9.936 | −11.765 | 1.00 | 42.97 | A | O |
| ATOM | 2262 | OD2 | ASP | A | 278 | 55.939 | −11.050 | −13.205 | 1.00 | 36.86 | A | O |
| ATOM | 2263 | C | ASP | A | 278 | 55.471 | −11.953 | −8.504 | 1.00 | 25.59 | A | C |
| ATOM | 2264 | O | ASP | A | 278 | 54.816 | −11.148 | −7.825 | 1.00 | 22.68 | A | O |
| ATOM | 2265 | N | CYS | A | 279 | 55.405 | −13.272 | −8.344 | 1.00 | 22.18 | A | N |
| ATOM | 2266 | CA | CYS | A | 279 | 54.622 | −13.844 | −7.273 | 1.00 | 21.60 | A | C |
| ATOM | 2267 | CB | CYS | A | 279 | 54.597 | −15.388 | −7.344 | 1.00 | 19.92 | A | C |
| ATOM | 2268 | SG | CYS | A | 279 | 53.431 | −16.131 | −6.153 | 1.00 | 23.77 | A | S |
| ATOM | 2269 | C | CYS | A | 279 | 55.135 | −13.390 | −5.924 | 1.00 | 20.82 | A | C |
| ATOM | 2270 | O | CYS | A | 279 | 54.342 | −12.991 | −5.083 | 1.00 | 21.23 | A | O |
| ATOM | 2271 | N | ARG | A | 280 | 56.447 | −13.452 | −5.698 | 1.00 | 18.39 | A | N |
| ATOM | 2272 | CA | ARG | A | 280 | 57.012 | −13.025 | −4.415 | 1.00 | 20.79 | A | C |
| ATOM | 2273 | CB | ARG | A | 280 | 58.523 | −13.245 | −4.374 | 1.00 | 20.57 | A | C |
| ATOM | 2274 | CG | ARG | A | 280 | 58.951 | −14.720 | −4.243 | 1.00 | 19.51 | A | C |
| ATOM | 2275 | CD | ARG | A | 280 | 60.433 | −14.790 | −4.036 | 1.00 | 18.20 | A | C |
| ATOM | 2276 | NE | ARG | A | 280 | 61.198 | −14.498 | −5.229 | 1.00 | 18.16 | A | N |
| ATOM | 2277 | CZ | ARG | A | 280 | 61.384 | −15.345 | −6.235 | 1.00 | 19.97 | A | C |
| ATOM | 2278 | NH1 | ARG | A | 280 | 60.834 | −16.552 | −6.227 | 1.00 | 22.51 | A | N |
| ATOM | 2279 | NH2 | ARG | A | 280 | 62.147 | −14.994 | −7.256 | 1.00 | 24.20 | A | N |
| ATOM | 2280 | C | ARG | A | 280 | 56.745 | −11.537 | −4.141 | 1.00 | 21.71 | A | C |
| ATOM | 2281 | O | ARG | A | 280 | 56.348 | −11.178 | −3.055 | 1.00 | 19.91 | A | O |
| ATOM | 2282 | N | ASN | A | 281 | 56.950 | −10.700 | −5.144 | 1.00 | 21.08 | A | N |
| ATOM | 2283 | CA | ASN | A | 281 | 56.628 | −9.282 | −5.027 | 1.00 | 21.89 | A | C |
| ATOM | 2284 | CB | ASN | A | 281 | 57.088 | −8.530 | −6.269 | 1.00 | 26.68 | A | C |
| ATOM | 2285 | CG | ASN | A | 281 | 58.615 | −8.479 | −6.380 | 1.00 | 36.64 | A | C |
| ATOM | 2286 | OD1 | ASN | A | 281 | 59.339 | −8.753 | −5.410 | 1.00 | 35.43 | A | O |
| ATOM | 2287 | ND2 | ASN | A | 281 | 59.107 | −8.145 | −7.567 | 1.00 | 33.86 | A | N |
| ATOM | 2288 | C | ASN | A | 281 | 55.156 | −9.001 | −4.704 | 1.00 | 21.55 | A | C |
| ATOM | 2289 | O | ASN | A | 281 | 54.874 | −8.236 | −3.782 | 1.00 | 21.28 | A | O |
| ATOM | 2290 | N | SER | A | 282 | 54.220 | −9.669 | −5.387 | 1.00 | 20.26 | A | N |
| ATOM | 2291 | CA | SER | A | 282 | 52.802 | −9.522 | −5.085 | 1.00 | 23.60 | A | C |
| ATOM | 2292 | CB | SER | A | 282 | 51.946 | −10.354 | −6.043 | 1.00 | 26.14 | A | C |
| ATOM | 2293 | OG | SER | A | 282 | 51.551 | −9.582 | −7.129 | 1.00 | 31.01 | A | O |
| ATOM | 2294 | C | SER | A | 282 | 52.448 | −9.961 | −3.678 | 1.00 | 21.74 | A | C |
| ATOM | 2295 | O | SER | A | 282 | 51.746 | −9.270 | −2.964 | 1.00 | 20.53 | A | O |
| ATOM | 2296 | N | VAL | A | 283 | 52.895 | −11.146 | −3.302 | 1.00 | 20.71 | A | N |
| ATOM | 2297 | CA | VAL | A | 283 | 52.621 | −11.663 | −1.974 | 1.00 | 17.85 | A | C |
| ATOM | 2298 | CB | VAL | A | 283 | 53.055 | −13.132 | −1.855 | 1.00 | 20.08 | A | C |
| ATOM | 2299 | CG1 | VAL | A | 283 | 52.977 | −13.611 | −0.395 | 1.00 | 19.46 | A | C |
| ATOM | 2300 | CG2 | VAL | A | 283 | 52.150 | −13.967 | −2.709 | 1.00 | 19.85 | A | C |
| ATOM | 2301 | C | VAL | A | 283 | 53.198 | −10.775 | −0.891 | 1.00 | 17.07 | A | C |
| ATOM | 2302 | O | VAL | A | 283 | 52.506 | −10.479 | 0.094 | 1.00 | 16.85 | A | O |
| ATOM | 2303 | N | ALA | A | 284 | 54.434 | −10.306 | −1.059 | 1.00 | 15.81 | A | N |
| ATOM | 2304 | CA | ALA | A | 284 | 55.050 | −9.476 | −0.028 | 1.00 | 17.39 | A | C |
| ATOM | 2305 | CB | ALA | A | 284 | 56.522 | −9.255 | −0.317 | 1.00 | 17.17 | A | C |
| ATOM | 2306 | C | ALA | A | 284 | 54.301 | −8.119 | 0.088 | 1.00 | 17.57 | A | C |
| ATOM | 2307 | O | ALA | A | 284 | 54.009 | −7.625 | 1.216 | 1.00 | 17.20 | A | O |
| ATOM | 2308 | N | LYS | A | 285 | 53.977 | −7.511 | −1.058 | 1.00 | 17.42 | A | N |
| ATOM | 2309 | CA | LYS | A | 285 | 53.155 | −6.272 | −1.062 | 1.00 | 18.85 | A | C |
| ATOM | 2310 | CB | LYS | A | 285 | 52.884 | −5.789 | −2.487 | 1.00 | 18.52 | A | C |
| ATOM | 2311 | CG | LYS | A | 285 | 54.103 | −5.210 | −3.181 | 1.00 | 19.50 | A | C |
| ATOM | 2312 | CD | LYS | A | 285 | 53.771 | −4.777 | −4.622 | 1.00 | 24.80 | A | C |

APPENDIX A-continued

*P. alba* 3T288C coordinates

| ATOM | 2313 | CE  | LYS | A | 285 | 54.911 | −3.939  | −5.170  | 1.00 | 29.57 | A | C |
|------|------|-----|-----|---|-----|--------|---------|---------|------|-------|---|---|
| ATOM | 2314 | NZ  | LYS | A | 285 | 54.911 | −3.908  | −6.624  | 1.00 | 45.89 | A | N |
| ATOM | 2315 | C   | LYS | A | 285 | 51.805 | −6.474  | −0.329  | 1.00 | 19.27 | A | C |
| ATOM | 2316 | O   | LYS | A | 285 | 51.427 | −5.669  | 0.529   | 1.00 | 19.71 | A | O |
| ATOM | 2317 | N   | MET | A | 286 | 51.080 | −7.538  | −0.673  | 1.00 | 17.23 | A | N |
| ATOM | 2318 | CA  | MET | A | 286 | 49.811 | −7.824  | −0.014  | 1.00 | 18.12 | A | C |
| ATOM | 2319 | CB  | MET | A | 286 | 49.107 | −9.038  | −0.597  | 1.00 | 21.82 | A | C |
| ATOM | 2320 | CG  | MET | A | 286 | 48.651 | −8.866  | −2.034  | 1.00 | 22.74 | A | C |
| ATOM | 2321 | SD  | MET | A | 286 | 47.766 | −7.321  | −2.298  | 1.00 | 26.21 | A | S |
| ATOM | 2322 | CE  | MET | A | 286 | 48.995 | −6.119  | −2.880  | 1.00 | 18.48 | A | C |
| ATOM | 2323 | C   | MET | A | 286 | 50.008 | −8.024  | 1.486   | 1.00 | 18.96 | A | C |
| ATOM | 2324 | O   | MET | A | 286 | 49.244 | −7.494  | 2.316   | 1.00 | 22.71 | A | O |
| ATOM | 2325 | N   | PHE | A | 287 | 51.039 | −8.764  | 1.849   | 1.00 | 19.84 | A | N |
| ATOM | 2326 | CA  | PHE | A | 287 | 51.292 | −8.955  | 3.279   | 1.00 | 23.52 | A | C |
| ATOM | 2327 | CB  | PHE | A | 287 | 52.377 | −9.994  | 3.603   | 1.00 | 29.12 | A | C |
| ATOM | 2328 | CG  | PHE | A | 287 | 51.983 | −10.939 | 4.745   | 1.00 | 42.44 | A | C |
| ATOM | 2329 | CD1 | PHE | A | 287 | 50.761 | −10.768 | 5.464   | 1.00 | 62.09 | A | C |
| ATOM | 2330 | CE1 | PHE | A | 287 | 50.368 | −11.651 | 6.509   | 1.00 | 52.92 | A | C |
| ATOM | 2331 | CZ  | PHE | A | 287 | 51.186 | −12.705 | 6.838   | 1.00 | 49.40 | A | C |
| ATOM | 2332 | CE2 | PHE | A | 287 | 52.409 | −12.884 | 6.145   | 1.00 | 59.69 | A | C |
| ATOM | 2333 | CD2 | PHE | A | 287 | 52.804 | −11.993 | 5.110   | 1.00 | 42.43 | A | C |
| ATOM | 2334 | C   | PHE | A | 287 | 51.590 | −7.700  | 4.029   | 1.00 | 21.35 | A | C |
| ATOM | 2335 | O   | PHE | A | 287 | 51.140 | −7.560  | 5.167   | 1.00 | 20.18 | A | O |
| ATOM | 2336 | N   | CYS | A | 288 | 52.300 | −6.760  | 3.395   | 1.00 | 19.81 | A | N |
| ATOM | 2337 | CA  | CYS | A | 288 | 52.546 | −5.464  | 4.016   | 1.00 | 20.01 | A | C |
| ATOM | 2338 | CB  | CYS | A | 288 | 53.430 | −4.568  | 3.152   | 1.00 | 24.96 | A | C |
| ATOM | 2339 | SG  | CYS | A | 288 | 55.186 | −5.053  | 3.151   | 1.00 | 27.36 | A | S |
| ATOM | 2340 | C   | CYS | A | 288 | 51.265 | −4.720  | 4.304   | 1.00 | 21.13 | A | C |
| ATOM | 2341 | O   | CYS | A | 288 | 51.118 | −4.110  | 5.367   | 1.00 | 19.04 | A | O |
| ATOM | 2342 | N   | PHE | A | 289 | 50.353 | −4.719  | 3.340   | 1.00 | 16.53 | A | N |
| ATOM | 2343 | CA  | PHE | A | 289 | 49.049 | −4.074  | 3.552   | 1.00 | 16.27 | A | C |
| ATOM | 2344 | CB  | PHE | A | 289 | 48.312 | −3.898  | 2.239   | 1.00 | 15.49 | A | C |
| ATOM | 2345 | CG  | PHE | A | 289 | 48.736 | −2.675  | 1.491   | 1.00 | 16.61 | A | C |
| ATOM | 2346 | CD1 | PHE | A | 289 | 48.413 | −1.421  | 1.957   | 1.00 | 18.72 | A | C |
| ATOM | 2347 | CE1 | PHE | A | 289 | 48.818 | −0.296  | 1.269   | 1.00 | 18.70 | A | C |
| ATOM | 2348 | CZ  | PHE | A | 289 | 49.543 | −0.424  | 0.109   | 1.00 | 18.93 | A | C |
| ATOM | 2473 | CG  | ASP | A | 304 | 30.689 | 4.873   | 14.493  | 1.00 | 35.20 | A | C |
| ATOM | 2474 | OD1 | ASP | A | 304 | 29.830 | 3.981   | 14.300  | 1.00 | 31.47 | A | O |
| ATOM | 2475 | OD2 | ASP | A | 304 | 30.547 | 5.751   | 15.375  | 1.00 | 38.27 | A | O |
| ATOM | 2476 | C   | ASP | A | 304 | 33.353 | 3.814   | 11.863  | 1.00 | 20.30 | A | C |
| ATOM | 2477 | O   | ASP | A | 304 | 32.998 | 3.846   | 10.683  | 1.00 | 17.82 | A | O |
| ATOM | 2478 | N   | GLU | A | 305 | 34.626 | 3.993   | 12.212  | 1.00 | 15.41 | A | N |
| ATOM | 2479 | CA  | GLU | A | 305 | 35.650 | 4.171   | 11.182  | 1.00 | 14.29 | A | C |
| ATOM | 2480 | CB  | GLU | A | 305 | 37.008 | 4.559   | 11.816  | 1.00 | 15.22 | A | C |
| ATOM | 2481 | CG  | GLU | A | 305 | 37.032 | 5.928   | 12.462  | 1.00 | 17.43 | A | C |
| ATOM | 2482 | CD  | GLU | A | 305 | 38.312 | 6.178   | 13.263  | 1.00 | 19.71 | A | C |
| ATOM | 2483 | OE1 | GLU | A | 305 | 38.970 | 5.222   | 13.736  | 1.00 | 17.09 | A | O |
| ATOM | 2484 | OE2 | GLU | A | 305 | 38.691 | 7.339   | 13.399  | 1.00 | 20.00 | A | O |
| ATOM | 2485 | C   | GLU | A | 305 | 35.819 | 2.918   | 10.345  | 1.00 | 14.09 | A | C |
| ATOM | 2486 | O   | GLU | A | 305 | 35.994 | 2.971   | 9.109   | 1.00 | 14.06 | A | O |
| ATOM | 2487 | N   | LEU | A | 306 | 35.788 | 1.764   | 11.006  | 1.00 | 13.12 | A | N |
| ATOM | 2488 | CA  | LEU | A | 306 | 36.012 | 0.521   | 10.306  | 1.00 | 12.82 | A | C |
| ATOM | 2489 | CB  | LEU | A | 306 | 36.129 | −0.638  | 11.315  | 1.00 | 12.26 | A | C |
| ATOM | 2490 | CG  | LEU | A | 306 | 37.275 | −0.474  | 12.341  | 1.00 | 13.73 | A | C |
| ATOM | 2491 | CD1 | LEU | A | 306 | 37.292 | −1.686  | 13.329  | 1.00 | 14.11 | A | C |
| ATOM | 2492 | CD2 | LEU | A | 306 | 38.622 | −0.339  | 11.638  | 1.00 | 11.07 | A | C |
| ATOM | 2493 | C   | LEU | A | 306 | 34.864 | 0.281   | 9.314   | 1.00 | 15.39 | A | C |
| ATOM | 2494 | O   | LEU | A | 306 | 35.069 | −0.300  | 8.262   | 1.00 | 16.92 | A | O |
| ATOM | 2495 | N   | GLU | A | 307 | 33.649 | 0.700   | 9.678   | 1.00 | 16.87 | A | N |
| ATOM | 2496 | CA  | GLU | A | 307 | 32.506 | 0.557   | 8.770   | 1.00 | 17.68 | A | C |
| ATOM | 2497 | CB  | GLU | A | 307 | 31.207 | 0.986   | 9.444   | 1.00 | 20.36 | A | C |
| ATOM | 2498 | CG  | GLU | A | 307 | 30.719 | 0.021   | 10.484  | 1.00 | 28.93 | A | C |
| ATOM | 2499 | CD  | GLU | A | 307 | 29.932 | −1.139  | 9.887   | 1.00 | 37.37 | A | C |
| ATOM | 2500 | OE1 | GLU | A | 307 | 29.757 | −1.178  | 8.640   | 1.00 | 38.07 | A | O |
| ATOM | 2501 | OE2 | GLU | A | 307 | 29.481 | −2.002  | 10.674  | 1.00 | 38.86 | A | O |
| ATOM | 2502 | C   | GLU | A | 307 | 32.759 | 1.393   | 7.529   | 1.00 | 17.79 | A | C |
| ATOM | 2503 | O   | GLU | A | 307 | 32.521 | 0.925   | 6.416   | 1.00 | 18.41 | A | O |
| ATOM | 2504 | N   | LEU | A | 308 | 33.305 | 2.599   | 7.709   | 1.00 | 16.45 | A | N |
| ATOM | 2505 | CA  | LEU | A | 308 | 33.621 | 3.481   | 6.560   | 1.00 | 18.98 | A | C |
| ATOM | 2506 | CB  | LEU | A | 308 | 34.068 | 4.869   | 7.014   | 1.00 | 18.90 | A | C |
| ATOM | 2507 | CG  | LEU | A | 308 | 33.028 | 5.811   | 7.618   | 1.00 | 28.08 | A | C |
| ATOM | 2508 | CD1 | LEU | A | 308 | 33.737 | 7.021   | 8.304   | 1.00 | 26.55 | A | C |
| ATOM | 2509 | CD2 | LEU | A | 308 | 32.061 | 6.267   | 6.534   | 1.00 | 26.63 | A | C |
| ATOM | 2510 | C   | LEU | A | 308 | 34.702 | 2.892   | 5.668   | 1.00 | 18.24 | A | C |
| ATOM | 2511 | O   | LEU | A | 308 | 34.626 | 2.940   | 4.436   | 1.00 | 17.72 | A | O |
| ATOM | 2512 | N   | PHE | A | 309 | 35.730 | 2.329   | 6.290   | 1.00 | 18.59 | A | N |
| ATOM | 2513 | CA  | PHE | A | 309 | 36.816 | 1.768   | 5.506   | 1.00 | 16.74 | A | C |
| ATOM | 2514 | CB  | PHE | A | 309 | 37.991 | 1.339   | 6.397   | 1.00 | 14.25 | A | C |

APPENDIX A-continued

*P. alba* 3T288C coordinates

| ATOM | 2515 | CG | PHE | A | 309 | 39.246 | 1.079 | 5.632 | 1.00 | 13.41 | A | C |
|------|------|------|------|---|-----|--------|--------|--------|------|-------|---|---|
| ATOM | 2516 | CD1 | PHE | A | 309 | 40.125 | 2.098 | 5.370 | 1.00 | 15.08 | A | C |
| ATOM | 2517 | CE1 | PHE | A | 309 | 41.275 | 1.879 | 4.720 | 1.00 | 15.28 | A | C |
| ATOM | 2518 | CZ | PHE | A | 309 | 41.573 | 0.638 | 4.260 | 1.00 | 16.06 | A | C |
| ATOM | 2519 | CE2 | PHE | A | 309 | 40.706 | −0.399 | 4.491 | 1.00 | 16.55 | A | C |
| ATOM | 2520 | CD2 | PHE | A | 309 | 39.564 | −0.185 | 5.206 | 1.00 | 14.73 | A | C |
| ATOM | 2521 | C | PHE | A | 309 | 36.339 | 0.612 | 4.679 | 1.00 | 17.02 | A | C |
| ATOM | 2522 | O | PHE | A | 309 | 36.698 | 0.499 | 3.508 | 1.00 | 16.41 | A | O |
| ATOM | 2523 | N | THR | A | 310 | 35.567 | −0.273 | 5.312 | 1.00 | 17.03 | A | N |
| ATOM | 2524 | CA | THR | A | 310 | 35.042 | −1.481 | 4.644 | 1.00 | 15.57 | A | C |
| ATOM | 2525 | CB | THR | A | 310 | 34.254 | −2.379 | 5.611 | 1.00 | 16.94 | A | C |
| ATOM | 2526 | OG1 | THR | A | 310 | 35.064 | −2.617 | 6.764 | 1.00 | 17.27 | A | O |
| ATOM | 2527 | CG2 | THR | A | 310 | 33.868 | −3.727 | 4.976 | 1.00 | 14.06 | A | C |
| ATOM | 2528 | C | THR | A | 310 | 34.165 | −1.121 | 3.464 | 1.00 | 14.32 | A | C |
| ATOM | 2529 | O | THR | A | 310 | 34.320 | −1.695 | 2.395 | 1.00 | 14.04 | A | O |
| ATOM | 2530 | N | ASP | A | 311 | 33.312 | −0.119 | 3.647 | 1.00 | 16.34 | A | N |
| ATOM | 2531 | CA | ASP | A | 311 | 32.457 | 0.399 | 2.571 | 1.00 | 19.21 | A | C |
| ATOM | 2532 | CB | ASP | A | 311 | 31.456 | 1.401 | 3.158 | 1.00 | 21.06 | A | C |
| ATOM | 2533 | CG | ASP | A | 311 | 30.602 | 2.056 | 2.106 | 1.00 | 25.80 | A | C |
| ATOM | 2534 | OD1 | ASP | A | 311 | 29.749 | 1.365 | 1.516 | 1.00 | 27.76 | A | O |
| ATOM | 2535 | OD2 | ASP | A | 311 | 30.805 | 3.261 | 1.851 | 1.00 | 29.96 | A | O |
| ATOM | 2536 | C | ASP | A | 311 | 33.277 | 1.007 | 1.420 | 1.00 | 19.30 | A | C |
| ATOM | 2537 | O | ASP | A | 311 | 32.964 | 0.797 | 0.251 | 1.00 | 17.59 | A | O |
| ATOM | 2538 | N | ALA | A | 312 | 34.345 | 1.724 | 1.755 | 1.00 | 16.06 | A | N |
| ATOM | 2539 | CA | ALA | A | 312 | 35.227 | 2.322 | 0.751 | 1.00 | 16.73 | A | C |
| ATOM | 2540 | CB | ALA | A | 312 | 36.273 | 3.210 | 1.412 | 1.00 | 14.46 | A | C |
| ATOM | 2541 | C | ALA | A | 312 | 35.897 | 1.270 | −0.109 | 1.00 | 16.20 | A | C |
| ATOM | 2542 | O | ALA | A | 312 | 35.982 | 1.436 | −1.330 | 1.00 | 16.25 | A | O |
| ATOM | 2543 | N | VAL | A | 313 | 36.369 | 0.187 | 0.518 | 1.00 | 15.49 | A | N |
| ATOM | 2544 | CA | VAL | A | 313 | 36.957 | −0.925 | −0.200 | 1.00 | 15.70 | A | C |
| ATOM | 2545 | CB | VAL | A | 313 | 37.658 | −1.919 | 0.749 | 1.00 | 15.23 | A | C |
| ATOM | 2546 | CG1 | VAL | A | 313 | 38.040 | −3.196 | 0.026 | 1.00 | 13.55 | A | C |
| ATOM | 2547 | CG2 | VAL | A | 313 | 38.910 | −1.242 | 1.389 | 1.00 | 15.29 | A | C |
| ATOM | 2548 | C | VAL | A | 313 | 35.928 | −1.637 | −1.069 | 1.00 | 16.66 | A | C |
| ATOM | 2549 | O | VAL | A | 313 | 36.216 | −1.976 | −2.236 | 1.00 | 14.48 | A | O |
| ATOM | 2550 | N | GLU | A | 314 | 34.744 | −1.861 | −0.528 | 1.00 | 17.83 | A | N |
| ATOM | 2551 | CA | GLU | A | 314 | 33.635 | −2.427 | −1.327 | 1.00 | 18.81 | A | C |
| ATOM | 2552 | CB | GLU | A | 314 | 32.376 | −2.598 | −0.478 | 1.00 | 21.15 | A | C |
| ATOM | 2553 | CG | GLU | A | 314 | 32.502 | −3.730 | 0.572 | 1.00 | 26.43 | A | C |
| ATOM | 2554 | CD | GLU | A | 314 | 31.275 | −3.846 | 1.486 | 1.00 | 29.94 | A | C |
| ATOM | 2555 | OE1 | GLU | A | 314 | 30.460 | −2.909 | 1.524 | 1.00 | 31.98 | A | O |
| ATOM | 2556 | OE2 | GLU | A | 314 | 31.135 | −4.858 | 2.187 | 1.00 | 28.42 | A | O |
| ATOM | 2557 | C | GLU | A | 314 | 33.297 | −1.593 | −2.539 | 1.00 | 18.03 | A | C |
| ATOM | 2558 | O | GLU | A | 314 | 33.116 | −2.129 | −3.610 | 1.00 | 20.81 | A | O |
| ATOM | 2559 | N | ARG | A | 315 | 33.226 | −0.289 | −2.389 | 1.00 | 15.47 | A | N |
| ATOM | 2560 | CA | AARG | A | 315 | 32.841 | 0.611 | −3.487 | 0.50 | 18.54 | A | C |
| ATOM | 2561 | CA | BARG | A | 315 | 32.839 | 0.563 | −3.515 | 0.50 | 19.14 | A | C |
| ATOM | 2562 | CB | AARG | A | 315 | 32.383 | 1.976 | −2.940 | 0.50 | 18.77 | A | C |
| ATOM | 2563 | CB | BARG | A | 315 | 32.243 | 1.871 | −3.013 | 0.50 | 20.09 | A | C |
| ATOM | 2564 | CG | AARG | A | 315 | 31.037 | 1.960 | −2.161 | 0.50 | 21.10 | A | C |
| ATOM | 2565 | CG | BARG | A | 315 | 30.830 | 1.674 | −2.471 | 0.50 | 23.70 | A | C |
| ATOM | 2566 | CD | AARG | A | 315 | 30.504 | 3.375 | −1.817 | 0.50 | 21.65 | A | C |
| ATOM | 2567 | CD | BARG | A | 315 | 30.324 | 2.865 | −1.681 | 0.50 | 24.91 | A | C |
| ATOM | 2568 | NE | AARG | A | 315 | 31.132 | 3.980 | −0.634 | 0.50 | 23.68 | A | N |
| ATOM | 2569 | NE | BARG | A | 315 | 29.008 | 2.591 | −1.126 | 0.50 | 29.79 | A | N |
| ATOM | 2570 | CZ | AARG | A | 315 | 32.199 | 4.775 | −0.664 | 0.50 | 20.63 | A | C |
| ATOM | 2571 | CZ | BARG | A | 315 | 27.887 | 2.612 | −1.837 | 0.50 | 36.61 | A | C |
| ATOM | 2572 | NH1 | AARG | A | 315 | 32.691 | 5.268 | 0.460 | 0.50 | 23.51 | A | N |
| ATOM | 2573 | NH1 | BARG | A | 315 | 27.927 | 2.897 | −3.129 | 0.50 | 38.35 | A | N |
| ATOM | 2574 | NH2 | BARG | A | 315 | 26.727 | 2.345 | −1.259 | 0.50 | 38.64 | A | N |
| ATOM | 2575 | NH2 | AARG | A | 315 | 32.780 | 5.075 | −1.811 | 0.50 | 19.97 | A | N |
| ATOM | 2576 | C | ARG | A | 315 | 33.991 | 0.809 | −4.497 | 1.00 | 21.60 | A | C |
| ATOM | 2577 | O | ARG | A | 315 | 33.767 | 1.030 | −5.674 | 1.00 | 16.65 | A | O |
| ATOM | 2578 | N | TRP | A | 316 | 35.229 | 0.771 | −4.018 | 1.00 | 17.56 | A | N |
| ATOM | 2579 | CA | TRP | A | 316 | 36.390 | 0.927 | −4.889 | 1.00 | 14.98 | A | C |
| ATOM | 2580 | CB | TRP | A | 316 | 36.592 | −0.288 | −5.758 | 1.00 | 16.79 | A | C |
| ATOM | 2581 | CG | TRP | A | 316 | 38.049 | −0.433 | −6.158 | 1.00 | 17.07 | A | C |
| ATOM | 2582 | CD1 | TRP | A | 316 | 38.638 | −0.174 | −7.390 | 1.00 | 14.99 | A | C |
| ATOM | 2583 | NE1 | TRP | A | 316 | 39.991 | −0.401 | −7.336 | 1.00 | 14.25 | A | N |
| ATOM | 2584 | CE2 | TRP | A | 316 | 40.345 | −0.805 | −6.118 | 1.00 | 12.86 | A | C |
| ATOM | 2585 | CD2 | TRP | A | 316 | 39.135 | −0.831 | −5.299 | 1.00 | 13.85 | A | C |
| ATOM | 2586 | CE3 | TRP | A | 316 | 39.226 | −1.236 | −3.987 | 1.00 | 15.44 | A | C |
| ATOM | 2587 | CZ3 | TRP | A | 316 | 40.479 | −1.594 | −3.486 | 1.00 | 15.61 | A | C |
| ATOM | 2588 | CH2 | TRP | A | 316 | 41.628 | −1.540 | −4.285 | 1.00 | 15.25 | A | C |
| ATOM | 2589 | CZ2 | TRP | A | 316 | 41.575 | −1.143 | −5.609 | 1.00 | 14.44 | A | C |
| ATOM | 2590 | C | TRP | A | 316 | 36.276 | 2.163 | −5.712 | 1.00 | 14.89 | A | C |
| ATOM | 2591 | O | TRP | A | 316 | 36.419 | 2.143 | −6.917 | 1.00 | 15.76 | A | O |
| ATOM | 2592 | N | ASP | A | 317 | 36.032 | 3.262 | −5.035 | 1.00 | 16.96 | A | N |

APPENDIX A-continued

*P. alba* 3T288C coordinates

| ATOM | 2593 | CA | ASP | A | 317 | 35.800 | 4.537 | −5.687 | 1.00 | 18.34 | A | C |
| ATOM | 2594 | CB | ASP | A | 317 | 34.358 | 4.911 | −5.441 | 1.00 | 18.08 | A | C |
| ATOM | 2595 | CG | ASP | A | 317 | 33.984 | 6.287 | −6.000 | 1.00 | 24.63 | A | C |
| ATOM | 2596 | OD1 | ASP | A | 317 | 34.793 | 6.935 | −6.711 | 1.00 | 27.57 | A | O |
| ATOM | 2597 | OD2 | ASP | A | 317 | 32.833 | 6.690 | −5.740 | 1.00 | 28.48 | A | O |
| ATOM | 2598 | C | ASP | A | 317 | 36.731 | 5.605 | −5.133 | 1.00 | 20.19 | A | C |
| ATOM | 2599 | O | ASP | A | 317 | 36.512 | 6.114 | −4.018 | 1.00 | 20.93 | A | O |
| ATOM | 2600 | N | VAL | A | 318 | 37.711 | 6.006 | −5.939 | 1.00 | 18.34 | A | N |
| ATOM | 2601 | CA | VAL | A | 318 | 38.710 | 6.991 | −5.503 | 1.00 | 19.63 | A | C |
| ATOM | 2602 | CB | VAL | A | 318 | 39.861 | 7.145 | −6.538 | 1.00 | 19.36 | A | C |
| ATOM | 2603 | CG1 | VAL | A | 318 | 39.498 | 8.102 | −7.663 | 1.00 | 21.41 | A | C |
| ATOM | 2604 | CG2 | VAL | A | 318 | 41.139 | 7.632 | −5.874 | 1.00 | 19.12 | A | C |
| ATOM | 2605 | C | VAL | A | 318 | 38.088 | 8.369 | −5.277 | 1.00 | 29.46 | A | C |
| ATOM | 2606 | O | VAL | A | 318 | 38.605 | 9.168 | −4.488 | 1.00 | 29.09 | A | O |
| ATOM | 2607 | N | ASN | A | 319 | 37.018 | 8.664 | −6.018 | 1.00 | 26.29 | A | N |
| ATOM | 2608 | CA | ASN | A | 319 | 36.374 | 9.983 | −5.980 | 1.00 | 31.77 | A | C |
| ATOM | 2609 | CB | ASN | A | 319 | 35.483 | 10.228 | −7.232 | 1.00 | 28.73 | A | C |
| ATOM | 2610 | CG | ASN | A | 319 | 36.280 | 10.184 | −8.574 | 1.00 | 31.03 | A | C |
| ATOM | 2611 | OD1 | ASN | A | 319 | 37.240 | 10.959 | −8.786 | 1.00 | 25.79 | A | O |
| ATOM | 2612 | ND2 | ASN | A | 319 | 35.836 | 9.314 | −9.500 | 1.00 | 16.89 | A | N |
| ATOM | 2613 | C | ASN | A | 319 | 35.540 | 10.153 | −4.724 | 1.00 | 27.47 | A | C |
| ATOM | 2614 | O | ASN | A | 319 | 34.901 | 11.182 | −4.589 | 1.00 | 31.81 | A | O |
| ATOM | 2615 | N | ALA | A | 320 | 35.537 | 9.156 | −3.832 | 1.00 | 25.56 | A | N |
| ATOM | 2616 | CA | ALA | A | 320 | 34.920 | 9.253 | −2.474 | 1.00 | 35.70 | A | C |
| ATOM | 2617 | CB | ALA | A | 320 | 33.740 | 8.259 | −2.370 | 1.00 | 30.73 | A | C |
| ATOM | 2618 | C | ALA | A | 320 | 35.890 | 9.032 | −1.269 | 1.00 | 35.09 | A | C |
| ATOM | 2619 | O | ALA | A | 320 | 35.446 | 8.708 | −0.177 | 1.00 | 42.99 | A | O |
| ATOM | 2620 | N | ILE | A | 321 | 37.204 | 9.178 | −1.449 | 1.00 | 35.73 | A | N |
| ATOM | 2621 | CA | ILE | A | 321 | 38.153 | 9.042 | −0.313 | 1.00 | 25.46 | A | C |
| ATOM | 2622 | CB | ILE | A | 321 | 39.658 | 8.885 | −0.768 | 1.00 | 31.72 | A | C |
| ATOM | 2623 | CG1 | ILE | A | 321 | 40.230 | 10.186 | −1.351 | 1.00 | 35.99 | A | C |
| ATOM | 2624 | CD1 | ILE | A | 321 | 41.644 | 10.023 | −1.980 | 1.00 | 41.27 | A | C |
| ATOM | 2625 | CG2 | ILE | A | 321 | 39.813 | 7.709 | −1.779 | 1.00 | 34.61 | A | C |
| ATOM | 2626 | C | ILE | A | 321 | 38.039 | 10.199 | 0.704 | 1.00 | 39.12 | A | C |
| ATOM | 2627 | O | ILE | A | 321 | 38.426 | 10.049 | 1.867 | 1.00 | 36.11 | A | O |
| ATOM | 2628 | N | ASN | A | 322 | 37.509 | 11.351 | 0.273 | 1.00 | 32.92 | A | N |
| ATOM | 2629 | CA | ASN | A | 322 | 37.210 | 12.447 | 1.197 | 1.00 | 31.27 | A | C |
| ATOM | 2630 | CB | ASN | A | 322 | 36.903 | 13.743 | 0.404 | 1.00 | 30.22 | A | C |
| ATOM | 2631 | CG | ASN | A | 322 | 38.191 | 14.408 | −0.185 | 1.00 | 33.53 | A | C |
| ATOM | 2632 | OD1 | ASN | A | 322 | 39.337 | 14.000 | 0.108 | 1.00 | 29.13 | A | O |
| ATOM | 2633 | ND2 | ASN | A | 322 | 38.000 | 15.458 | −0.974 | 1.00 | 32.82 | A | N |
| ATOM | 2634 | C | ASN | A | 322 | 36.143 | 12.121 | 2.303 | 1.00 | 29.49 | A | C |
| ATOM | 2635 | O | ASN | A | 322 | 36.017 | 12.864 | 3.259 | 1.00 | 28.36 | A | O |
| ATOM | 2636 | N | ASP | A | 323 | 35.446 | 10.986 | 2.228 | 1.00 | 31.55 | A | N |
| ATOM | 2637 | CA | ASP | A | 323 | 34.609 | 10.518 | 3.378 | 1.00 | 36.24 | A | C |
| ATOM | 2638 | CB | ASP | A | 323 | 33.601 | 9.414 | 2.946 | 1.00 | 51.90 | A | C |
| ATOM | 2639 | CG | ASP | A | 323 | 32.960 | 9.644 | 1.559 | 1.00 | 53.60 | A | C |
| ATOM | 2640 | OD1 | ASP | A | 323 | 32.937 | 10.788 | 1.060 | 1.00 | 51.28 | A | O |
| ATOM | 2641 | OD2 | ASP | A | 323 | 32.468 | 8.645 | 0.970 | 1.00 | 51.14 | A | O |
| ATOM | 2642 | C | ASP | A | 323 | 35.422 | 9.913 | 4.589 | 1.00 | 30.18 | A | C |
| ATOM | 2643 | O | ASP | A | 323 | 34.897 | 9.759 | 5.680 | 1.00 | 31.04 | A | O |
| ATOM | 2644 | N | LEU | A | 324 | 36.674 | 9.520 | 4.377 | 1.00 | 24.50 | A | N |
| ATOM | 2645 | CA | LEU | A | 324 | 37.419 | 8.730 | 5.377 | 1.00 | 19.57 | A | C |
| ATOM | 2646 | CB | LEU | A | 324 | 38.435 | 7.858 | 4.653 | 1.00 | 18.49 | A | C |
| ATOM | 2647 | CG | LEU | A | 324 | 37.837 | 6.719 | 3.832 | 1.00 | 21.24 | A | C |
| ATOM | 2648 | CD1 | LEU | A | 324 | 38.864 | 6.103 | 2.908 | 1.00 | 16.54 | A | C |
| ATOM | 2649 | CD2 | LEU | A | 324 | 37.287 | 5.677 | 4.774 | 1.00 | 22.23 | A | C |
| ATOM | 2650 | C | LEU | A | 324 | 38.162 | 9.642 | 6.333 | 1.00 | 17.96 | A | C |
| ATOM | 2651 | O | LEU | A | 324 | 38.552 | 10.704 | 5.926 | 1.00 | 16.89 | A | O |
| ATOM | 2652 | N | PRO | A | 325 | 38.414 | 9.216 | 7.588 | 1.00 | 17.81 | A | N |
| ATOM | 2653 | CA | PRO | A | 325 | 39.338 | 10.029 | 8.402 | 1.00 | 20.53 | A | C |
| ATOM | 2654 | CB | PRO | A | 325 | 39.333 | 9.323 | 9.772 | 1.00 | 22.81 | A | C |
| ATOM | 2655 | CG | PRO | A | 325 | 38.873 | 7.979 | 9.501 | 1.00 | 21.72 | A | C |
| ATOM | 2656 | CD | PRO | A | 325 | 37.934 | 8.046 | 8.322 | 1.00 | 20.29 | A | C |
| ATOM | 2657 | C | PRO | A | 325 | 40.740 | 10.065 | 7.808 | 1.00 | 15.43 | A | C |
| ATOM | 2658 | O | PRO | A | 325 | 41.092 | 9.176 | 7.053 | 1.00 | 14.99 | A | O |
| ATOM | 2659 | N | ASP | A | 326 | 41.538 | 11.069 | 8.166 | 1.00 | 13.83 | A | N |
| ATOM | 2660 | CA | ASP | A | 326 | 42.831 | 11.314 | 7.484 | 1.00 | 16.63 | A | C |
| ATOM | 2661 | CB | ASP | A | 326 | 43.571 | 12.457 | 8.150 | 1.00 | 20.34 | A | C |
| ATOM | 2662 | CG | ASP | A | 326 | 42.919 | 13.819 | 7.867 | 1.00 | 22.99 | A | C |
| ATOM | 2663 | OD1 | ASP | A | 326 | 42.066 | 13.906 | 6.956 | 1.00 | 27.29 | A | O |
| ATOM | 2664 | OD2 | ASP | A | 326 | 43.277 | 14.778 | 8.567 | 1.00 | 25.92 | A | O |
| ATOM | 2665 | C | ASP | A | 326 | 43.750 | 10.090 | 7.405 | 1.00 | 18.36 | A | C |
| ATOM | 2666 | O | ASP | A | 326 | 44.271 | 9.757 | 6.326 | 1.00 | 14.64 | A | O |
| ATOM | 2667 | N | TYR | A | 327 | 43.925 | 9.374 | 8.516 | 1.00 | 16.45 | A | N |
| ATOM | 2668 | CA | TYR | A | 327 | 44.789 | 8.191 | 8.458 | 1.00 | 17.44 | A | C |
| ATOM | 2669 | CB | TYR | A | 327 | 45.028 | 7.627 | 9.845 | 1.00 | 18.71 | A | C |
| ATOM | 2670 | CG | TYR | A | 327 | 43.903 | 6.798 | 10.411 | 1.00 | 19.90 | A | C |

APPENDIX A-continued

*P. alba* 3T288C coordinates

| ATOM | 2671 | CD1 | TYR | A | 327 | 42.801 | 7.382 | 11.069 | 1.00 | 17.57 | A | C |
|---|---|---|---|---|---|---|---|---|---|---|---|---|
| ATOM | 2672 | CE1 | TYR | A | 327 | 41.781 | 6.566 | 11.617 | 1.00 | 18.13 | A | C |
| ATOM | 2673 | CZ | TYR | A | 327 | 41.902 | 5.186 | 11.552 | 1.00 | 21.33 | A | C |
| ATOM | 2674 | OH | TYR | A | 327 | 40.931 | 4.323 | 12.067 | 1.00 | 20.25 | A | O |
| ATOM | 2675 | CE2 | TYR | A | 327 | 42.985 | 4.623 | 10.923 | 1.00 | 20.79 | A | C |
| ATOM | 2676 | CD2 | TYR | A | 327 | 43.977 | 5.418 | 10.362 | 1.00 | 20.19 | A | C |
| ATOM | 2677 | C | TYR | A | 327 | 44.273 | 7.116 | 7.496 | 1.00 | 16.83 | A | C |
| ATOM | 2678 | O | TYR | A | 327 | 45.056 | 6.419 | 6.831 | 1.00 | 18.49 | A | O |
| ATOM | 2679 | N | MET | A | 328 | 42.957 | 6.943 | 7.414 | 1.00 | 13.77 | A | N |
| ATOM | 2680 | CA | MET | A | 328 | 42.407 | 5.982 | 6.460 | 1.00 | 13.61 | A | C |
| ATOM | 2681 | CB | MET | A | 328 | 40.978 | 5.630 | 6.807 | 1.00 | 14.88 | A | C |
| ATOM | 2682 | CG | MET | A | 328 | 40.877 | 4.751 | 8.063 | 1.00 | 14.77 | A | C |
| ATOM | 2683 | SD | MET | A | 328 | 39.182 | 4.362 | 8.436 | 1.00 | 16.72 | A | S |
| ATOM | 2684 | CE | MET | A | 328 | 39.456 | 2.802 | 9.383 | 1.00 | 11.78 | A | C |
| ATOM | 2685 | C | MET | A | 328 | 42.437 | 6.430 | 4.985 | 1.00 | 16.66 | A | C |
| ATOM | 2686 | O | MET | A | 328 | 42.492 | 5.587 | 4.112 | 1.00 | 17.33 | A | O |
| ATOM | 2687 | N | LYS | A | 329 | 42.369 | 7.737 | 4.712 | 1.00 | 18.49 | A | N |
| ATOM | 2688 | CA | LYS | A | 329 | 42.474 | 8.244 | 3.329 | 1.00 | 19.66 | A | C |
| ATOM | 2689 | CB | LYS | A | 329 | 42.521 | 9.780 | 3.268 | 1.00 | 25.10 | A | C |
| ATOM | 2690 | CG | LYS | A | 329 | 41.299 | 10.557 | 3.662 | 1.00 | 39.00 | A | C |
| ATOM | 2691 | CD | LYS | A | 329 | 41.464 | 12.012 | 3.167 | 1.00 | 38.07 | A | C |
| ATOM | 2692 | CE | LYS | A | 329 | 40.322 | 12.928 | 3.565 | 1.00 | 44.10 | A | C |
| ATOM | 2693 | NZ | LYS | A | 329 | 40.381 | 14.163 | 2.715 | 1.00 | 35.97 | A | N |
| ATOM | 2694 | C | LYS | A | 329 | 43.777 | 7.807 | 2.743 | 1.00 | 15.39 | A | C |
| ATOM | 2695 | O | LYS | A | 329 | 43.840 | 7.348 | 1.612 | 1.00 | 15.48 | A | O |
| ATOM | 2696 | N | LEU | A | 330 | 44.844 | 7.976 | 3.521 | 1.00 | 13.32 | A | N |
| ATOM | 2697 | CA | LEU | A | 330 | 46.174 | 7.646 | 3.063 | 1.00 | 15.58 | A | C |
| ATOM | 2698 | CB | LEU | A | 330 | 47.214 | 8.193 | 4.060 | 1.00 | 19.08 | A | C |
| ATOM | 2699 | CG | LEU | A | 330 | 48.663 | 8.198 | 3.585 | 1.00 | 20.74 | A | C |
| ATOM | 2700 | CD1 | LEU | A | 330 | 48.827 | 9.359 | 2.531 | 1.00 | 16.60 | A | C |
| ATOM | 2701 | CD2 | LEU | A | 330 | 49.680 | 8.377 | 4.787 | 1.00 | 19.71 | A | C |
| ATOM | 2702 | C | LEU | A | 330 | 46.332 | 6.172 | 2.871 | 1.00 | 16.37 | A | C |
| ATOM | 2703 | O | LEU | A | 330 | 46.825 | 5.723 | 1.825 | 1.00 | 15.79 | A | O |
| ATOM | 2704 | N | CYS | A | 331 | 45.901 | 5.387 | 3.870 | 1.00 | 15.05 | A | N |
| ATOM | 2705 | CA | ACYS | A | 331 | 45.980 | 3.935 | 3.762 | 0.70 | 14.81 | A | C |
| ATOM | 2706 | CA | BCYS | A | 331 | 45.934 | 3.917 | 3.778 | 0.30 | 14.73 | A | C |
| ATOM | 2707 | CB | ACYS | A | 331 | 45.506 | 3.277 | 5.069 | 0.70 | 17.32 | A | C |
| ATOM | 2708 | CB | BCYS | A | 331 | 45.314 | 3.292 | 5.035 | 0.30 | 15.28 | A | C |
| ATOM | 2709 | SG | ACYS | A | 331 | 45.829 | 1.513 | 5.086 | 0.70 | 25.66 | A | S |
| ATOM | 2710 | SG | BCYS | A | 331 | 46.397 | 3.282 | 6.443 | 0.30 | 17.26 | A | S |
| ATOM | 2711 | C | CYS | A | 331 | 45.169 | 3.397 | 2.564 | 1.00 | 14.98 | A | C |
| ATOM | 2712 | O | CYS | A | 331 | 45.667 | 2.584 | 1.765 | 1.00 | 14.34 | A | O |
| ATOM | 2713 | N | PHE | A | 332 | 43.934 | 3.835 | 2.448 | 1.00 | 15.08 | A | N |
| ATOM | 2714 | CA | PHE | A | 332 | 43.086 | 3.462 | 1.324 | 1.00 | 15.82 | A | C |
| ATOM | 2715 | CB | PHE | A | 332 | 41.716 | 4.117 | 1.443 | 1.00 | 19.85 | A | C |
| ATOM | 2716 | CG | PHE | A | 332 | 40.816 | 3.771 | 0.300 | 1.00 | 22.23 | A | C |
| ATOM | 2717 | CD1 | PHE | A | 332 | 40.144 | 2.592 | 0.302 | 1.00 | 19.24 | A | C |
| ATOM | 2718 | CE1 | PHE | A | 332 | 39.323 | 2.244 | −0.761 | 1.00 | 23.63 | A | C |
| ATOM | 2719 | CZ | PHE | A | 332 | 39.188 | 3.073 | −1.830 | 1.00 | 17.47 | A | C |
| ATOM | 2720 | CE2 | PHE | A | 332 | 39.879 | 4.249 | −1.880 | 1.00 | 18.18 | A | C |
| ATOM | 2721 | CD2 | PHE | A | 332 | 40.706 | 4.605 | −0.811 | 1.00 | 19.50 | A | C |
| ATOM | 2722 | C | PHE | A | 332 | 43.678 | 3.823 | −0.051 | 1.00 | 13.90 | A | C |
| ATOM | 2723 | O | PHE | A | 332 | 43.704 | 2.981 | −0.938 | 1.00 | 13.13 | A | O |
| ATOM | 2724 | N | LEU | A | 333 | 44.182 | 5.038 | −0.223 | 1.00 | 13.85 | A | N |
| ATOM | 2725 | CA | LEU | A | 333 | 44.677 | 5.452 | −1.561 | 1.00 | 14.29 | A | C |
| ATOM | 2726 | CB | LEU | A | 333 | 44.865 | 6.948 | −1.655 | 1.00 | 12.13 | A | C |
| ATOM | 2727 | CG | LEU | A | 333 | 45.367 | 7.557 | −2.976 | 1.00 | 13.38 | A | C |
| ATOM | 2728 | CD1 | LEU | A | 333 | 44.438 | 7.120 | −4.114 | 1.00 | 12.36 | A | C |
| ATOM | 2729 | CD2 | LEU | A | 333 | 45.483 | 9.094 | −2.883 | 1.00 | 10.36 | A | C |
| ATOM | 2730 | C | LEU | A | 333 | 45.959 | 4.665 | −1.899 | 1.00 | 14.16 | A | C |
| ATOM | 2731 | O | LEU | A | 333 | 46.157 | 4.224 | −3.055 | 1.00 | 11.14 | A | O |
| ATOM | 2732 | N | ALA | A | 334 | 46.789 | 4.409 | −0.883 | 1.00 | 12.87 | A | N |
| ATOM | 2733 | CA | ALA | A | 334 | 47.977 | 3.554 | −1.090 | 1.00 | 16.15 | A | C |
| ATOM | 2734 | CB | ALA | A | 334 | 48.840 | 3.454 | 0.173 | 1.00 | 15.82 | A | C |
| ATOM | 2735 | C | ALA | A | 334 | 47.576 | 2.165 | −1.562 | 1.00 | 13.62 | A | C |
| ATOM | 2736 | O | ALA | A | 334 | 48.135 | 1.663 | −2.498 | 1.00 | 14.28 | A | O |
| ATOM | 2737 | N | LEU | A | 335 | 46.593 | 1.564 | −0.924 | 1.00 | 14.24 | A | N |
| ATOM | 2738 | CA | LEU | A | 335 | 46.123 | 0.216 | −1.302 | 1.00 | 16.91 | A | C |
| ATOM | 2739 | CB | LEU | A | 335 | 45.090 | −0.277 | −0.299 | 1.00 | 14.05 | A | C |
| ATOM | 2740 | CG | LEU | A | 335 | 44.334 | −1.570 | −0.507 | 1.00 | 19.27 | A | C |
| ATOM | 2741 | CD1 | LEU | A | 335 | 45.331 | −2.720 | −0.481 | 1.00 | 18.50 | A | C |
| ATOM | 2742 | CD2 | LEU | A | 335 | 43.181 | −1.768 | 0.501 | 1.00 | 19.37 | A | C |
| ATOM | 2743 | C | LEU | A | 335 | 45.486 | 0.251 | −2.686 | 1.00 | 14.42 | A | C |
| ATOM | 2744 | O | LEU | A | 335 | 45.750 | −0.604 | −3.523 | 1.00 | 16.54 | A | O |
| ATOM | 2745 | N | TYR | A | 336 | 44.624 | 1.238 | −2.889 | 1.00 | 14.24 | A | N |
| ATOM | 2746 | CA | TYR | A | 336 | 43.909 | 1.458 | −4.153 | 1.00 | 13.22 | A | C |
| ATOM | 2747 | CB | TYR | A | 336 | 43.129 | 2.755 | −4.043 | 1.00 | 12.76 | A | C |
| ATOM | 2748 | CG | TYR | A | 336 | 42.168 | 3.066 | −5.171 | 1.00 | 14.14 | A | C |

APPENDIX A-continued

*P. alba* 3T288C coordinates

| ATOM | 2749 | CD1 | TYR | A | 336 | 40.915 | 2.497 | −5.220 | 1.00 | 15.26 | A | C |
|---|---|---|---|---|---|---|---|---|---|---|---|---|
| ATOM | 2750 | CE1 | TYR | A | 336 | 40.032 | 2.790 | −6.264 | 1.00 | 16.12 | A | C |
| ATOM | 2751 | CZ | TYR | A | 336 | 40.389 | 3.682 | −7.208 | 1.00 | 17.61 | A | C |
| ATOM | 2752 | OH | TYR | A | 336 | 39.521 | 4.011 | −8.230 | 1.00 | 19.27 | A | O |
| ATOM | 2753 | CE2 | TYR | A | 336 | 41.620 | 4.279 | −7.162 | 1.00 | 15.70 | A | C |
| ATOM | 2754 | CD2 | TYR | A | 336 | 42.497 | 3.974 | −6.154 | 1.00 | 14.82 | A | C |
| ATOM | 2755 | C | TYR | A | 336 | 44.860 | 1.497 | −5.345 | 1.00 | 12.46 | A | C |
| ATOM | 2756 | O | TYR | A | 336 | 44.689 | 0.722 | −6.318 | 1.00 | 11.23 | A | O |
| ATOM | 2757 | N | ASN | A | 337 | 45.867 | 2.376 | −5.267 | 1.00 | 11.05 | A | N |
| ATOM | 2758 | CA | ASN | A | 337 | 46.913 | 2.477 | −6.325 | 1.00 | 10.92 | A | C |
| ATOM | 2759 | CB | ASN | A | 337 | 47.864 | 3.662 | −6.045 | 1.00 | 13.08 | A | C |
| ATOM | 2760 | CG | ASN | A | 337 | 47.178 | 5.011 | −6.226 | 1.00 | 16.67 | A | C |
| ATOM | 2761 | OD1 | ASN | A | 337 | 46.117 | 5.089 | −6.859 | 1.00 | 14.21 | A | O |
| ATOM | 2762 | ND2 | ASN | A | 337 | 47.749 | 6.078 | −5.629 | 1.00 | 12.56 | A | N |
| ATOM | 2763 | C | ASN | A | 337 | 47.718 | 1.200 | −6.538 | 1.00 | 13.12 | A | C |
| ATOM | 2764 | O | ASN | A | 337 | 47.994 | 0.825 | −7.671 | 1.00 | 11.66 | A | O |
| ATOM | 2765 | N | THR | A | 338 | 48.097 | 0.524 | −5.446 | 1.00 | 10.90 | A | N |
| ATOM | 2766 | CA | THR | A | 338 | 48.859 | −0.714 | −5.539 | 1.00 | 11.86 | A | C |
| ATOM | 2767 | CB | THR | A | 338 | 49.291 | −1.196 | −4.096 | 1.00 | 13.78 | A | C |
| ATOM | 2768 | OG1 | THR | A | 338 | 50.031 | −0.117 | −3.493 | 1.00 | 13.95 | A | O |
| ATOM | 2769 | CG2 | THR | A | 338 | 50.138 | −2.535 | −4.140 | 1.00 | 16.03 | A | C |
| ATOM | 2770 | C | THR | A | 338 | 48.053 | −1.802 | −6.268 | 1.00 | 12.45 | A | C |
| ATOM | 2771 | O | THR | A | 338 | 48.577 | −2.461 | −7.149 | 1.00 | 13.56 | A | O |
| ATOM | 2772 | N | ILE | A | 339 | 46.785 | −1.961 | −5.929 | 1.00 | 13.24 | A | N |
| ATOM | 2773 | CA | ILE | A | 339 | 45.953 | −2.999 | −6.549 | 1.00 | 14.77 | A | C |
| ATOM | 2774 | CB | ILE | A | 339 | 44.613 | −3.228 | −5.817 | 1.00 | 15.84 | A | C |
| ATOM | 2775 | CG1 | ILE | A | 339 | 44.805 | −3.733 | −4.366 | 1.00 | 22.56 | A | C |
| ATOM | 2776 | CD1 | ILE | A | 339 | 46.091 | −4.409 | −4.060 | 1.00 | 25.24 | A | C |
| ATOM | 2777 | CG2 | ILE | A | 339 | 43.713 | −4.206 | −6.587 | 1.00 | 16.00 | A | C |
| ATOM | 2778 | C | ILE | A | 339 | 45.683 | −2.616 | −8.021 | 1.00 | 16.22 | A | C |
| ATOM | 2779 | O | ILE | A | 339 | 45.803 | −3.467 | −8.907 | 1.00 | 15.73 | A | O |
| ATOM | 2780 | N | ASN | A | 340 | 45.338 | −1.354 | −8.272 | 1.00 | 13.61 | A | N |
| ATOM | 2781 | CA | ASN | A | 340 | 45.132 | −0.858 | −9.633 | 1.00 | 13.64 | A | C |
| ATOM | 2782 | CB | ASN | A | 340 | 44.643 | 0.610 | −9.648 | 1.00 | 14.73 | A | C |
| ATOM | 2783 | CG | ASN | A | 340 | 43.212 | 0.767 | −9.124 | 1.00 | 14.26 | A | C |
| ATOM | 2784 | OD1 | ASN | A | 340 | 42.491 | −0.210 | −8.962 | 1.00 | 14.11 | A | O |
| ATOM | 2785 | ND2 | ASN | A | 340 | 42.814 | 1.994 | −8.837 | 1.00 | 12.66 | A | N |
| ATOM | 2786 | C | ASN | A | 340 | 46.366 | −1.081 | −10.536 | 1.00 | 15.34 | A | C |
| ATOM | 2787 | O | ASN | A | 340 | 46.246 | −1.359 | −11.737 | 1.00 | 15.44 | A | O |
| ATOM | 2788 | N | GLU | A | 341 | 47.554 | −0.973 | −9.961 | 1.00 | 14.07 | A | N |
| ATOM | 2789 | CA | AGLU | A | 341 | 48.806 | −1.157 | −10.703 | 0.50 | 13.47 | A | C |
| ATOM | 2790 | CA | BGLU | A | 341 | 48.772 | −1.131 | −10.741 | 0.50 | 13.96 | A | C |
| ATOM | 2791 | CB | AGLU | A | 341 | 49.993 | −0.618 | −9.887 | 0.50 | 16.02 | A | C |
| ATOM | 2792 | CB | BGLU | A | 341 | 49.949 | −0.382 | −10.060 | 0.50 | 17.37 | A | C |
| ATOM | 2793 | CG | AGLU | A | 341 | 51.368 | −0.951 | −10.447 | 0.50 | 17.69 | A | C |
| ATOM | 2794 | CG | BGLU | A | 341 | 49.804 | 1.161 | −10.206 | 0.50 | 22.08 | A | C |
| ATOM | 2795 | CD | AGLU | A | 341 | 52.459 | −0.118 | −9.803 | 0.50 | 20.91 | A | C |
| ATOM | 2796 | CD | BGLU | A | 341 | 50.629 | 2.019 | −9.226 | 0.50 | 27.60 | A | C |
| ATOM | 2797 | OE1 | BGLU | A | 341 | 51.572 | 1.483 | −8.603 | 0.50 | 23.51 | A | O |
| ATOM | 2798 | OE1 | AGLU | A | 341 | 53.226 | 0.497 | −10.561 | 0.50 | 25.96 | A | O |
| ATOM | 2799 | OE2 | AGLU | A | 341 | 52.521 | −0.056 | −8.544 | 0.50 | 24.48 | A | O |
| ATOM | 2800 | OE2 | BGLU | A | 341 | 50.328 | 3.245 | −9.094 | 0.50 | 24.19 | A | O |
| ATOM | 2801 | C | GLU | A | 341 | 49.026 | −2.631 | −11.054 | 1.00 | 12.91 | A | C |
| ATOM | 2802 | O | GLU | A | 341 | 49.462 | −2.961 | −12.159 | 1.00 | 12.81 | A | O |
| ATOM | 2803 | N | ILE | A | 342 | 48.697 | −3.516 | −10.127 | 1.00 | 13.30 | A | N |
| ATOM | 2804 | CA | ILE | A | 342 | 48.748 | −4.965 | −10.378 | 1.00 | 15.54 | A | C |
| ATOM | 2805 | CB | ILE | A | 342 | 48.523 | −5.766 | −9.104 | 1.00 | 13.99 | A | C |
| ATOM | 2806 | CG1 | ILE | A | 342 | 49.746 | −5.616 | −8.187 | 1.00 | 14.53 | A | C |
| ATOM | 2807 | CD1 | ILE | A | 342 | 49.481 | −6.036 | −6.734 | 1.00 | 14.11 | A | C |
| ATOM | 2808 | CG2 | ILE | A | 342 | 48.296 | −7.246 | −9.408 | 1.00 | 16.66 | A | C |
| ATOM | 2809 | C | ILE | A | 342 | 47.733 | −5.337 | −11.469 | 1.00 | 18.15 | A | C |
| ATOM | 2810 | O | ILE | A | 342 | 48.076 | −6.076 | −12.401 | 1.00 | 17.80 | A | O |
| ATOM | 2811 | N | ALA | A | 343 | 46.533 | −4.762 | −11.400 | 1.00 | 16.13 | A | N |
| ATOM | 2812 | CA | ALA | A | 343 | 45.528 | −4.937 | −12.481 | 1.00 | 14.03 | A | C |
| ATOM | 2813 | CB | ALA | A | 343 | 44.234 | −4.211 | −12.169 | 1.00 | 11.91 | A | C |
| ATOM | 2814 | C | ALA | A | 343 | 46.092 | −4.480 | −13.786 | 1.00 | 14.80 | A | C |
| ATOM | 2815 | O | ALA | A | 343 | 45.925 | −5.172 | −14.784 | 1.00 | 14.81 | A | O |
| ATOM | 2816 | N | TYR | A | 344 | 46.755 | −3.312 | −13.810 | 1.00 | 12.84 | A | N |
| ATOM | 2817 | CA | TYR | A | 344 | 47.363 | −2.802 | −15.039 | 1.00 | 13.86 | A | C |
| ATOM | 2818 | CB | TYR | A | 344 | 48.045 | −1.423 | −14.850 | 1.00 | 11.49 | A | C |
| ATOM | 2819 | CG | TYR | A | 344 | 48.692 | −0.929 | −16.100 | 1.00 | 9.85 | A | C |
| ATOM | 2820 | CD1 | TYR | A | 344 | 47.939 | −0.286 | −17.074 | 1.00 | 9.93 | A | C |
| ATOM | 2821 | CE1 | TYR | A | 344 | 48.493 | 0.161 | −18.240 | 1.00 | 8.79 | A | C |
| ATOM | 2822 | CZ | TYR | A | 344 | 49.824 | −0.027 | −18.469 | 1.00 | 9.72 | A | C |
| ATOM | 2823 | OH | TYR | A | 344 | 50.296 | 0.416 | −19.655 | 1.00 | 11.12 | A | O |
| ATOM | 2824 | CE2 | TYR | A | 344 | 50.618 | −0.658 | −17.532 | 1.00 | 10.17 | A | C |
| ATOM | 2825 | CD2 | TYR | A | 344 | 50.042 | −1.071 | −16.324 | 1.00 | 9.90 | A | C |
| ATOM | 2826 | C | TYR | A | 344 | 48.377 | −3.790 | −15.620 | 1.00 | 14.30 | A | C |

APPENDIX A-continued

*P. alba* 3T288C coordinates

| ATOM | 2827 | O | TYR | A | 344 | 48.350 | −4.081 | −16.799 | 1.00 | 11.84 | A | O |
|---|---|---|---|---|---|---|---|---|---|---|---|---|
| ATOM | 2828 | N | ASP | A | 345 | 49.286 | −4.277 | −14.791 | 1.00 | 15.91 | A | N |
| ATOM | 2829 | CA | ASP | A | 345 | 50.307 | −5.205 | −15.280 | 1.00 | 17.61 | A | C |
| ATOM | 2830 | CB | ASP | A | 345 | 51.222 | −5.703 | −14.157 | 1.00 | 22.91 | A | C |
| ATOM | 2831 | CG | ASP | A | 345 | 52.054 | −4.585 | −13.478 | 1.00 | 24.91 | A | C |
| ATOM | 2832 | OD1 | ASP | A | 345 | 52.328 | −3.540 | −14.082 | 1.00 | 29.76 | A | O |
| ATOM | 2833 | OD2 | ASP | A | 345 | 52.410 | −4.789 | −12.296 | 1.00 | 40.11 | A | O |
| ATOM | 2834 | C | ASP | A | 345 | 49.638 | −6.444 | −15.929 | 1.00 | 17.32 | A | C |
| ATOM | 2835 | O | ASP | A | 345 | 50.124 | −6.957 | −16.929 | 1.00 | 16.55 | A | O |
| ATOM | 2836 | N | ASN | A | 346 | 48.552 | −6.925 | −15.331 | 1.00 | 16.63 | A | N |
| ATOM | 2837 | CA | ASN | A | 346 | 47.836 | −8.075 | −15.869 | 1.00 | 15.25 | A | C |
| ATOM | 2838 | CB | ASN | A | 346 | 46.897 | −8.661 | −14.839 | 1.00 | 18.38 | A | C |
| ATOM | 2839 | CG | ASN | A | 346 | 47.595 | −9.570 | −13.917 | 1.00 | 25.49 | A | C |
| ATOM | 2840 | OD1 | ASN | A | 346 | 47.711 | −10.781 | −14.186 | 1.00 | 19.59 | A | O |
| ATOM | 2841 | ND2 | ASN | A | 346 | 48.093 | −9.015 | −12.810 | 1.00 | 23.37 | A | N |
| ATOM | 2842 | C | ASN | A | 346 | 47.078 | −7.787 | −17.158 | 1.00 | 16.76 | A | C |
| ATOM | 2843 | O | ASN | A | 346 | 47.093 | −8.610 | −18.062 | 1.00 | 19.88 | A | O |
| ATOM | 2844 | N | LEU | A | 347 | 46.490 | −6.597 | −17.266 | 1.00 | 15.52 | A | N |
| ATOM | 2845 | CA | LEU | A | 347 | 45.902 | −6.120 | −18.514 | 1.00 | 13.62 | A | C |
| ATOM | 2846 | CB | LEU | A | 347 | 45.198 | −4.779 | −18.323 | 1.00 | 11.95 | A | C |
| ATOM | 2847 | CG | LEU | A | 347 | 44.492 | −4.169 | −19.533 | 1.00 | 11.99 | A | C |
| ATOM | 2848 | CD1 | LEU | A | 347 | 43.413 | −5.129 | −20.038 | 1.00 | 13.90 | A | C |
| ATOM | 2849 | CD2 | LEU | A | 347 | 43.932 | −2.771 | −19.199 | 1.00 | 13.13 | A | C |
| ATOM | 2850 | C | LEU | A | 347 | 46.940 | −6.078 | −19.629 | 1.00 | 17.97 | A | C |
| ATOM | 2851 | O | LEU | A | 347 | 46.736 | −6.649 | −20.730 | 1.00 | 16.03 | A | O |
| ATOM | 2852 | N | LYS | A | 348 | 48.081 | −5.472 | −19.332 | 1.00 | 13.81 | A | N |
| ATOM | 2853 | CA | LYS | A | 348 | 49.117 | −5.318 | −20.306 | 1.00 | 14.92 | A | C |
| ATOM | 2854 | CB | LYS | A | 348 | 50.236 | −4.463 | −19.738 | 1.00 | 18.92 | A | C |
| ATOM | 2855 | CG | LYS | A | 348 | 51.303 | −4.159 | −20.734 | 1.00 | 22.39 | A | C |
| ATOM | 2856 | CD | LYS | A | 348 | 52.244 | −3.064 | −20.262 | 1.00 | 25.50 | A | C |
| ATOM | 2857 | CE | LYS | A | 348 | 53.608 | −3.563 | −19.902 | 1.00 | 30.70 | A | C |
| ATOM | 2858 | NZ | LYS | A | 348 | 53.587 | −4.143 | −18.593 | 1.00 | 33.98 | A | N |
| ATOM | 2859 | C | LYS | A | 348 | 49.713 | −6.659 | −20.779 | 1.00 | 15.93 | A | C |
| ATOM | 2860 | O | LYS | A | 348 | 49.978 | −6.835 | −21.970 | 1.00 | 15.69 | A | O |
| ATOM | 2861 | N | ASP | A | 349 | 49.985 | −7.533 | −19.830 | 1.00 | 15.10 | A | N |
| ATOM | 2862 | CA | ASP | A | 349 | 50.727 | −8.774 | −20.103 | 1.00 | 22.90 | A | C |
| ATOM | 2863 | CB | ASP | A | 349 | 51.600 | −9.157 | −18.888 | 1.00 | 18.72 | A | C |
| ATOM | 2864 | CG | ASP | A | 349 | 52.706 | −8.090 | −18.606 | 1.00 | 28.43 | A | C |
| ATOM | 2865 | OD1 | ASP | A | 349 | 53.075 | −7.326 | −19.532 | 1.00 | 31.35 | A | O |
| ATOM | 2866 | OD2 | ASP | A | 349 | 53.179 | −7.993 | −17.459 | 1.00 | 49.50 | A | O |
| ATOM | 2867 | C | ASP | A | 349 | 49.826 | −9.928 | −20.532 | 1.00 | 22.68 | A | C |
| ATOM | 2868 | O | ASP | A | 349 | 50.226 | −10.709 | −21.348 | 1.00 | 22.80 | A | O |
| ATOM | 2869 | N | LYS | A | 350 | 48.616 | −10.020 | −19.982 | 1.00 | 21.26 | A | N |
| ATOM | 2870 | CA | LYS | A | 350 | 47.716 | −11.160 | −20.247 | 1.00 | 21.09 | A | C |
| ATOM | 2871 | CB | LYS | A | 350 | 47.238 | −11.768 | −18.935 | 1.00 | 25.36 | A | C |
| ATOM | 2872 | CG | LYS | A | 350 | 48.324 | −12.371 | −18.044 | 1.00 | 25.43 | A | C |
| ATOM | 2873 | CD | LYS | A | 350 | 47.703 | −12.850 | −16.709 | 1.00 | 44.76 | A | C |
| ATOM | 2874 | CE | LYS | A | 350 | 48.773 | −13.100 | −15.605 | 1.00 | 41.38 | A | C |
| ATOM | 2875 | NZ | LYS | A | 350 | 49.841 | −13.998 | −16.126 | 1.00 | 67.10 | A | N |
| ATOM | 2876 | C | LYS | A | 350 | 46.481 | −10.754 | −21.045 | 1.00 | 25.46 | A | C |
| ATOM | 2877 | O | LYS | A | 350 | 45.727 | −11.597 | −21.473 | 1.00 | 22.82 | A | O |
| ATOM | 2878 | N | GLY | A | 351 | 46.217 | −9.458 | −21.184 | 1.00 | 17.25 | A | N |
| ATOM | 2879 | CA | GLY | A | 351 | 45.118 | −9.004 | −22.002 | 1.00 | 19.61 | A | C |
| ATOM | 2880 | C | GLY | A | 351 | 43.774 | −9.129 | −21.322 | 1.00 | 19.39 | A | C |
| ATOM | 2881 | O | GLY | A | 351 | 42.753 | −8.986 | −21.972 | 1.00 | 20.33 | A | O |
| ATOM | 2882 | N | GLU | A | 352 | 43.764 | −9.287 | −20.006 | 1.00 | 17.50 | A | N |
| ATOM | 2883 | CA | GLU | A | 352 | 42.529 | −9.442 | −19.253 | 1.00 | 20.07 | A | C |
| ATOM | 2884 | CB | GLU | A | 352 | 42.542 | −10.806 | −18.546 | 1.00 | 23.74 | A | C |
| ATOM | 2885 | CG | GLU | A | 352 | 42.695 | −12.044 | −19.444 | 1.00 | 36.13 | A | C |
| ATOM | 2886 | CD | GLU | A | 352 | 41.454 | −12.383 | −20.264 | 1.00 | 42.77 | A | C |
| ATOM | 2887 | OE1 | GLU | A | 352 | 40.402 | −11.710 | −20.115 | 1.00 | 44.84 | A | O |
| ATOM | 2888 | OE2 | GLU | A | 352 | 41.551 | −13.335 | −21.074 | 1.00 | 62.66 | A | O |
| ATOM | 2889 | C | GLU | A | 352 | 42.423 | −8.383 | −18.166 | 1.00 | 19.66 | A | C |
| ATOM | 2890 | O | GLU | A | 352 | 43.444 | −8.030 | −17.542 | 1.00 | 15.51 | A | O |
| ATOM | 2891 | N | ASN | A | 353 | 41.203 | −7.934 | −17.898 | 1.00 | 20.74 | A | N |
| ATOM | 2892 | CA | ASN | A | 353 | 40.918 | −7.090 | −16.739 | 1.00 | 22.43 | A | C |
| ATOM | 2893 | CB | ASN | A | 353 | 39.822 | −6.099 | −17.083 | 1.00 | 23.62 | A | C |
| ATOM | 2894 | CG | ASN | A | 353 | 39.486 | −5.180 | −15.917 | 1.00 | 19.76 | A | C |
| ATOM | 2895 | OD1 | ASN | A | 353 | 40.047 | −5.295 | −14.821 | 1.00 | 20.21 | A | O |
| ATOM | 2896 | ND2 | ASN | A | 353 | 38.565 | −4.287 | −16.141 | 1.00 | 23.44 | A | N |
| ATOM | 2897 | C | ASN | A | 353 | 40.535 | −7.929 | −15.510 | 1.00 | 23.59 | A | C |
| ATOM | 2898 | O | ASN | A | 353 | 39.426 | −8.430 | −15.432 | 1.00 | 23.24 | A | O |
| ATOM | 2899 | N | ILE | A | 354 | 41.448 | −8.068 | −14.551 | 1.00 | 16.39 | A | N |
| ATOM | 2900 | CA | ILE | A | 354 | 41.213 | −8.909 | −13.377 | 1.00 | 18.18 | A | C |
| ATOM | 2901 | CB | ILE | A | 354 | 42.471 | −9.826 | −13.071 | 1.00 | 20.87 | A | C |
| ATOM | 2902 | CG1 | ILE | A | 354 | 43.685 | −8.961 | −12.679 | 1.00 | 23.86 | A | C |
| ATOM | 2903 | CD1 | ILE | A | 354 | 44.869 | −9.681 | −12.114 | 1.00 | 22.04 | A | C |
| ATOM | 2904 | CG2 | ILE | A | 354 | 42.818 | −10.649 | −14.246 | 1.00 | 26.49 | A | C |

APPENDIX A-continued

*P. alba* 3T288C coordinates

| ATOM | 2905 | C | ILE | A | 354 | 40.863 | −8.076 | −12.134 | 1.00 | 17.05 | A | C |
|---|---|---|---|---|---|---|---|---|---|---|---|---|
| ATOM | 2906 | O | ILE | A | 354 | 40.740 | −8.614 | −11.023 | 1.00 | 16.63 | A | O |
| ATOM | 2907 | N | LEU | A | 355 | 40.698 | −6.776 | −12.313 | 1.00 | 15.40 | A | N |
| ATOM | 2908 | CA | LEU | A | 355 | 40.503 | −5.870 | −11.179 | 1.00 | 16.59 | A | C |
| ATOM | 2909 | CB | LEU | A | 355 | 40.312 | −4.422 | −11.658 | 1.00 | 15.17 | A | C |
| ATOM | 2910 | CG | LEU | A | 355 | 40.244 | −3.371 | −10.554 | 1.00 | 16.92 | A | C |
| ATOM | 2911 | CD1 | LEU | A | 355 | 41.444 | −3.440 | −9.684 | 1.00 | 12.65 | A | C |
| ATOM | 2912 | CD2 | LEU | A | 355 | 40.076 | −1.969 | −11.169 | 1.00 | 15.94 | A | C |
| ATOM | 2913 | C | LEU | A | 355 | 39.307 | −6.277 | −10.343 | 1.00 | 19.71 | A | C |
| ATOM | 2914 | O | LEU | A | 355 | 39.411 | −6.270 | −9.125 | 1.00 | 20.01 | A | O |
| ATOM | 2915 | N | PRO | A | 356 | 38.197 | −6.733 | −10.994 | 1.00 | 19.04 | A | N |
| ATOM | 2916 | CA | PRO | A | 356 | 37.082 | −7.168 | −10.157 | 1.00 | 22.46 | A | C |
| ATOM | 2917 | CB | PRO | A | 356 | 36.016 | −7.617 | −11.181 | 1.00 | 27.85 | A | C |
| ATOM | 2918 | CG | PRO | A | 356 | 36.381 | −6.909 | −12.466 | 1.00 | 26.81 | A | C |
| ATOM | 2919 | CD | PRO | A | 356 | 37.871 | −6.785 | −12.440 | 1.00 | 18.70 | A | C |
| ATOM | 2920 | C | PRO | A | 356 | 37.425 | −8.284 | −9.165 | 1.00 | 17.63 | A | C |
| ATOM | 2921 | O | PRO | A | 356 | 36.912 | −8.276 | −8.056 | 1.00 | 19.64 | A | O |
| ATOM | 2922 | N | TYR | A | 357 | 38.292 | −9.222 | −9.535 | 1.00 | 17.75 | A | N |
| ATOM | 2923 | CA | TYR | A | 357 | 38.639 | −10.313 | −8.666 | 1.00 | 18.75 | A | C |
| ATOM | 2924 | CB | TYR | A | 357 | 39.296 | −11.463 | −9.439 | 1.00 | 23.81 | A | C |
| ATOM | 2925 | CG | TYR | A | 357 | 38.510 | −11.780 | −10.695 | 1.00 | 27.29 | A | C |
| ATOM | 2926 | CD1 | TYR | A | 357 | 37.253 | −12.358 | −10.623 | 1.00 | 43.84 | A | C |
| ATOM | 2927 | CE1 | TYR | A | 357 | 36.495 | −12.599 | −11.777 | 1.00 | 48.29 | A | C |
| ATOM | 2928 | CZ | TYR | A | 357 | 36.998 | −12.243 | −13.007 | 1.00 | 43.38 | A | C |
| ATOM | 2929 | OH | TYR | A | 357 | 36.278 | −12.488 | −14.147 | 1.00 | 57.79 | A | O |
| ATOM | 2930 | CE2 | TYR | A | 357 | 38.240 | −11.670 | −13.109 | 1.00 | 35.02 | A | C |
| ATOM | 2931 | CD2 | TYR | A | 357 | 38.992 | −11.438 | −11.941 | 1.00 | 30.70 | A | C |
| ATOM | 2932 | C | TYR | A | 357 | 39.569 | −9.861 | −7.539 | 1.00 | 20.46 | A | C |
| ATOM | 2933 | O | TYR | A | 357 | 39.448 | −10.336 | −6.424 | 1.00 | 17.34 | A | O |
| ATOM | 2934 | N | LEU | A | 358 | 40.505 | −8.963 | −7.837 | 1.00 | 19.62 | A | N |
| ATOM | 2935 | CA | LEU | A | 358 | 41.416 | −8.435 | −6.816 | 1.00 | 18.46 | A | C |
| ATOM | 2936 | CB | LEU | A | 358 | 42.504 | −7.567 | −7.462 | 1.00 | 17.42 | A | C |
| ATOM | 2937 | CG | LEU | A | 358 | 43.342 | −8.234 | −8.557 | 1.00 | 18.52 | A | C |
| ATOM | 2938 | CD1 | LEU | A | 358 | 44.447 | −7.314 | −9.129 | 1.00 | 13.44 | A | C |
| ATOM | 2939 | CD2 | LEU | A | 358 | 43.965 | −9.585 | −8.082 | 1.00 | 15.36 | A | C |
| ATOM | 2940 | C | LEU | A | 358 | 40.643 | −7.607 | −5.802 | 1.00 | 18.16 | A | C |
| ATOM | 2941 | O | LEU | A | 358 | 40.897 | −7.703 | −4.621 | 1.00 | 18.07 | A | O |
| ATOM | 2942 | N | THR | A | 359 | 39.706 | −6.769 | −6.258 | 1.00 | 17.16 | A | N |
| ATOM | 2943 | CA | THR | A | 359 | 38.970 | −5.910 | −5.340 | 1.00 | 19.21 | A | C |
| ATOM | 2944 | CB | THR | A | 359 | 38.265 | −4.733 | −6.053 | 1.00 | 19.64 | A | C |
| ATOM | 2945 | OG1 | THR | A | 359 | 37.306 | −5.211 | −7.012 | 1.00 | 17.02 | A | O |
| ATOM | 2946 | CG2 | THR | A | 359 | 39.292 | −3.852 | −6.759 | 1.00 | 17.09 | A | C |
| ATOM | 2947 | C | THR | A | 359 | 37.986 | −6.703 | −4.461 | 1.00 | 20.32 | A | C |
| ATOM | 2948 | O | THR | A | 359 | 37.809 | −6.396 | −3.291 | 1.00 | 17.74 | A | O |
| ATOM | 2949 | N | LYS | A | 360 | 37.426 | −7.774 | −5.000 | 1.00 | 21.30 | A | N |
| ATOM | 2950 | CA | LYS | A | 360 | 36.511 | −8.616 | −4.227 | 1.00 | 20.03 | A | C |
| ATOM | 2951 | CB | LYS | A | 360 | 35.804 | −9.623 | −5.139 | 1.00 | 21.21 | A | C |
| ATOM | 2952 | CG | LYS | A | 360 | 34.793 | −10.541 | −4.420 | 1.00 | 24.65 | A | C |
| ATOM | 2953 | CD | LYS | A | 360 | 33.613 | −9.722 | −3.911 | 1.00 | 35.48 | A | C |
| ATOM | 2954 | CE | LYS | A | 360 | 32.377 | −10.588 | −3.593 | 1.00 | 39.73 | A | C |
| ATOM | 2955 | NZ | LYS | A | 360 | 32.596 | −11.358 | −2.350 | 1.00 | 34.91 | A | N |
| ATOM | 2956 | C | LYS | A | 360 | 37.269 | −9.304 | −3.108 | 1.00 | 18.87 | A | C |
| ATOM | 2957 | O | LYS | A | 360 | 36.755 | −9.380 | −2.000 | 1.00 | 16.32 | A | O |
| ATOM | 2958 | N | ALA | A | 361 | 38.484 | −9.787 | −3.390 | 1.00 | 17.75 | A | N |
| ATOM | 2959 | CA | ALA | A | 361 | 39.342 | −10.403 | −2.377 | 1.00 | 17.01 | A | C |
| ATOM | 2960 | CB | ALA | A | 361 | 40.691 | −10.895 | −2.975 | 1.00 | 16.89 | A | C |
| ATOM | 2961 | C | ALA | A | 361 | 39.581 | −9.431 | −1.254 | 1.00 | 21.37 | A | C |
| ATOM | 2962 | O | ALA | A | 361 | 39.459 | −9.793 | −0.086 | 1.00 | 18.78 | A | O |
| ATOM | 2963 | N | TRP | A | 362 | 39.869 | −8.168 | −1.589 | 1.00 | 16.02 | A | N |
| ATOM | 2964 | CA | TRP | A | 362 | 40.057 | −7.156 | −0.530 | 1.00 | 16.57 | A | C |
| ATOM | 2965 | CB | TRP | A | 362 | 40.683 | −5.842 | −1.117 | 1.00 | 15.44 | A | C |
| ATOM | 2966 | CG | TRP | A | 362 | 42.175 | −6.013 | −1.080 | 1.00 | 15.77 | A | C |
| ATOM | 2967 | CD1 | TRP | A | 362 | 43.022 | −6.410 | −2.106 | 1.00 | 15.92 | A | C |
| ATOM | 2968 | NE1 | TRP | A | 362 | 44.291 | −6.530 | −1.649 | 1.00 | 16.94 | A | N |
| ATOM | 2969 | CE2 | TRP | A | 362 | 44.346 | −6.288 | −0.320 | 1.00 | 17.44 | A | C |
| ATOM | 2970 | CD2 | TRP | A | 362 | 43.006 | −5.980 | 0.113 | 1.00 | 14.82 | A | C |
| ATOM | 2971 | CE3 | TRP | A | 362 | 42.779 | −5.658 | 1.442 | 1.00 | 14.35 | A | C |
| ATOM | 2972 | CZ3 | TRP | A | 362 | 43.853 | −5.674 | 2.323 | 1.00 | 16.82 | A | C |
| ATOM | 2973 | CH2 | TRP | A | 362 | 45.132 | −5.996 | 1.892 | 1.00 | 18.89 | A | C |
| ATOM | 2974 | CZ2 | TRP | A | 362 | 45.406 | −6.316 | 0.563 | 1.00 | 17.80 | A | C |
| ATOM | 2975 | C | TRP | A | 362 | 38.778 | −6.870 | 0.258 | 1.00 | 16.02 | A | C |
| ATOM | 2976 | O | TRP | A | 362 | 38.825 | −6.702 | 1.479 | 1.00 | 17.20 | A | O |
| ATOM | 2977 | N | ALA | A | 363 | 37.635 | −6.790 | −0.425 | 1.00 | 15.47 | A | N |
| ATOM | 2978 | CA | ALA | A | 363 | 36.345 | −6.545 | 0.264 | 1.00 | 15.85 | A | C |
| ATOM | 2979 | CB | ALA | A | 363 | 35.192 | −6.378 | −0.737 | 1.00 | 13.63 | A | C |
| ATOM | 2980 | C | ALA | A | 363 | 36.043 | −7.692 | 1.209 | 1.00 | 17.54 | A | C |
| ATOM | 2981 | O | ALA | A | 363 | 35.605 | −7.482 | 2.357 | 1.00 | 15.67 | A | O |
| ATOM | 2982 | N | ASP | A | 364 | 36.266 | −8.912 | 0.730 | 1.00 | 17.17 | A | N |

APPENDIX A-continued

P. alba 3T288C coordinates

| ATOM | 2983 | CA | ASP | A | 364 | 36.021 | −10.081 | 1.558 | 1.00 | 19.58 | A | C |
|---|---|---|---|---|---|---|---|---|---|---|---|---|
| ATOM | 2984 | CB | ASP | A | 364 | 36.261 | −11.379 | 0.777 | 1.00 | 18.80 | A | C |
| ATOM | 2985 | CG | ASP | A | 364 | 35.186 | −11.654 | −0.277 | 1.00 | 25.03 | A | C |
| ATOM | 2986 | OD1 | ASP | A | 364 | 34.163 | −10.933 | −0.313 | 1.00 | 24.08 | A | O |
| ATOM | 2987 | OD2 | ASP | A | 364 | 35.411 | −12.586 | −1.089 | 1.00 | 30.13 | A | O |
| ATOM | 2988 | C | ASP | A | 364 | 36.923 | −10.077 | 2.775 | 1.00 | 21.21 | A | C |
| ATOM | 2989 | O | ASP | A | 364 | 36.488 | −10.396 | 3.879 | 1.00 | 22.54 | A | O |
| ATOM | 2990 | N | LEU | A | 365 | 38.180 | −9.700 | 2.602 | 1.00 | 17.93 | A | N |
| ATOM | 2991 | CA | LEU | A | 365 | 39.091 | −9.657 | 3.759 | 1.00 | 15.56 | A | C |
| ATOM | 2992 | CB | LEU | A | 365 | 40.539 | −9.491 | 3.316 | 1.00 | 18.51 | A | C |
| ATOM | 2993 | CG | LEU | A | 365 | 41.573 | −9.334 | 4.445 | 1.00 | 19.97 | A | C |
| ATOM | 2994 | CD1 | LEU | A | 365 | 41.577 | −10.605 | 5.310 | 1.00 | 18.02 | A | C |
| ATOM | 2995 | CD2 | LEU | A | 365 | 42.952 | −9.086 | 3.812 | 1.00 | 18.89 | A | C |
| ATOM | 2996 | C | LEU | A | 365 | 38.705 | −8.584 | 4.751 | 1.00 | 15.45 | A | C |
| ATOM | 2997 | O | LEU | A | 365 | 38.648 | −8.831 | 5.949 | 1.00 | 16.28 | A | O |
| ATOM | 2998 | N | CYS | A | 366 | 38.450 | −7.376 | 4.253 | 1.00 | 16.26 | A | N |
| ATOM | 2999 | CA | CYS | A | 366 | 37.990 | −6.297 | 5.112 | 1.00 | 17.29 | A | C |
| ATOM | 3000 | CB | CYS | A | 366 | 37.850 | −4.994 | 4.322 | 1.00 | 17.89 | A | C |
| ATOM | 3001 | SG | CYS | A | 366 | 39.503 | −4.353 | 3.920 | 1.00 | 21.78 | A | S |
| ATOM | 3002 | C | CYS | A | 366 | 36.698 | −6.658 | 5.838 | 1.00 | 17.80 | A | C |
| ATOM | 3003 | O | CYS | A | 366 | 36.572 | −6.362 | 7.025 | 1.00 | 16.43 | A | O |
| ATOM | 3004 | N | ASN | A | 367 | 35.776 | −7.340 | 5.157 | 1.00 | 18.27 | A | N |
| ATOM | 3005 | CA | ASN | A | 367 | 34.563 | −7.799 | 5.849 | 1.00 | 19.89 | A | C |
| ATOM | 3006 | CB | ASN | A | 367 | 33.480 | −8.314 | 4.879 | 1.00 | 19.83 | A | C |
| ATOM | 3007 | CG | ASN | A | 367 | 32.559 | −7.191 | 4.413 | 1.00 | 22.39 | A | C |
| ATOM | 3008 | OD1 | ASN | A | 367 | 31.795 | −6.645 | 5.211 | 1.00 | 25.95 | A | O |
| ATOM | 3009 | ND2 | ASN | A | 367 | 32.654 | −6.820 | 3.141 | 1.00 | 21.60 | A | N |
| ATOM | 3010 | C | ASN | A | 367 | 34.838 | −8.831 | 6.930 | 1.00 | 17.90 | A | C |
| ATOM | 3011 | O | ASN | A | 367 | 34.139 | −8.845 | 7.947 | 1.00 | 19.27 | A | O |
| ATOM | 3012 | N | ALA | A | 368 | 35.835 | −9.690 | 6.724 | 1.00 | 17.50 | A | N |
| ATOM | 3013 | CA | ALA | A | 368 | 36.199 | −10.694 | 7.735 | 1.00 | 16.98 | A | C |
| ATOM | 3014 | CB | ALA | A | 368 | 37.171 | −11.765 | 7.159 | 1.00 | 15.68 | A | C |
| ATOM | 3015 | C | ALA | A | 368 | 36.829 | −9.969 | 8.953 | 1.00 | 17.79 | A | C |
| ATOM | 3016 | O | ALA | A | 368 | 36.525 | −10.318 | 10.104 | 1.00 | 15.50 | A | O |
| ATOM | 3017 | N | PHE | A | 369 | 37.692 | −8.966 | 8.714 | 1.00 | 17.82 | A | N |
| ATOM | 3018 | CA | PHE | A | 369 | 38.229 | −8.147 | 9.824 | 1.00 | 16.77 | A | C |
| ATOM | 3019 | CB | PHE | A | 369 | 39.221 | −7.071 | 9.339 | 1.00 | 18.30 | A | C |
| ATOM | 3020 | CG | PHE | A | 369 | 40.568 | −7.590 | 8.837 | 1.00 | 19.24 | A | C |
| ATOM | 3021 | CD1 | PHE | A | 369 | 41.131 | −8.763 | 9.306 | 1.00 | 19.40 | A | C |
| ATOM | 3022 | CE1 | PHE | A | 369 | 42.396 | −9.193 | 8.869 | 1.00 | 26.18 | A | C |
| ATOM | 3023 | CZ | PHE | A | 369 | 43.111 | −8.439 | 7.950 | 1.00 | 23.12 | A | C |
| ATOM | 3024 | CE2 | PHE | A | 369 | 42.564 | −7.263 | 7.477 | 1.00 | 22.91 | A | C |
| ATOM | 3025 | CD2 | PHE | A | 369 | 41.304 | −6.828 | 7.940 | 1.00 | 22.68 | A | C |
| ATOM | 3026 | C | PHE | A | 369 | 37.092 | −7.420 | 10.562 | 1.00 | 16.24 | A | C |
| ATOM | 3027 | O | PHE | A | 369 | 37.101 | −7.327 | 11.798 | 1.00 | 16.27 | A | O |
| ATOM | 3028 | N | LEU | A | 370 | 36.156 | −6.842 | 9.815 | 1.00 | 16.48 | A | N |
| ATOM | 3029 | CA | LEU | A | 370 | 35.027 | −6.121 | 10.447 | 1.00 | 16.80 | A | C |
| ATOM | 3030 | CB | LEU | A | 370 | 34.116 | −5.493 | 9.387 | 1.00 | 17.12 | A | C |
| ATOM | 3031 | CG | LEU | A | 370 | 32.976 | −4.592 | 9.855 | 1.00 | 18.29 | A | C |
| ATOM | 3032 | CD1 | LEU | A | 370 | 33.490 | −3.370 | 10.629 | 1.00 | 15.76 | A | C |
| ATOM | 3033 | CD2 | LEU | A | 370 | 32.150 | −4.145 | 8.629 | 1.00 | 18.79 | A | C |
| ATOM | 3034 | C | LEU | A | 370 | 34.220 | −7.045 | 11.361 | 1.00 | 15.54 | A | C |
| ATOM | 3035 | O | LEU | A | 370 | 33.890 | −6.677 | 12.490 | 1.00 | 14.64 | A | O |
| ATOM | 3036 | N | GLN | A | 371 | 33.947 | −8.263 | 10.896 | 1.00 | 16.12 | A | N |
| ATOM | 3037 | CA | GLN | A | 371 | 33.151 | −9.219 | 11.699 | 1.00 | 14.85 | A | C |
| ATOM | 3038 | CB | GLN | A | 371 | 32.855 | −10.487 | 10.893 | 1.00 | 17.23 | A | C |
| ATOM | 3039 | CG | GLN | A | 371 | 32.175 | −11.586 | 11.707 | 1.00 | 20.63 | A | C |
| ATOM | 3040 | CD | GLN | A | 371 | 30.784 | −11.161 | 12.089 | 1.00 | 22.06 | A | C |
| ATOM | 3041 | OE1 | GLN | A | 371 | 30.550 | −10.601 | 13.173 | 1.00 | 21.46 | A | O |
| ATOM | 3042 | NE2 | GLN | A | 371 | 29.874 | −11.320 | 11.162 | 1.00 | 21.27 | A | N |
| ATOM | 3043 | C | GLN | A | 371 | 33.886 | −9.539 | 12.994 | 1.00 | 14.40 | A | C |
| ATOM | 3044 | O | GLN | A | 371 | 33.276 | −9.607 | 14.067 | 1.00 | 14.54 | A | O |
| ATOM | 3045 | N | GLU | A | 372 | 35.212 | −9.653 | 12.932 | 1.00 | 16.62 | A | N |
| ATOM | 3046 | CA | GLU | A | 372 | 36.005 | −9.834 | 14.162 | 1.00 | 19.01 | A | C |
| ATOM | 3047 | CB | GLU | A | 372 | 37.491 | −10.119 | 13.857 | 1.00 | 20.98 | A | C |
| ATOM | 3048 | CG | GLU | A | 372 | 37.711 | −11.554 | 13.396 | 1.00 | 29.08 | A | C |
| ATOM | 3049 | CD | GLU | A | 372 | 39.158 | −11.908 | 12.942 | 1.00 | 33.39 | A | C |
| ATOM | 3050 | OE1 | GLU | A | 372 | 40.011 | −10.990 | 12.711 | 1.00 | 34.79 | A | O |
| ATOM | 3051 | OE2 | GLU | A | 372 | 39.407 | −13.143 | 12.811 | 1.00 | 29.74 | A | O |
| ATOM | 3052 | C | GLU | A | 372 | 35.918 | −8.648 | 15.108 | 1.00 | 17.90 | A | C |
| ATOM | 3053 | O | GLU | A | 372 | 35.813 | −8.810 | 16.310 | 1.00 | 15.75 | A | O |
| ATOM | 3054 | N | ALA | A | 373 | 36.024 | −7.455 | 14.552 | 1.00 | 17.76 | A | N |
| ATOM | 3055 | CA | ALA | A | 373 | 35.941 | −6.235 | 15.352 | 1.00 | 19.33 | A | C |
| ATOM | 3056 | CB | ALA | A | 373 | 36.161 | −5.006 | 14.449 | 1.00 | 17.45 | A | C |
| ATOM | 3057 | C | ALA | A | 373 | 34.559 | −6.177 | 16.042 | 1.00 | 18.40 | A | C |
| ATOM | 3058 | O | ALA | A | 373 | 34.439 | −5.813 | 17.217 | 1.00 | 18.25 | A | O |
| ATOM | 3059 | N | LYS | A | 374 | 33.523 | −6.533 | 15.304 | 1.00 | 18.27 | A | N |
| ATOM | 3060 | CA | LYS | A | 374 | 32.148 | −6.485 | 15.839 | 1.00 | 23.07 | A | C |

APPENDIX A-continued

*P. alba* 3T288C coordinates

| ATOM | 3061 | CB | LYS | A | 374 | 31.127 | −6.708 | 14.722 | 1.00 | 25.62 | A | C |
|---|---|---|---|---|---|---|---|---|---|---|---|---|
| ATOM | 3062 | CG | LYS | A | 374 | 30.946 | −5.491 | 13.852 | 1.00 | 30.72 | A | C |
| ATOM | 3063 | CD | LYS | A | 374 | 29.908 | −5.715 | 12.751 | 1.00 | 33.77 | A | C |
| ATOM | 3064 | CE | LYS | A | 374 | 29.633 | −4.423 | 11.995 | 1.00 | 32.01 | A | C |
| ATOM | 3065 | NZ | LYS | A | 374 | 28.908 | −4.688 | 10.703 | 1.00 | 28.44 | A | N |
| ATOM | 3066 | C | LYS | A | 374 | 31.922 | −7.489 | 16.970 | 1.00 | 21.53 | A | C |
| ATOM | 3067 | O | LYS | A | 374 | 31.345 | −7.148 | 17.994 | 1.00 | 22.96 | A | O |
| ATOM | 3068 | N | TRP | A | 375 | 32.343 | −8.731 | 16.773 | 1.00 | 21.14 | A | N |
| ATOM | 3069 | CA | TRP | A | 375 | 32.234 | −9.734 | 17.824 | 1.00 | 20.44 | A | C |
| ATOM | 3070 | CB | TRP | A | 375 | 32.831 | −11.056 | 17.375 | 1.00 | 17.79 | A | C |
| ATOM | 3071 | CG | TRP | A | 375 | 31.969 | −11.869 | 16.458 | 1.00 | 17.05 | A | C |
| ATOM | 3072 | CD1 | TRP | A | 375 | 30.592 | −11.922 | 16.408 | 1.00 | 19.16 | A | C |
| ATOM | 3073 | NE1 | TRP | A | 375 | 30.175 | −12.815 | 15.454 | 1.00 | 20.51 | A | N |
| ATOM | 3074 | CE2 | TRP | A | 375 | 31.207 | −13.387 | 14.862 | 1.00 | 19.06 | A | C |
| ATOM | 3075 | CD2 | TRP | A | 375 | 32.413 | −12.826 | 15.465 | 1.00 | 16.94 | A | C |
| ATOM | 3076 | CE3 | TRP | A | 375 | 33.651 | −13.251 | 15.017 | 1.00 | 18.68 | A | C |
| ATOM | 3077 | CZ3 | TRP | A | 375 | 33.692 | −14.221 | 14.022 | 1.00 | 18.14 | A | C |
| ATOM | 3078 | CH2 | TRP | A | 375 | 32.516 | −14.753 | 13.457 | 1.00 | 20.50 | A | C |
| ATOM | 3079 | CZ2 | TRP | A | 375 | 31.256 | −14.357 | 13.863 | 1.00 | 18.39 | A | C |
| ATOM | 3080 | C | TRP | A | 375 | 32.934 | −9.300 | 19.096 | 1.00 | 24.17 | A | C |
| ATOM | 3081 | O | TRP | A | 375 | 32.446 | −9.538 | 20.197 | 1.00 | 23.79 | A | O |
| ATOM | 3082 | N | LEU | A | 376 | 34.094 | −8.684 | 18.954 | 1.00 | 21.61 | A | N |
| ATOM | 3083 | CA | LEU | A | 376 | 34.879 | −8.243 | 20.111 | 1.00 | 25.50 | A | C |
| ATOM | 3084 | CB | LEU | A | 376 | 36.252 | −7.756 | 19.649 | 1.00 | 29.13 | A | C |
| ATOM | 3085 | CG | LEU | A | 376 | 37.352 | −7.786 | 20.704 | 1.00 | 40.86 | A | C |
| ATOM | 3086 | CD1 | LEU | A | 376 | 37.818 | −9.236 | 20.886 | 1.00 | 47.30 | A | C |
| ATOM | 3087 | CD2 | LEU | A | 376 | 38.521 | −6.872 | 20.313 | 1.00 | 40.17 | A | C |
| ATOM | 3088 | C | LEU | A | 376 | 34.173 | −7.108 | 20.853 | 1.00 | 24.00 | A | C |
| ATOM | 3089 | O | LEU | A | 376 | 34.076 | −7.113 | 22.072 | 1.00 | 24.75 | A | O |
| ATOM | 3090 | N | TYR | A | 377 | 33.682 | −6.135 | 20.094 | 1.00 | 21.41 | A | N |
| ATOM | 3091 | CA | TYR | A | 377 | 33.004 | −4.999 | 20.663 | 1.00 | 22.87 | A | C |
| ATOM | 3092 | CB | TYR | A | 377 | 32.630 | −4.002 | 19.556 | 1.00 | 25.18 | A | C |
| ATOM | 3093 | CG | TYR | A | 377 | 31.858 | −2.792 | 20.054 | 1.00 | 27.72 | A | C |
| ATOM | 3094 | CD1 | TYR | A | 377 | 32.491 | −1.794 | 20.806 | 1.00 | 34.13 | A | C |
| ATOM | 3095 | CE1 | TYR | A | 377 | 31.777 | −0.673 | 21.288 | 1.00 | 36.47 | A | C |
| ATOM | 3096 | CZ | TYR | A | 377 | 30.425 | −0.549 | 21.001 | 1.00 | 38.76 | A | C |
| ATOM | 3097 | OH | TYR | A | 377 | 29.719 | 0.539 | 21.465 | 1.00 | 46.84 | A | O |
| ATOM | 3098 | CE2 | TYR | A | 377 | 29.773 | −1.526 | 20.248 | 1.00 | 38.56 | A | C |
| ATOM | 3099 | CD2 | TYR | A | 377 | 30.499 | −2.641 | 19.776 | 1.00 | 33.27 | A | C |
| ATOM | 3100 | C | TYR | A | 377 | 31.742 | −5.446 | 21.425 | 1.00 | 26.24 | A | C |
| ATOM | 3101 | O | TYR | A | 377 | 31.482 | −4.971 | 22.514 | 1.00 | 26.71 | A | O |
| ATOM | 3102 | N | ASN | A | 378 | 30.958 | −6.344 | 20.829 | 1.00 | 24.22 | A | N |
| ATOM | 3103 | CA | ASN | A | 378 | 29.704 | −6.794 | 21.429 | 1.00 | 27.32 | A | C |
| ATOM | 3104 | CB | ASN | A | 378 | 28.724 | −7.198 | 20.341 | 1.00 | 28.78 | A | C |
| ATOM | 3105 | CG | ASN | A | 378 | 28.337 | −6.036 | 19.460 | 1.00 | 28.02 | A | C |
| ATOM | 3106 | OD1 | ASN | A | 378 | 28.096 | −4.938 | 19.937 | 1.00 | 36.83 | A | O |
| ATOM | 3107 | ND2 | ASN | A | 378 | 28.263 | −6.275 | 18.176 | 1.00 | 34.11 | A | N |
| ATOM | 3108 | C | ASN | A | 378 | 29.896 | −7.947 | 22.393 | 1.00 | 26.44 | A | C |
| ATOM | 3109 | O | ASN | A | 378 | 28.933 | −8.441 | 22.949 | 1.00 | 22.29 | A | O |
| ATOM | 3110 | N | LYS | A | 379 | 31.144 | −8.371 | 22.584 | 1.00 | 27.62 | A | N |
| ATOM | 3111 | CA | LYS | A | 379 | 31.454 | −9.531 | 23.411 | 1.00 | 28.83 | A | C |
| ATOM | 3112 | CB | LYS | A | 379 | 31.256 | −9.169 | 24.895 | 1.00 | 31.31 | A | C |
| ATOM | 3113 | CG | LYS | A | 379 | 32.247 | −8.093 | 25.353 | 1.00 | 38.56 | A | C |
| ATOM | 3114 | CD | LYS | A | 379 | 31.787 | −7.303 | 26.564 | 1.00 | 45.70 | A | C |
| ATOM | 3115 | CE | LYS | A | 379 | 32.906 | −6.401 | 27.055 | 1.00 | 47.62 | A | C |
| ATOM | 3116 | NZ | LYS | A | 379 | 32.469 | −5.534 | 28.178 | 1.00 | 57.66 | A | N |
| ATOM | 3117 | C | LYS | A | 379 | 30.638 | −10.765 | 22.980 | 1.00 | 25.15 | A | C |
| ATOM | 3118 | O | LYS | A | 379 | 30.102 | −11.492 | 23.807 | 1.00 | 28.12 | A | O |
| ATOM | 3119 | N | SER | A | 380 | 30.545 | −10.992 | 21.675 | 1.00 | 24.80 | A | N |
| ATOM | 3120 | CA | SER | A | 380 | 29.787 | −12.121 | 21.144 | 1.00 | 22.46 | A | C |
| ATOM | 3121 | CB | SER | A | 380 | 29.565 | −11.957 | 19.645 | 1.00 | 24.96 | A | C |
| ATOM | 3122 | OG | SER | A | 380 | 29.059 | −10.652 | 19.336 | 1.00 | 20.52 | A | O |
| ATOM | 3123 | C | SER | A | 380 | 30.510 | −13.425 | 21.458 | 1.00 | 22.51 | A | C |
| ATOM | 3124 | O | SER | A | 380 | 31.691 | −13.437 | 21.764 | 1.00 | 27.18 | A | O |
| ATOM | 3125 | N | THR | A | 381 | 29.773 | −14.520 | 21.429 | 1.00 | 22.40 | A | N |
| ATOM | 3126 | CA | THR | A | 381 | 30.302 | −15.827 | 21.715 | 1.00 | 22.08 | A | C |
| ATOM | 3127 | CB | THR | A | 381 | 29.715 | −16.422 | 23.058 | 1.00 | 24.95 | A | C |
| ATOM | 3128 | OG1 | THR | A | 381 | 28.288 | −16.450 | 22.963 | 1.00 | 26.79 | A | O |
| ATOM | 3129 | CG2 | THR | A | 381 | 30.081 | −15.588 | 24.317 | 1.00 | 21.92 | A | C |
| ATOM | 3130 | C | THR | A | 381 | 29.868 | −16.700 | 20.537 | 1.00 | 23.52 | A | C |
| ATOM | 3131 | O | THR | A | 381 | 29.037 | −17.575 | 20.699 | 1.00 | 23.64 | A | O |
| ATOM | 3132 | N | PRO | A | 382 | 30.413 | −16.462 | 19.333 | 1.00 | 22.31 | A | N |
| ATOM | 3133 | CA | PRO | A | 382 | 30.015 | −17.325 | 18.219 | 1.00 | 18.54 | A | C |
| ATOM | 3134 | CB | PRO | A | 382 | 30.707 | −16.680 | 17.017 | 1.00 | 22.53 | A | C |
| ATOM | 3135 | CG | PRO | A | 382 | 31.991 | −16.111 | 17.629 | 1.00 | 22.28 | A | C |
| ATOM | 3136 | CD | PRO | A | 382 | 31.444 | −15.491 | 18.934 | 1.00 | 22.64 | A | C |
| ATOM | 3137 | C | PRO | A | 382 | 30.536 | −18.749 | 18.416 | 1.00 | 21.29 | A | C |
| ATOM | 3138 | O | PRO | A | 382 | 31.526 | −18.964 | 19.124 | 1.00 | 24.96 | A | O |

APPENDIX A-continued

*P. alba* 3T288C coordinates

| ATOM | 3139 | N | THR | A | 383 | 29.893 | −19.707 | 17.763 | 1.00 | 20.15 | A | N |
|---|---|---|---|---|---|---|---|---|---|---|---|---|
| ATOM | 3140 | CA | THR | A | 383 | 30.333 | −21.085 | 17.802 | 1.00 | 23.53 | A | C |
| ATOM | 3141 | CB | THR | A | 383 | 29.357 | −21.983 | 17.034 | 1.00 | 28.25 | A | C |
| ATOM | 3142 | OG1 | THR | A | 383 | 29.399 | −21.622 | 15.645 | 1.00 | 23.26 | A | O |
| ATOM | 3143 | CG2 | THR | A | 383 | 27.905 | −21.865 | 17.595 | 1.00 | 24.27 | A | C |
| ATOM | 3144 | C | THR | A | 383 | 31.706 | −21.213 | 17.128 | 1.00 | 25.20 | A | C |
| ATOM | 3145 | O | THR | A | 383 | 32.118 | −20.315 | 16.401 | 1.00 | 22.28 | A | O |
| ATOM | 3146 | N | PHE | A | 384 | 32.397 | −22.329 | 17.372 | 1.00 | 24.54 | A | N |
| ATOM | 3147 | CA | PHE | A | 384 | 33.639 | −22.623 | 16.685 | 1.00 | 23.44 | A | C |
| ATOM | 3148 | CB | PHE | A | 384 | 34.224 | −23.977 | 17.066 | 1.00 | 24.59 | A | C |
| ATOM | 3149 | CG | PHE | A | 384 | 35.441 | −24.332 | 16.261 | 1.00 | 22.84 | A | C |
| ATOM | 3150 | CD1 | PHE | A | 384 | 36.661 | −23.788 | 16.571 | 1.00 | 22.31 | A | C |
| ATOM | 3151 | CE1 | PHE | A | 384 | 37.787 | −24.069 | 15.826 | 1.00 | 22.72 | A | C |
| ATOM | 3152 | CZ | PHE | A | 384 | 37.705 | −24.897 | 14.743 | 1.00 | 23.44 | A | C |
| ATOM | 3153 | CE2 | PHE | A | 384 | 36.490 | −25.439 | 14.390 | 1.00 | 23.71 | A | C |
| ATOM | 3154 | CD2 | PHE | A | 384 | 35.350 | −25.152 | 15.155 | 1.00 | 21.29 | A | C |
| ATOM | 3155 | C | PHE | A | 384 | 33.479 | −22.568 | 15.188 | 1.00 | 21.88 | A | C |
| ATOM | 3156 | O | PHE | A | 384 | 34.320 | −21.991 | 14.505 | 1.00 | 20.61 | A | O |
| ATOM | 3157 | N | ASP | A | 385 | 32.456 | −23.210 | 14.652 | 1.00 | 20.33 | A | N |
| ATOM | 3158 | CA | ASP | A | 385 | 32.313 | −23.230 | 13.193 | 1.00 | 23.64 | A | C |
| ATOM | 3159 | CB | ASP | A | 385 | 31.123 | −24.069 | 12.735 | 1.00 | 28.59 | A | C |
| ATOM | 3160 | CG | ASP | A | 385 | 31.343 | −25.578 | 12.918 | 1.00 | 34.42 | A | C |
| ATOM | 3161 | OD1 | ASP | A | 385 | 32.495 | −26.056 | 12.965 | 1.00 | 30.99 | A | O |
| ATOM | 3162 | OD2 | ASP | A | 385 | 30.332 | −26.289 | 13.005 | 1.00 | 39.78 | A | O |
| ATOM | 3163 | C | ASP | A | 385 | 32.186 | −21.821 | 12.612 | 1.00 | 24.06 | A | C |
| ATOM | 3164 | O | ASP | A | 385 | 32.748 | −21.550 | 11.562 | 1.00 | 21.14 | A | O |
| ATOM | 3165 | N | ASP | A | 386 | 31.429 | −20.951 | 13.269 | 1.00 | 20.63 | A | N |
| ATOM | 3166 | CA | ASP | A | 386 | 31.252 | −19.587 | 12.770 | 1.00 | 22.72 | A | C |
| ATOM | 3167 | CB | ASP | A | 386 | 30.090 | −18.890 | 13.457 | 1.00 | 23.71 | A | C |
| ATOM | 3168 | CG | ASP | A | 386 | 28.732 | −19.369 | 12.936 | 1.00 | 32.71 | A | C |
| ATOM | 3169 | OD1 | ASP | A | 386 | 28.706 | −20.087 | 11.917 | 1.00 | 33.39 | A | O |
| ATOM | 3170 | OD2 | ASP | A | 386 | 27.696 | −19.008 | 13.532 | 1.00 | 37.76 | A | O |
| ATOM | 3171 | C | ASP | A | 386 | 32.525 | −18.757 | 12.913 | 1.00 | 22.35 | A | C |
| ATOM | 3172 | O | ASP | A | 386 | 32.924 | −18.085 | 11.951 | 1.00 | 21.45 | A | O |
| ATOM | 3173 | N | TYR | A | 387 | 33.150 | −18.819 | 14.095 | 1.00 | 19.24 | A | N |
| ATOM | 3174 | CA | TYR | A | 387 | 34.385 | −18.120 | 14.344 | 1.00 | 18.73 | A | C |
| ATOM | 3175 | CB | TYR | A | 387 | 34.912 | −18.343 | 15.766 | 1.00 | 21.24 | A | C |
| ATOM | 3176 | CG | TYR | A | 387 | 36.143 | −17.508 | 16.016 | 1.00 | 20.82 | A | C |
| ATOM | 3177 | CD1 | TYR | A | 387 | 36.025 | −16.151 | 16.308 | 1.00 | 24.25 | A | C |
| ATOM | 3178 | CE1 | TYR | A | 387 | 37.148 | −15.359 | 16.491 | 1.00 | 27.11 | A | C |
| ATOM | 3179 | CZ | TYR | A | 387 | 38.411 | −15.922 | 16.349 | 1.00 | 24.94 | A | C |
| ATOM | 3180 | OH | TYR | A | 387 | 39.505 | −15.131 | 16.526 | 1.00 | 25.59 | A | O |
| ATOM | 3181 | CE2 | TYR | A | 387 | 38.555 | −17.257 | 16.033 | 1.00 | 24.64 | A | C |
| ATOM | 3182 | CD2 | TYR | A | 387 | 37.423 | −18.044 | 15.861 | 1.00 | 24.24 | A | C |
| ATOM | 3183 | C | TYR | A | 387 | 35.455 | −18.539 | 13.355 | 1.00 | 20.98 | A | C |
| ATOM | 3184 | O | TYR | A | 387 | 36.068 | −17.699 | 12.693 | 1.00 | 15.42 | A | O |
| ATOM | 3185 | N | PHE | A | 388 | 35.679 | −19.843 | 13.247 | 1.00 | 19.21 | A | N |
| ATOM | 3186 | CA | PHE | A | 388 | 36.772 | −20.357 | 12.411 | 1.00 | 19.17 | A | C |
| ATOM | 3187 | CB | PHE | A | 388 | 36.991 | −21.843 | 12.681 | 1.00 | 20.60 | A | C |
| ATOM | 3188 | CG | PHE | A | 388 | 38.101 | −22.427 | 11.904 | 1.00 | 19.86 | A | C |
| ATOM | 3189 | CD1 | PHE | A | 388 | 39.403 | −22.056 | 12.155 | 1.00 | 21.76 | A | C |
| ATOM | 3190 | CE1 | PHE | A | 388 | 40.433 | −22.577 | 11.410 | 1.00 | 22.56 | A | C |
| ATOM | 3191 | CZ | PHE | A | 388 | 40.172 | −23.493 | 10.430 | 1.00 | 19.58 | A | C |
| ATOM | 3192 | CE2 | PHE | A | 388 | 38.899 | −23.862 | 10.156 | 1.00 | 20.94 | A | C |
| ATOM | 3193 | CD2 | PHE | A | 388 | 37.849 | −23.317 | 10.890 | 1.00 | 20.92 | A | C |
| ATOM | 3194 | C | PHE | A | 388 | 36.539 | −20.100 | 10.935 | 1.00 | 19.06 | A | C |
| ATOM | 3195 | O | PHE | A | 388 | 37.497 | −19.788 | 10.188 | 1.00 | 17.17 | A | O |
| ATOM | 3196 | N | GLY | A | 389 | 35.272 | −20.191 | 10.528 | 1.00 | 19.37 | A | N |
| ATOM | 3197 | CA | GLY | A | 389 | 34.882 | −19.911 | 9.159 | 1.00 | 22.43 | A | C |
| ATOM | 3198 | C | GLY | A | 389 | 35.304 | −18.514 | 8.761 | 1.00 | 19.92 | A | C |
| ATOM | 3199 | O | GLY | A | 389 | 35.929 | −18.307 | 7.713 | 1.00 | 20.11 | A | O |
| ATOM | 3200 | N | ASN | A | 390 | 35.047 | −17.560 | 9.644 | 1.00 | 19.07 | A | N |
| ATOM | 3201 | CA | ASN | A | 390 | 35.560 | −16.207 | 9.435 | 1.00 | 18.25 | A | C |
| ATOM | 3202 | CB | ASN | A | 390 | 34.861 | −15.268 | 10.395 | 1.00 | 17.19 | A | C |
| ATOM | 3203 | CG | ASN | A | 390 | 35.081 | −13.821 | 10.048 | 1.00 | 16.60 | A | C |
| ATOM | 3204 | OD1 | ASN | A | 390 | 34.530 | −13.343 | 9.095 | 1.00 | 16.51 | A | O |
| ATOM | 3205 | ND2 | ASN | A | 390 | 35.892 | −13.121 | 10.836 | 1.00 | 13.78 | A | N |
| ATOM | 3206 | C | ASN | A | 390 | 37.098 | −16.077 | 9.543 | 1.00 | 17.48 | A | C |
| ATOM | 3207 | O | ASN | A | 390 | 37.734 | −15.345 | 8.758 | 1.00 | 18.21 | A | O |
| ATOM | 3208 | N | ALA | A | 391 | 37.684 | −16.754 | 10.531 | 1.00 | 18.86 | A | N |
| ATOM | 3209 | CA | ALA | A | 391 | 39.105 | −16.616 | 10.877 | 1.00 | 17.38 | A | C |
| ATOM | 3210 | CB | ALA | A | 391 | 39.410 | −17.321 | 12.235 | 1.00 | 17.83 | A | C |
| ATOM | 3211 | C | ALA | A | 391 | 40.057 | −17.117 | 9.793 | 1.00 | 16.51 | A | C |
| ATOM | 3212 | O | ALA | A | 391 | 41.133 | −16.558 | 9.609 | 1.00 | 16.69 | A | O |
| ATOM | 3213 | N | TRP | A | 392 | 39.708 | −18.166 | 9.070 | 1.00 | 17.06 | A | N |
| ATOM | 3214 | CA | TRP | A | 392 | 40.571 | −18.582 | 7.987 | 1.00 | 17.60 | A | C |
| ATOM | 3215 | CB | TRP | A | 392 | 40.433 | −20.048 | 7.559 | 1.00 | 16.27 | A | C |
| ATOM | 3216 | CG | TRP | A | 392 | 39.154 | −20.481 | 6.953 | 1.00 | 16.13 | A | C |

APPENDIX A-continued

*P. alba* 3T288C coordinates

| ATOM | 3217 | CD1 | TRP | A | 392 | 38.125 | −21.201 | 7.565 | 1.00 | 21.78 | A | C |
|---|---|---|---|---|---|---|---|---|---|---|---|---|
| ATOM | 3218 | NE1 | TRP | A | 392 | 37.101 | −21.404 | 6.705 | 1.00 | 19.34 | A | N |
| ATOM | 3219 | CE2 | TRP | A | 392 | 37.397 | −20.927 | 5.496 | 1.00 | 20.92 | A | C |
| ATOM | 3220 | CD2 | TRP | A | 392 | 38.704 | −20.278 | 5.591 | 1.00 | 18.15 | A | C |
| ATOM | 3221 | CE3 | TRP | A | 392 | 39.256 | −19.693 | 4.463 | 1.00 | 16.56 | A | C |
| ATOM | 3222 | CZ3 | TRP | A | 392 | 38.521 | −19.736 | 3.287 | 1.00 | 19.13 | A | C |
| ATOM | 3223 | CH2 | TRP | A | 392 | 37.256 | −20.360 | 3.222 | 1.00 | 21.25 | A | C |
| ATOM | 3224 | CZ2 | TRP | A | 392 | 36.681 | −20.974 | 4.320 | 1.00 | 21.97 | A | C |
| ATOM | 3225 | C | TRP | A | 392 | 40.507 | −17.626 | 6.846 | 1.00 | 18.28 | A | C |
| ATOM | 3226 | O | TRP | A | 392 | 41.498 | −17.497 | 6.152 | 1.00 | 18.17 | A | O |
| ATOM | 3227 | N | LYS | A | 393 | 39.399 | −16.918 | 6.649 | 1.00 | 18.78 | A | N |
| ATOM | 3228 | CA | ALYS | A | 393 | 39.388 | −15.804 | 5.681 | 0.50 | 20.43 | A | C |
| ATOM | 3229 | CA | BLYS | A | 393 | 39.371 | −15.803 | 5.682 | 0.50 | 20.39 | A | C |
| ATOM | 3230 | CB | ALYS | A | 393 | 37.957 | −15.372 | 5.372 | 0.50 | 20.93 | A | C |
| ATOM | 3231 | CB | BLYS | A | 393 | 37.926 | −15.367 | 5.411 | 0.50 | 20.85 | A | C |
| ATOM | 3232 | CG | ALYS | A | 393 | 37.194 | −16.439 | 4.616 | 0.50 | 25.28 | A | C |
| ATOM | 3233 | CG | BLYS | A | 393 | 37.100 | −16.414 | 4.649 | 0.50 | 25.10 | A | C |
| ATOM | 3234 | CD | ALYS | A | 393 | 35.912 | −15.946 | 3.994 | 0.50 | 25.25 | A | C |
| ATOM | 3235 | CD | BLYS | A | 393 | 35.588 | −16.182 | 4.735 | 0.50 | 25.71 | A | C |
| ATOM | 3236 | CE | ALYS | A | 393 | 35.147 | −17.080 | 3.303 | 0.50 | 28.64 | A | C |
| ATOM | 3237 | CE | BLYS | A | 393 | 34.747 | −17.391 | 4.218 | 0.50 | 29.85 | A | C |
| ATOM | 3238 | NZ | ALYS | A | 393 | 33.835 | −16.643 | 2.731 | 0.50 | 30.37 | A | N |
| ATOM | 3239 | NZ | BLYS | A | 393 | 34.371 | −18.403 | 5.275 | 0.50 | 26.32 | A | N |
| ATOM | 3240 | C | LYS | A | 393 | 40.215 | −14.594 | 6.157 | 1.00 | 21.19 | A | C |
| ATOM | 3241 | O | LYS | A | 393 | 40.978 | −13.980 | 5.370 | 1.00 | 19.62 | A | O |
| ATOM | 3242 | N | SER | A | 394 | 40.081 | −14.258 | 7.435 | 1.00 | 18.93 | A | N |
| ATOM | 3243 | CA | SER | A | 394 | 40.788 | −13.129 | 8.020 | 1.00 | 18.32 | A | C |
| ATOM | 3244 | CB | SER | A | 394 | 40.208 | −12.768 | 9.390 | 1.00 | 19.03 | A | C |
| ATOM | 3245 | OG | SER | A | 394 | 40.696 | −13.614 | 10.427 | 1.00 | 21.24 | A | O |
| ATOM | 3246 | C | SER | A | 394 | 42.274 | −13.343 | 8.152 | 1.00 | 20.59 | A | C |
| ATOM | 3247 | O | SER | A | 394 | 43.010 | −12.383 | 8.365 | 1.00 | 18.07 | A | O |
| ATOM | 3248 | N | SER | A | 395 | 42.742 | −14.588 | 8.032 | 1.00 | 17.06 | A | N |
| ATOM | 3249 | CA | SER | A | 395 | 44.179 | −14.855 | 7.974 | 1.00 | 17.63 | A | C |
| ATOM | 3250 | CB | SER | A | 395 | 44.442 | −16.380 | 7.806 | 1.00 | 18.39 | A | C |
| ATOM | 3251 | OG | SER | A | 395 | 44.064 | −16.824 | 6.517 | 1.00 | 17.46 | A | O |
| ATOM | 3252 | C | SER | A | 395 | 44.844 | −14.108 | 6.831 | 1.00 | 15.64 | A | C |
| ATOM | 3253 | O | SER | A | 395 | 46.028 | −13.801 | 6.885 | 1.00 | 16.53 | A | O |
| ATOM | 3254 | N | SER | A | 396 | 44.084 | −13.900 | 5.774 | 1.00 | 13.99 | A | N |
| ATOM | 3255 | CA | SER | A | 396 | 44.517 | −13.353 | 4.485 | 1.00 | 16.21 | A | C |
| ATOM | 3256 | CB | SER | A | 396 | 45.480 | −12.161 | 4.627 | 1.00 | 19.71 | A | C |
| ATOM | 3257 | OG | SER | A | 396 | 46.832 | −12.545 | 4.880 | 1.00 | 18.63 | A | O |
| ATOM | 3258 | C | SER | A | 396 | 45.086 | −14.424 | 3.541 | 1.00 | 18.46 | A | C |
| ATOM | 3259 | O | SER | A | 396 | 45.476 | −14.115 | 2.407 | 1.00 | 18.03 | A | O |
| ATOM | 3260 | N | GLY | A | 397 | 45.096 | −15.681 | 3.985 | 1.00 | 20.43 | A | N |
| ATOM | 3261 | CA | GLY | A | 397 | 45.534 | −16.792 | 3.112 | 1.00 | 17.12 | A | C |
| ATOM | 3262 | C | GLY | A | 397 | 44.851 | −16.817 | 1.771 | 1.00 | 18.07 | A | C |
| ATOM | 3263 | O | GLY | A | 397 | 45.497 | −16.922 | 0.700 | 1.00 | 20.20 | A | O |
| ATOM | 3264 | N | PRO | A | 398 | 43.530 | −16.729 | 1.775 | 1.00 | 14.60 | A | N |
| ATOM | 3265 | CA | PRO | A | 398 | 42.879 | −16.744 | 0.495 | 1.00 | 15.16 | A | C |
| ATOM | 3266 | CB | PRO | A | 398 | 41.396 | −16.743 | 0.852 | 1.00 | 15.38 | A | C |
| ATOM | 3267 | CG | PRO | A | 398 | 41.355 | −17.315 | 2.211 | 1.00 | 17.75 | A | C |
| ATOM | 3268 | CD | PRO | A | 398 | 42.564 | −16.797 | 2.877 | 1.00 | 14.99 | A | C |
| ATOM | 3269 | C | PRO | A | 398 | 43.195 | −15.562 | −0.417 | 1.00 | 15.54 | A | C |
| ATOM | 3270 | O | PRO | A | 398 | 43.388 | −15.756 | −1.632 | 1.00 | 19.95 | A | O |
| ATOM | 3271 | N | LEU | A | 399 | 43.227 | −14.368 | 0.139 | 1.00 | 16.00 | A | N |
| ATOM | 3272 | CA | LEU | A | 399 | 43.647 | −13.182 | −0.626 | 1.00 | 15.47 | A | C |
| ATOM | 3273 | CB | LEU | A | 399 | 43.569 | −11.934 | 0.257 | 1.00 | 16.63 | A | C |
| ATOM | 3274 | CG | LEU | A | 399 | 43.910 | −10.633 | −0.493 | 1.00 | 16.79 | A | C |
| ATOM | 3275 | CD1 | LEU | A | 399 | 42.989 | −9.511 | −0.045 | 1.00 | 18.57 | A | C |
| ATOM | 3276 | CD2 | LEU | A | 399 | 45.414 | −10.269 | −0.216 | 1.00 | 15.49 | A | C |
| ATOM | 3277 | C | LEU | A | 399 | 45.051 | −13.336 | −1.210 | 1.00 | 14.23 | A | C |
| ATOM | 3278 | O | LEU | A | 399 | 45.267 | −13.094 | −2.399 | 1.00 | 15.49 | A | O |
| ATOM | 3279 | N | GLN | A | 400 | 45.999 | −13.803 | −0.397 | 1.00 | 15.09 | A | N |
| ATOM | 3280 | CA | GLN | A | 400 | 47.363 | −13.983 | −0.888 | 1.00 | 17.64 | A | C |
| ATOM | 3281 | CB | GLN | A | 400 | 48.268 | −14.492 | 0.234 | 1.00 | 20.37 | A | C |
| ATOM | 3282 | CG | GLN | A | 400 | 48.579 | −13.424 | 1.234 | 1.00 | 23.95 | A | C |
| ATOM | 3283 | CD | GLN | A | 400 | 49.511 | −13.940 | 2.292 | 1.00 | 27.25 | A | C |
| ATOM | 3284 | OE1 | GLN | A | 400 | 50.419 | −14.720 | 1.985 | 1.00 | 26.60 | A | O |
| ATOM | 3285 | NE2 | GLN | A | 400 | 49.238 | −13.594 | 3.557 | 1.00 | 26.70 | A | N |
| ATOM | 3286 | C | GLN | A | 400 | 47.416 | −14.931 | −2.047 | 1.00 | 18.18 | A | C |
| ATOM | 3287 | O | GLN | A | 400 | 48.123 | −14.697 | −3.043 | 1.00 | 16.77 | A | O |
| ATOM | 3288 | N | LEU | A | 401 | 46.636 | −16.000 | −1.944 | 1.00 | 18.75 | A | N |
| ATOM | 3289 | CA | LEU | A | 401 | 46.602 | −17.008 | −3.001 | 1.00 | 18.96 | A | C |
| ATOM | 3290 | CB | LEU | A | 401 | 46.059 | −18.360 | −2.475 | 1.00 | 16.12 | A | C |
| ATOM | 3291 | CG | LEU | A | 401 | 47.039 | −18.982 | −1.457 | 1.00 | 18.92 | A | C |
| ATOM | 3292 | CD1 | LEU | A | 401 | 46.386 | −20.203 | −0.807 | 1.00 | 19.18 | A | C |
| ATOM | 3293 | CD2 | LEU | A | 401 | 48.402 | −19.322 | −2.151 | 1.00 | 20.53 | A | C |
| ATOM | 3294 | C | LEU | A | 401 | 45.870 | −16.554 | −4.264 | 1.00 | 19.96 | A | C |

APPENDIX A-continued

P. alba 3T288C coordinates

| ATOM | 3295 | O | LEU | A | 401 | 46.218 | −17.023 | −5.345 | 1.00 | 21.04 | A | O |
|------|------|------|------|---|-----|--------|---------|--------|------|--------|---|---|
| ATOM | 3296 | N | VAL | A | 402 | 44.849 | −15.683 | −4.153 | 1.00 | 20.26 | A | N |
| ATOM | 3297 | CA | VAL | A | 402 | 44.254 | −15.057 | −5.356 | 1.00 | 19.68 | A | C |
| ATOM | 3298 | CB | VAL | A | 402 | 43.032 | −14.169 | −5.008 | 1.00 | 24.51 | A | C |
| ATOM | 3299 | CG1 | VAL | A | 402 | 42.644 | −13.289 | −6.187 | 1.00 | 24.17 | A | C |
| ATOM | 3300 | CG2 | VAL | A | 402 | 41.867 | −15.025 | −4.516 | 1.00 | 21.62 | A | C |
| ATOM | 3301 | C | VAL | A | 402 | 45.314 | −14.226 | −6.095 | 1.00 | 18.36 | A | C |
| ATOM | 3302 | O | VAL | A | 402 | 45.444 | −14.323 | −7.336 | 1.00 | 21.99 | A | O |
| ATOM | 3303 | N | PHE | A | 403 | 46.073 | −13.399 | −5.351 | 1.00 | 19.82 | A | N |
| ATOM | 3304 | CA | PHE | A | 403 | 47.158 | −12.610 | −5.987 | 1.00 | 18.45 | A | C |
| ATOM | 3305 | CB | PHE | A | 403 | 47.726 | −11.592 | −5.012 | 1.00 | 19.39 | A | C |
| ATOM | 3306 | CG | PHE | A | 403 | 46.873 | −10.346 | −4.913 | 1.00 | 16.10 | A | C |
| ATOM | 3307 | CD1 | PHE | A | 403 | 45.717 | −10.339 | −4.154 | 1.00 | 14.60 | A | C |
| ATOM | 3308 | CE1 | PHE | A | 403 | 44.902 | −9.224 | −4.075 | 1.00 | 17.25 | A | C |
| ATOM | 3309 | CZ | PHE | A | 403 | 45.257 | −8.087 | −4.779 | 1.00 | 17.90 | A | C |
| ATOM | 3310 | CE2 | PHE | A | 403 | 46.410 | −8.092 | −5.581 | 1.00 | 16.80 | A | C |
| ATOM | 3311 | CD2 | PHE | A | 403 | 47.197 | −9.219 | −5.662 | 1.00 | 17.29 | A | C |
| ATOM | 3312 | C | PHE | A | 403 | 48.246 | −13.532 | −6.558 | 1.00 | 23.74 | A | C |
| ATOM | 3313 | O | PHE | A | 403 | 48.750 | −13.312 | −7.675 | 1.00 | 19.63 | A | O |
| ATOM | 3314 | N | ALA | A | 404 | 48.593 | −14.580 | −5.817 | 1.00 | 20.65 | A | N |
| ATOM | 3315 | CA | ALA | A | 404 | 49.583 | −15.566 | −6.308 | 1.00 | 21.07 | A | C |
| ATOM | 3316 | CB | ALA | A | 404 | 49.949 | −16.642 | −5.195 | 1.00 | 19.70 | A | C |
| ATOM | 3317 | C | ALA | A | 404 | 49.143 | −16.225 | −7.610 | 1.00 | 19.16 | A | C |
| ATOM | 3318 | O | ALA | A | 404 | 49.966 | −16.411 | −8.526 | 1.00 | 20.37 | A | O |
| ATOM | 3319 | N | TYR | A | 405 | 47.860 | −16.564 | −7.714 | 1.00 | 17.02 | A | N |
| ATOM | 3320 | CA | TYR | A | 405 | 47.319 | −17.163 | −8.894 | 1.00 | 18.48 | A | C |
| ATOM | 3321 | CB | TYR | A | 405 | 45.804 | −17.389 | −8.788 | 1.00 | 18.61 | A | C |
| ATOM | 3322 | CG | TYR | A | 405 | 45.193 | −17.855 | −10.085 | 1.00 | 22.58 | A | C |
| ATOM | 3323 | CD1 | TYR | A | 405 | 45.158 | −19.214 | −10.433 | 1.00 | 25.30 | A | C |
| ATOM | 3324 | CE1 | TYR | A | 405 | 44.627 | −19.625 | −11.636 | 1.00 | 27.03 | A | C |
| ATOM | 3325 | CZ | TYR | A | 405 | 44.104 | −18.691 | −12.493 | 1.00 | 25.58 | A | C |
| ATOM | 3326 | OH | TYR | A | 405 | 43.547 | −19.037 | −13.713 | 1.00 | 26.03 | A | O |
| ATOM | 3327 | CE2 | TYR | A | 405 | 44.114 | −17.358 | −12.143 | 1.00 | 25.76 | A | C |
| ATOM | 3328 | CD2 | TYR | A | 405 | 44.640 | −16.961 | −10.959 | 1.00 | 23.26 | A | C |
| ATOM | 3329 | C | TYR | A | 405 | 47.652 | −16.319 | −10.106 | 1.00 | 24.78 | A | C |
| ATOM | 3330 | O | TYR | A | 405 | 48.141 | −16.840 | −11.120 | 1.00 | 21.81 | A | O |
| ATOM | 3331 | N | PHE | A | 406 | 47.401 | −15.009 | −10.030 | 1.00 | 19.07 | A | N |
| ATOM | 3332 | CA | PHE | A | 406 | 47.605 | −14.172 | −11.232 | 1.00 | 21.54 | A | C |
| ATOM | 3333 | CB | PHE | A | 406 | 46.856 | −12.857 | −11.077 | 1.00 | 20.15 | A | C |
| ATOM | 3334 | CG | PHE | A | 406 | 45.371 | −13.037 | −11.081 | 1.00 | 18.61 | A | C |
| ATOM | 3335 | CD1 | PHE | A | 406 | 44.724 | −13.352 | −12.235 | 1.00 | 19.65 | A | C |
| ATOM | 3336 | CE1 | PHE | A | 406 | 43.366 | −13.523 | −12.253 | 1.00 | 18.37 | A | C |
| ATOM | 3337 | CZ | PHE | A | 406 | 42.654 | −13.379 | −11.125 | 1.00 | 20.24 | A | C |
| ATOM | 3338 | CE2 | PHE | A | 406 | 43.274 | −13.065 | −9.969 | 1.00 | 17.42 | A | C |
| ATOM | 3339 | CD2 | PHE | A | 406 | 44.624 | −12.876 | −9.937 | 1.00 | 18.30 | A | C |
| ATOM | 3340 | C | PHE | A | 406 | 49.074 | −13.976 | −11.547 | 1.00 | 22.70 | A | C |
| ATOM | 3341 | O | PHE | A | 406 | 49.442 | −13.709 | −12.676 | 1.00 | 23.27 | A | O |
| ATOM | 3342 | N | ALA | A | 407 | 49.937 | −14.144 | −10.550 | 1.00 | 22.55 | A | N |
| ATOM | 3343 | CA | ALA | A | 407 | 51.363 | −14.019 | −10.772 | 1.00 | 21.36 | A | C |
| ATOM | 3344 | CB | ALA | A | 407 | 52.017 | −13.537 | −9.485 | 1.00 | 19.87 | A | C |
| ATOM | 3345 | C | ALA | A | 407 | 52.040 | −15.321 | −11.244 | 1.00 | 23.19 | A | C |
| ATOM | 3346 | O | ALA | A | 407 | 53.142 | −15.272 | −11.727 | 1.00 | 30.24 | A | O |
| ATOM | 3347 | N | VAL | A | 408 | 51.413 | −16.481 | −11.056 | 1.00 | 27.45 | A | N |
| ATOM | 3348 | CA | AVAL | A | 408 | 52.071 | −17.741 | −11.425 | 0.50 | 28.57 | A | C |
| ATOM | 3349 | CA | BVAL | A | 408 | 52.017 | −17.787 | −11.354 | 0.50 | 29.31 | A | C |
| ATOM | 3350 | CB | AVAL | A | 408 | 52.198 | −18.715 | −10.251 | 0.50 | 28.56 | A | C |
| ATOM | 3351 | CB | BVAL | A | 408 | 51.854 | −18.730 | −10.138 | 0.50 | 30.65 | A | C |
| ATOM | 3352 | CG1 | AVAL | A | 408 | 52.982 | −18.047 | −9.141 | 0.50 | 27.11 | A | C |
| ATOM | 3353 | CG1 | BVAL | A | 408 | 51.792 | −20.194 | −10.544 | 0.50 | 29.44 | A | C |
| ATOM | 3354 | CG2 | AVAL | A | 408 | 50.843 | −19.186 | −9.768 | 0.50 | 24.84 | A | C |
| ATOM | 3355 | CG2 | BVAL | A | 408 | 52.990 | −18.493 | −9.170 | 0.50 | 33.29 | A | C |
| ATOM | 3356 | C | VAL | A | 408 | 51.427 | −18.421 | −12.618 | 1.00 | 30.97 | A | C |
| ATOM | 3357 | O | VAL | A | 408 | 52.107 | −19.095 | −13.352 | 1.00 | 34.90 | A | O |
| ATOM | 3358 | N | VAL | A | 409 | 50.141 | −18.201 | −12.855 | 1.00 | 29.54 | A | N |
| ATOM | 3359 | CA | VAL | A | 409 | 49.475 | −18.838 | −13.987 | 1.00 | 38.14 | A | C |
| ATOM | 3360 | CB | VAL | A | 409 | 48.014 | −19.112 | −13.672 | 1.00 | 35.38 | A | C |
| ATOM | 3361 | CG1 | VAL | A | 409 | 47.287 | −19.625 | −14.897 | 1.00 | 40.56 | A | C |
| ATOM | 3362 | CG2 | VAL | A | 409 | 47.918 | −20.114 | −12.513 | 1.00 | 35.95 | A | C |
| ATOM | 3363 | C | VAL | A | 409 | 49.578 | −17.952 | −15.212 | 1.00 | 49.01 | A | C |
| ATOM | 3364 | O | VAL | A | 409 | 49.168 | −16.800 | −15.169 | 1.00 | 55.44 | A | O |
| ATOM | 3365 | N | GLN | A | 410 | 50.094 | −18.517 | −16.303 | 1.00 | 54.11 | A | N |
| ATOM | 3366 | CA | GLN | A | 410 | 50.314 | −17.775 | −17.555 | 1.00 | 58.29 | A | C |
| ATOM | 3367 | CB | GLN | A | 410 | 51.272 | −18.540 | −18.455 | 1.00 | 74.97 | A | C |
| ATOM | 3368 | CG | GLN | A | 410 | 52.676 | −18.656 | −17.877 | 1.00 | 104.40 | A | C |
| ATOM | 3369 | CD | GLN | A | 410 | 53.553 | −19.633 | −18.641 | 1.00 | 121.42 | A | C |
| ATOM | 3370 | OE1 | GLN | A | 410 | 53.131 | −20.746 | −18.967 | 1.00 | 129.81 | A | O |
| ATOM | 3371 | NE2 | GLN | A | 410 | 54.788 | −19.224 | −18.920 | 1.00 | 113.30 | A | N |
| ATOM | 3372 | C | GLN | A | 410 | 49.033 | −17.489 | −18.324 | 1.00 | 40.60 | A | C |

APPENDIX A-continued

*P. alba* 3T288C coordinates

| ATOM | 3373 | O | GLN | A | 410 | 48.835 | −16.385 | −18.826 | 1.00 | 45.84 | A | O |
|------|------|------|------|---|-----|--------|---------|---------|------|-------|---|---|
| ATOM | 3374 | N | ASN | A | 411 | 48.171 | −18.486 | −18.422 | 1.00 | 39.87 | A | N |
| ATOM | 3375 | CA | ASN | A | 411 | 46.881 | −18.321 | −19.069 | 1.00 | 39.51 | A | C |
| ATOM | 3376 | CB | ASN | A | 411 | 46.755 | −19.283 | −20.246 | 1.00 | 43.94 | A | C |
| ATOM | 3377 | CG | ASN | A | 411 | 47.619 | −18.860 | −21.408 | 1.00 | 45.54 | A | C |
| ATOM | 3378 | OD1 | ASN | A | 411 | 47.330 | −17.879 | −22.071 | 1.00 | 43.48 | A | O |
| ATOM | 3379 | ND2 | ASN | A | 411 | 48.706 | −19.566 | −21.623 | 1.00 | 47.40 | A | N |
| ATOM | 3380 | C | ASN | A | 411 | 45.777 | −18.566 | −18.074 | 1.00 | 41.61 | A | C |
| ATOM | 3381 | O | ASN | A | 411 | 45.513 | −19.704 | −17.671 | 1.00 | 36.11 | A | O |
| ATOM | 3382 | N | ILE | A | 412 | 45.089 | −17.495 | −17.720 | 1.00 | 37.06 | A | N |
| ATOM | 3383 | CA | ILE | A | 412 | 44.059 | −17.591 | −16.717 | 1.00 | 40.38 | A | C |
| ATOM | 3384 | CB | ILE | A | 412 | 43.803 | −16.228 | −16.041 | 1.00 | 39.90 | A | C |
| ATOM | 3385 | CG1 | ILE | A | 412 | 42.967 | −15.322 | −16.913 | 1.00 | 41.14 | A | C |
| ATOM | 3386 | CD1 | ILE | A | 412 | 42.480 | −14.114 | −16.169 | 1.00 | 49.82 | A | C |
| ATOM | 3387 | CG2 | ILE | A | 412 | 45.146 | −15.584 | −15.717 | 1.00 | 37.62 | A | C |
| ATOM | 3388 | C | ILE | A | 412 | 42.832 | −18.175 | −17.355 | 1.00 | 38.84 | A | C |
| ATOM | 3389 | O | ILE | A | 412 | 42.647 | −18.038 | −18.562 | 1.00 | 37.29 | A | O |
| ATOM | 3390 | N | LYS | A | 413 | 42.037 | −18.877 | −16.551 | 1.00 | 35.54 | A | N |
| ATOM | 3391 | CA | ALYS | A | 413 | 40.821 | −19.542 | −17.017 | 0.50 | 37.84 | A | C |
| ATOM | 3392 | CA | BLYS | A | 413 | 40.815 | −19.515 | −17.033 | 0.50 | 37.03 | A | C |
| ATOM | 3393 | CB | ALYS | A | 413 | 40.980 | −21.064 | −16.928 | 0.50 | 39.81 | A | C |
| ATOM | 3394 | CB | BLYS | A | 413 | 40.974 | −21.039 | −17.055 | 0.50 | 37.45 | A | C |
| ATOM | 3395 | CG | ALYS | A | 413 | 42.102 | −21.647 | −17.800 | 0.50 | 45.41 | A | C |
| ATOM | 3396 | CG | BLYS | A | 413 | 42.303 | −21.485 | −17.667 | 0.50 | 41.11 | A | C |
| ATOM | 3397 | CD | ALYS | A | 413 | 42.385 | −23.114 | −17.437 | 0.50 | 54.08 | A | C |
| ATOM | 3398 | CD | BLYS | A | 413 | 42.279 | −22.919 | −18.203 | 0.50 | 47.86 | A | C |
| ATOM | 3399 | CE | ALYS | A | 413 | 43.184 | −23.853 | −18.515 | 0.50 | 54.67 | A | C |
| ATOM | 3400 | CE | BLYS | A | 413 | 41.782 | −23.933 | −17.173 | 0.50 | 48.03 | A | C |
| ATOM | 3401 | NZ | ALYS | A | 413 | 44.525 | −23.255 | −18.745 | 0.50 | 52.77 | A | N |
| ATOM | 3402 | NZ | BLYS | A | 413 | 40.299 | −24.089 | −17.187 | 0.50 | 44.70 | A | N |
| ATOM | 3403 | C | LYS | A | 413 | 39.644 | −19.071 | −16.167 | 1.00 | 37.05 | A | C |
| ATOM | 3404 | O | LYS | A | 413 | 39.757 | −18.944 | −14.934 | 1.00 | 28.26 | A | O |
| ATOM | 3405 | N | LYS | A | 414 | 38.522 | −18.795 | −16.818 | 1.00 | 32.05 | A | N |
| ATOM | 3406 | CA | LYS | A | 414 | 37.363 | −18.243 | −16.148 | 1.00 | 35.17 | A | C |
| ATOM | 3407 | CB | LYS | A | 414 | 36.244 | −17.952 | −17.162 | 1.00 | 42.50 | A | C |
| ATOM | 3408 | CG | LYS | A | 414 | 34.967 | −17.374 | −16.532 | 1.00 | 58.00 | A | C |
| ATOM | 3409 | CD | LYS | A | 414 | 33.942 | −16.848 | −17.562 | 1.00 | 70.13 | A | C |
| ATOM | 3410 | CE | LYS | A | 414 | 33.549 | −17.894 | −18.610 | 1.00 | 76.49 | A | C |
| ATOM | 3411 | NZ | LYS | A | 414 | 33.122 | −19.206 | −18.034 | 1.00 | 79.30 | A | N |
| ATOM | 3412 | C | LYS | A | 414 | 36.869 | −19.184 | −15.049 | 1.00 | 30.94 | A | C |
| ATOM | 3413 | O | LYS | A | 414 | 36.458 | −18.749 | −13.978 | 1.00 | 33.29 | A | O |
| ATOM | 3414 | N | GLU | A | 415 | 36.936 | −20.475 | −15.309 | 1.00 | 29.17 | A | N |
| ATOM | 3415 | CA | GLU | A | 415 | 36.503 | −21.464 | −14.340 | 1.00 | 29.56 | A | C |
| ATOM | 3416 | CB | GLU | A | 415 | 36.455 | −22.821 | −15.005 | 1.00 | 36.10 | A | C |
| ATOM | 3417 | CG | GLU | A | 415 | 35.755 | −23.839 | −14.185 | 1.00 | 47.28 | A | C |
| ATOM | 3418 | CD | GLU | A | 415 | 35.920 | −25.229 | −14.755 | 1.00 | 65.80 | A | C |
| ATOM | 3419 | OE1 | GLU | A | 415 | 36.443 | −25.354 | −15.885 | 1.00 | 99.10 | A | O |
| ATOM | 3420 | OE2 | GLU | A | 415 | 35.539 | −26.194 | −14.066 | 1.00 | 53.16 | A | O |
| ATOM | 3421 | C | GLU | A | 415 | 37.409 | −21.520 | −13.102 | 1.00 | 26.70 | A | C |
| ATOM | 3422 | O | GLU | A | 415 | 36.934 | −21.688 | −11.975 | 1.00 | 27.05 | A | O |
| ATOM | 3423 | N | GLU | A | 416 | 38.704 | −21.379 | −13.315 | 1.00 | 22.01 | A | N |
| ATOM | 3424 | CA | GLU | A | 416 | 39.636 | −21.231 | −12.204 | 1.00 | 28.96 | A | C |
| ATOM | 3425 | CB | GLU | A | 416 | 41.059 | −21.196 | −12.729 | 1.00 | 29.30 | A | C |
| ATOM | 3426 | CG | GLU | A | 416 | 41.445 | −22.546 | −13.360 | 1.00 | 35.82 | A | C |
| ATOM | 3427 | CD | GLU | A | 416 | 42.902 | −22.633 | −13.766 | 1.00 | 38.67 | A | C |
| ATOM | 3428 | OE1 | GLU | A | 416 | 43.543 | −21.587 | −14.001 | 1.00 | 34.53 | A | O |
| ATOM | 3429 | OE2 | GLU | A | 416 | 43.410 | −23.762 | −13.857 | 1.00 | 49.04 | A | O |
| ATOM | 3430 | C | GLU | A | 416 | 39.323 | −20.006 | −11.368 | 1.00 | 24.91 | A | C |
| ATOM | 3431 | O | GLU | A | 416 | 39.190 | −20.087 | −10.150 | 1.00 | 25.36 | A | O |
| ATOM | 3432 | N | ILE | A | 417 | 39.162 | −18.864 | −12.013 | 1.00 | 25.14 | A | N |
| ATOM | 3433 | CA | AILE | A | 417 | 38.954 | −17.658 | −11.222 | 0.50 | 25.62 | A | C |
| ATOM | 3434 | CA | BILE | A | 417 | 38.864 | −17.587 | −11.339 | 0.50 | 27.40 | A | C |
| ATOM | 3435 | CB | AILE | A | 417 | 39.296 | −16.353 | −11.998 | 0.50 | 25.97 | A | C |
| ATOM | 3436 | CB | BILE | A | 417 | 38.703 | −16.454 | −12.392 | 0.50 | 28.46 | A | C |
| ATOM | 3437 | CG1 | AILE | A | 417 | 38.397 | −16.153 | −13.210 | 0.50 | 24.13 | A | C |
| ATOM | 3438 | CG1 | BILE | A | 417 | 40.059 | −16.125 | −13.015 | 0.50 | 28.41 | A | C |
| ATOM | 3439 | CD1 | AILE | A | 417 | 38.647 | −14.818 | −13.903 | 0.50 | 31.10 | A | C |
| ATOM | 3440 | CD1 | BILE | A | 417 | 39.965 | −15.233 | −14.243 | 0.50 | 32.20 | A | C |
| ATOM | 3441 | CG2 | AILE | A | 417 | 40.755 | −16.378 | −12.431 | 0.50 | 21.28 | A | C |
| ATOM | 3442 | CG2 | BILE | A | 417 | 38.081 | −15.207 | −11.771 | 0.50 | 26.97 | A | C |
| ATOM | 3443 | C | ILE | A | 417 | 37.573 | −17.670 | −10.532 | 1.00 | 26.52 | A | C |
| ATOM | 3444 | O | ILE | A | 417 | 37.487 | −17.251 | −9.379 | 1.00 | 29.89 | A | O |
| ATOM | 3445 | N | GLU | A | 418 | 36.544 | −18.217 | −11.169 | 1.00 | 26.91 | A | N |
| ATOM | 3446 | CA | GLU | A | 418 | 35.234 | −18.397 | −10.519 | 1.00 | 28.93 | A | C |
| ATOM | 3447 | CB | GLU | A | 418 | 34.231 | −19.058 | −11.472 | 1.00 | 34.19 | A | C |
| ATOM | 3448 | CG | GLU | A | 418 | 33.560 | −18.105 | −12.449 | 1.00 | 53.05 | A | C |
| ATOM | 3449 | CD | GLU | A | 418 | 32.603 | −18.811 | −13.425 | 1.00 | 66.68 | A | C |
| ATOM | 3450 | OE1 | GLU | A | 418 | 32.687 | −20.057 | −13.603 | 1.00 | 57.67 | A | O |

APPENDIX A-continued

*P. alba* 3T288C coordinates

| ATOM | 3451 | OE2 | GLU | A | 418 | 31.765 | −18.102 | −14.025 | 1.00 | 78.77 | A | O |
|---|---|---|---|---|---|---|---|---|---|---|---|---|
| ATOM | 3452 | C | GLU | A | 418 | 35.342 | −19.259 | −9.247 | 1.00 | 30.46 | A | C |
| ATOM | 3453 | O | GLU | A | 418 | 34.675 | −18.996 | −8.248 | 1.00 | 32.98 | A | O |
| ATOM | 3454 | N | ASN | A | 419 | 36.185 | −20.282 | −9.295 | 1.00 | 25.76 | A | N |
| ATOM | 3455 | CA | ASN | A | 419 | 36.413 | −21.134 | −8.131 | 1.00 | 27.38 | A | C |
| ATOM | 3456 | CB | ASN | A | 419 | 37.004 | −22.473 | −8.579 | 1.00 | 28.62 | A | C |
| ATOM | 3457 | CG | ASN | A | 419 | 35.920 | −23.449 | −8.982 | 1.00 | 33.85 | A | C |
| ATOM | 3458 | OD1 | ASN | A | 419 | 35.304 | −24.059 | −8.127 | 1.00 | 32.06 | A | O |
| ATOM | 3459 | ND2 | ASN | A | 419 | 35.621 | −23.527 | −10.272 | 1.00 | 29.04 | A | N |
| ATOM | 3460 | C | ASN | A | 419 | 37.241 | −20.483 | −7.021 | 1.00 | 21.01 | A | C |
| ATOM | 3461 | O | ASN | A | 419 | 37.001 | −20.725 | −5.855 | 1.00 | 24.32 | A | O |
| ATOM | 3462 | N | LEU | A | 420 | 38.171 | −19.621 | −7.392 | 1.00 | 23.30 | A | N |
| ATOM | 3463 | CA | LEU | A | 420 | 38.880 | −18.803 | −6.417 | 1.00 | 26.86 | A | C |
| ATOM | 3464 | CB | LEU | A | 420 | 39.939 | −17.948 | −7.094 | 1.00 | 30.50 | A | C |
| ATOM | 3465 | CG | LEU | A | 420 | 41.192 | −18.585 | −7.691 | 1.00 | 29.17 | A | C |
| ATOM | 3466 | CD1 | LEU | A | 420 | 41.932 | −17.455 | −8.424 | 1.00 | 29.98 | A | C |
| ATOM | 3467 | CD2 | LEU | A | 420 | 42.052 | −19.214 | −6.627 | 1.00 | 27.85 | A | C |
| ATOM | 3468 | C | LEU | A | 420 | 37.894 | −17.914 | −5.655 | 1.00 | 27.14 | A | C |
| ATOM | 3469 | O | LEU | A | 420 | 37.968 | −17.811 | −4.438 | 1.00 | 27.87 | A | O |
| ATOM | 3470 | N | GLN | A | 421 | 36.925 | −17.344 | −6.357 | 1.00 | 28.53 | A | N |
| ATOM | 3471 | CA | GLN | A | 421 | 35.952 | −16.477 | −5.710 | 1.00 | 36.09 | A | C |
| ATOM | 3472 | CB | GLN | A | 421 | 35.090 | −15.747 | −6.726 | 1.00 | 38.74 | A | C |
| ATOM | 3473 | CG | GLN | A | 421 | 35.881 | −14.837 | −7.596 | 1.00 | 41.97 | A | C |
| ATOM | 3474 | CD | GLN | A | 421 | 35.071 | −13.634 | −8.005 | 1.00 | 51.05 | A | C |
| ATOM | 3475 | OE1 | GLN | A | 421 | 34.064 | −13.769 | −8.686 | 1.00 | 42.51 | A | O |
| ATOM | 3476 | NE2 | GLN | A | 421 | 35.500 | −12.455 | −7.582 | 1.00 | 34.40 | A | N |
| ATOM | 3477 | C | GLN | A | 421 | 35.034 | −17.200 | −4.765 | 1.00 | 32.47 | A | C |
| ATOM | 3478 | O | GLN | A | 421 | 34.573 | −16.616 | −3.795 | 1.00 | 27.79 | A | O |
| ATOM | 3479 | N | LYS | A | 422 | 34.782 | −18.476 | −5.025 | 1.00 | 25.83 | A | N |
| ATOM | 3480 | CA | LYS | A | 422 | 34.003 | −19.278 | −4.115 | 1.00 | 22.56 | A | C |
| ATOM | 3481 | CB | LYS | A | 422 | 33.154 | −20.284 | −4.923 | 1.00 | 33.44 | A | C |
| ATOM | 3482 | CG | LYS | A | 422 | 32.134 | −19.596 | −5.816 | 1.00 | 45.98 | A | C |
| ATOM | 3483 | CD | LYS | A | 422 | 31.728 | −20.416 | −7.049 | 1.00 | 63.36 | A | C |
| ATOM | 3484 | CE | LYS | A | 422 | 30.833 | −19.557 | −7.974 | 1.00 | 73.27 | A | C |
| ATOM | 3485 | NZ | LYS | A | 422 | 30.447 | −20.198 | −9.275 | 1.00 | 66.66 | A | N |
| ATOM | 3486 | C | LYS | A | 422 | 34.880 | −20.014 | −3.107 | 1.00 | 23.96 | A | C |
| ATOM | 3487 | O | LYS | A | 422 | 34.412 | −20.944 | −2.457 | 1.00 | 25.32 | A | O |
| ATOM | 3488 | N | TYR | A | 423 | 36.148 | −19.633 | −2.965 | 1.00 | 24.30 | A | N |
| ATOM | 3489 | CA | TYR | A | 423 | 37.034 | −20.295 | −1.983 | 1.00 | 24.51 | A | C |
| ATOM | 3490 | CB | TYR | A | 423 | 36.551 | −20.040 | −0.567 | 1.00 | 27.30 | A | C |
| ATOM | 3491 | CG | TYR | A | 423 | 36.497 | −18.583 | −0.259 | 1.00 | 30.64 | A | C |
| ATOM | 3492 | CD1 | TYR | A | 423 | 37.628 | −17.915 | 0.119 | 1.00 | 32.19 | A | C |
| ATOM | 3493 | CE1 | TYR | A | 423 | 37.596 | −16.571 | 0.425 | 1.00 | 40.57 | A | C |
| ATOM | 3494 | CZ | TYR | A | 423 | 36.408 | −15.873 | 0.331 | 1.00 | 45.26 | A | C |
| ATOM | 3495 | OH | TYR | A | 423 | 36.397 | −14.533 | 0.619 | 1.00 | 45.20 | A | O |
| ATOM | 3496 | CE2 | TYR | A | 423 | 35.254 | −16.513 | −0.057 | 1.00 | 38.81 | A | C |
| ATOM | 3497 | CD2 | TYR | A | 423 | 35.301 | −17.874 | −0.349 | 1.00 | 43.23 | A | C |
| ATOM | 3498 | C | TYR | A | 423 | 37.169 | −21.796 | −2.162 | 1.00 | 23.71 | A | C |
| ATOM | 3499 | O | TYR | A | 423 | 36.979 | −22.565 | −1.223 | 1.00 | 23.89 | A | O |
| ATOM | 3500 | N | HIS | A | 424 | 37.537 | −22.204 | −3.365 | 1.00 | 22.42 | A | N |
| ATOM | 3501 | CA | HIS | A | 424 | 37.810 | −23.617 | −3.654 | 1.00 | 25.69 | A | C |
| ATOM | 3502 | CB | HIS | A | 424 | 38.434 | −23.688 | −5.041 | 1.00 | 28.03 | A | C |
| ATOM | 3503 | CG | HIS | A | 424 | 38.579 | −25.068 | −5.589 | 1.00 | 26.61 | A | C |
| ATOM | 3504 | ND1 | HIS | A | 424 | 39.719 | −25.801 | −5.448 | 1.00 | 26.17 | A | N |
| ATOM | 3505 | CE1 | HIS | A | 424 | 39.554 | −27.000 | −6.057 | 1.00 | 33.18 | A | C |
| ATOM | 3506 | NE2 | HIS | A | 424 | 38.346 | −27.003 | −6.639 | 1.00 | 30.75 | A | N |
| ATOM | 3507 | CD2 | HIS | A | 424 | 37.721 | −25.819 | −6.366 | 1.00 | 27.10 | A | C |
| ATOM | 3508 | C | HIS | A | 424 | 38.776 | −24.183 | −2.649 | 1.00 | 24.11 | A | C |
| ATOM | 3509 | O | HIS | A | 424 | 39.680 | −23.484 | −2.130 | 1.00 | 19.88 | A | O |
| ATOM | 3510 | N | ASP | A | 425 | 38.640 | −25.478 | −2.388 | 1.00 | 23.19 | A | N |
| ATOM | 3511 | CA | ASP | A | 425 | 39.546 | −26.229 | −1.525 | 1.00 | 24.75 | A | C |
| ATOM | 3512 | CB | ASP | A | 425 | 39.349 | −27.730 | −1.751 | 1.00 | 28.91 | A | C |
| ATOM | 3513 | CG | ASP | A | 425 | 37.961 | −28.223 | −1.351 | 1.00 | 34.79 | A | C |
| ATOM | 3514 | OD1 | ASP | A | 425 | 37.338 | −27.632 | −0.461 | 1.00 | 38.40 | A | O |
| ATOM | 3515 | OD2 | ASP | A | 425 | 37.510 | −29.218 | −1.954 | 1.00 | 42.28 | A | O |
| ATOM | 3516 | C | ASP | A | 425 | 41.041 | −25.973 | −1.709 | 1.00 | 21.70 | A | C |
| ATOM | 3517 | O | ASP | A | 425 | 41.813 | −26.049 | −0.766 | 1.00 | 20.92 | A | O |
| ATOM | 3518 | N | THR | A | 426 | 41.462 | −25.772 | −2.943 | 1.00 | 19.82 | A | N |
| ATOM | 3519 | CA | THR | A | 426 | 42.836 | −25.508 | −3.232 | 1.00 | 19.64 | A | C |
| ATOM | 3520 | CB | THR | A | 426 | 42.974 | −25.165 | −4.734 | 1.00 | 21.99 | A | C |
| ATOM | 3521 | OG1 | THR | A | 426 | 42.497 | −26.284 | −5.475 | 1.00 | 31.41 | A | O |
| ATOM | 3522 | CG2 | THR | A | 426 | 44.411 | −24.887 | −5.087 | 1.00 | 21.42 | A | C |
| ATOM | 3523 | C | THR | A | 426 | 43.366 | −24.323 | −2.407 | 1.00 | 20.34 | A | C |
| ATOM | 3524 | O | THR | A | 426 | 44.529 | −24.327 | −2.031 | 1.00 | 20.11 | A | O |
| ATOM | 3525 | N | ILE | A | 427 | 42.538 | −23.284 | −2.203 | 1.00 | 18.12 | A | N |
| ATOM | 3526 | CA | ILE | A | 427 | 42.955 | −22.142 | −1.396 | 1.00 | 17.33 | A | C |
| ATOM | 3527 | CB | ILE | A | 427 | 42.765 | −20.794 | −2.111 | 1.00 | 21.38 | A | C |
| ATOM | 3528 | CG1 | ILE | A | 427 | 41.327 | −20.360 | −2.144 | 1.00 | 18.39 | A | C |

APPENDIX A-continued

*P. alba* 3T288C coordinates

| ATOM | 3529 | CD1 | ILE | A | 427 | 41.189 | −18.919 | −2.801 | 1.00 | 20.52 | A | C |
|---|---|---|---|---|---|---|---|---|---|---|---|---|
| ATOM | 3530 | CG2 | ILE | A | 427 | 43.361 | −20.870 | −3.526 | 1.00 | 19.29 | A | C |
| ATOM | 3531 | C | ILE | A | 427 | 42.413 | −22.102 | 0.010 | 1.00 | 16.88 | A | C |
| ATOM | 3532 | O | ILE | A | 427 | 43.095 | −21.588 | 0.917 | 1.00 | 20.78 | A | O |
| ATOM | 3533 | N | SER | A | 428 | 41.287 | −22.761 | 0.268 | 1.00 | 16.24 | A | N |
| ATOM | 3534 | CA | SER | A | 428 | 40.728 | −22.677 | 1.587 | 1.00 | 18.26 | A | C |
| ATOM | 3535 | CB | SER | A | 428 | 39.260 | −23.061 | 1.561 | 1.00 | 22.20 | A | C |
| ATOM | 3536 | OG | SER | A | 428 | 39.129 | −24.406 | 1.151 | 1.00 | 23.46 | A | O |
| ATOM | 3537 | C | SER | A | 428 | 41.525 | −23.567 | 2.547 | 1.00 | 19.47 | A | C |
| ATOM | 3538 | O | SER | A | 428 | 41.822 | −23.181 | 3.671 | 1.00 | 18.98 | A | O |
| ATOM | 3539 | N | ARG | A | 429 | 41.929 | −24.754 | 2.119 | 1.00 | 19.92 | A | N |
| ATOM | 3540 | CA | AARG | A | 429 | 42.582 | −25.692 | 3.049 | 0.50 | 17.38 | A | C |
| ATOM | 3541 | CA | BARG | A | 429 | 42.548 | −25.696 | 3.052 | 0.50 | 18.39 | A | C |
| ATOM | 3542 | CB | AARG | A | 429 | 42.756 | −27.069 | 2.409 | 0.50 | 19.41 | A | C |
| ATOM | 3543 | CB | BARG | A | 429 | 42.596 | −27.113 | 2.430 | 0.50 | 22.82 | A | C |
| ATOM | 3544 | CG | AARG | A | 429 | 41.488 | −27.872 | 2.518 | 0.50 | 19.06 | A | C |
| ATOM | 3545 | CG | BARG | A | 429 | 41.176 | −27.620 | 1.991 | 0.50 | 22.48 | A | C |
| ATOM | 3546 | CD | AARG | A | 429 | 41.548 | −28.993 | 1.550 | 0.50 | 22.31 | A | C |
| ATOM | 3547 | CD | BARG | A | 429 | 40.778 | −28.905 | 2.690 | 0.50 | 31.48 | A | C |
| ATOM | 3548 | NE | AARG | A | 429 | 40.271 | −29.672 | 1.469 | 0.50 | 23.52 | A | N |
| ATOM | 3549 | NE | BARG | A | 429 | 39.575 | −29.554 | 2.140 | 0.50 | 30.27 | A | N |
| ATOM | 3550 | CZ | AARG | A | 429 | 39.930 | −30.402 | 0.439 | 0.50 | 15.63 | A | C |
| ATOM | 3551 | CZ | BARG | A | 429 | 38.399 | −29.587 | 2.763 | 0.50 | 34.86 | A | C |
| ATOM | 3552 | NH1 | AARG | A | 429 | 40.782 | −30.524 | −0.568 | 0.50 | 19.41 | A | N |
| ATOM | 3553 | NH1 | BARG | A | 429 | 38.279 | −29.014 | 3.956 | 0.50 | 26.08 | A | N |
| ATOM | 3554 | NH2 | AARG | A | 429 | 38.776 | −30.963 | 0.435 | 0.50 | 17.28 | A | N |
| ATOM | 3555 | NH2 | BARG | A | 429 | 37.361 | −30.237 | 2.218 | 0.50 | 27.64 | A | N |
| ATOM | 3556 | C | ARG | A | 429 | 43.918 | −25.198 | 3.588 | 1.00 | 16.22 | A | C |
| ATOM | 3557 | O | ARG | A | 429 | 44.183 | −25.282 | 4.780 | 1.00 | 16.19 | A | O |
| ATOM | 3558 | N | PRO | A | 430 | 44.762 | −24.642 | 2.726 | 1.00 | 16.98 | A | N |
| ATOM | 3559 | CA | PRO | A | 430 | 46.018 | −24.145 | 3.283 | 1.00 | 19.48 | A | C |
| ATOM | 3560 | CB | PRO | A | 430 | 46.830 | −23.764 | 2.056 | 1.00 | 24.27 | A | C |
| ATOM | 3561 | CG | PRO | A | 430 | 45.963 | −23.936 | 0.930 | 1.00 | 26.12 | A | C |
| ATOM | 3562 | CD | PRO | A | 430 | 44.812 | −24.737 | 1.263 | 1.00 | 23.07 | A | C |
| ATOM | 3563 | C | PRO | A | 430 | 45.778 | −22.938 | 4.192 | 1.00 | 17.44 | A | C |
| ATOM | 3564 | O | PRO | A | 430 | 46.536 | −22.713 | 5.146 | 1.00 | 16.01 | A | O |
| ATOM | 3565 | N | SER | A | 431 | 44.699 | −22.214 | 3.936 | 1.00 | 16.23 | A | N |
| ATOM | 3566 | CA | SER | A | 431 | 44.291 | −21.083 | 4.806 | 1.00 | 16.47 | A | C |
| ATOM | 3567 | CB | SER | A | 431 | 43.250 | −20.232 | 4.083 | 1.00 | 17.77 | A | C |
| ATOM | 3568 | OG | SER | A | 431 | 43.801 | −19.694 | 2.865 | 1.00 | 18.39 | A | O |
| ATOM | 3569 | C | SER | A | 431 | 43.777 | −21.582 | 6.164 | 1.00 | 18.22 | A | C |
| ATOM | 3570 | O | SER | A | 431 | 43.993 | −20.908 | 7.174 | 1.00 | 18.59 | A | O |
| ATOM | 3571 | N | HIS | A | 432 | 43.156 | −22.780 | 6.204 | 1.00 | 15.86 | A | N |
| ATOM | 3572 | CA | HIS | A | 432 | 42.780 | −23.405 | 7.448 | 1.00 | 16.36 | A | C |
| ATOM | 3573 | CB | HIS | A | 432 | 42.110 | −24.770 | 7.287 | 1.00 | 16.77 | A | C |
| ATOM | 3574 | CG | HIS | A | 432 | 40.776 | −24.777 | 6.567 | 1.00 | 20.10 | A | C |
| ATOM | 3575 | ND1 | HIS | A | 432 | 40.132 | −23.664 | 6.137 | 1.00 | 25.10 | A | N |
| ATOM | 3576 | CE1 | HIS | A | 432 | 38.961 | −24.023 | 5.537 | 1.00 | 20.22 | A | C |
| ATOM | 3577 | NE2 | HIS | A | 432 | 38.867 | −25.348 | 5.579 | 1.00 | 27.66 | A | N |
| ATOM | 3578 | CD2 | HIS | A | 432 | 39.974 | −25.846 | 6.202 | 1.00 | 23.79 | A | C |
| ATOM | 3579 | C | HIS | A | 432 | 44.030 | −23.620 | 8.282 | 1.00 | 14.57 | A | C |
| ATOM | 3580 | O | HIS | A | 432 | 44.070 | −23.311 | 9.467 | 1.00 | 17.94 | A | O |
| ATOM | 3581 | N | ILE | A | 433 | 45.067 | −24.158 | 7.661 | 1.00 | 15.54 | A | N |
| ATOM | 3582 | CA | ILE | A | 433 | 46.306 | −24.452 | 8.352 | 1.00 | 16.10 | A | C |
| ATOM | 3583 | CB | ILE | A | 433 | 47.233 | −25.278 | 7.483 | 1.00 | 17.95 | A | C |
| ATOM | 3584 | CG1 | ILE | A | 433 | 46.632 | −26.708 | 7.366 | 1.00 | 20.19 | A | C |
| ATOM | 3585 | CD1 | ILE | A | 433 | 47.196 | −27.406 | 6.192 | 1.00 | 26.65 | A | C |
| ATOM | 3586 | CG2 | ILE | A | 433 | 48.609 | −25.425 | 8.153 | 1.00 | 16.48 | A | C |
| ATOM | 3587 | C | ILE | A | 433 | 47.017 | −23.187 | 8.812 | 1.00 | 17.80 | A | C |
| ATOM | 3588 | O | ILE | A | 433 | 47.544 | −23.147 | 9.920 | 1.00 | 19.64 | A | O |
| ATOM | 3589 | N | PHE | A | 434 | 47.023 | −22.176 | 7.963 | 1.00 | 17.18 | A | N |
| ATOM | 3590 | CA | PHE | A | 434 | 47.604 | −20.870 | 8.304 | 1.00 | 17.38 | A | C |
| ATOM | 3591 | CB | PHE | A | 434 | 47.400 | −19.972 | 7.085 | 1.00 | 19.35 | A | C |
| ATOM | 3592 | CG | PHE | A | 434 | 47.927 | −18.537 | 7.224 | 1.00 | 19.98 | A | C |
| ATOM | 3593 | CD1 | PHE | A | 434 | 48.715 | −18.114 | 8.279 | 1.00 | 22.63 | A | C |
| ATOM | 3594 | CE1 | PHE | A | 434 | 49.148 | −16.776 | 8.353 | 1.00 | 24.62 | A | C |
| ATOM | 3595 | CZ | PHE | A | 434 | 48.870 | −15.921 | 7.348 | 1.00 | 20.63 | A | C |
| ATOM | 3596 | CE2 | PHE | A | 434 | 48.102 | −16.345 | 6.274 | 1.00 | 24.11 | A | C |
| ATOM | 3597 | CD2 | PHE | A | 434 | 47.651 | −17.633 | 6.219 | 1.00 | 23.72 | A | C |
| ATOM | 3598 | C | PHE | A | 434 | 46.959 | −20.325 | 9.604 | 1.00 | 18.74 | A | C |
| ATOM | 3599 | O | PHE | A | 434 | 47.659 | −19.969 | 10.581 | 1.00 | 18.92 | A | O |
| ATOM | 3600 | N | ARG | A | 435 | 45.632 | −20.304 | 9.645 | 1.00 | 17.74 | A | N |
| ATOM | 3601 | CA | ARG | A | 435 | 44.922 | −19.799 | 10.824 | 1.00 | 16.89 | A | C |
| ATOM | 3602 | CB | ARG | A | 435 | 43.436 | −19.607 | 10.511 | 1.00 | 15.62 | A | C |
| ATOM | 3603 | CG | ARG | A | 435 | 42.545 | −19.325 | 11.731 | 1.00 | 15.59 | A | C |
| ATOM | 3604 | CD | ARG | A | 435 | 43.046 | −18.111 | 12.556 | 1.00 | 17.62 | A | C |
| ATOM | 3605 | NE | ARG | A | 435 | 42.921 | −16.870 | 11.800 | 1.00 | 19.60 | A | N |
| ATOM | 3606 | CZ | ARG | A | 435 | 43.489 | −15.717 | 12.143 | 1.00 | 20.76 | A | C |

APPENDIX A-continued

*P. alba* 3T288C coordinates

| ATOM | 3607 | NH1 | ARG | A | 435 | 44.232 | −15.628 | 13.228 | 1.00 | 20.32 | A | N |
|---|---|---|---|---|---|---|---|---|---|---|---|---|
| ATOM | 3608 | NH2 | ARG | A | 435 | 43.277 | −14.639 | 11.409 | 1.00 | 20.79 | A | N |
| ATOM | 3609 | C | ARG | A | 435 | 45.162 | −20.661 | 12.053 | 1.00 | 18.87 | A | C |
| ATOM | 3610 | O | ARG | A | 435 | 45.423 | −20.145 | 13.168 | 1.00 | 18.81 | A | O |
| ATOM | 3611 | N | LEU | A | 436 | 45.152 | −21.979 | 11.871 | 1.00 | 17.30 | A | N |
| ATOM | 3612 | CA | LEU | A | 436 | 45.320 | −22.879 | 13.015 | 1.00 | 18.57 | A | C |
| ATOM | 3613 | CB | LEU | A | 436 | 44.898 | −24.321 | 12.637 | 1.00 | 18.56 | A | C |
| ATOM | 3614 | CG | LEU | A | 436 | 43.378 | −24.533 | 12.413 | 1.00 | 20.39 | A | C |
| ATOM | 3615 | CD1 | LEU | A | 436 | 43.085 | −25.939 | 11.814 | 1.00 | 19.89 | A | C |
| ATOM | 3616 | CD2 | LEU | A | 436 | 42.511 | −24.299 | 13.677 | 1.00 | 19.00 | A | C |
| ATOM | 3617 | C | LEU | A | 436 | 46.734 | −22.825 | 13.616 | 1.00 | 18.56 | A | C |
| ATOM | 3618 | O | LEU | A | 436 | 46.890 | −22.862 | 14.826 | 1.00 | 22.85 | A | O |
| ATOM | 3619 | N | CYS | A | 437 | 47.752 | −22.733 | 12.771 | 1.00 | 18.27 | A | N |
| ATOM | 3620 | CA | CYS | A | 437 | 49.124 | −22.609 | 13.221 | 1.00 | 18.06 | A | C |
| ATOM | 3621 | CB | CYS | A | 437 | 50.051 | −22.581 | 12.031 | 1.00 | 20.66 | A | C |
| ATOM | 3622 | SG | CYS | A | 437 | 50.305 | −24.213 | 11.297 | 1.00 | 24.31 | A | S |
| ATOM | 3623 | C | CYS | A | 437 | 49.300 | −21.305 | 14.012 | 1.00 | 20.39 | A | C |
| ATOM | 3624 | O | CYS | A | 437 | 49.927 | −21.286 | 15.042 | 1.00 | 23.46 | A | O |
| ATOM | 3625 | N | ASN | A | 438 | 48.738 | −20.233 | 13.487 | 1.00 | 18.39 | A | N |
| ATOM | 3626 | CA | ASN | A | 438 | 48.801 | −18.903 | 14.099 | 1.00 | 19.69 | A | C |
| ATOM | 3627 | CB | ASN | A | 438 | 48.116 | −17.871 | 13.172 | 1.00 | 19.76 | A | C |
| ATOM | 3628 | CG | ASN | A | 438 | 48.286 | −16.435 | 13.678 | 1.00 | 27.64 | A | C |
| ATOM | 3629 | OD1 | ASN | A | 438 | 48.974 | −16.224 | 14.631 | 1.00 | 29.01 | A | O |
| ATOM | 3630 | ND2 | ASN | A | 438 | 47.730 | −15.473 | 12.988 | 1.00 | 23.97 | A | N |
| ATOM | 3631 | C | ASN | A | 438 | 48.120 | −18.944 | 15.451 | 1.00 | 21.36 | A | C |
| ATOM | 3632 | O | ASN | A | 438 | 48.694 | −18.536 | 16.480 | 1.00 | 23.50 | A | O |
| ATOM | 3633 | N | ASP | A | 439 | 46.902 | −19.473 | 15.473 | 1.00 | 19.55 | A | N |
| ATOM | 3634 | CA | ASP | A | 439 | 46.146 | −19.487 | 16.702 | 1.00 | 19.28 | A | C |
| ATOM | 3635 | CB | ASP | A | 439 | 44.661 | −19.756 | 16.448 | 1.00 | 19.28 | A | C |
| ATOM | 3636 | CG | ASP | A | 439 | 43.932 | −18.546 | 15.925 | 1.00 | 21.53 | A | C |
| ATOM | 3637 | OD1 | ASP | A | 439 | 44.580 | −17.555 | 15.494 | 1.00 | 19.39 | A | O |
| ATOM | 3638 | OD2 | ASP | A | 439 | 42.672 | −18.593 | 15.921 | 1.00 | 23.22 | A | O |
| ATOM | 3639 | C | ASP | A | 439 | 46.732 | −20.438 | 17.731 | 1.00 | 22.35 | A | C |
| ATOM | 3640 | O | ASP | A | 439 | 46.658 | −20.158 | 18.952 | 1.00 | 24.01 | A | O |
| ATOM | 3641 | N | LEU | A | 440 | 47.316 | −21.547 | 17.286 | 1.00 | 22.14 | A | N |
| ATOM | 3642 | CA | LEU | A | 440 | 48.029 | −22.441 | 18.221 | 1.00 | 23.93 | A | C |
| ATOM | 3643 | CB | LEU | A | 440 | 48.523 | −23.732 | 17.555 | 1.00 | 23.86 | A | C |
| ATOM | 3644 | CG | LEU | A | 440 | 47.537 | −24.862 | 17.307 | 1.00 | 25.59 | A | C |
| ATOM | 3645 | CD1 | LEU | A | 440 | 48.140 | −25.874 | 16.284 | 1.00 | 22.82 | A | C |
| ATOM | 3646 | CD2 | LEU | A | 440 | 47.097 | −25.559 | 18.609 | 1.00 | 21.71 | A | C |
| ATOM | 3647 | C | LEU | A | 440 | 49.218 | −21.755 | 18.890 | 1.00 | 27.52 | A | C |
| ATOM | 3648 | O | LEU | A | 440 | 49.452 | −21.962 | 20.077 | 1.00 | 26.63 | A | O |
| ATOM | 3649 | N | ALA | A | 441 | 49.969 | −20.967 | 18.123 | 1.00 | 26.98 | A | N |
| ATOM | 3650 | CA | ALA | A | 441 | 51.138 | −20.229 | 18.651 | 1.00 | 28.39 | A | C |
| ATOM | 3651 | CB | ALA | A | 441 | 51.774 | −19.412 | 17.571 | 1.00 | 25.07 | A | C |
| ATOM | 3652 | C | ALA | A | 441 | 50.786 | −19.306 | 19.815 | 1.00 | 31.85 | A | C |
| ATOM | 3653 | O | ALA | A | 441 | 51.517 | −19.248 | 20.779 | 1.00 | 30.87 | A | O |
| ATOM | 3654 | N | SER | A | 442 | 49.654 | −18.613 | 19.737 | 1.00 | 34.55 | A | N |
| ATOM | 3655 | CA | SER | A | 442 | 49.272 | −17.614 | 20.753 | 1.00 | 31.17 | A | C |
| ATOM | 3656 | CB | SER | A | 442 | 48.827 | −16.328 | 20.058 | 1.00 | 32.51 | A | C |
| ATOM | 3657 | OG | SER | A | 442 | 47.744 | −16.577 | 19.187 | 1.00 | 37.82 | A | O |
| ATOM | 3658 | C | SER | A | 442 | 48.178 | −18.061 | 21.716 | 1.00 | 32.18 | A | C |
| ATOM | 3659 | O | SER | A | 442 | 47.830 | −17.330 | 22.649 | 1.00 | 37.74 | A | O |
| ATOM | 3660 | N | ALA | A | 443 | 47.658 | −19.268 | 21.535 | 1.00 | 26.46 | A | N |
| ATOM | 3661 | CA | ALA | A | 443 | 46.509 | −19.710 | 22.326 | 1.00 | 25.17 | A | C |
| ATOM | 3662 | CB | ALA | A | 443 | 46.080 | −21.107 | 21.915 | 1.00 | 26.66 | A | C |
| ATOM | 3663 | C | ALA | A | 443 | 46.758 | −19.676 | 23.845 | 1.00 | 28.97 | A | C |
| ATOM | 3664 | O | ALA | A | 443 | 45.877 | −19.257 | 24.585 | 1.00 | 27.44 | A | O |
| ATOM | 3665 | N | SER | A | 444 | 47.924 | −20.138 | 24.301 | 1.00 | 29.81 | A | N |
| ATOM | 3666 | CA | SER | A | 444 | 48.189 | −20.243 | 25.761 | 1.00 | 38.24 | A | C |
| ATOM | 3667 | CB | SER | A | 444 | 49.524 | −20.940 | 26.042 | 1.00 | 44.57 | A | C |
| ATOM | 3668 | OG | SER | A | 444 | 49.417 | −22.333 | 25.821 | 1.00 | 50.77 | A | O |
| ATOM | 3669 | C | SER | A | 444 | 48.176 | −18.886 | 26.459 | 1.00 | 31.44 | A | C |
| ATOM | 3670 | O | SER | A | 444 | 47.522 | −18.717 | 27.486 | 1.00 | 42.99 | A | O |
| ATOM | 3671 | N | ALA | A | 445 | 48.910 | −17.940 | 25.893 | 1.00 | 31.00 | A | N |
| ATOM | 3672 | CA | ALA | A | 445 | 48.970 | −16.578 | 26.389 | 1.00 | 37.39 | A | C |
| ATOM | 3673 | CB | ALA | A | 445 | 49.981 | −15.766 | 25.579 | 1.00 | 31.84 | A | C |
| ATOM | 3674 | C | ALA | A | 445 | 47.595 | −15.905 | 26.358 | 1.00 | 45.10 | A | C |
| ATOM | 3675 | O | ALA | A | 445 | 47.218 | −15.249 | 27.318 | 1.00 | 37.87 | A | O |
| ATOM | 3676 | N | GLU | A | 446 | 46.842 | −16.071 | 25.272 | 1.00 | 31.27 | A | N |
| ATOM | 3677 | CA | GLU | A | 446 | 45.536 | −15.411 | 25.147 | 1.00 | 33.60 | A | C |
| ATOM | 3678 | CB | GLU | A | 446 | 45.028 | −15.489 | 23.704 | 1.00 | 38.49 | A | C |
| ATOM | 3679 | CG | GLU | A | 446 | 45.802 | −14.564 | 22.754 | 1.00 | 40.53 | A | C |
| ATOM | 3680 | CD | GLU | A | 446 | 45.507 | −14.810 | 21.278 | 1.00 | 47.65 | A | C |
| ATOM | 3681 | OE1 | GLU | A | 446 | 44.636 | −15.647 | 20.955 | 1.00 | 46.48 | A | O |
| ATOM | 3682 | OE2 | GLU | A | 446 | 46.166 | −14.164 | 20.429 | 1.00 | 54.74 | A | O |
| ATOM | 3683 | C | GLU | A | 446 | 44.496 | −15.971 | 26.108 | 1.00 | 33.60 | A | C |
| ATOM | 3684 | O | GLU | A | 446 | 43.726 | −15.224 | 26.716 | 1.00 | 35.20 | A | O |

APPENDIX A-continued

*P. alba* 3T288C coordinates

| ATOM | 3685 | N | ILE | A | 447 | 44.473 | −17.290 | 26.222 | 1.00 | 30.36 | A | N |
|---|---|---|---|---|---|---|---|---|---|---|---|---|
| ATOM | 3686 | CA | ILE | A | 447 | 43.622 | −17.986 | 27.168 | 1.00 | 33.01 | A | C |
| ATOM | 3687 | CB | ILE | A | 447 | 43.782 | −19.509 | 27.020 | 1.00 | 33.51 | A | C |
| ATOM | 3688 | CG1 | ILE | A | 447 | 43.047 | −19.991 | 25.764 | 1.00 | 36.07 | A | C |
| ATOM | 3689 | CD1 | ILE | A | 447 | 43.514 | −21.342 | 25.254 | 1.00 | 32.96 | A | C |
| ATOM | 3690 | CG2 | ILE | A | 447 | 43.290 | −20.243 | 28.265 | 1.00 | 28.15 | A | C |
| ATOM | 3691 | C | ILE | A | 447 | 43.957 | −17.592 | 28.618 | 1.00 | 41.30 | A | C |
| ATOM | 3692 | O | ILE | A | 447 | 43.061 | −17.514 | 29.451 | 1.00 | 35.18 | A | O |
| ATOM | 3693 | N | ALA | A | 448 | 45.241 | −17.358 | 28.900 | 1.00 | 35.98 | A | N |
| ATOM | 3694 | CA | ALA | A | 448 | 45.701 | −16.935 | 30.232 | 1.00 | 39.88 | A | C |
| ATOM | 3695 | CB | ALA | A | 448 | 47.227 | −17.079 | 30.326 | 1.00 | 38.54 | A | C |
| ATOM | 3696 | C | ALA | A | 448 | 45.281 | −15.498 | 30.575 | 1.00 | 41.45 | A | C |
| ATOM | 3697 | O | ALA | A | 448 | 45.055 | −15.183 | 31.734 | 1.00 | 49.52 | A | O |
| ATOM | 3698 | N | ARG | A | 449 | 45.180 | −14.633 | 29.568 | 1.00 | 43.05 | A | N |
| ATOM | 3699 | CA | ARG | A | 449 | 44.694 | −13.266 | 29.752 | 1.00 | 37.79 | A | C |
| ATOM | 3700 | CB | ARG | A | 449 | 45.231 | −12.346 | 28.651 | 1.00 | 45.66 | A | C |
| ATOM | 3701 | CG | ARG | A | 449 | 46.748 | −12.245 | 28.560 | 1.00 | 48.52 | A | C |
| ATOM | 3702 | CD | ARG | A | 449 | 47.155 | −11.295 | 27.435 | 1.00 | 52.98 | A | C |
| ATOM | 3703 | NE | ARG | A | 449 | 48.158 | −11.903 | 26.560 | 1.00 | 65.22 | A | N |
| ATOM | 3704 | CZ | ARG | A | 449 | 48.074 | −12.008 | 25.230 | 1.00 | 67.12 | A | C |
| ATOM | 3705 | NH1 | ARG | A | 449 | 47.034 | −11.523 | 24.553 | 1.00 | 54.25 | A | N |
| ATOM | 3706 | NH2 | ARG | A | 449 | 49.058 | −12.601 | 24.556 | 1.00 | 72.81 | A | N |
| ATOM | 3707 | C | ARG | A | 449 | 43.163 | −13.183 | 29.734 | 1.00 | 41.63 | A | C |
| ATOM | 3708 | O | ARG | A | 449 | 42.606 | −12.085 | 29.794 | 1.00 | 38.89 | A | O |
| ATOM | 3709 | N | GLY | A | 450 | 42.484 | −14.325 | 29.641 | 1.00 | 36.28 | A | N |
| ATOM | 3710 | CA | GLY | A | 450 | 41.026 | −14.357 | 29.604 | 1.00 | 36.62 | A | C |
| ATOM | 3711 | C | GLY | A | 450 | 40.380 | −14.056 | 28.259 | 1.00 | 42.78 | A | C |
| ATOM | 3712 | O | GLY | A | 450 | 39.166 | −13.923 | 28.186 | 1.00 | 43.69 | A | O |
| ATOM | 3713 | N | GLU | A | 451 | 41.182 | −13.961 | 27.198 | 1.00 | 47.14 | A | N |
| ATOM | 3714 | CA | GLU | A | 451 | 40.686 | −13.682 | 25.848 | 1.00 | 43.60 | A | C |
| ATOM | 3715 | CB | GLU | A | 451 | 41.829 | −13.194 | 24.959 | 1.00 | 44.90 | A | C |
| ATOM | 3716 | CG | GLU | A | 451 | 42.482 | −11.927 | 25.491 | 1.00 | 54.21 | A | C |
| ATOM | 3717 | CD | GLU | A | 451 | 43.585 | −11.404 | 24.600 | 1.00 | 62.45 | A | C |
| ATOM | 3718 | OE1 | GLU | A | 451 | 43.462 | −11.514 | 23.355 | 1.00 | 60.04 | A | O |
| ATOM | 3719 | OE2 | GLU | A | 451 | 44.574 | −10.876 | 25.154 | 1.00 | 64.85 | A | O |
| ATOM | 3720 | C | GLU | A | 451 | 40.031 | −14.898 | 25.198 | 1.00 | 41.18 | A | C |
| ATOM | 3721 | O | GLU | A | 451 | 40.341 | −16.034 | 25.534 | 1.00 | 44.70 | A | O |
| ATOM | 3722 | N | THR | A | 452 | 39.119 | −14.637 | 24.267 | 1.00 | 33.47 | A | N |
| ATOM | 3723 | CA | THR | A | 452 | 38.338 | −15.687 | 23.611 | 1.00 | 32.68 | A | C |
| ATOM | 3724 | CB | THR | A | 452 | 36.834 | −15.582 | 23.983 | 1.00 | 33.03 | A | C |
| ATOM | 3725 | OG1 | THR | A | 452 | 36.309 | −14.334 | 23.509 | 1.00 | 34.61 | A | O |
| ATOM | 3726 | CG2 | THR | A | 452 | 36.623 | −15.701 | 25.502 | 1.00 | 29.34 | A | C |
| ATOM | 3727 | C | THR | A | 452 | 38.442 | −15.658 | 22.077 | 1.00 | 27.61 | A | C |
| ATOM | 3728 | O | THR | A | 452 | 37.873 | −16.518 | 21.417 | 1.00 | 35.74 | A | O |
| ATOM | 3729 | N | ALA | A | 453 | 39.153 | −14.672 | 21.533 | 1.00 | 27.23 | A | N |
| ATOM | 3730 | CA | ALA | A | 453 | 39.261 | −14.441 | 20.103 | 1.00 | 28.56 | A | C |
| ATOM | 3731 | CB | ALA | A | 453 | 39.508 | −12.945 | 19.807 | 1.00 | 24.78 | A | C |
| ATOM | 3732 | C | ALA | A | 453 | 40.389 | −15.278 | 19.550 | 1.00 | 28.41 | A | C |
| ATOM | 3733 | O | ALA | A | 453 | 41.394 | −14.745 | 19.086 | 1.00 | 30.61 | A | O |
| ATOM | 3734 | N | ASN | A | 454 | 40.210 | −16.594 | 19.599 | 1.00 | 26.38 | A | N |
| ATOM | 3735 | CA | ASN | A | 454 | 41.236 | −17.554 | 19.193 | 1.00 | 25.56 | A | C |
| ATOM | 3736 | CB | ASN | A | 454 | 42.239 | −17.757 | 20.338 | 1.00 | 22.98 | A | C |
| ATOM | 3737 | CG | ASN | A | 454 | 43.376 | −18.724 | 19.989 | 1.00 | 24.74 | A | C |
| ATOM | 3738 | OD1 | ASN | A | 454 | 43.207 | −19.938 | 20.050 | 1.00 | 30.88 | A | O |
| ATOM | 3739 | ND2 | ASN | A | 454 | 44.553 | −18.187 | 19.677 | 1.00 | 22.05 | A | N |
| ATOM | 3740 | C | ASN | A | 454 | 40.533 | −18.863 | 18.842 | 1.00 | 23.41 | A | C |
| ATOM | 3741 | O | ASN | A | 454 | 39.613 | −19.269 | 19.531 | 1.00 | 23.44 | A | O |
| ATOM | 3742 | N | SER | A | 455 | 40.980 | −19.535 | 17.795 | 1.00 | 20.52 | A | N |
| ATOM | 3743 | CA | SER | A | 455 | 40.342 | −20.775 | 17.361 | 1.00 | 19.85 | A | C |
| ATOM | 3744 | CB | SER | A | 455 | 41.030 | −21.305 | 16.083 | 1.00 | 20.87 | A | C |
| ATOM | 3745 | OG | SER | A | 455 | 40.892 | −20.344 | 15.030 | 1.00 | 24.90 | A | O |
| ATOM | 3746 | C | SER | A | 455 | 40.315 | −21.867 | 18.445 | 1.00 | 23.31 | A | C |
| ATOM | 3747 | O | SER | A | 455 | 39.291 | −22.553 | 18.629 | 1.00 | 21.73 | A | O |
| ATOM | 3748 | N | VAL | A | 456 | 41.436 | −22.042 | 19.143 | 1.00 | 19.77 | A | N |
| ATOM | 3749 | CA | VAL | A | 456 | 41.538 | −23.023 | 20.247 | 1.00 | 20.62 | A | C |
| ATOM | 3750 | CB | VAL | A | 456 | 42.961 | −23.046 | 20.861 | 1.00 | 26.15 | A | C |
| ATOM | 3751 | CG1 | VAL | A | 456 | 43.031 | −24.075 | 21.993 | 1.00 | 24.79 | A | C |
| ATOM | 3752 | CG2 | VAL | A | 456 | 44.013 | −23.297 | 19.785 | 1.00 | 22.76 | A | C |
| ATOM | 3753 | C | VAL | A | 456 | 40.577 | −22.721 | 21.398 | 1.00 | 22.08 | A | C |
| ATOM | 3754 | O | VAL | A | 456 | 39.960 | −23.635 | 21.969 | 1.00 | 22.97 | A | O |
| ATOM | 3755 | N | SER | A | 457 | 40.440 | −21.447 | 21.756 | 1.00 | 21.17 | A | N |
| ATOM | 3756 | CA | SER | A | 457 | 39.540 | −21.119 | 22.863 | 1.00 | 27.43 | A | C |
| ATOM | 3757 | CB | SER | A | 457 | 39.903 | −19.775 | 23.537 | 1.00 | 25.66 | A | C |
| ATOM | 3758 | OG | SER | A | 457 | 39.705 | −18.689 | 22.677 | 1.00 | 36.62 | A | O |
| ATOM | 3759 | C | SER | A | 457 | 38.079 | −21.195 | 22.410 | 1.00 | 25.99 | A | C |
| ATOM | 3760 | O | SER | A | 457 | 37.211 | −21.576 | 23.198 | 1.00 | 26.64 | A | O |
| ATOM | 3761 | N | CYS | A | 458 | 37.784 | −20.907 | 21.139 | 1.00 | 23.94 | A | N |
| ATOM | 3762 | CA | CYS | A | 458 | 36.407 | −21.151 | 20.649 | 1.00 | 21.80 | A | C |

APPENDIX A-continued

*P. alba* 3T288C coordinates

| ATOM | 3763 | CB | CYS | A | 458 | 36.109 | −20.521 | 19.299 | 1.00 | 21.16 | A | C |
|---|---|---|---|---|---|---|---|---|---|---|---|---|
| ATOM | 3764 | SG | CYS | A | 458 | 35.996 | −18.776 | 19.430 | 1.00 | 32.42 | A | S |
| ATOM | 3765 | C | CYS | A | 458 | 36.070 | −22.644 | 20.613 | 1.00 | 23.65 | A | C |
| ATOM | 3766 | O | CYS | A | 458 | 34.923 | −23.023 | 20.854 | 1.00 | 24.55 | A | O |
| ATOM | 3767 | N | TYR | A | 459 | 37.058 | −23.483 | 20.347 | 1.00 | 20.39 | A | N |
| ATOM | 3768 | CA | TYR | A | 459 | 36.814 | −24.922 | 20.314 | 1.00 | 24.45 | A | C |
| ATOM | 3769 | CB | TYR | A | 459 | 37.990 | −25.655 | 19.702 | 1.00 | 23.46 | A | C |
| ATOM | 3770 | CG | TYR | A | 459 | 37.667 | −27.042 | 19.198 | 1.00 | 28.55 | A | C |
| ATOM | 3771 | CD1 | TYR | A | 459 | 37.784 | −28.153 | 20.037 | 1.00 | 27.38 | A | C |
| ATOM | 3772 | CE1 | TYR | A | 459 | 37.503 | −29.441 | 19.585 | 1.00 | 31.49 | A | C |
| ATOM | 3773 | CZ | TYR | A | 459 | 37.096 | −29.635 | 18.266 | 1.00 | 31.60 | A | C |
| ATOM | 3774 | OH | TYR | A | 459 | 36.813 | −30.900 | 17.824 | 1.00 | 37.28 | A | O |
| ATOM | 3775 | CE2 | TYR | A | 459 | 36.969 | −28.555 | 17.407 | 1.00 | 26.89 | A | C |
| ATOM | 3776 | CD2 | TYR | A | 459 | 37.255 | −27.251 | 17.882 | 1.00 | 32.62 | A | C |
| ATOM | 3777 | C | TYR | A | 459 | 36.541 | −25.427 | 21.738 | 1.00 | 23.84 | A | C |
| ATOM | 3778 | O | TYR | A | 459 | 35.589 | −26.171 | 21.966 | 1.00 | 21.78 | A | O |
| ATOM | 3779 | N | MET | A | 460 | 37.359 | −24.978 | 22.691 | 1.00 | 24.24 | A | N |
| ATOM | 3780 | CA | MET | A | 460 | 37.134 | −25.253 | 24.120 | 1.00 | 23.73 | A | C |
| ATOM | 3781 | CB | MET | A | 460 | 38.093 | −24.432 | 24.979 | 1.00 | 24.01 | A | C |
| ATOM | 3782 | CG | MET | A | 460 | 39.520 | −24.918 | 24.935 | 1.00 | 28.42 | A | C |
| ATOM | 3783 | SD | MET | A | 460 | 40.629 | −23.759 | 25.730 | 1.00 | 34.44 | A | S |
| ATOM | 3784 | CE | MET | A | 460 | 40.012 | −23.901 | 27.446 | 1.00 | 27.52 | A | C |
| ATOM | 3785 | C | MET | A | 460 | 35.699 | −24.952 | 24.575 | 1.00 | 24.85 | A | C |
| ATOM | 3786 | O | MET | A | 460 | 35.056 | −25.765 | 25.259 | 1.00 | 26.64 | A | O |
| ATOM | 3787 | N | ARG | A | 461 | 35.218 | −23.775 | 24.188 | 1.00 | 26.93 | A | N |
| ATOM | 3788 | CA | ARG | A | 461 | 33.922 | −23.276 | 24.596 | 1.00 | 26.56 | A | C |
| ATOM | 3789 | CB | ARG | A | 461 | 33.789 | −21.798 | 24.236 | 1.00 | 25.65 | A | C |
| ATOM | 3790 | CG | ARG | A | 461 | 32.444 | −21.163 | 24.577 | 1.00 | 34.73 | A | C |
| ATOM | 3791 | CD | ARG | A | 461 | 32.528 | −19.649 | 24.477 | 1.00 | 36.40 | A | C |
| ATOM | 3792 | NE | ARG | A | 461 | 32.808 | −19.191 | 23.111 | 1.00 | 34.87 | A | N |
| ATOM | 3793 | CZ | ARG | A | 461 | 33.253 | −17.977 | 22.788 | 1.00 | 36.31 | A | C |
| ATOM | 3794 | NH1 | ARG | A | 461 | 33.494 | −17.073 | 23.740 | 1.00 | 37.11 | A | N |
| ATOM | 3795 | NH2 | ARG | A | 461 | 33.461 | −17.654 | 21.504 | 1.00 | 35.17 | A | N |
| ATOM | 3796 | C | ARG | A | 461 | 32.809 | −24.077 | 23.943 | 1.00 | 29.33 | A | C |
| ATOM | 3797 | O | ARG | A | 461 | 31.876 | −24.458 | 24.610 | 1.00 | 26.80 | A | O |
| ATOM | 3798 | N | THR | A | 462 | 32.908 | −24.340 | 22.645 | 1.00 | 25.41 | A | N |
| ATOM | 3799 | CA | THR | A | 462 | 31.825 | −25.025 | 21.931 | 1.00 | 25.70 | A | C |
| ATOM | 3800 | CB | THR | A | 462 | 31.999 | −24.938 | 20.395 | 1.00 | 28.39 | A | C |
| ATOM | 3801 | OG1 | THR | A | 462 | 31.983 | −23.565 | 19.979 | 1.00 | 19.95 | A | O |
| ATOM | 3802 | CG2 | THR | A | 462 | 30.869 | −25.735 | 19.679 | 1.00 | 28.51 | A | C |
| ATOM | 3803 | C | THR | A | 462 | 31.712 | −26.501 | 22.310 | 1.00 | 26.92 | A | C |
| ATOM | 3804 | O | THR | A | 462 | 30.617 | −27.028 | 22.429 | 1.00 | 25.53 | A | O |
| ATOM | 3805 | N | LYS | A | 463 | 32.847 | −27.168 | 22.474 | 1.00 | 31.10 | A | N |
| ATOM | 3806 | CA | LYS | A | 463 | 32.851 | −28.580 | 22.838 | 1.00 | 33.80 | A | C |
| ATOM | 3807 | CB | LYS | A | 463 | 34.072 | −29.287 | 22.264 | 1.00 | 35.18 | A | C |
| ATOM | 3808 | CG | LYS | A | 463 | 34.167 | −29.257 | 20.764 | 1.00 | 41.17 | A | C |
| ATOM | 3809 | CD | LYS | A | 463 | 32.996 | −29.915 | 20.082 | 1.00 | 45.55 | A | C |
| ATOM | 3810 | CE | LYS | A | 463 | 33.373 | −30.271 | 18.648 | 1.00 | 45.12 | A | C |
| ATOM | 3811 | NZ | LYS | A | 463 | 32.209 | −30.829 | 17.923 | 1.00 | 43.29 | A | N |
| ATOM | 3812 | C | LYS | A | 463 | 32.839 | −28.775 | 24.348 | 1.00 | 34.33 | A | C |
| ATOM | 3813 | O | LYS | A | 463 | 32.583 | −29.881 | 24.811 | 1.00 | 34.14 | A | O |
| ATOM | 3814 | N | GLY | A | 464 | 33.129 | −27.716 | 25.103 | 1.00 | 33.67 | A | N |
| ATOM | 3815 | CA | GLY | A | 464 | 33.148 | −27.780 | 26.570 | 1.00 | 37.10 | A | C |
| ATOM | 3816 | C | GLY | A | 464 | 34.308 | −28.622 | 27.070 | 1.00 | 33.81 | A | C |
| ATOM | 3817 | O | GLY | A | 464 | 34.111 | −29.505 | 27.883 | 1.00 | 28.67 | A | O |
| ATOM | 3818 | N | ILE | A | 465 | 35.519 | −28.366 | 26.579 | 1.00 | 26.69 | A | N |
| ATOM | 3819 | CA | ILE | A | 465 | 36.658 | −29.192 | 26.955 | 1.00 | 22.86 | A | C |
| ATOM | 3820 | CB | ILE | A | 465 | 37.034 | −30.183 | 25.818 | 1.00 | 25.64 | A | C |
| ATOM | 3821 | CG1 | ILE | A | 465 | 37.358 | −29.446 | 24.511 | 1.00 | 24.83 | A | C |
| ATOM | 3822 | CD1 | ILE | A | 465 | 37.700 | −30.355 | 23.334 | 1.00 | 22.74 | A | C |
| ATOM | 3823 | CG2 | ILE | A | 465 | 35.893 | −31.178 | 25.581 | 1.00 | 29.07 | A | C |
| ATOM | 3824 | C | ILE | A | 465 | 37.860 | −28.354 | 27.338 | 1.00 | 24.61 | A | C |
| ATOM | 3825 | O | ILE | A | 465 | 37.915 | −27.143 | 27.073 | 1.00 | 25.73 | A | O |
| ATOM | 3826 | N | SER | A | 466 | 38.845 | −29.020 | 27.923 | 1.00 | 24.33 | A | N |
| ATOM | 3827 | CA | SER | A | 466 | 40.073 | −28.378 | 28.353 | 1.00 | 28.81 | A | C |
| ATOM | 3828 | CB | SER | A | 466 | 40.935 | −29.366 | 29.140 | 1.00 | 28.18 | A | C |
| ATOM | 3829 | OG | SER | A | 466 | 41.359 | −30.428 | 28.295 | 1.00 | 25.24 | A | O |
| ATOM | 3830 | C | SER | A | 466 | 40.891 | −27.888 | 27.177 | 1.00 | 28.41 | A | C |
| ATOM | 3831 | O | SER | A | 466 | 40.745 | −28.391 | 26.052 | 1.00 | 30.75 | A | O |
| ATOM | 3832 | N | GLU | A | 467 | 41.775 | −26.933 | 27.460 | 1.00 | 27.64 | A | N |
| ATOM | 3833 | CA | GLU | A | 467 | 42.778 | −26.491 | 26.518 | 1.00 | 33.68 | A | C |
| ATOM | 3834 | CB | GLU | A | 467 | 43.713 | −25.437 | 27.142 | 1.00 | 32.28 | A | C |
| ATOM | 3835 | CG | GLU | A | 467 | 44.726 | −24.910 | 26.108 | 1.00 | 36.53 | A | C |
| ATOM | 3836 | CD | GLU | A | 467 | 45.627 | −23.809 | 26.617 | 1.00 | 45.60 | A | C |
| ATOM | 3837 | OE1 | GLU | A | 467 | 45.418 | −23.326 | 27.751 | 1.00 | 44.86 | A | O |
| ATOM | 3838 | OE2 | GLU | A | 467 | 46.555 | −23.424 | 25.865 | 1.00 | 43.13 | A | O |
| ATOM | 3839 | C | GLU | A | 467 | 43.601 | −27.655 | 25.933 | 1.00 | 36.62 | A | C |
| ATOM | 3840 | O | GLU | A | 467 | 43.874 | −27.683 | 24.732 | 1.00 | 28.59 | A | O |

APPENDIX A-continued

*P. alba* 3T288C coordinates

| ATOM | 3841 | N | GLU | A | 468 | 43.979 | −28.617 | 26.766 | 1.00 | 28.32 | A | N |
|---|---|---|---|---|---|---|---|---|---|---|---|---|
| ATOM | 3842 | CA | GLU | A | 468 | 44.820 | −29.694 | 26.301 | 1.00 | 33.91 | A | C |
| ATOM | 3843 | CB | GLU | A | 468 | 45.284 | −30.563 | 27.465 | 1.00 | 41.97 | A | C |
| ATOM | 3844 | CG | GLU | A | 468 | 46.394 | −31.522 | 27.070 | 1.00 | 58.39 | A | C |
| ATOM | 3845 | CD | GLU | A | 468 | 47.010 | −32.247 | 28.251 | 1.00 | 72.95 | A | C |
| ATOM | 3846 | OE1 | GLU | A | 468 | 46.592 | −31.996 | 29.404 | 1.00 | 83.55 | A | O |
| ATOM | 3847 | OE2 | GLU | A | 468 | 47.920 | −33.073 | 28.016 | 1.00 | 76.95 | A | O |
| ATOM | 3848 | C | GLU | A | 468 | 44.106 | −30.548 | 25.237 | 1.00 | 31.82 | A | C |
| ATOM | 3849 | O | GLU | A | 468 | 44.697 | −30.877 | 24.209 | 1.00 | 29.90 | A | O |
| ATOM | 3850 | N | LEU | A | 469 | 42.850 | −30.900 | 25.496 | 1.00 | 31.05 | A | N |
| ATOM | 3851 | CA | LEU | A | 469 | 42.065 | −31.697 | 24.551 | 1.00 | 30.37 | A | C |
| ATOM | 3852 | CB | LEU | A | 469 | 40.771 | −32.189 | 25.190 | 1.00 | 34.71 | A | C |
| ATOM | 3853 | CG | LEU | A | 469 | 40.867 | −33.374 | 26.156 | 1.00 | 46.07 | A | C |
| ATOM | 3854 | CD1 | LEU | A | 469 | 39.488 | −33.690 | 26.782 | 1.00 | 35.79 | A | C |
| ATOM | 3855 | CD2 | LEU | A | 469 | 41.438 | −34.600 | 25.441 | 1.00 | 39.75 | A | C |
| ATOM | 3856 | C | LEU | A | 469 | 41.722 | −30.888 | 23.289 | 1.00 | 29.53 | A | C |
| ATOM | 3857 | O | LEU | A | 469 | 41.668 | −31.440 | 22.211 | 1.00 | 28.42 | A | O |
| ATOM | 3858 | N | ALA | A | 470 | 41.467 | −29.592 | 23.442 | 1.00 | 25.77 | A | N |
| ATOM | 3859 | CA | ALA | A | 470 | 41.116 | −28.735 | 22.309 | 1.00 | 28.38 | A | C |
| ATOM | 3860 | CB | ALA | A | 470 | 40.642 | −27.366 | 22.767 | 1.00 | 21.67 | A | C |
| ATOM | 3861 | C | ALA | A | 470 | 42.328 | −28.626 | 21.406 | 1.00 | 28.76 | A | C |
| ATOM | 3862 | O | ALA | A | 470 | 42.199 | −28.735 | 20.194 | 1.00 | 27.45 | A | O |
| ATOM | 3863 | N | THR | A | 471 | 43.506 | −28.473 | 22.010 | 1.00 | 23.17 | A | N |
| ATOM | 3864 | CA | THR | A | 471 | 44.751 | −28.407 | 21.284 | 1.00 | 24.26 | A | C |
| ATOM | 3865 | CB | THR | A | 471 | 45.886 | −28.155 | 22.259 | 1.00 | 24.13 | A | C |
| ATOM | 3866 | OG1 | THR | A | 471 | 45.651 | −26.890 | 22.876 | 1.00 | 25.52 | A | O |
| ATOM | 3867 | CG2 | THR | A | 471 | 47.229 | −28.118 | 21.572 | 1.00 | 24.56 | A | C |
| ATOM | 3868 | C | THR | A | 471 | 45.009 | −29.668 | 20.445 | 1.00 | 29.77 | A | C |
| ATOM | 3869 | O | THR | A | 471 | 45.344 | −29.588 | 19.253 | 1.00 | 22.06 | A | O |
| ATOM | 3870 | N | GLU | A | 472 | 44.855 | −30.824 | 21.064 | 1.00 | 22.52 | A | N |
| ATOM | 3871 | CA | GLU | A | 472 | 44.944 | −32.083 | 20.369 | 1.00 | 27.11 | A | C |
| ATOM | 3872 | CB | GLU | A | 472 | 44.727 | −33.204 | 21.387 | 1.00 | 30.22 | A | C |
| ATOM | 3873 | CG | GLU | A | 472 | 44.802 | −34.608 | 20.851 | 1.00 | 38.12 | A | C |
| ATOM | 3874 | CD | GLU | A | 472 | 44.752 | −35.666 | 21.965 | 1.00 | 53.74 | A | C |
| ATOM | 3875 | OE1 | GLU | A | 472 | 44.133 | −35.428 | 23.039 | 1.00 | 54.00 | A | O |
| ATOM | 3876 | OE2 | GLU | A | 472 | 45.342 | −36.745 | 21.754 | 1.00 | 63.63 | A | O |
| ATOM | 3877 | C | GLU | A | 472 | 43.938 | −32.192 | 19.198 | 1.00 | 25.58 | A | C |
| ATOM | 3878 | O | GLU | A | 472 | 44.285 | −32.658 | 18.105 | 1.00 | 24.92 | A | O |
| ATOM | 3879 | N | SER | A | 473 | 42.705 | −31.767 | 19.414 | 1.00 | 20.39 | A | N |
| ATOM | 3880 | CA | SER | A | 473 | 41.719 | −31.768 | 18.333 | 1.00 | 25.72 | A | C |
| ATOM | 3881 | CB | SER | A | 473 | 40.355 | −31.332 | 18.814 | 1.00 | 26.44 | A | C |
| ATOM | 3882 | OG | SER | A | 473 | 39.941 | −32.144 | 19.881 | 1.00 | 34.79 | A | O |
| ATOM | 3883 | C | SER | A | 473 | 42.141 | −30.835 | 17.195 | 1.00 | 19.41 | A | C |
| ATOM | 3884 | O | SER | A | 473 | 41.921 | −31.148 | 16.044 | 1.00 | 17.90 | A | O |
| ATOM | 3885 | N | VAL | A | 474 | 42.720 | −29.698 | 17.516 | 1.00 | 19.66 | A | N |
| ATOM | 3886 | CA | VAL | A | 474 | 43.154 | −28.780 | 16.494 | 1.00 | 19.80 | A | C |
| ATOM | 3887 | CB | VAL | A | 474 | 43.533 | −27.425 | 17.074 | 1.00 | 21.08 | A | C |
| ATOM | 3888 | CG1 | VAL | A | 474 | 44.344 | −26.594 | 16.023 | 1.00 | 19.39 | A | C |
| ATOM | 3889 | CG2 | VAL | A | 474 | 42.271 | −26.706 | 17.477 | 1.00 | 22.82 | A | C |
| ATOM | 3890 | C | VAL | A | 474 | 44.290 | −29.380 | 15.656 | 1.00 | 22.88 | A | C |
| ATOM | 3891 | O | VAL | A | 474 | 44.303 | −29.227 | 14.422 | 1.00 | 22.10 | A | O |
| ATOM | 3892 | N | MET | A | 475 | 45.210 | −30.066 | 16.330 | 1.00 | 23.45 | A | N |
| ATOM | 3893 | CA | MET | A | 475 | 46.330 | −30.754 | 15.683 | 1.00 | 26.71 | A | C |
| ATOM | 3894 | CB | MET | A | 475 | 47.260 | −31.391 | 16.730 | 1.00 | 30.53 | A | C |
| ATOM | 3895 | CG | MET | A | 475 | 47.905 | −30.421 | 17.692 | 1.00 | 36.44 | A | C |
| ATOM | 3896 | SD | MET | A | 475 | 49.127 | −29.516 | 16.796 | 1.00 | 41.54 | A | S |
| ATOM | 3897 | CE | MET | A | 475 | 50.421 | −30.764 | 16.673 | 1.00 | 51.84 | A | C |
| ATOM | 3898 | C | MET | A | 475 | 45.818 | −31.839 | 14.759 | 1.00 | 23.38 | A | C |
| ATOM | 3899 | O | MET | A | 475 | 46.339 | −32.029 | 13.659 | 1.00 | 25.85 | A | O |
| ATOM | 3900 | N | ASN | A | 476 | 44.817 | −32.571 | 15.219 | 1.00 | 21.43 | A | N |
| ATOM | 3901 | CA | ASN | A | 476 | 44.176 | −33.555 | 14.373 | 1.00 | 25.46 | A | C |
| ATOM | 3902 | CB | ASN | A | 476 | 43.201 | −34.431 | 15.160 | 1.00 | 28.65 | A | C |
| ATOM | 3903 | CG | ASN | A | 476 | 43.891 | −35.297 | 16.218 | 1.00 | 31.36 | A | C |
| ATOM | 3904 | OD1 | ASN | A | 476 | 45.102 | −35.492 | 16.204 | 1.00 | 38.00 | A | O |
| ATOM | 3905 | ND2 | ASN | A | 476 | 43.097 | −35.826 | 17.141 | 1.00 | 27.91 | A | N |
| ATOM | 3906 | C | ASN | A | 476 | 43.475 | −32.919 | 13.176 | 1.00 | 21.71 | A | C |
| ATOM | 3907 | O | ASN | A | 476 | 43.482 | −33.507 | 12.094 | 1.00 | 19.35 | A | O |
| ATOM | 3908 | N | LEU | A | 477 | 42.887 | −31.731 | 13.351 | 1.00 | 20.67 | A | N |
| ATOM | 3909 | CA | ALEU | A | 477 | 42.311 | −30.995 | 12.215 | 0.50 | 19.61 | A | C |
| ATOM | 3910 | CA | BLEU | A | 477 | 42.309 | −30.983 | 12.221 | 0.50 | 22.54 | A | C |
| ATOM | 3911 | CB | ALEU | A | 477 | 41.581 | −29.741 | 12.677 | 0.50 | 18.09 | A | C |
| ATOM | 3912 | CB | BLEU | A | 477 | 41.574 | −29.721 | 12.691 | 0.50 | 25.47 | A | C |
| ATOM | 3913 | CG | ALEU | A | 477 | 40.866 | −28.940 | 11.586 | 0.50 | 18.16 | A | C |
| ATOM | 3914 | CG | BLEU | A | 477 | 40.038 | −29.768 | 12.688 | 0.50 | 33.95 | A | C |
| ATOM | 3915 | CD1 | ALEU | A | 477 | 40.121 | −29.860 | 10.614 | 0.50 | 21.10 | A | C |
| ATOM | 3916 | CD1 | BLEU | A | 477 | 39.458 | −28.519 | 13.367 | 0.50 | 29.79 | A | C |
| ATOM | 3917 | CD2 | ALEU | A | 477 | 39.912 | −27.901 | 12.226 | 0.50 | 16.24 | A | C |
| ATOM | 3918 | CD2 | BLEU | A | 477 | 39.506 | −29.905 | 11.257 | 0.50 | 35.02 | A | C |

APPENDIX A-continued

*P. alba* 3T288C coordinates

| ATOM | 3919 | C | LEU | A | 477 | 43.396 | −30.616 | 11.194 | 1.00 | 21.48 | A | C |
|---|---|---|---|---|---|---|---|---|---|---|---|---|
| ATOM | 3920 | O | LEU | A | 477 | 43.184 | −30.706 | 9.980 | 1.00 | 18.70 | A | O |
| ATOM | 3921 | N | ILE | A | 478 | 44.553 | −30.224 | 11.684 | 1.00 | 17.10 | A | N |
| ATOM | 3922 | CA | ILE | A | 478 | 45.705 | −29.917 | 10.800 | 1.00 | 16.49 | A | C |
| ATOM | 3923 | CB | ILE | A | 478 | 46.905 | −29.359 | 11.577 | 1.00 | 16.79 | A | C |
| ATOM | 3924 | CG1 | ILE | A | 478 | 46.568 | −27.911 | 12.029 | 1.00 | 18.33 | A | C |
| ATOM | 3925 | CD1 | ILE | A | 478 | 47.611 | −27.299 | 13.009 | 1.00 | 22.73 | A | C |
| ATOM | 3926 | CG2 | ILE | A | 478 | 48.224 | −29.287 | 10.695 | 1.00 | 12.76 | A | C |
| ATOM | 3927 | C | ILE | A | 478 | 46.117 | −31.151 | 10.005 | 1.00 | 19.00 | A | C |
| ATOM | 3928 | O | ILE | A | 478 | 46.283 | −31.068 | 8.781 | 1.00 | 16.79 | A | O |
| ATOM | 3929 | N | ASP | A | 479 | 46.235 | −32.294 | 10.679 | 1.00 | 15.78 | A | N |
| ATOM | 3930 | CA | ASP | A | 479 | 46.574 | −33.527 | 9.978 | 1.00 | 17.49 | A | C |
| ATOM | 3931 | CB | ASP | A | 479 | 46.714 | −34.691 | 10.947 | 1.00 | 20.17 | A | C |
| ATOM | 3932 | CG | ASP | A | 479 | 47.988 | −34.598 | 11.800 | 1.00 | 33.33 | A | C |
| ATOM | 3933 | OD1 | ASP | A | 479 | 48.979 | −33.880 | 11.465 | 1.00 | 37.08 | A | O |
| ATOM | 3934 | OD2 | ASP | A | 479 | 47.986 | −35.279 | 12.834 | 1.00 | 31.99 | A | O |
| ATOM | 3935 | C | ASP | A | 479 | 45.568 | −33.909 | 8.907 | 1.00 | 16.09 | A | C |
| ATOM | 3936 | O | ASP | A | 479 | 45.956 | −34.308 | 7.800 | 1.00 | 16.06 | A | O |
| ATOM | 3937 | N | GLU | A | 480 | 44.288 | −33.873 | 9.265 | 1.00 | 17.62 | A | N |
| ATOM | 3938 | CA | GLU | A | 480 | 43.212 | −34.154 | 8.308 | 1.00 | 19.20 | A | C |
| ATOM | 3939 | CB | GLU | A | 480 | 41.862 | −34.092 | 9.028 | 1.00 | 22.65 | A | C |
| ATOM | 3940 | CG | GLU | A | 480 | 40.652 | −34.191 | 8.172 | 1.00 | 37.11 | A | C |
| ATOM | 3941 | CD | GLU | A | 480 | 39.410 | −33.735 | 8.938 | 1.00 | 52.61 | A | C |
| ATOM | 3942 | OE1 | GLU | A | 480 | 39.183 | −34.254 | 10.046 | 1.00 | 53.08 | A | O |
| ATOM | 3943 | OE2 | GLU | A | 480 | 38.689 | −32.839 | 8.451 | 1.00 | 51.93 | A | O |
| ATOM | 3944 | C | GLU | A | 480 | 43.227 | −33.238 | 7.101 | 1.00 | 16.53 | A | C |
| ATOM | 3945 | O | GLU | A | 480 | 43.033 | −33.694 | 5.970 | 1.00 | 14.41 | A | O |
| ATOM | 3946 | N | THR | A | 481 | 43.461 | −31.947 | 7.340 | 1.00 | 15.80 | A | N |
| ATOM | 3947 | CA | THR | A | 481 | 43.569 | −30.981 | 6.290 | 1.00 | 13.89 | A | C |
| ATOM | 3948 | CB | THR | A | 481 | 43.657 | −29.560 | 6.890 | 1.00 | 17.77 | A | C |
| ATOM | 3949 | OG1 | THR | A | 481 | 42.509 | −29.362 | 7.753 | 1.00 | 19.40 | A | O |
| ATOM | 3950 | CG2 | THR | A | 481 | 43.759 | −28.502 | 5.761 | 1.00 | 16.74 | A | C |
| ATOM | 3951 | C | THR | A | 481 | 44.753 | −31.287 | 5.358 | 1.00 | 16.12 | A | C |
| ATOM | 3952 | O | THR | A | 481 | 44.613 | −31.231 | 4.136 | 1.00 | 13.98 | A | O |
| ATOM | 3953 | N | TRP | A | 482 | 45.912 | −31.626 | 5.919 | 1.00 | 15.23 | A | N |
| ATOM | 3954 | CA | TRP | A | 482 | 47.020 | −32.110 | 5.088 | 1.00 | 14.38 | A | C |
| ATOM | 3955 | CB | TRP | A | 482 | 48.225 | −32.441 | 5.967 | 1.00 | 15.52 | A | C |
| ATOM | 3956 | CG | TRP | A | 482 | 49.119 | −31.248 | 6.112 | 1.00 | 16.43 | A | C |
| ATOM | 3957 | CD1 | TRP | A | 482 | 49.158 | −30.313 | 7.151 | 1.00 | 17.00 | A | C |
| ATOM | 3958 | NE1 | TRP | A | 482 | 50.107 | −29.366 | 6.895 | 1.00 | 18.88 | A | N |
| ATOM | 3959 | CE2 | TRP | A | 482 | 50.679 | −29.572 | 5.689 | 1.00 | 16.63 | A | C |
| ATOM | 3960 | CD2 | TRP | A | 482 | 50.076 | −30.767 | 5.126 | 1.00 | 13.73 | A | C |
| ATOM | 3961 | CE3 | TRP | A | 482 | 50.490 | −31.211 | 3.881 | 1.00 | 18.76 | A | C |
| ATOM | 3962 | CZ3 | TRP | A | 482 | 51.471 | −30.491 | 3.201 | 1.00 | 20.35 | A | C |
| ATOM | 3963 | CH2 | TRP | A | 482 | 52.048 | −29.341 | 3.769 | 1.00 | 15.16 | A | C |
| ATOM | 3964 | CZ2 | TRP | A | 482 | 51.645 | −28.849 | 5.004 | 1.00 | 17.19 | A | C |
| ATOM | 3965 | C | TRP | A | 482 | 46.663 | −33.309 | 4.206 | 1.00 | 15.56 | A | C |
| ATOM | 3966 | O | TRP | A | 482 | 47.020 | −33.322 | 3.043 | 1.00 | 14.64 | A | O |
| ATOM | 3967 | N | LYS | A | 483 | 45.952 | −34.292 | 4.738 | 1.00 | 12.09 | A | N |
| ATOM | 3968 | CA | LYS | A | 483 | 45.562 | −35.442 | 3.931 | 1.00 | 14.07 | A | C |
| ATOM | 3969 | CB | LYS | A | 483 | 44.834 | −36.468 | 4.751 | 1.00 | 12.95 | A | C |
| ATOM | 3970 | CG | LYS | A | 483 | 45.695 | −37.214 | 5.710 | 1.00 | 15.23 | A | C |
| ATOM | 3971 | CD | LYS | A | 483 | 44.778 | −38.101 | 6.628 | 1.00 | 16.87 | A | C |
| ATOM | 3972 | CE | LYS | A | 483 | 45.546 | −38.727 | 7.744 | 1.00 | 20.92 | A | C |
| ATOM | 3973 | NZ | LYS | A | 483 | 44.621 | −39.452 | 8.640 | 1.00 | 19.13 | A | N |
| ATOM | 3974 | C | LYS | A | 483 | 44.679 | −35.024 | 2.743 | 1.00 | 13.93 | A | C |
| ATOM | 3975 | O | LYS | A | 483 | 44.848 | −35.547 | 1.644 | 1.00 | 13.27 | A | O |
| ATOM | 3976 | N | LYS | A | 484 | 43.810 | −34.043 | 2.959 | 1.00 | 14.49 | A | N |
| ATOM | 3977 | CA | LYS | A | 484 | 42.973 | −33.514 | 1.868 | 1.00 | 16.83 | A | C |
| ATOM | 3978 | CB | LYS | A | 484 | 41.829 | −32.688 | 2.407 | 1.00 | 15.87 | A | C |
| ATOM | 3979 | CG | LYS | A | 484 | 40.884 | −33.521 | 3.224 | 1.00 | 19.52 | A | C |
| ATOM | 3980 | CD | LYS | A | 484 | 39.799 | −32.667 | 3.808 | 1.00 | 28.94 | A | C |
| ATOM | 3981 | CE | LYS | A | 484 | 38.915 | −33.469 | 4.724 | 1.00 | 33.21 | A | C |
| ATOM | 3982 | NZ | LYS | A | 484 | 37.962 | −32.556 | 5.364 | 1.00 | 37.29 | A | N |
| ATOM | 3983 | C | LYS | A | 484 | 43.764 | −32.752 | 0.835 | 1.00 | 15.35 | A | C |
| ATOM | 3984 | O | LYS | A | 484 | 43.563 | −32.937 | −0.367 | 1.00 | 16.38 | A | O |
| ATOM | 3985 | N | MET | A | 485 | 44.729 | −31.963 | 1.274 | 1.00 | 15.56 | A | N |
| ATOM | 3986 | CA | MET | A | 485 | 45.564 | −31.230 | 0.338 | 1.00 | 18.45 | A | C |
| ATOM | 3987 | CB | MET | A | 485 | 46.475 | −30.224 | 1.047 | 1.00 | 17.39 | A | C |
| ATOM | 3988 | CG | MET | A | 485 | 45.772 | −29.041 | 1.663 | 1.00 | 21.79 | A | C |
| ATOM | 3989 | SD | MET | A | 485 | 46.944 | −27.785 | 2.264 | 1.00 | 23.85 | A | S |
| ATOM | 3990 | CE | MET | A | 485 | 47.995 | −28.677 | 3.419 | 1.00 | 21.57 | A | C |
| ATOM | 3991 | C | MET | A | 485 | 46.434 | −32.213 | −0.445 | 1.00 | 17.61 | A | C |
| ATOM | 3992 | O | MET | A | 485 | 46.626 | −32.015 | −1.645 | 1.00 | 17.08 | A | O |
| ATOM | 3993 | N | ASN | A | 486 | 46.885 | −33.299 | 0.199 | 1.00 | 18.25 | A | N |
| ATOM | 3994 | CA | ASN | A | 486 | 47.701 | −34.305 | −0.469 | 1.00 | 15.51 | A | C |
| ATOM | 3995 | CB | ASN | A | 486 | 48.192 | −35.399 | 0.497 | 1.00 | 16.05 | A | C |
| ATOM | 3996 | CG | ASN | A | 486 | 49.299 | −34.941 | 1.463 | 1.00 | 15.97 | A | C |

APPENDIX A-continued

*P. alba* 3T288C coordinates

| ATOM | 3997 | OD1 | ASN | A | 486 | 49.975 | −33.950 | 1.250 | 1.00 | 17.54 | A | O |
|---|---|---|---|---|---|---|---|---|---|---|---|---|
| ATOM | 3998 | ND2 | ASN | A | 486 | 49.468 | −35.706 | 2.557 | 1.00 | 13.12 | A | N |
| ATOM | 3999 | C | ASN | A | 486 | 46.912 | −34.966 | −1.621 | 1.00 | 17.24 | A | C |
| ATOM | 4000 | O | ASN | A | 486 | 47.464 | −35.234 | −2.698 | 1.00 | 18.56 | A | O |
| ATOM | 4001 | N | LYS | A | 487 | 45.635 | −35.236 | −1.388 | 1.00 | 14.64 | A | N |
| ATOM | 4002 | CA | LYS | A | 487 | 44.782 | −35.818 | −2.419 | 1.00 | 15.66 | A | C |
| ATOM | 4003 | CB | LYS | A | 487 | 43.422 | −36.234 | −1.867 | 1.00 | 16.91 | A | C |
| ATOM | 4004 | CG | LYS | A | 487 | 42.572 | −36.969 | −2.854 | 1.00 | 20.96 | A | C |
| ATOM | 4005 | CD | LYS | A | 487 | 41.260 | −37.370 | −2.247 | 1.00 | 25.53 | A | C |
| ATOM | 4006 | CE | LYS | A | 487 | 40.344 | −37.998 | −3.327 | 1.00 | 30.21 | A | C |
| ATOM | 4007 | NZ | LYS | A | 487 | 39.154 | −38.633 | −2.706 | 1.00 | 25.05 | A | N |
| ATOM | 4008 | C | LYS | A | 487 | 44.591 | −34.861 | −3.579 | 1.00 | 17.27 | A | C |
| ATOM | 4009 | O | LYS | A | 487 | 44.624 | −35.272 | −4.753 | 1.00 | 17.38 | A | O |
| ATOM | 4010 | N | GLU | A | 488 | 44.425 | −33.593 | −3.264 | 1.00 | 18.99 | A | N |
| ATOM | 4011 | CA | GLU | A | 488 | 44.215 | −32.556 | −4.296 | 1.00 | 22.07 | A | C |
| ATOM | 4012 | CB | GLU | A | 488 | 43.954 | −31.191 | −3.649 | 1.00 | 26.40 | A | C |
| ATOM | 4013 | CG | GLU | A | 488 | 43.568 | −30.048 | −4.605 | 1.00 | 37.28 | A | C |
| ATOM | 4014 | CD | GLU | A | 488 | 42.097 | −30.103 | −5.022 | 1.00 | 48.74 | A | C |
| ATOM | 4015 | OE1 | GLU | A | 488 | 41.260 | −30.584 | −4.221 | 1.00 | 54.85 | A | O |
| ATOM | 4016 | OE2 | GLU | A | 488 | 41.783 | −29.666 | −6.155 | 1.00 | 50.63 | A | O |
| ATOM | 4017 | C | GLU | A | 488 | 45.434 | −32.435 | −5.209 | 1.00 | 19.80 | A | C |
| ATOM | 4018 | O | GLU | A | 488 | 45.281 | −32.265 | −6.408 | 1.00 | 21.01 | A | O |
| ATOM | 4019 | N | LYS | A | 489 | 46.630 | −32.486 | −4.640 | 1.00 | 17.29 | A | N |
| ATOM | 4020 | CA | LYS | A | 489 | 47.851 | −32.400 | −5.422 | 1.00 | 18.72 | A | C |
| ATOM | 4021 | CB | LYS | A | 489 | 49.063 | −32.222 | −4.520 | 1.00 | 20.27 | A | C |
| ATOM | 4022 | CG | LYS | A | 489 | 50.438 | −32.185 | −5.212 | 1.00 | 20.51 | A | C |
| ATOM | 4023 | CD | LYS | A | 489 | 50.631 | −30.930 | −6.069 | 1.00 | 23.34 | A | C |
| ATOM | 4024 | CE | LYS | A | 489 | 51.862 | −31.036 | −6.979 | 1.00 | 23.63 | A | C |
| ATOM | 4025 | NZ | LYS | A | 489 | 53.084 | −31.210 | −6.198 | 1.00 | 21.67 | A | N |
| ATOM | 4026 | C | LYS | A | 489 | 48.039 | −33.629 | −6.331 | 1.00 | 23.93 | A | C |
| ATOM | 4027 | O | LYS | A | 489 | 48.576 | −33.512 | −7.443 | 1.00 | 21.37 | A | O |
| ATOM | 4028 | N | LEU | A | 490 | 47.647 | −34.796 | −5.828 | 1.00 | 22.66 | A | N |
| ATOM | 4029 | CA | ALEU | A | 490 | 47.865 | −36.062 | −6.550 | 0.50 | 27.19 | A | C |
| ATOM | 4030 | CA | BLEU | A | 490 | 47.823 | −36.076 | −6.542 | 0.50 | 27.96 | A | C |
| ATOM | 4031 | CB | ALEU | A | 490 | 47.834 | −37.243 | −5.558 | 0.50 | 22.47 | A | C |
| ATOM | 4032 | CB | BLEU | A | 490 | 47.607 | −37.256 | −5.594 | 0.50 | 24.24 | A | C |
| ATOM | 4033 | CG | ALEU | A | 490 | 48.080 | −38.692 | −6.004 | 0.50 | 21.71 | A | C |
| ATOM | 4034 | CG | BLEU | A | 490 | 48.829 | −37.831 | −4.913 | 0.50 | 23.81 | A | C |
| ATOM | 4035 | CD1 | ALEU | A | 490 | 49.436 | −38.888 | −6.644 | 0.50 | 19.67 | A | C |
| ATOM | 4036 | CD1 | BLEU | A | 490 | 48.403 | −38.959 | −3.950 | 0.50 | 21.79 | A | C |
| ATOM | 4037 | CD2 | ALEU | A | 490 | 47.951 | −39.598 | −4.798 | 0.50 | 21.41 | A | C |
| ATOM | 4038 | CD2 | BLEU | A | 490 | 49.805 | −38.359 | −5.955 | 0.50 | 25.26 | A | C |
| ATOM | 4039 | C | LEU | A | 490 | 46.848 | −36.248 | −7.682 | 1.00 | 30.53 | A | C |
| ATOM | 4040 | O | LEU | A | 490 | 47.218 | −36.645 | −8.763 | 1.00 | 32.66 | A | O |
| ATOM | 4041 | N | GLY | A | 491 | 45.590 | −35.927 | −7.409 | 1.00 | 31.34 | A | N |
| ATOM | 4042 | CA | GLY | A | 491 | 44.478 | −36.293 | −8.226 | 1.00 | 48.80 | A | C |
| ATOM | 4043 | C | GLY | A | 491 | 44.065 | −35.322 | −9.283 | 1.00 | 60.28 | A | C |
| ATOM | 4044 | O | GLY | A | 491 | 44.860 | −34.939 | −10.135 | 1.00 | 79.14 | A | O |
| ATOM | 4045 | N | GLY | A | 492 | 42.796 | −34.962 | −9.245 | 1.00 | 55.84 | A | N |
| ATOM | 4046 | CA | GLY | A | 492 | 42.162 | −34.344 | −10.379 | 1.00 | 72.32 | A | C |
| ATOM | 4047 | C | GLY | A | 492 | 41.713 | −32.969 | −9.983 | 1.00 | 72.34 | A | C |
| ATOM | 4048 | O | GLY | A | 492 | 40.510 | −32.700 | −9.894 | 1.00 | 67.55 | A | O |
| ATOM | 4049 | N | SER | A | 493 | 42.671 | −32.096 | −9.721 | 1.00 | 53.00 | A | N |
| ATOM | 4050 | CA | SER | A | 493 | 42.298 | −30.727 | −9.363 | 1.00 | 59.50 | A | C |
| ATOM | 4051 | CB | SER | A | 493 | 43.453 | −29.918 | −8.737 | 1.00 | 47.61 | A | C |
| ATOM | 4052 | OG | SER | A | 493 | 42.991 | −28.645 | −8.187 | 1.00 | 43.51 | A | O |
| ATOM | 4053 | C | SER | A | 493 | 41.800 | −30.003 | −10.604 | 1.00 | 44.76 | A | C |
| ATOM | 4054 | O | SER | A | 493 | 42.211 | −30.287 | −11.727 | 1.00 | 34.61 | A | O |
| ATOM | 4055 | N | LEU | A | 494 | 40.917 | −29.055 | −10.362 | 1.00 | 41.66 | A | N |
| ATOM | 4056 | CA | LEU | A | 494 | 40.589 | −28.025 | −11.325 | 1.00 | 42.41 | A | C |
| ATOM | 4057 | CB | LEU | A | 494 | 39.490 | −27.156 | −10.730 | 1.00 | 40.97 | A | C |
| ATOM | 4058 | CG | LEU | A | 494 | 39.214 | −25.832 | −11.437 | 1.00 | 60.70 | A | C |
| ATOM | 4059 | CD1 | LEU | A | 494 | 38.647 | −26.045 | −12.862 | 1.00 | 62.77 | A | C |
| ATOM | 4060 | CD2 | LEU | A | 494 | 38.276 | −25.030 | −10.568 | 1.00 | 49.79 | A | C |
| ATOM | 4061 | C | LEU | A | 494 | 41.827 | −27.172 | −11.689 | 1.00 | 37.14 | A | C |
| ATOM | 4062 | O | LEU | A | 494 | 41.975 | −26.729 | −12.810 | 1.00 | 41.80 | A | O |
| ATOM | 4063 | N | PHE | A | 495 | 42.733 | −26.965 | −10.743 | 1.00 | 26.68 | A | N |
| ATOM | 4064 | CA | PHE | A | 495 | 43.867 | −26.105 | −10.990 | 1.00 | 26.09 | A | C |
| ATOM | 4065 | CB | PHE | A | 495 | 44.190 | −25.371 | −9.706 | 1.00 | 23.48 | A | C |
| ATOM | 4066 | CG | PHE | A | 495 | 43.181 | −24.338 | −9.344 | 1.00 | 25.42 | A | C |
| ATOM | 4067 | CD1 | PHE | A | 495 | 43.301 | −23.059 | −9.816 | 1.00 | 26.17 | A | C |
| ATOM | 4068 | CE1 | PHE | A | 495 | 42.353 | −22.089 | −9.484 | 1.00 | 25.96 | A | C |
| ATOM | 4069 | CZ | PHE | A | 495 | 41.269 | −22.428 | −8.689 | 1.00 | 27.04 | A | C |
| ATOM | 4070 | CE2 | PHE | A | 495 | 41.139 | −23.719 | −8.235 | 1.00 | 29.85 | A | C |
| ATOM | 4071 | CD2 | PHE | A | 495 | 42.085 | −24.664 | −8.560 | 1.00 | 27.59 | A | C |
| ATOM | 4072 | C | PHE | A | 495 | 45.085 | −26.910 | −11.471 | 1.00 | 25.94 | A | C |
| ATOM | 4073 | O | PHE | A | 495 | 45.203 | −28.077 | −11.170 | 1.00 | 28.09 | A | O |
| ATOM | 4074 | N | ALA | A | 496 | 46.009 | −26.247 | −12.138 | 1.00 | 33.05 | A | N |

APPENDIX A-continued

P. alba 3T288C coordinates

| ATOM | 4075 | CA | ALA | A | 496 | 47.250 | −26.868 | −12.577 | 1.00 | 39.94 | A | C |
|---|---|---|---|---|---|---|---|---|---|---|---|---|
| ATOM | 4076 | CB | ALA | A | 496 | 47.945 | −25.966 | −13.574 | 1.00 | 42.98 | A | C |
| ATOM | 4077 | C | ALA | A | 496 | 48.150 | −27.120 | −11.352 | 1.00 | 36.62 | A | C |
| ATOM | 4078 | O | ALA | A | 496 | 48.121 | −26.349 | −10.389 | 1.00 | 31.86 | A | O |
| ATOM | 4079 | N | LYS | A | 497 | 48.963 | −28.167 | −11.419 | 1.00 | 34.08 | A | N |
| ATOM | 4080 | CA | LYS | A | 497 | 49.732 | −28.637 | −10.272 | 1.00 | 37.33 | A | C |
| ATOM | 4081 | CB | LYS | A | 497 | 50.470 | −29.961 | −10.588 | 1.00 | 41.75 | A | C |
| ATOM | 4082 | CG | LYS | A | 497 | 49.512 | −31.161 | −10.633 | 1.00 | 47.85 | A | C |
| ATOM | 4083 | CD | LYS | A | 497 | 50.233 | −32.512 | −10.638 | 1.00 | 56.61 | A | C |
| ATOM | 4084 | CE | LYS | A | 497 | 49.212 | −33.653 | −10.765 | 1.00 | 64.54 | A | C |
| ATOM | 4085 | NZ | LYS | A | 497 | 49.773 | −35.007 | −10.458 | 1.00 | 65.22 | A | N |
| ATOM | 4086 | C | LYS | A | 497 | 50.672 | −27.606 | −9.670 | 1.00 | 31.87 | A | C |
| ATOM | 4087 | O | LYS | A | 497 | 50.822 | −27.580 | −8.463 | 1.00 | 27.56 | A | O |
| ATOM | 4088 | N | PRO | A | 498 | 51.264 | −26.716 | −10.492 | 1.00 | 33.97 | A | N |
| ATOM | 4089 | CA | PRO | A | 498 | 52.093 | −25.671 | −9.909 | 1.00 | 32.61 | A | C |
| ATOM | 4090 | CB | PRO | A | 498 | 52.631 | −24.912 | −11.132 | 1.00 | 34.93 | A | C |
| ATOM | 4091 | CG | PRO | A | 498 | 52.536 | −25.882 | −12.254 | 1.00 | 42.21 | A | C |
| ATOM | 4092 | CD | PRO | A | 498 | 51.324 | −26.709 | −11.966 | 1.00 | 41.65 | A | C |
| ATOM | 4093 | C | PRO | A | 498 | 51.318 | −24.707 | −9.011 | 1.00 | 29.86 | A | C |
| ATOM | 4094 | O | PRO | A | 498 | 51.840 | −24.290 | −7.986 | 1.00 | 26.30 | A | O |
| ATOM | 4095 | N | PHE | A | 499 | 50.101 | −24.322 | −9.389 | 1.00 | 26.07 | A | N |
| ATOM | 4096 | CA | PHE | A | 499 | 49.324 | −23.478 | −8.486 | 1.00 | 25.20 | A | C |
| ATOM | 4097 | CB | PHE | A | 499 | 48.116 | −22.836 | −9.142 | 1.00 | 21.86 | A | C |
| ATOM | 4098 | CG | PHE | A | 499 | 47.358 | −21.964 | −8.214 | 1.00 | 20.70 | A | C |
| ATOM | 4099 | CD1 | PHE | A | 499 | 47.912 | −20.795 | −7.748 | 1.00 | 22.74 | A | C |
| ATOM | 4100 | CE1 | PHE | A | 499 | 47.240 | −20.000 | −6.837 | 1.00 | 24.76 | A | C |
| ATOM | 4101 | CZ | PHE | A | 499 | 45.980 | −20.372 | −6.418 | 1.00 | 22.15 | A | C |
| ATOM | 4102 | CE2 | PHE | A | 499 | 45.434 | −21.558 | −6.872 | 1.00 | 22.89 | A | C |
| ATOM | 4103 | CD2 | PHE | A | 499 | 46.121 | −22.328 | −7.767 | 1.00 | 21.48 | A | C |
| ATOM | 4104 | C | PHE | A | 499 | 48.901 | −24.256 | −7.209 | 1.00 | 19.68 | A | C |
| ATOM | 4105 | O | PHE | A | 499 | 48.967 | −23.680 | −6.103 | 1.00 | 20.69 | A | O |
| ATOM | 4106 | N | VAL | A | 500 | 48.510 | −25.536 | −7.353 | 1.00 | 20.38 | A | N |
| ATOM | 4107 | CA | VAL | A | 500 | 48.142 | −26.363 | −6.192 | 1.00 | 19.51 | A | C |
| ATOM | 4108 | CB | VAL | A | 500 | 47.691 | −27.750 | −6.568 | 1.00 | 22.11 | A | C |
| ATOM | 4109 | CG1 | VAL | A | 500 | 47.420 | −28.597 | −5.314 | 1.00 | 20.63 | A | C |
| ATOM | 4110 | CG2 | VAL | A | 500 | 46.418 | −27.684 | −7.500 | 1.00 | 19.82 | A | C |
| ATOM | 4111 | C | VAL | A | 500 | 49.310 | −26.414 | −5.237 | 1.00 | 17.74 | A | C |
| ATOM | 4112 | O | VAL | A | 500 | 49.139 | −26.210 | −4.051 | 1.00 | 19.47 | A | O |
| ATOM | 4113 | N | GLU | A | 501 | 50.518 | −26.572 | −5.769 | 1.00 | 21.36 | A | N |
| ATOM | 4114 | CA | GLU | A | 501 | 51.722 | −26.617 | −4.965 | 1.00 | 21.86 | A | C |
| ATOM | 4115 | CB | GLU | A | 501 | 52.903 | −27.076 | −5.811 | 1.00 | 26.57 | A | C |
| ATOM | 4116 | CG | GLU | A | 501 | 54.218 | −27.318 | −5.036 | 1.00 | 24.39 | A | C |
| ATOM | 4117 | CD | GLU | A | 501 | 54.178 | −28.541 | −4.079 | 1.00 | 31.48 | A | C |
| ATOM | 4118 | OE1 | GLU | A | 501 | 53.186 | −29.319 | −4.025 | 1.00 | 26.98 | A | O |
| ATOM | 4119 | OE2 | GLU | A | 501 | 55.198 | −28.741 | −3.395 | 1.00 | 27.65 | A | O |
| ATOM | 4120 | C | GLU | A | 501 | 52.062 | −25.283 | −4.272 | 1.00 | 20.56 | A | C |
| ATOM | 4121 | O | GLU | A | 501 | 52.447 | −25.272 | −3.078 | 1.00 | 16.73 | A | O |
| ATOM | 4122 | N | THR | A | 502 | 51.945 | −24.178 | −4.998 | 1.00 | 20.57 | A | N |
| ATOM | 4123 | CA | THR | A | 502 | 52.097 | −22.845 | −4.413 | 1.00 | 19.79 | A | C |
| ATOM | 4124 | CB | THR | A | 502 | 51.803 | −21.761 | −5.462 | 1.00 | 24.29 | A | C |
| ATOM | 4125 | OG1 | THR | A | 502 | 52.690 | −21.934 | −6.551 | 1.00 | 25.00 | A | O |
| ATOM | 4126 | CG2 | THR | A | 502 | 51.981 | −20.353 | −4.890 | 1.00 | 22.68 | A | C |
| ATOM | 4127 | C | THR | A | 502 | 51.146 | −22.669 | −3.198 | 1.00 | 18.49 | A | C |
| ATOM | 4128 | O | THR | A | 502 | 51.534 | −22.190 | −2.142 | 1.00 | 19.11 | A | O |
| ATOM | 4129 | N | ALA | A | 503 | 49.914 | −23.098 | −3.371 | 1.00 | 15.97 | A | N |
| ATOM | 4130 | CA | ALA | A | 503 | 48.885 | −23.042 | −2.315 | 1.00 | 17.68 | A | C |
| ATOM | 4131 | CB | ALA | A | 503 | 47.546 | −23.517 | −2.854 | 1.00 | 13.94 | A | C |
| ATOM | 4132 | C | ALA | A | 503 | 49.316 | −23.870 | −1.123 | 1.00 | 18.81 | A | C |
| ATOM | 4133 | O | ALA | A | 503 | 49.323 | −23.384 | 0.011 | 1.00 | 17.14 | A | O |
| ATOM | 4134 | N | ILE | A | 504 | 49.763 | −25.091 | −1.373 | 1.00 | 20.50 | A | N |
| ATOM | 4135 | CA | ILE | A | 504 | 50.294 | −25.926 | −0.282 | 1.00 | 18.42 | A | C |
| ATOM | 4136 | CB | ILE | A | 504 | 50.622 | −27.364 | −0.791 | 1.00 | 19.01 | A | C |
| ATOM | 4137 | CG1 | ILE | A | 504 | 49.347 | −28.068 | −1.267 | 1.00 | 20.65 | A | C |
| ATOM | 4138 | CD1 | ILE | A | 504 | 49.622 | −29.508 | −1.880 | 1.00 | 19.60 | A | C |
| ATOM | 4139 | CG2 | ILE | A | 504 | 51.328 | −28.229 | 0.336 | 1.00 | 16.48 | A | C |
| ATOM | 4140 | C | ILE | A | 504 | 51.523 | −25.271 | 0.360 | 1.00 | 20.66 | A | C |
| ATOM | 4141 | O | ILE | A | 504 | 51.692 | −25.327 | 1.586 | 1.00 | 17.24 | A | O |
| ATOM | 4142 | N | ASN | A | 505 | 52.367 | −24.592 | −0.423 | 1.00 | 18.20 | A | N |
| ATOM | 4143 | CA | ASN | A | 505 | 53.481 | −23.874 | 0.207 | 1.00 | 16.22 | A | C |
| ATOM | 4144 | CB | ASN | A | 505 | 54.419 | −23.250 | −0.825 | 1.00 | 19.40 | A | C |
| ATOM | 4145 | CG | ASN | A | 505 | 55.224 | −24.278 | −1.587 | 1.00 | 20.36 | A | C |
| ATOM | 4146 | OD1 | ASN | A | 505 | 55.464 | −25.400 | −1.111 | 1.00 | 19.80 | A | O |
| ATOM | 4147 | ND2 | ASN | A | 505 | 55.697 | −23.880 | −2.757 | 1.00 | 16.17 | A | N |
| ATOM | 4148 | C | ASN | A | 505 | 53.077 | −22.811 | 1.245 | 1.00 | 18.67 | A | C |
| ATOM | 4149 | O | ASN | A | 505 | 53.839 | −22.536 | 2.172 | 1.00 | 19.55 | A | O |
| ATOM | 4150 | N | LEU | A | 506 | 51.883 | −22.250 | 1.130 | 1.00 | 19.40 | A | N |
| ATOM | 4151 | CA | LEU | A | 506 | 51.415 | −21.299 | 2.133 | 1.00 | 18.37 | A | C |
| ATOM | 4152 | CB | LEU | A | 506 | 50.113 | −20.649 | 1.673 | 1.00 | 20.58 | A | C |

APPENDIX A-continued

| | | | | | P. alba 3T288C coordinates | | | | | | |
|---|---|---|---|---|---|---|---|---|---|---|---|
| ATOM | 4153 | CG | LEU | A | 506 | 49.487 | −19.672 | 2.701 | 1.00 | 30.53 | A | C |
| ATOM | 4154 | CD1 | LEU | A | 506 | 49.656 | −18.279 | 2.175 | 1.00 | 29.62 | A | C |
| ATOM | 4155 | CD2 | LEU | A | 506 | 47.982 | −19.947 | 2.935 | 1.00 | 26.29 | A | C |
| ATOM | 4156 | C | LEU | A | 506 | 51.227 | −22.024 | 3.469 | 1.00 | 17.76 | A | C |
| ATOM | 4157 | O | LEU | A | 506 | 51.540 | −21.481 | 4.551 | 1.00 | 16.64 | A | O |
| ATOM | 4158 | N | ALA | A | 507 | 50.753 | −23.271 | 3.422 | 1.00 | 17.78 | A | N |
| ATOM | 4159 | CA | ALA | A | 507 | 50.632 | −24.062 | 4.636 | 1.00 | 18.31 | A | C |
| ATOM | 4160 | CB | ALA | A | 507 | 49.809 | −25.373 | 4.398 | 1.00 | 16.33 | A | C |
| ATOM | 4161 | C | ALA | A | 507 | 52.016 | −24.374 | 5.220 | 1.00 | 17.60 | A | C |
| ATOM | 4162 | O | ALA | A | 507 | 52.224 | −24.289 | 6.430 | 1.00 | 18.28 | A | O |
| ATOM | 4163 | N | ARG | A | 508 | 52.962 | −24.758 | 4.373 | 1.00 | 14.94 | A | N |
| ATOM | 4164 | CA | ARG | A | 508 | 54.331 | −25.035 | 4.816 | 1.00 | 15.68 | A | C |
| ATOM | 4165 | CB | ARG | A | 508 | 55.193 | −25.438 | 3.624 | 1.00 | 15.05 | A | C |
| ATOM | 4166 | CG | ARG | A | 508 | 54.765 | −26.752 | 2.994 | 1.00 | 15.52 | A | C |
| ATOM | 4167 | CD | ARG | A | 508 | 55.742 | −27.210 | 1.937 | 1.00 | 17.52 | A | C |
| ATOM | 4168 | NE | ARG | A | 508 | 55.436 | −28.586 | 1.540 | 1.00 | 18.72 | A | N |
| ATOM | 4169 | CZ | ARG | A | 508 | 55.023 | −28.998 | 0.347 | 1.00 | 20.99 | A | C |
| ATOM | 4170 | NH1 | ARG | A | 508 | 54.826 | −28.175 | −0.666 | 1.00 | 20.60 | A | N |
| ATOM | 4171 | NH2 | ARG | A | 508 | 54.796 | −30.287 | 0.167 | 1.00 | 19.00 | A | N |
| ATOM | 4172 | C | ARG | A | 508 | 54.947 | −23.817 | 5.531 | 1.00 | 17.54 | A | C |
| ATOM | 4173 | O | ARG | A | 508 | 55.547 | −23.955 | 6.610 | 1.00 | 19.20 | A | O |
| ATOM | 4174 | N | GLN | A | 509 | 54.763 | −22.640 | 4.922 | 1.00 | 18.14 | A | N |
| ATOM | 4175 | CA | GLN | A | 509 | 55.322 | −21.402 | 5.475 | 1.00 | 18.23 | A | C |
| ATOM | 4176 | CB | GLN | A | 509 | 55.141 | −20.227 | 4.487 | 1.00 | 22.05 | A | C |
| ATOM | 4177 | CG | GLN | A | 509 | 55.731 | −18.902 | 5.006 | 1.00 | 22.47 | A | C |
| ATOM | 4178 | CD | GLN | A | 509 | 57.226 | −18.986 | 5.232 | 1.00 | 27.68 | A | C |
| ATOM | 4179 | OE1 | GLN | A | 509 | 57.930 | −19.557 | 4.446 | 1.00 | 26.27 | A | O |
| ATOM | 4180 | NE2 | GLN | A | 509 | 57.699 | −18.403 | 6.302 | 1.00 | 34.33 | A | N |
| ATOM | 4181 | C | GLN | A | 509 | 54.662 | −21.115 | 6.802 | 1.00 | 19.66 | A | C |
| ATOM | 4182 | O | GLN | A | 509 | 55.298 | −20.639 | 7.723 | 1.00 | 18.58 | A | O |
| ATOM | 4183 | N | SER | A | 510 | 53.376 | −21.435 | 6.935 | 1.00 | 19.88 | A | N |
| ATOM | 4184 | CA | SER | A | 510 | 52.698 | −21.304 | 8.224 | 1.00 | 16.74 | A | C |
| ATOM | 4185 | CB | SER | A | 510 | 51.214 | −21.683 | 8.074 | 1.00 | 20.01 | A | C |
| ATOM | 4186 | OG | SER | A | 510 | 50.580 | −20.747 | 7.203 | 1.00 | 21.40 | A | O |
| ATOM | 4187 | C | SER | A | 510 | 53.356 | −22.117 | 9.312 | 1.00 | 18.45 | A | C |
| ATOM | 4188 | O | SER | A | 510 | 53.611 | −21.625 | 10.436 | 1.00 | 20.32 | A | O |
| ATOM | 4189 | N | HIS | A | 511 | 53.617 | −23.388 | 9.021 | 1.00 | 16.45 | A | N |
| ATOM | 4190 | CA | HIS | A | 511 | 54.270 | −24.277 | 9.988 | 1.00 | 16.17 | A | C |
| ATOM | 4191 | CB | HIS | A | 511 | 54.446 | −25.675 | 9.395 | 1.00 | 18.95 | A | C |
| ATOM | 4192 | CG | HIS | A | 511 | 53.170 | −26.485 | 9.362 | 1.00 | 16.31 | A | C |
| ATOM | 4193 | ND1 | HIS | A | 511 | 52.624 | −27.021 | 10.495 | 1.00 | 20.09 | A | N |
| ATOM | 4194 | CE1 | HIS | A | 511 | 51.483 | −27.682 | 10.169 | 1.00 | 22.64 | A | C |
| ATOM | 4195 | NE2 | HIS | A | 511 | 51.314 | −27.611 | 8.847 | 1.00 | 18.17 | A | N |
| ATOM | 4196 | CD2 | HIS | A | 511 | 52.341 | −26.877 | 8.305 | 1.00 | 20.21 | A | C |
| ATOM | 4197 | C | HIS | A | 511 | 55.625 | −23.734 | 10.319 | 1.00 | 20.90 | A | C |
| ATOM | 4198 | O | HIS | A | 511 | 56.060 | −23.820 | 11.444 | 1.00 | 19.36 | A | O |
| ATOM | 4199 | N | CYS | A | 512 | 56.303 | −23.147 | 9.340 | 1.00 | 19.93 | A | N |
| ATOM | 4200 | CA | CYS | A | 512 | 57.658 | −22.668 | 9.560 | 1.00 | 20.84 | A | C |
| ATOM | 4201 | CB | CYS | A | 512 | 58.434 | −22.617 | 8.239 | 1.00 | 21.43 | A | C |
| ATOM | 4202 | SG | CYS | A | 512 | 58.833 | −24.343 | 7.612 | 1.00 | 26.02 | A | S |
| ATOM | 4203 | C | CYS | A | 512 | 57.742 | −21.291 | 10.272 | 1.00 | 21.58 | A | C |
| ATOM | 4204 | O | CYS | A | 512 | 58.748 | −20.991 | 10.842 | 1.00 | 26.11 | A | O |
| ATOM | 4205 | N | THR | A | 513 | 56.703 | −20.481 | 10.179 | 1.00 | 23.47 | A | N |
| ATOM | 4206 | CA | THR | A | 513 | 56.676 | −19.162 | 10.788 | 1.00 | 27.58 | A | C |
| ATOM | 4207 | CB | THR | A | 513 | 55.758 | −18.254 | 10.019 | 1.00 | 29.85 | A | C |
| ATOM | 4208 | OG1 | THR | A | 513 | 56.247 | −18.183 | 8.682 | 1.00 | 27.20 | A | O |
| ATOM | 4209 | CG2 | THR | A | 513 | 55.692 | −16.840 | 10.630 | 1.00 | 30.28 | A | C |
| ATOM | 4210 | C | THR | A | 513 | 56.197 | −19.254 | 12.215 | 1.00 | 37.01 | A | C |
| ATOM | 4211 | O | THR | A | 513 | 56.735 | −18.556 | 13.068 | 1.00 | 27.92 | A | O |
| ATOM | 4212 | N | TYR | A | 514 | 55.216 | −20.124 | 12.484 | 1.00 | 27.85 | A | N |
| ATOM | 4213 | CA | TYR | A | 514 | 54.604 | −20.210 | 13.819 | 1.00 | 32.83 | A | C |
| ATOM | 4214 | CB | TYR | A | 514 | 53.062 | −20.286 | 13.738 | 1.00 | 26.86 | A | C |
| ATOM | 4215 | CG | TYR | A | 514 | 52.532 | −19.034 | 13.105 | 1.00 | 22.85 | A | C |
| ATOM | 4216 | CD1 | TYR | A | 514 | 52.511 | −17.835 | 13.795 | 1.00 | 31.96 | A | C |
| ATOM | 4217 | CE1 | TYR | A | 514 | 52.084 | −16.673 | 13.177 | 1.00 | 30.33 | A | C |
| ATOM | 4218 | CZ | TYR | A | 514 | 51.698 | −16.708 | 11.868 | 1.00 | 31.28 | A | C |
| ATOM | 4219 | OH | TYR | A | 514 | 51.286 | −15.590 | 11.216 | 1.00 | 31.35 | A | O |
| ATOM | 4220 | CE2 | TYR | A | 514 | 51.730 | −17.875 | 11.170 | 1.00 | 26.60 | A | C |
| ATOM | 4221 | CD2 | TYR | A | 514 | 52.160 | −19.017 | 11.786 | 1.00 | 23.31 | A | C |
| ATOM | 4222 | C | TYR | A | 514 | 55.242 | −21.324 | 14.605 | 1.00 | 37.07 | A | C |
| ATOM | 4223 | O | TYR | A | 514 | 54.763 | −22.428 | 14.644 | 1.00 | 41.12 | A | O |
| ATOM | 4224 | N | HIS | A | 515 | 56.369 | −20.998 | 15.220 | 1.00 | 52.59 | A | N |
| ATOM | 4225 | CA | HIS | A | 515 | 57.199 | −21.961 | 15.943 | 1.00 | 47.40 | A | C |
| ATOM | 4226 | CB | HIS | A | 515 | 58.533 | −22.132 | 15.211 | 1.00 | 47.12 | A | C |
| ATOM | 4227 | CG | HIS | A | 515 | 59.339 | −20.849 | 15.076 | 1.00 | 44.49 | A | C |
| ATOM | 4228 | ND1 | HIS | A | 515 | 59.938 | −20.250 | 16.125 | 1.00 | 48.30 | A | N |
| ATOM | 4229 | CE1 | HIS | A | 515 | 60.575 | −19.133 | 15.700 | 1.00 | 37.04 | A | C |
| ATOM | 4230 | NE2 | HIS | A | 515 | 60.397 | −19.027 | 14.376 | 1.00 | 44.22 | A | N |

APPENDIX A-continued

P. alba 3T288C coordinates

| ATOM | 4231 | CD2 | HIS | A | 515 | 59.641 | −20.068 | 13.957 | 1.00 | 42.54 | A | C |
|---|---|---|---|---|---|---|---|---|---|---|---|---|
| ATOM | 4232 | C | HIS | A | 515 | 57.428 | −21.458 | 17.335 | 1.00 | 60.34 | A | C |
| ATOM | 4233 | O | HIS | A | 515 | 56.873 | −20.424 | 17.726 | 1.00 | 60.05 | A | O |
| ATOM | 4234 | N | ASN | A | 516 | 58.253 | −22.176 | 18.098 | 1.00 | 73.61 | A | N |
| ATOM | 4235 | CA | ASN | A | 516 | 58.653 | −21.727 | 19.429 | 1.00 | 78.32 | A | C |
| ATOM | 4236 | CB | ASN | A | 516 | 57.754 | −22.402 | 20.469 | 1.00 | 76.01 | A | C |
| ATOM | 4237 | CG | ASN | A | 516 | 57.642 | −21.597 | 21.738 | 1.00 | 80.70 | A | C |
| ATOM | 4238 | OD1 | ASN | A | 516 | 57.469 | −20.379 | 21.694 | 1.00 | 92.46 | A | O |
| ATOM | 4239 | ND2 | ASN | A | 516 | 57.753 | −22.266 | 22.879 | 1.00 | 69.09 | A | N |
| ATOM | 4240 | C | ASN | A | 516 | 60.146 | −21.938 | 19.790 | 1.00 | 71.29 | A | C |
| ATOM | 4241 | O | ASN | A | 516 | 60.498 | −21.929 | 20.967 | 1.00 | 72.15 | A | O |
| ATOM | 4242 | N | GLY | A | 517 | 61.015 | −22.113 | 18.790 | 1.00 | 73.55 | A | N |
| ATOM | 4243 | CA | GLY | A | 517 | 62.453 | −22.324 | 19.023 | 1.00 | 69.30 | A | C |
| ATOM | 4244 | C | GLY | A | 517 | 62.882 | −23.776 | 18.899 | 1.00 | 67.94 | A | C |
| ATOM | 4245 | O | GLY | A | 517 | 63.971 | −24.159 | 19.346 | 1.00 | 52.43 | A | O |
| ATOM | 4246 | N | THR | A | 521 | 67.697 | −22.083 | 21.593 | 1.00 | 48.19 | A | N |
| ATOM | 4247 | CA | THR | A | 521 | 67.278 | −20.802 | 21.017 | 1.00 | 61.81 | A | C |
| ATOM | 4248 | CB | THR | A | 521 | 67.383 | −20.783 | 19.459 | 1.00 | 70.39 | A | C |
| ATOM | 4249 | OG1 | THR | A | 521 | 66.575 | −21.828 | 18.907 | 1.00 | 93.82 | A | O |
| ATOM | 4250 | CG2 | THR | A | 521 | 68.823 | −20.966 | 18.990 | 1.00 | 66.62 | A | C |
| ATOM | 4251 | C | THR | A | 521 | 65.840 | −20.448 | 21.409 | 1.00 | 61.14 | A | C |
| ATOM | 4252 | O | THR | A | 521 | 65.037 | −21.330 | 21.732 | 1.00 | 64.90 | A | O |
| ATOM | 4253 | N | SER | A | 522 | 65.535 | −19.150 | 21.372 | 1.00 | 54.62 | A | N |
| ATOM | 4254 | CA | SER | A | 522 | 64.209 | −18.614 | 21.715 | 1.00 | 58.24 | A | C |
| ATOM | 4255 | CB | SER | A | 522 | 64.388 | −17.390 | 22.594 | 1.00 | 53.59 | A | C |
| ATOM | 4256 | OG | SER | A | 522 | 64.988 | −16.352 | 21.835 | 1.00 | 46.59 | A | O |
| ATOM | 4257 | C | SER | A | 522 | 63.452 | −18.213 | 20.435 | 1.00 | 54.40 | A | C |
| ATOM | 4258 | O | SER | A | 522 | 64.060 | −18.147 | 19.365 | 1.00 | 52.75 | A | O |
| ATOM | 4259 | N | PRO | A | 523 | 62.136 | −17.931 | 20.537 | 1.00 | 59.75 | A | N |
| ATOM | 4260 | CA | PRO | A | 523 | 61.363 | −17.599 | 19.329 | 1.00 | 67.72 | A | C |
| ATOM | 4261 | CB | PRO | A | 523 | 60.025 | −17.100 | 19.895 | 1.00 | 67.43 | A | C |
| ATOM | 4262 | CG | PRO | A | 523 | 59.858 | −17.915 | 21.128 | 1.00 | 61.02 | A | C |
| ATOM | 4263 | CD | PRO | A | 523 | 61.251 | −18.079 | 21.710 | 1.00 | 60.09 | A | C |
| ATOM | 4264 | C | PRO | A | 523 | 62.000 | −16.576 | 18.375 | 1.00 | 63.23 | A | C |
| ATOM | 4265 | O | PRO | A | 523 | 62.426 | −16.965 | 17.289 | 1.00 | 65.32 | A | O |
| ATOM | 4266 | N | ASP | A | 524 | 62.098 | −15.301 | 18.751 | 1.00 | 53.76 | A | N |
| ATOM | 4267 | CA | ASP | A | 524 | 62.463 | −14.292 | 17.746 | 1.00 | 56.64 | A | C |
| ATOM | 4268 | CB | ASP | A | 524 | 61.997 | −12.888 | 18.126 | 1.00 | 72.74 | A | C |
| ATOM | 4269 | CG | ASP | A | 524 | 61.249 | −12.221 | 16.980 | 1.00 | 90.60 | A | C |
| ATOM | 4270 | OD1 | ASP | A | 524 | 61.879 | −11.892 | 15.952 | 1.00 | 92.92 | A | O |
| ATOM | 4271 | OD2 | ASP | A | 524 | 60.017 | −12.076 | 17.088 | 1.00 | 99.57 | A | O |
| ATOM | 4272 | C | ASP | A | 524 | 63.938 | −14.318 | 17.345 | 1.00 | 43.11 | A | C |
| ATOM | 4273 | O | ASP | A | 524 | 64.314 | −13.682 | 16.370 | 1.00 | 45.57 | A | O |
| ATOM | 4274 | N | GLU | A | 525 | 64.758 | −15.053 | 18.093 | 1.00 | 38.74 | A | N |
| ATOM | 4275 | CA | GLU | A | 525 | 66.127 | −15.348 | 17.683 | 1.00 | 47.99 | A | C |
| ATOM | 4276 | CB | GLU | A | 525 | 66.966 | −15.818 | 18.879 | 1.00 | 57.18 | A | C |
| ATOM | 4277 | CG | GLU | A | 525 | 68.471 | −15.653 | 18.703 | 1.00 | 76.26 | A | C |
| ATOM | 4278 | CD | GLU | A | 525 | 68.893 | −14.230 | 18.331 | 1.00 | 86.79 | A | C |
| ATOM | 4279 | OE1 | GLU | A | 525 | 68.255 | −13.251 | 18.780 | 1.00 | 83.59 | A | O |
| ATOM | 4280 | OE2 | GLU | A | 525 | 69.877 | −14.096 | 17.577 | 1.00 | 87.42 | A | O |
| ATOM | 4281 | C | GLU | A | 525 | 66.144 | −16.417 | 16.569 | 1.00 | 38.28 | A | C |
| ATOM | 4282 | O | GLU | A | 525 | 66.952 | −16.332 | 15.656 | 1.00 | 42.11 | A | O |
| ATOM | 4283 | N | LEU | A | 526 | 65.269 | −17.414 | 16.656 | 1.00 | 42.35 | A | N |
| ATOM | 4284 | CA | LEU | A | 526 | 65.125 | −18.397 | 15.570 | 1.00 | 41.74 | A | C |
| ATOM | 4285 | CB | LEU | A | 526 | 64.186 | −19.549 | 15.974 | 1.00 | 41.93 | A | C |
| ATOM | 4286 | CG | LEU | A | 526 | 64.128 | −20.773 | 15.034 | 1.00 | 47.17 | A | C |
| ATOM | 4287 | CD1 | LEU | A | 526 | 65.540 | −21.285 | 14.673 | 1.00 | 39.29 | A | C |
| ATOM | 4288 | CD2 | LEU | A | 526 | 63.265 | −21.912 | 15.626 | 1.00 | 42.53 | A | C |
| ATOM | 4289 | C | LEU | A | 526 | 64.658 | −17.701 | 14.282 | 1.00 | 37.23 | A | C |
| ATOM | 4290 | O | LEU | A | 526 | 65.289 | −17.850 | 13.223 | 1.00 | 38.03 | A | O |
| ATOM | 4291 | N | THR | A | 527 | 63.588 | −16.915 | 14.376 | 1.00 | 34.27 | A | N |
| ATOM | 4292 | CA | THR | A | 527 | 63.107 | −16.129 | 13.231 | 1.00 | 35.49 | A | C |
| ATOM | 4293 | CB | THR | A | 527 | 61.935 | −15.222 | 13.639 | 1.00 | 37.44 | A | C |
| ATOM | 4294 | OG1 | THR | A | 527 | 60.916 | −16.040 | 14.216 | 1.00 | 37.80 | A | O |
| ATOM | 4295 | CG2 | THR | A | 527 | 61.357 | −14.444 | 12.439 | 1.00 | 30.44 | A | C |
| ATOM | 4296 | C | THR | A | 527 | 64.200 | −15.275 | 12.611 | 1.00 | 46.48 | A | C |
| ATOM | 4297 | O | THR | A | 527 | 64.328 | −15.218 | 11.388 | 1.00 | 46.01 | A | O |
| ATOM | 4298 | N | ARG | A | 528 | 64.996 | −14.617 | 13.452 | 1.00 | 41.37 | A | N |
| ATOM | 4299 | CA | ARG | A | 528 | 66.030 | −13.727 | 12.944 | 1.00 | 40.07 | A | C |
| ATOM | 4300 | CB | ARG | A | 528 | 66.596 | −12.873 | 14.074 | 1.00 | 49.72 | A | C |
| ATOM | 4301 | CG | ARG | A | 528 | 67.347 | −11.637 | 13.603 | 1.00 | 68.35 | A | C |
| ATOM | 4302 | CD | ARG | A | 528 | 68.111 | −10.980 | 14.753 | 1.00 | 72.05 | A | C |
| ATOM | 4303 | NE | ARG | A | 528 | 69.010 | −11.933 | 15.411 | 1.00 | 84.73 | A | N |
| ATOM | 4304 | CZ | ARG | A | 528 | 70.157 | −12.384 | 14.896 | 1.00 | 84.45 | A | C |
| ATOM | 4305 | NH1 | ARG | A | 528 | 70.581 | −11.975 | 13.702 | 1.00 | 92.83 | A | N |
| ATOM | 4306 | NH2 | ARG | A | 528 | 70.890 | −13.258 | 15.579 | 1.00 | 68.97 | A | N |
| ATOM | 4307 | C | ARG | A | 528 | 67.150 | −14.510 | 12.254 | 1.00 | 37.77 | A | C |
| ATOM | 4308 | O | ARG | A | 528 | 67.717 | −14.045 | 11.265 | 1.00 | 36.26 | A | O |

APPENDIX A-continued

*P. alba* 3T288C coordinates

| ATOM | 4309 | N | LYS | A | 529 | 67.502 | −15.670 | 12.800 | 1.00 | 32.17 | A | N |
|------|------|-----|-----|---|-----|--------|---------|--------|------|-------|---|---|
| ATOM | 4310 | CA | LYS | A | 529 | 68.492 | −16.536 | 12.148 | 1.00 | 43.23 | A | C |
| ATOM | 4311 | CB | LYS | A | 529 | 68.929 | −17.676 | 13.068 | 1.00 | 44.04 | A | C |
| ATOM | 4312 | CG | LYS | A | 529 | 69.925 | −17.250 | 14.143 | 1.00 | 61.21 | A | C |
| ATOM | 4313 | CD | LYS | A | 529 | 70.050 | −18.326 | 15.206 | 1.00 | 65.83 | A | C |
| ATOM | 4314 | CE | LYS | A | 529 | 70.831 | −17.849 | 16.414 | 1.00 | 83.82 | A | C |
| ATOM | 4315 | NZ | LYS | A | 529 | 70.540 | −18.727 | 17.589 | 1.00 | 91.28 | A | N |
| ATOM | 4316 | C | LYS | A | 529 | 67.955 | −17.097 | 10.808 | 1.00 | 31.54 | A | C |
| ATOM | 4317 | O | LYS | A | 529 | 68.703 | −17.225 | 9.845 | 1.00 | 42.10 | A | O |
| ATOM | 4318 | N | ARG | A | 530 | 66.668 | −17.399 | 10.748 | 1.00 | 36.46 | A | N |
| ATOM | 4319 | CA | ARG | A | 530 | 66.092 | −17.952 | 9.515 | 1.00 | 37.01 | A | C |
| ATOM | 4320 | CB | ARG | A | 530 | 64.741 | −18.562 | 9.786 | 1.00 | 36.05 | A | C |
| ATOM | 4321 | CG | ARG | A | 530 | 64.872 | −19.834 | 10.584 | 1.00 | 32.99 | A | C |
| ATOM | 4322 | CD | ARG | A | 530 | 63.544 | −20.448 | 10.839 | 1.00 | 35.75 | A | C |
| ATOM | 4323 | NE | ARG | A | 530 | 63.709 | −21.788 | 11.389 | 1.00 | 34.23 | A | N |
| ATOM | 4324 | CZ | ARG | A | 530 | 62.714 | −22.560 | 11.804 | 1.00 | 33.65 | A | C |
| ATOM | 4325 | NH1 | ARG | A | 530 | 61.455 | −22.164 | 11.696 | 1.00 | 35.22 | A | N |
| ATOM | 4326 | NH2 | ARG | A | 530 | 62.987 | −23.750 | 12.325 | 1.00 | 40.16 | A | N |
| ATOM | 4327 | C | ARG | A | 530 | 66.048 | −16.897 | 8.425 | 1.00 | 40.32 | A | C |
| ATOM | 4328 | O | ARG | A | 530 | 66.475 | −17.148 | 7.291 | 1.00 | 32.17 | A | O |
| ATOM | 4329 | N | VAL | A | 531 | 65.612 | −15.697 | 8.796 | 1.00 | 33.10 | A | N |
| ATOM | 4330 | CA | VAL | A | 531 | 65.576 | −14.584 | 7.866 | 1.00 | 35.68 | A | C |
| ATOM | 4331 | CB | VAL | A | 531 | 64.874 | −13.355 | 8.497 | 1.00 | 42.31 | A | C |
| ATOM | 4332 | CG1 | VAL | A | 531 | 64.901 | −12.166 | 7.547 | 1.00 | 41.62 | A | C |
| ATOM | 4333 | CG2 | VAL | A | 531 | 63.425 | −13.716 | 8.878 | 1.00 | 37.84 | A | C |
| ATOM | 4334 | C | VAL | A | 531 | 66.979 | −14.256 | 7.357 | 1.00 | 41.35 | A | C |
| ATOM | 4335 | O | VAL | A | 531 | 67.170 | −13.964 | 6.172 | 1.00 | 46.12 | A | O |
| ATOM | 4336 | N | LEU | A | 532 | 67.970 | −14.325 | 8.234 | 1.00 | 40.42 | A | N |
| ATOM | 4337 | CA | LEU | A | 532 | 69.344 | −14.093 | 7.811 | 1.00 | 39.71 | A | C |
| ATOM | 4338 | CB | LEU | A | 532 | 70.300 | −14.000 | 9.004 | 1.00 | 43.42 | A | C |
| ATOM | 4339 | CG | LEU | A | 532 | 70.692 | −12.579 | 9.478 | 1.00 | 53.48 | A | C |
| ATOM | 4340 | CD1 | LEU | A | 532 | 69.496 | −11.619 | 9.718 | 1.00 | 47.39 | A | C |
| ATOM | 4341 | CD2 | LEU | A | 532 | 71.538 | −12.720 | 10.726 | 1.00 | 45.63 | A | C |
| ATOM | 4342 | C | LEU | A | 532 | 69.837 | −15.180 | 6.838 | 1.00 | 46.33 | A | C |
| ATOM | 4343 | O | LEU | A | 532 | 70.445 | −14.862 | 5.825 | 1.00 | 44.36 | A | O |
| ATOM | 4344 | N | SER | A | 533 | 69.576 | −16.454 | 7.141 | 1.00 | 35.58 | A | N |
| ATOM | 4345 | CA | SER | A | 533 | 70.105 | −17.555 | 6.316 | 1.00 | 34.63 | A | C |
| ATOM | 4346 | CB | SER | A | 533 | 70.076 | −18.850 | 7.112 | 1.00 | 31.52 | A | C |
| ATOM | 4347 | OG | SER | A | 533 | 68.746 | −19.297 | 7.268 | 1.00 | 33.57 | A | O |
| ATOM | 4348 | C | SER | A | 533 | 69.358 | −17.712 | 4.982 | 1.00 | 25.58 | A | C |
| ATOM | 4349 | O | SER | A | 533 | 69.916 | −18.225 | 4.001 | 1.00 | 27.36 | A | O |
| ATOM | 4350 | N | VAL | A | 534 | 68.113 | −17.254 | 4.925 | 1.00 | 26.19 | A | N |
| ATOM | 4351 | CA | VAL | A | 534 | 67.324 | −17.302 | 3.667 | 1.00 | 23.87 | A | C |
| ATOM | 4352 | CB | VAL | A | 534 | 65.824 | −17.504 | 3.957 | 1.00 | 24.85 | A | C |
| ATOM | 4353 | CG1 | VAL | A | 534 | 64.962 | −17.401 | 2.688 | 1.00 | 19.21 | A | C |
| ATOM | 4354 | CG2 | VAL | A | 534 | 65.589 | −18.861 | 4.600 | 1.00 | 26.32 | A | C |
| ATOM | 4355 | C | VAL | A | 534 | 67.525 | −16.070 | 2.765 | 1.00 | 26.84 | A | C |
| ATOM | 4356 | O | VAL | A | 534 | 67.650 | −16.194 | 1.550 | 1.00 | 28.14 | A | O |
| ATOM | 4357 | N | ILE | A | 535 | 67.540 | −14.874 | 3.349 | 1.00 | 28.94 | A | N |
| ATOM | 4358 | CA | ILE | A | 535 | 67.516 | −13.635 | 2.563 | 1.00 | 28.39 | A | C |
| ATOM | 4359 | CB | ILE | A | 535 | 66.538 | −12.596 | 3.171 | 1.00 | 34.98 | A | C |
| ATOM | 4360 | CG1 | ILE | A | 535 | 65.113 | −13.130 | 3.251 | 1.00 | 35.70 | A | C |
| ATOM | 4361 | CD1 | ILE | A | 535 | 64.479 | −13.463 | 1.911 | 1.00 | 44.01 | A | C |
| ATOM | 4362 | CG2 | ILE | A | 535 | 66.582 | −11.268 | 2.372 | 1.00 | 35.77 | A | C |
| ATOM | 4363 | C | ILE | A | 535 | 68.882 | −12.956 | 2.465 | 1.00 | 32.00 | A | C |
| ATOM | 4364 | O | ILE | A | 535 | 69.306 | −12.535 | 1.385 | 1.00 | 38.68 | A | O |
| ATOM | 4365 | N | THR | A | 536 | 69.570 | −12.825 | 3.589 | 1.00 | 35.57 | A | N |
| ATOM | 4366 | CA | THR | A | 536 | 70.650 | −11.815 | 3.680 | 1.00 | 35.50 | A | C |
| ATOM | 4367 | CB | THR | A | 536 | 70.440 | −10.922 | 4.927 | 1.00 | 44.42 | A | C |
| ATOM | 4368 | OG1 | THR | A | 536 | 70.630 | −11.686 | 6.120 | 1.00 | 46.85 | A | O |
| ATOM | 4369 | CG2 | THR | A | 536 | 69.023 | −10.376 | 4.936 | 1.00 | 34.58 | A | C |
| ATOM | 4370 | C | THR | A | 536 | 72.080 | −12.379 | 3.578 | 1.00 | 35.15 | A | C |
| ATOM | 4371 | O | THR | A | 536 | 72.899 | −11.856 | 2.819 | 1.00 | 32.71 | A | O |
| ATOM | 4372 | N | GLU | A | 537 | 72.375 | −13.460 | 4.287 | 1.00 | 31.94 | A | N |
| ATOM | 4373 | CA | GLU | A | 537 | 73.728 | −14.005 | 4.299 | 1.00 | 38.13 | A | C |
| ATOM | 4374 | CB | GLU | A | 537 | 74.089 | −14.472 | 5.704 | 1.00 | 44.29 | A | C |
| ATOM | 4375 | CG | GLU | A | 537 | 74.061 | −13.369 | 6.740 | 1.00 | 56.93 | A | C |
| ATOM | 4376 | CD | GLU | A | 537 | 74.966 | −13.668 | 7.913 | 1.00 | 59.02 | A | C |
| ATOM | 4377 | OE1 | GLU | A | 537 | 75.055 | −14.854 | 8.296 | 1.00 | 56.89 | A | O |
| ATOM | 4378 | OE2 | GLU | A | 537 | 75.588 | −12.723 | 8.447 | 1.00 | 59.60 | A | O |
| ATOM | 4379 | C | GLU | A | 537 | 73.884 | −15.190 | 3.346 | 1.00 | 32.80 | A | C |
| ATOM | 4380 | O | GLU | A | 537 | 73.136 | −16.127 | 3.443 | 1.00 | 29.57 | A | O |
| ATOM | 4381 | N | PRO | A | 538 | 74.877 | −15.153 | 2.447 | 1.00 | 29.81 | A | N |
| ATOM | 4382 | CA | PRO | A | 538 | 75.135 | −16.339 | 1.643 | 1.00 | 27.02 | A | C |
| ATOM | 4383 | CB | PRO | A | 538 | 76.189 | −15.876 | 0.625 | 1.00 | 28.93 | A | C |
| ATOM | 4384 | CG | PRO | A | 538 | 76.740 | −14.597 | 1.160 | 1.00 | 34.72 | A | C |
| ATOM | 4385 | CD | PRO | A | 538 | 75.672 | −13.990 | 2.011 | 1.00 | 34.41 | A | C |
| ATOM | 4386 | C | PRO | A | 538 | 75.664 | −17.498 | 2.457 | 1.00 | 26.35 | A | C |

APPENDIX A-continued

*P. alba* 3T288C coordinates

| ATOM | 4387 | O | PRO | A | 538 | 76.199 | −17.301 | 3.526 | 1.00 | 20.63 | A | O |
|------|------|------|-----|---|-----|--------|---------|-------|------|-------|---|---|
| ATOM | 4388 | N | ILE | A | 539 | 75.474 | −18.709 | 1.942 | 1.00 | 24.14 | A | N |
| ATOM | 4389 | CA | ILE | A | 539 | 76.119 | −19.895 | 2.469 | 1.00 | 22.55 | A | C |
| ATOM | 4390 | CB | ILE | A | 539 | 75.580 | −21.185 | 1.795 | 1.00 | 23.63 | A | C |
| ATOM | 4391 | CG1 | ILE | A | 539 | 74.110 | −21.388 | 2.197 | 1.00 | 23.50 | A | C |
| ATOM | 4392 | CD1 | ILE | A | 539 | 73.484 | −22.693 | 1.716 | 1.00 | 20.21 | A | C |
| ATOM | 4393 | CG2 | ILE | A | 539 | 76.433 | −22.376 | 2.151 | 1.00 | 20.66 | A | C |
| ATOM | 4394 | C | ILE | A | 539 | 77.603 | −19.760 | 2.176 | 1.00 | 24.55 | A | C |
| ATOM | 4395 | O | ILE | A | 539 | 77.995 | −19.240 | 1.116 | 1.00 | 17.55 | A | O |
| ATOM | 4396 | N | LEU | A | 540 | 78.415 | −20.260 | 3.099 | 1.00 | 20.97 | A | N |
| ATOM | 4397 | CA | LEU | A | 540 | 79.866 | −20.080 | 3.033 | 1.00 | 23.53 | A | C |
| ATOM | 4398 | CB | LEU | A | 540 | 80.554 | −20.454 | 4.361 | 1.00 | 25.37 | A | C |
| ATOM | 4399 | CG | LEU | A | 540 | 80.573 | −19.421 | 5.505 | 1.00 | 37.87 | A | C |
| ATOM | 4400 | CD1 | LEU | A | 540 | 81.220 | −20.026 | 6.753 | 1.00 | 41.81 | A | C |
| ATOM | 4401 | CD2 | LEU | A | 540 | 81.320 | −18.094 | 5.146 | 1.00 | 33.15 | A | C |
| ATOM | 4402 | C | LEU | A | 540 | 80.381 | −20.922 | 1.888 | 1.00 | 24.37 | A | C |
| ATOM | 4403 | O | LEU | A | 540 | 79.937 | −22.063 | 1.713 | 1.00 | 26.94 | A | O |
| ATOM | 4404 | N | PRO | A | 541 | 81.312 | −20.366 | 1.092 | 1.00 | 26.27 | A | N |
| ATOM | 4405 | CA | PRO | A | 541 | 81.687 | −20.986 | −0.188 | 1.00 | 23.27 | A | C |
| ATOM | 4406 | CB | PRO | A | 541 | 82.687 | −19.997 | −0.800 | 1.00 | 28.51 | A | C |
| ATOM | 4407 | CG | PRO | A | 541 | 83.029 | −19.016 | 0.303 | 1.00 | 29.70 | A | C |
| ATOM | 4408 | CD | PRO | A | 541 | 81.901 | −19.021 | 1.266 | 1.00 | 29.11 | A | C |
| ATOM | 4409 | C | PRO | A | 541 | 82.278 | −22.374 | −0.058 | 1.00 | 24.70 | A | C |
| ATOM | 4410 | O | PRO | A | 541 | 82.858 | −22.721 | 0.971 | 1.00 | 25.93 | A | O |
| ATOM | 4411 | N | PHE | A | 542 | 82.098 | −23.185 | −1.095 | 1.00 | 24.37 | A | N |
| ATOM | 4412 | CA | PHE | A | 542 | 82.703 | −24.513 | −1.151 | 1.00 | 21.75 | A | C |
| ATOM | 4413 | CB | PHE | A | 542 | 82.437 | −25.081 | −2.522 | 1.00 | 21.15 | A | C |
| ATOM | 4414 | CG | PHE | A | 542 | 83.008 | −26.416 | −2.729 | 1.00 | 22.86 | A | C |
| ATOM | 4415 | CD1 | PHE | A | 542 | 82.505 | −27.496 | −2.037 | 1.00 | 23.96 | A | C |
| ATOM | 4416 | CE1 | PHE | A | 542 | 83.011 | −28.753 | −2.231 | 1.00 | 26.40 | A | C |
| ATOM | 4417 | CZ | PHE | A | 542 | 84.050 | −28.953 | −3.127 | 1.00 | 29.66 | A | C |
| ATOM | 4418 | CE2 | PHE | A | 542 | 84.574 | −27.875 | −3.826 | 1.00 | 28.49 | A | C |
| ATOM | 4419 | CD2 | PHE | A | 542 | 84.048 | −26.613 | −3.629 | 1.00 | 26.57 | A | C |
| ATOM | 4420 | C | PHE | A | 542 | 84.225 | −24.449 | −0.980 | 1.00 | 25.16 | A | C |
| ATOM | 4421 | O | PHE | A | 542 | 84.829 | −23.566 | −1.544 | 1.00 | 21.55 | A | O |
| ATOM | 4422 | N | GLU | A | 543 | 84.827 | −25.395 | −0.253 | 1.00 | 34.39 | A | N |
| ATOM | 4423 | CA | GLU | A | 543 | 86.302 | −25.457 | −0.097 | 1.00 | 47.54 | A | C |
| ATOM | 4424 | CB | GLU | A | 543 | 86.720 | −25.276 | 1.373 | 1.00 | 57.01 | A | C |
| ATOM | 4425 | CG | GLU | A | 543 | 86.935 | −23.819 | 1.792 | 1.00 | 59.28 | A | C |
| ATOM | 4426 | CD | GLU | A | 543 | 87.824 | −23.691 | 3.025 | 1.00 | 71.22 | A | C |
| ATOM | 4427 | OE1 | GLU | A | 543 | 88.980 | −24.175 | 3.003 | 1.00 | 69.03 | A | O |
| ATOM | 4428 | OE2 | GLU | A | 543 | 87.368 | −23.092 | 4.018 | 1.00 | 82.75 | A | O |
| ATOM | 4429 | C | GLU | A | 543 | 86.981 | −26.698 | −0.714 | 1.00 | 50.91 | A | C |
| ATOM | 4430 | O | GLU | A | 543 | 87.247 | −26.713 | −1.913 | 1.00 | 56.87 | A | O |
| ATOM | 4431 | N | ARG | A | 544 | 87.287 | −27.720 | 0.085 | 1.00 | 67.82 | A | N |
| ATOM | 4432 | CA | ARG | A | 544 | 88.181 | −28.797 | −0.371 | 1.00 | 70.50 | A | C |
| ATOM | 4433 | CB | ARG | A | 544 | 89.581 | −28.230 | −0.696 | 1.00 | 76.08 | A | C |
| ATOM | 4434 | CG | ARG | A | 544 | 90.546 | −29.200 | −1.391 | 1.00 | 90.28 | A | C |
| ATOM | 4435 | CD | ARG | A | 544 | 89.885 | −30.008 | −2.515 | 1.00 | 101.63 | A | C |
| ATOM | 4436 | NE | ARG | A | 544 | 89.111 | −29.177 | −3.442 | 1.00 | 99.45 | A | N |
| ATOM | 4437 | CZ | ARG | A | 544 | 88.374 | −29.647 | −4.448 | 1.00 | 93.65 | A | C |
| ATOM | 4438 | NH1 | ARG | A | 544 | 88.292 | −30.950 | −4.678 | 1.00 | 95.79 | A | N |
| ATOM | 4439 | NH2 | ARG | A | 544 | 87.710 | −28.808 | −5.235 | 1.00 | 91.46 | A | N |
| ATOM | 4440 | C | ARG | A | 544 | 88.309 | −29.910 | 0.662 | 1.00 | 65.35 | A | C |
| ATOM | 4441 | O | ARG | A | 544 | 89.318 | −30.003 | 1.364 | 1.00 | 66.29 | A | O |
| ATOM | 4442 | N | SER | B | 6 | 66.028 | 35.448 | 11.860 | 1.00 | 47.07 | B | N |
| ATOM | 4443 | CA | SER | B | 6 | 66.385 | 36.705 | 11.127 | 1.00 | 58.24 | B | C |
| ATOM | 4444 | CB | SER | B | 6 | 66.400 | 37.899 | 12.073 | 1.00 | 56.45 | B | C |
| ATOM | 4445 | OG | SER | B | 6 | 66.861 | 39.069 | 11.413 | 1.00 | 72.79 | B | O |
| ATOM | 4446 | C | SER | B | 6 | 67.715 | 36.596 | 10.348 | 1.00 | 60.55 | B | C |
| ATOM | 4447 | O | SER | B | 6 | 67.735 | 36.911 | 9.153 | 1.00 | 56.56 | B | O |
| ATOM | 4448 | N | ALA | B | 7 | 68.816 | 36.179 | 11.000 | 1.00 | 42.85 | B | N |
| ATOM | 4449 | CA | ALA | B | 7 | 69.983 | 35.673 | 10.240 | 1.00 | 35.66 | B | C |
| ATOM | 4450 | CB | ALA | B | 7 | 71.252 | 35.554 | 11.104 | 1.00 | 30.55 | B | C |
| ATOM | 4451 | C | ALA | B | 7 | 69.550 | 34.315 | 9.718 | 1.00 | 31.48 | B | C |
| ATOM | 4452 | O | ALA | B | 7 | 68.673 | 33.684 | 10.306 | 1.00 | 28.34 | B | O |
| ATOM | 4453 | N | ASN | B | 8 | 70.119 | 33.860 | 8.607 | 1.00 | 37.62 | B | N |
| ATOM | 4454 | CA | ASN | B | 8 | 69.707 | 32.579 | 8.041 | 1.00 | 36.50 | B | C |
| ATOM | 4455 | CB | ASN | B | 8 | 68.925 | 32.796 | 6.739 | 1.00 | 40.61 | B | C |
| ATOM | 4456 | CG | ASN | B | 8 | 68.518 | 31.498 | 6.081 | 1.00 | 39.92 | B | C |
| ATOM | 4457 | OD1 | ASN | B | 8 | 68.472 | 30.436 | 6.712 | 1.00 | 47.46 | B | O |
| ATOM | 4458 | ND2 | ASN | B | 8 | 68.215 | 31.577 | 4.798 | 1.00 | 59.84 | B | N |
| ATOM | 4459 | C | ASN | B | 8 | 70.866 | 31.612 | 7.813 | 1.00 | 35.29 | B | C |
| ATOM | 4460 | O | ASN | B | 8 | 71.528 | 31.650 | 6.779 | 1.00 | 39.53 | B | O |
| ATOM | 4461 | N | TYR | B | 9 | 71.066 | 30.709 | 8.767 | 1.00 | 32.98 | B | N |
| ATOM | 4462 | CA | TYR | B | 9 | 72.154 | 29.740 | 8.692 | 1.00 | 31.48 | B | C |
| ATOM | 4463 | CB | TYR | B | 9 | 72.806 | 29.570 | 10.075 | 1.00 | 25.69 | B | C |
| ATOM | 4464 | CG | TYR | B | 9 | 73.331 | 30.877 | 10.652 | 1.00 | 21.84 | B | C |

APPENDIX A-continued

P. alba 3T288C coordinates

| ATOM | 4465 | CD1 | TYR | B | 9 | 74.259 | 31.663 | 9.945 | 1.00 | 22.23 | B | C |
|---|---|---|---|---|---|---|---|---|---|---|---|---|
| ATOM | 4466 | CE1 | TYR | B | 9 | 74.748 | 32.876 | 10.495 | 1.00 | 18.59 | B | C |
| ATOM | 4467 | CZ | TYR | B | 9 | 74.268 | 33.313 | 11.720 | 1.00 | 14.14 | B | C |
| ATOM | 4468 | OH | TYR | B | 9 | 74.738 | 34.483 | 12.270 | 1.00 | 15.10 | B | O |
| ATOM | 4469 | CE2 | TYR | B | 9 | 73.328 | 32.554 | 12.420 | 1.00 | 13.57 | B | C |
| ATOM | 4470 | CD2 | TYR | B | 9 | 72.875 | 31.350 | 11.887 | 1.00 | 17.61 | B | C |
| ATOM | 4471 | C | TYR | B | 9 | 71.703 | 28.390 | 8.131 | 1.00 | 35.04 | B | C |
| ATOM | 4472 | O | TYR | B | 9 | 72.488 | 27.448 | 8.105 | 1.00 | 39.68 | B | O |
| ATOM | 4473 | N | GLU | B | 10 | 70.459 | 28.296 | 7.660 | 1.00 | 42.28 | B | N |
| ATOM | 4474 | CA | GLU | B | 10 | 69.933 | 27.015 | 7.152 | 1.00 | 47.58 | B | C |
| ATOM | 4475 | CB | GLU | B | 10 | 68.391 | 26.999 | 7.200 | 1.00 | 51.50 | B | C |
| ATOM | 4476 | CG | GLU | B | 10 | 67.797 | 27.312 | 8.605 | 1.00 | 60.77 | B | C |
| ATOM | 4477 | CD | GLU | B | 10 | 68.474 | 26.526 | 9.740 | 1.00 | 69.74 | B | C |
| ATOM | 4478 | OE1 | GLU | B | 10 | 68.629 | 25.294 | 9.600 | 1.00 | 71.24 | B | O |
| ATOM | 4479 | OE2 | GLU | B | 10 | 68.858 | 27.137 | 10.766 | 1.00 | 81.34 | B | O |
| ATOM | 4480 | C | GLU | B | 10 | 70.481 | 26.715 | 5.741 | 1.00 | 38.79 | B | C |
| ATOM | 4481 | O | GLU | B | 10 | 70.707 | 27.644 | 4.952 | 1.00 | 35.80 | B | O |
| ATOM | 4482 | N | PRO | B | 11 | 70.740 | 25.425 | 5.435 | 1.00 | 48.23 | B | N |
| ATOM | 4483 | CA | PRO | B | 11 | 71.364 | 25.091 | 4.154 | 1.00 | 45.24 | B | C |
| ATOM | 4484 | CB | PRO | B | 11 | 71.760 | 23.621 | 4.329 | 1.00 | 53.83 | B | C |
| ATOM | 4485 | CG | PRO | B | 11 | 70.740 | 23.077 | 5.276 | 1.00 | 58.80 | B | C |
| ATOM | 4486 | CD | PRO | B | 11 | 70.432 | 24.214 | 6.227 | 1.00 | 57.54 | B | C |
| ATOM | 4487 | C | PRO | B | 11 | 70.363 | 25.244 | 3.011 | 1.00 | 38.09 | B | C |
| ATOM | 4488 | O | PRO | B | 11 | 69.158 | 25.173 | 3.242 | 1.00 | 37.80 | B | O |
| ATOM | 4489 | N | ASN | B | 12 | 70.862 | 25.500 | 1.809 | 1.00 | 35.42 | B | N |
| ATOM | 4490 | CA | ASN | B | 12 | 70.033 | 25.475 | 0.594 | 1.00 | 36.63 | B | C |
| ATOM | 4491 | CB | ASN | B | 12 | 70.491 | 26.541 | −0.406 | 1.00 | 44.07 | B | C |
| ATOM | 4492 | CG | ASN | B | 12 | 70.595 | 27.907 | 0.215 | 1.00 | 48.52 | B | C |
| ATOM | 4493 | OD1 | ASN | B | 12 | 69.591 | 28.482 | 0.615 | 1.00 | 57.64 | B | O |
| ATOM | 4494 | ND2 | ASN | B | 12 | 71.816 | 28.437 | 0.311 | 1.00 | 44.25 | B | N |
| ATOM | 4495 | C | ASN | B | 12 | 70.058 | 24.097 | −0.068 | 1.00 | 33.77 | B | C |
| ATOM | 4496 | O | ASN | B | 12 | 71.034 | 23.324 | 0.058 | 1.00 | 34.32 | B | O |
| ATOM | 4497 | N | SER | B | 13 | 68.967 | 23.772 | −0.758 | 1.00 | 43.14 | B | N |
| ATOM | 4498 | CA | SER | B | 13 | 68.857 | 22.493 | −1.483 | 1.00 | 41.27 | B | C |
| ATOM | 4499 | CB | SER | B | 13 | 67.454 | 22.324 | −2.091 | 1.00 | 35.20 | B | C |
| ATOM | 4500 | OG | SER | B | 13 | 67.033 | 23.498 | −2.759 | 1.00 | 39.06 | B | O |
| ATOM | 4501 | C | SER | B | 13 | 69.923 | 22.356 | −2.586 | 1.00 | 40.57 | B | C |
| ATOM | 4502 | O | SER | B | 13 | 70.258 | 21.243 | −2.991 | 1.00 | 43.94 | B | O |
| ATOM | 4503 | N | TRP | B | 14 | 70.462 | 23.489 | −3.039 | 1.00 | 30.52 | B | N |
| ATOM | 4504 | CA | TRP | B | 14 | 71.523 | 23.518 | −4.062 | 1.00 | 35.59 | B | C |
| ATOM | 4505 | CB | TRP | B | 14 | 71.226 | 24.606 | −5.107 | 1.00 | 32.98 | B | C |
| ATOM | 4506 | CG | TRP | B | 14 | 70.716 | 25.912 | −4.544 | 1.00 | 36.10 | B | C |
| ATOM | 4507 | CD1 | TRP | B | 14 | 69.387 | 26.315 | −4.410 | 1.00 | 45.32 | B | C |
| ATOM | 4508 | NE1 | TRP | B | 14 | 69.306 | 27.561 | −3.841 | 1.00 | 45.60 | B | N |
| ATOM | 4509 | CE2 | TRP | B | 14 | 70.538 | 28.040 | −3.577 | 1.00 | 38.78 | B | C |
| ATOM | 4510 | CD2 | TRP | B | 14 | 71.503 | 27.017 | −4.006 | 1.00 | 34.57 | B | C |
| ATOM | 4511 | CE3 | TRP | B | 14 | 72.849 | 27.256 | −3.838 | 1.00 | 41.97 | B | C |
| ATOM | 4512 | CZ3 | TRP | B | 14 | 73.250 | 28.469 | −3.262 | 1.00 | 55.13 | B | C |
| ATOM | 4513 | CH2 | TRP | B | 14 | 72.317 | 29.432 | −2.863 | 1.00 | 53.40 | B | C |
| ATOM | 4514 | CZ2 | TRP | B | 14 | 70.937 | 29.230 | −3.015 | 1.00 | 42.74 | B | C |
| ATOM | 4515 | C | TRP | B | 14 | 72.950 | 23.665 | −3.521 | 1.00 | 36.47 | B | C |
| ATOM | 4516 | O | TRP | B | 14 | 73.909 | 23.621 | −4.304 | 1.00 | 28.14 | B | O |
| ATOM | 4517 | N | ASP | B | 15 | 73.128 | 23.825 | −2.203 | 1.00 | 31.81 | B | N |
| ATOM | 4518 | CA | ASP | B | 15 | 74.491 | 23.876 | −1.611 | 1.00 | 28.30 | B | C |
| ATOM | 4519 | CB | ASP | B | 15 | 74.425 | 23.877 | −0.071 | 1.00 | 33.88 | B | C |
| ATOM | 4520 | CG | ASP | B | 15 | 74.011 | 25.218 | 0.518 | 1.00 | 40.45 | B | C |
| ATOM | 4521 | OD1 | ASP | B | 15 | 73.764 | 26.174 | −0.234 | 1.00 | 42.94 | B | O |
| ATOM | 4522 | OD2 | ASP | B | 15 | 73.930 | 25.309 | 1.763 | 1.00 | 54.72 | B | O |
| ATOM | 4523 | C | ASP | B | 15 | 75.319 | 22.637 | −2.029 | 1.00 | 33.86 | B | C |
| ATOM | 4524 | O | ASP | B | 15 | 74.784 | 21.523 | −2.110 | 1.00 | 26.74 | B | O |
| ATOM | 4525 | N | TYR | B | 16 | 76.625 | 22.819 | −2.228 | 1.00 | 28.03 | B | N |
| ATOM | 4526 | CA | TYR | B | 16 | 77.536 | 21.728 | −2.628 | 1.00 | 27.83 | B | C |
| ATOM | 4527 | CB | TYR | B | 16 | 78.917 | 22.286 | −3.056 | 1.00 | 25.77 | B | C |
| ATOM | 4528 | CG | TYR | B | 16 | 78.893 | 23.078 | −4.351 | 1.00 | 24.05 | B | C |
| ATOM | 4529 | CD1 | TYR | B | 16 | 78.370 | 22.517 | −5.531 | 1.00 | 22.17 | B | C |
| ATOM | 4530 | CE1 | TYR | B | 16 | 78.355 | 23.234 | −6.721 | 1.00 | 17.53 | B | C |
| ATOM | 4531 | CZ | TYR | B | 16 | 78.814 | 24.517 | −6.732 | 1.00 | 20.83 | B | C |
| ATOM | 4532 | OH | TYR | B | 16 | 78.770 | 25.206 | −7.896 | 1.00 | 19.17 | B | O |
| ATOM | 4533 | CE2 | TYR | B | 16 | 79.329 | 25.107 | −5.579 | 1.00 | 24.55 | B | C |
| ATOM | 4534 | CD2 | TYR | B | 16 | 79.364 | 24.379 | −4.399 | 1.00 | 24.85 | B | C |
| ATOM | 4535 | C | TYR | B | 16 | 77.714 | 20.649 | −1.525 | 1.00 | 35.70 | B | C |
| ATOM | 4536 | O | TYR | B | 16 | 77.945 | 19.473 | −1.835 | 1.00 | 32.15 | B | O |
| ATOM | 4537 | N | ASP | B | 17 | 77.618 | 21.053 | −0.255 | 1.00 | 30.24 | B | N |
| ATOM | 4538 | CA | ASP | B | 17 | 77.597 | 20.080 | 0.869 | 1.00 | 42.23 | B | C |
| ATOM | 4539 | CB | ASP | B | 17 | 77.534 | 20.812 | 2.219 | 1.00 | 38.98 | B | C |
| ATOM | 4540 | CG | ASP | B | 17 | 78.841 | 21.499 | 2.587 | 1.00 | 44.68 | B | C |
| ATOM | 4541 | OD1 | ASP | B | 17 | 79.926 | 20.995 | 2.204 | 1.00 | 44.13 | B | O |
| ATOM | 4542 | OD2 | ASP | B | 17 | 78.770 | 22.546 | 3.275 | 1.00 | 44.42 | B | O |

APPENDIX A-continued

*P. alba* 3T288C coordinates

| ATOM | 4543 | C | ASP | B | 17 | 76.400 | 19.110 | 0.748 | 1.00 | 45.86 | B | C |
|---|---|---|---|---|---|---|---|---|---|---|---|---|
| ATOM | 4544 | O | ASP | B | 17 | 76.523 | 17.919 | 1.008 | 1.00 | 51.23 | B | O |
| ATOM | 4545 | N | TYR | B | 18 | 75.259 | 19.647 | 0.329 | 1.00 | 49.27 | B | N |
| ATOM | 4546 | CA | TYR | B | 18 | 74.025 | 18.877 | 0.133 | 1.00 | 50.51 | B | C |
| ATOM | 4547 | CB | TYR | B | 18 | 72.840 | 19.861 | 0.083 | 1.00 | 60.94 | B | C |
| ATOM | 4548 | CG | TYR | B | 18 | 71.471 | 19.297 | 0.384 | 1.00 | 82.34 | B | C |
| ATOM | 4549 | CD1 | TYR | B | 18 | 70.797 | 18.508 | −0.555 | 1.00 | 91.64 | B | C |
| ATOM | 4550 | CE1 | TYR | B | 18 | 69.531 | 18.007 | −0.293 | 1.00 | 96.76 | B | C |
| ATOM | 4551 | CZ | TYR | B | 18 | 68.916 | 18.307 | 0.913 | 1.00 | 100.88 | B | C |
| ATOM | 4552 | OH | TYR | B | 18 | 67.662 | 17.809 | 1.169 | 1.00 | 105.08 | B | O |
| ATOM | 4553 | CE2 | TYR | B | 18 | 69.553 | 19.103 | 1.858 | 1.00 | 92.37 | B | C |
| ATOM | 4554 | CD2 | TYR | B | 18 | 70.821 | 19.598 | 1.586 | 1.00 | 87.10 | B | C |
| ATOM | 4555 | C | TYR | B | 18 | 74.116 | 18.045 | −1.158 | 1.00 | 48.99 | B | C |
| ATOM | 4556 | O | TYR | B | 18 | 73.977 | 16.828 | −1.127 | 1.00 | 44.28 | B | O |
| ATOM | 4557 | N | LEU | B | 19 | 74.383 | 18.704 | −2.287 | 1.00 | 43.39 | B | N |
| ATOM | 4558 | CA | LEU | B | 19 | 74.349 | 18.061 | −3.610 | 1.00 | 39.30 | B | C |
| ATOM | 4559 | CB | LEU | B | 19 | 74.222 | 19.115 | −4.734 | 1.00 | 40.10 | B | C |
| ATOM | 4560 | CG | LEU | B | 19 | 72.909 | 19.881 | −4.924 | 1.00 | 36.96 | B | C |
| ATOM | 4561 | CD1 | LEU | B | 19 | 73.106 | 20.911 | −6.037 | 1.00 | 33.51 | B | C |
| ATOM | 4562 | CD2 | LEU | B | 19 | 71.702 | 18.942 | −5.242 | 1.00 | 35.19 | B | C |
| ATOM | 4563 | C | LEU | B | 19 | 75.530 | 17.131 | −3.931 | 1.00 | 38.74 | B | C |
| ATOM | 4564 | O | LEU | B | 19 | 75.448 | 16.358 | −4.870 | 1.00 | 33.93 | B | O |
| ATOM | 4565 | N | LEU | B | 20 | 76.626 | 17.207 | −3.184 | 1.00 | 43.02 | B | N |
| ATOM | 4566 | CA | LEU | B | 20 | 77.784 | 16.337 | −3.446 | 1.00 | 48.34 | B | C |
| ATOM | 4567 | CB | LEU | B | 20 | 78.956 | 17.186 | −3.980 | 1.00 | 48.91 | B | C |
| ATOM | 4568 | CG | LEU | B | 20 | 78.737 | 17.933 | −5.311 | 1.00 | 42.22 | B | C |
| ATOM | 4569 | CD1 | LEU | B | 20 | 79.941 | 18.813 | −5.681 | 1.00 | 32.75 | B | C |
| ATOM | 4570 | CD2 | LEU | B | 20 | 78.427 | 16.957 | −6.428 | 1.00 | 41.67 | B | C |
| ATOM | 4571 | C | LEU | B | 20 | 78.159 | 15.566 | −2.162 | 1.00 | 53.90 | B | C |
| ATOM | 4572 | O | LEU | B | 20 | 78.522 | 16.183 | −1.166 | 1.00 | 50.11 | B | O |
| ATOM | 4573 | N | SER | B | 21 | 78.064 | 14.229 | −2.185 | 1.00 | 73.10 | B | N |
| ATOM | 4574 | CA | SER | B | 21 | 78.141 | 13.417 | −0.947 | 1.00 | 87.01 | B | C |
| ATOM | 4575 | CB | SER | B | 21 | 76.733 | 13.253 | −0.351 | 1.00 | 82.80 | B | C |
| ATOM | 4576 | OG | SER | B | 21 | 76.250 | 14.465 | 0.191 | 1.00 | 87.39 | B | O |
| ATOM | 4577 | C | SER | B | 21 | 78.772 | 12.011 | −1.059 | 1.00 | 105.74 | B | C |
| ATOM | 4578 | O | SER | B | 21 | 79.742 | 11.697 | −0.360 | 1.00 | 95.58 | B | O |
| ATOM | 4579 | N | SER | B | 22 | 78.198 | 11.160 | −1.905 | 1.00 | 118.22 | B | N |
| ATOM | 4580 | CA | SER | B | 22 | 78.488 | 9.719 | −1.861 | 1.00 | 113.76 | B | C |
| ATOM | 4581 | CB | SER | B | 22 | 77.376 | 8.940 | −2.574 | 1.00 | 109.60 | B | C |
| ATOM | 4582 | OG | SER | B | 22 | 77.051 | 9.533 | −3.823 | 1.00 | 113.06 | B | O |
| ATOM | 4583 | C | SER | B | 22 | 79.857 | 9.357 | −2.439 | 1.00 | 101.67 | B | C |
| ATOM | 4584 | O | SER | B | 22 | 80.196 | 9.751 | −3.552 | 1.00 | 111.02 | B | O |
| ATOM | 4585 | N | ILE | B | 28 | 83.597 | 12.639 | −5.109 | 1.00 | 85.65 | B | N |
| ATOM | 4586 | CA | ILE | B | 28 | 82.666 | 13.752 | −4.965 | 1.00 | 86.60 | B | C |
| ATOM | 4587 | CB | ILE | B | 28 | 81.164 | 13.263 | −5.008 | 1.00 | 93.39 | B | C |
| ATOM | 4588 | CG1 | ILE | B | 28 | 80.923 | 12.256 | −6.149 | 1.00 | 83.16 | B | C |
| ATOM | 4589 | CD1 | ILE | B | 28 | 79.442 | 12.122 | −6.580 | 1.00 | 61.20 | B | C |
| ATOM | 4590 | CG2 | ILE | B | 28 | 80.211 | 14.427 | −5.205 | 1.00 | 98.61 | B | C |
| ATOM | 4591 | C | ILE | B | 28 | 82.985 | 14.552 | −3.680 | 1.00 | 83.50 | B | C |
| ATOM | 4592 | O | ILE | B | 28 | 82.171 | 15.365 | −3.233 | 1.00 | 79.32 | B | O |
| ATOM | 4593 | N | GLU | B | 29 | 84.180 | 14.325 | −3.117 | 1.00 | 76.18 | B | N |
| ATOM | 4594 | CA | GLU | B | 29 | 84.667 | 15.025 | −1.915 | 1.00 | 76.21 | B | C |
| ATOM | 4595 | CB | GLU | B | 29 | 85.131 | 14.003 | −0.865 | 1.00 | 76.32 | B | C |
| ATOM | 4596 | CG | GLU | B | 29 | 85.858 | 14.579 | 0.372 | 1.00 | 72.53 | B | C |
| ATOM | 4597 | CD | GLU | B | 29 | 84.923 | 15.133 | 1.438 | 1.00 | 70.19 | B | C |
| ATOM | 4598 | OE1 | GLU | B | 29 | 83.782 | 15.526 | 1.121 | 1.00 | 71.77 | B | O |
| ATOM | 4599 | OE2 | GLU | B | 29 | 85.338 | 15.175 | 2.611 | 1.00 | 63.15 | B | O |
| ATOM | 4600 | C | GLU | B | 29 | 85.815 | 15.997 | −2.242 | 1.00 | 83.08 | B | C |
| ATOM | 4601 | O | GLU | B | 29 | 85.858 | 17.125 | −1.734 | 1.00 | 68.15 | B | O |
| ATOM | 4602 | N | VAL | B | 30 | 86.761 | 15.543 | −3.060 | 1.00 | 82.68 | B | N |
| ATOM | 4603 | CA | VAL | B | 30 | 87.825 | 16.416 | −3.557 | 1.00 | 72.16 | B | C |
| ATOM | 4604 | CB | VAL | B | 30 | 88.928 | 15.620 | −4.327 | 1.00 | 69.91 | B | C |
| ATOM | 4605 | CG1 | VAL | B | 30 | 88.342 | 14.879 | −5.566 | 1.00 | 57.81 | B | C |
| ATOM | 4606 | CG2 | VAL | B | 30 | 90.079 | 16.544 | −4.719 | 1.00 | 50.91 | B | C |
| ATOM | 4607 | C | VAL | B | 30 | 87.217 | 17.503 | −4.454 | 1.00 | 59.36 | B | C |
| ATOM | 4608 | O | VAL | B | 30 | 87.598 | 18.665 | −4.356 | 1.00 | 50.25 | B | O |
| ATOM | 4609 | N | TYR | B | 31 | 86.264 | 17.096 | −5.297 | 1.00 | 47.13 | B | N |
| ATOM | 4610 | CA | TYR | B | 31 | 85.540 | 17.957 | −6.261 | 1.00 | 52.78 | B | C |
| ATOM | 4611 | CB | TYR | B | 31 | 84.753 | 17.013 | −7.199 | 1.00 | 53.13 | B | C |
| ATOM | 4612 | CG | TYR | B | 31 | 83.853 | 17.527 | −8.333 | 1.00 | 51.24 | B | C |
| ATOM | 4613 | CD1 | TYR | B | 31 | 84.321 | 17.610 | −9.653 | 1.00 | 53.18 | B | C |
| ATOM | 4614 | CE1 | TYR | B | 31 | 83.460 | 18.012 | −10.722 | 1.00 | 52.11 | B | C |
| ATOM | 4615 | CZ | TYR | B | 31 | 82.099 | 18.293 | −10.468 | 1.00 | 63.53 | B | C |
| ATOM | 4616 | OH | TYR | B | 31 | 81.214 | 18.693 | −11.496 | 1.00 | 34.19 | B | O |
| ATOM | 4617 | CE2 | TYR | B | 31 | 81.620 | 18.175 | −9.158 | 1.00 | 63.84 | B | C |
| ATOM | 4618 | CD2 | TYR | B | 31 | 82.489 | 17.772 | −8.111 | 1.00 | 58.51 | B | C |
| ATOM | 4619 | C | TYR | B | 31 | 84.628 | 18.966 | −5.526 | 1.00 | 45.55 | B | C |
| ATOM | 4620 | O | TYR | B | 31 | 84.466 | 20.108 | −5.978 | 1.00 | 32.99 | B | O |

APPENDIX A-continued

*P. alba* 3T288C coordinates

| ATOM | 4621 | N   | LYS | B | 32 | 84.073 | 18.547 | −4.382 | 1.00 | 39.91 | B | N |
|------|------|-----|-----|---|----|--------|--------|--------|------|-------|---|---|
| ATOM | 4622 | CA  | LYS | B | 32 | 83.222 | 19.401 | −3.535 | 1.00 | 37.60 | B | C |
| ATOM | 4623 | CB  | LYS | B | 32 | 82.581 | 18.578 | −2.406 | 1.00 | 35.13 | B | C |
| ATOM | 4624 | CG  | LYS | B | 32 | 81.635 | 19.380 | −1.518 | 1.00 | 37.69 | B | C |
| ATOM | 4625 | CD  | LYS | B | 32 | 81.148 | 18.584 | −0.328 | 1.00 | 46.73 | B | C |
| ATOM | 4626 | CE  | LYS | B | 32 | 82.243 | 18.417 | 0.707  | 1.00 | 54.45 | B | C |
| ATOM | 4627 | NZ  | LYS | B | 32 | 81.709 | 18.007 | 2.029  | 1.00 | 58.88 | B | N |
| ATOM | 4628 | C   | LYS | B | 32 | 84.009 | 20.563 | −2.929 | 1.00 | 29.15 | B | C |
| ATOM | 4629 | O   | LYS | B | 32 | 83.567 | 21.704 | −2.945 | 1.00 | 26.62 | B | O |
| ATOM | 4630 | N   | ASP | B | 33 | 85.171 | 20.262 | −2.380 | 1.00 | 26.85 | B | N |
| ATOM | 4631 | CA  | ASP | B | 33 | 86.043 | 21.304 | −1.850 | 1.00 | 31.14 | B | C |
| ATOM | 4632 | CB  | ASP | B | 33 | 87.244 | 20.694 | −1.112 | 1.00 | 40.70 | B | C |
| ATOM | 4633 | CG  | ASP | B | 33 | 86.860 | 20.052 | 0.234  | 1.00 | 51.84 | B | C |
| ATOM | 4634 | OD1 | ASP | B | 33 | 85.654 | 20.001 | 0.587  | 1.00 | 46.52 | B | O |
| ATOM | 4635 | OD2 | ASP | B | 33 | 87.783 | 19.596 | 0.943  | 1.00 | 66.19 | B | O |
| ATOM | 4636 | C   | ASP | B | 33 | 86.522 | 22.273 | −2.944 | 1.00 | 27.80 | B | C |
| ATOM | 4637 | O   | ASP | B | 33 | 86.731 | 23.460 | −2.661 | 1.00 | 19.96 | B | O |
| ATOM | 4638 | N   | LYS | B | 34 | 86.701 | 21.784 | −4.179 | 1.00 | 28.92 | B | N |
| ATOM | 4639 | CA  | LYS | B | 34 | 87.096 | 22.666 | −5.288 | 1.00 | 30.71 | B | C |
| ATOM | 4640 | CB  | LYS | B | 34 | 87.463 | 21.925 | −6.581 | 1.00 | 40.79 | B | C |
| ATOM | 4641 | CG  | LYS | B | 34 | 88.951 | 21.833 | −6.793 | 1.00 | 62.22 | B | C |
| ATOM | 4642 | CD  | LYS | B | 34 | 89.356 | 20.754 | −7.790 | 1.00 | 73.27 | B | C |
| ATOM | 4643 | CE  | LYS | B | 34 | 90.722 | 20.184 | −7.405 | 1.00 | 75.22 | B | C |
| ATOM | 4644 | NZ  | LYS | B | 34 | 91.222 | 19.199 | −8.395 | 1.00 | 77.49 | B | N |
| ATOM | 4645 | C   | LYS | B | 34 | 85.957 | 23.595 | −5.552 | 1.00 | 19.79 | B | C |
| ATOM | 4646 | O   | LYS | B | 34 | 86.165 | 24.802 | −5.613 | 1.00 | 21.44 | B | O |
| ATOM | 4647 | N   | ALA | B | 35 | 84.752 | 23.041 | −5.657 | 1.00 | 17.70 | B | N |
| ATOM | 4648 | CA  | ALA | B | 35 | 83.578 | 23.838 | −5.959 | 1.00 | 17.27 | B | C |
| ATOM | 4649 | CB  | ALA | B | 35 | 82.324 | 22.968 | −6.139 | 1.00 | 21.47 | B | C |
| ATOM | 4650 | C   | ALA | B | 35 | 83.346 | 24.917 | −4.902 | 1.00 | 14.58 | B | C |
| ATOM | 4651 | O   | ALA | B | 35 | 83.132 | 26.055 | −5.249 | 1.00 | 13.40 | B | O |
| ATOM | 4652 | N   | LYS | B | 36 | 83.412 | 24.566 | −3.628 | 1.00 | 13.58 | B | N |
| ATOM | 4653 | CA  | LYS | B | 36 | 83.192 | 25.542 | −2.571 | 1.00 | 16.14 | B | C |
| ATOM | 4654 | CB  | LYS | B | 36 | 83.192 | 24.844 | −1.209 | 1.00 | 22.56 | B | C |
| ATOM | 4655 | CG  | LYS | B | 36 | 81.867 | 24.120 | −0.931 | 1.00 | 25.63 | B | C |
| ATOM | 4656 | CD  | LYS | B | 36 | 82.003 | 22.927 | 0.008  | 1.00 | 27.13 | B | C |
| ATOM | 4657 | CE  | LYS | B | 36 | 82.113 | 23.335 | 1.455  | 1.00 | 27.92 | B | C |
| ATOM | 4658 | NZ  | LYS | B | 36 | 82.483 | 22.191 | 2.365  | 1.00 | 34.58 | B | N |
| ATOM | 4659 | C   | LYS | B | 36 | 84.201 | 26.716 | −2.577 | 1.00 | 16.08 | B | C |
| ATOM | 4660 | O   | LYS | B | 36 | 83.808 | 27.852 | −2.389 | 1.00 | 14.45 | B | O |
| ATOM | 4661 | N   | LYS | B | 37 | 85.490 | 26.438 | −2.789 | 1.00 | 16.82 | B | N |
| ATOM | 4662 | CA  | LYS | B | 37 | 86.513 | 27.496 | −2.841 | 1.00 | 15.72 | B | C |
| ATOM | 4663 | CB  | LYS | B | 37 | 87.887 | 26.871 | −3.009 | 1.00 | 18.50 | B | C |
| ATOM | 4664 | CG  | LYS | B | 37 | 89.029 | 27.830 | −2.842 | 1.00 | 24.53 | B | C |
| ATOM | 4665 | CD  | LYS | B | 37 | 90.353 | 27.059 | −2.666 | 1.00 | 28.56 | B | C |
| ATOM | 4666 | CE  | LYS | B | 37 | 91.523 | 27.969 | −2.240 | 1.00 | 36.91 | B | C |
| ATOM | 4667 | NZ  | LYS | B | 37 | 91.795 | 29.070 | −3.227 | 1.00 | 35.36 | B | N |
| ATOM | 4668 | C   | LYS | B | 37 | 86.258 | 28.476 | −4.000 | 1.00 | 14.34 | B | C |
| ATOM | 4669 | O   | LYS | B | 37 | 86.366 | 29.696 | −3.831 | 1.00 | 14.98 | B | O |
| ATOM | 4670 | N   | LEU | B | 38 | 85.948 | 27.927 | −5.173 | 1.00 | 12.95 | B | N |
| ATOM | 4671 | CA  | LEU | B | 38 | 85.584 | 28.724 | −6.356 | 1.00 | 13.59 | B | C |
| ATOM | 4672 | CB  | LEU | B | 38 | 85.367 | 27.815 | −7.579 | 1.00 | 13.70 | B | C |
| ATOM | 4673 | CG  | LEU | B | 38 | 86.576 | 26.956 | −8.026 | 1.00 | 14.80 | B | C |
| ATOM | 4674 | CD1 | LEU | B | 38 | 86.156 | 25.994 | −9.138 | 1.00 | 15.35 | B | C |
| ATOM | 4675 | CD2 | LEU | B | 38 | 87.708 | 27.807 | −8.496 | 1.00 | 16.16 | B | C |
| ATOM | 4676 | C   | LEU | B | 38 | 84.331 | 29.580 | −6.128 | 1.00 | 11.73 | B | C |
| ATOM | 4677 | O   | LEU | B | 38 | 84.312 | 30.774 | −6.434 | 1.00 | 10.49 | B | O |
| ATOM | 4678 | N   | GLU | B | 39 | 83.284 | 28.957 | −5.593 | 1.00 | 11.44 | B | N |
| ATOM | 4679 | CA  | GLU | B | 39 | 82.039 | 29.651 | −5.285 | 1.00 | 10.93 | B | C |
| ATOM | 4680 | CB  | GLU | B | 39 | 81.024 | 28.641 | −4.707 | 1.00 | 14.27 | B | C |
| ATOM | 4681 | CG  | GLU | B | 39 | 79.661 | 29.208 | −4.277 | 1.00 | 15.52 | B | C |
| ATOM | 4682 | CD  | GLU | B | 39 | 78.760 | 28.118 | −3.648 | 1.00 | 21.97 | B | C |
| ATOM | 4683 | OE1 | GLU | B | 39 | 79.308 | 27.233 | −2.932 | 1.00 | 20.74 | B | O |
| ATOM | 4684 | OE2 | GLU | B | 39 | 77.519 | 28.145 | −3.871 | 1.00 | 19.35 | B | O |
| ATOM | 4685 | C   | GLU | B | 39 | 82.260 | 30.782 | −4.295 | 1.00 | 10.22 | B | C |
| ATOM | 4686 | O   | GLU | B | 39 | 81.707 | 31.874 | −4.441 | 1.00 | 11.77 | B | O |
| ATOM | 4687 | N   | ALA | B | 40 | 83.049 | 30.514 | −3.263 | 1.00 | 11.24 | B | N |
| ATOM | 4688 | CA  | ALA | B | 40 | 83.413 | 31.549 | −2.275 | 1.00 | 10.54 | B | C |
| ATOM | 4689 | CB  | ALA | B | 40 | 84.445 | 30.961 | −1.271 | 1.00 | 8.92  | B | C |
| ATOM | 4690 | C   | ALA | B | 40 | 83.988 | 32.820 | −2.922 | 1.00 | 11.00 | B | C |
| ATOM | 4691 | O   | ALA | B | 40 | 83.643 | 33.967 | −2.573 | 1.00 | 10.39 | B | O |
| ATOM | 4692 | N   | GLU | B | 41 | 84.921 | 32.593 | −3.832 | 1.00 | 11.84 | B | N |
| ATOM | 4693 | CA  | GLU | B | 41 | 85.642 | 33.679 | −4.482 | 1.00 | 13.73 | B | C |
| ATOM | 4694 | CB  | GLU | B | 41 | 86.845 | 33.130 | −5.257 | 1.00 | 16.77 | B | C |
| ATOM | 4695 | CG  | GLU | B | 41 | 87.556 | 34.171 | −6.075 | 1.00 | 23.70 | B | C |
| ATOM | 4696 | CD  | GLU | B | 41 | 88.983 | 33.774 | −6.425 | 1.00 | 26.91 | B | C |
| ATOM | 4697 | OE1 | GLU | B | 41 | 89.536 | 32.847 | −5.786 | 1.00 | 28.61 | B | O |
| ATOM | 4698 | OE2 | GLU | B | 41 | 89.524 | 34.397 | −7.361 | 1.00 | 28.33 | B | O |

APPENDIX A-continued

*P. alba* 3T288C coordinates

| ATOM | 4699 | C | GLU | B | 41 | 84.700 | 34.465 | −5.371 | 1.00 | 11.19 | B | C |
|---|---|---|---|---|---|---|---|---|---|---|---|---|
| ATOM | 4700 | O | GLU | B | 41 | 84.766 | 35.677 | −5.373 | 1.00 | 12.00 | B | O |
| ATOM | 4701 | N | VAL | B | 42 | 83.789 | 33.793 | −6.078 | 1.00 | 11.09 | B | N |
| ATOM | 4702 | CA | VAL | B | 42 | 82.786 | 34.501 | −6.891 | 1.00 | 10.93 | B | C |
| ATOM | 4703 | CB | VAL | B | 42 | 81.997 | 33.525 | −7.747 | 1.00 | 9.55 | B | C |
| ATOM | 4704 | CG1 | VAL | B | 42 | 80.857 | 34.255 | −8.496 | 1.00 | 9.17 | B | C |
| ATOM | 4705 | CG2 | VAL | B | 42 | 82.928 | 32.811 | −8.738 | 1.00 | 8.08 | B | C |
| ATOM | 4706 | C | VAL | B | 42 | 81.839 | 35.323 | −5.990 | 1.00 | 12.84 | B | C |
| ATOM | 4707 | O | VAL | B | 42 | 81.520 | 36.490 | −6.260 | 1.00 | 8.45 | B | O |
| ATOM | 4708 | N | ARG | B | 43 | 81.461 | 34.738 | −4.855 | 1.00 | 13.35 | B | N |
| ATOM | 4709 | CA | ARG | B | 43 | 80.627 | 35.466 | −3.894 | 1.00 | 12.68 | B | C |
| ATOM | 4710 | CB | ARG | B | 43 | 80.256 | 34.564 | −2.678 | 1.00 | 16.05 | B | C |
| ATOM | 4711 | CG | ARG | B | 43 | 79.596 | 35.299 | −1.520 | 1.00 | 15.98 | B | C |
| ATOM | 4712 | CD | ARG | B | 43 | 80.551 | 36.025 | −0.555 | 1.00 | 14.84 | B | C |
| ATOM | 4713 | NE | ARG | B | 43 | 79.792 | 36.738 | 0.477 | 1.00 | 12.83 | B | N |
| ATOM | 4714 | CZ | ARG | B | 43 | 80.287 | 37.581 | 1.367 | 1.00 | 13.48 | B | C |
| ATOM | 4715 | NH1 | ARG | B | 43 | 81.604 | 37.873 | 1.419 | 1.00 | 12.76 | B | N |
| ATOM | 4716 | NH2 | ARG | B | 43 | 79.450 | 38.143 | 2.236 | 1.00 | 13.52 | B | N |
| ATOM | 4717 | C | ARG | B | 43 | 81.333 | 36.719 | −3.455 | 1.00 | 10.00 | B | C |
| ATOM | 4718 | O | ARG | B | 43 | 80.724 | 37.800 | −3.453 | 1.00 | 9.91 | B | O |
| ATOM | 4719 | N | ARG | B | 44 | 82.622 | 36.610 | −3.095 | 1.00 | 10.02 | B | N |
| ATOM | 4720 | CA | ARG | B | 44 | 83.403 | 37.766 | −2.649 | 1.00 | 11.29 | B | C |
| ATOM | 4721 | CB | ARG | B | 44 | 84.859 | 37.387 | −2.317 | 1.00 | 11.05 | B | C |
| ATOM | 4722 | CG | ARG | B | 44 | 85.738 | 38.573 | −1.939 | 1.00 | 12.30 | B | C |
| ATOM | 4723 | CD | ARG | B | 44 | 87.177 | 38.170 | −1.662 | 1.00 | 13.93 | B | C |
| ATOM | 4724 | NE | ARG | B | 44 | 87.816 | 37.720 | −2.879 | 1.00 | 13.54 | B | N |
| ATOM | 4725 | CZ | ARG | B | 44 | 88.955 | 37.037 | −2.934 | 1.00 | 15.26 | B | C |
| ATOM | 4726 | NH1 | ARG | B | 44 | 89.639 | 36.695 | −1.820 | 1.00 | 15.94 | B | N |
| ATOM | 4727 | NH2 | ARG | B | 44 | 89.434 | 36.723 | −4.136 | 1.00 | 17.40 | B | N |
| ATOM | 4728 | C | ARG | B | 44 | 83.405 | 38.901 | −3.711 | 1.00 | 13.01 | B | C |
| ATOM | 4729 | O | ARG | B | 44 | 83.240 | 40.084 | −3.381 | 1.00 | 12.57 | B | O |
| ATOM | 4730 | N | GLU | B | 45 | 83.640 | 38.530 | −4.957 | 1.00 | 12.75 | B | N |
| ATOM | 4731 | CA | GLU | B | 45 | 83.748 | 39.520 | −6.062 | 1.00 | 13.49 | B | C |
| ATOM | 4732 | CB | GLU | B | 45 | 84.261 | 38.852 | −7.335 | 1.00 | 14.55 | B | C |
| ATOM | 4733 | CG | GLU | B | 45 | 85.693 | 38.391 | −7.210 | 1.00 | 20.78 | B | C |
| ATOM | 4734 | CD | GLU | B | 45 | 86.595 | 39.480 | −6.687 | 1.00 | 22.05 | B | C |
| ATOM | 4735 | OE1 | GLU | B | 45 | 86.700 | 40.507 | −7.381 | 1.00 | 30.70 | B | O |
| ATOM | 4736 | OE2 | GLU | B | 45 | 87.156 | 39.348 | −5.565 | 1.00 | 23.89 | B | O |
| ATOM | 4737 | C | GLU | B | 45 | 82.411 | 40.195 | −6.356 | 1.00 | 11.85 | B | C |
| ATOM | 4738 | O | GLU | B | 45 | 82.383 | 41.369 | −6.652 | 1.00 | 13.11 | B | O |
| ATOM | 4739 | N | ILE | B | 46 | 81.303 | 39.476 | −6.257 | 1.00 | 13.19 | B | N |
| ATOM | 4740 | CA | ILE | B | 46 | 79.982 | 40.124 | −6.405 | 1.00 | 13.57 | B | C |
| ATOM | 4741 | CB | ILE | B | 46 | 78.837 | 39.124 | −6.541 | 1.00 | 13.61 | B | C |
| ATOM | 4742 | CG1 | ILE | B | 46 | 78.999 | 38.312 | −7.834 | 1.00 | 14.91 | B | C |
| ATOM | 4743 | CD1 | ILE | B | 46 | 78.232 | 36.993 | −7.820 | 1.00 | 15.21 | B | C |
| ATOM | 4744 | CG2 | ILE | B | 46 | 77.406 | 39.838 | −6.519 | 1.00 | 13.13 | B | C |
| ATOM | 4745 | C | ILE | B | 46 | 79.704 | 41.089 | −5.248 | 1.00 | 15.53 | B | C |
| ATOM | 4746 | O | ILE | B | 46 | 79.070 | 42.114 | −5.447 | 1.00 | 16.29 | B | O |
| ATOM | 4747 | N | ASN | B | 47 | 80.211 | 40.779 | −4.055 | 1.00 | 14.45 | B | N |
| ATOM | 4748 | CA | ASN | B | 47 | 79.945 | 41.573 | −2.857 | 1.00 | 13.64 | B | C |
| ATOM | 4749 | CB | ASN | B | 47 | 79.982 | 40.663 | −1.616 | 1.00 | 13.48 | B | C |
| ATOM | 4750 | CG | ASN | B | 47 | 78.682 | 39.912 | −1.409 | 1.00 | 15.18 | B | C |
| ATOM | 4751 | OD1 | ASN | B | 47 | 77.783 | 40.444 | −0.809 | 1.00 | 19.56 | B | O |
| ATOM | 4752 | ND2 | ASN | B | 47 | 78.562 | 38.700 | −1.935 | 1.00 | 14.68 | B | N |
| ATOM | 4753 | C | ASN | B | 47 | 80.920 | 42.729 | −2.689 | 1.00 | 14.30 | B | C |
| ATOM | 4754 | O | ASN | B | 47 | 80.787 | 43.524 | −1.753 | 1.00 | 15.59 | B | O |
| ATOM | 4755 | N | ASN | B | 48 | 81.935 | 42.782 | −3.553 | 1.00 | 12.89 | B | N |
| ATOM | 4756 | CA | ASN | B | 48 | 83.002 | 43.732 | −3.436 | 1.00 | 14.23 | B | C |
| ATOM | 4757 | CB | ASN | B | 48 | 84.104 | 43.415 | −4.452 | 1.00 | 15.10 | B | C |
| ATOM | 4758 | CG | ASN | B | 48 | 85.190 | 44.481 | −4.524 | 1.00 | 14.60 | B | C |
| ATOM | 4759 | OD1 | ASN | B | 48 | 85.436 | 45.247 | −3.582 | 1.00 | 14.32 | B | O |
| ATOM | 4760 | ND2 | ASN | B | 48 | 85.876 | 44.499 | −5.640 | 1.00 | 14.84 | B | N |
| ATOM | 4761 | C | ASN | B | 48 | 82.461 | 45.145 | −3.657 | 1.00 | 18.92 | B | C |
| ATOM | 4762 | O | ASN | B | 48 | 82.064 | 45.520 | −4.743 | 1.00 | 18.59 | B | O |
| ATOM | 4763 | N | GLU | B | 49 | 82.526 | 45.894 | −2.579 | 1.00 | 16.96 | B | N |
| ATOM | 4764 | CA | AGLU | B | 49 | 81.891 | 47.222 | −2.595 | 0.50 | 20.16 | B | C |
| ATOM | 4765 | CA | BGLU | B | 49 | 82.012 | 47.211 | −2.332 | 0.50 | 20.40 | B | C |
| ATOM | 4766 | CB | AGLU | B | 49 | 81.283 | 47.614 | −1.246 | 0.50 | 20.23 | B | C |
| ATOM | 4767 | CB | BGLU | B | 49 | 82.092 | 47.349 | −0.763 | 0.50 | 20.55 | B | C |
| ATOM | 4768 | CG | AGLU | B | 49 | 79.871 | 47.057 | −1.095 | 0.50 | 18.95 | B | C |
| ATOM | 4769 | CG | BGLU | B | 49 | 82.748 | 46.010 | 0.056 | 0.50 | 17.18 | B | C |
| ATOM | 4770 | CD | AGLU | B | 49 | 79.177 | 47.488 | 0.179 | 0.50 | 20.35 | B | C |
| ATOM | 4771 | CD | BGLU | B | 49 | 82.014 | 45.559 | 1.354 | 0.50 | 20.63 | B | C |
| ATOM | 4772 | OE1 | AGLU | B | 49 | 79.264 | 48.678 | 0.538 | 0.50 | 18.79 | B | O |
| ATOM | 4773 | OE1 | BGLU | B | 49 | 81.815 | 44.321 | 1.607 | 0.50 | 12.18 | B | O |
| ATOM | 4774 | OE2 | AGLU | B | 49 | 78.516 | 46.636 | 0.804 | 0.50 | 20.33 | B | O |
| ATOM | 4775 | OE2 | BGLU | B | 49 | 81.659 | 46.441 | 2.165 | 0.50 | 35.93 | B | O |
| ATOM | 4776 | C | GLU | B | 49 | 82.806 | 48.297 | −3.137 | 1.00 | 23.82 | B | C |

APPENDIX A-continued

P. alba 3T288C coordinates

| ATOM | 4777 | O | GLU | B | 49 | 82.351 | 49.413 | −3.361 | 1.00 | 23.93 | B | O |
|---|---|---|---|---|---|---|---|---|---|---|---|---|
| ATOM | 4778 | N | LYS | B | 50 | 84.041 | 47.946 | −3.496 | 1.00 | 23.25 | B | N |
| ATOM | 4779 | CA | LYS | B | 50 | 84.950 | 48.858 | −4.183 | 1.00 | 25.39 | B | C |
| ATOM | 4780 | CB | LYS | B | 50 | 86.360 | 48.773 | −3.582 | 1.00 | 26.32 | B | C |
| ATOM | 4781 | CG | LYS | B | 50 | 86.467 | 49.109 | −2.104 | 1.00 | 30.70 | B | C |
| ATOM | 4782 | CD | LYS | B | 50 | 87.925 | 49.077 | −1.631 | 1.00 | 36.98 | B | C |
| ATOM | 4783 | CE | LYS | B | 50 | 88.324 | 47.760 | −0.997 | 1.00 | 36.26 | B | C |
| ATOM | 4784 | NZ | LYS | B | 50 | 87.920 | 47.744 | 0.432 | 1.00 | 37.46 | B | N |
| ATOM | 4785 | C | LYS | B | 50 | 85.056 | 48.586 | −5.683 | 1.00 | 21.74 | B | C |
| ATOM | 4786 | O | LYS | B | 50 | 85.849 | 49.221 | −6.341 | 1.00 | 19.87 | B | O |
| ATOM | 4787 | N | ALA | B | 51 | 84.298 | 47.641 | −6.228 | 1.00 | 20.75 | B | N |
| ATOM | 4788 | CA | ALA | B | 51 | 84.388 | 47.339 | −7.670 | 1.00 | 23.95 | B | C |
| ATOM | 4789 | CB | ALA | B | 51 | 83.564 | 46.099 | −8.031 | 1.00 | 24.01 | B | C |
| ATOM | 4790 | C | ALA | B | 51 | 83.889 | 48.533 | −8.483 | 1.00 | 26.40 | B | C |
| ATOM | 4791 | O | ALA | B | 51 | 83.035 | 49.262 | −8.019 | 1.00 | 19.87 | B | O |
| ATOM | 4792 | N | GLU | B | 52 | 84.429 | 48.726 | −9.685 | 1.00 | 30.89 | B | N |
| ATOM | 4793 | CA | GLU | B | 52 | 83.891 | 49.712 | −10.619 | 1.00 | 32.03 | B | C |
| ATOM | 4794 | CB | GLU | B | 52 | 84.814 | 49.918 | −11.826 | 1.00 | 34.13 | B | C |
| ATOM | 4795 | CG | GLU | B | 52 | 86.179 | 50.492 | −11.479 | 1.00 | 48.84 | B | C |
| ATOM | 4796 | CD | GLU | B | 52 | 86.105 | 51.808 | −10.703 | 1.00 | 55.69 | B | C |
| ATOM | 4797 | OE1 | GLU | B | 52 | 85.026 | 52.439 | −10.662 | 1.00 | 59.80 | B | O |
| ATOM | 4798 | OE2 | GLU | B | 52 | 87.135 | 52.216 | −10.129 | 1.00 | 73.34 | B | O |
| ATOM | 4799 | C | GLU | B | 52 | 82.539 | 49.221 | −11.096 | 1.00 | 30.95 | B | C |
| ATOM | 4800 | O | GLU | B | 52 | 82.356 | 48.028 | −11.327 | 1.00 | 23.44 | B | O |
| ATOM | 4801 | N | PHE | B | 53 | 81.596 | 50.141 | −11.252 | 1.00 | 30.12 | B | N |
| ATOM | 4802 | CA | PHE | B | 53 | 80.218 | 49.742 | −11.473 | 1.00 | 32.98 | B | C |
| ATOM | 4803 | CB | PHE | B | 53 | 79.251 | 50.936 | −11.338 | 1.00 | 43.11 | B | C |
| ATOM | 4804 | CG | PHE | B | 53 | 78.867 | 51.269 | −9.878 | 1.00 | 55.16 | B | C |
| ATOM | 4805 | CD1 | PHE | B | 53 | 78.505 | 50.251 | −8.961 | 1.00 | 64.23 | B | C |
| ATOM | 4806 | CE1 | PHE | B | 53 | 78.139 | 50.555 | −7.624 | 1.00 | 59.12 | B | C |
| ATOM | 4807 | CZ | PHE | B | 53 | 78.126 | 51.883 | −7.199 | 1.00 | 55.08 | B | C |
| ATOM | 4808 | CE2 | PHE | B | 53 | 78.477 | 52.909 | −8.101 | 1.00 | 60.25 | B | C |
| ATOM | 4809 | CD2 | PHE | B | 53 | 78.843 | 52.598 | −9.429 | 1.00 | 60.00 | B | C |
| ATOM | 4810 | C | PHE | B | 53 | 80.066 | 48.968 | −12.786 | 1.00 | 28.16 | B | C |
| ATOM | 4811 | O | PHE | B | 53 | 79.474 | 47.890 | −12.797 | 1.00 | 21.25 | B | O |
| ATOM | 4812 | N | LEU | B | 54 | 80.665 | 49.435 | −13.868 | 1.00 | 23.34 | B | N |
| ATOM | 4813 | CA | LEU | B | 54 | 80.566 | 48.668 | −15.134 | 1.00 | 25.10 | B | C |
| ATOM | 4814 | CB | LEU | B | 54 | 81.148 | 49.457 | −16.309 | 1.00 | 29.41 | B | C |
| ATOM | 4815 | CG | LEU | B | 54 | 80.706 | 49.050 | −17.729 | 1.00 | 44.51 | B | C |
| ATOM | 4816 | CD1 | LEU | B | 54 | 80.836 | 50.213 | −18.709 | 1.00 | 41.57 | B | C |
| ATOM | 4817 | CD2 | LEU | B | 54 | 81.510 | 47.879 | −18.233 | 1.00 | 45.75 | B | C |
| ATOM | 4818 | C | LEU | B | 54 | 81.165 | 47.235 | −15.058 | 1.00 | 23.44 | B | C |
| ATOM | 4819 | O | LEU | B | 54 | 80.552 | 46.288 | −15.538 | 1.00 | 20.26 | B | O |
| ATOM | 4820 | N | ATHR | B | 55 | 82.338 | 47.073 | −14.451 | 0.50 | 23.03 | B | N |
| ATOM | 4821 | N | BTHR | B | 55 | 82.340 | 47.092 | −14.444 | 0.50 | 21.21 | B | N |
| ATOM | 4822 | CA | ATHR | B | 55 | 82.943 | 45.737 | −14.351 | 0.50 | 22.88 | B | C |
| ATOM | 4823 | CA | BTHR | B | 55 | 82.990 | 45.778 | −14.298 | 0.50 | 19.98 | B | C |
| ATOM | 4824 | CB | ATHR | B | 55 | 84.383 | 45.784 | −13.810 | 0.50 | 24.47 | B | C |
| ATOM | 4825 | CB | BTHR | B | 55 | 84.402 | 45.909 | −13.662 | 0.50 | 19.41 | B | C |
| ATOM | 4826 | OG1 | ATHR | B | 55 | 84.365 | 46.120 | −12.417 | 0.50 | 26.50 | B | O |
| ATOM | 4827 | OG1 | BTHR | B | 55 | 85.192 | 46.839 | −14.419 | 0.50 | 20.82 | B | O |
| ATOM | 4828 | CG2 | ATHR | B | 55 | 85.214 | 46.808 | −14.582 | 0.50 | 26.31 | B | C |
| ATOM | 4829 | CG2 | BTHR | B | 55 | 85.124 | 44.551 | −13.597 | 0.50 | 16.45 | B | C |
| ATOM | 4830 | C | ATHR | B | 55 | 82.095 | 44.802 | −13.473 | 0.50 | 20.01 | B | C |
| ATOM | 4831 | C | BTHR | B | 55 | 82.126 | 44.817 | −13.460 | 0.50 | 18.73 | B | C |
| ATOM | 4832 | O | ATHR | B | 55 | 82.031 | 43.600 | −13.727 | 0.50 | 18.26 | B | O |
| ATOM | 4833 | O | BTHR | B | 55 | 82.081 | 43.618 | −13.731 | 0.50 | 17.39 | B | O |
| ATOM | 4834 | N | LEU | B | 56 | 81.436 | 45.359 | −12.458 | 1.00 | 17.88 | B | N |
| ATOM | 4835 | CA | LEU | B | 56 | 80.542 | 44.585 | −11.603 | 1.00 | 17.45 | B | C |
| ATOM | 4836 | CB | LEU | B | 56 | 80.154 | 45.405 | −10.388 | 1.00 | 20.45 | B | C |
| ATOM | 4837 | CG | LEU | B | 56 | 79.231 | 44.795 | −9.353 | 1.00 | 23.80 | B | C |
| ATOM | 4838 | CD1 | LEU | B | 56 | 79.791 | 43.459 | −8.827 | 1.00 | 29.79 | B | C |
| ATOM | 4839 | CD2 | LEU | B | 56 | 79.051 | 45.812 | −8.210 | 1.00 | 26.50 | B | C |
| ATOM | 4840 | C | LEU | B | 56 | 79.283 | 44.148 | −12.341 | 1.00 | 16.79 | B | C |
| ATOM | 4841 | O | LEU | B | 56 | 78.850 | 43.012 | −12.204 | 1.00 | 13.84 | B | O |
| ATOM | 4842 | N | LEU | B | 57 | 78.704 | 45.055 | −13.124 | 1.00 | 14.24 | B | N |
| ATOM | 4843 | CA | LEU | B | 57 | 77.538 | 44.719 | −13.947 | 1.00 | 14.52 | B | C |
| ATOM | 4844 | CB | LEU | B | 57 | 77.060 | 45.936 | −14.751 | 1.00 | 15.36 | B | C |
| ATOM | 4845 | CG | LEU | B | 57 | 76.387 | 47.077 | −13.990 | 1.00 | 16.40 | B | C |
| ATOM | 4846 | CD1 | LEU | B | 57 | 76.057 | 48.244 | −14.958 | 1.00 | 17.56 | B | C |
| ATOM | 4847 | CD2 | LEU | B | 57 | 75.162 | 46.595 | −13.228 | 1.00 | 17.05 | B | C |
| ATOM | 4848 | C | LEU | B | 57 | 77.911 | 43.571 | −14.881 | 1.00 | 14.74 | B | C |
| ATOM | 4849 | O | LEU | B | 57 | 77.140 | 42.624 | −15.036 | 1.00 | 15.04 | B | O |
| ATOM | 4850 | N | GLU | B | 58 | 79.102 | 43.640 | −15.476 | 1.00 | 13.97 | B | N |
| ATOM | 4851 | CA | GLU | B | 58 | 79.543 | 42.614 | −16.415 | 1.00 | 17.92 | B | C |
| ATOM | 4852 | CB | GLU | B | 58 | 80.792 | 43.088 | −17.193 | 1.00 | 23.28 | B | C |
| ATOM | 4853 | CG | GLU | B | 58 | 80.402 | 43.969 | −18.383 | 1.00 | 35.09 | B | C |
| ATOM | 4854 | CD | GLU | B | 58 | 81.588 | 44.709 | −19.053 | 1.00 | 48.05 | B | C |

APPENDIX A-continued

*P. alba* 3T288C coordinates

| ATOM | 4855 | OE1 | GLU | B | 58 | 82.767 | 44.585 | −18.615 | 1.00 | 43.16 | B | O |
|---|---|---|---|---|---|---|---|---|---|---|---|---|
| ATOM | 4856 | OE2 | GLU | B | 58 | 81.306 | 45.439 | −20.028 | 1.00 | 53.26 | B | O |
| ATOM | 4857 | C | GLU | B | 58 | 79.810 | 41.265 | −15.733 | 1.00 | 15.56 | B | C |
| ATOM | 4858 | O | GLU | B | 58 | 79.535 | 40.216 | −16.309 | 1.00 | 14.28 | B | O |
| ATOM | 4859 | N | LEU | B | 59 | 80.376 | 41.302 | −14.529 | 1.00 | 15.21 | B | N |
| ATOM | 4860 | CA | LEU | B | 59 | 80.525 | 40.113 | −13.709 | 1.00 | 14.80 | B | C |
| ATOM | 4861 | CB | LEU | B | 59 | 81.201 | 40.430 | −12.359 | 1.00 | 14.28 | B | C |
| ATOM | 4862 | CG | LEU | B | 59 | 81.338 | 39.248 | −11.371 | 1.00 | 15.64 | B | C |
| ATOM | 4863 | CD1 | LEU | B | 59 | 82.113 | 38.051 | −11.985 | 1.00 | 15.94 | B | C |
| ATOM | 4864 | CD2 | LEU | B | 59 | 82.038 | 39.695 | −10.068 | 1.00 | 12.84 | B | C |
| ATOM | 4865 | C | LEU | B | 59 | 79.169 | 39.485 | −13.477 | 1.00 | 12.28 | B | C |
| ATOM | 4866 | O | LEU | B | 59 | 79.000 | 38.318 | −13.718 | 1.00 | 16.70 | B | O |
| ATOM | 4867 | N | ILE | B | 60 | 78.195 | 40.264 | −13.037 | 1.00 | 13.86 | B | N |
| ATOM | 4868 | CA | ILE | B | 60 | 76.850 | 39.737 | −12.792 | 1.00 | 14.00 | B | C |
| ATOM | 4869 | CB | ILE | B | 60 | 75.887 | 40.823 | −12.271 | 1.00 | 14.84 | B | C |
| ATOM | 4870 | CG1 | ILE | B | 60 | 76.307 | 41.274 | −10.857 | 1.00 | 18.96 | B | C |
| ATOM | 4871 | CD1 | ILE | B | 60 | 75.489 | 42.427 | −10.344 | 1.00 | 17.63 | B | C |
| ATOM | 4872 | CG2 | ILE | B | 60 | 74.454 | 40.313 | −12.265 | 1.00 | 14.38 | B | C |
| ATOM | 4873 | C | ILE | B | 60 | 76.299 | 39.130 | −14.068 | 1.00 | 13.84 | B | C |
| ATOM | 4874 | O | ILE | B | 60 | 75.797 | 38.018 | −14.073 | 1.00 | 12.23 | B | O |
| ATOM | 4875 | N | ASP | B | 61 | 76.416 | 39.834 | −15.167 | 1.00 | 13.78 | B | N |
| ATOM | 4876 | CA | ASP | B | 61 | 75.892 | 39.295 | −16.431 | 1.00 | 16.74 | B | C |
| ATOM | 4877 | CB | ASP | B | 61 | 76.118 | 40.317 | −17.541 | 1.00 | 18.93 | B | C |
| ATOM | 4878 | CG | ASP | B | 61 | 75.411 | 39.955 | −18.827 | 1.00 | 25.31 | B | C |
| ATOM | 4879 | OD1 | ASP | B | 61 | 74.304 | 39.329 | −18.796 | 1.00 | 22.11 | B | O |
| ATOM | 4880 | OD2 | ASP | B | 61 | 75.967 | 40.325 | −19.890 | 1.00 | 28.39 | B | O |
| ATOM | 4881 | C | ASP | B | 61 | 76.562 | 37.969 | −16.806 | 1.00 | 14.33 | B | C |
| ATOM | 4882 | O | ASP | B | 61 | 75.891 | 37.038 | −17.262 | 1.00 | 16.51 | B | O |
| ATOM | 4883 | N | ASN | B | 62 | 77.876 | 37.869 | −16.620 | 1.00 | 13.41 | B | N |
| ATOM | 4884 | CA | ASN | B | 62 | 78.601 | 36.620 | −16.937 | 1.00 | 11.85 | B | C |
| ATOM | 4885 | CB | ASN | B | 62 | 80.111 | 36.814 | −16.876 | 1.00 | 13.90 | B | C |
| ATOM | 4886 | CG | ASN | B | 62 | 80.664 | 37.577 | −18.075 | 1.00 | 18.63 | B | C |
| ATOM | 4887 | OD1 | ASN | B | 62 | 80.209 | 37.395 | −19.169 | 1.00 | 19.52 | B | O |
| ATOM | 4888 | ND2 | ASN | B | 62 | 81.674 | 38.399 | −17.852 | 1.00 | 15.65 | B | N |
| ATOM | 4889 | C | ASN | B | 62 | 78.203 | 35.483 | −16.006 | 1.00 | 13.00 | B | C |
| ATOM | 4890 | O | ASN | B | 62 | 77.999 | 34.347 | −16.453 | 1.00 | 11.41 | B | O |
| ATOM | 4891 | N | VAL | B | 63 | 78.095 | 35.783 | −14.711 | 1.00 | 11.96 | B | N |
| ATOM | 4892 | CA | VAL | B | 63 | 77.655 | 34.790 | −13.739 | 1.00 | 11.92 | B | C |
| ATOM | 4893 | CB | VAL | B | 63 | 77.584 | 35.386 | −12.313 | 1.00 | 12.40 | B | C |
| ATOM | 4894 | CG1 | VAL | B | 63 | 76.769 | 34.486 | −11.352 | 1.00 | 12.19 | B | C |
| ATOM | 4895 | CG2 | VAL | B | 63 | 79.056 | 35.621 | −11.770 | 1.00 | 12.49 | B | C |
| ATOM | 4896 | C | VAL | B | 63 | 76.322 | 34.191 | −14.169 | 1.00 | 13.22 | B | C |
| ATOM | 4897 | O | VAL | B | 63 | 76.172 | 32.980 | −14.167 | 1.00 | 16.56 | B | O |
| ATOM | 4898 | N | GLN | B | 64 | 75.383 | 35.046 | −14.583 | 1.00 | 14.63 | B | N |
| ATOM | 4899 | CA | GLN | B | 64 | 74.054 | 34.606 | −15.033 | 1.00 | 14.98 | B | C |
| ATOM | 4900 | CB | GLN | B | 64 | 73.090 | 35.802 | −15.166 | 1.00 | 14.41 | B | C |
| ATOM | 4901 | CG | GLN | B | 64 | 72.771 | 36.400 | −13.788 | 1.00 | 15.48 | B | C |
| ATOM | 4902 | CD | GLN | B | 64 | 71.677 | 37.443 | −13.761 | 1.00 | 19.08 | B | C |
| ATOM | 4903 | OE1 | GLN | B | 64 | 71.079 | 37.652 | −12.704 | 1.00 | 21.09 | B | O |
| ATOM | 4904 | NE2 | GLN | B | 64 | 71.393 | 38.089 | −14.900 | 1.00 | 14.44 | B | N |
| ATOM | 4905 | C | GLN | B | 64 | 74.058 | 33.796 | −16.325 | 1.00 | 13.55 | B | C |
| ATOM | 4906 | O | GLN | B | 64 | 73.489 | 32.713 | −16.372 | 1.00 | 13.68 | B | O |
| ATOM | 4907 | N | ARG | B | 65 | 74.739 | 34.295 | −17.346 | 1.00 | 14.94 | B | N |
| ATOM | 4908 | CA | AARG | B | 65 | 74.767 | 33.639 | −18.651 | 0.50 | 14.67 | B | C |
| ATOM | 4909 | CA | BARG | B | 65 | 74.736 | 33.628 | −18.642 | 0.50 | 15.55 | B | C |
| ATOM | 4910 | CB | AARG | B | 65 | 75.499 | 34.509 | −19.676 | 0.50 | 14.34 | B | C |
| ATOM | 4911 | CB | BARG | B | 65 | 75.371 | 34.512 | −19.716 | 0.50 | 16.50 | B | C |
| ATOM | 4912 | CG | AARG | B | 65 | 74.750 | 35.784 | −20.027 | 0.50 | 14.56 | B | C |
| ATOM | 4913 | CG | BARG | B | 65 | 74.581 | 35.792 | −19.964 | 0.50 | 18.15 | B | C |
| ATOM | 4914 | CD | AARG | B | 65 | 75.330 | 36.436 | −21.285 | 0.50 | 14.40 | B | C |
| ATOM | 4915 | CD | BARG | B | 65 | 74.774 | 36.325 | −21.386 | 0.50 | 19.88 | B | C |
| ATOM | 4916 | NE | AARG | B | 65 | 75.153 | 35.573 | −22.455 | 0.50 | 13.78 | B | N |
| ATOM | 4917 | NE | BARG | B | 65 | 75.104 | 37.740 | −21.397 | 0.50 | 21.26 | B | N |
| ATOM | 4918 | CZ | AARG | B | 65 | 75.573 | 35.871 | −23.679 | 0.50 | 15.22 | B | C |
| ATOM | 4919 | CZ | BARG | B | 65 | 75.107 | 38.496 | −22.496 | 0.50 | 20.33 | B | C |
| ATOM | 4920 | NH1 | AARG | B | 65 | 76.201 | 37.015 | −23.905 | 0.50 | 15.86 | B | N |
| ATOM | 4921 | NH1 | BARG | B | 65 | 74.760 | 37.965 | −23.662 | 0.50 | 18.24 | B | N |
| ATOM | 4922 | NH2 | AARG | B | 65 | 75.356 | 35.027 | −24.676 | 0.50 | 13.84 | B | N |
| ATOM | 4923 | NH2 | BARG | B | 65 | 75.445 | 39.776 | −22.417 | 0.50 | 16.33 | B | N |
| ATOM | 4924 | C | ARG | B | 65 | 75.410 | 32.264 | −18.579 | 1.00 | 14.29 | B | C |
| ATOM | 4925 | O | ARG | B | 65 | 74.968 | 31.342 | −19.254 | 1.00 | 15.76 | B | O |
| ATOM | 4926 | N | LEU | B | 66 | 76.445 | 32.139 | −17.738 | 1.00 | 13.64 | B | N |
| ATOM | 4927 | CA | LEU | B | 66 | 77.165 | 30.873 | −17.562 | 1.00 | 12.80 | B | C |
| ATOM | 4928 | CB | LEU | B | 66 | 78.506 | 31.117 | −16.836 | 1.00 | 13.34 | B | C |
| ATOM | 4929 | CG | LEU | B | 66 | 79.559 | 31.861 | −17.629 | 1.00 | 14.00 | B | C |
| ATOM | 4930 | CD1 | LEU | B | 66 | 80.711 | 32.272 | −16.735 | 1.00 | 13.19 | B | C |
| ATOM | 4931 | CD2 | LEU | B | 66 | 80.026 | 31.017 | −18.797 | 1.00 | 15.81 | B | C |
| ATOM | 4932 | C | LEU | B | 66 | 76.348 | 29.838 | −16.785 | 1.00 | 12.95 | B | C |

APPENDIX A-continued

*P. alba* 3T288C coordinates

| ATOM | 4933 | O | LEU | B | 66 | 76.792 | 28.713 | −16.596 | 1.00 | 15.25 | B | O |
|------|------|------|------|---|----|--------|--------|---------|------|-------|---|---|
| ATOM | 4934 | N | GLY | B | 67 | 75.183 | 30.236 | −16.295 | 1.00 | 12.63 | B | N |
| ATOM | 4935 | CA | GLY | B | 67 | 74.259 | 29.321 | −15.643 | 1.00 | 11.80 | B | C |
| ATOM | 4936 | C | GLY | B | 67 | 74.279 | 29.330 | −14.139 | 1.00 | 12.81 | B | C |
| ATOM | 4937 | O | GLY | B | 67 | 73.648 | 28.486 | −13.528 | 1.00 | 16.75 | B | O |
| ATOM | 4938 | N | LEU | B | 68 | 74.982 | 30.292 | −13.520 | 1.00 | 15.63 | B | N |
| ATOM | 4939 | CA | LEU | B | 68 | 75.209 | 30.261 | −12.081 | 1.00 | 14.06 | B | C |
| ATOM | 4940 | CB | LEU | B | 68 | 76.690 | 30.497 | −11.750 | 1.00 | 14.42 | B | C |
| ATOM | 4941 | CG | LEU | B | 68 | 77.713 | 29.432 | −12.162 | 1.00 | 15.73 | B | C |
| ATOM | 4942 | CD1 | LEU | B | 68 | 79.114 | 30.010 | −12.224 | 1.00 | 14.70 | B | C |
| ATOM | 4943 | CD2 | LEU | B | 68 | 77.694 | 28.268 | −11.190 | 1.00 | 12.66 | B | C |
| ATOM | 4944 | C | LEU | B | 68 | 74.333 | 31.259 | −11.311 | 1.00 | 15.70 | B | C |
| ATOM | 4945 | O | LEU | B | 68 | 74.470 | 31.366 | −10.087 | 1.00 | 13.51 | B | O |
| ATOM | 4946 | N | GLY | B | 69 | 73.418 | 31.959 | −11.996 | 1.00 | 15.68 | B | N |
| ATOM | 4947 | CA | GLY | B | 69 | 72.570 | 32.988 | −11.342 | 1.00 | 17.75 | B | C |
| ATOM | 4948 | C | GLY | B | 69 | 71.803 | 32.506 | −10.116 | 1.00 | 18.82 | B | C |
| ATOM | 4949 | O | GLY | B | 69 | 71.745 | 33.208 | −9.086 | 1.00 | 21.69 | B | O |
| ATOM | 4950 | N | TYR | B | 70 | 71.282 | 31.280 | −10.210 | 1.00 | 15.94 | B | N |
| ATOM | 4951 | CA | TYR | B | 70 | 70.471 | 30.667 | −9.161 | 1.00 | 19.27 | B | C |
| ATOM | 4952 | CB | TYR | B | 70 | 69.927 | 29.293 | −9.621 | 1.00 | 17.09 | B | C |
| ATOM | 4953 | CG | TYR | B | 70 | 70.942 | 28.141 | −9.574 | 1.00 | 15.13 | B | C |
| ATOM | 4954 | CD1 | TYR | B | 70 | 71.898 | 27.965 | −10.586 | 1.00 | 14.78 | B | C |
| ATOM | 4955 | CE1 | TYR | B | 70 | 72.831 | 26.932 | −10.541 | 1.00 | 14.99 | B | C |
| ATOM | 4956 | CZ | TYR | B | 70 | 72.823 | 26.068 | −9.445 | 1.00 | 19.35 | B | C |
| ATOM | 4957 | OH | TYR | B | 70 | 73.748 | 25.067 | −9.313 | 1.00 | 15.46 | B | O |
| ATOM | 4958 | CE2 | TYR | B | 70 | 71.869 | 26.238 | −8.426 | 1.00 | 18.36 | B | C |
| ATOM | 4959 | CD2 | TYR | B | 70 | 70.959 | 27.259 | −8.500 | 1.00 | 17.04 | B | C |
| ATOM | 4960 | C | TYR | B | 70 | 71.268 | 30.533 | −7.851 | 1.00 | 21.65 | B | C |
| ATOM | 4961 | O | TYR | B | 70 | 70.673 | 30.525 | −6.786 | 1.00 | 25.79 | B | O |
| ATOM | 4962 | N | ARG | B | 71 | 72.603 | 30.401 | −7.943 | 1.00 | 18.29 | B | N |
| ATOM | 4963 | CA | AARG | B | 71 | 73.446 | 30.173 | −6.776 | 0.50 | 19.57 | B | C |
| ATOM | 4964 | CA | BARG | B | 71 | 73.457 | 30.183 | −6.759 | 0.50 | 18.98 | B | C |
| ATOM | 4965 | CB | AARG | B | 71 | 74.713 | 29.448 | −7.251 | 0.50 | 20.81 | B | C |
| ATOM | 4966 | CB | BARG | B | 71 | 74.799 | 29.522 | −7.129 | 0.50 | 19.07 | B | C |
| ATOM | 4967 | CG | AARG | B | 71 | 75.669 | 29.003 | −6.186 | 0.50 | 19.46 | B | C |
| ATOM | 4968 | CG | BARG | B | 71 | 74.723 | 28.171 | −7.779 | 0.50 | 17.63 | B | C |
| ATOM | 4969 | CD | AARG | B | 71 | 76.649 | 27.983 | −6.782 | 0.50 | 18.97 | B | C |
| ATOM | 4970 | CD | BARG | B | 71 | 76.055 | 27.469 | −7.708 | 0.50 | 15.61 | B | C |
| ATOM | 4971 | NE | AARG | B | 71 | 75.968 | 26.746 | −7.137 | 0.50 | 15.99 | B | N |
| ATOM | 4972 | NE | BARG | B | 71 | 76.367 | 27.021 | −6.358 | 0.50 | 15.15 | B | N |
| ATOM | 4973 | CZ | AARG | B | 71 | 75.615 | 25.816 | −6.259 | 0.50 | 17.57 | B | C |
| ATOM | 4974 | CZ | BARG | B | 71 | 75.804 | 25.972 | −5.769 | 0.50 | 15.78 | B | C |
| ATOM | 4975 | NH1 | AARG | B | 71 | 74.986 | 24.717 | −6.670 | 0.50 | 17.39 | B | N |
| ATOM | 4976 | NH1 | BARG | B | 71 | 74.896 | 25.247 | −6.419 | 0.50 | 16.27 | B | N |
| ATOM | 4977 | NH2 | AARG | B | 71 | 75.894 | 25.982 | −4.967 | 0.50 | 18.25 | B | N |
| ATOM | 4978 | NH2 | BARG | B | 71 | 76.150 | 25.645 | −4.524 | 0.50 | 14.04 | B | N |
| ATOM | 4979 | C | ARG | B | 71 | 73.814 | 31.488 | −6.067 | 1.00 | 18.17 | B | C |
| ATOM | 4980 | O | ARG | B | 71 | 74.263 | 31.476 | −4.940 | 1.00 | 17.84 | B | O |
| ATOM | 4981 | N | PHE | B | 72 | 73.658 | 32.606 | −6.763 | 1.00 | 16.59 | B | N |
| ATOM | 4982 | CA | PHE | B | 72 | 74.128 | 33.897 | −6.263 | 1.00 | 17.05 | B | C |
| ATOM | 4983 | CB | PHE | B | 72 | 75.302 | 34.386 | −7.148 | 1.00 | 17.06 | B | C |
| ATOM | 4984 | CG | PHE | B | 72 | 76.518 | 33.505 | −7.065 | 1.00 | 15.19 | B | C |
| ATOM | 4985 | CD1 | PHE | B | 72 | 77.291 | 33.492 | −5.908 | 1.00 | 14.85 | B | C |
| ATOM | 4986 | CE1 | PHE | B | 72 | 78.382 | 32.681 | −5.810 | 1.00 | 13.25 | B | C |
| ATOM | 4987 | CZ | PHE | B | 72 | 78.729 | 31.844 | −6.882 | 1.00 | 13.18 | B | C |
| ATOM | 4988 | CE2 | PHE | B | 72 | 77.945 | 31.823 | −8.018 | 1.00 | 13.45 | B | C |
| ATOM | 4989 | CD2 | PHE | B | 72 | 76.848 | 32.659 | −8.102 | 1.00 | 13.58 | B | C |
| ATOM | 4990 | C | PHE | B | 72 | 73.041 | 34.961 | −6.200 | 1.00 | 17.89 | B | C |
| ATOM | 4991 | O | PHE | B | 72 | 73.344 | 36.158 | −6.201 | 1.00 | 15.78 | B | O |
| ATOM | 4992 | N | GLU | B | 73 | 71.782 | 34.542 | −6.127 | 1.00 | 21.33 | B | N |
| ATOM | 4993 | CA | GLU | B | 73 | 70.708 | 35.501 | −6.306 | 1.00 | 24.20 | B | C |
| ATOM | 4994 | CB | GLU | B | 73 | 69.324 | 34.862 | −6.298 | 1.00 | 27.63 | B | C |
| ATOM | 4995 | CG | GLU | B | 73 | 68.238 | 35.887 | −6.529 | 1.00 | 32.36 | B | C |
| ATOM | 4996 | CD | GLU | B | 73 | 66.884 | 35.260 | −6.841 | 1.00 | 44.63 | B | C |
| ATOM | 4997 | OE1 | GLU | B | 73 | 66.833 | 34.092 | −7.280 | 1.00 | 43.71 | B | O |
| ATOM | 4998 | OE2 | GLU | B | 73 | 65.872 | 35.955 | −6.653 | 1.00 | 43.69 | B | O |
| ATOM | 4999 | C | GLU | B | 73 | 70.731 | 36.591 | −5.264 | 1.00 | 23.08 | B | C |
| ATOM | 5000 | O | GLU | B | 73 | 70.546 | 37.755 | −5.604 | 1.00 | 21.72 | B | O |
| ATOM | 5001 | N | SER | B | 74 | 70.958 | 36.262 | −4.003 | 1.00 | 21.31 | B | N |
| ATOM | 5002 | CA | SER | B | 74 | 70.868 | 37.305 | −3.025 | 1.00 | 25.45 | B | C |
| ATOM | 5003 | CB | SER | B | 74 | 70.662 | 36.730 | −1.637 | 1.00 | 30.25 | B | C |
| ATOM | 5004 | OG | SER | B | 74 | 71.856 | 36.148 | −1.173 | 1.00 | 38.94 | B | O |
| ATOM | 5005 | C | SER | B | 74 | 72.120 | 38.207 | −3.126 | 1.00 | 25.84 | B | C |
| ATOM | 5006 | O | SER | B | 74 | 72.064 | 39.392 | −2.813 | 1.00 | 23.71 | B | O |
| ATOM | 5007 | N | ASP | B | 75 | 73.255 | 37.646 | −3.554 | 1.00 | 20.01 | B | N |
| ATOM | 5008 | CA | ASP | B | 75 | 74.460 | 38.467 | −3.744 | 1.00 | 18.98 | B | C |
| ATOM | 5009 | CB | ASP | B | 75 | 75.678 | 37.580 | −4.059 | 1.00 | 18.31 | B | C |
| ATOM | 5010 | CG | ASP | B | 75 | 75.953 | 36.557 | −2.962 | 1.00 | 24.11 | B | C |

APPENDIX A-continued

*P. alba* 3T288C coordinates

| ATOM | 5011 | OD1 | ASP | B | 75 | 76.184 | 36.968 | −1.810 | 1.00 | 21.46 | B | O |
|---|---|---|---|---|---|---|---|---|---|---|---|---|
| ATOM | 5012 | OD2 | ASP | B | 75 | 75.916 | 35.339 | −3.246 | 1.00 | 31.41 | B | O |
| ATOM | 5013 | C | ASP | B | 75 | 74.228 | 39.482 | −4.879 | 1.00 | 13.74 | B | C |
| ATOM | 5014 | O | ASP | B | 75 | 74.605 | 40.657 | −4.777 | 1.00 | 16.30 | B | O |
| ATOM | 5015 | N | ILE | B | 76 | 73.635 | 38.997 | −5.969 | 1.00 | 15.12 | B | N |
| ATOM | 5016 | CA | ILE | B | 76 | 73.334 | 39.841 | −7.134 | 1.00 | 15.07 | B | C |
| ATOM | 5017 | CB | ILE | B | 76 | 72.804 | 39.005 | −8.296 | 1.00 | 15.73 | B | C |
| ATOM | 5018 | CG1 | ILE | B | 76 | 73.932 | 38.106 | −8.838 | 1.00 | 16.42 | B | C |
| ATOM | 5019 | CD1 | ILE | B | 76 | 73.471 | 36.938 | −9.708 | 1.00 | 16.94 | B | C |
| ATOM | 5020 | CG2 | ILE | B | 76 | 72.198 | 39.922 | −9.393 | 1.00 | 12.45 | B | C |
| ATOM | 5021 | C | ILE | B | 76 | 72.338 | 40.932 | −6.736 | 1.00 | 15.52 | B | C |
| ATOM | 5022 | O | ILE | B | 76 | 72.543 | 42.077 | −7.029 | 1.00 | 13.57 | B | O |
| ATOM | 5023 | N | ARG | B | 77 | 71.294 | 40.586 | −5.998 | 1.00 | 17.87 | B | N |
| ATOM | 5024 | CA | AARG | B | 77 | 70.303 | 41.571 | −5.548 | 0.50 | 19.33 | B | C |
| ATOM | 5025 | CA | BARG | B | 77 | 70.327 | 41.607 | −5.606 | 0.50 | 21.73 | B | C |
| ATOM | 5026 | CB | AARG | B | 77 | 69.183 | 40.903 | −4.730 | 0.50 | 18.50 | B | C |
| ATOM | 5027 | CB | BARG | B | 77 | 69.065 | 41.007 | −4.978 | 0.50 | 24.67 | B | C |
| ATOM | 5028 | CG | AARG | B | 77 | 68.257 | 39.962 | −5.492 | 0.50 | 18.79 | B | C |
| ATOM | 5029 | CG | BARG | B | 77 | 67.932 | 40.869 | −5.962 | 0.50 | 31.93 | B | C |
| ATOM | 5030 | CD | AARG | B | 77 | 67.061 | 39.485 | −4.594 | 0.50 | 18.26 | B | C |
| ATOM | 5031 | CD | BARG | B | 77 | 66.571 | 41.085 | −5.291 | 0.50 | 41.21 | B | C |
| ATOM | 5032 | NE | AARG | B | 77 | 66.301 | 40.638 | −4.130 | 0.50 | 22.01 | B | N |
| ATOM | 5033 | NE | BARG | B | 77 | 66.552 | 40.594 | −3.914 | 0.50 | 43.53 | B | N |
| ATOM | 5034 | CZ | AARG | B | 77 | 65.456 | 41.338 | −4.891 | 0.50 | 23.05 | B | C |
| ATOM | 5035 | CZ | BARG | B | 77 | 66.554 | 39.311 | −3.580 | 0.50 | 41.07 | B | C |
| ATOM | 5036 | NH1 | AARG | B | 77 | 65.227 | 40.967 | −6.143 | 0.50 | 18.41 | B | N |
| ATOM | 5037 | NH1 | BARG | B | 77 | 66.580 | 38.379 | −4.520 | 0.50 | 43.20 | B | N |
| ATOM | 5038 | NH2 | AARG | B | 77 | 64.833 | 42.401 | −4.392 | 0.50 | 23.08 | B | N |
| ATOM | 5039 | NH2 | BARG | B | 77 | 66.534 | 38.958 | −2.304 | 0.50 | 51.19 | B | N |
| ATOM | 5040 | C | ARG | B | 77 | 70.952 | 42.656 | −4.697 | 1.00 | 19.64 | B | C |
| ATOM | 5041 | O | ARG | B | 77 | 70.680 | 43.840 | −4.863 | 1.00 | 22.88 | B | O |
| ATOM | 5042 | N | GLY | B | 78 | 71.819 | 42.240 | −3.775 | 1.00 | 20.09 | B | N |
| ATOM | 5043 | CA | GLY | B | 78 | 72.515 | 43.204 | −2.929 | 1.00 | 20.98 | B | C |
| ATOM | 5044 | C | GLY | B | 78 | 73.364 | 44.174 | −3.731 | 1.00 | 20.75 | B | C |
| ATOM | 5045 | O | GLY | B | 78 | 73.381 | 45.377 | −3.461 | 1.00 | 22.15 | B | O |
| ATOM | 5046 | N | ALA | B | 79 | 74.089 | 43.655 | −4.720 | 1.00 | 18.78 | B | N |
| ATOM | 5047 | CA | ALA | B | 79 | 74.924 | 44.489 | −5.572 | 1.00 | 18.42 | B | C |
| ATOM | 5048 | CB | ALA | B | 79 | 75.778 | 43.612 | −6.495 | 1.00 | 17.86 | B | C |
| ATOM | 5049 | C | ALA | B | 79 | 74.072 | 45.457 | −6.361 | 1.00 | 15.85 | B | C |
| ATOM | 5050 | O | ALA | B | 79 | 74.398 | 46.630 | −6.489 | 1.00 | 14.18 | B | O |
| ATOM | 5051 | N | LEU | B | 80 | 72.953 | 44.983 | −6.896 | 1.00 | 17.36 | B | N |
| ATOM | 5052 | CA | LEU | B | 80 | 72.102 | 45.859 | −7.714 | 1.00 | 18.93 | B | C |
| ATOM | 5053 | CB | LEU | B | 80 | 71.048 | 45.045 | −8.449 | 1.00 | 17.55 | B | C |
| ATOM | 5054 | CG | LEU | B | 80 | 71.587 | 44.131 | −9.546 | 1.00 | 17.15 | B | C |
| ATOM | 5055 | CD1 | LEU | B | 80 | 70.465 | 43.255 | −10.060 | 1.00 | 16.24 | B | C |
| ATOM | 5056 | CD2 | LEU | B | 80 | 72.209 | 44.964 | −10.668 | 1.00 | 15.59 | B | C |
| ATOM | 5057 | C | LEU | B | 80 | 71.429 | 46.957 | −6.878 | 1.00 | 22.83 | B | C |
| ATOM | 5058 | O | LEU | B | 80 | 71.268 | 48.090 | −7.337 | 1.00 | 20.36 | B | O |
| ATOM | 5059 | N | ASP | B | 81 | 71.031 | 46.607 | −5.660 | 1.00 | 26.31 | B | N |
| ATOM | 5060 | CA | ASP | B | 81 | 70.407 | 47.565 | −4.753 | 1.00 | 32.97 | B | C |
| ATOM | 5061 | CB | ASP | B | 81 | 69.943 | 46.842 | −3.483 | 1.00 | 36.50 | B | C |
| ATOM | 5062 | CG | ASP | B | 81 | 69.066 | 47.710 | −2.608 | 1.00 | 44.23 | B | C |
| ATOM | 5063 | OD1 | ASP | B | 81 | 67.937 | 48.029 | −3.026 | 1.00 | 48.95 | B | O |
| ATOM | 5064 | OD2 | ASP | B | 81 | 69.504 | 48.068 | −1.496 | 1.00 | 48.03 | B | O |
| ATOM | 5065 | C | ASP | B | 81 | 71.376 | 48.702 | −4.422 | 1.00 | 28.91 | B | C |
| ATOM | 5066 | O | ASP | B | 81 | 71.000 | 49.874 | −4.421 | 1.00 | 31.14 | B | O |
| ATOM | 5067 | N | ARG | B | 82 | 72.624 | 48.346 | −4.126 | 1.00 | 27.25 | B | N |
| ATOM | 5068 | CA | ARG | B | 82 | 73.659 | 49.337 | −3.836 | 1.00 | 28.22 | B | C |
| ATOM | 5069 | CB | ARG | B | 82 | 74.954 | 48.676 | −3.355 | 1.00 | 28.94 | B | C |
| ATOM | 5070 | CG | ARG | B | 82 | 74.907 | 48.182 | −1.923 | 1.00 | 36.06 | B | C |
| ATOM | 5071 | CD | ARG | B | 82 | 76.297 | 47.764 | −1.463 | 1.00 | 40.01 | B | C |
| ATOM | 5072 | NE | ARG | B | 82 | 76.837 | 46.648 | −2.246 | 1.00 | 38.93 | B | N |
| ATOM | 5073 | CZ | ARG | B | 82 | 76.499 | 45.365 | −2.078 | 1.00 | 39.77 | B | C |
| ATOM | 5074 | NH1 | ARG | B | 82 | 75.598 | 45.013 | −1.159 | 1.00 | 41.64 | B | N |
| ATOM | 5075 | NH2 | ARG | B | 82 | 77.057 | 44.422 | −2.839 | 1.00 | 30.99 | B | N |
| ATOM | 5076 | C | ARG | B | 82 | 73.961 | 50.193 | −5.051 | 1.00 | 24.69 | B | C |
| ATOM | 5077 | O | ARG | B | 82 | 74.162 | 51.379 | −4.920 | 1.00 | 24.76 | B | O |
| ATOM | 5078 | N | PHE | B | 83 | 73.977 | 49.587 | −6.235 | 1.00 | 23.39 | B | N |
| ATOM | 5079 | CA | PHE | B | 83 | 74.153 | 50.328 | −7.480 | 1.00 | 22.29 | B | C |
| ATOM | 5080 | CB | PHE | B | 83 | 74.075 | 49.369 | −8.666 | 1.00 | 24.15 | B | C |
| ATOM | 5081 | CG | PHE | B | 83 | 74.217 | 50.024 | −10.007 | 1.00 | 23.55 | B | C |
| ATOM | 5082 | CD1 | PHE | B | 83 | 75.406 | 50.644 | −10.367 | 1.00 | 30.81 | B | C |
| ATOM | 5083 | CE1 | PHE | B | 83 | 75.551 | 51.249 | −11.615 | 1.00 | 26.93 | B | C |
| ATOM | 5084 | CZ | PHE | B | 83 | 74.501 | 51.224 | −12.512 | 1.00 | 29.70 | B | C |
| ATOM | 5085 | CE2 | PHE | B | 83 | 73.317 | 50.621 | −12.156 | 1.00 | 25.36 | B | C |
| ATOM | 5086 | CD2 | PHE | B | 83 | 73.184 | 50.021 | −10.908 | 1.00 | 25.59 | B | C |
| ATOM | 5087 | C | PHE | B | 83 | 73.080 | 51.402 | −7.617 | 1.00 | 28.13 | B | C |
| ATOM | 5088 | O | PHE | B | 83 | 73.362 | 52.530 | −8.036 | 1.00 | 32.31 | B | O |

APPENDIX A-continued

*P. alba* 3T288C coordinates

| ATOM | 5089 | N | VAL | B | 84 | 71.850 | 51.063 | −7.264 | 1.00 | 25.80 | B | N |
|---|---|---|---|---|---|---|---|---|---|---|---|---|
| ATOM | 5090 | CA | VAL | B | 84 | 70.783 | 52.044 | −7.360 | 1.00 | 32.46 | B | C |
| ATOM | 5091 | CB | VAL | B | 84 | 69.401 | 51.419 | −7.237 | 1.00 | 34.87 | B | C |
| ATOM | 5092 | CG1 | VAL | B | 84 | 68.364 | 52.505 | −6.892 | 1.00 | 35.85 | B | C |
| ATOM | 5093 | CG2 | VAL | B | 84 | 69.052 | 50.687 | −8.530 | 1.00 | 26.81 | B | C |
| ATOM | 5094 | C | VAL | B | 84 | 70.960 | 53.073 | −6.266 | 1.00 | 36.84 | B | C |
| ATOM | 5095 | O | VAL | B | 84 | 71.291 | 54.206 | −6.550 | 1.00 | 30.70 | B | O |
| ATOM | 5096 | N | SER | B | 85 | 70.790 | 52.647 | −5.017 | 1.00 | 43.24 | B | N |
| ATOM | 5097 | CA | SER | B | 85 | 70.754 | 53.564 | −3.876 | 1.00 | 42.00 | B | C |
| ATOM | 5098 | CB | SER | B | 85 | 70.548 | 52.782 | −2.575 | 1.00 | 41.82 | B | C |
| ATOM | 5099 | OG | SER | B | 85 | 71.758 | 52.172 | −2.170 | 1.00 | 45.68 | B | O |
| ATOM | 5100 | C | SER | B | 85 | 71.987 | 54.478 | −3.762 | 1.00 | 42.81 | B | C |
| ATOM | 5101 | O | SER | B | 85 | 71.910 | 55.543 | −3.151 | 1.00 | 47.04 | B | O |
| ATOM | 5102 | N | SER | B | 86 | 73.110 | 54.090 | −4.356 | 1.00 | 35.93 | B | N |
| ATOM | 5103 | CA | SER | B | 86 | 74.283 | 54.951 | −4.359 | 1.00 | 33.92 | B | C |
| ATOM | 5104 | CB | SER | B | 86 | 75.548 | 54.112 | −4.499 | 1.00 | 32.14 | B | C |
| ATOM | 5105 | OG | SER | B | 86 | 75.729 | 53.707 | −5.842 | 1.00 | 33.64 | B | O |
| ATOM | 5106 | C | SER | B | 86 | 74.268 | 56.013 | −5.478 | 1.00 | 38.88 | B | C |
| ATOM | 5107 | O | SER | B | 86 | 75.231 | 56.746 | −5.622 | 1.00 | 39.84 | B | O |
| ATOM | 5108 | N | GLY | B | 87 | 73.200 | 56.086 | −6.272 | 1.00 | 39.23 | B | N |
| ATOM | 5109 | CA | GLY | B | 87 | 73.160 | 56.987 | −7.436 | 1.00 | 36.38 | B | C |
| ATOM | 5110 | C | GLY | B | 87 | 73.901 | 56.455 | −8.659 | 1.00 | 40.92 | B | C |
| ATOM | 5111 | O | GLY | B | 87 | 74.032 | 57.161 | −9.663 | 1.00 | 31.51 | B | O |
| ATOM | 5112 | N | GLY | B | 88 | 74.369 | 55.203 | −8.596 | 1.00 | 39.83 | B | N |
| ATOM | 5113 | CA | GLY | B | 88 | 75.122 | 54.595 | −9.692 | 1.00 | 31.43 | B | C |
| ATOM | 5114 | C | GLY | B | 88 | 74.314 | 54.463 | −10.962 | 1.00 | 33.31 | B | C |
| ATOM | 5115 | O | GLY | B | 88 | 74.849 | 54.605 | −12.066 | 1.00 | 37.29 | B | O |
| ATOM | 5116 | N | PHE | B | 89 | 73.019 | 54.205 | −10.824 | 1.00 | 35.85 | B | N |
| ATOM | 5117 | CA | PHE | B | 89 | 72.158 | 54.073 | −12.009 | 1.00 | 36.71 | B | C |
| ATOM | 5118 | CB | PHE | B | 89 | 70.828 | 53.383 | −11.649 | 1.00 | 31.01 | B | C |
| ATOM | 5119 | CG | PHE | B | 89 | 69.943 | 53.122 | −12.832 | 1.00 | 32.04 | B | C |
| ATOM | 5120 | CD1 | PHE | B | 89 | 70.408 | 52.394 | −13.927 | 1.00 | 30.41 | B | C |
| ATOM | 5121 | CE1 | PHE | B | 89 | 69.592 | 52.172 | −15.029 | 1.00 | 29.24 | B | C |
| ATOM | 5122 | CZ | PHE | B | 89 | 68.316 | 52.656 | −15.040 | 1.00 | 30.11 | B | C |
| ATOM | 5123 | CE2 | PHE | B | 89 | 67.844 | 53.383 | −13.961 | 1.00 | 33.17 | B | C |
| ATOM | 5124 | CD2 | PHE | B | 89 | 68.655 | 53.612 | −12.866 | 1.00 | 31.62 | B | C |
| ATOM | 5125 | C | PHE | B | 89 | 71.966 | 55.438 | −12.716 | 1.00 | 34.35 | B | C |
| ATOM | 5126 | O | PHE | B | 89 | 71.972 | 55.512 | −13.944 | 1.00 | 35.68 | B | O |
| ATOM | 5127 | N | ASP | B | 90 | 71.831 | 56.515 | −11.951 | 1.00 | 47.99 | B | N |
| ATOM | 5128 | CA | ASP | B | 90 | 71.864 | 57.873 | −12.534 | 1.00 | 47.41 | B | C |
| ATOM | 5129 | CB | ASP | B | 90 | 71.851 | 58.947 | −11.450 | 1.00 | 63.15 | B | C |
| ATOM | 5130 | CG | ASP | B | 90 | 70.460 | 59.379 | −11.085 | 1.00 | 75.50 | B | C |
| ATOM | 5131 | OD1 | ASP | B | 90 | 69.558 | 58.515 | −11.089 | 1.00 | 55.04 | B | O |
| ATOM | 5132 | OD2 | ASP | B | 90 | 70.273 | 60.583 | −10.798 | 1.00 | 83.17 | B | O |
| ATOM | 5133 | C | ASP | B | 90 | 73.099 | 58.096 | −13.376 | 1.00 | 39.65 | B | C |
| ATOM | 5134 | O | ASP | B | 90 | 72.997 | 58.504 | −14.532 | 1.00 | 47.01 | B | O |
| ATOM | 5135 | N | ALA | B | 91 | 74.256 | 57.840 | −12.770 | 1.00 | 38.64 | B | N |
| ATOM | 5136 | CA | ALA | B | 91 | 75.557 | 58.067 | −13.402 | 1.00 | 37.96 | B | C |
| ATOM | 5137 | CB | ALA | B | 91 | 76.689 | 57.509 | −12.536 | 1.00 | 36.86 | B | C |
| ATOM | 5138 | C | ALA | B | 91 | 75.615 | 57.459 | −14.790 | 1.00 | 38.02 | B | C |
| ATOM | 5139 | O | ALA | B | 91 | 75.941 | 58.162 | −15.753 | 1.00 | 26.33 | B | O |
| ATOM | 5140 | N | VAL | B | 92 | 75.271 | 56.169 | −14.912 | 1.00 | 32.42 | B | N |
| ATOM | 5141 | CA | VAL | B | 92 | 75.437 | 55.495 | −16.197 | 1.00 | 28.95 | B | C |
| ATOM | 5142 | CB | VAL | B | 92 | 75.332 | 53.942 | −16.123 | 1.00 | 31.66 | B | C |
| ATOM | 5143 | CG1 | VAL | B | 92 | 76.404 | 53.387 | −15.168 | 1.00 | 37.05 | B | C |
| ATOM | 5144 | CG2 | VAL | B | 92 | 73.933 | 53.505 | −15.726 | 1.00 | 26.45 | B | C |
| ATOM | 5145 | C | VAL | B | 92 | 74.499 | 56.067 | −17.256 | 1.00 | 24.25 | B | C |
| ATOM | 5146 | O | VAL | B | 92 | 74.873 | 56.119 | −18.422 | 1.00 | 26.79 | B | O |
| ATOM | 5147 | N | THR | B | 93 | 73.311 | 56.522 | −16.864 | 1.00 | 27.09 | B | N |
| ATOM | 5148 | CA | THR | B | 93 | 72.349 | 57.050 | −17.847 | 1.00 | 29.51 | B | C |
| ATOM | 5149 | CB | THR | B | 93 | 70.917 | 57.196 | −17.276 | 1.00 | 31.52 | B | C |
| ATOM | 5150 | OG1 | THR | B | 93 | 70.912 | 58.154 | −16.215 | 1.00 | 37.00 | B | O |
| ATOM | 5151 | CG2 | THR | B | 93 | 70.381 | 55.842 | −16.756 | 1.00 | 30.63 | B | C |
| ATOM | 5152 | C | THR | B | 93 | 72.813 | 58.375 | −18.497 | 1.00 | 28.69 | B | C |
| ATOM | 5153 | O | THR | B | 93 | 72.271 | 58.769 | −19.530 | 1.00 | 26.16 | B | O |
| ATOM | 5154 | N | LYS | B | 94 | 73.830 | 59.021 | −17.923 | 1.00 | 34.87 | B | N |
| ATOM | 5155 | CA | LYS | B | 94 | 74.462 | 60.213 | −18.540 | 1.00 | 39.05 | B | C |
| ATOM | 5156 | CB | LYS | B | 94 | 74.944 | 61.223 | −17.488 | 1.00 | 40.76 | B | C |
| ATOM | 5157 | CG | LYS | B | 94 | 74.018 | 61.479 | −16.315 | 1.00 | 48.73 | B | C |
| ATOM | 5158 | CD | LYS | B | 94 | 72.655 | 61.989 | −16.739 | 1.00 | 55.16 | B | C |
| ATOM | 5159 | CE | LYS | B | 94 | 71.900 | 62.521 | −15.529 | 1.00 | 59.95 | B | C |
| ATOM | 5160 | NZ | LYS | B | 94 | 70.454 | 62.656 | −15.807 | 1.00 | 68.55 | B | N |
| ATOM | 5161 | C | LYS | B | 94 | 75.673 | 59.870 | −19.400 | 1.00 | 37.62 | B | C |
| ATOM | 5162 | O | LYS | B | 94 | 76.036 | 60.639 | −20.278 | 1.00 | 42.15 | B | O |
| ATOM | 5163 | N | THR | B | 95 | 76.315 | 58.739 | −19.123 | 1.00 | 35.13 | B | N |
| ATOM | 5164 | CA | THR | B | 95 | 77.645 | 58.453 | −19.667 | 1.00 | 31.61 | B | C |
| ATOM | 5165 | CB | THR | B | 95 | 78.643 | 58.170 | −18.522 | 1.00 | 30.78 | B | C |
| ATOM | 5166 | OG1 | THR | B | 95 | 78.293 | 56.950 | −17.848 | 1.00 | 30.43 | B | O |

APPENDIX A-continued

*P. alba* 3T288C coordinates

| ATOM | 5167 | CG2 | THR | B | 95 | 78.647 | 59.332 | −17.500 | 1.00 | 30.18 | B | C |
|---|---|---|---|---|---|---|---|---|---|---|---|---|
| ATOM | 5168 | C | THR | B | 95 | 77.696 | 57.305 | −20.690 | 1.00 | 33.47 | B | C |
| ATOM | 5169 | O | THR | B | 95 | 78.454 | 57.390 | −21.659 | 1.00 | 33.96 | B | O |
| ATOM | 5170 | N | SER | B | 96 | 76.884 | 56.252 | −20.487 | 1.00 | 30.71 | B | N |
| ATOM | 5171 | CA | SER | B | 96 | 77.113 | 54.954 | −21.139 | 1.00 | 26.68 | B | C |
| ATOM | 5172 | CB | SER | B | 96 | 77.999 | 54.103 | −20.208 | 1.00 | 26.33 | B | C |
| ATOM | 5173 | OG | SER | B | 96 | 78.094 | 52.750 | −20.606 | 1.00 | 28.02 | B | O |
| ATOM | 5174 | C | SER | B | 96 | 75.801 | 54.201 | −21.526 | 1.00 | 28.35 | B | C |
| ATOM | 5175 | O | SER | B | 96 | 74.996 | 53.790 | −20.658 | 1.00 | 21.83 | B | O |
| ATOM | 5176 | N | LEU | B | 97 | 75.608 | 54.003 | −22.832 | 1.00 | 24.62 | B | N |
| ATOM | 5177 | CA | LEU | B | 97 | 74.475 | 53.217 | −23.336 | 1.00 | 26.38 | B | C |
| ATOM | 5178 | CB | LEU | B | 97 | 74.395 | 53.258 | −24.865 | 1.00 | 24.22 | B | C |
| ATOM | 5179 | CG | LEU | B | 97 | 73.301 | 52.390 | −25.504 | 1.00 | 23.98 | B | C |
| ATOM | 5180 | CD1 | LEU | B | 97 | 71.912 | 52.882 | −25.098 | 1.00 | 23.33 | B | C |
| ATOM | 5181 | CD2 | LEU | B | 97 | 73.456 | 52.362 | −27.022 | 1.00 | 24.44 | B | C |
| ATOM | 5182 | C | LEU | B | 97 | 74.582 | 51.770 | −22.870 | 1.00 | 25.26 | B | C |
| ATOM | 5183 | O | LEU | B | 97 | 73.606 | 51.211 | −22.399 | 1.00 | 23.11 | B | O |
| ATOM | 5184 | N | HIS | B | 98 | 75.762 | 51.174 | −23.029 | 1.00 | 23.74 | B | N |
| ATOM | 5185 | CA | HIS | B | 98 | 76.022 | 49.808 | −22.571 | 1.00 | 23.36 | B | C |
| ATOM | 5186 | CB | HIS | B | 98 | 77.471 | 49.427 | −22.857 | 1.00 | 23.90 | B | C |
| ATOM | 5187 | CG | HIS | B | 98 | 77.854 | 48.056 | −22.369 | 1.00 | 28.17 | B | C |
| ATOM | 5188 | ND1 | HIS | B | 98 | 77.018 | 46.996 | −22.448 | 1.00 | 32.87 | B | N |
| ATOM | 5189 | CE1 | HIS | B | 98 | 77.624 | 45.910 | −21.935 | 1.00 | 31.82 | B | C |
| ATOM | 5190 | NE2 | HIS | B | 98 | 78.855 | 46.271 | −21.537 | 1.00 | 38.65 | B | N |
| ATOM | 5191 | CD2 | HIS | B | 98 | 79.029 | 47.588 | −21.795 | 1.00 | 30.71 | B | C |
| ATOM | 5192 | C | HIS | B | 98 | 75.711 | 49.673 | −21.103 | 1.00 | 22.84 | B | C |
| ATOM | 5193 | O | HIS | B | 98 | 74.971 | 48.773 | −20.701 | 1.00 | 20.22 | B | O |
| ATOM | 5194 | N | GLY | B | 99 | 76.250 | 50.572 | −20.283 | 1.00 | 19.58 | B | N |
| ATOM | 5195 | CA | GLY | B | 99 | 75.972 | 50.557 | −18.836 | 1.00 | 19.66 | B | C |
| ATOM | 5196 | C | GLY | B | 99 | 74.482 | 50.668 | −18.520 | 1.00 | 20.65 | B | C |
| ATOM | 5197 | O | GLY | B | 99 | 73.955 | 49.949 | −17.650 | 1.00 | 16.40 | B | O |
| ATOM | 5198 | N | THR | B | 100 | 73.803 | 51.564 | −19.236 | 1.00 | 16.08 | B | N |
| ATOM | 5199 | CA | THR | B | 100 | 72.399 | 51.804 | −19.018 | 1.00 | 16.75 | B | C |
| ATOM | 5200 | CB | THR | B | 100 | 71.936 | 53.097 | −19.719 | 1.00 | 18.78 | B | C |
| ATOM | 5201 | OG1 | THR | B | 100 | 72.623 | 54.221 | −19.144 | 1.00 | 22.13 | B | O |
| ATOM | 5202 | CG2 | THR | B | 100 | 70.458 | 53.296 | −19.554 | 1.00 | 18.90 | B | C |
| ATOM | 5203 | C | THR | B | 100 | 71.544 | 50.611 | −19.462 | 1.00 | 18.44 | B | C |
| ATOM | 5204 | O | THR | B | 100 | 70.656 | 50.192 | −18.725 | 1.00 | 16.59 | B | O |
| ATOM | 5205 | N | ALA | B | 101 | 71.840 | 50.058 | −20.637 | 1.00 | 17.28 | B | N |
| ATOM | 5206 | CA | ALA | B | 101 | 71.060 | 48.965 | −21.187 | 1.00 | 19.07 | B | C |
| ATOM | 5207 | CB | ALA | B | 101 | 71.445 | 48.722 | −22.648 | 1.00 | 18.01 | B | C |
| ATOM | 5208 | C | ALA | B | 101 | 71.268 | 47.705 | −20.333 | 1.00 | 16.43 | B | C |
| ATOM | 5209 | O | ALA | B | 101 | 70.329 | 46.972 | −20.047 | 1.00 | 18.06 | B | O |
| ATOM | 5210 | N | LEU | B | 102 | 72.500 | 47.470 | −19.915 | 1.00 | 15.43 | B | N |
| ATOM | 5211 | CA | LEU | B | 102 | 72.785 | 46.284 | −19.108 | 1.00 | 16.88 | B | C |
| ATOM | 5212 | CB | LEU | B | 102 | 74.307 | 46.070 | −18.984 | 1.00 | 18.21 | B | C |
| ATOM | 5213 | CG | LEU | B | 102 | 74.770 | 44.887 | −18.124 | 1.00 | 16.60 | B | C |
| ATOM | 5214 | CD1 | LEU | B | 102 | 74.090 | 43.606 | −18.521 | 1.00 | 17.56 | B | C |
| ATOM | 5215 | CD2 | LEU | B | 102 | 76.308 | 44.767 | −18.207 | 1.00 | 20.27 | B | C |
| ATOM | 5216 | C | LEU | B | 102 | 72.126 | 46.418 | −17.725 | 1.00 | 16.97 | B | C |
| ATOM | 5217 | O | LEU | B | 102 | 71.450 | 45.499 | −17.238 | 1.00 | 14.04 | B | O |
| ATOM | 5218 | N | SER | B | 103 | 72.304 | 47.574 | −17.096 | 1.00 | 18.21 | B | N |
| ATOM | 5219 | CA | SER | B | 103 | 71.771 | 47.752 | −15.763 | 1.00 | 17.35 | B | C |
| ATOM | 5220 | CB | SER | B | 103 | 72.333 | 49.003 | −15.089 | 1.00 | 18.75 | B | C |
| ATOM | 5221 | OG | SER | B | 103 | 72.042 | 50.151 | −15.843 | 1.00 | 18.72 | B | O |
| ATOM | 5222 | C | SER | B | 103 | 70.242 | 47.749 | −15.785 | 1.00 | 18.14 | B | C |
| ATOM | 5223 | O | SER | B | 103 | 69.630 | 47.214 | −14.885 | 1.00 | 18.58 | B | O |
| ATOM | 5224 | N | PHE | B | 104 | 69.641 | 48.329 | −16.818 | 1.00 | 18.14 | B | N |
| ATOM | 5225 | CA | PHE | B | 104 | 68.199 | 48.322 | −16.971 | 1.00 | 18.85 | B | C |
| ATOM | 5226 | CB | PHE | B | 104 | 67.813 | 49.009 | −18.289 | 1.00 | 19.22 | B | C |
| ATOM | 5227 | CG | PHE | B | 104 | 66.323 | 49.037 | −18.548 | 1.00 | 19.65 | B | C |
| ATOM | 5228 | CD1 | PHE | B | 104 | 65.693 | 47.984 | −19.200 | 1.00 | 20.74 | B | C |
| ATOM | 5229 | CE1 | PHE | B | 104 | 64.314 | 47.998 | −19.439 | 1.00 | 19.71 | B | C |
| ATOM | 5230 | CZ | PHE | B | 104 | 63.567 | 49.056 | −19.033 | 1.00 | 18.71 | B | C |
| ATOM | 5231 | CE2 | PHE | B | 104 | 64.183 | 50.127 | −18.407 | 1.00 | 24.37 | B | C |
| ATOM | 5232 | CD2 | PHE | B | 104 | 65.563 | 50.114 | −18.167 | 1.00 | 22.21 | B | C |
| ATOM | 5233 | C | PHE | B | 104 | 67.689 | 46.882 | −16.973 | 1.00 | 17.17 | B | C |
| ATOM | 5234 | O | PHE | B | 104 | 66.741 | 46.526 | −16.245 | 1.00 | 16.32 | B | O |
| ATOM | 5235 | N | ARG | B | 105 | 68.336 | 46.043 | −17.778 | 1.00 | 13.42 | B | N |
| ATOM | 5236 | CA | ARG | B | 105 | 67.919 | 44.645 | −17.873 | 1.00 | 15.63 | B | C |
| ATOM | 5237 | CB | ARG | B | 105 | 68.641 | 43.918 | −19.024 | 1.00 | 13.02 | B | C |
| ATOM | 5238 | CG | ARG | B | 105 | 68.333 | 42.452 | −19.081 | 1.00 | 14.74 | B | C |
| ATOM | 5239 | CD | ARG | B | 105 | 68.877 | 41.808 | −20.362 | 1.00 | 16.05 | B | C |
| ATOM | 5240 | NE | ARG | B | 105 | 70.330 | 41.836 | −20.500 | 1.00 | 16.37 | B | N |
| ATOM | 5241 | CZ | ARG | B | 105 | 71.161 | 40.984 | −19.914 | 1.00 | 17.27 | B | C |
| ATOM | 5242 | NH1 | ARG | B | 105 | 70.697 | 40.030 | −19.116 | 1.00 | 17.40 | B | N |
| ATOM | 5243 | NH2 | ARG | B | 105 | 72.454 | 41.085 | −20.139 | 1.00 | 20.81 | B | N |
| ATOM | 5244 | C | ARG | B | 105 | 68.075 | 43.891 | −16.551 | 1.00 | 15.32 | B | C |

APPENDIX A-continued

*P. alba* 3T288C coordinates

| ATOM | 5245 | O | ARG | B | 105 | 67.152 | 43.225 | −16.110 | 1.00 | 14.27 | B | O |
|------|------|-----|-----|---|-----|--------|--------|---------|------|-------|---|---|
| ATOM | 5246 | N | LEU | B | 106 | 69.229 | 44.025 | −15.901 | 1.00 | 12.51 | B | N |
| ATOM | 5247 | CA | LEU | B | 106 | 69.477 | 43.304 | −14.683 | 1.00 | 13.49 | B | C |
| ATOM | 5248 | CB | LEU | B | 106 | 70.965 | 43.433 | −14.243 | 1.00 | 12.09 | B | C |
| ATOM | 5249 | CG | LEU | B | 106 | 72.010 | 42.909 | −15.238 | 1.00 | 12.53 | B | C |
| ATOM | 5250 | CD1 | LEU | B | 106 | 73.418 | 43.201 | −14.689 | 1.00 | 10.73 | B | C |
| ATOM | 5251 | CD2 | LEU | B | 106 | 71.819 | 41.373 | −15.502 | 1.00 | 11.52 | B | C |
| ATOM | 5252 | C | LEU | B | 106 | 68.525 | 43.797 | −13.602 | 1.00 | 12.64 | B | C |
| ATOM | 5253 | O | LEU | B | 106 | 67.965 | 42.992 | −12.851 | 1.00 | 13.50 | B | O |
| ATOM | 5254 | N | LEU | B | 107 | 68.343 | 45.107 | −13.521 | 1.00 | 16.05 | B | N |
| ATOM | 5255 | CA | LEU | B | 107 | 67.468 | 45.692 | −12.507 | 1.00 | 16.98 | B | C |
| ATOM | 5256 | CB | LEU | B | 107 | 67.541 | 47.222 | −12.557 | 1.00 | 18.29 | B | C |
| ATOM | 5257 | CG | LEU | B | 107 | 68.810 | 47.803 | −11.933 | 1.00 | 19.58 | B | C |
| ATOM | 5258 | CD1 | LEU | B | 107 | 69.009 | 49.257 | −12.356 | 1.00 | 18.58 | B | C |
| ATOM | 5259 | CD2 | LEU | B | 107 | 68.701 | 47.653 | −10.424 | 1.00 | 21.10 | B | C |
| ATOM | 5260 | C | LEU | B | 107 | 66.038 | 45.203 | −12.708 | 1.00 | 17.38 | B | C |
| ATOM | 5261 | O | LEU | B | 107 | 65.402 | 44.690 | −11.777 | 1.00 | 16.00 | B | O |
| ATOM | 5262 | N | ARG | B | 108 | 65.546 | 45.305 | −13.936 | 1.00 | 16.53 | B | N |
| ATOM | 5263 | CA | ARG | B | 108 | 64.191 | 44.837 | −14.199 | 1.00 | 16.64 | B | C |
| ATOM | 5264 | CB | ARG | B | 108 | 63.695 | 45.245 | −15.585 | 1.00 | 17.67 | B | C |
| ATOM | 5265 | CG | ARG | B | 108 | 62.248 | 44.770 | −15.818 | 1.00 | 22.71 | B | C |
| ATOM | 5266 | CD | ARG | B | 108 | 61.545 | 45.480 | −16.945 | 1.00 | 22.49 | B | C |
| ATOM | 5267 | NE | ARG | B | 108 | 61.208 | 46.877 | −16.656 | 1.00 | 17.35 | B | N |
| ATOM | 5268 | CZ | ARG | B | 108 | 60.598 | 47.687 | −17.524 | 1.00 | 19.22 | B | C |
| ATOM | 5269 | NH1 | ARG | B | 108 | 60.236 | 47.262 | −18.727 | 1.00 | 18.94 | B | N |
| ATOM | 5270 | NH2 | ARG | B | 108 | 60.345 | 48.935 | −17.195 | 1.00 | 18.38 | B | N |
| ATOM | 5271 | C | ARG | B | 108 | 64.068 | 43.326 | −13.992 | 1.00 | 15.93 | B | C |
| ATOM | 5272 | O | ARG | B | 108 | 63.082 | 42.852 | −13.439 | 1.00 | 15.19 | B | O |
| ATOM | 5273 | N | GLN | B | 109 | 65.066 | 42.552 | −14.403 | 1.00 | 16.08 | B | N |
| ATOM | 5274 | CA | GLN | B | 109 | 65.036 | 41.101 | −14.168 | 1.00 | 16.94 | B | C |
| ATOM | 5275 | CB | GLN | B | 109 | 66.363 | 40.481 | −14.657 | 1.00 | 18.02 | B | C |
| ATOM | 5276 | CG | GLN | B | 109 | 66.470 | 38.977 | −14.403 | 1.00 | 20.52 | B | C |
| ATOM | 5277 | CD | GLN | B | 109 | 67.881 | 38.431 | −14.647 | 1.00 | 21.88 | B | C |
| ATOM | 5278 | OE1 | GLN | B | 109 | 68.756 | 39.140 | −15.161 | 1.00 | 17.04 | B | O |
| ATOM | 5279 | NE2 | GLN | B | 109 | 68.104 | 37.159 | −14.259 | 1.00 | 19.73 | B | N |
| ATOM | 5280 | C | GLN | B | 109 | 64.829 | 40.744 | −12.667 | 1.00 | 17.41 | B | C |
| ATOM | 5281 | O | GLN | B | 109 | 64.139 | 39.781 | −12.307 | 1.00 | 16.39 | B | O |
| ATOM | 5282 | N | HIS | B | 110 | 65.462 | 41.524 | −11.809 | 1.00 | 16.32 | B | N |
| ATOM | 5283 | CA | HIS | B | 110 | 65.458 | 41.278 | −10.395 | 1.00 | 19.70 | B | C |
| ATOM | 5284 | CB | HIS | B | 110 | 66.885 | 41.520 | −9.843 | 1.00 | 18.76 | B | C |
| ATOM | 5285 | CG | HIS | B | 110 | 67.825 | 40.397 | −10.201 | 1.00 | 19.50 | B | C |
| ATOM | 5286 | ND1 | HIS | B | 110 | 67.819 | 39.207 | −9.534 | 1.00 | 20.72 | B | N |
| ATOM | 5287 | CE1 | HIS | B | 110 | 68.724 | 38.374 | −10.105 | 1.00 | 20.86 | B | C |
| ATOM | 5288 | NE2 | HIS | B | 110 | 69.259 | 39.005 | −11.175 | 1.00 | 18.25 | B | N |
| ATOM | 5289 | CD2 | HIS | B | 110 | 68.732 | 40.260 | −11.251 | 1.00 | 15.44 | B | C |
| ATOM | 5290 | C | HIS | B | 110 | 64.378 | 42.100 | −9.712 | 1.00 | 23.42 | B | C |
| ATOM | 5291 | O | HIS | B | 110 | 64.443 | 42.349 | −8.519 | 1.00 | 23.26 | B | O |
| ATOM | 5292 | N | GLY | B | 111 | 63.376 | 42.531 | −10.475 | 1.00 | 21.81 | B | N |
| ATOM | 5293 | CA | GLY | B | 111 | 62.171 | 43.131 | −9.890 | 1.00 | 20.16 | B | C |
| ATOM | 5294 | C | GLY | B | 111 | 62.273 | 44.581 | −9.440 | 1.00 | 26.24 | B | C |
| ATOM | 5295 | O | GLY | B | 111 | 61.360 | 45.060 | −8.790 | 1.00 | 27.12 | B | O |
| ATOM | 5296 | N | PHE | B | 112 | 63.376 | 45.271 | −9.753 | 1.00 | 18.84 | B | N |
| ATOM | 5297 | CA | PHE | B | 112 | 63.499 | 46.674 | −9.445 | 1.00 | 21.69 | B | C |
| ATOM | 5298 | CB | PHE | B | 112 | 64.953 | 47.135 | −9.492 | 1.00 | 22.76 | B | C |
| ATOM | 5299 | CG | PHE | B | 112 | 65.794 | 46.565 | −8.408 | 1.00 | 24.54 | B | C |
| ATOM | 5300 | CD1 | PHE | B | 112 | 66.375 | 45.310 | −8.545 | 1.00 | 23.28 | B | C |
| ATOM | 5301 | CE1 | PHE | B | 112 | 67.165 | 44.784 | −7.549 | 1.00 | 25.68 | B | C |
| ATOM | 5302 | CZ | PHE | B | 112 | 67.357 | 45.492 | −6.378 | 1.00 | 30.15 | B | C |
| ATOM | 5303 | CE2 | PHE | B | 112 | 66.771 | 46.735 | −6.222 | 1.00 | 30.82 | B | C |
| ATOM | 5304 | CD2 | PHE | B | 112 | 65.999 | 47.270 | −7.233 | 1.00 | 29.06 | B | C |
| ATOM | 5305 | C | PHE | B | 112 | 62.698 | 47.477 | −10.446 | 1.00 | 23.68 | B | C |
| ATOM | 5306 | O | PHE | B | 112 | 62.494 | 47.050 | −11.584 | 1.00 | 24.90 | B | O |
| ATOM | 5307 | N | GLU | B | 113 | 62.249 | 48.639 | −9.991 | 1.00 | 28.56 | B | N |
| ATOM | 5308 | CA | GLU | B | 113 | 61.517 | 49.574 | −10.801 | 1.00 | 29.69 | B | C |
| ATOM | 5309 | CB | GLU | B | 113 | 60.602 | 50.447 | −9.933 | 1.00 | 37.49 | B | C |
| ATOM | 5310 | CG | GLU | B | 113 | 59.510 | 51.122 | −10.751 | 1.00 | 47.65 | B | C |
| ATOM | 5311 | CD | GLU | B | 113 | 58.598 | 52.026 | −9.935 | 1.00 | 69.63 | B | C |
| ATOM | 5312 | OE1 | GLU | B | 113 | 59.086 | 52.679 | −8.989 | 1.00 | 75.21 | B | O |
| ATOM | 5313 | OE2 | GLU | B | 113 | 57.387 | 52.090 | −10.254 | 1.00 | 70.93 | B | O |
| ATOM | 5314 | C | GLU | B | 113 | 62.480 | 50.453 | −11.600 | 1.00 | 23.60 | B | C |
| ATOM | 5315 | O | GLU | B | 113 | 63.218 | 51.264 | −11.057 | 1.00 | 31.81 | B | O |
| ATOM | 5316 | N | VAL | B | 114 | 62.474 | 50.274 | −12.908 | 1.00 | 20.86 | B | N |
| ATOM | 5317 | CA | VAL | B | 114 | 63.187 | 51.163 | −13.817 | 1.00 | 21.32 | B | C |
| ATOM | 5318 | CB | VAL | B | 114 | 64.453 | 50.479 | −14.383 | 1.00 | 23.76 | B | C |
| ATOM | 5319 | CG1 | VAL | B | 114 | 65.526 | 50.343 | −13.282 | 1.00 | 20.01 | B | C |
| ATOM | 5320 | CG2 | VAL | B | 114 | 64.110 | 49.127 | −14.983 | 1.00 | 21.05 | B | C |
| ATOM | 5321 | C | VAL | B | 114 | 62.231 | 51.605 | −14.947 | 1.00 | 21.51 | B | C |
| ATOM | 5322 | O | VAL | B | 114 | 61.294 | 50.891 | −15.332 | 1.00 | 20.01 | B | O |

APPENDIX A-continued

*P. alba* 3T288C coordinates

| ATOM | 5323 | N | SER | B | 115 | 62.474 | 52.789 | −15.465 | 1.00 | 17.24 | B | N |
|---|---|---|---|---|---|---|---|---|---|---|---|---|
| ATOM | 5324 | CA | SER | B | 115 | 61.633 | 53.413 | −16.476 | 1.00 | 21.29 | B | C |
| ATOM | 5325 | CB | SER | B | 115 | 61.302 | 54.859 | −16.017 | 1.00 | 22.76 | B | C |
| ATOM | 5326 | OG | SER | B | 115 | 60.931 | 55.680 | −17.115 | 1.00 | 27.64 | B | O |
| ATOM | 5327 | C | SER | B | 115 | 62.354 | 53.459 | −17.824 | 1.00 | 21.00 | B | C |
| ATOM | 5328 | O | SER | B | 115 | 63.582 | 53.591 | −17.885 | 1.00 | 17.43 | B | O |
| ATOM | 5329 | N | GLN | B | 116 | 61.586 | 53.412 | −18.906 | 1.00 | 20.95 | B | N |
| ATOM | 5330 | CA | GLN | B | 116 | 62.156 | 53.577 | −20.255 | 1.00 | 25.47 | B | C |
| ATOM | 5331 | CB | GLN | B | 116 | 61.095 | 53.316 | −21.348 | 1.00 | 28.24 | B | C |
| ATOM | 5332 | CG | GLN | B | 116 | 59.871 | 54.267 | −21.348 | 1.00 | 28.04 | B | C |
| ATOM | 5333 | CD | GLN | B | 116 | 59.077 | 54.234 | −22.640 | 1.00 | 27.34 | B | C |
| ATOM | 5334 | OE1 | GLN | B | 116 | 59.359 | 53.446 | −23.535 | 1.00 | 29.10 | B | O |
| ATOM | 5335 | NE2 | GLN | B | 116 | 58.079 | 55.102 | −22.741 | 1.00 | 22.35 | B | N |
| ATOM | 5336 | C | GLN | B | 116 | 62.812 | 54.942 | −20.479 | 1.00 | 28.20 | B | C |
| ATOM | 5337 | O | GLN | B | 116 | 63.601 | 55.104 | −21.414 | 1.00 | 23.76 | B | O |
| ATOM | 5338 | N | GLU | B | 117 | 62.497 | 55.917 | −19.622 | 1.00 | 31.18 | B | N |
| ATOM | 5339 | CA | GLU | B | 117 | 63.149 | 57.240 | −19.678 | 1.00 | 36.90 | B | C |
| ATOM | 5340 | CB | GLU | B | 117 | 62.524 | 58.228 | −18.676 | 1.00 | 41.23 | B | C |
| ATOM | 5341 | CG | GLU | B | 117 | 61.061 | 58.577 | −18.936 | 1.00 | 43.94 | B | C |
| ATOM | 5342 | CD | GLU | B | 117 | 60.827 | 59.150 | −20.321 | 1.00 | 50.10 | B | C |
| ATOM | 5343 | OE1 | GLU | B | 117 | 61.675 | 59.929 | −20.808 | 1.00 | 62.87 | B | O |
| ATOM | 5344 | OE2 | GLU | B | 117 | 59.789 | 58.817 | −20.931 | 1.00 | 60.89 | B | O |
| ATOM | 5345 | C | GLU | B | 117 | 64.659 | 57.150 | −19.434 | 1.00 | 30.52 | B | C |
| ATOM | 5346 | O | GLU | B | 117 | 65.385 | 58.038 | −19.801 | 1.00 | 21.21 | B | O |
| ATOM | 5347 | N | ALA | B | 118 | 65.126 | 56.052 | −18.854 | 1.00 | 26.64 | B | N |
| ATOM | 5348 | CA | ALA | B | 118 | 66.555 | 55.806 | −18.676 | 1.00 | 24.31 | B | C |
| ATOM | 5349 | CB | ALA | B | 118 | 66.763 | 54.394 | −18.052 | 1.00 | 23.93 | B | C |
| ATOM | 5350 | C | ALA | B | 118 | 67.339 | 55.936 | −19.987 | 1.00 | 21.81 | B | C |
| ATOM | 5351 | O | ALA | B | 118 | 68.532 | 56.230 | −19.976 | 1.00 | 20.44 | B | O |
| ATOM | 5352 | N | PHE | B | 119 | 66.680 | 55.712 | −21.116 | 1.00 | 23.54 | B | N |
| ATOM | 5353 | CA | PHE | B | 119 | 67.342 | 55.831 | −22.412 | 1.00 | 29.59 | B | C |
| ATOM | 5354 | CB | PHE | B | 119 | 66.847 | 54.728 | −23.335 | 1.00 | 29.29 | B | C |
| ATOM | 5355 | CG | PHE | B | 119 | 67.164 | 53.348 | −22.833 | 1.00 | 27.07 | B | C |
| ATOM | 5356 | CD1 | PHE | B | 119 | 68.415 | 52.781 | −23.076 | 1.00 | 26.61 | B | C |
| ATOM | 5357 | CE1 | PHE | B | 119 | 68.721 | 51.515 | −22.614 | 1.00 | 24.31 | B | C |
| ATOM | 5358 | CZ | PHE | B | 119 | 67.785 | 50.801 | −21.891 | 1.00 | 23.77 | B | C |
| ATOM | 5359 | CE2 | PHE | B | 119 | 66.539 | 51.350 | −21.624 | 1.00 | 28.37 | B | C |
| ATOM | 5360 | CD2 | PHE | B | 119 | 66.233 | 52.634 | −22.099 | 1.00 | 26.90 | B | C |
| ATOM | 5361 | C | PHE | B | 119 | 67.144 | 57.186 | −23.112 | 1.00 | 34.14 | B | C |
| ATOM | 5362 | O | PHE | B | 119 | 67.561 | 57.340 | −24.267 | 1.00 | 31.83 | B | O |
| ATOM | 5363 | N | SER | B | 120 | 66.536 | 58.164 | −22.443 | 1.00 | 34.61 | B | N |
| ATOM | 5364 | CA | ASER | B | 120 | 66.218 | 59.461 | −23.082 | 0.50 | 37.13 | B | C |
| ATOM | 5365 | CA | BSER | B | 120 | 66.216 | 59.426 | −23.131 | 0.50 | 40.94 | B | C |
| ATOM | 5366 | CB | ASER | B | 120 | 65.327 | 60.320 | −22.177 | 0.50 | 33.88 | B | C |
| ATOM | 5367 | CB | BSER | B | 120 | 65.169 | 60.234 | −22.357 | 0.50 | 42.91 | B | C |
| ATOM | 5368 | OG | ASER | B | 120 | 66.010 | 60.728 | −21.007 | 0.50 | 24.33 | B | O |
| ATOM | 5369 | OG | BSER | B | 120 | 63.881 | 59.640 | −22.507 | 0.50 | 38.32 | B | O |
| ATOM | 5370 | C | SER | B | 120 | 67.470 | 60.252 | −23.446 | 1.00 | 38.63 | B | C |
| ATOM | 5371 | O | SER | B | 120 | 67.493 | 60.979 | −24.434 | 1.00 | 45.53 | B | O |
| ATOM | 5372 | N | GLY | B | 121 | 68.515 | 60.106 | −22.637 | 1.00 | 38.31 | B | N |
| ATOM | 5373 | CA | GLY | B | 121 | 69.784 | 60.780 | −22.881 | 1.00 | 41.06 | B | C |
| ATOM | 5374 | C | GLY | B | 121 | 70.494 | 60.384 | −24.169 | 1.00 | 41.78 | B | C |
| ATOM | 5375 | O | GLY | B | 121 | 71.424 | 61.066 | −24.585 | 1.00 | 43.25 | B | O |
| ATOM | 5376 | N | PHE | B | 122 | 70.061 | 59.297 | −24.807 | 1.00 | 38.87 | B | N |
| ATOM | 5377 | CA | PHE | B | 122 | 70.718 | 58.783 | −26.021 | 1.00 | 39.39 | B | C |
| ATOM | 5378 | CB | PHE | B | 122 | 71.017 | 57.285 | −25.843 | 1.00 | 38.14 | B | C |
| ATOM | 5379 | CG | PHE | B | 122 | 71.710 | 56.979 | −24.551 | 1.00 | 37.60 | B | C |
| ATOM | 5380 | CD1 | PHE | B | 122 | 73.091 | 57.030 | −24.466 | 1.00 | 35.88 | B | C |
| ATOM | 5381 | CE1 | PHE | B | 122 | 73.736 | 56.783 | −23.262 | 1.00 | 38.04 | B | C |
| ATOM | 5382 | CZ | PHE | B | 122 | 72.997 | 56.494 | −22.132 | 1.00 | 36.17 | B | C |
| ATOM | 5383 | CE2 | PHE | B | 122 | 71.618 | 56.448 | −22.202 | 1.00 | 44.59 | B | C |
| ATOM | 5384 | CD2 | PHE | B | 122 | 70.978 | 56.692 | −23.405 | 1.00 | 39.21 | B | C |
| ATOM | 5385 | C | PHE | B | 122 | 69.937 | 59.036 | −27.320 | 1.00 | 36.51 | B | C |
| ATOM | 5386 | O | PHE | B | 122 | 70.289 | 58.491 | −28.367 | 1.00 | 37.34 | B | O |
| ATOM | 5387 | N | LYS | B | 123 | 68.890 | 59.857 | −27.251 | 1.00 | 38.74 | B | N |
| ATOM | 5388 | CA | LYS | B | 123 | 68.112 | 60.229 | −28.438 | 1.00 | 46.15 | B | C |
| ATOM | 5389 | CB | LYS | B | 123 | 66.612 | 60.183 | −28.125 | 1.00 | 51.47 | B | C |
| ATOM | 5390 | CG | LYS | B | 123 | 66.067 | 58.761 | −27.913 | 1.00 | 54.05 | B | C |
| ATOM | 5391 | CD | LYS | B | 123 | 64.842 | 58.698 | −26.965 | 1.00 | 59.06 | B | C |
| ATOM | 5392 | CE | LYS | B | 123 | 63.518 | 59.033 | −27.656 | 1.00 | 55.33 | B | C |
| ATOM | 5393 | NZ | LYS | B | 123 | 62.999 | 57.931 | −28.521 | 1.00 | 52.50 | B | N |
| ATOM | 5394 | C | LYS | B | 123 | 68.523 | 61.625 | −28.928 | 1.00 | 53.18 | B | C |
| ATOM | 5395 | O | LYS | B | 123 | 68.897 | 62.486 | −28.129 | 1.00 | 46.65 | B | O |
| ATOM | 5396 | N | ASP | B | 124 | 68.469 | 61.837 | −30.243 | 1.00 | 54.74 | B | N |
| ATOM | 5397 | CA | ASP | B | 124 | 68.799 | 63.145 | −30.844 | 1.00 | 48.78 | B | C |
| ATOM | 5398 | CB | ASP | B | 124 | 69.229 | 62.982 | −32.323 | 1.00 | 41.62 | B | C |
| ATOM | 5399 | CG | ASP | B | 124 | 68.121 | 62.412 | −33.219 | 1.00 | 39.32 | B | C |
| ATOM | 5400 | OD1 | ASP | B | 124 | 66.927 | 62.460 | −32.844 | 1.00 | 36.69 | B | O |

APPENDIX A-continued

*P. alba* 3T288C coordinates

| ATOM | 5401 | OD2 | ASP | B | 124 | 68.448 | 61.901 | −34.309 | 1.00 | 43.22 | B | O |
|------|------|-----|-----|---|-----|--------|--------|---------|------|-------|---|---|
| ATOM | 5402 | C | ASP | B | 124 | 67.624 | 64.125 | −30.707 | 1.00 | 52.38 | B | C |
| ATOM | 5403 | O | ASP | B | 124 | 66.642 | 63.834 | −30.017 | 1.00 | 48.79 | B | O |
| ATOM | 5404 | N | GLN | B | 125 | 67.736 | 65.281 | −31.364 | 1.00 | 54.13 | B | N |
| ATOM | 5405 | CA | GLN | B | 125 | 66.648 | 66.268 | −31.441 | 1.00 | 58.11 | B | C |
| ATOM | 5406 | CB | GLN | B | 125 | 67.048 | 67.430 | −32.342 | 1.00 | 57.23 | B | C |
| ATOM | 5407 | CG | GLN | B | 125 | 68.219 | 68.223 | −31.829 | 1.00 | 66.12 | B | C |
| ATOM | 5408 | CD | GLN | B | 125 | 68.351 | 69.568 | −32.513 | 1.00 | 75.22 | B | C |
| ATOM | 5409 | OE1 | GLN | B | 125 | 69.145 | 70.404 | −32.095 | 1.00 | 91.78 | B | O |
| ATOM | 5410 | NE2 | GLN | B | 125 | 67.568 | 69.786 | −33.569 | 1.00 | 72.21 | B | N |
| ATOM | 5411 | C | GLN | B | 125 | 65.342 | 65.694 | −31.983 | 1.00 | 58.06 | B | C |
| ATOM | 5412 | O | GLN | B | 125 | 64.274 | 65.920 | −31.412 | 1.00 | 50.39 | B | O |
| ATOM | 5413 | N | ASN | B | 126 | 65.432 | 64.959 | −33.091 | 1.00 | 53.50 | B | N |
| ATOM | 5414 | CA | ASN | B | 126 | 64.255 | 64.335 | −33.701 | 1.00 | 54.83 | B | C |
| ATOM | 5415 | CB | ASN | B | 126 | 64.621 | 63.686 | −35.039 | 1.00 | 48.62 | B | C |
| ATOM | 5416 | CG | ASN | B | 126 | 64.985 | 64.701 | −36.090 | 1.00 | 48.04 | B | C |
| ATOM | 5417 | OD1 | ASN | B | 126 | 65.360 | 65.831 | −35.776 | 1.00 | 37.87 | B | O |
| ATOM | 5418 | ND2 | ASN | B | 126 | 64.885 | 64.305 | −37.352 | 1.00 | 53.77 | B | N |
| ATOM | 5419 | C | ASN | B | 126 | 63.556 | 63.302 | −32.806 | 1.00 | 55.85 | B | C |
| ATOM | 5420 | O | ASN | B | 126 | 62.418 | 62.921 | −33.082 | 1.00 | 51.34 | B | O |
| ATOM | 5421 | N | GLY | B | 127 | 64.230 | 62.867 | −31.740 | 1.00 | 50.88 | B | N |
| ATOM | 5422 | CA | GLY | B | 127 | 63.692 | 61.855 | −30.828 | 1.00 | 53.73 | B | C |
| ATOM | 5423 | C | GLY | B | 127 | 64.049 | 60.439 | −31.243 | 1.00 | 47.40 | B | C |
| ATOM | 5424 | O | GLY | B | 127 | 63.411 | 59.484 | −30.809 | 1.00 | 50.16 | B | O |
| ATOM | 5425 | N | ASN | B | 128 | 65.065 | 60.319 | −32.093 | 1.00 | 40.27 | B | N |
| ATOM | 5426 | CA | ASN | B | 128 | 65.569 | 59.042 | −32.568 | 1.00 | 45.14 | B | C |
| ATOM | 5427 | CB | ASN | B | 128 | 65.719 | 59.037 | −34.094 | 1.00 | 44.88 | B | C |
| ATOM | 5428 | CG | ASN | B | 128 | 64.480 | 59.550 | −34.806 | 1.00 | 48.63 | B | C |
| ATOM | 5429 | OD1 | ASN | B | 128 | 64.569 | 60.360 | −35.733 | 1.00 | 49.05 | B | O |
| ATOM | 5430 | ND2 | ASN | B | 128 | 63.317 | 59.094 | −34.366 | 1.00 | 49.33 | B | N |
| ATOM | 5431 | C | ASN | B | 128 | 66.922 | 58.801 | −31.926 | 1.00 | 46.12 | B | C |
| ATOM | 5432 | O | ASN | B | 128 | 67.652 | 59.744 | −31.626 | 1.00 | 49.12 | B | O |
| ATOM | 5433 | N | PHE | B | 129 | 67.250 | 57.536 | −31.707 | 1.00 | 42.63 | B | N |
| ATOM | 5434 | CA | PHE | B | 129 | 68.544 | 57.172 | −31.137 | 1.00 | 42.17 | B | C |
| ATOM | 5435 | CB | PHE | B | 129 | 68.658 | 55.648 | −31.006 | 1.00 | 38.64 | B | C |
| ATOM | 5436 | CG | PHE | B | 129 | 67.878 | 55.080 | −29.837 | 1.00 | 36.83 | B | C |
| ATOM | 5437 | CD1 | PHE | B | 129 | 68.415 | 55.106 | −28.557 | 1.00 | 33.99 | B | C |
| ATOM | 5438 | CE1 | PHE | B | 129 | 67.709 | 54.596 | −27.477 | 1.00 | 36.82 | B | C |
| ATOM | 5439 | CZ | PHE | B | 129 | 66.453 | 54.061 | −27.670 | 1.00 | 33.55 | B | C |
| ATOM | 5440 | CE2 | PHE | B | 129 | 65.895 | 54.033 | −28.942 | 1.00 | 34.20 | B | C |
| ATOM | 5441 | CD2 | PHE | B | 129 | 66.608 | 54.536 | −30.018 | 1.00 | 33.13 | B | C |
| ATOM | 5442 | C | PHE | B | 129 | 69.688 | 57.729 | −31.985 | 1.00 | 37.32 | B | C |
| ATOM | 5443 | O | PHE | B | 129 | 69.673 | 57.598 | −33.209 | 1.00 | 36.11 | B | O |
| ATOM | 5444 | N | LEU | B | 130 | 70.662 | 58.353 | −31.329 | 1.00 | 35.07 | B | N |
| ATOM | 5445 | CA | LEU | B | 130 | 71.816 | 58.939 | −32.024 | 1.00 | 40.07 | B | C |
| ATOM | 5446 | CB | LEU | B | 130 | 72.803 | 59.533 | −31.008 | 1.00 | 40.58 | B | C |
| ATOM | 5447 | CG | LEU | B | 130 | 72.306 | 60.765 | −30.227 | 1.00 | 39.82 | B | C |
| ATOM | 5448 | CD1 | LEU | B | 130 | 72.966 | 60.870 | −28.861 | 1.00 | 36.33 | B | C |
| ATOM | 5449 | CD2 | LEU | B | 130 | 72.531 | 62.060 | −31.028 | 1.00 | 35.72 | B | C |
| ATOM | 5450 | C | LEU | B | 130 | 72.494 | 57.876 | −32.902 | 1.00 | 39.82 | B | C |
| ATOM | 5451 | O | LEU | B | 130 | 72.670 | 56.735 | −32.480 | 1.00 | 32.74 | B | O |
| ATOM | 5452 | N | GLU | B | 131 | 72.856 | 58.251 | −34.124 | 1.00 | 37.28 | B | N |
| ATOM | 5453 | CA | GLU | B | 131 | 73.355 | 57.301 | −35.125 | 1.00 | 40.60 | B | C |
| ATOM | 5454 | CB | GLU | B | 131 | 73.428 | 57.974 | −36.507 | 1.00 | 47.10 | B | C |
| ATOM | 5455 | CG | GLU | B | 131 | 73.804 | 57.043 | −37.674 | 1.00 | 52.91 | B | C |
| ATOM | 5456 | CD | GLU | B | 131 | 72.682 | 56.082 | −38.070 | 1.00 | 56.45 | B | C |
| ATOM | 5457 | OE1 | GLU | B | 131 | 71.773 | 55.832 | −37.250 | 1.00 | 74.91 | B | O |
| ATOM | 5458 | OE2 | GLU | B | 131 | 72.703 | 55.569 | −39.210 | 1.00 | 54.24 | B | O |
| ATOM | 5459 | C | GLU | B | 131 | 74.725 | 56.728 | −34.782 | 1.00 | 39.38 | B | C |
| ATOM | 5460 | O | GLU | B | 131 | 74.966 | 55.545 | −35.003 | 1.00 | 40.85 | B | O |
| ATOM | 5461 | N | ASN | B | 132 | 75.614 | 57.569 | −34.259 | 1.00 | 36.12 | B | N |
| ATOM | 5462 | CA | ASN | B | 132 | 76.977 | 57.148 | −33.891 | 1.00 | 42.27 | B | C |
| ATOM | 5463 | CB | ASN | B | 132 | 77.784 | 58.352 | −33.406 | 1.00 | 46.73 | B | C |
| ATOM | 5464 | CG | ASN | B | 132 | 77.083 | 59.117 | −32.292 | 1.00 | 48.09 | B | C |
| ATOM | 5465 | OD1 | ASN | B | 132 | 76.466 | 58.533 | −31.405 | 1.00 | 50.95 | B | O |
| ATOM | 5466 | ND2 | ASN | B | 132 | 77.176 | 60.432 | −32.341 | 1.00 | 50.02 | B | N |
| ATOM | 5467 | C | ASN | B | 132 | 77.067 | 56.024 | −32.834 | 1.00 | 41.78 | B | C |
| ATOM | 5468 | O | ASN | B | 132 | 78.110 | 55.389 | −32.682 | 1.00 | 37.33 | B | O |
| ATOM | 5469 | N | LEU | B | 133 | 75.983 | 55.797 | −32.096 | 1.00 | 38.52 | B | N |
| ATOM | 5470 | CA | LEU | B | 133 | 75.903 | 54.664 | −31.154 | 1.00 | 38.43 | B | C |
| ATOM | 5471 | CB | LEU | B | 133 | 74.553 | 54.670 | −30.433 | 1.00 | 34.51 | B | C |
| ATOM | 5472 | CG | LEU | B | 133 | 74.363 | 55.868 | −29.482 | 1.00 | 38.72 | B | C |
| ATOM | 5473 | CD1 | LEU | B | 133 | 72.888 | 56.026 | −29.067 | 1.00 | 34.84 | B | C |
| ATOM | 5474 | CD2 | LEU | B | 133 | 75.264 | 55.742 | −28.268 | 1.00 | 29.27 | B | C |
| ATOM | 5475 | C | LEU | B | 133 | 76.134 | 53.317 | −31.857 | 1.00 | 34.69 | B | C |
| ATOM | 5476 | O | LEU | B | 133 | 76.678 | 52.395 | −31.257 | 1.00 | 36.37 | B | O |
| ATOM | 5477 | N | LYS | B | 134 | 75.779 | 53.234 | −33.141 | 1.00 | 33.33 | B | N |
| ATOM | 5478 | CA | LYS | B | 134 | 75.993 | 52.018 | −33.945 | 1.00 | 35.81 | B | C |

APPENDIX A-continued

*P. alba* 3T288C coordinates

| ATOM | 5479 | CB | LYS | B | 134 | 75.509 | 52.237 | −35.386 | 1.00 | 37.14 | B | C |
|---|---|---|---|---|---|---|---|---|---|---|---|---|
| ATOM | 5480 | CG | LYS | B | 134 | 76.432 | 53.141 | −36.211 | 1.00 | 46.43 | B | C |
| ATOM | 5481 | CD | LYS | B | 134 | 75.885 | 53.431 | −37.607 | 1.00 | 44.56 | B | C |
| ATOM | 5482 | CE | LYS | B | 134 | 77.004 | 53.816 | −38.580 | 1.00 | 41.71 | B | C |
| ATOM | 5483 | NZ | LYS | B | 134 | 76.650 | 53.405 | −39.957 | 1.00 | 41.67 | B | N |
| ATOM | 5484 | C | LYS | B | 134 | 77.452 | 51.512 | −33.952 | 1.00 | 35.23 | B | C |
| ATOM | 5485 | O | LYS | B | 134 | 77.698 | 50.337 | −34.223 | 1.00 | 40.09 | B | O |
| ATOM | 5486 | N | GLU | B | 135 | 78.404 | 52.390 | −33.650 | 1.00 | 32.63 | B | N |
| ATOM | 5487 | CA | AGLU | B | 135 | 79.821 | 52.022 | −33.698 | 0.50 | 36.56 | B | C |
| ATOM | 5488 | CA | BGLU | B | 135 | 79.829 | 52.050 | −33.676 | 0.50 | 36.80 | B | C |
| ATOM | 5489 | CB | AGLU | B | 135 | 80.703 | 53.267 | −33.858 | 0.50 | 37.02 | B | C |
| ATOM | 5490 | CB | BGLU | B | 135 | 80.674 | 53.331 | −33.756 | 0.50 | 37.58 | B | C |
| ATOM | 5491 | CG | AGLU | B | 135 | 80.304 | 54.221 | −35.015 | 0.50 | 37.03 | B | C |
| ATOM | 5492 | CG | BGLU | B | 135 | 80.422 | 54.168 | −35.027 | 0.50 | 38.50 | B | C |
| ATOM | 5493 | CD | AGLU | B | 135 | 80.492 | 53.627 | −36.407 | 0.50 | 38.03 | B | C |
| ATOM | 5494 | CD | BGLU | B | 135 | 81.151 | 55.509 | −35.032 | 0.50 | 39.75 | B | C |
| ATOM | 5495 | OE1 | AGLU | B | 135 | 80.976 | 52.481 | −36.518 | 0.50 | 36.37 | B | O |
| ATOM | 5496 | OE1 | BGLU | B | 135 | 81.194 | 56.191 | −33.984 | 0.50 | 40.21 | B | O |
| ATOM | 5497 | OE2 | BGLU | B | 135 | 81.672 | 55.892 | −36.099 | 0.50 | 41.10 | B | O |
| ATOM | 5498 | OE2 | AGLU | B | 135 | 80.156 | 54.318 | −37.397 | 0.50 | 38.97 | B | O |
| ATOM | 5499 | C | GLU | B | 135 | 80.227 | 51.222 | −32.448 | 1.00 | 39.96 | B | C |
| ATOM | 5500 | O | GLU | B | 135 | 81.279 | 50.566 | −32.431 | 1.00 | 34.56 | B | O |
| ATOM | 5501 | N | ASP | B | 136 | 79.386 | 51.262 | −31.415 | 1.00 | 33.09 | B | N |
| ATOM | 5502 | CA | ASP | B | 136 | 79.635 | 50.527 | −30.173 | 1.00 | 31.38 | B | C |
| ATOM | 5503 | CB | ASP | B | 136 | 79.316 | 51.423 | −28.980 | 1.00 | 31.58 | B | C |
| ATOM | 5504 | CG | ASP | B | 136 | 79.714 | 50.799 | −27.655 | 1.00 | 35.43 | B | C |
| ATOM | 5505 | OD1 | ASP | B | 136 | 80.066 | 49.594 | −27.612 | 1.00 | 44.94 | B | O |
| ATOM | 5506 | OD2 | ASP | B | 136 | 79.675 | 51.530 | −26.646 | 1.00 | 39.28 | B | O |
| ATOM | 5507 | C | ASP | B | 136 | 78.772 | 49.262 | −30.127 | 1.00 | 28.89 | B | C |
| ATOM | 5508 | O | ASP | B | 136 | 77.660 | 49.289 | −29.610 | 1.00 | 26.68 | B | O |
| ATOM | 5509 | N | ILE | B | 137 | 79.302 | 48.161 | −30.653 | 1.00 | 30.70 | B | N |
| ATOM | 5510 | CA | ILE | B | 137 | 78.533 | 46.934 | −30.846 | 1.00 | 26.61 | B | C |
| ATOM | 5511 | CB | ILE | B | 137 | 79.298 | 45.911 | −31.720 | 1.00 | 33.94 | B | C |
| ATOM | 5512 | CG1 | ILE | B | 137 | 79.657 | 46.515 | −33.085 | 1.00 | 35.20 | B | C |
| ATOM | 5513 | CD1 | ILE | B | 137 | 78.435 | 46.944 | −33.870 | 1.00 | 34.22 | B | C |
| ATOM | 5514 | CG2 | ILE | B | 137 | 78.445 | 44.688 | −31.994 | 1.00 | 32.75 | B | C |
| ATOM | 5515 | C | ILE | B | 137 | 78.104 | 46.291 | −29.514 | 1.00 | 28.02 | B | C |
| ATOM | 5516 | O | ILE | B | 137 | 77.012 | 45.741 | −29.427 | 1.00 | 26.31 | B | O |
| ATOM | 5517 | N | LYS | B | 138 | 78.952 | 46.374 | −28.494 | 1.00 | 27.68 | B | N |
| ATOM | 5518 | CA | LYS | B | 138 | 78.595 | 45.940 | −27.147 | 1.00 | 29.84 | B | C |
| ATOM | 5519 | CB | LYS | B | 138 | 79.701 | 46.263 | −26.146 | 1.00 | 34.20 | B | C |
| ATOM | 5520 | CG | LYS | B | 138 | 80.582 | 45.100 | −25.778 | 1.00 | 44.02 | B | C |
| ATOM | 5521 | CD | LYS | B | 138 | 81.442 | 45.464 | −24.571 | 1.00 | 51.03 | B | C |
| ATOM | 5522 | CE | LYS | B | 138 | 81.980 | 44.226 | −23.880 | 1.00 | 58.48 | B | C |
| ATOM | 5523 | NZ | LYS | B | 138 | 81.557 | 44.189 | −22.456 | 1.00 | 57.19 | B | N |
| ATOM | 5524 | C | LYS | B | 138 | 77.319 | 46.610 | −26.672 | 1.00 | 26.53 | B | C |
| ATOM | 5525 | O | LYS | B | 138 | 76.383 | 45.942 | −26.230 | 1.00 | 24.26 | B | O |
| ATOM | 5526 | N | ALA | B | 139 | 77.294 | 47.934 | −26.775 | 1.00 | 26.02 | B | N |
| ATOM | 5527 | CA | ALA | B | 139 | 76.172 | 48.719 | −26.304 | 1.00 | 22.77 | B | C |
| ATOM | 5528 | CB | ALA | B | 139 | 76.506 | 50.229 | −26.326 | 1.00 | 17.44 | B | C |
| ATOM | 5529 | C | ALA | B | 139 | 74.921 | 48.429 | −27.112 | 1.00 | 24.29 | B | C |
| ATOM | 5530 | O | ALA | B | 139 | 73.821 | 48.392 | −26.547 | 1.00 | 22.75 | B | O |
| ATOM | 5531 | N | ILE | B | 140 | 75.076 | 48.208 | −28.420 | 1.00 | 23.37 | B | N |
| ATOM | 5532 | CA | ILE | B | 140 | 73.914 | 47.921 | −29.284 | 1.00 | 22.15 | B | C |
| ATOM | 5533 | CB | ILE | B | 140 | 74.262 | 47.983 | −30.794 | 1.00 | 21.48 | B | C |
| ATOM | 5534 | CG1 | ILE | B | 140 | 74.636 | 49.407 | −31.183 | 1.00 | 27.65 | B | C |
| ATOM | 5535 | CD1 | ILE | B | 140 | 73.572 | 50.458 | −30.836 | 1.00 | 25.53 | B | C |
| ATOM | 5536 | CG2 | ILE | B | 140 | 73.077 | 47.542 | −31.634 | 1.00 | 22.55 | B | C |
| ATOM | 5537 | C | ILE | B | 140 | 73.305 | 46.561 | −28.957 | 1.00 | 20.16 | B | C |
| ATOM | 5538 | O | ILE | B | 140 | 72.093 | 46.440 | −28.858 | 1.00 | 22.67 | B | O |
| ATOM | 5539 | N | LEU | B | 141 | 74.151 | 45.549 | −28.820 | 1.00 | 19.51 | B | N |
| ATOM | 5540 | CA | LEU | B | 141 | 73.729 | 44.264 | −28.291 | 1.00 | 24.91 | B | C |
| ATOM | 5541 | CB | LEU | B | 141 | 74.928 | 43.352 | −28.058 | 1.00 | 27.39 | B | C |
| ATOM | 5542 | CG | LEU | B | 141 | 75.220 | 42.377 | −29.184 | 1.00 | 34.95 | B | C |
| ATOM | 5543 | CD1 | LEU | B | 141 | 76.646 | 41.835 | −29.109 | 1.00 | 31.07 | B | C |
| ATOM | 5544 | CD2 | LEU | B | 141 | 74.202 | 41.262 | −29.108 | 1.00 | 33.04 | B | C |
| ATOM | 5545 | C | LEU | B | 141 | 72.975 | 44.416 | −26.977 | 1.00 | 20.67 | B | C |
| ATOM | 5546 | O | LEU | B | 141 | 71.924 | 43.802 | −26.798 | 1.00 | 20.92 | B | O |
| ATOM | 5547 | N | SER | B | 142 | 73.539 | 45.170 | −26.034 | 1.00 | 20.17 | B | N |
| ATOM | 5548 | CA | SER | B | 142 | 72.915 | 45.332 | −24.718 | 1.00 | 20.30 | B | C |
| ATOM | 5549 | CB | SER | B | 142 | 73.777 | 46.155 | −23.768 | 1.00 | 23.23 | B | C |
| ATOM | 5550 | OG | SER | B | 142 | 74.802 | 45.361 | −23.230 | 1.00 | 30.11 | B | O |
| ATOM | 5551 | C | SER | B | 142 | 71.563 | 45.988 | −24.829 | 1.00 | 18.07 | B | C |
| ATOM | 5552 | O | SER | B | 142 | 70.623 | 45.598 | −24.143 | 1.00 | 15.63 | B | O |
| ATOM | 5553 | N | LEU | B | 143 | 71.466 | 46.976 | −25.707 | 1.00 | 16.54 | B | N |
| ATOM | 5554 | CA | LEU | B | 143 | 70.191 | 47.630 | −25.962 | 1.00 | 17.71 | B | C |
| ATOM | 5555 | CB | LEU | B | 143 | 70.407 | 48.821 | −26.885 | 1.00 | 18.73 | B | C |
| ATOM | 5556 | CG | LEU | B | 143 | 69.179 | 49.672 | −27.189 | 1.00 | 21.91 | B | C |

APPENDIX A-continued

*P. alba* 3T288C coordinates

| ATOM | 5557 | CD1 | LEU | B | 143 | 68.586 | 50.367 | −25.946 | 1.00 | 20.22 | B | C |
|---|---|---|---|---|---|---|---|---|---|---|---|---|
| ATOM | 5558 | CD2 | LEU | B | 143 | 69.575 | 50.688 | −28.256 | 1.00 | 18.60 | B | C |
| ATOM | 5559 | C | LEU | B | 143 | 69.147 | 46.678 | −26.558 | 1.00 | 17.90 | B | C |
| ATOM | 5560 | O | LEU | B | 143 | 67.997 | 46.671 | −26.113 | 1.00 | 19.28 | B | O |
| ATOM | 5561 | N | TYR | B | 144 | 69.539 | 45.899 | −27.568 | 1.00 | 17.16 | B | N |
| ATOM | 5562 | CA | TYR | B | 144 | 68.674 | 44.855 | −28.118 | 1.00 | 19.80 | B | C |
| ATOM | 5563 | CB | TYR | B | 144 | 69.422 | 44.127 | −29.224 | 1.00 | 19.05 | B | C |
| ATOM | 5564 | CG | TYR | B | 144 | 68.797 | 42.874 | −29.747 | 1.00 | 22.04 | B | C |
| ATOM | 5565 | CD1 | TYR | B | 144 | 67.817 | 42.912 | −30.727 | 1.00 | 23.03 | B | C |
| ATOM | 5566 | CE1 | TYR | B | 144 | 67.264 | 41.752 | −31.222 | 1.00 | 25.33 | B | C |
| ATOM | 5567 | CZ | TYR | B | 144 | 67.707 | 40.533 | −30.727 | 1.00 | 27.46 | B | C |
| ATOM | 5568 | OH | TYR | B | 144 | 67.193 | 39.332 | −31.164 | 1.00 | 37.98 | B | O |
| ATOM | 5569 | CE2 | TYR | B | 144 | 68.664 | 40.489 | −29.746 | 1.00 | 27.56 | B | C |
| ATOM | 5570 | CD2 | TYR | B | 144 | 69.197 | 41.648 | −29.266 | 1.00 | 25.78 | B | C |
| ATOM | 5571 | C | TYR | B | 144 | 68.220 | 43.876 | −27.016 | 1.00 | 19.27 | B | C |
| ATOM | 5572 | O | TYR | B | 144 | 67.031 | 43.595 | −26.893 | 1.00 | 16.16 | B | O |
| ATOM | 5573 | N | GLU | B | 145 | 69.146 | 43.409 | −26.172 | 1.00 | 16.42 | B | N |
| ATOM | 5574 | CA | GLU | B | 145 | 68.756 | 42.458 | −25.120 | 1.00 | 16.71 | B | C |
| ATOM | 5575 | CB | GLU | B | 145 | 69.958 | 41.934 | −24.342 | 1.00 | 17.86 | B | C |
| ATOM | 5576 | CG | GLU | B | 145 | 70.968 | 41.099 | −25.175 | 1.00 | 23.74 | B | C |
| ATOM | 5577 | CD | GLU | B | 145 | 70.433 | 39.735 | −25.637 | 1.00 | 27.87 | B | C |
| ATOM | 5578 | OE1 | GLU | B | 145 | 69.241 | 39.407 | −25.369 | 1.00 | 29.72 | B | O |
| ATOM | 5579 | OE2 | GLU | B | 145 | 71.222 | 38.977 | −26.262 | 1.00 | 22.17 | B | O |
| ATOM | 5580 | C | GLU | B | 145 | 67.733 | 43.076 | −24.149 | 1.00 | 15.36 | B | C |
| ATOM | 5581 | O | GLU | B | 145 | 66.758 | 42.433 | −23.782 | 1.00 | 17.00 | B | O |
| ATOM | 5582 | N | ALA | B | 146 | 67.953 | 44.331 | −23.772 | 1.00 | 15.19 | B | N |
| ATOM | 5583 | CA | ALA | B | 146 | 67.097 | 45.031 | −22.816 | 1.00 | 16.77 | B | C |
| ATOM | 5584 | CB | ALA | B | 146 | 67.754 | 46.372 | −22.403 | 1.00 | 15.90 | B | C |
| ATOM | 5585 | C | ALA | B | 146 | 65.670 | 45.259 | −23.376 | 1.00 | 18.70 | B | C |
| ATOM | 5586 | O | ALA | B | 146 | 64.674 | 45.219 | −22.630 | 1.00 | 16.44 | B | O |
| ATOM | 5587 | N | SER | B | 147 | 65.575 | 45.472 | −24.684 | 1.00 | 17.99 | B | N |
| ATOM | 5588 | CA | SER | B | 147 | 64.289 | 45.771 | −25.309 | 1.00 | 19.54 | B | C |
| ATOM | 5589 | CB | SER | B | 147 | 64.482 | 46.091 | −26.810 | 1.00 | 21.52 | B | C |
| ATOM | 5590 | OG | SER | B | 147 | 64.753 | 44.911 | −27.566 | 1.00 | 22.75 | B | O |
| ATOM | 5591 | C | SER | B | 147 | 63.224 | 44.657 | −25.108 | 1.00 | 18.90 | B | C |
| ATOM | 5592 | O | SER | B | 147 | 62.018 | 44.936 | −25.070 | 1.00 | 20.51 | B | O |
| ATOM | 5593 | N | PHE | B | 148 | 63.662 | 43.415 | −24.930 | 1.00 | 17.55 | B | N |
| ATOM | 5594 | CA | PHE | B | 148 | 62.754 | 42.301 | −24.758 | 1.00 | 18.08 | B | C |
| ATOM | 5595 | CB | PHE | B | 148 | 63.436 | 40.969 | −25.122 | 1.00 | 19.55 | B | C |
| ATOM | 5596 | CG | PHE | B | 148 | 63.713 | 40.846 | −26.593 | 1.00 | 17.56 | B | C |
| ATOM | 5597 | CD1 | PHE | B | 148 | 62.733 | 40.350 | −27.460 | 1.00 | 17.90 | B | C |
| ATOM | 5598 | CE1 | PHE | B | 148 | 62.947 | 40.282 | −28.835 | 1.00 | 19.84 | B | C |
| ATOM | 5599 | CZ | PHE | B | 148 | 64.142 | 40.672 | −29.355 | 1.00 | 22.18 | B | C |
| ATOM | 5600 | CE2 | PHE | B | 148 | 65.147 | 41.165 | −28.489 | 1.00 | 21.23 | B | C |
| ATOM | 5601 | CD2 | PHE | B | 148 | 64.908 | 41.241 | −27.113 | 1.00 | 18.18 | B | C |
| ATOM | 5602 | C | PHE | B | 148 | 62.131 | 42.286 | −23.373 | 1.00 | 20.15 | B | C |
| ATOM | 5603 | O | PHE | B | 148 | 61.179 | 41.550 | −23.139 | 1.00 | 16.91 | B | O |
| ATOM | 5604 | N | LEU | B | 149 | 62.610 | 43.146 | −22.466 | 1.00 | 19.45 | B | N |
| ATOM | 5605 | CA | LEU | B | 149 | 61.991 | 43.233 | −21.136 | 1.00 | 17.46 | B | C |
| ATOM | 5606 | CB | LEU | B | 149 | 63.058 | 43.450 | −20.074 | 1.00 | 17.26 | B | C |
| ATOM | 5607 | CG | LEU | B | 149 | 63.793 | 42.153 | −19.705 | 1.00 | 17.95 | B | C |
| ATOM | 5608 | CD1 | LEU | B | 149 | 64.991 | 41.884 | −20.643 | 1.00 | 18.08 | B | C |
| ATOM | 5609 | CD2 | LEU | B | 149 | 64.241 | 42.230 | −18.227 | 1.00 | 16.84 | B | C |
| ATOM | 5610 | C | LEU | B | 149 | 60.885 | 44.267 | −21.062 | 1.00 | 18.68 | B | C |
| ATOM | 5611 | O | LEU | B | 149 | 60.398 | 44.581 | −19.969 | 1.00 | 16.29 | B | O |
| ATOM | 5612 | N | ALA | B | 150 | 60.452 | 44.760 | −22.232 | 1.00 | 18.92 | B | N |
| ATOM | 5613 | CA | ALA | B | 150 | 59.486 | 45.834 | −22.293 | 1.00 | 21.18 | B | C |
| ATOM | 5614 | CB | ALA | B | 150 | 59.368 | 46.350 | −23.730 | 1.00 | 20.05 | B | C |
| ATOM | 5615 | C | ALA | B | 150 | 58.108 | 45.418 | −21.764 | 1.00 | 21.68 | B | C |
| ATOM | 5616 | O | ALA | B | 150 | 57.698 | 44.242 | −21.839 | 1.00 | 21.33 | B | O |
| ATOM | 5617 | N | LEU | B | 151 | 57.405 | 46.408 | −21.241 | 1.00 | 19.58 | B | N |
| ATOM | 5618 | CA | LEU | B | 151 | 56.006 | 46.317 | −20.869 | 1.00 | 21.35 | B | C |
| ATOM | 5619 | CB | LEU | B | 151 | 55.788 | 46.978 | −19.504 | 1.00 | 23.78 | B | C |
| ATOM | 5620 | CG | LEU | B | 151 | 56.706 | 46.538 | −18.361 | 1.00 | 27.90 | B | C |
| ATOM | 5621 | CD1 | LEU | B | 151 | 56.345 | 47.224 | −17.046 | 1.00 | 23.70 | B | C |
| ATOM | 5622 | CD2 | LEU | B | 151 | 56.694 | 45.043 | −18.178 | 1.00 | 22.80 | B | C |
| ATOM | 5623 | C | LEU | B | 151 | 55.156 | 47.052 | −21.920 | 1.00 | 20.12 | B | C |
| ATOM | 5624 | O | LEU | B | 151 | 55.680 | 47.794 | −22.746 | 1.00 | 24.87 | B | O |
| ATOM | 5625 | N | GLU | B | 152 | 53.846 | 46.847 | −21.889 | 1.00 | 19.20 | B | N |
| ATOM | 5626 | CA | GLU | B | 152 | 52.956 | 47.556 | −22.823 | 1.00 | 23.41 | B | C |
| ATOM | 5627 | CB | GLU | B | 152 | 51.509 | 47.169 | −22.577 | 1.00 | 29.93 | B | C |
| ATOM | 5628 | CG | GLU | B | 152 | 51.081 | 45.890 | −23.215 | 1.00 | 42.29 | B | C |
| ATOM | 5629 | CD | GLU | B | 152 | 49.564 | 45.763 | −23.216 | 1.00 | 51.02 | B | C |
| ATOM | 5630 | OE1 | GLU | B | 152 | 48.910 | 46.406 | −24.063 | 1.00 | 46.01 | B | O |
| ATOM | 5631 | OE2 | GLU | B | 152 | 49.036 | 45.042 | −22.350 | 1.00 | 48.21 | B | O |
| ATOM | 5632 | C | GLU | B | 152 | 53.082 | 49.065 | −22.609 | 1.00 | 22.58 | B | C |
| ATOM | 5633 | O | GLU | B | 152 | 53.146 | 49.515 | −21.465 | 1.00 | 21.70 | B | O |
| ATOM | 5634 | N | GLY | B | 153 | 53.146 | 49.822 | −23.695 | 1.00 | 24.58 | B | N |

APPENDIX A-continued

P. alba 3T288C coordinates

| ATOM | 5635 | CA | GLY | B | 153 | 53.226 | 51.285 | −23.635 | 1.00 | 24.61 | B | C |
| ATOM | 5636 | C | GLY | B | 153 | 54.660 | 51.812 | −23.622 | 1.00 | 27.73 | B | C |
| ATOM | 5637 | O | GLY | B | 153 | 54.876 | 53.011 | −23.701 | 1.00 | 26.02 | B | O |
| ATOM | 5638 | N | GLU | B | 154 | 55.657 | 50.929 | −23.517 | 1.00 | 23.81 | B | N |
| ATOM | 5639 | CA | GLU | B | 154 | 57.041 | 51.368 | −23.509 | 1.00 | 22.75 | B | C |
| ATOM | 5640 | CB | GLU | B | 154 | 57.900 | 50.488 | −22.600 | 1.00 | 27.37 | B | C |
| ATOM | 5641 | CG | GLU | B | 154 | 57.580 | 50.713 | −21.102 | 1.00 | 27.77 | B | C |
| ATOM | 5642 | CD | GLU | B | 154 | 58.439 | 49.874 | −20.166 | 1.00 | 28.06 | B | C |
| ATOM | 5643 | OE1 | GLU | B | 154 | 58.954 | 48.821 | −20.597 | 1.00 | 28.68 | B | O |
| ATOM | 5644 | OE2 | GLU | B | 154 | 58.601 | 50.253 | −18.984 | 1.00 | 27.35 | B | O |
| ATOM | 5645 | C | GLU | B | 154 | 57.555 | 51.450 | −24.949 | 1.00 | 26.56 | B | C |
| ATOM | 5646 | O | GLU | B | 154 | 58.352 | 50.647 | −25.410 | 1.00 | 19.20 | B | O |
| ATOM | 5647 | N | ASN | B | 155 | 57.086 | 52.480 | −25.648 | 1.00 | 30.84 | B | N |
| ATOM | 5648 | CA | ASN | B | 155 | 57.417 | 52.689 | −27.050 | 1.00 | 25.67 | B | C |
| ATOM | 5649 | CB | ASN | B | 155 | 56.641 | 53.907 | −27.574 | 1.00 | 28.27 | B | C |
| ATOM | 5650 | CG | ASN | B | 155 | 56.924 | 55.162 | −26.758 | 1.00 | 32.90 | B | C |
| ATOM | 5651 | OD1 | ASN | B | 155 | 56.439 | 55.307 | −25.636 | 1.00 | 31.26 | B | O |
| ATOM | 5652 | ND2 | ASN | B | 155 | 57.741 | 56.055 | −27.303 | 1.00 | 36.59 | B | N |
| ATOM | 5653 | C | ASN | B | 155 | 58.913 | 52.902 | −27.304 | 1.00 | 23.66 | B | C |
| ATOM | 5654 | O | ASN | B | 155 | 59.417 | 52.539 | −28.365 | 1.00 | 27.16 | B | O |
| ATOM | 5655 | N | ILE | B | 156 | 59.626 | 53.500 | −26.351 | 1.00 | 22.77 | B | N |
| ATOM | 5656 | CA | ILE | B | 156 | 61.063 | 53.706 | −26.506 | 1.00 | 21.62 | B | C |
| ATOM | 5657 | CB | ILE | B | 156 | 61.690 | 54.544 | −25.351 | 1.00 | 27.45 | B | C |
| ATOM | 5658 | CG1 | ILE | B | 156 | 61.075 | 55.949 | −25.305 | 1.00 | 27.27 | B | C |
| ATOM | 5659 | CD1 | ILE | B | 156 | 61.899 | 56.951 | −24.487 | 1.00 | 26.26 | B | C |
| ATOM | 5660 | CG2 | ILE | B | 156 | 63.182 | 54.702 | −25.563 | 1.00 | 22.98 | B | C |
| ATOM | 5661 | C | ILE | B | 156 | 61.805 | 52.384 | −26.634 | 1.00 | 22.91 | B | C |
| ATOM | 5662 | O | ILE | B | 156 | 62.715 | 52.268 | −27.456 | 1.00 | 24.66 | B | O |
| ATOM | 5663 | N | LEU | B | 157 | 61.409 | 51.382 | −25.843 | 1.00 | 24.03 | B | N |
| ATOM | 5664 | CA | LEU | B | 157 | 62.023 | 50.062 | −25.927 | 1.00 | 24.42 | B | C |
| ATOM | 5665 | CB | LEU | B | 157 | 61.569 | 49.153 | −24.770 | 1.00 | 21.56 | B | C |
| ATOM | 5666 | CG | LEU | B | 157 | 61.977 | 49.634 | −23.378 | 1.00 | 26.08 | B | C |
| ATOM | 5667 | CD1 | LEU | B | 157 | 61.751 | 48.552 | −22.330 | 1.00 | 27.55 | B | C |
| ATOM | 5668 | CD2 | LEU | B | 157 | 63.413 | 50.040 | −23.385 | 1.00 | 26.42 | B | C |
| ATOM | 5669 | C | LEU | B | 157 | 61.722 | 49.397 | −27.254 | 1.00 | 23.32 | B | C |
| ATOM | 5670 | O | LEU | B | 157 | 62.597 | 48.762 | −27.832 | 1.00 | 23.85 | B | O |
| ATOM | 5671 | N | ASP | B | 158 | 60.492 | 49.545 | −27.740 | 1.00 | 22.27 | B | N |
| ATOM | 5672 | CA | ASP | B | 158 | 60.148 | 49.059 | −29.075 | 1.00 | 25.95 | B | C |
| ATOM | 5673 | CB | ASP | B | 158 | 58.651 | 49.287 | −29.352 | 1.00 | 27.41 | B | C |
| ATOM | 5674 | CG | ASP | B | 158 | 57.754 | 48.257 | −28.632 | 1.00 | 41.98 | B | C |
| ATOM | 5675 | OD1 | ASP | B | 158 | 58.256 | 47.220 | −28.150 | 1.00 | 46.41 | B | O |
| ATOM | 5676 | OD2 | ASP | B | 158 | 56.535 | 48.476 | −28.544 | 1.00 | 45.63 | B | O |
| ATOM | 5677 | C | ASP | B | 158 | 61.017 | 49.710 | −30.155 | 1.00 | 22.57 | B | C |
| ATOM | 5678 | O | ASP | B | 158 | 61.518 | 49.045 | −31.062 | 1.00 | 22.80 | B | O |
| ATOM | 5679 | N | GLU | B | 159 | 61.216 | 51.007 | −30.022 | 1.00 | 25.58 | B | N |
| ATOM | 5680 | CA | GLU | B | 159 | 62.062 | 51.764 | −30.941 | 1.00 | 29.22 | B | C |
| ATOM | 5681 | CB | GLU | B | 159 | 61.980 | 53.261 | −30.619 | 1.00 | 33.36 | B | C |
| ATOM | 5682 | CG | GLU | B | 159 | 60.610 | 53.898 | −30.909 | 1.00 | 42.11 | B | C |
| ATOM | 5683 | CD | GLU | B | 159 | 60.382 | 55.249 | −30.206 | 1.00 | 43.81 | B | C |
| ATOM | 5684 | OE1 | GLU | B | 159 | 61.347 | 56.017 | −29.991 | 1.00 | 48.43 | B | O |
| ATOM | 5685 | OE2 | GLU | B | 159 | 59.213 | 55.547 | −29.882 | 1.00 | 51.64 | B | O |
| ATOM | 5686 | C | GLU | B | 159 | 63.513 | 51.275 | −30.836 | 1.00 | 26.50 | B | C |
| ATOM | 5687 | O | GLU | B | 159 | 64.193 | 51.124 | −31.843 | 1.00 | 22.26 | B | O |
| ATOM | 5688 | N | ALA | B | 160 | 63.971 | 51.011 | −29.614 | 1.00 | 22.74 | B | N |
| ATOM | 5689 | CA | ALA | B | 160 | 65.339 | 50.514 | −29.408 | 1.00 | 25.08 | B | C |
| ATOM | 5690 | CB | ALA | B | 160 | 65.658 | 50.332 | −27.919 | 1.00 | 26.19 | B | C |
| ATOM | 5691 | C | ALA | B | 160 | 65.571 | 49.214 | −30.143 | 1.00 | 25.21 | B | C |
| ATOM | 5692 | O | ALA | B | 160 | 66.610 | 49.051 | −30.778 | 1.00 | 24.90 | B | O |
| ATOM | 5693 | N | LYS | B | 161 | 64.607 | 48.295 | −30.060 | 1.00 | 22.51 | B | N |
| ATOM | 5694 | CA | LYS | B | 161 | 64.740 | 47.011 | −30.734 | 1.00 | 24.00 | B | C |
| ATOM | 5695 | CB | LYS | B | 161 | 63.550 | 46.091 | −30.422 | 1.00 | 24.85 | B | C |
| ATOM | 5696 | CG | LYS | B | 161 | 63.715 | 44.676 | −30.956 | 1.00 | 25.57 | B | C |
| ATOM | 5697 | CD | LYS | B | 161 | 62.422 | 43.873 | −30.927 | 1.00 | 30.04 | B | C |
| ATOM | 5698 | CE | LYS | B | 161 | 61.946 | 43.588 | −29.482 | 1.00 | 30.85 | B | C |
| ATOM | 5699 | NZ | LYS | B | 161 | 60.562 | 42.972 | −29.451 | 1.00 | 32.20 | B | N |
| ATOM | 5700 | C | LYS | B | 161 | 64.884 | 47.200 | −32.245 | 1.00 | 21.81 | B | C |
| ATOM | 5701 | O | LYS | B | 161 | 65.754 | 46.590 | −32.866 | 1.00 | 21.50 | B | O |
| ATOM | 5702 | N | VAL | B | 162 | 64.036 | 48.052 | −32.813 | 1.00 | 23.96 | B | N |
| ATOM | 5703 | CA | VAL | B | 162 | 64.039 | 48.303 | −34.258 | 1.00 | 24.15 | B | C |
| ATOM | 5704 | CB | VAL | B | 162 | 62.855 | 49.245 | −34.678 | 1.00 | 22.34 | B | C |
| ATOM | 5705 | CG1 | VAL | B | 162 | 63.017 | 49.744 | −36.132 | 1.00 | 21.25 | B | C |
| ATOM | 5706 | CG2 | VAL | B | 162 | 61.506 | 48.522 | −34.475 | 1.00 | 21.74 | B | C |
| ATOM | 5707 | C | VAL | B | 162 | 65.395 | 48.884 | −34.642 | 1.00 | 25.05 | B | C |
| ATOM | 5708 | O | VAL | B | 162 | 66.068 | 48.377 | −35.545 | 1.00 | 26.49 | B | O |
| ATOM | 5709 | N | PHE | B | 163 | 65.804 | 49.924 | −33.923 | 1.00 | 24.34 | B | N |
| ATOM | 5710 | CA | PHE | B | 163 | 67.139 | 50.515 | −34.082 | 1.00 | 24.16 | B | C |
| ATOM | 5711 | CB | PHE | B | 163 | 67.339 | 51.619 | −33.040 | 1.00 | 24.78 | B | C |
| ATOM | 5712 | CG | PHE | B | 163 | 68.696 | 52.250 | −33.061 | 1.00 | 24.62 | B | C |

APPENDIX A-continued

*P. alba* 3T288C coordinates

| ATOM | 5713 | CD1 | PHE | B | 163 | 69.011 | 53.217 | −34.004 | 1.00 | 31.24 | B | C |
|------|------|-----|-----|---|-----|--------|--------|---------|------|-------|---|---|
| ATOM | 5714 | CE1 | PHE | B | 163 | 70.252 | 53.814 | −34.016 | 1.00 | 29.93 | B | C |
| ATOM | 5715 | CZ | PHE | B | 163 | 71.214 | 53.454 | −33.065 | 1.00 | 32.86 | B | C |
| ATOM | 5716 | CE2 | PHE | B | 163 | 70.919 | 52.494 | −32.121 | 1.00 | 31.64 | B | C |
| ATOM | 5717 | CD2 | PHE | B | 163 | 69.655 | 51.901 | −32.115 | 1.00 | 29.49 | B | C |
| ATOM | 5718 | C | PHE | B | 163 | 68.271 | 49.495 | −33.981 | 1.00 | 26.28 | B | C |
| ATOM | 5719 | O | PHE | B | 163 | 69.100 | 49.391 | −34.889 | 1.00 | 24.95 | B | O |
| ATOM | 5720 | N | ALA | B | 164 | 68.320 | 48.751 | −32.876 | 1.00 | 25.01 | B | N |
| ATOM | 5721 | CA | ALA | B | 164 | 69.425 | 47.832 | −32.638 | 1.00 | 21.33 | B | C |
| ATOM | 5722 | CB | ALA | B | 164 | 69.322 | 47.173 | −31.206 | 1.00 | 21.86 | B | C |
| ATOM | 5723 | C | ALA | B | 164 | 69.504 | 46.751 | −33.704 | 1.00 | 19.03 | B | C |
| ATOM | 5724 | O | ALA | B | 164 | 70.586 | 46.467 | −34.213 | 1.00 | 21.68 | B | O |
| ATOM | 5725 | N | ILE | B | 165 | 68.373 | 46.131 | −34.026 | 1.00 | 21.18 | B | N |
| ATOM | 5726 | CA | ILE | B | 165 | 68.323 | 45.060 | −35.045 | 1.00 | 25.74 | B | C |
| ATOM | 5727 | CB | ILE | B | 165 | 66.890 | 44.534 | −35.246 | 1.00 | 32.13 | B | C |
| ATOM | 5728 | CG1 | ILE | B | 165 | 66.488 | 43.594 | −34.114 | 1.00 | 37.00 | B | C |
| ATOM | 5729 | CD1 | ILE | B | 165 | 64.986 | 43.262 | −34.103 | 1.00 | 31.74 | B | C |
| ATOM | 5730 | CG2 | ILE | B | 165 | 66.749 | 43.785 | −36.570 | 1.00 | 36.42 | B | C |
| ATOM | 5731 | C | ILE | B | 165 | 68.871 | 45.550 | −36.405 | 1.00 | 28.32 | B | C |
| ATOM | 5732 | O | ILE | B | 165 | 69.575 | 44.812 | −37.100 | 1.00 | 25.65 | B | O |
| ATOM | 5733 | N | SER | B | 166 | 68.572 | 46.800 | −36.757 | 1.00 | 31.22 | B | N |
| ATOM | 5734 | CA | ASER | B | 166 | 69.023 | 47.393 | −38.027 | 0.50 | 31.91 | B | C |
| ATOM | 5735 | CA | BSER | B | 166 | 69.022 | 47.367 | −38.033 | 0.50 | 33.95 | B | C |
| ATOM | 5736 | CB | ASER | B | 166 | 68.533 | 48.843 | −38.167 | 0.50 | 27.64 | B | C |
| ATOM | 5737 | CB | BSER | B | 166 | 68.491 | 48.787 | −38.213 | 0.50 | 31.99 | B | C |
| ATOM | 5738 | OG | ASER | B | 166 | 69.361 | 49.750 | −37.451 | 0.50 | 23.79 | B | O |
| ATOM | 5739 | OG | BSER | B | 166 | 67.081 | 48.793 | −38.137 | 0.50 | 32.33 | B | O |
| ATOM | 5740 | C | SER | B | 166 | 70.539 | 47.374 | −38.154 | 1.00 | 33.66 | B | C |
| ATOM | 5741 | O | SER | B | 166 | 71.077 | 47.051 | −39.205 | 1.00 | 34.05 | B | O |
| ATOM | 5742 | N | HIS | B | 167 | 71.223 | 47.729 | −37.074 | 1.00 | 33.02 | B | N |
| ATOM | 5743 | CA | HIS | B | 167 | 72.675 | 47.835 | −37.121 | 1.00 | 34.21 | B | C |
| ATOM | 5744 | CB | HIS | B | 167 | 73.151 | 48.973 | −36.214 | 1.00 | 33.91 | B | C |
| ATOM | 5745 | CG | HIS | B | 167 | 72.612 | 50.339 | −36.628 | 1.00 | 45.20 | B | C |
| ATOM | 5746 | ND1 | HIS | B | 167 | 72.967 | 50.938 | −37.785 | 1.00 | 48.79 | B | N |
| ATOM | 5747 | CE1 | HIS | B | 167 | 72.322 | 52.119 | −37.898 | 1.00 | 47.04 | B | C |
| ATOM | 5748 | NE2 | HIS | B | 167 | 71.547 | 52.277 | −36.812 | 1.00 | 50.51 | B | N |
| ATOM | 5749 | CD2 | HIS | B | 167 | 71.697 | 51.197 | −36.009 | 1.00 | 48.48 | B | C |
| ATOM | 5750 | C | HIS | B | 167 | 73.355 | 46.525 | −36.836 | 1.00 | 34.42 | B | C |
| ATOM | 5751 | O | HIS | B | 167 | 74.508 | 46.339 | −37.218 | 1.00 | 37.01 | B | O |
| ATOM | 5752 | N | LEU | B | 168 | 72.646 | 45.588 | −36.204 | 1.00 | 32.96 | B | N |
| ATOM | 5753 | CA | LEU | B | 168 | 73.216 | 44.270 | −35.896 | 1.00 | 28.12 | B | C |
| ATOM | 5754 | CB | LEU | B | 168 | 72.470 | 43.593 | −34.725 | 1.00 | 25.45 | B | C |
| ATOM | 5755 | CG | LEU | B | 168 | 72.682 | 44.212 | −33.331 | 1.00 | 26.35 | B | C |
| ATOM | 5756 | CD1 | LEU | B | 168 | 71.704 | 43.639 | −32.309 | 1.00 | 26.86 | B | C |
| ATOM | 5757 | CD2 | LEU | B | 168 | 74.113 | 44.036 | −32.855 | 1.00 | 21.75 | B | C |
| ATOM | 5758 | C | LEU | B | 168 | 73.262 | 43.328 | −37.108 | 1.00 | 32.22 | B | C |
| ATOM | 5759 | O | LEU | B | 168 | 74.273 | 42.653 | −37.329 | 1.00 | 36.39 | B | O |
| ATOM | 5760 | N | LYS | B | 169 | 72.191 | 43.259 | −37.889 | 1.00 | 34.18 | B | N |
| ATOM | 5761 | CA | LYS | B | 169 | 72.147 | 42.236 | −38.950 | 1.00 | 48.30 | B | C |
| ATOM | 5762 | CB | LYS | B | 169 | 70.714 | 41.853 | −39.357 | 1.00 | 53.20 | B | C |
| ATOM | 5763 | CG | LYS | B | 169 | 69.813 | 42.939 | −39.906 | 1.00 | 58.88 | B | C |
| ATOM | 5764 | CD | LYS | B | 169 | 68.360 | 42.442 | −39.832 | 1.00 | 68.90 | B | C |
| ATOM | 5765 | CE | LYS | B | 169 | 67.344 | 43.516 | −40.162 | 1.00 | 70.33 | B | C |
| ATOM | 5766 | NZ | LYS | B | 169 | 67.345 | 43.859 | −41.605 | 1.00 | 68.49 | B | N |
| ATOM | 5767 | C | LYS | B | 169 | 73.025 | 42.535 | −40.167 | 1.00 | 45.13 | B | C |
| ATOM | 5768 | O | LYS | B | 169 | 73.391 | 41.630 | −40.912 | 1.00 | 43.68 | B | O |
| ATOM | 5769 | N | GLU | B | 170 | 73.417 | 43.783 | −40.342 | 1.00 | 42.63 | B | N |
| ATOM | 5770 | CA | GLU | B | 170 | 74.257 | 44.114 | −41.484 | 1.00 | 56.02 | B | C |
| ATOM | 5771 | CB | GLU | B | 170 | 73.871 | 45.483 | −42.039 | 1.00 | 60.46 | B | C |
| ATOM | 5772 | CG | GLU | B | 170 | 74.152 | 46.645 | −41.096 | 1.00 | 69.20 | B | C |
| ATOM | 5773 | CD | GLU | B | 170 | 73.483 | 47.941 | −41.527 | 1.00 | 77.95 | B | C |
| ATOM | 5774 | OE1 | GLU | B | 170 | 72.775 | 47.954 | −42.559 | 1.00 | 83.41 | B | O |
| ATOM | 5775 | OE2 | GLU | B | 170 | 73.667 | 48.955 | −40.823 | 1.00 | 76.71 | B | O |
| ATOM | 5776 | C | GLU | B | 170 | 75.745 | 44.062 | −41.126 | 1.00 | 54.62 | B | C |
| ATOM | 5777 | O | GLU | B | 170 | 76.570 | 44.610 | −41.852 | 1.00 | 59.09 | B | O |
| ATOM | 5778 | N | LEU | B | 171 | 76.089 | 43.398 | −40.023 | 1.00 | 52.49 | B | N |
| ATOM | 5779 | CA | LEU | B | 171 | 77.473 | 43.384 | −39.535 | 1.00 | 48.96 | B | C |
| ATOM | 5780 | CB | LEU | B | 171 | 77.527 | 43.246 | −38.012 | 1.00 | 47.66 | B | C |
| ATOM | 5781 | CG | LEU | B | 171 | 77.149 | 44.474 | −37.190 | 1.00 | 50.18 | B | C |
| ATOM | 5782 | CD1 | LEU | B | 171 | 77.310 | 44.165 | −35.705 | 1.00 | 52.90 | B | C |
| ATOM | 5783 | CD2 | LEU | B | 171 | 77.975 | 45.689 | −37.577 | 1.00 | 40.88 | B | C |
| ATOM | 5784 | C | LEU | B | 171 | 78.299 | 42.265 | −40.151 | 1.00 | 50.12 | B | C |
| ATOM | 5785 | O | LEU | B | 171 | 77.885 | 41.107 | −40.152 | 1.00 | 47.31 | B | O |
| ATOM | 5786 | N | SER | B | 172 | 79.484 | 42.632 | −40.640 | 1.00 | 50.94 | B | N |
| ATOM | 5787 | CA | SER | B | 172 | 80.434 | 41.693 | −41.222 | 1.00 | 51.81 | B | C |
| ATOM | 5788 | CB | SER | B | 172 | 81.237 | 42.397 | −42.327 | 1.00 | 55.69 | B | C |
| ATOM | 5789 | OG | SER | B | 172 | 82.034 | 41.484 | −43.058 | 1.00 | 57.01 | B | O |
| ATOM | 5790 | C | SER | B | 172 | 81.387 | 41.182 | −40.146 | 1.00 | 42.54 | B | C |

APPENDIX A-continued

*P. alba* 3T288C coordinates

| ATOM | 5791 | O | SER | B | 172 | 81.985 | 41.983 | −39.419 | 1.00 | 44.20 | B | O |
|---|---|---|---|---|---|---|---|---|---|---|---|---|
| ATOM | 5792 | N | GLU | B | 173 | 81.533 | 39.858 | −40.048 | 1.00 | 42.14 | B | N |
| ATOM | 5793 | CA | GLU | B | 173 | 82.523 | 39.245 | −39.148 | 1.00 | 49.56 | B | C |
| ATOM | 5794 | CB | GLU | B | 173 | 82.579 | 37.724 | −39.349 | 1.00 | 58.65 | B | C |
| ATOM | 5795 | CG | GLU | B | 173 | 83.863 | 37.069 | −38.808 | 1.00 | 69.97 | B | C |
| ATOM | 5796 | CD | GLU | B | 173 | 83.738 | 35.574 | −38.576 | 1.00 | 74.14 | B | C |
| ATOM | 5797 | OE1 | GLU | B | 173 | 82.704 | 34.977 | −38.947 | 1.00 | 77.61 | B | O |
| ATOM | 5798 | OE2 | GLU | B | 173 | 84.688 | 34.994 | −38.011 | 1.00 | 83.80 | B | O |
| ATOM | 5799 | C | GLU | B | 173 | 83.909 | 39.851 | −39.367 | 1.00 | 51.07 | B | C |
| ATOM | 5800 | O | GLU | B | 173 | 84.649 | 40.113 | −38.410 | 1.00 | 40.49 | B | O |
| ATOM | 5801 | N | GLU | B | 174 | 84.241 | 40.048 | −40.642 | 1.00 | 59.07 | B | N |
| ATOM | 5802 | CA | GLU | B | 174 | 85.445 | 40.753 | −41.054 | 1.00 | 57.26 | B | C |
| ATOM | 5803 | CB | GLU | B | 174 | 85.308 | 41.184 | −42.514 | 1.00 | 70.84 | B | C |
| ATOM | 5804 | CG | GLU | B | 174 | 85.534 | 40.070 | −43.512 | 1.00 | 75.42 | B | C |
| ATOM | 5805 | CD | GLU | B | 174 | 87.006 | 39.780 | −43.695 | 1.00 | 76.79 | B | C |
| ATOM | 5806 | OE1 | GLU | B | 174 | 87.636 | 40.410 | −44.571 | 1.00 | 71.71 | B | O |
| ATOM | 5807 | OE2 | GLU | B | 174 | 87.536 | 38.931 | −42.949 | 1.00 | 74.53 | B | O |
| ATOM | 5808 | C | GLU | B | 174 | 85.696 | 41.986 | −40.202 | 1.00 | 55.82 | B | C |
| ATOM | 5809 | O | GLU | B | 174 | 86.756 | 42.128 | −39.589 | 1.00 | 53.13 | B | O |
| ATOM | 5810 | N | LYS | B | 175 | 84.703 | 42.865 | −40.155 | 1.00 | 59.43 | B | N |
| ATOM | 5811 | CA | LYS | B | 175 | 84.865 | 44.163 | −39.511 | 1.00 | 59.17 | B | C |
| ATOM | 5812 | CB | LYS | B | 175 | 83.782 | 45.132 | −39.989 | 1.00 | 67.78 | B | C |
| ATOM | 5813 | CG | LYS | B | 175 | 83.866 | 45.355 | −41.489 | 1.00 | 79.99 | B | C |
| ATOM | 5814 | CD | LYS | B | 175 | 82.941 | 46.430 | −42.009 | 1.00 | 87.78 | B | C |
| ATOM | 5815 | CE | LYS | B | 175 | 83.024 | 46.483 | −43.530 | 1.00 | 79.47 | B | C |
| ATOM | 5816 | NZ | LYS | B | 175 | 82.498 | 47.758 | −44.087 | 1.00 | 82.96 | B | N |
| ATOM | 5817 | C | LYS | B | 175 | 84.898 | 44.074 | −37.990 | 1.00 | 52.80 | B | C |
| ATOM | 5818 | O | LYS | B | 175 | 85.698 | 44.756 | −37.354 | 1.00 | 46.32 | B | O |
| ATOM | 5819 | N | ILE | B | 176 | 84.065 | 43.216 | −37.403 | 1.00 | 47.03 | B | N |
| ATOM | 5820 | CA | ILE | B | 176 | 83.947 | 43.172 | −35.934 | 1.00 | 41.39 | B | C |
| ATOM | 5821 | CB | ILE | B | 176 | 82.467 | 43.162 | −35.483 | 1.00 | 37.31 | B | C |
| ATOM | 5822 | CG1 | ILE | B | 176 | 81.765 | 41.858 | −35.896 | 1.00 | 40.17 | B | C |
| ATOM | 5823 | CD1 | ILE | B | 176 | 80.314 | 41.783 | −35.465 | 1.00 | 36.72 | B | C |
| ATOM | 5824 | CG2 | ILE | B | 176 | 81.740 | 44.395 | −36.034 | 1.00 | 32.47 | B | C |
| ATOM | 5825 | C | ILE | B | 176 | 84.721 | 42.042 | −35.233 | 1.00 | 38.72 | B | C |
| ATOM | 5826 | O | ILE | B | 176 | 84.978 | 42.124 | −34.029 | 1.00 | 36.23 | B | O |
| ATOM | 5827 | N | GLY | B | 177 | 85.083 | 40.996 | −35.974 | 1.00 | 37.16 | B | N |
| ATOM | 5828 | CA | GLY | B | 177 | 85.806 | 39.860 | −35.401 | 1.00 | 38.29 | B | C |
| ATOM | 5829 | C | GLY | B | 177 | 84.880 | 38.695 | −35.094 | 1.00 | 44.77 | B | C |
| ATOM | 5830 | O | GLY | B | 177 | 83.673 | 38.878 | −34.937 | 1.00 | 41.96 | B | O |
| ATOM | 5831 | N | LYS | B | 178 | 85.468 | 37.504 | −34.985 | 1.00 | 43.62 | B | N |
| ATOM | 5832 | CA | LYS | B | 178 | 84.735 | 36.235 | −34.868 | 1.00 | 41.16 | B | C |
| ATOM | 5833 | CB | LYS | B | 178 | 85.733 | 35.073 | −34.955 | 1.00 | 45.58 | B | C |
| ATOM | 5834 | CG | LYS | B | 178 | 85.133 | 33.675 | −34.886 | 1.00 | 52.04 | B | C |
| ATOM | 5835 | CD | LYS | B | 178 | 86.235 | 32.622 | −34.939 | 1.00 | 60.26 | B | C |
| ATOM | 5836 | CE | LYS | B | 178 | 85.712 | 31.238 | −34.594 | 1.00 | 65.99 | B | C |
| ATOM | 5837 | NZ | LYS | B | 178 | 84.777 | 30.719 | −35.620 | 1.00 | 68.96 | B | N |
| ATOM | 5838 | C | LYS | B | 178 | 83.910 | 36.127 | −33.578 | 1.00 | 33.31 | B | C |
| ATOM | 5839 | O | LYS | B | 178 | 82.724 | 35.832 | −33.619 | 1.00 | 33.33 | B | O |
| ATOM | 5840 | N | GLU | B | 179 | 84.563 | 36.366 | −32.447 | 1.00 | 35.34 | B | N |
| ATOM | 5841 | CA | GLU | B | 179 | 83.946 | 36.349 | −31.121 | 1.00 | 42.45 | B | C |
| ATOM | 5842 | CB | GLU | B | 179 | 85.001 | 36.767 | −30.100 | 1.00 | 45.16 | B | C |
| ATOM | 5843 | CG | GLU | B | 179 | 84.500 | 37.192 | −28.740 | 1.00 | 57.61 | B | C |
| ATOM | 5844 | CD | GLU | B | 179 | 85.651 | 37.498 | −27.792 | 1.00 | 71.05 | B | C |
| ATOM | 5845 | OE1 | GLU | B | 179 | 86.814 | 37.166 | −28.129 | 1.00 | 62.84 | B | O |
| ATOM | 5846 | OE2 | GLU | B | 179 | 85.398 | 38.077 | −26.713 | 1.00 | 92.44 | B | O |
| ATOM | 5847 | C | GLU | B | 179 | 82.705 | 37.247 | −31.028 | 1.00 | 43.58 | B | C |
| ATOM | 5848 | O | GLU | B | 179 | 81.631 | 36.815 | −30.558 | 1.00 | 34.19 | B | O |
| ATOM | 5849 | N | LEU | B | 180 | 82.846 | 38.483 | −31.497 | 1.00 | 36.50 | B | N |
| ATOM | 5850 | CA | LEU | B | 180 | 81.737 | 39.417 | −31.473 | 1.00 | 35.40 | B | C |
| ATOM | 5851 | CB | LEU | B | 180 | 82.231 | 40.848 | −31.626 | 1.00 | 38.16 | B | C |
| ATOM | 5852 | CG | LEU | B | 180 | 81.318 | 41.863 | −30.940 | 1.00 | 40.07 | B | C |
| ATOM | 5853 | CD1 | LEU | B | 180 | 81.242 | 41.604 | −29.421 | 1.00 | 37.91 | B | C |
| ATOM | 5854 | CD2 | LEU | B | 180 | 81.786 | 43.286 | −31.253 | 1.00 | 37.86 | B | C |
| ATOM | 5855 | C | LEU | B | 180 | 80.645 | 39.067 | −32.508 | 1.00 | 37.86 | B | C |
| ATOM | 5856 | O | LEU | B | 180 | 79.455 | 39.223 | −32.224 | 1.00 | 34.14 | B | O |
| ATOM | 5857 | N | ALA | B | 181 | 81.027 | 38.554 | −33.677 | 1.00 | 38.02 | B | N |
| ATOM | 5858 | CA | ALA | B | 181 | 80.029 | 38.064 | −34.650 | 1.00 | 30.09 | B | C |
| ATOM | 5859 | CB | ALA | B | 181 | 80.692 | 37.689 | −35.963 | 1.00 | 29.54 | B | C |
| ATOM | 5860 | C | ALA | B | 181 | 79.244 | 36.869 | −34.099 | 1.00 | 28.27 | B | C |
| ATOM | 5861 | O | ALA | B | 181 | 78.053 | 36.704 | −34.385 | 1.00 | 23.95 | B | O |
| ATOM | 5862 | N | GLU | B | 182 | 79.908 | 36.013 | −33.331 | 1.00 | 27.80 | B | N |
| ATOM | 5863 | CA | GLU | B | 182 | 79.213 | 34.871 | −32.740 | 1.00 | 31.93 | B | C |
| ATOM | 5864 | CB | GLU | B | 182 | 80.199 | 33.842 | −32.161 | 1.00 | 37.75 | B | C |
| ATOM | 5865 | CG | GLU | B | 182 | 80.576 | 32.728 | −33.159 | 1.00 | 46.68 | B | C |
| ATOM | 5866 | CD | GLU | B | 182 | 82.013 | 32.202 | −32.999 | 1.00 | 56.06 | B | C |
| ATOM | 5867 | OE1 | GLU | B | 182 | 82.650 | 32.451 | −31.950 | 1.00 | 57.60 | B | O |
| ATOM | 5868 | OE2 | GLU | B | 182 | 82.510 | 31.538 | −33.937 | 1.00 | 62.66 | B | O |

APPENDIX A-continued

*P. alba* 3T288C coordinates

| ATOM | 5869 | C | GLU | B | 182 | 78.214 | 35.371 | −31.687 | 1.00 | 25.88 | B | C |
|------|------|------|------|---|-----|--------|--------|---------|------|-------|---|---|
| ATOM | 5870 | O | GLU | B | 182 | 77.116 | 34.850 | −31.595 | 1.00 | 26.72 | B | O |
| ATOM | 5871 | N | GLN | B | 183 | 78.590 | 36.398 | −30.925 | 1.00 | 24.20 | B | N |
| ATOM | 5872 | CA | GLN | B | 183 | 77.686 | 36.984 | −29.935 | 1.00 | 22.87 | B | C |
| ATOM | 5873 | CB | GLN | B | 183 | 78.387 | 38.040 | −29.052 | 1.00 | 23.49 | B | C |
| ATOM | 5874 | CG | GLN | B | 183 | 79.385 | 37.484 | −27.988 | 1.00 | 25.76 | B | C |
| ATOM | 5875 | CD | GLN | B | 183 | 78.718 | 36.735 | −26.796 | 1.00 | 36.22 | B | C |
| ATOM | 5876 | OE1 | GLN | B | 183 | 77.488 | 36.781 | −26.581 | 1.00 | 39.28 | B | O |
| ATOM | 5877 | NE2 | GLN | B | 183 | 79.547 | 36.040 | −26.010 | 1.00 | 27.88 | B | N |
| ATOM | 5878 | C | GLN | B | 183 | 76.462 | 37.581 | −30.641 | 1.00 | 20.79 | B | C |
| ATOM | 5879 | O | GLN | B | 183 | 75.328 | 37.342 | −30.231 | 1.00 | 18.96 | B | O |
| ATOM | 5880 | N | VAL | B | 184 | 76.699 | 38.317 | −31.723 | 1.00 | 18.41 | B | N |
| ATOM | 5881 | CA | VAL | B | 184 | 75.615 | 38.956 | −32.459 | 1.00 | 22.44 | B | C |
| ATOM | 5882 | CB | VAL | B | 184 | 76.134 | 39.908 | −33.560 | 1.00 | 21.83 | B | C |
| ATOM | 5883 | CG1 | VAL | B | 184 | 74.959 | 40.418 | −34.416 | 1.00 | 25.83 | B | C |
| ATOM | 5884 | CG2 | VAL | B | 184 | 76.922 | 41.070 | −32.924 | 1.00 | 21.84 | B | C |
| ATOM | 5885 | C | VAL | B | 184 | 74.690 | 37.916 | −33.059 | 1.00 | 22.10 | B | C |
| ATOM | 5886 | O | VAL | B | 184 | 73.473 | 38.058 | −32.971 | 1.00 | 27.26 | B | O |
| ATOM | 5887 | N | ASN | B | 185 | 75.256 | 36.858 | −33.646 | 1.00 | 24.42 | B | N |
| ATOM | 5888 | CA | ASN | B | 185 | 74.431 | 35.789 | −34.243 | 1.00 | 22.70 | B | C |
| ATOM | 5889 | CB | ASN | B | 185 | 75.286 | 34.822 | −35.055 | 1.00 | 25.47 | B | C |
| ATOM | 5890 | CG | ASN | B | 185 | 75.910 | 35.487 | −36.292 | 1.00 | 33.07 | B | C |
| ATOM | 5891 | OD1 | ASN | B | 185 | 75.334 | 36.406 | −36.882 | 1.00 | 34.50 | B | O |
| ATOM | 5892 | ND2 | ASN | B | 185 | 77.112 | 35.044 | −36.655 | 1.00 | 27.32 | B | N |
| ATOM | 5893 | C | ASN | B | 185 | 73.624 | 35.022 | −33.207 | 1.00 | 22.45 | B | C |
| ATOM | 5894 | O | ASN | B | 185 | 72.478 | 34.684 | −33.438 | 1.00 | 21.71 | B | O |
| ATOM | 5895 | N | HIS | B | 186 | 74.215 | 34.770 | −32.050 | 1.00 | 19.36 | B | N |
| ATOM | 5896 | CA | HIS | B | 186 | 73.499 | 34.086 | −30.992 | 1.00 | 21.89 | B | C |
| ATOM | 5897 | CB | HIS | B | 186 | 74.465 | 33.852 | −29.845 | 1.00 | 20.44 | B | C |
| ATOM | 5898 | CG | HIS | B | 186 | 73.887 | 33.118 | −28.679 | 1.00 | 20.44 | B | C |
| ATOM | 5899 | ND1 | HIS | B | 186 | 73.618 | 31.798 | −28.715 | 1.00 | 18.19 | B | N |
| ATOM | 5900 | CE1 | HIS | B | 186 | 73.153 | 31.411 | −27.516 | 1.00 | 22.14 | B | C |
| ATOM | 5901 | NE2 | HIS | B | 186 | 73.154 | 32.481 | −26.694 | 1.00 | 19.30 | B | N |
| ATOM | 5902 | CD2 | HIS | B | 186 | 73.606 | 33.548 | −27.379 | 1.00 | 23.03 | B | C |
| ATOM | 5903 | C | HIS | B | 186 | 72.304 | 34.932 | −30.579 | 1.00 | 22.29 | B | C |
| ATOM | 5904 | O | HIS | B | 186 | 71.182 | 34.436 | −30.457 | 1.00 | 22.93 | B | O |
| ATOM | 5905 | N | ALA | B | 187 | 72.534 | 36.235 | −30.422 | 1.00 | 21.36 | B | N |
| ATOM | 5906 | CA | ALA | B | 187 | 71.490 | 37.178 | −30.007 | 1.00 | 20.58 | B | C |
| ATOM | 5907 | CB | ALA | B | 187 | 72.124 | 38.559 | −29.786 | 1.00 | 18.30 | B | C |
| ATOM | 5908 | C | ALA | B | 187 | 70.331 | 37.265 | −31.017 | 1.00 | 22.35 | B | C |
| ATOM | 5909 | O | ALA | B | 187 | 69.153 | 37.323 | −30.633 | 1.00 | 20.93 | B | O |
| ATOM | 5910 | N | LEU | B | 188 | 70.681 | 37.291 | −32.302 | 1.00 | 22.80 | B | N |
| ATOM | 5911 | CA | LEU | B | 188 | 69.690 | 37.432 | −33.372 | 1.00 | 24.02 | B | C |
| ATOM | 5912 | CB | LEU | B | 188 | 70.352 | 37.870 | −34.690 | 1.00 | 25.03 | B | C |
| ATOM | 5913 | CG | LEU | B | 188 | 70.966 | 39.274 | −34.681 | 1.00 | 25.80 | B | C |
| ATOM | 5914 | CD1 | LEU | B | 188 | 71.784 | 39.523 | −35.920 | 1.00 | 25.59 | B | C |
| ATOM | 5915 | CD2 | LEU | B | 188 | 69.896 | 40.343 | −34.546 | 1.00 | 26.13 | B | C |
| ATOM | 5916 | C | LEU | B | 188 | 68.918 | 36.139 | −33.529 | 1.00 | 25.43 | B | C |
| ATOM | 5917 | O | LEU | B | 188 | 67.736 | 36.173 | −33.805 | 1.00 | 28.67 | B | O |
| ATOM | 5918 | N | GLU | B | 189 | 69.556 | 35.000 | −33.279 | 1.00 | 25.97 | B | N |
| ATOM | 5919 | CA | GLU | B | 189 | 68.823 | 33.739 | −33.192 | 1.00 | 24.23 | B | C |
| ATOM | 5920 | CB | GLU | B | 189 | 69.789 | 32.591 | −32.848 | 1.00 | 22.91 | B | C |
| ATOM | 5921 | CG | GLU | B | 189 | 69.154 | 31.206 | −32.838 | 1.00 | 27.18 | B | C |
| ATOM | 5922 | CD | GLU | B | 189 | 70.073 | 30.113 | −32.302 | 1.00 | 37.99 | B | C |
| ATOM | 5923 | OE1 | GLU | B | 189 | 70.636 | 30.254 | −31.179 | 1.00 | 34.64 | B | O |
| ATOM | 5924 | OE2 | GLU | B | 189 | 70.220 | 29.090 | −33.003 | 1.00 | 38.22 | B | O |
| ATOM | 5925 | C | GLU | B | 189 | 67.659 | 33.839 | −32.160 | 1.00 | 26.47 | B | C |
| ATOM | 5926 | O | GLU | B | 189 | 66.497 | 33.540 | −32.467 | 1.00 | 21.27 | B | O |
| ATOM | 5927 | N | LEU | B | 190 | 67.968 | 34.235 | −30.932 | 1.00 | 22.17 | B | N |
| ATOM | 5928 | CA | LEU | B | 190 | 66.943 | 34.387 | −29.896 | 1.00 | 20.33 | B | C |
| ATOM | 5929 | CB | LEU | B | 190 | 66.553 | 33.018 | −29.345 | 1.00 | 17.23 | B | C |
| ATOM | 5930 | CG | LEU | B | 190 | 65.348 | 32.872 | −28.434 | 1.00 | 18.56 | B | C |
| ATOM | 5931 | CD1 | LEU | B | 190 | 64.025 | 33.102 | −29.244 | 1.00 | 19.80 | B | C |
| ATOM | 5932 | CD2 | LEU | B | 190 | 65.366 | 31.442 | −27.832 | 1.00 | 18.21 | B | C |
| ATOM | 5933 | C | LEU | B | 190 | 67.575 | 35.203 | −28.765 | 1.00 | 20.27 | B | C |
| ATOM | 5934 | O | LEU | B | 190 | 68.699 | 34.959 | −28.379 | 1.00 | 17.38 | B | O |
| ATOM | 5935 | N | PRO | B | 191 | 66.858 | 36.149 | −28.221 | 1.00 | 17.86 | B | N |
| ATOM | 5936 | CA | PRO | B | 191 | 67.456 | 36.948 | −27.164 | 1.00 | 16.52 | B | C |
| ATOM | 5937 | CB | PRO | B | 191 | 66.496 | 38.137 | −27.063 | 1.00 | 19.92 | B | C |
| ATOM | 5938 | CG | PRO | B | 191 | 65.224 | 37.601 | −27.464 | 1.00 | 19.34 | B | C |
| ATOM | 5939 | CD | PRO | B | 191 | 65.550 | 36.666 | −28.621 | 1.00 | 19.66 | B | C |
| ATOM | 5940 | C | PRO | B | 191 | 67.511 | 36.262 | −25.844 | 1.00 | 18.58 | B | C |
| ATOM | 5941 | O | PRO | B | 191 | 66.763 | 35.292 | −25.605 | 1.00 | 21.63 | B | O |
| ATOM | 5942 | N | LEU | B | 192 | 68.375 | 36.772 | −24.967 | 1.00 | 19.06 | B | N |
| ATOM | 5943 | CA | LEU | B | 192 | 68.601 | 36.175 | −23.667 | 1.00 | 19.22 | B | C |
| ATOM | 5944 | CB | LEU | B | 192 | 69.528 | 37.033 | −22.797 | 1.00 | 24.31 | B | C |
| ATOM | 5945 | CG | LEU | B | 192 | 71.015 | 36.962 | −23.073 | 1.00 | 33.33 | B | C |
| ATOM | 5946 | CD1 | LEU | B | 192 | 71.710 | 38.156 | −22.370 | 1.00 | 30.34 | B | C |

APPENDIX A-continued

*P. alba* 3T288C coordinates

| ATOM | 5947 | CD2 | LEU | B | 192 | 71.565 | 35.596 | −22.603 | 1.00 | 26.99 | B | C |
|---|---|---|---|---|---|---|---|---|---|---|---|---|
| ATOM | 5948 | C | LEU | B | 192 | 67.322 | 35.980 | −22.898 | 1.00 | 19.34 | B | C |
| ATOM | 5949 | O | LEU | B | 192 | 67.139 | 34.963 | −22.257 | 1.00 | 16.96 | B | O |
| ATOM | 5950 | N | HIS | B | 193 | 66.459 | 36.983 | −22.949 | 1.00 | 15.46 | B | N |
| ATOM | 5951 | CA | HIS | B | 193 | 65.235 | 36.966 | −22.174 | 1.00 | 18.69 | B | C |
| ATOM | 5952 | CB | HIS | B | 193 | 64.544 | 38.336 | −22.282 | 1.00 | 15.11 | B | C |
| ATOM | 5953 | CG | HIS | B | 193 | 63.405 | 38.528 | −21.297 | 1.00 | 15.94 | B | C |
| ATOM | 5954 | ND1 | HIS | B | 193 | 63.574 | 38.450 | −19.952 | 1.00 | 18.12 | B | N |
| ATOM | 5955 | CE1 | HIS | B | 193 | 62.387 | 38.650 | −19.339 | 1.00 | 17.94 | B | C |
| ATOM | 5956 | NE2 | HIS | B | 193 | 61.468 | 38.902 | −20.292 | 1.00 | 18.67 | B | N |
| ATOM | 5957 | CD2 | HIS | B | 193 | 62.071 | 38.835 | −21.506 | 1.00 | 16.13 | B | C |
| ATOM | 5958 | C | HIS | B | 193 | 64.294 | 35.838 | −22.558 | 1.00 | 13.46 | B | C |
| ATOM | 5959 | O | HIS | B | 193 | 63.440 | 35.441 | −21.772 | 1.00 | 15.85 | B | O |
| ATOM | 5960 | N | ARG | B | 194 | 64.435 | 35.332 | −23.771 | 1.00 | 13.24 | B | N |
| ATOM | 5961 | CA | ARG | B | 194 | 63.605 | 34.246 | −24.281 | 1.00 | 14.54 | B | C |
| ATOM | 5962 | CB | ARG | B | 194 | 63.098 | 34.605 | −25.686 | 1.00 | 15.59 | B | C |
| ATOM | 5963 | CG | ARG | B | 194 | 62.187 | 35.795 | −25.690 | 1.00 | 15.21 | B | C |
| ATOM | 5964 | CD | ARG | B | 194 | 61.533 | 36.037 | −27.017 | 1.00 | 17.56 | B | C |
| ATOM | 5965 | NE | ARG | B | 194 | 60.702 | 37.247 | −26.963 | 1.00 | 19.45 | B | N |
| ATOM | 5966 | CZ | ARG | B | 194 | 60.048 | 37.772 | −27.995 | 1.00 | 22.26 | B | C |
| ATOM | 5967 | NH1 | ARG | B | 194 | 60.111 | 37.194 | −29.191 | 1.00 | 20.50 | B | N |
| ATOM | 5968 | NH2 | ARG | B | 194 | 59.276 | 38.847 | −27.803 | 1.00 | 19.22 | B | N |
| ATOM | 5969 | C | ARG | B | 194 | 64.269 | 32.862 | −24.328 | 1.00 | 15.56 | B | C |
| ATOM | 5970 | O | ARG | B | 194 | 63.579 | 31.874 | −24.549 | 1.00 | 18.90 | B | O |
| ATOM | 5971 | N | ARG | B | 195 | 65.573 | 32.781 | −24.102 | 1.00 | 17.67 | B | N |
| ATOM | 5972 | CA | ARG | B | 195 | 66.306 | 31.507 | −24.154 | 1.00 | 17.08 | B | C |
| ATOM | 5973 | CB | ARG | B | 195 | 67.754 | 31.754 | −24.595 | 1.00 | 19.12 | B | C |
| ATOM | 5974 | CG | ARG | B | 195 | 68.465 | 30.472 | −25.018 | 1.00 | 20.16 | B | C |
| ATOM | 5975 | CD | ARG | B | 195 | 69.877 | 30.743 | −25.510 | 1.00 | 18.78 | B | C |
| ATOM | 5976 | NE | ARG | B | 195 | 69.946 | 31.704 | −26.624 | 1.00 | 21.88 | B | N |
| ATOM | 5977 | CZ | ARG | B | 195 | 69.991 | 31.384 | −27.920 | 1.00 | 27.25 | B | C |
| ATOM | 5978 | NH1 | ARG | B | 195 | 69.990 | 30.116 | −28.303 | 1.00 | 25.88 | B | N |
| ATOM | 5979 | NH2 | ARG | B | 195 | 70.068 | 32.335 | −28.847 | 1.00 | 28.28 | B | N |
| ATOM | 5980 | C | ARG | B | 195 | 66.257 | 30.789 | −22.798 | 1.00 | 16.57 | B | C |
| ATOM | 5981 | O | ARG | B | 195 | 66.281 | 31.432 | −21.726 | 1.00 | 15.80 | B | O |
| ATOM | 5982 | N | THR | B | 196 | 66.158 | 29.470 | −22.830 | 1.00 | 15.49 | B | N |
| ATOM | 5983 | CA | THR | B | 196 | 66.133 | 28.692 | −21.605 | 1.00 | 15.97 | B | C |
| ATOM | 5984 | CB | THR | B | 196 | 65.787 | 27.202 | −21.860 | 1.00 | 20.73 | B | C |
| ATOM | 5985 | OG1 | THR | B | 196 | 66.683 | 26.672 | −22.813 | 1.00 | 23.79 | B | O |
| ATOM | 5986 | CG2 | THR | B | 196 | 64.342 | 27.043 | −22.414 | 1.00 | 18.21 | B | C |
| ATOM | 5987 | C | THR | B | 196 | 67.509 | 28.817 | −20.947 | 1.00 | 14.24 | B | C |
| ATOM | 5988 | O | THR | B | 196 | 68.506 | 29.050 | −21.614 | 1.00 | 14.38 | B | O |
| ATOM | 5989 | N | GLN | B | 197 | 67.552 | 28.610 | −19.650 | 1.00 | 15.82 | B | N |
| ATOM | 5990 | CA | GLN | B | 197 | 68.779 | 28.794 | −18.872 | 1.00 | 15.13 | B | C |
| ATOM | 5991 | CB | GLN | B | 197 | 68.398 | 28.731 | −17.388 | 1.00 | 16.40 | B | C |
| ATOM | 5992 | CG | GLN | B | 197 | 69.313 | 29.536 | −16.402 | 1.00 | 23.34 | B | C |
| ATOM | 5993 | CD | GLN | B | 197 | 70.400 | 28.668 | −15.827 | 1.00 | 19.25 | B | C |
| ATOM | 5994 | OE1 | GLN | B | 197 | 70.750 | 27.639 | −16.413 | 1.00 | 17.54 | B | O |
| ATOM | 5995 | NE2 | GLN | B | 197 | 70.933 | 29.055 | −14.672 | 1.00 | 19.64 | B | N |
| ATOM | 5996 | C | GLN | B | 197 | 69.912 | 27.794 | −19.253 | 1.00 | 15.38 | B | C |
| ATOM | 5997 | O | GLN | B | 197 | 71.040 | 28.214 | −19.543 | 1.00 | 15.99 | B | O |
| ATOM | 5998 | N | ARG | B | 198 | 69.631 | 26.487 | −19.261 | 1.00 | 15.88 | B | N |
| ATOM | 5999 | CA | ARG | B | 198 | 70.650 | 25.503 | −19.628 | 1.00 | 15.76 | B | C |
| ATOM | 6000 | CB | ARG | B | 198 | 70.151 | 24.068 | −19.495 | 1.00 | 17.18 | B | C |
| ATOM | 6001 | CG | ARG | B | 198 | 69.747 | 23.686 | −18.071 | 1.00 | 17.17 | B | C |
| ATOM | 6002 | CD | ARG | B | 198 | 70.987 | 23.505 | −17.154 | 1.00 | 18.00 | B | C |
| ATOM | 6003 | NE | ARG | B | 198 | 71.390 | 24.755 | −16.491 | 1.00 | 17.03 | B | N |
| ATOM | 6004 | CZ | ARG | B | 198 | 72.436 | 24.877 | −15.679 | 1.00 | 18.12 | B | C |
| ATOM | 6005 | NH1 | ARG | B | 198 | 73.201 | 23.837 | −15.422 | 1.00 | 18.07 | B | N |
| ATOM | 6006 | NH2 | ARG | B | 198 | 72.714 | 26.047 | −15.111 | 1.00 | 18.32 | B | N |
| ATOM | 6007 | C | ARG | B | 198 | 71.191 | 25.712 | −21.020 | 1.00 | 14.67 | B | C |
| ATOM | 6008 | O | ARG | B | 198 | 72.393 | 25.618 | −21.196 | 1.00 | 16.24 | B | O |
| ATOM | 6009 | N | LEU | B | 199 | 70.345 | 26.007 | −22.008 | 1.00 | 15.86 | B | N |
| ATOM | 6010 | CA | LEU | B | 199 | 70.846 | 26.282 | −23.373 | 1.00 | 17.59 | B | C |
| ATOM | 6011 | CB | LEU | B | 199 | 69.741 | 26.411 | −24.414 | 1.00 | 23.09 | B | C |
| ATOM | 6012 | CG | LEU | B | 199 | 69.172 | 25.097 | −24.927 | 1.00 | 25.48 | B | C |
| ATOM | 6013 | CD1 | LEU | B | 199 | 68.001 | 25.403 | −25.846 | 1.00 | 29.15 | B | C |
| ATOM | 6014 | CD2 | LEU | B | 199 | 70.249 | 24.258 | −25.668 | 1.00 | 23.01 | B | C |
| ATOM | 6015 | C | LEU | B | 199 | 71.728 | 27.501 | −23.423 | 1.00 | 14.99 | B | C |
| ATOM | 6016 | O | LEU | B | 199 | 72.779 | 27.465 | −24.043 | 1.00 | 17.26 | B | O |
| ATOM | 6017 | N | GLU | B | 200 | 71.365 | 28.574 | −22.717 | 1.00 | 17.19 | B | N |
| ATOM | 6018 | CA | GLU | B | 200 | 72.262 | 29.716 | −22.634 | 1.00 | 16.80 | B | C |
| ATOM | 6019 | CB | GLU | B | 200 | 71.603 | 30.885 | −21.903 | 1.00 | 18.56 | B | C |
| ATOM | 6020 | CG | GLU | B | 200 | 72.470 | 32.138 | −21.838 | 1.00 | 19.52 | B | C |
| ATOM | 6021 | CD | GLU | B | 200 | 73.011 | 32.611 | −23.208 | 1.00 | 23.00 | B | C |
| ATOM | 6022 | OE1 | GLU | B | 200 | 72.365 | 32.402 | −24.243 | 1.00 | 28.08 | B | O |
| ATOM | 6023 | OE2 | GLU | B | 200 | 74.115 | 33.177 | −23.238 | 1.00 | 26.36 | B | O |
| ATOM | 6024 | C | GLU | B | 200 | 73.598 | 29.332 | −21.962 | 1.00 | 15.03 | B | C |

APPENDIX A-continued

*P. alba* 3T288C coordinates

| ATOM | 6025 | O   | GLU | B | 200 | 74.654 | 29.744 | −22.419 | 1.00 | 16.93 | B | O |
| ATOM | 6026 | N   | ALA | B | 201 | 73.537 | 28.572 | −20.869 | 1.00 | 16.50 | B | N |
| ATOM | 6027 | CA  | ALA | B | 201 | 74.741 | 28.162 | −20.131 | 1.00 | 14.91 | B | C |
| ATOM | 6028 | CB  | ALA | B | 201 | 74.376 | 27.366 | −18.864 | 1.00 | 15.26 | B | C |
| ATOM | 6029 | C   | ALA | B | 201 | 75.712 | 27.386 | −21.014 | 1.00 | 14.98 | B | C |
| ATOM | 6030 | O   | ALA | B | 201 | 76.902 | 27.711 | −21.065 | 1.00 | 16.94 | B | O |
| ATOM | 6031 | N   | VAL | B | 202 | 75.223 | 26.385 | −21.734 | 1.00 | 16.65 | B | N |
| ATOM | 6032 | CA  | VAL | B | 202 | 76.110 | 25.533 | −22.524 | 1.00 | 18.24 | B | C |
| ATOM | 6033 | CB  | VAL | B | 202 | 75.413 | 24.228 | −23.033 | 1.00 | 20.43 | B | C |
| ATOM | 6034 | CG1 | VAL | B | 202 | 74.512 | 24.514 | −24.187 | 1.00 | 19.20 | B | C |
| ATOM | 6035 | CG2 | VAL | B | 202 | 76.542 | 23.142 | −23.429 | 1.00 | 18.68 | B | C |
| ATOM | 6036 | C   | VAL | B | 202 | 76.767 | 26.327 | −23.641 | 1.00 | 18.74 | B | C |
| ATOM | 6037 | O   | VAL | B | 202 | 77.952 | 26.163 | −23.923 | 1.00 | 19.25 | B | O |
| ATOM | 6038 | N   | TRP | B | 203 | 76.046 | 27.280 | −24.200 | 1.00 | 20.00 | B | N |
| ATOM | 6039 | CA  | TRP | B | 203 | 76.616 | 28.127 | −25.231 | 1.00 | 19.92 | B | C |
| ATOM | 6040 | CB  | TRP | B | 203 | 75.497 | 28.878 | −25.969 | 1.00 | 23.20 | B | C |
| ATOM | 6041 | CG  | TRP | B | 203 | 76.048 | 29.658 | −27.134 | 1.00 | 22.71 | B | C |
| ATOM | 6042 | CD1 | TRP | B | 203 | 76.157 | 29.240 | −28.460 | 1.00 | 23.74 | B | C |
| ATOM | 6043 | NE1 | TRP | B | 203 | 76.707 | 30.213 | −29.236 | 1.00 | 21.14 | B | N |
| ATOM | 6044 | CE2 | TRP | B | 203 | 77.022 | 31.290 | −28.488 | 1.00 | 22.74 | B | C |
| ATOM | 6045 | CD2 | TRP | B | 203 | 76.600 | 31.001 | −27.115 | 1.00 | 21.85 | B | C |
| ATOM | 6046 | CE3 | TRP | B | 203 | 76.800 | 31.961 | −26.132 | 1.00 | 26.65 | B | C |
| ATOM | 6047 | CZ3 | TRP | B | 203 | 77.379 | 33.179 | −26.499 | 1.00 | 22.71 | B | C |
| ATOM | 6048 | CH2 | TRP | B | 203 | 77.788 | 33.427 | −27.820 | 1.00 | 24.24 | B | C |
| ATOM | 6049 | CZ2 | TRP | B | 203 | 77.604 | 32.487 | −28.838 | 1.00 | 23.57 | B | C |
| ATOM | 6050 | C   | TRP | B | 203 | 77.601 | 29.110 | −24.635 | 1.00 | 20.87 | B | C |
| ATOM | 6051 | O   | TRP | B | 203 | 78.734 | 29.297 | −25.144 | 1.00 | 17.52 | B | O |
| ATOM | 6052 | N   | SER | B | 204 | 77.199 | 29.771 | −23.546 | 1.00 | 15.45 | B | N |
| ATOM | 6053 | CA  | SER | B | 204 | 78.083 | 30.775 | −22.940 | 1.00 | 16.11 | B | C |
| ATOM | 6054 | CB  | SER | B | 204 | 77.362 | 31.546 | −21.819 | 1.00 | 17.27 | B | C |
| ATOM | 6055 | OG  | SER | B | 204 | 76.568 | 32.572 | −22.375 | 1.00 | 19.39 | B | O |
| ATOM | 6056 | C   | SER | B | 204 | 79.370 | 30.173 | −22.395 | 1.00 | 15.39 | B | C |
| ATOM | 6057 | O   | SER | B | 204 | 80.394 | 30.835 | −22.391 | 1.00 | 16.11 | B | O |
| ATOM | 6058 | N   | ILE | B | 205 | 79.319 | 28.938 | −21.899 | 1.00 | 16.43 | B | N |
| ATOM | 6059 | CA  | ILE | B | 205 | 80.503 | 28.343 | −21.295 | 1.00 | 16.59 | B | C |
| ATOM | 6060 | CB  | ILE | B | 205 | 80.192 | 27.060 | −20.494 | 1.00 | 14.72 | B | C |
| ATOM | 6061 | CG1 | ILE | B | 205 | 79.467 | 27.430 | −19.188 | 1.00 | 15.63 | B | C |
| ATOM | 6062 | CD1 | ILE | B | 205 | 78.694 | 26.305 | −18.505 | 1.00 | 15.15 | B | C |
| ATOM | 6063 | CG2 | ILE | B | 205 | 81.507 | 26.330 | −20.134 | 1.00 | 16.76 | B | C |
| ATOM | 6064 | C   | ILE | B | 205 | 81.523 | 28.084 | −22.404 | 1.00 | 20.64 | B | C |
| ATOM | 6065 | O   | ILE | B | 205 | 82.699 | 28.395 | −22.254 | 1.00 | 15.38 | B | O |
| ATOM | 6066 | N   | GLU | B | 206 | 81.056 | 27.531 | −23.517 | 1.00 | 21.81 | B | N |
| ATOM | 6067 | CA  | GLU | B | 206 | 81.889 | 27.373 | −24.707 | 1.00 | 22.45 | B | C |
| ATOM | 6068 | CB  | GLU | B | 206 | 81.087 | 26.726 | −25.840 | 1.00 | 24.56 | B | C |
| ATOM | 6069 | CG  | GLU | B | 206 | 81.899 | 26.453 | −27.146 | 1.00 | 31.17 | B | C |
| ATOM | 6070 | CD  | GLU | B | 206 | 83.163 | 25.580 | −26.937 | 1.00 | 42.25 | B | C |
| ATOM | 6071 | OE1 | GLU | B | 206 | 83.240 | 24.815 | −25.947 | 1.00 | 39.81 | B | O |
| ATOM | 6072 | OE2 | GLU | B | 206 | 84.087 | 25.656 | −27.780 | 1.00 | 51.64 | B | O |
| ATOM | 6073 | C   | GLU | B | 206 | 82.446 | 28.714 | −25.167 | 1.00 | 20.41 | B | C |
| ATOM | 6074 | O   | GLU | B | 206 | 83.636 | 28.830 | −25.447 | 1.00 | 23.72 | B | O |
| ATOM | 6075 | N   | ALA | B | 207 | 81.617 | 29.746 | −25.249 | 1.00 | 17.21 | B | N |
| ATOM | 6076 | CA  | ALA | B | 207 | 82.128 | 31.050 | −25.707 | 1.00 | 17.73 | B | C |
| ATOM | 6077 | CB  | ALA | B | 207 | 81.011 | 32.050 | −25.881 | 1.00 | 16.31 | B | C |
| ATOM | 6078 | C   | ALA | B | 207 | 83.152 | 31.592 | −24.731 | 1.00 | 21.22 | B | C |
| ATOM | 6079 | O   | ALA | B | 207 | 84.192 | 32.115 | −25.126 | 1.00 | 21.97 | B | O |
| ATOM | 6080 | N   | TYR | B | 208 | 82.868 | 31.451 | −23.433 | 1.00 | 17.91 | B | N |
| ATOM | 6081 | CA  | TYR | B | 208 | 83.709 | 32.070 | −22.430 | 1.00 | 19.00 | B | C |
| ATOM | 6082 | CB  | TYR | B | 208 | 83.017 | 32.016 | −21.068 | 1.00 | 17.47 | B | C |
| ATOM | 6083 | CG  | TYR | B | 208 | 83.563 | 32.956 | −20.061 | 1.00 | 17.44 | B | C |
| ATOM | 6084 | CD1 | TYR | B | 208 | 83.470 | 34.325 | −20.231 | 1.00 | 22.19 | B | C |
| ATOM | 6085 | CE1 | TYR | B | 208 | 84.002 | 35.205 | −19.275 | 1.00 | 22.79 | B | C |
| ATOM | 6086 | CZ  | TYR | B | 208 | 84.618 | 34.696 | −18.160 | 1.00 | 20.52 | B | C |
| ATOM | 6087 | OH  | TYR | B | 208 | 85.160 | 35.517 | −17.199 | 1.00 | 22.16 | B | O |
| ATOM | 6088 | CE2 | TYR | B | 208 | 84.712 | 33.343 | −17.982 | 1.00 | 22.62 | B | C |
| ATOM | 6089 | CD2 | TYR | B | 208 | 84.191 | 32.482 | −18.924 | 1.00 | 20.39 | B | C |
| ATOM | 6090 | C   | TYR | B | 208 | 85.121 | 31.455 | −22.382 | 1.00 | 21.14 | B | C |
| ATOM | 6091 | O   | TYR | B | 208 | 86.094 | 32.163 | −22.176 | 1.00 | 23.19 | B | O |
| ATOM | 6092 | N   | ARG | B | 209 | 85.230 | 30.141 | −22.570 | 1.00 | 23.40 | B | N |
| ATOM | 6093 | CA  | ARG | B | 209 | 86.503 | 29.467 | −22.415 | 1.00 | 23.18 | B | C |
| ATOM | 6094 | CB  | ARG | B | 209 | 86.333 | 27.956 | −22.281 | 1.00 | 22.22 | B | C |
| ATOM | 6095 | CG  | ARG | B | 209 | 85.955 | 27.249 | −23.546 | 1.00 | 22.39 | B | C |
| ATOM | 6096 | CD  | ARG | B | 209 | 85.367 | 25.888 | −23.242 | 1.00 | 21.92 | B | C |
| ATOM | 6097 | NE  | ARG | B | 209 | 86.318 | 25.065 | −22.510 | 1.00 | 19.65 | B | N |
| ATOM | 6098 | CZ  | ARG | B | 209 | 86.010 | 23.941 | −21.872 | 1.00 | 19.54 | B | C |
| ATOM | 6099 | NH1 | ARG | B | 209 | 84.767 | 23.478 | −21.825 | 1.00 | 18.84 | B | N |
| ATOM | 6100 | NH2 | ARG | B | 209 | 86.945 | 23.290 | −21.230 | 1.00 | 19.02 | B | N |
| ATOM | 6101 | C   | ARG | B | 209 | 87.437 | 29.794 | −23.570 | 1.00 | 23.18 | B | C |
| ATOM | 6102 | O   | ARG | B | 209 | 88.616 | 29.604 | −23.442 | 1.00 | 26.17 | B | O |

APPENDIX A-continued

*P. alba* 3T288C coordinates

| ATOM | 6103 | N | LYS | B | 210 | 86.903 | 30.300 | −24.674 | 1.00 | 25.22 | B | N |
|---|---|---|---|---|---|---|---|---|---|---|---|---|
| ATOM | 6104 | CA | LYS | B | 210 | 87.726 | 30.739 | −25.797 | 1.00 | 29.87 | B | C |
| ATOM | 6105 | CB | LYS | B | 210 | 86.933 | 30.694 | −27.098 | 1.00 | 26.62 | B | C |
| ATOM | 6106 | CG | LYS | B | 210 | 86.471 | 29.315 | −27.446 | 1.00 | 28.26 | B | C |
| ATOM | 6107 | CD | LYS | B | 210 | 86.122 | 29.195 | −28.922 | 1.00 | 27.77 | B | C |
| ATOM | 6108 | CE | LYS | B | 210 | 84.884 | 28.370 | −29.132 | 1.00 | 28.89 | B | C |
| ATOM | 6109 | NZ | LYS | B | 210 | 83.709 | 29.236 | −29.267 | 1.00 | 28.19 | B | N |
| ATOM | 6110 | C | LYS | B | 210 | 88.299 | 32.128 | −25.637 | 1.00 | 30.55 | B | C |
| ATOM | 6111 | O | LYS | B | 210 | 89.179 | 32.493 | −26.386 | 1.00 | 34.12 | B | O |
| ATOM | 6112 | N | LYS | B | 211 | 87.806 | 32.915 | −24.690 | 1.00 | 31.31 | B | N |
| ATOM | 6113 | CA | LYS | B | 211 | 88.390 | 34.236 | −24.440 | 1.00 | 37.33 | B | C |
| ATOM | 6114 | CB | LYS | B | 211 | 87.432 | 35.096 | −23.629 | 1.00 | 38.53 | B | C |
| ATOM | 6115 | CG | LYS | B | 211 | 86.127 | 35.407 | −24.298 | 1.00 | 38.75 | B | C |
| ATOM | 6116 | CD | LYS | B | 211 | 85.194 | 36.134 | −23.326 | 1.00 | 48.24 | B | C |
| ATOM | 6117 | CE | LYS | B | 211 | 85.650 | 37.563 | −23.032 | 1.00 | 61.03 | B | C |
| ATOM | 6118 | NZ | LYS | B | 211 | 85.287 | 37.988 | −21.653 | 1.00 | 72.73 | B | N |
| ATOM | 6119 | C | LYS | B | 211 | 89.701 | 34.097 | −23.667 | 1.00 | 34.45 | B | C |
| ATOM | 6120 | O | LYS | B | 211 | 89.743 | 33.398 | −22.650 | 1.00 | 33.64 | B | O |
| ATOM | 6121 | N | GLU | B | 212 | 90.759 | 34.771 | −24.126 | 1.00 | 35.44 | B | N |
| ATOM | 6122 | CA | GLU | B | 212 | 92.064 | 34.717 | −23.441 | 1.00 | 40.21 | B | C |
| ATOM | 6123 | CB | GLU | B | 212 | 93.157 | 35.413 | −24.264 | 1.00 | 44.48 | B | C |
| ATOM | 6124 | CG | GLU | B | 212 | 94.488 | 35.596 | −23.507 | 1.00 | 49.74 | B | C |
| ATOM | 6125 | CD | GLU | B | 212 | 95.705 | 35.662 | −24.412 | 1.00 | 50.52 | B | C |
| ATOM | 6126 | OE1 | GLU | B | 212 | 95.560 | 36.001 | −25.603 | 1.00 | 48.70 | B | O |
| ATOM | 6127 | OE2 | GLU | B | 212 | 96.814 | 35.368 | −23.923 | 1.00 | 55.77 | B | O |
| ATOM | 6128 | C | GLU | B | 212 | 92.022 | 35.318 | −22.029 | 1.00 | 36.75 | B | C |
| ATOM | 6129 | O | GLU | B | 212 | 92.768 | 34.897 | −21.139 | 1.00 | 34.64 | B | O |
| ATOM | 6130 | N | ASP | B | 213 | 91.138 | 36.287 | −21.834 | 1.00 | 33.09 | B | N |
| ATOM | 6131 | CA | ASP | B | 213 | 91.023 | 37.008 | −20.568 | 1.00 | 30.97 | B | C |
| ATOM | 6132 | CB | ASP | B | 213 | 90.829 | 38.488 | −20.878 | 1.00 | 33.35 | B | C |
| ATOM | 6133 | CG | ASP | B | 213 | 89.668 | 38.718 | −21.827 | 1.00 | 43.49 | B | C |
| ATOM | 6134 | OD1 | ASP | B | 213 | 89.547 | 37.944 | −22.806 | 1.00 | 50.90 | B | O |
| ATOM | 6135 | OD2 | ASP | B | 213 | 88.868 | 39.639 | −21.587 | 1.00 | 52.59 | B | O |
| ATOM | 6136 | C | ASP | B | 213 | 89.842 | 36.515 | −19.703 | 1.00 | 29.08 | B | C |
| ATOM | 6137 | O | ASP | B | 213 | 89.426 | 37.227 | −18.793 | 1.00 | 29.45 | B | O |
| ATOM | 6138 | N | ALA | B | 214 | 89.304 | 35.324 | −19.983 | 1.00 | 21.49 | B | N |
| ATOM | 6139 | CA | ALA | B | 214 | 88.231 | 34.735 | −19.170 | 1.00 | 23.04 | B | C |
| ATOM | 6140 | CB | ALA | B | 214 | 87.829 | 33.366 | −19.727 | 1.00 | 24.25 | B | C |
| ATOM | 6141 | C | ALA | B | 214 | 88.686 | 34.574 | −17.737 | 1.00 | 21.97 | B | C |
| ATOM | 6142 | O | ALA | B | 214 | 89.812 | 34.165 | −17.490 | 1.00 | 18.38 | B | O |
| ATOM | 6143 | N | ASN | B | 215 | 87.822 | 34.865 | −16.772 | 1.00 | 21.39 | B | N |
| ATOM | 6144 | CA | ASN | B | 215 | 88.184 | 34.596 | −15.380 | 1.00 | 20.57 | B | C |
| ATOM | 6145 | CB | ASN | B | 215 | 87.172 | 35.209 | −14.413 | 1.00 | 21.21 | B | C |
| ATOM | 6146 | CG | ASN | B | 215 | 87.631 | 35.118 | −12.990 | 1.00 | 23.78 | B | C |
| ATOM | 6147 | OD1 | ASN | B | 215 | 87.544 | 34.067 | −12.352 | 1.00 | 21.84 | B | O |
| ATOM | 6148 | ND2 | ASN | B | 215 | 88.160 | 36.213 | −12.483 | 1.00 | 30.68 | B | N |
| ATOM | 6149 | C | ASN | B | 215 | 88.245 | 33.083 | −15.185 | 1.00 | 19.49 | B | C |
| ATOM | 6150 | O | ASN | B | 215 | 87.251 | 32.411 | −15.394 | 1.00 | 17.69 | B | O |
| ATOM | 6151 | N | GLN | B | 216 | 89.388 | 32.554 | −14.771 | 1.00 | 15.50 | B | N |
| ATOM | 6152 | CA | GLN | B | 216 | 89.567 | 31.099 | −14.674 | 1.00 | 17.45 | B | C |
| ATOM | 6153 | CB | GLN | B | 216 | 91.057 | 30.710 | −14.607 | 1.00 | 19.58 | B | C |
| ATOM | 6154 | CG | GLN | B | 216 | 91.873 | 31.067 | −15.868 | 1.00 | 23.01 | B | C |
| ATOM | 6155 | CD | GLN | B | 216 | 91.223 | 30.547 | −17.164 | 1.00 | 27.82 | B | C |
| ATOM | 6156 | OE1 | GLN | B | 216 | 91.277 | 29.346 | −17.475 | 1.00 | 28.73 | B | O |
| ATOM | 6157 | NE2 | GLN | B | 216 | 90.588 | 31.453 | −17.914 | 1.00 | 26.91 | B | N |
| ATOM | 6158 | C | GLN | B | 216 | 88.800 | 30.499 | −13.490 | 1.00 | 16.75 | B | C |
| ATOM | 6159 | O | GLN | B | 216 | 88.333 | 29.345 | −13.555 | 1.00 | 14.88 | B | O |
| ATOM | 6160 | N | VAL | B | 217 | 88.654 | 31.273 | −12.416 | 1.00 | 13.21 | B | N |
| ATOM | 6161 | CA | VAL | B | 217 | 87.857 | 30.809 | −11.286 | 1.00 | 13.06 | B | C |
| ATOM | 6162 | CB | VAL | B | 217 | 87.984 | 31.751 | −10.040 | 1.00 | 14.93 | B | C |
| ATOM | 6163 | CG1 | VAL | B | 217 | 86.939 | 31.390 | −8.994 | 1.00 | 12.99 | B | C |
| ATOM | 6164 | CG2 | VAL | B | 217 | 89.391 | 31.674 | −9.443 | 1.00 | 12.34 | B | C |
| ATOM | 6165 | C | VAL | B | 217 | 86.403 | 30.651 | −11.709 | 1.00 | 13.42 | B | C |
| ATOM | 6166 | O | VAL | B | 217 | 85.782 | 29.594 | −11.470 | 1.00 | 13.08 | B | O |
| ATOM | 6167 | N | LEU | B | 218 | 85.867 | 31.665 | −12.384 | 1.00 | 12.11 | B | N |
| ATOM | 6168 | CA | LEU | B | 218 | 84.466 | 31.647 | −12.768 | 1.00 | 13.87 | B | C |
| ATOM | 6169 | CB | LEU | B | 218 | 84.045 | 33.022 | −13.323 | 1.00 | 14.78 | B | C |
| ATOM | 6170 | CG | LEU | B | 218 | 82.600 | 33.252 | −13.772 | 1.00 | 16.06 | B | C |
| ATOM | 6171 | CD1 | LEU | B | 218 | 81.654 | 33.022 | −12.598 | 1.00 | 14.64 | B | C |
| ATOM | 6172 | CD2 | LEU | B | 218 | 82.436 | 34.651 | −14.330 | 1.00 | 13.89 | B | C |
| ATOM | 6173 | C | LEU | B | 218 | 84.238 | 30.559 | −13.810 | 1.00 | 15.09 | B | C |
| ATOM | 6174 | O | LEU | B | 218 | 83.244 | 29.833 | −13.757 | 1.00 | 15.71 | B | O |
| ATOM | 6175 | N | LEU | B | 219 | 85.139 | 30.459 | −14.781 | 1.00 | 14.94 | B | N |
| ATOM | 6176 | CA | LEU | B | 219 | 85.027 | 29.452 | −15.827 | 1.00 | 15.31 | B | C |
| ATOM | 6177 | CB | LEU | B | 219 | 86.161 | 29.580 | −16.840 | 1.00 | 16.77 | B | C |
| ATOM | 6178 | CG | LEU | B | 219 | 86.283 | 28.499 | −17.925 | 1.00 | 17.35 | B | C |
| ATOM | 6179 | CD1 | LEU | B | 219 | 84.975 | 28.362 | −18.681 | 1.00 | 16.73 | B | C |
| ATOM | 6180 | CD2 | LEU | B | 219 | 87.489 | 28.794 | −18.869 | 1.00 | 19.01 | B | C |

APPENDIX A-continued

*P. alba* 3T288C coordinates

| ATOM | 6181 | C | LEU | B | 219 | 85.030 | 28.057 | −15.230 | 1.00 | 13.44 | B | C |
|---|---|---|---|---|---|---|---|---|---|---|---|---|
| ATOM | 6182 | O | LEU | B | 219 | 84.175 | 27.236 | −15.559 | 1.00 | 16.42 | B | O |
| ATOM | 6183 | N | GLU | B | 220 | 85.986 | 27.779 | −14.362 | 1.00 | 12.24 | B | N |
| ATOM | 6184 | CA | GLU | B | 220 | 86.071 | 26.453 | −13.760 | 1.00 | 14.83 | B | C |
| ATOM | 6185 | CB | GLU | B | 220 | 87.308 | 26.297 | −12.882 | 1.00 | 16.56 | B | C |
| ATOM | 6186 | CG | GLU | B | 220 | 87.391 | 24.892 | −12.308 | 1.00 | 18.99 | B | C |
| ATOM | 6187 | CD | GLU | B | 220 | 88.677 | 24.606 | −11.570 | 1.00 | 23.45 | B | C |
| ATOM | 6188 | OE1 | GLU | B | 220 | 89.457 | 25.554 | −11.301 | 1.00 | 23.25 | B | O |
| ATOM | 6189 | OE2 | GLU | B | 220 | 88.882 | 23.412 | −11.258 | 1.00 | 23.06 | B | O |
| ATOM | 6190 | C | GLU | B | 220 | 84.803 | 26.118 | −12.958 | 1.00 | 15.88 | B | C |
| ATOM | 6191 | O | GLU | B | 220 | 84.271 | 25.018 | −13.082 | 1.00 | 14.54 | B | O |
| ATOM | 6192 | N | LEU | B | 221 | 84.285 | 27.079 | −12.190 | 1.00 | 14.47 | B | N |
| ATOM | 6193 | CA | LEU | B | 221 | 83.028 | 26.866 | −11.436 | 1.00 | 12.29 | B | C |
| ATOM | 6194 | CB | LEU | B | 221 | 82.737 | 28.081 | −10.553 | 1.00 | 11.47 | B | C |
| ATOM | 6195 | CG | LEU | B | 221 | 81.493 | 27.994 | −9.676 | 1.00 | 10.80 | B | C |
| ATOM | 6196 | CD1 | LEU | B | 221 | 81.598 | 26.866 | −8.638 | 1.00 | 10.25 | B | C |
| ATOM | 6197 | CD2 | LEU | B | 221 | 81.160 | 29.353 | −8.998 | 1.00 | 11.71 | B | C |
| ATOM | 6198 | C | LEU | B | 221 | 81.842 | 26.603 | −12.364 | 1.00 | 12.09 | B | C |
| ATOM | 6199 | O | LEU | B | 221 | 81.046 | 25.681 | −12.123 | 1.00 | 15.58 | B | O |
| ATOM | 6200 | N | ALA | B | 222 | 81.728 | 27.383 | −13.432 | 1.00 | 11.03 | B | N |
| ATOM | 6201 | CA | ALA | B | 222 | 80.635 | 27.213 | −14.378 | 1.00 | 14.42 | B | C |
| ATOM | 6202 | CB | ALA | B | 222 | 80.686 | 28.281 | −15.467 | 1.00 | 11.29 | B | C |
| ATOM | 6203 | C | ALA | B | 222 | 80.626 | 25.796 | −14.981 | 1.00 | 15.15 | B | C |
| ATOM | 6204 | O | ALA | B | 222 | 79.575 | 25.199 | −15.130 | 1.00 | 14.67 | B | O |
| ATOM | 6205 | N | ILE | B | 223 | 81.795 | 25.250 | −15.289 | 1.00 | 16.15 | B | N |
| ATOM | 6206 | CA | ILE | B | 223 | 81.880 | 23.889 | −15.831 | 1.00 | 15.33 | B | C |
| ATOM | 6207 | CB | ILE | B | 223 | 83.302 | 23.575 | −16.340 | 1.00 | 15.08 | B | C |
| ATOM | 6208 | CG1 | ILE | B | 223 | 83.590 | 24.391 | −17.596 | 1.00 | 13.36 | B | C |
| ATOM | 6209 | CD1 | ILE | B | 223 | 85.065 | 24.343 | −18.024 | 1.00 | 15.70 | B | C |
| ATOM | 6210 | CG2 | ILE | B | 223 | 83.453 | 22.071 | −16.630 | 1.00 | 13.45 | B | C |
| ATOM | 6211 | C | ILE | B | 223 | 81.491 | 22.862 | −14.774 | 1.00 | 14.47 | B | C |
| ATOM | 6212 | O | ILE | B | 223 | 80.665 | 21.992 | −15.007 | 1.00 | 14.34 | B | O |
| ATOM | 6213 | N | LEU | B | 224 | 82.062 | 23.009 | −13.587 | 1.00 | 15.34 | B | N |
| ATOM | 6214 | CA | ALEU | B | 224 | 81.784 | 22.109 | −12.486 | 0.50 | 16.13 | B | C |
| ATOM | 6215 | CA | BLEU | B | 224 | 81.779 | 22.060 | −12.526 | 0.50 | 16.37 | B | C |
| ATOM | 6216 | CB | ALEU | B | 224 | 82.552 | 22.593 | −11.262 | 0.50 | 16.37 | B | C |
| ATOM | 6217 | CB | BLEU | B | 224 | 82.640 | 22.335 | −11.290 | 0.50 | 16.95 | B | C |
| ATOM | 6218 | CG | ALEU | B | 224 | 82.640 | 21.657 | −10.072 | 0.50 | 16.80 | B | C |
| ATOM | 6219 | CG | BLEU | B | 224 | 84.152 | 22.112 | −11.454 | 0.50 | 17.31 | B | C |
| ATOM | 6220 | CD1 | ALEU | B | 224 | 83.895 | 22.006 | −9.297 | 0.50 | 15.21 | B | C |
| ATOM | 6221 | CD1 | BLEU | B | 224 | 84.830 | 22.348 | −10.119 | 0.50 | 16.93 | B | C |
| ATOM | 6222 | CD2 | ALEU | B | 224 | 81.395 | 21.740 | −9.189 | 0.50 | 14.02 | B | C |
| ATOM | 6223 | CD2 | BLEU | B | 224 | 84.502 | 20.713 | −12.008 | 0.50 | 17.10 | B | C |
| ATOM | 6224 | C | LEU | B | 224 | 80.276 | 22.060 | −12.196 | 1.00 | 17.10 | B | C |
| ATOM | 6225 | O | LEU | B | 224 | 79.666 | 20.988 | −12.081 | 1.00 | 14.62 | B | O |
| ATOM | 6226 | N | ASP | B | 225 | 79.678 | 23.237 | −12.062 | 1.00 | 14.86 | B | N |
| ATOM | 6227 | CA | ASP | B | 225 | 78.271 | 23.337 | −11.693 | 1.00 | 14.10 | B | C |
| ATOM | 6228 | CB | ASP | B | 225 | 77.864 | 24.805 | −11.425 | 1.00 | 14.24 | B | C |
| ATOM | 6229 | CG | ASP | B | 225 | 76.624 | 24.906 | −10.544 | 1.00 | 15.89 | B | C |
| ATOM | 6230 | OD1 | ASP | B | 225 | 76.787 | 24.757 | −9.307 | 1.00 | 16.14 | B | O |
| ATOM | 6231 | OD2 | ASP | B | 225 | 75.494 | 25.104 | −11.079 | 1.00 | 16.81 | B | O |
| ATOM | 6232 | C | ASP | B | 225 | 77.365 | 22.750 | −12.777 | 1.00 | 13.39 | B | C |
| ATOM | 6233 | O | ASP | B | 225 | 76.487 | 21.982 | −12.464 | 1.00 | 15.58 | B | O |
| ATOM | 6234 | N | TYR | B | 226 | 77.603 | 23.096 | −14.044 | 1.00 | 11.94 | B | N |
| ATOM | 6235 | CA | TYR | B | 226 | 76.825 | 22.573 | −15.154 | 1.00 | 15.44 | B | C |
| ATOM | 6236 | CB | TYR | B | 226 | 77.342 | 23.140 | −16.461 | 1.00 | 14.71 | B | C |
| ATOM | 6237 | CG | TYR | B | 226 | 76.434 | 22.785 | −17.603 | 1.00 | 15.95 | B | C |
| ATOM | 6238 | CD1 | TYR | B | 226 | 76.558 | 21.559 | −18.265 | 1.00 | 16.89 | B | C |
| ATOM | 6239 | CE1 | TYR | B | 226 | 75.730 | 21.218 | −19.309 | 1.00 | 19.42 | B | C |
| ATOM | 6240 | CZ | TYR | B | 226 | 74.746 | 22.102 | −19.716 | 1.00 | 21.14 | B | C |
| ATOM | 6241 | OH | TYR | B | 226 | 73.902 | 21.754 | −20.731 | 1.00 | 22.75 | B | O |
| ATOM | 6242 | CE2 | TYR | B | 226 | 74.592 | 23.324 | −19.066 | 1.00 | 21.14 | B | C |
| ATOM | 6243 | CD2 | TYR | B | 226 | 75.450 | 23.658 | −18.023 | 1.00 | 18.76 | B | C |
| ATOM | 6244 | C | TYR | B | 226 | 76.814 | 21.032 | −15.199 | 1.00 | 18.55 | B | C |
| ATOM | 6245 | O | TYR | B | 226 | 75.751 | 20.403 | −15.340 | 1.00 | 14.96 | B | O |
| ATOM | 6246 | N | ASN | B | 227 | 77.993 | 20.438 | −15.054 | 1.00 | 17.61 | B | N |
| ATOM | 6247 | CA | ASN | B | 227 | 78.132 | 18.972 | −15.059 | 1.00 | 18.83 | B | C |
| ATOM | 6248 | CB | ASN | B | 227 | 79.592 | 18.545 | −15.274 | 1.00 | 19.64 | B | C |
| ATOM | 6249 | CG | ASN | B | 227 | 80.065 | 18.832 | −16.685 | 1.00 | 18.15 | B | C |
| ATOM | 6250 | OD1 | ASN | B | 227 | 79.248 | 19.019 | −17.608 | 1.00 | 20.61 | B | O |
| ATOM | 6251 | ND2 | ASN | B | 227 | 81.370 | 18.933 | −16.861 | 1.00 | 16.37 | B | N |
| ATOM | 6252 | C | ASN | B | 227 | 77.496 | 18.337 | −13.828 | 1.00 | 20.83 | B | C |
| ATOM | 6253 | O | ASN | B | 227 | 76.846 | 17.296 | −13.957 | 1.00 | 19.81 | B | O |
| ATOM | 6254 | N | MET | B | 228 | 77.571 | 19.001 | −12.673 | 1.00 | 17.33 | B | N |
| ATOM | 6255 | CA | AMET | B | 228 | 76.866 | 18.537 | −11.479 | 0.50 | 16.75 | B | C |
| ATOM | 6256 | CA | BMET | B | 228 | 76.865 | 18.495 | −11.491 | 0.50 | 22.51 | B | C |
| ATOM | 6257 | CB | AMET | B | 228 | 77.225 | 19.420 | −10.287 | 0.50 | 14.37 | B | C |
| ATOM | 6258 | CB | BMET | B | 228 | 77.300 | 19.200 | −10.188 | 0.50 | 29.14 | B | C |

APPENDIX A-continued

P. alba 3T288C coordinates

| ATOM | 6259 | CG | AMET | B | 228 | 76.537 | 19.072 | −8.975 | 0.50 | 12.77 | B | C |
|------|------|------|------|---|-----|--------|--------|--------|------|-------|---|---|
| ATOM | 6260 | CG | BMET | B | 228 | 76.514 | 20.447 | −9.749 | 0.50 | 44.80 | B | C |
| ATOM | 6261 | SD | AMET | B | 228 | 76.760 | 20.399 | −7.762 | 0.50 | 12.66 | B | S |
| ATOM | 6262 | SD | BMET | B | 228 | 75.395 | 20.226 | −8.333 | 0.50 | 54.35 | B | S |
| ATOM | 6263 | CE | AMET | B | 228 | 75.682 | 21.683 | −8.474 | 0.50 | 15.49 | B | C |
| ATOM | 6264 | CE | BMET | B | 228 | 74.091 | 19.223 | −9.003 | 0.50 | 42.65 | B | C |
| ATOM | 6265 | C | MET | B | 228 | 75.342 | 18.530 | −11.708 | 1.00 | 20.48 | B | C |
| ATOM | 6266 | O | MET | B | 228 | 74.653 | 17.559 | −11.394 | 1.00 | 18.56 | B | O |
| ATOM | 6267 | N | ILE | B | 229 | 74.799 | 19.611 | −12.268 | 1.00 | 17.89 | B | N |
| ATOM | 6268 | CA | ILE | B | 229 | 73.350 | 19.661 | −12.469 | 1.00 | 15.86 | B | C |
| ATOM | 6269 | CB | ILE | B | 229 | 72.858 | 21.076 | −12.870 | 1.00 | 16.15 | B | C |
| ATOM | 6270 | CG1 | ILE | B | 229 | 73.043 | 22.035 | −11.687 | 1.00 | 15.99 | B | C |
| ATOM | 6271 | CD1 | ILE | B | 229 | 72.699 | 23.482 | −11.988 | 1.00 | 18.39 | B | C |
| ATOM | 6272 | CG2 | ILE | B | 229 | 71.358 | 21.045 | −13.274 | 1.00 | 15.61 | B | C |
| ATOM | 6273 | C | ILE | B | 229 | 72.943 | 18.596 | −13.495 | 1.00 | 17.35 | B | C |
| ATOM | 6274 | O | ILE | B | 229 | 71.971 | 17.909 | −13.306 | 1.00 | 23.75 | B | O |
| ATOM | 6275 | N | GLN | B | 230 | 73.701 | 18.459 | −14.570 | 1.00 | 17.03 | B | N |
| ATOM | 6276 | CA | GLN | B | 230 | 73.427 | 17.433 | −15.545 | 1.00 | 22.65 | B | C |
| ATOM | 6277 | CB | GLN | B | 230 | 74.469 | 17.433 | −16.630 | 1.00 | 23.17 | B | C |
| ATOM | 6278 | CG | GLN | B | 230 | 74.036 | 16.671 | −17.840 | 1.00 | 24.09 | B | C |
| ATOM | 6279 | CD | GLN | B | 230 | 75.124 | 16.660 | −18.876 | 1.00 | 25.69 | B | C |
| ATOM | 6280 | OE1 | GLN | B | 230 | 76.207 | 16.159 | −18.617 | 1.00 | 24.23 | B | O |
| ATOM | 6281 | NE2 | GLN | B | 230 | 74.854 | 17.238 | −20.050 | 1.00 | 23.11 | B | N |
| ATOM | 6282 | C | GLN | B | 230 | 73.368 | 16.037 | −14.929 | 1.00 | 23.04 | B | C |
| ATOM | 6283 | O | GLN | B | 230 | 72.565 | 15.234 | −15.356 | 1.00 | 23.54 | B | O |
| ATOM | 6284 | N | SER | B | 231 | 74.200 | 15.745 | −13.941 | 1.00 | 21.41 | B | N |
| ATOM | 6285 | CA | SER | B | 231 | 74.193 | 14.412 | −13.319 | 1.00 | 23.65 | B | C |
| ATOM | 6286 | CB | SER | B | 231 | 75.471 | 14.168 | −12.468 | 1.00 | 23.19 | B | C |
| ATOM | 6287 | OG | SER | B | 231 | 75.384 | 14.886 | −11.237 | 1.00 | 32.62 | B | O |
| ATOM | 6288 | C | SER | B | 231 | 72.896 | 14.223 | −12.512 | 1.00 | 24.26 | B | C |
| ATOM | 6289 | O | SER | B | 231 | 72.344 | 13.112 | −12.459 | 1.00 | 20.75 | B | O |
| ATOM | 6290 | N | VAL | B | 232 | 72.381 | 15.302 | −11.929 | 1.00 | 21.48 | B | N |
| ATOM | 6291 | CA | VAL | B | 232 | 71.037 | 15.279 | −11.328 | 1.00 | 21.24 | B | C |
| ATOM | 6292 | CB | VAL | B | 232 | 70.692 | 16.603 | −10.628 | 1.00 | 23.83 | B | C |
| ATOM | 6293 | CG1 | VAL | B | 232 | 69.270 | 16.592 | −10.059 | 1.00 | 24.12 | B | C |
| ATOM | 6294 | CG2 | VAL | B | 232 | 71.681 | 16.880 | −9.532 | 1.00 | 20.84 | B | C |
| ATOM | 6295 | C | VAL | B | 232 | 69.986 | 14.952 | −12.413 | 1.00 | 24.74 | B | C |
| ATOM | 6296 | O | VAL | B | 232 | 69.136 | 14.097 | −12.209 | 1.00 | 24.73 | B | O |
| ATOM | 6297 | N | TYR | B | 233 | 70.071 | 15.579 | −13.583 | 1.00 | 23.53 | B | N |
| ATOM | 6298 | CA | TYR | B | 233 | 69.100 | 15.288 | −14.644 | 1.00 | 23.90 | B | C |
| ATOM | 6299 | CB | TYR | B | 233 | 69.310 | 16.184 | −15.861 | 1.00 | 19.78 | B | C |
| ATOM | 6300 | CG | TYR | B | 233 | 69.165 | 17.700 | −15.638 | 1.00 | 15.82 | B | C |
| ATOM | 6301 | CD1 | TYR | B | 233 | 68.412 | 18.220 | −14.594 | 1.00 | 14.87 | B | C |
| ATOM | 6302 | CE1 | TYR | B | 233 | 68.281 | 19.609 | −14.438 | 1.00 | 16.04 | B | C |
| ATOM | 6303 | CZ | TYR | B | 233 | 68.900 | 20.445 | −15.347 | 1.00 | 15.46 | B | C |
| ATOM | 6304 | OH | TYR | B | 233 | 68.778 | 21.816 | −15.227 | 1.00 | 19.31 | B | O |
| ATOM | 6305 | CE2 | TYR | B | 233 | 69.633 | 19.934 | −16.393 | 1.00 | 16.43 | B | C |
| ATOM | 6306 | CD2 | TYR | B | 233 | 69.760 | 18.597 | −16.540 | 1.00 | 15.50 | B | C |
| ATOM | 6307 | C | TYR | B | 233 | 69.201 | 13.806 | −15.097 | 1.00 | 29.65 | B | C |
| ATOM | 6308 | O | TYR | B | 233 | 68.182 | 13.176 | −15.436 | 1.00 | 24.75 | B | O |
| ATOM | 6309 | N | GLN | B | 234 | 70.415 | 13.260 | −15.122 | 1.00 | 23.59 | B | N |
| ATOM | 6310 | CA | GLN | B | 234 | 70.614 | 11.879 | −15.605 | 1.00 | 27.67 | B | C |
| ATOM | 6311 | CB | GLN | B | 234 | 72.083 | 11.615 | −15.914 | 1.00 | 26.53 | B | C |
| ATOM | 6312 | CG | GLN | B | 234 | 72.547 | 12.384 | −17.157 | 1.00 | 26.79 | B | C |
| ATOM | 6313 | CD | GLN | B | 234 | 74.045 | 12.416 | −17.285 | 1.00 | 29.18 | B | C |
| ATOM | 6314 | OE1 | GLN | B | 234 | 74.758 | 12.085 | −16.338 | 1.00 | 32.91 | B | O |
| ATOM | 6315 | NE2 | GLN | B | 234 | 74.541 | 12.814 | −18.458 | 1.00 | 29.56 | B | N |
| ATOM | 6316 | C | GLN | B | 234 | 70.021 | 10.888 | −14.609 | 1.00 | 23.60 | B | C |
| ATOM | 6317 | O | GLN | B | 234 | 69.391 | 9.907 | −15.012 | 1.00 | 30.92 | B | O |
| ATOM | 6318 | N | ARG | B | 235 | 70.150 | 11.174 | −13.319 | 1.00 | 25.13 | B | N |
| ATOM | 6319 | CA | ARG | B | 235 | 69.448 | 10.394 | −12.303 | 1.00 | 29.36 | B | C |
| ATOM | 6320 | CB | ARG | B | 235 | 69.922 | 10.758 | −10.898 | 1.00 | 30.29 | B | C |
| ATOM | 6321 | CG | ARG | B | 235 | 69.373 | 9.840 | −9.811 | 1.00 | 39.19 | B | C |
| ATOM | 6322 | CD | ARG | B | 235 | 70.021 | 10.065 | −8.460 | 1.00 | 56.79 | B | C |
| ATOM | 6323 | NE | ARG | B | 235 | 69.818 | 11.434 | −7.971 | 1.00 | 77.67 | B | N |
| ATOM | 6324 | CZ | ARG | B | 235 | 70.759 | 12.383 | −7.879 | 1.00 | 76.44 | B | C |
| ATOM | 6325 | NH1 | ARG | B | 235 | 72.024 | 12.147 | −8.232 | 1.00 | 76.63 | B | N |
| ATOM | 6326 | NH2 | ARG | B | 235 | 70.430 | 13.592 | −7.421 | 1.00 | 56.91 | B | N |
| ATOM | 6327 | C | ARG | B | 235 | 67.908 | 10.518 | −12.423 | 1.00 | 30.66 | B | C |
| ATOM | 6328 | O | ARG | B | 235 | 67.200 | 9.523 | −12.395 | 1.00 | 26.67 | B | O |
| ATOM | 6329 | N | ASP | B | 236 | 67.391 | 11.726 | −12.567 | 1.00 | 29.85 | B | N |
| ATOM | 6330 | CA | ASP | B | 236 | 65.944 | 11.945 | −12.764 | 1.00 | 25.23 | B | C |
| ATOM | 6331 | CB | ASP | B | 236 | 65.644 | 13.409 | −13.134 | 1.00 | 30.33 | B | C |
| ATOM | 6332 | CG | ASP | B | 236 | 65.904 | 14.414 | −12.004 | 1.00 | 36.62 | B | C |
| ATOM | 6333 | OD1 | ASP | B | 236 | 65.910 | 14.039 | −10.810 | 1.00 | 31.93 | B | O |
| ATOM | 6334 | OD2 | ASP | B | 236 | 66.050 | 15.627 | −12.336 | 1.00 | 28.75 | B | O |
| ATOM | 6335 | C | ASP | B | 236 | 65.437 | 11.096 | −13.924 | 1.00 | 24.79 | B | C |
| ATOM | 6336 | O | ASP | B | 236 | 64.449 | 10.412 | −13.797 | 1.00 | 27.76 | B | O |

APPENDIX A-continued

P. alba 3T288C coordinates

| ATOM | 6337 | N | LEU | B | 237 | 66.126 | 11.191 | −15.058 | 1.00 | 21.17 | B | N |
|---|---|---|---|---|---|---|---|---|---|---|---|---|
| ATOM | 6338 | CA | LEU | B | 237 | 65.758 | 10.541 | −16.298 | 1.00 | 24.76 | B | C |
| ATOM | 6339 | CB | LEU | B | 237 | 66.664 | 11.028 | −17.431 | 1.00 | 24.56 | B | C |
| ATOM | 6340 | CG | LEU | B | 237 | 66.562 | 10.373 | −18.805 | 1.00 | 29.01 | B | C |
| ATOM | 6341 | CD1 | LEU | B | 237 | 65.215 | 10.683 | −19.447 | 1.00 | 30.62 | B | C |
| ATOM | 6342 | CD2 | LEU | B | 237 | 67.720 | 10.818 | −19.706 | 1.00 | 31.68 | B | C |
| ATOM | 6343 | C | LEU | B | 237 | 65.849 | 9.017 | −16.213 | 1.00 | 31.40 | B | C |
| ATOM | 6344 | O | LEU | B | 237 | 65.066 | 8.326 | −16.851 | 1.00 | 24.72 | B | O |
| ATOM | 6345 | N | ARG | B | 238 | 66.832 | 8.503 | −15.484 | 1.00 | 28.78 | B | N |
| ATOM | 6346 | CA | AARG | B | 238 | 66.936 | 7.058 | −15.276 | 0.50 | 33.73 | B | C |
| ATOM | 6347 | CA | BARG | B | 238 | 66.945 | 7.057 | −15.247 | 0.50 | 35.56 | B | C |
| ATOM | 6348 | CB | AARG | B | 238 | 68.255 | 6.681 | −14.581 | 0.50 | 31.17 | B | C |
| ATOM | 6349 | CB | BARG | B | 238 | 68.215 | 6.706 | −14.454 | 0.50 | 35.57 | B | C |
| ATOM | 6350 | CG | AARG | B | 238 | 69.474 | 6.716 | −15.506 | 0.50 | 30.21 | B | C |
| ATOM | 6351 | CG | BARG | B | 238 | 69.457 | 6.476 | −15.299 | 0.50 | 37.44 | B | C |
| ATOM | 6352 | CD | AARG | B | 238 | 70.728 | 6.119 | −14.842 | 0.50 | 33.56 | B | C |
| ATOM | 6353 | CD | BARG | B | 238 | 70.558 | 5.769 | −14.481 | 0.50 | 41.07 | B | C |
| ATOM | 6354 | NE | AARG | B | 238 | 71.117 | 6.845 | −13.633 | 0.50 | 32.43 | B | N |
| ATOM | 6355 | NE | BARG | B | 238 | 71.197 | 6.676 | −13.525 | 0.50 | 42.64 | B | N |
| ATOM | 6356 | CZ | AARG | B | 238 | 72.064 | 7.776 | −13.591 | 0.50 | 25.66 | B | C |
| ATOM | 6357 | CZ | BARG | B | 238 | 70.981 | 6.679 | −12.210 | 0.50 | 36.62 | B | C |
| ATOM | 6358 | NH1 | AARG | B | 238 | 72.731 | 8.098 | −14.692 | 0.50 | 21.79 | B | N |
| ATOM | 6359 | NH1 | BARG | B | 238 | 70.145 | 5.812 | −11.649 | 0.50 | 30.78 | B | N |
| ATOM | 6360 | NH2 | AARG | B | 238 | 72.339 | 8.381 | −12.446 | 0.50 | 23.30 | B | N |
| ATOM | 6361 | NH2 | BARG | B | 238 | 71.616 | 7.557 | −11.450 | 0.50 | 35.02 | B | N |
| ATOM | 6362 | C | ARG | B | 238 | 65.723 | 6.562 | −14.485 | 1.00 | 36.07 | B | C |
| ATOM | 6363 | O | ARG | B | 238 | 65.155 | 5.526 | −14.817 | 1.00 | 32.64 | B | O |
| ATOM | 6364 | N | GLU | B | 239 | 65.307 | 7.314 | −13.468 | 1.00 | 33.02 | B | N |
| ATOM | 6365 | CA | GLU | B | 239 | 64.140 | 6.922 | −12.679 | 1.00 | 39.52 | B | C |
| ATOM | 6366 | CB | GLU | B | 239 | 64.051 | 7.764 | −11.416 | 1.00 | 50.36 | B | C |
| ATOM | 6367 | CG | GLU | B | 239 | 62.899 | 7.375 | −10.495 | 1.00 | 67.79 | B | C |
| ATOM | 6368 | CD | GLU | B | 239 | 62.986 | 8.033 | −9.123 | 1.00 | 87.78 | B | C |
| ATOM | 6369 | OE1 | GLU | B | 239 | 64.032 | 8.639 | −8.798 | 1.00 | 81.07 | B | O |
| ATOM | 6370 | OE2 | GLU | B | 239 | 61.998 | 7.943 | −8.363 | 1.00 | 105.74 | B | O |
| ATOM | 6371 | C | GLU | B | 239 | 62.825 | 7.017 | −13.483 | 1.00 | 44.14 | B | C |
| ATOM | 6372 | O | GLU | B | 239 | 61.941 | 6.160 | −13.360 | 1.00 | 37.48 | B | O |
| ATOM | 6373 | N | THR | B | 240 | 62.709 | 8.058 | −14.299 | 1.00 | 35.32 | B | N |
| ATOM | 6374 | CA | THR | B | 240 | 61.537 | 8.246 | −15.162 | 1.00 | 32.81 | B | C |
| ATOM | 6375 | CB | THR | B | 240 | 61.473 | 9.688 | −15.647 | 1.00 | 33.62 | B | C |
| ATOM | 6376 | OG1 | THR | B | 240 | 61.233 | 10.512 | −14.498 | 1.00 | 32.31 | B | O |
| ATOM | 6377 | CG2 | THR | B | 240 | 60.347 | 9.909 | −16.683 | 1.00 | 28.21 | B | C |
| ATOM | 6378 | C | THR | B | 240 | 61.555 | 7.265 | −16.334 | 1.00 | 32.29 | B | C |
| ATOM | 6379 | O | THR | B | 240 | 60.508 | 6.883 | −16.842 | 1.00 | 30.87 | B | O |
| ATOM | 6380 | N | SER | B | 241 | 62.742 | 6.866 | −16.775 | 1.00 | 35.89 | B | N |
| ATOM | 6381 | CA | SER | B | 241 | 62.876 | 5.813 | −17.801 | 1.00 | 36.95 | B | C |
| ATOM | 6382 | CB | SER | B | 241 | 64.332 | 5.642 | −18.239 | 1.00 | 41.95 | B | C |
| ATOM | 6383 | OG | SER | B | 241 | 64.659 | 6.570 | −19.256 | 1.00 | 43.35 | B | O |
| ATOM | 6384 | C | SER | B | 241 | 62.369 | 4.479 | −17.284 | 1.00 | 30.92 | B | C |
| ATOM | 6385 | O | SER | B | 241 | 61.673 | 3.751 | −17.983 | 1.00 | 31.23 | B | O |
| ATOM | 6386 | N | ARG | B | 242 | 62.720 | 4.158 | −16.056 | 1.00 | 31.06 | B | N |
| ATOM | 6387 | CA | ARG | B | 242 | 62.264 | 2.918 | −15.487 | 1.00 | 43.04 | B | C |
| ATOM | 6388 | CB | ARG | B | 242 | 62.894 | 2.633 | −14.122 | 1.00 | 49.17 | B | C |
| ATOM | 6389 | CG | ARG | B | 242 | 64.246 | 1.896 | −14.196 | 1.00 | 63.90 | B | C |
| ATOM | 6390 | CD | ARG | B | 242 | 64.647 | 1.303 | −12.835 | 1.00 | 65.15 | B | C |
| ATOM | 6391 | NE | ARG | B | 242 | 64.177 | 2.139 | −11.721 | 1.00 | 71.29 | B | N |
| ATOM | 6392 | CZ | ARG | B | 242 | 64.864 | 3.126 | −11.141 | 1.00 | 77.59 | B | C |
| ATOM | 6393 | NH1 | ARG | B | 242 | 66.099 | 3.431 | −11.532 | 1.00 | 83.44 | B | N |
| ATOM | 6394 | NH2 | ARG | B | 242 | 64.309 | 3.814 | −10.147 | 1.00 | 76.69 | B | N |
| ATOM | 6395 | C | ARG | B | 242 | 60.762 | 2.955 | −15.381 | 1.00 | 31.28 | B | C |
| ATOM | 6396 | O | ARG | B | 242 | 60.123 | 1.965 | −15.642 | 1.00 | 36.75 | B | O |
| ATOM | 6397 | N | TRP | B | 243 | 60.202 | 4.081 | −14.965 | 1.00 | 30.04 | B | N |
| ATOM | 6398 | CA | TRP | B | 243 | 58.751 | 4.277 | −14.948 | 1.00 | 24.61 | B | C |
| ATOM | 6399 | CB | TRP | B | 243 | 58.397 | 5.692 | −14.474 | 1.00 | 29.93 | B | C |
| ATOM | 6400 | CG | TRP | B | 243 | 56.955 | 6.076 | −14.721 | 1.00 | 20.51 | B | C |
| ATOM | 6401 | CD1 | TRP | B | 243 | 55.854 | 5.661 | −13.998 | 1.00 | 24.00 | B | C |
| ATOM | 6402 | NE1 | TRP | B | 243 | 54.712 | 6.162 | −14.525 | 1.00 | 27.60 | B | N |
| ATOM | 6403 | CE2 | TRP | B | 243 | 54.967 | 6.875 | −15.624 | 1.00 | 19.22 | B | C |
| ATOM | 6404 | CD2 | TRP | B | 243 | 56.412 | 6.868 | −15.811 | 1.00 | 19.39 | B | C |
| ATOM | 6405 | CE3 | TRP | B | 243 | 56.949 | 7.527 | −16.889 | 1.00 | 19.69 | B | C |
| ATOM | 6406 | CZ3 | TRP | B | 243 | 56.099 | 8.225 | −17.740 | 1.00 | 22.15 | B | C |
| ATOM | 6407 | CH2 | TRP | B | 243 | 54.712 | 8.236 | −17.526 | 1.00 | 25.82 | B | C |
| ATOM | 6408 | CZ2 | TRP | B | 243 | 54.132 | 7.543 | −16.456 | 1.00 | 20.93 | B | C |
| ATOM | 6409 | C | TRP | B | 243 | 58.132 | 4.039 | −16.310 | 1.00 | 24.26 | B | C |
| ATOM | 6410 | O | TRP | B | 243 | 57.138 | 3.322 | −16.441 | 1.00 | 24.17 | B | O |
| ATOM | 6411 | N | TRP | B | 244 | 58.691 | 4.659 | −17.342 | 1.00 | 20.84 | B | N |
| ATOM | 6412 | CA | TRP | B | 244 | 58.099 | 4.583 | −18.675 | 1.00 | 19.39 | B | C |
| ATOM | 6413 | CB | TRP | B | 244 | 58.793 | 5.572 | −19.606 | 1.00 | 22.08 | B | C |
| ATOM | 6414 | CG | TRP | B | 244 | 58.136 | 5.798 | −20.943 | 1.00 | 24.58 | B | C |

APPENDIX A-continued

*P. alba* 3T288C coordinates

| ATOM | 6415 | CD1 | TRP | B | 244 | 58.744 | 5.714 | −22.189 | 1.00 | 33.52 | B | C |
| ATOM | 6416 | NE1 | TRP | B | 244 | 57.842 | 5.994 | −23.184 | 1.00 | 32.99 | B | N |
| ATOM | 6417 | CE2 | TRP | B | 244 | 56.626 | 6.277 | −22.674 | 1.00 | 25.24 | B | C |
| ATOM | 6418 | CD2 | TRP | B | 244 | 56.729 | 6.170 | −21.233 | 1.00 | 24.61 | B | C |
| ATOM | 6419 | CE3 | TRP | B | 244 | 55.597 | 6.387 | −20.467 | 1.00 | 22.17 | B | C |
| ATOM | 6420 | CZ3 | TRP | B | 244 | 54.404 | 6.694 | −21.102 | 1.00 | 28.89 | B | C |
| ATOM | 6421 | CH2 | TRP | B | 244 | 54.327 | 6.798 | −22.486 | 1.00 | 30.43 | B | C |
| ATOM | 6422 | CZ2 | TRP | B | 244 | 55.438 | 6.596 | −23.299 | 1.00 | 29.37 | B | C |
| ATOM | 6423 | C | TRP | B | 244 | 58.160 | 3.178 | −19.209 | 1.00 | 19.52 | B | C |
| ATOM | 6424 | O | TRP | B | 244 | 57.231 | 2.709 | −19.844 | 1.00 | 15.68 | B | O |
| ATOM | 6425 | N | ARG | B | 245 | 59.256 | 2.487 | −18.948 | 1.00 | 21.43 | B | N |
| ATOM | 6426 | CA | ARG | B | 245 | 59.400 | 1.083 | −19.391 | 1.00 | 26.75 | B | C |
| ATOM | 6427 | CB | ARG | B | 245 | 60.834 | 0.594 | −19.143 | 1.00 | 29.07 | B | C |
| ATOM | 6428 | CG | ARG | B | 245 | 61.766 | 0.748 | −20.349 | 1.00 | 46.10 | B | C |
| ATOM | 6429 | CD | ARG | B | 245 | 63.055 | −0.075 | −20.152 | 1.00 | 52.27 | B | C |
| ATOM | 6430 | NE | ARG | B | 245 | 63.735 | 0.329 | −18.919 | 1.00 | 64.17 | B | N |
| ATOM | 6431 | CZ | ARG | B | 245 | 64.460 | 1.444 | −18.777 | 1.00 | 60.45 | B | C |
| ATOM | 6432 | NH1 | ARG | B | 245 | 64.629 | 2.282 | −19.802 | 1.00 | 61.89 | B | N |
| ATOM | 6433 | NH2 | ARG | B | 245 | 65.017 | 1.732 | −17.602 | 1.00 | 47.28 | B | N |
| ATOM | 6434 | C | ARG | B | 245 | 58.397 | 0.139 | −18.696 | 1.00 | 28.71 | B | C |
| ATOM | 6435 | O | ARG | B | 245 | 57.820 | −0.740 | −19.320 | 1.00 | 25.38 | B | O |
| ATOM | 6436 | N | ARG | B | 246 | 58.216 | 0.320 | −17.396 | 1.00 | 32.47 | B | N |
| ATOM | 6437 | CA | ARG | B | 246 | 57.112 | −0.300 | −16.645 | 1.00 | 37.98 | B | C |
| ATOM | 6438 | CB | ARG | B | 246 | 57.043 | 0.306 | −15.234 | 1.00 | 56.60 | B | C |
| ATOM | 6439 | CG | ARG | B | 246 | 56.231 | −0.484 | −14.220 | 1.00 | 67.23 | B | C |
| ATOM | 6440 | CD | ARG | B | 246 | 57.128 | −1.273 | −13.267 | 1.00 | 74.38 | B | C |
| ATOM | 6441 | NE | ARG | B | 246 | 56.697 | −2.665 | −13.121 | 1.00 | 94.33 | B | N |
| ATOM | 6442 | CZ | ARG | B | 246 | 57.313 | −3.572 | −12.368 | 1.00 | 96.83 | B | C |
| ATOM | 6443 | NH1 | ARG | B | 246 | 58.394 | −3.246 | −11.664 | 1.00 | 103.34 | B | N |
| ATOM | 6444 | NH2 | ARG | B | 246 | 56.844 | −4.810 | −12.311 | 1.00 | 93.77 | B | N |
| ATOM | 6445 | C | ARG | B | 246 | 55.753 | −0.116 | −17.318 | 1.00 | 26.40 | B | C |
| ATOM | 6446 | O | ARG | B | 246 | 55.060 | −1.073 | −17.549 | 1.00 | 29.09 | B | O |
| ATOM | 6447 | N | VAL | B | 247 | 55.385 | 1.123 | −17.622 | 1.00 | 20.94 | B | N |
| ATOM | 6448 | CA | VAL | B | 247 | 54.100 | 1.447 | −18.239 | 1.00 | 19.96 | B | C |
| ATOM | 6449 | CB | VAL | B | 247 | 53.895 | 2.953 | −18.359 | 1.00 | 22.94 | B | C |
| ATOM | 6450 | CG1 | VAL | B | 247 | 52.618 | 3.271 | −19.077 | 1.00 | 23.70 | B | C |
| ATOM | 6451 | CG2 | VAL | B | 247 | 53.861 | 3.621 | −16.969 | 1.00 | 28.91 | B | C |
| ATOM | 6452 | C | VAL | B | 247 | 53.969 | 0.743 | −19.597 | 1.00 | 22.21 | B | C |
| ATOM | 6453 | O | VAL | B | 247 | 52.930 | 0.127 | −19.893 | 1.00 | 19.85 | B | O |
| ATOM | 6454 | N | GLY | B | 248 | 55.038 | 0.804 | −20.399 | 1.00 | 26.35 | B | N |
| ATOM | 6455 | CA | GLY | B | 248 | 55.212 | −0.050 | −21.602 | 1.00 | 25.85 | B | C |
| ATOM | 6456 | C | GLY | B | 248 | 54.266 | 0.239 | −22.739 | 1.00 | 22.97 | B | C |
| ATOM | 6457 | O | GLY | B | 248 | 53.999 | −0.599 | −23.598 | 1.00 | 27.66 | B | O |
| ATOM | 6458 | N | LEU | B | 249 | 53.749 | 1.430 | −22.753 | 1.00 | 24.10 | B | N |
| ATOM | 6459 | CA | LEU | B | 249 | 52.654 | 1.793 | −23.645 | 1.00 | 30.34 | B | C |
| ATOM | 6460 | CB | LEU | B | 249 | 52.002 | 3.042 | −23.086 | 1.00 | 31.09 | B | C |
| ATOM | 6461 | CG | LEU | B | 249 | 50.500 | 3.297 | −23.109 | 1.00 | 36.14 | B | C |
| ATOM | 6462 | CD1 | LEU | B | 249 | 49.670 | 2.120 | −22.704 | 1.00 | 34.85 | B | C |
| ATOM | 6463 | CD2 | LEU | B | 249 | 50.227 | 4.513 | −22.209 | 1.00 | 35.23 | B | C |
| ATOM | 6464 | C | LEU | B | 249 | 53.133 | 1.991 | −25.101 | 1.00 | 46.24 | B | C |
| ATOM | 6465 | O | LEU | B | 249 | 52.454 | 1.568 | −26.054 | 1.00 | 38.44 | B | O |
| ATOM | 6466 | N | ALA | B | 250 | 54.305 | 2.602 | −25.276 | 1.00 | 52.20 | B | N |
| ATOM | 6467 | CA | ALA | B | 250 | 54.887 | 2.779 | −26.614 | 1.00 | 63.15 | B | C |
| ATOM | 6468 | CB | ALA | B | 250 | 56.153 | 3.635 | −26.545 | 1.00 | 60.43 | B | C |
| ATOM | 6469 | C | ALA | B | 250 | 55.179 | 1.429 | −27.298 | 1.00 | 64.10 | B | C |
| ATOM | 6470 | O | ALA | B | 250 | 55.044 | 1.311 | −28.512 | 1.00 | 64.56 | B | O |
| ATOM | 6471 | N | THR | B | 251 | 55.566 | 0.427 | −26.507 | 1.00 | 50.70 | B | N |
| ATOM | 6472 | CA | THR | B | 251 | 55.744 | −0.947 | −26.971 | 1.00 | 41.78 | B | C |
| ATOM | 6473 | CB | THR | B | 251 | 56.377 | −1.808 | −25.860 | 1.00 | 42.75 | B | C |
| ATOM | 6474 | OG1 | THR | B | 251 | 57.705 | −1.349 | −25.620 | 1.00 | 59.83 | B | O |
| ATOM | 6475 | CG2 | THR | B | 251 | 56.414 | −3.278 | −26.243 | 1.00 | 44.05 | B | C |
| ATOM | 6476 | C | THR | B | 251 | 54.458 | −1.679 | −27.377 | 1.00 | 42.26 | B | C |
| ATOM | 6477 | O | THR | B | 251 | 54.463 | −2.481 | −28.304 | 1.00 | 53.14 | B | O |
| ATOM | 6478 | N | LYS | B | 252 | 53.377 | −1.430 | −26.648 | 1.00 | 33.76 | B | N |
| ATOM | 6479 | CA | LYS | B | 252 | 52.133 | −2.199 | −26.779 | 1.00 | 35.99 | B | C |
| ATOM | 6480 | CB | LYS | B | 252 | 51.520 | −2.436 | −25.385 | 1.00 | 33.65 | B | C |
| ATOM | 6481 | CG | LYS | B | 252 | 52.400 | −3.297 | −24.446 | 1.00 | 32.18 | B | C |
| ATOM | 6482 | CD | LYS | B | 252 | 52.228 | −4.791 | −24.691 | 1.00 | 34.71 | B | C |
| ATOM | 6483 | CE | LYS | B | 252 | 53.099 | −5.652 | −23.754 | 1.00 | 36.30 | B | C |
| ATOM | 6484 | NZ | LYS | B | 252 | 52.740 | −7.131 | −23.821 | 1.00 | 35.73 | B | N |
| ATOM | 6485 | C | LYS | B | 252 | 51.117 | −1.533 | −27.710 | 1.00 | 31.67 | B | C |
| ATOM | 6486 | O | LYS | B | 252 | 50.178 | −2.167 | −28.160 | 1.00 | 43.55 | B | O |
| ATOM | 6487 | N | LEU | B | 253 | 51.315 | −0.252 | −27.983 | 1.00 | 27.89 | B | N |
| ATOM | 6488 | CA | LEU | B | 253 | 50.466 | 0.507 | −28.899 | 1.00 | 31.51 | B | C |
| ATOM | 6489 | CB | LEU | B | 253 | 50.054 | 1.851 | −28.287 | 1.00 | 29.45 | B | C |
| ATOM | 6490 | CG | LEU | B | 253 | 48.676 | 2.020 | −27.621 | 1.00 | 36.86 | B | C |
| ATOM | 6491 | CD1 | LEU | B | 253 | 48.212 | 0.812 | −26.830 | 1.00 | 38.75 | B | C |
| ATOM | 6492 | CD2 | LEU | B | 253 | 48.707 | 3.285 | −26.767 | 1.00 | 33.51 | B | C |

APPENDIX A-continued

*P. alba* 3T288C coordinates

| ATOM | 6493 | C | LEU | B | 253 | 51.313 | 0.720 | −30.160 | 1.00 | 35.74 | B | C |
|---|---|---|---|---|---|---|---|---|---|---|---|---|
| ATOM | 6494 | O | LEU | B | 253 | 52.301 | 1.454 | −30.135 | 1.00 | 37.08 | B | O |
| ATOM | 6495 | N | HIS | B | 254 | 50.903 | 0.076 | −31.249 | 1.00 | 33.84 | B | N |
| ATOM | 6496 | CA | AHIS | B | 254 | 51.728 | −0.000 | −32.446 | 0.50 | 33.25 | B | C |
| ATOM | 6497 | CA | BHIS | B | 254 | 51.678 | −0.001 | −32.501 | 0.50 | 34.84 | B | C |
| ATOM | 6498 | CB | AHIS | B | 254 | 51.245 | −1.162 | −33.334 | 0.50 | 34.73 | B | C |
| ATOM | 6499 | CB | BHIS | B | 254 | 51.067 | −1.032 | −33.482 | 0.50 | 37.53 | B | C |
| ATOM | 6500 | CG | AHIS | B | 254 | 51.052 | −2.474 | −32.569 | 0.50 | 36.94 | B | C |
| ATOM | 6501 | CG | BHIS | B | 254 | 49.813 | −0.555 | −34.199 | 0.50 | 43.00 | B | C |
| ATOM | 6502 | ND1 | AHIS | B | 254 | 50.299 | −3.497 | −33.039 | 0.50 | 37.35 | B | N |
| ATOM | 6503 | ND1 | BHIS | B | 254 | 48.588 | −1.038 | −33.918 | 0.50 | 48.80 | B | N |
| ATOM | 6504 | CE1 | AHIS | B | 254 | 50.307 | −4.506 | −32.148 | 0.50 | 33.86 | B | C |
| ATOM | 6505 | CE1 | BHIS | B | 254 | 47.677 | −0.434 | −34.704 | 0.50 | 47.74 | B | C |
| ATOM | 6506 | NE2 | AHIS | B | 254 | 51.054 | −4.127 | −31.097 | 0.50 | 38.53 | B | N |
| ATOM | 6507 | NE2 | BHIS | B | 254 | 48.321 | 0.439 | −35.497 | 0.50 | 39.38 | B | N |
| ATOM | 6508 | CD2 | AHIS | B | 254 | 51.528 | −2.881 | −31.323 | 0.50 | 33.37 | B | C |
| ATOM | 6509 | CD2 | BHIS | B | 254 | 49.638 | 0.385 | −35.217 | 0.50 | 46.45 | B | C |
| ATOM | 6510 | C | HIS | B | 254 | 51.807 | 1.330 | −33.183 | 1.00 | 33.53 | B | C |
| ATOM | 6511 | O | HIS | B | 254 | 52.796 | 1.603 | −33.858 | 1.00 | 25.82 | B | O |
| ATOM | 6512 | N | PHE | B | 255 | 50.793 | 2.184 | −33.031 | 1.00 | 27.23 | B | N |
| ATOM | 6513 | CA | PHE | B | 255 | 50.822 | 3.525 | −33.632 | 1.00 | 29.21 | B | C |
| ATOM | 6514 | CB | PHE | B | 255 | 49.380 | 4.066 | −33.854 | 1.00 | 29.73 | B | C |
| ATOM | 6515 | CG | PHE | B | 255 | 48.607 | 4.271 | −32.575 | 1.00 | 27.91 | B | C |
| ATOM | 6516 | CD1 | PHE | B | 255 | 48.736 | 5.449 | −31.865 | 1.00 | 29.74 | B | C |
| ATOM | 6517 | CE1 | PHE | B | 255 | 48.058 | 5.637 | −30.661 | 1.00 | 35.80 | B | C |
| ATOM | 6518 | CZ | PHE | B | 255 | 47.262 | 4.611 | −30.142 | 1.00 | 36.41 | B | C |
| ATOM | 6519 | CE2 | PHE | B | 255 | 47.144 | 3.411 | −30.838 | 1.00 | 37.91 | B | C |
| ATOM | 6520 | CD2 | PHE | B | 255 | 47.817 | 3.245 | −32.046 | 1.00 | 31.88 | B | C |
| ATOM | 6521 | C | PHE | B | 255 | 51.653 | 4.574 | −32.841 | 1.00 | 35.02 | B | C |
| ATOM | 6522 | O | PHE | B | 255 | 51.930 | 5.653 | −33.380 | 1.00 | 32.16 | B | O |
| ATOM | 6523 | N | ALA | B | 256 | 52.024 | 4.287 | −31.583 | 1.00 | 36.94 | B | N |
| ATOM | 6524 | CA | ALA | B | 256 | 52.473 | 5.361 | −30.660 | 1.00 | 44.62 | B | C |
| ATOM | 6525 | CB | ALA | B | 256 | 52.189 | 5.002 | −29.178 | 1.00 | 38.64 | B | C |
| ATOM | 6526 | C | ALA | B | 256 | 53.939 | 5.730 | −30.831 | 1.00 | 41.50 | B | C |
| ATOM | 6527 | O | ALA | B | 256 | 54.791 | 4.866 | −31.042 | 1.00 | 32.37 | B | O |
| ATOM | 6528 | N | ARG | B | 257 | 54.206 | 7.030 | −30.748 | 1.00 | 42.55 | B | N |
| ATOM | 6529 | CA | ARG | B | 257 | 55.560 | 7.566 | −30.699 | 1.00 | 55.66 | B | C |
| ATOM | 6530 | CB | ARG | B | 257 | 55.563 | 9.058 | −31.074 | 1.00 | 61.07 | B | C |
| ATOM | 6531 | CG | ARG | B | 257 | 55.225 | 9.398 | −32.526 | 1.00 | 63.21 | B | C |
| ATOM | 6532 | CD | ARG | B | 257 | 55.159 | 10.932 | −32.719 | 1.00 | 66.34 | B | C |
| ATOM | 6533 | NE | ARG | B | 257 | 53.937 | 11.526 | −32.146 | 1.00 | 55.10 | B | N |
| ATOM | 6534 | CZ | ARG | B | 257 | 53.814 | 12.782 | −31.707 | 1.00 | 68.91 | B | C |
| ATOM | 6535 | NH1 | ARG | B | 257 | 54.841 | 13.630 | −31.738 | 1.00 | 80.51 | B | N |
| ATOM | 6536 | NH2 | ARG | B | 257 | 52.652 | 13.200 | −31.206 | 1.00 | 69.46 | B | N |
| ATOM | 6537 | C | ARG | B | 257 | 56.107 | 7.437 | −29.275 | 1.00 | 58.53 | B | C |
| ATOM | 6538 | O | ARG | B | 257 | 55.422 | 7.816 | −28.316 | 1.00 | 50.74 | B | O |
| ATOM | 6539 | N | ASP | B | 258 | 57.329 | 6.911 | −29.145 | 1.00 | 56.60 | B | N |
| ATOM | 6540 | CA | ASP | B | 258 | 58.114 | 7.044 | −27.906 | 1.00 | 54.48 | B | C |
| ATOM | 6541 | CB | ASP | B | 258 | 59.108 | 5.883 | −27.776 | 1.00 | 45.90 | B | C |
| ATOM | 6542 | CG | ASP | B | 258 | 59.879 | 5.897 | −26.438 | 1.00 | 60.08 | B | C |
| ATOM | 6543 | OD1 | ASP | B | 258 | 60.038 | 6.974 | −25.810 | 1.00 | 55.44 | B | O |
| ATOM | 6544 | OD2 | ASP | B | 258 | 60.340 | 4.813 | −26.012 | 1.00 | 61.30 | B | O |
| ATOM | 6545 | C | ASP | B | 258 | 58.855 | 8.420 | −27.908 | 1.00 | 53.21 | B | C |
| ATOM | 6546 | O | ASP | B | 258 | 59.700 | 8.681 | −28.777 | 1.00 | 54.31 | B | O |
| ATOM | 6547 | N | ARG | B | 259 | 58.529 | 9.285 | −26.943 | 1.00 | 39.90 | B | N |
| ATOM | 6548 | CA | AARG | B | 259 | 59.112 | 10.631 | −26.889 | 0.50 | 40.52 | B | C |
| ATOM | 6549 | CA | BARG | B | 259 | 59.083 | 10.634 | −26.879 | 0.50 | 40.15 | B | C |
| ATOM | 6550 | CB | AARG | B | 259 | 58.062 | 11.680 | −27.306 | 0.50 | 43.68 | B | C |
| ATOM | 6551 | CB | BARG | B | 259 | 57.973 | 11.635 | −27.224 | 0.50 | 42.16 | B | C |
| ATOM | 6552 | CG | AARG | B | 259 | 57.732 | 11.710 | −28.815 | 0.50 | 51.56 | B | C |
| ATOM | 6553 | CG | BARG | B | 259 | 57.503 | 11.561 | −28.680 | 0.50 | 50.00 | B | C |
| ATOM | 6554 | CD | AARG | B | 259 | 58.823 | 12.403 | −29.649 | 0.50 | 50.35 | B | C |
| ATOM | 6555 | CD | BARG | B | 259 | 58.131 | 12.661 | −29.517 | 0.50 | 47.88 | B | C |
| ATOM | 6556 | NE | AARG | B | 259 | 58.527 | 12.394 | −31.084 | 0.50 | 46.77 | B | N |
| ATOM | 6557 | NE | BARG | B | 259 | 57.393 | 13.904 | −29.360 | 0.50 | 46.89 | B | N |
| ATOM | 6558 | CZ | AARG | B | 259 | 58.843 | 11.397 | −31.910 | 0.50 | 41.60 | B | C |
| ATOM | 6559 | CZ | BARG | B | 259 | 57.948 | 15.108 | −29.313 | 0.50 | 43.09 | B | C |
| ATOM | 6560 | NH1 | AARG | B | 259 | 59.478 | 10.330 | −31.449 | 0.50 | 40.52 | B | N |
| ATOM | 6561 | NH1 | BARG | B | 259 | 59.259 | 15.257 | −29.410 | 0.50 | 39.41 | B | N |
| ATOM | 6562 | NH2 | AARG | B | 259 | 58.525 | 11.464 | −33.195 | 0.50 | 37.19 | B | N |
| ATOM | 6563 | NH2 | BARG | B | 259 | 57.177 | 16.165 | −29.165 | 0.50 | 35.24 | B | N |
| ATOM | 6564 | C | ARG | B | 259 | 59.665 | 10.943 | −25.492 | 1.00 | 36.58 | B | C |
| ATOM | 6565 | O | ARG | B | 259 | 59.645 | 12.110 | −25.032 | 1.00 | 28.62 | B | O |
| ATOM | 6566 | N | LEU | B | 260 | 60.177 | 9.928 | −24.805 | 1.00 | 31.08 | B | N |
| ATOM | 6567 | CA | LEU | B | 260 | 60.619 | 10.149 | −23.406 | 1.00 | 34.96 | B | C |
| ATOM | 6568 | CB | LEU | B | 260 | 61.009 | 8.858 | −22.674 | 1.00 | 37.76 | B | C |
| ATOM | 6569 | CG | LEU | B | 260 | 61.451 | 9.053 | −21.202 | 1.00 | 35.28 | B | C |
| ATOM | 6570 | CD1 | LEU | B | 260 | 60.369 | 9.711 | −20.327 | 1.00 | 43.36 | B | C |

APPENDIX A-continued

P. alba 3T288C coordinates

| ATOM | 6571 | CD2 | LEU | B | 260 | 61.853 | 7.776 | −20.575 | 1.00 | 46.40 | B | C |
|---|---|---|---|---|---|---|---|---|---|---|---|---|
| ATOM | 6572 | C | LEU | B | 260 | 61.767 | 11.133 | −23.264 | 1.00 | 36.19 | B | C |
| ATOM | 6573 | O | LEU | B | 260 | 61.702 | 12.034 | −22.412 | 1.00 | 32.69 | B | O |
| ATOM | 6574 | N | ILE | B | 261 | 62.821 | 10.955 | −24.064 | 1.00 | 31.53 | B | N |
| ATOM | 6575 | CA | ILE | B | 261 | 64.025 | 11.787 | −23.909 | 1.00 | 30.92 | B | C |
| ATOM | 6576 | CB | ILE | B | 261 | 65.243 | 11.293 | −24.781 | 1.00 | 30.88 | B | C |
| ATOM | 6577 | CG1 | ILE | B | 261 | 65.698 | 9.894 | −24.338 | 1.00 | 39.52 | B | C |
| ATOM | 6578 | CD1 | ILE | B | 261 | 66.531 | 9.099 | −25.417 | 1.00 | 39.51 | B | C |
| ATOM | 6579 | CG2 | ILE | B | 261 | 66.433 | 12.250 | −24.639 | 1.00 | 33.59 | B | C |
| ATOM | 6580 | C | ILE | B | 261 | 63.633 | 13.247 | −24.202 | 1.00 | 21.15 | B | C |
| ATOM | 6581 | O | ILE | B | 261 | 63.937 | 14.128 | −23.402 | 1.00 | 24.35 | B | O |
| ATOM | 6582 | N | GLU | B | 262 | 62.893 | 13.466 | −25.294 | 1.00 | 23.43 | B | N |
| ATOM | 6583 | CA | GLU | B | 262 | 62.398 | 14.791 | −25.667 | 1.00 | 29.00 | B | C |
| ATOM | 6584 | CB | GLU | B | 262 | 61.608 | 14.772 | −26.987 | 1.00 | 37.83 | B | C |
| ATOM | 6585 | CG | GLU | B | 262 | 62.406 | 14.298 | −28.231 | 1.00 | 50.13 | B | C |
| ATOM | 6586 | CD | GLU | B | 262 | 62.232 | 12.788 | −28.595 | 1.00 | 58.78 | B | C |
| ATOM | 6587 | OE1 | GLU | B | 262 | 62.453 | 11.867 | −27.752 | 1.00 | 43.65 | B | O |
| ATOM | 6588 | OE2 | GLU | B | 262 | 61.903 | 12.525 | −29.767 | 1.00 | 64.04 | B | O |
| ATOM | 6589 | C | GLU | B | 262 | 61.533 | 15.402 | −24.562 | 1.00 | 25.19 | B | C |
| ATOM | 6590 | O | GLU | B | 262 | 61.622 | 16.598 | −24.319 | 1.00 | 24.01 | B | O |
| ATOM | 6591 | N | SER | B | 263 | 60.719 | 14.584 | −23.884 | 1.00 | 24.94 | B | N |
| ATOM | 6592 | CA | ASER | B | 263 | 59.826 | 15.026 | −22.799 | 0.50 | 20.12 | B | C |
| ATOM | 6593 | CA | BSER | B | 263 | 59.830 | 15.116 | −22.868 | 0.50 | 21.08 | B | C |
| ATOM | 6594 | CB | ASER | B | 263 | 58.970 | 13.859 | −22.267 | 0.50 | 19.81 | B | C |
| ATOM | 6595 | CB | BSER | B | 263 | 58.731 | 14.108 | −22.525 | 0.50 | 21.88 | B | C |
| ATOM | 6596 | OG | ASER | B | 263 | 59.731 | 12.961 | −21.442 | 0.50 | 18.14 | B | O |
| ATOM | 6597 | OG | BSER | B | 263 | 57.782 | 14.044 | −23.590 | 0.50 | 25.34 | B | O |
| ATOM | 6598 | C | SER | B | 263 | 60.664 | 15.570 | −21.651 | 1.00 | 22.12 | B | C |
| ATOM | 6599 | O | SER | B | 263 | 60.340 | 16.582 | −21.015 | 1.00 | 18.32 | B | O |
| ATOM | 6600 | N | PHE | B | 264 | 61.750 | 14.885 | −21.379 | 1.00 | 21.21 | B | N |
| ATOM | 6601 | CA | PHE | B | 264 | 62.627 | 15.295 | −20.301 | 1.00 | 21.14 | B | C |
| ATOM | 6602 | CB | PHE | B | 264 | 63.533 | 14.152 | −19.848 | 1.00 | 25.11 | B | C |
| ATOM | 6603 | CG | PHE | B | 264 | 64.021 | 14.362 | −18.483 | 1.00 | 21.53 | B | C |
| ATOM | 6604 | CD1 | PHE | B | 264 | 63.229 | 14.001 | −17.411 | 1.00 | 26.88 | B | C |
| ATOM | 6605 | CE1 | PHE | B | 264 | 63.615 | 14.266 | −16.116 | 1.00 | 32.05 | B | C |
| ATOM | 6606 | CZ | PHE | B | 264 | 64.803 | 14.957 | −15.886 | 1.00 | 30.00 | B | C |
| ATOM | 6607 | CE2 | PHE | B | 264 | 65.579 | 15.347 | −16.948 | 1.00 | 26.11 | B | C |
| ATOM | 6608 | CD2 | PHE | B | 264 | 65.161 | 15.075 | −18.256 | 1.00 | 29.07 | B | C |
| ATOM | 6609 | C | PHE | B | 264 | 63.428 | 16.566 | −20.598 | 1.00 | 20.61 | B | C |
| ATOM | 6610 | O | PHE | B | 264 | 63.547 | 17.464 | −19.744 | 1.00 | 20.73 | B | O |
| ATOM | 6611 | N | TYR | B | 265 | 63.946 | 16.665 | −21.815 | 1.00 | 20.09 | B | N |
| ATOM | 6612 | CA | TYR | B | 265 | 64.607 | 17.881 | −22.298 | 1.00 | 17.15 | B | C |
| ATOM | 6613 | CB | TYR | B | 265 | 65.040 | 17.662 | −23.748 | 1.00 | 19.86 | B | C |
| ATOM | 6614 | CG | TYR | B | 265 | 65.504 | 18.895 | −24.472 | 1.00 | 23.47 | B | C |
| ATOM | 6615 | CD1 | TYR | B | 265 | 66.800 | 19.361 | −24.310 | 1.00 | 31.92 | B | C |
| ATOM | 6616 | CE1 | TYR | B | 265 | 67.244 | 20.493 | −24.966 | 1.00 | 30.60 | B | C |
| ATOM | 6617 | CZ | TYR | B | 265 | 66.400 | 21.181 | −25.794 | 1.00 | 34.74 | B | C |
| ATOM | 6618 | OH | TYR | B | 265 | 66.885 | 22.293 | −26.426 | 1.00 | 38.69 | B | O |
| ATOM | 6619 | CE2 | TYR | B | 265 | 65.092 | 20.737 | −25.993 | 1.00 | 32.63 | B | C |
| ATOM | 6620 | CD2 | TYR | B | 265 | 64.659 | 19.590 | −25.330 | 1.00 | 24.71 | B | C |
| ATOM | 6621 | C | TYR | B | 265 | 63.665 | 19.074 | −22.169 | 1.00 | 18.92 | B | C |
| ATOM | 6622 | O | TYR | B | 265 | 64.051 | 20.158 | −21.734 | 1.00 | 19.31 | B | O |
| ATOM | 6623 | N | TRP | B | 266 | 62.409 | 18.853 | −22.526 | 1.00 | 16.41 | B | N |
| ATOM | 6624 | CA | TRP | B | 266 | 61.377 | 19.870 | −22.400 | 1.00 | 18.68 | B | C |
| ATOM | 6625 | CB | TRP | B | 266 | 60.081 | 19.335 | −23.011 | 1.00 | 19.17 | B | C |
| ATOM | 6626 | CG | TRP | B | 266 | 58.915 | 20.266 | −22.847 | 1.00 | 19.86 | B | C |
| ATOM | 6627 | CD1 | TRP | B | 266 | 58.060 | 20.383 | −21.776 | 1.00 | 20.93 | B | C |
| ATOM | 6628 | NE1 | TRP | B | 266 | 57.139 | 21.348 | −22.002 | 1.00 | 20.77 | B | N |
| ATOM | 6629 | CE2 | TRP | B | 266 | 57.358 | 21.940 | −23.183 | 1.00 | 20.01 | B | C |
| ATOM | 6630 | CD2 | TRP | B | 266 | 58.475 | 21.268 | −23.797 | 1.00 | 16.68 | B | C |
| ATOM | 6631 | CE3 | TRP | B | 266 | 58.902 | 21.664 | −25.057 | 1.00 | 19.39 | B | C |
| ATOM | 6632 | CZ3 | TRP | B | 266 | 58.218 | 22.692 | −25.686 | 1.00 | 20.94 | B | C |
| ATOM | 6633 | CH2 | TRP | B | 266 | 57.136 | 23.310 | −25.085 | 1.00 | 20.17 | B | C |
| ATOM | 6634 | CZ2 | TRP | B | 266 | 56.677 | 22.941 | −23.824 | 1.00 | 25.72 | B | C |
| ATOM | 6635 | C | TRP | B | 266 | 61.225 | 20.265 | −20.965 | 1.00 | 17.64 | B | C |
| ATOM | 6636 | O | TRP | B | 266 | 61.259 | 21.454 | −20.624 | 1.00 | 15.67 | B | O |
| ATOM | 6637 | N | ALA | B | 267 | 61.101 | 19.272 | −20.079 | 1.00 | 18.06 | B | N |
| ATOM | 6638 | CA | ALA | B | 267 | 60.975 | 19.552 | −18.649 | 1.00 | 20.03 | B | C |
| ATOM | 6639 | CB | ALA | B | 267 | 60.791 | 18.268 | −17.842 | 1.00 | 22.95 | B | C |
| ATOM | 6640 | C | ALA | B | 267 | 62.131 | 20.366 | −18.054 | 1.00 | 17.74 | B | C |
| ATOM | 6641 | O | ALA | B | 267 | 61.905 | 21.206 | −17.172 | 1.00 | 16.57 | B | O |
| ATOM | 6642 | N | VAL | B | 268 | 63.347 | 20.114 | −18.522 | 1.00 | 17.36 | B | N |
| ATOM | 6643 | CA | VAL | B | 268 | 64.519 | 20.826 | −18.021 | 1.00 | 15.22 | B | C |
| ATOM | 6644 | CB | VAL | B | 268 | 65.836 | 20.263 | −18.636 | 1.00 | 16.11 | B | C |
| ATOM | 6645 | CG1 | VAL | B | 268 | 67.029 | 21.251 | −18.463 | 1.00 | 14.19 | B | C |
| ATOM | 6646 | CG2 | VAL | B | 268 | 66.188 | 18.882 | −18.025 | 1.00 | 18.11 | B | C |
| ATOM | 6647 | C | VAL | B | 268 | 64.381 | 22.342 | −18.282 | 1.00 | 20.16 | B | C |
| ATOM | 6648 | O | VAL | B | 268 | 64.812 | 23.166 | −17.472 | 1.00 | 17.44 | B | O |

APPENDIX A-continued

*P. alba* 3T288C coordinates

| ATOM | 6649 | N   | GLY | B | 269 | 63.760 | 22.699 | −19.406 | 1.00 | 18.75 | B | N |
| ---- | ---- | --- | --- | - | --- | ------ | ------ | ------- | ---- | ----- | - | - |
| ATOM | 6650 | CA  | GLY | B | 269 | 63.566 | 24.128 | −19.765 | 1.00 | 18.20 | B | C |
| ATOM | 6651 | C   | GLY | B | 269 | 62.541 | 24.803 | −18.882 | 1.00 | 18.02 | B | C |
| ATOM | 6652 | O   | GLY | B | 269 | 62.657 | 25.990 | −18.590 | 1.00 | 18.41 | B | O |
| ATOM | 6653 | N   | VAL | B | 270 | 61.532 | 24.038 | −18.447 | 1.00 | 18.51 | B | N |
| ATOM | 6654 | CA  | VAL | B | 270 | 60.502 | 24.543 | −17.550 | 1.00 | 17.42 | B | C |
| ATOM | 6655 | CB  | VAL | B | 270 | 59.273 | 23.618 | −17.547 | 1.00 | 17.32 | B | C |
| ATOM | 6656 | CG1 | VAL | B | 270 | 58.273 | 24.056 | −16.526 | 1.00 | 15.84 | B | C |
| ATOM | 6657 | CG2 | VAL | B | 270 | 58.650 | 23.582 | −19.014 | 1.00 | 17.61 | B | C |
| ATOM | 6658 | C   | VAL | B | 270 | 61.038 | 24.725 | −16.121 | 1.00 | 19.45 | B | C |
| ATOM | 6659 | O   | VAL | B | 270 | 60.746 | 25.732 | −15.473 | 1.00 | 17.68 | B | O |
| ATOM | 6660 | N   | ALA | B | 271 | 61.799 | 23.751 | −15.618 | 1.00 | 15.53 | B | N |
| ATOM | 6661 | CA  | ALA | B | 271 | 62.329 | 23.853 | −14.252 | 1.00 | 18.34 | B | C |
| ATOM | 6662 | CB  | ALA | B | 271 | 61.370 | 23.161 | −13.275 | 1.00 | 20.38 | B | C |
| ATOM | 6663 | C   | ALA | B | 271 | 63.734 | 23.255 | −14.171 | 1.00 | 21.27 | B | C |
| ATOM | 6664 | O   | ALA | B | 271 | 63.903 | 22.013 | −14.018 | 1.00 | 19.31 | B | O |
| ATOM | 6665 | N   | PHE | B | 272 | 64.753 | 24.102 | −14.304 | 1.00 | 15.12 | B | N |
| ATOM | 6666 | CA  | PHE | B | 272 | 66.125 | 23.605 | −14.456 | 1.00 | 17.09 | B | C |
| ATOM | 6667 | CB  | PHE | B | 272 | 66.958 | 24.540 | −15.326 | 1.00 | 19.46 | B | C |
| ATOM | 6668 | CG  | PHE | B | 272 | 67.462 | 25.746 | −14.582 | 1.00 | 25.15 | B | C |
| ATOM | 6669 | CD1 | PHE | B | 272 | 68.674 | 25.709 | −13.922 | 1.00 | 31.93 | B | C |
| ATOM | 6670 | CE1 | PHE | B | 272 | 69.121 | 26.832 | −13.211 | 1.00 | 34.44 | B | C |
| ATOM | 6671 | CZ  | PHE | B | 272 | 68.344 | 27.985 | −13.178 | 1.00 | 27.74 | B | C |
| ATOM | 6672 | CE2 | PHE | B | 272 | 67.148 | 28.022 | −13.836 | 1.00 | 36.19 | B | C |
| ATOM | 6673 | CD2 | PHE | B | 272 | 66.701 | 26.896 | −14.523 | 1.00 | 31.96 | B | C |
| ATOM | 6674 | C   | PHE | B | 272 | 66.872 | 23.409 | −13.128 | 1.00 | 19.83 | B | C |
| ATOM | 6675 | O   | PHE | B | 272 | 67.880 | 22.670 | −13.108 | 1.00 | 19.24 | B | O |
| ATOM | 6676 | N   | GLU | B | 273 | 66.433 | 24.104 | −12.070 | 1.00 | 19.54 | B | N |
| ATOM | 6677 | CA  | GLU | B | 273 | 67.218 | 24.156 | −10.822 | 1.00 | 25.70 | B | C |
| ATOM | 6678 | CB  | GLU | B | 273 | 66.643 | 25.121 | −9.795  | 1.00 | 23.52 | B | C |
| ATOM | 6679 | CG  | GLU | B | 273 | 66.692 | 26.586 | −10.212 | 1.00 | 29.09 | B | C |
| ATOM | 6680 | CD  | GLU | B | 273 | 65.428 | 27.067 | −10.970 | 1.00 | 37.43 | B | C |
| ATOM | 6681 | OE1 | GLU | B | 273 | 64.703 | 26.283 | −11.672 | 1.00 | 32.92 | B | O |
| ATOM | 6682 | OE2 | GLU | B | 273 | 65.168 | 28.280 | −10.865 | 1.00 | 42.12 | B | O |
| ATOM | 6683 | C   | GLU | B | 273 | 67.269 | 22.747 | −10.233 | 1.00 | 26.94 | B | C |
| ATOM | 6684 | O   | GLU | B | 273 | 66.280 | 22.009 | −10.309 | 1.00 | 22.77 | B | O |
| ATOM | 6685 | N   | PRO | B | 274 | 68.412 | 22.370 | −9.645  | 1.00 | 24.26 | B | N |
| ATOM | 6686 | CA  | PRO | B | 274 | 68.579 | 20.985 | −9.233  | 1.00 | 25.14 | B | C |
| ATOM | 6687 | CB  | PRO | B | 274 | 69.980 | 20.957 | −8.589  | 1.00 | 27.41 | B | C |
| ATOM | 6688 | CG  | PRO | B | 274 | 70.373 | 22.350 | −8.413  | 1.00 | 27.95 | B | C |
| ATOM | 6689 | CD  | PRO | B | 274 | 69.630 | 23.165 | −9.418  | 1.00 | 25.84 | B | C |
| ATOM | 6690 | C   | PRO | B | 274 | 67.504 | 20.495 | −8.265  | 1.00 | 24.47 | B | C |
| ATOM | 6691 | O   | PRO | B | 274 | 67.119 | 19.342 | −8.326  | 1.00 | 27.78 | B | O |
| ATOM | 6692 | N   | GLN | B | 275 | 66.958 | 21.376 | −7.448  | 1.00 | 23.27 | B | N |
| ATOM | 6693 | CA  | GLN | B | 275 | 65.948 | 20.961 | −6.466  | 1.00 | 26.52 | B | C |
| ATOM | 6694 | CB  | GLN | B | 275 | 65.773 | 22.025 | −5.373  | 1.00 | 25.42 | B | C |
| ATOM | 6695 | CG  | GLN | B | 275 | 65.269 | 23.415 | −5.793  | 1.00 | 28.04 | B | C |
| ATOM | 6696 | CD  | GLN | B | 275 | 66.375 | 24.384 | −6.239  | 1.00 | 33.28 | B | C |
| ATOM | 6697 | OE1 | GLN | B | 275 | 67.456 | 23.974 | −6.698  | 1.00 | 29.99 | B | O |
| ATOM | 6698 | NE2 | GLN | B | 275 | 66.101 | 25.689 | −6.110  | 1.00 | 33.44 | B | N |
| ATOM | 6699 | C   | GLN | B | 275 | 64.566 | 20.626 | −7.038  | 1.00 | 25.38 | B | C |
| ATOM | 6700 | O   | GLN | B | 275 | 63.718 | 20.145 | −6.298  | 1.00 | 28.33 | B | O |
| ATOM | 6701 | N   | TYR | B | 276 | 64.327 | 20.886 | −8.330  | 1.00 | 24.88 | B | N |
| ATOM | 6702 | CA  | TYR | B | 276 | 62.980 | 20.695 | −8.935  | 1.00 | 22.85 | B | C |
| ATOM | 6703 | CB  | TYR | B | 276 | 62.654 | 21.874 | −9.882  | 1.00 | 21.39 | B | C |
| ATOM | 6704 | CG  | TYR | B | 276 | 62.398 | 23.193 | −9.161  | 1.00 | 27.30 | B | C |
| ATOM | 6705 | CD1 | TYR | B | 276 | 61.533 | 23.261 | −8.066  | 1.00 | 29.89 | B | C |
| ATOM | 6706 | CE1 | TYR | B | 276 | 61.304 | 24.472 | −7.396  | 1.00 | 31.01 | B | C |
| ATOM | 6707 | CZ  | TYR | B | 276 | 61.929 | 25.618 | −7.831  | 1.00 | 36.98 | B | C |
| ATOM | 6708 | OH  | TYR | B | 276 | 61.697 | 26.789 | −7.167  | 1.00 | 41.65 | B | O |
| ATOM | 6709 | CE2 | TYR | B | 276 | 62.773 | 25.586 | −8.919  | 1.00 | 36.74 | B | C |
| ATOM | 6710 | CD2 | TYR | B | 276 | 63.007 | 24.366 | −9.580  | 1.00 | 31.75 | B | C |
| ATOM | 6711 | C   | TYR | B | 276 | 62.810 | 19.374 | −9.682  | 1.00 | 25.69 | B | C |
| ATOM | 6712 | O   | TYR | B | 276 | 62.140 | 19.320 | −10.698 | 1.00 | 18.56 | B | O |
| ATOM | 6713 | N   | SER | B | 277 | 63.400 | 18.315 | −9.156  | 1.00 | 20.78 | B | N |
| ATOM | 6714 | CA  | SER | B | 277 | 63.267 | 16.995 | −9.690  | 1.00 | 20.77 | B | C |
| ATOM | 6715 | CB  | SER | B | 277 | 64.023 | 16.001 | −8.789  | 1.00 | 28.26 | B | C |
| ATOM | 6716 | OG  | SER | B | 277 | 65.369 | 15.907 | −9.232  | 1.00 | 32.73 | B | O |
| ATOM | 6717 | C   | SER | B | 277 | 61.837 | 16.574 | −9.856  | 1.00 | 20.62 | B | C |
| ATOM | 6718 | O   | SER | B | 277 | 61.491 | 16.016 | −10.904 | 1.00 | 20.18 | B | O |
| ATOM | 6719 | N   | ASP | B | 278 | 61.001 | 16.838 | −8.855  | 1.00 | 19.70 | B | N |
| ATOM | 6720 | CA  | ASP | B | 278 | 59.601 | 16.441 | −8.904  | 1.00 | 21.39 | B | C |
| ATOM | 6721 | CB  | ASP | B | 278 | 58.881 | 16.772 | −7.615  | 1.00 | 27.49 | B | C |
| ATOM | 6722 | CG  | ASP | B | 278 | 59.286 | 15.867 | −6.481  | 1.00 | 35.28 | B | C |
| ATOM | 6723 | OD1 | ASP | B | 278 | 60.058 | 14.915 | −6.727  | 1.00 | 45.25 | B | O |
| ATOM | 6724 | OD2 | ASP | B | 278 | 58.838 | 16.116 | −5.344  | 1.00 | 49.36 | B | O |
| ATOM | 6725 | C   | ASP | B | 278 | 58.885 | 17.184 | −10.012 | 1.00 | 24.04 | B | C |
| ATOM | 6726 | O   | ASP | B | 278 | 58.095 | 16.584 | −10.728 | 1.00 | 23.33 | B | O |

APPENDIX A-continued

*P. alba* 3T288C coordinates

| ATOM | 6727 | N | CYS | B | 279 | 59.148 | 18.491 | −10.129 | 1.00 | 19.17 | B | N |
|---|---|---|---|---|---|---|---|---|---|---|---|---|
| ATOM | 6728 | CA | CYS | B | 279 | 58.561 | 19.249 | −11.208 | 1.00 | 21.15 | B | C |
| ATOM | 6729 | CB | CYS | B | 279 | 58.962 | 20.740 | −11.171 | 1.00 | 20.42 | B | C |
| ATOM | 6730 | SG | CYS | B | 279 | 57.972 | 21.692 | −12.360 | 1.00 | 23.47 | B | S |
| ATOM | 6731 | C | CYS | B | 279 | 58.942 | 18.625 | −12.531 | 1.00 | 19.45 | B | C |
| ATOM | 6732 | O | CYS | B | 279 | 58.079 | 18.409 | −13.379 | 1.00 | 20.55 | B | O |
| ATOM | 6733 | N | ARG | B | 280 | 60.229 | 18.352 | −12.740 | 1.00 | 15.98 | B | N |
| ATOM | 6734 | CA | ARG | B | 280 | 60.655 | 17.808 | −14.028 | 1.00 | 18.83 | B | C |
| ATOM | 6735 | CB | ARG | B | 280 | 62.175 | 17.634 | −14.116 | 1.00 | 17.83 | B | C |
| ATOM | 6736 | CG | ARG | B | 280 | 62.977 | 18.950 | −14.224 | 1.00 | 19.13 | B | C |
| ATOM | 6737 | CD | ARG | B | 280 | 64.438 | 18.697 | −14.456 | 1.00 | 19.75 | B | C |
| ATOM | 6738 | NE | ARG | B | 280 | 65.103 | 18.174 | −13.272 | 1.00 | 16.55 | B | N |
| ATOM | 6739 | CZ | ARG | B | 280 | 65.525 | 18.928 | −12.252 | 1.00 | 18.61 | B | C |
| ATOM | 6740 | NH1 | ARG | B | 280 | 65.329 | 20.238 | −12.274 | 1.00 | 17.30 | B | N |
| ATOM | 6741 | NH2 | ARG | B | 280 | 66.148 | 18.371 | −11.211 | 1.00 | 19.56 | B | N |
| ATOM | 6742 | C | ARG | B | 280 | 60.040 | 16.454 | −14.320 | 1.00 | 21.11 | B | C |
| ATOM | 6743 | O | ARG | B | 280 | 59.685 | 16.164 | −15.467 | 1.00 | 18.91 | B | O |
| ATOM | 6744 | N | ASN | B | 281 | 59.990 | 15.610 | −13.300 | 1.00 | 19.83 | B | N |
| ATOM | 6745 | CA | ASN | B | 281 | 59.389 | 14.284 | −13.429 | 1.00 | 20.75 | B | C |
| ATOM | 6746 | CB | ASN | B | 281 | 59.656 | 13.442 | −12.196 | 1.00 | 24.86 | B | C |
| ATOM | 6747 | CG | ASN | B | 281 | 61.119 | 13.072 | −12.056 | 1.00 | 35.79 | B | C |
| ATOM | 6748 | OD1 | ASN | B | 281 | 61.902 | 13.110 | −13.030 | 1.00 | 38.79 | B | O |
| ATOM | 6749 | ND2 | ASN | B | 281 | 61.500 | 12.696 | −10.843 | 1.00 | 31.24 | B | N |
| ATOM | 6750 | C | ASN | B | 281 | 57.899 | 14.329 | −13.758 | 1.00 | 17.43 | B | C |
| ATOM | 6751 | O | ASN | B | 281 | 57.465 | 13.643 | −14.687 | 1.00 | 20.51 | B | O |
| ATOM | 6752 | N | SER | B | 282 | 57.136 | 15.163 | −13.061 | 1.00 | 20.69 | B | N |
| ATOM | 6753 | CA | SER | B | 282 | 55.736 | 15.391 | −13.391 | 1.00 | 22.52 | B | C |
| ATOM | 6754 | CB | SER | B | 282 | 55.156 | 16.453 | −12.473 | 1.00 | 29.52 | B | C |
| ATOM | 6755 | OG | SER | B | 282 | 54.323 | 15.891 | −11.515 | 1.00 | 36.99 | B | O |
| ATOM | 6756 | C | SER | B | 282 | 55.522 | 15.905 | −14.818 | 1.00 | 21.80 | B | C |
| ATOM | 6757 | O | SER | B | 282 | 54.669 | 15.420 | −15.565 | 1.00 | 19.88 | B | O |
| ATOM | 6758 | N | VAL | B | 283 | 56.272 | 16.932 | −15.170 | 1.00 | 18.27 | B | N |
| ATOM | 6759 | CA | VAL | B | 283 | 56.138 | 17.518 | −16.473 | 1.00 | 16.31 | B | C |
| ATOM | 6760 | CB | VAL | B | 283 | 56.903 | 18.849 | −16.607 | 1.00 | 18.31 | B | C |
| ATOM | 6761 | CG1 | VAL | B | 283 | 56.910 | 19.316 | −18.088 | 1.00 | 15.14 | B | C |
| ATOM | 6762 | CG2 | VAL | B | 283 | 56.253 | 19.885 | −15.718 | 1.00 | 18.23 | B | C |
| ATOM | 6763 | C | VAL | B | 283 | 56.497 | 16.537 | −17.557 | 1.00 | 19.38 | B | C |
| ATOM | 6764 | O | VAL | B | 283 | 55.760 | 16.445 | −18.546 | 1.00 | 15.39 | B | O |
| ATOM | 6765 | N | ALA | B | 284 | 57.586 | 15.773 | −17.380 | 1.00 | 17.29 | B | N |
| ATOM | 6766 | CA | ALA | B | 284 | 57.987 | 14.781 | −18.383 | 1.00 | 17.24 | B | C |
| ATOM | 6767 | CB | ALA | B | 284 | 59.375 | 14.198 | −18.029 | 1.00 | 18.23 | B | C |
| ATOM | 6768 | C | ALA | B | 284 | 56.940 | 13.662 | −18.528 | 1.00 | 17.47 | B | C |
| ATOM | 6769 | O | ALA | B | 284 | 56.590 | 13.217 | −19.657 | 1.00 | 16.74 | B | O |
| ATOM | 6770 | N | LYS | B | 285 | 56.436 | 13.175 | −17.399 | 1.00 | 16.38 | B | N |
| ATOM | 6771 | CA | LYS | B | 285 | 55.369 | 12.155 | −17.427 | 1.00 | 15.42 | B | C |
| ATOM | 6772 | CB | LYS | B | 285 | 54.982 | 11.727 | −16.010 | 1.00 | 15.54 | B | C |
| ATOM | 6773 | CG | LYS | B | 285 | 56.019 | 10.886 | −15.343 | 1.00 | 20.92 | B | C |
| ATOM | 6774 | CD | LYS | B | 285 | 55.558 | 10.490 | −13.930 | 1.00 | 26.64 | B | C |
| ATOM | 6775 | CE | LYS | B | 285 | 56.471 | 9.484 | −13.263 | 1.00 | 30.58 | B | C |
| ATOM | 6776 | NZ | LYS | B | 285 | 56.066 | 9.445 | −11.827 | 1.00 | 42.27 | B | N |
| ATOM | 6777 | C | LYS | B | 285 | 54.139 | 12.664 | −18.182 | 1.00 | 15.13 | B | C |
| ATOM | 6778 | O | LYS | B | 285 | 53.560 | 11.958 | −19.018 | 1.00 | 16.43 | B | O |
| ATOM | 6779 | N | MET | B | 286 | 53.739 | 13.889 | −17.904 | 1.00 | 18.03 | B | N |
| ATOM | 6780 | CA | MET | B | 286 | 52.537 | 14.415 | −18.534 | 1.00 | 19.05 | B | C |
| ATOM | 6781 | CB | MET | B | 286 | 52.053 | 15.724 | −17.936 | 1.00 | 19.10 | B | C |
| ATOM | 6782 | CG | MET | B | 286 | 51.543 | 15.612 | −16.503 | 1.00 | 19.96 | B | C |
| ATOM | 6783 | SD | MET | B | 286 | 50.293 | 14.375 | −16.265 | 1.00 | 25.05 | B | S |
| ATOM | 6784 | CE | MET | B | 286 | 51.185 | 12.968 | −15.611 | 1.00 | 23.35 | B | C |
| ATOM | 6785 | C | MET | B | 286 | 52.794 | 14.590 | −20.012 | 1.00 | 20.13 | B | C |
| ATOM | 6786 | O | MET | B | 286 | 51.932 | 14.265 | −20.823 | 1.00 | 20.15 | B | O |
| ATOM | 6787 | N | PHE | B | 287 | 53.981 | 15.051 | −20.374 | 1.00 | 17.26 | B | N |
| ATOM | 6788 | CA | PHE | B | 287 | 54.260 | 15.220 | −21.806 | 1.00 | 17.95 | B | C |
| ATOM | 6789 | CB | PHE | B | 287 | 55.548 | 15.984 | −22.074 | 1.00 | 28.34 | B | C |
| ATOM | 6790 | CG | PHE | B | 287 | 55.446 | 16.967 | −23.231 | 1.00 | 44.47 | B | C |
| ATOM | 6791 | CD1 | PHE | B | 287 | 54.194 | 17.252 | −23.856 | 1.00 | 56.86 | B | C |
| ATOM | 6792 | CE1 | PHE | B | 287 | 54.081 | 18.161 | −24.926 | 1.00 | 41.77 | B | C |
| ATOM | 6793 | CZ | PHE | B | 287 | 55.210 | 18.832 | −25.367 | 1.00 | 45.38 | B | C |
| ATOM | 6794 | CE2 | PHE | B | 287 | 56.470 | 18.563 | −24.755 | 1.00 | 57.85 | B | C |
| ATOM | 6795 | CD2 | PHE | B | 287 | 56.576 | 17.637 | −23.688 | 1.00 | 41.58 | B | C |
| ATOM | 6796 | C | PHE | B | 287 | 54.249 | 13.922 | −22.558 | 1.00 | 16.03 | B | C |
| ATOM | 6797 | O | PHE | B | 287 | 53.789 | 13.874 | −23.715 | 1.00 | 15.83 | B | O |
| ATOM | 6798 | N | CYS | B | 288 | 54.685 | 12.847 | −21.909 | 1.00 | 14.89 | B | N |
| ATOM | 6799 | CA | CYS | B | 288 | 54.586 | 11.519 | −22.509 | 1.00 | 14.98 | B | C |
| ATOM | 6800 | CB | CYS | B | 288 | 55.247 | 10.449 | −21.636 | 1.00 | 21.40 | B | C |
| ATOM | 6801 | SG | CYS | B | 288 | 57.050 | 10.528 | −21.550 | 1.00 | 25.90 | B | S |
| ATOM | 6802 | C | CYS | B | 288 | 53.150 | 11.096 | −22.809 | 1.00 | 18.56 | B | C |
| ATOM | 6803 | O | CYS | B | 288 | 52.843 | 10.623 | −23.899 | 1.00 | 17.61 | B | O |
| ATOM | 6804 | N | PHE | B | 289 | 52.272 | 11.229 | −21.827 | 1.00 | 15.35 | B | N |

APPENDIX A-continued

*P. alba* 3T288C coordinates

| ATOM | 6805 | CA  | PHE | B | 289 | 50.857 | 10.959 | −22.052 | 1.00 | 16.35 | B | C |
| ---- | ---- | --- | --- | - | --- | ------ | ------ | ------- | ---- | ----- | - | - |
| ATOM | 6806 | CB  | PHE | B | 289 | 50.088 | 10.988 | −20.705 | 1.00 | 15.27 | B | C |
| ATOM | 6807 | CG  | PHE | B | 289 | 50.203 | 9.706  | −19.972 | 1.00 | 17.14 | B | C |
| ATOM | 6808 | CD1 | PHE | B | 289 | 49.626 | 8.573  | −20.486 | 1.00 | 20.13 | B | C |
| ATOM | 6809 | CE1 | PHE | B | 289 | 49.783 | 7.349  | −19.837 | 1.00 | 21.56 | B | C |
| ATOM | 6810 | CZ  | PHE | B | 289 | 50.523 | 7.270  | −18.699 | 1.00 | 18.36 | B | C |
| ATOM | 6811 | CE2 | PHE | B | 289 | 51.122 | 8.381  | −18.197 | 1.00 | 20.87 | B | C |
| ATOM | 6812 | CD2 | PHE | B | 289 | 50.984 | 9.594  | −18.830 | 1.00 | 23.02 | B | C |
| ATOM | 6813 | C   | PHE | B | 289 | 50.211 | 11.900 | −23.043 | 1.00 | 15.41 | B | C |
| ATOM | 6814 | O   | PHE | B | 289 | 49.451 | 11.459 | −23.898 | 1.00 | 17.63 | B | O |
| ATOM | 6815 | N   | VAL | B | 290 | 50.525 | 13.195 | −22.955 | 1.00 | 15.98 | B | N |
| ATOM | 6816 | CA  | VAL | B | 290 | 49.986 | 14.129 | −23.933 | 1.00 | 15.11 | B | C |
| ATOM | 6817 | CB  | VAL | B | 290 | 50.467 | 15.588 | −23.701 | 1.00 | 16.79 | B | C |
| ATOM | 6818 | CG1 | VAL | B | 290 | 50.133 | 16.477 | −24.909 | 1.00 | 15.60 | B | C |
| ATOM | 6819 | CG2 | VAL | B | 290 | 49.837 | 16.138 | −22.433 | 1.00 | 13.84 | B | C |
| ATOM | 6820 | C   | VAL | B | 290 | 50.294 | 13.682 | −25.341 | 1.00 | 16.81 | B | C |
| ATOM | 6821 | O   | VAL | B | 290 | 49.416 | 13.687 | −26.193 | 1.00 | 17.52 | B | O |
| ATOM | 6822 | N   | THR | B | 291 | 51.529 | 13.294 | −25.601 | 1.00 | 19.53 | B | N |
| ATOM | 6823 | CA  | THR | B | 291 | 51.912 | 12.949 | −26.980 | 1.00 | 22.80 | B | C |
| ATOM | 6824 | CB  | THR | B | 291 | 53.428 | 12.631 | −27.106 | 1.00 | 25.06 | B | C |
| ATOM | 6825 | OG1 | THR | B | 291 | 53.723 | 11.394 | −26.472 | 1.00 | 44.14 | B | O |
| ATOM | 6826 | CG2 | THR | B | 291 | 54.302 | 13.691 | −26.473 | 1.00 | 19.46 | B | C |
| ATOM | 6827 | C   | THR | B | 291 | 51.128 | 11.733 | −27.510 | 1.00 | 23.54 | B | C |
| ATOM | 6828 | O   | THR | B | 291 | 50.706 | 11.710 | −28.669 | 1.00 | 20.69 | B | O |
| ATOM | 6829 | N   | ILE | B | 292 | 50.976 | 10.707 | −26.674 | 1.00 | 18.62 | B | N |
| ATOM | 6830 | CA  | ILE | B | 292 | 50.199 | 9.511  | −27.040 | 1.00 | 17.16 | B | C |
| ATOM | 6831 | CB  | ILE | B | 292 | 50.337 | 8.423  | −25.941 | 1.00 | 20.53 | B | C |
| ATOM | 6832 | CG1 | ILE | B | 292 | 51.780 | 7.968  | −25.861 | 1.00 | 27.07 | B | C |
| ATOM | 6833 | CD1 | ILE | B | 292 | 52.015 | 6.951  | −24.785 | 1.00 | 33.53 | B | C |
| ATOM | 6834 | CG2 | ILE | B | 292 | 49.424 | 7.239  | −26.257 | 1.00 | 23.47 | B | C |
| ATOM | 6835 | C   | ILE | B | 292 | 48.708 | 9.796  | −27.207 | 1.00 | 13.31 | B | C |
| ATOM | 6836 | O   | ILE | B | 292 | 48.090 | 9.376  | −28.172 | 1.00 | 15.77 | B | O |
| ATOM | 6837 | N   | ILE | B | 293 | 48.126 | 10.512 | −26.269 | 1.00 | 13.87 | B | N |
| ATOM | 6838 | CA  | ILE | B | 293 | 46.708 | 10.848 | −26.334 | 1.00 | 14.79 | B | C |
| ATOM | 6839 | CB  | ILE | B | 293 | 46.218 | 11.378 | −24.992 | 1.00 | 14.65 | B | C |
| ATOM | 6840 | CG1 | ILE | B | 293 | 46.253 | 10.221 | −23.968 | 1.00 | 19.35 | B | C |
| ATOM | 6841 | CD1 | ILE | B | 293 | 46.061 | 10.663 | −22.555 | 1.00 | 20.43 | B | C |
| ATOM | 6842 | CG2 | ILE | B | 293 | 44.751 | 11.910 | −25.141 | 1.00 | 14.75 | B | C |
| ATOM | 6843 | C   | ILE | B | 293 | 46.379 | 11.819 | −27.489 | 1.00 | 18.92 | B | C |
| ATOM | 6844 | O   | ILE | B | 293 | 45.380 | 11.641 | −28.221 | 1.00 | 16.07 | B | O |
| ATOM | 6845 | N   | ASP | B | 294 | 47.265 | 12.767 | −27.720 | 1.00 | 17.62 | B | N |
| ATOM | 6846 | CA  | ASP | B | 294 | 47.146 | 13.669 | −28.911 | 1.00 | 20.00 | B | C |
| ATOM | 6847 | CB  | ASP | B | 294 | 48.345 | 14.612 | −28.967 | 1.00 | 25.16 | B | C |
| ATOM | 6848 | CG  | ASP | B | 294 | 48.176 | 15.781 | −29.984 | 1.00 | 36.99 | B | C |
| ATOM | 6849 | OD1 | ASP | B | 294 | 47.380 | 15.706 | −30.906 | 1.00 | 37.88 | B | O |
| ATOM | 6850 | OD2 | ASP | B | 294 | 48.880 | 16.800 | −29.836 | 1.00 | 58.01 | B | O |
| ATOM | 6851 | C   | ASP | B | 294 | 47.098 | 12.826 | −30.188 | 1.00 | 18.94 | B | C |
| ATOM | 6852 | O   | ASP | B | 294 | 46.244 | 13.039 | −31.021 | 1.00 | 16.12 | B | O |
| ATOM | 6853 | N   | ASP | B | 295 | 47.997 | 11.861 | −30.327 | 1.00 | 18.01 | B | N |
| ATOM | 6854 | CA  | ASP | B | 295 | 47.973 | 10.931 | −31.468 | 1.00 | 20.14 | B | C |
| ATOM | 6855 | CB  | ASP | B | 295 | 49.096 | 9.911  | −31.363 | 1.00 | 27.52 | B | C |
| ATOM | 6856 | CG  | ASP | B | 295 | 50.486 | 10.484 | −31.700 | 1.00 | 44.28 | B | C |
| ATOM | 6857 | OD1 | ASP | B | 295 | 50.547 | 11.583 | −32.293 | 1.00 | 40.05 | B | O |
| ATOM | 6858 | OD2 | ASP | B | 295 | 51.515 | 9.815  | −31.359 | 1.00 | 41.64 | B | O |
| ATOM | 6859 | C   | ASP | B | 295 | 46.634 | 10.158 | −31.640 | 1.00 | 21.15 | B | C |
| ATOM | 6860 | O   | ASP | B | 295 | 46.148 | 9.966  | −32.777 | 1.00 | 19.75 | B | O |
| ATOM | 6861 | N   | ILE | B | 296 | 46.075 | 9.679  | −30.532 | 1.00 | 16.24 | B | N |
| ATOM | 6862 | CA  | ILE | B | 296 | 44.775 | 8.990  | −30.554 | 1.00 | 15.66 | B | C |
| ATOM | 6863 | CB  | ILE | B | 296 | 44.413 | 8.461  | −29.122 | 1.00 | 16.02 | B | C |
| ATOM | 6864 | CG1 | ILE | B | 296 | 45.371 | 7.284  | −28.781 | 1.00 | 18.95 | B | C |
| ATOM | 6865 | CD1 | ILE | B | 296 | 45.180 | 6.693  | −27.375 | 1.00 | 17.17 | B | C |
| ATOM | 6866 | CG2 | ILE | B | 296 | 42.958 | 7.993  | −29.072 | 1.00 | 14.97 | B | C |
| ATOM | 6867 | C   | ILE | B | 296 | 43.703 | 9.890  | −31.152 | 1.00 | 13.43 | B | C |
| ATOM | 6868 | O   | ILE | B | 296 | 43.037 | 9.517  | −32.125 | 1.00 | 14.63 | B | O |
| ATOM | 6869 | N   | TYR | B | 297 | 43.568 | 11.117 | −30.624 | 1.00 | 15.09 | B | N |
| ATOM | 6870 | CA  | TYR | B | 297 | 42.578 | 12.057 | −31.121 | 1.00 | 15.87 | B | C |
| ATOM | 6871 | CB  | TYR | B | 297 | 42.421 | 13.260 | −30.200 | 1.00 | 16.95 | B | C |
| ATOM | 6872 | CG  | TYR | B | 297 | 41.637 | 12.975 | −28.960 | 1.00 | 16.22 | B | C |
| ATOM | 6873 | CD1 | TYR | B | 297 | 42.233 | 12.369 | −27.876 | 1.00 | 18.96 | B | C |
| ATOM | 6874 | CE1 | TYR | B | 297 | 41.533 | 12.122 | −26.734 | 1.00 | 19.27 | B | C |
| ATOM | 6875 | CZ  | TYR | B | 297 | 40.226 | 12.519 | −26.653 | 1.00 | 16.55 | B | C |
| ATOM | 6876 | OH  | TYR | B | 297 | 39.540 | 12.273 | −25.481 | 1.00 | 17.47 | B | O |
| ATOM | 6877 | CE2 | TYR | B | 297 | 39.631 | 13.175 | −27.708 | 1.00 | 15.00 | B | C |
| ATOM | 6878 | CD2 | TYR | B | 297 | 40.340 | 13.379 | −28.847 | 1.00 | 14.40 | B | C |
| ATOM | 6879 | C   | TYR | B | 297 | 42.881 | 12.578 | −32.516 | 1.00 | 17.77 | B | C |
| ATOM | 6880 | O   | TYR | B | 297 | 41.953 | 12.807 | −33.292 | 1.00 | 16.97 | B | O |
| ATOM | 6881 | N   | ASP | B | 298 | 44.160 | 12.742 | −32.815 | 1.00 | 19.99 | B | N |
| ATOM | 6882 | CA  | ASP | B | 298 | 44.596 | 13.278 | −34.118 | 1.00 | 23.26 | B | C |

APPENDIX A-continued

*P. alba* 3T288C coordinates

| ATOM | 6883 | CB  | ASP | B | 298 | 46.045 | 13.731 | −34.047 | 1.00 | 28.34 | B | C |
| ATOM | 6884 | CG  | ASP | B | 298 | 46.509 | 14.437 | −35.321 | 1.00 | 38.75 | B | C |
| ATOM | 6885 | OD1 | ASP | B | 298 | 45.730 | 15.246 | −35.868 | 1.00 | 36.91 | B | O |
| ATOM | 6886 | OD2 | ASP | B | 298 | 47.654 | 14.182 | −35.766 | 1.00 | 42.81 | B | O |
| ATOM | 6887 | C   | ASP | B | 298 | 44.408 | 12.330 | −35.296 | 1.00 | 23.75 | B | C |
| ATOM | 6888 | O   | ASP | B | 298 | 43.861 | 12.730 | −36.342 | 1.00 | 22.43 | B | O |
| ATOM | 6889 | N   | VAL | B | 299 | 44.861 | 11.077 | −35.168 | 1.00 | 18.23 | B | N |
| ATOM | 6890 | CA  | VAL | B | 299 | 44.821 | 10.178 | −36.314 | 1.00 | 19.25 | B | C |
| ATOM | 6891 | CB  | VAL | B | 299 | 46.219 | 9.979  | −36.949 | 1.00 | 24.81 | B | C |
| ATOM | 6892 | CG1 | VAL | B | 299 | 46.692 | 11.299 | −37.581 | 1.00 | 29.19 | B | C |
| ATOM | 6893 | CG2 | VAL | B | 299 | 47.221 | 9.421  | −35.934 | 1.00 | 22.46 | B | C |
| ATOM | 6894 | C   | VAL | B | 299 | 44.202 | 8.826  | −36.081 | 1.00 | 17.35 | B | C |
| ATOM | 6895 | O   | VAL | B | 299 | 43.577 | 8.296  | −36.985 | 1.00 | 17.18 | B | O |
| ATOM | 6896 | N   | TYR | B | 300 | 44.364 | 8.243  | −34.899 | 1.00 | 16.33 | B | N |
| ATOM | 6897 | CA  | TYR | B | 300 | 43.998 | 6.828  | −34.736 | 1.00 | 18.61 | B | C |
| ATOM | 6898 | CB  | TYR | B | 300 | 44.908 | 6.202  | −33.677 | 1.00 | 19.79 | B | C |
| ATOM | 6899 | CG  | TYR | B | 300 | 44.840 | 4.699  | −33.651 | 1.00 | 19.73 | B | C |
| ATOM | 6900 | CD1 | TYR | B | 300 | 45.633 | 3.917  | −34.507 | 1.00 | 18.54 | B | C |
| ATOM | 6901 | CE1 | TYR | B | 300 | 45.557 | 2.496  | −34.474 | 1.00 | 19.58 | B | C |
| ATOM | 6902 | CZ  | TYR | B | 300 | 44.654 | 1.890  | −33.597 | 1.00 | 17.68 | B | C |
| ATOM | 6903 | OH  | TYR | B | 300 | 44.559 | 0.552  | −33.522 | 1.00 | 21.00 | B | O |
| ATOM | 6904 | CE2 | TYR | B | 300 | 43.861 | 2.640  | −32.763 | 1.00 | 21.49 | B | C |
| ATOM | 6905 | CD2 | TYR | B | 300 | 43.942 | 4.049  | −32.804 | 1.00 | 22.94 | B | C |
| ATOM | 6906 | C   | TYR | B | 300 | 42.500 | 6.598  | −34.396 | 1.00 | 15.66 | B | C |
| ATOM | 6907 | O   | TYR | B | 300 | 41.855 | 5.745  | −34.978 | 1.00 | 16.10 | B | O |
| ATOM | 6908 | N   | GLY | B | 301 | 41.961 | 7.349  | −33.464 | 1.00 | 14.35 | B | N |
| ATOM | 6909 | CA  | GLY | B | 301 | 40.617 | 7.084  | −32.929 | 1.00 | 13.88 | B | C |
| ATOM | 6910 | C   | GLY | B | 301 | 39.486 | 7.560  | −33.795 | 1.00 | 19.41 | B | C |
| ATOM | 6911 | O   | GLY | B | 301 | 39.578 | 8.639  | −34.396 | 1.00 | 17.02 | B | O |
| ATOM | 6912 | N   | THR | B | 302 | 38.415 | 6.761  | −33.889 | 1.00 | 17.51 | B | N |
| ATOM | 6913 | CA  | THR | B | 302 | 37.184 | 7.246  | −34.519 | 1.00 | 16.58 | B | C |
| ATOM | 6914 | CB  | THR | B | 302 | 36.168 | 6.117  | −34.850 | 1.00 | 16.55 | B | C |
| ATOM | 6915 | OG1 | THR | B | 302 | 35.689 | 5.542  | −33.635 | 1.00 | 17.13 | B | O |
| ATOM | 6916 | CG2 | THR | B | 302 | 36.770 | 5.007  | −35.748 | 1.00 | 12.41 | B | C |
| ATOM | 6917 | C   | THR | B | 302 | 36.489 | 8.211  | −33.581 | 1.00 | 16.89 | B | C |
| ATOM | 6918 | O   | THR | B | 302 | 36.696 | 8.191  | −32.392 | 1.00 | 17.51 | B | O |
| ATOM | 6919 | N   | LEU | B | 303 | 35.595 | 9.039  | −34.112 | 1.00 | 18.82 | B | N |
| ATOM | 6920 | CA  | LEU | B | 303 | 34.924 | 10.002 | −33.280 | 1.00 | 18.70 | B | C |
| ATOM | 6921 | CB  | LEU | B | 303 | 34.040 | 10.902 | −34.140 | 1.00 | 25.89 | B | C |
| ATOM | 6922 | CG  | LEU | B | 303 | 33.922 | 12.395 | −33.907 | 1.00 | 33.97 | B | C |
| ATOM | 6923 | CD1 | LEU | B | 303 | 35.238 | 13.063 | −33.530 | 1.00 | 26.30 | B | C |
| ATOM | 6924 | CD2 | LEU | B | 303 | 33.287 | 13.024 | −35.186 | 1.00 | 29.85 | B | C |
| ATOM | 6925 | C   | LEU | B | 303 | 34.112 | 9.354  | −32.156 | 1.00 | 18.45 | B | C |
| ATOM | 6926 | O   | LEU | B | 303 | 34.101 | 9.852  | −31.031 | 1.00 | 18.10 | B | O |
| ATOM | 6927 | N   | ASP | B | 304 | 33.454 | 8.233  | −32.441 | 1.00 | 18.11 | B | N |
| ATOM | 6928 | CA  | ASP | B | 304 | 32.737 | 7.445  | −31.405 | 1.00 | 19.14 | B | C |
| ATOM | 6929 | CB  | ASP | B | 304 | 32.027 | 6.217  | −32.020 | 1.00 | 24.92 | B | C |
| ATOM | 6930 | CG  | ASP | B | 304 | 30.770 | 6.589  | −32.888 | 1.00 | 37.62 | B | C |
| ATOM | 6931 | OD1 | ASP | B | 304 | 30.233 | 7.725  | −32.793 | 1.00 | 36.17 | B | O |
| ATOM | 6932 | OD2 | ASP | B | 304 | 30.316 | 5.728  | −33.674 | 1.00 | 42.17 | B | O |
| ATOM | 6933 | C   | ASP | B | 304 | 33.674 | 6.976  | −30.264 | 1.00 | 17.27 | B | C |
| ATOM | 6934 | O   | ASP | B | 304 | 33.298 | 7.015  | −29.098 | 1.00 | 15.49 | B | O |
| ATOM | 6935 | N   | GLU | B | 305 | 34.883 | 6.536  | −30.610 | 1.00 | 17.49 | B | N |
| ATOM | 6936 | CA  | GLU | B | 305 | 35.858 | 6.090  | −29.613 | 1.00 | 15.60 | B | C |
| ATOM | 6937 | CB  | GLU | B | 305 | 37.055 | 5.401  | −30.301 | 1.00 | 16.67 | B | C |
| ATOM | 6938 | CG  | GLU | B | 305 | 36.732 | 4.136  | −31.078 | 1.00 | 17.92 | B | C |
| ATOM | 6939 | CD  | GLU | B | 305 | 37.954 | 3.572  | −31.821 | 1.00 | 18.92 | B | C |
| ATOM | 6940 | OE1 | GLU | B | 305 | 38.882 | 4.342  | −32.205 | 1.00 | 17.92 | B | O |
| ATOM | 6941 | OE2 | GLU | B | 305 | 38.046 | 2.336  | −31.953 | 1.00 | 19.32 | B | O |
| ATOM | 6942 | C   | GLU | B | 305 | 36.352 | 7.284  | −28.803 | 1.00 | 14.90 | B | C |
| ATOM | 6943 | O   | GLU | B | 305 | 36.552 | 7.186  | −27.608 | 1.00 | 14.85 | B | O |
| ATOM | 6944 | N   | LEU | B | 306 | 36.560 | 8.417  | −29.476 | 1.00 | 14.91 | B | N |
| ATOM | 6945 | CA  | LEU | B | 306 | 37.066 | 9.604  | −28.826 | 1.00 | 13.56 | B | C |
| ATOM | 6946 | CB  | LEU | B | 306 | 37.460 | 10.651 | −29.876 | 1.00 | 13.42 | B | C |
| ATOM | 6947 | CG  | LEU | B | 306 | 38.586 | 10.284 | −30.878 | 1.00 | 14.82 | B | C |
| ATOM | 6948 | CD1 | LEU | B | 306 | 38.847 | 11.573 | −31.746 | 1.00 | 14.84 | B | C |
| ATOM | 6949 | CD2 | LEU | B | 306 | 39.834 | 9.840  | −30.171 | 1.00 | 15.93 | B | C |
| ATOM | 6950 | C   | LEU | B | 306 | 36.048 | 10.161 | −27.816 | 1.00 | 13.30 | B | C |
| ATOM | 6951 | O   | LEU | B | 306 | 36.411 | 10.666 | −26.751 | 1.00 | 14.09 | B | O |
| ATOM | 6952 | N   | GLU | B | 307 | 34.762 | 10.034 | −28.125 | 1.00 | 14.71 | B | N |
| ATOM | 6953 | CA  | GLU | B | 307 | 33.729 | 10.442 | −27.179 | 1.00 | 16.27 | B | C |
| ATOM | 6954 | CB  | GLU | B | 307 | 32.331 | 10.356 | −27.807 | 1.00 | 23.38 | B | C |
| ATOM | 6955 | CG  | GLU | B | 307 | 32.111 | 11.353 | −28.928 | 1.00 | 26.61 | B | C |
| ATOM | 6956 | CD  | GLU | B | 307 | 31.648 | 12.688 | −28.409 | 1.00 | 37.36 | B | C |
| ATOM | 6957 | OE1 | GLU | B | 307 | 31.531 | 12.827 | −27.163 | 1.00 | 34.44 | B | O |
| ATOM | 6958 | OE2 | GLU | B | 307 | 31.397 | 13.588 | −29.240 | 1.00 | 39.03 | B | O |
| ATOM | 6959 | C   | GLU | B | 307 | 33.763 | 9.556  | −25.955 | 1.00 | 17.30 | B | C |
| ATOM | 6960 | O   | GLU | B | 307 | 33.624 | 10.048 | −24.860 | 1.00 | 16.25 | B | O |

APPENDIX A-continued

*P. alba* 3T288C coordinates

| ATOM | 6961 | N | LEU | B | 308 | 33.958 | 8.246 | −26.136 | 1.00 | 17.52 | B | N |
|---|---|---|---|---|---|---|---|---|---|---|---|---|
| ATOM | 6962 | CA | LEU | B | 308 | 34.075 | 7.326 | −24.986 | 1.00 | 20.67 | B | C |
| ATOM | 6963 | CB | LEU | B | 308 | 34.267 | 5.863 | −25.451 | 1.00 | 23.47 | B | C |
| ATOM | 6964 | CG | LEU | B | 308 | 33.023 | 5.193 | −26.041 | 1.00 | 25.34 | B | C |
| ATOM | 6965 | CD1 | LEU | B | 308 | 33.350 | 3.738 | −26.465 | 1.00 | 23.64 | B | C |
| ATOM | 6966 | CD2 | LEU | B | 308 | 31.862 | 5.193 | −25.028 | 1.00 | 27.52 | B | C |
| ATOM | 6967 | C | LEU | B | 308 | 35.240 | 7.674 | −24.111 | 1.00 | 17.44 | B | C |
| ATOM | 6968 | O | LEU | B | 308 | 35.124 | 7.703 | −22.887 | 1.00 | 15.08 | B | O |
| ATOM | 6969 | N | PHE | B | 309 | 36.386 | 7.934 | −24.736 | 1.00 | 15.50 | B | N |
| ATOM | 6970 | CA | PHE | B | 309 | 37.597 | 8.288 | −23.969 | 1.00 | 14.42 | B | C |
| ATOM | 6971 | CB | PHE | B | 309 | 38.816 | 8.407 | −24.893 | 1.00 | 13.51 | B | C |
| ATOM | 6972 | CG | PHE | B | 309 | 40.141 | 8.375 | −24.170 | 1.00 | 13.46 | B | C |
| ATOM | 6973 | CD1 | PHE | B | 309 | 40.722 | 9.533 | −23.699 | 1.00 | 14.51 | B | C |
| ATOM | 6974 | CE1 | PHE | B | 309 | 41.940 | 9.504 | −23.011 | 1.00 | 16.19 | B | C |
| ATOM | 6975 | CZ | PHE | B | 309 | 42.567 | 8.281 | −22.809 | 1.00 | 16.97 | B | C |
| ATOM | 6976 | CE2 | PHE | B | 309 | 41.999 | 7.155 | −23.238 | 1.00 | 15.71 | B | C |
| ATOM | 6977 | CD2 | PHE | B | 309 | 40.772 | 7.180 | −23.927 | 1.00 | 16.06 | B | C |
| ATOM | 6978 | C | PHE | B | 309 | 37.409 | 9.563 | −23.164 | 1.00 | 14.01 | B | C |
| ATOM | 6979 | O | PHE | B | 309 | 37.782 | 9.622 | −21.979 | 1.00 | 14.02 | B | O |
| ATOM | 6980 | N | THR | B | 310 | 36.886 | 10.610 | −23.812 | 1.00 | 17.04 | B | N |
| ATOM | 6981 | CA | THR | B | 310 | 36.645 | 11.889 | −23.157 | 1.00 | 15.23 | B | C |
| ATOM | 6982 | CB | THR | B | 310 | 36.062 | 12.936 | −24.140 | 1.00 | 17.00 | B | C |
| ATOM | 6983 | OG1 | THR | B | 310 | 36.923 | 13.003 | −25.280 | 1.00 | 18.07 | B | O |
| ATOM | 6984 | CG2 | THR | B | 310 | 35.942 | 14.349 | −23.506 | 1.00 | 14.76 | B | C |
| ATOM | 6985 | C | THR | B | 310 | 35.729 | 11.735 | −21.948 | 1.00 | 17.85 | B | C |
| ATOM | 6986 | O | THR | B | 310 | 36.039 | 12.243 | −20.871 | 1.00 | 14.66 | B | O |
| ATOM | 6987 | N | ASP | B | 311 | 34.649 | 10.979 | −22.130 | 1.00 | 19.67 | B | N |
| ATOM | 6988 | CA | ASP | B | 311 | 33.699 | 10.657 | −21.075 | 1.00 | 19.68 | B | C |
| ATOM | 6989 | CB | ASP | B | 311 | 32.534 | 9.817 | −21.647 | 1.00 | 22.14 | B | C |
| ATOM | 6990 | CG | ASP | B | 311 | 31.516 | 9.414 | −20.579 | 1.00 | 28.93 | B | C |
| ATOM | 6991 | OD1 | ASP | B | 311 | 30.837 | 10.310 | −19.997 | 1.00 | 31.55 | B | O |
| ATOM | 6992 | OD2 | ASP | B | 311 | 31.429 | 8.209 | −20.261 | 1.00 | 32.04 | B | O |
| ATOM | 6993 | C | ASP | B | 311 | 34.372 | 9.886 | −19.944 | 1.00 | 19.06 | B | C |
| ATOM | 6994 | O | ASP | B | 311 | 34.114 | 10.168 | −18.785 | 1.00 | 16.44 | B | O |
| ATOM | 6995 | N | ALA | B | 312 | 35.229 | 8.914 | −20.281 | 1.00 | 18.62 | B | N |
| ATOM | 6996 | CA | ALA | B | 312 | 35.926 | 8.147 | −19.275 | 1.00 | 17.19 | B | C |
| ATOM | 6997 | CB | ALA | B | 312 | 36.664 | 6.912 | −19.892 | 1.00 | 13.49 | B | C |
| ATOM | 6998 | C | ALA | B | 312 | 36.859 | 9.028 | −18.440 | 1.00 | 13.94 | B | C |
| ATOM | 6999 | O | ALA | B | 312 | 36.894 | 8.886 | −17.229 | 1.00 | 15.40 | B | O |
| ATOM | 7000 | N | VAL | B | 313 | 37.541 | 9.998 | −19.063 | 1.00 | 13.78 | B | N |
| ATOM | 7001 | CA | VAL | B | 313 | 38.380 | 10.912 | −18.337 | 1.00 | 14.72 | B | C |
| ATOM | 7002 | CB | VAL | B | 313 | 39.314 | 11.724 | −19.271 | 1.00 | 12.81 | B | C |
| ATOM | 7003 | CG1 | VAL | B | 313 | 40.012 | 12.823 | −18.484 | 1.00 | 16.22 | B | C |
| ATOM | 7004 | CG2 | VAL | B | 313 | 40.344 | 10.765 | −19.930 | 1.00 | 12.97 | B | C |
| ATOM | 7005 | C | VAL | B | 313 | 37.556 | 11.845 | −17.413 | 1.00 | 17.12 | B | C |
| ATOM | 7006 | O | VAL | B | 313 | 37.895 | 11.995 | −16.248 | 1.00 | 13.85 | B | O |
| ATOM | 7007 | N | GLU | B | 314 | 36.446 | 12.384 | −17.914 | 1.00 | 19.70 | B | N |
| ATOM | 7008 | CA | GLU | B | 314 | 35.519 | 13.203 | −17.116 | 1.00 | 17.71 | B | C |
| ATOM | 7009 | CB | GLU | B | 314 | 34.314 | 13.642 | −17.987 | 1.00 | 18.63 | B | C |
| ATOM | 7010 | CG | GLU | B | 314 | 34.732 | 14.588 | −19.117 | 1.00 | 22.12 | B | C |
| ATOM | 7011 | CD | GLU | B | 314 | 33.579 | 15.065 | −20.023 | 1.00 | 28.37 | B | C |
| ATOM | 7012 | OE1 | GLU | B | 314 | 32.565 | 14.380 | −20.150 | 1.00 | 33.47 | B | O |
| ATOM | 7013 | OE2 | GLU | B | 314 | 33.738 | 16.100 | −20.679 | 1.00 | 28.18 | B | O |
| ATOM | 7014 | C | GLU | B | 314 | 34.992 | 12.469 | −15.881 | 1.00 | 20.83 | B | C |
| ATOM | 7015 | O | GLU | B | 314 | 34.964 | 13.042 | −14.820 | 1.00 | 18.78 | B | O |
| ATOM | 7016 | N | ARG | B | 315 | 34.624 | 11.195 | −16.017 | 1.00 | 17.42 | B | N |
| ATOM | 7017 | CA | ARG | B | 315 | 34.045 | 10.428 | −14.888 | 1.00 | 21.50 | B | C |
| ATOM | 7018 | CB | ARG | B | 315 | 33.193 | 9.299 | −15.421 | 1.00 | 24.86 | B | C |
| ATOM | 7019 | CG | ARG | B | 315 | 31.882 | 9.782 | −16.058 | 1.00 | 31.82 | B | C |
| ATOM | 7020 | CD | ARG | B | 315 | 31.120 | 8.651 | −16.749 | 1.00 | 38.64 | B | C |
| ATOM | 7021 | NE | ARG | B | 315 | 30.075 | 9.168 | −17.641 | 1.00 | 56.06 | B | N |
| ATOM | 7022 | CZ | ARG | B | 315 | 28.896 | 9.671 | −17.251 | 1.00 | 63.18 | B | C |
| ATOM | 7023 | NH1 | ARG | B | 315 | 28.557 | 9.724 | −15.966 | 1.00 | 58.00 | B | N |
| ATOM | 7024 | NH2 | ARG | B | 315 | 28.034 | 10.116 | −18.164 | 1.00 | 62.54 | B | N |
| ATOM | 7025 | C | ARG | B | 315 | 35.107 | 9.879 | −13.924 | 1.00 | 20.36 | B | C |
| ATOM | 7026 | O | ARG | B | 315 | 34.860 | 9.690 | −12.725 | 1.00 | 16.97 | B | O |
| ATOM | 7027 | N | TRP | B | 316 | 36.295 | 9.608 | −14.445 | 1.00 | 15.84 | B | N |
| ATOM | 7028 | CA | TRP | B | 316 | 37.393 | 9.138 | −13.622 | 1.00 | 14.10 | B | C |
| ATOM | 7029 | CB | TRP | B | 316 | 37.925 | 10.258 | −12.740 | 1.00 | 15.69 | B | C |
| ATOM | 7030 | CG | TRP | B | 316 | 39.359 | 10.072 | −12.373 | 1.00 | 12.64 | B | C |
| ATOM | 7031 | CD1 | TRP | B | 316 | 39.871 | 9.691 | −11.155 | 1.00 | 13.71 | B | C |
| ATOM | 7032 | NE1 | TRP | B | 316 | 41.226 | 9.613 | −11.213 | 1.00 | 11.47 | B | N |
| ATOM | 7033 | CE2 | TRP | B | 316 | 41.677 | 9.923 | −12.429 | 1.00 | 10.57 | B | C |
| ATOM | 7034 | CD2 | TRP | B | 316 | 40.532 | 10.242 | −13.240 | 1.00 | 11.76 | B | C |
| ATOM | 7035 | CE3 | TRP | B | 316 | 40.720 | 10.599 | −14.556 | 1.00 | 12.19 | B | C |
| ATOM | 7036 | CZ3 | TRP | B | 316 | 41.996 | 10.637 | −15.048 | 1.00 | 14.49 | B | C |
| ATOM | 7037 | CH2 | TRP | B | 316 | 43.103 | 10.344 | −14.234 | 1.00 | 14.28 | B | C |
| ATOM | 7038 | CZ2 | TRP | B | 316 | 42.958 | 9.993 | −12.914 | 1.00 | 12.17 | B | C |

APPENDIX A-continued

*P. alba* 3T288C coordinates

| ATOM | 7039 | C | TRP | B | 316 | 36.997 | 7.951 | −12.817 | 1.00 | 13.75 | B | C |
|------|------|------|-----|---|-----|--------|--------|---------|------|-------|---|---|
| ATOM | 7040 | O | TRP | B | 316 | 37.127 | 7.945 | −11.613 | 1.00 | 15.54 | B | O |
| ATOM | 7041 | N | ASP | B | 317 | 36.470 | 6.939 | −13.485 | 1.00 | 14.60 | B | N |
| ATOM | 7042 | CA | ASP | B | 317 | 35.944 | 5.750 | −12.810 | 1.00 | 18.60 | B | C |
| ATOM | 7043 | CB | ASP | B | 317 | 34.439 | 5.688 | −13.112 | 1.00 | 18.39 | B | C |
| ATOM | 7044 | CG | ASP | B | 317 | 33.744 | 4.490 | −12.526 | 1.00 | 23.79 | B | C |
| ATOM | 7045 | OD1 | ASP | B | 317 | 34.291 | 3.728 | −11.691 | 1.00 | 28.29 | B | O |
| ATOM | 7046 | OD2 | ASP | B | 317 | 32.578 | 4.326 | −12.918 | 1.00 | 29.79 | B | O |
| ATOM | 7047 | C | ASP | B | 317 | 36.655 | 4.521 | −13.365 | 1.00 | 17.48 | B | C |
| ATOM | 7048 | O | ASP | B | 317 | 36.458 | 4.195 | −14.532 | 1.00 | 21.17 | B | O |
| ATOM | 7049 | N | VAL | B | 318 | 37.449 | 3.844 | −12.535 | 1.00 | 20.98 | B | N |
| ATOM | 7050 | CA | VAL | B | 318 | 38.216 | 2.676 | −12.970 | 1.00 | 18.72 | B | C |
| ATOM | 7051 | CB | VAL | B | 318 | 39.303 | 2.293 | −11.952 | 1.00 | 22.93 | B | C |
| ATOM | 7052 | CG1 | VAL | B | 318 | 38.693 | 1.638 | −10.707 | 1.00 | 22.40 | B | C |
| ATOM | 7053 | CG2 | VAL | B | 318 | 40.351 | 1.365 | −12.578 | 1.00 | 21.60 | B | C |
| ATOM | 7054 | C | VAL | B | 318 | 37.276 | 1.489 | −13.145 | 1.00 | 26.77 | B | C |
| ATOM | 7055 | O | VAL | B | 318 | 37.547 | 0.597 | −13.934 | 1.00 | 24.06 | B | O |
| ATOM | 7056 | N | ASN | B | 319 | 36.167 | 1.476 | −12.407 | 1.00 | 24.55 | B | N |
| ATOM | 7057 | CA | ASN | B | 319 | 35.197 | 0.365 | −12.484 | 1.00 | 25.94 | B | C |
| ATOM | 7058 | CB | ASN | B | 319 | 34.261 | 0.385 | −11.275 | 1.00 | 26.17 | B | C |
| ATOM | 7059 | CG | ASN | B | 319 | 35.018 | 0.199 | −9.952 | 1.00 | 28.06 | B | C |
| ATOM | 7060 | OD1 | ASN | B | 319 | 35.796 | −0.761 | −9.803 | 1.00 | 27.13 | B | O |
| ATOM | 7061 | ND2 | ASN | B | 319 | 34.789 | 1.100 | −8.988 | 1.00 | 20.00 | B | N |
| ATOM | 7062 | C | ASN | B | 319 | 34.393 | 0.345 | −13.769 | 1.00 | 23.58 | B | C |
| ATOM | 7063 | O | ASN | B | 319 | 33.598 | −0.555 | −13.949 | 1.00 | 23.76 | B | O |
| ATOM | 7064 | N | ALA | B | 320 | 34.636 | 1.308 | −14.663 | 1.00 | 23.98 | B | N |
| ATOM | 7065 | CA | ALA | B | 320 | 33.974 | 1.397 | −15.984 | 1.00 | 29.16 | B | C |
| ATOM | 7066 | CB | ALA | B | 320 | 33.189 | 2.730 | −16.067 | 1.00 | 26.97 | B | C |
| ATOM | 7067 | C | ALA | B | 320 | 34.936 | 1.331 | −17.199 | 1.00 | 33.61 | B | C |
| ATOM | 7068 | O | ALA | B | 320 | 34.527 | 1.638 | −18.303 | 1.00 | 29.23 | B | O |
| ATOM | 7069 | N | ILE | B | 321 | 36.209 | 0.965 | −17.021 | 1.00 | 33.27 | B | N |
| ATOM | 7070 | CA | ILE | B | 321 | 37.157 | 0.884 | −18.166 | 1.00 | 22.33 | B | C |
| ATOM | 7071 | CB | ILE | B | 321 | 38.641 | 0.637 | −17.725 | 1.00 | 25.50 | B | C |
| ATOM | 7072 | CG1 | ILE | B | 321 | 38.835 | −0.765 | −17.202 | 1.00 | 23.16 | B | C |
| ATOM | 7073 | CD1 | ILE | B | 321 | 40.201 | −0.992 | −16.573 | 1.00 | 33.57 | B | C |
| ATOM | 7074 | CG2 | ILE | B | 321 | 39.096 | 1.664 | −16.636 | 1.00 | 22.17 | B | C |
| ATOM | 7075 | C | ILE | B | 321 | 36.784 | −0.196 | −19.191 | 1.00 | 29.18 | B | C |
| ATOM | 7076 | O | ILE | B | 321 | 37.217 | −0.143 | −20.339 | 1.00 | 33.50 | B | O |
| ATOM | 7077 | N | ASN | B | 322 | 35.992 | −1.186 | −18.789 | 1.00 | 26.39 | B | N |
| ATOM | 7078 | CA | ASN | B | 322 | 35.492 | −2.174 | −19.744 | 1.00 | 28.36 | B | C |
| ATOM | 7079 | CB | ASN | B | 322 | 34.846 | −3.373 | −19.019 | 1.00 | 29.64 | B | C |
| ATOM | 7080 | CG | ASN | B | 322 | 35.896 | −4.329 | −18.370 | 1.00 | 28.34 | B | C |
| ATOM | 7081 | OD1 | ASN | B | 322 | 37.100 | −4.289 | −18.666 | 1.00 | 22.33 | B | O |
| ATOM | 7082 | ND2 | ASN | B | 322 | 35.421 | −5.182 | −17.500 | 1.00 | 23.59 | B | N |
| ATOM | 7083 | C | ASN | B | 322 | 34.547 | −1.591 | −20.842 | 1.00 | 24.07 | B | C |
| ATOM | 7084 | O | ASN | B | 322 | 34.299 | −2.245 | −21.813 | 1.00 | 22.82 | B | O |
| ATOM | 7085 | N | ASP | B | 323 | 34.086 | −0.358 | −20.713 | 1.00 | 26.94 | B | N |
| ATOM | 7086 | CA | ASP | B | 323 | 33.367 | 0.317 | −21.834 | 1.00 | 34.72 | B | C |
| ATOM | 7087 | CB | ASP | B | 323 | 32.720 | 1.634 | −21.343 | 1.00 | 42.84 | B | C |
| ATOM | 7088 | CG | ASP | B | 323 | 31.791 | 1.459 | −20.127 | 1.00 | 42.61 | B | C |
| ATOM | 7089 | OD1 | ASP | B | 323 | 31.199 | 0.384 | −19.955 | 1.00 | 44.74 | B | O |
| ATOM | 7090 | OD2 | ASP | B | 323 | 31.641 | 2.433 | −19.353 | 1.00 | 43.15 | B | O |
| ATOM | 7091 | C | ASP | B | 323 | 34.292 | 0.705 | −23.032 | 1.00 | 27.41 | B | C |
| ATOM | 7092 | O | ASP | B | 323 | 33.835 | 1.019 | −24.125 | 1.00 | 27.02 | B | O |
| ATOM | 7093 | N | LEU | B | 324 | 35.594 | 0.723 | −22.806 | 1.00 | 21.91 | B | N |
| ATOM | 7094 | CA | LEU | B | 324 | 36.520 | 1.263 | −23.795 | 1.00 | 21.35 | B | C |
| ATOM | 7095 | CB | LEU | B | 324 | 37.699 | 1.905 | −23.075 | 1.00 | 18.13 | B | C |
| ATOM | 7096 | CG | LEU | B | 324 | 37.394 | 3.110 | −22.196 | 1.00 | 19.17 | B | C |
| ATOM | 7097 | CD1 | LEU | B | 324 | 38.555 | 3.482 | −21.265 | 1.00 | 17.09 | B | C |
| ATOM | 7098 | CD2 | LEU | B | 324 | 37.033 | 4.301 | −23.103 | 1.00 | 15.35 | B | C |
| ATOM | 7099 | C | LEU | B | 324 | 37.058 | 0.190 | −24.738 | 1.00 | 20.92 | B | C |
| ATOM | 7100 | O | LEU | B | 324 | 37.287 | −0.944 | −24.307 | 1.00 | 19.02 | B | O |
| ATOM | 7101 | N | PRO | B | 325 | 37.350 | 0.556 | −26.009 | 1.00 | 18.20 | B | N |
| ATOM | 7102 | CA | PRO | B | 325 | 38.042 | −0.408 | −26.878 | 1.00 | 21.89 | B | C |
| ATOM | 7103 | CB | PRO | B | 325 | 38.135 | 0.326 | −28.230 | 1.00 | 21.00 | B | C |
| ATOM | 7104 | CG | PRO | B | 325 | 38.016 | 1.718 | −27.914 | 1.00 | 20.12 | B | C |
| ATOM | 7105 | CD | PRO | B | 325 | 37.143 | 1.842 | −26.684 | 1.00 | 18.81 | B | C |
| ATOM | 7106 | C | PRO | B | 325 | 39.426 | −0.741 | −26.304 | 1.00 | 19.63 | B | C |
| ATOM | 7107 | O | PRO | B | 325 | 39.976 | 0.057 | −25.533 | 1.00 | 15.57 | B | O |
| ATOM | 7108 | N | ASP | B | 326 | 39.964 | −1.908 | −26.656 | 1.00 | 16.21 | B | N |
| ATOM | 7109 | CA | ASP | B | 326 | 41.121 | −2.488 | −25.940 | 1.00 | 17.77 | B | C |
| ATOM | 7110 | CB | ASP | B | 326 | 41.543 | −3.815 | −26.570 | 1.00 | 22.34 | B | C |
| ATOM | 7111 | CG | ASP | B | 326 | 40.567 | −4.979 | −26.255 | 1.00 | 24.51 | B | C |
| ATOM | 7112 | OD1 | ASP | B | 326 | 39.698 | −4.857 | −25.367 | 1.00 | 28.55 | B | O |
| ATOM | 7113 | OD2 | ASP | B | 326 | 40.673 | −6.028 | −26.910 | 1.00 | 29.72 | B | O |
| ATOM | 7114 | C | ASP | B | 326 | 42.322 | −1.526 | −25.867 | 1.00 | 16.53 | B | C |
| ATOM | 7115 | O | ASP | B | 326 | 42.909 | −1.335 | −24.792 | 1.00 | 13.99 | B | O |
| ATOM | 7116 | N | TYR | B | 327 | 42.654 | −0.857 | −26.972 | 1.00 | 15.60 | B | N |

APPENDIX A-continued

*P. alba* 3T288C coordinates

| ATOM | 7117 | CA | TYR | B | 327 | 43.804 | 0.098 | −26.924 | 1.00 | 17.04 | B | C |
| ATOM | 7118 | CB | TYR | B | 327 | 44.214 | 0.584 | −28.316 | 1.00 | 17.03 | B | C |
| ATOM | 7119 | CG | TYR | B | 327 | 43.315 | 1.659 | −28.914 | 1.00 | 17.73 | B | C |
| ATOM | 7120 | CD1 | TYR | B | 327 | 42.132 | 1.343 | −29.557 | 1.00 | 18.37 | B | C |
| ATOM | 7121 | CE1 | TYR | B | 327 | 41.316 | 2.363 | −30.095 | 1.00 | 19.68 | B | C |
| ATOM | 7122 | CZ | TYR | B | 327 | 41.741 | 3.685 | −30.012 | 1.00 | 19.30 | B | C |
| ATOM | 7123 | OH | TYR | B | 327 | 41.008 | 4.703 | −30.533 | 1.00 | 17.39 | B | O |
| ATOM | 7124 | CE2 | TYR | B | 327 | 42.902 | 3.998 | −29.399 | 1.00 | 21.08 | B | C |
| ATOM | 7125 | CD2 | TYR | B | 327 | 43.684 | 2.991 | −28.842 | 1.00 | 19.32 | B | C |
| ATOM | 7126 | C | TYR | B | 327 | 43.563 | 1.274 | −25.978 | 1.00 | 15.40 | B | C |
| ATOM | 7127 | O | TYR | B | 327 | 44.494 | 1.753 | −25.289 | 1.00 | 17.13 | B | O |
| ATOM | 7128 | N | MET | B | 328 | 42.326 | 1.737 | −25.879 | 1.00 | 15.12 | B | N |
| ATOM | 7129 | CA | MET | B | 328 | 42.043 | 2.839 | −24.944 | 1.00 | 13.87 | B | C |
| ATOM | 7130 | CB | MET | B | 328 | 40.746 | 3.533 | −25.291 | 1.00 | 16.27 | B | C |
| ATOM | 7131 | CG | MET | B | 328 | 40.878 | 4.478 | −26.468 | 1.00 | 17.30 | B | C |
| ATOM | 7132 | SD | MET | B | 328 | 39.258 | 5.116 | −26.958 | 1.00 | 16.70 | B | S |
| ATOM | 7133 | CE | MET | B | 328 | 39.865 | 6.551 | −27.939 | 1.00 | 15.53 | B | C |
| ATOM | 7134 | C | MET | B | 328 | 41.994 | 2.405 | −23.485 | 1.00 | 13.82 | B | C |
| ATOM | 7135 | O | MET | B | 328 | 42.280 | 3.190 | −22.595 | 1.00 | 15.80 | B | O |
| ATOM | 7136 | N | LYS | B | 329 | 41.647 | 1.157 | −23.258 | 1.00 | 15.99 | B | N |
| ATOM | 7137 | CA | LYS | B | 329 | 41.602 | 0.607 | −21.905 | 1.00 | 18.78 | B | C |
| ATOM | 7138 | CB | LYS | B | 329 | 41.141 | −0.836 | −21.963 | 1.00 | 18.76 | B | C |
| ATOM | 7139 | CG | LYS | B | 329 | 40.485 | −1.341 | −20.692 | 1.00 | 29.84 | B | C |
| ATOM | 7140 | CD | LYS | B | 329 | 39.870 | −2.750 | −20.875 | 1.00 | 29.88 | B | C |
| ATOM | 7141 | CE | LYS | B | 329 | 39.085 | −2.869 | −22.175 | 1.00 | 34.22 | B | C |
| ATOM | 7142 | NZ | LYS | B | 329 | 38.141 | −4.004 | −22.166 | 1.00 | 33.90 | B | N |
| ATOM | 7143 | C | LYS | B | 329 | 42.982 | 0.688 | −21.275 | 1.00 | 15.84 | B | C |
| ATOM | 7144 | O | LYS | B | 329 | 43.124 | 1.102 | −20.145 | 1.00 | 13.96 | B | O |
| ATOM | 7145 | N | LEU | B | 330 | 43.988 | 0.286 | −22.040 | 1.00 | 13.82 | B | N |
| ATOM | 7146 | CA | LEU | B | 330 | 45.348 | 0.326 | −21.593 | 1.00 | 14.18 | B | C |
| ATOM | 7147 | CB | LEU | B | 330 | 46.220 | −0.428 | −22.591 | 1.00 | 14.87 | B | C |
| ATOM | 7148 | CG | LEU | B | 330 | 47.602 | −0.861 | −22.123 | 1.00 | 17.60 | B | C |
| ATOM | 7149 | CD1 | LEU | B | 330 | 47.498 | −1.976 | −21.081 | 1.00 | 17.42 | B | C |
| ATOM | 7150 | CD2 | LEU | B | 330 | 48.411 | −1.377 | −23.338 | 1.00 | 19.62 | B | C |
| ATOM | 7151 | C | LEU | B | 330 | 45.839 | 1.739 | −21.374 | 1.00 | 15.98 | B | C |
| ATOM | 7152 | O | LEU | B | 330 | 46.381 | 2.064 | −20.296 | 1.00 | 14.92 | B | O |
| ATOM | 7153 | N | CYS | B | 331 | 45.638 | 2.607 | −22.372 | 1.00 | 15.80 | B | N |
| ATOM | 7154 | CA | ACYS | B | 331 | 46.049 | 4.000 | −22.251 | 0.50 | 14.90 | B | C |
| ATOM | 7155 | CA | BCYS | B | 331 | 46.018 | 4.013 | −22.258 | 0.50 | 16.77 | B | C |
| ATOM | 7156 | CB | ACYS | B | 331 | 45.751 | 4.763 | −23.555 | 0.50 | 16.03 | B | C |
| ATOM | 7157 | CB | BCYS | B | 331 | 45.609 | 4.772 | −23.525 | 0.50 | 21.14 | B | C |
| ATOM | 7158 | SG | ACYS | B | 331 | 46.485 | 6.421 | −23.637 | 0.50 | 17.14 | B | S |
| ATOM | 7159 | SG | BCYS | B | 331 | 46.673 | 4.456 | −24.908 | 0.50 | 30.01 | B | S |
| ATOM | 7160 | C | CYS | B | 331 | 45.360 | 4.680 | −21.061 | 1.00 | 14.16 | B | C |
| ATOM | 7161 | O | CYS | B | 331 | 46.017 | 5.344 | −20.269 | 1.00 | 14.78 | B | O |
| ATOM | 7162 | N | PHE | B | 332 | 44.040 | 4.517 | −20.956 | 1.00 | 12.94 | B | N |
| ATOM | 7163 | CA | PHE | B | 332 | 43.289 | 5.070 | −19.843 | 1.00 | 12.85 | B | C |
| ATOM | 7164 | CB | PHE | B | 332 | 41.792 | 4.785 | −19.934 | 1.00 | 14.46 | B | C |
| ATOM | 7165 | CG | PHE | B | 332 | 40.993 | 5.396 | −18.801 | 1.00 | 17.76 | B | C |
| ATOM | 7166 | CD1 | PHE | B | 332 | 40.638 | 6.716 | −18.836 | 1.00 | 17.42 | B | C |
| ATOM | 7167 | CE1 | PHE | B | 332 | 39.921 | 7.282 | −17.798 | 1.00 | 21.26 | B | C |
| ATOM | 7168 | CZ | PHE | B | 332 | 39.554 | 6.517 | −16.719 | 1.00 | 17.35 | B | C |
| ATOM | 7169 | CE2 | PHE | B | 332 | 39.930 | 5.236 | −16.639 | 1.00 | 20.18 | B | C |
| ATOM | 7170 | CD2 | PHE | B | 332 | 40.641 | 4.650 | −17.689 | 1.00 | 21.54 | B | C |
| ATOM | 7171 | C | PHE | B | 332 | 43.816 | 4.591 | −18.496 | 1.00 | 10.49 | B | C |
| ATOM | 7172 | O | PHE | B | 332 | 44.073 | 5.398 | −17.613 | 1.00 | 11.44 | B | O |
| ATOM | 7173 | N | LEU | B | 333 | 44.002 | 3.293 | −18.351 | 1.00 | 11.57 | B | N |
| ATOM | 7174 | CA | LEU | B | 333 | 44.347 | 2.762 | −17.044 | 1.00 | 10.73 | B | C |
| ATOM | 7175 | CB | LEU | B | 333 | 44.170 | 1.256 | −16.957 | 1.00 | 11.15 | B | C |
| ATOM | 7176 | CG | LEU | B | 333 | 44.494 | 0.599 | −15.595 | 1.00 | 11.32 | B | C |
| ATOM | 7177 | CD1 | LEU | B | 333 | 43.650 | 1.232 | −14.483 | 1.00 | 9.46 | B | C |
| ATOM | 7178 | CD2 | LEU | B | 333 | 44.261 | −0.957 | −15.619 | 1.00 | 9.98 | B | C |
| ATOM | 7179 | C | LEU | B | 333 | 45.771 | 3.231 | −16.673 | 1.00 | 13.03 | B | C |
| ATOM | 7180 | O | LEU | B | 333 | 46.024 | 3.606 | −15.507 | 1.00 | 10.42 | B | O |
| ATOM | 7181 | N | ALA | B | 334 | 46.664 | 3.338 | −17.663 | 1.00 | 11.93 | B | N |
| ATOM | 7182 | CA | ALA | B | 334 | 48.011 | 3.853 | −17.368 | 1.00 | 13.38 | B | C |
| ATOM | 7183 | CB | ALA | B | 334 | 48.913 | 3.685 | −18.575 | 1.00 | 15.36 | B | C |
| ATOM | 7184 | C | ALA | B | 334 | 47.984 | 5.312 | −16.906 | 1.00 | 12.41 | B | C |
| ATOM | 7185 | O | ALA | B | 334 | 48.691 | 5.696 | −15.978 | 1.00 | 12.48 | B | O |
| ATOM | 7186 | N | LEU | B | 335 | 47.156 | 6.123 | −17.548 | 1.00 | 14.27 | B | N |
| ATOM | 7187 | CA | LEU | B | 335 | 47.000 | 7.544 | −17.184 | 1.00 | 14.27 | B | C |
| ATOM | 7188 | CB | LEU | B | 335 | 46.099 | 8.266 | −18.217 | 1.00 | 13.34 | B | C |
| ATOM | 7189 | CG | LEU | B | 335 | 45.755 | 9.740 | −17.994 | 1.00 | 19.00 | B | C |
| ATOM | 7190 | CD1 | LEU | B | 335 | 47.010 | 10.582 | −18.057 | 1.00 | 16.63 | B | C |
| ATOM | 7191 | CD2 | LEU | B | 335 | 44.695 | 10.245 | −18.956 | 1.00 | 21.42 | B | C |
| ATOM | 7192 | C | LEU | B | 335 | 46.396 | 7.663 | −15.779 | 1.00 | 13.65 | B | C |
| ATOM | 7193 | O | LEU | B | 335 | 46.898 | 8.412 | −14.942 | 1.00 | 15.12 | B | O |
| ATOM | 7194 | N | TYR | B | 336 | 45.309 | 6.926 | −15.574 | 1.00 | 14.28 | B | N |

APPENDIX A-continued

P. alba 3T288C coordinates

| ATOM | 7195 | CA | TYR | B | 336 | 44.563 | 6.865 | −14.329 | 1.00 | 13.79 | B | C |
|---|---|---|---|---|---|---|---|---|---|---|---|---|
| ATOM | 7196 | CB | TYR | B | 336 | 43.503 | 5.777 | −14.448 | 1.00 | 13.43 | B | C |
| ATOM | 7197 | CG | TYR | B | 336 | 42.499 | 5.696 | −13.337 | 1.00 | 12.12 | B | C |
| ATOM | 7198 | CD1 | TYR | B | 336 | 41.410 | 6.570 | −13.286 | 1.00 | 14.48 | B | C |
| ATOM | 7199 | CE1 | TYR | B | 336 | 40.461 | 6.486 | −12.232 | 1.00 | 15.49 | B | C |
| ATOM | 7200 | CZ | TYR | B | 336 | 40.618 | 5.543 | −11.262 | 1.00 | 17.58 | B | C |
| ATOM | 7201 | OH | TYR | B | 336 | 39.706 | 5.404 | −10.223 | 1.00 | 20.26 | B | O |
| ATOM | 7202 | CE2 | TYR | B | 336 | 41.705 | 4.678 | −11.313 | 1.00 | 16.06 | B | C |
| ATOM | 7203 | CD2 | TYR | B | 336 | 42.636 | 4.775 | −12.328 | 1.00 | 12.06 | B | C |
| ATOM | 7204 | C | TYR | B | 336 | 45.474 | 6.574 | −13.173 | 1.00 | 13.04 | B | C |
| ATOM | 7205 | O | TYR | B | 336 | 45.535 | 7.368 | −12.217 | 1.00 | 10.25 | B | O |
| ATOM | 7206 | N | ASN | B | 337 | 46.268 | 5.507 | −13.279 | 1.00 | 11.68 | B | N |
| ATOM | 7207 | CA | ASN | B | 337 | 47.194 | 5.162 | −12.199 | 1.00 | 11.43 | B | C |
| ATOM | 7208 | CB | ASN | B | 337 | 47.852 | 3.796 | −12.409 | 1.00 | 10.75 | B | C |
| ATOM | 7209 | CG | ASN | B | 337 | 46.888 | 2.659 | −12.265 | 1.00 | 13.68 | B | C |
| ATOM | 7210 | OD1 | ASN | B | 337 | 45.820 | 2.821 | −11.681 | 1.00 | 15.73 | B | O |
| ATOM | 7211 | ND2 | ASN | B | 337 | 47.246 | 1.475 | −12.815 | 1.00 | 12.01 | B | N |
| ATOM | 7212 | C | ASN | B | 337 | 48.268 | 6.230 | −12.014 | 1.00 | 12.56 | B | C |
| ATOM | 7213 | O | ASN | B | 337 | 48.669 | 6.532 | −10.907 | 1.00 | 9.49 | B | O |
| ATOM | 7214 | N | THR | B | 338 | 48.762 | 6.796 | −13.114 | 1.00 | 11.89 | B | N |
| ATOM | 7215 | CA | THR | B | 338 | 49.845 | 7.794 | −13.007 | 1.00 | 13.27 | B | C |
| ATOM | 7216 | CB | THR | B | 338 | 50.380 | 8.190 | −14.415 | 1.00 | 13.32 | B | C |
| ATOM | 7217 | OG1 | THR | B | 338 | 50.891 | 7.025 | −15.072 | 1.00 | 11.43 | B | O |
| ATOM | 7218 | CG2 | THR | B | 338 | 51.537 | 9.254 | −14.292 | 1.00 | 11.47 | B | C |
| ATOM | 7219 | C | THR | B | 338 | 49.354 | 9.039 | −12.245 | 1.00 | 11.70 | B | C |
| ATOM | 7220 | O | THR | B | 338 | 50.025 | 9.546 | −11.331 | 1.00 | 10.36 | B | O |
| ATOM | 7221 | N | ILE | B | 339 | 48.151 | 9.488 | −12.577 | 1.00 | 13.01 | B | N |
| ATOM | 7222 | CA | ILE | B | 339 | 47.617 | 10.696 | −11.960 | 1.00 | 14.00 | B | C |
| ATOM | 7223 | CB | ILE | B | 339 | 46.396 | 11.246 | −12.721 | 1.00 | 14.99 | B | C |
| ATOM | 7224 | CG1 | ILE | B | 339 | 46.747 | 11.682 | −14.146 | 1.00 | 18.07 | B | C |
| ATOM | 7225 | CD1 | ILE | B | 339 | 48.106 | 12.170 | −14.359 | 1.00 | 20.10 | B | C |
| ATOM | 7226 | CG2 | ILE | B | 339 | 45.768 | 12.404 | −11.959 | 1.00 | 14.32 | B | C |
| ATOM | 7227 | C | ILE | B | 339 | 47.242 | 10.398 | −10.485 | 1.00 | 13.46 | B | C |
| ATOM | 7228 | O | ILE | B | 339 | 47.538 | 11.205 | −9.621 | 1.00 | 11.31 | B | O |
| ATOM | 7229 | N | ASN | B | 340 | 46.644 | 9.230 | −10.215 | 1.00 | 13.92 | B | N |
| ATOM | 7230 | CA | ASN | B | 340 | 46.307 | 8.829 | −8.836 | 1.00 | 13.55 | B | C |
| ATOM | 7231 | CB | ASN | B | 340 | 45.468 | 7.553 | −8.764 | 1.00 | 12.74 | B | C |
| ATOM | 7232 | CG | ASN | B | 340 | 44.074 | 7.755 | −9.301 | 1.00 | 15.12 | B | C |
| ATOM | 7233 | OD1 | ASN | B | 340 | 43.648 | 8.889 | −9.555 | 1.00 | 13.91 | B | O |
| ATOM | 7234 | ND2 | ASN | B | 340 | 43.364 | 6.666 | −9.520 | 1.00 | 12.09 | B | N |
| ATOM | 7235 | C | ASN | B | 340 | 47.539 | 8.718 | −7.965 | 1.00 | 14.94 | B | C |
| ATOM | 7236 | O | ASN | B | 340 | 47.471 | 9.006 | −6.759 | 1.00 | 12.07 | B | O |
| ATOM | 7237 | N | GLU | B | 341 | 48.656 | 8.300 | −8.559 | 1.00 | 13.96 | B | N |
| ATOM | 7238 | CA | GLU | B | 341 | 49.949 | 8.274 | −7.847 | 1.00 | 12.04 | B | C |
| ATOM | 7239 | CB | GLU | B | 341 | 50.982 | 7.440 | −8.654 | 1.00 | 16.76 | B | C |
| ATOM | 7240 | CG | GLU | B | 341 | 52.351 | 7.360 | −8.012 | 1.00 | 27.37 | B | C |
| ATOM | 7241 | CD | GLU | B | 341 | 53.300 | 6.365 | −8.704 | 1.00 | 40.42 | B | C |
| ATOM | 7242 | OE1 | GLU | B | 341 | 53.521 | 6.477 | −9.939 | 1.00 | 50.64 | B | O |
| ATOM | 7243 | OE2 | GLU | B | 341 | 53.825 | 5.477 | −8.000 | 1.00 | 41.15 | B | O |
| ATOM | 7244 | C | GLU | B | 341 | 50.483 | 9.651 | −7.494 | 1.00 | 11.88 | B | C |
| ATOM | 7245 | O | GLU | B | 341 | 50.999 | 9.868 | −6.379 | 1.00 | 11.32 | B | O |
| ATOM | 7246 | N | ILE | B | 342 | 50.377 | 10.589 | −8.421 | 1.00 | 11.62 | B | N |
| ATOM | 7247 | CA | ILE | B | 342 | 50.815 | 11.964 | −8.141 | 1.00 | 13.66 | B | C |
| ATOM | 7248 | CB | ILE | B | 342 | 50.798 | 12.812 | −9.390 | 1.00 | 14.05 | B | C |
| ATOM | 7249 | CG1 | ILE | B | 342 | 51.936 | 12.339 | −10.318 | 1.00 | 14.25 | B | C |
| ATOM | 7250 | CD1 | ILE | B | 342 | 51.739 | 12.813 | −11.820 | 1.00 | 13.16 | B | C |
| ATOM | 7251 | CG2 | ILE | B | 342 | 50.943 | 14.326 | −9.035 | 1.00 | 13.52 | B | C |
| ATOM | 7252 | C | ILE | B | 342 | 49.927 | 12.546 | −7.060 | 1.00 | 12.69 | B | C |
| ATOM | 7253 | O | ILE | B | 342 | 50.446 | 13.164 | −6.143 | 1.00 | 12.41 | B | O |
| ATOM | 7254 | N | ALA | B | 343 | 48.612 | 12.272 | −7.119 | 1.00 | 13.09 | B | N |
| ATOM | 7255 | CA | ALA | B | 343 | 47.690 | 12.675 | −6.016 | 1.00 | 13.78 | B | C |
| ATOM | 7256 | CB | ALA | B | 343 | 46.251 | 12.353 | −6.322 | 1.00 | 10.48 | B | C |
| ATOM | 7257 | C | ALA | B | 343 | 48.088 | 12.082 | −4.680 | 1.00 | 14.93 | B | C |
| ATOM | 7258 | O | ALA | B | 343 | 48.080 | 12.776 | −3.639 | 1.00 | 12.57 | B | O |
| ATOM | 7259 | N | TYR | B | 344 | 48.450 | 10.802 | −4.685 | 1.00 | 13.63 | B | N |
| ATOM | 7260 | CA | TYR | B | 344 | 48.910 | 10.153 | −3.477 | 1.00 | 10.64 | B | C |
| ATOM | 7261 | CB | TYR | B | 344 | 49.202 | 8.632 | −3.662 | 1.00 | 9.56 | B | C |
| ATOM | 7262 | CG | TYR | B | 344 | 49.722 | 8.019 | −2.401 | 1.00 | 8.14 | B | C |
| ATOM | 7263 | CD1 | TYR | B | 344 | 48.845 | 7.584 | −1.425 | 1.00 | 8.38 | B | C |
| ATOM | 7264 | CE1 | TYR | B | 344 | 49.276 | 7.038 | −0.280 | 1.00 | 7.58 | B | C |
| ATOM | 7265 | CZ | TYR | B | 344 | 50.627 | 6.927 | −0.020 | 1.00 | 8.20 | B | C |
| ATOM | 7266 | OH | TYR | B | 344 | 50.992 | 6.367 | 1.189 | 1.00 | 8.47 | B | O |
| ATOM | 7267 | CE2 | TYR | B | 344 | 51.540 | 7.361 | −0.959 | 1.00 | 8.57 | B | C |
| ATOM | 7268 | CD2 | TYR | B | 344 | 51.078 | 7.891 | −2.157 | 1.00 | 7.92 | B | C |
| ATOM | 7269 | C | TYR | B | 344 | 50.148 | 10.855 | −2.903 | 1.00 | 11.53 | B | C |
| ATOM | 7270 | O | TYR | B | 344 | 50.207 | 11.110 | −1.717 | 1.00 | 8.74 | B | O |
| ATOM | 7271 | N | ASP | B | 345 | 51.118 | 11.169 | −3.744 | 1.00 | 12.70 | B | N |
| ATOM | 7272 | CA | ASP | B | 345 | 52.347 | 11.824 | −3.292 | 1.00 | 14.02 | B | C |

APPENDIX A-continued

*P. alba* 3T288C coordinates

| ATOM | 7273 | CB | ASP | B | 345 | 53.313 | 12.105 | −4.464 | 1.00 | 18.53 | B | C |
|---|---|---|---|---|---|---|---|---|---|---|---|---|
| ATOM | 7274 | CG | ASP | B | 345 | 53.945 | 10.831 | −5.042 | 1.00 | 27.30 | B | C |
| ATOM | 7275 | OD1 | ASP | B | 345 | 53.971 | 9.815 | −4.337 | 1.00 | 28.65 | B | O |
| ATOM | 7276 | OD2 | ASP | B | 345 | 54.395 | 10.863 | −6.211 | 1.00 | 40.96 | B | O |
| ATOM | 7277 | C | ASP | B | 345 | 52.011 | 13.157 | −2.607 | 1.00 | 15.72 | B | C |
| ATOM | 7278 | O | ASP | B | 345 | 52.598 | 13.497 | −1.579 | 1.00 | 13.12 | B | O |
| ATOM | 7279 | N | ASN | B | 346 | 51.055 | 13.878 | −3.173 | 1.00 | 16.72 | B | N |
| ATOM | 7280 | CA | ASN | B | 346 | 50.683 | 15.159 | −2.628 | 1.00 | 16.11 | B | C |
| ATOM | 7281 | CB | ASN | B | 346 | 49.923 | 15.942 | −3.654 | 1.00 | 17.94 | B | C |
| ATOM | 7282 | CG | ASN | B | 346 | 50.806 | 16.715 | −4.511 | 1.00 | 31.41 | B | C |
| ATOM | 7283 | OD1 | ASN | B | 346 | 51.179 | 17.863 | −4.162 | 1.00 | 25.07 | B | O |
| ATOM | 7284 | ND2 | ASN | B | 346 | 51.187 | 16.121 | −5.669 | 1.00 | 29.47 | B | N |
| ATOM | 7285 | C | ASN | B | 346 | 49.870 | 15.054 | −1.342 | 1.00 | 16.09 | B | C |
| ATOM | 7286 | O | ASN | B | 346 | 50.053 | 15.856 | −0.437 | 1.00 | 16.82 | B | O |
| ATOM | 7287 | N | LEU | B | 347 | 49.016 | 14.043 | −1.237 | 1.00 | 14.19 | B | N |
| ATOM | 7288 | CA | LEU | B | 347 | 48.279 | 13.810 | −0.010 | 1.00 | 15.35 | B | C |
| ATOM | 7289 | CB | LEU | B | 347 | 47.269 | 12.671 | −0.191 | 1.00 | 13.99 | B | C |
| ATOM | 7290 | CG | LEU | B | 347 | 46.433 | 12.274 | 1.017 | 1.00 | 14.99 | B | C |
| ATOM | 7291 | CD1 | LEU | B | 347 | 45.598 | 13.471 | 1.531 | 1.00 | 15.83 | B | C |
| ATOM | 7292 | CD2 | LEU | B | 347 | 45.561 | 11.037 | 0.756 | 1.00 | 14.36 | B | C |
| ATOM | 7293 | C | LEU | B | 347 | 49.271 | 13.518 | 1.099 | 1.00 | 17.90 | B | C |
| ATOM | 7294 | O | LEU | B | 347 | 49.217 | 14.116 | 2.208 | 1.00 | 14.50 | B | O |
| ATOM | 7295 | N | LYS | B | 348 | 50.214 | 12.636 | 0.795 | 1.00 | 15.21 | B | N |
| ATOM | 7296 | CA | LYS | B | 348 | 51.180 | 12.206 | 1.787 | 1.00 | 19.60 | B | C |
| ATOM | 7297 | CB | LYS | B | 348 | 52.069 | 11.083 | 1.225 | 1.00 | 20.15 | B | C |
| ATOM | 7298 | CG | LYS | B | 348 | 53.053 | 10.521 | 2.188 | 1.00 | 23.64 | B | C |
| ATOM | 7299 | CD | LYS | B | 348 | 53.725 | 9.259 | 1.636 | 1.00 | 28.85 | B | C |
| ATOM | 7300 | CE | LYS | B | 348 | 55.190 | 9.441 | 1.319 | 1.00 | 36.11 | B | C |
| ATOM | 7301 | NZ | LYS | B | 348 | 55.383 | 10.058 | 0.015 | 1.00 | 38.70 | B | N |
| ATOM | 7302 | C | LYS | B | 348 | 52.051 | 13.350 | 2.244 | 1.00 | 16.80 | B | C |
| ATOM | 7303 | O | LYS | B | 348 | 52.398 | 13.439 | 3.429 | 1.00 | 16.67 | B | O |
| ATOM | 7304 | N | ASP | B | 349 | 52.484 | 14.170 | 1.291 | 1.00 | 18.71 | B | N |
| ATOM | 7305 | CA | ASP | B | 349 | 53.558 | 15.121 | 1.555 | 1.00 | 20.44 | B | C |
| ATOM | 7306 | CB | ASP | B | 349 | 54.430 | 15.332 | 0.304 | 1.00 | 23.50 | B | C |
| ATOM | 7307 | CG | ASP | B | 349 | 55.315 | 14.111 | −0.042 | 1.00 | 32.24 | B | C |
| ATOM | 7308 | OD1 | ASP | B | 349 | 55.586 | 13.246 | 0.842 | 1.00 | 32.69 | B | O |
| ATOM | 7309 | OD2 | ASP | B | 349 | 55.722 | 14.020 | −1.223 | 1.00 | 43.22 | B | O |
| ATOM | 7310 | C | ASP | B | 349 | 53.005 | 16.479 | 2.011 | 1.00 | 23.89 | B | C |
| ATOM | 7311 | O | ASP | B | 349 | 53.632 | 17.161 | 2.793 | 1.00 | 22.40 | B | O |
| ATOM | 7312 | N | LYS | B | 350 | 51.842 | 16.861 | 1.511 | 1.00 | 21.29 | B | N |
| ATOM | 7313 | CA | LYS | B | 350 | 51.274 | 18.175 | 1.791 | 1.00 | 22.34 | B | C |
| ATOM | 7314 | CB | LYS | B | 350 | 51.010 | 18.888 | 0.479 | 1.00 | 27.25 | B | C |
| ATOM | 7315 | CG | LYS | B | 350 | 52.261 | 19.230 | −0.327 | 1.00 | 29.83 | B | C |
| ATOM | 7316 | CD | LYS | B | 350 | 51.788 | 19.978 | −1.562 | 1.00 | 45.65 | B | C |
| ATOM | 7317 | CE | LYS | B | 350 | 52.786 | 20.029 | −2.703 | 1.00 | 44.16 | B | C |
| ATOM | 7318 | NZ | LYS | B | 350 | 52.019 | 20.581 | −3.865 | 1.00 | 42.33 | B | N |
| ATOM | 7319 | C | LYS | B | 350 | 49.964 | 18.091 | 2.567 | 1.00 | 26.95 | B | C |
| ATOM | 7320 | O | LYS | B | 350 | 49.430 | 19.108 | 2.998 | 1.00 | 20.13 | B | O |
| ATOM | 7321 | N | GLY | B | 351 | 49.427 | 16.890 | 2.735 | 1.00 | 18.56 | B | N |
| ATOM | 7322 | CA | GLY | B | 351 | 48.193 | 16.717 | 3.487 | 1.00 | 19.14 | B | C |
| ATOM | 7323 | C | GLY | B | 351 | 46.946 | 17.172 | 2.759 | 1.00 | 18.66 | B | C |
| ATOM | 7324 | O | GLY | B | 351 | 45.922 | 17.388 | 3.386 | 1.00 | 21.25 | B | O |
| ATOM | 7325 | N | GLU | B | 352 | 47.017 | 17.307 | 1.438 | 1.00 | 17.28 | B | N |
| ATOM | 7326 | CA | GLU | B | 352 | 45.875 | 17.795 | 0.649 | 1.00 | 20.07 | B | C |
| ATOM | 7327 | CB | GLU | B | 352 | 46.277 | 19.103 | −0.050 | 1.00 | 25.44 | B | C |
| ATOM | 7328 | CG | GLU | B | 352 | 46.764 | 20.227 | 0.882 | 1.00 | 34.41 | B | C |
| ATOM | 7329 | CD | GLU | B | 352 | 45.648 | 21.027 | 1.532 | 1.00 | 40.95 | B | C |
| ATOM | 7330 | OE1 | GLU | B | 352 | 44.479 | 20.596 | 1.468 | 1.00 | 43.14 | B | O |
| ATOM | 7331 | OE2 | GLU | B | 352 | 45.957 | 22.097 | 2.119 | 1.00 | 53.99 | B | O |
| ATOM | 7332 | C | GLU | B | 352 | 45.491 | 16.839 | −0.452 | 1.00 | 17.35 | B | C |
| ATOM | 7333 | O | GLU | B | 352 | 46.371 | 16.306 | −1.119 | 1.00 | 15.99 | B | O |
| ATOM | 7334 | N | ASN | B | 353 | 44.198 | 16.692 | −0.693 | 1.00 | 20.08 | B | N |
| ATOM | 7335 | CA | ASN | B | 353 | 43.687 | 15.949 | −1.826 | 1.00 | 24.17 | B | C |
| ATOM | 7336 | CB | ASN | B | 353 | 42.344 | 15.291 | −1.505 | 1.00 | 24.41 | B | C |
| ATOM | 7337 | CG | ASN | B | 353 | 41.823 | 14.425 | −2.660 | 1.00 | 28.25 | B | C |
| ATOM | 7338 | OD1 | ASN | B | 353 | 42.443 | 14.351 | −3.726 | 1.00 | 19.89 | B | O |
| ATOM | 7339 | ND2 | ASN | B | 353 | 40.711 | 13.719 | −2.426 | 1.00 | 28.61 | B | N |
| ATOM | 7340 | C | ASN | B | 353 | 43.523 | 16.860 | −3.035 | 1.00 | 24.82 | B | C |
| ATOM | 7341 | O | ASN | B | 353 | 42.539 | 17.565 | −3.142 | 1.00 | 20.76 | B | O |
| ATOM | 7342 | N | ILE | B | 354 | 44.464 | 16.788 | −3.962 | 1.00 | 17.07 | B | N |
| ATOM | 7343 | CA | ILE | B | 354 | 44.447 | 17.612 | −5.161 | 1.00 | 16.52 | B | C |
| ATOM | 7344 | CB | ILE | B | 354 | 45.875 | 18.138 | −5.458 | 1.00 | 19.20 | B | C |
| ATOM | 7345 | CG1 | ILE | B | 354 | 46.813 | 16.975 | −5.801 | 1.00 | 20.65 | B | C |
| ATOM | 7346 | CD1 | ILE | B | 354 | 48.124 | 17.359 | −6.405 | 1.00 | 19.75 | B | C |
| ATOM | 7347 | CG2 | ILE | B | 354 | 46.394 | 18.954 | −4.308 | 1.00 | 20.17 | B | C |
| ATOM | 7348 | C | ILE | B | 354 | 43.878 | 16.873 | −6.406 | 1.00 | 14.87 | B | C |
| ATOM | 7349 | O | ILE | B | 354 | 43.858 | 17.419 | −7.510 | 1.00 | 14.28 | B | O |
| ATOM | 7350 | N | LEU | B | 355 | 43.395 | 15.655 | −6.233 | 1.00 | 14.49 | B | N |

APPENDIX A-continued

*P. alba* 3T288C coordinates

| ATOM | 7351 | CA | LEU | B | 355 | 42.992 | 14.814 | −7.380 | 1.00 | 16.72 | B | C |
|------|------|-----|-----|---|-----|--------|--------|---------|------|-------|---|---|
| ATOM | 7352 | CB | LEU | B | 355 | 42.503 | 13.437 | −6.905 | 1.00 | 16.17 | B | C |
| ATOM | 7353 | CG | LEU | B | 355 | 42.124 | 12.443 | −8.018 | 1.00 | 20.13 | B | C |
| ATOM | 7354 | CD1 | LEU | B | 355 | 43.327 | 12.200 | −8.933 | 1.00 | 16.30 | B | C |
| ATOM | 7355 | CD2 | LEU | B | 355 | 41.576 | 11.152 | −7.429 | 1.00 | 19.09 | B | C |
| ATOM | 7356 | C | LEU | B | 355 | 41.932 | 15.525 | −8.255 | 1.00 | 17.42 | B | C |
| ATOM | 7357 | O | LEU | B | 355 | 42.073 | 15.554 | −9.498 | 1.00 | 17.72 | B | O |
| ATOM | 7358 | N | PRO | B | 356 | 40.919 | 16.176 | −7.616 | 1.00 | 19.20 | B | N |
| ATOM | 7359 | CA | PRO | B | 356 | 39.907 | 16.857 | −8.447 | 1.00 | 20.49 | B | C |
| ATOM | 7360 | CB | PRO | B | 356 | 39.011 | 17.570 | −7.427 | 1.00 | 25.18 | B | C |
| ATOM | 7361 | CG | PRO | B | 356 | 39.195 | 16.766 | −6.140 | 1.00 | 22.46 | B | C |
| ATOM | 7362 | CD | PRO | B | 356 | 40.646 | 16.349 | −6.176 | 1.00 | 16.95 | B | C |
| ATOM | 7363 | C | PRO | B | 356 | 40.531 | 17.846 | −9.417 | 1.00 | 16.26 | B | C |
| ATOM | 7364 | O | PRO | B | 356 | 40.087 | 17.924 | −10.549 | 1.00 | 15.34 | B | O |
| ATOM | 7365 | N | TYR | B | 357 | 41.588 | 18.532 | −9.021 | 1.00 | 15.15 | B | N |
| ATOM | 7366 | CA | TYR | B | 357 | 42.214 | 19.540 | −9.920 | 1.00 | 18.77 | B | C |
| ATOM | 7367 | CB | TYR | B | 357 | 43.092 | 20.465 | −9.121 | 1.00 | 24.64 | B | C |
| ATOM | 7368 | CG | TYR | B | 357 | 42.401 | 20.969 | −7.856 | 1.00 | 25.80 | B | C |
| ATOM | 7369 | CD1 | TYR | B | 357 | 41.238 | 21.715 | −7.918 | 1.00 | 35.57 | B | C |
| ATOM | 7370 | CE1 | TYR | B | 357 | 40.594 | 22.159 | −6.749 | 1.00 | 34.51 | B | C |
| ATOM | 7371 | CZ | TYR | B | 357 | 41.141 | 21.848 | −5.528 | 1.00 | 34.02 | B | C |
| ATOM | 7372 | OH | TYR | B | 357 | 40.570 | 22.254 | −4.355 | 1.00 | 40.33 | B | O |
| ATOM | 7373 | CE2 | TYR | B | 357 | 42.290 | 21.112 | −5.458 | 1.00 | 30.39 | B | C |
| ATOM | 7374 | CD2 | TYR | B | 357 | 42.914 | 20.684 | −6.621 | 1.00 | 25.62 | B | C |
| ATOM | 7375 | C | TYR | B | 357 | 43.028 | 18.907 | −11.061 | 1.00 | 19.51 | B | C |
| ATOM | 7376 | O | TYR | B | 357 | 43.054 | 19.415 | −12.191 | 1.00 | 14.78 | B | O |
| ATOM | 7377 | N | LEU | B | 358 | 43.688 | 17.793 | −10.758 | 1.00 | 16.40 | B | N |
| ATOM | 7378 | CA | LEU | B | 358 | 44.472 | 17.065 | −11.759 | 1.00 | 14.91 | B | C |
| ATOM | 7379 | CB | LEU | B | 358 | 45.363 | 16.019 | −11.095 | 1.00 | 16.54 | B | C |
| ATOM | 7380 | CG | LEU | B | 358 | 46.329 | 16.457 | −9.988 | 1.00 | 18.96 | B | C |
| ATOM | 7381 | CD1 | LEU | B | 358 | 47.129 | 15.226 | −9.464 | 1.00 | 15.05 | B | C |
| ATOM | 7382 | CD2 | LEU | B | 358 | 47.237 | 17.613 | −10.471 | 1.00 | 17.94 | B | C |
| ATOM | 7383 | C | LEU | B | 358 | 43.563 | 16.413 | −12.781 | 1.00 | 12.49 | B | C |
| ATOM | 7384 | O | LEU | B | 358 | 43.850 | 16.409 | −13.985 | 1.00 | 14.97 | B | O |
| ATOM | 7385 | N | THR | B | 359 | 42.470 | 15.823 | −12.327 | 1.00 | 14.36 | B | N |
| ATOM | 7386 | CA | THR | B | 359 | 41.552 | 15.178 | −13.273 | 1.00 | 15.09 | B | C |
| ATOM | 7387 | CB | THR | B | 359 | 40.646 | 14.193 | −12.575 | 1.00 | 17.38 | B | C |
| ATOM | 7388 | OG1 | THR | B | 359 | 39.798 | 14.921 | −11.679 | 1.00 | 20.37 | B | O |
| ATOM | 7389 | CG2 | THR | B | 359 | 41.516 | 13.140 | −11.799 | 1.00 | 13.68 | B | C |
| ATOM | 7390 | C | THR | B | 359 | 40.754 | 16.185 | −14.129 | 1.00 | 16.20 | B | C |
| ATOM | 7391 | O | THR | B | 359 | 40.454 | 15.917 | −15.302 | 1.00 | 17.64 | B | O |
| ATOM | 7392 | N | LYS | B | 360 | 40.458 | 17.360 | −13.583 | 1.00 | 16.58 | B | N |
| ATOM | 7393 | CA | LYS | B | 360 | 39.785 | 18.406 | −14.375 | 1.00 | 15.55 | B | C |
| ATOM | 7394 | CB | LYS | B | 360 | 39.361 | 19.567 | −13.475 | 1.00 | 20.66 | B | C |
| ATOM | 7395 | CG | LYS | B | 360 | 38.529 | 20.692 | −14.207 | 1.00 | 25.93 | B | C |
| ATOM | 7396 | CD | LYS | B | 360 | 37.361 | 20.084 | −14.960 | 1.00 | 33.77 | B | C |
| ATOM | 7397 | CE | LYS | B | 360 | 36.242 | 21.101 | −15.274 | 1.00 | 45.52 | B | C |
| ATOM | 7398 | NZ | LYS | B | 360 | 36.763 | 22.220 | −16.100 | 1.00 | 38.16 | B | N |
| ATOM | 7399 | C | LYS | B | 360 | 40.699 | 18.905 | −15.461 | 1.00 | 14.49 | B | C |
| ATOM | 7400 | O | LYS | B | 360 | 40.254 | 19.149 | −16.573 | 1.00 | 17.23 | B | O |
| ATOM | 7401 | N | ALA | B | 361 | 41.979 | 19.061 | −15.161 | 1.00 | 13.46 | B | N |
| ATOM | 7402 | CA | ALA | B | 361 | 42.921 | 19.464 | −16.193 | 1.00 | 13.85 | B | C |
| ATOM | 7403 | CB | ALA | B | 361 | 44.341 | 19.705 | −15.653 | 1.00 | 12.78 | B | C |
| ATOM | 7404 | C | ALA | B | 361 | 42.949 | 18.475 | −17.308 | 1.00 | 13.54 | B | C |
| ATOM | 7405 | O | ALA | B | 361 | 42.932 | 18.866 | −18.470 | 1.00 | 16.50 | B | O |
| ATOM | 7406 | N | TRP | B | 362 | 42.995 | 17.190 | −16.991 | 1.00 | 13.97 | B | N |
| ATOM | 7407 | CA | TRP | B | 362 | 42.897 | 16.167 | −18.043 | 1.00 | 12.24 | B | C |
| ATOM | 7408 | CB | TRP | B | 362 | 43.208 | 14.737 | −17.493 | 1.00 | 13.20 | B | C |
| ATOM | 7409 | CG | TRP | B | 362 | 44.683 | 14.537 | −17.560 | 1.00 | 13.43 | B | C |
| ATOM | 7410 | CD1 | TRP | B | 362 | 45.605 | 14.660 | −16.550 | 1.00 | 13.75 | B | C |
| ATOM | 7411 | NE1 | TRP | B | 362 | 46.870 | 14.488 | −17.041 | 1.00 | 14.85 | B | N |
| ATOM | 7412 | CE2 | TRP | B | 362 | 46.844 | 14.249 | −18.354 | 1.00 | 14.41 | B | C |
| ATOM | 7413 | CD2 | TRP | B | 362 | 45.463 | 14.256 | −18.762 | 1.00 | 13.93 | B | C |
| ATOM | 7414 | CE3 | TRP | B | 362 | 45.151 | 14.037 | −20.090 | 1.00 | 16.46 | B | C |
| ATOM | 7415 | CZ3 | TRP | B | 362 | 46.186 | 13.803 | −20.982 | 1.00 | 16.27 | B | C |
| ATOM | 7416 | CH2 | TRP | B | 362 | 47.523 | 13.789 | −20.551 | 1.00 | 15.56 | B | C |
| ATOM | 7417 | CZ2 | TRP | B | 362 | 47.861 | 14.032 | −19.238 | 1.00 | 17.59 | B | C |
| ATOM | 7418 | C | TRP | B | 362 | 41.599 | 16.203 | −18.798 | 1.00 | 13.44 | B | C |
| ATOM | 7419 | O | TRP | B | 362 | 41.609 | 16.075 | −20.027 | 1.00 | 14.23 | B | O |
| ATOM | 7420 | N | ALA | B | 363 | 40.478 | 16.402 | −18.102 | 1.00 | 13.92 | B | N |
| ATOM | 7421 | CA | ALA | B | 363 | 39.158 | 16.453 | −18.789 | 1.00 | 14.98 | B | C |
| ATOM | 7422 | CB | ALA | B | 363 | 37.987 | 16.519 | −17.760 | 1.00 | 14.86 | B | C |
| ATOM | 7423 | C | ALA | B | 363 | 39.102 | 17.644 | −19.755 | 1.00 | 14.71 | B | C |
| ATOM | 7424 | O | ALA | B | 363 | 38.680 | 17.507 | −20.896 | 1.00 | 16.67 | B | O |
| ATOM | 7425 | N | ASP | B | 364 | 39.616 | 18.781 | −19.317 | 1.00 | 15.71 | B | N |
| ATOM | 7426 | CA | ASP | B | 364 | 39.727 | 19.985 | −20.160 | 1.00 | 18.73 | B | C |
| ATOM | 7427 | CB | ASP | B | 364 | 40.258 | 21.179 | −19.337 | 1.00 | 19.66 | B | C |
| ATOM | 7428 | CG | ASP | B | 364 | 39.270 | 21.699 | −18.300 | 1.00 | 23.82 | B | C |

APPENDIX A-continued

*P. alba* 3T288C coordinates

| ATOM | 7429 | OD1 | ASP | B | 364 | 38.093 | 21.286 | −18.300 | 1.00 | 26.70 | B | O |
|---|---|---|---|---|---|---|---|---|---|---|---|---|
| ATOM | 7430 | OD2 | ASP | B | 364 | 39.678 | 22.544 | −17.462 | 1.00 | 26.89 | B | O |
| ATOM | 7431 | C | ASP | B | 364 | 40.622 | 19.783 | −21.371 | 1.00 | 17.83 | B | C |
| ATOM | 7432 | O | ASP | B | 364 | 40.269 | 20.171 | −22.474 | 1.00 | 15.74 | B | O |
| ATOM | 7433 | N | LEU | B | 365 | 41.771 | 19.117 | −21.197 | 1.00 | 16.80 | B | N |
| ATOM | 7434 | CA | LEU | B | 365 | 42.614 | 18.812 | −22.342 | 1.00 | 15.51 | B | C |
| ATOM | 7435 | CB | LEU | B | 365 | 43.949 | 18.247 | −21.909 | 1.00 | 16.12 | B | C |
| ATOM | 7436 | CG | LEU | B | 365 | 44.923 | 17.884 | −23.016 | 1.00 | 16.24 | B | C |
| ATOM | 7437 | CD1 | LEU | B | 365 | 45.225 | 19.093 | −23.874 | 1.00 | 17.38 | B | C |
| ATOM | 7438 | CD2 | LEU | B | 365 | 46.195 | 17.331 | −22.400 | 1.00 | 16.63 | B | C |
| ATOM | 7439 | C | LEU | B | 365 | 41.939 | 17.856 | −23.329 | 1.00 | 16.21 | B | C |
| ATOM | 7440 | O | LEU | B | 365 | 41.941 | 18.110 | −24.529 | 1.00 | 14.92 | B | O |
| ATOM | 7441 | N | CYS | B | 366 | 41.383 | 16.738 | −22.842 | 1.00 | 15.29 | B | N |
| ATOM | 7442 | CA | CYS | B | 366 | 40.700 | 15.796 | −23.756 | 1.00 | 15.91 | B | C |
| ATOM | 7443 | CB | CYS | B | 366 | 40.216 | 14.541 | −23.025 | 1.00 | 17.87 | B | C |
| ATOM | 7444 | SG | CYS | B | 366 | 41.641 | 13.556 | −22.499 | 1.00 | 21.04 | B | S |
| ATOM | 7445 | C | CYS | B | 366 | 39.542 | 16.464 | −24.490 | 1.00 | 16.85 | B | C |
| ATOM | 7446 | O | CYS | B | 366 | 39.350 | 16.198 | −25.671 | 1.00 | 14.79 | B | O |
| ATOM | 7447 | N | ASN | B | 367 | 38.817 | 17.362 | −23.800 | 1.00 | 16.38 | B | N |
| ATOM | 7448 | CA | ASN | B | 367 | 37.761 | 18.157 | −24.457 | 1.00 | 16.79 | B | C |
| ATOM | 7449 | CB | ASN | B | 367 | 36.849 | 18.878 | −23.445 | 1.00 | 16.17 | B | C |
| ATOM | 7450 | CG | ASN | B | 367 | 35.713 | 17.976 | −22.965 | 1.00 | 23.08 | B | C |
| ATOM | 7451 | OD1 | ASN | B | 367 | 34.854 | 17.609 | −23.760 | 1.00 | 21.90 | B | O |
| ATOM | 7452 | ND2 | ASN | B | 367 | 35.738 | 17.563 | −21.705 | 1.00 | 21.53 | B | N |
| ATOM | 7453 | C | ASN | B | 367 | 38.281 | 19.095 | −25.545 | 1.00 | 17.97 | B | C |
| ATOM | 7454 | O | ASN | B | 367 | 37.636 | 19.231 | −26.580 | 1.00 | 16.45 | B | O |
| ATOM | 7455 | N | ALA | B | 368 | 39.457 | 19.688 | −25.352 | 1.00 | 18.77 | B | N |
| ATOM | 7456 | CA | ALA | B | 368 | 40.067 | 20.493 | −26.405 | 1.00 | 16.37 | B | C |
| ATOM | 7457 | CB | ALA | B | 368 | 41.212 | 21.352 | −25.878 | 1.00 | 13.38 | B | C |
| ATOM | 7458 | C | ALA | B | 368 | 40.513 | 19.603 | −27.576 | 1.00 | 16.09 | B | C |
| ATOM | 7459 | O | ALA | B | 368 | 40.299 | 19.951 | −28.736 | 1.00 | 13.68 | B | O |
| ATOM | 7460 | N | PHE | B | 369 | 41.105 | 18.445 | −27.303 | 1.00 | 14.01 | B | N |
| ATOM | 7461 | CA | PHE | B | 369 | 41.413 | 17.512 | −28.384 | 1.00 | 14.80 | B | C |
| ATOM | 7462 | CB | PHE | B | 369 | 42.087 | 16.242 | −27.875 | 1.00 | 15.59 | B | C |
| ATOM | 7463 | CG | PHE | B | 369 | 43.516 | 16.425 | −27.358 | 1.00 | 17.49 | B | C |
| ATOM | 7464 | CD1 | PHE | B | 369 | 44.361 | 17.399 | −27.860 | 1.00 | 18.60 | B | C |
| ATOM | 7465 | CE1 | PHE | B | 369 | 45.671 | 17.512 | −27.402 | 1.00 | 23.68 | B | C |
| ATOM | 7466 | CZ | PHE | B | 369 | 46.167 | 16.617 | −26.442 | 1.00 | 19.70 | B | C |
| ATOM | 7467 | CE2 | PHE | B | 369 | 45.347 | 15.633 | −25.954 | 1.00 | 18.87 | B | C |
| ATOM | 7468 | CD2 | PHE | B | 369 | 44.012 | 15.536 | −26.419 | 1.00 | 20.51 | B | C |
| ATOM | 7469 | C | PHE | B | 369 | 40.162 | 17.065 | −29.148 | 1.00 | 14.30 | B | C |
| ATOM | 7470 | O | PHE | B | 369 | 40.203 | 16.956 | −30.379 | 1.00 | 12.66 | B | O |
| ATOM | 7471 | N | LEU | B | 370 | 39.085 | 16.757 | −28.414 | 1.00 | 12.34 | B | N |
| ATOM | 7472 | CA | LEU | B | 370 | 37.833 | 16.326 | −29.048 | 1.00 | 14.00 | B | C |
| ATOM | 7473 | CB | LEU | B | 370 | 36.811 | 15.941 | −27.991 | 1.00 | 14.86 | B | C |
| ATOM | 7474 | CG | LEU | B | 370 | 35.478 | 15.350 | −28.436 | 1.00 | 16.58 | B | C |
| ATOM | 7475 | CD1 | LEU | B | 370 | 35.694 | 14.023 | −29.171 | 1.00 | 15.46 | B | C |
| ATOM | 7476 | CD2 | LEU | B | 370 | 34.467 | 15.214 | −27.237 | 1.00 | 14.12 | B | C |
| ATOM | 7477 | C | LEU | B | 370 | 37.265 | 17.409 | −29.973 | 1.00 | 14.60 | B | C |
| ATOM | 7478 | O | LEU | B | 370 | 36.800 | 17.127 | −31.074 | 1.00 | 13.28 | B | O |
| ATOM | 7479 | N | GLN | B | 371 | 37.296 | 18.664 | −29.515 | 1.00 | 14.38 | B | N |
| ATOM | 7480 | CA | GLN | B | 371 | 36.862 | 19.765 | −30.364 | 1.00 | 12.58 | B | C |
| ATOM | 7481 | CB | GLN | B | 371 | 36.935 | 21.136 | −29.624 | 1.00 | 13.91 | B | C |
| ATOM | 7482 | CG | GLN | B | 371 | 36.525 | 22.344 | −30.491 | 1.00 | 15.05 | B | C |
| ATOM | 7483 | CD | GLN | B | 371 | 35.083 | 22.250 | −30.923 | 1.00 | 21.08 | B | C |
| ATOM | 7484 | OE1 | GLN | B | 371 | 34.747 | 21.704 | −31.985 | 1.00 | 23.31 | B | O |
| ATOM | 7485 | NE2 | GLN | B | 371 | 34.228 | 22.663 | −30.062 | 1.00 | 15.07 | B | N |
| ATOM | 7486 | C | GLN | B | 371 | 37.659 | 19.793 | −31.661 | 1.00 | 12.40 | B | C |
| ATOM | 7487 | O | GLN | B | 371 | 37.072 | 19.961 | −32.712 | 1.00 | 16.60 | B | O |
| ATOM | 7488 | N | GLU | B | 372 | 38.977 | 19.620 | −31.619 | 1.00 | 12.63 | B | N |
| ATOM | 7489 | CA | GLU | B | 372 | 39.777 | 19.560 | −32.852 | 1.00 | 14.19 | B | C |
| ATOM | 7490 | CB | GLU | B | 372 | 41.297 | 19.436 | −32.553 | 1.00 | 15.96 | B | C |
| ATOM | 7491 | CG | GLU | B | 372 | 41.827 | 20.751 | −31.939 | 1.00 | 24.27 | B | C |
| ATOM | 7492 | CD | GLU | B | 372 | 43.324 | 20.791 | −31.593 | 1.00 | 29.35 | B | C |
| ATOM | 7493 | OE1 | GLU | B | 372 | 44.002 | 19.716 | −31.433 | 1.00 | 38.38 | B | O |
| ATOM | 7494 | OE2 | GLU | B | 372 | 43.808 | 21.931 | −31.418 | 1.00 | 32.54 | B | O |
| ATOM | 7495 | C | GLU | B | 372 | 39.373 | 18.416 | −33.787 | 1.00 | 14.37 | B | C |
| ATOM | 7496 | O | GLU | B | 372 | 39.254 | 18.619 | −35.001 | 1.00 | 12.45 | B | O |
| ATOM | 7497 | N | ALA | B | 373 | 39.171 | 17.235 | −33.203 | 1.00 | 15.48 | B | N |
| ATOM | 7498 | CA | ALA | B | 373 | 38.776 | 16.051 | −33.966 | 1.00 | 16.23 | B | C |
| ATOM | 7499 | CB | ALA | B | 373 | 38.745 | 14.825 | −33.070 | 1.00 | 15.65 | B | C |
| ATOM | 7500 | C | ALA | B | 373 | 37.422 | 16.287 | −34.616 | 1.00 | 16.98 | B | C |
| ATOM | 7501 | O | ALA | B | 373 | 37.219 | 15.908 | −35.767 | 1.00 | 13.16 | B | O |
| ATOM | 7502 | N | LYS | B | 374 | 36.502 | 16.946 | −33.906 | 1.00 | 14.90 | B | N |
| ATOM | 7503 | CA | LYS | B | 374 | 35.180 | 17.201 | −34.476 | 1.00 | 15.49 | B | C |
| ATOM | 7504 | CB | LYS | B | 374 | 34.195 | 17.686 | −33.435 | 1.00 | 18.32 | B | C |
| ATOM | 7505 | CG | LYS | B | 374 | 33.717 | 16.658 | −32.506 | 1.00 | 21.64 | B | C |
| ATOM | 7506 | CD | LYS | B | 374 | 32.830 | 17.267 | −31.416 | 1.00 | 32.78 | B | C |

APPENDIX A-continued

*P. alba* 3T288C coordinates

| ATOM | 7507 | CE  | LYS | B | 374 | 32.172 | 16.151 | −30.614 | 1.00 | 30.52 | B | C |
| ---- | ---- | --- | --- | - | --- | ------ | ------ | ------- | ---- | ----- | - | - |
| ATOM | 7508 | NZ  | LYS | B | 374 | 31.629 | 16.620 | −29.322 | 1.00 | 27.14 | B | N |
| ATOM | 7509 | C   | LYS | B | 374 | 35.254 | 18.204 | −35.604 | 1.00 | 16.34 | B | C |
| ATOM | 7510 | O   | LYS | B | 374 | 34.628 | 18.042 | −36.663 | 1.00 | 13.85 | B | O |
| ATOM | 7511 | N   | TRP | B | 375 | 36.001 | 19.278 | −35.401 | 1.00 | 14.40 | B | N |
| ATOM | 7512 | CA  | TRP | B | 375 | 36.148 | 20.242 | −36.484 | 1.00 | 14.42 | B | C |
| ATOM | 7513 | CB  | TRP | B | 375 | 37.068 | 21.370 | −36.043 | 1.00 | 12.63 | B | C |
| ATOM | 7514 | CG  | TRP | B | 375 | 36.412 | 22.448 | −35.167 | 1.00 | 11.41 | B | C |
| ATOM | 7515 | CD1 | TRP | B | 375 | 35.092 | 22.888 | −35.154 | 1.00 | 13.11 | B | C |
| ATOM | 7516 | NE1 | TRP | B | 375 | 34.950 | 23.935 | −34.256 | 1.00 | 12.24 | B | N |
| ATOM | 7517 | CE2 | TRP | B | 375 | 36.132 | 24.227 | −33.685 | 1.00 | 12.65 | B | C |
| ATOM | 7518 | CD2 | TRP | B | 375 | 37.116 | 23.330 | −34.238 | 1.00 | 11.48 | B | C |
| ATOM | 7519 | CE3 | TRP | B | 375 | 38.432 | 23.413 | −33.799 | 1.00 | 13.19 | B | C |
| ATOM | 7520 | CZ3 | TRP | B | 375 | 38.751 | 24.416 | −32.864 | 1.00 | 14.17 | B | C |
| ATOM | 7521 | CH2 | TRP | B | 375 | 37.772 | 25.253 | −32.354 | 1.00 | 14.32 | B | C |
| ATOM | 7522 | CZ2 | TRP | B | 375 | 36.463 | 25.181 | −32.739 | 1.00 | 14.31 | B | C |
| ATOM | 7523 | C   | TRP | B | 375 | 36.705 | 19.597 | −37.727 | 1.00 | 18.06 | B | C |
| ATOM | 7524 | O   | TRP | B | 375 | 36.269 | 19.888 | −38.837 | 1.00 | 14.97 | B | O |
| ATOM | 7525 | N   | LEU | B | 376 | 37.714 | 18.756 | −37.541 | 1.00 | 20.64 | B | N |
| ATOM | 7526 | CA  | LEU | B | 376 | 38.375 | 18.079 | −38.660 | 1.00 | 21.54 | B | C |
| ATOM | 7527 | CB  | LEU | B | 376 | 39.560 | 17.240 | −38.181 | 1.00 | 23.28 | B | C |
| ATOM | 7528 | CG  | LEU | B | 376 | 40.494 | 16.750 | −39.299 | 1.00 | 34.36 | B | C |
| ATOM | 7529 | CD1 | LEU | B | 376 | 41.152 | 17.935 | −40.050 | 1.00 | 35.82 | B | C |
| ATOM | 7530 | CD2 | LEU | B | 376 | 41.565 | 15.804 | −38.729 | 1.00 | 33.84 | B | C |
| ATOM | 7531 | C   | LEU | B | 376 | 37.379 | 17.181 | −39.386 | 1.00 | 19.90 | B | C |
| ATOM | 7532 | O   | LEU | B | 376 | 37.250 | 17.255 | −40.603 | 1.00 | 20.49 | B | O |
| ATOM | 7533 | N   | TYR | B | 377 | 36.639 | 16.402 | −38.623 | 1.00 | 20.22 | B | N |
| ATOM | 7534 | CA  | TYR | B | 377 | 35.662 | 15.486 | −39.189 | 1.00 | 23.40 | B | C |
| ATOM | 7535 | CB  | TYR | B | 377 | 35.028 | 14.624 | −38.095 | 1.00 | 22.36 | B | C |
| ATOM | 7536 | CG  | TYR | B | 377 | 33.973 | 13.666 | −38.628 | 1.00 | 23.93 | B | C |
| ATOM | 7537 | CD1 | TYR | B | 377 | 34.339 | 12.418 | −39.158 | 1.00 | 30.84 | B | C |
| ATOM | 7538 | CE1 | TYR | B | 377 | 33.379 | 11.541 | −39.666 | 1.00 | 35.98 | B | C |
| ATOM | 7539 | CZ  | TYR | B | 377 | 32.038 | 11.900 | −39.640 | 1.00 | 38.89 | B | C |
| ATOM | 7540 | OH  | TYR | B | 377 | 31.092 | 11.026 | −40.129 | 1.00 | 48.41 | B | O |
| ATOM | 7541 | CE2 | TYR | B | 377 | 31.643 | 13.121 | −39.118 | 1.00 | 31.81 | B | C |
| ATOM | 7542 | CD2 | TYR | B | 377 | 32.615 | 13.999 | −38.611 | 1.00 | 31.71 | B | C |
| ATOM | 7543 | C   | TYR | B | 377 | 34.551 | 16.219 | −39.943 | 1.00 | 28.67 | B | C |
| ATOM | 7544 | O   | TYR | B | 377 | 34.164 | 15.812 | −41.028 | 1.00 | 20.24 | B | O |
| ATOM | 7545 | N   | ASN | B | 378 | 34.026 | 17.290 | −39.358 | 1.00 | 21.29 | B | N |
| ATOM | 7546 | CA  | ASN | B | 378 | 32.915 | 18.021 | −39.969 | 1.00 | 20.45 | B | C |
| ATOM | 7547 | CB  | ASN | B | 378 | 32.084 | 18.701 | −38.907 | 1.00 | 25.71 | B | C |
| ATOM | 7548 | CG  | ASN | B | 378 | 31.390 | 17.736 | −38.033 | 1.00 | 27.08 | B | C |
| ATOM | 7549 | OD1 | ASN | B | 378 | 30.769 | 16.819 | −38.512 | 1.00 | 29.20 | B | O |
| ATOM | 7550 | ND2 | ASN | B | 378 | 31.467 | 17.941 | −36.740 | 1.00 | 26.32 | B | N |
| ATOM | 7551 | C   | ASN | B | 378 | 33.373 | 19.026 | −41.002 | 1.00 | 18.69 | B | C |
| ATOM | 7552 | O   | ASN | B | 378 | 32.564 | 19.718 | −41.587 | 1.00 | 22.16 | B | O |
| ATOM | 7553 | N   | LYS | B | 379 | 34.669 | 19.103 | −41.244 | 1.00 | 17.02 | B | N |
| ATOM | 7554 | CA  | LYS | B | 379 | 35.215 | 20.060 | −42.185 | 1.00 | 24.24 | B | C |
| ATOM | 7555 | CB  | LYS | B | 379 | 34.732 | 19.735 | −43.601 | 1.00 | 27.41 | B | C |
| ATOM | 7556 | CG  | LYS | B | 379 | 35.424 | 18.460 | −44.172 | 1.00 | 39.50 | B | C |
| ATOM | 7557 | CD  | LYS | B | 379 | 34.587 | 17.811 | −45.284 | 1.00 | 48.10 | B | C |
| ATOM | 7558 | CE  | LYS | B | 379 | 35.455 | 17.117 | −46.317 | 1.00 | 62.70 | B | C |
| ATOM | 7559 | NZ  | LYS | B | 379 | 36.439 | 16.191 | −45.693 | 1.00 | 70.83 | B | N |
| ATOM | 7560 | C   | LYS | B | 379 | 34.897 | 21.515 | −41.780 | 1.00 | 21.35 | B | C |
| ATOM | 7561 | O   | LYS | B | 379 | 34.567 | 22.351 | −42.612 | 1.00 | 21.06 | B | O |
| ATOM | 7562 | N   | SER | B | 380 | 34.986 | 21.795 | −40.489 | 1.00 | 18.96 | B | N |
| ATOM | 7563 | CA  | SER | B | 380 | 34.621 | 23.098 | −39.988 | 1.00 | 20.28 | B | C |
| ATOM | 7564 | CB  | SER | B | 380 | 34.452 | 23.048 | −38.487 | 1.00 | 22.63 | B | C |
| ATOM | 7565 | OG  | SER | B | 380 | 33.428 | 22.172 | −38.167 | 1.00 | 17.13 | B | O |
| ATOM | 7566 | C   | SER | B | 380 | 35.694 | 24.078 | −40.322 | 1.00 | 19.57 | B | C |
| ATOM | 7567 | O   | SER | B | 380 | 36.837 | 23.715 | −40.449 | 1.00 | 17.94 | B | O |
| ATOM | 7568 | N   | THR | B | 381 | 35.344 | 25.357 | −40.390 | 1.00 | 19.95 | B | N |
| ATOM | 7569 | CA  | THR | B | 381 | 36.314 | 26.389 | −40.691 | 1.00 | 14.29 | B | C |
| ATOM | 7570 | CB  | THR | B | 381 | 35.996 | 26.981 | −42.067 | 1.00 | 14.00 | B | C |
| ATOM | 7571 | OG1 | THR | B | 381 | 34.621 | 27.374 | −42.061 | 1.00 | 17.82 | B | O |
| ATOM | 7572 | CG2 | THR | B | 381 | 36.214 | 25.883 | −43.219 | 1.00 | 20.33 | B | C |
| ATOM | 7573 | C   | THR | B | 381 | 36.179 | 27.510 | −39.624 | 1.00 | 17.48 | B | C |
| ATOM | 7574 | O   | THR | B | 381 | 35.743 | 28.602 | −39.943 | 1.00 | 14.56 | B | O |
| ATOM | 7575 | N   | PRO | B | 382 | 36.518 | 27.225 | −38.365 | 1.00 | 14.21 | B | N |
| ATOM | 7576 | CA  | PRO | B | 382 | 36.366 | 28.257 | −37.335 | 1.00 | 16.47 | B | C |
| ATOM | 7577 | CB  | PRO | B | 382 | 36.777 | 27.532 | −36.051 | 1.00 | 15.71 | B | C |
| ATOM | 7578 | CG  | PRO | B | 382 | 37.580 | 26.381 | −36.501 | 1.00 | 16.62 | B | C |
| ATOM | 7579 | CD  | PRO | B | 382 | 37.117 | 25.993 | −37.834 | 1.00 | 15.97 | B | C |
| ATOM | 7580 | C   | PRO | B | 382 | 37.233 | 29.492 | −37.524 | 1.00 | 14.79 | B | C |
| ATOM | 7581 | O   | PRO | B | 382 | 38.319 | 29.419 | −38.086 | 1.00 | 14.02 | B | O |
| ATOM | 7582 | N   | THR | B | 383 | 36.786 | 30.616 | −36.968 | 1.00 | 12.94 | B | N |
| ATOM | 7583 | CA  | THR | B | 383 | 37.565 | 31.826 | −36.989 | 1.00 | 11.18 | B | C |
| ATOM | 7584 | CB  | THR | B | 383 | 36.805 | 33.013 | −36.303 | 1.00 | 10.38 | B | C |

APPENDIX A-continued

*P. alba* 3T288C coordinates

| ATOM | 7585 | OG1 | THR | B | 383 | 36.684 | 32.722 | −34.903 | 1.00 | 10.91 | B | O |
|------|------|-----|-----|---|-----|--------|--------|---------|------|-------|---|---|
| ATOM | 7586 | CG2 | THR | B | 383 | 35.411 | 33.234 | −36.931 | 1.00 | 8.96 | B | C |
| ATOM | 7587 | C | THR | B | 383 | 38.852 | 31.604 | −36.256 | 1.00 | 12.11 | B | C |
| ATOM | 7588 | O | THR | B | 383 | 38.966 | 30.692 | −35.402 | 1.00 | 10.33 | B | O |
| ATOM | 7589 | N | PHE | B | 384 | 39.817 | 32.490 | −36.500 | 1.00 | 10.85 | B | N |
| ATOM | 7590 | CA | PHE | B | 384 | 41.054 | 32.439 | −35.731 | 1.00 | 11.66 | B | C |
| ATOM | 7591 | CB | PHE | B | 384 | 42.020 | 33.553 | −36.132 | 1.00 | 12.97 | B | C |
| ATOM | 7592 | CG | PHE | B | 384 | 43.236 | 33.622 | −35.252 | 1.00 | 11.75 | B | C |
| ATOM | 7593 | CD1 | PHE | B | 384 | 44.344 | 32.803 | −35.508 | 1.00 | 12.41 | B | C |
| ATOM | 7594 | CE1 | PHE | B | 384 | 45.424 | 32.806 | −34.679 | 1.00 | 13.91 | B | C |
| ATOM | 7595 | CZ | PHE | B | 384 | 45.456 | 33.656 | −33.552 | 1.00 | 13.96 | B | C |
| ATOM | 7596 | CE2 | PHE | B | 384 | 44.372 | 34.464 | −33.291 | 1.00 | 13.02 | B | C |
| ATOM | 7597 | CD2 | PHE | B | 384 | 43.264 | 34.449 | −34.159 | 1.00 | 12.10 | B | C |
| ATOM | 7598 | C | PHE | B | 384 | 40.811 | 32.476 | −34.213 | 1.00 | 13.50 | B | C |
| ATOM | 7599 | O | PHE | B | 384 | 41.417 | 31.689 | −33.464 | 1.00 | 11.60 | B | O |
| ATOM | 7600 | N | ASP | B | 385 | 39.985 | 33.410 | −33.735 | 1.00 | 11.08 | B | N |
| ATOM | 7601 | CA | ASP | B | 385 | 39.685 | 33.468 | −32.292 | 1.00 | 11.99 | B | C |
| ATOM | 7602 | CB | ASP | B | 385 | 38.682 | 34.576 | −31.961 | 1.00 | 13.98 | B | C |
| ATOM | 7603 | CG | ASP | B | 385 | 39.316 | 35.984 | −32.088 | 1.00 | 16.22 | B | C |
| ATOM | 7604 | OD1 | ASP | B | 385 | 40.548 | 36.066 | −32.040 | 1.00 | 17.51 | B | O |
| ATOM | 7605 | OD2 | ASP | B | 385 | 38.610 | 36.967 | −32.290 | 1.00 | 16.80 | B | O |
| ATOM | 7606 | C | ASP | B | 385 | 39.151 | 32.169 | −31.722 | 1.00 | 10.77 | B | C |
| ATOM | 7607 | O | ASP | B | 385 | 39.547 | 31.776 | −30.631 | 1.00 | 11.38 | B | O |
| ATOM | 7608 | N | ASP | B | 386 | 38.210 | 31.545 | −32.396 | 1.00 | 11.91 | B | N |
| ATOM | 7609 | CA | ASP | B | 386 | 37.682 | 30.240 | −31.921 | 1.00 | 12.63 | B | C |
| ATOM | 7610 | CB | ASP | B | 386 | 36.481 | 29.824 | −32.750 | 1.00 | 14.45 | B | C |
| ATOM | 7611 | CG | ASP | B | 386 | 35.210 | 30.550 | −32.337 | 1.00 | 25.95 | B | C |
| ATOM | 7612 | OD1 | ASP | B | 386 | 35.272 | 31.290 | −31.342 | 1.00 | 26.16 | B | O |
| ATOM | 7613 | OD2 | ASP | B | 386 | 34.173 | 30.382 | −33.014 | 1.00 | 26.70 | B | O |
| ATOM | 7614 | C | ASP | B | 386 | 38.722 | 29.134 | −31.997 | 1.00 | 13.21 | B | C |
| ATOM | 7615 | O | ASP | B | 386 | 38.902 | 28.343 | −31.042 | 1.00 | 14.69 | B | O |
| ATOM | 7616 | N | TYR | B | 387 | 39.412 | 29.058 | −33.132 | 1.00 | 12.07 | B | N |
| ATOM | 7617 | CA | TYR | B | 387 | 40.425 | 27.998 | −33.316 | 1.00 | 12.49 | B | C |
| ATOM | 7618 | CB | TYR | B | 387 | 41.030 | 28.016 | −34.718 | 1.00 | 16.80 | B | C |
| ATOM | 7619 | CG | TYR | B | 387 | 42.023 | 26.899 | −34.880 | 1.00 | 20.99 | B | C |
| ATOM | 7620 | CD1 | TYR | B | 387 | 41.564 | 25.606 | −35.143 | 1.00 | 23.33 | B | C |
| ATOM | 7621 | CE1 | TYR | B | 387 | 42.427 | 24.550 | −35.298 | 1.00 | 28.23 | B | C |
| ATOM | 7622 | CZ | TYR | B | 387 | 43.781 | 24.757 | −35.146 | 1.00 | 27.53 | B | C |
| ATOM | 7623 | OH | TYR | B | 387 | 44.588 | 23.648 | −35.278 | 1.00 | 30.12 | B | O |
| ATOM | 7624 | CE2 | TYR | B | 387 | 44.288 | 26.017 | −34.851 | 1.00 | 22.49 | B | C |
| ATOM | 7625 | CD2 | TYR | B | 387 | 43.382 | 27.103 | −34.720 | 1.00 | 22.96 | B | C |
| ATOM | 7626 | C | TYR | B | 387 | 41.540 | 28.122 | −32.305 | 1.00 | 14.93 | B | C |
| ATOM | 7627 | O | TYR | B | 387 | 41.889 | 27.138 | −31.572 | 1.00 | 12.65 | B | O |
| ATOM | 7628 | N | PHE | B | 388 | 42.079 | 29.332 | −32.216 | 1.00 | 14.05 | B | N |
| ATOM | 7629 | CA | PHE | B | 388 | 43.221 | 29.590 | −31.324 | 1.00 | 12.82 | B | C |
| ATOM | 7630 | CB | PHE | B | 388 | 43.815 | 31.007 | −31.576 | 1.00 | 14.30 | B | C |
| ATOM | 7631 | CG | PHE | B | 388 | 45.008 | 31.331 | −30.729 | 1.00 | 12.87 | B | C |
| ATOM | 7632 | CD1 | PHE | B | 388 | 46.168 | 30.597 | −30.846 | 1.00 | 15.58 | B | C |
| ATOM | 7633 | CE1 | PHE | B | 388 | 47.275 | 30.848 | −30.003 | 1.00 | 18.48 | B | C |
| ATOM | 7634 | CZ | PHE | B | 388 | 47.233 | 31.905 | −29.073 | 1.00 | 15.76 | B | C |
| ATOM | 7635 | CE2 | PHE | B | 388 | 46.056 | 32.630 | −28.933 | 1.00 | 19.27 | B | C |
| ATOM | 7636 | CD2 | PHE | B | 388 | 44.954 | 32.352 | −29.774 | 1.00 | 17.96 | B | C |
| ATOM | 7637 | C | PHE | B | 388 | 42.787 | 29.430 | −29.870 | 1.00 | 12.87 | B | C |
| ATOM | 7638 | O | PHE | B | 388 | 43.571 | 28.959 | −29.055 | 1.00 | 14.74 | B | O |
| ATOM | 7639 | N | GLY | B | 389 | 41.589 | 29.903 | −29.525 | 1.00 | 15.26 | B | N |
| ATOM | 7640 | CA | GLY | B | 389 | 41.008 | 29.764 | −28.133 | 1.00 | 14.49 | B | C |
| ATOM | 7641 | C | GLY | B | 389 | 41.056 | 28.311 | −27.654 | 1.00 | 14.82 | B | C |
| ATOM | 7642 | O | GLY | B | 389 | 41.467 | 28.020 | −26.530 | 1.00 | 18.64 | B | O |
| ATOM | 7643 | N | ASN | B | 390 | 40.697 | 27.379 | −28.541 | 1.00 | 17.04 | B | N |
| ATOM | 7644 | CA | ASN | B | 390 | 40.862 | 25.959 | −28.269 | 1.00 | 13.61 | B | C |
| ATOM | 7645 | CB | ASN | B | 390 | 39.942 | 25.148 | −29.207 | 1.00 | 15.14 | B | C |
| ATOM | 7646 | CG | ASN | B | 390 | 39.832 | 23.706 | −28.801 | 1.00 | 14.66 | B | C |
| ATOM | 7647 | OD1 | ASN | B | 390 | 39.156 | 23.393 | −27.874 | 1.00 | 14.99 | B | O |
| ATOM | 7648 | ND2 | ASN | B | 390 | 40.470 | 22.825 | −29.523 | 1.00 | 11.39 | B | N |
| ATOM | 7649 | C | ASN | B | 390 | 42.333 | 25.450 | −28.372 | 1.00 | 15.73 | B | C |
| ATOM | 7650 | O | ASN | B | 390 | 42.754 | 24.625 | −27.566 | 1.00 | 13.70 | B | O |
| ATOM | 7651 | N | ALA | B | 391 | 43.093 | 25.932 | −29.361 | 1.00 | 14.07 | B | N |
| ATOM | 7652 | CA | ALA | B | 391 | 44.421 | 25.428 | −29.637 | 1.00 | 14.55 | B | C |
| ATOM | 7653 | CB | ALA | B | 391 | 44.909 | 25.965 | −31.011 | 1.00 | 12.31 | B | C |
| ATOM | 7654 | C | ALA | B | 391 | 45.432 | 25.719 | −28.528 | 1.00 | 17.05 | B | C |
| ATOM | 7655 | O | ALA | B | 391 | 46.364 | 24.922 | −28.297 | 1.00 | 14.56 | B | O |
| ATOM | 7656 | N | TRP | B | 392 | 45.317 | 26.860 | −27.841 | 1.00 | 14.34 | B | N |
| ATOM | 7657 | CA | TRP | B | 392 | 46.234 | 27.067 | −26.731 | 1.00 | 16.32 | B | C |
| ATOM | 7658 | CB | TRP | B | 392 | 46.401 | 28.542 | −26.313 | 1.00 | 16.63 | B | C |
| ATOM | 7659 | CG | TRP | B | 392 | 45.226 | 29.273 | −25.710 | 1.00 | 14.95 | B | C |
| ATOM | 7660 | CD1 | TRP | B | 392 | 44.435 | 30.228 | −26.314 | 1.00 | 14.59 | B | C |
| ATOM | 7661 | NE1 | TRP | B | 392 | 43.499 | 30.687 | −25.468 | 1.00 | 16.87 | B | N |
| ATOM | 7662 | CE2 | TRP | B | 392 | 43.655 | 30.167 | −24.259 | 1.00 | 19.26 | B | C |

APPENDIX A-continued

*P. alba* 3T288C coordinates

| ATOM | 7663 | CD2 | TRP | B | 392 | 44.745 | 29.204 | −24.349 | 1.00 | 13.74 | B | C |
|---|---|---|---|---|---|---|---|---|---|---|---|---|
| ATOM | 7664 | CE3 | TRP | B | 392 | 45.123 | 28.505 | −23.221 | 1.00 | 16.86 | B | C |
| ATOM | 7665 | CZ3 | TRP | B | 392 | 44.399 | 28.704 | −22.048 | 1.00 | 19.49 | B | C |
| ATOM | 7666 | CH2 | TRP | B | 392 | 43.324 | 29.607 | −21.992 | 1.00 | 21.16 | B | C |
| ATOM | 7667 | CZ2 | TRP | B | 392 | 42.933 | 30.360 | −23.096 | 1.00 | 20.28 | B | C |
| ATOM | 7668 | C | TRP | B | 392 | 45.969 | 26.147 | −25.577 | 1.00 | 16.74 | B | C |
| ATOM | 7669 | O | TRP | B | 392 | 46.896 | 25.820 | −24.849 | 1.00 | 16.66 | B | O |
| ATOM | 7670 | N | LYS | B | 393 | 44.732 | 25.697 | −25.403 | 1.00 | 13.97 | B | N |
| ATOM | 7671 | CA | ALYS | B | 393 | 44.432 | 24.701 | −24.391 | 0.50 | 16.29 | B | C |
| ATOM | 7672 | CA | BLYS | B | 393 | 44.409 | 24.679 | −24.402 | 0.50 | 16.84 | B | C |
| ATOM | 7673 | CB | ALYS | B | 393 | 42.925 | 24.689 | −24.066 | 0.50 | 17.23 | B | C |
| ATOM | 7674 | CB | BLYS | B | 393 | 42.892 | 24.547 | −24.178 | 0.50 | 18.43 | B | C |
| ATOM | 7675 | CG | ALYS | B | 393 | 42.407 | 26.061 | −23.590 | 0.50 | 19.87 | B | C |
| ATOM | 7676 | CG | BLYS | B | 393 | 42.227 | 25.745 | −23.524 | 0.50 | 22.26 | B | C |
| ATOM | 7677 | CD | ALYS | B | 393 | 40.926 | 26.081 | −23.145 | 0.50 | 19.59 | B | C |
| ATOM | 7678 | CD | BLYS | B | 393 | 40.698 | 25.675 | −23.664 | 0.50 | 22.54 | B | C |
| ATOM | 7679 | CE | ALYS | B | 393 | 40.439 | 27.520 | −22.818 | 0.50 | 24.24 | B | C |
| ATOM | 7680 | CE | BLYS | B | 393 | 40.020 | 26.968 | −23.255 | 0.50 | 30.19 | B | C |
| ATOM | 7681 | NZ | ALYS | B | 393 | 40.026 | 28.379 | −24.047 | 0.50 | 26.04 | B | N |
| ATOM | 7682 | NZ | BLYS | B | 393 | 39.565 | 27.013 | −21.834 | 0.50 | 26.38 | B | N |
| ATOM | 7683 | C | LYS | B | 393 | 44.927 | 23.309 | −24.837 | 1.00 | 16.19 | B | C |
| ATOM | 7684 | O | LYS | B | 393 | 45.524 | 22.588 | −24.050 | 1.00 | 17.75 | B | O |
| ATOM | 7685 | N | SER | B | 394 | 44.690 | 22.967 | −26.097 | 1.00 | 14.65 | B | N |
| ATOM | 7686 | CA | SER | B | 394 | 45.108 | 21.697 | −26.664 | 1.00 | 16.05 | B | C |
| ATOM | 7687 | CB | SER | B | 394 | 44.487 | 21.443 | −28.053 | 1.00 | 15.63 | B | C |
| ATOM | 7688 | OG | SER | B | 394 | 45.175 | 22.134 | −29.095 | 1.00 | 16.43 | B | O |
| ATOM | 7689 | C | SER | B | 394 | 46.603 | 21.561 | −26.781 | 1.00 | 16.75 | B | C |
| ATOM | 7690 | O | SER | B | 394 | 47.069 | 20.463 | −26.981 | 1.00 | 14.84 | B | O |
| ATOM | 7691 | N | SER | B | 395 | 47.351 | 22.660 | −26.683 | 1.00 | 17.02 | B | N |
| ATOM | 7692 | CA | SER | B | 395 | 48.819 | 22.574 | −26.593 | 1.00 | 17.94 | B | C |
| ATOM | 7693 | CB | SER | B | 395 | 49.437 | 23.941 | −26.370 | 1.00 | 17.30 | B | C |
| ATOM | 7694 | OG | SER | B | 395 | 49.134 | 24.510 | −25.088 | 1.00 | 13.55 | B | O |
| ATOM | 7695 | C | SER | B | 395 | 49.291 | 21.677 | −25.431 | 1.00 | 15.76 | B | C |
| ATOM | 7696 | O | SER | B | 395 | 50.376 | 21.123 | −25.489 | 1.00 | 16.76 | B | O |
| ATOM | 7697 | N | SER | B | 396 | 48.489 | 21.642 | −24.373 | 1.00 | 13.76 | B | N |
| ATOM | 7698 | CA | SER | B | 396 | 48.762 | 21.022 | −23.076 | 1.00 | 17.04 | B | C |
| ATOM | 7699 | CB | SER | B | 396 | 49.445 | 19.653 | −23.161 | 1.00 | 17.48 | B | C |
| ATOM | 7700 | OG | SER | B | 396 | 50.853 | 19.741 | −23.382 | 1.00 | 15.38 | B | O |
| ATOM | 7701 | C | SER | B | 396 | 49.534 | 21.961 | −22.140 | 1.00 | 17.50 | B | C |
| ATOM | 7702 | O | SER | B | 396 | 49.784 | 21.614 | −21.002 | 1.00 | 16.88 | B | O |
| ATOM | 7703 | N | GLY | B | 397 | 49.874 | 23.171 | −22.606 | 1.00 | 16.26 | B | N |
| ATOM | 7704 | CA | GLY | B | 397 | 50.504 | 24.184 | −21.738 | 1.00 | 14.34 | B | C |
| ATOM | 7705 | C | GLY | B | 397 | 49.824 | 24.358 | −20.397 | 1.00 | 15.51 | B | C |
| ATOM | 7706 | O | GLY | B | 397 | 50.472 | 24.259 | −19.348 | 1.00 | 16.30 | B | O |
| ATOM | 7707 | N | PRO | B | 398 | 48.508 | 24.565 | −20.401 | 1.00 | 14.57 | B | N |
| ATOM | 7708 | CA | PRO | B | 398 | 47.852 | 24.807 | −19.120 | 1.00 | 17.72 | B | C |
| ATOM | 7709 | CB | PRO | B | 398 | 46.417 | 25.177 | −19.517 | 1.00 | 18.32 | B | C |
| ATOM | 7710 | CG | PRO | B | 398 | 46.618 | 25.755 | −20.932 | 1.00 | 17.69 | B | C |
| ATOM | 7711 | CD | PRO | B | 398 | 47.646 | 24.918 | −21.540 | 1.00 | 18.38 | B | C |
| ATOM | 7712 | C | PRO | B | 398 | 47.893 | 23.595 | −18.210 | 1.00 | 16.14 | B | C |
| ATOM | 7713 | O | PRO | B | 398 | 48.128 | 23.739 | −17.006 | 1.00 | 19.03 | B | O |
| ATOM | 7714 | N | LEU | B | 399 | 47.734 | 22.406 | −18.786 | 1.00 | 17.00 | B | N |
| ATOM | 7715 | CA | LEU | B | 399 | 47.787 | 21.185 | −17.997 | 1.00 | 16.02 | B | C |
| ATOM | 7716 | CB | LEU | B | 399 | 47.384 | 19.950 | −18.846 | 1.00 | 14.75 | B | C |
| ATOM | 7717 | CG | LEU | B | 399 | 47.440 | 18.620 | −18.074 | 1.00 | 15.21 | B | C |
| ATOM | 7718 | CD1 | LEU | B | 399 | 46.325 | 17.703 | −18.504 | 1.00 | 15.91 | B | C |
| ATOM | 7719 | CD2 | LEU | B | 399 | 48.798 | 17.906 | −18.311 | 1.00 | 14.96 | B | C |
| ATOM | 7720 | C | LEU | B | 399 | 49.187 | 21.015 | −17.402 | 1.00 | 17.23 | B | C |
| ATOM | 7721 | O | LEU | B | 399 | 49.334 | 20.686 | −16.233 | 1.00 | 15.66 | B | O |
| ATOM | 7722 | N | GLN | B | 400 | 50.222 | 21.227 | −18.204 | 1.00 | 14.25 | B | N |
| ATOM | 7723 | CA | GLN | B | 400 | 51.571 | 21.062 | −17.692 | 1.00 | 16.46 | B | C |
| ATOM | 7724 | CB | GLN | B | 400 | 52.571 | 21.338 | −18.804 | 1.00 | 17.14 | B | C |
| ATOM | 7725 | CG | GLN | B | 400 | 52.574 | 20.251 | −19.891 | 1.00 | 22.36 | B | C |
| ATOM | 7726 | CD | GLN | B | 400 | 53.679 | 20.470 | −20.915 | 1.00 | 23.80 | B | C |
| ATOM | 7727 | OE1 | GLN | B | 400 | 54.753 | 20.953 | −20.570 | 1.00 | 26.17 | B | O |
| ATOM | 7728 | NE2 | GLN | B | 400 | 53.403 | 20.144 | −22.200 | 1.00 | 21.26 | B | N |
| ATOM | 7729 | C | GLN | B | 400 | 51.831 | 21.996 | −16.505 | 1.00 | 16.03 | B | C |
| ATOM | 7730 | O | GLN | B | 400 | 52.461 | 21.638 | −15.492 | 1.00 | 17.98 | B | O |
| ATOM | 7731 | N | LEU | B | 401 | 51.323 | 23.202 | −16.612 | 1.00 | 16.36 | B | N |
| ATOM | 7732 | CA | LEU | B | 401 | 51.580 | 24.189 | −15.573 | 1.00 | 16.93 | B | C |
| ATOM | 7733 | CB | LEU | B | 401 | 51.406 | 25.621 | −16.137 | 1.00 | 16.62 | B | C |
| ATOM | 7734 | CG | LEU | B | 401 | 52.510 | 26.026 | −17.139 | 1.00 | 16.58 | B | C |
| ATOM | 7735 | CD1 | LEU | B | 401 | 52.218 | 27.399 | −17.812 | 1.00 | 16.43 | B | C |
| ATOM | 7736 | CD2 | LEU | B | 401 | 53.956 | 25.978 | −16.555 | 1.00 | 17.12 | B | C |
| ATOM | 7737 | C | LEU | B | 401 | 50.738 | 23.940 | −14.323 | 1.00 | 16.36 | B | C |
| ATOM | 7738 | O | LEU | B | 401 | 51.161 | 24.321 | −13.223 | 1.00 | 17.21 | B | O |
| ATOM | 7739 | N | VAL | B | 402 | 49.560 | 23.291 | −14.455 | 1.00 | 15.44 | B | N |
| ATOM | 7740 | CA | VAL | B | 402 | 48.783 | 22.891 | −13.271 | 1.00 | 16.82 | B | C |

APPENDIX A-continued

*P. alba* 3T288C coordinates

| ATOM | 7741 | CB | VAL | B | 402 | 47.409 | 22.358 | −13.638 | 1.00 | 19.24 | B | C |
|------|------|------|-----|---|-----|--------|--------|---------|------|--------|---|---|
| ATOM | 7742 | CG1 | VAL | B | 402 | 46.785 | 21.555 | −12.475 | 1.00 | 21.42 | B | C |
| ATOM | 7743 | CG2 | VAL | B | 402 | 46.523 | 23.505 | −14.109 | 1.00 | 18.39 | B | C |
| ATOM | 7744 | C | VAL | B | 402 | 49.611 | 21.831 | −12.539 | 1.00 | 17.32 | B | C |
| ATOM | 7745 | O | VAL | B | 402 | 49.825 | 21.939 | −11.352 | 1.00 | 19.90 | B | O |
| ATOM | 7746 | N | PHE | B | 403 | 50.152 | 20.853 | −13.265 | 1.00 | 16.42 | B | N |
| ATOM | 7747 | CA | PHE | B | 403 | 51.010 | 19.849 | −12.627 | 1.00 | 15.92 | B | C |
| ATOM | 7748 | CB | PHE | B | 403 | 51.306 | 18.711 | −13.596 | 1.00 | 16.25 | B | C |
| ATOM | 7749 | CG | PHE | B | 403 | 50.205 | 17.685 | −13.654 | 1.00 | 18.43 | B | C |
| ATOM | 7750 | CD1 | PHE | B | 403 | 49.101 | 17.874 | −14.470 | 1.00 | 16.84 | B | C |
| ATOM | 7751 | CE1 | PHE | B | 403 | 48.073 | 16.956 | −14.498 | 1.00 | 17.95 | B | C |
| ATOM | 7752 | CZ | PHE | B | 403 | 48.150 | 15.813 | −13.720 | 1.00 | 17.55 | B | C |
| ATOM | 7753 | CE2 | PHE | B | 403 | 49.274 | 15.600 | −12.930 | 1.00 | 17.75 | B | C |
| ATOM | 7754 | CD2 | PHE | B | 403 | 50.281 | 16.534 | −12.888 | 1.00 | 16.36 | B | C |
| ATOM | 7755 | C | PHE | B | 403 | 52.296 | 20.451 | −12.034 | 1.00 | 20.51 | B | C |
| ATOM | 7756 | O | PHE | B | 403 | 52.710 | 20.097 | −10.921 | 1.00 | 18.15 | B | O |
| ATOM | 7757 | N | ALA | B | 404 | 52.869 | 21.427 | −12.731 | 1.00 | 18.27 | B | N |
| ATOM | 7758 | CA | ALA | B | 404 | 54.068 | 22.116 | −12.256 | 1.00 | 21.22 | B | C |
| ATOM | 7759 | CB | ALA | B | 404 | 54.650 | 23.019 | −13.338 | 1.00 | 19.30 | B | C |
| ATOM | 7760 | C | ALA | B | 404 | 53.763 | 22.906 | −10.986 | 1.00 | 19.19 | B | C |
| ATOM | 7761 | O | ALA | B | 404 | 54.575 | 22.905 | −10.069 | 1.00 | 18.68 | B | O |
| ATOM | 7762 | N | TYR | B | 405 | 52.598 | 23.544 | −10.913 | 1.00 | 17.24 | B | N |
| ATOM | 7763 | CA | TYR | B | 405 | 52.178 | 24.284 | −9.704 | 1.00 | 19.01 | B | C |
| ATOM | 7764 | CB | TYR | B | 405 | 50.737 | 24.823 | −9.830 | 1.00 | 17.43 | B | C |
| ATOM | 7765 | CG | TYR | B | 405 | 50.197 | 25.462 | −8.549 | 1.00 | 18.45 | B | C |
| ATOM | 7766 | CD1 | TYR | B | 405 | 50.452 | 26.809 | −8.228 | 1.00 | 18.58 | B | C |
| ATOM | 7767 | CE1 | TYR | B | 405 | 49.964 | 27.364 | −7.046 | 1.00 | 21.18 | B | C |
| ATOM | 7768 | CZ | TYR | B | 405 | 49.243 | 26.585 | −6.174 | 1.00 | 27.35 | B | C |
| ATOM | 7769 | OH | TYR | B | 405 | 48.769 | 27.080 | −4.969 | 1.00 | 24.53 | B | O |
| ATOM | 7770 | CE2 | TYR | B | 405 | 48.984 | 25.269 | −6.489 | 1.00 | 26.69 | B | C |
| ATOM | 7771 | CD2 | TYR | B | 405 | 49.456 | 24.725 | −7.653 | 1.00 | 19.95 | B | C |
| ATOM | 7772 | C | TYR | B | 405 | 52.293 | 23.391 | −8.462 | 1.00 | 22.99 | B | C |
| ATOM | 7773 | O | TYR | B | 405 | 52.935 | 23.745 | −7.461 | 1.00 | 19.04 | B | O |
| ATOM | 7774 | N | PHE | B | 406 | 51.698 | 22.206 | −8.526 | 1.00 | 21.16 | B | N |
| ATOM | 7775 | CA | PHE | B | 406 | 51.714 | 21.337 | −7.356 | 1.00 | 19.33 | B | C |
| ATOM | 7776 | CB | PHE | B | 406 | 50.673 | 20.225 | −7.474 | 1.00 | 20.00 | B | C |
| ATOM | 7777 | CG | PHE | B | 406 | 49.263 | 20.733 | −7.528 | 1.00 | 18.99 | B | C |
| ATOM | 7778 | CD1 | PHE | B | 406 | 48.657 | 21.211 | −6.385 | 1.00 | 16.83 | B | C |
| ATOM | 7779 | CE1 | PHE | B | 406 | 47.361 | 21.704 | −6.425 | 1.00 | 17.64 | B | C |
| ATOM | 7780 | CZ | PHE | B | 406 | 46.658 | 21.696 | −7.624 | 1.00 | 21.27 | B | C |
| ATOM | 7781 | CE2 | PHE | B | 406 | 47.266 | 21.186 | −8.771 | 1.00 | 18.93 | B | C |
| ATOM | 7782 | CD2 | PHE | B | 406 | 48.548 | 20.734 | −8.718 | 1.00 | 18.22 | B | C |
| ATOM | 7783 | C | PHE | B | 406 | 53.081 | 20.762 | −7.044 | 1.00 | 24.99 | B | C |
| ATOM | 7784 | O | PHE | B | 406 | 53.328 | 20.393 | −5.905 | 1.00 | 22.61 | B | O |
| ATOM | 7785 | N | ALA | B | 407 | 53.970 | 20.673 | −8.029 | 1.00 | 21.48 | B | N |
| ATOM | 7786 | CA | ALA | B | 407 | 55.318 | 20.191 | −7.778 | 1.00 | 21.13 | B | C |
| ATOM | 7787 | CB | ALA | B | 407 | 55.844 | 19.442 | −8.997 | 1.00 | 17.54 | B | C |
| ATOM | 7788 | C | ALA | B | 407 | 56.313 | 21.275 | −7.358 | 1.00 | 26.36 | B | C |
| ATOM | 7789 | O | ALA | B | 407 | 57.410 | 20.940 | −6.889 | 1.00 | 31.08 | B | O |
| ATOM | 7790 | N | VAL | B | 408 | 55.977 | 22.552 | −7.546 | 1.00 | 29.15 | B | N |
| ATOM | 7791 | CA | VAL | B | 408 | 56.893 | 23.616 | −7.148 | 1.00 | 25.79 | B | C |
| ATOM | 7792 | CB | VAL | B | 408 | 57.283 | 24.618 | −8.287 | 1.00 | 29.33 | B | C |
| ATOM | 7793 | CG1 | VAL | B | 408 | 57.817 | 23.898 | −9.520 | 1.00 | 26.70 | B | C |
| ATOM | 7794 | CG2 | VAL | B | 408 | 56.148 | 25.509 | −8.613 | 1.00 | 29.67 | B | C |
| ATOM | 7795 | C | VAL | B | 408 | 56.425 | 24.448 | −5.969 | 1.00 | 28.18 | B | C |
| ATOM | 7796 | O | VAL | B | 408 | 57.251 | 25.061 | −5.355 | 1.00 | 30.90 | B | O |
| ATOM | 7797 | N | VAL | B | 409 | 55.134 | 24.495 | −5.658 | 1.00 | 28.79 | B | N |
| ATOM | 7798 | CA | VAL | B | 409 | 54.639 | 25.344 | −4.572 | 1.00 | 35.25 | B | C |
| ATOM | 7799 | CB | VAL | B | 409 | 53.292 | 26.011 | −4.958 | 1.00 | 34.13 | B | C |
| ATOM | 7800 | CG1 | VAL | B | 409 | 52.508 | 26.477 | −3.738 | 1.00 | 38.15 | B | C |
| ATOM | 7801 | CG2 | VAL | B | 409 | 53.545 | 27.173 | −5.914 | 1.00 | 33.80 | B | C |
| ATOM | 7802 | C | VAL | B | 409 | 54.470 | 24.512 | −3.293 | 1.00 | 43.84 | B | C |
| ATOM | 7803 | O | VAL | B | 409 | 53.712 | 23.547 | −3.285 | 1.00 | 49.99 | B | O |
| ATOM | 7804 | N | GLN | B | 410 | 55.147 | 24.914 | −2.218 | 1.00 | 46.58 | B | N |
| ATOM | 7805 | CA | GLN | B | 410 | 55.111 | 24.168 | −0.939 | 1.00 | 51.15 | B | C |
| ATOM | 7806 | CB | GLN | B | 410 | 56.196 | 24.665 | 0.017 | 1.00 | 62.44 | B | C |
| ATOM | 7807 | CG | GLN | B | 410 | 57.608 | 24.223 | −0.368 | 1.00 | 85.53 | B | C |
| ATOM | 7808 | CD | GLN | B | 410 | 58.693 | 24.878 | 0.483 | 1.00 | 98.51 | B | C |
| ATOM | 7809 | OE1 | GLN | B | 410 | 58.437 | 25.837 | 1.212 | 1.00 | 115.04 | B | O |
| ATOM | 7810 | NE2 | GLN | B | 410 | 59.913 | 24.361 | 0.387 | 1.00 | 96.93 | B | N |
| ATOM | 7811 | C | GLN | B | 410 | 53.746 | 24.235 | −0.259 | 1.00 | 34.26 | B | C |
| ATOM | 7812 | O | GLN | B | 410 | 53.184 | 23.204 | 0.136 | 1.00 | 41.14 | B | O |
| ATOM | 7813 | N | ASN | B | 411 | 53.193 | 25.440 | −0.170 | 1.00 | 36.04 | B | N |
| ATOM | 7814 | CA | ASN | B | 411 | 51.879 | 25.655 | 0.431 | 1.00 | 36.24 | B | C |
| ATOM | 7815 | CB | ASN | B | 411 | 51.993 | 26.656 | 1.586 | 1.00 | 39.41 | B | C |
| ATOM | 7816 | CG | ASN | B | 411 | 52.858 | 26.121 | 2.700 | 1.00 | 44.31 | B | C |
| ATOM | 7817 | OD1 | ASN | B | 411 | 54.002 | 26.539 | 2.868 | 1.00 | 52.88 | B | O |
| ATOM | 7818 | ND2 | ASN | B | 411 | 52.345 | 25.135 | 3.414 | 1.00 | 37.57 | B | N |

APPENDIX A-continued

*P. alba* 3T288C coordinates

| ATOM | 7819 | C | ASN | B | 411 | 50.851 | 26.127 | −0.577 | 1.00 | 34.78 | B | C |
|---|---|---|---|---|---|---|---|---|---|---|---|---|
| ATOM | 7820 | O | ASN | B | 411 | 50.806 | 27.315 | −0.947 | 1.00 | 33.95 | B | O |
| ATOM | 7821 | N | ILE | B | 412 | 49.989 | 25.202 | −0.974 | 1.00 | 32.83 | B | N |
| ATOM | 7822 | CA | ILE | B | 412 | 49.002 | 25.486 | −1.986 | 1.00 | 30.16 | B | C |
| ATOM | 7823 | CB | ILE | B | 412 | 48.372 | 24.173 | −2.580 | 1.00 | 39.38 | B | C |
| ATOM | 7824 | CG1 | ILE | B | 412 | 47.327 | 23.547 | −1.664 | 1.00 | 36.76 | B | C |
| ATOM | 7825 | CD1 | ILE | B | 412 | 46.506 | 22.420 | −2.347 | 1.00 | 30.79 | B | C |
| ATOM | 7826 | CG2 | ILE | B | 412 | 49.455 | 23.141 | −2.892 | 1.00 | 39.51 | B | C |
| ATOM | 7827 | C | ILE | B | 412 | 47.961 | 26.397 | −1.377 | 1.00 | 33.47 | B | C |
| ATOM | 7828 | O | ILE | B | 412 | 47.693 | 26.325 | −0.182 | 1.00 | 30.49 | B | O |
| ATOM | 7829 | N | LYS | B | 413 | 47.367 | 27.250 | −2.190 | 1.00 | 28.56 | B | N |
| ATOM | 7830 | CA | LYS | B | 413 | 46.293 | 28.111 | −1.728 | 1.00 | 31.18 | B | C |
| ATOM | 7831 | CB | LYS | B | 413 | 46.742 | 29.567 | −1.724 | 1.00 | 33.98 | B | C |
| ATOM | 7832 | CG | LYS | B | 413 | 47.863 | 29.824 | −0.747 | 1.00 | 39.78 | B | C |
| ATOM | 7833 | CD | LYS | B | 413 | 48.596 | 31.111 | −1.062 | 1.00 | 50.58 | B | C |
| ATOM | 7834 | CE | LYS | B | 413 | 49.785 | 31.288 | −0.148 | 1.00 | 49.79 | B | C |
| ATOM | 7835 | NZ | LYS | B | 413 | 50.396 | 32.600 | −0.413 | 1.00 | 53.85 | B | N |
| ATOM | 7836 | C | LYS | B | 413 | 45.077 | 27.957 | −2.597 | 1.00 | 31.66 | B | C |
| ATOM | 7837 | O | LYS | B | 413 | 45.172 | 27.893 | −3.818 | 1.00 | 29.12 | B | O |
| ATOM | 7838 | N | LYS | B | 414 | 43.929 | 27.915 | −1.936 | 1.00 | 28.79 | B | N |
| ATOM | 7839 | CA | LYS | B | 414 | 42.638 | 27.829 | −2.568 | 1.00 | 40.86 | B | C |
| ATOM | 7840 | CB | LYS | B | 414 | 41.532 | 28.075 | −1.524 | 1.00 | 51.07 | B | C |
| ATOM | 7841 | CG | LYS | B | 414 | 40.102 | 28.244 | −2.085 | 1.00 | 66.21 | B | C |
| ATOM | 7842 | CD | LYS | B | 414 | 39.612 | 27.042 | −2.909 | 1.00 | 79.46 | B | C |
| ATOM | 7843 | CE | LYS | B | 414 | 39.427 | 25.788 | −2.073 | 1.00 | 89.72 | B | C |
| ATOM | 7844 | NZ | LYS | B | 414 | 38.431 | 25.988 | −0.988 | 1.00 | 98.92 | B | N |
| ATOM | 7845 | C | LYS | B | 414 | 42.469 | 28.799 | −3.733 | 1.00 | 32.82 | B | C |
| ATOM | 7846 | O | LYS | B | 414 | 42.016 | 28.394 | −4.798 | 1.00 | 24.44 | B | O |
| ATOM | 7847 | N | GLU | B | 415 | 42.780 | 30.076 | −3.537 | 1.00 | 27.69 | B | N |
| ATOM | 7848 | CA | GLU | B | 415 | 42.501 | 31.041 | −4.589 | 1.00 | 32.63 | B | C |
| ATOM | 7849 | CB | GLU | B | 415 | 42.482 | 32.489 | −4.055 | 1.00 | 36.78 | B | C |
| ATOM | 7850 | CG | GLU | B | 415 | 43.682 | 33.333 | −4.394 | 1.00 | 59.26 | B | C |
| ATOM | 7851 | CD | GLU | B | 415 | 43.532 | 34.800 | −3.967 | 1.00 | 65.67 | B | C |
| ATOM | 7852 | OE1 | GLU | B | 415 | 42.448 | 35.405 | −4.161 | 1.00 | 47.51 | B | O |
| ATOM | 7853 | OE2 | GLU | B | 415 | 44.530 | 35.348 | −3.460 | 1.00 | 66.03 | B | O |
| ATOM | 7854 | C | GLU | B | 415 | 43.453 | 30.855 | −5.800 | 1.00 | 22.84 | B | C |
| ATOM | 7855 | O | GLU | B | 415 | 43.078 | 31.143 | −6.917 | 1.00 | 28.14 | B | O |
| ATOM | 7856 | N | GLU | B | 416 | 44.675 | 30.412 | −5.557 | 1.00 | 23.46 | B | N |
| ATOM | 7857 | CA | GLU | B | 416 | 45.592 | 30.094 | −6.634 | 1.00 | 26.32 | B | C |
| ATOM | 7858 | CB | GLU | B | 416 | 46.983 | 29.771 | −6.092 | 1.00 | 27.26 | B | C |
| ATOM | 7859 | CG | GLU | B | 416 | 47.672 | 30.981 | −5.449 | 1.00 | 33.55 | B | C |
| ATOM | 7860 | CD | GLU | B | 416 | 49.106 | 30.692 | −5.016 | 1.00 | 35.88 | B | C |
| ATOM | 7861 | OE1 | GLU | B | 416 | 49.435 | 29.528 | −4.697 | 1.00 | 33.22 | B | O |
| ATOM | 7862 | OE2 | GLU | B | 416 | 49.912 | 31.637 | −4.995 | 1.00 | 44.51 | B | O |
| ATOM | 7863 | C | GLU | B | 416 | 45.052 | 28.936 | −7.454 | 1.00 | 27.30 | B | C |
| ATOM | 7864 | O | GLU | B | 416 | 44.998 | 29.040 | −8.661 | 1.00 | 26.85 | B | O |
| ATOM | 7865 | N | ILE | B | 417 | 44.611 | 27.870 | −6.784 | 1.00 | 31.08 | B | N |
| ATOM | 7866 | CA | AILE | B | 417 | 44.073 | 26.700 | −7.488 | 0.50 | 30.71 | B | C |
| ATOM | 7867 | CA | BILE | B | 417 | 44.016 | 26.696 | −7.432 | 0.50 | 31.36 | B | C |
| ATOM | 7868 | CB | AILE | B | 417 | 43.699 | 25.514 | −6.566 | 0.50 | 31.05 | B | C |
| ATOM | 7869 | CB | BILE | B | 417 | 43.501 | 25.688 | −6.388 | 0.50 | 32.70 | B | C |
| ATOM | 7870 | CG1 | AILE | B | 417 | 44.820 | 25.146 | −5.612 | 0.50 | 28.12 | B | C |
| ATOM | 7871 | CG1 | BILE | B | 417 | 44.676 | 25.067 | −5.670 | 0.50 | 27.91 | B | C |
| ATOM | 7872 | CD1 | AILE | B | 417 | 44.335 | 24.332 | −4.406 | 0.50 | 26.96 | B | C |
| ATOM | 7873 | CD1 | BILE | B | 417 | 45.850 | 24.919 | −6.546 | 0.50 | 24.89 | B | C |
| ATOM | 7874 | CG2 | AILE | B | 417 | 43.401 | 24.278 | −7.415 | 0.50 | 33.62 | B | C |
| ATOM | 7875 | CG2 | BILE | B | 417 | 42.665 | 24.601 | −7.051 | 0.50 | 42.31 | B | C |
| ATOM | 7876 | C | ILE | B | 417 | 42.841 | 27.083 | −8.286 | 1.00 | 27.12 | B | C |
| ATOM | 7877 | O | ILE | B | 417 | 42.709 | 26.665 | −9.426 | 1.00 | 30.48 | B | O |
| ATOM | 7878 | N | GLU | B | 418 | 41.962 | 27.891 | −7.705 | 1.00 | 31.07 | B | N |
| ATOM | 7879 | CA | GLU | B | 418 | 40.757 | 28.339 | −8.415 | 1.00 | 34.04 | B | C |
| ATOM | 7880 | CB | GLU | B | 418 | 39.864 | 29.176 | −7.499 | 1.00 | 40.60 | B | C |
| ATOM | 7881 | CG | GLU | B | 418 | 39.146 | 28.377 | −6.415 | 1.00 | 52.16 | B | C |
| ATOM | 7882 | CD | GLU | B | 418 | 38.224 | 29.253 | −5.553 | 1.00 | 61.73 | B | C |
| ATOM | 7883 | OE1 | GLU | B | 418 | 38.642 | 30.362 | −5.126 | 1.00 | 53.45 | B | O |
| ATOM | 7884 | OE2 | GLU | B | 418 | 37.080 | 28.821 | −5.297 | 1.00 | 78.65 | B | O |
| ATOM | 7885 | C | GLU | B | 418 | 41.102 | 29.165 | −9.644 | 1.00 | 31.84 | B | C |
| ATOM | 7886 | O | GLU | B | 418 | 40.425 | 29.087 | −10.676 | 1.00 | 27.15 | B | O |
| ATOM | 7887 | N | ASN | B | 419 | 42.141 | 29.984 | −9.540 | 1.00 | 23.18 | B | N |
| ATOM | 7888 | CA | ASN | B | 419 | 42.545 | 30.753 | −10.703 | 1.00 | 28.59 | B | C |
| ATOM | 7889 | CB | ASN | B | 419 | 43.419 | 31.902 | −10.275 | 1.00 | 26.05 | B | C |
| ATOM | 7890 | CG | ASN | B | 419 | 42.584 | 33.055 | −9.825 | 1.00 | 32.56 | B | C |
| ATOM | 7891 | OD1 | ASN | B | 419 | 42.071 | 33.785 | −10.651 | 1.00 | 32.13 | B | O |
| ATOM | 7892 | ND2 | ASN | B | 419 | 42.360 | 33.167 | −8.515 | 1.00 | 26.49 | B | N |
| ATOM | 7893 | C | ASN | B | 419 | 43.183 | 29.953 | −11.842 | 1.00 | 21.02 | B | C |
| ATOM | 7894 | O | ASN | B | 419 | 42.954 | 30.273 | −13.021 | 1.00 | 23.89 | B | O |
| ATOM | 7895 | N | LEU | B | 420 | 43.965 | 28.933 | −11.482 | 1.00 | 21.54 | B | N |
| ATOM | 7896 | CA | LEU | B | 420 | 44.461 | 27.967 | −12.448 | 1.00 | 26.65 | B | C |

APPENDIX A-continued

*P. alba* 3T288C coordinates

| ATOM | 7897 | CB | LEU | B | 420 | 45.247 | 26.839 | −11.769 | 1.00 | 25.17 | B | C |
|------|------|-----|------|---|-----|--------|--------|---------|------|-------|---|---|
| ATOM | 7898 | CG | LEU | B | 420 | 46.577 | 27.175 | −11.077 | 1.00 | 32.36 | B | C |
| ATOM | 7899 | CD1 | LEU | B | 420 | 47.067 | 25.963 | −10.301 | 1.00 | 30.40 | B | C |
| ATOM | 7900 | CD2 | LEU | B | 420 | 47.619 | 27.666 | −12.058 | 1.00 | 28.07 | B | C |
| ATOM | 7901 | C | LEU | B | 420 | 43.300 | 27.353 | −13.238 | 1.00 | 28.82 | B | C |
| ATOM | 7902 | O | LEU | B | 420 | 43.356 | 27.280 | −14.461 | 1.00 | 26.51 | B | O |
| ATOM | 7903 | N | GLN | B | 421 | 42.243 | 26.937 | −12.539 | 1.00 | 28.46 | B | N |
| ATOM | 7904 | CA | GLN | B | 421 | 41.100 | 26.291 | −13.193 | 1.00 | 28.02 | B | C |
| ATOM | 7905 | CB | GLN | B | 421 | 40.088 | 25.791 | −12.166 | 1.00 | 35.06 | B | C |
| ATOM | 7906 | CG | GLN | B | 421 | 40.638 | 24.713 | −11.299 | 1.00 | 37.28 | B | C |
| ATOM | 7907 | CD | GLN | B | 421 | 39.609 | 23.675 | −10.893 | 1.00 | 39.96 | B | C |
| ATOM | 7908 | OE1 | GLN | B | 421 | 39.746 | 22.499 | −11.216 | 1.00 | 36.36 | B | O |
| ATOM | 7909 | NE2 | GLN | B | 421 | 38.604 | 24.092 | −10.162 | 1.00 | 28.86 | B | N |
| ATOM | 7910 | C | GLN | B | 421 | 40.398 | 27.211 | −14.140 | 1.00 | 25.93 | B | C |
| ATOM | 7911 | O | GLN | B | 421 | 39.787 | 26.761 | −15.107 | 1.00 | 28.33 | B | O |
| ATOM | 7912 | N | LYS | B | 422 | 40.458 | 28.511 | −13.866 | 1.00 | 24.57 | B | N |
| ATOM | 7913 | CA | LYS | B | 422 | 39.885 | 29.512 | −14.765 | 1.00 | 25.71 | B | C |
| ATOM | 7914 | CB | LYS | B | 422 | 39.296 | 30.684 | −13.943 | 1.00 | 31.56 | B | C |
| ATOM | 7915 | CG | LYS | B | 422 | 38.012 | 30.279 | −13.227 | 1.00 | 51.62 | B | C |
| ATOM | 7916 | CD | LYS | B | 422 | 37.660 | 31.126 | −11.988 | 1.00 | 60.90 | B | C |
| ATOM | 7917 | CE | LYS | B | 422 | 36.364 | 30.571 | −11.331 | 1.00 | 65.83 | B | C |
| ATOM | 7918 | NZ | LYS | B | 422 | 36.046 | 31.096 | −9.972 | 1.00 | 54.30 | B | N |
| ATOM | 7919 | C | LYS | B | 422 | 40.920 | 30.032 | −15.765 | 1.00 | 23.39 | B | C |
| ATOM | 7920 | O | LYS | B | 422 | 40.695 | 31.032 | −16.443 | 1.00 | 28.46 | B | O |
| ATOM | 7921 | N | TYR | B | 423 | 42.063 | 29.372 | −15.872 | 1.00 | 22.71 | B | N |
| ATOM | 7922 | CA | TYR | B | 423 | 43.074 | 29.773 | −16.864 | 1.00 | 20.56 | B | C |
| ATOM | 7923 | CB | TYR | B | 423 | 42.574 | 29.603 | −18.283 | 1.00 | 21.24 | B | C |
| ATOM | 7924 | CG | TYR | B | 423 | 42.196 | 28.181 | −18.626 | 1.00 | 25.60 | B | C |
| ATOM | 7925 | CD1 | TYR | B | 423 | 43.149 | 27.273 | −19.024 | 1.00 | 23.47 | B | C |
| ATOM | 7926 | CE1 | TYR | B | 423 | 42.792 | 25.962 | −19.367 | 1.00 | 28.05 | B | C |
| ATOM | 7927 | CZ | TYR | B | 423 | 41.454 | 25.577 | −19.260 | 1.00 | 32.51 | B | C |
| ATOM | 7928 | OH | TYR | B | 423 | 41.037 | 24.313 | −19.566 | 1.00 | 34.46 | B | O |
| ATOM | 7929 | CE2 | TYR | B | 423 | 40.495 | 26.487 | −18.859 | 1.00 | 34.11 | B | C |
| ATOM | 7930 | CD2 | TYR | B | 423 | 40.864 | 27.770 | −18.566 | 1.00 | 27.96 | B | C |
| ATOM | 7931 | C | TYR | B | 423 | 43.532 | 31.214 | −16.705 | 1.00 | 21.71 | B | C |
| ATOM | 7932 | O | TYR | B | 423 | 43.536 | 31.989 | −17.650 | 1.00 | 20.05 | B | O |
| ATOM | 7933 | N | HIS | B | 424 | 43.991 | 31.518 | −15.506 | 1.00 | 22.59 | B | N |
| ATOM | 7934 | CA | HIS | B | 424 | 44.562 | 32.815 | −15.181 | 1.00 | 21.09 | B | C |
| ATOM | 7935 | CB | HIS | B | 424 | 45.067 | 32.740 | −13.750 | 1.00 | 23.23 | B | C |
| ATOM | 7936 | CG | HIS | B | 424 | 45.673 | 34.023 | −13.239 | 1.00 | 26.81 | B | C |
| ATOM | 7937 | ND1 | HIS | B | 424 | 44.935 | 34.992 | −12.625 | 1.00 | 31.97 | B | N |
| ATOM | 7938 | CE1 | HIS | B | 424 | 45.748 | 36.011 | −12.278 | 1.00 | 22.71 | B | C |
| ATOM | 7939 | NE2 | HIS | B | 424 | 46.988 | 35.715 | −12.678 | 1.00 | 31.93 | B | N |
| ATOM | 7940 | CD2 | HIS | B | 424 | 46.970 | 34.489 | −13.281 | 1.00 | 25.44 | B | C |
| ATOM | 7941 | C | HIS | B | 424 | 45.707 | 33.105 | −16.133 | 1.00 | 21.91 | B | C |
| ATOM | 7942 | O | HIS | B | 424 | 46.430 | 32.196 | −16.599 | 1.00 | 17.91 | B | O |
| ATOM | 7943 | N | ASP | B | 425 | 45.883 | 34.374 | −16.429 | 1.00 | 17.02 | B | N |
| ATOM | 7944 | CA | ASP | B | 425 | 46.957 | 34.854 | −17.305 | 1.00 | 22.29 | B | C |
| ATOM | 7945 | CB | ASP | B | 425 | 47.130 | 36.361 | −17.128 | 1.00 | 31.01 | B | C |
| ATOM | 7946 | CG | ASP | B | 425 | 45.940 | 37.145 | −17.611 | 1.00 | 35.91 | B | C |
| ATOM | 7947 | OD1 | ASP | B | 425 | 45.264 | 36.690 | −18.559 | 1.00 | 43.87 | B | O |
| ATOM | 7948 | OD2 | ASP | B | 425 | 45.688 | 38.218 | −17.020 | 1.00 | 43.05 | B | O |
| ATOM | 7949 | C | ASP | B | 425 | 48.338 | 34.264 | −17.087 | 1.00 | 21.04 | B | C |
| ATOM | 7950 | O | ASP | B | 425 | 49.110 | 34.165 | −18.025 | 1.00 | 17.11 | B | O |
| ATOM | 7951 | N | THR | B | 426 | 48.667 | 33.940 | −15.844 | 1.00 | 20.31 | B | N |
| ATOM | 7952 | CA | THR | B | 426 | 49.951 | 33.336 | −15.488 | 1.00 | 19.84 | B | C |
| ATOM | 7953 | CB | THR | B | 426 | 50.004 | 33.029 | −13.970 | 1.00 | 23.34 | B | C |
| ATOM | 7954 | OG1 | THR | B | 426 | 49.890 | 34.283 | −13.256 | 1.00 | 27.25 | B | O |
| ATOM | 7955 | CG2 | THR | B | 426 | 51.301 | 32.410 | −13.590 | 1.00 | 24.23 | B | C |
| ATOM | 7956 | C | THR | B | 426 | 50.242 | 32.088 | −16.290 | 1.00 | 20.14 | B | C |
| ATOM | 7957 | O | THR | B | 426 | 51.399 | 31.857 | −16.665 | 1.00 | 18.00 | B | O |
| ATOM | 7958 | N | ILE | B | 427 | 49.194 | 31.295 | −16.554 | 1.00 | 17.26 | B | N |
| ATOM | 7959 | CA | ILE | B | 427 | 49.339 | 30.057 | −17.301 | 1.00 | 16.26 | B | C |
| ATOM | 7960 | CB | ILE | B | 427 | 48.749 | 28.814 | −16.594 | 1.00 | 17.08 | B | C |
| ATOM | 7961 | CG1 | ILE | B | 427 | 47.227 | 28.781 | −16.579 | 1.00 | 19.40 | B | C |
| ATOM | 7962 | CD1 | ILE | B | 427 | 46.679 | 27.474 | −15.907 | 1.00 | 20.08 | B | C |
| ATOM | 7963 | CG2 | ILE | B | 427 | 49.293 | 28.697 | −15.175 | 1.00 | 18.97 | B | C |
| ATOM | 7964 | C | ILE | B | 427 | 48.829 | 30.182 | −18.710 | 1.00 | 17.22 | B | C |
| ATOM | 7965 | O | ILE | B | 427 | 49.347 | 29.520 | −19.604 | 1.00 | 20.85 | B | O |
| ATOM | 7966 | N | SER | B | 428 | 47.842 | 31.045 | −18.962 | 1.00 | 20.43 | B | N |
| ATOM | 7967 | CA | SER | B | 428 | 47.309 | 31.113 | −20.321 | 1.00 | 15.80 | B | C |
| ATOM | 7968 | CB | SER | B | 428 | 45.945 | 31.785 | −20.348 | 1.00 | 21.10 | B | C |
| ATOM | 7969 | OG | SER | B | 428 | 46.037 | 33.132 | −20.023 | 1.00 | 20.25 | B | O |
| ATOM | 7970 | C | SER | B | 428 | 48.290 | 31.806 | −21.264 | 1.00 | 17.17 | B | C |
| ATOM | 7971 | O | SER | B | 428 | 48.473 | 31.356 | −22.380 | 1.00 | 18.80 | B | O |
| ATOM | 7972 | N | ARG | B | 429 | 48.995 | 32.852 | −20.835 | 1.00 | 16.72 | B | N |
| ATOM | 7973 | CA | AARG | B | 429 | 49.828 | 33.594 | −21.788 | 0.50 | 15.43 | B | C |
| ATOM | 7974 | CA | BARG | B | 429 | 49.833 | 33.608 | −21.780 | 0.50 | 16.11 | B | C |

APPENDIX A-continued

*P. alba* 3T288C coordinates

| ATOM | 7975 | CB | AARG | B | 429 | 50.238 | 34.952 | −21.233 | 0.50 | 18.21 | B | C |
|------|------|------|------|---|-----|--------|--------|---------|------|-------|---|---|
| ATOM | 7976 | CB | BARG | B | 429 | 50.291 | 34.946 | −21.195 | 0.50 | 20.44 | B | C |
| ATOM | 7977 | CG | AARG | B | 429 | 49.080 | 35.944 | −21.200 | 0.50 | 18.18 | B | C |
| ATOM | 7978 | CG | BARG | B | 429 | 49.166 | 35.882 | −20.723 | 0.50 | 22.04 | B | C |
| ATOM | 7979 | CD | AARG | B | 429 | 49.539 | 37.351 | −20.892 | 0.50 | 21.00 | B | C |
| ATOM | 7980 | CD | BARG | B | 429 | 48.398 | 36.559 | −21.847 | 0.50 | 26.45 | B | C |
| ATOM | 7981 | NE | AARG | B | 429 | 48.441 | 38.247 | −20.522 | 0.50 | 22.76 | B | N |
| ATOM | 7982 | NE | BARG | B | 429 | 47.476 | 37.580 | −21.324 | 0.50 | 28.17 | B | N |
| ATOM | 7983 | CZ | AARG | B | 429 | 48.322 | 38.845 | −19.342 | 0.50 | 20.32 | B | C |
| ATOM | 7984 | CZ | BARG | B | 429 | 46.530 | 38.181 | −22.036 | 0.50 | 25.21 | B | C |
| ATOM | 7985 | NH1 | AARG | B | 429 | 49.219 | 38.662 | −18.389 | 0.50 | 27.90 | B | N |
| ATOM | 7986 | NH1 | BARG | B | 429 | 46.361 | 37.881 | −23.304 | 0.50 | 22.10 | B | N |
| ATOM | 7987 | NH2 | AARG | B | 429 | 47.315 | 39.640 | −19.133 | 0.50 | 22.88 | B | N |
| ATOM | 7988 | NH2 | BARG | B | 429 | 45.768 | 39.099 | −21.472 | 0.50 | 32.07 | B | N |
| ATOM | 7989 | C | ARG | B | 429 | 51.015 | 32.767 | −22.274 | 1.00 | 17.61 | B | C |
| ATOM | 7990 | O | ARG | B | 429 | 51.282 | 32.725 | −23.457 | 1.00 | 14.57 | B | O |
| ATOM | 7991 | N | PRO | B | 430 | 51.712 | 32.054 | −21.363 | 1.00 | 14.73 | B | N |
| ATOM | 7992 | CA | PRO | B | 430 | 52.757 | 31.188 | −21.898 | 1.00 | 15.75 | B | C |
| ATOM | 7993 | CB | PRO | B | 430 | 53.397 | 30.550 | −20.652 | 1.00 | 17.07 | B | C |
| ATOM | 7994 | CG | PRO | B | 430 | 52.846 | 31.249 | −19.511 | 1.00 | 20.36 | B | C |
| ATOM | 7995 | CD | PRO | B | 430 | 51.730 | 32.117 | −19.892 | 1.00 | 16.63 | B | C |
| ATOM | 7996 | C | PRO | B | 430 | 52.243 | 30.083 | −22.815 | 1.00 | 14.70 | B | C |
| ATOM | 7997 | O | PRO | B | 430 | 52.975 | 29.648 | −23.726 | 1.00 | 15.79 | B | O |
| ATOM | 7998 | N | SER | B | 431 | 51.012 | 29.633 | −22.582 | 1.00 | 14.43 | B | N |
| ATOM | 7999 | CA | SER | B | 431 | 50.356 | 28.622 | −23.449 | 1.00 | 14.37 | B | C |
| ATOM | 8000 | CB | SER | B | 431 | 49.083 | 28.084 | −22.762 | 1.00 | 13.13 | B | C |
| ATOM | 8001 | OG | SER | B | 431 | 49.502 | 27.415 | −21.527 | 1.00 | 18.20 | B | O |
| ATOM | 8002 | C | SER | B | 431 | 50.054 | 29.198 | −24.822 | 1.00 | 17.17 | B | C |
| ATOM | 8003 | O | SER | B | 431 | 50.140 | 28.494 | −25.833 | 1.00 | 16.81 | B | O |
| ATOM | 8004 | N | HIS | B | 432 | 49.737 | 30.499 | −24.859 | 1.00 | 14.64 | B | N |
| ATOM | 8005 | CA | HIS | B | 432 | 49.577 | 31.190 | −26.130 | 1.00 | 15.68 | B | C |
| ATOM | 8006 | CB | HIS | B | 432 | 49.223 | 32.656 | −25.968 | 1.00 | 14.64 | B | C |
| ATOM | 8007 | CG | HIS | B | 432 | 47.877 | 32.917 | −25.321 | 1.00 | 18.93 | B | C |
| ATOM | 8008 | ND1 | HIS | B | 432 | 47.439 | 34.166 | −25.059 | 1.00 | 22.86 | B | N |
| ATOM | 8009 | CE1 | HIS | B | 432 | 46.212 | 34.100 | −24.472 | 1.00 | 25.01 | B | C |
| ATOM | 8010 | NE2 | HIS | B | 432 | 45.881 | 32.819 | −24.357 | 1.00 | 19.96 | B | N |
| ATOM | 8011 | CD2 | HIS | B | 432 | 46.910 | 32.063 | −24.846 | 1.00 | 17.39 | B | C |
| ATOM | 8012 | C | HIS | B | 432 | 50.825 | 31.072 | −26.925 | 1.00 | 14.11 | B | C |
| ATOM | 8013 | O | HIS | B | 432 | 50.805 | 30.707 | −28.110 | 1.00 | 13.66 | B | O |
| ATOM | 8014 | N | ILE | B | 433 | 51.940 | 31.399 | −26.286 | 1.00 | 15.75 | B | N |
| ATOM | 8015 | CA | ILE | B | 433 | 53.232 | 31.332 | −26.955 | 1.00 | 14.75 | B | C |
| ATOM | 8016 | CB | ILE | B | 433 | 54.329 | 32.001 | −26.067 | 1.00 | 15.98 | B | C |
| ATOM | 8017 | CG1 | ILE | B | 433 | 54.013 | 33.539 | −26.056 | 1.00 | 18.75 | B | C |
| ATOM | 8018 | CD1 | ILE | B | 433 | 54.706 | 34.306 | −25.048 | 1.00 | 24.29 | B | C |
| ATOM | 8019 | CG2 | ILE | B | 433 | 55.727 | 31.742 | −26.691 | 1.00 | 15.81 | B | C |
| ATOM | 8020 | C | ILE | B | 433 | 53.609 | 29.929 | −27.451 | 1.00 | 14.07 | B | C |
| ATOM | 8021 | O | ILE | B | 433 | 54.129 | 29.767 | −28.587 | 1.00 | 15.08 | B | O |
| ATOM | 8022 | N | PHE | B | 434 | 53.366 | 28.931 | −26.611 | 1.00 | 14.80 | B | N |
| ATOM | 8023 | CA | PHE | B | 434 | 53.631 | 27.514 | −26.921 | 1.00 | 14.96 | B | C |
| ATOM | 8024 | CB | PHE | B | 434 | 53.164 | 26.715 | −25.697 | 1.00 | 15.79 | B | C |
| ATOM | 8025 | CG | PHE | B | 434 | 53.298 | 25.222 | −25.792 | 1.00 | 16.92 | B | C |
| ATOM | 8026 | CD1 | PHE | B | 434 | 54.039 | 24.579 | −26.793 | 1.00 | 19.94 | B | C |
| ATOM | 8027 | CE1 | PHE | B | 434 | 54.158 | 23.160 | −26.796 | 1.00 | 19.87 | B | C |
| ATOM | 8028 | CZ | PHE | B | 434 | 53.576 | 22.407 | −25.787 | 1.00 | 22.06 | B | C |
| ATOM | 8029 | CE2 | PHE | B | 434 | 52.850 | 23.042 | −24.785 | 1.00 | 19.60 | B | C |
| ATOM | 8030 | CD2 | PHE | B | 434 | 52.730 | 24.453 | −24.791 | 1.00 | 17.79 | B | C |
| ATOM | 8031 | C | PHE | B | 434 | 52.907 | 27.120 | −28.228 | 1.00 | 14.03 | B | C |
| ATOM | 8032 | O | PHE | B | 434 | 53.528 | 26.604 | −29.165 | 1.00 | 16.19 | B | O |
| ATOM | 8033 | N | ARG | B | 435 | 51.622 | 27.445 | −28.307 | 1.00 | 14.78 | B | N |
| ATOM | 8034 | CA | ARG | B | 435 | 50.819 | 27.116 | −29.488 | 1.00 | 12.98 | B | C |
| ATOM | 8035 | CB | ARG | B | 435 | 49.327 | 27.369 | −29.195 | 1.00 | 14.24 | B | C |
| ATOM | 8036 | CG | ARG | B | 435 | 48.375 | 27.168 | −30.367 | 1.00 | 13.52 | B | C |
| ATOM | 8037 | CD | ARG | B | 435 | 48.591 | 25.871 | −31.145 | 1.00 | 14.92 | B | C |
| ATOM | 8038 | NE | ARG | B | 435 | 48.185 | 24.704 | −30.372 | 1.00 | 16.56 | B | N |
| ATOM | 8039 | CZ | ARG | B | 435 | 48.453 | 23.449 | −30.711 | 1.00 | 19.64 | B | C |
| ATOM | 8040 | NH1 | ARG | B | 435 | 49.195 | 23.185 | −31.782 | 1.00 | 19.87 | B | N |
| ATOM | 8041 | NH2 | ARG | B | 435 | 47.963 | 22.460 | −29.973 | 1.00 | 18.55 | B | N |
| ATOM | 8042 | C | ARG | B | 435 | 51.291 | 27.886 | −30.683 | 1.00 | 14.00 | B | C |
| ATOM | 8043 | O | ARG | B | 435 | 51.409 | 27.317 | −31.759 | 1.00 | 14.38 | B | O |
| ATOM | 8044 | N | LEU | B | 436 | 51.581 | 29.188 | −30.529 | 1.00 | 14.56 | B | N |
| ATOM | 8045 | CA | LEU | B | 436 | 51.968 | 29.977 | −31.682 | 1.00 | 13.42 | B | C |
| ATOM | 8046 | CB | LEU | B | 436 | 51.924 | 31.485 | −31.419 | 1.00 | 14.94 | B | C |
| ATOM | 8047 | CG | LEU | B | 436 | 50.544 | 32.075 | −31.099 | 1.00 | 14.41 | B | C |
| ATOM | 8048 | CD1 | LEU | B | 436 | 50.640 | 33.516 | −30.626 | 1.00 | 14.92 | B | C |
| ATOM | 8049 | CD2 | LEU | B | 436 | 49.602 | 31.922 | −32.295 | 1.00 | 13.74 | B | C |
| ATOM | 8050 | C | LEU | B | 436 | 53.344 | 29.555 | −32.203 | 1.00 | 15.66 | B | C |
| ATOM | 8051 | O | LEU | B | 436 | 53.532 | 29.483 | −33.418 | 1.00 | 19.19 | B | O |
| ATOM | 8052 | N | CYS | B | 437 | 54.293 | 29.272 | −31.301 | 1.00 | 16.96 | B | N |

APPENDIX A-continued

P. alba 3T288C coordinates

| ATOM | 8053 | CA | CYS | B | 437 | 55.603 | 28.766 | −31.734 | 1.00 | 16.93 | B | C |
|---|---|---|---|---|---|---|---|---|---|---|---|---|
| ATOM | 8054 | CB | CYS | B | 437 | 56.536 | 28.577 | −30.559 | 1.00 | 17.77 | B | C |
| ATOM | 8055 | SG | CYS | B | 437 | 57.150 | 30.113 | −29.871 | 1.00 | 22.06 | B | S |
| ATOM | 8056 | C | CYS | B | 437 | 55.503 | 27.451 | −32.498 | 1.00 | 14.77 | B | C |
| ATOM | 8057 | O | CYS | B | 437 | 56.099 | 27.296 | −33.550 | 1.00 | 18.12 | B | O |
| ATOM | 8058 | N | ASN | B | 438 | 54.727 | 26.520 | −31.966 | 1.00 | 17.15 | B | N |
| ATOM | 8059 | CA | ASN | B | 438 | 54.519 | 25.218 | −32.568 | 1.00 | 16.89 | B | C |
| ATOM | 8060 | CB | ASN | B | 438 | 53.649 | 24.381 | −31.646 | 1.00 | 16.59 | B | C |
| ATOM | 8061 | CG | ASN | B | 438 | 53.345 | 22.972 | −32.214 | 1.00 | 24.82 | B | C |
| ATOM | 8062 | OD1 | ASN | B | 438 | 53.826 | 22.576 | −33.265 | 1.00 | 33.49 | B | O |
| ATOM | 8063 | ND2 | ASN | B | 438 | 52.657 | 22.205 | −31.447 | 1.00 | 22.35 | B | N |
| ATOM | 8064 | C | ASN | B | 438 | 53.900 | 25.390 | −33.951 | 1.00 | 20.33 | B | C |
| ATOM | 8065 | O | ASN | B | 438 | 54.399 | 24.838 | −34.952 | 1.00 | 19.00 | B | O |
| ATOM | 8066 | N | ASP | B | 439 | 52.857 | 26.214 | −34.033 | 1.00 | 15.44 | B | N |
| ATOM | 8067 | CA | ASP | B | 439 | 52.159 | 26.398 | −35.307 | 1.00 | 15.06 | B | C |
| ATOM | 8068 | CB | ASP | B | 439 | 50.765 | 27.022 | −35.120 | 1.00 | 16.90 | B | C |
| ATOM | 8069 | CG | ASP | B | 439 | 49.744 | 26.019 | −34.541 | 1.00 | 19.98 | B | C |
| ATOM | 8070 | OD1 | ASP | B | 439 | 50.174 | 24.934 | −34.065 | 1.00 | 17.50 | B | O |
| ATOM | 8071 | OD2 | ASP | B | 439 | 48.513 | 26.315 | −34.523 | 1.00 | 18.13 | B | O |
| ATOM | 8072 | C | ASP | B | 439 | 52.989 | 27.155 | −36.326 | 1.00 | 16.19 | B | C |
| ATOM | 8073 | O | ASP | B | 439 | 52.888 | 26.870 | −37.516 | 1.00 | 17.47 | B | O |
| ATOM | 8074 | N | LEU | B | 440 | 53.820 | 28.094 | −35.882 | 1.00 | 15.61 | B | N |
| ATOM | 8075 | CA | LEU | B | 440 | 54.676 | 28.794 | −36.811 | 1.00 | 18.75 | B | C |
| ATOM | 8076 | CB | LEU | B | 440 | 55.471 | 29.906 | −36.122 | 1.00 | 21.99 | B | C |
| ATOM | 8077 | CG | LEU | B | 440 | 54.750 | 31.220 | −35.858 | 1.00 | 20.97 | B | C |
| ATOM | 8078 | CD1 | LEU | B | 440 | 55.562 | 31.999 | −34.845 | 1.00 | 19.22 | B | C |
| ATOM | 8079 | CD2 | LEU | B | 440 | 54.559 | 32.027 | −37.128 | 1.00 | 17.97 | B | C |
| ATOM | 8080 | C | LEU | B | 440 | 55.688 | 27.811 | −37.451 | 1.00 | 19.73 | B | C |
| ATOM | 8081 | O | LEU | B | 440 | 56.004 | 27.961 | −38.621 | 1.00 | 18.40 | B | O |
| ATOM | 8082 | N | ALA | B | 441 | 56.182 | 26.845 | −36.674 | 1.00 | 20.07 | B | N |
| ATOM | 8083 | CA | ALA | B | 441 | 57.214 | 25.894 | −37.157 | 1.00 | 23.25 | B | C |
| ATOM | 8084 | CB | ALA | B | 441 | 57.813 | 25.077 | −35.983 | 1.00 | 19.15 | B | C |
| ATOM | 8085 | C | ALA | B | 441 | 56.640 | 24.971 | −38.228 | 1.00 | 25.11 | B | C |
| ATOM | 8086 | O | ALA | B | 441 | 57.327 | 24.606 | −39.161 | 1.00 | 23.98 | B | O |
| ATOM | 8087 | N | SER | B | 442 | 55.359 | 24.639 | −38.137 | 1.00 | 23.43 | B | N |
| ATOM | 8088 | CA | SER | B | 442 | 54.767 | 23.738 | −39.119 | 1.00 | 27.50 | B | C |
| ATOM | 8089 | CB | SER | B | 442 | 53.991 | 22.640 | −38.385 | 1.00 | 26.04 | B | C |
| ATOM | 8090 | OG | SER | B | 442 | 52.935 | 23.180 | −37.640 | 1.00 | 34.78 | B | O |
| ATOM | 8091 | C | SER | B | 442 | 53.889 | 24.429 | −40.180 | 1.00 | 24.60 | B | C |
| ATOM | 8092 | O | SER | B | 442 | 53.387 | 23.763 | −41.103 | 1.00 | 23.82 | B | O |
| ATOM | 8093 | N | ALA | B | 443 | 53.741 | 25.755 | −40.088 | 1.00 | 26.78 | B | N |
| ATOM | 8094 | CA | ALA | B | 443 | 52.788 | 26.481 | −40.938 | 1.00 | 25.34 | B | C |
| ATOM | 8095 | CB | ALA | B | 443 | 52.813 | 27.978 | −40.637 | 1.00 | 22.95 | B | C |
| ATOM | 8096 | C | ALA | B | 443 | 53.062 | 26.247 | −42.431 | 1.00 | 28.89 | B | C |
| ATOM | 8097 | O | ALA | B | 443 | 52.157 | 25.916 | −43.185 | 1.00 | 22.42 | B | O |
| ATOM | 8098 | N | SER | B | 444 | 54.300 | 26.458 | −42.868 | 1.00 | 27.66 | B | N |
| ATOM | 8099 | CA | SER | B | 444 | 54.589 | 26.373 | −44.312 | 1.00 | 33.85 | B | C |
| ATOM | 8100 | CB | SER | B | 444 | 56.058 | 26.640 | −44.598 | 1.00 | 36.92 | B | C |
| ATOM | 8101 | OG | SER | B | 444 | 56.346 | 28.011 | −44.385 | 1.00 | 47.06 | B | O |
| ATOM | 8102 | C | SER | B | 444 | 54.180 | 25.031 | −44.901 | 1.00 | 30.05 | B | C |
| ATOM | 8103 | O | SER | B | 444 | 53.466 | 24.980 | −45.900 | 1.00 | 30.05 | B | O |
| ATOM | 8104 | N | ALA | B | 445 | 54.602 | 23.945 | −44.263 | 1.00 | 29.24 | B | N |
| ATOM | 8105 | CA | ALA | B | 445 | 54.315 | 22.616 | −44.793 | 1.00 | 35.03 | B | C |
| ATOM | 8106 | CB | ALA | B | 445 | 55.129 | 21.522 | −44.045 | 1.00 | 32.05 | B | C |
| ATOM | 8107 | C | ALA | B | 445 | 52.807 | 22.332 | −44.755 | 1.00 | 37.09 | B | C |
| ATOM | 8108 | O | ALA | B | 445 | 52.257 | 21.787 | −45.704 | 1.00 | 33.84 | B | O |
| ATOM | 8109 | N | GLU | B | 446 | 52.124 | 22.734 | −43.685 | 1.00 | 30.46 | B | N |
| ATOM | 8110 | CA | GLU | B | 446 | 50.697 | 22.475 | −43.579 | 1.00 | 28.45 | B | C |
| ATOM | 8111 | CB | GLU | B | 446 | 50.218 | 22.656 | −42.139 | 1.00 | 37.91 | B | C |
| ATOM | 8112 | CG | GLU | B | 446 | 50.638 | 21.476 | −41.256 | 1.00 | 42.02 | B | C |
| ATOM | 8113 | CD | GLU | B | 446 | 50.457 | 21.692 | −39.740 | 1.00 | 42.41 | B | C |
| ATOM | 8114 | OE1 | GLU | B | 446 | 49.785 | 22.643 | −39.310 | 1.00 | 45.73 | B | O |
| ATOM | 8115 | OE2 | GLU | B | 446 | 51.005 | 20.887 | −38.958 | 1.00 | 43.12 | B | O |
| ATOM | 8116 | C | GLU | B | 446 | 49.890 | 23.315 | −44.573 | 1.00 | 33.90 | B | C |
| ATOM | 8117 | O | GLU | B | 446 | 48.937 | 22.819 | −45.169 | 1.00 | 31.66 | B | O |
| ATOM | 8118 | N | ILE | B | 447 | 50.293 | 24.568 | −44.794 | 1.00 | 27.20 | B | N |
| ATOM | 8119 | CA | ILE | B | 447 | 49.579 | 25.424 | −45.737 | 1.00 | 27.83 | B | C |
| ATOM | 8120 | CB | ILE | B | 447 | 50.055 | 26.895 | −45.659 | 1.00 | 28.75 | B | C |
| ATOM | 8121 | CG1 | ILE | B | 447 | 49.600 | 27.490 | −44.320 | 1.00 | 27.61 | B | C |
| ATOM | 8122 | CD1 | ILE | B | 447 | 50.393 | 28.640 | −43.844 | 1.00 | 26.97 | B | C |
| ATOM | 8123 | CG2 | ILE | B | 447 | 49.500 | 27.723 | −46.845 | 1.00 | 28.72 | B | C |
| ATOM | 8124 | C | ILE | B | 447 | 49.705 | 24.847 | −47.155 | 1.00 | 36.77 | B | C |
| ATOM | 8125 | O | ILE | B | 447 | 48.703 | 24.713 | −47.863 | 1.00 | 38.04 | B | O |
| ATOM | 8126 | N | ALA | B | 448 | 50.919 | 24.442 | −47.526 | 1.00 | 31.66 | B | N |
| ATOM | 8127 | CA | ALA | B | 448 | 51.194 | 23.890 | −48.854 | 1.00 | 36.12 | B | C |
| ATOM | 8128 | CB | ALA | B | 448 | 52.707 | 23.879 | −49.127 | 1.00 | 26.57 | B | C |
| ATOM | 8129 | C | ALA | B | 448 | 50.592 | 22.493 | −49.052 | 1.00 | 39.86 | B | C |
| ATOM | 8130 | O | ALA | B | 448 | 50.465 | 22.039 | −50.180 | 1.00 | 48.95 | B | O |

APPENDIX A-continued

P. alba 3T288C coordinates

| ATOM | 8131 | N | ARG | B | 449 | 50.238 | 21.817 | −47.960 | 1.00 | 40.90 | B | N |
|------|------|-----|-----|---|-----|--------|--------|---------|------|-------|---|---|
| ATOM | 8132 | CA | ARG | B | 449 | 49.462 | 20.574 | −48.014 | 1.00 | 43.27 | B | C |
| ATOM | 8133 | CB | ARG | B | 449 | 49.719 | 19.719 | −46.767 | 1.00 | 45.19 | B | C |
| ATOM | 8134 | CG | ARG | B | 449 | 50.845 | 18.718 | −46.901 | 1.00 | 46.47 | B | C |
| ATOM | 8135 | CD | ARG | B | 449 | 51.014 | 17.908 | −45.619 | 1.00 | 54.26 | B | C |
| ATOM | 8136 | NE | ARG | B | 449 | 52.120 | 18.386 | −44.785 | 1.00 | 65.38 | B | N |
| ATOM | 8137 | CZ | ARG | B | 449 | 52.152 | 18.377 | −43.446 | 1.00 | 64.14 | B | C |
| ATOM | 8138 | NH1 | ARG | B | 449 | 51.126 | 17.936 | −42.726 | 1.00 | 67.70 | B | N |
| ATOM | 8139 | NH2 | ARG | B | 449 | 53.228 | 18.834 | −42.814 | 1.00 | 67.87 | B | N |
| ATOM | 8140 | C | ARG | B | 449 | 47.954 | 20.814 | −48.115 | 1.00 | 44.23 | B | C |
| ATOM | 8141 | O | ARG | B | 449 | 47.186 | 19.862 | −48.221 | 1.00 | 47.36 | B | O |
| ATOM | 8142 | N | GLY | B | 450 | 47.519 | 22.065 | −48.044 | 1.00 | 42.67 | B | N |
| ATOM | 8143 | CA | GLY | B | 450 | 46.083 | 22.375 | −48.002 | 1.00 | 40.45 | B | C |
| ATOM | 8144 | C | GLY | B | 450 | 45.411 | 22.196 | −46.641 | 1.00 | 45.63 | B | C |
| ATOM | 8145 | O | GLY | B | 450 | 44.193 | 22.253 | −46.544 | 1.00 | 39.65 | B | O |
| ATOM | 8146 | N | GLU | B | 451 | 46.191 | 21.995 | −45.578 | 1.00 | 46.83 | B | N |
| ATOM | 8147 | CA | GLU | B | 451 | 45.620 | 21.874 | −44.236 | 1.00 | 43.73 | B | C |
| ATOM | 8148 | CB | GLU | B | 451 | 46.578 | 21.142 | −43.299 | 1.00 | 57.06 | B | C |
| ATOM | 8149 | CG | GLU | B | 451 | 46.765 | 19.683 | −43.695 | 1.00 | 61.57 | B | C |
| ATOM | 8150 | CD | GLU | B | 451 | 47.876 | 19.009 | −42.931 | 1.00 | 64.10 | B | C |
| ATOM | 8151 | OE1 | GLU | B | 451 | 47.993 | 19.254 | −41.714 | 1.00 | 65.34 | B | O |
| ATOM | 8152 | OE2 | GLU | B | 451 | 48.627 | 18.227 | −43.550 | 1.00 | 61.42 | B | O |
| ATOM | 8153 | C | GLU | B | 451 | 45.258 | 23.234 | −43.663 | 1.00 | 38.50 | B | C |
| ATOM | 8154 | O | GLU | B | 451 | 45.840 | 24.259 | −44.026 | 1.00 | 45.27 | B | O |
| ATOM | 8155 | N | THR | B | 452 | 44.258 | 23.246 | −42.793 | 1.00 | 31.58 | B | N |
| ATOM | 8156 | CA | THR | B | 452 | 43.761 | 24.488 | −42.242 | 1.00 | 31.96 | B | C |
| ATOM | 8157 | CB | THR | B | 452 | 42.312 | 24.772 | −42.689 | 1.00 | 34.79 | B | C |
| ATOM | 8158 | OG1 | THR | B | 452 | 41.462 | 23.731 | −42.199 | 1.00 | 34.40 | B | O |
| ATOM | 8159 | CG2 | THR | B | 452 | 42.202 | 24.905 | −44.225 | 1.00 | 30.65 | B | C |
| ATOM | 8160 | C | THR | B | 452 | 43.828 | 24.477 | −40.717 | 1.00 | 28.29 | B | C |
| ATOM | 8161 | O | THR | B | 452 | 43.566 | 25.508 | −40.090 | 1.00 | 28.98 | B | O |
| ATOM | 8162 | N | ALA | B | 453 | 44.223 | 23.337 | −40.135 | 1.00 | 29.72 | B | N |
| ATOM | 8163 | CA | ALA | B | 453 | 44.308 | 23.177 | −38.684 | 1.00 | 27.93 | B | C |
| ATOM | 8164 | CB | ALA | B | 453 | 44.159 | 21.712 | −38.293 | 1.00 | 26.92 | B | C |
| ATOM | 8165 | C | ALA | B | 453 | 45.650 | 23.716 | −38.179 | 1.00 | 31.25 | B | C |
| ATOM | 8166 | O | ALA | B | 453 | 46.482 | 22.957 | −37.723 | 1.00 | 25.19 | B | O |
| ATOM | 8167 | N | ASN | B | 454 | 45.828 | 25.023 | −38.276 | 1.00 | 23.93 | B | N |
| ATOM | 8168 | CA | ASN | B | 454 | 47.045 | 25.699 | −37.889 | 1.00 | 21.21 | B | C |
| ATOM | 8169 | CB | ASN | B | 454 | 48.083 | 25.582 | −39.014 | 1.00 | 21.74 | B | C |
| ATOM | 8170 | CG | ASN | B | 454 | 49.394 | 26.258 | −38.685 | 1.00 | 21.29 | B | C |
| ATOM | 8171 | OD1 | ASN | B | 454 | 49.513 | 27.465 | −38.794 | 1.00 | 22.92 | B | O |
| ATOM | 8172 | ND2 | ASN | B | 454 | 50.413 | 25.473 | −38.365 | 1.00 | 18.97 | B | N |
| ATOM | 8173 | C | ASN | B | 454 | 46.705 | 27.151 | −37.638 | 1.00 | 18.41 | B | C |
| ATOM | 8174 | O | ASN | B | 454 | 46.035 | 27.771 | −38.450 | 1.00 | 16.21 | B | O |
| ATOM | 8175 | N | SER | B | 455 | 47.221 | 27.711 | −36.543 | 1.00 | 19.01 | B | N |
| ATOM | 8176 | CA | SER | B | 455 | 47.002 | 29.113 | −36.202 | 1.00 | 16.68 | B | C |
| ATOM | 8177 | CB | SER | B | 455 | 47.781 | 29.488 | −34.921 | 1.00 | 20.45 | B | C |
| ATOM | 8178 | OG | SER | B | 455 | 47.301 | 28.678 | −33.853 | 1.00 | 19.49 | B | O |
| ATOM | 8179 | C | SER | B | 455 | 47.319 | 30.099 | −37.316 | 1.00 | 19.30 | B | C |
| ATOM | 8180 | O | SER | B | 455 | 46.540 | 31.034 | −37.548 | 1.00 | 15.67 | B | O |
| ATOM | 8181 | N | VAL | B | 456 | 48.432 | 29.915 | −38.024 | 1.00 | 15.11 | B | N |
| ATOM | 8182 | CA | VAL | B | 456 | 48.828 | 30.843 | −39.062 | 1.00 | 15.74 | B | C |
| ATOM | 8183 | CB | VAL | B | 456 | 50.299 | 30.596 | −39.541 | 1.00 | 19.50 | B | C |
| ATOM | 8184 | CG1 | VAL | B | 456 | 50.688 | 31.606 | −40.590 | 1.00 | 20.50 | B | C |
| ATOM | 8185 | CG2 | VAL | B | 456 | 51.251 | 30.648 | −38.368 | 1.00 | 15.54 | B | C |
| ATOM | 8186 | C | VAL | B | 456 | 47.852 | 30.763 | −40.237 | 1.00 | 16.05 | B | C |
| ATOM | 8187 | O | VAL | B | 456 | 47.410 | 31.785 | −40.806 | 1.00 | 14.34 | B | O |
| ATOM | 8188 | N | SER | B | 457 | 47.490 | 29.544 | −40.583 | 1.00 | 15.10 | B | N |
| ATOM | 8189 | CA | SER | B | 457 | 46.511 | 29.323 | −41.616 | 1.00 | 18.41 | B | C |
| ATOM | 8190 | CB | SER | B | 457 | 46.293 | 27.846 | −41.869 | 1.00 | 20.92 | B | C |
| ATOM | 8191 | OG | SER | B | 457 | 45.167 | 27.772 | −42.724 | 1.00 | 26.24 | B | O |
| ATOM | 8192 | C | SER | B | 457 | 45.158 | 29.949 | −41.284 | 1.00 | 17.65 | B | C |
| ATOM | 8193 | O | SER | B | 457 | 44.531 | 30.564 | −42.146 | 1.00 | 14.43 | B | O |
| ATOM | 8194 | N | CYS | B | 458 | 44.704 | 29.804 | −40.043 | 1.00 | 15.66 | B | N |
| ATOM | 8195 | CA | CYS | B | 458 | 43.444 | 30.453 | −39.640 | 1.00 | 18.01 | B | C |
| ATOM | 8196 | CB | CYS | B | 458 | 43.054 | 30.160 | −38.192 | 1.00 | 25.62 | B | C |
| ATOM | 8197 | SG | CYS | B | 458 | 42.256 | 28.699 | −38.041 | 1.00 | 35.73 | B | S |
| ATOM | 8198 | C | CYS | B | 458 | 43.517 | 31.929 | −39.741 | 1.00 | 12.07 | B | C |
| ATOM | 8199 | O | CYS | B | 458 | 42.566 | 32.557 | −40.176 | 1.00 | 16.64 | B | O |
| ATOM | 8200 | N | TYR | B | 459 | 44.629 | 32.503 | −39.306 | 1.00 | 14.40 | B | N |
| ATOM | 8201 | CA | TYR | B | 459 | 44.794 | 33.931 | −39.350 | 1.00 | 14.44 | B | C |
| ATOM | 8202 | CB | TYR | B | 459 | 46.096 | 34.315 | −38.667 | 1.00 | 17.94 | B | C |
| ATOM | 8203 | CG | TYR | B | 459 | 46.120 | 35.710 | −38.123 | 1.00 | 18.08 | B | C |
| ATOM | 8204 | CD1 | TYR | B | 459 | 46.388 | 36.781 | −38.958 | 1.00 | 23.82 | B | C |
| ATOM | 8205 | CE1 | TYR | B | 459 | 46.419 | 38.077 | −38.479 | 1.00 | 25.57 | B | C |
| ATOM | 8206 | CZ | TYR | B | 459 | 46.213 | 38.329 | −37.149 | 1.00 | 25.18 | B | C |
| ATOM | 8207 | OH | TYR | B | 459 | 46.262 | 39.634 | −36.748 | 1.00 | 37.10 | B | O |
| ATOM | 8208 | CE2 | TYR | B | 459 | 45.977 | 37.300 | −36.272 | 1.00 | 24.97 | B | C |

APPENDIX A-continued

*P. alba* 3T288C coordinates

| ATOM | 8209 | CD2 | TYR | B | 459 | 45.932 | 35.967 | −36.772 | 1.00 | 25.54 | B | C |
|---|---|---|---|---|---|---|---|---|---|---|---|---|
| ATOM | 8210 | C | TYR | B | 459 | 44.740 | 34.421 | −40.797 | 1.00 | 16.51 | B | C |
| ATOM | 8211 | O | TYR | B | 459 | 44.078 | 35.445 | −41.132 | 1.00 | 14.82 | B | O |
| ATOM | 8212 | N | MET | B | 460 | 45.433 | 33.718 | −41.686 | 1.00 | 13.76 | B | N |
| ATOM | 8213 | CA | MET | B | 460 | 45.348 | 34.057 | −43.117 | 1.00 | 14.07 | B | C |
| ATOM | 8214 | CB | MET | B | 460 | 46.056 | 33.032 | −44.002 | 1.00 | 15.60 | B | C |
| ATOM | 8215 | CG | MET | B | 460 | 47.540 | 33.067 | −43.937 | 1.00 | 21.56 | B | C |
| ATOM | 8216 | SD | MET | B | 460 | 48.225 | 31.608 | −44.774 | 1.00 | 24.76 | B | S |
| ATOM | 8217 | CE | MET | B | 460 | 47.831 | 31.926 | −46.477 | 1.00 | 15.99 | B | C |
| ATOM | 8218 | C | MET | B | 460 | 43.917 | 34.084 | −43.642 | 1.00 | 14.98 | B | C |
| ATOM | 8219 | O | MET | B | 460 | 43.527 | 34.991 | −44.393 | 1.00 | 15.96 | B | O |
| ATOM | 8220 | N | ARG | B | 461 | 43.162 | 33.048 | −43.329 | 1.00 | 13.68 | B | N |
| ATOM | 8221 | CA | ARG | B | 461 | 41.796 | 32.938 | −43.848 | 1.00 | 16.87 | B | C |
| ATOM | 8222 | CB | ARG | B | 461 | 41.283 | 31.518 | −43.727 | 1.00 | 23.77 | B | C |
| ATOM | 8223 | CG | ARG | B | 461 | 41.747 | 30.676 | −44.914 | 1.00 | 32.85 | B | C |
| ATOM | 8224 | CD | ARG | B | 461 | 41.446 | 29.197 | −44.770 | 1.00 | 34.57 | B | C |
| ATOM | 8225 | NE | ARG | B | 461 | 41.992 | 28.629 | −43.532 | 1.00 | 34.16 | B | N |
| ATOM | 8226 | CZ | ARG | B | 461 | 41.289 | 28.392 | −42.420 | 1.00 | 44.41 | B | C |
| ATOM | 8227 | NH1 | ARG | B | 461 | 39.972 | 28.674 | −42.354 | 1.00 | 33.15 | B | N |
| ATOM | 8228 | NH2 | ARG | B | 461 | 41.917 | 27.875 | −41.352 | 1.00 | 33.81 | B | N |
| ATOM | 8229 | C | ARG | B | 461 | 40.840 | 33.891 | −43.167 | 1.00 | 13.78 | B | C |
| ATOM | 8230 | O | ARG | B | 461 | 39.967 | 34.412 | −43.785 | 1.00 | 14.11 | B | O |
| ATOM | 8231 | N | THR | B | 462 | 41.018 | 34.106 | −41.875 | 1.00 | 13.65 | B | N |
| ATOM | 8232 | CA | THR | B | 462 | 40.207 | 35.071 | −41.150 | 1.00 | 12.52 | B | C |
| ATOM | 8233 | CB | THR | B | 462 | 40.442 | 34.981 | −39.640 | 1.00 | 11.17 | B | C |
| ATOM | 8234 | OG1 | THR | B | 462 | 39.831 | 33.778 | −39.180 | 1.00 | 10.66 | B | O |
| ATOM | 8235 | CG2 | THR | B | 462 | 39.844 | 36.207 | −38.911 | 1.00 | 10.76 | B | C |
| ATOM | 8236 | C | THR | B | 462 | 40.396 | 36.491 | −41.666 | 1.00 | 14.81 | B | C |
| ATOM | 8237 | O | THR | B | 462 | 39.421 | 37.173 | −41.877 | 1.00 | 13.55 | B | O |
| ATOM | 8238 | N | LYS | B | 463 | 41.631 | 36.921 | −41.872 | 1.00 | 16.92 | B | N |
| ATOM | 8239 | CA | ALYS | B | 463 | 41.919 | 38.298 | −42.288 | 0.50 | 16.81 | B | C |
| ATOM | 8240 | CA | BLYS | B | 463 | 41.908 | 38.302 | −42.277 | 0.50 | 16.46 | B | C |
| ATOM | 8241 | CB | ALYS | B | 463 | 43.207 | 38.775 | −41.647 | 0.50 | 17.82 | B | C |
| ATOM | 8242 | CB | BLYS | B | 463 | 43.179 | 38.803 | −41.607 | 0.50 | 16.89 | B | C |
| ATOM | 8243 | CG | ALYS | B | 463 | 43.039 | 39.156 | −40.201 | 0.50 | 20.60 | B | C |
| ATOM | 8244 | CG | BLYS | B | 463 | 43.217 | 38.634 | −40.073 | 0.50 | 18.51 | B | C |
| ATOM | 8245 | CD | ALYS | B | 463 | 42.486 | 40.556 | −40.116 | 0.50 | 20.99 | B | C |
| ATOM | 8246 | CD | BLYS | B | 463 | 42.193 | 39.525 | −39.394 | 0.50 | 19.15 | B | C |
| ATOM | 8247 | CE | ALYS | B | 463 | 42.523 | 41.081 | −38.718 | 0.50 | 19.52 | B | C |
| ATOM | 8248 | CE | BLYS | B | 463 | 42.692 | 40.035 | −38.046 | 0.50 | 21.93 | B | C |
| ATOM | 8249 | NZ | ALYS | B | 463 | 41.763 | 42.322 | −38.646 | 0.50 | 18.07 | B | N |
| ATOM | 8250 | NZ | BLYS | B | 463 | 42.390 | 39.101 | −36.923 | 0.50 | 22.18 | B | N |
| ATOM | 8251 | C | LYS | B | 463 | 42.015 | 38.480 | −43.794 | 1.00 | 15.05 | B | C |
| ATOM | 8252 | O | LYS | B | 463 | 42.054 | 39.591 | −44.284 | 1.00 | 18.45 | B | O |
| ATOM | 8253 | N | GLY | B | 464 | 42.040 | 37.393 | −44.535 | 1.00 | 15.19 | B | N |
| ATOM | 8254 | CA | GLY | B | 464 | 42.135 | 37.464 | −45.988 | 1.00 | 14.92 | B | C |
| ATOM | 8255 | C | GLY | B | 464 | 43.506 | 37.936 | −46.454 | 1.00 | 15.23 | B | C |
| ATOM | 8256 | O | GLY | B | 464 | 43.601 | 38.672 | −47.409 | 1.00 | 16.94 | B | O |
| ATOM | 8257 | N | ILE | B | 465 | 44.568 | 37.493 | −45.787 | 1.00 | 16.53 | B | N |
| ATOM | 8258 | CA | ILE | B | 465 | 45.947 | 37.941 | −46.099 | 1.00 | 15.71 | B | C |
| ATOM | 8259 | CB | ILE | B | 465 | 46.571 | 38.763 | −44.951 | 1.00 | 14.86 | B | C |
| ATOM | 8260 | CG1 | ILE | B | 465 | 46.690 | 37.925 | −43.667 | 1.00 | 15.16 | B | C |
| ATOM | 8261 | CD1 | ILE | B | 465 | 47.295 | 38.642 | −42.526 | 1.00 | 17.97 | B | C |
| ATOM | 8262 | CG2 | ILE | B | 465 | 45.772 | 40.069 | −44.760 | 1.00 | 15.44 | B | C |
| ATOM | 8263 | C | ILE | B | 465 | 46.884 | 36.782 | −46.442 | 1.00 | 16.44 | B | C |
| ATOM | 8264 | O | ILE | B | 465 | 46.605 | 35.603 | −46.158 | 1.00 | 17.69 | B | O |
| ATOM | 8265 | N | SER | B | 466 | 48.032 | 37.143 | −46.998 | 1.00 | 20.92 | B | N |
| ATOM | 8266 | CA | SER | B | 466 | 49.070 | 36.187 | −47.379 | 1.00 | 20.24 | B | C |
| ATOM | 8267 | CB | SER | B | 466 | 50.179 | 36.913 | −48.133 | 1.00 | 22.24 | B | C |
| ATOM | 8268 | OG | SER | B | 466 | 50.843 | 37.794 | −47.243 | 1.00 | 20.55 | B | O |
| ATOM | 8269 | C | SER | B | 466 | 49.711 | 35.550 | −46.160 | 1.00 | 19.68 | B | C |
| ATOM | 8270 | O | SER | B | 466 | 49.690 | 36.113 | −45.036 | 1.00 | 17.72 | B | O |
| ATOM | 8271 | N | GLU | B | 467 | 50.332 | 34.400 | −46.404 | 1.00 | 19.75 | B | N |
| ATOM | 8272 | CA | GLU | B | 467 | 51.117 | 33.716 | −45.403 | 1.00 | 24.19 | B | C |
| ATOM | 8273 | CB | GLU | B | 467 | 51.714 | 32.423 | −45.969 | 1.00 | 26.22 | B | C |
| ATOM | 8274 | CG | GLU | B | 467 | 52.518 | 31.664 | −44.911 | 1.00 | 29.10 | B | C |
| ATOM | 8275 | CD | GLU | B | 467 | 53.050 | 30.306 | −45.365 | 1.00 | 36.05 | B | C |
| ATOM | 8276 | OE1 | GLU | B | 467 | 52.638 | 29.809 | −46.434 | 1.00 | 35.86 | B | O |
| ATOM | 8277 | OE2 | GLU | B | 467 | 53.887 | 29.733 | −44.622 | 1.00 | 33.33 | B | O |
| ATOM | 8278 | C | GLU | B | 467 | 52.203 | 34.601 | −44.777 | 1.00 | 22.33 | B | C |
| ATOM | 8279 | O | GLU | B | 467 | 52.410 | 34.537 | −43.575 | 1.00 | 23.79 | B | O |
| ATOM | 8280 | N | GLU | B | 468 | 52.845 | 35.464 | −45.564 | 1.00 | 22.39 | B | N |
| ATOM | 8281 | CA | GLU | B | 468 | 53.918 | 36.330 | −45.038 | 1.00 | 27.65 | B | C |
| ATOM | 8282 | CB | GLU | B | 468 | 54.631 | 37.123 | −46.147 | 1.00 | 33.61 | B | C |
| ATOM | 8283 | CG | GLU | B | 468 | 55.397 | 36.289 | −47.150 | 1.00 | 50.09 | B | C |
| ATOM | 8284 | CD | GLU | B | 468 | 54.509 | 35.368 | −48.016 | 1.00 | 66.40 | B | C |
| ATOM | 8285 | OE1 | GLU | B | 468 | 53.401 | 35.772 | −48.447 | 1.00 | 49.17 | B | O |
| ATOM | 8286 | OE2 | GLU | B | 468 | 54.925 | 34.216 | −48.262 | 1.00 | 85.08 | B | O |

APPENDIX A-continued

P. alba 3T288C coordinates

| ATOM | 8287 | C | GLU | B | 468 | 53.358 | 37.328 | −44.049 | 1.00 | 21.77 | B | C |
|------|------|------|------|---|-----|--------|--------|---------|------|-------|---|---|
| ATOM | 8288 | O | GLU | B | 468 | 53.929 | 37.539 | −42.995 | 1.00 | 20.88 | B | O |
| ATOM | 8289 | N | LEU | B | 469 | 52.230 | 37.947 | −44.398 | 1.00 | 19.47 | B | N |
| ATOM | 8290 | CA | LEU | B | 469 | 51.601 | 38.915 | −43.508 | 1.00 | 19.05 | B | C |
| ATOM | 8291 | CB | LEU | B | 469 | 50.547 | 39.747 | −44.229 | 1.00 | 23.07 | B | C |
| ATOM | 8292 | CG | LEU | B | 469 | 51.089 | 40.827 | −45.164 | 1.00 | 29.43 | B | C |
| ATOM | 8293 | CD1 | LEU | B | 469 | 50.033 | 41.218 | −46.221 | 1.00 | 24.90 | B | C |
| ATOM | 8294 | CD2 | LEU | B | 469 | 51.578 | 42.023 | −44.341 | 1.00 | 33.35 | B | C |
| ATOM | 8295 | C | LEU | B | 469 | 50.998 | 38.235 | −42.269 | 1.00 | 16.57 | B | C |
| ATOM | 8296 | O | LEU | B | 469 | 51.095 | 38.760 | −41.196 | 1.00 | 16.59 | B | O |
| ATOM | 8297 | N | ALA | B | 470 | 50.414 | 37.059 | −42.417 | 1.00 | 16.46 | B | N |
| ATOM | 8298 | CA | ALA | B | 470 | 49.867 | 36.352 | −41.268 | 1.00 | 17.72 | B | C |
| ATOM | 8299 | CB | ALA | B | 470 | 49.099 | 35.112 | −41.714 | 1.00 | 14.43 | B | C |
| ATOM | 8300 | C | ALA | B | 470 | 51.005 | 35.984 | −40.307 | 1.00 | 19.08 | B | C |
| ATOM | 8301 | O | ALA | B | 470 | 50.889 | 36.125 | −39.090 | 1.00 | 16.48 | B | O |
| ATOM | 8302 | N | THR | B | 471 | 52.123 | 35.534 | −40.868 | 1.00 | 17.61 | B | N |
| ATOM | 8303 | CA | THR | B | 471 | 53.299 | 35.178 | −40.068 | 1.00 | 16.26 | B | C |
| ATOM | 8304 | CB | THR | B | 471 | 54.441 | 34.621 | −40.963 | 1.00 | 17.28 | B | C |
| ATOM | 8305 | OG1 | THR | B | 471 | 53.916 | 33.497 | −41.675 | 1.00 | 18.87 | B | O |
| ATOM | 8306 | CG2 | THR | B | 471 | 55.661 | 34.220 | −40.120 | 1.00 | 17.17 | B | C |
| ATOM | 8307 | C | THR | B | 471 | 53.800 | 36.342 | −39.244 | 1.00 | 17.20 | B | C |
| ATOM | 8308 | O | THR | B | 471 | 54.001 | 36.218 | −38.024 | 1.00 | 14.80 | B | O |
| ATOM | 8309 | N | GLU | B | 472 | 53.991 | 37.473 | −39.904 | 1.00 | 18.72 | B | N |
| ATOM | 8310 | CA | GLU | B | 472 | 54.323 | 38.729 | −39.230 | 1.00 | 23.12 | B | C |
| ATOM | 8311 | CB | GLU | B | 472 | 54.502 | 39.824 | −40.305 | 1.00 | 26.44 | B | C |
| ATOM | 8312 | CG | GLU | B | 472 | 54.573 | 41.278 | −39.863 | 1.00 | 37.27 | B | C |
| ATOM | 8313 | CD | GLU | B | 472 | 54.716 | 42.236 | −41.077 | 1.00 | 41.81 | B | C |
| ATOM | 8314 | OE1 | GLU | B | 472 | 55.849 | 42.428 | −41.548 | 1.00 | 46.89 | B | O |
| ATOM | 8315 | OE2 | GLU | B | 472 | 53.699 | 42.774 | −41.573 | 1.00 | 42.94 | B | O |
| ATOM | 8316 | C | GLU | B | 472 | 53.313 | 39.124 | −38.101 | 1.00 | 22.60 | B | C |
| ATOM | 8317 | O | GLU | B | 472 | 53.735 | 39.469 | −36.977 | 1.00 | 19.81 | B | O |
| ATOM | 8318 | N | SER | B | 473 | 52.007 | 39.018 | −38.360 | 1.00 | 19.86 | B | N |
| ATOM | 8319 | CA | SER | B | 473 | 51.014 | 39.293 | −37.299 | 1.00 | 20.06 | B | C |
| ATOM | 8320 | CB | SER | B | 473 | 49.572 | 39.208 | −37.815 | 1.00 | 22.53 | B | C |
| ATOM | 8321 | OG | SER | B | 473 | 49.304 | 40.264 | −38.673 | 1.00 | 29.40 | B | O |
| ATOM | 8322 | C | SER | B | 473 | 51.152 | 38.316 | −36.143 | 1.00 | 15.27 | B | C |
| ATOM | 8323 | O | SER | B | 473 | 51.038 | 38.697 | −35.001 | 1.00 | 17.14 | B | O |
| ATOM | 8324 | N | VAL | B | 474 | 51.398 | 37.055 | −36.438 | 1.00 | 15.88 | B | N |
| ATOM | 8325 | CA | VAL | B | 474 | 51.594 | 36.093 | −35.377 | 1.00 | 15.12 | B | C |
| ATOM | 8326 | CB | VAL | B | 474 | 51.608 | 34.665 | −35.926 | 1.00 | 15.21 | B | C |
| ATOM | 8327 | CG1 | VAL | B | 474 | 52.067 | 33.652 | −34.800 | 1.00 | 13.14 | B | C |
| ATOM | 8328 | CG2 | VAL | B | 474 | 50.228 | 34.299 | −36.427 | 1.00 | 15.92 | B | C |
| ATOM | 8329 | C | VAL | B | 474 | 52.846 | 36.414 | −34.522 | 1.00 | 15.98 | B | C |
| ATOM | 8330 | O | VAL | B | 474 | 52.795 | 36.410 | −33.272 | 1.00 | 16.50 | B | O |
| ATOM | 8331 | N | MET | B | 475 | 53.934 | 36.796 | −35.165 | 1.00 | 19.87 | B | N |
| ATOM | 8332 | CA | MET | B | 475 | 55.127 | 37.241 | −34.424 | 1.00 | 18.38 | B | C |
| ATOM | 8333 | CB | MET | B | 475 | 56.282 | 37.591 | −35.376 | 1.00 | 21.15 | B | C |
| ATOM | 8334 | CG | MET | B | 475 | 56.744 | 36.508 | −36.344 | 1.00 | 31.58 | B | C |
| ATOM | 8335 | SD | MET | B | 475 | 57.511 | 35.151 | −35.483 | 1.00 | 49.68 | B | S |
| ATOM | 8336 | CE | MET | B | 475 | 58.323 | 34.357 | −36.907 | 1.00 | 50.34 | B | C |
| ATOM | 8337 | C | MET | B | 475 | 54.842 | 38.479 | −33.552 | 1.00 | 22.82 | B | C |
| ATOM | 8338 | O | MET | B | 475 | 55.349 | 38.556 | −32.430 | 1.00 | 19.84 | B | O |
| ATOM | 8339 | N | ASN | B | 476 | 54.046 | 39.440 | −34.052 | 1.00 | 17.77 | B | N |
| ATOM | 8340 | CA | ASN | B | 476 | 53.659 | 40.582 | −33.228 | 1.00 | 18.07 | B | C |
| ATOM | 8341 | CB | ASN | B | 476 | 52.880 | 41.650 | −34.014 | 1.00 | 23.11 | B | C |
| ATOM | 8342 | CG | ASN | B | 476 | 53.723 | 42.332 | −35.068 | 1.00 | 29.55 | B | C |
| ATOM | 8343 | OD1 | ASN | B | 476 | 54.943 | 42.257 | −35.033 | 1.00 | 28.97 | B | O |
| ATOM | 8344 | ND2 | ASN | B | 476 | 53.068 | 43.011 | −36.025 | 1.00 | 29.79 | B | N |
| ATOM | 8345 | C | ASN | B | 476 | 52.819 | 40.151 | −32.047 | 1.00 | 18.90 | B | C |
| ATOM | 8346 | O | ASN | B | 476 | 52.973 | 40.698 | −30.950 | 1.00 | 18.05 | B | O |
| ATOM | 8347 | N | LEU | B | 477 | 51.924 | 39.177 | −32.261 | 1.00 | 17.13 | B | N |
| ATOM | 8348 | CA | LEU | B | 477 | 51.104 | 38.673 | −31.160 | 1.00 | 18.26 | B | C |
| ATOM | 8349 | CB | LEU | B | 477 | 50.109 | 37.654 | −31.688 | 1.00 | 20.23 | B | C |
| ATOM | 8350 | CG | LEU | B | 477 | 49.119 | 37.025 | −30.729 | 1.00 | 28.85 | B | C |
| ATOM | 8351 | CD1 | LEU | B | 477 | 48.451 | 38.109 | −29.830 | 1.00 | 27.90 | B | C |
| ATOM | 8352 | CD2 | LEU | B | 477 | 48.055 | 36.211 | −31.571 | 1.00 | 22.42 | B | C |
| ATOM | 8353 | C | LEU | B | 477 | 51.985 | 38.048 | −30.058 | 1.00 | 14.52 | B | C |
| ATOM | 8354 | O | LEU | B | 477 | 51.742 | 38.219 | −28.855 | 1.00 | 15.43 | B | O |
| ATOM | 8355 | N | ILE | B | 478 | 53.007 | 37.305 | −30.478 | 1.00 | 16.26 | B | N |
| ATOM | 8356 | CA | ILE | B | 478 | 53.996 | 36.766 | −29.538 | 1.00 | 14.82 | B | C |
| ATOM | 8357 | CB | ILE | B | 478 | 55.024 | 35.865 | −30.248 | 1.00 | 15.10 | B | C |
| ATOM | 8358 | CG1 | ILE | B | 478 | 54.300 | 34.569 | −30.691 | 1.00 | 15.74 | B | C |
| ATOM | 8359 | CD1 | ILE | B | 478 | 55.145 | 33.621 | −31.585 | 1.00 | 18.13 | B | C |
| ATOM | 8360 | CG2 | ILE | B | 478 | 56.258 | 35.554 | −29.342 | 1.00 | 13.94 | B | C |
| ATOM | 8361 | C | ILE | B | 478 | 54.660 | 37.904 | −28.752 | 1.00 | 14.69 | B | C |
| ATOM | 8362 | O | ILE | B | 478 | 54.752 | 37.795 | −27.524 | 1.00 | 15.56 | B | O |
| ATOM | 8363 | N | ASP | B | 479 | 55.094 | 38.980 | −29.430 | 1.00 | 14.82 | B | N |
| ATOM | 8364 | CA | ASP | B | 479 | 55.705 | 40.149 | −28.738 | 1.00 | 15.47 | B | C |

APPENDIX A-continued

*P. alba* 3T288C coordinates

| ATOM | 8365 | CB | ASP | B | 479 | 56.139 | 41.213 | −29.742 | 1.00 | 22.03 | B | C |
|---|---|---|---|---|---|---|---|---|---|---|---|---|
| ATOM | 8366 | CG | ASP | B | 479 | 57.356 | 40.787 | −30.542 | 1.00 | 30.54 | B | C |
| ATOM | 8367 | OD1 | ASP | B | 479 | 58.065 | 39.847 | −30.114 | 1.00 | 31.87 | B | O |
| ATOM | 8368 | OD2 | ASP | B | 479 | 57.612 | 41.393 | −31.600 | 1.00 | 30.28 | B | O |
| ATOM | 8369 | C | ASP | B | 479 | 54.781 | 40.779 | −27.692 | 1.00 | 16.99 | B | C |
| ATOM | 8370 | O | ASP | B | 479 | 55.185 | 41.056 | −26.563 | 1.00 | 16.06 | B | O |
| ATOM | 8371 | N | GLU | B | 480 | 53.531 | 41.003 | −28.073 | 1.00 | 16.84 | B | N |
| ATOM | 8372 | CA | GLU | B | 480 | 52.565 | 41.593 | −27.173 | 1.00 | 17.96 | B | C |
| ATOM | 8373 | CB | GLU | B | 480 | 51.256 | 41.896 | −27.927 | 1.00 | 19.41 | B | C |
| ATOM | 8374 | CG | GLU | B | 480 | 51.372 | 43.053 | −28.936 | 1.00 | 30.52 | B | C |
| ATOM | 8375 | CD | GLU | B | 480 | 51.945 | 44.350 | −28.305 | 1.00 | 34.11 | B | C |
| ATOM | 8376 | OE1 | GLU | B | 480 | 51.388 | 44.805 | −27.282 | 1.00 | 36.99 | B | O |
| ATOM | 8377 | OE2 | GLU | B | 480 | 52.974 | 44.879 | −28.796 | 1.00 | 41.37 | B | O |
| ATOM | 8378 | C | GLU | B | 480 | 52.305 | 40.686 | −25.974 | 1.00 | 17.57 | B | C |
| ATOM | 8379 | O | GLU | B | 480 | 52.169 | 41.164 | −24.855 | 1.00 | 15.62 | B | O |
| ATOM | 8380 | N | THR | B | 481 | 52.256 | 39.375 | −26.206 | 1.00 | 14.91 | B | N |
| ATOM | 8381 | CA | THR | B | 481 | 52.072 | 38.432 | −25.121 | 1.00 | 16.01 | B | C |
| ATOM | 8382 | CB | THR | B | 481 | 51.847 | 37.006 | −25.655 | 1.00 | 16.05 | B | C |
| ATOM | 8383 | OG1 | THR | B | 481 | 50.733 | 37.017 | −26.574 | 1.00 | 19.54 | B | O |
| ATOM | 8384 | CG2 | THR | B | 481 | 51.550 | 36.061 | −24.491 | 1.00 | 18.71 | B | C |
| ATOM | 8385 | C | THR | B | 481 | 53.248 | 38.456 | −24.151 | 1.00 | 16.16 | B | C |
| ATOM | 8386 | O | THR | B | 481 | 53.053 | 38.430 | −22.954 | 1.00 | 16.06 | B | O |
| ATOM | 8387 | N | TRP | B | 482 | 54.467 | 38.549 | −24.655 | 1.00 | 13.23 | B | N |
| ATOM | 8388 | CA | TRP | B | 482 | 55.602 | 38.694 | −23.776 | 1.00 | 13.54 | B | C |
| ATOM | 8389 | CB | TRP | B | 482 | 56.897 | 38.722 | −24.586 | 1.00 | 14.51 | B | C |
| ATOM | 8390 | CG | TRP | B | 482 | 57.515 | 37.346 | −24.682 | 1.00 | 17.52 | B | C |
| ATOM | 8391 | CD1 | TRP | B | 482 | 57.458 | 36.446 | −25.752 | 1.00 | 16.21 | B | C |
| ATOM | 8392 | NE1 | TRP | B | 482 | 58.141 | 35.294 | −25.441 | 1.00 | 16.16 | B | N |
| ATOM | 8393 | CE2 | TRP | B | 482 | 58.681 | 35.367 | −24.216 | 1.00 | 17.21 | B | C |
| ATOM | 8394 | CD2 | TRP | B | 482 | 58.306 | 36.670 | −23.656 | 1.00 | 14.61 | B | C |
| ATOM | 8395 | CE3 | TRP | B | 482 | 58.749 | 37.006 | −22.375 | 1.00 | 18.50 | B | C |
| ATOM | 8396 | CZ3 | TRP | B | 482 | 59.537 | 36.077 | −21.674 | 1.00 | 18.54 | B | C |
| ATOM | 8397 | CH2 | TRP | B | 482 | 59.853 | 34.823 | −22.214 | 1.00 | 17.57 | B | C |
| ATOM | 8398 | CZ2 | TRP | B | 482 | 59.437 | 34.443 | −23.492 | 1.00 | 16.54 | B | C |
| ATOM | 8399 | C | TRP | B | 482 | 55.518 | 39.936 | −22.906 | 1.00 | 14.61 | B | C |
| ATOM | 8400 | O | TRP | B | 482 | 55.886 | 39.903 | −21.742 | 1.00 | 15.95 | B | O |
| ATOM | 8401 | N | LYS | B | 483 | 55.022 | 41.024 | −23.453 | 1.00 | 14.90 | B | N |
| ATOM | 8402 | CA | LYS | B | 483 | 54.925 | 42.281 | −22.674 | 1.00 | 16.98 | B | C |
| ATOM | 8403 | CB | LYS | B | 483 | 54.442 | 43.426 | −23.532 | 1.00 | 17.74 | B | C |
| ATOM | 8404 | CG | LYS | B | 483 | 55.379 | 43.817 | −24.655 | 1.00 | 20.23 | B | C |
| ATOM | 8405 | CD | LYS | B | 483 | 54.759 | 44.930 | −25.530 | 1.00 | 21.43 | B | C |
| ATOM | 8406 | CE | LYS | B | 483 | 55.736 | 45.408 | −26.595 | 1.00 | 21.93 | B | C |
| ATOM | 8407 | NZ | LYS | B | 483 | 55.119 | 46.410 | −27.482 | 1.00 | 28.30 | B | N |
| ATOM | 8408 | C | LYS | B | 483 | 54.016 | 42.105 | −21.489 | 1.00 | 17.58 | B | C |
| ATOM | 8409 | O | LYS | B | 483 | 54.306 | 42.584 | −20.391 | 1.00 | 16.44 | B | O |
| ATOM | 8410 | N | LYS | B | 484 | 52.959 | 41.332 | −21.697 | 1.00 | 18.31 | B | N |
| ATOM | 8411 | CA | LYS | B | 484 | 52.006 | 41.058 | −20.654 | 1.00 | 17.54 | B | C |
| ATOM | 8412 | CB | LYS | B | 484 | 50.691 | 40.578 | −21.275 | 1.00 | 21.90 | B | C |
| ATOM | 8413 | CG | LYS | B | 484 | 50.042 | 41.658 | −22.116 | 1.00 | 26.76 | B | C |
| ATOM | 8414 | CD | LYS | B | 484 | 48.735 | 41.239 | −22.728 | 1.00 | 34.55 | B | C |
| ATOM | 8415 | CE | LYS | B | 484 | 48.116 | 42.432 | −23.459 | 1.00 | 38.13 | B | C |
| ATOM | 8416 | NZ | LYS | B | 484 | 47.234 | 41.967 | −24.542 | 1.00 | 66.26 | B | N |
| ATOM | 8417 | C | LYS | B | 484 | 52.550 | 40.099 | −19.605 | 1.00 | 19.69 | B | C |
| ATOM | 8418 | O | LYS | B | 484 | 52.321 | 40.274 | −18.425 | 1.00 | 17.32 | B | O |
| ATOM | 8419 | N | MET | B | 485 | 53.344 | 39.130 | −20.033 | 1.00 | 17.84 | B | N |
| ATOM | 8420 | CA | MET | B | 485 | 53.991 | 38.211 | −19.107 | 1.00 | 16.90 | B | C |
| ATOM | 8421 | CB | MET | B | 485 | 54.695 | 37.076 | −19.873 | 1.00 | 16.46 | B | C |
| ATOM | 8422 | CG | MET | B | 485 | 53.741 | 36.144 | −20.549 | 1.00 | 19.65 | B | C |
| ATOM | 8423 | SD | MET | B | 485 | 54.501 | 34.543 | −20.977 | 1.00 | 23.37 | B | S |
| ATOM | 8424 | CE | MET | B | 485 | 55.900 | 35.004 | −22.009 | 1.00 | 19.59 | B | C |
| ATOM | 8425 | C | MET | B | 485 | 55.001 | 38.974 | −18.294 | 1.00 | 16.66 | B | C |
| ATOM | 8426 | O | MET | B | 485 | 55.185 | 38.669 | −17.118 | 1.00 | 18.87 | B | O |
| ATOM | 8427 | N | ASN | B | 486 | 55.686 | 39.927 | −18.931 | 1.00 | 18.20 | B | N |
| ATOM | 8428 | CA | ASN | B | 486 | 56.694 | 40.724 | −18.231 | 1.00 | 19.00 | B | C |
| ATOM | 8429 | CB | ASN | B | 486 | 57.437 | 41.646 | −19.175 | 1.00 | 17.48 | B | C |
| ATOM | 8430 | CG | ASN | B | 486 | 58.421 | 40.912 | −20.103 | 1.00 | 16.17 | B | C |
| ATOM | 8431 | OD1 | ASN | B | 486 | 58.786 | 39.783 | −19.864 | 1.00 | 15.97 | B | O |
| ATOM | 8432 | ND2 | ASN | B | 486 | 58.821 | 41.580 | −21.198 | 1.00 | 14.17 | B | N |
| ATOM | 8433 | C | ASN | B | 486 | 56.051 | 41.538 | −17.090 | 1.00 | 19.96 | B | C |
| ATOM | 8434 | O | ASN | B | 486 | 56.617 | 41.623 | −15.996 | 1.00 | 20.11 | B | O |
| ATOM | 8435 | N | LYS | B | 487 | 54.873 | 42.112 | −17.348 | 1.00 | 19.54 | B | N |
| ATOM | 8436 | CA | LYS | B | 487 | 54.162 | 42.870 | −16.322 | 1.00 | 22.85 | B | C |
| ATOM | 8437 | CB | LYS | B | 487 | 52.925 | 43.572 | −16.867 | 1.00 | 26.20 | B | C |
| ATOM | 8438 | CG | LYS | B | 487 | 52.250 | 44.443 | −15.810 | 1.00 | 33.19 | B | C |
| ATOM | 8439 | CD | LYS | B | 487 | 51.323 | 45.475 | −16.438 | 1.00 | 44.95 | B | C |
| ATOM | 8440 | CE | LYS | B | 487 | 50.482 | 46.180 | −15.378 | 1.00 | 51.82 | B | C |
| ATOM | 8441 | NZ | LYS | B | 487 | 49.214 | 46.702 | −15.950 | 1.00 | 58.53 | B | N |
| ATOM | 8442 | C | LYS | B | 487 | 53.731 | 41.979 | −15.176 | 1.00 | 23.67 | B | C |

APPENDIX A-continued

*P. alba* 3T288C coordinates

| ATOM | 8443 | O | LYS | B | 487 | 53.802 | 42.377 | −14.020 | 1.00 | 25.23 | B | O |
|---|---|---|---|---|---|---|---|---|---|---|---|---|
| ATOM | 8444 | N | GLU | B | 488 | 53.284 | 40.779 | −15.496 | 1.00 | 23.22 | B | N |
| ATOM | 8445 | CA | GLU | B | 488 | 52.847 | 39.837 | −14.480 | 1.00 | 26.06 | B | C |
| ATOM | 8446 | CB | GLU | B | 488 | 52.305 | 38.562 | −15.152 | 1.00 | 29.47 | B | C |
| ATOM | 8447 | CG | GLU | B | 488 | 51.579 | 37.591 | −14.230 | 1.00 | 34.00 | B | C |
| ATOM | 8448 | CD | GLU | B | 488 | 50.172 | 38.088 | −13.807 | 1.00 | 43.28 | B | C |
| ATOM | 8449 | OE1 | GLU | B | 488 | 49.541 | 38.871 | −14.550 | 1.00 | 42.03 | B | O |
| ATOM | 8450 | OE2 | GLU | B | 488 | 49.697 | 37.699 | −12.724 | 1.00 | 49.73 | B | O |
| ATOM | 8451 | C | GLU | B | 488 | 54.001 | 39.482 | −13.525 | 1.00 | 24.22 | B | C |
| ATOM | 8452 | O | GLU | B | 488 | 53.818 | 39.397 | −12.309 | 1.00 | 23.72 | B | O |
| ATOM | 8453 | N | LYS | B | 489 | 55.186 | 39.255 | −14.078 | 1.00 | 20.78 | B | N |
| ATOM | 8454 | CA | LYS | B | 489 | 56.346 | 38.886 | −13.283 | 1.00 | 19.45 | B | C |
| ATOM | 8455 | CB | LYS | B | 489 | 57.493 | 38.501 | −14.207 | 1.00 | 19.09 | B | C |
| ATOM | 8456 | CG | LYS | B | 489 | 58.778 | 38.061 | −13.510 | 1.00 | 22.98 | B | C |
| ATOM | 8457 | CD | LYS | B | 489 | 58.559 | 36.815 | −12.685 | 1.00 | 25.02 | B | C |
| ATOM | 8458 | CE | LYS | B | 489 | 59.697 | 36.599 | −11.687 | 1.00 | 24.62 | B | C |
| ATOM | 8459 | NZ | LYS | B | 489 | 60.996 | 36.422 | −12.344 | 1.00 | 20.33 | B | N |
| ATOM | 8460 | C | LYS | B | 489 | 56.829 | 40.035 | −12.368 | 1.00 | 22.49 | B | C |
| ATOM | 8461 | O | LYS | B | 489 | 57.313 | 39.801 | −11.257 | 1.00 | 24.69 | B | O |
| ATOM | 8462 | N | LEU | B | 490 | 56.739 | 41.259 | −12.876 | 1.00 | 28.37 | B | N |
| ATOM | 8463 | CA | LEU | B | 490 | 57.153 | 42.446 | −12.137 | 1.00 | 31.85 | B | C |
| ATOM | 8464 | CB | LEU | B | 490 | 57.239 | 43.646 | −13.072 | 1.00 | 28.43 | B | C |
| ATOM | 8465 | CG | LEU | B | 490 | 58.610 | 43.878 | −13.638 | 1.00 | 37.28 | B | C |
| ATOM | 8466 | CD1 | LEU | B | 490 | 58.501 | 44.897 | −14.750 | 1.00 | 36.27 | B | C |
| ATOM | 8467 | CD2 | LEU | B | 490 | 59.540 | 44.358 | −12.493 | 1.00 | 31.43 | B | C |
| ATOM | 8468 | C | LEU | B | 490 | 56.135 | 42.821 | −11.107 | 1.00 | 38.82 | B | C |
| ATOM | 8469 | O | LEU | B | 490 | 56.482 | 43.239 | −10.009 | 1.00 | 48.72 | B | O |
| ATOM | 8470 | N | GLY | B | 491 | 54.877 | 42.694 | −11.516 | 1.00 | 44.34 | B | N |
| ATOM | 8471 | CA | GLY | B | 491 | 53.764 | 43.360 | −10.897 | 1.00 | 53.36 | B | C |
| ATOM | 8472 | C | GLY | B | 491 | 53.198 | 42.581 | −9.749 | 1.00 | 65.53 | B | C |
| ATOM | 8473 | O | GLY | B | 491 | 53.934 | 42.042 | −8.924 | 1.00 | 88.54 | B | O |
| ATOM | 8474 | N | GLY | B | 492 | 51.880 | 42.525 | −9.691 | 1.00 | 68.71 | B | N |
| ATOM | 8475 | CA | GLY | B | 492 | 51.217 | 42.067 | −8.490 | 1.00 | 75.80 | B | C |
| ATOM | 8476 | C | GLY | B | 492 | 50.470 | 40.803 | −8.777 | 1.00 | 67.99 | B | C |
| ATOM | 8477 | O | GLY | B | 492 | 49.253 | 40.743 | −8.594 | 1.00 | 62.39 | B | O |
| ATOM | 8478 | N | SER | B | 493 | 51.179 | 39.784 | −9.244 | 1.00 | 58.58 | B | N |
| ATOM | 8479 | CA | SER | B | 493 | 50.486 | 38.539 | −9.522 | 1.00 | 58.70 | B | C |
| ATOM | 8480 | CB | SER | B | 493 | 51.395 | 37.458 | −10.150 | 1.00 | 58.29 | B | C |
| ATOM | 8481 | OG | SER | B | 493 | 50.630 | 36.373 | −10.739 | 1.00 | 37.84 | B | O |
| ATOM | 8482 | C | SER | B | 493 | 49.858 | 38.034 | −8.219 | 1.00 | 52.46 | B | C |
| ATOM | 8483 | O | SER | B | 493 | 50.355 | 38.275 | −7.110 | 1.00 | 44.13 | B | O |
| ATOM | 8484 | N | LEU | B | 494 | 48.728 | 37.372 | −8.397 | 1.00 | 43.71 | B | N |
| ATOM | 8485 | CA | LEU | B | 494 | 48.161 | 36.479 | −7.423 | 1.00 | 40.14 | B | C |
| ATOM | 8486 | CB | LEU | B | 494 | 46.941 | 35.833 | −8.075 | 1.00 | 46.56 | B | C |
| ATOM | 8487 | CG | LEU | B | 494 | 46.008 | 34.991 | −7.227 | 1.00 | 49.26 | B | C |
| ATOM | 8488 | CD1 | LEU | B | 494 | 45.033 | 35.910 | −6.522 | 1.00 | 65.09 | B | C |
| ATOM | 8489 | CD2 | LEU | B | 494 | 45.281 | 34.031 | −8.111 | 1.00 | 48.58 | B | C |
| ATOM | 8490 | C | LEU | B | 494 | 49.196 | 35.414 | −7.023 | 1.00 | 39.04 | B | C |
| ATOM | 8491 | O | LEU | B | 494 | 49.296 | 35.040 | −5.855 | 1.00 | 41.27 | B | O |
| ATOM | 8492 | N | PHE | B | 495 | 50.001 | 34.956 | −7.985 | 1.00 | 28.85 | B | N |
| ATOM | 8493 | CA | PHE | B | 495 | 50.954 | 33.855 | −7.746 | 1.00 | 26.55 | B | C |
| ATOM | 8494 | CB | PHE | B | 495 | 51.106 | 33.021 | −9.026 | 1.00 | 22.08 | B | C |
| ATOM | 8495 | CG | PHE | B | 495 | 49.857 | 32.286 | −9.410 | 1.00 | 20.12 | B | C |
| ATOM | 8496 | CD1 | PHE | B | 495 | 48.909 | 32.889 | −10.218 | 1.00 | 22.68 | B | C |
| ATOM | 8497 | CE1 | PHE | B | 495 | 47.742 | 32.225 | −10.575 | 1.00 | 27.54 | B | C |
| ATOM | 8498 | CZ | PHE | B | 495 | 47.519 | 30.929 | −10.131 | 1.00 | 31.42 | B | C |
| ATOM | 8499 | CE2 | PHE | B | 495 | 48.466 | 30.309 | −9.333 | 1.00 | 24.27 | B | C |
| ATOM | 8500 | CD2 | PHE | B | 495 | 49.637 | 30.998 | −8.973 | 1.00 | 23.92 | B | C |
| ATOM | 8501 | C | PHE | B | 495 | 52.333 | 34.332 | −7.286 | 1.00 | 25.17 | B | C |
| ATOM | 8502 | O | PHE | B | 495 | 52.749 | 35.423 | −7.626 | 1.00 | 26.71 | B | O |
| ATOM | 8503 | N | ALA | B | 496 | 53.042 | 33.486 | −6.552 | 1.00 | 30.68 | B | N |
| ATOM | 8504 | CA | ALA | B | 496 | 54.394 | 33.797 | −6.122 | 1.00 | 39.90 | B | C |
| ATOM | 8505 | CB | ALA | B | 496 | 54.884 | 32.751 | −5.097 | 1.00 | 34.91 | B | C |
| ATOM | 8506 | C | ALA | B | 496 | 55.318 | 33.849 | −7.351 | 1.00 | 44.23 | B | C |
| ATOM | 8507 | O | ALA | B | 496 | 55.126 | 33.089 | −8.305 | 1.00 | 32.16 | B | O |
| ATOM | 8508 | N | LYS | B | 497 | 56.314 | 34.737 | −7.307 | 1.00 | 39.12 | B | N |
| ATOM | 8509 | CA | LYS | B | 497 | 57.260 | 34.937 | −8.406 | 1.00 | 40.13 | B | C |
| ATOM | 8510 | CB | LYS | B | 497 | 58.315 | 36.017 | −8.053 | 1.00 | 40.35 | B | C |
| ATOM | 8511 | CG | LYS | B | 497 | 57.805 | 37.487 | −8.172 | 1.00 | 46.61 | B | C |
| ATOM | 8512 | CD | LYS | B | 497 | 58.913 | 38.495 | −7.741 | 1.00 | 50.16 | B | C |
| ATOM | 8513 | CE | LYS | B | 497 | 58.560 | 39.989 | −7.960 | 1.00 | 58.07 | B | C |
| ATOM | 8514 | NZ | LYS | B | 497 | 59.154 | 40.584 | −9.230 | 1.00 | 51.75 | B | N |
| ATOM | 8515 | C | LYS | B | 497 | 57.928 | 33.648 | −8.951 | 1.00 | 33.09 | B | C |
| ATOM | 8516 | O | LYS | B | 497 | 58.100 | 33.541 | −10.154 | 1.00 | 32.79 | B | O |
| ATOM | 8517 | N | PRO | B | 498 | 58.272 | 32.666 | −8.097 | 1.00 | 34.88 | B | N |
| ATOM | 8518 | CA | PRO | B | 498 | 58.857 | 31.424 | −8.626 | 1.00 | 34.68 | B | C |
| ATOM | 8519 | CB | PRO | B | 498 | 59.171 | 30.602 | −7.371 | 1.00 | 31.62 | B | C |
| ATOM | 8520 | CG | PRO | B | 498 | 59.308 | 31.635 | −6.278 | 1.00 | 33.00 | B | C |

APPENDIX A-continued

*P. alba* 3T288C coordinates

| ATOM | 8521 | CD | PRO | B | 498 | 58.349 | 32.723 | −6.621 | 1.00 | 37.97 | B | C |
|------|------|-----|-----|---|-----|--------|--------|---------|------|-------|---|---|
| ATOM | 8522 | C | PRO | B | 498 | 57.935 | 30.611 | −9.535 | 1.00 | 33.03 | B | C |
| ATOM | 8523 | O | PRO | B | 498 | 58.401 | 30.016 | −10.490 | 1.00 | 29.69 | B | O |
| ATOM | 8524 | N | PHE | B | 499 | 56.641 | 30.575 | −9.242 | 1.00 | 26.45 | B | N |
| ATOM | 8525 | CA | PHE | B | 499 | 55.722 | 29.917 | −10.144 | 1.00 | 23.83 | B | C |
| ATOM | 8526 | CB | PHE | B | 499 | 54.387 | 29.588 | −9.476 | 1.00 | 23.35 | B | C |
| ATOM | 8527 | CG | PHE | B | 499 | 53.423 | 28.939 | −10.407 | 1.00 | 22.11 | B | C |
| ATOM | 8528 | CD1 | PHE | B | 499 | 53.633 | 27.653 | −10.857 | 1.00 | 23.76 | B | C |
| ATOM | 8529 | CE1 | PHE | B | 499 | 52.736 | 27.068 | −11.742 | 1.00 | 23.42 | B | C |
| ATOM | 8530 | CZ | PHE | B | 499 | 51.648 | 27.756 | −12.177 | 1.00 | 20.10 | B | C |
| ATOM | 8531 | CE2 | PHE | B | 499 | 51.450 | 29.024 | −11.762 | 1.00 | 22.67 | B | C |
| ATOM | 8532 | CD2 | PHE | B | 499 | 52.338 | 29.624 | −10.882 | 1.00 | 22.37 | B | C |
| ATOM | 8533 | C | PHE | B | 499 | 55.487 | 30.763 | −11.390 | 1.00 | 18.06 | B | C |
| ATOM | 8534 | O | PHE | B | 499 | 55.382 | 30.219 | −12.471 | 1.00 | 21.21 | B | O |
| ATOM | 8535 | N | VAL | B | 500 | 55.413 | 32.083 | −11.247 | 1.00 | 17.55 | B | N |
| ATOM | 8536 | CA | VAL | B | 500 | 55.247 | 32.942 | −12.418 | 1.00 | 19.54 | B | C |
| ATOM | 8537 | CB | VAL | B | 500 | 55.106 | 34.462 | −12.096 | 1.00 | 23.69 | B | C |
| ATOM | 8538 | CG1 | VAL | B | 500 | 54.996 | 35.282 | −13.401 | 1.00 | 18.81 | B | C |
| ATOM | 8539 | CG2 | VAL | B | 500 | 53.876 | 34.723 | −11.201 | 1.00 | 24.37 | B | C |
| ATOM | 8540 | C | VAL | B | 500 | 56.397 | 32.687 | −13.374 | 1.00 | 19.76 | B | C |
| ATOM | 8541 | O | VAL | B | 500 | 56.198 | 32.551 | −14.579 | 1.00 | 18.23 | B | O |
| ATOM | 8542 | N | GLU | B | 501 | 57.602 | 32.548 | −12.832 | 1.00 | 19.34 | B | N |
| ATOM | 8543 | CA | GLU | B | 501 | 58.788 | 32.338 | −13.640 | 1.00 | 18.85 | B | C |
| ATOM | 8544 | CB | GLU | B | 501 | 60.056 | 32.535 | −12.787 | 1.00 | 23.38 | B | C |
| ATOM | 8545 | CG | GLU | B | 501 | 61.376 | 32.483 | −13.558 | 1.00 | 26.47 | B | C |
| ATOM | 8546 | CD | GLU | B | 501 | 61.598 | 33.666 | −14.504 | 1.00 | 29.42 | B | C |
| ATOM | 8547 | OE1 | GLU | B | 501 | 60.802 | 34.625 | −14.546 | 1.00 | 28.81 | B | O |
| ATOM | 8548 | OE2 | GLU | B | 501 | 62.598 | 33.632 | −15.223 | 1.00 | 30.94 | B | O |
| ATOM | 8549 | C | GLU | B | 501 | 58.796 | 30.942 | −14.291 | 1.00 | 19.55 | B | C |
| ATOM | 8550 | O | GLU | B | 501 | 59.231 | 30.792 | −15.437 | 1.00 | 19.89 | B | O |
| ATOM | 8551 | N | THR | B | 502 | 58.349 | 29.919 | −13.556 | 1.00 | 18.37 | B | N |
| ATOM | 8552 | CA | THR | B | 502 | 58.256 | 28.569 | −14.109 | 1.00 | 16.92 | B | C |
| ATOM | 8553 | CB | THR | B | 502 | 57.718 | 27.587 | −13.057 | 1.00 | 21.51 | B | C |
| ATOM | 8554 | OG1 | THR | B | 502 | 58.621 | 27.588 | −11.958 | 1.00 | 24.18 | B | O |
| ATOM | 8555 | CG2 | THR | B | 502 | 57.562 | 26.158 | −13.617 | 1.00 | 20.21 | B | C |
| ATOM | 8556 | C | THR | B | 502 | 57.319 | 28.595 | −15.326 | 1.00 | 16.37 | B | C |
| ATOM | 8557 | O | THR | B | 502 | 57.600 | 27.981 | −16.357 | 1.00 | 18.24 | B | O |
| ATOM | 8558 | N | ALA | B | 503 | 56.225 | 29.319 | −15.195 | 1.00 | 15.53 | B | N |
| ATOM | 8559 | CA | ALA | B | 503 | 55.261 | 29.465 | −16.303 | 1.00 | 17.36 | B | C |
| ATOM | 8560 | CB | ALA | B | 503 | 53.998 | 30.172 | −15.822 | 1.00 | 15.56 | B | C |
| ATOM | 8561 | C | ALA | B | 503 | 55.853 | 30.181 | −17.522 | 1.00 | 14.65 | B | C |
| ATOM | 8562 | O | ALA | B | 503 | 55.721 | 29.727 | −18.661 | 1.00 | 14.63 | B | O |
| ATOM | 8563 | N | ILE | B | 504 | 56.554 | 31.267 | −17.285 | 1.00 | 15.97 | B | N |
| ATOM | 8564 | CA | ILE | B | 504 | 57.295 | 31.919 | −18.352 | 1.00 | 14.89 | B | C |
| ATOM | 8565 | CB | ILE | B | 504 | 57.949 | 33.259 | −17.883 | 1.00 | 16.17 | B | C |
| ATOM | 8566 | CG1 | ILE | B | 504 | 56.853 | 34.250 | −17.464 | 1.00 | 18.62 | B | C |
| ATOM | 8567 | CD1 | ILE | B | 504 | 57.334 | 35.541 | −16.733 | 1.00 | 20.52 | B | C |
| ATOM | 8568 | CG2 | ILE | B | 504 | 58.846 | 33.848 | −19.042 | 1.00 | 18.16 | B | C |
| ATOM | 8569 | C | ILE | B | 504 | 58.321 | 31.018 | −18.995 | 1.00 | 15.33 | B | C |
| ATOM | 8570 | O | ILE | B | 504 | 58.513 | 31.077 | −20.217 | 1.00 | 15.15 | B | O |
| ATOM | 8571 | N | ASN | B | 505 | 58.972 | 30.158 | −18.206 | 1.00 | 17.39 | B | N |
| ATOM | 8572 | CA | ASN | B | 505 | 59.914 | 29.185 | −18.775 | 1.00 | 15.96 | B | C |
| ATOM | 8573 | CB | ASN | B | 505 | 60.586 | 28.382 | −17.665 | 1.00 | 18.93 | B | C |
| ATOM | 8574 | CG | ASN | B | 505 | 61.632 | 29.183 | −16.921 | 1.00 | 21.82 | B | C |
| ATOM | 8575 | OD1 | ASN | B | 505 | 62.105 | 30.224 | −17.411 | 1.00 | 18.32 | B | O |
| ATOM | 8576 | ND2 | ASN | B | 505 | 62.015 | 28.691 | −15.728 | 1.00 | 15.07 | B | N |
| ATOM | 8577 | C | ASN | B | 505 | 59.292 | 28.226 | −19.830 | 1.00 | 17.21 | B | C |
| ATOM | 8578 | O | ASN | B | 505 | 59.933 | 27.843 | −20.826 | 1.00 | 16.83 | B | O |
| ATOM | 8579 | N | LEU | B | 506 | 58.025 | 27.917 | −19.664 | 1.00 | 16.82 | B | N |
| ATOM | 8580 | CA | LEU | B | 506 | 57.351 | 27.116 | −20.676 | 1.00 | 17.93 | B | C |
| ATOM | 8581 | CB | LEU | B | 506 | 55.939 | 26.753 | −20.219 | 1.00 | 17.53 | B | C |
| ATOM | 8582 | CG | LEU | B | 506 | 55.205 | 25.851 | −21.226 | 1.00 | 24.77 | B | C |
| ATOM | 8583 | CD1 | LEU | B | 506 | 54.696 | 24.591 | −20.494 | 1.00 | 25.28 | B | C |
| ATOM | 8584 | CD2 | LEU | B | 506 | 54.067 | 26.637 | −21.819 | 1.00 | 23.39 | B | C |
| ATOM | 8585 | C | LEU | B | 506 | 57.326 | 27.853 | −22.028 | 1.00 | 19.12 | B | C |
| ATOM | 8586 | O | LEU | B | 506 | 57.513 | 27.231 | −23.076 | 1.00 | 15.80 | B | O |
| ATOM | 8587 | N | ALA | B | 507 | 57.108 | 29.171 | −22.012 | 1.00 | 18.26 | B | N |
| ATOM | 8588 | CA | ALA | B | 507 | 57.230 | 29.954 | −23.223 | 1.00 | 16.87 | B | C |
| ATOM | 8589 | CB | ALA | B | 507 | 56.810 | 31.430 | −22.970 | 1.00 | 18.33 | B | C |
| ATOM | 8590 | C | ALA | B | 507 | 58.645 | 29.923 | −23.732 | 1.00 | 15.87 | B | C |
| ATOM | 8591 | O | ALA | B | 507 | 58.868 | 29.815 | −24.924 | 1.00 | 13.91 | B | O |
| ATOM | 8592 | N | ARG | B | 508 | 59.630 | 30.045 | −22.837 | 1.00 | 16.77 | B | N |
| ATOM | 8593 | CA | ARG | B | 508 | 61.035 | 29.991 | −23.310 | 1.00 | 14.86 | B | C |
| ATOM | 8594 | CB | ARG | B | 508 | 62.050 | 30.236 | −22.196 | 1.00 | 14.69 | B | C |
| ATOM | 8595 | CG | ARG | B | 508 | 61.932 | 31.621 | −21.599 | 1.00 | 16.39 | B | C |
| ATOM | 8596 | CD | ARG | B | 508 | 62.920 | 31.867 | −20.511 | 1.00 | 17.09 | B | C |
| ATOM | 8597 | NE | ARG | B | 508 | 62.956 | 33.301 | −20.135 | 1.00 | 18.33 | B | N |
| ATOM | 8598 | CZ | ARG | B | 508 | 62.597 | 33.803 | −18.962 | 1.00 | 18.87 | B | C |

APPENDIX A-continued

*P. alba* 3T288C coordinates

| ATOM | 8599 | NH1 | ARG | B | 508 | 62.152 | 33.027 | −17.977 | 1.00 | 19.08 | B | N |
|---|---|---|---|---|---|---|---|---|---|---|---|---|
| ATOM | 8600 | NH2 | ARG | B | 508 | 62.699 | 35.117 | −18.755 | 1.00 | 22.71 | B | N |
| ATOM | 8601 | C | ARG | B | 508 | 61.330 | 28.671 | −23.972 | 1.00 | 13.08 | B | C |
| ATOM | 8602 | O | ARG | B | 508 | 61.946 | 28.637 | −25.019 | 1.00 | 14.84 | B | O |
| ATOM | 8603 | N | GLN | B | 509 | 60.919 | 27.574 | −23.334 | 1.00 | 12.57 | B | N |
| ATOM | 8604 | CA | GLN | B | 509 | 61.156 | 26.274 | −23.918 | 1.00 | 14.65 | B | C |
| ATOM | 8605 | CB | GLN | B | 509 | 60.720 | 25.147 | −22.959 | 1.00 | 15.26 | B | C |
| ATOM | 8606 | CG | GLN | B | 509 | 61.024 | 23.770 | −23.521 | 1.00 | 17.12 | B | C |
| ATOM | 8607 | CD | GLN | B | 509 | 62.537 | 23.515 | −23.650 | 1.00 | 21.81 | B | C |
| ATOM | 8608 | OE1 | GLN | B | 509 | 63.275 | 23.824 | −22.759 | 1.00 | 28.15 | B | O |
| ATOM | 8609 | NE2 | GLN | B | 509 | 62.966 | 22.966 | −24.755 | 1.00 | 32.54 | B | N |
| ATOM | 8610 | C | GLN | B | 509 | 60.492 | 26.108 | −25.299 | 1.00 | 16.44 | B | C |
| ATOM | 8611 | O | GLN | B | 509 | 61.043 | 25.458 | −26.195 | 1.00 | 17.20 | B | O |
| ATOM | 8612 | N | SER | B | 510 | 59.331 | 26.731 | −25.478 | 1.00 | 17.03 | B | N |
| ATOM | 8613 | CA | SER | B | 510 | 58.645 | 26.721 | −26.761 | 1.00 | 16.45 | B | C |
| ATOM | 8614 | CB | SER | B | 510 | 57.277 | 27.454 | −26.650 | 1.00 | 17.44 | B | C |
| ATOM | 8615 | OG | SER | B | 510 | 56.458 | 26.798 | −25.692 | 1.00 | 20.37 | B | O |
| ATOM | 8616 | C | SER | B | 510 | 59.494 | 27.358 | −27.830 | 1.00 | 17.70 | B | C |
| ATOM | 8617 | O | SER | B | 510 | 59.638 | 26.815 | −28.941 | 1.00 | 15.61 | B | O |
| ATOM | 8618 | N | HIS | B | 511 | 60.059 | 28.522 | −27.499 | 1.00 | 18.37 | B | N |
| ATOM | 8619 | CA | HIS | B | 511 | 60.914 | 29.239 | −28.419 | 1.00 | 15.76 | B | C |
| ATOM | 8620 | CB | HIS | B | 511 | 61.379 | 30.593 | −27.842 | 1.00 | 19.17 | B | C |
| ATOM | 8621 | CG | HIS | B | 511 | 60.337 | 31.704 | −27.906 | 1.00 | 18.73 | B | C |
| ATOM | 8622 | ND1 | HIS | B | 511 | 59.990 | 32.312 | −29.061 | 1.00 | 18.45 | B | N |
| ATOM | 8623 | CE1 | HIS | B | 511 | 59.071 | 33.270 | −28.810 | 1.00 | 20.71 | B | C |
| ATOM | 8624 | NE2 | HIS | B | 511 | 58.839 | 33.296 | −27.491 | 1.00 | 17.90 | B | N |
| ATOM | 8625 | CD2 | HIS | B | 511 | 59.622 | 32.357 | −26.893 | 1.00 | 20.37 | B | C |
| ATOM | 8626 | C | HIS | B | 511 | 62.115 | 28.418 | −28.800 | 1.00 | 21.48 | B | C |
| ATOM | 8627 | O | HIS | B | 511 | 62.519 | 28.441 | −29.945 | 1.00 | 17.20 | B | O |
| ATOM | 8628 | N | CYS | B | 512 | 62.697 | 27.694 | −27.853 | 1.00 | 16.84 | B | N |
| ATOM | 8629 | CA | CYS | B | 512 | 63.918 | 26.933 | −28.125 | 1.00 | 19.38 | B | C |
| ATOM | 8630 | CB | CYS | B | 512 | 64.687 | 26.692 | −26.805 | 1.00 | 19.41 | B | C |
| ATOM | 8631 | SG | CYS | B | 512 | 65.249 | 28.250 | −26.057 | 1.00 | 25.23 | B | S |
| ATOM | 8632 | C | CYS | B | 512 | 63.617 | 25.580 | −28.842 | 1.00 | 21.62 | B | C |
| ATOM | 8633 | O | CYS | B | 512 | 64.416 | 25.108 | −29.623 | 1.00 | 27.01 | B | O |
| ATOM | 8634 | N | THR | B | 513 | 62.454 | 24.995 | −28.580 | 1.00 | 22.77 | B | N |
| ATOM | 8635 | CA | THR | B | 513 | 62.062 | 23.732 | −29.192 | 1.00 | 24.80 | B | C |
| ATOM | 8636 | CB | THR | B | 513 | 60.948 | 23.125 | −28.403 | 1.00 | 27.16 | B | C |
| ATOM | 8637 | OG1 | THR | B | 513 | 61.455 | 22.833 | −27.122 | 1.00 | 26.52 | B | O |
| ATOM | 8638 | CG2 | THR | B | 513 | 60.451 | 21.824 | −29.037 | 1.00 | 30.46 | B | C |
| ATOM | 8639 | C | THR | B | 513 | 61.615 | 23.859 | −30.652 | 1.00 | 27.78 | B | C |
| ATOM | 8640 | O | THR | B | 513 | 61.930 | 23.007 | −31.472 | 1.00 | 24.42 | B | O |
| ATOM | 8641 | N | TYR | B | 514 | 60.903 | 24.931 | −30.982 | 1.00 | 22.91 | B | N |
| ATOM | 8642 | CA | TYR | B | 514 | 60.314 | 25.070 | −32.308 | 1.00 | 28.13 | B | C |
| ATOM | 8643 | CB | TYR | B | 514 | 58.837 | 25.457 | −32.209 | 1.00 | 22.64 | B | C |
| ATOM | 8644 | CG | TYR | B | 514 | 58.040 | 24.384 | −31.524 | 1.00 | 24.67 | B | C |
| ATOM | 8645 | CD1 | TYR | B | 514 | 57.749 | 23.174 | −32.166 | 1.00 | 27.20 | B | C |
| ATOM | 8646 | CE1 | TYR | B | 514 | 57.040 | 22.177 | −31.516 | 1.00 | 25.06 | B | C |
| ATOM | 8647 | CZ | TYR | B | 514 | 56.620 | 22.390 | −30.252 | 1.00 | 25.30 | B | C |
| ATOM | 8648 | OH | TYR | B | 514 | 55.932 | 21.420 | −29.578 | 1.00 | 25.40 | B | O |
| ATOM | 8649 | CE2 | TYR | B | 514 | 56.924 | 23.584 | −29.593 | 1.00 | 22.38 | B | C |
| ATOM | 8650 | CD2 | TYR | B | 514 | 57.605 | 24.544 | −30.230 | 1.00 | 24.03 | B | C |
| ATOM | 8651 | C | TYR | B | 514 | 61.116 | 26.060 | −33.107 | 1.00 | 34.01 | B | C |
| ATOM | 8652 | O | TYR | B | 514 | 60.846 | 27.240 | −33.093 | 1.00 | 41.72 | B | O |
| ATOM | 8653 | N | HIS | B | 515 | 62.112 | 25.527 | −33.808 | 1.00 | 49.16 | B | N |
| ATOM | 8654 | CA | HIS | B | 515 | 63.076 | 26.288 | −34.597 | 1.00 | 47.01 | B | C |
| ATOM | 8655 | CB | HIS | B | 515 | 64.427 | 26.142 | −33.925 | 1.00 | 42.91 | B | C |
| ATOM | 8656 | CG | HIS | B | 515 | 64.872 | 24.700 | −33.790 | 1.00 | 44.52 | B | C |
| ATOM | 8657 | ND1 | HIS | B | 515 | 64.972 | 24.077 | −32.597 | 1.00 | 42.52 | B | N |
| ATOM | 8658 | CE1 | HIS | B | 515 | 65.346 | 22.800 | −32.789 | 1.00 | 37.27 | B | C |
| ATOM | 8659 | NE2 | HIS | B | 515 | 65.496 | 22.605 | −34.112 | 1.00 | 49.63 | B | N |
| ATOM | 8660 | CD2 | HIS | B | 515 | 65.194 | 23.748 | −34.758 | 1.00 | 38.43 | B | C |
| ATOM | 8661 | C | HIS | B | 515 | 63.108 | 25.718 | −36.014 | 1.00 | 55.54 | B | C |
| ATOM | 8662 | O | HIS | B | 515 | 62.259 | 24.870 | −36.346 | 1.00 | 42.46 | B | O |
| ATOM | 8663 | N | ASN | B | 516 | 64.073 | 26.174 | −36.841 | 1.00 | 69.26 | B | N |
| ATOM | 8664 | CA | ASN | B | 516 | 64.386 | 25.594 | −38.181 | 1.00 | 70.09 | B | C |
| ATOM | 8665 | CB | ASN | B | 516 | 63.740 | 26.423 | −39.291 | 1.00 | 77.49 | B | C |
| ATOM | 8666 | CG | ASN | B | 516 | 62.232 | 26.459 | −39.195 | 1.00 | 88.07 | B | C |
| ATOM | 8667 | OD1 | ASN | B | 516 | 61.560 | 25.453 | −39.418 | 1.00 | 92.86 | B | O |
| ATOM | 8668 | ND2 | ASN | B | 516 | 61.689 | 27.627 | −38.876 | 1.00 | 90.10 | B | N |
| ATOM | 8669 | C | ASN | B | 516 | 65.886 | 25.510 | −38.508 | 1.00 | 51.85 | B | C |
| ATOM | 8670 | O | ASN | B | 516 | 66.686 | 24.937 | −37.766 | 1.00 | 53.73 | B | O |
| ATOM | 8671 | N | THR | B | 521 | 73.370 | 24.373 | −39.725 | 1.00 | 72.27 | B | N |
| ATOM | 8672 | CA | THR | B | 521 | 72.845 | 23.006 | −39.683 | 1.00 | 70.10 | B | C |
| ATOM | 8673 | CB | THR | B | 521 | 73.400 | 22.213 | −38.468 | 1.00 | 69.26 | B | C |
| ATOM | 8674 | OG1 | THR | B | 521 | 72.791 | 22.682 | −37.254 | 1.00 | 53.07 | B | O |
| ATOM | 8675 | CG2 | THR | B | 521 | 74.955 | 22.328 | −38.403 | 1.00 | 50.45 | B | C |
| ATOM | 8676 | C | THR | B | 521 | 71.304 | 23.002 | −39.715 | 1.00 | 67.88 | B | C |

APPENDIX A-continued

P. alba 3T288C coordinates

| ATOM | 8677 | O   | THR | B | 521 | 70.686 | 24.063 | −39.849 | 1.00 | 74.48 | B | O |
|------|------|-----|-----|---|-----|--------|--------|---------|------|-------|---|---|
| ATOM | 8678 | N   | SER | B | 522 | 70.698 | 21.815 | −39.611 | 1.00 | 56.47 | B | N |
| ATOM | 8679 | CA  | SER | B | 522 | 69.273 | 21.617 | −39.923 | 1.00 | 54.25 | B | C |
| ATOM | 8680 | CB  | SER | B | 522 | 69.116 | 20.434 | −40.877 | 1.00 | 54.80 | B | C |
| ATOM | 8681 | OG  | SER | B | 522 | 68.903 | 19.225 | −40.162 | 1.00 | 48.21 | B | O |
| ATOM | 8682 | C   | SER | B | 522 | 68.420 | 21.353 | −38.671 | 1.00 | 70.09 | B | C |
| ATOM | 8683 | O   | SER | B | 522 | 68.974 | 21.157 | −37.590 | 1.00 | 65.77 | B | O |
| ATOM | 8684 | N   | PRO | B | 523 | 67.071 | 21.325 | −38.823 | 1.00 | 69.30 | B | N |
| ATOM | 8685 | CA  | PRO | B | 523 | 66.136 | 21.170 | −37.693 | 1.00 | 69.67 | B | C |
| ATOM | 8686 | CB  | PRO | B | 523 | 64.762 | 21.160 | −38.374 | 1.00 | 63.00 | B | C |
| ATOM | 8687 | CG  | PRO | B | 523 | 64.958 | 21.930 | −39.609 | 1.00 | 63.11 | B | C |
| ATOM | 8688 | CD  | PRO | B | 523 | 66.338 | 21.591 | −40.077 | 1.00 | 69.18 | B | C |
| ATOM | 8689 | C   | PRO | B | 523 | 66.316 | 19.907 | −36.834 | 1.00 | 68.39 | B | C |
| ATOM | 8690 | O   | PRO | B | 523 | 66.474 | 20.009 | −35.604 | 1.00 | 45.02 | B | O |
| ATOM | 8691 | N   | ASP | B | 524 | 66.286 | 18.735 | −37.461 | 1.00 | 58.00 | B | N |
| ATOM | 8692 | CA  | ASP | B | 524 | 66.439 | 17.479 | −36.717 | 1.00 | 59.59 | B | C |
| ATOM | 8693 | CB  | ASP | B | 524 | 66.231 | 16.258 | −37.625 | 1.00 | 65.22 | B | C |
| ATOM | 8694 | CG  | ASP | B | 524 | 64.765 | 15.999 | −37.929 | 1.00 | 72.73 | B | C |
| ATOM | 8695 | OD1 | ASP | B | 524 | 63.895 | 16.413 | −37.126 | 1.00 | 73.64 | B | O |
| ATOM | 8696 | OD2 | ASP | B | 524 | 64.483 | 15.376 | −38.973 | 1.00 | 63.61 | B | O |
| ATOM | 8697 | C   | ASP | B | 524 | 67.796 | 17.380 | −36.047 | 1.00 | 47.88 | B | C |
| ATOM | 8698 | O   | ASP | B | 524 | 67.895 | 16.867 | −34.935 | 1.00 | 40.13 | B | O |
| ATOM | 8699 | N   | GLU | B | 525 | 68.832 | 17.867 | −36.728 | 1.00 | 42.68 | B | N |
| ATOM | 8700 | CA  | GLU | B | 525 | 70.191 | 17.832 | −36.191 | 1.00 | 43.58 | B | C |
| ATOM | 8701 | CB  | GLU | B | 525 | 71.236 | 18.059 | −37.299 | 1.00 | 50.60 | B | C |
| ATOM | 8702 | CG  | GLU | B | 525 | 72.085 | 16.818 | −37.598 | 1.00 | 65.78 | B | C |
| ATOM | 8703 | CD  | GLU | B | 525 | 72.920 | 16.384 | −36.395 | 1.00 | 73.95 | B | C |
| ATOM | 8704 | OE1 | GLU | B | 525 | 73.972 | 17.004 | −36.150 | 1.00 | 81.89 | B | O |
| ATOM | 8705 | OE2 | GLU | B | 525 | 72.521 | 15.434 | −35.688 | 1.00 | 69.88 | B | O |
| ATOM | 8706 | C   | GLU | B | 525 | 70.397 | 18.822 | −35.033 | 1.00 | 37.64 | B | C |
| ATOM | 8707 | O   | GLU | B | 525 | 71.010 | 18.477 | −34.026 | 1.00 | 40.61 | B | O |
| ATOM | 8708 | N   | LEU | B | 526 | 69.894 | 20.041 | −35.182 | 1.00 | 42.79 | B | N |
| ATOM | 8709 | CA  | LEU | B | 526 | 69.943 | 21.033 | −34.098 | 1.00 | 42.76 | B | C |
| ATOM | 8710 | CB  | LEU | B | 526 | 69.300 | 22.355 | −34.541 | 1.00 | 39.65 | B | C |
| ATOM | 8711 | CG  | LEU | B | 526 | 69.491 | 23.607 | −33.677 | 1.00 | 35.52 | B | C |
| ATOM | 8712 | CD1 | LEU | B | 526 | 70.952 | 23.927 | −33.408 | 1.00 | 35.56 | B | C |
| ATOM | 8713 | CD2 | LEU | B | 526 | 68.793 | 24.781 | −34.375 | 1.00 | 36.01 | B | C |
| ATOM | 8714 | C   | LEU | B | 526 | 69.250 | 20.487 | −32.838 | 1.00 | 40.04 | B | C |
| ATOM | 8715 | O   | LEU | B | 526 | 69.803 | 20.593 | −31.741 | 1.00 | 30.06 | B | O |
| ATOM | 8716 | N   | THR | B | 527 | 68.066 | 19.880 | −32.994 | 1.00 | 33.52 | B | N |
| ATOM | 8717 | CA  | THR | B | 527 | 67.353 | 19.288 | −31.841 | 1.00 | 36.91 | B | C |
| ATOM | 8718 | CB  | THR | B | 527 | 65.984 | 18.666 | −32.211 | 1.00 | 35.04 | B | C |
| ATOM | 8719 | OG1 | THR | B | 527 | 65.115 | 19.689 | −32.691 | 1.00 | 38.19 | B | O |
| ATOM | 8720 | CG2 | THR | B | 527 | 65.325 | 18.003 | −30.998 | 1.00 | 30.65 | B | C |
| ATOM | 8721 | C   | THR | B | 527 | 68.188 | 18.226 | −31.157 | 1.00 | 39.79 | B | C |
| ATOM | 8722 | O   | THR | B | 527 | 68.293 | 18.197 | −29.931 | 1.00 | 34.09 | B | O |
| ATOM | 8723 | N   | ARG | B | 528 | 68.804 | 17.349 | −31.936 | 1.00 | 37.41 | B | N |
| ATOM | 8724 | CA  | ARG | B | 528 | 69.547 | 16.269 | −31.307 | 1.00 | 36.55 | B | C |
| ATOM | 8725 | CB  | ARG | B | 528 | 69.831 | 15.137 | −32.294 | 1.00 | 52.60 | B | C |
| ATOM | 8726 | CG  | ARG | B | 528 | 69.701 | 13.738 | −31.660 | 1.00 | 69.87 | B | C |
| ATOM | 8727 | CD  | ARG | B | 528 | 70.156 | 12.662 | −32.631 | 1.00 | 87.21 | B | C |
| ATOM | 8728 | NE  | ARG | B | 528 | 71.397 | 13.075 | −33.283 | 1.00 | 95.91 | B | N |
| ATOM | 8729 | CZ  | ARG | B | 528 | 72.604 | 13.062 | −32.715 | 1.00 | 88.77 | B | C |
| ATOM | 8730 | NH1 | ARG | B | 528 | 72.775 | 12.631 | −31.465 | 1.00 | 82.15 | B | N |
| ATOM | 8731 | NH2 | ARG | B | 528 | 73.655 | 13.481 | −33.413 | 1.00 | 77.77 | B | N |
| ATOM | 8732 | C   | ARG | B | 528 | 70.841 | 16.771 | −30.634 | 1.00 | 32.41 | B | C |
| ATOM | 8733 | O   | ARG | B | 528 | 71.224 | 16.238 | −29.600 | 1.00 | 32.77 | B | O |
| ATOM | 8734 | N   | LYS | B | 529 | 71.496 | 17.776 | −31.220 | 1.00 | 28.56 | B | N |
| ATOM | 8735 | CA  | LYS | B | 529 | 72.665 | 18.432 | −30.595 | 1.00 | 38.61 | B | C |
| ATOM | 8736 | CB  | LYS | B | 529 | 73.287 | 19.491 | −31.528 | 1.00 | 41.18 | B | C |
| ATOM | 8737 | CG  | LYS | B | 529 | 74.196 | 18.949 | −32.605 | 1.00 | 50.54 | B | C |
| ATOM | 8738 | CD  | LYS | B | 529 | 74.880 | 20.083 | −33.355 | 1.00 | 54.89 | B | C |
| ATOM | 8739 | CE  | LYS | B | 529 | 75.945 | 19.563 | −34.303 | 1.00 | 56.41 | B | C |
| ATOM | 8740 | NZ  | LYS | B | 529 | 76.220 | 20.534 | −35.406 | 1.00 | 61.61 | B | N |
| ATOM | 8741 | C   | LYS | B | 529 | 72.292 | 19.099 | −29.261 | 1.00 | 31.73 | B | C |
| ATOM | 8742 | O   | LYS | B | 529 | 72.981 | 18.930 | −28.259 | 1.00 | 43.25 | B | O |
| ATOM | 8743 | N   | ARG | B | 530 | 71.213 | 19.867 | −29.262 | 1.00 | 37.56 | B | N |
| ATOM | 8744 | CA  | ARG | B | 530 | 70.752 | 20.526 | −28.043 | 1.00 | 37.61 | B | C |
| ATOM | 8745 | CB  | ARG | B | 530 | 69.570 | 21.442 | −28.328 | 1.00 | 38.98 | B | C |
| ATOM | 8746 | CG  | ARG | B | 530 | 69.957 | 22.687 | −29.108 | 1.00 | 32.36 | B | C |
| ATOM | 8747 | CD  | ARG | B | 530 | 68.774 | 23.588 | −29.298 | 1.00 | 32.92 | B | C |
| ATOM | 8748 | NE  | ARG | B | 530 | 69.178 | 24.845 | −29.909 | 1.00 | 33.71 | B | N |
| ATOM | 8749 | CZ  | ARG | B | 530 | 68.344 | 25.793 | −30.318 | 1.00 | 38.82 | B | C |
| ATOM | 8750 | NH1 | ARG | B | 530 | 67.033 | 25.649 | −30.179 | 1.00 | 45.15 | B | N |
| ATOM | 8751 | NH2 | ARG | B | 530 | 68.825 | 26.897 | −30.887 | 1.00 | 42.27 | B | N |
| ATOM | 8752 | C   | ARG | B | 530 | 70.398 | 19.489 | −26.987 | 1.00 | 41.72 | B | C |
| ATOM | 8753 | O   | ARG | B | 530 | 70.853 | 19.595 | −25.852 | 1.00 | 39.24 | B | O |
| ATOM | 8754 | N   | VAL | B | 531 | 69.624 | 18.469 | −27.360 | 1.00 | 36.28 | B | N |

APPENDIX A-continued

P. alba 3T288C coordinates

| ATOM | 8755 | CA  | VAL | B | 531 | 69.275 | 17.393 | −26.406 | 1.00 | 42.76 | B | C |
|------|------|-----|-----|---|-----|--------|--------|---------|------|-------|---|---|
| ATOM | 8756 | CB  | VAL | B | 531 | 68.363 | 16.297 | −27.037 | 1.00 | 42.52 | B | C |
| ATOM | 8757 | CG1 | VAL | B | 531 | 68.414 | 15.007 | −26.226 | 1.00 | 43.01 | B | C |
| ATOM | 8758 | CG2 | VAL | B | 531 | 66.938 | 16.807 | −27.152 | 1.00 | 36.09 | B | C |
| ATOM | 8759 | C   | VAL | B | 531 | 70.512 | 16.756 | −25.791 | 1.00 | 38.29 | B | C |
| ATOM | 8760 | O   | VAL | B | 531 | 70.561 | 16.501 | −24.590 | 1.00 | 47.98 | B | O |
| ATOM | 8761 | N   | LEU | B | 532 | 71.520 | 16.505 | −26.617 | 1.00 | 45.39 | B | N |
| ATOM | 8762 | CA  | LEU | B | 532 | 72.771 | 15.923 | −26.146 | 1.00 | 42.10 | B | C |
| ATOM | 8763 | CB  | LEU | B | 532 | 73.647 | 15.501 | −27.333 | 1.00 | 52.99 | B | C |
| ATOM | 8764 | CG  | LEU | B | 532 | 73.599 | 14.022 | −27.730 | 1.00 | 55.07 | B | C |
| ATOM | 8765 | CD1 | LEU | B | 532 | 72.167 | 13.491 | −27.918 | 1.00 | 53.47 | B | C |
| ATOM | 8766 | CD2 | LEU | B | 532 | 74.409 | 13.851 | −28.987 | 1.00 | 50.51 | B | C |
| ATOM | 8767 | C   | LEU | B | 532 | 73.592 | 16.835 | −25.214 | 1.00 | 43.28 | B | C |
| ATOM | 8768 | O   | LEU | B | 532 | 74.228 | 16.348 | −24.268 | 1.00 | 37.39 | B | O |
| ATOM | 8769 | N   | SER | B | 533 | 73.608 | 18.140 | −25.498 | 1.00 | 35.64 | B | N |
| ATOM | 8770 | CA  | SER | B | 533 | 74.416 | 19.084 | −24.725 | 1.00 | 30.10 | B | C |
| ATOM | 8771 | CB  | SER | B | 533 | 74.637 | 20.371 | −25.517 | 1.00 | 31.45 | B | C |
| ATOM | 8772 | OG  | SER | B | 533 | 73.422 | 21.073 | −25.710 | 1.00 | 35.60 | B | O |
| ATOM | 8773 | C   | SER | B | 533 | 73.734 | 19.408 | −23.410 | 1.00 | 25.74 | B | C |
| ATOM | 8774 | O   | SER | B | 533 | 74.375 | 19.842 | −22.464 | 1.00 | 27.81 | B | O |
| ATOM | 8775 | N   | VAL | B | 534 | 72.416 | 19.227 | −23.351 | 1.00 | 26.13 | B | N |
| ATOM | 8776 | CA  | VAL | B | 534 | 71.686 | 19.472 | −22.117 | 1.00 | 22.57 | B | C |
| ATOM | 8777 | CB  | VAL | B | 534 | 70.295 | 20.062 | −22.402 | 1.00 | 20.39 | B | C |
| ATOM | 8778 | CG1 | VAL | B | 534 | 69.458 | 20.157 | −21.128 | 1.00 | 20.01 | B | C |
| ATOM | 8779 | CG2 | VAL | B | 534 | 70.435 | 21.421 | −23.049 | 1.00 | 21.72 | B | C |
| ATOM | 8780 | C   | VAL | B | 534 | 71.590 | 18.219 | −21.242 | 1.00 | 27.30 | B | C |
| ATOM | 8781 | O   | VAL | B | 534 | 71.820 | 18.299 | −20.041 | 1.00 | 25.45 | B | O |
| ATOM | 8782 | N   | ILE | B | 535 | 71.276 | 17.062 | −21.835 | 1.00 | 27.49 | B | N |
| ATOM | 8783 | CA  | ILE | B | 535 | 71.005 | 15.850 | −21.048 | 1.00 | 28.80 | B | C |
| ATOM | 8784 | CB  | ILE | B | 535 | 69.805 | 15.028 | −21.613 | 1.00 | 35.69 | B | C |
| ATOM | 8785 | CG1 | ILE | B | 535 | 68.533 | 15.879 | −21.713 | 1.00 | 35.37 | B | C |
| ATOM | 8786 | CD1 | ILE | B | 535 | 68.029 | 16.446 | −20.395 | 1.00 | 35.74 | B | C |
| ATOM | 8787 | CG2 | ILE | B | 535 | 69.548 | 13.793 | −20.741 | 1.00 | 36.67 | B | C |
| ATOM | 8788 | C   | ILE | B | 535 | 72.178 | 14.879 | −20.940 | 1.00 | 27.66 | B | C |
| ATOM | 8789 | O   | ILE | B | 535 | 72.493 | 14.392 | −19.857 | 1.00 | 31.72 | B | O |
| ATOM | 8790 | N   | THR | B | 536 | 72.826 | 14.571 | −22.053 | 1.00 | 32.60 | B | N |
| ATOM | 8791 | CA  | THR | B | 536 | 73.616 | 13.337 | −22.083 | 1.00 | 32.47 | B | C |
| ATOM | 8792 | CB  | THR | B | 536 | 73.151 | 12.420 | −23.235 | 1.00 | 46.51 | B | C |
| ATOM | 8793 | OG1 | THR | B | 536 | 72.860 | 13.200 | −24.393 | 1.00 | 38.77 | B | O |
| ATOM | 8794 | CG2 | THR | B | 536 | 71.850 | 11.698 | −22.839 | 1.00 | 42.92 | B | C |
| ATOM | 8795 | C   | THR | B | 536 | 75.138 | 13.530 | −21.989 | 1.00 | 33.92 | B | C |
| ATOM | 8796 | O   | THR | B | 536 | 75.786 | 12.819 | −21.227 | 1.00 | 31.82 | B | O |
| ATOM | 8797 | N   | GLU | B | 537 | 75.708 | 14.503 | −22.691 | 1.00 | 34.30 | B | N |
| ATOM | 8798 | CA  | GLU | B | 537 | 77.162 | 14.695 | −22.683 | 1.00 | 38.05 | B | C |
| ATOM | 8799 | CB  | GLU | B | 537 | 77.630 | 15.026 | −24.093 | 1.00 | 47.74 | B | C |
| ATOM | 8800 | CG  | GLU | B | 537 | 77.392 | 13.899 | −25.087 | 1.00 | 61.00 | B | C |
| ATOM | 8801 | CD  | GLU | B | 537 | 77.678 | 14.319 | −26.508 | 1.00 | 66.39 | B | C |
| ATOM | 8802 | OE1 | GLU | B | 537 | 78.858 | 14.554 | −26.826 | 1.00 | 64.96 | B | O |
| ATOM | 8803 | OE2 | GLU | B | 537 | 76.721 | 14.421 | −27.303 | 1.00 | 86.24 | B | O |
| ATOM | 8804 | C   | GLU | B | 537 | 77.596 | 15.814 | −21.727 | 1.00 | 36.26 | B | C |
| ATOM | 8805 | O   | GLU | B | 537 | 77.059 | 16.903 | −21.796 | 1.00 | 34.09 | B | O |
| ATOM | 8806 | N   | PRO | B | 538 | 78.570 | 15.554 | −20.837 | 1.00 | 32.46 | B | N |
| ATOM | 8807 | CA  | PRO | B | 538 | 79.053 | 16.656 | −20.014 | 1.00 | 30.79 | B | C |
| ATOM | 8808 | CB  | PRO | B | 538 | 79.882 | 15.959 | −18.940 | 1.00 | 29.64 | B | C |
| ATOM | 8809 | CG  | PRO | B | 538 | 80.360 | 14.729 | −19.591 | 1.00 | 33.98 | B | C |
| ATOM | 8810 | CD  | PRO | B | 538 | 79.264 | 14.298 | −20.523 | 1.00 | 39.03 | B | C |
| ATOM | 8811 | C   | PRO | B | 538 | 79.883 | 17.654 | −20.818 | 1.00 | 28.97 | B | C |
| ATOM | 8812 | O   | PRO | B | 538 | 80.301 | 17.358 | −21.933 | 1.00 | 31.95 | B | O |
| ATOM | 8813 | N   | ILE | B | 539 | 80.041 | 18.857 | −20.277 | 1.00 | 24.60 | B | N |
| ATOM | 8814 | CA  | ILE | B | 539 | 80.912 | 19.871 | −20.859 | 1.00 | 25.40 | B | C |
| ATOM | 8815 | CB  | ILE | B | 539 | 80.671 | 21.276 | −20.198 | 1.00 | 24.58 | B | C |
| ATOM | 8816 | CG1 | ILE | B | 539 | 79.328 | 21.825 | −20.687 | 1.00 | 20.47 | B | C |
| ATOM | 8817 | CD1 | ILE | B | 539 | 78.935 | 23.187 | −20.171 | 1.00 | 18.78 | B | C |
| ATOM | 8818 | CG2 | ILE | B | 539 | 81.789 | 22.265 | −20.533 | 1.00 | 21.75 | B | C |
| ATOM | 8819 | C   | ILE | B | 539 | 82.333 | 19.422 | −20.609 | 1.00 | 23.93 | B | C |
| ATOM | 8820 | O   | ILE | B | 539 | 82.615 | 18.892 | −19.530 | 1.00 | 22.47 | B | O |
| ATOM | 8821 | N   | LEU | B | 540 | 83.219 | 19.647 | −21.578 | 1.00 | 23.76 | B | N |
| ATOM | 8822 | CA  | LEU | B | 540 | 84.613 | 19.165 | −21.483 | 1.00 | 29.28 | B | C |
| ATOM | 8823 | CB  | LEU | B | 540 | 85.426 | 19.455 | −22.770 | 1.00 | 31.78 | B | C |
| ATOM | 8824 | CG  | LEU | B | 540 | 85.142 | 18.637 | −24.047 | 1.00 | 37.56 | B | C |
| ATOM | 8825 | CD1 | LEU | B | 540 | 86.028 | 19.094 | −25.222 | 1.00 | 35.30 | B | C |
| ATOM | 8826 | CD2 | LEU | B | 540 | 85.330 | 17.126 | −23.810 | 1.00 | 35.88 | B | C |
| ATOM | 8827 | C   | LEU | B | 540 | 85.284 | 19.824 | −20.287 | 1.00 | 28.87 | B | C |
| ATOM | 8828 | O   | LEU | B | 540 | 85.139 | 21.032 | −20.076 | 1.00 | 28.27 | B | O |
| ATOM | 8829 | N   | PRO | B | 541 | 86.032 | 19.039 | −19.503 | 1.00 | 30.18 | B | N |
| ATOM | 8830 | CA  | PRO | B | 541 | 86.569 | 19.564 | −18.256 | 1.00 | 27.81 | B | C |
| ATOM | 8831 | CB  | PRO | B | 541 | 87.372 | 18.392 | −17.677 | 1.00 | 31.70 | B | C |
| ATOM | 8832 | CG  | PRO | B | 541 | 87.511 | 17.412 | −18.771 | 1.00 | 31.03 | B | C |

APPENDIX A-continued

*P. alba* 3T288C coordinates

| ATOM | 8833 | CD | PRO | B | 541 | 86.440 | 17.643 | −19.752 | 1.00 | 30.45 | B | C |
|------|------|----|-----|---|-----|--------|--------|---------|------|-------|---|---|
| ATOM | 8834 | C | PRO | B | 541 | 87.465 | 20.781 | −18.420 | 1.00 | 23.81 | B | C |
| ATOM | 8835 | O | PRO | B | 541 | 88.036 | 21.023 | −19.493 | 1.00 | 23.24 | B | O |
| ATOM | 8836 | N | PHE | B | 542 | 87.570 | 21.544 | −17.340 | 1.00 | 23.63 | B | N |
| ATOM | 8837 | CA | PHE | B | 542 | 88.428 | 22.719 | −17.303 | 1.00 | 25.63 | B | C |
| ATOM | 8838 | CB | PHE | B | 542 | 88.188 | 23.461 | −15.992 | 1.00 | 20.98 | B | C |
| ATOM | 8839 | CG | PHE | B | 542 | 89.075 | 24.646 | −15.805 | 1.00 | 22.67 | B | C |
| ATOM | 8840 | CD1 | PHE | B | 542 | 88.875 | 25.798 | −16.545 | 1.00 | 24.18 | B | C |
| ATOM | 8841 | CE1 | PHE | B | 542 | 89.696 | 26.892 | −16.381 | 1.00 | 26.40 | B | C |
| ATOM | 8842 | CZ | PHE | B | 542 | 90.745 | 26.847 | −15.464 | 1.00 | 26.09 | B | C |
| ATOM | 8843 | CE2 | PHE | B | 542 | 90.956 | 25.700 | −14.730 | 1.00 | 28.04 | B | C |
| ATOM | 8844 | CD2 | PHE | B | 542 | 90.118 | 24.607 | −14.901 | 1.00 | 24.54 | B | C |
| ATOM | 8845 | C | PHE | B | 542 | 89.923 | 22.335 | −17.404 | 1.00 | 24.57 | B | C |
| ATOM | 8846 | O | PHE | B | 542 | 90.354 | 21.435 | −16.718 | 1.00 | 26.15 | B | O |
| ATOM | 8847 | N | GLU | B | 543 | 90.691 | 23.048 | −18.229 | 1.00 | 30.05 | B | N |
| ATOM | 8848 | CA | GLU | B | 543 | 92.144 | 22.847 | −18.358 | 1.00 | 45.33 | B | C |
| ATOM | 8849 | CB | GLU | B | 543 | 92.475 | 22.331 | −19.754 | 1.00 | 51.76 | B | C |
| ATOM | 8850 | CG | GLU | B | 543 | 92.258 | 20.848 | −19.967 | 1.00 | 58.60 | B | C |
| ATOM | 8851 | CD | GLU | B | 543 | 92.868 | 20.385 | −21.281 | 1.00 | 70.33 | B | C |
| ATOM | 8852 | OE1 | GLU | B | 543 | 92.308 | 20.724 | −22.346 | 1.00 | 78.28 | B | O |
| ATOM | 8853 | OE2 | GLU | B | 543 | 93.915 | 19.701 | −21.249 | 1.00 | 62.47 | B | O |
| ATOM | 8854 | C | GLU | B | 543 | 92.921 | 24.154 | −18.139 | 1.00 | 55.07 | B | C |
| ATOM | 8855 | O | GLU | B | 543 | 92.409 | 25.240 | −18.410 | 1.00 | 68.55 | B | O |
| ATOM | 8856 | N | ARG | B | 544 | 94.161 | 24.048 | −17.673 | 1.00 | 66.21 | B | N |
| ATOM | 8857 | CA | ARG | B | 544 | 95.063 | 25.206 | −17.600 | 1.00 | 66.46 | B | C |
| ATOM | 8858 | CB | ARG | B | 544 | 96.449 | 24.783 | −17.115 | 1.00 | 72.05 | B | C |
| ATOM | 8859 | CG | ARG | B | 544 | 96.630 | 24.852 | −15.618 | 1.00 | 82.51 | B | C |
| ATOM | 8860 | CD | ARG | B | 544 | 96.466 | 26.273 | −15.082 | 1.00 | 82.85 | B | C |
| ATOM | 8861 | NE | ARG | B | 544 | 95.163 | 26.517 | −14.456 | 1.00 | 83.68 | B | N |
| ATOM | 8862 | CZ | ARG | B | 544 | 94.775 | 26.005 | −13.287 | 1.00 | 88.75 | B | C |
| ATOM | 8863 | NH1 | ARG | B | 544 | 95.564 | 25.183 | −12.604 | 1.00 | 105.01 | B | N |
| ATOM | 8864 | NH2 | ARG | B | 544 | 93.583 | 26.307 | −12.791 | 1.00 | 82.97 | B | N |
| ATOM | 8865 | C | ARG | B | 544 | 95.208 | 25.906 | −18.947 | 1.00 | 60.40 | B | C |
| ATOM | 8866 | O | ARG | B | 544 | 95.633 | 27.055 | −19.008 | 1.00 | 50.23 | B | O |
| ATOM | 8867 | O2 | EDO | C | 1 | 50.210 | −34.939 | 6.459 | 1.00 | 38.13 | | O |
| ATOM | 8868 | C2 | EDO | C | 1 | 49.011 | −35.682 | 6.773 | 1.00 | 41.21 | | C |
| ATOM | 8869 | C1 | EDO | C | 1 | 49.054 | −36.235 | 8.192 | 1.00 | 45.53 | | C |
| ATOM | 8870 | O1 | EDO | C | 1 | 49.986 | −37.333 | 8.219 | 1.00 | 44.71 | | O |
| ATOM | 8871 | O2 | EDO | C | 2 | 63.438 | −31.727 | 17.582 | 1.00 | 45.81 | | O |
| ATOM | 8872 | C2 | EDO | C | 2 | 62.577 | −30.665 | 18.072 | 1.00 | 74.69 | | C |
| ATOM | 8873 | C1 | EDO | C | 2 | 61.818 | −31.103 | 19.324 | 1.00 | 83.94 | | C |
| ATOM | 8874 | O1 | EDO | C | 2 | 60.663 | −31.864 | 18.957 | 1.00 | 82.22 | | O |
| ATOM | 8875 | O2 | EDO | C | 3 | 35.774 | −12.724 | 19.459 | 1.00 | 49.91 | | O |
| ATOM | 8876 | C2 | EDO | C | 3 | 34.695 | −13.626 | 19.183 | 1.00 | 51.62 | | C |
| ATOM | 8877 | C1 | EDO | C | 3 | 35.066 | −15.056 | 19.586 | 1.00 | 50.18 | | C |
| ATOM | 8878 | O1 | EDO | C | 3 | 34.908 | −15.275 | 20.995 | 1.00 | 52.38 | | O |
| ATOM | 8879 | O2 | EDO | C | 4 | 55.664 | −31.020 | −7.478 | 1.00 | 62.16 | | O |
| ATOM | 8880 | C2 | EDO | C | 4 | 56.447 | −32.199 | −7.745 | 1.00 | 55.16 | | C |
| ATOM | 8881 | C1 | EDO | C | 4 | 57.841 | −32.025 | −7.181 | 1.00 | 46.79 | | C |
| ATOM | 8882 | O1 | EDO | C | 4 | 57.749 | −31.794 | −5.762 | 1.00 | 44.89 | | O |
| ATOM | 8883 | O2 | EDO | C | 5 | 59.390 | 40.828 | −24.889 | 1.00 | 46.90 | | O |
| ATOM | 8884 | C2 | EDO | C | 5 | 58.426 | 41.563 | −25.689 | 1.00 | 52.84 | | C |
| ATOM | 8885 | C1 | EDO | C | 5 | 58.953 | 42.947 | −26.019 | 1.00 | 60.33 | | C |
| ATOM | 8886 | O1 | EDO | C | 5 | 59.696 | 42.902 | −27.239 | 1.00 | 52.81 | | O |
| ATOM | 8887 | O2 | EDO | C | 6 | 67.159 | 24.576 | −21.207 | 1.00 | 44.76 | | O |
| ATOM | 8888 | C2 | EDO | C | 6 | 67.371 | 23.331 | −21.847 | 1.00 | 79.38 | | C |
| ATOM | 8889 | C1 | EDO | C | 6 | 66.232 | 23.107 | −22.819 | 1.00 | 81.18 | | C |
| ATOM | 8890 | O1 | EDO | C | 6 | 65.631 | 21.876 | −22.429 | 1.00 | 57.51 | | O |
| ATOM | 8891 | O2 | EDO | C | 7 | 42.814 | 23.197 | −18.005 | 1.00 | 43.20 | | O |
| ATOM | 8892 | C2 | EDO | C | 7 | 43.711 | 23.598 | −16.933 | 1.00 | 55.67 | | C |
| ATOM | 8893 | C1 | EDO | C | 7 | 42.980 | 23.928 | −15.622 | 1.00 | 49.52 | | C |
| ATOM | 8894 | O1 | EDO | C | 7 | 41.983 | 22.938 | −15.314 | 1.00 | 49.06 | | O |
| ATOM | 8895 | O2 | EDO | C | 8 | 65.887 | 35.660 | −13.297 | 1.00 | 64.73 | | O |
| ATOM | 8896 | C2 | EDO | C | 8 | 66.494 | 35.632 | −11.997 | 1.00 | 60.39 | | C |
| ATOM | 8897 | C1 | EDO | C | 8 | 65.653 | 36.461 | −11.041 | 1.00 | 51.23 | | C |
| ATOM | 8898 | O1 | EDO | C | 8 | 64.285 | 36.084 | −11.242 | 1.00 | 63.87 | | O |
| ATOM | 8899 | O2 | EDO | C | 9 | 75.025 | −15.092 | −7.645 | 1.00 | 73.04 | | O |
| ATOM | 8900 | C2 | EDO | C | 9 | 75.916 | −15.591 | −6.618 | 1.00 | 54.13 | | C |
| ATOM | 8901 | C1 | EDO | C | 9 | 76.282 | −14.481 | −5.629 | 1.00 | 62.03 | | C |
| ATOM | 8902 | O1 | EDO | C | 9 | 76.476 | −15.036 | −4.307 | 1.00 | 71.74 | | O |
| ATOM | 8903 | O2 | EDO | C | 10 | 37.539 | −13.647 | −3.807 | 1.00 | 56.73 | | O |
| ATOM | 8904 | C2 | EDO | C | 10 | 38.572 | −14.413 | −3.187 | 1.00 | 53.33 | | C |
| ATOM | 8905 | C1 | EDO | C | 10 | 38.080 | −14.845 | −1.828 | 1.00 | 66.57 | | C |
| ATOM | 8906 | O1 | EDO | C | 10 | 38.329 | −13.862 | −0.808 | 1.00 | 43.72 | | O |
| ATOM | 8907 | O2 | EDO | C | 11 | 62.286 | 22.846 | −3.976 | 1.00 | 95.27 | | O |
| ATOM | 8908 | C2 | EDO | C | 11 | 61.432 | 21.701 | −3.837 | 1.00 | 78.37 | | C |
| ATOM | 8909 | C1 | EDO | C | 11 | 60.151 | 21.921 | −4.633 | 1.00 | 74.32 | | C |
| ATOM | 8910 | O1 | EDO | C | 11 | 59.125 | 22.519 | −3.825 | 1.00 | 66.41 | | O |

APPENDIX A-continued

*P. alba* 3T288C coordinates

| ATOM | 8911 | O | HOH | W | 1 | 34.048 | 30.209 | −35.713 | 1.00 | 30.57 | O |
|---|---|---|---|---|---|---|---|---|---|---|---|
| ATOM | 8912 | O | HOH | W | 2 | 72.221 | 30.561 | −18.308 | 1.00 | 34.52 | O |
| ATOM | 8913 | O | HOH | W | 3 | 42.922 | −37.541 | 1.254 | 1.00 | 24.96 | O |
| ATOM | 8914 | O | HOH | W | 4 | 50.386 | 5.471 | −4.647 | 1.00 | 32.49 | O |
| ATOM | 8915 | O | HOH | W | 5 | 33.078 | 3.362 | −9.383 | 1.00 | 54.39 | O |
| ATOM | 8916 | O | HOH | W | 6 | 52.914 | 44.981 | −20.022 | 1.00 | 38.76 | O |
| ATOM | 8917 | O | HOH | W | 7 | 46.727 | −46.708 | −0.071 | 1.00 | 28.55 | O |
| ATOM | 8918 | O | HOH | W | 8 | 43.693 | 28.326 | 0.980 | 1.00 | 60.87 | O |
| ATOM | 8919 | O | HOH | W | 9 | 40.812 | 33.780 | −15.967 | 1.00 | 55.29 | O |
| ATOM | 8920 | O | HOH | W | 10 | 34.233 | −15.102 | −12.393 | 1.00 | 69.73 | O |
| ATOM | 8921 | O | HOH | W | 11 | 60.558 | −41.349 | 3.050 | 1.00 | 30.19 | O |
| ATOM | 8922 | O | HOH | W | 12 | 51.686 | −35.679 | −4.930 | 1.00 | 30.59 | O |
| ATOM | 8923 | O | HOH | W | 13 | 41.009 | 10.787 | −34.962 | 1.00 | 32.13 | O |
| ATOM | 8924 | O | HOH | W | 14 | 72.510 | −28.244 | 9.403 | 1.00 | 47.03 | O |
| ATOM | 8925 | O | HOH | W | 15 | 58.976 | 52.860 | −18.688 | 1.00 | 44.24 | O |
| ATOM | 8926 | O | HOH | W | 16 | 38.872 | −12.021 | 23.356 | 1.00 | 57.68 | O |
| ATOM | 8927 | O | HOH | W | 17 | 52.746 | 17.543 | −10.057 | 1.00 | 29.72 | O |
| ATOM | 8928 | O | HOH | W | 18 | 51.072 | −32.904 | −1.376 | 1.00 | 29.37 | O |
| ATOM | 8929 | O | HOH | W | 19 | 63.526 | −35.430 | −0.774 | 1.00 | 28.10 | O |
| ATOM | 8930 | O | HOH | W | 20 | 68.058 | 39.373 | −17.925 | 1.00 | 39.37 | O |
| ATOM | 8931 | O | HOH | W | 21 | 33.554 | −10.585 | −11.360 | 1.00 | 67.19 | O |
| ATOM | 8932 | O | HOH | W | 22 | 37.063 | 12.291 | −2.365 | 1.00 | 51.31 | O |
| ATOM | 8933 | O | HOH | W | 23 | 37.950 | −12.663 | −6.107 | 1.00 | 35.96 | O |
| ATOM | 8934 | O | HOH | W | 24 | 59.883 | 20.188 | −7.683 | 1.00 | 40.62 | O |
| ATOM | 8935 | O | HOH | W | 25 | 64.280 | 31.472 | −14.859 | 1.00 | 54.99 | O |
| ATOM | 8936 | O | HOH | W | 26 | 50.836 | −23.573 | 23.569 | 1.00 | 61.82 | O |
| ATOM | 8937 | O | HOH | W | 27 | 44.198 | 36.276 | −15.221 | 1.00 | 47.21 | O |
| ATOM | 8938 | O | HOH | W | 28 | 27.068 | −13.991 | 20.678 | 1.00 | 58.53 | O |
| ATOM | 8939 | O | HOH | W | 29 | 59.191 | 6.102 | 3.877 | 1.00 | 52.78 | O |
| ATOM | 8940 | O | HOH | W | 30 | 56.173 | 43.466 | −32.287 | 1.00 | 55.42 | O |
| ATOM | 8941 | O | HOH | W | 31 | 48.255 | 36.614 | −25.882 | 1.00 | 35.33 | O |
| ATOM | 8942 | O | HOH | W | 32 | 52.907 | 8.991 | −11.103 | 1.00 | 35.35 | O |
| ATOM | 8943 | O | HOH | W | 33 | 78.772 | 40.802 | −19.806 | 1.00 | 64.63 | O |
| ATOM | 8944 | O | HOH | W | 34 | 35.785 | 6.639 | −16.100 | 1.00 | 38.23 | O |
| ATOM | 8945 | O | HOH | W | 35 | 34.929 | 18.983 | −26.361 | 1.00 | 36.02 | O |
| ATOM | 8946 | O | HOH | W | 36 | 65.094 | −28.160 | −0.117 | 1.00 | 30.19 | O |
| ATOM | 8947 | O | HOH | W | 37 | 39.427 | −1.601 | 16.456 | 1.00 | 37.99 | O |
| ATOM | 8948 | O | HOH | W | 38 | 55.902 | −54.816 | 1.904 | 1.00 | 37.57 | O |
| ATOM | 8949 | O | HOH | W | 39 | 61.453 | 35.126 | −30.488 | 1.00 | 46.77 | O |
| ATOM | 8950 | O | HOH | W | 40 | 44.942 | 4.117 | −9.297 | 1.00 | 26.04 | O |
| ATOM | 8951 | O | HOH | W | 41 | 41.406 | −41.347 | 0.269 | 1.00 | 28.33 | O |
| ATOM | 8952 | O | HOH | W | 42 | 57.974 | −52.022 | −9.497 | 1.00 | 40.95 | O |
| ATOM | 8953 | O | HOH | W | 43 | 42.050 | 21.939 | −12.530 | 1.00 | 33.98 | O |
| ATOM | 8954 | O | HOH | W | 44 | 41.003 | −33.274 | −1.457 | 1.00 | 33.03 | O |
| ATOM | 8955 | O | HOH | W | 45 | 40.926 | −47.571 | 5.365 | 1.00 | 32.94 | O |
| ATOM | 8956 | O | HOH | W | 46 | 49.424 | −10.782 | −8.514 | 1.00 | 29.03 | O |
| ATOM | 8957 | O | HOH | W | 47 | 45.277 | −21.798 | −15.931 | 1.00 | 55.04 | O |
| ATOM | 8958 | O | HOH | W | 48 | 51.511 | −44.053 | −11.372 | 1.00 | 34.36 | O |
| ATOM | 8959 | O | HOH | W | 49 | 44.630 | 14.779 | −38.339 | 1.00 | 50.75 | O |
| ATOM | 8960 | O | HOH | W | 50 | 67.819 | −51.366 | 2.851 | 1.00 | 60.07 | O |
| ATOM | 8961 | O | HOH | W | 51 | 38.599 | 22.223 | −22.766 | 1.00 | 36.92 | O |
| ATOM | 8962 | O | HOH | W | 52 | 74.566 | −28.008 | −17.386 | 1.00 | 37.79 | O |
| ATOM | 8963 | O | HOH | W | 53 | 64.915 | 27.603 | −18.440 | 1.00 | 30.85 | O |
| ATOM | 8964 | O | HOH | W | 54 | 47.207 | −13.782 | 9.500 | 1.00 | 40.97 | O |
| ATOM | 8965 | O | HOH | W | 55 | 66.176 | −37.909 | 3.811 | 1.00 | 46.95 | O |
| ATOM | 8966 | O | HOH | W | 56 | 53.336 | 16.841 | −7.459 | 1.00 | 37.81 | O |
| ATOM | 8967 | O | HOH | W | 57 | 73.333 | 30.235 | −30.752 | 1.00 | 43.63 | O |
| ATOM | 8968 | O | HOH | W | 58 | 33.230 | 18.696 | −28.428 | 1.00 | 45.03 | O |
| ATOM | 8969 | O | HOH | W | 59 | 66.175 | −39.931 | −15.870 | 1.00 | 39.41 | O |
| ATOM | 8970 | O | HOH | W | 60 | 35.995 | 14.593 | −42.897 | 1.00 | 65.27 | O |
| ATOM | 8971 | O | HOH | W | 61 | 58.757 | 13.049 | −4.982 | 1.00 | 66.66 | O |
| ATOM | 8972 | O | HOH | W | 62 | 37.415 | 9.573 | 12.896 | 1.00 | 51.12 | O |
| ATOM | 8973 | O | HOH | W | 63 | 47.051 | 24.023 | −34.571 | 1.00 | 47.66 | O |
| ATOM | 8974 | O | HOH | W | 64 | 72.806 | −37.016 | 2.957 | 1.00 | 47.83 | O |
| ATOM | 8975 | O | HOH | W | 65 | 73.786 | 10.617 | −12.312 | 1.00 | 52.20 | O |
| ATOM | 8976 | O | HOH | W | 66 | 40.427 | 12.828 | 10.123 | 1.00 | 52.56 | O |
| ATOM | 8977 | O | HOH | W | 67 | 35.371 | −1.990 | −16.124 | 1.00 | 43.14 | O |
| ATOM | 8978 | O | HOH | W | 68 | 38.863 | −4.985 | 16.991 | 1.00 | 38.62 | O |
| ATOM | 8979 | O | HOH | W | 69 | 35.770 | −4.210 | −3.569 | 1.00 | 35.17 | O |
| ATOM | 8980 | O | HOH | W | 70 | 68.324 | −43.580 | −13.697 | 1.00 | 43.83 | O |
| ATOM | 8981 | O | HOH | W | 71 | 33.955 | −13.890 | 2.042 | 1.00 | 40.37 | O |
| ATOM | 8982 | O | HOH | W | 72 | 61.227 | −29.698 | 2.658 | 1.00 | 35.13 | O |
| ATOM | 8983 | O | HOH | W | 73 | 65.711 | −50.865 | 5.677 | 1.00 | 43.64 | O |
| ATOM | 8984 | O | HOH | W | 74 | 74.357 | −42.812 | −10.884 | 1.00 | 44.35 | O |
| ATOM | 8985 | O | HOH | W | 75 | 45.510 | −11.279 | 9.183 | 1.00 | 53.55 | O |
| ATOM | 8986 | O | HOH | W | 76 | 58.068 | 37.458 | −31.933 | 1.00 | 45.05 | O |
| ATOM | 8987 | O | HOH | W | 77 | 29.944 | −7.112 | 9.777 | 1.00 | 50.98 | O |
| ATOM | 8988 | O | HOH | W | 78 | 70.628 | 32.182 | −4.862 | 1.00 | 50.28 | O |

APPENDIX A-continued

*P. alba* 3T288C coordinates

| ATOM | 8989 | O | HOH | W | 79 | 49.706 | −31.542 | 13.259 | 1.00 | 37.73 | O |
|---|---|---|---|---|---|---|---|---|---|---|---|
| ATOM | 8990 | O | HOH | W | 80 | 39.571 | 27.621 | −39.892 | 1.00 | 36.81 | O |
| ATOM | 8991 | O | HOH | W | 81 | 49.230 | 40.718 | −34.169 | 1.00 | 39.33 | O |
| ATOM | 8992 | O | HOH | W | 82 | 63.542 | 44.164 | −6.413 | 1.00 | 48.75 | O |
| ATOM | 8993 | O | HOH | W | 83 | 75.927 | −38.606 | −1.097 | 1.00 | 47.25 | O |
| ATOM | 8994 | O | HOH | W | 84 | 76.193 | 41.852 | −2.775 | 1.00 | 42.75 | O |
| ATOM | 8995 | O | HOH | W | 85 | 70.942 | 44.418 | −21.606 | 1.00 | 42.30 | O |
| ATOM | 8996 | O | HOH | W | 86 | 73.469 | −41.972 | −3.523 | 1.00 | 38.48 | O |
| ATOM | 8997 | O | HOH | W | 87 | 69.367 | −31.467 | −16.366 | 1.00 | 53.89 | O |
| ATOM | 8998 | O | HOH | W | 88 | 54.386 | 16.085 | −3.461 | 1.00 | 52.54 | O |
| ATOM | 8999 | O | HOH | W | 89 | 66.132 | 31.872 | −19.085 | 1.00 | 35.71 | O |
| ATOM | 9000 | O | HOH | W | 90 | 66.404 | −41.771 | 6.383 | 1.00 | 38.20 | O |
| ATOM | 9001 | O | HOH | W | 91 | 50.092 | 22.669 | 0.190 | 1.00 | 51.87 | O |
| ATOM | 9002 | O | HOH | W | 92 | 39.373 | −39.231 | 0.174 | 1.00 | 35.92 | O |
| ATOM | 9003 | O | HOH | W | 93 | 65.979 | −23.272 | 11.936 | 1.00 | 69.59 | O |
| ATOM | 9004 | O | HOH | W | 94 | 48.792 | −13.384 | 21.980 | 1.00 | 74.36 | O |
| ATOM | 9005 | O | HOH | W | 95 | 71.412 | −24.600 | −16.671 | 1.00 | 36.24 | O |
| ATOM | 9006 | O | HOH | W | 96 | 56.586 | 26.740 | −41.218 | 1.00 | 41.19 | O |
| ATOM | 9007 | O | HOH | W | 97 | 39.489 | −7.587 | 16.107 | 1.00 | 51.95 | O |
| ATOM | 9008 | O | HOH | W | 98 | 53.647 | −55.615 | −0.148 | 1.00 | 51.86 | O |
| ATOM | 9009 | O | HOH | W | 99 | 46.171 | −56.680 | −2.479 | 1.00 | 35.43 | O |
| ATOM | 9010 | O | HOH | W | 100 | 39.972 | −32.522 | 15.077 | 1.00 | 48.51 | O |
| ATOM | 9011 | O | HOH | W | 101 | 48.922 | −24.272 | 21.614 | 1.00 | 54.16 | O |
| ATOM | 9012 | O | HOH | W | 102 | 74.982 | 40.128 | −38.250 | 1.00 | 66.19 | O |
| ATOM | 9013 | O | HOH | W | 103 | 61.120 | 47.767 | −13.833 | 1.00 | 40.35 | O |
| ATOM | 9014 | O | HOH | W | 104 | 41.768 | −16.179 | 15.677 | 1.00 | 50.58 | O |
| ATOM | 9015 | O | HOH | W | 105 | 60.972 | −37.487 | −17.532 | 1.00 | 53.12 | O |
| ATOM | 9016 | O | HOH | W | 106 | 41.668 | −1.875 | −29.376 | 1.00 | 40.10 | O |
| ATOM | 9017 | O | HOH | W | 107 | 62.308 | 38.576 | −13.930 | 1.00 | 39.71 | O |
| ATOM | 9018 | O | HOH | W | 108 | 52.023 | −49.412 | −4.168 | 1.00 | 38.73 | O |
| ATOM | 9019 | O | HOH | W | 109 | 44.425 | −14.470 | −21.023 | 1.00 | 59.71 | O |
| ATOM | 9020 | O | HOH | W | 110 | 68.249 | −40.733 | 1.635 | 1.00 | 51.87 | O |
| ATOM | 9021 | O | HOH | W | 111 | 58.014 | 40.360 | −34.091 | 1.00 | 58.79 | O |
| ATOM | 9022 | O | HOH | W | 112 | 65.473 | −25.959 | 8.283 | 1.00 | 37.98 | O |
| ATOM | 9023 | O | HOH | W | 113 | 58.376 | 28.638 | −34.072 | 1.00 | 37.08 | O |
| ATOM | 9024 | O | HOH | W | 114 | 40.956 | 20.759 | −36.052 | 1.00 | 34.09 | O |
| ATOM | 9025 | O | HOH | W | 115 | 53.523 | −30.166 | 11.765 | 1.00 | 47.29 | O |
| ATOM | 9026 | O | HOH | W | 116 | 81.018 | −22.161 | −3.491 | 1.00 | 48.31 | O |
| ATOM | 9027 | O | HOH | W | 117 | 77.989 | 31.942 | −1.939 | 1.00 | 52.87 | O |
| ATOM | 9028 | O | HOH | W | 118 | 30.031 | −4.641 | 5.412 | 1.00 | 52.50 | O |
| ATOM | 9029 | O | HOH | W | 119 | 49.668 | 41.842 | −31.710 | 1.00 | 52.92 | O |
| ATOM | 9030 | O | HOH | W | 120 | 46.700 | 19.419 | −30.652 | 1.00 | 53.45 | O |
| ATOM | 9031 | O | HOH | W | 121 | 63.076 | −29.920 | 0.218 | 1.00 | 34.61 | O |
| ATOM | 9032 | O | HOH | W | 122 | 63.859 | 26.049 | −4.564 | 1.00 | 64.19 | O |
| ATOM | 9033 | O | HOH | W | 123 | 69.023 | −54.334 | 7.222 | 1.00 | 83.51 | O |
| ATOM | 9034 | O | HOH | W | 124 | 65.415 | −27.642 | −23.447 | 1.00 | 60.02 | O |
| ATOM | 9035 | O | HOH | W | 125 | 55.626 | 50.586 | −29.608 | 1.00 | 55.69 | O |
| ATOM | 9036 | O | HOH | W | 126 | 66.593 | 44.060 | −2.954 | 1.00 | 68.62 | O |
| ATOM | 9037 | O | HOH | W | 127 | 58.391 | −28.842 | 16.508 | 1.00 | 57.64 | O |
| ATOM | 9038 | O | HOH | W | 128 | 53.900 | −39.356 | −12.313 | 1.00 | 43.15 | O |
| ATOM | 9039 | O | HOH | W | 129 | 74.782 | 37.164 | −27.479 | 1.00 | 44.49 | O |
| ATOM | 9040 | O | HOH | W | 130 | 90.863 | 34.951 | −9.722 | 1.00 | 62.59 | O |
| ATOM | 9041 | O | HOH | W | 131 | 52.472 | −48.905 | −6.906 | 1.00 | 56.63 | O |
| ATOM | 9042 | O | HOH | W | 132 | 43.350 | 10.560 | 11.057 | 1.00 | 38.08 | O |
| ATOM | 9043 | O | HOH | W | 133 | 52.074 | −50.711 | 14.213 | 1.00 | 54.06 | O |
| ATOM | 9044 | O | HOH | W | 134 | 70.265 | −31.997 | 17.051 | 1.00 | 57.08 | O |
| ATOM | 9045 | O | HOH | W | 135 | 82.367 | −22.862 | −5.771 | 1.00 | 53.41 | O |
| ATOM | 9046 | O | HOH | W | 136 | 73.877 | −43.074 | −1.202 | 1.00 | 52.04 | O |
| ATOM | 9047 | O | HOH | W | 137 | 61.815 | 36.018 | −7.588 | 1.00 | 66.58 | O |
| ATOM | 9048 | O | HOH | W | 138 | 36.147 | −3.135 | −8.569 | 1.00 | 54.25 | O |
| ATOM | 9049 | O | HOH | W | 139 | 38.569 | −3.334 | −28.598 | 1.00 | 46.22 | O |
| ATOM | 9050 | O | HOH | W | 140 | 30.675 | 4.623 | 10.151 | 1.00 | 44.33 | O |
| ATOM | 9051 | O | HOH | W | 141 | 34.344 | −12.039 | 4.162 | 1.00 | 35.56 | O |
| ATOM | 9052 | O | HOH | W | 142 | 66.321 | −28.096 | 12.287 | 1.00 | 44.18 | O |
| ATOM | 9053 | O | HOH | W | 143 | 39.877 | 17.457 | −2.554 | 1.00 | 57.30 | O |
| ATOM | 9054 | O | HOH | W | 144 | 37.888 | 20.717 | −9.842 | 1.00 | 50.69 | O |
| ATOM | 9055 | O | HOH | W | 145 | 36.597 | −25.323 | 28.278 | 1.00 | 54.67 | O |
| ATOM | 9056 | O | HOH | W | 146 | 57.161 | 18.828 | −5.002 | 1.00 | 58.07 | O |
| ATOM | 9057 | O | HOH | W | 147 | 62.481 | −31.446 | 7.726 | 1.00 | 41.64 | O |
| ATOM | 9058 | O | HOH | W | 148 | 76.571 | 43.616 | −24.789 | 1.00 | 44.73 | O |
| ATOM | 9059 | O | HOH | W | 149 | 30.688 | −1.114 | 6.069 | 1.00 | 56.57 | O |
| ATOM | 9060 | O | HOH | W | 150 | 81.407 | 28.142 | −1.050 | 1.00 | 38.72 | O |
| ATOM | 9061 | O | HOH | W | 151 | 77.076 | 36.019 | 0.324 | 1.00 | 42.72 | O |
| ATOM | 9062 | O | HOH | W | 152 | 51.332 | 29.535 | −2.522 | 1.00 | 49.96 | O |
| ATOM | 9063 | O | HOH | W | 153 | 39.612 | −34.777 | 16.884 | 1.00 | 52.30 | O |
| ATOM | 9064 | O | HOH | W | 154 | 79.194 | 43.959 | 0.289 | 1.00 | 43.48 | O |
| ATOM | 9065 | O | HOH | W | 155 | 38.215 | 13.169 | −10.040 | 1.00 | 64.98 | O |
| ATOM | 9066 | O | HOH | W | 156 | 56.920 | 35.850 | −4.782 | 1.00 | 60.82 | O |

APPENDIX A-continued

*P. alba* 3T288C coordinates

| ATOM | 9067 | O | HOH | W | 157 | 47.053 | −24.557 | 23.296 | 1.00 | 49.95 | O |
|---|---|---|---|---|---|---|---|---|---|---|---|
| ATOM | 9068 | O | HOH | W | 158 | 58.327 | 5.069 | −30.924 | 1.00 | 79.38 | O |
| ATOM | 9069 | O | HOH | W | 159 | 64.930 | 46.968 | −37.558 | 1.00 | 56.21 | O |
| ATOM | 9070 | O | HOH | W | 160 | 57.306 | −26.687 | −3.825 | 1.00 | 45.16 | O |
| ATOM | 9071 | O | HOH | W | 161 | 36.627 | −11.455 | 17.346 | 1.00 | 37.75 | O |
| ATOM | 9072 | O | HOH | W | 162 | 50.199 | 44.936 | −19.825 | 1.00 | 51.53 | O |
| ATOM | 9073 | O | HOH | W | 163 | 54.531 | 9.807 | −8.888 | 1.00 | 57.92 | O |
| ATOM | 9074 | O | HOH | W | 164 | 78.331 | 52.654 | −23.946 | 1.00 | 46.37 | O |
| ATOM | 9075 | O | HOH | W | 165 | 73.905 | −38.892 | −3.033 | 1.00 | 49.22 | O |
| ATOM | 9076 | O | HOH | W | 166 | 50.113 | −10.237 | −11.005 | 1.00 | 29.80 | O |
| ATOM | 9077 | O | HOH | W | 167 | 36.232 | 0.508 | −31.397 | 1.00 | 45.29 | O |
| ATOM | 9078 | O | HOH | W | 168 | 43.592 | 39.061 | −19.142 | 1.00 | 63.60 | O |
| ATOM | 9079 | O | HOH | W | 169 | 40.214 | −33.998 | 12.608 | 1.00 | 57.97 | O |
| ATOM | 9080 | O | HOH | W | 170 | 75.916 | −38.941 | −4.757 | 1.00 | 58.71 | O |
| ATOM | 9081 | O | HOH | W | 171 | 50.926 | 30.569 | −48.782 | 1.00 | 68.05 | O |
| ATOM | 9082 | O | HOH | W | 172 | 30.965 | 12.611 | −18.907 | 1.00 | 48.18 | O |
| ATOM | 9083 | O | HOH | W | 173 | 65.768 | 32.879 | −34.997 | 1.00 | 59.97 | O |
| ATOM | 9084 | O | HOH | W | 174 | 67.132 | −46.375 | −14.735 | 1.00 | 63.90 | O |
| ATOM | 9085 | O | HOH | W | 175 | 30.868 | −31.797 | 22.531 | 1.00 | 71.45 | O |
| ATOM | 9086 | O | HOH | W | 176 | 37.574 | 17.226 | −11.259 | 1.00 | 44.53 | O |
| ATOM | 9087 | O | HOH | W | 177 | 67.951 | 28.566 | −6.687 | 1.00 | 62.21 | O |
| ATOM | 9088 | O | HOH | W | 178 | 51.731 | −23.089 | 15.681 | 1.00 | 44.07 | O |
| ATOM | 9089 | O | HOH | W | 179 | 61.714 | 18.275 | −6.221 | 1.00 | 41.96 | O |
| ATOM | 9090 | O | HOH | W | 180 | 38.431 | 13.065 | −7.226 | 1.00 | 51.80 | O |
| ATOM | 9091 | O | HOH | W | 181 | 54.783 | 3.722 | 12.486 | 1.00 | 49.70 | O |
| ATOM | 9092 | O | HOH | W | 182 | 81.778 | 31.669 | −29.328 | 1.00 | 70.71 | O |
| ATOM | 9093 | O | HOH | W | 183 | 72.037 | 35.490 | 7.499 | 1.00 | 52.36 | O |
| ATOM | 9094 | O | HOH | W | 184 | 30.818 | 6.946 | −28.568 | 1.00 | 42.29 | O |
| ATOM | 9095 | O | HOH | W | 185 | 89.548 | 24.910 | −20.320 | 1.00 | 60.31 | O |
| ATOM | 9096 | O | HOH | W | 186 | 31.480 | −7.942 | 7.728 | 1.00 | 41.20 | O |
| ATOM | 9097 | O | HOH | W | 187 | 35.972 | 10.716 | 8.864 | 1.00 | 61.98 | O |
| ATOM | 9098 | O | HOH | W | 188 | 73.905 | −14.913 | −2.316 | 1.00 | 46.00 | O |
| ATOM | 9099 | O | HOH | W | 189 | 78.890 | 44.704 | −4.758 | 1.00 | 47.35 | O |
| ATOM | 9100 | O | HOH | W | 190 | 47.865 | 33.986 | −3.697 | 1.00 | 71.46 | O |
| ATOM | 9101 | O | HOH | W | 191 | 55.489 | −51.636 | −8.793 | 1.00 | 51.44 | O |
| ATOM | 9102 | O | HOH | W | 192 | 44.629 | 34.253 | −47.662 | 1.00 | 52.49 | O |
| ATOM | 9103 | O | HOH | W | 193 | 36.321 | −3.150 | −11.179 | 1.00 | 53.77 | O |
| ATOM | 9104 | O | HOH | W | 194 | 75.543 | 27.909 | −1.152 | 1.00 | 62.47 | O |
| ATOM | 9105 | O | HOH | W | 195 | 68.920 | 32.752 | −21.140 | 1.00 | 42.66 | O |
| ATOM | 9106 | O | HOH | W | 196 | 56.053 | 16.201 | 4.167 | 1.00 | 64.28 | O |
| ATOM | 9107 | O | HOH | W | 197 | 70.643 | 32.752 | −18.624 | 1.00 | 40.54 | O |
| ATOM | 9108 | O | HOH | W | 198 | 42.990 | 18.891 | −36.337 | 1.00 | 43.70 | O |
| ATOM | 9109 | O | HOH | W | 199 | 32.339 | 21.015 | −35.934 | 1.00 | 46.78 | O |
| ATOM | 9110 | O | HOH | W | 200 | 64.041 | −53.498 | 6.127 | 1.00 | 45.10 | O |
| ATOM | 9111 | O | HOH | W | 201 | 37.492 | −2.289 | −14.229 | 1.00 | 43.61 | O |
| ATOM | 9112 | O | HOH | W | 202 | 54.643 | 2.234 | −30.940 | 1.00 | 54.31 | O |
| ATOM | 9113 | O | HOH | W | 203 | 81.792 | 34.267 | −28.947 | 1.00 | 63.73 | O |
| ATOM | 9114 | O | HOH | W | 204 | 51.574 | −47.862 | 15.312 | 1.00 | 52.96 | O |
| ATOM | 9115 | O | HOH | W | 205 | 66.116 | −0.774 | −1.663 | 1.00 | 57.05 | O |
| ATOM | 9116 | O | HOH | W | 206 | 63.489 | −29.240 | −13.484 | 1.00 | 47.17 | O |
| ATOM | 9117 | O | HOH | W | 207 | 33.774 | −11.564 | 21.850 | 1.00 | 53.05 | O |
| ATOM | 9118 | O | HOH | W | 208 | 33.410 | 5.065 | 2.929 | 1.00 | 51.28 | O |
| ATOM | 9119 | O | HOH | W | 209 | 89.488 | 19.709 | −15.078 | 1.00 | 67.84 | O |
| ATOM | 9120 | O | HOH | W | 210 | 51.136 | −34.897 | −7.810 | 1.00 | 46.73 | O |
| ATOM | 9121 | O | HOH | W | 211 | 39.578 | 31.108 | −40.140 | 1.00 | 39.00 | O |
| ATOM | 9122 | O | HOH | W | 212 | 55.752 | −41.092 | 20.935 | 1.00 | 51.13 | O |
| ATOM | 9123 | O | HOH | W | 213 | 63.192 | 38.662 | −8.121 | 1.00 | 46.18 | O |
| ATOM | 9124 | O | HOH | W | 214 | 75.303 | −41.780 | −5.954 | 1.00 | 63.51 | O |
| ATOM | 9125 | O | HOH | W | 215 | 67.066 | −29.506 | 14.424 | 1.00 | 48.90 | O |
| ATOM | 9126 | O | HOH | W | 216 | 84.007 | −41.435 | 3.877 | 1.00 | 84.50 | O |
| ATOM | 9127 | O | HOH | W | 217 | 33.659 | −6.085 | −4.081 | 1.00 | 58.14 | O |
| ATOM | 9128 | O | HOH | W | 218 | 54.424 | 51.143 | −27.170 | 1.00 | 66.78 | O |
| ATOM | 9129 | O | HOH | W | 219 | 31.233 | 14.822 | −42.523 | 1.00 | 66.06 | O |
| ATOM | 9130 | O | HOH | W | 220 | 59.996 | 46.699 | −32.009 | 1.00 | 48.66 | O |
| ATOM | 9131 | O | HOH | W | 221 | 30.554 | 13.140 | −16.210 | 1.00 | 61.86 | O |
| ATOM | 9132 | O | HOH | W | 222 | 44.203 | −28.493 | −14.505 | 1.00 | 77.63 | O |
| ATOM | 9133 | O | HOH | W | 223 | 30.289 | 8.081 | −13.588 | 1.00 | 54.11 | O |
| ATOM | 9134 | O | HOH | W | 224 | 50.274 | −42.317 | −4.855 | 1.00 | 26.53 | O |
| ATOM | 9135 | O | HOH | W | 225 | 28.651 | −3.712 | 7.966 | 1.00 | 54.69 | O |
| ATOM | 9136 | O | HOH | W | 226 | 67.116 | 39.647 | −23.789 | 1.00 | 37.76 | O |
| ATOM | 9137 | O | HOH | W | 227 | 37.656 | −21.694 | −17.940 | 1.00 | 61.68 | O |
| ATOM | 9138 | O | HOH | W | 228 | 91.647 | 34.394 | −14.107 | 1.00 | 45.15 | O |
| ATOM | 9139 | O | HOH | W | 229 | 41.028 | 35.508 | −7.118 | 1.00 | 61.75 | O |
| ATOM | 9140 | O | HOH | W | 230 | 40.248 | −28.559 | 6.969 | 1.00 | 38.66 | O |
| ATOM | 9141 | O | HOH | W | 231 | 54.162 | −42.641 | 18.951 | 1.00 | 41.38 | O |
| ATOM | 9142 | O | HOH | W | 232 | 81.228 | −32.085 | −13.074 | 1.00 | 41.35 | O |
| ATOM | 9143 | O | HOH | W | 233 | 50.268 | −35.358 | −2.701 | 1.00 | 28.38 | O |
| ATOM | 9144 | O | HOH | W | 234 | 64.857 | 30.043 | −17.341 | 1.00 | 34.77 | O |

APPENDIX A-continued

P. alba 3T288C coordinates

| ATOM | 9145 | O | HOH | W | 235 | 62.674 | 9.209 | −26.807 | 1.00 | 58.76 | O |
|---|---|---|---|---|---|---|---|---|---|---|---|
| ATOM | 9146 | O | HOH | W | 236 | 82.184 | 52.975 | −10.392 | 1.00 | 61.52 | O |
| ATOM | 9147 | O | HOH | W | 237 | 36.482 | −4.133 | 18.202 | 1.00 | 41.73 | O |
| ATOM | 9148 | O | HOH | W | 238 | 74.033 | 16.183 | −7.064 | 1.00 | 71.16 | O |
| ATOM | 9149 | O | HOH | W | 239 | 65.741 | −38.019 | 19.761 | 1.00 | 57.50 | O |
| ATOM | 9150 | O | HOH | W | 240 | 49.937 | −21.240 | 22.807 | 1.00 | 46.67 | O |
| ATOM | 9151 | O | HOH | W | 241 | 34.731 | −6.689 | −7.318 | 1.00 | 48.62 | O |
| ATOM | 9152 | O | HOH | W | 242 | 65.731 | 38.382 | −18.155 | 1.00 | 44.68 | O |
| ATOM | 9153 | O | HOH | W | 243 | 29.862 | −2.337 | 4.065 | 1.00 | 59.55 | O |
| ATOM | 9154 | O | HOH | W | 244 | 45.836 | −15.023 | −19.205 | 1.00 | 49.02 | O |
| ATOM | 9155 | O | HOH | W | 245 | 36.589 | −1.619 | 17.193 | 1.00 | 40.23 | O |
| ATOM | 9156 | O | HOH | W | 246 | 34.323 | −10.323 | −8.877 | 1.00 | 58.54 | O |
| ATOM | 9157 | O | HOH | W | 247 | 62.139 | 39.167 | −10.432 | 1.00 | 45.40 | O |
| ATOM | 9158 | O | HOH | W | 248 | 49.939 | 41.406 | −17.501 | 1.00 | 46.80 | O |
| ATOM | 9159 | O | HOH | W | 249 | 53.513 | 48.260 | −26.270 | 1.00 | 60.43 | O |
| ATOM | 9160 | O | HOH | W | 250 | 73.526 | 23.237 | −27.444 | 1.00 | 61.10 | O |
| ATOM | 9161 | O | HOH | W | 251 | 69.211 | −30.970 | 14.209 | 1.00 | 53.73 | O |
| ATOM | 9162 | O | HOH | W | 252 | 49.336 | 18.864 | −28.048 | 1.00 | 57.51 | O |
| ATOM | 9163 | O | HOH | W | 253 | 49.935 | 1.484 | −13.946 | 1.00 | 37.90 | O |
| ATOM | 9164 | O | HOH | W | 254 | 30.096 | 3.893 | 5.083 | 1.00 | 66.59 | O |
| ATOM | 9165 | O | HOH | W | 255 | 39.758 | −7.496 | 13.501 | 1.00 | 56.93 | O |
| ATOM | 9166 | O | HOH | W | 256 | 82.305 | −35.291 | −6.599 | 1.00 | 51.37 | O |
| ATOM | 9167 | O | HOH | W | 257 | 49.782 | −39.950 | 8.443 | 1.00 | 31.76 | O |
| ATOM | 9168 | O | HOH | W | 258 | 27.976 | −9.654 | 14.307 | 1.00 | 48.06 | O |
| ATOM | 9169 | O | HOH | W | 259 | 47.094 | −21.051 | 28.763 | 1.00 | 63.75 | O |
| ATOM | 9170 | O | HOH | W | 260 | 41.251 | 14.226 | −35.483 | 1.00 | 35.07 | O |
| ATOM | 9171 | O | HOH | W | 261 | 42.481 | 24.274 | −1.324 | 1.00 | 69.59 | O |
| ATOM | 9172 | O | HOH | W | 262 | 51.446 | 20.748 | −28.017 | 1.00 | 45.64 | O |
| ATOM | 9173 | O | HOH | W | 263 | 72.148 | 25.241 | −29.773 | 1.00 | 65.72 | O |
| ATOM | 9174 | O | HOH | W | 264 | 39.401 | 11.992 | −4.214 | 1.00 | 49.54 | O |
| ATOM | 9175 | O | HOH | W | 265 | 32.275 | 12.617 | −24.662 | 1.00 | 50.59 | O |
| ATOM | 9176 | O | HOH | W | 266 | 55.250 | 9.269 | −25.684 | 1.00 | 52.64 | O |
| ATOM | 9177 | O | HOH | W | 267 | 58.661 | 44.938 | −30.151 | 1.00 | 61.24 | O |
| ATOM | 9178 | O | HOH | W | 268 | 83.116 | −36.414 | −4.312 | 1.00 | 46.83 | O |
| ATOM | 9179 | O | HOH | W | 269 | 42.839 | 15.510 | 2.646 | 1.00 | 50.23 | O |
| ATOM | 9180 | O | HOH | W | 270 | 53.273 | −7.575 | −8.127 | 1.00 | 59.58 | O |
| ATOM | 9181 | O | HOH | W | 271 | 32.659 | 16.190 | −23.905 | 1.00 | 38.99 | O |
| ATOM | 9182 | O | HOH | W | 272 | 30.130 | −12.373 | 8.961 | 1.00 | 56.13 | O |
| ATOM | 9183 | O | HOH | W | 273 | 38.784 | 13.668 | −36.645 | 1.00 | 35.13 | O |
| ATOM | 9184 | O | HOH | W | 274 | 31.104 | 1.559 | 23.598 | 1.00 | 57.27 | O |
| ATOM | 9185 | O | HOH | W | 275 | 81.657 | −36.807 | −8.531 | 1.00 | 61.00 | O |
| ATOM | 9186 | O | HOH | W | 276 | 28.259 | −9.123 | 17.061 | 1.00 | 66.33 | O |
| ATOM | 9187 | O | HOH | W | 277 | 74.640 | 10.010 | −14.448 | 1.00 | 58.66 | O |
| ATOM | 9188 | O | HOH | W | 278 | 51.672 | 47.624 | −28.267 | 1.00 | 83.54 | O |
| ATOM | 9189 | O | HOH | W | 279 | 31.801 | 14.035 | −22.697 | 1.00 | 56.21 | O |
| ATOM | 9190 | O | HOH | W | 280 | 48.965 | −56.394 | 1.074 | 1.00 | 52.99 | O |
| ATOM | 9191 | O | HOH | W | 281 | 35.984 | 12.918 | 7.155 | 1.00 | 73.87 | O |
| ATOM | 9192 | O | HOH | W | 282 | 39.220 | 24.103 | −15.411 | 1.00 | 56.10 | O |
| ATOM | 9193 | O | HOH | W | 283 | 82.513 | 24.091 | −23.548 | 1.00 | 46.49 | O |
| ATOM | 9194 | O | HOH | W | 284 | 71.235 | −14.567 | −9.579 | 1.00 | 63.27 | O |
| ATOM | 9195 | O | HOH | W | 285 | 40.489 | 24.887 | −39.134 | 1.00 | 41.29 | O |
| ATOM | 9196 | O | HOH | W | 286 | 31.217 | 5.552 | −3.887 | 1.00 | 54.56 | O |
| ATOM | 9197 | O | HOH | W | 287 | 43.073 | −12.113 | 14.437 | 1.00 | 67.38 | O |
| ATOM | 9198 | O | HOH | W | 288 | 41.797 | −9.307 | 15.285 | 1.00 | 77.90 | O |
| ATOM | 9199 | O | HOH | W | 289 | 81.627 | −42.055 | −15.117 | 1.00 | 54.24 | O |
| ATOM | 9200 | O | HOH | W | 290 | 62.244 | −32.737 | −7.755 | 1.00 | 40.89 | O |
| ATOM | 9201 | O | HOH | W | 291 | 64.210 | −29.885 | −4.076 | 1.00 | 32.81 | O |
| ATOM | 9202 | O | HOH | W | 292 | 58.895 | −35.573 | −0.679 | 1.00 | 32.40 | O |
| ATOM | 9203 | O | HOH | W | 293 | 56.735 | −34.166 | −0.445 | 1.00 | 38.48 | O |
| ATOM | 9204 | O | HOH | W | 294 | 58.151 | −30.292 | 0.958 | 1.00 | 47.10 | O |
| ATOM | 9205 | O | HOH | W | 295 | 55.143 | −32.877 | −2.640 | 1.00 | 40.38 | O |
| ATOM | 9206 | O | HOH | W | 296 | 53.725 | −33.616 | −4.826 | 1.00 | 30.71 | O |
| ATOM | 9207 | O | HOH | W | 297 | 53.204 | −31.192 | −1.960 | 1.00 | 27.95 | O |
| ATOM | 9208 | O | HOH | W | 298 | 64.773 | −39.562 | 5.940 | 1.00 | 37.11 | O |
| ATOM | 9209 | O | HOH | W | 299 | 63.454 | −40.346 | 3.719 | 1.00 | 33.48 | O |
| ATOM | 9210 | O | HOH | W | 300 | 70.929 | −25.565 | −3.552 | 1.00 | 30.91 | O |
| ATOM | 9211 | O | HOH | W | 301 | 69.251 | −23.763 | −4.761 | 1.00 | 28.53 | O |
| ATOM | 9212 | O | HOH | W | 302 | 68.454 | −19.371 | −2.053 | 1.00 | 30.58 | O |
| ATOM | 9213 | O | HOH | W | 303 | 67.364 | −18.575 | 0.260 | 1.00 | 38.26 | O |
| ATOM | 9214 | O | HOH | W | 304 | 57.160 | −34.364 | −10.979 | 1.00 | 33.18 | O |
| ATOM | 9215 | O | HOH | W | 305 | 61.204 | −57.454 | 4.268 | 1.00 | 75.63 | O |
| ATOM | 9216 | O | HOH | W | 306 | 56.730 | −31.024 | −3.793 | 1.00 | 48.17 | O |
| ATOM | 9217 | O | HOH | W | 307 | 47.415 | −47.036 | −5.422 | 1.00 | 57.71 | O |
| ATOM | 9218 | O | HOH | W | 308 | 46.209 | −46.389 | −3.069 | 1.00 | 47.74 | O |
| ATOM | 9219 | O | HOH | W | 309 | 45.713 | −44.103 | −2.107 | 1.00 | 41.00 | O |
| ATOM | 9220 | O | HOH | W | 310 | 43.110 | −43.797 | −2.091 | 1.00 | 33.44 | O |
| ATOM | 9221 | O | HOH | W | 311 | 42.141 | −41.451 | −2.487 | 1.00 | 40.62 | O |
| ATOM | 9222 | O | HOH | W | 312 | 43.871 | −40.170 | −4.616 | 1.00 | 45.61 | O |

APPENDIX A-continued

*P. alba* 3T288C coordinates

| ATOM | 9223 | O | HOH | W | 313 | 50.240 | −52.391 | 4.392 | 1.00 | 48.19 | O |
|---|---|---|---|---|---|---|---|---|---|---|---|
| ATOM | 9224 | O | HOH | W | 314 | 45.922 | −53.351 | −4.156 | 1.00 | 60.44 | O |
| ATOM | 9225 | O | HOH | W | 315 | 45.630 | −50.143 | −2.403 | 1.00 | 58.28 | O |
| ATOM | 9226 | O | HOH | W | 316 | 45.142 | −50.949 | 0.350 | 1.00 | 45.00 | O |
| ATOM | 9227 | O | HOH | W | 317 | 45.313 | −51.628 | 2.682 | 1.00 | 43.29 | O |
| ATOM | 9228 | O | HOH | W | 318 | 57.968 | −35.760 | 5.378 | 1.00 | 30.72 | O |
| ATOM | 9229 | O | HOH | W | 319 | 40.306 | −36.855 | 1.232 | 1.00 | 35.14 | O |
| ATOM | 9230 | O | HOH | W | 320 | 36.996 | −35.972 | 6.611 | 1.00 | 51.01 | O |
| ATOM | 9231 | O | HOH | W | 321 | 35.419 | −34.298 | 4.601 | 1.00 | 64.21 | O |
| ATOM | 9232 | O | HOH | W | 322 | 42.265 | −41.053 | 7.654 | 1.00 | 35.63 | O |
| ATOM | 9233 | O | HOH | W | 323 | 42.932 | −43.525 | 8.391 | 1.00 | 47.39 | O |
| ATOM | 9234 | O | HOH | W | 324 | 49.568 | −41.121 | 13.413 | 1.00 | 38.52 | O |
| ATOM | 9235 | O | HOH | W | 325 | 51.888 | −40.050 | 15.225 | 1.00 | 54.02 | O |
| ATOM | 9236 | O | HOH | W | 326 | 52.387 | −40.621 | 17.982 | 1.00 | 51.86 | O |
| ATOM | 9237 | O | HOH | W | 327 | 47.514 | −44.885 | 13.940 | 1.00 | 42.74 | O |
| ATOM | 9238 | O | HOH | W | 328 | 51.324 | −35.459 | 12.667 | 1.00 | 45.33 | O |
| ATOM | 9239 | O | HOH | W | 329 | 53.700 | −33.540 | 13.321 | 1.00 | 63.89 | O |
| ATOM | 9240 | O | HOH | W | 330 | 55.987 | −31.141 | 13.723 | 1.00 | 65.46 | O |
| ATOM | 9241 | O | HOH | W | 331 | 58.756 | −23.502 | −0.119 | 1.00 | 27.18 | O |
| ATOM | 9242 | O | HOH | W | 332 | 58.087 | −25.850 | −1.205 | 1.00 | 32.88 | O |
| ATOM | 9243 | O | HOH | W | 333 | 61.110 | −21.801 | 0.234 | 1.00 | 28.97 | O |
| ATOM | 9244 | O | HOH | W | 334 | 61.686 | −20.886 | 2.780 | 1.00 | 36.67 | O |
| ATOM | 9245 | O | HOH | W | 335 | 73.897 | −23.796 | 4.991 | 1.00 | 44.56 | O |
| ATOM | 9246 | O | HOH | W | 336 | 74.045 | −21.212 | 6.006 | 1.00 | 54.18 | O |
| ATOM | 9247 | O | HOH | W | 337 | 76.577 | −24.196 | 5.079 | 1.00 | 42.85 | O |
| ATOM | 9248 | O | HOH | W | 338 | 76.437 | −37.129 | −8.119 | 1.00 | 57.89 | O |
| ATOM | 9249 | O | HOH | W | 339 | 53.634 | −3.371 | 7.101 | 1.00 | 53.10 | O |
| ATOM | 9250 | O | HOH | W | 340 | 54.187 | −10.567 | 7.280 | 1.00 | 58.39 | O |
| ATOM | 9251 | O | HOH | W | 341 | 60.617 | −18.738 | 10.723 | 1.00 | 58.51 | O |
| ATOM | 9252 | O | HOH | W | 342 | 56.086 | −22.336 | −5.812 | 1.00 | 46.26 | O |
| ATOM | 9253 | O | HOH | W | 343 | 55.844 | −24.396 | −7.238 | 1.00 | 47.67 | O |
| ATOM | 9254 | O | HOH | W | 344 | 55.734 | −15.022 | −10.656 | 1.00 | 37.65 | O |
| ATOM | 9255 | O | HOH | W | 345 | 32.227 | 3.493 | 16.889 | 1.00 | 41.69 | O |
| ATOM | 9256 | O | HOH | W | 346 | 32.995 | 6.036 | 17.187 | 1.00 | 38.26 | O |
| ATOM | 9257 | O | HOH | W | 347 | 43.855 | −6.680 | −15.301 | 1.00 | 31.82 | O |
| ATOM | 9258 | O | HOH | W | 348 | 52.777 | −10.540 | −22.744 | 1.00 | 57.84 | O |
| ATOM | 9259 | O | HOH | W | 349 | 32.973 | −8.777 | 0.726 | 1.00 | 43.68 | O |
| ATOM | 9260 | O | HOH | W | 350 | 31.795 | −7.152 | −0.910 | 1.00 | 52.97 | O |
| ATOM | 9261 | O | HOH | W | 351 | 39.854 | −12.449 | 0.769 | 1.00 | 29.30 | O |
| ATOM | 9262 | O | HOH | W | 352 | 41.632 | −13.591 | 2.624 | 1.00 | 27.96 | O |
| ATOM | 9263 | O | HOH | W | 353 | 37.139 | −14.688 | 12.920 | 1.00 | 35.82 | O |
| ATOM | 9264 | O | HOH | W | 354 | 38.976 | −12.566 | 16.101 | 1.00 | 43.62 | O |
| ATOM | 9265 | O | HOH | W | 355 | 30.926 | −25.033 | 15.928 | 1.00 | 38.28 | O |
| ATOM | 9266 | O | HOH | W | 356 | 32.642 | −27.492 | 16.851 | 1.00 | 59.83 | O |
| ATOM | 9267 | O | HOH | W | 357 | 33.558 | −28.347 | 14.344 | 1.00 | 58.12 | O |
| ATOM | 9268 | O | HOH | W | 358 | 35.977 | −29.130 | 13.344 | 1.00 | 58.73 | O |
| ATOM | 9269 | O | HOH | W | 359 | 37.818 | −27.617 | 8.908 | 1.00 | 58.44 | O |
| ATOM | 9270 | O | HOH | W | 360 | 34.483 | −25.533 | 11.257 | 1.00 | 47.88 | O |
| ATOM | 9271 | O | HOH | W | 361 | 33.652 | −23.329 | 9.812 | 1.00 | 38.74 | O |
| ATOM | 9272 | O | HOH | W | 362 | 34.737 | −22.982 | 7.515 | 1.00 | 44.25 | O |
| ATOM | 9273 | O | HOH | W | 363 | 31.499 | −17.415 | 9.894 | 1.00 | 44.12 | O |
| ATOM | 9274 | O | HOH | W | 364 | 51.399 | −14.940 | −14.522 | 1.00 | 53.24 | O |
| ATOM | 9275 | O | HOH | W | 365 | 45.855 | −23.406 | −12.555 | 1.00 | 48.01 | O |
| ATOM | 9276 | O | HOH | W | 366 | 46.195 | −26.619 | −2.424 | 1.00 | 35.47 | O |
| ATOM | 9277 | O | HOH | W | 367 | 48.585 | −13.372 | 16.041 | 1.00 | 79.24 | O |
| ATOM | 9278 | O | HOH | W | 368 | 48.885 | −16.067 | 17.071 | 1.00 | 56.25 | O |
| ATOM | 9279 | O | HOH | W | 369 | 46.367 | −15.771 | 16.682 | 1.00 | 41.39 | O |
| ATOM | 9280 | O | HOH | W | 370 | 42.851 | −37.419 | 9.601 | 1.00 | 43.78 | O |
| ATOM | 9281 | O | HOH | W | 371 | 43.598 | −36.638 | 12.092 | 1.00 | 51.81 | O |
| ATOM | 9282 | O | HOH | W | 372 | 37.469 | −38.201 | −4.913 | 1.00 | 57.09 | O |
| ATOM | 9283 | O | HOH | W | 373 | 53.585 | −34.115 | −8.277 | 1.00 | 39.64 | O |
| ATOM | 9284 | O | HOH | W | 374 | 54.662 | −34.020 | −10.670 | 1.00 | 47.00 | O |
| ATOM | 9285 | O | HOH | W | 375 | 56.958 | −28.402 | −7.616 | 1.00 | 49.88 | O |
| ATOM | 9286 | O | HOH | W | 376 | 88.727 | 30.365 | −5.469 | 1.00 | 42.14 | O |
| ATOM | 9287 | O | HOH | W | 377 | 92.020 | 32.548 | −6.742 | 1.00 | 60.45 | O |
| ATOM | 9288 | O | HOH | W | 378 | 84.725 | 42.573 | −7.609 | 1.00 | 40.48 | O |
| ATOM | 9289 | O | HOH | W | 379 | 85.252 | 41.889 | −11.799 | 1.00 | 64.42 | O |
| ATOM | 9290 | O | HOH | W | 380 | 85.092 | 49.969 | 0.422 | 1.00 | 64.39 | O |
| ATOM | 9291 | O | HOH | W | 381 | 85.911 | 45.396 | 0.491 | 1.00 | 38.83 | O |
| ATOM | 9292 | O | HOH | W | 382 | 87.802 | 41.943 | −1.434 | 1.00 | 36.71 | O |
| ATOM | 9293 | O | HOH | W | 383 | 89.519 | 40.344 | 0.174 | 1.00 | 32.44 | O |
| ATOM | 9294 | O | HOH | W | 384 | 84.286 | 49.819 | −14.844 | 1.00 | 74.07 | O |
| ATOM | 9295 | O | HOH | W | 385 | 83.672 | 41.939 | −14.940 | 1.00 | 39.80 | O |
| ATOM | 9296 | O | HOH | W | 386 | 83.295 | 38.973 | −15.352 | 1.00 | 55.46 | O |
| ATOM | 9297 | O | HOH | W | 387 | 85.204 | 37.793 | −17.488 | 1.00 | 58.96 | O |
| ATOM | 9298 | O | HOH | W | 388 | 72.365 | 37.973 | −17.684 | 1.00 | 32.25 | O |
| ATOM | 9299 | O | HOH | W | 389 | 71.257 | 35.561 | −18.476 | 1.00 | 40.70 | O |
| ATOM | 9300 | O | HOH | W | 390 | 71.807 | 32.311 | −14.434 | 1.00 | 31.88 | O |

APPENDIX A-continued

*P. alba* 3T288C coordinates

| ATOM | 9301 | O | HOH | W | 391 | 69.838 | 34.721 | −14.719 | 1.00 | 45.42 | O |
|---|---|---|---|---|---|---|---|---|---|---|---|
| ATOM | 9302 | O | HOH | W | 392 | 70.340 | 35.612 | −11.135 | 1.00 | 44.21 | O |
| ATOM | 9303 | O | HOH | W | 393 | 65.944 | 38.414 | −7.631 | 1.00 | 38.17 | O |
| ATOM | 9304 | O | HOH | W | 394 | 77.200 | 26.681 | −14.865 | 1.00 | 32.87 | O |
| ATOM | 9305 | O | HOH | W | 395 | 75.188 | 25.234 | −13.739 | 1.00 | 31.92 | O |
| ATOM | 9306 | O | HOH | W | 396 | 73.371 | 21.193 | −16.417 | 1.00 | 33.68 | O |
| ATOM | 9307 | O | HOH | W | 397 | 72.126 | 20.703 | −18.786 | 1.00 | 38.26 | O |
| ATOM | 9308 | O | HOH | W | 398 | 73.634 | 42.793 | −22.468 | 1.00 | 42.63 | O |
| ATOM | 9309 | O | HOH | W | 399 | 74.545 | 41.623 | −24.513 | 1.00 | 42.65 | O |
| ATOM | 9310 | O | HOH | W | 400 | 60.949 | 41.087 | −13.743 | 1.00 | 32.39 | O |
| ATOM | 9311 | O | HOH | W | 401 | 59.269 | 41.117 | −15.968 | 1.00 | 33.16 | O |
| ATOM | 9312 | O | HOH | W | 402 | 59.573 | 38.606 | −17.369 | 1.00 | 37.23 | O |
| ATOM | 9313 | O | HOH | W | 403 | 61.334 | 36.357 | −16.624 | 1.00 | 34.12 | O |
| ATOM | 9314 | O | HOH | W | 404 | 65.431 | 37.913 | −32.478 | 1.00 | 72.71 | O |
| ATOM | 9315 | O | HOH | W | 405 | 74.252 | 31.182 | −33.075 | 1.00 | 54.89 | O |
| ATOM | 9316 | O | HOH | W | 406 | 66.162 | 34.417 | −19.631 | 1.00 | 41.16 | O |
| ATOM | 9317 | O | HOH | W | 407 | 70.541 | 34.371 | −26.179 | 1.00 | 49.35 | O |
| ATOM | 9318 | O | HOH | W | 408 | 72.160 | 36.584 | −26.563 | 1.00 | 44.65 | O |
| ATOM | 9319 | O | HOH | W | 409 | 66.812 | 25.333 | −18.755 | 1.00 | 30.19 | O |
| ATOM | 9320 | O | HOH | W | 410 | 86.491 | 35.390 | −9.504 | 1.00 | 58.45 | O |
| ATOM | 9321 | O | HOH | W | 411 | 90.048 | 27.970 | −11.850 | 1.00 | 44.02 | O |
| ATOM | 9322 | O | HOH | W | 412 | 62.171 | 10.320 | −31.392 | 1.00 | 77.96 | O |
| ATOM | 9323 | O | HOH | W | 413 | 61.847 | 27.094 | −12.737 | 1.00 | 54.30 | O |
| ATOM | 9324 | O | HOH | W | 414 | 47.375 | 17.474 | −33.175 | 1.00 | 62.08 | O |
| ATOM | 9325 | O | HOH | W | 415 | 44.847 | 16.856 | −34.410 | 1.00 | 66.00 | O |
| ATOM | 9326 | O | HOH | W | 416 | 42.338 | 16.500 | −34.798 | 1.00 | 44.22 | O |
| ATOM | 9327 | O | HOH | W | 417 | 46.428 | 14.822 | −3.242 | 1.00 | 31.09 | O |
| ATOM | 9328 | O | HOH | W | 418 | 44.072 | 21.336 | −19.449 | 1.00 | 24.93 | O |
| ATOM | 9329 | O | HOH | W | 419 | 45.933 | 21.946 | −21.305 | 1.00 | 25.92 | O |
| ATOM | 9330 | O | HOH | W | 420 | 36.477 | 19.634 | −19.350 | 1.00 | 38.85 | O |
| ATOM | 9331 | O | HOH | W | 421 | 35.761 | 21.880 | −22.296 | 1.00 | 54.28 | O |
| ATOM | 9332 | O | HOH | W | 422 | 38.598 | 24.261 | −20.814 | 1.00 | 34.09 | O |
| ATOM | 9333 | O | HOH | W | 423 | 42.073 | 24.026 | −31.807 | 1.00 | 32.62 | O |
| ATOM | 9334 | O | HOH | W | 424 | 43.629 | 21.308 | −34.851 | 1.00 | 46.44 | O |
| ATOM | 9335 | O | HOH | W | 425 | 38.238 | 12.974 | −39.130 | 1.00 | 43.81 | O |
| ATOM | 9336 | O | HOH | W | 426 | 39.118 | 35.646 | −35.292 | 1.00 | 25.51 | O |
| ATOM | 9337 | O | HOH | W | 427 | 42.266 | 35.370 | −30.119 | 1.00 | 37.45 | O |
| ATOM | 9338 | O | HOH | W | 428 | 40.813 | 33.402 | −28.894 | 1.00 | 33.01 | O |
| ATOM | 9339 | O | HOH | W | 429 | 41.930 | 32.862 | −26.596 | 1.00 | 32.89 | O |
| ATOM | 9340 | O | HOH | W | 430 | 45.994 | 36.920 | −27.628 | 1.00 | 49.65 | O |
| ATOM | 9341 | O | HOH | W | 431 | 44.666 | 38.262 | −32.062 | 1.00 | 50.17 | O |
| ATOM | 9342 | O | HOH | W | 432 | 44.748 | 36.296 | −29.774 | 1.00 | 48.50 | O |
| ATOM | 9343 | O | HOH | W | 433 | 41.893 | 38.285 | −33.098 | 1.00 | 59.37 | O |
| ATOM | 9344 | O | HOH | W | 434 | 41.389 | 37.610 | −35.338 | 1.00 | 44.70 | O |
| ATOM | 9345 | O | HOH | W | 435 | 37.463 | 28.292 | −28.977 | 1.00 | 35.01 | O |
| ATOM | 9346 | O | HOH | W | 436 | 37.525 | 31.016 | −27.801 | 1.00 | 60.63 | O |
| ATOM | 9347 | O | HOH | W | 437 | 43.596 | 33.620 | −22.636 | 1.00 | 43.67 | O |
| ATOM | 9348 | O | HOH | W | 438 | 42.528 | 32.919 | −20.253 | 1.00 | 49.09 | O |
| ATOM | 9349 | O | HOH | W | 439 | 39.951 | 31.335 | −21.011 | 1.00 | 58.00 | O |
| ATOM | 9350 | O | HOH | W | 440 | 48.590 | 40.251 | −26.117 | 1.00 | 55.18 | O |
| ATOM | 9351 | O | HOH | W | 441 | 51.164 | 36.110 | −17.925 | 1.00 | 49.35 | O |
| ATOM | 9352 | O | HOH | W | 442 | 53.569 | 33.635 | −16.169 | 1.00 | 35.61 | O |
| ATOM | 9353 | O | HOH | W | 443 | 60.658 | 22.781 | −34.989 | 1.00 | 62.99 | O |
| ATOM | 9354 | O | HOH | W | 444 | 67.055 | 28.403 | −32.430 | 1.00 | 71.44 | O |
| ATOM | 9355 | O | HOH | W | 445 | 64.929 | 28.511 | −31.436 | 1.00 | 65.11 | O |
| ATOM | 9356 | O | HOH | W | 446 | 31.261 | 2.328 | −12.309 | 1.00 | 60.56 | O |
| ATOM | 9357 | O | HOH | W | 447 | 62.959 | −32.696 | −0.260 | 1.00 | 37.45 | O |
| ATOM | 9358 | O | HOH | W | 448 | 32.942 | 6.020 | −16.822 | 1.00 | 50.50 | O |
| ATOM | 9359 | O | HOH | W | 449 | 39.358 | −34.872 | −0.178 | 1.00 | 40.87 | O |
| ATOM | 9360 | O | HOH | W | 450 | 49.185 | 17.331 | −39.030 | 1.00 | 85.64 | O |
| ATOM | 9361 | O | HOH | W | 451 | 34.510 | 7.195 | 15.541 | 1.00 | 40.34 | O |
| ATOM | 9362 | O | HOH | W | 452 | 47.514 | 20.262 | −33.130 | 1.00 | 70.32 | O |
| ATOM | 9363 | O | HOH | W | 453 | 55.771 | 22.486 | −35.412 | 1.00 | 55.29 | O |
| ATOM | 9364 | O | HOH | W | 454 | 51.628 | 22.787 | −35.224 | 1.00 | 43.15 | O |
| ATOM | 9365 | O | HOH | W | 455 | 70.247 | −33.650 | 4.619 | 1.00 | 44.86 | O |
| ATOM | 9366 | O | HOH | W | 456 | 56.201 | −31.455 | 16.228 | 1.00 | 70.20 | O |
| ATOM | 9367 | O | HOH | W | 457 | 53.402 | −26.502 | 13.095 | 1.00 | 43.52 | O |
| ATOM | 9368 | O | HOH | W | 458 | 50.905 | −29.097 | 13.293 | 1.00 | 51.50 | O |
| ATOM | 9369 | O | HOH | W | 459 | 58.406 | −24.593 | 13.085 | 1.00 | 64.84 | O |
| ATOM | 9370 | O | HOH | W | 460 | 33.095 | −1.824 | −7.051 | 1.00 | 53.88 | O |
| ATOM | 9371 | O | HOH | W | 461 | 33.672 | −5.051 | −9.420 | 1.00 | 80.71 | O |
| ATOM | 9372 | O | HOH | W | 462 | 31.765 | −1.950 | −9.780 | 1.00 | 62.59 | O |
| ATOM | 9373 | O | HOH | W | 463 | 28.204 | 6.068 | 17.286 | 1.00 | 70.37 | O |
| ATOM | 9374 | O | HOH | W | 464 | 27.676 | 1.116 | 7.983 | 1.00 | 72.76 | O |
| ATOM | 9375 | O | HOH | W | 465 | 60.829 | −28.277 | −6.075 | 1.00 | 46.61 | O |
| ATOM | 9376 | O | HOH | W | 466 | 63.126 | −27.902 | −5.719 | 1.00 | 45.15 | O |
| ATOM | 9377 | O | HOH | W | 467 | 30.807 | −10.665 | 7.011 | 1.00 | 54.47 | O |
| ATOM | 9378 | O | HOH | W | 468 | 52.783 | −44.340 | 20.735 | 1.00 | 61.14 | O |

APPENDIX A-continued

P. alba 3T288C coordinates

| ATOM | 9379 | O | HOH | W | 469 | 53.681 | −46.710 | 20.274 | 1.00 | 63.66 | O |
|---|---|---|---|---|---|---|---|---|---|---|---|
| ATOM | 9380 | O | HOH | W | 470 | 47.228 | −42.064 | 14.688 | 1.00 | 51.18 | O |
| ATOM | 9381 | O | HOH | W | 471 | 45.107 | −40.588 | 13.641 | 1.00 | 70.66 | O |
| ATOM | 9382 | O | HOH | W | 472 | 42.635 | −41.371 | 12.545 | 1.00 | 64.29 | O |
| ATOM | 9383 | O | HOH | W | 473 | 35.539 | 3.814 | −2.340 | 1.00 | 37.60 | O |
| ATOM | 9384 | O | HOH | W | 474 | 73.492 | 25.649 | 6.524 | 1.00 | 67.76 | O |
| ATOM | 9385 | O | HOH | W | 475 | 76.443 | 30.265 | −3.269 | 1.00 | 48.17 | O |
| ATOM | 9386 | O | HOH | W | 476 | 54.665 | 30.777 | −42.169 | 1.00 | 51.03 | O |
| ATOM | 9387 | O | HOH | W | 477 | 62.072 | −26.897 | −29.645 | 1.00 | 60.54 | O |
| ATOM | 9388 | O | HOH | W | 478 | 83.395 | −25.719 | −18.311 | 1.00 | 61.12 | O |
| ATOM | 9389 | O | HOH | W | 479 | 69.296 | −29.080 | −15.067 | 1.00 | 52.55 | O |
| ATOM | 9390 | O | HOH | W | 480 | 68.450 | −34.644 | −18.846 | 1.00 | 41.82 | O |
| ATOM | 9391 | O | HOH | W | 481 | 68.844 | −42.933 | −18.854 | 1.00 | 46.36 | O |
| ATOM | 9392 | O | HOH | W | 482 | 74.779 | −51.629 | −18.945 | 1.00 | 82.33 | O |
| ATOM | 9393 | O | HOH | W | 483 | 61.814 | −31.687 | −3.538 | 1.00 | 39.24 | O |
| ATOM | 9394 | O | HOH | W | 484 | 60.409 | −33.103 | −0.222 | 1.00 | 45.78 | O |
| ATOM | 9395 | O | HOH | W | 485 | 58.893 | −27.935 | 0.472 | 1.00 | 37.41 | O |
| ATOM | 9396 | O | HOH | W | 486 | 64.559 | −37.400 | 7.582 | 1.00 | 36.43 | O |
| ATOM | 9397 | O | HOH | W | 487 | 59.482 | −60.439 | 1.522 | 1.00 | 74.62 | O |
| ATOM | 9398 | O | HOH | W | 488 | 68.935 | −48.617 | 6.285 | 1.00 | 57.38 | O |
| ATOM | 9399 | O | HOH | W | 489 | 45.518 | −41.693 | 6.827 | 1.00 | 48.99 | O |
| ATOM | 9400 | O | HOH | W | 490 | 73.965 | −30.043 | 10.858 | 1.00 | 57.30 | O |
| ATOM | 9401 | O | HOH | W | 491 | 60.705 | −18.803 | 3.885 | 1.00 | 48.85 | O |
| ATOM | 9402 | O | HOH | W | 492 | 58.316 | −21.884 | −13.444 | 1.00 | 54.51 | O |
| ATOM | 9403 | O | HOH | W | 493 | 51.463 | −2.633 | −7.386 | 1.00 | 35.03 | O |
| ATOM | 9404 | O | HOH | W | 494 | 33.079 | −3.931 | 24.409 | 1.00 | 63.38 | O |
| ATOM | 9405 | O | HOH | W | 495 | 27.735 | −22.892 | 14.172 | 1.00 | 53.70 | O |
| ATOM | 9406 | O | HOH | W | 496 | 29.069 | −16.433 | 10.323 | 1.00 | 66.96 | O |
| ATOM | 9407 | O | HOH | W | 497 | 38.888 | −20.098 | −19.891 | 1.00 | 65.74 | O |
| ATOM | 9408 | O | HOH | W | 498 | 46.039 | −37.082 | 13.291 | 1.00 | 56.96 | O |
| ATOM | 9409 | O | HOH | W | 499 | 90.450 | 25.023 | −8.885 | 1.00 | 62.54 | O |
| ATOM | 9410 | O | HOH | W | 500 | 87.188 | 44.513 | −1.400 | 1.00 | 60.58 | O |
| ATOM | 9411 | O | HOH | W | 501 | 88.088 | 41.534 | −3.683 | 1.00 | 51.73 | O |
| ATOM | 9412 | O | HOH | W | 502 | 84.472 | 43.474 | −10.213 | 1.00 | 58.23 | O |
| ATOM | 9413 | O | HOH | W | 503 | 60.288 | 45.674 | −27.170 | 1.00 | 52.90 | O |
| ATOM | 9414 | O | HOH | W | 504 | 60.503 | 38.801 | −24.799 | 1.00 | 54.90 | O |
| ATOM | 9415 | O | HOH | W | 505 | 65.628 | 22.382 | −28.961 | 1.00 | 55.27 | O |

What is claimed is:

1. An isolated polypeptide variant having isoprene synthase activity, wherein the polypeptide variant comprises a substitution at residue X288 corresponding to SEQ ID NO:1, and wherein the polypeptide has increased protein solubility compared a parent polypeptide which does not comprise the substitution at residue X288, wherein said polypeptide variant is 90% identical to isoprene synthase polypeptide of SEQ ID NO: 1.

2. The polypeptide variant of claim 1 wherein the substitution is at S288.

3. The polypeptide variant of claim 2 wherein the substitution is S288C.

4. The polypeptide variant of claim 1, where the polypeptide has at least 5% to at least 75% increased protein solubility compared to the parent polypeptide.

5. The polypeptide variant of claim 1 wherein the polypeptide is derived from a parent polypeptide isolated from a plant.

6. The polypeptide variant of claim 5 wherein the parent polypeptide is isolated from a plant species selected from poplar (*Populus* sp.), kudzu (*Pueraria* sp.), English oak (*Quercus* sp.) or willow (*Salix* sp.).

7. The polypeptide variant of claim 6 wherein the species is *Populus* sp.

8. The polypeptide variant of claim 7 wherein the species is *P. alba, P. tremuloides, P. trichocharpa,* or *P. nigra*.

9. The polypeptide variant of claim 6 wherein the species is *Pueraria* sp.

10. The polypeptide variant of claim 9 wherein the species is *Pueraria montana*.

11. The polypeptide variant of claim 6 wherein the species is *Quercus* sp.

12. The polypeptide variant of claim 11 wherein the species is *Quercus rubur*.

13. The polypeptide variant of claim 6 wherein the species is *Salix* sp.

14. The polypeptide variant of claim 13 wherein the species is *S. alba* or *S. baylonica*.

* * * * *

SEQUENCE LISTING

<160> NUMBER OF SEQ ID NOS: 47

<210> SEQ ID NO 1
<211> LENGTH: 544
<212> TYPE: PRT
<213> ORGANISM: Artificial Sequence
<220> FEATURE:
<223> OTHER INFORMATION: Synthetic Construct

<400> SEQUENCE: 1

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
```

-continued

```
              115                 120                 125
Phe Leu Glu Asn Leu Lys Glu Asp Ile Lys Ala Ile Leu Ser Leu Tyr
130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                    165                 170                 175
Gly Lys Glu Leu Ala Glu Gln Val Asn His Ala Leu Glu Leu Pro Leu
                180                 185                 190
His Arg Arg Thr Gln Arg Leu Glu Ala Val Trp Ser Ile Glu Ala Tyr
                    195                 200                 205
Arg Lys Lys Glu Asp Ala Asn Gln Val Leu Leu Glu Leu Ala Ile Leu
210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                    245                 250                 255
Arg Asp Arg Leu Ile Glu Ser Phe Tyr Trp Ala Val Gly Val Ala Phe
                260                 265                 270
Glu Pro Gln Tyr Ser Asp Cys Arg Asn Ser Val Ala Lys Met Phe Ser
                    275                 280                 285
Phe Val Thr Ile Ile Asp Asp Ile Tyr Asp Val Tyr Gly Thr Leu Asp
290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                    325                 330                 335
Asn Thr Ile Asn Glu Ile Ala Tyr Asp Asn Leu Lys Asp Lys Gly Glu
                340                 345                 350
Asn Ile Leu Pro Tyr Leu Thr Lys Ala Trp Ala Asp Leu Cys Asn Ala
                    355                 360                 365
Phe Leu Gln Glu Ala Lys Trp Leu Tyr Asn Lys Ser Thr Pro Thr Phe
370                 375                 380
Asp Asp Tyr Phe Gly Asn Ala Trp Lys Ser Ser Ser Gly Pro Leu Gln
385                 390                 395                 400
Leu Val Phe Ala Tyr Phe Ala Val Val Gln Asn Ile Lys Lys Glu Glu
                    405                 410                 415
Ile Glu Asn Leu Gln Lys Tyr His Asp Thr Ile Ser Arg Pro Ser His
                420                 425                 430
Ile Phe Arg Leu Cys Asn Asp Leu Ala Ser Ala Ser Ala Glu Ile Ala
                    435                 440                 445
Arg Gly Glu Thr Ala Asn Ser Val Ser Cys Tyr Met Arg Thr Lys Gly
                450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                    485                 490                 495
Lys Pro Phe Val Glu Thr Ala Ile Asn Leu Ala Arg Gln Ser His Cys
                500                 505                 510
Thr Tyr His Asn Gly Asp Ala His Thr Ser Pro Asp Glu Leu Thr Arg
                    515                 520                 525
Lys Arg Val Leu Ser Val Ile Thr Glu Pro Ile Leu Pro Phe Glu Arg
530                 535                 540
```

<210> SEQ ID NO 2
<211> LENGTH: 553
<212> TYPE: PRT
<213> ORGANISM: Artificial Sequence
<220> FEATURE:
<223> OTHER INFORMATION: Synthetic Construct

<400> SEQUENCE: 2

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Cys
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365
```

Phe Leu Gln Glu Ala Lys Trp Leu Tyr Asn Lys Ser Thr Pro Thr Phe
         370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                    405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
        450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Gly Pro Ile Leu Pro Phe Glu Arg
        530                 535                 540

Glu Asn Leu Tyr Phe Gln Gly Leu Glu
545                 550

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
gaaaaactga gtggtagcct gttcgcgaaa c                              31

<210> SEQ ID NO 4
<211> LENGTH: 31
<212> TYPE: DNA
<213> ORGANISM: Artificial Sequence
<220> FEATURE:
<223> OTHER INFORMATION: Synthetic Construct

<400> SEQUENCE: 4
aggctaccac tcagtttttc cttgttcatc t                              31

<210> SEQ ID NO 5
<211> LENGTH: 33
<212> TYPE: DNA
<213> ORGANISM: Artificial Sequence
<220> FEATURE:
<223> OTHER INFORMATION: Synthetic Construct

<400> SEQUENCE: 5
aaaaatgttt tgtttcgtaa ccattatcga cga                            33

<210> SEQ ID NO 6
<211> LENGTH: 33
<212> TYPE: DNA
<213> ORGANISM: Artificial Sequence
<220> FEATURE:

<223> OTHER INFORMATION: Synthetic Construct

<400> SEQUENCE: 6
tggttacgaa acaaaacatt tttgcgacgg agt                33

<210> SEQ ID NO 7
<211> LENGTH: 544
<212> TYPE: PRT
<213> ORGANISM: Artificial Sequence
<220> FEATURE:
<223> OTHER INFORMATION: Synthetic Construct

<400> SEQUENCE: 7

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Cys
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335
```

```
Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
        370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

<210> SEQ ID NO 8
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 8
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttttagg    180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggttat caagtgaga     780 aatcaccatg agtgacgact gaatccggtg agaatggcaa agtttatgc atttctttcc     840 agacttgttc aacaggccag ccattacgct cgtcatcaaa atcactcgca tcaaccaaac     900
```

-continued

```
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggga acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca gggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
```

```
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcgggaa tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat tgattgcgca gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagca cgtcgctctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gttcctccg gcggcttcga    5340 tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
```

| | |
|---|---|
| gccactgcat cgccgtactc agcgtctgga agcagtatgg tctatcgagg cctaccgtaa | 5700 |
| aaaggaggac gcgaatcagg ttctgctgga gctggcaatt ctggattaca acatgatcca | 5760 |
| gtctgtatac cagcgtgatc tgcgtgaaac gtcccgttgg tggcgtcgtg tgggtctggc | 5820 |
| gaccaaactg cactttgctc gtgaccgcct gattgagagc ttctactggg ccgtgggtgt | 5880 |
| agcattcgaa ccgcaatact ccgactgccg taactccgtc gcaaaaatgt tttgtttcgt | 5940 |
| aaccattatc gacgatatct acgatgtata cggcaccctg gacgaactgg agctgtttac | 6000 |
| tgatgcagtt gagcgttggg acgtaaacgc catcaacgac ctgccggatt acatgaaact | 6060 |
| gtgcttctg gctctgtata acactattaa cgaaatcgcc tacgacaacc tgaaagataa | 6120 |
| aggtgagaac atcctgccgt atctgaccaa agcctgggct gacctgtgca acgctttcct | 6180 |
| gcaagaagcc aagtggctgt acaacaaatc tactccgacc tttgacgact acttcggcaa | 6240 |
| cgcatggaaa tcctcttctg gcccgctgca actggtgttc gcttacttcg ctgtcgtgca | 6300 |
| gaacattaaa aaggaagaga tcgaaaacct gcaaaaatac catgacacca tctctcgtcc | 6360 |
| ttcccatatc ttccgtctgt gcaatgacct ggctagcgcg tctgcggaaa ttgcgcgtgg | 6420 |
| tgaaaccgca aatagcgttt cttgttacat gcgcactaaa ggtatctccg aagaactggc | 6480 |
| taccgaaagc gtgatgaatc tgatcgatga acctgaaaa aagatgaaca aggaaaaact | 6540 |
| gggtggtagc ctgttcgcga aaccgttcgt ggaaaccgcg atcaacctgg cacgtcaatc | 6600 |
| tcactgcact tatcataacg gcgacgcgca tacctctccg gatgagctga cccgcaaacg | 6660 |
| cgttctgtct gtaatcactg aaccgattct gccgtttgaa cgctaaggat ccgaattcga | 6720 |
| gctccgtcga caagcttgcg gccgcactcg agcaccacca ccaccaccac tgagatccgg | 6780 |
| ctgctaacaa agcccgaaag gaagctgagt tggctgctgc caccgctgag caataactag | 6840 |
| cataacccct tggggcctct aaacgggtct gaggggtttt ttgctgaaa ggaggaacta | 6900 |
| tatccggat | 6909 |

<210> SEQ ID NO 9
<211> LENGTH: 6858
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggaagc | 420 |
| tcgtcgttct gcgaactacg aacctaacag ctgggactat gattacctgc tgtcctccga | 480 |
| cacggacgag tccatcgaag tatacaaaga caaagcgaaa aagctggaag ccgaagttcg | 540 |
| tcgcgagatt aataacgaaa agcagaatt tctgaccctg ctggaactga ttgacaacgt | 600 |
| ccagcgcctg ggcctgggtt accgtttcga gtctgatatc cgtggtgcgc tggatcgctt | 660 |
| cgtttcctcc ggcggcttcg atgcggtaac caagacttcc tgcacggta cggcactgtc | 720 |
| tttccgtctg ctgcgtcaac acggttttga ggtttctcag gaagcgttca gcggcttcaa | 780 |

```
agaccaaaac ggcaacttcc tggagaacct gaaggaagat atcaaagcta tcctgagcct    840
gtacgaggcc agcttcctgg ctctggaagg cgaaaacatc ctggacgagg cgaaggtttt    900
cgcaatctct catctgaaag aactgtctga agaaaagatc ggtaaagagc tggcagaaca    960
ggtgaaccat gcactggaac tgccactgca tcgccgtact cagcgtctgg aagcagtatg   1020
gtctatcgag gcctaccgta aaaggagga cgcgaatcag gttctgctgg agctggcaat   1080
tctggattac aacatgatcc agtctgtata ccagcgtgat ctgcgtgaaa cgtcccgttg   1140
gtggcgtcgt gtgggtctgg cgaccaaact gcactttgct cgtgaccgcc tgattgagag   1200
cttctactgg gccgtgggtg tagcattcga accgcaatac tccgactgcc gtaactccgt   1260
cgcaaaaatg ttttctttcg taaccattat cgacgatatc tacgatgtat acggcaccct   1320
ggacgaactg gagctgttta ctgatgcagt tgagcgttgg gacgtaaacg ccatcaacga   1380
cctgccggat tacatgaaac tgtgcttcct ggctctgtat aacactatta cgaaatcgc   1440
ctacgacaac ctgaaagata aggtgagaa catcctgccg tatctgacca agcctgggc   1500
tgacctgtgc aacgctttcc tgcaagaagc caagtggctg tacaacaaat ctactccgac   1560
ctttgacgac tacttcggca acgcatggaa atcctcttct ggcccgctgc aactggtgtt   1620
cgcttacttc gctgtcgtgc agaacattaa aaaggaagag atcgaaaacc tgcaaaaata   1680
ccatgacacc atctctcgtc cttcccatat cttccgtctg tgcaatgacc tggctagcgc   1740
gtctgcggaa attgcgcgtg gtgaaaccgc aaatagcgtt tcttgttaca tgcgcactaa   1800
aggtatctcc gaagaactgg ctaccgaaag cgtgatgaat ctgatcgatg aaacctggaa   1860
aaagatgaac aaggaaaaac tgagtggtag cctgttcgcg aaaccgttcg tggaaaccgc   1920
gatcaacctg gcacgtcaat ctcactgcac ttatcataac ggcgacgcgc atacctctcc   1980
ggatgagctg acccgcaaac gcgttctgtc tgtaatcact gaaccgattc tgccgtttga   2040
acgctaactg cataaaggag gtaaaaaaac atggtatcct gttctgcgcc gggtaagatt   2100
tacctgttcg gtgaacacgc cgtagtttat ggcgaaactg caattgcgtg tgcggtggaa   2160
ctgcgtaccc gtgttcgcgc ggaactcaat gactctatca ctattcagag ccagatcggc   2220
cgcaccggtc tggatttcga aaagcaccct tatgtgtctg cggtaattga aaaatgcgc   2280
aaatctattc ctattaacgg tgttttcttg accgtcgatt ccgacatccc ggtgggctcc   2340
ggtctgggta gcagcgcagc cgttactatc gcgtctattg gtgcgctgaa cgagctgttc   2400
ggctttggcc tcagcctgca gaaaatcgct aaactgggcc acgaaatcga attaaagta   2460
cagggtgccg cgtccccaac cgatacgtat gtttctacct tcggcggcgt ggttaccatc   2520
ccggaacgtc gcaaactgaa aactccggac tgcggcattg tgattggcga taccggcgtt   2580
ttctcctcca ccaaagagtt agtagctaac gtacgtcagc tgcgcgaaag ctacccggat   2640
ttgatcgaac cgctgatgac ctctattggc aaaatctctc gtatcggcga caactggtt   2700
ctgtctggcg actacgcatc catcggccgc ctgatgaacg tcaaccaggg tctcctggac   2760
gccctgggcg ttaacatctt agaactgagc cagctgatct attccgctcg tgcggcaggt   2820
gcgtttggcg ctaaaatcac gggcgctggc ggcggtggct gtatggttgc gctgaccgct   2880
ccggaaaaat gcaaccaagt ggcagaagcg gtagcaggcg ctggcggtaa agtgactatc   2940
actaaaccga ccgagcaagg tctgaaagta gattaaagtc tagttaaagt ttaaacggtc   3000
tccagcttgg ctgttttggc ggatgagaga agatttcag cctgatacag attaaatcag   3060
aacgcagaag cggtctgata aaacagaatt tgcctggcgg cagtagcgcg gtggtcccac   3120
```

```
ctgaccccat gccgaactca gaagtgaaac gccgtagcgc cgatggtagt gtggggtctc   3180
cccatgcgag agtagggaac tgccaggcat caaataaaac gaaaggctca gtcgaaagac   3240
tgggcctttc gttttatctg ttgtttgtcg gtgaacgctc tcctgagtag gacaaatccg   3300
ccgggagcgg atttgaacgt tgcgaagcaa cggcccggag ggtggcgggc aggacgcccg   3360
ccataaactg ccaggcatca aattaagcag aaggccatcc tgacggatgg ccttttttgcg  3420 tttctacaaa ctctttttgt ttattttct aaatacattc aaatatgtat ccgctcatga    3480
gacaataacc ctgataaatg cttcaataat attgaaaaag gaagagtatg agtattcaac   3540
atttccgtgt cgcccttatt cccttttttg cggcattttg ccttcctgtt tttgctcacc   3600
cagaaacgct ggtgaaagta aaagatgctg aagatcagtt gggtgcacga gtgggttaca   3660
tcgaactgga tctcaacagc ggtaagatcc ttgagagttt tcgccccgaa gaacgttttc   3720
caatgatgag cacttttaaa gttctgctat gtggcgcggt attatcccgt gttgacgccg   3780
ggcaagagca actcggtcgc cgcatacact attctcagaa tgacttggtt gagtactcac   3840
cagtcacaga aaagcatctt acggatggca tgacagtaag agaattatgc agtgctgcca   3900
taaccatgag tgataacact gcggccaact tacttctgac aacgatcgga ggaccgaagg   3960
agctaaccgc ttttttgcac aacatggggg atcatgtaac tcgccttgat cgttgggaac   4020
cggagctgaa tgaagccata ccaaacgacg agcgtgacac cacgatgcct gtagcaatgg   4080
caacaacgtt gcgcaaacta ttaactggcg aactacttac tctagcttcc cggcaacaat   4140
taatagactg gatggaggcg gataaagttg caggaccact tctgcgctcg gcccttccgg   4200
ctggctggtt tattgctgat aaatctggag ccggtgagcg tgggtctcgc ggtatcattg   4260
cagcactggg gccagatggt aagccctccc gtatcgtagt tatctacacg acggggagtc   4320
aggcaactat ggatgaacga aatagacaga tcgctgagat aggtgcctca ctgattaagc   4380
attggtaact gtcagaccaa gtttactcat atatacttta gattgattta aaacttcatt   4440
tttaatttaa aaggatctag gtgaagatcc tttttgataa tctcatgacc aaaatccctt   4500
aacgtgagtt ttcgttccac tgagcgtcag accccgtaga aaagatcaaa ggatcttctt   4560
gagatccttt ttttctgcgc gtaatctgct gcttgcaaac aaaaaaacca ccgctaccag   4620
cggtggtttg tttgccggat caagagctac caactctttt tccgaaggta actggcttca   4680
gcagagcgca gataccaaat actgtccttc tagtgtagcc gtagttaggc caccacttca   4740
agaactctgt agcaccgcct acatacctcg ctctgctaat cctgttacca gtggctgctg   4800
ccagtggcga taagtcgtgt cttaccgggt tggactcaag acgatagtta ccggataagg   4860
cgcagcggtc gggctgaacg gggggttcgt gcacacagcc cagcttggag cgaacgacct   4920
acaccgaact gagataccta cagcgtgagc tatgagaaag cgccacgctt cccgaaggga   4980
gaaaggcgga caggtatccg gtaagcggca gggtcggaac aggagagcgc acgagggagc   5040
ttccaggggg aaacgcctgg tatctttata gtcctgtcgg gtttcgccac ctctgacttg   5100
agcgtcgatt tttgtgatgc tcgtcagggg ggcggagcct atggaaaaac gccagcaacg   5160
cggccttttt acggttcctg gccttttgct ggccttttgc tcacatgttc tttcctgcgt   5220
tatcccctga ttctgtggat aaccgtatta ccgcctttga gtgagctgat accgctcgcc   5280
gcagccgaac gaccgagcgc agcgagtcag tgagcgagga agcggaagag cgcctgatgc   5340
ggtattttct ccttacgcat ctgtgcggta tttcacaccg catatggtgc actctcagta   5400
caatctgctc tgatgccgca tagttaagcc agtatacact ccgctatcgc tacgtgactg   5460
ggtcatggct gcgccccgac acccgccaac acccgctgac gcgccctgac gggcttgtct   5520
```

```
gctcccggca tccgcttaca gacaagctgt gaccgtctcc gggagctgca tgtgtcagag    5580
gttttcaccg tcatcaccga aacgcgcgag gcagcagatc aattcgcgcg cgaaggcgaa    5640
gcggcatgca tttacgttga caccatcgaa tggtgcaaaa cctttcgcgg tatggcatga    5700
tagcgcccgg aagagagtca attcaggtgt gtgaatgtga aaccagtaac gttatacgat    5760
gtcgcagagt atgccggtgt ctcttatcag accgtttccc gcgtggtgaa ccaggccagc    5820
cacgtttctg cgaaaacgcg ggaaaaagtg gaagcggcga tggcggagct gaattacatt    5880
cccaaccgcg tggcacaaca actggcgggc aaacagtcgt tgctgattgg cgttgccacc    5940
tccagtctgg ccctgcacgc gccgtcgcaa attgtcgcgg cgattaaatc tcgcgccgat    6000
caactgggtg ccagcgtggt ggtgtcgatg gtagaacgaa gcggcgtcga agcctgtaaa    6060
gcggcggtgc acaatcttct cgcgcaacgc gtcagtgggc tgatcattaa ctatccgctg    6120
gatgaccagg atgccattgc tgtggaagct gcctgcacta atgttccggc gttatttctt    6180
gatgtctctg accagacacc catcaacagt attattttct cccatgaaga cggtacgcga    6240
ctgggcgtgg agcatctggt cgcattgggt caccagcaaa tcgcgctgtt agcgggccca    6300
ttaagttctg tctcggcgcg tctgcgtctg gctggctggc ataaatatct cactcgcaat    6360
caaattcagc cgatagcgga acgggaaggc gactggagtg ccatgtccgg ttttcaacaa    6420
accatgcaaa tgctgaatga gggcatcgtt cccactgcga tgctggttgc aacgatcag    6480 atggcgctgg gcgcaatgcg cgccattacc gagtccgggc tgcgcgttgg tgcggatatc    6540
tcggtagtgg gatacgacga taccgaagac agctcatgtt atatcccgcc gtcaaccacc    6600
atcaaacagg attttcgcct gctggggcaa accagcgtgg accgcttgct gcaactctct    6660
cagggccagg cggtgaaggg caatcagctg ttgcccgtct cactggtgaa aagaaaaacc    6720
accctggcgc ccaatacgca aaccgcctct ccccgcgcgt tggccgattc attaatgcag    6780
ctggcacgac aggtttcccg actggaaagc gggcagtgag cgcaacgcaa ttaatgtgag    6840
ttagcgcgaa ttgatctg                                                  6858
```

<210> SEQ ID NO 10
<211> LENGTH: 544
<212> TYPE: PRT
<213> ORGANISM: Artificial Sequence
<220> FEATURE:
<223> OTHER INFORMATION: Synthetic Construct

<400> SEQUENCE: 10

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
```

```
              115                 120                 125
Phe Leu Glu Asn Leu Lys Glu Asp Ile Lys Ala Ile Leu Ser Leu Tyr
    130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                165                 170                 175
Gly Lys Glu Leu Ala Glu Gln Val Asn His Ala Leu Glu Leu Pro Leu
                180                 185                 190
His Arg Arg Thr Gln Arg Leu Glu Ala Val Trp Ser Ile Glu Ala Tyr
                195                 200                 205
Arg Lys Lys Glu Asp Ala Asn Gln Val Leu Leu Glu Leu Ala Ile Leu
    210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                245                 250                 255
Arg Asp Arg Leu Ile Glu Ser Phe Tyr Trp Ala Val Gly Val Ala Phe
                260                 265                 270
Glu Pro Gln Tyr Ser Asp Cys Arg Asn Ser Val Ala Lys Met Phe Cys
                275                 280                 285
Phe Val Thr Ile Ile Asp Asp Ile Tyr Asp Val Tyr Gly Thr Leu Asp
                290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
                340                 345                 350
Asn Ile Leu Pro Tyr Leu Thr Lys Ala Trp Ala Asp Leu Cys Asn Ala
                355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
                420                 425                 430
Ile Phe Arg Leu Cys Asn Asp Leu Ala Ser Ala Ser Ala Glu Ile Ala
                435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Ser Gly Ser Leu Phe Ala
                485                 490                 495
Lys Pro Phe Val Glu Thr Ala Ile Asn Leu Ala Arg Gln Ser His Cys
                500                 505                 510
Thr Tyr His Asn Gly Asp Ala His Thr Ser Pro Asp Glu Leu Thr Arg
                515                 520                 525
Lys Arg Val Leu Ser Val Ile Thr Glu Pro Ile Leu Pro Phe Glu Arg
                530                 535                 540
```

<210> SEQ ID NO 11
<211> LENGTH: 6858
<212> TYPE: DNA
<213> ORGANISM: Artificial Sequence
<220> FEATURE:
<223> OTHER INFORMATION: Synthetic Construct

<400> SEQUENCE: 11

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggaagc     420
tcgtcgttct gcgaactacg aacctaacag ctgggactat gattacctgc tgtcctccga     480
cacggacgag tccatcgaag tatacaaaga caaagcgaaa aagctggaag ccgaagttcg     540
tcgcgagatt aataacgaaa agcagaattc tgaccctg ctggaactga ttgacaacgt     600
ccagcgcctg ggcctgggtt accgtttcga gtctgatatc cgtggtgcgc tggatcgctt     660
cgtttcctcc ggcggcttcg atgcggtaac caagacttcc ctgcacggta cggcactgtc     720
tttccgtctg ctgcgtcaac acggttttga ggtttctcag gaagcgttca gcggcttcaa     780
agaccaaaac ggcaacttcc tggagaacct gaaggaagat atcaaagcta tcctgagcct     840
gtacgaggcc agcttcctgg ctctggaagg cgaaaacatc ctggacgagg cgaaggtttt     900
cgcaatctct catctgaaag aactgtctga agaaagatc ggtaaagagc tggcagaaca     960
ggtgaaccat gcactggaac tgccactgca tcgccgtact cagcgtctgg aagcagtatg    1020
gtctatcgag gcctaccgta aaaggagga gcgaatcag gttctgctgg agctggcaat    1080
tctggattac aacatgatcc agtctgtata ccagcgtgat ctgcgtgaaa cgtcccgttg    1140
gtggcgtcgt gtgggtctgg cgaccaaact gcactttgct cgtgaccgcc tgattgagag    1200
cttctactgg gccgtgggtg tagcattcga accgcaatac tccgactgcc gtaactccgt    1260
cgcaaaaatg tttttgtttcg taaccattat cgacgatatc tacgatgtat acggcacccct   1320
ggacgaactg gagctgttta ctgatgcagt tgagcgttgg gacgtaaacg ccatcaacga    1380
cctgccggat tacatgaaac tgtgctttct ggctctgtat aacactatta acgaaatcgc    1440
ctacgacaac ctgaaagata aggtgagaa catcctgccg tatctgacca agcctgggc    1500
tgacctgtgc aacgctttcc tgcaagaagc caagtggctg tacaacaaat ctactccgac    1560
ctttgacgac tacttcggca acgcatggaa atcctcttct ggcccgctgc aactggtgtt    1620
cgcttacttc gctgtcgtgc agaacattaa aaaggaagag atcgaaaacc tgcaaaaata    1680
ccatgacacc atctctcgtc cttcccatat cttccgtctg tgcaatgacc tggctagcgc    1740
gtctgcggaa attgcgcgtg gtgaaaccgc aaatagcgtt tcttgttaca tgcgcactaa    1800
aggtatctcc gaagaactgg ctaccgaaag cgtgatgaat ctgatcgatg aaacctggaa    1860
aaagatgaac aaggaaaaac tgagtggtag cctgttcgcg aaaccgttcg tggaaaccgc    1920
gatcaacctg gcacgtcaat ctcactgcac ttatcataac ggcgacgcgc ataccttctcc    1980
ggatgagctg acccgcaaac gcgttctgtc tgtaataact gaaccgattc tgccgtttga    2040
```

```
acgctaactg cataaaggag gtaaaaaaac atggtatcct gttctgcgcc gggtaagatt    2100
tacctgttcg gtgaacacgc cgtagtttat ggcgaaactg caattgcgtg tgcggtggaa    2160
ctgcgtaccc gtgttcgcgc ggaactcaat gactctatca ctattcagag ccagatcggc    2220
cgcaccggtc tggatttcga aaagcaccct tatgtgtctg cggtaattga aaaatgcgc    2280
aaatctattc ctattaacgg tgttttcttg accgtcgatt ccgacatccc ggtgggctcc    2340
ggtctgggta gcagcgcagc cgttactatc gcgtctattg gtgcgctgaa cgagctgttc    2400
ggctttggcc tcagcctgca agaaatcgct aaactgggcc acgaaatcga aattaaagta    2460
cagggtgccg cgtccccaac cgatacgtat gtttctacct tcggcggcgt ggttaccatc    2520
ccggaacgtc gcaaactgaa aactccggac tgcggcattg tgattggcga taccggcgtt    2580
ttctcctcca ccaaagagtt agtagctaac gtacgtcagc tgcgcgaaag ctacccggat    2640
ttgatcgaac cgctgatgac ctctattggc aaaatctctc gtatcggcga acaactggtt    2700
ctgtctggcg actacgcatc catcggccgc ctgatgaacg tcaaccaggg tctcctggac    2760
gccctgggcg ttaacatctt agaactgagc cagctgatct attccgctcg tgcggcaggt    2820
gcgtttggcg ctaaaatcac gggcgctggc ggcggtggct gtatggttgc gctgaccgct    2880
ccggaaaaat gcaaccaagt ggcagaagcg gtagcaggcg ctggcggtaa agtgactatc    2940
actaaaccga ccgagcaagg tctgaaagta gattaaagtc tagttaaagt ttaaacggtc    3000
tccagcttgg ctgttttggc ggatgagaga agattttcag cctgatacag attaaatcag    3060
aacgcagaag cggtctgata aaacagaatt tgcctggcgg cagtagcgcg gtggtcccac    3120
ctgaccccat gccgaactca gaagtgaaac gccgtagcgc cgatggtagt gtggggtctc    3180
cccatgcgag agtagggaac tgccaggcat caaataaaac gaaaggctca gtcgaaagac    3240
tgggcctttc gttttatctg ttgtttgtcg gtgaacgctc tcctgagtag acaaatccg    3300
ccgggagcgg atttgaacgt tgcgaagcaa cggcccggag ggtggcgggc aggacgcccg    3360
ccataaactg ccaggcatca aattaagcag aaggccatcc tgacggatgg cctttttgcg    3420
tttctacaaa ctcttttttgt ttattttct aaatacattc aaatatgtat ccgctcatga    3480
gacaataacc ctgataaatg cttcaataat attgaaaaag gaagagtatg agtattcaac    3540
atttccgtgt cgcccttatt cccttttttg cggcattttg ccttcctgtt tttgctcacc    3600
cagaaacgct ggtgaaagta aaagatgctg aagatcagtt gggtgcacga gtgggttaca    3660
tcgaactgga tctcaacagc ggtaagatcc ttgagagttt tcgccccgaa gaacgttttc    3720
caatgatgag cacttttaaa gttctgctat gtggcgcggt attatcccgt gttgacgccg    3780
ggcaagagca actcggtcgc cgcatacact attctcagaa tgacttggtt gagtactcac    3840
cagtcacaga aaagcatctt acggatggca tgacagtaag agaattatgc agtgctgcca    3900
taaccatgag tgataacact gcggccaact tacttctgac aacgatcgga ggaccgaagg    3960
agctaaccgc ttttttgcac aacatggggg atcatgtaac tcgccttgat cgttgggaac    4020
cggagctgaa tgaagccata ccaaacgacg agcgtgacac cacgatgcct gtagcaatgg    4080
caacaacgtt gcgcaaacta ttaactggcg aactacttac tctagcttcc cggcaacaat    4140
taatagactg gatggaggcg gataaagttg caggaccact tctgcgctcg gcccttccgg    4200
ctggctggtt tattgctgat aaatctggag ccggtgagcg tgggtctcgc ggtatcattg    4260
cagcactggg gccagatggt aagccctccc gtatcgtagt tatctacacg acggggagtc    4320
aggcaactat ggatgaacga aatagacaga tcgctgagat aggtgcctca ctgattaagc    4380
attggtaact gtcagaccaa gtttactcat atatacttta gattgattta aaacttcatt    4440
```

```
tttaatttaa aaggatctag gtgaagatcc tttttgataa tctcatgacc aaaatccctt    4500
aacgtgagtt ttcgttccac tgagcgtcag accccgtaga aaagatcaaa ggatcttctt    4560
gagatccttt ttttctgcgc gtaatctgct gcttgcaaac aaaaaaacca ccgctaccag    4620
cggtggtttg tttgccggat caagagctac caactctttt tccgaaggta actggcttca    4680
gcagagcgca gataccaaat actgtccttc tagtgtagcc gtagttaggc caccacttca    4740
agaactctgt agcaccgcct acatacccg ctctgctaat cctgttacca gtggctgctg    4800
ccagtggcga taagtcgtgt cttaccgggt tggactcaag acgatagtta ccggataagg    4860
cgcagcggtc gggctgaacg gggggttcgt gcacacagcc cagcttggag cgaacgacct    4920
acaccgaact gagataccta cagcgtgagc tatgagaaag cgccacgctt cccgaaggga    4980
gaaaggcgga caggtatccg gtaagcggca gggtcggaac aggagagcgc acgagggagc    5040
ttccaggggg aaacgcctgg tatctttata gtcctgtcgg gtttcgccac ctctgacttg    5100
agcgtcgatt tttgtgatgc tcgtcagggg gcggagcct atggaaaaac gccagcaacg    5160
cggccttttt acggttcctg gccttttgct ggccttttgc tcacatgttc tttcctgcgt    5220
tatcccctga ttctgtggat aaccgtatta ccgcctttga gtgagctgat accgctcgcc    5280
gcagccgaac gaccgagcgc agcgagtcag tgagcgagga gcggaagag cgcctgatgc    5340
ggtattttct ccttacgcat ctgtgcggta tttcacaccg catatggtgc actctcagta    5400
caatctgctc tgatgccgca tagttaagcc agtatacact ccgctatcgc tacgtgactg    5460
ggtcatggct gcgccccgac acccgccaac acccgctgac gcgccctgac gggcttgtct    5520
gctcccggca tccgcttaca gacaagctgt gaccgtctcc gggagctgca tgtgtcagag    5580
gttttcaccg tcatcaccga aacgcgcgag gcagcagatc aattcgcgcg cgaaggcgaa    5640
gcggcatgca tttacgttga caccatcgaa tggtgcaaaa cctttcgcgg tatggcatga    5700
tagcgcccgg aagagagtca attcagggtg gtgaatgtga aaccagtaac gttatacgat    5760
gtcgcagagt atgccggtgt ctcttatcag accgtttccc gcgtggtgaa ccaggccagc    5820
cacgtttctg cgaaaacgcg ggaaaaagtg gaagcggcga tggcggagct gaattacatt    5880
cccaaccgcg tggcacaaca actggcgggc aaacagtcgt tgctgattgg cgttgccacc    5940
tccagtctgg ccctgcacgc gccgtcgcaa attgtcgcgg cgattaaatc tcgcgccgat    6000
caactgggtg ccagcgtggt ggtgtcgatg gtagaacgaa gcggcgtcga agcctgtaaa    6060
gcggcggtgc acaatcttct cgcgcaacgc gtcagtgggc tgatcattaa ctatccgctg    6120
gatgaccagg atgccattgc tgtggaagct gcctgcacta atgttccggc gttatttctt    6180
gatgtctctg accagacacc catcaacagt attattttct cccatgaaga cggtacgcga    6240
ctgggcgtga agcatctggt cgcattgggt caccagcaaa tcgcgctgtt agcgggccca    6300
ttaagttctg tctcggcgcg tctgcgtctg gctggctggc ataaatatct cactcgcaat    6360
caaattcagc cgatagcgga acgggaaggc gactggagtg ccatgtccgg ttttcaacaa    6420
accatgcaaa tgctgaatga gggcatcgtt cccactgcga tgctggttgc caacgatcag    6480
atggcgctgg gcgcaatgcg cgccattacc gagtccgggc tgcgcgttgg tgcggatatc    6540
tcggtagtgg gatacgacga taccgaagac agctcatgtt atatcccgcc gtcaaccacc    6600
atcaaacagg attttcgcct gctggggcaa accagcgtgg accgcttgct gcaactctct    6660
cagggccagg cggtgaaggg caatcagctg ttgcccgtct cactggtgaa agaaaaaacc    6720
accctggcgc ccaatacgca aaccgcctct ccccgcgcgt tggccgattc attaatgcag    6780
```

```
ctggcacgac aggtttcccg actggaaagc gggcagtgag cgcaacgcaa ttaatgtgag    6840
ttagcgcgaa ttgatctg                                                  6858
```

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12

```
gatagtaacg gctgcgctgc tacc                                              24
```

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13

```
acaatttcac acaggaaaca gc                                                22
```

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14

```
ccaggcaaat tctgttttat cag                                               23
```

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15

```
gacagcttat catcgactgc acg                                               23
```

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16

```
cctcctttca cttcacgaag c                                                 21
```

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17

```
gcttttcact gacgcagttg ag                                                22
```

<210> SEQ ID NO 18
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 18
gataaacaat gagaccgcag                                               20

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
ggagaacttg aaagaggac                                                19

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gtacaacaca atcaatgaga tag                                           23

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
gatgcacata catcacctga tg                                            22

<210> SEQ ID NO 22
<211> LENGTH: 50
<212> TYPE: DNA
<213> ORGANISM: Artificial Sequence
<220> FEATURE:
<223> OTHER INFORMATION: Synthetic Construct

<400> SEQUENCE: 22
gcagaatttc tgtcgctaag atgttctgtt tcgtaaccat tatcgacgac              50

<210> SEQ ID NO 23
<211> LENGTH: 50
<212> TYPE: DNA
<213> ORGANISM: Artificial Sequence
<220> FEATURE:
<223> OTHER INFORMATION: Synthetic Construct

<400> SEQUENCE: 23
gtcgtcgata atggttacga aacagaacat cttagcgaca gaaattctgc              50

<210> SEQ ID NO 24
<211> LENGTH: 48
<212> TYPE: DNA
<213> ORGANISM: Artificial Sequence
<220> FEATURE:
<223> OTHER INFORMATION: Synthetic Construct

<400> SEQUENCE: 24
```

```
cgcaaatctg tggctaaaat gttttgtttc gtgaccataa ttgatgac                 48
```

<210> SEQ ID NO 25
<211> LENGTH: 48
<212> TYPE: DNA
<213> ORGANISM: Artificial Sequence
<220> FEATURE:
<223> OTHER INFORMATION: Synthetic Construct

<400> SEQUENCE: 25

```
gtcatcaatt atggtcacga acaaaacat tttagccaca gatttgcg                  48
```

<210> SEQ ID NO 26
<211> LENGTH: 66
<212> TYPE: DNA
<213> ORGANISM: Artificial Sequence
<220> FEATURE:
<223> OTHER INFORMATION: Synthetic Construct

<400> SEQUENCE: 26

```
gcgaacgatg cataaaggag gtaaaaaaac atggtatcct gttctgcgcc gggtaagatt    60
tacctg                                                               66
```

<210> SEQ ID NO 27
<211> LENGTH: 48
<212> TYPE: DNA
<213> ORGANISM: Artificial Sequence
<220> FEATURE:
<223> OTHER INFORMATION: Synthetic construct

<400> SEQUENCE: 27

```
gggcccgttt aaactttaac tagactttaa tctactttca gaccttgc                 48
```

<210> SEQ ID NO 28
<211> LENGTH: 1643
<212> TYPE: DNA
<213> ORGANISM: Artificial Sequence
<220> FEATURE:
<223> OTHER INFORMATION: Synthetic Construct

<400> SEQUENCE: 28

```
ccatggaaac cagacggtcc gctaattatg aaccgaacag ttgggattac gattacctgc    60
tttcttcgga tacgaagat gccatagagg tatacaaaga caaagcgaag aaactggatg    120
ctgaagtacg ctcgaagata aacaatgaga ccgcagaatt tttaacgcaa ttagaactga   180
ttgacactat ccagcgcctg ggtttgggtt atcgtttcga aagcgacatt agacgcgcct   240
tggatcgttt cgtgagtagt ggtgggttcg aggctgtcgc gaaaacttca ctgcaagcta   300
cagcactgtc ttttcggctg ctgcgtcaac atggtttcga ggttagtcaa gaagtgttta   360
atggtttcaa agaccagaac ggtaacttta tggaggattt aaaagaagat attaaggccc   420
tcctttcact tcacgaagca tcttttttag ctctggaagg cgagaatatt ctggacgagg   480
caaaggtatt cacaattagc cacctcaaag aactgaacga ggagaaaatt ggcaaagaca   540
tggtggaaca agtgaaccat gctctggaat taccccttca tcgtcgtacg cagcgtttgg   600
aggctgtgtg gtctattgaa gcgtatcgga agaaggaaga tgcaaaccgc gtccttctgg   660
aacttgcaat cctcgattat aatatggtcc aatctgtgta tcagcgcgat ttgcgcgaaa   720
cttcgagatg gtggcgccgc gtgggattag ccactaagtt gcatttcgcc agagacagac   780
ttatcgaatc cttctattgg gcggttggcg tcgcctttga accgcaatac tcagattgca   840
gaatttctgt cgctaagatg ttctctttcg taaccattat cgacgacatt tatgatgtgt   900
```

| | |
|---|---|
| atgggacgtt ggaagagctg gagcttttca ctgacgcagt tgagagatgg gatgtgagcg | 960 |
| ccattgacga tttacccgat tatatgaaac tgtgcttctt ggcgttgtac aatactataa | 1020 |
| acgaaatcgc ttatgacaat cttaaagaaa aaggcgaaaa tattctgccg tatctgacta | 1080 |
| aagcctgggc ggatctttgc aatgctttcc tgcaagaggc acgttttta tataacaagt | 1140 |
| cgacacctac cttctcagat tattttggca atgcgtggaa atctagttct gggccacttc | 1200 |
| aactggtttt tgcttacttt gccgtagtgc aaaacatcaa aaaggaagaa accgaaaatc | 1260 |
| tgctgaaata tcatgatata atctcttggc catcgtacat atttcggctg tgtaatgatc | 1320 |
| tggcttccgc atcggcagaa attgcgcggg gtgagactgc aaacagcgtt tcttgttaca | 1380 |
| tgcggacgaa gggaatttcc gaagaactgg caaccgaatc agtgatgaat cttattgatg | 1440 |
| aaacgtggaa aaagatgaac aaggaaaaat tgggggactc actctttgca aaacactttg | 1500 |
| tggagaccgc gataaaacctt gctcgccaat cgcattgtac gtatcataat ggagatgcgc | 1560 |
| atacttcgcc tgacgaatta acccgcaaac gcgtactgtc agtgatcact gaaccgatac | 1620 |
| tgccattgga acggtgactg cag | 1643 |

<210> SEQ ID NO 29
<211> LENGTH: 6019
<212> TYPE: DNA
<213> ORGANISM: Artificial Sequence
<220> FEATURE:
<223> OTHER INFORMATION: Synthetic construct

<400> SEQUENCE: 29

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg caaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggaaac | 420 |
| cagacggtcc gctaattatg aaccgaacag ttgggattac gattacctgc tttcttcgga | 480 |
| tacgaagat gccatagagg tatacaaaga caaagcgaag aaactggatg ctgaagtacg | 540 |
| ctcgaagata aacaatgaga ccgcagaatt tttaacgcaa ttagaactga ttgacactat | 600 |
| ccagcgcctg ggttggggtt atcgtttcga agcgacatt agacgcgcct ggatcgtttt | 660 |
| cgtgagtagt ggtgggttcg aggctgtcgc gaaaacttca ctgcaagcta cagcactgtc | 720 |
| ttttcggctg ctgcgtcaac atggtttcga ggttagtcaa gaagtgttta atggtttcaa | 780 |
| agaccagaac ggtaacttta tggaggattt aaaagaagat attaaggccc cctttcact | 840 |
| tcacgaagca tcttttttag ctctggaagg cgagaatatt ctggacgagg caaaggtatt | 900 |
| cacaattagc cacctcaaag aactgaacga ggagaaaatt ggcaaagaca tggtggaaca | 960 |
| agtgaaccat gctctggaat tacccttca tcgtcgtacg cagcgtttgg aggctgtgtg | 1020 |
| gtctattgaa gcgtatcgga agaaggaaga tgcaaaccgc gtccttctgg aacttgcaat | 1080 |
| cctcgattat aatatggtcc aatctgtgta tcagcgcgat ttgcgcgaaa cttcgagatg | 1140 |
| gtggcgccgc gtgggattag ccactaagtt gcatttcgcc agagacagac ttatcgaatc | 1200 |
| cttctattgg gcggttggcg tcgccttga accgcaatac tcagattgca gaatttctgt | 1260 |

```
cgctaagatg ttctctttcg taaccattat cgacgacatt tatgatgtgt atgggacgtt    1320
ggaagagctg gagcttttca ctgacgcagt tgagagatgg gatgtgagcg ccattgacga    1380
tttacccgat tatatgaaac tgtgcttctt ggcgttgtac aatactataa acgaaatcgc    1440
ttatgacaat cttaaagaaa aaggcgaaaa tattctgccg tatctgacta aagcctgggc    1500
ggatctttgc aatgctttcc tgcaagaggc acgttttta tataacaagt cgacacctac    1560
cttctcagat tattttggca atgcgtggaa atctagttct gggccacttc aactggtttt    1620
tgcttacttt gccgtagtgc aaaacatcaa aaaggaagaa accgaaaatc tgctgaaata    1680
tcatgatata atctcttggc catcgtacat atttcggctg tgtaatgatc tggcttccgc    1740
atcggcagaa attgcgcggg gtgagactgc aaacagcgtt tcttgttaca tgcggacgaa    1800
gggaatttcc gaagaactgg caaccgaatc agtgatgaat cttattgatg aaacgtggaa    1860
aaagatgaac aaggaaaaat tgggggactc actctttgca aaacactttg tggagaccgc    1920
gataaacctt gctcgccaat cgcattgtac gtatcataat ggagatgcgc atacttcgcc    1980
tgacgaatta acccgcaaac gcgtactgtc agtgatcact gaaccgatac tgccattgga    2040
acggtgactg cagctggtac catatgggaa ttcgaagctt tctagaacaa aaactcatct    2100
cagaagagga tctgaatagc gccgtcgacc atcatcatca tcatcattga gtttaaacgg    2160
tctccagctt ggctgttttg gcggatgaga agattttc agcctgatac agattaaatc    2220
agaacgcaga agcggtctga taaaacagaa tttgcctggc ggcagtagcg cggtggtccc    2280
acctgacccc atgccgaact cagaagtgaa acgccgtagc gccgatggta gtgtggggtc    2340
tccccatgcg agagtaggga actgccaggc atcaaataaa acgaaaggct cagtcgaaag    2400
actgggcctt tcgttttatc tgttgtttgt cggtgaacgc tctcctgagt aggacaaatc    2460
cgccgggagc ggatttgaac gttgcgaagc aacggcccgg agggtggcgg gcaggacgcc    2520
cgccataaac tgccaggcat caaattaagc agaaggccat cctgacggat ggccttttg    2580
cgtttctaca aactcttttg tttatttttc taaatacatt caaatatgta tccgctcatg    2640
agacaataac cctgataaat gcttcaataa tattgaaaaa ggaagagtat gagtattcaa    2700
catttccgtg tcgcccttat tcccttttt gcggcatttt gccttcctgt ttttgctcac    2760
ccagaaacgc tggtgaaagt aaaagatgct gaagatcagt tgggtgcacg agtgggttac    2820
atcgaactgg atctcaacag cggtaagatc cttgagagtt ttcgccccga gaacgttttt    2880
ccaatgatga gcacttttaa agttctgcta tgtggcgcgg tattatcccg tgttgacgcc    2940
gggcaagagc aactcggtcg ccgcatacac tattctcaga tgacttggt tgagtactca    3000
ccagtcacag aaaagcatct tacggatggc atgacagtaa gagaattatg cagtgctgcc    3060
ataaccatga gtgataacac tgcggccaac ttacttctga caacgatcgg aggaccgaag    3120
gagctaaccg ctttttgca caacatgggg gatcatgtaa ctcgccttga tcgttgggaa    3180
ccggagctga atgaagccat accaaacgac gagcgtgaca ccacgatgcc tgtagcaatg    3240
gcaacaacgt tgcgcaaact attaactggc gaactactta ctctagcttc ccggcaacaa    3300
ttaatagact ggatggaggc ggataaagtt gcaggaccac ttctgcgctc ggcccttccg    3360
gctggctggt ttattgctga taaatctgga gccggtgagc gtgggtctcg cggtatcatt    3420
gcagcactgg ggccagatgg taagccctcc cgtatcgtag ttatctacac gacggggagt    3480
caggcaacta tggatgaacg aaatagacag atcgctgaga taggtgcctc actgattaag    3540
cattggtaac tgtcagacca gtttactca tatatacttt agattgattt aaaacttcat    3600
ttttaattta aaaggatcta ggtgaagatc cttttgata atctcatgac caaatccct    3660
```

```
taacgtgagt tttcgttcca ctgagcgtca gacccgtag aaaagatcaa aggatcttct   3720
tgagatcctt tttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag ctatgagaaa gcgccacgct tcccgaaggg   4140
agaaaggcgg acaggtatcc ggtaagcggc agggtcggaa caggagagcg cacgagggag   4200
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatcccctg attctgtgga taaccgtatt accgcctttg agtgagctga taccgctcgc   4440
cgcagccgaa cgaccgagcg cagcgagtca gtgagcgagg aagcggaaga gcgcctgatg   4500
cggtattttc tccttacgca tctgtgcggt atttcacacc gcatatggtg cactctcagt   4560
acaatctgct ctgatgccgc atagttaagc cagtatacac tccgctatcg ctacgtgact   4620
gggtcatggc tgcgcccga cacccgccaa cacccgctga cgcgccctga cgggcttgtc   4680
tgctcccggc atccgcttac agacaagctg tgaccgtctc cgggagctgc atgtgtcaga   4740
ggttttcacc gtcatcaccg aaacgcgcga ggcagcagat caattcgcgc gcgaaggcga   4800
agcggcatgc atttacgttg acaccatcga atggtgcaaa acctttcgcg gtatggcatg   4860
atagcgcccg gaagagagtc aattcagggt ggtgaatgtg aaaccagtaa cgttatacga   4920
tgtcgcagag tatgccggtg tctcttatca gaccgtttcc cgcgtggtga accaggccag   4980
ccacgtttct gcgaaaacgc gggaaaaagt ggaagcggcg atggcggagc tgaattacat   5040
tcccaaccgc gtggcacaac aactggcggg caaacagtcg ttgctgattg gcgttgccac   5100
ctccagtctg gccctgcacg cgccgtcgca aattgtcgcg gcgattaaat ctcgcgccga   5160
tcaactgggt gccagcgtgg tggtgtcgat ggtagaacga agcggcgtcg aagcctgtaa   5220
agcggcggtg cacaatcttc tcgcgcaacg cgtcagtggg ctgatcatta actatccgct   5280
ggatgaccag gatgccattg ctgtggaagc tgcctgcact aatgttccgg cgttatttct   5340
tgatgtctct gaccagacac ccatcaacag tattatttc tcccatgaag acggtacgcg   5400
actgggcgtg gagcatctgg tcgcattggg tcaccagcaa atcgcgctgt agcgggccc    5460
attaagttct gtctcggcgc gtctgcgtct ggctggctgg cataaatatc tcactcgcaa   5520
tcaaattcag ccgatagcgg aacgggaagg cgactggagt gccatgtccg gttttcaaca   5580
aaccatgcaa atgctgaatg agggcatcgt tcccactgcg atgctggttg ccaacgatca   5640
gatggcgctg ggcgcaatgc gcgccattac cgagtccggg ctgcgcgttg gtgcggatat   5700
ctcggtagtg ggatacgacg ataccgaaga cagctcatgt tatatcccgc cgtcaaccac   5760
catcaaacag gattttcgcc tgctggggca accagcgtgg accgcttgc tgcaactctc   5820
tcagggccag gcggtgaagg gcaatcagct gttgcccgtc tcactggtga aaagaaaaac   5880
caccctggcg cccaatacgc aaaccgcctc tccccgcgcg ttggccgatt cattaatgca   5940
gctggcacga caggtttccc gactggaaag cgggcagtga gcgcaacgca attaatgtga   6000
```

| gttagcgcga attgatctg | 6019 |

<210> SEQ ID NO 30
<211> LENGTH: 6857
<212> TYPE: DNA
<213> ORGANISM: Artificial Sequence
<220> FEATURE:
<223> OTHER INFORMATION: Synthetic Construct

<400> SEQUENCE: 30

| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggaaac | 420 |
| cagacggtcc gctaattatg aaccgaacag ttgggattac gattacctgc tttcttcgga | 480 |
| tacggaagat gccatagagg tatacaaaga caaagcgaag aaactggatg ctgaagtacg | 540 |
| ctcgaagata aacaatgaga ccgcagaatt tttaacgcaa ttagaactga ttgacactat | 600 |
| ccagcgcctg ggtttgggtt atcgtttcga agcgacatt agacgcgcct tggatcgttt | 660 |
| cgtgagtagt ggtgggttcg aggctgtcgc gaaaacttca ctgcaagcta cagcactgtc | 720 |
| ttttcggctg ctgcgtcaac atggtttcga ggttagtcaa gaagtgttta atggtttcaa | 780 |
| agaccagaac ggtaacttta tggaggattt aaaagaagat attaaggccc tcctttcact | 840 |
| tcacgaagca tcttttttag ctctggaagg cgagaatatt ctggacgagg caaaggtatt | 900 |
| cacaattagc cacctcaaag aactgaacga ggagaaaatt ggcaaagaca tggtggaaca | 960 |
| agtgaaccat gctctggaat taccccttca tcgtcgtacg cagcgtttgg aggctgtgtg | 1020 |
| gtctattgaa gcgtatcgga agaaggaaga tgcaaaccgc gtccttctgg aacttgcaat | 1080 |
| cctcgattat aatatggtcc aatctgtgta tcagcgcgat ttgcgcgaaa cttcgagatg | 1140 |
| gtggcgccgc gtgggattag ccactaagtt gcatttcgcc agagacagac ttatcgaatc | 1200 |
| cttctattgg gcggttggcg tcgcctttga accgcaatac tcagattgca gaatttctgt | 1260 |
| cgctaagatg ttctctttcg taaccattat cgacgacatt tatgatgtgt atgggacgtt | 1320 |
| ggaagagctg gagcttttca ctgacgcagt tgagagatgg gatgtgagcg ccattgacga | 1380 |
| tttacccgat tatatgaaac tgtgcttctt ggcgttgtac aatactataa acgaaatcgc | 1440 |
| ttatgacaat cttaaagaaa aaggcgaaaa tattctgccg tatctgacta agcctgggc | 1500 |
| ggatctttgc aatgctttcc tgcaagaggc acgtttttta tataacaagt cgacacctac | 1560 |
| cttctcagat tatttggca atgcgtgaa atctagttct gggccacttc aactggtttt | 1620 |
| tgcttacttt gccgtagtgc aaaacatcaa aaaggaagaa accgaaaatc tgctgaaata | 1680 |
| tcatgatata atctcttggc catcgtacat atttcggctg tgtaatgatc tggcttccgc | 1740 |
| atcggcagaa attgcgcggg gtgagactgc aaacagcgtt tcttgttaca tgcggacgaa | 1800 |
| gggaatttcc gaagaactgg caaccgaatc agtgatgaat cttattgatg aaacgtggaa | 1860 |
| aaagatgaac aaggaaaaat tgggggactc actctttgca aaacactttg tggagaccgc | 1920 |
| gataaacctt gctcgccaat cgcattgtac gtatcataat ggagatgcgc atacttcgcc | 1980 |
| tgacgaatta acccgcaaac gcgtactgtc agtgatcact gaaccgatac tgccattgga | 2040 |

```
acggtgactg cataaaggag gtaaaaaaac atggtatcct gttctgcgcc gggtaagatt    2100
tacctgttcg gtgaacacgc cgtagtttat ggcgaaactg caattgcgtg tgcggtggaa    2160
ctgcgtaccc gtgttcgcgc ggaactcaat gactctatca ctattcagag ccagatcggc    2220
cgcaccggtc tggatttcga aaagcaccct tatgtgtctg cggtaattga aaaatgcgc    2280 aaatctattc ctattaacgg tgttttcttg accgtcgatt ccgacatccc ggtgggctcc    2340
ggtctgggta gcagcgcagc cgttactatc gcgtctattg gtgcgctgaa cgagctgttc    2400
ggctttggcc tcagcctgca agaaatcgct aaactgggcc acgaaatcga attaaagta    2460 cagggtgccg cgtccccaac cgatacgtat gtttctacct tcggcggcgt ggttaccatc    2520
ccggaacgtc gcaaactgaa aactccggac tgcggcattg tgattggcga taccggcgtt    2580
ttctcctcca ccaaagagtt agtagctaac gtacgtcagc tgcgcgaaag ctacccggat    2640
ttgatcgaac cgctgatgac ctctattggc aaaatctctc gtatcggcga caactggtt    2700 ctgtctggcg actacgcatc catcggccgc ctgatgaacg tcaaccaggg tctcctggac    2760
gccctgggcg ttaacatctt agaactgagc cagctgatct attccgctcg tgcggcaggt    2820
gcgtttggcg ctaaaatcac gggcgctggc ggcggtggct gtatggttgc gctgaccgct    2880
ccggaaaaat gcaaccaagt ggcagaagcg gtagcaggcg ctggcggtaa agtgactatc    2940
actaaaccga ccgagcaagg tctgaaagta gattaaagtc tagttaaagt ttaaacggtc    3000
tccagcttgg ctgttttggc ggatgagaga agattttcag cctgatacag attaaatcag    3060
aacgcagaag cggtctgata aaacagaatt tgcctggcgg cagtagcgcg gtggtcccac    3120
ctgaccccat gccgaactca gaagtgaaac gccgtagcgc cgatggtagt gtggggtctc    3180
cccatgcgag agtagggaac tgccaggcat caaataaaac gaaaggctca gtcgaaagac    3240
tgggcctttc gttttatctg ttgtttgtcg gtgaacgctc tcctgagtag acaaatccg    3300 ccgggagcgg atttgaacgt tgcgaagcaa cggcccggag ggtggcgggc aggacgcccg    3360
ccataaactg ccaggcatca aattaagcag aaggccatcc tgacggatgg ccttttttgcg    3420 tttctacaaa ctcttttgtt tatttttcta aatacattca aatatgtatc cgctcatgag    3480
acaataaccc tgataaatgc ttcaataata ttgaaaaagg aagagtatga gtattcaaca    3540
tttccgtgtc gcccttattc cctttttttgc ggcattttgc cttcctgttt ttgctcaccc    3600
agaaacgctg gtgaaagtaa aagatgctga agatcagttg ggtgcacgag tgggttacat    3660
cgaactggat ctcaacagcg gtaagatcct tgagagtttt cgccccgaag aacgttttcc    3720
aatgatgagc acttttaaag ttctgctatg tggcgcggta ttatcccgtg ttgacgccgg    3780
gcaagagcaa ctcggtcgcc gcatacacta ttctcagaat gacttggttg agtactcacc    3840
agtcacagaa aagcatctta cggatggcat gacagtaaga gaattatgca gtgctgccat    3900
aaccatgagt gataacactg cggccaactt acttctgaca acgatcggag gaccgaagga    3960
gctaaccgct tttttgcaca acatggggga tcatgtaact cgccttgatc gttgggaacc    4020
ggagctgaat gaagccatac caaacgacga gcgtgacacc acgatgcctg tagcaatggc    4080
aacaacgttg cgcaaactat taactggcga actacttact ctagcttccc ggcaacaatt    4140
aatagactgg atggaggcgg ataaagttgc aggaccactt ctgcgctcgg cccttccggc    4200
tggctggttt attgctgata aatctggagc cggtgagcgt gggtctcgcg gtatcattgc    4260
agcactgggg ccagatggta agccctcccg tatcgtagtt atctacacga cggggagtca    4320
ggcaactatg gatgaacgaa atagacagat cgctgagata ggtgcctcac tgattaagca    4380
```

-continued

```
ttggtaactg tcagaccaag tttactcata tatactttag attgatttaa aacttcattt    4440
ttaatttaaa aggatctagg tgaagatcct ttttgataat ctcatgacca aaatcccttaa   4500 acgtgagttt tcgttccact gagcgtcaga ccccgtagaa aagatcaaag gatcttcttg   4560
agatcctttt tttctgcgcg taatctgctg cttgcaaaca aaaaaaccac cgctaccagc   4620
ggtggtttgt ttgccggatc aagagctacc aactcttttt ccgaaggtaa ctggcttcag   4680
cagagcgcag ataccaaata ctgtccttct agtgtagccg tagttaggcc accacttcaa   4740
gaactctgta gcaccgccta catacctcgc tctgctaatc ctgttaccag tggctgctgc   4800
cagtggcgat aagtcgtgtc ttaccgggtt ggactcaaga cgatagttac cggataaggc   4860
gcagcggtcg ggctgaacgg ggggttcgtg cacacagccc agcttggagc gaacgaccta   4920
caccgaactg agatacctac agcgtgagct atgagaaagc gccacgcttc ccgaagggag   4980
aaaggcggac aggtatccgg taagcggcag ggtcggaaca ggagagcgca cgagggagct   5040
tccaggggga aacgcctggt atctttatag tcctgtcggg tttcgccacc tctgacttga   5100
gcgtcgattt ttgtgatgct cgtcaggggg gcggagccta tggaaaaacg ccagcaacgc   5160
ggccttttta cggttcctgg ccttttgctg gccttttgct cacatgttct ttcctgcgtt   5220
atcccctgat tctgtggata accgtattac cgcctttgag tgagctgata ccgctcgccg   5280
cagccgaacg accgagcgca gcgagtcagt gagcgaggaa gcggaagagc gcctgatgcg   5340
gtattttctc cttacgcatc tgtgcggtat ttcacaccgc atatggtgca ctctcagtac   5400
aatctgctct gatgccgcat agttaagcca gtatacactc cgctatcgct acgtgactgg   5460
gtcatggctg cgccccgaca cccgccaaca cccgctgacg cgccctgacg gcttgtctg    5520 ctcccggcat ccgcttacag acaagctgtg accgtctccg ggagctgcat gtgtcagagg   5580
ttttcaccgt catcaccgaa acgcgcgagg cagcagatca attcgcgcgc gaaggcgaag   5640
cggcatgcat ttacgttgac accatcgaat ggtgcaaaac ctttcgcggt atggcatgat   5700
agcgcccgga agagagtcaa ttcagggtgg tgaatgtgaa accagtaacg ttatacgatg   5760
tcgcagagta tgccggtgtc tcttatcaga ccgtttcccg cgtggtgaac caggccagcc   5820
acgtttctgc gaaaacgcgg gaaaaagtgg aagcggcgat ggcggagctg aattacattc   5880
ccaaccgcgt ggcacaacaa ctggcgggca aacagtcgtt gctgattggc gttgccacct   5940
ccagtctggc cctgcacgcg ccgtcgcaaa ttgtcgcggc gattaaatct cgcgccgatc   6000
aactgggtgc cagcgtggtg gtgtcgatgg tagaacgaag cggcgtcgaa gcctgtaaag   6060
cggcggtgca caatcttctc gcgcaacgcg tcagtgggct gatcattaac tatccgctgg   6120
atgaccagga tgccattgct gtggaagctg cctgcactaa tgttccggcg ttatttcttg   6180
atgtctctga ccagacaccc atcaacagta ttattttctc ccatgaagac ggtacgcgac   6240
tgggcgtgga gcatctggtc gcattgggtc accagcaaat cgcgctgtta gcgggcccat   6300
taagttctgt ctcggcgcgt ctgcgtctgg ctggctggca taaatatctc actcgcaatc   6360
aaattcagcc gatagcggaa cgggaaggcg actggagtgc catgtccggt tttcaacaaa   6420
ccatgcaaat gctgaatgag gcatcgttc ccactgcgat gctggttgcc aacgatcaga   6480
tggcgctggg cgcaatgcgc gccattaccg agtccgggct gcgcgttggt gcggatatct   6540
cggtagtggg atacgacgat accgaagaca gctcatgtta tatcccgccg tcaaccacca   6600
tcaaacagga ttttcgcctg ctggggcaaa ccagcgtgga ccgcttgctg caactctctc   6660
agggccaggc ggtgaagggc aatcagctgt tgcccgtctc actggtgaaa agaaaaacca   6720
ccctggcgcc caatacgcaa accgcctctc cccgcgcgtt ggccgattca ttaatgcagc   6780
```

<210> SEQ ID NO 31
<211> LENGTH: 1643
<212> TYPE: DNA
<213> ORGANISM: Artificial Sequence
<220> FEATURE:
<223> OTHER INFORMATION: Synthetic Construct

<400> SEQUENCE: 31

```
tggcacgaca ggtttcccga ctggaaagcg ggcagtgagc gcaacgcaat taatgtgagt    6840
tagcgcgaat tgatctg                                                   6857
```

<210> SEQ ID NO 31
<211> LENGTH: 1643
<212> TYPE: DNA
<213> ORGANISM: Artificial Sequence
<220> FEATURE:
<223> OTHER INFORMATION: Synthetic Construct

<400> SEQUENCE: 31

```
ccatggaaac ccgcagaacc gccaattatg aacccaattc ctgggattac gattacctttt     60 tgagtagcga taacgatgac gccatagaac tgtacaaaga taaagccaag aaacttgatg    120
cagaagtgcg tagtaaaatt aataacgaaa agcagaatt tcttacacaa cttgaactca    180
ttgatactat ccaacgtctc ggcctcggat accgcttcga atcagatata cggcgcgcta    240
tcgatagata tgtttcatcg gcggattcg aggcagtggc taaaacgtcg ttacacgcaa    300
cagcactcag ttttcgtttg ttacgccaac atggattcga agtgagccaa gaggtatttt    360
cgggtttcaa ggaccaaaat ggaaacttta tggagaactt gaaagaggac ataaaggcaa    420
ttcttagtct ctatgaagcg agtttccttg ctttagaagg cgagaatata ttggacgaag    480
ccaaggtctt tacaatctcc cacctgaaag agctgaatga ggaaaaaatt ggaaaagacc    540
tggccgacca agtgaatcat cgcgctggaa cttcctctgca tcggcgtacc cagcgtcttg    600
aagcggtatg gtcgatagaa gcctatcgca aaaggaagg agcgaatcgc gcattactgg    660
aactggcgat cttggactac aatatggtcc aatcagtcta ccaacgcgat ttgcgcgaaa    720
cctcccgctg gtggcgccgt gtaggcttag caactaaatt gcattttgca cgtgaccggc    780
tgattgaatc ttctattgg gcggtcggcg ttgccttga gccgcaatat tctgactgtc    840
gcaaatctgt ggctaaaatg ttttcattcg tgaccataat tgatgacata tatgatgttt    900
atgggacgtt agatgagtta gagttgttta ccgacgcagt tgaacgctgg gacgtttctg    960
ccgtggatga cctcccggat tatatgaaat tatgctttct ggccctgtac aacacaatca   1020
atgagatagc atacgacaat ctgaaagaaa aaggtgaaaa catcctgcct tacctgacta   1080
aagcatgggc tgacttatgc aacgcatttc tgcaagaggc gaaatttctg tacaacaaat   1140
ccactccaac cttcgatgac tactttgca atgcctggaa aagtagcagt ggcccgttgc   1200
agttagtgtt cgcttatttt gcggtcgttc aaaacattaa gaaggaggag acggagaacc   1260
ttcagaagta ccacgacatt atttcgtggc caagttatat ttttcgctta tgtaatgatc   1320
tggcctctgc gtcagccgaa atcgctcggg gagagaccgc aaattctgtt tcttgctaca   1380
ttagaactaa gggcatctct gaggagttag caacggaatc tgttatgaat ctgattgatg   1440
agacttggaa aaagatgaat aaagagaagg tgggcgattc actgttcgct aaacaatttg   1500
tagaaacagc tattaatctg gctcgtcagt cacattgcac gtatcataat ggtgatgcac   1560
atacatcacc tgatgagctg actcgtaaac gtgtcttatc tgtgatcacc gaaccgatcc   1620 ttccgttttga aagatgactg cag                                          1643
```

<210> SEQ ID NO 32
<211> LENGTH: 6019
<212> TYPE: DNA
<213> ORGANISM: Artificial Sequence
<220> FEATURE:
<223> OTHER INFORMATION: Synthetic Construct

```
<400> SEQUENCE: 32
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg caaatattc    180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggaaac   420
ccgcagaacc gccaattatg aacccaattc ctgggattac gattaccttt tgagtagcga   480
taacgatgac gccatagaac tgtacaaaga taaagccaag aaacttgatg cagaagtgcg   540
tagtaaaatt aataacgaaa aagcagaatt tcttacacaa cttgaactca ttgatactat   600
ccaacgtctc ggcctcggat accgcttcga atcagatata cggcgcgcta tcgatagata   660
tgtttcatcg ggcggattcg aggcagtggc taaaacgtcg ttacacgcaa cagcactcag   720
ttttcgtttg ttacgccaac atggattcga agtgagccaa gaggtatttt cgggtttcaa   780
ggaccaaaat ggaaacttta tggagaactt gaaagaggac ataaaggcaa ttcttagtct   840
ctatgaagcg agtttccttg ctttagaagg cgagaatata ttggacgaag ccaaggtctt   900
tacaatctcc cacctgaaag agctgaatga ggaaaaaatt ggaaaagacc tggccgacca   960
agtgaatcat gcgctggaac ttcctctgca tcggcgtacc cagcgtcttg aagcggtatg  1020
gtcgatagaa gcctatcgca aaaggaagg agcgaatcgc gcattactgg aactggcgat  1080
cttggactac aatatggtcc aatcagtcta ccaacgcgat ttgcgcgaaa cctcccgctg  1140
gtggcgccgt gtaggcttag caactaaatt gcattttgca cgtgaccggc tgattgaatc  1200
tttctattgg gcggtcggcg ttgcctttga gccgcaatat tctgactgtc gcaaatctgt  1260
ggctaaaatg ttttcattcg tgaccataat tgatgacata tatgatgttt atgggacgtt  1320
agatgagtta gagttgttta ccgacgcagt tgaacgctgg gacgtttctg ccgtggatga  1380
cctcccggat tatatgaaat tatgcttttct ggccctgtac aacacaatca atgagatagc  1440
atacgacaat ctgaaagaaa aaggtgaaaa catcctgcct tacctgacta agcatgggc  1500
tgacttatgc aacgcatttc tgcaagaggc gaaatttctg tacaacaaat ccactccaac  1560
cttcgatgac tactttggca atgcctggaa aagtagcagt ggcccgttgc agttagtgtt  1620
cgcttatttt gcggtcgttc aaaacattaa gaaggaggag acggagaacc ttcagaagta  1680
ccacgacatt atttcgtggc caagttatat ttttcgctta tgtaatgatc tggcctctgc  1740
gtcagccgaa atcgctcggg gagagaccgc aaattctgtt tcttgctaca ttagaactaa  1800
gggcatctct gaggagttag caacggaatc tgttatgaat ctgattgatg agacttggaa  1860
aaagatgaat aaagagaagg tgggcgattc actgttcgct aaacaatttg tagaaacagc  1920
tattaatctg gctcgtcagt cacattgcac gtatcataat ggtgatgcac atacatcacc  1980
tgatgagctg actcgtaaac gtgtcttatc tgtgatcacc gaaccgatcc ttccgtttga  2040
aagatgactg cagctggtac catatgggaa ttcgaagctt tctagaacaa aaactcatct  2100
cagaagagga tctgaatagc gccgtcgacc atcatcatca tcatcattga gtttaaacgg  2160
tctccagctt ggctgttttg gcggatgaga agattttc agcctgatac agattaaatc  2220
agaacgcaga agcggtctga taaacagaa tttgcctggc ggcagtagcg cggtggtccc  2280
acctgacccc atgccgaact cagaagtgaa acgccgtagc gccgatggta gtgtggggtc  2340
```

```
tccccatgcg agagtaggga actgccaggc atcaaataaa acgaaaggct cagtcgaaag    2400
actgggcctt tcgttttatc tgttgtttgt cggtgaacgc tctcctgagt aggacaaatc    2460
cgccgggagc ggatttgaac gttgcgaagc aacggcccgg agggtggcgg gcaggacgcc    2520
cgccataaac tgccaggcat caaattaagc agaaggccat cctgacggat ggccttttg     2580 cgtttctaca aactcttttg tttattttc taaatacatt caaatatgta tccgctcatg     2640
agacaataac cctgataaat gcttcaataa tattgaaaaa ggaagagtat gagtattcaa    2700
catttccgtg tcgcccttat tcccttttttt gcggcatttt gccttcctgt ttttgctcac    2760
ccagaaacgt tggtgaaagt aaaagatgct gaagatcagt tgggtgcacg agtgggttac    2820
atcgaactgg atctcaacag cggtaagatc cttgagagtt ttcgccccga agaacgtttt    2880
ccaatgatga gcacttttaa agttctgcta tgtggcgcgg tattatcccg tgttgacgcc    2940
gggcaagagc aactcggtcg ccgcatacac tattctcaga atgacttggt tgagtactca    3000
ccagtcacag aaaagcatct tacgatggca tgacagtaaa agaattatg cagtgctgcc     3060 ataaccatga gtgataacac tgcggccaac ttacttctga caacgatcgg aggaccgaag    3120
gagctaaccg cttttttgca caacatgggg gatcatgtaa ctcgccttga tcgttgggaa    3180
ccggagctga atgaagccat accaaacgac gagcgtgaca ccacgatgcc tgtagcaatg    3240
gcaacaacgt tgcgcaaact attaactggc gaactactta ctctagcttc ccggcaacaa    3300
ttaatagact ggatggaggc ggataaagtt gcaggaccac ttctgcgctc ggcccttccg    3360
gctggctggt ttattgctga taaatctgga gccggtgagc gtgggtctcg cggtatcatt    3420
gcagcactgg ggccagatgg taagccctcc cgtatcgtag ttatctacac gacggggagt    3480
caggcaacta tggatgaacg aaatagacag atcgctgaga taggtgcctc actgattaag    3540
cattggtaac tgtcagacca agtttactca tatatacttt agattgattt aaaacttcat    3600
ttttaattta aaaggatcta ggtgaagatc ctttttgata atctcatgac caaaatccct    3660
taacgtgagt tttcgttcca ctgagcgtca gaccccgtag aaaagatcaa aggatcttct    3720
tgagatcctt ttttttctgcg cgtaatctgc tgcttgcaaa caaaaaaacc accgctacca    3780
gcggtggttt gtttgccgga tcaagagcta ccaactcttt ttccgaaggt aactggcttc    3840
agcagagcgc agataccaaa tactgtcctt ctagtgtagc cgtagttagg ccaccacttc    3900
aagaactctg tagcaccgcc tacatacctc gctctgctaa tcctgttacc agtggctgct    3960
gccagtggcg ataagtcgtg tcttaccggg ttggactcaa gacgatagtt accggataag    4020
gcgcagcggt cgggctgaac ggggggttcg tgcacacagc ccagcttgga gcgaacgacc    4080
tacaccgaac tgagatacct acagcgtgag ctatgagaaa gcgccacgct tcccgaaggg    4140
agaaaggcgg acaggtatcc ggtaagcggc agggtcggaa caggagagcg cacgagggag    4200
cttccagggg gaaacgcctg gtatctttat agtcctgtcg gtttcgccac cctctgactt    4260
gagcgtcgat ttttgtgatg ctcgtcaggg gggcggagcc tatggaaaaa cgccagcaac    4320
gcggcctttt tacggttcct ggccttttgc tggccttttg ctcacatgtt ctttcctgcg    4380
ttatcccctg attctgtgga taaccgtatt accgcctttg agtgagctga taccgctcgc    4440
cgcagccgaa cgaccgagcg cagcgagtca gtgagcgagg aagcggaaga gcgcctgatg    4500
cggtattttc tccttacgca tctgtgcggt atttcacacc gcatatggtg cactctcagt    4560
acaatctgct ctgatgccgc atagttaagc cagtatacac tccgctatcg ctacgtgact    4620
gggtcatggc tgcgccccga cacccgccaa cacccgctga cgcgccctga cgggcttgtc    4680
```

```
tgctcccggc atccgcttac agacaagctg tgaccgtctc cgggagctgc atgtgtcaga    4740
ggttttcacc gtcatcaccg aaacgcgcga ggcagcagat caattcgcgc gcgaaggcga    4800
agcggcatgc atttacgttg acaccatcga atggtgcaaa acctttcgcg gtatggcatg    4860
atagcgcccg gaagagagtc aattcagggt ggtgaatgtg aaaccagtaa cgttatacga    4920
tgtcgcagag tatgccggtg tctcttatca gaccgtttcc cgcgtggtga accaggccag    4980
ccacgtttct gcgaaaacgc gggaaaaagt ggaagcggcg atggcggagc tgaattacat    5040
tcccaaccgc gtggcacaac aactggcggg caaacagtcg ttgctgattg gcgttgccac    5100
ctccagtctg gccctgcacg cgccgtcgca aattgtcgcg gcgattaaat ctcgcgccga    5160
tcaactgggt gccagcgtgg tggtgtcgat ggtagaacga agcggcgtcg aagcctgtaa    5220
agcggcggtg cacaatcttc tcgcgcaacg cgtcagtggg ctgatcatta actatccgct    5280
ggatgaccag gatgccattg ctgtggaagc tgcctgcact aatgttccgg cgttatttct    5340
tgatgtctct gaccagacac ccatcaacag tattattttc tcccatgaag acggtacgcg    5400
actgggcgtg gagcatctgg tcgcattggg tcaccagcaa atcgcgctgt tagcgggccc    5460
attaagttct gtctcggcgc gtctgcgtct ggctggctgg cataaatatc tcactcgcaa    5520
tcaaattcag ccgatagcgg aacgggaagg cgactggagt gccatgtccg ttttcaaca    5580 aaccatgcaa atgctgaatg agggcatcgt tcccactgcg atgctggttg ccaacgatca    5640
gatggcgctg gcgcaatgc gcgccattac cgagtccggg ctgcgcgttg gtgcggatat    5700
ctcggtagtg ggatacgacg ataccgaaga cagctcatgt tatatcccgc cgtcaaccac    5760
catcaaacag gattttcgcc tgctggggca accagcgtg gaccgcttgc tgcaactctc    5820
tcagggccag gcggtgaagg gcaatcagct gttgcccgtc tcactggtga aagaaaaac    5880 cacccctggcg cccaatacgc aaaccgcctc tccccgcgcg ttggccgatt cattaatgca    5940
gctggcacga caggtttccc gactggaaag cgggcagtga gcgcaacgca attaatgtga    6000
gttagcgcga attgatctg                                                 6019

<210> SEQ ID NO 33
<211> LENGTH: 6857
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatggaaac    420
ccgcagaacc gccaattatg aacccaattc ctgggattac gattaccttt tgagtagcga    480
taacgatgac gccatagaac tgtacaaaga taaagccaag aaacttgatg cagaagtgcg    540
tagtaaaatt aataacgaaa agcagaatt tcttacacaa cttgaactca ttgatactat    600
ccaacgtctc ggcctcggat accgcttcga atcagatata cggcgcgcta tcgatagata    660
tgtttcatcg ggcggattcg aggcagtggc taaaacgtcg ttacacgcaa cagcactcag    720
```

```
ttttcgtttg ttacgccaac atggattcga agtgagccaa gaggtatttt cgggtttcaa    780
ggaccaaaat ggaaacttta tgagaacctt gaaagaggac ataaaggcaa ttcttagtct    840
ctatgaagcg agtttccttg ctttagaagg cgagaatata ttggacgaag ccaaggtctt    900
tacaatctcc cacctgaaag agctgaatga ggaaaaaatt ggaaaagacc tggccgacca    960
agtgaatcat gcgctggaac ttcctctgca tcggcgtacc cagcgtcttg aagcggtatg   1020
gtcgatagaa gcctatcgca aaaggaagg agcgaatcgc gcattactgg aactggcgat    1080
cttggactac aatatggtcc aatcagtcta ccaacgcgat ttgcgcgaaa cctcccgctg   1140
gtggcgccgt gtaggcttag caactaaatt gcattttgca cgtgaccggc tgattgaatc   1200
tttctattgg gcggtcggcg ttgccttga gccgcaatat tctgactgtc gcaaatctgt    1260
ggctaaaatg ttttcattcg tgaccataat tgatgacata tatgatgttt atgggacgtt   1320
agatgagtta gagttgttta ccgacgcagt tgaacgctgg gacgtttctg ccgtggatga   1380
cctcccggat tatatgaaat tatgctttct ggccctgtac aacacaatca atgagatagc   1440
atacgacaat ctgaaagaaa aaggtgaaaa catcctgcct tacctgacta aagcatgggc   1500
tgacttatgc aacgcatttc tgcaagaggc gaaatttctg tacaacaaat ccactccaac   1560
cttcgatgac tactttggca atgcctggaa aagtagcagt ggcccgttgc agttagtgtt   1620
cgcttatttt gcggtcgttc aaaacattaa gaaggaggag acggagaacc ttcagaagta   1680
ccacgacatt atttcgtggc caagttatat ttttcgctta tgtaatgatc tggcctctgc   1740
gtcagccgaa atcgctcggg gagagaccgc aaattctgtt tcttgctaca ttagaactaa   1800
gggcatctct gaggagttag caacggaatc tgttatgaat ctgattgatg agacttggaa   1860
aaagatgaat aaagaaagg tgggcgattc actgttcgct aaacaatttg tagaaacagc   1920
tattaatctg gctcgtcagt cacattgcac gtatcataat ggtgatgcac atacatcacc   1980
tgatgagctg actcgtaaac gtgtcttatc tgtgatcacc gaaccgatcc ttccgtttga   2040
aagatgactg cataaaggag gtaaaaaaac atggtatcct gttctgcgcc gggtaagatt   2100
tacctgttcg gtgaacacgc cgtagtttat ggcgaaactg caattgcgtg tgcggtggaa   2160
ctgcgtaccc gtgttcgcgc ggaactcaat gactctatca ctattcagag ccagatcggc   2220
cgcaccggtc tggatttcga aaagcaccct tatgtgtctg cggtaattga aaaatgcgc    2280
aaatctattc ctattaacgg tgttttcttg accgtcgatt ccgacatccc ggtgggctcc   2340
ggtctgggta gcagcgcagc cgttactatc gcgtctattg gtgcgctgaa cgagctgttc   2400
ggctttggcc tcagcctgca agaaatcgct aaactgggcc acgaaatcga aattaaagta   2460
cagggtgccg cgtccccaac cgatacgtat gtttctacct tcggcggcgt ggttaccatc   2520
ccggaacgtc gcaaactgaa aactccggac tgcggcattg tgattggcga taccggcgtt   2580
ttctcctcca ccaaagagtt agtagctaac gtacgtcagc tgcgcgaaag ctacccggat   2640
ttgatcgaac cgctgatgac ctctattggc aaaatctctc gtatcggcga caactggtt    2700
ctgtctggcg actacgcatc catcggccgc ctgatgaacg tcaaccaggg tctcctggac   2760
gccctgggcg ttaacatctt agaactgagc cagctgatct attccgctcg tgcggcaggt   2820
gcgtttggcc ctaaaatcac gggcgctggc ggcggtggct gtatggttgc gctgaccgct   2880
ccggaaaaat gcaaccaagt ggcagaagcg gtagcaggcg ctggcggtaa agtgactatc   2940
actaaaccga ccgagcaagg tctgaaagta gattaaagtc tagttaaagt ttaaacggtc   3000
tccagcttgg ctgttttggc ggatgagaga agattttcag cctgatacag attaaatcag   3060
```

```
aacgcagaag cggtctgata aaacagaatt tgcctggcgg cagtagcgcg gtggtcccac    3120
ctgaccccat gccgaactca gaagtgaaac gccgtagcgc cgatggtagt gtggggtctc    3180
cccatgcgag agtagggaac tgccaggcat caaataaaac gaaaggctca gtcgaaagac    3240
tgggcctttc gttttatctg ttgtttgtcg gtgaacgctc tcctgagtag gacaaatccg    3300
ccgggagcgg atttgaacgt tgcgaagcaa cggcccggag ggtggcgggc aggacgcccg    3360
ccataaactg ccaggcatca aattaagcag aaggccatcc tgacggatgg ccttttttgcg   3420 tttctacaaa ctcttttgtt tattttttcta aatacattca aatatgtatc cgctcatgag   3480
acaataaccc tgataaatgc ttcaataata ttgaaaaagg aagagtatga gtattcaaca    3540
tttccgtgtc gcccttattc cctttttttgc ggcattttgc cttcctgttt ttgctcaccc   3600
agaaacgctg gtgaaagtaa aagatgctga agatcagttg ggtgcacgag tgggttacat    3660
cgaactggat ctcaacagcg gtaagatcct tgagagtttt cgccccgaag aacgttttcc    3720
aatgatgagc acttttaaag ttctgctatg tggcgcggta ttatcccgtg ttgacgccgg    3780
gcaagagcaa ctcggtcgcc gcatacacta ttctcagaat gacttggttg agtactcacc    3840
agtcacagaa aagcatctta cggatggcat gacagtaaga gaattatgca gtgctgccat    3900
aaccatgagt gataacactg cggccaactt acttctgaca acgatcggag gaccgaagga    3960
gctaaccgct tttttgcaca acatggggga tcatgtaact cgccttgatc gttgggaacc    4020
ggagctgaat gaagccatac caaacgacga gcgtgacacc acgatgcctg tagcaatggc    4080
aacaacgttg cgcaaactat taactggcga actacttact ctagcttccc ggcaacaatt    4140
aatagactgg atggaggcgg ataaagttgc aggaccactt ctgcgctcgg cccttccggc    4200
tggctggttt attgctgata aatctggagc cggtgagcgt gggtctcgcg gtatcattgc    4260
agcactgggg ccagatggta agccctcccg tatcgtagtt atctacacga cggggagtca    4320
ggcaactatg gatgaacgaa atagacagat cgctgagata ggtgcctcac tgattaagca    4380
ttggtaactg tcagaccaag tttactcata tatactttag attgatttaa aacttcattt    4440
ttaatttaaa aggatctagg tgaagatcct ttttgataat ctcatgacca aaatccctta    4500
acgtgagttt tcgttccact gagcgtcaga ccccgtagaa aagatcaaag gatcttcttg    4560
agatcctttt tttctgcgcg taatctgctg cttgcaaaca aaaaaaccac cgctaccagc    4620
ggtggtttgt ttgccggatc aagagctacc aactctttt ccgaaggtaa ctggcttcag    4680
cagagcgcag ataccaaata ctgtccttct agtgtagccg tagttaggcc accacttcaa    4740
gaactctgta gcaccgccta catacctcgc tctgctaatc ctgttaccag tggctgctgc    4800
cagtggcgat aagtcgtgtc ttaccgggtt ggactcaaga cgatagttac cggataaggc    4860
gcagcggtcg ggctgaacgg ggggttcgtg cacacagccc agcttggagc gaacgaccta    4920
caccgaactg agatacctac agcgtgagct atgagaaagc gccacgcttc ccgaagggag    4980
aaaggcggac aggtatccgg taagcggcag ggtcggaaca ggagagcgca cgagggagct    5040 tccagggga aacgcctggt atctttatag tcctgtcggg tttcgccacc tctgacttga    5100
gcgtcgattt ttgtgatgct cgtcaggggg gcggagccta tggaaaaacg ccagcaacgc    5160
ggccttttta cggttcctgg ccttttgctg gccttttgct cacatgttct ttcctgcgtt    5220
atcccctgat tctgtggata accgtattac cgcctttgag tgagctgata ccgctcgccg    5280
cagccgaacg accgagcgca gcgagtcagt gagcgaggaa gcggaagagc gcctgatgcg    5340
gtattttctc cttacgcatc tgtgcggtat ttcacaccgc atatggtgca ctctcagtac    5400
aatctgctct gatgccgcat agttaagcca gtatacactc cgctatcgct acgtgactgg    5460
```

```
gtcatggctg cgccccgaca cccgccaaca cccgctgacg cgccctgacg ggcttgtctg      5520
ctcccggcat ccgcttacag acaagctgtg accgtcccg ggagctgcat gtgtcagagg       5580
ttttcaccgt catcaccgaa acgcgcgagg cagcagatca attcgcgcgc gaaggcgaag      5640
cggcatgcat ttacgttgac accatcgaat ggtgcaaaac ctttcgcggt atggcatgat     5700
agcgcccgga agagagtcaa ttcagggtgg tgaatgtgaa accagtaacg ttatacgatg     5760
tcgcagagta tgccggtgtc tcttatcaga ccgtttcccg cgtggtgaac caggccagcc     5820
acgtttctgc gaaaacgcgg gaaaagtgg aagcggcgat ggcggagctg aattacattc      5880
ccaaccgcgt ggcacaacaa ctggcgggca aacagtcgtt gctgattggc gttgccacct    5940
ccagtctggc cctgcacgcg ccgtcgcaaa ttgtcgcggc gattaaatct cgcgccgatc     6000
aactgggtgc cagcgtggtg gtgtcgatgg tagaacgaag cggcgtcgaa gcctgtaaag    6060
cggcggtgca caatcttctc gcgcaacgcg tcagtgggct gatcattaac tatccgctgg    6120
atgaccagga tgccattgct gtggaagctg cctgcactaa tgttccggcg ttatttcttg    6180
atgtctctga ccagacaccc atcaacagta ttatttctc ccatgaagac ggtacgcgac     6240
tgggcgtgga gcatctggtc gcattgggtc accagcaaat cgcgctgtta gcgggcccat    6300
taagttctgt ctcggcgcgt ctgcgtctgg ctggctggca taaatatctc actcgcaatc    6360
aaattcagcc gatagcggaa cgggaaggcg actggagtgc catgtccggt tttcaacaaa    6420
ccatgcaaat gctgaatgag ggcatcgttc ccactgcgat gctggttgcc aacgatcaga    6480
tggcgctggg cgcaatgcgc gccattaccg agtccgggct gcgcgttggt gcggatatct    6540
cggtagtggg atacgacgat accgaagaca gctcatgtta tatcccgccg tcaaccacca   6600
tcaaacagga ttttcgcctg ctggggcaaa ccagcgtgga ccgcttgctg caactctctc    6660
agggccaggc ggtgaagggc aatcagctgt tgcccgtctc actggtgaaa agaaaaacca   6720
ccctggcgcc caatacgcaa accgcctctc cccgcgcgtt ggccgattca ttaatgcagc    6780
tggcacgaca ggtttcccga ctggaaagcg ggcagtgagc gcaacgcaat taatgtgagt    6840
tagcgcgaat tgatctg                                                    6857
```

<210> SEQ ID NO 34
<211> LENGTH: 6019
<212> TYPE: DNA
<213> ORGANISM: Artificial Sequence
<220> FEATURE:
<223> OTHER INFORMATION: Synthetic Construct

<400> SEQUENCE: 34

```
gtttgacagc ttatcatcga ctgcacggtg caccaatgct tctggcgtca ggcagccatc       60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa     300
caatttatca gacaatctgt gtgggcactc gaccggaatt atcgattaac tttattatta    360
aaaattaaag aggtatatat taatgtatcg attaaataag gaggaataaa ccatggaaac    420
cagacggtcc gctaattatg aaccgaacag ttgggattac gattacctgc tttcttcgga    480
tacggaagat gccatagagg tatacaaaga caaagcgaag aaactggatg ctgaagtacg    540
ctcgaagata aacaatgaga ccgcagaatt tttaacgcaa ttagaactga ttgacactat   600
```

```
ccagcgcctg ggtttgggtt atcgtttcga aagcgacatt agacgcgcct tggatcgttt    660
cgtgagtagt ggtgggttcg aggctgtcgc gaaaacttca ctgcaagcta cagcactgtc    720
ttttcggctg ctgcgtcaac atggtttcga ggttagtcaa gaagtgttta atggtttcaa    780
agaccagaac ggtaacttta tggaggattt aaaagaagat attaaggccc tcctttcact    840
tcacgaagca tcttttttag ctctggaagg cgagaatatt ctggacgagg caaaggtatt    900
cacaattagc cacctcaaag aactgaacga ggagaaaatt ggcaaagaca tggtggaaca    960
agtgaaccat gctctggaat tacccottca tcgtcgtacg cagcgtttgg aggctgtgtg   1020
gtctattgaa gcgtatcgga agaaggaaga tgcaaaccgc gtccttctgg aacttgcaat   1080
cctcgattat aatatggtcc aatctgtgta tcagcgcgat ttgcgcgaaa cttcgagatg   1140
gtggcgccgc gtgggattag ccactaagtt gcatttcgcc agagacagac ttatcgaatc   1200
cttctattgg gcggttggcg tcgccttrga accgcaatac tcagattgca gaatttctgt   1260
cgctaagatg ttctgtttcg taaccattat cgacgacatt tatgatgtgt atgggacgtt   1320
ggaagagctg gagcttttca ctgacgcagt tgagagatgg gatgtgagcg ccattgacga   1380
tttacccgat tatatgaaac tgtgcttctt ggcgttgtac aatactataa acgaaatcgc   1440
ttatgacaat cttaaagaaa aaggcgaaaa tattctgccg tatctgacta aagcctgggc   1500
ggatctttgc aatgctttcc tgcaagaggc acgttttta taacaagt cgacacctac   1560 cttctcagat tattttggca atgcgtggaa atctagttct gggccacttc aactgggttt   1620
tgcttacttt gccgtagtgc aaaacatcaa aaaggaagaa accgaaaatc tgctgaaata   1680
tcatgatata atctcttggc catcgtacat atttcggctg tgtaatgatc tggcttccgc   1740
atcggcagaa attgcgcggg gtgagactgc aaacagcgtt tcttgttaca tgcggacgaa   1800
gggaatttcc gaagaactgg caaccgaatc agtgatgaat cttattgatg aaacgtggaa   1860
aaagatgaac aaggaaaaat tgggggactc actctttgca aaacactttg tggagaccgc   1920
gataaaccrt gctcgccaat cgcattgtac gtatcataat ggagatgcgc atacttcgcc   1980
tgacgaatta acccgcaaac gcgtactgtc agtgatcact gaaccgatac tgccattgga   2040
acggtgactg cagctggtac catatgggaa ttcgaagctt tctagaacaa aaactcatct   2100
cagaagagga tctgaatagc gccgtcgacc atcatcatca tcatcattga gtttaaacgg   2160
tctccagctt ggctgttttg gcggatgaga agattttc agcctgatac agattaaatc   2220
agaacgcaga agcggtctga taaaacagaa tttgcctggc ggcagtagcg cggtggtccc   2280
acctgacccc atgccgaact cagaagtgaa acgccgtagc gccgatggta gtgtggggtc   2340
tccccatgcg agagtaggga actgccaggc atcaaataaa acgaaaggct cagtcgaaag   2400
actgggcctt tcgttttatc tgttgtttgt cggtgaacgc tctcctgagt aggacaaatc   2460
cgccgggagc ggatttgaac gttgcgaagc aacggcccgg agggtggcgg gcaggacgcc   2520
cgccataaac tgccaggcat caaattaagc agaaggccat cctgacggat ggcctttttg   2580
cgtttctaca aactcttttg tttatttttc taaatacatt caaatatgta tccgctcatg   2640
agacaataac cctgataaat gcttcaataa tattgaaaaa ggaagagtat gagtattcaa   2700
catttccgtg tcgcccttat tcccttttt gcggcatttt gccttcctgt ttttgctcac   2760
ccagaaacgc tggtgaaagt aaaagatgct gaagatcagt tgggtgcacg agtgggttac   2820
atcgaactgg atctcaacag cggtaagatc cttgagagtt ttcgccccga gaacgttttt   2880
ccaatgatga gcacttttaa agttctgcta tgtggcgcgg tattatcccg tgttgacgcc   2940
gggcaagagc aactcggtcg ccgcatacac tattctcaga atgacttggt tgagtactca   3000
```

```
ccagtcacag aaaagcatct tacggatggc atgacagtaa agaaattatg cagtgctgcc    3060
ataaccatga gtgataacac tgcggccaac ttacttctga caacgatcgg aggaccgaag    3120
gagctaaccg cttttttgca caacatgggg gatcatgtaa ctcgccttga tcgttgggaa    3180
ccggagctga atgaagccat accaaacgac gagcgtgaca ccacgatgcc tgtagcaatg    3240
gcaacaacgt tgcgcaaact attaactggc gaactactta ctctagcttc ccggcaacaa    3300
ttaatagact ggatggaggc ggataaagtt gcaggaccac ttctgcgctc ggcccttccg    3360
gctggctggt ttattgctga taaatctgga gccggtgagc gtgggtctcg cggtatcatt    3420
gcagcactgg ggccagatgg taagccctcc cgtatcgtag ttatctacac gacggggagt    3480
caggcaacta tggatgaacg aaatagacag atcgctgaga taggtgcctc actgattaag    3540
cattggtaac tgtcagacca agtttactca tatatacttt agattgattt aaaacttcat    3600
ttttaattta aaaggatcta ggtgaagatc ctttttgata atctcatgac caaaatccct    3660
taacgtgagt tttcgttcca ctgagcgtca gaccccgtag aaaagatcaa aggatcttct    3720
tgagatcctt tttttctgcg cgtaatctgc tgcttgcaaa caaaaaaacc accgctacca    3780
gcggtggttt gtttgccgga tcaagagcta ccaactcttt ttccgaaggt aactggcttc    3840
agcagagcgc agataccaaa tactgtcctt ctagtgtagc cgtagttagg ccaccacttc    3900
aagaactctg tagcaccgcc tacatacctc gctctgctaa tcctgttacc agtggctgct    3960
gccagtggcg ataagtcgtg tcttaccggg ttggactcaa gacgatagtt accggataag    4020
gcgcagcggt cgggctgaac ggggggttcg tgcacacagc ccagcttgga gcgaacgacc    4080
tacaccgaac tgagatacct acagcgtgag ctatgagaaa gcgccacgct tcccgaaggg    4140
agaaaggcgg acaggtatcc ggtaagcggc agggtcggaa caggagagcg cacgagggag    4200
cttccagggg gaaacgcctg gtatctttat agtcctgtcg ggtttcgcca cctctgactt    4260
gagcgtcgat ttttgtgatg ctcgtcaggg gggcggagcc tatggaaaaa cgccagcaac    4320
gcggcctttt tacggttcct ggccttttgc tggccttttg ctcacatgtt ctttcctgcg    4380
ttatccctg attctgtgga taaccgtatt accgcctttg agtgagctga taccgctcgc    4440
cgcagccgaa cgaccgagcg cagcgagtca gtgagcgagg aagcggaaga gcgcctgatg    4500
cggtattttc tccttacgca tctgtgcggt atttcacacc gcatatggtg cactctcagt    4560
acaatctgct ctgatgccgc atagttaagc cagtatacac tccgctatcg ctacgtgact    4620
gggtcatggc tgcgccccga cacccgccaa cacccgctga cgcgccctga cgggcttgtc    4680
tgctcccggc atccgcttac agacaagctg tgaccgtctc cgggagctgc atgtgtcaga    4740
ggttttcacc gtcatcaccg aaacgcgcga ggcagcagat caattcgcgc gcgaaggcga    4800
agcggcatgc atttacgttg acaccatcga atggtgcaaa acctttcgcg gtatggcatg    4860
atagcgcccg gaagagagtc aattcagggt ggtgaatgtg aaaccagtaa cgttatacga    4920
tgtcgcagag tatgccggtg tctcttatca gaccgtttcc cgcgtggtga accaggccag    4980
ccacgtttct gcgaaaacgc gggaaaaagt ggaagcggcg atggcggagc tgaattacat    5040
tcccaaccgc gtggcacaac aactggcggg caaacagtcg ttgctgattg gcgttgccac    5100
ctccagtctg gccctgcacg cgccgtcgca aattgtcgcg gcgattaaat ctcgcgccga    5160
tcaactgggt gccagcgtgg tggtgtcgat ggtagaacga agcggcgtcg aagcctgtaa    5220
agcggcggtg cacaatcttc tcgcgcaacg cgtcagtggg ctgatcatta actatccgct    5280
ggatgaccag gatgccattg ctgtggaagc tgcctgcact aatgttccgg cgttatttct    5340
```

```
tgatgtctct gaccagacac ccatcaacag tattattttc tcccatgaag acggtacgcg    5400
actgggcgtg gagcatctgg tcgcattggg tcaccagcaa atcgcgctgt tagcgggccc    5460
attaagttct gtctcggcgc gtctgcgtct ggctggctgg cataaatatc tcactcgcaa    5520
tcaaattcag ccgatagcgg aacgggaagg cgactggagt gccatgtccg gttttcaaca    5580
aaccatgcaa atgctgaatg agggcatcgt tcccactgcg atgctggttg ccaacgatca    5640
gatggcgctg ggcgcaatgc gcgccattac cgagtccggg ctgcgcgttg gtgcggatat    5700
ctcggtagtg ggatacgacg ataccgaaga cagctcatgt tatatcccgc cgtcaaccac    5760
catcaaacag gattttcgcc tgctgggggca accagcgtgg accgcttgc tgcaactctc    5820 tcagggccag gcggtgaagg gcaatcagct gttgcccgtc tcactggtga aagaaaaac    5880 caccctggcg cccaatacgc aaaccgcctc tccccgcgcg ttggccgatt cattaatgca    5940
gctggcacga caggtttccc gactggaaag cgggcagtga gcgcaacgca attaatgtga    6000
gttagcgcga attgatctg                                                 6019

<210> SEQ ID NO 35
<211> LENGTH: 6019
<212> TYPE: DNA
<213> ORGANISM: Artificial Sequence
<220> FEATURE:
<223> OTHER INFORMATION: Synthetic Construct

<400> SEQUENCE: 35
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggaaac     420
ccgcagaacc gccaattatg aacccaattc ctgggattac gattaccttt tgagtagcga     480
taacgatgac gccatagaac tgtacaaaga taaagccaag aaacttgatg cagaagtgcg     540
tagtaaaatt aataacgaaa aagcagaatt tcttacacaa cttgaactca ttgatactat     600
ccaacgtctc ggcctcggat accgcttcga atcagatata cggcgcgcta tcgatagata     660
tgtttcatcg gcggattcg aggcagtggc taaaacgtcg ttacacgcaa cagcactcag     720
ttttcgtttg ttacgccaac atggattcga agtgagccaa gaggtatttt cgggtttcaa     780
ggaccaaaat ggaaacttta tggagaactt gaaagaggac ataaaggcaa ttcttagtct     840
ctatgaagcg agtttccttg ctttagaagg cgagaatata ttggacgaag ccaaggtctt     900
tacaatctcc cacctgaaag agctgaatga ggaaaaaatt ggaaaagacc tggccgacca     960
agtgaatcat gcgctggaac ttcctctgca tcggcgtacc cagcgtcttg aagcggtatg    1020
gtcgatagaa gcctatcgca aaaggaagg agcgaatcgc gcattactgg aactggcgat    1080
cttggactac aatatggtcc aatcagtcta ccaacgcgat ttgcgcgaaa cctcccgctg    1140
gtggcgccgt gtaggcttag caactaaatt gcattttgca cgtgaccggc tgattgaatc    1200
tttctattgg gcggtcggcg ttgccttga gccgcaatat tctgactgtc gcaaatctgt    1260
ggctaaaatg ttttgtttcg tgaccataat tgatgacata tatgatgttt atgggacgtt    1320
agatgagtta gagttgttta ccgacgcagt tgaacgctgg gacgtttctg ccgtggatga    1380
```

-continued

```
cctcccggat tatatgaaat tatgctttct ggccctgtac aacacaatca atgagatagc   1440
atacgacaat ctgaaagaaa aaggtgaaaa catcctgcct tacctgacta aagcatgggc   1500
tgacttatgc aacgcatttc tgcaagaggc gaaatttctg tacaacaaat ccactccaac   1560
cttcgatgac tactttggca atgcctggaa aagtagcagt ggcccgttgc agttagtgtt   1620
cgcttatttt gcggtcgttc aaaacattaa gaaggaggag acggagaacc ttcagaagta   1680
ccacgacatt atttcgtggc caagttatat ttttcgctta tgtaatgatc tggcctctgc   1740
gtcagccgaa atcgctcggg gagagaccgc aaattctgtt tcttgctaca ttagaactaa   1800
gggcatctct gaggagttag caacggaatc tgttatgaat ctgattgatg agacttggaa   1860
aaagatgaat aaagagaagg tgggcgattc actgttcgct aaacaatttg tagaaacagc   1920
tattaatctg gctcgtcagt cacattgcac gtatcataat ggtgatgcac atacatcacc   1980
tgatgagctg actcgtaaac gtgtcttatc tgtgatcacc gaaccgatcc ttccgtttga   2040
aagatgactg cagctggtac catatgggaa ttcgaagctt tctagaacaa aaactcatct   2100
cagaagagga tctgaatagc gccgtcgacc atcatcatca tcatcattga gtttaaacgg   2160
tctccagctt ggctgttttg gcggatgaga aagattttc agcctgatac agattaaatc   2220
agaacgcaga agcggtctga taaaacagaa tttgcctggc ggcagtagcg cggtggtccc   2280
acctgacccc atgccgaact cagaagtgaa acgccgtagc gccgatggta gtgtggggtc   2340
tccccatgcg agagtaggga actgccaggc atcaaataaa acgaaaggct cagtcgaaag   2400
actgggcctt tcgttttatc tgttgtttgt cggtgaacgc tctcctgagt aggacaaatc   2460
cgccgggagc ggatttgaac gttgcgaagc aacggcccgg agggtggcgg gcaggacgcc   2520
cgccataaac tgccaggcat caaattaagc agaaggccat cctgacggat ggcctttttg   2580
cgtttctaca aactcttttg tttatttttc taaatacatt caaatatgta tccgctcatg   2640
agacaataac cctgataaat gcttcaataa tattgaaaaa ggaagagtat gagtattcaa   2700
catttccgtg tcgcccttat tcccttttt gcggcatttt gccttcctgt ttttgctcac   2760
ccagaaacgc tggtgaaagt aaaagatgct gaagatcagt tgggtgcacg agtgggttac   2820
atcgaactgg atctcaacag cggtaagatc cttgagagtt ttcgccccga gaacgttttt   2880
ccaatgatga gcacttttaa agttctgcta tgtggcgcgg tattatcccg tgttgacgcc   2940
gggcaagagc aactcggtcg ccgcatacac tattctcaga atgacttggt tgagtactca   3000
ccagtcacag aaaagcatct tacggatggc atgacagtaa gagaattatg cagtgctgcc   3060
ataaccatga gtgataacac tgcggccaac ttacttctga caacgatcgg aggaccgaag   3120
gagctaaccg cttttttgca caacatgggg gatcatgtaa ctcgccttga tcgttgggaa   3180
ccggagctga atgaagccat accaaacgac gagcgtgaca ccacgatgcc tgtagcaatg   3240
gcaacaacgt tgcgcaaact attaactggc gaactactta ctctagcttc ccggcaacaa   3300
ttaatagact ggatggaggc ggataaagtt gcaggaccac ttctgcgctc ggcccttccg   3360
gctggctggt ttattgctga taaatctgga gccggtgagc gtgggtctcg cggtatcatt   3420
gcagcactgg ggccagatgg taagccctcc cgtatcgtag ttatctacac gacggggagt   3480
caggcaacta tggatgaacg aaatagacag atcgctgaga taggtgcctc actgattaag   3540
cattggtaac tgtcagacca agtttactca tatatacttt agattgattt aaaacttcat   3600
ttttaattta aaaggatcta ggtgaagatc ctttttgata atctcatgac caaaatccct   3660
taacgtgagt tttcgttcca ctgagcgtca gaccccgtag aaaagatcaa aggatcttct   3720
```

```
tgagatcctt ttttctgcg cgtaatctgc tgcttgcaaa caaaaaaacc accgctacca   3780
gcggtggttt gtttgccgga tcaagagcta ccaactcttt ttccgaaggt aactggcttc   3840
agcagagcgc agataccaaa tactgtcctt ctagtgtagc cgtagttagg ccaccacttc   3900
aagaactctg tagcaccgcc tacatacctc gctctgctaa tcctgttacc agtggctgct   3960
gccagtggcg ataagtcgtg tcttaccggg ttggactcaa gacgatagtt accggataag   4020
gcgcagcggt cgggctgaac ggggggttcg tgcacacagc ccagcttgga gcgaacgacc   4080
tacaccgaac tgagatacct acagcgtgag ctatgagaaa gcgccacgct tcccgaaggg   4140
agaaaggcgg acaggtatcc ggtaagcggc agggtcggaa caggagagcg cacgagggag   4200
cttccagggg gaaacgcctg gtatctttat agtcctgtcg ggtttcgcca cctctgactt   4260
gagcgtcgat ttttgtgatg ctcgtcaggg gggcggagcc tatggaaaaa cgccagcaac   4320
gcggcctttt tacggttcct ggccttttgc tggccttttg ctcacatgtt ctttcctgcg   4380
ttatccctg attctgtgga taaccgtatt accgcctttg agtgagctga taccgctcgc   4440
cgcagccgaa cgaccgagcg cagcgagtca gtgagcgagg aagcggaaga gcgcctgatg   4500
cggtattttc tccttacgca tctgtgcggt atttcacacc gcatatggtg cactctcagt   4560
acaatctgct ctgatgccgc atagttaagc cagtatacac tccgctatcg ctacgtgact   4620
gggtcatggc tgcgccccga cacccgccaa cacccgctga cgcgccctga cgggcttgtc   4680
tgctcccggc atccgcttac agacaagctg tgaccgtctc cggagctgc atgtgtcaga   4740
ggttttcacc gtcatcaccg aaacgcgcga ggcagcagat caattcgcgc gcgaaggcga   4800
agcggcatgc atttacgttg acaccatcga atggtgcaaa acctttcgcg gtatggcatg   4860
atagcgcccg gaagagagtc aattcagggt ggtgaatgtg aaaccagtaa cgttatacga   4920
tgtcgcagag tatgccggtg tctcttatca gaccgtttcc cgcgtggtga accaggccag   4980
ccacgtttct gcgaaaacgc gggaaaaagt ggaagcggcg atggcggagc tgaattacat   5040
tcccaaccgc gtggcacaac aactggcggg caaacagtcg ttgctgattg gcgttgccac   5100
ctccagtctg gccctgcacg cgccgtcgca aattgtcgcg gcgattaaat ctcgcgccga   5160
tcaactgggt gccagcgtgg tggtgtcgat ggtagaacga agcggcgtcg aagcctgtaa   5220
agcggcggtg cacaatcttc tcgcgcaacg cgtcagtggg ctgatcatta actatccgct   5280
ggatgaccag gatgccattg ctgtggaagc tgcctgcact aatgttccgg cgttatttct   5340
tgatgtctct gaccagacac ccatcaacag tattattttc tcccatgaag acggtacgcg   5400
actgggcgtg gagcatctgg tcgcattggg tcaccagcaa atcgcgctgt tagcgggccc   5460
attaagttct gtctcggcgc gtctgcgtct ggctggctgg cataaatatc tcactcgcaa   5520
tcaaattcag ccgatagcgg aacgggaagg cgactggagt gccatgtccg tttttcaaca   5580
aaccatgcaa atgctgaatg agggcatcgt tcccactgcg atgctggttg ccaacgatca   5640
gatggcgctg ggcgcaatgc gcgccattac cgagtccggg ctgcgcgttg gtgcggatat   5700
ctcggtagtg ggatacgacg ataccgaaga cagctcatgt tatatcccgc cgtcaaccac   5760
catcaaacag gattttcgcc tgctggggca accagcgtg gaccgcttgc tgcaactctc   5820
tcagggccag gcggtgaagg gcaatcagct gttgccgtc tcactggtga aagaaaaac    5880
caccctggcg cccaatacgc aaaccgcctc tccccgcgcg ttggccgatt cattaatgca   5940
gctggcacga caggtttccc gactggaaag cgggcagtga gcgcaacgca attaatgtga   6000
gttagcgcga attgatctg                                                6019
```

```
<210> SEQ ID NO 36
<211> LENGTH: 33
<212> TYPE: DNA
<213> ORGANISM: Artificial Sequence
<220> FEATURE:
<223> OTHER INFORMATION: Synthetic Construct

<400> SEQUENCE: 36
acatatggaa acgcgtcgtt ctgcgaacta cga                           33

<210> SEQ ID NO 37
<211> LENGTH: 33
<212> TYPE: DNA
<213> ORGANISM: Artificial Sequence
<220> FEATURE:
<223> OTHER INFORMATION: Synthetic Construct

<400> SEQUENCE: 37
cagaacgacg cgtttccata tgtatatctc ctt                           33

<210> SEQ ID NO 38
<211> LENGTH: 33
<212> TYPE: DNA
<213> ORGANISM: Artificial Sequence
<220> FEATURE:
<223> OTHER INFORMATION: Synthetic Construct

<400> SEQUENCE: 38
aaaaatgttt tgtttcgtaa ccattatcga cga                           33

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
tggttacgaa acaaaacatt tttgcgacgg agt                           33

<210> SEQ ID NO 40
<211> LENGTH: 559
<212> TYPE: PRT
<213> ORGANISM: Artificial Sequence
<220> FEATURE:
<223> OTHER INFORMATION: Synthetic Construct

<400> SEQUENCE: 40
```

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn

-continued

```
            115                 120                 125
Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
                180                 185                 190

His Arg Arg Thr Gln Arg Leu Glu Ala Val Trp Ser Ile Glu Ala Tyr
                195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Cys
                275                 280                 285

Phe Val Thr Ile Ile Asp Asp Ile Tyr Asp Val Tyr Gly Thr Leu Asp
                290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Phe Glu Arg
    530                 535                 540
```

Glu Asn Leu Tyr Phe Gln Gly Leu Glu His His His His His His
545 550 555

<210> SEQ ID NO 41
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 41

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggc tcccttagg     180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggatt tgccgatttc ggcctattgg ttaaaaaatg agctgattta     420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat  1020
tttcacctga tcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
```

```
ccaggggaa acgcctggta tctttatagt cctgtcgggt ttcgccacct ctgacttgag      2040
cgtcgatttt tgtgatgctc gtcaggggg cggagcctat ggaaaaacgc cagcaacgcg      2100 gccttttac ggttcctggc cttttgctgg ccttttgctc acatgttctt tcctgcgtta      2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280 tatttttctcc ttacgcatct gtgcggtatt tcacaccgca tatatggtgc actctcagta    2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aaggggatt tctgttcatg ggggtaatga taccgatgaa      2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagacttta     3000
cgaaacacgg aaaccgaaga ccattcatgt tgttgctcag gtcgcagacg ttttgcagca     3060
gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc     3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc     3300
gctccagcga aagcggtcct cgccgaaaat gacccagagc gctgccggca cctgtcctac     3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta     3480
atgagtgagc taacttacat taattgcgtt gcgctcactg cccgctttcc agtcgggaaa     3540
cctgtcgtgc cagctgcatt aatgaatcgg ccaacgcgcg gggagaggcg gtttgcgtat     3600
tgggcgccag ggtggttttt cttttcacca gtgagacggg caacagctga ttgcccttca     3660
ccgcctggcc ctgagagagt tgcagcaagc ggtccacgct ggtttgcccc agcaggcgaa     3720
aatcctgttt gatggtggtt aacggcggga tataacatga gctgtcttcg gtatcgtcgt     3780
atcccactac cgagatatcc gcaccaacgc gcagcccgga ctcggtaatg gcgcgcattg     3840
cgcccagcgc catctgatcg ttggcaacca gcatcgcagt gggaacgatg ccctcattca     3900
gcatttgcat ggtttgttga aaaccggaca tggcactcca gtcgccttcc cgttccgcta     3960
tcggctgaat ttgattgcga gtgagatatt tatgccagcc agccagacgc agacgcgccg     4020
agacagaact taatgggccc gctaacagcg cgatttgctg gtgacccaat gcgaccagat     4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
```

-continued

```
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg cgcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttgtttcgt    5940
aaccattatc gacgatatct acgatgtata cggcacccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
```

```
gggcctcgag caccaccacc accaccactg agatccggct gctaacaaag cccgaaagga      6780
agctgagttg gctgctgcca ccgctgagca ataactagca taaccccttg gggcctctaa      6840
acgggtcttg aggggttttt tgctgaaagg aggaactata tccggat                    6887
```

<210> SEQ ID NO 42
<211> LENGTH: 559
<212> TYPE: PRT
<213> ORGANISM: Artificial Sequence
<220> FEATURE:
<223> OTHER INFORMATION: Synthetic Construct

<400> SEQUENCE: 42

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Cys
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335
```

```
Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
            450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
            530                 535                 540

Glu Asn Leu Tyr Phe Gln Gly Leu Glu His His His His His His
545                 550                 555
```

<210> SEQ ID NO 43
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 43

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct tgacgttgg agtccacgtt    300
ctttaatagt ggactcttgt tccaaactgg aacaacactc aaccctatct cggtctattc   360
ttttgattta tagggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttc taaatacatt caaatatgta   540
tccgctcatg aattaattct tagaaaaact catcgagcat caaatgaaac tgcaatttat   600
tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa ataaggttat caagtgaga   780
```

```
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa acgcctggta tctttatagt cctgtcgggt ttcgccacct ctgacttgag   2040
cgtcgatttt tgtgatgctc gtcaggggg cggagcctat ggaaaaacgc cagcaacgcg   2100
gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
```

```
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaaacg cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gttctcagg aagcgttcag cggcttcaaa gaccaaaacg caacttcct    5460
ggagaacctg aaggaagata tcaaagctat cctgagcctg tacgaggcca gcttcctggc    5520
```

```
tctggaaggc gaaacatcc tggacgaggc gaaggttttc gcaatctctc atctgaaaga   5580
actgtctgaa gaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaatgt tttgtttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgcttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga acctgaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg ggcctctaa   6840
acgggtcttg aggggttttt tgctgaaagg aggaactata tccggat      6887
```

<210> SEQ ID NO 44
<211> LENGTH: 544
<212> TYPE: PRT
<213> ORGANISM: Artificial Sequence
<220> FEATURE:
<223> OTHER INFORMATION: Synthetic construct

<400> SEQUENCE: 44

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

```
Phe Leu Glu Asn Leu Lys Glu Asp Ile Lys Ala Ile Leu Ser Leu Tyr
    130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                    165                 170                 175
Gly Lys Glu Leu Ala Glu Gln Val Asn His Ala Leu Glu Leu Pro Leu
                180                 185                 190
His Arg Arg Thr Gln Arg Leu Glu Ala Val Trp Ser Ile Glu Ala Tyr
            195                 200                 205
Arg Lys Lys Glu Asp Ala Asn Gln Val Leu Leu Glu Leu Ala Ile Leu
    210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
    275                 280                 285
Phe Val Thr Ile Ile Asp Asp Ile Tyr Asp Val Tyr Gly Thr Leu Asp
290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Thr Glu Pro Ile Leu Pro Phe Glu Arg
    530                 535                 540
```

<210> SEQ ID NO 45
<211> LENGTH: 544
<212> TYPE: PRT
<213> ORGANISM: Artificial Sequence
<220> FEATURE:
<223> OTHER INFORMATION: Synthetic construct

<400> SEQUENCE: 45

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Glu Asp Ala Ile Glu Val Tyr Lys
            20                  25                  30

Asp Lys Ala Lys Lys Leu Asp Ala Glu Val Arg Ser Lys Ile Asn Asn
        35                  40                  45

Glu Thr Ala Glu Phe Leu Thr Gln Leu Glu Leu Ile Asp Thr Ile Gln
    50                  55                  60

Arg Leu Gly Leu Gly Tyr Arg Phe Glu Ser Asp Ile Arg Arg Ala Leu
65                  70                  75                  80

Asp Arg Phe Val Ser Ser Gly Gly Phe Glu Ala Val Ala Lys Thr Ser
                85                  90                  95

Leu Gln Ala Thr Ala Leu Ser Phe Arg Leu Leu Arg Gln His Gly Phe
            100                 105                 110

Glu Val Ser Gln Glu Val Phe Asn Gly Phe Lys Asp Gln Asn Gly Asn
        115                 120                 125

Phe Met Glu Asp Leu Lys Glu Asp Ile Lys Ala Leu Leu Ser Leu His
    130                 135                 140

Glu Ala Ser Phe Leu Ala Leu Glu Gly Glu Asn Ile Leu Asp Glu Ala
145                 150                 155                 160

Lys Val Phe Thr Ile Ser His Leu Lys Glu Leu Asn Glu Glu Lys Ile
                165                 170                 175

Gly Lys Asp Met Val Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Arg Val Leu Leu Glu Leu Ala Ile Leu
    210                 215                 220

Asp Tyr Asn Met Val Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Ile Ser Val Ala Lys Met Phe Ser
        275                 280                 285

Phe Val Thr Ile Ile Asp Asp Ile Tyr Asp Val Tyr Gly Thr Leu Glu
    290                 295                 300

Glu Leu Glu Leu Phe Thr Asp Ala Val Glu Arg Trp Asp Val Ser Ala
305                 310                 315                 320

Ile Asp Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Glu Lys Gly Glu
            340                 345                 350

Asn Ile Leu Pro Tyr Leu Thr Lys Ala Trp Ala Asp Leu Cys Asn Ala
        355                 360                 365
```

```
Phe Leu Gln Glu Ala Arg Phe Leu Tyr Asn Lys Ser Thr Pro Thr Phe
    370                 375                 380

Ser Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                    405                 410                 415

Thr Glu Asn Leu Leu Lys Tyr His Asp Ile Ile Ser Trp Pro Ser Tyr
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Asp Ser Leu Phe Ala
                485                 490                 495

Lys His Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Leu Glu Arg
530                 535                 540

<210> SEQ ID NO 46
<211> LENGTH: 544
<212> TYPE: PRT
<213> ORGANISM: Artificial Sequence
<220> FEATURE:
<223> OTHER INFORMATION: Synthetic construct

<400> SEQUENCE: 46

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
                20                  25                  30

Asp Lys Ala Lys Lys Leu Glu Ala Glu Val Arg Arg Glu Ile Asn Asn
            35                  40                  45

Glu Lys Ala Glu Phe Leu Thr Leu Leu Glu Leu Ile Asp Asn Val Gln
50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190
```

His Arg Arg Thr Gln Arg Leu Glu Ala Val Trp Ser Ile Glu Ala Tyr
            195                 200                 205

Arg Lys Lys Glu Asp Ala Asn Gln Val Leu Leu Glu Leu Ala Ile Leu
        210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

<210> SEQ ID NO 47
<211> LENGTH: 544
<212> TYPE: PRT
<213> ORGANISM: Artificial Sequence
<220> FEATURE:
<223> OTHER INFORMATION: Synthetic construct

<400> SEQUENCE: 47

Met Glu Thr Arg Arg Thr Ala Asn Tyr Glu Pro Asn Ser Trp Asp Tyr
1               5                   10                  15

```
Asp Tyr Leu Leu Ser Ser Asp Asn Asp Ala Ile Glu Leu Tyr Lys
            20                  25                  30

Asp Lys Ala Lys Lys Leu Asp Ala Glu Val Arg Ser Lys Ile Asn Asn
        35                  40                  45

Glu Lys Ala Glu Phe Leu Thr Gln Leu Glu Leu Ile Asp Thr Ile Gln
 50                  55                  60

Arg Leu Gly Leu Gly Tyr Arg Phe Glu Ser Asp Ile Arg Arg Ala Ile
 65                  70                  75                  80

Asp Arg Tyr Val Ser Ser Gly Gly Phe Glu Ala Val Ala Lys Thr Ser
                85                  90                  95

Leu His Ala Thr Ala Leu Ser Phe Arg Leu Leu Arg Gln His Gly Phe
            100                 105                 110

Glu Val Ser Gln Glu Val Phe Ser Gly Phe Lys Asp Gln Asn Gly Asn
            115                 120                 125

Phe Met Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Thr Ile Ser His Leu Lys Glu Leu Asn Glu Glu Lys Ile
                165                 170                 175

Gly Lys Asp Leu Ala Asp Gln Val Asn His Ala Leu Glu Leu Pro Leu
            180                 185                 190

His Arg Arg Thr Gln Arg Leu Glu Ala Val Trp Ser Ile Glu Ala Tyr
            195                 200                 205

Arg Lys Lys Glu Gly Ala Asn Arg Ala Leu Leu Glu Leu Ala Ile Leu
210                 215                 220

Asp Tyr Asn Met Val Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Lys Ser Val Ala Lys Met Phe Ser
            275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Ser Ala
305                 310                 315                 320

Val Asp Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Glu Lys Gly Glu
            340                 345                 350

Asn Ile Leu Pro Tyr Leu Thr Lys Ala Trp Ala Asp Leu Cys Asn Ala
            355                 360                 365

Phe Leu Gln Glu Ala Lys Phe Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Thr Glu Asn Leu Gln Lys Tyr His Asp Ile Ile Ser Trp Pro Ser Tyr
            420                 425                 430

Ile Phe Arg Leu Cys Asn Asp Leu Ala Ser Ala Ser Ala Glu Ile Ala
```

```
                    435                 440                 445
Arg Gly Glu Thr Ala Asn Ser Val Ser Cys Tyr Ile Arg Thr Lys Gly
        450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Val Gly Asp Ser Leu Phe Ala
                485                 490                 495

Lys Gln Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
530                 535                 540
```